United States Patent
Brown et al.

(10) Patent No.: US 9,428,752 B2
(45) Date of Patent: *Aug. 30, 2016

(54) METHODS AND COMPOSITIONS FOR THE SPECIFIC INHIBITION OF BETA-CATENIN BY DOUBLE-STRANDED RNA

(71) Applicant: Dicerna Pharmaceuticals, Inc., Cambridge, MA (US)

(72) Inventors: Bob D. Brown, Littleton, MA (US); Henryk T. Dudek, Wellesley, MA (US)

(73) Assignee: Dicerna Pharmaceuticals, Inc., Cambridge, MA (US)

(*) Notice: Subject to any disclaimer, the term of this patent is extended or adjusted under 35 U.S.C. 154(b) by 52 days.

This patent is subject to a terminal disclaimer.

(21) Appl. No.: 14/925,952

(22) Filed: Oct. 28, 2015

(65) Prior Publication Data

US 2016/0053263 A1    Feb. 25, 2016

Related U.S. Application Data

(60) Continuation of application No. 14/300,754, filed on Jun. 10, 2014, now Pat. No. 9,243,244, which is a division of application No. 13/718,525, filed on Dec. 18, 2012, now Pat. No. 8,815,825, which is a continuation of application No. PCT/US2011/042820, filed on Jul. 1, 2011.

(60) Provisional application No. 61/361,776, filed on Jul. 6, 2010.

(51) Int. Cl.
   *C12N 15/11* (2006.01)
   *C12N 15/113* (2010.01)

(52) U.S. Cl.
   CPC .......... *C12N 15/113* (2013.01); *C12N 2310/14* (2013.01); *C12N 2310/321* (2013.01)

(58) Field of Classification Search
   None
   See application file for complete search history.

(56) References Cited

U.S. PATENT DOCUMENTS

| | | |
|---|---|---|
| 2003/0064384 A1 | 4/2003 | Hung et al. |
| 2004/0175703 A1 | 9/2004 | Kreutzer et al. |
| 2008/0113351 A1 | 5/2008 | Naito et al. |
| 2009/0156533 A1 | 6/2009 | McSwiggen et al. |
| 2009/0176725 A1 | 7/2009 | Morrissey et al. |
| 2009/0203137 A1 | 8/2009 | Worm |

FOREIGN PATENT DOCUMENTS

WO    2007031091 A2    3/2007

OTHER PUBLICATIONS

Sun et al.; Asymmetric RNA duplexes mediate RNA interference in mammalian cells, Nature Biotechnology, vol. 26 (12), pp. 1379-1382.

International Search Report for corresponding International Application No. PCT/US2011/42820, dated Apr. 23, 2012, 6 pages.

*Primary Examiner* — Kate Poliakova-Georgantas

(74) *Attorney, Agent, or Firm* — Mintz Levin Cohn Ferris Glovsky and Popeo, P.C.; Christopher R. Crowles

(57) ABSTRACT

This invention relates to compounds, compositions, and methods useful for reducing β-catenin target RNA and protein levels via use of dsRNAs, e.g., Dicer substrate siRNA (DsiRNA) agents.

14 Claims, 32 Drawing Sheets

Figure 11
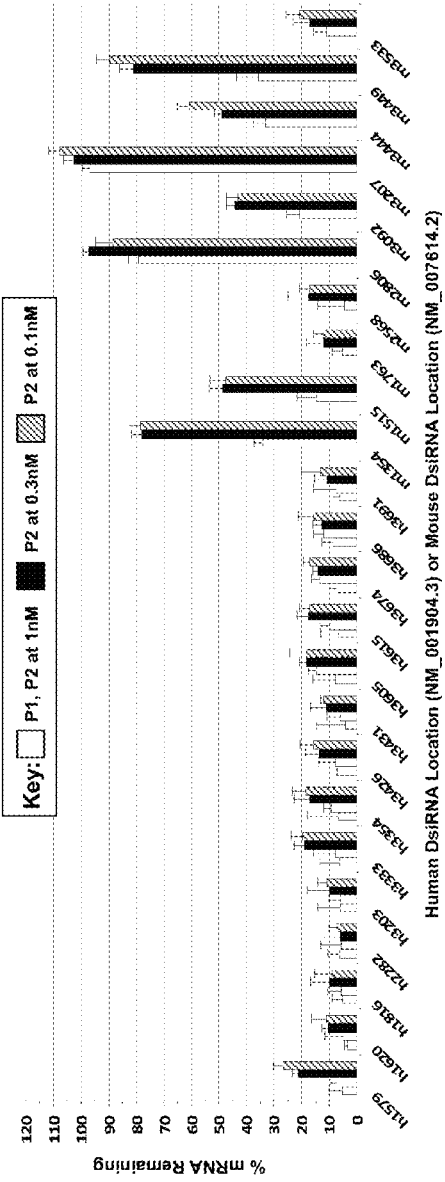

Figure 25
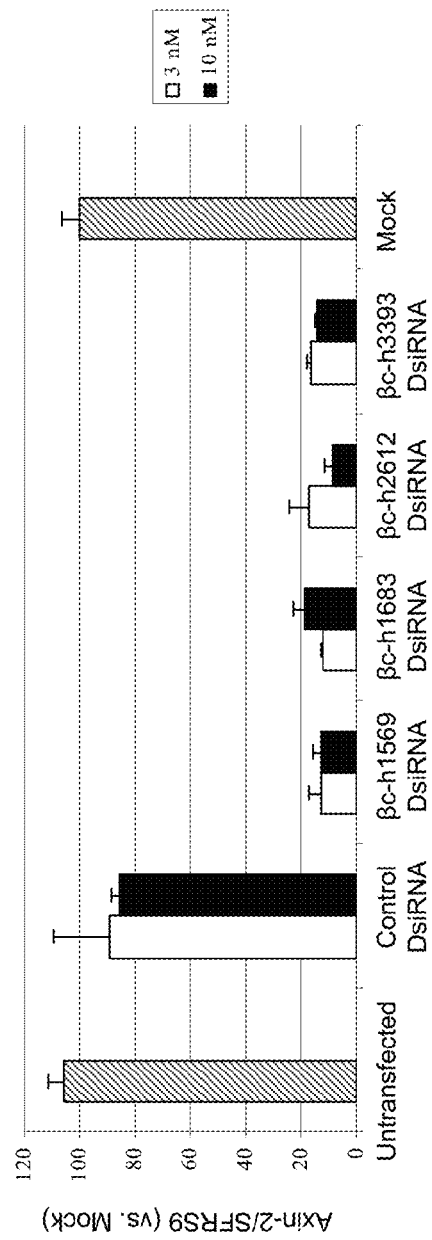
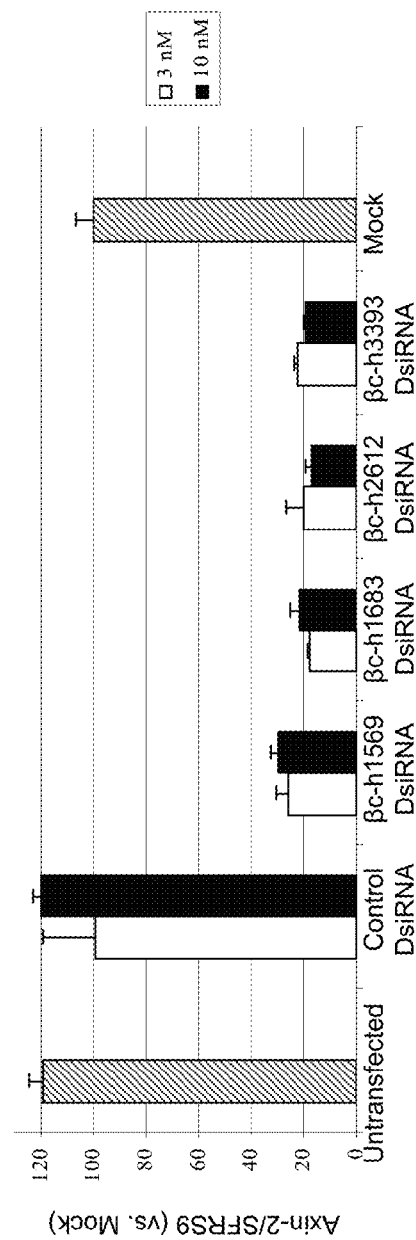

METHODS AND COMPOSITIONS FOR THE SPECIFIC INHIBITION OF BETA-CATENIN BY DOUBLE-STRANDED RNA

CROSS-REFERENCE TO RELATED APPLICATIONS

The present application is a continuation of U.S. patent application Ser. No. 14/300,754, filed Jun. 10, 2014, pending, which is a divisional of U.S. patent application Ser. No. 13/718,525, filed Dec. 18, 2012, granted, which is a continuation of PCT international application Ser. No. PCT/US2011/042820, filed Jul. 1, 2011, designating the United States, which claims benefit under 35 U.S.C. §119(e) of U.S. provisional patent application No. 61/361,776, filed Jul. 6, 2010. The entire contents of the aforementioned patent applications are incorporated herein by this reference.

FIELD OF THE INVENTION

The present invention relates to compounds, compositions, and methods for the study, diagnosis, and treatment of traits, diseases and conditions that respond to the modulation of CTNNB1 (β-catenin) gene expression and/or activity.

BACKGROUND OF THE INVENTION

Wnt pathway signaling mediates development, regeneration, cellular proliferation and stem cell formation (Fuerer et al. *EMBO Rep* 9: 134-8). Abnormal Wnt pathway signaling has been associated with a wide range of diseases, including cancer (Moon et al. *Nat Rev Genet.* 5: 691-701). Mutations in β-catenin (encoded by the CTNNB1 gene in humans)—an oncogene that is the key mediator of Wnt signaling—have been specifically associated with colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers (Polakis P. *Genes Dev.* 14: 1837-51; Samowitz et al. *Cancer Res.* 59: 1442-4; Iwao et al. *Cancer Res.* 58: 1021-6; Mirabelli-Primdahl et al. *Cancer Res.* 59: 3346-51; Shitoh et al. *J Clin Path.* 52: 695-6; Tejpar et al. *Oncogene* 18: 6615-20; Kitaeva et al. *Cancer Res.* 57: 4478-81; Sparks et al. *Cancer Res.* 58: 1130-4; Miyaki et al. *Cancer Res.* 59: 4506-9; Park et al. *Cancer Res.* 59: 4257-60; Huang et al. *Am J Pathol.* 155: 1795-801; Nhieu et al. *Am J Pathol.* 155: 703-10; Legoix et al. *Oncogene* 18: 4044-6; Jeng et al. *Cancer Lett.* 152: 45-51; Koch et al. *Cancer Res.* 59: 269-73; Wei et al. *Oncogene* 19: 498-504; Koesters et al. *Cancer Res.* 59: 3880-2; Maiti et al. *Cancer Res.* 60: 6288-92; Zurawel et al. *Cancer Res.* 58: 896-9; Gamallo et al. *Am J Pathol.* 155: 527-36; Palacios and Gamallo *Cancer Res.* 58: 1344-7; Wright et al. *Int J Cancer* 82: 625-9; Gerdes et al. *Digestion* 60: 544-8; Chan et al. *Nat Genet.* 21: 410-3; Voeller et al. *Cancer Res.* 58: 2520-3; Garcia-Rostan et al. *Cancer Res.* 59: 1811-5; Fukuchi et al. *Cancer Res.* 58: 3526-8). Many such mutations in β-catenin are believed to impart increased stability to the β-catenin protein, making β-catenin an attractive target for development of therapeutics that inhibit and/or reduce levels of the β-catenin protein. Given the role of β-catenin in the development of cancer and other diseases and/or disorders (e.g., proper β-catenin activity is important for hair follicle/epithelial stem cell function, meaning that certain inhibitors of (β-catenin possess depilatory properties), there remains an unmet need for therapeutically effective inhibitors of β-catenin.

Double-stranded RNA (dsRNA) agents possessing strand lengths of 25 to 35 nucleotides have been described as effective inhibitors of target gene expression in mammalian cells (Rossi et al., U.S. Patent Application Nos. 2005/0244858 and US 2005/0277610). dsRNA agents of such length are believed to be processed by the Dicer enzyme of the RNA interference (RNAi) pathway, leading such agents to be termed "Dicer substrate siRNA" ("DsiRNA") agents. Additional modified structures of DsiRNA agents were previously described (Rossi et al., U.S. Patent Application No. 2007/0265220).

BRIEF SUMMARY OF THE INVENTION

The present invention is directed to compositions that contain double stranded RNA ("dsRNA"), and methods for preparing them. The dsRNAs of the invention are capable of reducing the expression of a target CTNNB1 gene (encoding (β-catenin) in a cell, either in vitro or in a mammalian subject. More particularly, the invention is directed to Dicer substrate siRNAs ("DsiRNAs") with structures and modification patterns which act as effective and highly potent β-catenin inhibitory agents, and also may possess extended duration of inhibitory effect. A number of such DsiRNAs possess target-specific inhibitory potencies and efficacies that are significantly enhanced relative to 21 nucleotide siRNAs directed against the same target RNA.

In one aspect, the invention provides an isolated double stranded ribonucleic acid (dsRNA) comprising first and second nucleic acid strands and a duplex region of at least 25 base pairs, wherein the first strand is 25-34 nucleotides in length and the second strand is 26-35 nucleotides in length and comprises 1-5 single-stranded nucleotides at its 3' terminus, where the second oligonucleotide strand is sufficiently complementary to a target β-catenin cDNA sequence of SEQ ID NOs: 2226-3334 along at least 15 nucleotides of the second oligonucleotide strand length to reduce β-catenin target gene expression when the double stranded nucleic acid is introduced into a mammalian cell. Optionally, the second oligonucleotide strand is complementary to a target β-catenin cDNA sequence of SEQ ID NOs: 1-3 and 5-6 along at most 27 nucleotides of its length.

In one embodiment, starting from the first nucleotide (position 1) at the 3' terminus of the first oligonucleotide strand, position 1, 2 and/or 3 is substituted with a modified nucleotide. In certain embodiments, the modified nucleotide residue of the 3' terminus of the first strand is a deoxyribonucleotide, an acyclonucleotide or a fluorescent molecule. In a related embodiment, position 1 of the 3' terminus of the first oligonucleotide strand is a deoxyribonucleotide.

In an additional embodiment, the 3' terminus of the first strand and the 5' terminus of the second strand form a blunt end.

In another embodiment, the first strand is 25 nucleotides in length and the second strand is 27 nucleotides in length.

In one embodiment, the second strand includes a sequence of SEQ ID NOs: 1117-2225.

In another embodiment, the first strand includes a sequence of SEQ ID NOs: 8-1116, 3335-3822 and 3823-4443.

In an additional embodiment, the dsRNA includes a pair of first strand/second strand sequences as shown for a DsiRNA agent of Tables 2-4, 6, 9 or 11.

In one embodiment, each of the first and the second strands has a length which is at least 26 nucleotides.

In another embodiment, the nucleotides of the 3' overhang include a modified nucleotide. Optionally, the modified nucleotide of the 3' overhang is a 2'-O-methyl ribonucleotide. In a related embodiment, all nucleotides of the 3' overhang are modified nucleotides.

In an additional embodiment, one or both of the first and second oligonucleotide strands includes a 5' phosphate.

In another embodiment, the modified nucleotide residues of the dsRNA are 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino or 2'-O—(N-methlycarbamate).

In one embodiment, the 3' overhang of the dsRNA is 1-3 nucleotides in length. Optionally, the 3' overhang is 1-2 nucleotides in length. In a related embodiment, the 3' overhang is two nucleotides in length and the modified nucleotide of the 3' overhang is a 2'-O-methyl modified ribonucleotide.

In a further embodiment, the second oligonucleotide strand, starting from the nucleotide residue of the second strand that is complementary to the 5' terminal nucleotide residue of the first oligonucleotide strand, includes alternating modified and unmodified nucleotide residues. In another embodiment, the second oligonucleotide strand, starting from the nucleotide residue of the second strand that is complementary to the 5' terminal nucleotide residue of the first oligonucleotide strand, includes unmodified nucleotide residues at all positions from position 18 to the 5' terminus of the second oligonucleotide strand.

In another embodiment, each of the first and the second strands has a length which is at least 26 and at most 30 nucleotides.

In one embodiment, the dsRNA is cleaved endogenously in the cell by Dicer.

In an additional embodiment, the amount of the isolated double stranded nucleic acid sufficient to reduce expression of the target gene is 1 nanomolar or less, 200 picomolar or less, 100 picomolar or less, 50 picomolar or less, 20 picomolar or less, 10 picomolar or less, 5 picomolar or less, 2 picomolar or less or 1 picomolar or less in the environment of the cell.

In a further embodiment, the isolated dsRNA possesses greater potency than isolated 21mer siRNAs directed to the identical at least 15 nucleotides of the target β-catenin cDNA in reducing target β-catenin gene expression when assayed in vitro in a mammalian cell at an effective concentration in the environment of a cell of 1 nanomolar or less, 200 picomolar or less, 100 picomolar or less, 50 picomolar or less, 20 picomolar or less, 10 picomolar or less, 5 picomolar or less, 2 picomolar or less or 1 picomolar or less.

In another embodiment, the isolated dsRNA is sufficiently complementary to the target β-catenin cDNA sequence to reduce β-catenin target gene expression by at least 10%, at least 50%, at least 80-90%, at least 95%, at least 98%, or at least 99% when the double stranded nucleic acid is introduced into a mammalian cell.

In a further embodiment, the first and second strands are joined by a chemical linker. In a related embodiment, the 3' terminus of the first strand and the 5' terminus of the second strand are joined by a chemical linker.

In one embodiment, a nucleotide of the second or first strand is substituted with a modified nucleotide that directs the orientation of Dicer cleavage.

In another embodiment, the dsRNA has a modified nucleotide that is a deoxyribonucleotide, a dideoxyribonucleotide, an acyclonucleotide, a 3'-deoxyadenosine (cordycepin), a 3'-azido-3'-deoxythymidine (AZT), a 2',3'-dideoxyinosine (ddI), a 2',3'-dideoxy-3'-thiacytidine (3TC), a 2',3'-didehydro-2',3'-dideoxythymidine (d4T), a monophosphate nucleotide of 3'-azido-3'-deoxythymidine (AZT), a 2',3'-dideoxy-3'-thiacytidine (3TC) and a monophosphate nucleotide of 2',3'-didehydro-2',3'-dideoxythymidine (d4T), a 4-thiouracil, a 5-bromouracil, a 5-iodouracil, a 5-(3-aminoallyl)-uracil, a 2'-O-alkyl ribonucleotide, a 2'-O-methyl ribonucleotide, a 2'-amino ribonucleotide, a 2'-fluoro ribonucleotide, or a locked nucleic acid.

In an additional embodiment, the dsRNA has a phosphonate, a phosphorothioate or a phosphotriesterphosphate backbone modification.

In one embodiment, the invention provides a method for reducing expression of a target β-catenin gene in a mammalian cell having contacting a mammalian cell in vitro with an isolated dsRNA as described in an amount sufficient to reduce expression of a target β-catenin gene in the cell.

In one embodiment, target β-catenin gene expression is reduced by at least 10%, at least 50%, or at least 80-90%. In another embodiment, target β-catenin mRNA levels are reduced at least 90% at least 8 days after the cell is contacted with the dsRNA. In a further embodiment, β-catenin mRNA levels are reduced by at least 70% at least 10 days after the cell is contacted with the dsRNA.

In a further embodiment, the invention provides a method for reducing expression of a target β-catenin gene in a mammal by administering an isolated dsRNA as described to a mammal in an amount sufficient to reduce expression of a target β-catenin gene in the mammal.

In one embodiment, the isolated dsRNA is administered at a dosage of 1 microgram to 5 milligrams per kilogram of the mammal per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In another embodiment, the isolated dsRNA possesses greater potency than isolated 21mer siRNAs directed to the identical at least 15 nucleotides of the target β-catenin cDNA in reducing target β-catenin gene expression when assayed in vitro in a mammalian cell at an effective concentration in the environment of a cell of 1 nanomolar or less.

In an additional embodiment, the administering step includes intravenous injection, intramuscular injection, intraperitoneal injection, infusion, subcutaneous injection, transdermal, aerosol, rectal, vaginal, topical, oral or inhaled delivery.

In a further embodiment, the invention provides a method for selectively inhibiting the growth of a cell by contacting a cell with an amount of an isolated dsRNA as described, in an amount sufficient to inhibit the growth of the cell.

In one embodiment, the cell is a tumor cell of a subject. Optionally, the cell is a tumor cell in vitro. In a related embodiment, the cell is a human cell.

In an additional embodiment, the invention provides a formulation which includes an isolated dsRNA as described, where the dsRNA is present in an amount effective to reduce target β-catenin RNA levels when the dsRNA is introduced into a mammalian cell in vitro by at least 10%, at least 50% or at least 80-90%, and where the dsRNA possesses greater potency than isolated 21mer siRNAs directed to the identical at least 15 nucleotides of the target β-catenin cDNA in reducing target β-catenin RNA levels when assayed in vitro in a mammalian cell at an effective concentration in the environment of a cell of 1 nanomolar or less.

In one embodiment, the effective amount is 1 nanomolar or less, 200 picomolar or less, 100 picomolar or less, 50 picomolar or less, 20 picomolar or less, 10 picomolar or less, 5 picomolar or less, 2 picomolar or less or 1 picomolar or less in the environment of the cell.

In another embodiment, the invention provides a formulation which includes an isolated dsRNA as described, where the dsRNA is present in an amount effective to reduce target RNA levels when the dsRNA is introduced into a cell of a mammalian subject by at least 10%, at least 50% or at least 80-90%, and where the dsRNA possesses greater potency than isolated 21mer siRNAs directed to the identical at least 15 nucleotides of the target β-catenin cDNA in reducing target β-catenin RNA levels when assayed in vitro in a mammalian cell at an effective concentration in the environment of a cell of 1 nanomolar or less.

In one embodiment, the effective amount is a dosage of 1 microgram to 5 milligrams per kilogram of the subject per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In an additional embodiment, the invention provides a mammalian cell containing an isolated dsRNA as described.

Another embodiment of the invention provides a pharmaceutical composition which includes an isolated dsRNA as described and a pharmaceutically acceptable carrier. A further embodiment of the invention provides a kit having an isolated dsRNA as described and instructions for its use.

In an additional aspect, the invention provides a composition possessing β-catenin inhibitory activity consisting essentially of an isolated double stranded ribonucleic acid (dsRNA) comprising first and second nucleic acid strands and a duplex region of at least 25 base pairs, where the first strand is 25-34 nucleotides in length and the second strand is 26-35 nucleotides in length and comprises 1-5 single-stranded nucleotides at its 3' terminus, where the second oligonucleotide strand is sufficiently complementary to a target β-catenin cDNA sequence of SEQ ID NOs: 2226-3334 along at least 15 nucleotides of the second oligonucleotide strand length to reduce β-catenin target gene expression when the double stranded nucleic acid is introduced into a mammalian cell.

In another embodiment, the invention provides a method for treating or preventing a β-catenin-associated disease or disorder in a subject by administering a dsRNA and/or dsRNA-containing composition of the invention and a pharmaceutically acceptable carrier to a subject in an amount sufficient to treat or prevent a β-catenin-associated disease or disorder in the subject. In a related embodiment, the β-catenin-associated disease or disorder is colorectal or hepatocellular cancer. Optionally, the β-catenin-associated disease or disorder is melanoma.

In another aspect, the invention provides an isolated double stranded ribonucleic acid (dsRNA) comprising first and second nucleic acid strands and a duplex region of at least 25 base pairs, wherein the dsRNA comprises blunt ends, where each of the first and second oligonucleotide strands consists of the same number of nucleotide residues and is at most 35 nucleotides in length, wherein the second oligonucleotide strand is sufficiently complementary to a target β-catenin cDNA sequence of SEQ ID NOs: 2226-3334 along at least 15 nucleotides of the second oligonucleotide strand length to reduce β-catenin target gene expression when the double stranded nucleic acid is introduced into a mammalian cell.

In one embodiment, the dsRNA is capable of reducing target gene expression at a concentration of less than 1 nanomolar in the environment of a cell. In another embodiment, each of the first and the second strands has a length which is at least 26 nucleotides. In a related embodiment, each of the first and the second strands has a length which is 26-30 nucleotides. Optionally, each of the first and the second strands has a length which is 27 nucleotides.

In certain embodiments, the second strand of the dsRNA includes a sequence selected from SEQ ID NOs: 1117-2225. (Optionally, the second strand is a sequence selected from SEQ ID NOs: 1117-2225.) In related embodiments, the first strand of the dsRNA includes a sequence selected from SEQ ID NOs: 5553-7770. (Optionally, the first strand is a sequence selected from SEQ ID NOs: 5553-7770.) In a further embodiment, the dsRNA includes a pair of first strand and corresponding second strand sequences selected from Tables 7-8 or 12-13.

Another aspect of the invention provides an isolated double stranded ribonucleic acid (dsRNA) comprising first and second nucleic acid strands and a duplex region of at least 25 base pairs, where the dsRNA comprises a blunt end, where each of the first and second oligonucleotide strands consists of the same number of nucleotide residues and is at most 35 nucleotides in length, where the ultimate and penultimate residues of the 3' terminus of the first strand and the ultimate and penultimate residues of said 5' terminus of the second strand form one or two mismatched based pairs. where the second oligonucleotide strand is sufficiently complementary to a target β-catenin cDNA sequence of SEQ ID NOs: 2226-3334 along at least 15 nucleotides of the second oligonucleotide strand length to reduce 3-catenin target gene expression when the double stranded nucleic acid is introduced into a mammalian cell.

In one embodiment, the first strand includes a sequence of SEQ ID NOs: 5553-6661.

In an additional aspect, the invention provides a composition possessing β-catenin inhibitory activity consisting essentially of an isolated double stranded ribonucleic acid (dsRNA) comprising first and second nucleic acid strands and a duplex region of at least 25 base pairs, where the dsRNA comprises blunt ends, where each of the first and second oligonucleotide strands consists of the same number of nucleotide residues and is at most 35 nucleotides in length, where the second oligonucleotide strand is sufficiently complementary to a target β-catenin cDNA sequence of SEQ ID NOs: 2226-3334 along at least 15 nucleotides of the second oligonucleotide strand length to reduce β-catenin target gene expression when the double stranded nucleic acid is introduced into a mammalian cell and the second oligonucleotide strand is complementary to a target β-catenin cDNA sequence of SEQ ID NOs: 1-3 and 5-6 along at most 35 nucleotides of its length.

In another aspect, the invention provides an isolated dsRNA molecule consisting of a sense region and an antisense region, where the sense region and the antisense region together form a duplex region consisting of 19-35 base pairs and the antisense region includes a sequence that is the complement of a sequence of SEQ ID NOs 4444-5552, and the isolated dsRNA further includes from zero to two 3' overhang regions where each overhang region is six or fewer nucleotides in length. Optionally, the duplex region consists of 25-35 base pairs.

In a further aspect, the invention provides a siRNA molecule consisting of a sense region and an antisense region, where the sense region and the antisense region together form a duplex region consisting of 19-23 base pairs and the antisense region includes a sequence that is the complement of a sequence of SEQ ID NOs 4444-5552, and the isolated dsRNA further includes from zero to four overhang regions, where each overhang region is six or fewer nucleotides in length.

In a further aspect, the invention provides an isolated double stranded ribonucleic acid (dsRNA) comprising first and second nucleic acid strands, wherein the first strand is 15-35 nucleotides in length and the second strand is 19-35 nucleotides in length, wherein the second oligonucleotide strand is sufficiently complementary to a target β-catenin cDNA sequence of Table 18 along at least 19 nucleotides of the second oligonucleotide strand length to reduce β-catenin target gene expression when the double stranded nucleic acid is introduced into a mammalian cell. In certain embodiments, the isolated dsRNA possesses a duplex region of at least 25 base pairs. In one embodiment, the second strand of the isolated dsRNA includes a one to five nucleotide single stranded overhang of the first strand at the 3' terminus of the second strand. In another embodiment, the first strand is 25-35 nucleotides in length. In an additional embodiment, the second strand is 25-35 nucleotides in length. Optionally, the second oligonucleotide strand is complementary to a target β-catenin cDNA sequence of GenBank Accession Nos. NM_001904.3, NM_001098209.1 or NM_001098210.1 along at most 27 nucleotides of the second oligonucleotide strand length.

In one embodiment, starting from the first nucleotide (position 1) at the 3' terminus of the first oligonucleotide strand, position 1, 2 and/or 3 is substituted with a modified nucleotide. In certain embodiments, the modified nucleotide residue of the 3' terminus of the first strand is a deoxyribonucleotide, an acyclonucleotide or a fluorescent molecule. In a related embodiment, position 1 of the 3' terminus of the first oligonucleotide strand is a deoxyribonucleotide.

In an additional embodiment, the 3' terminus of the first strand and the 5' terminus of the second strand form a blunt end.

In another embodiment, the first strand is 25 nucleotides in length and the second strand is 27 nucleotides in length.

In one embodiment, the second strand includes a sequence of SEQ ID NOs: 1122, 1126, 1216, 1239, 1282, 1368, 1165, 1509, 1536 and 1552.

In another embodiment, the first strand includes a sequence of SEQ ID NOs: 13, 17, 107, 130, 173, 259, 56, 400, 427 and 443.

In an additional embodiment, the dsRNA includes a pair of first strand/second strand sequences as shown for a DsiRNA agent of Tables 2-3, 6-9 and 11-13.

In one embodiment, each of the first and the second strands has a length which is at least 26 nucleotides.

In another embodiment, the nucleotides of the 3' overhang include a modified nucleotide. Optionally, the modified nucleotide of the 3' overhang is a 2'-O-methyl ribonucleotide. In a related embodiment, all nucleotides of the 3' overhang are modified nucleotides.

In an additional embodiment, one or both of the first and second oligonucleotide strands includes a 5' phosphate.

In another embodiment, the modified nucleotide residues of the dsRNA are 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino or 2'-O—(N-methlycarbamate).

In one embodiment, the 3' overhang of the dsRNA is 1-3 nucleotides in length. Optionally, the 3' overhang is 1-2 nucleotides in length. In a related embodiment, the 3' overhang is two nucleotides in length and the modified nucleotide of the 3' overhang is a 2'-O-methyl modified ribonucleotide.

In a further embodiment, the second oligonucleotide strand, starting from the nucleotide residue of the second strand that is complementary to the 5' terminal nucleotide residue of the first oligonucleotide strand, includes alternating modified and unmodified nucleotide residues. In another embodiment, the second oligonucleotide strand, starting from the nucleotide residue of the second strand that is complementary to the 5' terminal nucleotide residue of the first oligonucleotide strand, includes unmodified nucleotide residues at all positions from position 18 to the 5' terminus of the second oligonucleotide strand.

In another embodiment, each of the first and the second strands has a length which is at least 26 and at most 30 nucleotides.

In one embodiment, the dsRNA is cleaved endogenously in the cell by Dicer.

In an additional embodiment, the amount of the isolated double stranded nucleic acid sufficient to reduce expression of the target gene is 1 nanomolar or less, 200 picomolar or less, 100 picomolar or less, 50 picomolar or less, 20 picomolar or less, 10 picomolar or less, 5 picomolar or less, 2 picomolar or less or 1 picomolar or less in the environment of the cell.

In a further embodiment, the isolated dsRNA possesses greater potency than isolated 21mer siRNAs directed to the identical at least 19 nucleotides of the target β-catenin cDNA in reducing target β-catenin gene expression when assayed in vitro in a mammalian cell at an effective concentration in the environment of a cell of 1 nanomolar or less, 200 picomolar or less, 100 picomolar or less, 50 picomolar or less, 20 picomolar or less, 10 picomolar or less, 5 picomolar or less, 2 picomolar or less or 1 picomolar or less.

In another embodiment, the isolated dsRNA is sufficiently complementary to the target β-catenin cDNA sequence to reduce β-catenin target gene expression by at least 10%, at least 50%, at least 80-90%, at least 95%, at least 98%, or at least 99% when the double stranded nucleic acid is introduced into a mammalian cell.

In a further embodiment, the first and second strands are joined by a chemical linker. In a related embodiment, the 3' terminus of the first strand and the 5' terminus of the second strand are joined by a chemical linker.

In one embodiment, a nucleotide of the second or first strand is substituted with a modified nucleotide that directs the orientation of Dicer cleavage.

In another embodiment, the dsRNA has a modified nucleotide that is a deoxyribonucleotide, a dideoxyribonucleotide, an acyclonucleotide, a 3'-deoxyadenosine (cordycepin), a 3'-azido-3'-deoxythymidine (AZT), a 2',3'-dideoxyinosine (ddI), a 2',3'-dideoxy-3'-thiacytidine (3TC), a 2',3'-didehydro-2',3'-dideoxythymidine (d4T), a monophosphate nucleotide of 3'-azido-3'-deoxythymidine (AZT), a 2',3'-dideoxy-3'-thiacytidine (3TC) and a monophosphate nucleotide of 2',3'-didehydro-2',3'-dideoxythymidine (d4T), a 4-thiouracil, a 5-bromouracil, a 5-iodouracil, a 5-(3-aminoallyl)-uracil, a 2'-O-alkyl ribonucleotide, a 2'-O-methyl ribonucleotide, a 2'-amino ribonucleotide, a 2'-fluoro ribonucleotide, or a locked nucleic acid.

In an additional embodiment, the dsRNA has a phosphonate, a phosphorothioate or a phosphotriesterphosphate backbone modification.

In a further embodiment, the dsRNA contains a morpholino nucleic acid or oligonucleotide, or a peptide nucleic acid (PNA).

In one embodiment, the invention provides a method for reducing expression of a target β-catenin gene in a mammalian cell having contacting a mammalian cell in vitro with an isolated dsRNA as described in an amount sufficient to reduce expression of a target β-catenin gene in the cell.

In one embodiment, target β-catenin gene expression is reduced by at least 10%, at least 50%, or at least 80-90%. In another embodiment, target β-catenin mRNA levels are reduced at least 90% at least 8 days after the cell is contacted with the dsRNA. In a further embodiment, β-catenin mRNA levels are reduced by at least 70% at least 10 days after the cell is contacted with the dsRNA.

In a further embodiment, the invention provides a method for reducing expression of a target β-catenin gene in a mammal by administering an isolated dsRNA as described to a mammal in an amount sufficient to reduce expression of a target β-catenin gene in the mammal.

In one embodiment, the isolated dsRNA is administered at a dosage of 1 microgram to 5 milligrams per kilogram of the mammal per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In another embodiment, the isolated dsRNA possesses greater potency than isolated 21mer siRNAs directed to the identical at least 19 nucleotides of the target β-catenin cDNA in reducing target β-catenin gene expression when assayed in vitro in a mammalian cell at an effective concentration in the environment of a cell of 1 nanomolar or less.

In an additional embodiment, the administering step includes intravenous injection, intramuscular injection, intraperitoneal injection, infusion, subcutaneous injection, transdermal, aerosol, rectal, vaginal, topical, oral or inhaled delivery.

In a further embodiment, the invention provides a method for selectively inhibiting the growth of a cell by contacting a cell with an amount of an isolated dsRNA as described, in an amount sufficient to inhibit the growth of the cell.

In one embodiment, the cell is a tumor cell of a subject. Optionally, the cell is a tumor cell in vitro, e.g., a hepatocellular (e.g., HepG2 or HuH7) or colorectal (e.g., HCT116) cancer cell, or a HeLa or other cancer cell. In certain embodiments, the cell is a mammalian liver cell. In a related embodiment, the cell is a human cell.

In an additional embodiment, the invention provides a formulation which includes an isolated dsRNA as described, where the dsRNA is present in an amount effective to reduce target β-catenin RNA levels when the dsRNA is introduced into a mammalian cell in vitro by at least 10%, at least 50% or at least 80-90%, and where the dsRNA possesses greater potency than isolated 21mer siRNAs directed to the identical at least 19 nucleotides of the target β-catenin cDNA in reducing target β-catenin RNA levels when assayed in vitro in a mammalian cell at an effective concentration in the environment of a cell of 1 nanomolar or less.

In one embodiment, the effective amount is 1 nanomolar or less, 200 picomolar or less, 100 picomolar or less, 50 picomolar or less, 20 picomolar or less, 10 picomolar or less, 5 picomolar or less, 2 picomolar or less or 1 picomolar or less in the environment of the cell.

In another embodiment, the invention provides a formulation which includes an isolated dsRNA as described, where the dsRNA is present in an amount effective to reduce target RNA levels when the dsRNA is introduced into a cell of a mammalian subject by at least 10%, at least 50% or at least 80-90%, and where the dsRNA possesses greater potency than isolated 21mer siRNAs directed to the identical at least 19 nucleotides of the target β-catenin cDNA in reducing target β-catenin RNA levels when assayed in vitro in a mammalian cell at an effective concentration in the environment of a cell of 1 nanomolar or less.

In one embodiment, the effective amount is a dosage of 1 microgram to 5 milligrams per kilogram of the subject per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In an additional embodiment, the invention provides a mammalian cell containing an isolated dsRNA as described.

Another embodiment of the invention provides a pharmaceutical composition which includes an isolated dsRNA as described and a pharmaceutically acceptable carrier. A further embodiment of the invention provides a kit having an isolated dsRNA as described and instructions for its use.

In an additional aspect, the invention provides a composition possessing β-catenin inhibitory activity consisting essentially of an isolated double stranded ribonucleic acid (dsRNA) comprising first and second nucleic acid strands, wherein the first strand is 15-35 nucleotides in length and the second strand is 19-35 nucleotides in length, wherein the second oligonucleotide strand is sufficiently complementary to a target β-catenin cDNA sequence of Table 18 along at least 19 nucleotides of the second oligonucleotide strand length to reduce β-catenin target gene expression when the double stranded nucleic acid is introduced into a mammalian cell.

In another embodiment, the invention provides a method for treating or preventing a β-catenin-associated disease or disorder in a subject by administering a dsRNA and/or dsRNA-containing composition of the invention and a pharmaceutically acceptable carrier to a subject in an amount sufficient to treat or prevent a β-catenin-associated disease or disorder in the subject. In a related embodiment, the β-catenin-associated disease or disorder is hepatocellular or colorectal cancer, or, optionally, renal, breast, lung, ovarian, cervical, esophageal, oropharyngeal or pancreatic cancer.

In another aspect, the invention provides an isolated double stranded ribonucleic acid (dsRNA) comprising first and second nucleic acid strands, wherein the dsRNA comprises blunt ends, wherein each of the first and second oligonucleotide strands consists of the same number of nucleotide residues and is at most 35 nucleotides in length, wherein the second oligonucleotide strand is sufficiently complementary to a target β-catenin cDNA sequence of Table 18 along at least 19 nucleotides of the second oligonucleotide strand length to reduce β-catenin target gene expression when the double stranded nucleic acid is introduced into a mammalian cell.

In one embodiment, the dsRNA is capable of reducing target gene expression at a concentration of less than 1 nanomolar in the environment of a cell. In another embodiment, each of the first and the second strands has a length which is at least 26 nucleotides. In a related embodiment, each of the first and the second strands has a length which is 26-30 nucleotides. Optionally, each of the first and the second strands has a length which is 27 nucleotides.

In certain embodiments, the second strand of the dsRNA includes a sequence selected from SEQ ID NOs: 1122, 1126, 1216, 1239, 1282, 1368, 1165, 1509, 1536 and 1552. In related embodiments, the first strand of the dsRNA includes a sequence selected from SEQ ID NOs: 6667, 6671, 6761, 6784, 6827, 6913, 6710, 7054, 7081 and 7097. In a further embodiment, the dsRNA includes a pair of first strand and corresponding second strand sequences selected from Tables 2-3, 6-9 and 11-13.

Another aspect of the invention provides an isolated double stranded ribonucleic acid (dsRNA) comprising first and second nucleic acid strands, wherein the dsRNA comprises a blunt end, wherein each of the first and second oligonucleotide strands consists of the same number of nucleotide residues and is at most 35 nucleotides in length, wherein the ultimate and penultimate residues of the 3' terminus of the first strand and the ultimate and penultimate residues of said 5' terminus of the second strand form one or two mismatched based pairs, wherein the second oligonucleotide strand is sufficiently complementary to a target β-catenin cDNA sequence of Table 18 along at least 19 nucleotides of the second oligonucleotide strand length to reduce β-catenin target gene expression when the double stranded nucleic acid is introduced into a mammalian cell.

In one embodiment, the first strand includes a sequence of SEQ ID NOs: 5558, 5562, 5652, 5675, 5718, 5804, 5601, 5945, 5972 and 5988.

In an additional aspect, the invention provides a composition possessing β-catenin inhibitory activity consisting essentially of an isolated double stranded ribonucleic acid (dsRNA) comprising first and second nucleic acid strands, wherein the dsRNA comprises blunt ends, wherein each of the first and second oligonucleotide strands consists of the same number of nucleotide residues and is at most 35 nucleotides in length, wherein the second oligonucleotide strand is sufficiently complementary to a target β-catenin cDNA sequence of Table 18 along at least 19 nucleotides of the second oligonucleotide strand length to reduce β-catenin target gene expression when the double stranded nucleic acid is introduced into a mammalian cell.

In another aspect, the invention provides an isolated dsRNA molecule consisting of a sense region and an antisense region, where the sense region and the antisense region together form a duplex region consisting of 15-35 base pairs and the antisense region includes a sequence that is the complement of a sequence of Table 18, and the isolated dsRNA further includes from zero to two 3' overhang regions where each overhang region is six or fewer nucleotides in length. Optionally, the duplex region consists of 19-35 base pairs. In certain embodiments, the duplex region consists of 25-35 base pairs. In additional embodiments, the duplex region consists of 25-30 base pairs.

In a further aspect, the invention provides a siRNA molecule consisting of a sense region and an antisense region, where the sense region and the antisense region together form a duplex region consisting of 19-23 base pairs and the antisense region includes a sequence that is the complement of a sequence of Table 18, and the isolated dsRNA further includes from zero to four overhang regions, where each overhang region is six or fewer nucleotides in length.

In certain aspects, the invention is directed to Dicer substrate siRNAs ("DsiRNAs") with structures and modification patterns that act as effective and highly potent β-catenin inhibitory agents, optionally possessing extended duration of inhibitory effect. A number of such DsiRNAs possess target-specific inhibitory potencies and efficacies that are significantly enhanced relative to 19-23 base pair double stranded nucleic acids (e.g., 21 nucleotide siRNAs) directed against the same target RNA. In certain such embodiments, such a DsiRNA is more potent at reducing β-catenin target gene expression in a mammalian cell than a 19, 20, 21, 22 or 23 base pair sequence that is contained within it, when suitably formulated at a concentration of 1 nM or less.

The present invention is also directed to compounds, compositions, and methods relating to traits, diseases and conditions that respond to the modulation of expression and/or activity of genes involved in CTNNB1 gene expression pathways or other cellular processes that mediate the maintenance or development of such traits, diseases and conditions. Specifically, the invention relates to small nucleic acid molecules that are capable of being processed by the Dicer enzyme, such as Dicer substrate siRNAs (DsiRNAs) capable of mediating RNA interference (RNAi) against CTNNB1 (β-catenin) gene expression. Such anti-β-catenin DsiRNAs are useful, for example, in providing compositions for treatment of traits, diseases and conditions that can respond to modulation of β-catenin in a subject, such as cancer and/or other proliferative diseases, disorders, or conditions. Efficacy, potency, toxicity and other effects of an anti-β-catenin DsiRNA can be examined in one or more animal models of proliferative disease (exemplary suitable animal models of proliferative disease are recited below).

BRIEF DESCRIPTION OF THE DRAWINGS

FIGS. 8-11 show histograms of human β-catenin inhibitory efficacies observed for indicated DsiRNAs. "P1" indicates phase 1, while "P2" indicates phase 2. In phase 1, DsiRNAs were tested at 1 nM in the environment of HeLa cells. In phase 2, DsiRNAs were tested at 1 nM, at 0.3 nM and at 0.1 nM in the environment of HeLa cells. Individual bars represent average human β-catenin levels observed in triplicate, with standard errors shown. Human β-catenin levels were normalized to HPRT and SFRS9 levels. Expression levels were assayed with probe amplicons positioned at both positions 1297-1397 and 3506-3659 in Hs CTNNB1. (It is noted that the histograms of FIG. 8 reflect phase 2 values obtained for a subpar transfection.)

FIG. 25 shows that assayed DsiRNAs targeting human β-catenin (βcat-h1569, βcat-h1683, βcat-h2612 and βcat-h3393) effectively inhibited expression of Axin-2, a downstream target of β-catenin, in both HCT116 (colon carcinoma) and HepG2 (hepatocellular carcinoma) cell lines. Cells were assayed at two days post-transfection at indicated concentrations (3 nM and 10 nM) with designated DsiRNAs.

DETAILED DESCRIPTION OF THE INVENTION

Figure 1:
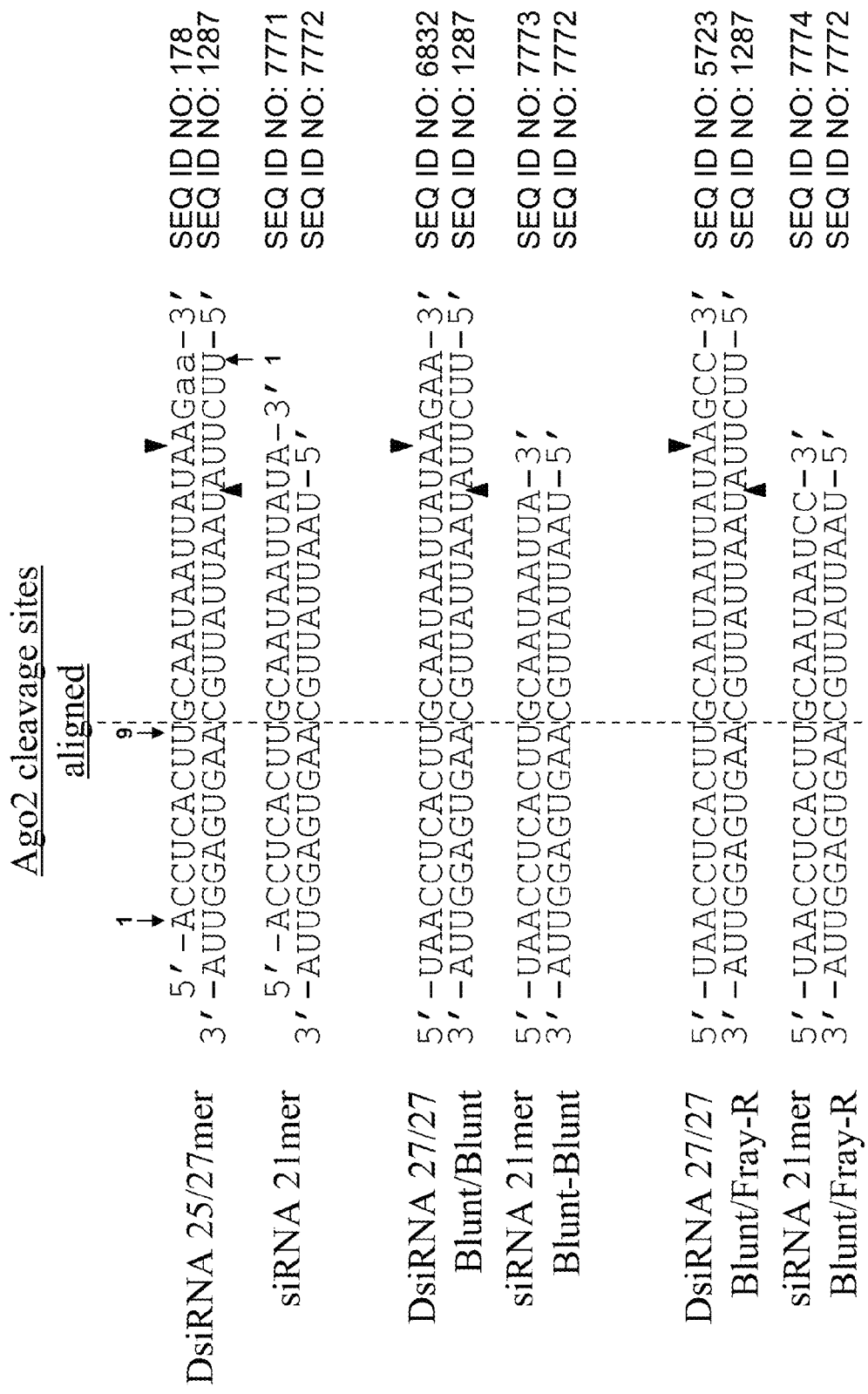
FIG. 1 shows the structures of exemplary DsiRNA agents targeting a site in the β-catenin RNA referred to herein as the "βc-1569" target site. UPPER case=unmodified RNA, lower case=DNA, Bold=mismatch base pair nucleotides; arrowheads indicate projected Dicer enzyme cleavage sites; dashed line indicates sense strand (top strand) sequences corresponding to the projected Argonaute 2 (Ago2) cleavage site within the targeted β-catenin sequence.

The present invention is directed to compositions that contain double stranded RNA ("dsRNA"), and methods for preparing them, that are capable of reducing the level and/or expression of the (β-catenin gene in vivo or in vitro. One of the strands of the dsRNA contains a region of nucleotide sequence that has a length that ranges from 19 to 35 nucleotides that can direct the destruction and/or translational inhibition of the targeted β-catenin transcript.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The present invention features one or more DsiRNA molecules that can modulate (e.g., inhibit) β-catenin expression. The DsiRNAs of the invention optionally can be used in combination with modulators of other genes and/or gene products associated with the maintenance or development of diseases or disorders associated with β-catenin misregulation (e.g., tumor formation and/or growth, etc.). The DsiRNA agents of the invention modulate β-catenin RNAs such as those corresponding to the cDNA sequences referred to by GenBank Accession Nos. NM_001904.3 (human β-catenin, transcript variant 1), NM_001098209.1 (human β-catenin, transcript variant 2), NM_001098210.1 (human (β-catenin, transcript variant 3) and NM_ 007614.2 & NM_007614.3 (mouse (β-catenin), which are recited below and referred to herein generally as "β-catenin."

The below description of the various aspects and embodiments of the invention is provided with reference to exemplary β-catenin RNAs, generally referred to herein as β-catenin However, such reference is meant to be exemplary only and the various aspects and embodiments of the invention are also directed to alternate β-catenin RNAs, such as mutant β-catenin RNAs or additional β-catenin splice variants. Certain aspects and embodiments are also directed to other genes involved in β-catenin pathways, including genes whose misregulation acts in association with that of β-catenin (or is affected or affects (β-catenin regulation) to produce phenotypic effects that may be targeted for treatment (e.g., tumor formation and/or growth, etc.). Such additional genes can be targeted using DsiRNA and the methods described herein for use of β-catenin targeting DsiRNAs. Thus, the inhibition and the effects of such inhibition of the other genes can be performed as described herein.

The terms "β-catenin" and "CTNNB1" refer to nucleic acid sequences encoding a β-catenin protein, peptide, or polypeptide (e.g., β-catenin transcripts, such as the sequences of β-catenin Genbank Accession Nos. NM_001904.3, NM_001098209.1, NM_001098210.1, NM_ 007614.2 and NM_007614.3). In certain embodiments, the term "β-catenin" is also meant to include other β-catenin encoding sequence, such as other β-catenin isoforms, mutant β-catenin genes, splice variants of β-catenin genes, and β-catenin gene polymorphisms. The term "β-catenin" is used to refer to the polypeptide gene product of a β-catenin gene/transript, e.g., a β-catenin protein, peptide, or polypeptide, such as those encoded by β-catenin Genbank Accession Nos. NM_001904.3, NM_001098209.1, NM_001098210.1, NM_007614.2 and NM_007614.3.

As used herein, a "β-catenin-associated disease or disorder" refers to a disease or disorder known in the art to be associated with altered β-catenin expression, level and/or activity. Notably, a "β-catenin-associated disease or disorder" includes cancer and/or proliferative diseases, conditions, or disorders. Two exemplary "β-catenin-associated diseases or disorders" are colorectal cancer and melanoma.

By "proliferative disease" or "cancer" as used herein is meant, a disease, condition, trait, genotype or phenotype characterized by unregulated cell growth or replication as is known in the art; including leukemias, for example, acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and other cancer or proliferative disease, condition, trait, genotype or phenotype that can respond to the modulation of disease related gene expression in a cell or tissue, alone or in combination with other therapies.

In certain embodiments, dsRNA-mediated inhibition of a β-catenin target sequence is assessed. In such embodiments, β-catenin RNA levels can be assessed by art-recognized methods (e.g., RT-PCR, Northern blot, expression array, etc.), optionally via comparison of β-catenin levels in the presence of an anti-β-catenin dsRNA of the invention relative to the absence of such an anti-β-catenin dsRNA. In certain embodiments, β-catenin levels in the presence of an anti-β-catenin dsRNA are compared to those observed in the presence of vehicle alone, in the presence of a dsRNA directed against an unrelated target RNA, or in the absence of any treatment.

It is also recognized that levels of β-catenin protein can be assessed as indicative of β-catenin RNA levels, but only to the extent that it is known, under a given set of cellular and/or tissue conditions, whether the level of β-catenin protein is directly or indirectly related to β-catenin RNA levels and/or the extent to which a dsRNA inhibits β-catenin expression, thus art-recognized methods of assessing β-catenin protein levels (e.g., Western blot, immunoprecipitation, other antibody-based methods, etc.) can also be employed to examine the inhibitory effect of a dsRNA of the invention.

An anti-β-catenin dsRNA of the invention is deemed to possess "β-catenin inhibitory activity" if a statistically significant reduction in β-catenin RNA level is seen when an anti-β-catenin dsRNA of the invention is administered to a system (e.g., cell-free in vitro system), cell, tissue or organism, as compared to a selected control. The distribution of experimental values and the number of replicate assays performed will tend to dictate the parameters of what levels of reduction in β-catenin RNA (either as a % or in absolute terms) is deemed statistically significant (as assessed by standard methods of determining statistical significance known in the art). However, in certain embodiments, "β-catenin inhibitory activity" is defined based upon a % or absolute level of reduction in the level of β-catenin mRNA in a system, cell, tissue or organism. For example, in certain embodiments, a DsiRNA of the invention is deemed to possess β-catenin inhibitory activity if at least a 5% reduction or at least a 10% reduction in β-catenin RNA is observed in the presence of a DsiRNA of the invention relative to β-catenin mRNA levels seen for a suitable control. (For example, in vivo β-catenin levels in a tissue and/or subject can, in certain embodiments, be deemed to be inhibited by a DsiRNA agent of the invention if, e.g., a 5% or 10% reduction in (β-catenin levels is observed relative to a control.) In certain other embodiments, a DsiRNA of the invention is deemed to possess β-catenin inhibitory activity if β-catenin RNA levels are observed to be reduced by at least 15% relative to a selected control, by at least 20% relative to a selected control, by at least 25% relative to a selected control, by at least 30% relative to a selected control, by at least 35% relative to a selected control, by at least 40% relative to a selected control, by at least 45% relative to a selected control, by at least 50% relative to a selected control, by at least 55% relative to a selected control, by at least 60% relative to a selected control, by at least 65% relative to a selected control, by at least 70% relative to a selected control, by at least 75% relative to a selected control, by at least 80% relative to a selected control, by at least 85% relative to a selected control, by at least 90% relative to a selected control, by at least 95% relative to a selected control, by at least 96% relative to a selected control, by at least 97% relative to a selected control, by at least 98% relative to a selected control or by at least 99% relative to a selected control. In some embodiments, complete inhibition of β-catenin is required for a DsiRNA to be deemed to possess β-catenin inhibitory activity. In certain models (e.g., cell culture), a DsiRNA is deemed to possess β-catenin inhibitory activity if at least a 50% reduction in β-catenin levels is observed relative to a suitable control. In certain other embodiments, a DsiRNA is deemed to possess β-catenin inhibitory activity if at least an 80% reduction in β-catenin levels is observed relative to a suitable control.

By way of specific example, in the Examples below, a series of DsiRNAs targeting β-catenin were tested for the ability to reduce β-catenin mRNA levels in human HeLa or mouse Hepa 1-6 cells in vitro, at 1 nM concentrations in the environment of such cells and in the presence of a transfection agent (Lipofectamine™ RNAiMAX, Invitrogen). Within the below Examples, β-catenin inhibitory activity was initially ascribed to those DsiRNAs that were observed to effect at least a 70% reduction of β-catenin mRNA levels under the assayed conditions. It is contemplated that β-catenin inhibitory activity could also be attributed to a dsRNA under either more or less stringent conditions than those employed for the Examples below, even when the same or a similar assay and conditions are employed. For example, in certain embodiments, a tested dsRNA of the invention is deemed to possess β-catenin inhibitory activity if at least a 10% reduction, at least a 20% reduction, at least a 30% reduction, at least a 40% reduction, at least a 50% reduction, at least a 60% reduction, at least a 75% reduction, at least an 80% reduction, at least an 85% reduction, at least a 90% reduction, or at least a 95% reduction in β-catenin mRNA levels is observed in a mammalian cell line in vitro at 1 nM dsRNA concentration or lower in the environment of a cell, relative to a suitable control.

Use of other endpoints for determination of whether a double stranded RNA of the invention possesses β-catenin inhibitory activity is also contemplated. Specifically, in one embodiment, in addition to or as an alternative to assessing β-catenin mRNA levels, the ability of a tested dsRNA to reduce β-catenin protein levels (e.g., at 48 hours after contacting a mammalian cell in vitro or in vivo) is assessed, and a tested dsRNA is deemed to possess β-catenin inhibitory activity if at least a 10% reduction, at least a 20% reduction, at least a 30% reduction, at least a 40% reduction, at least a 50% reduction, at least a 60% reduction, at least a 70% reduction, at least a 75% reduction, at least an 80% reduction, at least an 85% reduction, at least a 90% reduction, or at least a 95% reduction in β-catenin protein levels is observed in a mammalian cell contacted with the assayed double stranded RNA in vitro or in vivo, relative to a suitable control. Additional endpoints contemplated include, e.g., assessment of a phenotype associated with reduction of β-catenin levels— e.g., reduction of growth of a contacted mammalian cell line in vitro and/or reduction of growth of a tumor in vivo, including, e.g., halting or reducing the growth of tumor or cancer cell levels as described in greater detail elsewhere herein.

β-catenin inhibitory activity can also be evaluated over time (duration) and over concentration ranges (potency), with assessment of what constitutes a dsRNA possessing β-catenin inhibitory activity adjusted in accordance with concentrations administered and duration of time following administration. Thus, in certain embodiments, a DsiRNA of the invention is deemed to possess β-catenin inhibitory activity if at least a 50% reduction in β-catenin activity is observed at a duration of time of 2 hours, 5 hours, 10 hours, 1 day, 2 days, 3 days, 4 days, 5 days, 6 days, 7 days, 8 days, 9 days, 10 days or more after administration is observed/persists. In additional embodiments, a DsiRNA of the invention is deemed to be a potent β-catenin inhibitory agent if β-catenin inhibitory activity (e.g., in certain embodiments, at least 50% inhibition of (β-catenin) is observed at a concentration of 1 nM or less, 500 pM or less, 200 pM or less, 100 pM or less, 50 pM or less, 20 pM or less, 10 pM or less, 5 pM or less, 2 pM or less or even 1 pM or less in the environment of a cell, for example, within an in vitro assay for β-catenin inhibitory activity as described herein. In certain embodiments, a potent β-catenin inhibitory dsRNA of the invention is defined as one that is capable of β-catenin inhibitory activity (e.g., in certain embodiments, at least 20% reduction of (β-catenin levels) at a formulated concentration of 10 mg/kg or less when administered to a subject in an effective delivery vehicle (e.g., an effective lipid nanoparticle formulation). Preferably, a potent β-catenin inhibitory dsRNA of the invention is defined as one that is capable of β-catenin inhibitory activity (e.g., in certain embodiments, at least 50% reduction of (β-catenin levels) at a formulated concentration of 5 mg/kg or less when administered to a subject in an effective delivery vehicle. More preferably, a potent β-catenin inhibitory dsRNA of the invention is defined as one that is capable of β-catenin inhibitory activity (e.g., in certain embodiments, at least 50% reduction of (β-catenin levels) at a formulated concentration of 5 mg/kg or less when administered to a subject in an effective delivery vehicle. Optionally, a potent β-catenin inhibitory dsRNA of the invention is defined as one that is capable of β-catenin inhibitory activity (e.g., in certain embodiments, at least 50% reduction of (β-catenin levels) at a formulated concentration of 2 mg/kg or less, or even 1 mg/kg or less, when administered to a subject in an effective delivery vehicle.

In certain embodiments, potency of a dsRNA of the invention is determined in reference to the number of copies of a dsRNA present in the cytoplasm of a target cell that are required to achieve a certain level of target gene knockdown. For example, in certain embodiments, a potent dsRNA is one capable of causing 50% or greater knockdown of a target mRNA when present in the cytoplasm of a target cell at a copy number of 1000 or fewer RISC-loaded antisense strands per cell. More preferably, a potent dsRNA is one capable of producing 50% or greater knockdown of a target mRNA when present in the cytoplasm of a target cell at a copy number of 500 or fewer RISC-loaded antisense strands per cell. Optionally, a potent dsRNA is one capable of producing 50% or greater knockdown of a target mRNA when present in the cytoplasm of a target cell at a copy number of 300 or fewer RISC-loaded antisense strands per cell.

In further embodiments, the potency of a DsiRNA of the invention can be defined in reference to a 19 to 23mer dsRNA directed to the same target sequence within the same target gene. For example, a DsiRNA of the invention that possesses enhanced potency relative to a corresponding 19 to 23mer dsRNA can be a DsiRNA that reduces a target gene by an additional 5% or more, an additional 10% or more, an additional 20% or more, an additional 30% or more, an additional 40% or more, or an additional 50% or more as compared to a corresponding 19 to 23mer dsRNA, when assayed in an in vitro assay as described herein at a sufficiently low concentration to allow for detection of a potency difference (e.g., transfection concentrations at or below 1 nM in the environment of a cell, at or below 100 pM in the environment of a cell, at or below 10 pM in the environment of a cell, at or below 1 nM in the environment of a cell, in an in vitro assay as described herein; notably, it is recognized that potency differences can be best detected via performance of such assays across a range of concentrations—e.g., 0.1 pM to 10 nM—for purpose of generating a dose-response curve and identifying an IC50 value associated with a DsiRNA/dsRNA).

β-catenin inhibitory levels and/or β-catenin levels may also be assessed indirectly, e.g., measurement of a reduction in a β-catenin-associated disease marker protein or target gene, such as MYC, Cyclin D1, or Axin2, or reduction of the size or number of polyps or tumors (e.g., colon tumors) in a subject may be used to assess β-catenin levels and/or β-catenin inhibitory efficacy of a double-stranded nucleic acid of the instant invention.

In certain embodiments, the phrase "consists essentially of" is used in reference to the anti-β-catenin dsRNAs of the invention. In some such embodiments, "consists essentially of" refers to a composition that comprises a dsRNA of the invention which possesses at least a certain level of β-catenin inhibitory activity (e.g., at least 50% (β-catenin inhibitory activity) and that also comprises one or more additional components and/or modifications that do not significantly impact the β-catenin inhibitory activity of the dsRNA. For example, in certain embodiments, a composition "consists essentially of" a dsRNA of the invention where modifications of the dsRNA of the invention and/or dsRNA-associated components of the composition do not alter the β-catenin inhibitory activity (optionally including potency or duration of (β-catenin inhibitory activity) by greater than 3%, greater than 5%, greater than 10%, greater than 15%, greater than 20%, greater than 25%, greater than 30%, greater than 35%, greater than 40%, greater than 45%, or greater than 50% relative to the dsRNA of the invention in isolation. In certain embodiments, a composition is deemed to consist essentially of a dsRNA of the invention even if more dramatic reduction of β-catenin inhibitory activity (e.g., 80% reduction, 90% reduction, etc. in efficacy, duration and/or potency) occurs in the presence of additional components or modifications, yet where β-catenin inhibitory activity is not significantly elevated (e.g., observed levels of (β-catenin inhibitory activity are within 10% of those observed for the isolated dsRNA of the invention) in the presence of additional components and/or modifications.

As used herein, the phrase "dsRNA reduces β-catenin mRNA levels by at least X % when assayed in vitro in a mammalian cell at an effective concentration in the environment of said cell of 1 nanomolar or less" refers to a requirement for the dsRNA to reduce the native β-catenin mRNA levels of a HeLa cell population by at least X %, when assayed at a transfection concentration of 1 nanomolar or less in the presence of Lipofectamine™ RNAiMAX (Invitrogen) and following manufacturer's instructions. Such HeLa cells are obtained from ATCC and maintained in DMEM (HyClone) supplemented with 10% fetal bovine serum (HyClone) at 37° C. under 5% $CO_2$. β-catenin mRNA levels are then assayed at 24 h or 48 h post-transfection to assess % inhibition, with respect to an appropriate control as described elsewhere herein. In certain embodiments, the HeLa cells of such assays are replaced with HepG2, HCT116, HuH7 or other cell line.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen US 2009/0137500; Eckstein et al., International PCT Publication No. WO 92/07065; Usman et al., International PCT Publication No. WO 93/15187; Uhlman & Peyman U.S. Pat. No. 6,326,487, all are hereby incorporated by reference herein). There are several examples of modified nucleic acid bases known in the art as summarized by Limbach et al., *Nucleic Acids Res.* 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-allyl, 2'-O[2-(methylamino)-2-oxoethyl], 4'-thio, 4'-$CH_2$—O-2'-bridge, 4'-$(CH_2)_2$—O-2'-bridge, 2'-LNA, and 2'-O—(N-methylcarbamate) or those comprising base analogs. In connection with 2'-modified nucleotides as described for the present disclosure, by "amino" is meant 2'-$NH_2$ or 2'-O—$NH_2$, which can be modified or unmodified. Such modified groups are described, e.g., in Eckstein et al., U.S. Pat. No. 5,672,695 and Matulic-Adamic et al., U.S. Pat. No. 6,248,878.

In reference to the nucleic acid molecules of the present disclosure, modifications may exist upon these agents in patterns on one or both strands of the double stranded ribonucleic acid (dsRNA). As used herein, "alternating positions" refers to a pattern where every other nucleotide is a modified nucleotide or there is an unmodified nucleotide (e.g., an unmodified ribonucleotide) between every modified nucleotide over a defined length of a strand of the dsRNA (e.g., 5'-MNMNMN-3'; 3'-MNMNMN-5'; where M is a modified nucleotide and N is an unmodified nucleotide). The modification pattern starts from the first nucleotide position at either the 5' or 3' terminus according to a position numbering convention, e.g., as described herein (in certain embodiments, position 1 is designated in reference to the terminal residue of a strand following a projected Dicer cleavage event of a DsiRNA agent of the invention; thus, position 1 does not always constitute a 3' terminal residue of a pre-processed agent of the invention). The pattern of modified nucleotides at alternating positions may run the full length of the strand, but in certain embodiments includes at least 4, 6, 8, 10, 12, 14 nucleotides containing at least 2, 3, 4, 5, 6 or 7 modified nucleotides, respectively. As used herein, "alternating pairs of positions" refers to a pattern where two consecutive modified nucleotides are separated by two consecutive unmodified nucleotides over a defined length of a strand of the dsRNA (e.g., 5'-MMNNMMNNMMNN-3'; 3'-MMNNMMNNM-MNN-5'; where M is a modified nucleotide and N is an unmodified nucleotide). The modification pattern starts from the first nucleotide position at either the 5' or 3' terminus according to a position numbering convention such as those described herein. The pattern of modified nucleotides at alternating positions may run the full length of the strand, but preferably includes at least 8, 12, 16, 20, 24, 28 nucleotides containing at least 4, 6, 8, 10, 12 or 14 modified nucleotides, respectively. It is emphasized that the above modification patterns are exemplary and are not intended as limitations on the scope of the invention.

As used herein, "base analog" refers to a heterocyclic moiety which is located at the 1' position of a nucleotide sugar moiety in a modified nucleotide that can be incorporated into a nucleic acid duplex (or the equivalent position in a nucleotide sugar moiety substitution that can be incorporated into a nucleic acid duplex). In the dsRNAs of the invention, a base analog is generally either a purine or pyrimidine base excluding the common bases guanine (G), cytosine (C), adenine (A), thymine (T), and uracil (U). Base analogs can duplex with other bases or base analogs in dsRNAs. Base analogs include those useful in the compounds and methods of the invention, e.g., those disclosed in U.S. Pat. Nos. 5,432,272 and 6,001,983 to Benner and US Patent Publication No. 20080213891 to Manoharan, which are herein incorporated by reference. Non-limiting examples of bases include hypoxanthine (I), xanthine (X), 3β-D-ribofuranosyl-(2,6-diaminopyrimidine) (K), 3-β-D-ribofuranosyl-(1-methyl-pyrazolo[4,3-d]pyrimidine-5,7(4H,6H)-dione) (P), iso-cytosine (iso-C), iso-guanine (iso-G), 1-β-D-ribofuranosyl-(5-nitroindole), 1-β-D-ribofuranosyl-β-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S), 2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof (Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108.). Base analogs may also be a universal base.

As used herein, "universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid. The ability of a single stranded nucleic acid containing a universal base to duplex a target nucleic can be assayed by methods apparent to one in the art (e.g., UV absorbance, circular dichroism, gel shift, single stranded nuclease sensitivity, etc.). Additionally, conditions under which duplex formation is observed may be varied to determine duplex stability or formation, e.g., temperature, as melting temperature (Tm) correlates with the stability of nucleic acid duplexes. Compared to a reference single stranded nucleic acid that is exactly complementary to a target nucleic acid, the single stranded nucleic acid containing a universal base forms a duplex with the target nucleic acid that has a lower Tm than a duplex formed with the complementary nucleic acid. However, compared to a reference single stranded nucleic acid in which the universal base has been replaced with a base to generate a single mismatch, the single stranded nucleic acid containing the universal base forms a duplex with the target nucleic acid that has a higher Tm than a duplex formed with the nucleic acid having the mismatched base.

Some universal bases are capable of base pairing by forming hydrogen bonds between the universal base and all of the bases guanine (G), cytosine (C), adenine (A), thymine (T), and uracil (U) under base pair forming conditions. A universal base is not a base that forms a base pair with only one single complementary base. In a duplex, a universal base may form no hydrogen bonds, one hydrogen bond, or more than one hydrogen bond with each of G, C, A, T, and U opposite to it on the opposite strand of a duplex. Preferably, the universal base does not interact with the base opposite to it on the opposite strand of a duplex. In a duplex, base pairing involving a universal base occurs without altering the double helical structure of the phosphate backbone. A universal base may also interact with bases in adjacent nucleotides on the same nucleic acid strand by stacking interactions. Such stacking interactions stabilize the duplex, especially in situations where the universal base does not form any hydrogen bonds with the base positioned opposite to it on the opposite strand of the duplex. Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43).

As used herein, "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins, stem loops, or extended loops.

As used herein, "extended loop" in the context of a dsRNA refers to a single stranded loop and in addition 1, 2, 3, 4, 5, 6 or up to 20 base pairs or duplexes flanking the loop. In an extended loop, nucleotides that flank the loop on the 5' side form a duplex with nucleotides that flank the loop on the 3' side. An extended loop may form a hairpin or stem loop.

As used herein, "tetraloop" in the context of a dsRNA refers to a loop (a single stranded region) consisting of four nucleotides that forms a stable secondary structure that contributes to the stability of an adjacent Watson-Crick hybridized nucleotides. Without being limited to theory, a tetraloop may stabilize an adjacent Watson-Crick base pair by stacking interactions. In addition, interactions among the four nucleotides in a tetraloop include but are not limited to non-Watson-Crick base pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). A tetraloop confers an increase in the melting temperature (Tm) of an adjacent duplex that is higher than expected from a simple model loop sequence consisting of four random bases. For example, a tetraloop can confer a melting temperature of at least 55° C. in 10 mM $NaHPO_4$ to a hairpin comprising a duplex of at least 2 base pairs in length. A tetraloop may contain ribonucleotides, deoxyribonucleotides, modified nucleotides, and combinations thereof. Examples of RNA tetraloops include the UNCG family of tetraloops (e.g., UUCG), the GNRA family of tetraloops (e.g., GAAA), and the CUUG tetraloop. (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, the d(TNCG) family of tetraloops (e.g., d(TTCG)). (Nakano et al. Biochemistry, 41 (48), 14281-14292, 2002.; SHINJI et al. Nippon Kagakkai Koen Yokoshu VOL. 78th; NO. 2; PAGE. 731 (2000).)

As used herein, the term "siRNA" refers to a double stranded nucleic acid in which each strand comprises RNA, RNA analog(s) or RNA and DNA. The siRNA comprises between 19 and 23 nucleotides or comprises 21 nucleotides. The siRNA typically has 2 bp overhangs on the 3' ends of each strand such that the duplex region in the siRNA comprises 17-21 nucleotides, or 19 nucleotides. Typically, the antisense strand of the siRNA is sufficiently complementary with the target sequence of the β-catenin gene/RNA.

An anti-β-catenin DsiRNA of the instant invention possesses strand lengths of at least 25 nucleotides. Accordingly, in certain embodiments, an anti-β-catenin DsiRNA contains one oligonucleotide sequence, a first sequence, that is at least 25 nucleotides in length and no longer than 35 or up to 50 or more nucleotides. This sequence of RNA can be between 26 and 35, 26 and 34, 26 and 33, 26 and 32, 26 and 31, 26 and 30, and 26 and 29 nucleotides in length. This sequence can be 27 or 28 nucleotides in length or 27 nucleotides in length. The second sequence of the DsiRNA agent can be a sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotide sequence will have 21 or more complementary base pairs, or 25 or more complementary base pairs with the first oligonucleotide sequence. In one embodiment, the second sequence is the same length as the first sequence, and the DsiRNA agent is blunt ended. In another embodiment, the ends of the DsiRNA agent have one or more overhangs.

In certain embodiments, the first and second oligonucleotide sequences of the DsiRNA agent exist on separate oligonucleotide strands that can be and typically are chemically synthesized. In some embodiments, both strands are between 26 and 35 nucleotides in length. In other embodiments, both strands are between 25 and 30 or 26 and 30 nucleotides in length. In one embodiment, both strands are 27 nucleotides in length, are completely complementary and have blunt ends. In certain embodiments of the instant invention, the first and second sequences of an anti-β-catenin DsiRNA exist on separate RNA oligonucleotides (strands). In one embodiment, one or both oligonucleotide strands are capable of serving as a substrate for Dicer. In other embodiments, at least one modification is present that promotes Dicer to bind to the double-stranded RNA structure in an orientation that maximizes the double-stranded RNA structure's effectiveness in inhibiting gene expression. In certain embodiments of the instant invention, the anti-β-catenin DsiRNA agent is comprised of two oligonucleotide strands of differing lengths, with the anti-β-catenin DsiRNA possessing a blunt end at the 3' terminus of a first strand (sense strand) and a 3' overhang at the 3' terminus of a second strand (antisense strand). The DsiRNA can also contain one or more deoxyribonucleic acid (DNA) base substitutions.

Suitable DsiRNA compositions that contain two separate oligonucleotides can be chemically linked outside their annealing region by chemical linking groups. Many suitable chemical linking groups are known in the art and can be used. Suitable groups will not block Dicer activity on the DsiRNA and will not interfere with the directed destruction of the RNA transcribed from the target gene. Alternatively, the two separate oligonucleotides can be linked by a third oligonucleotide such that a hairpin structure is produced upon annealing of the two oligonucleotides making up the DsiRNA composition. The hairpin structure will not block Dicer activity on the DsiRNA and will not interfere with the directed destruction of the target RNA.

As used herein, a dsRNA, e.g., DsiRNA or siRNA, having a sequence "sufficiently complementary" to a target RNA or cDNA sequence (e.g., β-catenin mRNA) means that the dsRNA has a sequence sufficient to trigger the destruction of the target RNA (where a cDNA sequence is recited, the RNA sequence corresponding to the recited cDNA sequence) by the RNAi machinery (e.g., the RISC complex) or process. For example, a dsRNA that is "sufficiently complementary" to a target RNA or cDNA sequence to trigger the destruction of the target RNA by the RNAi machinery or process can be identified as a dsRNA that causes a detectable reduction in the level of the target RNA in an appropriate assay of dsRNA activity (e.g., an in vitro assay as described in Example 2 below), or, in further examples, a dsRNA that is sufficiently complementary to a target RNA or cDNA sequence to trigger the destruction of the target RNA by the RNAi machinery or process can be identified as a dsRNA that produces at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least a 70%, at least a 75%, at least a 80%, at least a 85%, at least a 90%, at least a 95%, at least a 98% or at least a 99% reduction in the level of the target RNA in an appropriate assay of dsRNA activity. In additional examples, a dsRNA that is sufficiently complementary to a target RNA or cDNA sequence to trigger the destruction of the target RNA by the RNAi machinery or process can be identified based upon assessment of the duration of a certain level of inhibitory activity with respect to the target RNA or protein levels in a cell or organism. For example, a dsRNA that is sufficiently complementary to a target RNA or cDNA sequence to trigger the destruction of the target RNA by the RNAi machinery or process can be identified as a dsRNA capable of reducing target mRNA levels by at least 20% at least 48 hours post-administration of said dsRNA to a cell or organism. Preferably, a dsRNA that is sufficiently complementary to a target RNA or cDNA sequence to trigger the destruction of the target RNA by the RNAi machinery or process is identified as a dsRNA capable of reducing target mRNA levels by at least 40% at least 72 hours post-administration of said dsRNA to a cell or organism, by at least 40% at least four, five or seven days post-administration of said dsRNA to a cell or organism, by at least 50% at least 48 hours post-administration of said dsRNA to a cell or organism, by at least 50% at least 72 hours post-administration of said dsRNA to a cell or organism, by at least 50% at least four, five or seven days post-administration of said dsRNA to a cell or organism, by at least 80% at least 48 hours post-administration of said dsRNA to a cell or organism, by at least 80% at least 72 hours post-administration of said dsRNA to a cell or organism, or by at least 80% at least four, five or seven days post-administration of said dsRNA to a cell or organism.

The dsRNA molecule can be designed such that every residue of the antisense strand is complementary to a residue in the target molecule. Alternatively, substitutions can be made within the molecule to increase stability and/or enhance processing activity of said molecule. Substitutions can be made within the strand or can be made to residues at the ends of the strand. In certain embodiments, substitutions and/or modifications are made at specific residues within a DsiRNA agent. Such substitutions and/or modifications can include, e.g., deoxy-modifications at one or more residues of positions 1, 2 and 3 when numbering from the 3' terminal position of the sense strand of a DsiRNA agent; and introduction of 2'-O-alkyl (e.g., 2'-O-methyl) modifications at the 3' terminal residue of the antisense strand of DsiRNA agents, with such modifications also being performed at overhang positions of the 3' portion of the antisense strand and at alternating residues of the antisense strand of the DsiRNA that are included within the region of a DsiRNA agent that is processed to form an active siRNA agent. The preceding modifications are offered as exemplary, and are not intended to be limiting in any manner. Further consideration of the structure of preferred DsiRNA agents, including further description of the modifications and substitutions that can be performed upon the anti-β-catenin DsiRNA agents of the instant invention, can be found below.

Where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where separate RNA molecules, such dsRNA are often referred to as siRNA ("short interfering RNA") or DsiRNA ("Dicer substrate siRNAs"). Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5'end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In addition, as used herein, "dsRNA" may include chemical modifications to ribonucleotides, internucleoside linkages, end-groups, caps, and conjugated moieties, including substantial modifications at multiple nucleotides and including all types of modifications disclosed herein or known in the art. Any such modifications, as used in an siRNA- or DsiRNA-type molecule, are encompassed by "dsRNA" for the purposes of this specification and claims.

The phrase "duplex region" refers to the region in two complementary or substantially complementary oligonucleotides that form base pairs with one another, either by Watson-Crick base pairing or other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

Single-stranded nucleic acids that base pair over a number of bases are said to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g. gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, i.e., (the melting temperature; Tm). Hybridization conditions are also conditions under which base pairs can form. Various conditions of stringency can be used to determine hybridization (see, e.g., Wahl, G. M. and S. L. Berger (1987) Methods Enzymol. 152:399; Kimmel, A. R. (1987) Methods Enzymol. 152:507). Stringent temperature conditions will ordinarily include temperatures of at least about 30° C., more preferably of at least about 37° C., and most preferably of at least about 42° C. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm(° C.)=2(\# \text{ of A+T bases})+4(\# \text{ of G+C bases})$. For hybrids between 18 and 49 base pairs in length, $Tm(° C.)=81.5+16.6(\log 10[Na+])+0.41 (\% G+C)-(600/N)$, where N is the number of bases in the hybrid, and [Na+] is the concentration of sodium ions in the hybridization buffer ([Na+] for 1×SSC=0.165 M). For example, a hybridization determination buffer is shown in Table 1.

TABLE 1

| | final conc. | | Vender | Cat# | Lot# | m.w./Stock | To make 50 mL solution | |
|---|---|---|---|---|---|---|---|---|
| NaCl | 100 | mM | Sigma | S-5150 | 41K8934 | 5M | 1 | mL |
| KCl | 80 | mM | Sigma | P-9541 | 70K0002 | 74.55 | 0.298 | g |
| MgCl$_2$ | 8 | mM | Sigma | M-1028 | 120K8933 | 1M | 0.4 | mL |
| sucrose | 2% | w/v | Fisher | BP220-212 | 907105 | 342.3 | 1 | g |
| Tris-HCl | 16 | mM | Fisher | BP1757-500 | 12419 | 1M | 0.8 | mL |
| NaH$_2$PO$_4$ | 1 | mM | Sigma | S-3193 | 52H-029515 | 120.0 | 0.006 | g |
| EDTA | 0.02 | mM | Sigma | E-7889 | 110K89271 | 0.5M | 2 | µL |
| H$_2$O | | | Sigma | W-4502 | 51K2359 | | to 50 | mL |
| pH = 7.0 at 20° C. | | | | | adjust with HCl | | | |

Useful variations on hybridization conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Antisense to Molecular Cloning Techniques, 1987, Academic Press, New York); and Sambrook et al., Molecular Cloning: A Laboratory Manual, Cold Spring Harbor Laboratory Press, New York.

As used herein, "oligonucleotide strand" is a single stranded nucleic acid molecule. An oligonucleotide may comprise ribonucleotides, deoxyribonucleotides, modified nucleotides (e.g., nucleotides with 2' modifications, synthetic base analogs, etc.) or combinations thereof. Such modified oligonucleotides can be preferred over native forms because of properties such as, for example, enhanced cellular uptake and increased stability in the presence of nucleases.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "ribonucleotide" specifically excludes a deoxyribonucleotide, which is a nucleotide possessing a single proton group at the 2' ribose ring position.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide. As used herein, the term "deoxyribonucleotide" also includes a modified ribonucleotide that does not permit Dicer cleavage of a dsRNA agent, e.g., a 2'-O-methyl ribonucleotide, a phosphorothioate-modified ribonucleotide residue, etc., that does not permit Dicer cleavage to occur at a bond of such a residue.

As used herein, the term "PS-NA" refers to a phosphorothioate-modified nucleotide residue. The term "PS-NA" therefore encompasses both phosphorothioate-modified ribonucleotides ("PS-RNAs") and phosphorothioate-modified deoxyribonucleotides ("PS-DNAs").

As used herein, "Dicer" refers to an endoribonuclease in the RNase III family that cleaves a dsRNA or dsRNA-containing molecule, e.g., double-stranded RNA (dsRNA) or pre-microRNA (miRNA), into double-stranded nucleic acid fragments 19-25 nucleotides long, usually with a two-base overhang on the 3' end. With respect to the dsRNAs of the invention, the duplex formed by a dsRNA region of an agent of the invention is recognized by Dicer and is a Dicer substrate on at least one strand of the duplex. Dicer catalyzes the first step in the RNA interference pathway, which consequently results in the degradation of a target RNA. The protein sequence of human Dicer is provided at the NCBI database under accession number NP_085124, hereby incorporated by reference.

Dicer "cleavage" is determined as follows (e.g., see Collingwood et al., Oligonucleotides 18:187-200 (2008)). In a Dicer cleavage assay, RNA duplexes (100 pmol) are incubated in 20 µL of 20 mM Tris pH 8.0, 200 mM NaCl, 2.5 mM MgCl2 with or without 1 unit of recombinant human Dicer (Stratagene, La Jolla, Calif.) at 37° C. for 18-24 hours. Samples are desalted using a Performa SR 96-well plate (Edge Biosystems, Gaithersburg, Md.). Electrospray-ionization liquid chromatography mass spectroscopy (ESI-LCMS) of duplex RNAs pre- and post-treatment with Dicer is done using an Oligo HTCS system (Novatia, Princeton, N.J.; Hail et al., 2004), which consists of a ThermoFinnigan TSQ7000, Xcalibur data system, ProMass data processing software and Paradigm MS4 HPLC (Michrom BioResources, Auburn, Calif.). In this assay, Dicer cleavage occurs where at least 5%, 10%, 20%, 30%, 40%, 50%, 60%, 70%, 80%, 90%, 95%, or even 100% of the Dicer substrate dsRNA, (i.e., 25-30 bp, dsRNA, preferably 26-30 bp dsRNA) is cleaved to a shorter dsRNA (e.g., 19-23 bp dsRNA, preferably, 21-23 bp dsRNA).

As used herein, "Dicer cleavage site" refers to the sites at which Dicer cleaves a dsRNA (e.g., the dsRNA region of a DsiRNA agent of the invention). Dicer contains two RNase III domains which typically cleave both the sense and antisense strands of a dsRNA. The average distance between the RNase III domains and the PAZ domain determines the length of the short double-stranded nucleic acid fragments it produces and this distance can vary (Macrae et al. (2006) *Science* 311: 195-8). As shown in FIG. 1, Dicer is projected to cleave certain double-stranded ribonucleic acids of the instant invention that possess an antisense strand having a 2 nucleotide 3' overhang at a site between the $21^{st}$ and $22^{nd}$ nucleotides removed from the 3' terminus of the antisense strand, and at a corresponding site between the $21^{st}$ and $22^{nd}$ nucleotides removed from the 5' terminus of the sense strand. The projected and/or prevalent Dicer cleavage site(s) for dsRNA molecules distinct from those depicted in FIG. 1 may be similarly identified via art-recognized methods, including those described in Macrae et al. While the Dicer cleavage events depicted in FIG. 1 generate 21 nucleotide siRNAs, it is noted that Dicer cleavage of a dsRNA (e.g., DsiRNA) can result in generation of Dicer-processed siRNA lengths of 19 to 23 nucleotides in length. Indeed, in certain embodiments, a double-stranded DNA region may be included within a dsRNA for purpose of directing prevalent Dicer excision of a typically non-preferred 19mer or 20mer siRNA, rather than a 21mer.

As used herein, "overhang" refers to unpaired nucleotides, in the context of a duplex having one or more free ends at the 5' terminus or 3' terminus of a dsRNA. In certain embodiments, the overhang is a 3' or 5' overhang on the antisense strand or sense strand. In some embodiments, the overhang is a 3' overhang having a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

A dsRNA of the invention comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of the β-catenin target gene, the other strand (the sense strand) comprises a region which is complementary to the antisense strand, such that the two strands hybridize and form a duplex structure when combined under suitable conditions. Generally, the duplex structure is between 15 and 35, optionally between 25 and 30, between 26 and 30, between 18 and 25, between 19 and 24, or between 19 and 21 base pairs in length. Similarly, the region of complementarity to the target sequence is between 15 and 35, optionally between 18 and 30, between 25 and 30, between 19 and 24, or between 19 and 21 nucleotides in length. The dsRNA of the invention may further comprise one or more single-stranded nucleotide overhang(s). It has been identified that dsRNAs comprising duplex structures of between 15 and 35 base pairs in length can be effective in inducing RNA interference, including DsiRNAs (generally of at least 25 base pairs in length) and siRNAs (in certain embodiments, duplex structures of siRNAs are between 20 and 23, and optionally, specifically 21 base pairs (Elbashir et al., *EMBO* 20: 6877-6888)). It has also been identified that dsRNAs possessing duplexes shorter than 20 base pairs can be effective as well (e.g., 15, 16, 17, 18 or 19 base pair duplexes). In certain embodiments, the dsRNAs of the invention can comprise at least one strand of a length of 19 nucleotides or more. In certain embodiments, it can be reasonably expected that shorter dsRNAs comprising a sequence complementary to one of the sequences of Table 10 below, minus only a few nucleotides on one or both ends may be similarly effective as compared to the dsRNAs described above and in Tables 2-5 and 7-10. Hence, dsRNAs comprising a partial sequence of at least 15, 16, 17, 18, 19, 20, or more contiguous nucleotides sufficiently complementary to one of the sequences of Table 10, and differing in their ability to inhibit the expression of the β-catenin target gene in an assay as described herein by not more than 5, 10, 15, 20, 25, or 30% inhibition from a dsRNA comprising the full sequence, are contemplated by the invention. In one embodiment, at least one end of the dsRNA has a single-stranded nucleotide overhang of 1 to 5, optionally 1 to 4, in certain embodiments, 1 or 2 nucleotides. Certain dsRNA structures having at least one nucleotide overhang possess superior inhibitory properties as compared to counterparts possessing base-paired blunt ends at both ends of the dsRNA molecule.

As used herein, the term "RNA processing" refers to processing activities performed by components of the siRNA, miRNA or RNase H pathways (e.g., Drosha, Dicer, Argonaute2 or other RISC endoribonucleases, and RNaseH), which are described in greater detail below (see "RNA Processing" section below). The term is explicitly distinguished from the post-transcriptional processes of 5' capping of RNA and degradation of RNA via non-RISC- or non-RNase H-mediated processes. Such "degradation" of an RNA can take several forms, e.g. deadenylation (removal of a 3' poly(A) tail), and/or nuclease digestion of part or all of the body of the RNA by one or more of several endo- or exo-nucleases (e.g., RNase III, RNase P, RNase T1, RNase A (1, 2, 3, 4/5), oligonucleotidase, etc.).

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.). Indeed, design and use of the DsiRNA agents of the instant invention contemplates the possibility of using such DsiRNA agents not only against target RNAs of β-catenin possessing perfect complementarity with the presently described DsiRNA agents, but also against target β-catenin RNAs possessing sequences that are, e.g., only 99%, 98%, 97%, 96%, 95%, 94%, 93%, 92%, 91%, 90%, 89%, 88%, 87%, 86%, 85%, 84%, 83%, 82%, 81%, 80% etc. complementary to said DsiRNA agents. Similarly, it is contemplated that the presently described DsiRNA agents of the instant invention might be readily altered by the skilled artisan to enhance the extent of complementarity between said DsiRNA agents and a target β-catenin RNA, e.g., of a specific allelic variant of β-catenin (e.g., an allele of enhanced therapeutic interest). Indeed, DsiRNA agent sequences with insertions, deletions, and single point mutations relative to the target β-catenin sequence can also be effective for inhibition. Alternatively, DsiRNA agent sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions.times.100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, a gapped alignment is formed by introducing gaps, and percent identity is determined over the length of the aligned sequences. To obtain gapped alignments for comparison purposes, Gapped BLAST can be utilized as described in Altschul et al., (1997) Nucleic Acids Res. 25(17): 3389-3402. In another embodiment, a global alignment is formed by introducing gaps, and percent identity is determined over the entire length of the sequences aligned. A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the DsiRNA antisense strand and the portion of the β-catenin RNA sequence is preferred. Alternatively, the DsiRNA may be defined functionally as a nucleotide sequence (or oligonucleotide sequence) that is capable of hybridizing with a portion of the β-catenin RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4. The length of the identical nucleotide sequences may be at least 10, 12, 15, 17, 20, 22, 25, 27 or 30 bases.

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of a DsiRNA molecule having complementarity to an antisense region of the DsiRNA molecule. In addition, the sense region of a DsiRNA molecule can comprise a nucleic acid sequence having homology with a target nucleic acid sequence.

By "antisense region" is meant a nucleotide sequence of a DsiRNA molecule having complementarity to a target nucleic acid sequence. In addition, the antisense region of a DsiRNA molecule comprises a nucleic acid sequence having complementarity to a sense region of the DsiRNA molecule.

As used herein, "antisense strand" refers to a single stranded nucleic acid molecule which has a sequence complementary to that of a target RNA. When the antisense strand contains modified nucleotides with base analogs, it is not necessarily complementary over its entire length, but must at least hybridize with a target RNA.

As used herein, "sense strand" refers to a single stranded nucleic acid molecule which has a sequence complementary to that of an antisense strand. When the antisense strand contains modified nucleotides with base analogs, the sense strand need not be complementary over the entire length of the antisense strand, but must at least duplex with the antisense strand.

As used herein, "guide strand" refers to a single stranded nucleic acid molecule of a dsRNA or dsRNA-containing molecule, which has a sequence sufficiently complementary to that of a target RNA to result in RNA interference. After cleavage of the dsRNA or dsRNA-containing molecule by Dicer, a fragment of the guide strand remains associated with RISC, binds a target RNA as a component of the RISC complex, and promotes cleavage of a target RNA by RISC. As used herein, the guide strand does not necessarily refer to a continuous single stranded nucleic acid and may comprise a discontinuity, preferably at a site that is cleaved by Dicer. A guide strand is an antisense strand.

As used herein, "passenger strand" refers to an oligonucleotide strand of a dsRNA or dsRNA-containing molecule, which has a sequence that is complementary to that of the guide strand. As used herein, the passenger strand does not necessarily refer to a continuous single stranded nucleic acid and may comprise a discontinuity, preferably at a site that is cleaved by Dicer. A passenger strand is a sense strand.

By "target nucleic acid" is meant a nucleic acid sequence whose expression, level or activity is to be modulated. The target nucleic acid can be DNA or RNA. For agents that target AR, in certain embodiments target nucleic acid is β-catenin RNA. β-catenin RNA target sites can also interchangeably be referenced by corresponding cDNA sequences. Levels of β-catenin may also be targeted via targeting of upstream effectors of β-catenin, or the effects of modulated or misregulated β-catenin may also be modulated by targeting of molecules downstream of β-catenin in the β-catenin signalling pathway.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence. In one embodiment, a DsiRNA molecule of the invention comprises 19 to 30 (e.g., 19, 20, 21, 22, 23, 24, 25, 26, 27, 28, 29, or 30 or more) nucleotides that are complementary to one or more target nucleic acid molecules or a portion thereof.

In one embodiment, DsiRNA molecules of the invention that down regulate or reduce β-catenin gene expression are used for treating, preventing or reducing 3-catenin-related diseases or disorders (e.g., cancer) in a subject or organism.

In one embodiment of the present invention, each sequence of a DsiRNA molecule of the invention is independently 25 to 35 nucleotides in length, in specific embodiments 25, 26, 27, 28, 29, 30, 31, 32, 33, 34 or 35 nucleotides in length. In another embodiment, the DsiRNA duplexes of the invention independently comprise 25 to 30 base pairs (e.g., 25, 26, 27, 28, 29, or 30). In another embodiment, one or more strands of the DsiRNA molecule of the invention independently comprises 19 to 35 nucleotides (e.g., 19, 20, 21, 22, 23, 24, 25, 26, 27, 28, 29, 30, 31, 32, 33, 34 or 35) that are complementary to a target (AR) nucleic acid molecule. In certain embodiments, a DsiRNA molecule of the invention possesses a length of duplexed nucleotides between 25 and 34 nucleotides in length (e.g., 25, 26, 27, 28, 29, 30, 31, 32, 33 or 34 nucleotides in length; optionally, all such nucleotides base pair with cognate nucleotides of the opposite strand). (Exemplary DsiRNA molecules of the invention are shown in FIG. 1, and below.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell. Within certain aspects, the term "cell" refers specifically to mammalian cells, such as human cells, that contain one or more isolated dsRNA molecules of the present disclosure. In particular aspects, a cell processes dsRNAs or dsRNA-containing molecules resulting in RNA interference of target nucleic acids, and contains proteins and protein complexes required for RNAi, e.g., Dicer and RISC.

In certain embodiments, dsRNAs of the invention are Dicer substrate siRNAs ("DsiRNAs"). DsiRNAs can possess certain advantages as compared to inhibitory nucleic acids that are not dicer substrates ("non-DsiRNAs"). Such advantages include, but are not limited to, enhanced duration of effect of a DsiRNA relative to a non-DsiRNA, as well as enhanced inhibitory activity of a DsiRNA as compared to a non-DsiRNA (e.g., a 19-23mer siRNA) when each inhibitory nucleic acid is suitably formulated and assessed for inhibitory activity in a mammalian cell at the same concentration (in this latter scenario, the DsiRNA would be identified as more potent than the non-DsiRNA). Detection of the enhanced potency of a DsiRNA relative to a non-DsiRNA is often most readily achieved at a formulated concentration (e.g., transfection concentration of the dsRNA) that results in the DsiRNA eliciting approximately 30-70% knockdown activity upon a target RNA (e.g., a mRNA). For active DsiRNAs, such levels of knockdown activity are most often achieved at in vitro mammalian cell DsiRNA transfection concentrations of 1 nM or less of as suitably formulated, and in certain instances are observed at DsiRNA transfection concentrations of 200 pM or less, 100 pM or less, 50 pM or less, 20 pM or less, 10 pM or less, 5 pM or less, or even 1 pM or less. Indeed, due to the variability among DsiRNAs of the precise concentration at which 30-70% knockdown of a target RNA is observed, construction of an IC50 curve via assessment of the inhibitory activity of DsiRNAs and non-DsiRNAs across a range of effective concentrations is a preferred method for detecting the enhanced potency of a DsiRNA relative to a non-DsiRNA inhibitory agent.

In certain embodiments, a DsiRNA (in a state as initially formed, prior to dicer cleavage) is more potent at reducing β-catenin target gene expression in a mammalian cell than a 19, 20, 21, 22 or 23 base pair sequence that is contained within it. In certain such embodiments, a DsiRNA prior to dicer cleavage is more potent than a 19-21mer contained within it. Optionally, a DsiRNA prior to dicer cleavage is more potent than a 19 base pair duplex contained within it that is synthesized with symmetric dTdT overhangs (thereby forming a siRNA possessing 21 nucleotide strand lengths having dTdT overhangs). In certain embodiments, the DsiRNA is more potent than a 19-23mer siRNA (e.g., a 19 base pair duplex with dTdT overhangs) that targets at least 15 nucleotides of the 21 nucleotide target sequence that is recited for a DsiRNA of the invention (without wishing to be bound by theory, the identity of a such a target site for a DsiRNA is identified via identification of the Ago2 cleavage site for the DsiRNA; once the Ago2 cleavage site of a DsiRNA is determined for a DsiRNA, identification of the Ago2 cleavage site for any other inhibitory dsRNA can be performed and these Ago2 cleavage sites can be aligned, thereby determining the alignment of projected target nucleotide sequences for multiple dsRNAs). In certain related embodiments, the DsiRNA is more potent than a 19-23mer siRNA that targets at least 20 nucleotides of the 21 nucleotide target sequence that is recited for a DsiRNA of the invention. Optionally, the DsiRNA is more potent than a 19-23mer siRNA that targets the same 21 nucleotide target sequence that is recited for a DsiRNA of the invention. In certain embodiments, the DsiRNA is more potent than any 21mer siRNA that targets the same 21 nucleotide target sequence that is recited for a DsiRNA of the invention. Optionally, the DsiRNA is more potent than any 21 or 22mer siRNA that targets the same 21 nucleotide target sequence that is recited for a DsiRNA of the invention. In certain embodiments, the DsiRNA is more potent than any 21, 22 or 23mer siRNA that targets the same 21 nucleotide target sequence that is recited for a DsiRNA of the invention. As noted above, such potency assessments are most effectively performed upon dsRNAs that are suitably formulated (e.g., formulated with an appropriate transfection reagent) at a concentration of 1 nM or less. Optionally, an IC50 assessment is performed to evaluate activity across a range of effective inhibitory concentrations, thereby allowing for robust comparison of the relative potencies of dsRNAs so assayed.

The dsRNA molecules of the invention are added directly, or can be complexed with lipids (e.g., cationic lipids), packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers. In particular embodiments, the nucleic acid molecules of the invention comprise sequences shown in FIG. 1, and the below exemplary structures. Examples of such nucleic acid molecules consist essentially of sequences defined in these figures and exemplary structures. Furthermore, where such agents are modified in accordance with the below description of modification patterning of DsiRNA agents, chemically modified forms of constructs described in FIG. 1, and the below exemplary structures can be used in all uses described for the DsiRNA agents of FIG. 1, and the below exemplary structures.

In another aspect, the invention provides mammalian cells containing one or more DsiRNA molecules of this invention. The one or more DsiRNA molecules can independently be targeted to the same or different sites.

By "RNA" is meant a molecule comprising at least one, and preferably at least 4, 8 and 12 ribonucleotide residues. The at least 4, 8 or 12 RNA residues may be contiguous. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the DsiRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the DsiRNA agents of the invention can be administered. A subject can be a mammal or mammalian cells, including a human or human cells.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA compositions may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Various methodologies of the instant invention include step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent (e.g., DsiRNA) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

"Treatment", or "treating" as used herein, is defined as the application or administration of a therapeutic agent (e.g., a DsiRNA agent or a vector or transgene encoding same) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

Structures of Anti-β-catenin DsiRNA Agents

In certain embodiments, the anti-β-catenin DsiRNA agents of the invention have the following structures:

In one such embodiment, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA and "Y" is an overhang domain comprised of 1-4 RNA monomers that are optionally 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand.

DsiRNAs of the invention can carry a broad range of modification patterns (e.g., 2'-O-methyl RNA patterns, e.g., within extended DsiRNA agents). Certain modification patterns of the second strand of DsiRNAs of the invention are presented below.

In one embodiment, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In another such embodiment, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand.

In additional embodiments, the DsiRNA comprises:

```
5'-XXXXXXXXXXXXXXXXXXXXXXXXX-3'
3'-YXXXXXXXXXXXXX̲X̲X̲XXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YX̲XXXXXXXXXXXXX̲X̲X̲XXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. The top strand is the sense strand, and the bottom strand is the antisense strand. In another related embodiment, the DsiRNA comprises:

```
5'-XXXXXXXXXXXXXXXXXXXXXXXXX-3'
3'-X̲XXXXXXXXXXXXX̲X̲X̲XXXXXXXXXX̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-X̲XXXXXXXXXXXXX̲X̲X̲XXXXXXXXXX̲-5'
``` wherein "X"=RNA, "X̲"=2'-O-methyl RNA, and "D"=DNA. The top strand is the sense strand, and the bottom strand is the antisense strand.

In other embodiments, the DsiRNA comprises:

```
5'-XXXXXXXXXXXXXXXXXXXXXXXXX-3'
3'-YX̲XXXXXXXXXXXX̲X̲X̲XXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXDD-3'
3'-YX̲XXXXXXXXXXXX̲X̲X̲XXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-XXXXXXXXXXXXXXXXXXXXXXXXX-3'
3'-X̲XXXXXXXXXXXXX̲X̲X̲XXXXXXXXXX̲-5'
``` wherein "X"=RNA and "X̲"=2'-O-methyl RNA. The top strand is the sense strand, and the bottom strand is the antisense strand. In another related embodiment, the DsiRNA comprises:

```
5'-XXXXXXXXXXXXXXXXXXXXXXXDD-3'
3'-X̲XXXXXXXXXXXXX̲X̲X̲XXXXXXXXXX̲-5'
``` wherein "X"=RNA, "X̲"=2'-O-methyl RNA, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YX̲XXXXXXXXXXXX̲X̲X̲XXXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXDD-3'
3'-YX̲XXXXXXXXXXXX̲X̲X̲XXXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-XXXXXXXXXXXXXXXXXXXXXXXXX-3'
3'-X̲XXXXXXXXXXXXX̲X̲X̲XXXXXXXXXX̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-X̲XXXXXXXXXXXXX̲X̲X̲XXXXXXXXXX̲-5'
``` wherein "X"=RNA, "X̲"=2'-O-methyl RNA, and "D"=DNA. The top strand is the sense strand, and the bottom strand is the antisense strand.

In additional embodiments, the DsiRNA comprises:

```
5'-XXXXXXXXXXXXXXXXXXXXXXXXX-3'
3'-YX̲XXXXXXXXXXXX̲X̲X̲XXXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXXXDD-3'
3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In other embodiments, the DsiRNA comprises:

```
5'-XXXXXXXXXXXXXXXXXXXXXXXXX-3'
3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In additional embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXXXDD-3'
3'-YXXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-X̲X̲X̲X̲X̲X̲X̲X̲X̲X̲X̲X̲X̲X̲X̲X̲X̲X̲X̲X̲X̲X̲X̲X̲X̲X̲X̲-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXXDD-3'

3'-X̲X̲X̲X̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, and "D"=DNA. The top strand is the sense strand, and the bottom strand is the antisense strand.

In additional embodiments, the DsiRNA comprises:

5'-XXXXXXXXXXXXXXXXXXXXXXXXX-3'

3'-YX̲X̲X̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXXDD-3'

3'-YX̲X̲X̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-XX̲X̲X̲X̲X̲X̲X̲X̲X̲X̲X̲X̲X̲X̲X̲X̲X̲X̲X̲X̲X̲X̲X̲X̲X̲-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXXDD-3'

3'-XXX̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, and "D"=DNA. The top strand is the sense strand, and the bottom strand is the antisense strand.

In other embodiments, the DsiRNA comprises:

5'-XXXXXXXXXXXXXXXXXXXXXXXXX-3'

3'-YX̲X̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

5'-XXXXXXXXXXXXXXXXXXXXXXXXDD-3'

3'-YX̲X̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-X̲X̲X̲X̲X̲X̲X̲X̲X̲X̲X̲X̲X̲X̲X̲X̲X̲X̲X̲X̲X̲X̲X̲X̲X̲X̲-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXXDD-3'

3'-X̲X̲X̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, and "D"=DNA. The top strand is the sense strand, and the bottom strand is the antisense strand.

In further embodiments, the DsiRNA comprises:

5'-XXXXXXXXXXXXXXXXXXXXXXXXX-3'

3'-YXXXXXXXXXXXXX̲X̲XXXXXXXXXXXX̲X̲X̲X̲-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXXDD-3'

3'-YX̲X̲X̲X̲X̲X̲X̲X̲X̲X̲X̲X̲X̲X̲X̲X̲X̲X̲X̲X̲X̲X̲X̲X̲X̲-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand.

In additional embodiments, the DsiRNA comprises:

```
5'-XXXXXXXXXXXXXXXXXXXXXXXXX-3'

3'-YXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand.

In further embodiments, the DsiRNA comprises:

```
5'-XXXXXXXXXXXXXXXXXXXXXXXXX-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand.

In other embodiments, the DsiRNA comprises:

```
5'-XXXXXXXXXXXXXXXXXXXXXXXXX-3'

3'-YXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In another related embodiment, the DsiRNA comprises:

```
5'-XXXXXXXXXXXXXXXXXXXXXXXDD-3'

3'-YXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In additional embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In additional embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In additional embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

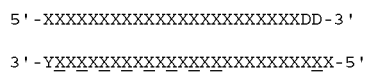

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

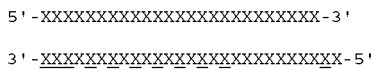

wherein "X"=RNA and "X"=2'-O-methyl RNA. The top strand is the sense strand, and the bottom strand is the antisense strand. In a further related embodiment, the DsiRNA comprises:

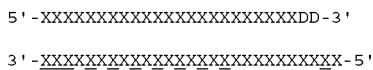

wherein "X"=RNA, "X"=2'-O-methyl RNA, and "D"=DNA. The top strand is the sense strand, and the bottom strand is the antisense strand.

In additional embodiments, the DsiRNA comprises:

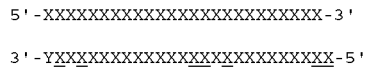

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

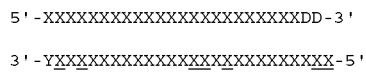

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

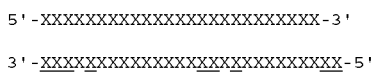

wherein "X"=RNA and "X"=2'-O-methyl RNA. The top strand is the sense strand, and the bottom strand is the antisense strand. In a further related embodiment, the DsiRNA comprises:

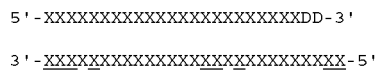

wherein "X"=RNA, "X"=2'-O-methyl RNA, and "D"=DNA. The top strand is the sense strand, and the bottom strand is the antisense strand.

The above modification patterns can also be incorporated into, e.g., the extended DsiRNA structures and mismatch and/or frayed DsiRNA structures described below.

In another embodiment, the DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary 27mer DsiRNA agent with two terminal mismatched residues is shown:

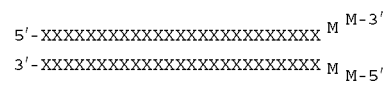

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand is the sense strand, and the bottom strand is the antisense strand. Alternatively, the bottom strand is the sense strand and the top strand is the antisense strand.

In certain additional embodiments, the present invention provides compositions for RNA interference (RNAi) that possess one or more base paired deoxyribonucleotides within a region of a double stranded ribonucleic acid (dsRNA) that is positioned 3' of a projected sense strand Dicer cleavage site and correspondingly 5' of a projected antisense strand Dicer cleavage site. The compositions of the invention comprise a dsRNA which is a precursor molecule, i.e., the dsRNA of the present invention is processed in vivo to produce an active small interfering nucleic acid (siRNA). The dsRNA is processed by Dicer to an active siRNA which is incorporated into RISC.

In certain embodiments, the DsiRNA agents of the invention can have the following exemplary structures (noting that any of the following exemplary structures can be combined, e.g., with the bottom strand modification patterns of the above-described structures—in one specific example, the bottom strand modification pattern shown in any of the above structures is applied to the 27 most 3' residues of the bottom strand of any of the following structures; in another specific example, the bottom strand modification pattern shown in any of the above structures upon the 23 most 3' residues of the bottom strand is applied to the 23 most 3' residues of the bottom strand of any of the following structures):

In one such embodiment, the DsiRNA comprises the following (an exemplary "right-extended", "DNA extended" DsiRNA):

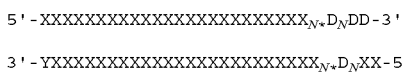

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

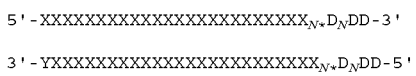

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

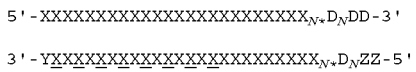

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

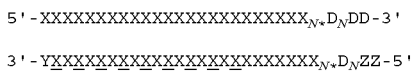

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

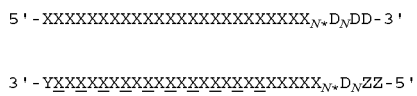

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

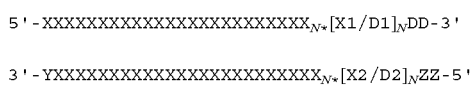

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In the structures depicted herein, the 5' end of either the sense strand or antisense strand can optionally comprise a phosphate group.

In another embodiment, a DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

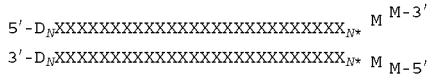

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-15 or, optionally, 1-8. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In one embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. An exemplary structure for such a molecule is shown:

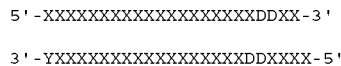

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand. The above structure is modeled to force Dicer to cleave a minimum of a 21mer duplex as its primary post-processing form. In embodiments where the bottom strand of the above structure is the antisense strand, the positioning of two deoxyribonucleotide residues at the ultimate and penultimate residues of the 5' end of the antisense strand may reduce off-target effects for a given compound.

In one embodiment, the DsiRNA comprises the following (an exemplary "left-extended", "DNA extended" DsiRNA):

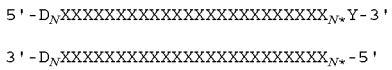

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

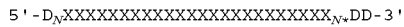
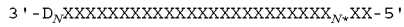

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

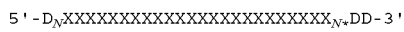
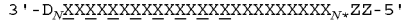

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

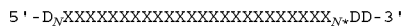
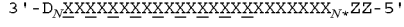

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

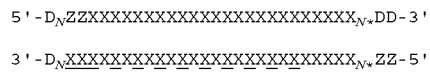

wherein "X"=RNA, "X"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

wherein "X"=RNA, "X"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

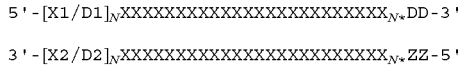

wherein "X"=RNA, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In a related embodiment, the DsiRNA comprises:

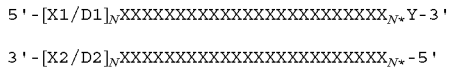

wherein "X"=RNA, "D"=DNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

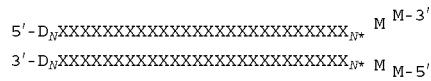

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-8 or 1-10. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In another embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. Exemplary structures for such a molecule are shown:

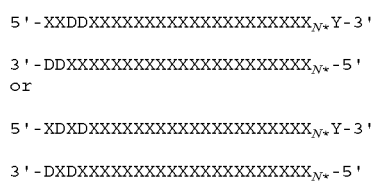

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In any of the above embodiments where the bottom strand of the above structure is the antisense strand, the positioning of two deoxyribonucleotide residues at the ultimate and penultimate residues of the 5' end of the antisense strand may reduce off-target effects.

In certain embodiments, the "D" residues of the above structures include at least one PS-DNA or PS-RNA. Optionally, the "D" residues of the above structures include at least one modified nucleotide that inhibits Dicer cleavage.

While the above-described "DNA-extended" DsiRNA agents can be categorized as either "left extended" or "right extended", DsiRNA agents comprising both left- and right-extended DNA-containing sequences within a single agent (e.g., both flanks surrounding a core dsRNA structure are dsDNA extensions) can also be generated and used in similar manner to those described herein for "right-extended" and "left-extended" agents.

In some embodiments, the DsiRNA of the instant invention further comprises a linking moiety or domain that joins the sense and antisense strands of a DNA:DNA-extended DsiRNA agent. Optionally, such a linking moiety domain joins the 3' end of the sense strand and the 5' end of the antisense strand. The linking moiety may be a chemical (non-nucleotide) linker, such as an oligomethylenediol linker, oligoethylene glycol linker, or other art-recognized linker moiety. Alternatively, the linker can be a nucleotide linker, optionally including an extended loop and/or tetraloop.

In one embodiment, the DsiRNA agent has an asymmetric structure, with the sense strand having a 25-base pair length, and the antisense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxynucleotides at the 3' end of the sense strand.

In another embodiment, the DsiRNA agent has an asymmetric structure, with the antisense strand having a 25-base pair length, and the sense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxyribonucleotides at the 3' end of the antisense strand.

Exemplary β-catenin targeting DsiRNA agents of the invention include the following:

TABLE 2

Selected Anti-β-catenin DsiRNAs, *Homo sapiens* Unique Duplexes

| | | |
|---|---|---|
| βc-240 Target: | 5'-CUGAGGGUAUUUGAAGUAUACCAta-3'<br>3'-GGGACUCCCAUAAACUUCAUAUGGUAU-5'<br>5'-CCCTGAGGGTATTTGAAGTATACCATA-3' | (SEQ ID NO: 8)<br>(SEQ ID NO: 1117)<br>(SEQ ID NO: 2226) |
| βc-244 Target: | 5'-GGGUAUUUGAAGUAUACCAUACAac-3'<br>3'-CUCCCAUAAACUUCAUAUGGUAUGUUG-5'<br>5'-GAGGGTATTTGAAGTATACCATACAAC-3' | (SEQ ID NO: 9)<br>(SEQ ID NO: 1118)<br>(SEQ ID NO: 2227) |
| βc-253 Target: | 5'-AAGUAUACCAUACAACUGUUUUGaa-3'<br>3'-ACUUCAUAUGGUAUGUUGACAAAACUU-5'<br>5'-TGAAGTATACCATACAACTGTTTTGAA-3' | (SEQ ID NO: 10)<br>(SEQ ID NO: 1119)<br>(SEQ ID NO: 2228) |
| βc-259 Target: | 5'-ACCAUACAACUGUUUUGAAAAUCca-3'<br>3'-UAUGGUAUGUUGACAAAACUUUUAGGU-5'<br>5'-ATACCATACAACTGTTTTGAAAATCCA-3' | (SEQ ID NO: 11)<br>(SEQ ID NO: 1120)<br>(SEQ ID NO: 2229) |
| βc-264 Target: | 5'-ACAACUGUUUUGAAAAUCCAGCGtg-3'<br>3'-UAUGUUGACAAAACUUUUAGGUCGCAC-5'<br>5'-ATACAACTGTTTTGAAAATCCAGCGTG-3' | (SEQ ID NO: 12)<br>(SEQ ID NO: 1121)<br>(SEQ ID NO: 2230) |
| βc-496 Target: | 5'-GGGAUUUUCUCAGUCCUUCACUCaa-3'<br>3'-GUCCCUAAAAGAGUCAGGAAGUGAGUU-5'<br>5'-CAGGGATTTTCTCAGTCCTTCACTCAA-3' | (SEQ ID NO: 13)<br>(SEQ ID NO: 1122)<br>(SEQ ID NO: 2231) |
| βc-516 Target: | 5'-CUCAAGAACAAGUAGCUGAUAUUga-3'<br>3'-GUGAGUUCUUGUUCAUCGACUAUAACU-5'<br>5'-CACTCAAGAACAAGTAGCTGATATTGA-3' | (SEQ ID NO: 14)<br>(SEQ ID NO: 1123)<br>(SEQ ID NO: 2232) |
| βc-522 Target: | 5'-AACAAGUAGCUGAUAUUGAUGGAca-3'<br>3'-UCUUGUUCAUCGACUAUAACUACCUGU-5'<br>5'-AGAACAAGTAGCTGATATTGATGGACA-3' | (SEQ ID NO: 15)<br>(SEQ ID NO: 1124)<br>(SEQ ID NO: 2233) |
| βc-524 Target: | 5'-CAAGUAGCUGAUAUUGAUGGACgt-3'<br>3'-UUGUUCAUCGACUAUAACUACCUGUCA-5'<br>5'-AACAAGTAGCTGATATTGATGGACAGT-3' | (SEQ ID NO: 16)<br>(SEQ ID NO: 1125)<br>(SEQ ID NO: 2234) |
| βc-540 Target: | 5'-AUGGACAGUAUGCAAUGACUCGAgc-3'<br>3'-ACUACCUGUCAUACGUUACUGAGCUCG-5'<br>5'-TGATGGACAGTATGCAATGACTCGAGC-3' | (SEQ ID NO: 17)<br>(SEQ ID NO: 1126)<br>(SEQ ID NO: 2235) |
| βc-582 Target: | 5'-CUAUGUUCCCUGAGACAUUAGAUga-3'<br>3'-ACGAUACAAGGGACUCUGUAAUCUACU-5'<br>5'-TGCTATGTTCCCTGAGACATTAGATGA-3' | (SEQ ID NO: 18)<br>(SEQ ID NO: 1127)<br>(SEQ ID NO: 2236) |
| βc-686 Target: | 5'-CUGAAACAUGCAGUUGUAAACUUga-3'<br>3'-ACGACUUUGUACGUCAACAUUUGAACU-5'<br>5'-TGCTGAAACATGCAGTTGTAAACTTGA-3' | (SEQ ID NO: 19)<br>(SEQ ID NO: 1128)<br>(SEQ ID NO: 2237) |
| βc-692 Target: | 5'-CAUGCAGUUGUAAACUUGAUUAAct-3'<br>3'-UUGUACGUCAACAUUUGAACUAAUUGA-5'<br>5'-AACATGCAGTTGTAAACTTGATTAACT-3' | (SEQ ID NO: 20)<br>(SEQ ID NO: 1129)<br>(SEQ ID NO: 2238) |
| βc-697 Target: | 5'-AGUUGUAAACUUGAUUAACUAUCaa-3'<br>3'-CGUCAACAUUUGAACUAAUUGAUAGUU-5'<br>5'-GCAGTTGTAAACTTGATTAACTATCAA-3' | (SEQ ID NO: 21)<br>(SEQ ID NO: 1130)<br>(SEQ ID NO: 2239) |

TABLE 2-continued

Selected Anti-β-catenin DsiRNAs, *Homo sapiens* Unique Duplexes

|  |  |  |
|---|---|---|
| | 5'-UUGAUUAACUAUCAAGAUGAUGCag-3' | (SEQ ID NO: 22) |
| | 3'-UGAACUAAUUGAUAGUUCUACUACGUC-5' | (SEQ ID NO: 1131) |
| βc-707 Target: | 5'-ACTTGATTAACTATCAAGATGATGCAG-3' | (SEQ ID NO: 2240) |
| | 5'-CUGAACUGACAAAACUGCUAAAUga-3' | (SEQ ID NO: 23) |
| | 3'-GGGACUUGACUGUUUUGACGAUUUACU-5' | (SEQ ID NO: 1132) |
| βc-753 Target: | 5'-CCCTGAACTGACAAAACTGCTAAATGA-3' | (SEQ ID NO: 2241) |
| | 5'-AGAUGGUGUCUGCUAUUGUACGUac-3' | (SEQ ID NO: 24) |
| | 3'-AGUCUACCACAGACGAUAACAUGCAUG-5' | (SEQ ID NO: 1133) |
| βc-870 Target: | 5'-TCAGATGGTGTCTGCTATTGTACGTAC-3' | (SEQ ID NO: 2242) |
| | 5'-ACGUACCAUGCAGAAUACAAAUGat-3' | (SEQ ID NO: 25) |
| | 3'-CAUGCAUGGUACGUCUUUAUGUUUACUA-5' | (SEQ ID NO: 1134) |
| βc-889 Target: | 5'-GTACGTACCATGCAGAATACAAATGAT-3' | (SEQ ID NO: 2243) |
| | 5'-UACAACUCUCCACAACCUUUUAUta-3' | (SEQ ID NO: 26) |
| | 3'-UAAUGUUGAGAGGUGUUGGAAAAUAAU-5' | (SEQ ID NO: 1135) |
| βc-1060 Target: | 5'-ATTACAACTCTCCACAACCTTTTATTA-3' | (SEQ ID NO: 2244) |
| | 5'-CUCUCCACAACCUUUUAUUACAUca-3' | (SEQ ID NO: 27) |
| | 3'-UUGAGAGGUGUUGGAAAAUAAUGUAGU-5' | (SEQ ID NO: 1136) |
| βc-1065 Target: | 5'-AACTCTCCACAACCTTTTATTACATCA-3' | (SEQ ID NO: 2245) |
| | 5'-CACAACCUUUUAUUACAUCAAGAag-3' | (SEQ ID NO: 28) |
| | 3'-AGGUGUUGGAAAAUAAUGUAGUUCUUC-5' | (SEQ ID NO: 1137) |
| βc-1070 Target: | 5'-TCCACAACCTTTTATTACATCAAGAAG-3' | (SEQ ID NO: 2246) |
| | 5'-CUUUUAUUACAUCAAGAAGGAGCta-3' | (SEQ ID NO: 29) |
| | 3'-UGGAAAAUAAUGUAGUUCUUCCUCGAU-5' | (SEQ ID NO: 1138) |
| βc-1076 Target: | 5'-ACCTTTTATTACATCAAGAAGGAGCTA-3' | (SEQ ID NO: 2247) |
| | 5'-AAAACAAAUGUUAAAUUCUUGGCta-3' | (SEQ ID NO: 30) |
| | 3'-UGUUUUGUUUACAAUUUAAGAACCGAU-5' | (SEQ ID NO: 1139) |
| βc-1154 Target: | 5'-ACAAAACAAATGTTAAATTCTTGGCTA-3' | (SEQ ID NO: 2248) |
| | 5'-UACGACAGACUGCCUUCAAAUUUta-3' | (SEQ ID NO: 31) |
| | 3'-UAAUGCUGUCUGACGGAAGUUUAAAAU-5' | (SEQ ID NO: 1140) |
| βc-1180 Target: | 5'-ATTACGACAGACTGCCTTCAAATTTTA-3' | (SEQ ID NO: 2249) |
| | 5'-CAGACUGCCUUCAAAUUUUAGCUta-3' | (SEQ ID NO: 32) |
| | 3'-CUGUCUGACGGAAGUUUAAAAUCGAAU-5' | (SEQ ID NO: 1141) |
| βc-1185 Target: | 5'-GACAGACTGCCTTCAAATTTTAGCTTA-3' | (SEQ ID NO: 2250) |
| | 5'-CUUUAGUAAAUAUAAUGAGGACCta-3' | (SEQ ID NO: 33) |
| | 3'-UCGAAAUCAUUUAUAUUACUCCUGGAU-5' | (SEQ ID NO: 1142) |
| βc-1260 Target: | 5'-AGCTTTAGTAAATATAATGAGGACCTA-3' | (SEQ ID NO: 2251) |
| | 5'-AAAACUACUGUGGACCACAAGCAga-3' | (SEQ ID NO: 34) |
| | 3'-CUUUUUGAUGACACCUGGUGUUCGUCU-5' | (SEQ ID NO: 1143) |
| βc-1294 Target: | 5'-GAAAAACTACTGTGGACCACAAGCAGA-3' | (SEQ ID NO: 2252) |
| | 5'-AGUCAACGUCUUGUUCAGAACUGtc-3' | (SEQ ID NO: 35) |
| | 3'-GUUCAGUUGCAGAACAAGUCUUGACAG-5' | (SEQ ID NO: 1144) |
| βc-1412 Target: | 5'-CAAGTCAACGTCTTGTTCAGAACTGTC-3' | (SEQ ID NO: 2253) |
| | 5'-CGUCUUGUUCAGAACUGUCUUUGga-3' | (SEQ ID NO: 36) |
| | 3'-UUGCAGAACAAGUCUUGACAGAAACCU-5' | (SEQ ID NO: 1145) |
| βc-1418 Target: | 5'-AACGTCTTGTTCAGAACTGTCTTTGGA-3' | (SEQ ID NO: 2254) |
| | 5'-UGUUCAGAACUGUCUUUGGACUCtc-3' | (SEQ ID NO: 37) |
| | 3'-GAACAAGUCUUGACAGAAACCUGAGAG-5' | (SEQ ID NO: 1146) |
| βc-1423 Target: | 5'-CTTGTTCAGAACTGTCTTTGGACTCTC-3' | (SEQ ID NO: 2255) |
| | 5'-GGUUCAGAUGAUAUAAAUGUGGUca-3' | (SEQ ID NO: 38) |
| | 3'-ACCCAAGUCUACUAUAUUUACACCAGU-5' | (SEQ ID NO: 1147) |
| βc-1520 Target: | 5'-TGGGTTCAGATGATATAAATGTGGTCA-3' | (SEQ ID NO: 2256) |
| | 5'-UCUUUCUAACCUCACUUGCAAUAat-3' | (SEQ ID NO: 39) |
| | 3'-UAAGAAAGAUUGGAGUGAACGUUAUUA-5' | (SEQ ID NO: 1148) |
| βc-1561 Target: | 5'-ATTCTTTCTAACCTCACTTGCAATAAT-3' | (SEQ ID NO: 2257) |
| | 5'-CUCACUUGCAAUAAUUAUAAGAAca-3' | (SEQ ID NO: 40) |
| | 3'-UGGAGUGAACGUUAUUAAUAUUCUUGU-5' | (SEQ ID NO: 1149) |
| βc-1571 Target: | 5'-ACCTCACTTGCAATAATTATAAGAACA-3' | (SEQ ID NO: 2258) |

TABLE 2-continued

Selected Anti-β-catenin DsiRNAs, *Homo sapiens* Unique Duplexes

| | | |
|---|---|---|
| βc-1579 Target: | 5'-CAAUAAUUAUAAGAACAAGAUGAtg-3'<br>3'-ACGUUAUUAAUAUUCUUGUUCUACUAC-5'<br>5'-TGCAATAATTATAAGAACAAGATGATG-3' | (SEQ ID NO: 41)<br>(SEQ ID NO: 1150)<br>(SEQ ID NO: 2259) |
| βc-1620 Target: | 5'-GUAUAGAGGCUCUUGUGCGUACUgt-3'<br>3'-ACCAUAUCUCCGAGAACACGCAUGACA-5'<br>5'-TGGTATAGAGGCTCTTGTGCGTACTGT-3' | (SEQ ID NO: 42)<br>(SEQ ID NO: 1151)<br>(SEQ ID NO: 2260) |
| βc-1816 Target: | 5'-GGCUACUGUUGGAUUGAUUCGAAat-3'<br>3'-UUCCGAUGACAACCUAACUAAGCUUUA-5'<br>5'-AAGGCTACTGTTGGATTGATTCGAAAT-3' | (SEQ ID NO: 43)<br>(SEQ ID NO: 1152)<br>(SEQ ID NO: 2261) |
| βc-1987 Target: | 5'-CAUGGAAGAAAUAGUUGAAGGUUgt-3'<br>3'-GCGUACCUUCUUUAUCAACUUCCAACA-5'<br>5'-CGCATGGAAGAAATAGTTGAAGGTTGT-3' | (SEQ ID NO: 44)<br>(SEQ ID NO: 1153)<br>(SEQ ID NO: 2262) |
| βc-1989 Target: | 5'-UGGAAGAAAUAGUUGAAGGUUGUac-3'<br>3'-GUACCUUCUUUAUCAACUUCCAACAUG-5'<br>5'-CATGGAAGAAATAGTTGAAGGTTGTAC-3' | (SEQ ID NO: 45)<br>(SEQ ID NO: 1154)<br>(SEQ ID NO: 2263) |
| βc-2111 Target: | 5'-AUUGAAAACAUCCAAAGAGUAGCtg-3'<br>3'-GGUAACUUUUGUAGGUUUCUCAUCGAC-5'<br>5'-CCATTGAAAACATCCAAAGAGTAGCTG-3' | (SEQ ID NO: 46)<br>(SEQ ID NO: 1155)<br>(SEQ ID NO: 2264) |
| βc-2282 Target: | 5'-GAGGACAAGCCACAAGAUUACAAga-3'<br>3'-GACUCCUGUUCGGUGUUCUAAUGUUCU-5'<br>5'-CTGAGGACAAGCCACAAGATTACAAGA-3' | (SEQ ID NO: 47)<br>(SEQ ID NO: 1156)<br>(SEQ ID NO: 2265) |
| βc-2624 Target: | 5'-GAUACUGACCUGUAAAUCAUCCUtt-3'<br>3'-AACUAUGACUGGACAUUUAGUAGGAAA-5'<br>5'-TTGATACTGACCTGTAAATCATCCTTT-3' | (SEQ ID NO: 48)<br>(SEQ ID NO: 1157)<br>(SEQ ID NO: 2266) |
| βc-2647 Target: | 5'-UUAGGUAAGAAGUUUUAAAAAGCca-3'<br>3'-GAAAUCCAUUCUUCAAAAUUUUUCGGU-5'<br>5'-CTTTAGGTAAGAAGTTTTAAAAAGCCA-3' | (SEQ ID NO: 49)<br>(SEQ ID NO: 1158)<br>(SEQ ID NO: 2267) |
| βc-2770 Target: | 5'-CAGGUAUAUACUUUGAAAGGAGAtg-3'<br>3'-UUGUCCAUAUAUGAAACUUUCCUCUAC-5'<br>5'-AACAGGTATATACTTTGAAAGGAGATG-3' | (SEQ ID NO: 50)<br>(SEQ ID NO: 1159)<br>(SEQ ID NO: 2268) |
| βc-2848 Target: | 5'-GAAGUUAUUAACUUUAAUGUUUUtt-3'<br>3'-ACCUUCAAUAAUUGAAAUUACAAAAAA-5'<br>5'-TGGAAGTTATTAACTTTAATGTTTTTT-3' | (SEQ ID NO: 51)<br>(SEQ ID NO: 1160)<br>(SEQ ID NO: 2269) |
| βc-2874 Target: | 5'-CCACAGCUUUUGCAACUUAAUACtc-3'<br>3'-ACGGUGUCGAAAACGUUGAAUUAUGAG-5'<br>5'-TGCCACAGCTTTTGCAACTTAATACTC-3' | (SEQ ID NO: 52)<br>(SEQ ID NO: 1161)<br>(SEQ ID NO: 2270) |
| βc-2909 Target: | 5'-CAUUUGCUGUUUUAAACAUUAAUag-3'<br>3'-UUGUAAACGACAAAAUUUGUAAUUAUC-5'<br>5'-AACATTTGCTGTTTTAAACATTAATAG-3' | (SEQ ID NO: 53)<br>(SEQ ID NO: 1162)<br>(SEQ ID NO: 2271) |
| βc-3074 Target: | 5'-CAAUUGAAGUAAACUUUUUGUUCtg-3'<br>3'-UUGUUAACUUCAUUUGAAAAACAAGAC-5'<br>5'-AACAATTGAAGTAAACTTTTGTTCTG-3' | (SEQ ID NO: 54)<br>(SEQ ID NO: 1163)<br>(SEQ ID NO: 2272) |
| βc-3197 Target: | 5'-ACCCUAGCCUUGCUUGUUAAAUUtt-3'<br>3'-UUUGGGAUCGGAACGAACAAUUUAAAA-5'<br>5'-AAACCCTAGCCTTGCTTGTTAAATTTT-3' | (SEQ ID NO: 55)<br>(SEQ ID NO: 1164)<br>(SEQ ID NO: 2273) |
| βc-3203 Target: | 5'-GCCUUGCUUGUUAAAUUUUUUUtt-3'<br>3'-AUCGGAACGAACAAUUUAAAAAAAAAA-5'<br>5'-TAGCCTTGCTTGTTAAATTTTTTTTT-3' | (SEQ ID NO: 56)<br>(SEQ ID NO: 1165)<br>(SEQ ID NO: 2274) |
| βc-3273 Target: | 5'-GAAGUAGCUCUUUUUUUUUUUUtt-3'<br>3'-AACUUCAUCGAGAAAAAAAAAAAAAAA-5'<br>5'-TTGAAGTAGCTCTTTTTTTTTTTTTT-3' | (SEQ ID NO: 57)<br>(SEQ ID NO: 1166)<br>(SEQ ID NO: 2275) |
| βc-3333 Target: | 5'-GUAGUGUUAAGUUAUAGUGAAUAct-3'<br>3'-AGCAUCACAAUUCAAUAUCACUUAUGA-5'<br>5'-TCGTAGTGTTAAGTTATAGTGAATACT-3' | (SEQ ID NO: 58)<br>(SEQ ID NO: 1167)<br>(SEQ ID NO: 2276) |
| βc-3349 Target: | 5'-GUGAAUACUGCUACAGCAAUUUCta-3'<br>3'-AUCACUUAUGACGAUGUCGUUAAAGAU-5'<br>5'-TAGTGAATACTGCTACAGCAATTTCTA-3' | (SEQ ID NO: 59)<br>(SEQ ID NO: 1168)<br>(SEQ ID NO: 2277) |

TABLE 2-continued

Selected Anti-β-catenin DsiRNAs, *Homo sapiens* Unique Duplexes

| | | |
|---|---|---|
| βc-3354 Target: | 5'-UACUGCUACAGCAAUUUCUAAUUtt-3'<br>3'-UUAUGACGAUGUCGUUAAAGAUUAAAA-5'<br>5'-AATACTGCTACAGCAATTTCTAATTTT-3' | (SEQ ID NO: 60)<br>(SEQ ID NO: 1169)<br>(SEQ ID NO: 2278) |
| βc-3371 Target: | 5'-CUAAUUUUAAGAAUUGAGUAAUgg-3'<br>3'-AAGAUUAAAAAUUCUUAACUCAUUACC-5'<br>5'-TTCTAATTTTAAGAATTGAGTAATGG-3' | (SEQ ID NO: 61)<br>(SEQ ID NO: 1170)<br>(SEQ ID NO: 2279) |
| βc-3376 Target: | 5'-UUUUAAGAAUUGAGUAAUGGUGUag-3'<br>3'-UAAAAAUUCUUAACUCAUUACCACAUC-5'<br>5'-ATTTTTAAGAATTGAGTAATGGTGTAG-3' | (SEQ ID NO: 62)<br>(SEQ ID NO: 1171)<br>(SEQ ID NO: 2280) |
| βc-3411 Target: | 5'-CAUAAUCACUCUAAUUAAUUGUAat-3'<br>3'-AAGUAUUAGUGAGAUUAAUUAACAUUA-5'<br>5'-TTCATAATCACTCTAATTAATTGTAAT-3' | (SEQ ID NO: 63)<br>(SEQ ID NO: 1172)<br>(SEQ ID NO: 2281) |
| βc-3426 Target: | 5'-UAAUUGUAAUCUGAAUAAAGUGUaa-3'<br>3'-UAAUUAACAUUAGACUUAUUUCACAUU-5'<br>5'-ATTAATTGTAATCTGAATAAAGTGTAA-3' | (SEQ ID NO: 64)<br>(SEQ ID NO: 1173)<br>(SEQ ID NO: 2282) |
| βc-3431 Target: | 5'-GUAAUCUGAAUAAAGUGUAACAAtt-3'<br>3'-AACAUUAGACUUAUUUCACAUUGUUAA-5'<br>5'-TTGTAATCTGAATAAAGTGTAACAATT-3' | (SEQ ID NO: 65)<br>(SEQ ID NO: 1174)<br>(SEQ ID NO: 2283) |
| βc-3437 Target: | 5'-UGAAUAAAGUGUAACAAUUGUGUag-3'<br>3'-AGACUUAUUUCACAUUGUUAACACAUC-5'<br>5'-TCTGAATAAAGTGTAACAATTGTGTAG-3' | (SEQ ID NO: 66)<br>(SEQ ID NO: 1175)<br>(SEQ ID NO: 2284) |
| βc-3458 Target: | 5'-GUAGCCUUUUUGUAUAAAAUAGAca-3'<br>3'-CACAUCGGAAAAACAUAUUUUAUCUGU-5'<br>5'-GTGTAGCCTTTTTGTATAAAATAGACA-3' | (SEQ ID NO: 67)<br>(SEQ ID NO: 1176)<br>(SEQ ID NO: 2285) |
| βc-3468 Target: | 5'-UGUAUAAAAUAGACAAAUAGAAAat-3'<br>3'-AAACAUAUUUUAUCUGUUUAUCUUUUA-5'<br>5'-TTTGTATAAAATAGACAAATAGAAAAT-3' | (SEQ ID NO: 68)<br>(SEQ ID NO: 1177)<br>(SEQ ID NO: 2286) |
| βc-3488 Target: | 5'-AAAAUGGUCCAAUUAGUUUCCUUtt-3'<br>3'-UCUUUUACCAGGUUAAUCAAAGGAAAA-5'<br>5'-AGAAAATGGTCCAATTAGTTTCCTTTT-3' | (SEQ ID NO: 69)<br>(SEQ ID NO: 1178)<br>(SEQ ID NO: 2287) |
| βc-3496 Target: | 5'-CCAAUUAGUUUCCUUUUUAAUAUGc-3'<br>3'-CAGGUUAAUCAAAGGAAAAAUUAUACG-5'<br>5'-GTCCAATTAGTTTCCTTTTTAATATGC-3' | (SEQ ID NO: 70)<br>(SEQ ID NO: 1179)<br>(SEQ ID NO: 2288) |
| βc-3552 Target: | 5'-UUUGAUCAAAAACUAUUUGGGAUat-3'<br>3'-AAAAACUAGUUUUUGAUAAACCCUAUA-5'<br>5'-TTTTTGATCAAAAACTATTTGGGATAT-3' | (SEQ ID NO: 71)<br>(SEQ ID NO: 1180)<br>(SEQ ID NO: 2289) |
| βc-3600 Target: | 5'-GAGGUGUUAUUUGGAACCUUGUUtt-3'<br>3'-UUCUCCACAAUAAACCUUGGAACAAAA-5'<br>5'-AAGAGGTGTTATTTGGAACCTTGTTTT-3' | (SEQ ID NO: 72)<br>(SEQ ID NO: 1181)<br>(SEQ ID NO: 2290) |
| βc-3605 Target: | 5'-GUUAUUUGGAACCUUGUUUUGGAca-3'<br>3'-CACAAUAAACCUUGGAACAAAACCUGU-5'<br>5'-GTGTTATTTGGAACCTTGTTTTGGACA-3' | (SEQ ID NO: 73)<br>(SEQ ID NO: 1182)<br>(SEQ ID NO: 2291) |
| βc-3615 Target: | 5'-ACCUUGUUUUGGACAGUUUACCAgt-3'<br>3'-CUUGGAACAAAACCUGUCAAAUGGUCA-5'<br>5'-GAACCTTGTTTTGGACAGTTTACCAGT-3' | (SEQ ID NO: 74)<br>(SEQ ID NO: 1183)<br>(SEQ ID NO: 2292) |
| βc-3674 Target: | 5'-GAUACGAUGCUUCAAGAGAAAAUgc-3'<br>3'-CACUAUGCUACGAAGUUCUCUUUUACG-5'<br>5'-GTGATACGATGCTTCAAGAGAAAATGC-3' | (SEQ ID NO: 75)<br>(SEQ ID NO: 1184)<br>(SEQ ID NO: 2293) |
| βc-3686 Target: | 5'-CAAGAGAAAAUGCGGUUAUAAAAaa-3'<br>3'-AAGUUCUCUUUUACGCCAAUAUUUUUU-5'<br>5'-TTCAAGAGAAAATGCGGTTATAAAAAA-3' | (SEQ ID NO: 76)<br>(SEQ ID NO: 1185)<br>(SEQ ID NO: 2294) |
| βc-3691 Target: | 5'-GAAAAUGCGGUUAUAAAAAUGGtt-3'<br>3'-CUCUUUUACGCCAAUAUUUUUUACCAA-5'<br>5'-GAGAAAATGCGGTTATAAAAAATGGTT-3' | (SEQ ID NO: 77)<br>(SEQ ID NO: 1186)<br>(SEQ ID NO: 2295) |
| βc-3700 Target: | 5'-GUUAUAAAAAUGGUUCAGAAUUaa-3'<br>3'-GCCAAUAUUUUUUACCAAGUCUUAAUU-5'<br>5'-CGGTTATAAAAAATGGTTCAGAATTAA-3' | (SEQ ID NO: 78)<br>(SEQ ID NO: 1187)<br>(SEQ ID NO: 2296) |

TABLE 2-continued

Selected Anti-β-catenin DsiRNAs, *Homo sapiens* Unique Duplexes

|  | 5'-AAAAUGGUUCAGAAUUAAACUUUta-3' | (SEQ ID NO: 79) |
|---|---|---|
|  | 3'-UUUUUUACCAAGUCUUAAUUUGAAAAU-5' | (SEQ ID NO: 1188) |
| βc-3707 Target: | 5'-AAAAAATGGTTCAGAATTAAACTTTTA-3' | (SEQ ID NO: 2297) |

TABLE 3

Selected Anti-β-catenin DsiRNAs, Duplexes Targeting Both Human and Mouse Sequences

|  | 5'-GCGUGGACAAUGGCUACUCAAGCtg-3' | (SEQ ID NO: 80) |
|---|---|---|
|  | 3'-GUCGCACCUGUUACCGAUGAGUUCGAC-5' | (SEQ ID NO: 1189) |
| βc-284 Target: | 5'-CAGCGTGGACAATGGCTACTCAAGCTG-3' | (SEQ ID NO: 2298) |
|  | 5'-CGUGGACAAUGGCUACUCAAGCUga-3' | (SEQ ID NO: 81) |
|  | 3'-UCGCACCUGUUACCGAUGAGUUCGACU-5' | (SEQ ID NO: 1190) |
| βc-285 Target: | 5'-AGCGTGGACAATGGCTACTCAAGCTGA-3' | (SEQ ID NO: 2299) |
|  | 5'-GUGGACAAUGGCUACUCAAGCUGat-3' | (SEQ ID NO: 82) |
|  | 3'-CGCACCUGUUACCGAUGAGUUCGACUA-5' | (SEQ ID NO: 1191) |
| βc-286 Target: | 5'-GCGTGGACAATGGCTACTCAAGCTGAT-3' | (SEQ ID NO: 2300) |
|  | 5'-UGGACAAUGGCUACUCAAGCUGAtt-3' | (SEQ ID NO: 83) |
|  | 3'-GCACCUGUUACCGAUGAGUUCGACUAA-5' | (SEQ ID NO: 1192) |
| βc-287 Target: | 5'-CGTGGACAATGGCTACTCAAGCTGATT-3' | (SEQ ID NO: 2301) |
|  | 5'-GGACAAUGGCUACUCAAGCUGAUtt-3' | (SEQ ID NO: 84) |
|  | 3'-CACCUGUUACCGAUGAGUUCGACUAAA-5' | (SEQ ID NO: 1193) |
| βc-288 Target: | 5'-GTGGACAATGGCTACTCAAGCTGATTT-3' | (SEQ ID NO: 2302) |
|  | 5'-GACAAUGGCUACUCAAGCUGAUUtg-3' | (SEQ ID NO: 85) |
|  | 3'-ACCUGUUACCGAUGAGUUCGACUAAAC-5' | (SEQ ID NO: 1194) |
| βc-289 Target: | 5'-TGGACAATGGCTACTCAAGCTGATTTG-3' | (SEQ ID NO: 2303) |
|  | 5'-ACAAUGGCUACUCAAGCUGAUUUga-3' | (SEQ ID NO: 86) |
|  | 3'-CCUGUUACCGAUGAGUUCGACUAAACU-5' | (SEQ ID NO: 1195) |
| βc-290 Target: | 5'-GGACAATGGCTACTCAAGCTGATTTGA-3' | (SEQ ID NO: 2304) |
|  | 5'-CAAUGGCUACUCAAGCUGAUUUGat-3' | (SEQ ID NO: 87) |
|  | 3'-CUGUUACCGAUGAGUUCGACUAAACUA-5' | (SEQ ID NO: 1196) |
| βc-291 Target: | 5'-GACAATGGCTACTCAAGCTGATTTGAT-3' | (SEQ ID NO: 2305) |
|  | 5'-UGAUGGAGUUGGACAUGGCCAUGga-3' | (SEQ ID NO: 88) |
|  | 3'-AAACUACCUCAACCUGUACCGGUACCU-5' | (SEQ ID NO: 1197) |
| βc-312 Target: | 5'-TTTGATGGAGTTGGACATGGCCATGGA-3' | (SEQ ID NO: 2306) |
|  | 5'-GAUGGAGUUGGACAUGGCCAUGGaa-3' | (SEQ ID NO: 89) |
|  | 3'-AACUACCUCAACCUGUACCGGUACCUU-5' | (SEQ ID NO: 1198) |
| βc-313 Target: | 5'-TTGATGGAGTTGGACATGGCCATGGAA-3' | (SEQ ID NO: 2307) |
|  | 5'-AUGGAGUUGGACAUGGCCAUGGAac-3' | (SEQ ID NO: 90) |
|  | 3'-ACUACCUCAACCUGUACCGGUACCUUG-5' | (SEQ ID NO: 1199) |
| βc-314 Target: | 5'-TGATGGAGTTGGACATGGCCATGGAAC-3' | (SEQ ID NO: 2308) |
|  | 5'-UGGAGUUGGACAUGGCCAUGGAAcc-3' | (SEQ ID NO: 91) |
|  | 3'-CUACCUCAACCUGUACCGGUACCUUGG-5' | (SEQ ID NO: 1200) |
| βc-315 Target: | 5'-GATGGAGTTGGACATGGCCATGGAACC-3' | (SEQ ID NO: 2309) |
|  | 5'-GGAGUUGGACAUGGCCAUGGAACca-3' | (SEQ ID NO: 92) |
|  | 3'-UACCUCAACCUGUACCGGUACCUUGGU-5' | (SEQ ID NO: 1201) |
| βc-316 Target: | 5'-ATGGAGTTGGACATGGCCATGGAACCA-3' | (SEQ ID NO: 2310) |
|  | 5'-GAGUUGGACAUGGCCAUGGAACCag-3' | (SEQ ID NO: 93) |
|  | 3'-ACCUCAACCUGUACCGGUACCUUGGUC-5' | (SEQ ID NO: 1202) |
| βc-317 Target: | 5'-TGGAGTTGGACATGGCCATGGAACCAG-3' | (SEQ ID NO: 2311) |
|  | 5'-AGUUGGACAUGGCCAUGGAACCAga-3' | (SEQ ID NO: 94) |
|  | 3'-CCUCAACCUGUACCGGUACCUUGGUCU-5' | (SEQ ID NO: 1203) |
| βc-318 Target: | 5'-GGAGTTGGACATGGCCATGGAACCAGA-3' | (SEQ ID NO: 2312) |
|  | 5'-UCUGGAAUCCAUUCUGGUGCCACta-3' | (SEQ ID NO: 95) |
|  | 3'-UGAGACCUUAGGUAAGACCACGGUGAU-5' | (SEQ ID NO: 1204) |
| βc-389 Target: | 5'-ACTCTGGAATCCATTCTGGTGCCACTA-3' | (SEQ ID NO: 2313) |

TABLE 3-continued

Selected Anti-β-catenin DsiRNAs, Duplexes Targeting Both Human and Mouse Sequences βc-390
```
         5'-CUGGAAUCCAUUCUGGUGCCACUac-3'      (SEQ ID NO: 96)
         3'-GAGACCUUAGGUAAGACCACGGUGAUG-5'    (SEQ ID NO: 1205)
 Target: 5'-CTCTGGAATCCATTCTGGTGCCACTAC-3'    (SEQ ID NO: 2314)
```

βc-391
```
         5'-UGGAAUCCAUUCUGGUGCCACUAcc-3'      (SEQ ID NO: 97)
         3'-AGACCUUAGGUAAGACCACGGUGAUGG-5'    (SEQ ID NO: 1206)
 Target: 5'-TCTGGAATCCATTCTGGTGCCACTACC-3'    (SEQ ID NO: 2315)
```

βc-392
```
         5'-GGAAUCCAUUCUGGUGCCACUACca-3'      (SEQ ID NO: 98)
         3'-GACCUUAGGUAAGACCACGGUGAUGGU-5'    (SEQ ID NO: 1207)
 Target: 5'-CTGGAATCCATTCTGGTGCCACTACCA-3'    (SEQ ID NO: 2316)
```

βc-393
```
         5'-GAAUCCAUUCUGGUGCCACUACCac-3'      (SEQ ID NO: 99)
         3'-ACCUUAGGUAAGACCACGGUGAUGGUG-5'    (SEQ ID NO: 1208)
 Target: 5'-TGGAATCCATTCTGGTGCCACTACCAC-3'    (SEQ ID NO: 2317)
```

βc-600
```
         5'-UAGAUGAGGGCAUGCAGAUCCCAtc-3'      (SEQ ID NO: 100)
         3'-UAAUCUACUCCCGUACGUCUAGGGUAG-5'    (SEQ ID NO: 1209)
 Target: 5'-ATTAGATGAGGGCATGCAGATCCCATC-3'    (SEQ ID NO: 2318)
```

βc-601
```
         5'-AGAUGAGGGCAUGCAGAUCCCAUct-3'      (SEQ ID NO: 101)
         3'-AAUCUACUCCCGUACGUCUAGGGUAGA-5'    (SEQ ID NO: 1210)
 Target: 5'-TTAGATGAGGGCATGCAGATCCCATCT-3'    (SEQ ID NO: 2319)
```

βc-602
```
         5'-GAUGAGGGCAUGCAGAUCCCAUCta-3'      (SEQ ID NO: 102)
         3'-AUCUACUCCCGUACGUCUAGGGUAGAU-5'    (SEQ ID NO: 1211)
 Target: 5'-TAGATGAGGGCATGCAGATCCCATCTA-3'    (SEQ ID NO: 2320)
```

βc-603
```
         5'-AUGAGGGCAUGCAGAUCCCAUCUac-3'      (SEQ ID NO: 103)
         3'-UCUACUCCCGUACGUCUAGGGUAGAUG-5'    (SEQ ID NO: 1212)
 Target: 5'-AGATGAGGGCATGCAGATCCCATCTAC-3'    (SEQ ID NO: 2321)
```

βc-604
```
         5'-UGAGGGCAUGCAGAUCCCAUCUACa-3'      (SEQ ID NO: 104)
         3'-CUACUCCCGUACGUCUAGGGUAGAUGU-5'    (SEQ ID NO: 1213)
 Target: 5'-GATGAGGGCATGCAGATCCCATCTACA-3'    (SEQ ID NO: 2322)
```

βc-605
```
         5'-GAGGGCAUGCAGAUCCCAUCUACac-3'      (SEQ ID NO: 105)
         3'-UACUCCCGUACGUCUAGGGUAGAUGUG-5'    (SEQ ID NO: 1214)
 Target: 5'-ATGAGGGCATGCAGATCCCATCTACAC-3'    (SEQ ID NO: 2323)
```

βc-638
```
         5'-GCUGCUCAUCCCACUAAUGUCCAgc-3'      (SEQ ID NO: 106)
         3'-UACGACGAGUAGGGUGAUUACAGGUCG-5'    (SEQ ID NO: 1215)
 Target: 5'-ATGCTGCTCATCCCACTAATGTCCAGC-3'    (SEQ ID NO: 2324)
```

βc-639
```
         5'-CUGCUCAUCCCACUAAUGUCCAGcg-3'      (SEQ ID NO: 107)
         3'-ACGACGAGUAGGGUGAUUACAGGUCGC-5'    (SEQ ID NO: 1216)
 Target: 5'-TGCTGCTCATCCCACTAATGTCCAGCG-3'    (SEQ ID NO: 2325)
```

βc-640
```
         5'-UGCUCAUCCCACUAAUGUCCAGCgt-3'      (SEQ ID NO: 108)
         3'-CGACGAGUAGGGUGAUUACAGGUCGCA-5'    (SEQ ID NO: 1217)
 Target: 5'-GCTGCTCATCCCACTAATGTCCAGCGT-3'    (SEQ ID NO: 2326)
```

βc-641
```
         5'-GCUCAUCCCACUAAUGUCCAGCGtt-3'      (SEQ ID NO: 109)
         3'-GACGAGUAGGGUGAUUACAGGUCGCAA-5'    (SEQ ID NO: 1218)
 Target: 5'-CTGCTCATCCCACTAATGTCCAGCGTT-3'    (SEQ ID NO: 2327)
```

βc-642
```
         5'-CUCAUCCCACUAAUGUCCAGCGUtt-3'      (SEQ ID NO: 110)
         3'-ACGAGUAGGGUGAUUACAGGUCGCAAA-5'    (SEQ ID NO: 1219)
 Target: 5'-TGCTCATCCCACTAATGTCCAGCGTTT-3'    (SEQ ID NO: 2328)
```

βc-643
```
         5'-UCAUCCCACUAAUGUCCAGCGUUtg-3'      (SEQ ID NO: 111)
         3'-CGAGUAGGGUGAUUACAGGUCGCAAAC-5'    (SEQ ID NO: 1220)
 Target: 5'-GCTCATCCCACTAATGTCCAGCGTTTG-3'    (SEQ ID NO: 2329)
```

βc-644
```
         5'-CAUCCCACUAAUGUCCAGCGUUUgg-3'      (SEQ ID NO: 112)
         3'-GAGUAGGGUGAUUACAGGUCGCAAACC-5'    (SEQ ID NO: 1221)
 Target: 5'-CTCATCCCACTAATGTCCAGCGTTTGG-3'    (SEQ ID NO: 2330)
```

βc-645
```
         5'-AUCCCACUAAUGUCCAGCGUUUGgc-3'      (SEQ ID NO: 113)
         3'-AGUAGGGUGAUUACAGGUCGCAAACCG-5'    (SEQ ID NO: 1222)
 Target: 5'-TCATCCCACTAATGTCCAGCGTTTGGC-3'    (SEQ ID NO: 2331)
```

βc-665
```
         5'-UUGGCUGAACCAUCACAGAUGCUga-3'      (SEQ ID NO: 114)
         3'-CAAACCGACUUGGUAGUGUCUACGACU-5'    (SEQ ID NO: 1223)
 Target: 5'-GTTTGGCTGAACCATCACAGATGCTGA-3'    (SEQ ID NO: 2332)
```

TABLE 3-continued

Selected Anti-β-catenin DsiRNAs, Duplexes Targeting Both Human and Mouse Sequences

| | | |
|---|---|---|
| βc-666 Target: | 5'-UGGCUGAACCAUCACAGAUGCUGAa-3'<br>3'-AAACCGACUUGGUAGUGUCUACGACUU-5'<br>5'-TTTGGCTGAACCATCACAGATGCTGAA-3' | (SEQ ID NO: 115)<br>(SEQ ID NO: 1224)<br>(SEQ ID NO: 2333) |
| βc-667 Target: | 5'-GGCUGAACCAUCACAGAUGCUGAa-3'<br>3'-AACCGACUUGGUAGUGUCUACGACUUU-5'<br>5'-TTGGCTGAACCATCACAGATGCTGAAA-3' | (SEQ ID NO: 116)<br>(SEQ ID NO: 1225)<br>(SEQ ID NO: 2334) |
| βc-731 Target: | 5'-GAACUUGCCACACGUGCAAUCCCtg-3'<br>3'-GUCUUGAACGGUGUGCACGUUAGGGAC-5'<br>5'-CAGAACTTGCCACACGTGCAATCCCTG-3' | (SEQ ID NO: 117)<br>(SEQ ID NO: 1226)<br>(SEQ ID NO: 2335) |
| βc-732 Target: | 5'-AACUUGCCACACGUGCAAUCCCUga-3'<br>3'-UCUUGAACGGUGUGCACGUUAGGGACU-5'<br>5'-AGAACTTGCCACACGTGCAATCCCTGA-3' | (SEQ ID NO: 118)<br>(SEQ ID NO: 1227)<br>(SEQ ID NO: 2336) |
| βc-809 Target: | 5'-GUUAUGGUCCAUCAGCUUUCUAAaa-3'<br>3'-GUCAAUACCAGGUAGUCGAAAGAUUUU-5'<br>5'-CAGTTATGGTCCATCAGCTTTCTAAAA-3' | (SEQ ID NO: 119)<br>(SEQ ID NO: 1228)<br>(SEQ ID NO: 2337) |
| βc-810 Target: | 5'-UUAUGGUCCAUCAGCUUUCUAAAaa-3'<br>3'-UCAAUACCAGGUAGUCGAAAGAUUUUU-5'<br>5'-AGTTATGGTCCATCAGCTTTCTAAAAA-3' | (SEQ ID NO: 120)<br>(SEQ ID NO: 1229)<br>(SEQ ID NO: 2338) |
| βc-830 Target: | 5'-AAAAAGGAAGCUUCCAGACACGCta-3'<br>3'-GAUUUUUCCUUCGAAGGUCUGUGCGAU-5'<br>5'-CTAAAAGGAAGCTTCCAGACACGCTA-3' | (SEQ ID NO: 121)<br>(SEQ ID NO: 1230)<br>(SEQ ID NO: 2339) |
| βc-831 Target: | 5'-AAAAGGAAGCUUCCAGACACGCUat-3'<br>3'-AUUUUUCCUUCGAAGGUCUGUGCGAUA-5'<br>5'-TAAAAAGGAAGCTTCCAGACACGCTAT-3' | (SEQ ID NO: 122)<br>(SEQ ID NO: 1231)<br>(SEQ ID NO: 2340) |
| βc-893 Target: | 5'-ACCAUGCAGAAUACAAAUGAUGUag-3'<br>3'-CAUGGUACGUCUUAUGUUUACUACAUC-5'<br>5'-GTACCATGCAGAATACAAATGATGTAG-3' | (SEQ ID NO: 123)<br>(SEQ ID NO: 1232)<br>(SEQ ID NO: 2341) |
| βc-894 Target: | 5'-CCAUGCAGAAUACAAAUGAUGUAga-3'<br>3'-AUGGUACGUCUUAUGUUUACUACAUCU-5'<br>5'-TACCATGCAGAATACAAATGATGTAGA-3' | (SEQ ID NO: 124)<br>(SEQ ID NO: 1233)<br>(SEQ ID NO: 2342) |
| βc-895 Target: | 5'-CAUGCAGAAUACAAAUGAUGUAGaa-3'<br>3'-UGGUACGUCUUAUGUUUACUACAUCUU-5'<br>5'-ACCATGCAGAATACAAATGATGTAGAA-3' | (SEQ ID NO: 125)<br>(SEQ ID NO: 1234)<br>(SEQ ID NO: 2343) |
| βc-896 Target: | 5'-AUGCAGAAUACAAAUGAUGUAGAaa-3'<br>3'-GGUACGUCUUAUGUUUACUACAUCUUU-5'<br>5'-CCATGCAGAATACAAATGATGTAGAAA-3' | (SEQ ID NO: 126)<br>(SEQ ID NO: 1235)<br>(SEQ ID NO: 2344) |
| βc-897 Target: | 5'-UGCAGAAUACAAAUGAUGUAGAAac-3'<br>3'-GUACGUCUUAUGUUUACUACAUCUUUG-5'<br>5'-CATGCAGAATACAAATGATGTAGAAAC-3' | (SEQ ID NO: 127)<br>(SEQ ID NO: 1236)<br>(SEQ ID NO: 2345) |
| βc-898 Target: | 5'-GCAGAAUACAAAUGAUGUAGAAAca-3'<br>3'-UACGUCUUAUGUUUACUACAUCUUUGU-5'<br>5'-ATGCAGAATACAAATGATGTAGAAACA-3' | (SEQ ID NO: 128)<br>(SEQ ID NO: 1237)<br>(SEQ ID NO: 2346) |
| βc-899 Target: | 5'-CAGAAUACAAAUGAUGUAGAAAcag-3'<br>3'-ACGUCUUAUGUUUACUACAUCUUUGUC-5'<br>5'-TGCAGAATACAAATGATGTAGAAACAG-3' | (SEQ ID NO: 129)<br>(SEQ ID NO: 1238)<br>(SEQ ID NO: 2347) |
| βc-900 Target: | 5'-AGAAUACAAAUGAUGUAGAAACAgc-3'<br>3'-CGUCUUAUGUUUACUACAUCUUUGUCG-5'<br>5'-GCAGAATACAAATGATGTAGAAACAGC-3' | (SEQ ID NO: 130)<br>(SEQ ID NO: 1239)<br>(SEQ ID NO: 2348) |
| βc-977 Target: | 5'-CUGGCCAUCUUUAAGUCUGGAGGca-3'<br>3'-AUGACCGGUAGAAAUUCAGACCUCCGU-5'<br>5'-TACTGGCCATCTTTAAGTCTGGAGGCA-3' | (SEQ ID NO: 131)<br>(SEQ ID NO: 1240)<br>(SEQ ID NO: 2349) |
| βc-978 Target: | 5'-UGGCCAUCUUUAAGUCUGGAGGCat-3'<br>3'-UGACCGGUAGAAAUUCAGACCUCCGUA-5'<br>5'-ACTGGCCATCTTTAAGTCTGGAGGC-3' | (SEQ ID NO: 132)<br>(SEQ ID NO: 1241)<br>(SEQ ID NO: 2350) |
| βc-1091 Target: | 5'-GAAGGAGCUAAAAUGGCAGUGCgtt-3'<br>3'-UUCUUCCUCGAUUUUACCGUCACGCAA-5'<br>5'-AAGAAGGAGCTAAAATGGCAGTGCGTT-3' | (SEQ ID NO: 133)<br>(SEQ ID NO: 1242)<br>(SEQ ID NO: 2351) |

TABLE 3-continued

Selected Anti-β-catenin DsiRNAs, Duplexes Targeting Both Human and Mouse Sequences

| | | |
|---|---|---|
| | 5'-AAGGAGCUAAAAUGGCAGUGCGUtt-3' | (SEQ ID NO: 134) |
| | 3'-UCUUCCUCGAUUUUACCGUCACGCAAA-5' | (SEQ ID NO: 1243) |
| βc-1092 Target: | 5'-AGAAGGAGCTAAAATGGCAGTGCGTTT-3' | (SEQ ID NO: 2352) |
| | 5'-AGGAGCUAAAAUGGCAGUGCGUUta-3' | (SEQ ID NO: 135) |
| | 3'-CUUCCUCGAUUUUACCGUCACGCAAAU-5' | (SEQ ID NO: 1244) |
| βc-1093 Target: | 5'-GAAGGAGCTAAAATGGCAGTGCGTTTA-3' | (SEQ ID NO: 2353) |
| | 5'-GGAGCUAAAAUGGCAGUGCGUUUag-3' | (SEQ ID NO: 136) |
| | 3'-UUCCUCGAUUUUACCGUCACGCAAAUC-5' | (SEQ ID NO: 1245) |
| βc-1094 Target: | 5'-AAGGAGCTAAAATGGCAGTGCGTTTAG-3' | (SEQ ID NO: 2354) |
| | 5'-GAGCUAAAAUGGCAGUGCGUUUAgc-3' | (SEQ ID NO: 137) |
| | 3'-UCCUCGAUUUUACCGUCACGCAAAUCG-5' | (SEQ ID NO: 1246) |
| βc-1095 Target: | 5'-AGGAGCTAAAATGGCAGTGCGTTTAGC-3' | (SEQ ID NO: 2355) |
| | 5'-CUGUGGACCACAAGCAGAGUGCUga-3' | (SEQ ID NO: 138) |
| | 3'-AUGACACCUGGUGUUCGUCUCACGACU-5' | (SEQ ID NO: 1247) |
| βc-1301 Target: | 5'-TACTGTGGACCACAAGCAGAGTGCTGA-3' | (SEQ ID NO: 2356) |
| | 5'-UGUGGACCACAAGCAGAGUGCUGaa-3' | (SEQ ID NO: 139) |
| | 3'-UGACACCUGGUGUUCGUCUCACGACUU-5' | (SEQ ID NO: 1248) |
| βc-1302 Target: | 5'-ACTGTGGACCACAAGCAGAGTGCTGAA-3' | (SEQ ID NO: 2357) |
| | 5'-GUGGACCACAAGCAGAGUGCUGAag-3' | (SEQ ID NO: 140) |
| | 3'-GACACCUGGUGUUCGUCUCACGACUUC-5' | (SEQ ID NO: 1249) |
| βc-1303 Target: | 5'-CTGTGGACCACAAGCAGAGTGCTGAAG-3' | (SEQ ID NO: 2358) |
| | 5'-UGGACCACAAGCAGAGUGCUGAAgg-3' | (SEQ ID NO: 141) |
| | 3'-ACACCUGGUGUUCGUCUCACGACUUCC-5' | (SEQ ID NO: 1250) |
| βc-1304 Target: | 5'-TGTGGACCACAAGCAGAGTGCTGAAGG-3' | (SEQ ID NO: 2359) |
| | 5'-GGACCACAAGCAGAGUGCUGAAGgt-3' | (SEQ ID NO: 142) |
| | 3'-CACCUGGUGUUCGUCUCACGACUUCCA-5' | (SEQ ID NO: 1251) |
| βc-1305 Target: | 5'-GTGGACCACAAGCAGAGTGCTGAAGGT-3' | (SEQ ID NO: 2360) |
| | 5'-GACCACAAGCAGAGUGCUGAAGGtg-3' | (SEQ ID NO: 143) |
| | 3'-ACCUGGUGUUCGUCUCACGACUUCCAC-5' | (SEQ ID NO: 1252) |
| βc-1306 Target: | 5'-TGGACCACAAGCAGAGTGCTGAAGGTG-3' | (SEQ ID NO: 2361) |
| | 5'-ACCACAAGCAGAGUGCUGAAGGUgc-3' | (SEQ ID NO: 144) |
| | 3'-CCUGGUGUUCGUCUCACGACUUCCACG-5' | (SEQ ID NO: 1253) |
| βc-1307 Target: | 5'-GGACCACAAGCAGAGTGCTGAAGGTGC-3' | (SEQ ID NO: 2362) |
| | 5'-CCACAAGCAGAGUGCUGAAGGUGct-3' | (SEQ ID NO: 145) |
| | 3'-CUGGUGUUCGUCUCACGACUUCCACGA-5' | (SEQ ID NO: 1254) |
| βc-1308 Target: | 5'-GACCACAAGCAGAGTGCTGAAGGTGCT-3' | (SEQ ID NO: 2363) |
| | 5'-CACAAGCAGAGUGCUGAAGGUGCta-3' | (SEQ ID NO: 146) |
| | 3'-UGGUGUUCGUCUCACGACUUCCACGAU-5' | (SEQ ID NO: 1255) |
| βc-1309 Target: | 5'-ACCACAAGCAGAGTGCTGAAGGTGCTA-3' | (SEQ ID NO: 2364) |
| | 5'-ACAAGCAGAGUGCUGAAGGUGCUat-3' | (SEQ ID NO: 147) |
| | 3'-GGUGUUCGUCUCACGACUUCCACGAUA-5' | (SEQ ID NO: 1256) |
| βc-1310 Target: | 5'-CCACAAGCAGAGTGCTGAAGGTGCTAT-3' | (SEQ ID NO: 2365) |
| | 5'-CAAGCAGAGUGCUGAAGGUGCUAtc-3' | (SEQ ID NO: 148) |
| | 3'-GUGUUCGUCUCACGACUUCCACGAUAG-5' | (SEQ ID NO: 1257) |
| βc-1311 Target: | 5'-CACAAGCAGAGTGCTGAAGGTGCTATC-3' | (SEQ ID NO: 2366) |
| | 5'-AAGCAGAGUGCUGAAGGUGCUAUct-3' | (SEQ ID NO: 149) |
| | 3'-UGUUCGUCUCACGACUUCCACGAUAGA-5' | (SEQ ID NO: 1258) |
| βc-1312 Target: | 5'-ACAAGCAGAGTGCTGAAGGTGCTATCT-3' | (SEQ ID NO: 2367) |
| | 5'-AGCAGAGUGCUGAAGGUGCUAUCtg-3' | (SEQ ID NO: 150) |
| | 3'-GUUCGUCUCACGACUUCCACGAUAGAC-5' | (SEQ ID NO: 1259) |
| βc-1313 Target: | 5'-CAAGCAGAGTGCTGAAGGTGCTATCTG-3' | (SEQ ID NO: 2368) |
| | 5'-GCAGAGUGCUGAAGGUGCUAUCUgt-3' | (SEQ ID NO: 151) |
| | 3'-UUCGUCUCACGACUUCCACGAUAGACA-5' | (SEQ ID NO: 1260) |
| βc-1314 Target: | 5'-AAGCAGAGTGCTGAAGGTGCTATCTGT-3' | (SEQ ID NO: 2369) |
| | 5'-AACUGUCUUUGGACUCUCAGGAAtc-3' | (SEQ ID NO: 152) |
| | 3'-UCUUGACAGAAACCUGAGAGUCCUUAG-5' | (SEQ ID NO: 1261) |
| βc-1430 Target: | 5'-AGAACTGTCTTTGGACTCTCAGGAATC-3' | (SEQ ID NO: 2370) |

TABLE 3-continued

Selected Anti-β-catenin DsiRNAs, Duplexes Targeting Both Human and Mouse Sequences

| | | |
|---|---|---|
| | 5'-ACUGUCUUUGGACUCUCAGGAAUct-3' | (SEQ ID NO: 153) |
| | 3'-<u>CUU</u>GACAGAAACCUGAGAGUCCUUAGA-5' | (SEQ ID NO: 1262) |
| βc-1431 Target: | 5'-GAACTGTCTTTGGACTCTCAGGAATCT-3' | (SEQ ID NO: 2371) |
| | 5'-GAUGAUAUAAAUGUGGUCACCUGtg-3' | (SEQ ID NO: 154) |
| | 3'-<u>GUC</u>UACUAUAUUUACACCAGUGGACAC-5' | (SEQ ID NO: 1263) |
| βc-1526 Target: | 5'-CAGATGATATAAATGTGGTCACCTGTG-3' | (SEQ ID NO: 2372) |
| | 5'-AUGAUAUAAAUGUGGUCACCUGUGc-3' | (SEQ ID NO: 155) |
| | 3'-<u>UCU</u>ACUAUAUUUACACCAGUGGACACG-5' | (SEQ ID NO: 1264) |
| βc-1527 Target: | 5'-AGATGATATAAATGTGGTCACCTGTGC-3' | (SEQ ID NO: 2373) |
| | 5'-UGAUAUAAAUGUGGUCACCUGUGca-3' | (SEQ ID NO: 156) |
| | 3'-<u>CUA</u>CUAUAUUUACACCAGUGGACACGU-5' | (SEQ ID NO: 1265) |
| βc-1528 Target: | 5'-GATGATATAAATGTGGTCACCTGTGCA-3' | (SEQ ID NO: 2374) |
| | 5'-GAUAUAAAUGUGGUCACCUGUGCag-3' | (SEQ ID NO: 157) |
| | 3'-<u>UAC</u>UAUAUUUACACCAGUGGACACGUC-5' | (SEQ ID NO: 1266) |
| βc-1529 Target: | 5'-ATGATATAAATGTGGTCACCTGTGCAG-3' | (SEQ ID NO: 2375) |
| | 5'-AUAUAAAUGUGGUCACCUGUGCAgc-3' | (SEQ ID NO: 158) |
| | 3'-<u>ACU</u>AUAUUUACACCAGUGGACACGUCG-5' | (SEQ ID NO: 1267) |
| βc-1530 Target: | 5'-TGATATAAATGTGGTCACCTGTGCAGC-3' | (SEQ ID NO: 2376) |
| | 5'-UAUAAAUGUGGUCACCUGUGCAGct-3' | (SEQ ID NO: 159) |
| | 3'-<u>CUA</u>UAUUUACACCAGUGGACACGUCGA-5' | (SEQ ID NO: 1268) |
| βc-1531 Target: | 5'-GATATAAATGTGGTCACCTGTGCAGCT-3' | (SEQ ID NO: 2377) |
| | 5'-AUAAAUGUGGUCACCUGUGCAGCtg-3' | (SEQ ID NO: 160) |
| | 3'-<u>UAU</u>AUUUACACCAGUGGACACGUCGAC-5' | (SEQ ID NO: 1269) |
| βc-1532 Target: | 5'-ATATAAATGTGGTCACCTGTGCAGCTG-3' | (SEQ ID NO: 2378) |
| | 5'-UAAAUGUGGUCACCUGUGCAGCUgg-3' | (SEQ ID NO: 161) |
| | 3'-<u>AUA</u>UUUACACCAGUGGACACGUCGACC-5' | (SEQ ID NO: 1270) |
| βc-1533 Target: | 5'-TATAAATGTGGTCACCTGTGCAGCTGG-3' | (SEQ ID NO: 2379) |
| | 5'-AAAUGUGGUCACCUGUGCAGCUGga-3' | (SEQ ID NO: 162) |
| | 3'-<u>UAU</u>UUACACCAGUGGACACGUCGACCU-5' | (SEQ ID NO: 1271) |
| βc-1534 Target: | 5'-ATAAATGTGGTCACCTGTGCAGCTGGA-3' | (SEQ ID NO: 2380) |
| | 5'-AAUGUGGUCACCUGUGCAGCUGGaa-3' | (SEQ ID NO: 163) |
| | 3'-<u>AUU</u>UACACCAGUGGACACGUCGACCUU-5' | (SEQ ID NO: 1272) |
| βc-1535 Target: | 5'-TAAATGTGGTCACCTGTGCAGCTGGAA-3' | (SEQ ID NO: 2381) |
| | 5'-AUGUGGUCACCUGUGCAGCUGGAat-3' | (SEQ ID NO: 164) |
| | 3'-<u>UUU</u>ACACCAGUGGACACGUCGACCUUA-5' | (SEQ ID NO: 1273) |
| βc-1536 Target: | 5'-AAATGTGGTCACCTGTGCAGCTGGAAT-3' | (SEQ ID NO: 2382) |
| | 5'-UGUGGUCACCUGUGCAGCUGGAAtt-3' | (SEQ ID NO: 165) |
| | 3'-<u>UUA</u>CACCAGUGGACACGUCGACCUUAA-5' | (SEQ ID NO: 1274) |
| βc-1537 Target: | 5'-AATGTGGTCACCTGTGCAGCTGGAATT-3' | (SEQ ID NO: 2383) |
| | 5'-GUGGUCACCUGUGCAGCUGGAAUtc-3' | (SEQ ID NO: 166) |
| | 3'-<u>UAC</u>ACCAGUGGACACGUCGACCUUAAG-5' | (SEQ ID NO: 1275) |
| βc-1538 Target: | 5'-ATGTGGTCACCTGTGCAGCTGGAATTC-3' | (SEQ ID NO: 2384) |
| | 5'-UGGUCACCUGUGCAGCUGGAAUUct-3' | (SEQ ID NO: 167) |
| | 3'-<u>ACA</u>CCAGUGGACACGUCGACCUUAAGA-5' | (SEQ ID NO: 1276) |
| βc-1539 Target: | 5'-TGTGGTCACCTGTGCAGCTGGAATTCT-3' | (SEQ ID NO: 2385) |
| | 5'-GGUCACCUGUGCAGCUGGAAUUCtt-3' | (SEQ ID NO: 168) |
| | 3'-<u>CAC</u>CAGUGGACACGUCGACCUUAAGAA-5' | (SEQ ID NO: 1277) |
| βc-1540 Target: | 5'-GTGGTCACCTGTGCAGCTGGAATTCTT-3' | (SEQ ID NO: 2386) |
| | 5'-GUCACCUGUGCAGCUGGAAUUCUtt-3' | (SEQ ID NO: 169) |
| | 3'-<u>ACC</u>AGUGGACACGUCGACCUUAAGAAA-5' | (SEQ ID NO: 1278) |
| βc-1541 Target: | 5'-TGGTCACCTGTGCAGCTGGAATTCTTT-3' | (SEQ ID NO: 2387) |
| | 5'-UCACCUGUGCAGCUGGAAUUCUUtc-3' | (SEQ ID NO: 170) |
| | 3'-<u>CCA</u>GUGGACACGUCGACCUUAAGAAAG-5' | (SEQ ID NO: 1279) |
| βc-1542 Target: | 5'-GGTCACCTGTGCAGCTGGAATTCTTTC-3' | (SEQ ID NO: 2388) |
| | 5'-CACCUGUGCAGCUGGAAUUCUUUct-3' | (SEQ ID NO: 171) |
| | 3'-<u>CAG</u>UGGACACGUCGACCUUAAGAAAGA-5' | (SEQ ID NO: 1280) |
| βc-1543 Target: | 5'-GTCACCTGTGCAGCTGGAATTCTTTCT-3' | (SEQ ID NO: 2389) |

TABLE 3-continued

Selected Anti-β-catenin DsiRNAs, Duplexes Targeting Both Human and Mouse Sequences

| | | |
|---|---|---|
| βc-1544 Target: | 5'-ACCUGUGCAGCUGGAAUUCUUUCta-3'<br>3'-AGUGGACACGUCGACCUUAAGAAAGAU-5'<br>5'-TCACCTGTGCAGCTGGAATTCTTTCTA-3' | (SEQ ID NO: 172)<br>(SEQ ID NO: 1281)<br>(SEQ ID NO: 2390) |
| βc-1545 Target: | 5'-CCUGUGCAGCUGGAAUUCUUUCUaa-3'<br>3'-GUGGACACGUCGACCUUAAGAAAGAUU-5'<br>5'-CACCTGTGCAGCTGGAATTCTTTCTAA-3' | (SEQ ID NO: 173)<br>(SEQ ID NO: 1282)<br>(SEQ ID NO: 2391) |
| βc-1565 Target: | 5'-UCUAACCUCACUUGCAAUAAUUAta-3'<br>3'-AAAGAUUGGAGUGAACGUUAUUAAUAU-5'<br>5'-TTTCTAACCTCACTTGCAATAATTATA-3' | (SEQ ID NO: 174)<br>(SEQ ID NO: 1283)<br>(SEQ ID NO: 2392) |
| βc-1566 Target: | 5'-CUAACCUCACUUGCAAUAAUUAUaa-3'<br>3'-AAGAUUGGAGUGAACGUUAUUAAUAUU-5'<br>5'-TTCTAACCTCACTTGCAATAATTATAA-3' | (SEQ ID NO: 175)<br>(SEQ ID NO: 1284)<br>(SEQ ID NO: 2393) |
| βc-1567 Target: | 5'-UAACCUCACUUGCAAUAAUUAUAag-3'<br>3'-AGAUUGGAGUGAACGUUAUUAAUAUUC-5'<br>5'-TCTAACCTCACTTGCAATAATTATAAG-3' | (SEQ ID NO: 176)<br>(SEQ ID NO: 1285)<br>(SEQ ID NO: 2394) |
| βc-1568 Target: | 5'-AACCUCACUUGCAAUAAUUAUAAga-3'<br>3'-GAUUGGAGUGAACGUUAUUAAUAUUCU-5'<br>5'-CTAACCTCACTTGCAATAATTATAAGA-3' | (SEQ ID NO: 177)<br>(SEQ ID NO: 1286)<br>(SEQ ID NO: 2395) |
| βc-1569 Target: | 5'-ACCUCACUUGCAAUAAUUAUAAGaa-3'<br>3'-AUUGGAGUGAACGUUAUUAAUAUUCUU-5'<br>5'-TAACCTCACTTGCAATAATTATAAGAA-3' | (SEQ ID NO: 178)<br>(SEQ ID NO: 1287)<br>(SEQ ID NO: 2396) |
| βc-1652 Target: | 5'-GCUGGUGACAGGGAAGACAUCACtg-3'<br>3'-CCCGACCACUGUCCCUUCUGUAGUGAC-5'<br>5'-GGGCTGGTGACAGGGAAGACATCACTG-3' | (SEQ ID NO: 179)<br>(SEQ ID NO: 1288)<br>(SEQ ID NO: 2397) |
| βc-1653 Target: | 5'-CUGGUGACAGGGAAGACAUCACUga-3'<br>3'-CCGACCACUGUCCCUUCUGUAGUGACU-5'<br>5'-GGCTGGTGACAGGGAAGACATCACTGA-3' | (SEQ ID NO: 180)<br>(SEQ ID NO: 1289)<br>(SEQ ID NO: 2398) |
| βc-1654 Target: | 5'-UGGUGACAGGGAAGACAUCACUGag-3'<br>3'-CGACCACUGUCCCUUCUGUAGUGACUC-5'<br>5'-GCTGGTGACAGGGAAGACATCACTGAG-3' | (SEQ ID NO: 181)<br>(SEQ ID NO: 1290)<br>(SEQ ID NO: 2399) |
| βc-1655 Target: | 5'-GGUGACAGGGAAGACAUCACUGAgc-3'<br>3'-GACCACUGUCCCUUCUGUAGUGACUCG-5'<br>5'-CTGGTGACAGGGAAGACATCACTGAGC-3' | (SEQ ID NO: 182)<br>(SEQ ID NO: 1291)<br>(SEQ ID NO: 2400) |
| βc-1656 Target: | 5'-GUGACAGGGAAGACAUCACUGAGcc-3'<br>3'-ACCACUGUCCCUUCUGUAGUGACUCGG-5'<br>5'-TGGTGACAGGGAAGACATCACTGAGCC-3' | (SEQ ID NO: 183)<br>(SEQ ID NO: 1292)<br>(SEQ ID NO: 2401) |
| βc-1657 Target: | 5'-UGACAGGGAAGACAUCACUGAGCct-3'<br>3'-CCACUGUCCCUUCUGUAGUGACUCGGA-5'<br>5'-GGTGACAGGGAAGACATCACTGAGCCT-3' | (SEQ ID NO: 184)<br>(SEQ ID NO: 1293)<br>(SEQ ID NO: 2402) |
| βc-1658 Target: | 5'-GACAGGGAAGACAUCACUGAGCCtg-3'<br>3'-CACUGUCCCUUCUGUAGUGACUCGGAC-5'<br>5'-GTGACAGGGAAGACATCACTGAGCCTG-3' | (SEQ ID NO: 185)<br>(SEQ ID NO: 1294)<br>(SEQ ID NO: 2403) |
| βc-1659 Target: | 5'-ACAGGGAAGACAUCACUGAGCCUgc-3'<br>3'-ACUGUCCCUUCUGUAGUGACUCGGACG-5'<br>5'-TGACAGGGAAGACATCACTGAGCCTGC-3' | (SEQ ID NO: 186)<br>(SEQ ID NO: 1295)<br>(SEQ ID NO: 2404) |
| βc-1660 Target: | 5'-CAGGGAAGACAUCACUGAGCCUGcc-3'<br>3'-CUGUCCCUUCUGUAGUGACUCGGACGG-5'<br>5'-GACAGGGAAGACATCACTGAGCCTGCC-3' | (SEQ ID NO: 187)<br>(SEQ ID NO: 1296)<br>(SEQ ID NO: 2405) |
| βc-1661 Target: | 5'-AGGGAAGACAUCACUGAGCCUGCca-3'<br>3'-UGUCCCUUCUGUAGUGACUCGGACGGU-5'<br>5'-ACAGGGAAGACATCACTGAGCCTGCCA-3' | (SEQ ID NO: 188)<br>(SEQ ID NO: 1297)<br>(SEQ ID NO: 2406) |
| βc-1662 Target: | 5'-GGGAAGACAUCACUGAGCCUGCCat-3'<br>3'-GUCCCUUCUGUAGUGACUCGGACGGUA-5'<br>5'-CAGGGAAGACATCACTGAGCCTGCC-3' | (SEQ ID NO: 189)<br>(SEQ ID NO: 1298)<br>(SEQ ID NO: 2407) |
| βc-1663 Target: | 5'-GGAAGACAUCACUGAGCCUGCCAtc-3'<br>3'-UCCCUUCUGUAGUGACUCGGACGGUAG-5'<br>5'-AGGGAAGACATCACTGAGCCTGCCATC-3' | (SEQ ID NO: 190)<br>(SEQ ID NO: 1299)<br>(SEQ ID NO: 2408) |

TABLE 3-continued

Selected Anti-β-catenin DsiRNAs, Duplexes Targeting Both Human and Mouse Sequences

| | | |
|---|---|---|
| βc-1664 | 5'-GAAGACAUCACUGAGCCUGCCAUCt-3'<br>3'-CCCUUCUGUAGUGACUCGGACGGUAGA-5'<br>Target: 5'-GGGAAGACATCACTGAGCCTGCCATCT-3' | (SEQ ID NO: 191)<br>(SEQ ID NO: 1300)<br>(SEQ ID NO: 2409) |
| βc-1665 | 5'-AAGACAUCACUGAGCCUGCCAUCtg-3'<br>3'-CCUUCUGUAGUGACUCGGACGGUAGAC-5'<br>Target: 5'-GGAAGACATCACTGAGCCTGCCATCTG-3' | (SEQ ID NO: 192)<br>(SEQ ID NO: 1301)<br>(SEQ ID NO: 2410) |
| βc-1666 | 5'-AGACAUCACUGAGCCUGCCAUCUgt-3'<br>3'-CUUCUGUAGUGACUCGGACGGUAGACA-5'<br>Target: 5'-GAAGACATCACTGAGCCTGCCATCTGT-3' | (SEQ ID NO: 193)<br>(SEQ ID NO: 1302)<br>(SEQ ID NO: 2411) |
| βc-1667 | 5'-GACAUCACUGAGCCUGCCAUCUGtg-3'<br>3'-UUCUGUAGUGACUCGGACGGUAGACAC-5'<br>Target: 5'-AAGACATCACTGAGCCTGCCATCTGTG-3' | (SEQ ID NO: 194)<br>(SEQ ID NO: 1303)<br>(SEQ ID NO: 2412) |
| βc-1668 | 5'-ACAUCACUGAGCCUGCCAUCUGUgc-3'<br>3'-UCUGUAGUGACUCGGACGGUAGACACG-5'<br>Target: 5'-AGACATCACTGAGCCTGCCATCTGTGC-3' | (SEQ ID NO: 195)<br>(SEQ ID NO: 1304)<br>(SEQ ID NO: 2413) |
| βc-1669 | 5'-CAUCACUGAGCCUGCCAUCUGUGct-3'<br>3'-CUGUAGUGACUCGGACGGUAGACACGA-5'<br>Target: 5'-GACATCACTGAGCCTGCCATCTGTGCT-3' | (SEQ ID NO: 196)<br>(SEQ ID NO: 1305)<br>(SEQ ID NO: 2414) |
| βc-1670 | 5'-AUCACUGAGCCUGCCAUCUGUGCtc-3'<br>3'-UGUAGUGACUCGGACGGUAGACACGAG-5'<br>Target: 5'-ACATCACTGAGCCTGCCATCTGTGCTC-3' | (SEQ ID NO: 197)<br>(SEQ ID NO: 1306)<br>(SEQ ID NO: 2415) |
| βc-1671 | 5'-UCACUGAGCCUGCCAUCUGUGCUct-3'<br>3'-GUAGUGACUCGGACGGUAGACACGAGA-5'<br>Target: 5'-CATCACTGAGCCTGCCATCTGTGCTCT-3' | (SEQ ID NO: 198)<br>(SEQ ID NO: 1307)<br>(SEQ ID NO: 2416) |
| βc-1672 | 5'-CACUGAGCCUGCCAUCUGUGCUCtt-3'<br>3'-UAGUGACUCGGACGGUAGACACGAGAA-5'<br>Target: 5'-ATCACTGAGCCTGCCATCTGTGCTCTT-3' | (SEQ ID NO: 199)<br>(SEQ ID NO: 1308)<br>(SEQ ID NO: 2417) |
| βc-1673 | 5'-ACUGAGCCUGCCAUCUGUGCUCUtc-3'<br>3'-AGUGACUCGGACGGUAGACACGAGAAG-5'<br>Target: 5'-TCACTGAGCCTGCCATCTGTGCTCTTC-3' | (SEQ ID NO: 200)<br>(SEQ ID NO: 1309)<br>(SEQ ID NO: 2418) |
| βc-1674 | 5'-CUGAGCCUGCCAUCUGUGCUCUUcg-3'<br>3'-GUGACUCGGACGGUAGACACGAGAAGC-5'<br>Target: 5'-CACTGAGCCTGCCATCTGTGCTCTTCG-3' | (SEQ ID NO: 201)<br>(SEQ ID NO: 1310)<br>(SEQ ID NO: 2419) |
| βc-1675 | 5'-UGAGCCUGCCAUCUGUGCUCUUCgt-3'<br>3'-UGACUCGGACGGUAGACACGAGAAGCA-5'<br>Target: 5'-ACTGAGCCTGCCATCTGTGCTCTTCGT-3' | (SEQ ID NO: 202)<br>(SEQ ID NO: 1311)<br>(SEQ ID NO: 2420) |
| βc-1676 | 5'-GAGCCUGCCAUCUGUGCUCUUCGtc-3'<br>3'-GACUCGGACGGUAGACACGAGAAGCAG-5'<br>Target: 5'-CTGAGCCTGCCATCTGTGCTCTTCGTC-3' | (SEQ ID NO: 203)<br>(SEQ ID NO: 1312)<br>(SEQ ID NO: 2421) |
| βc-1677 | 5'-AGCCUGCCAUCUGUGCUCUUCGUca-3'<br>3'-ACUCGGACGGUAGACACGAGAAGCAGU-5'<br>Target: 5'-TGAGCCTGCCATCTGTGCTCTTCGTCA-3' | (SEQ ID NO: 204)<br>(SEQ ID NO: 1313)<br>(SEQ ID NO: 2422) |
| βc-1678 | 5'-GCCUGCCAUCUGUGCUCUUCGUCat-3'<br>3'-CUCGGACGGUAGACACGAGAAGCAGUA-5'<br>Target: 5'-GAGCCTGCCATCTGTGCTCTTCGTC-3' | (SEQ ID NO: 205)<br>(SEQ ID NO: 1314)<br>(SEQ ID NO: 2423) |
| βc-1679 | 5'-CCUGCCAUCUGUGCUCUUCGUCAtc-3'<br>3'-UCGGACGGUAGACACGAGAAGCAGUAG-5'<br>Target: 5'-AGCCTGCCATCTGTGCTCTTCGTCATC-3' | (SEQ ID NO: 206)<br>(SEQ ID NO: 1315)<br>(SEQ ID NO: 2424) |
| βc-1680 | 5'-CUGCCAUCUGUGCUCUUCGUCAUct-3'<br>3'-CGGACGGUAGACACGAGAAGCAGUAGA-5'<br>Target: 5'-GCCTGCCATCTGTGCTCTTCGTCATCT-3' | (SEQ ID NO: 207)<br>(SEQ ID NO: 1316)<br>(SEQ ID NO: 2425) |
| βc-1681 | 5'-UGCCAUCUGUGCUCUUCGUCAUCtg-3'<br>3'-GGACGGUAGACACGAGAAGCAGUAGAC-5'<br>Target: 5'-CCTGCCATCTGTGCTCTTCGTCATCTG-3' | (SEQ ID NO: 208)<br>(SEQ ID NO: 1317)<br>(SEQ ID NO: 2426) |
| βc-1682 | 5'-GCCAUCUGUGCUCUUCGUCAUCUga-3'<br>3'-GACGGUAGACACGAGAAGCAGUAGACU-5'<br>Target: 5'-CTGCCATCTGTGCTCTTCGTCATCTGA-3' | (SEQ ID NO: 209)<br>(SEQ ID NO: 1318)<br>(SEQ ID NO: 2427) |

TABLE 3-continued

Selected Anti-β-catenin DsiRNAs, Duplexes Targeting Both Human and Mouse Sequences

| | | |
|---|---|---|
| βc-1683 | 5'-CCAUCUGUGCUCUUCGUCAUCUGAc-3'<br>3'-ACGGUAGACACGAGAAGCAGUAGACUG-5'<br>Target: 5'-TGCCATCTGTGCTCTTCGTCATCTGAC-3' | (SEQ ID NO: 210)<br>(SEQ ID NO: 1319)<br>(SEQ ID NO: 2428) |
| βc-1684 | 5'-CAUCUGUGCUCUUCGUCAUCUGAcc-3'<br>3'-CGGUAGACACGAGAAGCAGUAGACUGG-5'<br>Target: 5'-GCCATCTGTGCTCTTCGTCATCTGACC-3' | (SEQ ID NO: 211)<br>(SEQ ID NO: 1320)<br>(SEQ ID NO: 2429) |
| βc-1685 | 5'-AUCUGUGCUCUUCGUCAUCUGACca-3'<br>3'-GGUAGACACGAGAAGCAGUAGACUGGU-5'<br>Target: 5'-CCATCTGTGCTCTTCGTCATCTGACCA-3' | (SEQ ID NO: 212)<br>(SEQ ID NO: 1321)<br>(SEQ ID NO: 2430) |
| βc-1686 | 5'-UCUGUGCUCUUCGUCAUCUGACCag-3'<br>3'-GUAGACACGAGAAGCAGUAGACUGGUC-5'<br>Target: 5'-CATCTGTGCTCTTCGTCATCTGACCAG-3' | (SEQ ID NO: 213)<br>(SEQ ID NO: 1322)<br>(SEQ ID NO: 2431) |
| βc-1687 | 5'-CUGUGCUCUUCGUCAUCUGACCAgc-3'<br>3'-UAGACACGAGAAGCAGUAGACUGGUCG-5'<br>Target: 5'-ATCTGTGCTCTTCGTCATCTGACCAGC-3' | (SEQ ID NO: 214)<br>(SEQ ID NO: 1323)<br>(SEQ ID NO: 2432) |
| βc-1688 | 5'-UGUGCUCUUCGUCAUCUGACCAGcc-3'<br>3'-AGACACGAGAAGCAGUAGACUGGUCGG-5'<br>Target: 5'-TCTGTGCTCTTCGTCATCTGACCAGCC-3' | (SEQ ID NO: 215)<br>(SEQ ID NO: 1324)<br>(SEQ ID NO: 2433) |
| βc-1689 | 5'-GUGCUCUUCGUCAUCUGACCAGCcg-3'<br>3'-GACACGAGAAGCAGUAGACUGGUCGGC-5'<br>Target: 5'-CTGTGCTCTTCGTCATCTGACCAGCCG-3' | (SEQ ID NO: 216)<br>(SEQ ID NO: 1325)<br>(SEQ ID NO: 2434) |
| βc-1690 | 5'-UGCUCUUCGUCAUCUGACCAGCCga-3'<br>3'-ACACGAGAAGCAGUAGACUGGUCGGCU-5'<br>Target: 5'-TGTGCTCTTCGTCATCTGACCAGCCGA-3' | (SEQ ID NO: 217)<br>(SEQ ID NO: 1326)<br>(SEQ ID NO: 2435) |
| βc-1691 | 5'-GCUCUUCGUCAUCUGACCAGCCGac-3'<br>3'-CACGAGAAGCAGUAGACUGGUCGGCUG-5'<br>Target: 5'-GTGCTCTTCGTCATCTGACCAGCCGAC-3' | (SEQ ID NO: 218)<br>(SEQ ID NO: 1327)<br>(SEQ ID NO: 2436) |
| βc-1692 | 5'-CUCUUCGUCAUCUGACCAGCCGAca-3'<br>3'-ACGAGAAGCAGUAGACUGGUCGGCUGU-5'<br>Target: 5'-TGCTCTTCGTCATCTGACCAGCCGACA-3' | (SEQ ID NO: 219)<br>(SEQ ID NO: 1328)<br>(SEQ ID NO: 2437) |
| βc-1693 | 5'-UCUUCGUCAUCUGACCAGCCGACac-3'<br>3'-CGAGAAGCAGUAGACUGGUCGGCUGUG-5'<br>Target: 5'-GCTCTTCGTCATCTGACCAGCCGACAC-3' | (SEQ ID NO: 220)<br>(SEQ ID NO: 1329)<br>(SEQ ID NO: 2438) |
| βc-1694 | 5'-CUUCGUCAUCUGACCAGCCGACAcc-3'<br>3'-GAGAAGCAGUAGACUGGUCGGCUGUGG-5'<br>Target: 5'-CTCTTCGTCATCTGACCAGCCGACACC-3' | (SEQ ID NO: 221)<br>(SEQ ID NO: 1330)<br>(SEQ ID NO: 2439) |
| βc-1695 | 5'-UUCGUCAUCUGACCAGCCGACACca-3'<br>3'-AGAAGCAGUAGACUGGUCGGCUGUGGU-5'<br>Target: 5'-TCTTCGTCATCTGACCAGCCGACACCA-3' | (SEQ ID NO: 222)<br>(SEQ ID NO: 1331)<br>(SEQ ID NO: 2440) |
| βc-1787 | 5'-CACCCACCAUCCCACUGGCCUCUga-3'<br>3'-AUGUGGGUGGUAGGGUGACCGGAGACU-5'<br>Target: 5'-TACACCCACCATCCCACTGGCCTCTGA-3' | (SEQ ID NO: 223)<br>(SEQ ID NO: 1332)<br>(SEQ ID NO: 2441) |
| βc-1788 | 5'-ACCCACCAUCCCACUGGCCUCUGat-3'<br>3'-UGUGGGUGGUAGGGUGACCGGAGACUA-5'<br>Target: 5'-ACACCCACCATCCCACTGGCCTCTGAT-3' | (SEQ ID NO: 224)<br>(SEQ ID NO: 1333)<br>(SEQ ID NO: 2442) |
| βc-1789 | 5'-CCCACCAUCCCACUGGCCUCUGAta-3'<br>3'-GUGGGUGGUAGGGUGACCGGAGACUAU-5'<br>Target: 5'-CACCCACCATCCCACTGGCCTCTGATA-3' | (SEQ ID NO: 225)<br>(SEQ ID NO: 1334)<br>(SEQ ID NO: 2443) |
| βc-1790 | 5'-CCACCAUCCCACUGGCCUCUGAUaa-3'<br>3'-UGGGUGGUAGGGUGACCGGAGACUAUU-5'<br>Target: 5'-ACCCACCATCCCACTGGCCTCTGATAA-3' | (SEQ ID NO: 226)<br>(SEQ ID NO: 1335)<br>(SEQ ID NO: 2444) |
| βc-1791 | 5'-CACCAUCCCACUGGCCUCUGAUAaa-3'<br>3'-GGGUGGUAGGGUGACCGGAGACUAUUU-5'<br>Target: 5'-CCCACCATCCCACTGGCCTCTGATAAA-3' | (SEQ ID NO: 227)<br>(SEQ ID NO: 1336)<br>(SEQ ID NO: 2445) |
| βc-1792 | 5'-ACCAUCCCACUGGCCUCUGAUAAag-3'<br>3'-GGUGGUAGGGUGACCGGAGACUAUUUC-5'<br>Target: 5'-CCACCATCCCACTGGCCTCTGATAAAG-3' | (SEQ ID NO: 228)<br>(SEQ ID NO: 1337)<br>(SEQ ID NO: 2446) |

TABLE 3-continued

Selected Anti-β-catenin DsiRNAs, Duplexes Targeting Both Human and Mouse Sequences

| | | |
|---|---|---|
| βc-1793 | 5'-CCAUCCCACUGGCCUCUGAUAAAGg-3'<br>3'-GUGGUAGGGUGACCGGAGACUAUUUCC-5'<br>Target: 5'-CACCATCCCACTGGCCTCTGATAAAGG-3' | (SEQ ID NO: 229)<br>(SEQ ID NO: 1338)<br>(SEQ ID NO: 2447) |
| βc-1794 | 5'-CAUCCCACUGGCCUCUGAUAAAGgc-3'<br>3'-UGGUAGGGUGACCGGAGACUAUUUCCG-5'<br>Target: 5'-ACCATCCCACTGGCCTCTGATAAAGGC-3' | (SEQ ID NO: 230)<br>(SEQ ID NO: 1339)<br>(SEQ ID NO: 2448) |
| βc-1795 | 5'-AUCCCACUGGCCUCUGAUAAAGGct-3'<br>3'-GGUAGGGUGACCGGAGACUAUUUCCGA-5'<br>Target: 5'-CCATCCCACTGGCCTCTGATAAAGGCT-3' | (SEQ ID NO: 231)<br>(SEQ ID NO: 1340)<br>(SEQ ID NO: 2449) |
| βc-1796 | 5'-UCCCACUGGCCUCUGAUAAAGGCta-3'<br>3'-GUAGGGUGACCGGAGACUAUUUCCGAU-5'<br>Target: 5'-CATCCCACTGGCCTCTGATAAAGGCTA-3' | (SEQ ID NO: 232)<br>(SEQ ID NO: 1341)<br>(SEQ ID NO: 2450) |
| βc-1797 | 5'-CCCACUGGCCUCUGAUAAAGGCUac-3'<br>3'-UAGGGUGACCGGAGACUAUUUCCGAUG-5'<br>Target: 5'-ATCCCACTGGCCTCTGATAAAGGCTAC-3' | (SEQ ID NO: 233)<br>(SEQ ID NO: 1342)<br>(SEQ ID NO: 2451) |
| βc-1798 | 5'-CCACUGGCCUCUGAUAAAGGCUAct-3'<br>3'-AGGGUGACCGGAGACUAUUUCCGAUGA-5'<br>Target: 5'-TCCCACTGGCCTCTGATAAAGGCTACT-3' | (SEQ ID NO: 234)<br>(SEQ ID NO: 1343)<br>(SEQ ID NO: 2452) |
| βc-1799 | 5'-CACUGGCCUCUGAUAAAGGCUACtg-3'<br>3'-GGGUGACCGGAGACUAUUUCCGAUGAC-5'<br>Target: 5'-CCCACTGGCCTCTGATAAAGGCTACTG-3' | (SEQ ID NO: 235)<br>(SEQ ID NO: 1344)<br>(SEQ ID NO: 2453) |
| βc-1800 | 5'-ACUGGCCUCUGAUAAAGGCUACUgt-3'<br>3'-GGUGACCGGAGACUAUUUCCGAUGACA-5'<br>Target: 5'-CCACTGGCCTCTGATAAAGGCTACTGT-3' | (SEQ ID NO: 236)<br>(SEQ ID NO: 1345)<br>(SEQ ID NO: 2454) |
| βc-1820 | 5'-ACUGUUGGAUUGAUUCGAAAUCUtg-3'<br>3'-GAUGACAACCUAACUAAGCUUUAGAAC-5'<br>Target: 5'-CTACTGTTGGATTGATTCGAAATCTTG-3' | (SEQ ID NO: 237)<br>(SEQ ID NO: 1346)<br>(SEQ ID NO: 2455) |
| βc-1821 | 5'-CUGUUGGAUUGAUUCGAAAUCUUgc-3'<br>3'-AUGACAACCUAACUAAGCUUUAGAACG-5'<br>Target: 5'-TACTGTTGGATTGATTCGAAATCTTGC-3' | (SEQ ID NO: 238)<br>(SEQ ID NO: 1347)<br>(SEQ ID NO: 2456) |
| βc-2072 | 5'-AAUACCAUUCCAUUGUUUGUGCAgc-3'<br>3'-AUUUAUGGUAAGGUAACAAACACGUCG-5'<br>Target: 5'-TAAATACCATTCCATTGTTTGTGCAGC-3' | (SEQ ID NO: 239)<br>(SEQ ID NO: 1348)<br>(SEQ ID NO: 2457) |
| βc-2073 | 5'-AUACCAUUCCAUUGUUUGUGCAGct-3'<br>3'-UUUAUGGUAAGGUAACAAACACGUCGA-5'<br>Target: 5'-AAATACCATTCCATTGTTTGTGCAGCT-3' | (SEQ ID NO: 240)<br>(SEQ ID NO: 1349)<br>(SEQ ID NO: 2458) |
| βc-2074 | 5'-UACCAUUCCAUUGUUUGUGCAGCtg-3'<br>3'-UUAUGGUAAGGUAACAAACACGUCGAC-5'<br>Target: 5'-AATACCATTCCATTGTTTGTGCAGCTG-3' | (SEQ ID NO: 241)<br>(SEQ ID NO: 1350)<br>(SEQ ID NO: 2459) |
| βc-2075 | 5'-ACCAUUCCAUUGUUUGUGCAGCUgc-3'<br>3'-UAUGGUAAGGUAACAAACACGUCGACG-5'<br>Target: 5'-ATACCATTCCATTGTTTGTGCAGCTGC-3' | (SEQ ID NO: 242)<br>(SEQ ID NO: 1351)<br>(SEQ ID NO: 2460) |
| βc-2076 | 5'-CCAUUCCAUUGUUUGUGCAGCUGct-3'<br>3'-AUGGUAAGGUAACAAACACGUCGACGA-5'<br>Target: 5'-TACCATTCCATTGTTTGTGCAGCTGCT-3' | (SEQ ID NO: 243)<br>(SEQ ID NO: 1352)<br>(SEQ ID NO: 2461) |
| βc-2077 | 5'-CAUUCCAUUGUUUGUGCAGCUGCtt-3'<br>3'-UGGUAAGGUAACAAACACGUCGACGAA-5'<br>Target: 5'-ACCATTCCATTGTTTGTGCAGCTGCTT-3' | (SEQ ID NO: 244)<br>(SEQ ID NO: 1353)<br>(SEQ ID NO: 2462) |
| βc-2097 | 5'-UGCUUUAUUCUCCCAUUGAAAACat-3'<br>3'-CGACGAAAUAAGAGGGUAACUUUUGUA-5'<br>Target: 5'-GCTGCTTTATTCTCCCATTGAAAAC-3' | (SEQ ID NO: 245)<br>(SEQ ID NO: 1354)<br>(SEQ ID NO: 2463) |
| βc-2098 | 5'-GCUUUAUUCUCCCAUUGAAAACAtc-3'<br>3'-GACGAAAUAAGAGGGUAACUUUUGUAG-5'<br>Target: 5'-CTGCTTTATTCTCCCATTGAAAACATC-3' | (SEQ ID NO: 246)<br>(SEQ ID NO: 1355)<br>(SEQ ID NO: 2464) |
| βc-2099 | 5'-CUUUAUUCUCCCAUUGAAAACAUcc-3'<br>3'-ACGAAAUAAGAGGGUAACUUUUGUAGG-5'<br>Target: 5'-TGCTTTATTCTCCCATTGAAAACATCC-3' | (SEQ ID NO: 247)<br>(SEQ ID NO: 1356)<br>(SEQ ID NO: 2465) |

TABLE 3-continued

Selected Anti-β-catenin DsiRNAs, Duplexes Targeting Both Human and Mouse Sequences

| | | |
|---|---|---|
| | 5'-UUUAUUCUCCCAUUGAAAACAUCca-3' | (SEQ ID NO: 248) |
| | 3'-CGAAAUAAGAGGGUAACUUUUGUAGGU-5' | (SEQ ID NO: 1357) |
| βc-2100 Target: | 5'-GCTTTATTCTCCCATTGAAAACATCCA-3' | (SEQ ID NO: 2466) |
| | 5'-GUCCUCUGUGAACUUGCUCAGGAca-3' | (SEQ ID NO: 249) |
| | 3'-CCCAGGAGACACUUGAACGAGUCCUGU-5' | (SEQ ID NO: 1358) |
| βc-2141 Target: | 5'-GGGTCCTCTGTGAACTTGCTCAGGACA-3' | (SEQ ID NO: 2467) |
| | 5'-UCCUCUGUGAACUUGCUCAGGACaa-3' | (SEQ ID NO: 250) |
| | 3'-CCAGGAGACACUUGAACGAGUCCUGUU-5' | (SEQ ID NO: 1359) |
| βc-2142 Target: | 5'-GGTCCTCTGTGAACTTGCTCAGGACAA-3' | (SEQ ID NO: 2468) |
| | 5'-CCUCUGUGAACUUGCUCAGGACAag-3' | (SEQ ID NO: 251) |
| | 3'-CAGGAGACACUUGAACGAGUCCUGUUC-5' | (SEQ ID NO: 1360) |
| βc-2143 Target: | 5'-GTCCTCTGTGAACTTGCTCAGGACAAG-3' | (SEQ ID NO: 2469) |
| | 5'-CUCUGUGAACUUGCUCAGGACAAgg-3' | (SEQ ID NO: 252) |
| | 3'-AGGAGACACUUGAACGAGUCCUGUUCC-5' | (SEQ ID NO: 1361) |
| βc-2144 Target: | 5'-TCCTCTGTGAACTTGCTCAGGACAAGG-3' | (SEQ ID NO: 2470) |
| | 5'-UCUGUGAACUUGCUCAGGACAAGga-3' | (SEQ ID NO: 253) |
| | 3'-GGAGACACUUGAACGAGUCCUGUUCCU-5' | (SEQ ID NO: 1362) |
| βc-2145 Target: | 5'-CCTCTGTGAACTTGCTCAGGACAAGGA-3' | (SEQ ID NO: 2471) |
| | 5'-CUGUGAACUUGCUCAGGACAAGGaa-3' | (SEQ ID NO: 254) |
| | 3'-GAGACACUUGAACGAGUCCUGUUCCUU-5' | (SEQ ID NO: 1363) |
| βc-2146 Target: | 5'-CTCTGTGAACTTGCTCAGGACAAGGAA-3' | (SEQ ID NO: 2472) |
| | 5'-UGUGAACUUGCUCAGGACAAGGAag-3' | (SEQ ID NO: 255) |
| | 3'-AGACACUUGAACGAGUCCUGUUCCUUC-5' | (SEQ ID NO: 1364) |
| βc-2147 Target: | 5'-TCTGTGAACTTGCTCAGGACAAGGAAG-3' | (SEQ ID NO: 2473) |
| | 5'-GUGAACUUGCUCAGGACAAGGAAgc-3' | (SEQ ID NO: 256) |
| | 3'-GACACUUGAACGAGUCCUGUUCCUUCG-5' | (SEQ ID NO: 1365) |
| βc-2148 Target: | 5'-CTGTGAACTTGCTCAGGACAAGGAAGC-3' | (SEQ ID NO: 2474) |
| | 5'-UGAACUUGCUCAGGACAAGGAAGct-3' | (SEQ ID NO: 257) |
| | 3'-ACACUUGAACGAGUCCUGUUCCUUCGA-5' | (SEQ ID NO: 1366) |
| βc-2149 Target: | 5'-TGTGAACTTGCTCAGGACAAGGAAGCT-3' | (SEQ ID NO: 2475) |
| | 5'-GAACUUGCUCAGGACAAGGAAGCtg-3' | (SEQ ID NO: 258) |
| | 3'-CACUUGAACGAGUCCUGUUCCUUCGAC-5' | (SEQ ID NO: 1367) |
| βc-2150 Target: | 5'-GTGAACTTGCTCAGGACAAGGAAGCTG-3' | (SEQ ID NO: 2476) |
| | 5'-AACUUGCUCAGGACAAGGAAGCUgc-3' | (SEQ ID NO: 259) |
| | 3'-ACUUGAACGAGUCCUGUUCCUUCGACG-5' | (SEQ ID NO: 1368) |
| βc-2151 Target: | 5'-TGAACTTGCTCAGGACAAGGAAGCTGC-3' | (SEQ ID NO: 2477) |
| | 5'-AUUGAAGCUGAGGGAGCCACAGCtc-3' | (SEQ ID NO: 260) |
| | 3'-GAUAACUUCGACUCCCUCGGUGUCGAG-5' | (SEQ ID NO: 1369) |
| βc-2183 Target: | 5'-CTATTGAAGCTGAGGGAGCCACAGCTC-3' | (SEQ ID NO: 2478) |
| | 5'-UUGAAGCUGAGGGAGCCACAGCUcc-3' | (SEQ ID NO: 261) |
| | 3'-AUAACUUCGACUCCCUCGGUGUCGAGG-5' | (SEQ ID NO: 1370) |
| βc-2184 Target: | 5'-TATTGAAGCTGAGGGAGCCACAGCTCC-3' | (SEQ ID NO: 2479) |
| | 5'-UGAAGCUGAGGGAGCCACAGCUCct-3' | (SEQ ID NO: 262) |
| | 3'-UAACUUCGACUCCCUCGGUGUCGAGGA-5' | (SEQ ID NO: 1371) |
| βc-2185 Target: | 5'-ATTGAAGCTGAGGGAGCCACAGCTCCT-3' | (SEQ ID NO: 2480) |
| | 5'-UUCCGAAUGUCUGAGGACAAGCCac-3' | (SEQ ID NO: 263) |
| | 3'-ACAAGGCUUACAGACUCCUGUUCGGUG-5' | (SEQ ID NO: 1372) |
| βc-2270 Target: | 5'-TGTTCCGAATGTCTGAGGACAAGCCAC-3' | (SEQ ID NO: 2481) |
| | 5'-UCCGAAUGUCUGAGGACAAGCCAca-3' | (SEQ ID NO: 264) |
| | 3'-CAAGGCUUACAGACUCCUGUUCGGUGU-5' | (SEQ ID NO: 1373) |
| βc-2271 Target: | 5'-GTTCCGAATGTCTGAGGACAAGCCACA-3' | (SEQ ID NO: 2482) |
| | 5'-CCGAAUGUCUGAGGACAAGCCACaa-3' | (SEQ ID NO: 265) |
| | 3'-AAGGCUUACAGACUCCUGUUCGGUGUU-5' | (SEQ ID NO: 1374) |
| βc-2272 Target: | 5'-TTCCGAATGTCTGAGGACAAGCCACAA-3' | (SEQ ID NO: 2483) |
| | 5'-CGAAUGUCUGAGGACAAGCCACAag-3' | (SEQ ID NO: 266) |
| | 3'-AGGCUUACAGACUCCUGUUCGGUGUUC-5' | (SEQ ID NO: 1375) |
| βc-2273 Target: | 5'-TCCGAATGTCTGAGGACAAGCCACAAG-3' | (SEQ ID NO: 2484) |

TABLE 3-continued

Selected Anti-β-catenin DsiRNAs, Duplexes Targeting Both Human and Mouse Sequences

| | | |
|---|---|---|
| βc-2274 Target: | 5'-GAAUGUCUGAGGACAAGCCACAAga-3'<br>3'-GGCUUACAGACUCCUGUUCGGUGUUCU-5'<br>5'-CCGAATGTCTGAGGACAAGCCACAAGA-3' | (SEQ ID NO: 267)<br>(SEQ ID NO: 1376)<br>(SEQ ID NO: 2485) |
| βc-2275 Target: | 5'-AAUGUCUGAGGACAAGCCACAAGat-3'<br>3'-GCUUACAGACUCCUGUUCGGUGUUCUA-5'<br>5'-CGAATGTCTGAGGACAAGCCACAAGAT-3' | (SEQ ID NO: 268)<br>(SEQ ID NO: 1377)<br>(SEQ ID NO: 2486) |
| βc-2276 Target: | 5'-AUGUCUGAGGACAAGCCACAAGAtt-3'<br>3'-CUUACAGACUCCUGUUCGGUGUUCUAA-5'<br>5'-GAATGTCTGAGGACAAGCCACAAGATT-3' | (SEQ ID NO: 269)<br>(SEQ ID NO: 1378)<br>(SEQ ID NO: 2487) |
| βc-2277 Target: | 5'-UGUCUGAGGACAAGCCACAAGAUta-3'<br>3'-UUACAGACUCCUGUUCGGUGUUCUAAU-5'<br>5'-AATGTCTGAGGACAAGCCACAAGATTA-3' | (SEQ ID NO: 270)<br>(SEQ ID NO: 1379)<br>(SEQ ID NO: 2488) |
| βc-2345 Target: | 5'-ACAGAGCCAAUGGCUUGGAAUGAga-3'<br>3'-CUUGUCUCGGUUACCGAACCUUACUCU-5'<br>5'-GAACAGAGCCAATGGCTTGGAATGAGA-3' | (SEQ ID NO: 271)<br>(SEQ ID NO: 1380)<br>(SEQ ID NO: 2489) |
| βc-2346 Target: | 5'-CAGAGCCAAUGGCUUGGAAUGAGac-3'<br>3'-UUGUCUCGGUUACCGAACCUUACUCUG-5'<br>5'-AACAGAGCCAATGGCTTGGAATGAGAC-3' | (SEQ ID NO: 272)<br>(SEQ ID NO: 1381)<br>(SEQ ID NO: 2490) |
| βc-2347 Target: | 5'-AGAGCCAAUGGCUUGGAAUGAGAct-3'<br>3'-UGUCUCGGUUACCGAACCUUACUCUGA-5'<br>5'-ACAGAGCCAATGGCTTGGAATGAGACT-3' | (SEQ ID NO: 273)<br>(SEQ ID NO: 1382)<br>(SEQ ID NO: 2491) |
| βc-2348 Target: | 5'-GAGCCAAUGGCUUGGAAUGAGACtg-3'<br>3'-GUCUCGGUUACCGAACCUUACUCUGAC-5'<br>5'-CAGAGCCAATGGCTTGGAATGAGACTG-3' | (SEQ ID NO: 274)<br>(SEQ ID NO: 1383)<br>(SEQ ID NO: 2492) |
| βc-2349 Target: | 5'-AGCCAAUGGCUUGGAAUGAGACUgc-3'<br>3'-UCUCGGUUACCGAACCUUACUCUGACG-5'<br>5'-AGAGCCAATGGCTTGGAATGAGACTGC-3' | (SEQ ID NO: 275)<br>(SEQ ID NO: 1384)<br>(SEQ ID NO: 2493) |
| βc-2350 Target: | 5'-GCCAAUGGCUUGGAAUGAGACUGct-3'<br>3'-CUCGGUUACCGAACCUUACUCUGACGA-5'<br>5'-GAGCCAATGGCTTGGAATGAGACTGCT-3' | (SEQ ID NO: 276)<br>(SEQ ID NO: 1385)<br>(SEQ ID NO: 2494) |
| βc-2351 Target: | 5'-CCAAUGGCUUGGAAUGAGACUGCtg-3'<br>3'-UCGGUUACCGAACCUUACUCUGACGAC-5'<br>5'-AGCCAATGGCTTGGAATGAGACTGCTG-3' | (SEQ ID NO: 277)<br>(SEQ ID NO: 1386)<br>(SEQ ID NO: 2495) |
| βc-2352 Target: | 5'-CAAUGGCUUGGAAUGAGACUGCUga-3'<br>3'-CGGUUACCGAACCUUACUCUGACGACU-5'<br>5'-GCCAATGGCTTGGAATGAGACTGCTGA-3' | (SEQ ID NO: 278)<br>(SEQ ID NO: 1387)<br>(SEQ ID NO: 2496) |
| βc-2353 Target: | 5'-AAUGGCUUGGAAUGAGACUGCUGat-3'<br>3'-GGUUACCGAACCUUACUCUGACGACUA-5'<br>5'-CCAATGGCTTGGAATGAGACTGCTGAT-3' | (SEQ ID NO: 279)<br>(SEQ ID NO: 1388)<br>(SEQ ID NO: 2497) |
| βc-2354 Target: | 5'-AUGGCUUGGAAUGAGACUGCUGAtc-3'<br>3'-GUUACCGAACCUUACUCUGACGACUAG-5'<br>5'-CAATGGCTTGGAATGAGACTGCTGATC-3' | (SEQ ID NO: 280)<br>(SEQ ID NO: 1389)<br>(SEQ ID NO: 2498) |
| βc-2355 Target: | 5'-UGGCUUGGAAUGAGACUGCUGAUct-3'<br>3'-UUACCGAACCUUACUCUGACGACUAGA-5'<br>5'-AATGGCTTGGAATGAGACTGCTGATCT-3' | (SEQ ID NO: 281)<br>(SEQ ID NO: 1390)<br>(SEQ ID NO: 2499) |
| βc-2411 Target: | 5'-CUUGGAUAUCGCCAGGAUGAUCCta-3'<br>3'-GGGAACCUAUAGCGGUCCUACUAGGAU-5'<br>5'-CCCTTGGATATCGCCAGGATGATCCTA-3' | (SEQ ID NO: 282)<br>(SEQ ID NO: 1391)<br>(SEQ ID NO: 2500) |
| βc-2412 Target: | 5'-UUGGAUAUCGCCAGGAUGAUCCUag-3'<br>3'-GGAACCUAUAGCGGUCCUACUAGGAUC-5'<br>5'-CCTTGGATATCGCCAGGATGATCCTAG-3' | (SEQ ID NO: 283)<br>(SEQ ID NO: 1392)<br>(SEQ ID NO: 2501) |
| βc-2413 Target: | 5'-UGGAUAUCGCCAGGAUGAUCCUAgc-3'<br>3'-GAACCUAUAGCGGUCCUACUAGGAUCG-5'<br>5'-CTTGGATATCGCCAGGATGATCCTAGC-3' | (SEQ ID NO: 284)<br>(SEQ ID NO: 1393)<br>(SEQ ID NO: 2502) |
| βc-2414 Target: | 5'-GGAUAUCGCCAGGAUGAUCCUAGct-3'<br>3'-AACCUAUAGCGGUCCUACUAGGAUCGA-5'<br>5'-TTGGATATCGCCAGGATGATCCTAGCT-3' | (SEQ ID NO: 285)<br>(SEQ ID NO: 1394)<br>(SEQ ID NO: 2503) |

TABLE 3-continued

Selected Anti-β-catenin DsiRNAs, Duplexes Targeting Both Human and Mouse Sequences

| | | |
|---|---|---|
| | 5'-GAUAUCGCCAGGAUGAUCCUAGCta-3' | (SEQ ID NO: 286) |
| | 3'-ACCUAUAGCGGUCCUACUAGGAUCGAU-5' | (SEQ ID NO: 1395) |
| βc-2415 Target: | 5'-TGGATATCGCCAGGATGATCCTAGCTA-3' | (SEQ ID NO: 2504) |
| | 5'-CGUUCUUUUCACUCUGGUGGAUAtg-3' | (SEQ ID NO: 287) |
| | 3'-UAGCAAGAAAAGUGAGACCACCUAUAC-5' | (SEQ ID NO: 1396) |
| βc-2441 Target: | 5'-ATCGTTCTTTTCACTCTGGTGGATATG-3' | (SEQ ID NO: 2505) |
| | 5'-GUUCUUUUCACUCUGGUGGAUAUgg-3' | (SEQ ID NO: 288) |
| | 3'-AGCAAGAAAAGUGAGACCACCUAUACC-5' | (SEQ ID NO: 1397) |
| βc-2442 Target: | 5'-TCGTTCTTTTCACTCTGGTGGATATGG-3' | (SEQ ID NO: 2506) |
| | 5'-UUCUUUUCACUCUGGUGGAUAUGgc-3' | (SEQ ID NO: 289) |
| | 3'-GCAAGAAAAGUGAGACCACCUAUACCG-5' | (SEQ ID NO: 1398) |
| βc-2443 Target: | 5'-CGTTCTTTTCACTCTGGTGGATATGGC-3' | (SEQ ID NO: 2507) |
| | 5'-UCUUUUCACUCUGGUGGAUAUGGcc-3' | (SEQ ID NO: 290) |
| | 3'-CAAGAAAAGUGAGACCACCUAUACCGG-5' | (SEQ ID NO: 1399) |
| βc-2444 Target: | 5'-GTTCTTTTCACTCTGGTGGATATGGCC-3' | (SEQ ID NO: 2508) |
| | 5'-CUUUUCACUCUGGUGGAUAUGGCca-3' | (SEQ ID NO: 291) |
| | 3'-AAGAAAAGUGAGACCACCUAUACCGGU-5' | (SEQ ID NO: 1400) |
| βc-2445 Target: | 5'-TTCTTTTCACTCTGGTGGATATGGCCA-3' | (SEQ ID NO: 2509) |
| | 5'-CAUGAGAUGGGUGGCCACCACCCCtg-3' | (SEQ ID NO: 292) |
| | 3'-UUGUACUCUACCCACCGGUGGUGGGAC-5' | (SEQ ID NO: 1401) |
| βc-2501 Target: | 5'-AACATGAGATGGGTGGCCACCACCCTG-3' | (SEQ ID NO: 2510) |
| | 5'-AUGAGAUGGGUGGCCACCACCCCUgg-3' | (SEQ ID NO: 293) |
| | 3'-UGUACUCUACCCACCGGUGGUGGGACC-5' | (SEQ ID NO: 1402) |
| βc-2502 Target: | 5'-ACATGAGATGGGTGGCCACCACCCTGG-3' | (SEQ ID NO: 2511) |
| | 5'-UGAGAUGGGUGGCCACCACCCCUGgt-3' | (SEQ ID NO: 294) |
| | 3'-GUACUCUACCCACCGGUGGUGGGACCA-5' | (SEQ ID NO: 1403) |
| βc-2503 Target: | 5'-CATGAGATGGGTGGCCACCACCCTGGT-3' | (SEQ ID NO: 2512) |
| | 5'-GAGAUGGGUGGCCACCACCCCUGGtg-3' | (SEQ ID NO: 295) |
| | 3'-UACUCUACCCACCGGUGGUGGGACCAC-5' | (SEQ ID NO: 1404) |
| βc-2504 Target: | 5'-ATGAGATGGGTGGCCACCACCCTGGTG-3' | (SEQ ID NO: 2513) |
| | 5'-AGAUGGGUGGCCACCACCCCUGGUgc-3' | (SEQ ID NO: 296) |
| | 3'-ACUCUACCCACCGGUGGUGGGACCACG-5' | (SEQ ID NO: 1405) |
| βc-2505 Target: | 5'-TGAGATGGGTGGCCACCACCCTGGTGC-3' | (SEQ ID NO: 2514) |
| | 5'-GAUGGGUGGCCACCACCCCUGGUGct-3' | (SEQ ID NO: 297) |
| | 3'-CUCUACCCACCGGUGGUGGGACCACGA-5' | (SEQ ID NO: 1406) |
| βc-2506 Target: | 5'-GAGATGGGTGGCCACCACCCTGGTGCT-3' | (SEQ ID NO: 2515) |
| | 5'-AUGGGUGGCCACCACCCCUGGUGCtg-3' | (SEQ ID NO: 298) |
| | 3'-UCUACCCACCGGUGGUGGGACCACGAC-5' | (SEQ ID NO: 1407) |
| βc-2507 Target: | 5'-AGATGGGTGGCCACCACCCTGGTGCTG-3' | (SEQ ID NO: 2516) |
| | 5'-UGGGUGGCCACCACCCCUGGUGCUga-3' | (SEQ ID NO: 299) |
| | 3'-CUACCCACCGGUGGUGGGACCACGACU-5' | (SEQ ID NO: 1408) |
| βc-2508 Target: | 5'-GATGGGTGGCCACCACCCTGGTGCTGA-3' | (SEQ ID NO: 2517) |
| | 5'-GGGUGGCCACCACCCCUGGUGCUGac-3' | (SEQ ID NO: 300) |
| | 3'-UACCCACCGGUGGUGGGACCACGACUG-5' | (SEQ ID NO: 1409) |
| βc-2509 Target: | 5'-ATGGGTGGCCACCACCCTGGTGCTGAC-3' | (SEQ ID NO: 2518) |
| | 5'-GGUGGCCACCACCCCUGGUGCUGAct-3' | (SEQ ID NO: 301) |
| | 3'-ACCCACCGGUGGUGGGACCACGACUGA-5' | (SEQ ID NO: 1410) |
| βc-2510 Target: | 5'-TGGGTGGCCACCACCCTGGTGCTGACT-3' | (SEQ ID NO: 2519) |
| | 5'-GUGGCCACCACCCCUGGUGCUGACta-3' | (SEQ ID NO: 302) |
| | 3'-CCCACCGGUGGUGGGACCACGACUGAU-5' | (SEQ ID NO: 1411) |
| βc-2511 Target: | 5'-GGGTGGCCACCACCCTGGTGCTGACTA-3' | (SEQ ID NO: 2520) |
| | 5'-UGGCCACCACCCCUGGUGCUGACUat-3' | (SEQ ID NO: 303) |
| | 3'-CCACCGGUGGUGGGACCACGACUGAUA-5' | (SEQ ID NO: 1412) |
| βc-2512 Target: | 5'-GGTGGCCACCACCCTGGTGCTGACTAT-3' | (SEQ ID NO: 2521) |
| | 5'-GGCCACCACCCCUGGUGCUGACUAtc-3' | (SEQ ID NO: 304) |
| | 3'-CACCGGUGGUGGGACCACGACUGAUAG-5' | (SEQ ID NO: 1413) |
| βc-2513 Target: | 5'-GTGGCCACCACCCTGGTGCTGACTATC-3' | (SEQ ID NO: 2522) |

TABLE 3-continued

Selected Anti-β-catenin DsiRNAs, Duplexes Targeting Both Human and Mouse Sequences

| | | |
|---|---|---|
| | 5'-GCCACCACCCUGGUGCUGACUAUCc-3' | (SEQ ID NO: 305) |
| | 3'-ACCGGUGGUGGGACCACGACUGAUAGG-5' | (SEQ ID NO: 1414) |
| βc-2514 Target: | 5'-TGGCCACCACCCTGGTGCTGACTATCC-3' | (SEQ ID NO: 2523) |
| | 5'-CCACCACCCUGGUGCUGACUAUCca-3' | (SEQ ID NO: 306) |
| | 3'-CCGGUGGUGGGACCACGACUGAUAGGU-5' | (SEQ ID NO: 1415) |
| βc-2515 Target: | 5'-GGCCACCACCCTGGTGCTGACTATCCA-3' | (SEQ ID NO: 2524) |
| | 5'-CACCACCCUGGUGCUGACUAUCCag-3' | (SEQ ID NO: 307) |
| | 3'-CGGUGGUGGGACCACGACUGAUAGGUC-5' | (SEQ ID NO: 1416) |
| βc-2516 Target: | 5'-GCCACCACCCTGGTGCTGACTATCCAG-3' | (SEQ ID NO: 2525) |
| | 5'-ACCACCCUGGUGCUGACUAUCCAgt-3' | (SEQ ID NO: 308) |
| | 3'-GGUGGUGGGACCACGACUGAUAGGUCA-5' | (SEQ ID NO: 1417) |
| βc-2517 Target: | 5'-CCACCACCCTGGTGCTGACTATCCAGT-3' | (SEQ ID NO: 2526) |
| | 5'-CCACCCUGGUGCUGACUAUCCAGtt-3' | (SEQ ID NO: 309) |
| | 3'-GUGGUGGGACCACGACUGAUAGGUCAA-5' | (SEQ ID NO: 1418) |
| βc-2518 Target: | 5'-CACCACCCTGGTGCTGACTATCCAGTT-3' | (SEQ ID NO: 2527) |
| | 5'-CACCCUGGUGCUGACUAUCCAGUtg-3' | (SEQ ID NO: 310) |
| | 3'-UGGUGGGACCACGACUGAUAGGUCAAC-5' | (SEQ ID NO: 1419) |
| βc-2519 Target: | 5'-ACCACCCTGGTGCTGACTATCCAGTTG-3' | (SEQ ID NO: 2528) |
| | 5'-ACCCUGGUGCUGACUAUCCAGUUga-3' | (SEQ ID NO: 311) |
| | 3'-GGUGGGACCACGACUGAUAGGUCAACU-5' | (SEQ ID NO: 1420) |
| βc-2520 Target: | 5'-CCACCCTGGTGCTGACTATCCAGTTGA-3' | (SEQ ID NO: 2529) |
| | 5'-CCCUGGUGCUGACUAUCCAGUUGat-3' | (SEQ ID NO: 312) |
| | 3'-GUGGGACCACGACUGAUAGGUCAACUA-5' | (SEQ ID NO: 1421) |
| βc-2521 Target: | 5'-CACCCTGGTGCTGACTATCCAGTTGAT-3' | (SEQ ID NO: 2530) |
| | 5'-CCUGGUGCUGACUAUCCAGUUGAtg-3' | (SEQ ID NO: 313) |
| | 3'-UGGGACCACGACUGAUAGGUCAACUAC-5' | (SEQ ID NO: 1422) |
| βc-2522 Target: | 5'-ACCCTGGTGCTGACTATCCAGTTGATG-3' | (SEQ ID NO: 2531) |
| | 5'-CUGGUGCUGACUAUCCAGUUGAUgg-3' | (SEQ ID NO: 314) |
| | 3'-GGGACCACGACUGAUAGGUCAACUACC-5' | (SEQ ID NO: 1423) |
| βc-2523 Target: | 5'-CCCTGGTGCTGACTATCCAGTTGATGG-3' | (SEQ ID NO: 2532) |
| | 5'-UGGUGCUGACUAUCCAGUUGAUGgg-3' | (SEQ ID NO: 315) |
| | 3'-GGACCACGACUGAUAGGUCAACUACCC-5' | (SEQ ID NO: 1424) |
| βc-2524 Target: | 5'-CCTGGTGCTGACTATCCAGTTGATGGG-3' | (SEQ ID NO: 2533) |
| | 5'-GGUGCUGACUAUCCAGUUGAUGGgc-3' | (SEQ ID NO: 316) |
| | 3'-GACCACGACUGAUAGGUCAACUACCCG-5' | (SEQ ID NO: 1425) |
| βc-2525 Target: | 5'-CTGGTGCTGACTATCCAGTTGATGGGC-3' | (SEQ ID NO: 2534) |
| | 5'-GUGCUGACUAUCCAGUUGAUGGGct-3' | (SEQ ID NO: 317) |
| | 3'-ACCACGACUGAUAGGUCAACUACCCGA-5' | (SEQ ID NO: 1426) |
| βc-2526 Target: | 5'-TGGTGCTGACTATCCAGTTGATGGGCT-3' | (SEQ ID NO: 2535) |
| | 5'-UGCUGACUAUCCAGUUGAUGGGCtg-3' | (SEQ ID NO: 318) |
| | 3'-CCACGACUGAUAGGUCAACUACCCGAC-5' | (SEQ ID NO: 1427) |
| βc-2527 Target: | 5'-GGTGCTGACTATCCAGTTGATGGGCTG-3' | (SEQ ID NO: 2536) |
| | 5'-GCUGACUAUCCAGUUGAUGGGCUgc-3' | (SEQ ID NO: 319) |
| | 3'-CACGACUGAUAGGUCAACUACCCGACG-5' | (SEQ ID NO: 1428) |
| βc-2528 Target: | 5'-GTGCTGACTATCCAGTTGATGGGCTGC-3' | (SEQ ID NO: 2537) |
| | 5'-CUGACUAUCCAGUUGAUGGGCUGcc-3' | (SEQ ID NO: 320) |
| | 3'-ACGACUGAUAGGUCAACUACCCGACGG-5' | (SEQ ID NO: 1429) |
| βc-2529 Target: | 5'-TGCTGACTATCCAGTTGATGGGCTGCC-3' | (SEQ ID NO: 2538) |
| | 5'-UGACUAUCCAGUUGAUGGGCUGCca-3' | (SEQ ID NO: 321) |
| | 3'-CGACUGAUAGGUCAACUACCCGACGGU-5' | (SEQ ID NO: 1430) |
| βc-2530 Target: | 5'-GCTGACTATCCAGTTGATGGGCTGCCA-3' | (SEQ ID NO: 2539) |
| | 5'-GACUAUCCAGUUGAUGGGCUGCCag-3' | (SEQ ID NO: 322) |
| | 3'-GACUGAUAGGUCAACUACCCGACGGUC-5' | (SEQ ID NO: 1431) |
| βc-2531 Target: | 5'-CTGACTATCCAGTTGATGGGCTGCCAG-3' | (SEQ ID NO: 2540) |
| | 5'-ACUAUCCAGUUGAUGGGCUGCCAga-3' | (SEQ ID NO: 323) |
| | 3'-ACUGAUAGGUCAACUACCCGACGGUCU-5' | (SEQ ID NO: 1432) |
| βc-2532 Target: | 5'-TGACTATCCAGTTGATGGGCTGCCAGA-3' | (SEQ ID NO: 2541) |

TABLE 3-continued

Selected Anti-β-catenin DsiRNAs, Duplexes Targeting Both Human and Mouse Sequences

| | | |
|---|---|---|
| | 5'-CUAUCCAGUUGAUGGGCUGCCAGat-3' | (SEQ ID NO: 324) |
| | 3'-CUGAUAGGUCAACUACCCGACGGUCUA-5' | (SEQ ID NO: 1433) |
| βc-2533 Target: | 5'-GACTATCCAGTTGATGGGCTGCCAGAT-3' | (SEQ ID NO: 2542) |
| | 5'-UAUCCAGUUGAUGGGCUGCCAGAtc-3' | (SEQ ID NO: 325) |
| | 3'-UGAUAGGUCAACUACCCGACGGUCUAG-5' | (SEQ ID NO: 1434) |
| βc-2534 Target: | 5'-ACTATCCAGTTGATGGGCTGCCAGATC-3' | (SEQ ID NO: 2543) |
| | 5'-AUCCAGUUGAUGGGCUGCCAGAUct-3' | (SEQ ID NO: 326) |
| | 3'-GAUAGGUCAACUACCCGACGGUCUAGA-5' | (SEQ ID NO: 1435) |
| βc-2535 Target: | 5'-CTATCCAGTTGATGGGCTGCCAGATCT-3' | (SEQ ID NO: 2544) |
| | 5'-GCCCAGGACCUCAUGGAUGGGCUgc-3' | (SEQ ID NO: 327) |
| | 3'-UACGGGUCCUGGAGUACCUACCCGACG-5' | (SEQ ID NO: 1436) |
| βc-2567 Target: | 5'-ATGCCCAGGACCTCATGGATGGGCTGC-3' | (SEQ ID NO: 2545) |
| | 5'-CCCAGGACCUCAUGGAUGGGCUGcc-3' | (SEQ ID NO: 328) |
| | 3'-ACGGGUCCUGGAGUACCUACCCGACGG-5' | (SEQ ID NO: 1437) |
| βc-2568 Target: | 5'-TGCCCAGGACCTCATGGATGGGCTGCC-3' | (SEQ ID NO: 2546) |
| | 5'-CCAGGACCUCAUGGAUGGGCUGCct-3' | (SEQ ID NO: 329) |
| | 3'-CGGGUCCUGGAGUACCUACCCGACGGA-5' | (SEQ ID NO: 1438) |
| βc-2569 Target: | 5'-GCCCAGGACCTCATGGATGGGCTGCCT-3' | (SEQ ID NO: 2547) |
| | 5'-AGCAAUCAGCUGGCCUGGUUUGAta-3' | (SEQ ID NO: 330) |
| | 3'-UGUCGUUAGUCGACCGGACCAAACUAU-5' | (SEQ ID NO: 1439) |
| βc-2603 Target: | 5'-ACAGCAATCAGCTGGCCTGGTTTGATA-3' | (SEQ ID NO: 2548) |
| | 5'-GCAAUCAGCUGGCCUGGUUUGAUac-3' | (SEQ ID NO: 331) |
| | 3'-GUCGUUAGUCGACCGGACCAAACUAUG-5' | (SEQ ID NO: 1440) |
| βc-2604 Target: | 5'-CAGCAATCAGCTGGCCTGGTTTGATAC-3' | (SEQ ID NO: 2549) |
| | 5'-CAAUCAGCUGGCCUGGUUUGAUAct-3' | (SEQ ID NO: 332) |
| | 3'-UCGUUAGUCGACCGGACCAAACUAUGA-5' | (SEQ ID NO: 1441) |
| βc-2605 Target: | 5'-AGCAATCAGCTGGCCTGGTTTGATACT-3' | (SEQ ID NO: 2550) |
| | 5'-AAUCAGCUGGCCUGGUUUGAUACtg-3' | (SEQ ID NO: 333) |
| | 3'-CGUUAGUCGACCGGACCAAACUAUGAC-5' | (SEQ ID NO: 1442) |
| βc-2606 Target: | 5'-GCAATCAGCTGGCCTGGTTTGATACTG-3' | (SEQ ID NO: 2551) |
| | 5'-AUCAGCUGGCCUGGUUUGAUACUga-3' | (SEQ ID NO: 334) |
| | 3'-GUUAGUCGACCGGACCAAACUAUGACU-5' | (SEQ ID NO: 1443) |
| βc-2607 Target: | 5'-CAATCAGCTGGCCTGGTTTGATACTGA-3' | (SEQ ID NO: 2552) |
| | 5'-UCAGCUGGCCUGGUUUGAUACUGac-3' | (SEQ ID NO: 335) |
| | 3'-UUAGUCGACCGGACCAAACUAUGACUG-5' | (SEQ ID NO: 1444) |
| βc-2608 Target: | 5'-AATCAGCTGGCCTGGTTTGATACTGAC-3' | (SEQ ID NO: 2553) |
| | 5'-CAGCUGGCCUGGUUUGAUACUGAcc-3' | (SEQ ID NO: 336) |
| | 3'-UAGUCGACCGGACCAAACUAUGACUGG-5' | (SEQ ID NO: 1445) |
| βc-2609 Target: | 5'-ATCAGCTGGCCTGGTTTGATACTGACC-3' | (SEQ ID NO: 2554) |
| | 5'-AGCUGGCCUGGUUUGAUACUGACct-3' | (SEQ ID NO: 337) |
| | 3'-AGUCGACCGGACCAAACUAUGACUGGA-5' | (SEQ ID NO: 1446) |
| βc-2610 Target: | 5'-TCAGCTGGCCTGGTTTGATACTGACCT-3' | (SEQ ID NO: 2555) |
| | 5'-GCUGGCCUGGUUUGAUACUGACCtg-3' | (SEQ ID NO: 338) |
| | 3'-GUCGACCGGACCAAACUAUGACUGGAC-5' | (SEQ ID NO: 1447) |
| βc-2611 Target: | 5'-CAGCTGGCCTGGTTTGATACTGACCTG-3' | (SEQ ID NO: 2556) |
| | 5'-CUGGCCUGGUUUGAUACUGACCUgt-3' | (SEQ ID NO: 339) |
| | 3'-UCGACCGGACCAAACUAUGACUGGACA-5' | (SEQ ID NO: 1448) |
| βc-2612 Target: | 5'-AGCTGGCCTGGTTTGATACTGACCTGT-3' | (SEQ ID NO: 2557) |
| | 5'-UGGCCUGGUUUGAUACUGACCUGta-3' | (SEQ ID NO: 340) |
| | 3'-CGACCGGACCAAACUAUGACUGGACAU-5' | (SEQ ID NO: 1449) |
| βc-2613 Target: | 5'-GCTGGCCTGGTTTGATACTGACCTGTA-3' | (SEQ ID NO: 2558) |
| | 5'-GGCCUGGUUUGAUACUGACCUGUaa-3' | (SEQ ID NO: 341) |
| | 3'-GACCGGACCAAACUAUGACUGGACAUU-5' | (SEQ ID NO: 1450) |
| βc-2614 Target: | 5'-CTGGCCTGGTTTGATACTGACCTGTAA-3' | (SEQ ID NO: 2559) |
| | 5'-GCCUGGUUUGAUACUGACCUGUAaa-3' | (SEQ ID NO: 342) |
| | 3'-ACCGGACCAAACUAUGACUGGACAUUU-5' | (SEQ ID NO: 1451) |
| βc-2615 Target: | 5'-TGGCCTGGTTTGATACTGACCTGTAAA-3' | (SEQ ID NO: 2560) |

TABLE 3-continued

Selected Anti-β-catenin DsiRNAs, Duplexes Targeting Both Human and Mouse Sequences

| | | |
|---|---|---|
| | 5'-CCUGGUUUGAUACUGACCUGUAAat-3' | (SEQ ID NO: 343) |
| | 3'-CCGGACCAAACUAUGACUGGACAUUUA-5' | (SEQ ID NO: 1452) |
| βc-2616 Target: | 5'-GGCCTGGTTTGATACTGACCTGTAAAT-3' | (SEQ ID NO: 2561) |
| | 5'-CUGGUUUGAUACUGACCUGUAAAtc-3' | (SEQ ID NO: 344) |
| | 3'-CGGACCAAACUAUGACUGGACAUUUAG-5' | (SEQ ID NO: 1453) |
| βc-2617 Target: | 5'-GCCTGGTTTGATACTGACCTGTAAATC-3' | (SEQ ID NO: 2562) |
| | 5'-UGGUUUGAUACUGACCUGUAAAUCa-3' | (SEQ ID NO: 345) |
| | 3'-GGACCAAACUAUGACUGGACAUUUAGU-5' | (SEQ ID NO: 1454) |
| βc-2618 Target: | 5'-CCTGGTTTGATACTGACCTGTAAATCA-3' | (SEQ ID NO: 2563) |
| | 5'-GGUUUGAUACUGACCUGUAAAUCat-3' | (SEQ ID NO: 346) |
| | 3'-GACCAAACUAUGACUGGACAUUUAGUA-5' | (SEQ ID NO: 1455) |
| βc-2619 Target: | 5'-CTGGTTTGATACTGACCTGTAAATC-3' | (SEQ ID NO: 2564) |
| | 5'-GUUUGAUACUGACCUGUAAAUCAtc-3' | (SEQ ID NO: 347) |
| | 3'-ACCAAACUAUGACUGGACAUUUAGUAG-5' | (SEQ ID NO: 1456) |
| βc-2620 Target: | 5'-TGGTTTGATACTGACCTGTAAATCATC-3' | (SEQ ID NO: 2565) |
| | 5'-UUUGAUACUGACCUGUAAAUCAUcc-3' | (SEQ ID NO: 348) |
| | 3'-CCAAACUAUGACUGGACAUUUAGUAGG-5' | (SEQ ID NO: 1457) |
| βc-2621 Target: | 5'-GGTTTGATACTGACCTGTAAATCATCC-3' | (SEQ ID NO: 2566) |
| | 5'-UUGAUACUGACCUGUAAAUCAUCct-3' | (SEQ ID NO: 349) |
| | 3'-CAAACUAUGACUGGACAUUUAGUAGGA-5' | (SEQ ID NO: 1458) |
| βc-2622 Target: | 5'-GTTTGATACTGACCTGTAAATCATCCT-3' | (SEQ ID NO: 2567) |
| | 5'-UGAUACUGACCUGUAAAUCAUCCtt-3' | (SEQ ID NO: 350) |
| | 3'-AAACUAUGACUGGACAUUUAGUAGGAA-5' | (SEQ ID NO: 1459) |
| βc-2623 Target: | 5'-TTTGATACTGACCTGTAAATCATCCTT-3' | (SEQ ID NO: 2568) |
| | 5'-UUUUGCCACAGCUUUUGCAACUUaa-3' | (SEQ ID NO: 351) |
| | 3'-AAAAACGGUGUCGAAAACGUUGAAUU-5' | (SEQ ID NO: 1460) |
| βc-2869 Target: | 5'-TTTTTTGCCACAGCTTTTGCAACTTAA-3' | (SEQ ID NO: 2569) |
| | 5'-UGAGUAACAUUUGCUGUUUUAAAca-3' | (SEQ ID NO: 352) |
| | 3'-UUACUCAUUGUAAACGACAAAAUUUGU-5' | (SEQ ID NO: 1461) |
| βc-2902 Target: | 5'-AATGAGTAACATTTGCTGTTTTAAACA-3' | (SEQ ID NO: 2570) |
| | 5'-AACAUUAAUAGCAGCCUUUCUCUct-3' | (SEQ ID NO: 353) |
| | 3'-AUUUGUAAUUAUCGUCGGAAAGAGAGA-5' | (SEQ ID NO: 1462) |
| βc-2923 Target: | 5'-TAAACATTAATAGCAGCCTTTCTCTCT-3' | (SEQ ID NO: 2571) |
| | 5'-CAUUAAUAGCAGCCUUUCUCUCUtt-3' | (SEQ ID NO: 354) |
| | 3'-UUGUAAUUAUCGUCGGAAAGAGAGAAA-5' | (SEQ ID NO: 1463) |
| βc-2925 Target: | 5'-AACATTAATAGCAGCCTTTCTCTCTTT-3' | (SEQ ID NO: 2572) |
| | 5'-UUAAUAGCAGCCUUUCUCUCUUUat-3' | (SEQ ID NO: 355) |
| | 3'-GUAAUUAUCGUCGGAAAGAGAGAAAUA-5' | (SEQ ID NO: 1464) |
| βc-2927 Target: | 5'-CATTAATAGCAGCCTTTCTCTCTTTAT-3' | (SEQ ID NO: 2573) |
| | 5'-AAUAGCAGCCUUUCUCUCUUUAUac-3' | (SEQ ID NO: 356) |
| | 3'-AAUUAUCGUCGGAAAGAGAGAAAUAUG-5' | (SEQ ID NO: 1465) |
| βc-2929 Target: | 5'-TTAATAGCAGCCTTTCTCTCTTTATAC-3' | (SEQ ID NO: 2574) |
| | 5'-GCAUUGUGAUUGGCCUGUAGAGUtg-3' | (SEQ ID NO: 357) |
| | 3'-AACGUAACACUAACCGGACAUCUCAAC-5' | (SEQ ID NO: 1466) |
| βc-2973 Target: | 5'-TTGCATTGTGATTGGCCTGTAGAGTTG-3' | (SEQ ID NO: 2575) |
| | 5'-AUUGUGAUUGGCCUGUAGAGUUGct-3' | (SEQ ID NO: 358) |
| | 3'-CGUAACACUAACCGGACAUCUCAACGA-5' | (SEQ ID NO: 1467) |
| βc-2975 Target: | 5'-GCATTGTGATTGGCCTGTAGAGTTGCT-3' | (SEQ ID NO: 2576) |
| | 5'-UGUGAUUGGCCUGUAGAGUUGCUga-3' | (SEQ ID NO: 359) |
| | 3'-UAACACUAACCGGACAUCUCAACGACU-5' | (SEQ ID NO: 1468) |
| βc-2977 Target: | 5'-ATTGTGATTGGCCTGTAGAGTTGCTGA-3' | (SEQ ID NO: 2577) |
| | 5'-UGAUUGGCCUGUAGAGUUGCUGAga-3' | (SEQ ID NO: 360) |
| | 3'-ACACUAACCGGACAUCUCAACGACUCU-5' | (SEQ ID NO: 1469) |
| βc-2979 Target: | 5'-TGTGATTGGCCTGTAGAGTTGCTGAGA-3' | (SEQ ID NO: 2578) |
| | 5'-AUUGGCCUGUAGAGUUGCUGAGAgg-3' | (SEQ ID NO: 361) |
| | 3'-ACUAACCGGACAUCUCAACGACUCUCC-5' | (SEQ ID NO: 1470) |
| βc-2981 Target: | 5'-TGATTGGCCTGTAGAGTTGCTGAGAGG-3' | (SEQ ID NO: 2579) |

TABLE 3-continued

Selected Anti-β-catenin DsiRNAs, Duplexes Targeting Both Human and Mouse Sequences

| | | |
|---|---|---|
| βc-2983 | 5'-UGGCCUGUAGAGUUGCUGAGAGGGc-3'<br>3'-UAACCGGACAUCUCAACGACUCUCCCG-5'<br>Target: 5'-ATTGGCCTGTAGAGTTGCTGAGAGGGC-3' | (SEQ ID NO: 362)<br>(SEQ ID NO: 1471)<br>(SEQ ID NO: 2580) |
| βc-2985 | 5'-GCCUGUAGAGUUGCUGAGAGGGCtc-3'<br>3'-ACCGGACAUCUCAACGACUCUCCCGAG-5'<br>Target: 5'-TGGCCTGTAGAGTTGCTGAGAGGGCTC-3' | (SEQ ID NO: 363)<br>(SEQ ID NO: 1472)<br>(SEQ ID NO: 2581) |
| βc-2987 | 5'-CUGUAGAGUUGCUGAGAGGGCUCga-3'<br>3'-CGGACAUCUCAACGACUCUCCCGAGCU-5'<br>Target: 5'-GCCTGTAGAGTTGCTGAGAGGGCTCGA-3' | (SEQ ID NO: 364)<br>(SEQ ID NO: 1473)<br>(SEQ ID NO: 2582) |
| βc-2989 | 5'-GUAGAGUUGCUGAGAGGGCUCGagg-3'<br>3'-GACAUCUCAACGACUCUCCCGAGCUCC-5'<br>Target: 5'-CTGTAGAGTTGCTGAGAGGGCTCGAGG-3' | (SEQ ID NO: 365)<br>(SEQ ID NO: 1474)<br>(SEQ ID NO: 2583) |
| βc-3015 | 5'-GUGGGCUGGUAUCUCAGAAAGUGcc-3'<br>3'-CCCACCCGACCAUAGAGUCUUUCACGG-5'<br>Target: 5'-GGGTGGGCTGGTATCTCAGAAAGTGCC-3' | (SEQ ID NO: 366)<br>(SEQ ID NO: 1475)<br>(SEQ ID NO: 2584) |
| βc-3017 | 5'-GGGCUGGUAUCUCAGAAAGUGCCtg-3'<br>3'-CACCCGACCAUAGAGUCUUUCACGGAC-5'<br>Target: 5'-GTGGGCTGGTATCTCAGAAAGTGCCTG-3' | (SEQ ID NO: 367)<br>(SEQ ID NO: 1476)<br>(SEQ ID NO: 2585) |
| βc-3019 | 5'-GCUGGUAUCUCAGAAAGUGCCUGac-3'<br>3'-CCCGACCAUAGAGUCUUUCACGGACUG-5'<br>Target: 5'-GGGCTGGTATCTCAGAAAGTGCCTGAC-3' | (SEQ ID NO: 368)<br>(SEQ ID NO: 1477)<br>(SEQ ID NO: 2586) |
| βc-3021 | 5'-UGGUAUCUCAGAAAGUGCCUGACac-3'<br>3'-CGACCAUAGAGUCUUUCACGGACUGUG-5'<br>Target: 5'-GCTGGTATCTCAGAAAGTGCCTGACAC-3' | (SEQ ID NO: 369)<br>(SEQ ID NO: 1478)<br>(SEQ ID NO: 2587) |
| βc-3046 | 5'-ACUAACCAAGCUGAGUUUCCUAUgg-3'<br>3'-UGUGAUUGGUUCGACUCAAAGGAUACC-5'<br>Target: 5'-ACACTAACCAAGCTGAGTTTCCTATGG-3' | (SEQ ID NO: 370)<br>(SEQ ID NO: 1479)<br>(SEQ ID NO: 2588) |
| βc-3048 | 5'-UAACCAAGCUGAGUUUCCUAUGGga-3'<br>3'-UGAUUGGUUCGACUCAAAGGAUACCCU-5'<br>Target: 5'-ACTAACCAAGCTGAGTTTCCTATGGGA-3' | (SEQ ID NO: 371)<br>(SEQ ID NO: 1480)<br>(SEQ ID NO: 2589) |
| βc-3050 | 5'-ACCAAGCUGAGUUUCCUAUGGGAac-3'<br>3'-AUUGGUUCGACUCAAAGGAUACCCUUG-5'<br>Target: 5'-TAACCAAGCTGAGTTTCCTATGGGAAC-3' | (SEQ ID NO: 372)<br>(SEQ ID NO: 1481)<br>(SEQ ID NO: 2590) |
| βc-3052 | 5'-CAAGCUGAGUUUCCUAUGGGAACaa-3'<br>3'-UGGUUCGACUCAAAGGAUACCCUUGUU-5'<br>Target: 5'-ACCAAGCTGAGTTTCCTATGGGAACAA-3' | (SEQ ID NO: 373)<br>(SEQ ID NO: 1482)<br>(SEQ ID NO: 2591) |
| βc-3054 | 5'-AGCUGAGUUUCCUAUGGGAACAAtt-3'<br>3'-GUUCGACUCAAAGGAUACCCUUGUUAA-5'<br>Target: 5'-CAAGCTGAGTTTCCTATGGGAACAATT-3' | (SEQ ID NO: 374)<br>(SEQ ID NO: 1483)<br>(SEQ ID NO: 2592) |
| βc-3056 | 5'-CUGAGUUUCCUAUGGGAACAAUUga-3'<br>3'-UCGACUCAAAGGAUACCCUUGUUAACU-5'<br>Target: 5'-AGCTGAGTTTCCTATGGGAACAATTGA-3' | (SEQ ID NO: 375)<br>(SEQ ID NO: 1484)<br>(SEQ ID NO: 2593) |
| βc-3087 | 5'-CUUUUUGUUCUGGUCCUUUUUGGtc-3'<br>3'-UUGAAAAACAAGACCAGGAAAAACCAG-5'<br>Target: 5'-AACTTTTGTTCTGGTCCTTTTTGGTC-3' | (SEQ ID NO: 376)<br>(SEQ ID NO: 1485)<br>(SEQ ID NO: 2594) |
| βc-3089 | 5'-UUUUGUUCUGGUCCUUUUUGGUCga-3'<br>3'-GAAAAACAAGACCAGGAAAAACCAGCU-5'<br>Target: 5'-CTTTTGTTCTGGTCCTTTTTGGTCGA-3' | (SEQ ID NO: 377)<br>(SEQ ID NO: 1486)<br>(SEQ ID NO: 2595) |
| βc-3091 | 5'-UUGUUCUGGUCCUUUUUGGUCGAgg-3'<br>3'-AAAACAAGACCAGGAAAAACCAGCUCC-5'<br>Target: 5'-TTTTGTTCTGGTCCTTTTTGGTCGAGG-3' | (SEQ ID NO: 378)<br>(SEQ ID NO: 1487)<br>(SEQ ID NO: 2596) |
| βc-3093 | 5'-GUUCUGGUCCUUUUUGGUCGAGGag-3'<br>3'-AACAAGACCAGGAAAAACCAGCUCCUC-5'<br>Target: 5'-TTGTTCTGGTCCTTTTTGGTCGAGGAG-3' | (SEQ ID NO: 379)<br>(SEQ ID NO: 1488)<br>(SEQ ID NO: 2597) |
| βc-3095 | 5'-UCUGGUCCUUUUUGGUCGAGGAGta-3'<br>3'-CAAGACCAGGAAAAACCAGCUCCUCAU-5'<br>Target: 5'-GTTCTGGTCCTTTTTGGTCGAGGAGTA-3' | (SEQ ID NO: 380)<br>(SEQ ID NO: 1489)<br>(SEQ ID NO: 2598) |

TABLE 3-continued

Selected Anti-β-catenin DsiRNAs, Duplexes Targeting Both Human and Mouse Sequences

| | | |
|---|---|---|
| | 5'-UGGUCCUUUUUGGUCGAGGAGUAac-3' | (SEQ ID NO: 381) |
| | 3'-AGACCAGGAAAAACCAGCUCCUCAUUG-5' | (SEQ ID NO: 1490) |
| βc-3097 Target: | 5'-TCTGGTCCTTTTTGGTCGAGGAGTAAC-3' | (SEQ ID NO: 2599) |
| | 5'-GUCCUUUUUGGUCGAGGAGUAACaa-3' | (SEQ ID NO: 382) |
| | 3'-ACCAGGAAAAACCAGCUCCUCAUUGUU-5' | (SEQ ID NO: 1491) |
| βc-3099 Target: | 5'-TGGTCCTTTTTGGTCGAGGAGTAACAA-3' | (SEQ ID NO: 2600) |
| | 5'-CCUUUUUGGUCGAGGAGUAACAAta-3' | (SEQ ID NO: 383) |
| | 3'-CAGGAAAAACCAGCUCCUCAUUGUUAU-5' | (SEQ ID NO: 1492) |
| βc-3101 Target: | 5'-GTCCTTTTTGGTCGAGGAGTAACAATA-3' | (SEQ ID NO: 2601) |
| | 5'-UUUUUGGUCGAGGAGUAACAAUACa-3' | (SEQ ID NO: 384) |
| | 3'-GGAAAAACCAGCUCCUCAUUGUUAUGU-5' | (SEQ ID NO: 1493) |
| βc-3103 Target: | 5'-CCTTTTTGGTCGAGGAGTAACAATACA-3' | (SEQ ID NO: 2602) |
| | 5'-UUUGGUCGAGGAGUAACAAUACAaa-3' | (SEQ ID NO: 385) |
| | 3'-AAAACCAGCUCCUCAUUGUUAUGUUU-5' | (SEQ ID NO: 1494) |
| βc-3105 Target: | 5'-TTTTTGGTCGAGGAGTAACAATACAAA-3' | (SEQ ID NO: 2603) |
| | 5'-UGGUCGAGGAGUAACAAUACAAAtg-3' | (SEQ ID NO: 386) |
| | 3'-AAACCAGCUCCUCAUUGUUAUGUUUAC-5' | (SEQ ID NO: 1495) |
| βc-3107 Target: | 5'-TTTGGTCGAGGAGTAACAATACAAATG-3' | (SEQ ID NO: 2604) |
| | 5'-GUCGAGGAGUAACAAUACAAAUGga-3' | (SEQ ID NO: 387) |
| | 3'-ACCAGCUCCUCAUUGUUAUGUUUACCU-5' | (SEQ ID NO: 1496) |
| βc-3109 Target: | 5'-TGGTCGAGGAGTAACAATACAAATGGA-3' | (SEQ ID NO: 2605) |
| | 5'-CGAGGAGUAACAAUACAAAUGGAtt-3' | (SEQ ID NO: 388) |
| | 3'-CAGCUCCUCAUUGUUAUGUUUACCUAA-5' | (SEQ ID NO: 1497) |
| βc-3111 Target: | 5'-GTCGAGGAGTAACAATACAAATGGATT-3' | (SEQ ID NO: 2606) |
| | 5'-AGGAGUAACAAUACAAAUGGAUUtt-3' | (SEQ ID NO: 389) |
| | 3'-GCUCCUCAUUGUUAUGUUUACCUAAAA-5' | (SEQ ID NO: 1498) |
| βc-3113 Target: | 5'-CGAGGAGTAACAATACAAATGGATTTT-3' | (SEQ ID NO: 2607) |
| | 5'-GAGUAACAAUACAAAUGGAUUUUgg-3' | (SEQ ID NO: 390) |
| | 3'-UCCUCAUUGUUAUGUUUACCUAAAACC-5' | (SEQ ID NO: 1499) |
| βc-3115 Target: | 5'-AGGAGTAACAATACAAATGGATTTTGG-3' | (SEQ ID NO: 2608) |
| | 5'-UAUCAAACCCUAGCCUUGCUUGUta-3' | (SEQ ID NO: 391) |
| | 3'-AAAUAGUUUGGGAUCGGAACGAACAAU-5' | (SEQ ID NO: 1500) |
| βc-3191 Target: | 5'-TTTATCAAACCCTAGCCTTGCTTGTTA-3' | (SEQ ID NO: 2609) |
| | 5'-UCAAACCCUAGCCUUGCUUGUUAaa-3' | (SEQ ID NO: 392) |
| | 3'-AUAGUUUGGGAUCGGAACGAACAAUUU-5' | (SEQ ID NO: 1501) |
| βc-3193 Target: | 5'-TATCAAACCCTAGCCTTGCTTGTTAAA-3' | (SEQ ID NO: 2610) |
| | 5'-AAACCCUAGCCUUGCUUGUUAAAtt-3' | (SEQ ID NO: 393) |
| | 3'-AGUUUGGGAUCGGAACGAACAAUUUAA-5' | (SEQ ID NO: 1502) |
| βc-3195 Target: | 5'-TCAAACCCTAGCCTTGCTTGTTAAATT-3' | (SEQ ID NO: 2611) |
| | 5'-GAGUAAUGGUGUAGAACACUAAUtc-3' | (SEQ ID NO: 394) |
| | 3'-AACUCAUUACCACAUCUUGUGAUUAAG-5' | (SEQ ID NO: 1503) |
| βc-3387 Target: | 5'-TTGAGTAATGGTGTAGAACACTAATTC-3' | (SEQ ID NO: 2612) |
| | 5'-GUAAUGGUGUAGAACACUAAUUCat-3' | (SEQ ID NO: 395) |
| | 3'-CUCAUUACCACAUCUUGUGAUUAAGUA-5' | (SEQ ID NO: 1504) |
| βc-3389 Target: | 5'-GAGTAATGGTGTAGAACACTAATTC-3' | (SEQ ID NO: 2613) |
| | 5'-AAUGGUGUAGAACACUAAUUCAUaa-3' | (SEQ ID NO: 396) |
| | 3'-CAUUACCACAUCUUGUGAUUAAGUAUU-5' | (SEQ ID NO: 1505) |
| βc-3391 Target: | 5'-GTAATGGTGTAGAACACTAATTCATAA-3' | (SEQ ID NO: 2614) |
| | 5'-UGGUGUAGAACACUAAUUCAUAAtc-3' | (SEQ ID NO: 397) |
| | 3'-UUACCACAUCUUGUGAUUAAGUAUUAG-5' | (SEQ ID NO: 1506) |
| βc-3393 Target: | 5'-AATGGTGTAGAACACTAATTCATAATC-3' | (SEQ ID NO: 2615) |
| | 5'-GUGUAGAACACUAAUUCAUAAUCac-3' | (SEQ ID NO: 398) |
| | 3'-ACCACAUCUUGUGAUUAAGUAUUAGUG-5' | (SEQ ID NO: 1507) |
| βc-3395 Target: | 5'-TGGTGTAGAACACTAATTCATAATCAC-3' | (SEQ ID NO: 2616) |
| | 5'-GUAGAACACUAAUUCAUAAUCACtc-3' | (SEQ ID NO: 399) |
| | 3'-CACAUCUUGUGAUUAAGUAUUAGUGAG-5' | (SEQ ID NO: 1508) |
| βc-3397 Target: | 5'-GTGTAGAACACTAATTCATAATCACTC-3' | (SEQ ID NO: 2617) |

TABLE 3-continued

Selected Anti-β-catenin DsiRNAs, Duplexes Targeting Both Human and Mouse Sequences

|  |  |  |
|---|---|---|
|  | 5'-AGAACACUAAUUCAUAAUCACUCUa-3' | (SEQ ID NO: 400) |
|  | 3'-CAUCUUGUGAUUAAGUAUUAGUGAGAU-5' | (SEQ ID NO: 1509) |
| βc-3399 Target: | 5'-GTAGAACACTAATTCATAATCACTCTA-3' | (SEQ ID NO: 2618) |
|  | 5'-AACACUAAUUCAUAAUCACUCUAat-3' | (SEQ ID NO: 401) |
|  | 3'-UCUUGUGAUUAAGUAUUAGUGAGAUUA-5' | (SEQ ID NO: 1510) |
| βc-3401 Target: | 5'-AGAACACTAATTCATAATCACTCTAAT-3' | (SEQ ID NO: 2619) |
|  | 5'-UUAGUUUCCUUUUUAAUAUGCUUaa-3' | (SEQ ID NO: 402) |
|  | 3'-UUAAUCAAAGGAAAAAUUAUACGAAUU-5' | (SEQ ID NO: 1511) |
| βc-3500 Target: | 5'-AATTAGTTTCCTTTTTAATATGCTTAA-3' | (SEQ ID NO: 2620) |
|  | 5'-AGUUUCCUUUUUAAUAUGCUUAAaa-3' | (SEQ ID NO: 403) |
|  | 3'-AAUCAAAGGAAAAAUUAUACGAAUUUU-5' | (SEQ ID NO: 1512) |
| βc-3502 Target: | 5'-TTAGTTTCCTTTTTAATATGCTTAAAA-3' | (SEQ ID NO: 2621) |
|  | 5'-UUUCCUUUUUAAUAUGCUUAAAAUa-3' | (SEQ ID NO: 404) |
|  | 3'-UCAAAGGAAAAAUUAUACGAAUUUUAU-5' | (SEQ ID NO: 1513) |
| βc-3504 Target: | 5'-AGTTTCCTTTTTAATATGCTTAAAATA-3' | (SEQ ID NO: 2622) |
|  | 5'-UCCUUUUUAAUAUGCUUAAAAUAag-3' | (SEQ ID NO: 405) |
|  | 3'-AAAGGAAAAAUUAUACGAAUUUUAUUC-5' | (SEQ ID NO: 1514) |
| βc-3506 Target: | 5'-TTTCCTTTTTAATATGCTTAAAATAAG-3' | (SEQ ID NO: 2623) |
|  | 5'-CUUUUUAAUAUGCUUAAAAUAAGca-3' | (SEQ ID NO: 406) |
|  | 3'-AGGAAAAAUUAUACGAAUUUUAUUCGU-5' | (SEQ ID NO: 1515) |
| βc-3508 Target: | 5'-TCCTTTTTAATATGCTTAAAATAAGCA-3' | (SEQ ID NO: 2624) |
|  | 5'-UUUUUAAUAUGCUUAAAAUAAGCag-3' | (SEQ ID NO: 407) |
|  | 3'-GGAAAAAUUAUACGAAUUUUAUUCGUC-5' | (SEQ ID NO: 1516) |
| βc-3509 Target: | 5'-CCTTTTTAATATGCTTAAAATAAGCAG-3' | (SEQ ID NO: 2625) |
|  | 5'-UUUUAAUAUGCUUAAAAUAAGCAgg-3' | (SEQ ID NO: 408) |
|  | 3'-GAAAAAUUAUACGAAUUUUAUUCGUCC-5' | (SEQ ID NO: 1517) |
| βc-3510 Target: | 5'-CTTTTTAATATGCTTAAAATAAGCAGG-3' | (SEQ ID NO: 2626) |
|  | 5'-UUAAUAUGCUUAAAAUAAGCAGGtg-3' | (SEQ ID NO: 409) |
|  | 3'-AAAAUUAUACGAAUUUUAUUCGUCCAC-5' | (SEQ ID NO: 1518) |
| βc-3512 Target: | 5'-TTTTAATATGCTTAAAATAAGCAGGTG-3' | (SEQ ID NO: 2627) |
|  | 5'-AAUAUGCUUAAAAUAAGCAGGUGga-3' | (SEQ ID NO: 410) |
|  | 3'-AAUUAUACGAAUUUUAUUCGUCCACCU-5' | (SEQ ID NO: 1519) |
| βc-3514 Target: | 5'-TTAATATGCTTAAAATAAGCAGGTGGA-3' | (SEQ ID NO: 2628) |
|  | 5'-UAUGCUUAAAAUAAGCAGGUGGAtc-3' | (SEQ ID NO: 411) |
|  | 3'-UUAUACGAAUUUUAUUCGUCCACCUAG-5' | (SEQ ID NO: 1520) |
| βc-3516 Target: | 5'-AATATGCTTAAAATAAGCAGGTGGATC-3' | (SEQ ID NO: 2629) |
|  | 5'-UGCUUAAAAUAAGCAGGUGGAUCta-3' | (SEQ ID NO: 412) |
|  | 3'-AUACGAAUUUUAUUCGUCCACCUAGAU-5' | (SEQ ID NO: 1521) |
| βc-3518 Target: | 5'-TATGCTTAAAATAAGCAGGTGGATCTA-3' | (SEQ ID NO: 2630) |
|  | 5'-CUUAAAAUAAGCAGGUGGAUCUAtt-3' | (SEQ ID NO: 413) |
|  | 3'-ACGAAUUUUAUUCGUCCACCUAGAUAA-5' | (SEQ ID NO: 1522) |
| βc-3520 Target: | 5'-TGCTTAAAATAAGCAGGTGGATCTATT-3' | (SEQ ID NO: 2631) |
|  | 5'-UAAAAUAAGCAGGUGGAUCUAUUtc-3' | (SEQ ID NO: 414) |
|  | 3'-GAAUUUUAUUCGUCCACCUAGAUAAAG-5' | (SEQ ID NO: 1523) |
| βc-3522 Target: | 5'-CTTAAAATAAGCAGGTGGATCTATTTC-3' | (SEQ ID NO: 2632) |
|  | 5'-AAAUAAGCAGGUGGAUCUAUUUCat-3' | (SEQ ID NO: 415) |
|  | 3'-AUUUUAUUCGUCCACCUAGAUAAAGUA-5' | (SEQ ID NO: 1524) |
| βc-3524 Target: | 5'-TAAAATAAGCAGGTGGATCTATTTC-3' | (SEQ ID NO: 2633) |
|  | 5'-AUAAGCAGGUGGAUCUAUUUCAUgt-3' | (SEQ ID NO: 416) |
|  | 3'-UUUAUUCGUCCACCUAGAUAAAGUACA-5' | (SEQ ID NO: 1525) |
| βc-3526 Target: | 5'-AAATAAGCAGGTGGATCTATTTCATGT-3' | (SEQ ID NO: 2634) |
|  | 5'-AAGCAGGUGGAUCUAUUUCAUGUtt-3' | (SEQ ID NO: 417) |
|  | 3'-UAUUCGUCCACCUAGAUAAAGUACAAA-5' | (SEQ ID NO: 1526) |
| βc-3528 Target: | 5'-ATAAGCAGGTGGATCTATTTCATGTTT-3' | (SEQ ID NO: 2635) |
|  | 5'-GCAGGUGGAUCUAUUUCAUGUUUtt-3' | (SEQ ID NO: 418) |
|  | 3'-UUCGUCCACCUAGAUAAAGUACAAAAA-5' | (SEQ ID NO: 1527) |
| βc-3530 Target: | 5'-AAGCAGGTGGATCTATTTCATGTTTTT-3' | (SEQ ID NO: 2636) |

TABLE 3-continued

Selected Anti-β-catenin DsiRNAs, Duplexes Targeting Both Human and Mouse Sequences

| | | |
|---|---|---|
| βc-3532 Target: | 5'-AGGUGGAUCUAUUUCAUGUUUUUga-3'<br>3'-CGUCCACCUAGAUAAAGUACAAAAACU-5'<br>5'-GCAGGTGGATCTATTTCATGTTTTTGA-3' | (SEQ ID NO: 419)<br>(SEQ ID NO: 1528)<br>(SEQ ID NO: 2637) |
| βc-3534 Target: | 5'-GUGGAUCUAUUUCAUGUUUUUGAtc-3'<br>3'-UCCACCUAGAUAAAGUACAAAAACUAG-5'<br>5'-AGGTGGATCTATTTCATGTTTTTGATC-3' | (SEQ ID NO: 420)<br>(SEQ ID NO: 1529)<br>(SEQ ID NO: 2638) |
| βc-3536 Target: | 5'-GGAUCUAUUUCAUGUUUUUGAUCaa-3'<br>3'-CACCUAGAUAAAGUACAAAAACUAGUU-5'<br>5'-GTGGATCTATTTCATGTTTTTGATCAA-3' | (SEQ ID NO: 421)<br>(SEQ ID NO: 1530)<br>(SEQ ID NO: 2639) |
| βc-3538 Target: | 5'-AUCUAUUUCAUGUUUUUGAUCAAaa-3'<br>3'-CCUAGAUAAAGUACAAAAACUAGUUUU-5'<br>5'-GGATCTATTTCATGTTTTTGATCAAAA-3' | (SEQ ID NO: 422)<br>(SEQ ID NO: 1531)<br>(SEQ ID NO: 2640) |
| βc-3583 Target: | 5'-GUAGGGUAAAUCAGUAAGAGGUGUtt-3'<br>3'-CCCAUCCCAUUUAGUCAUUCUCCACAA-5'<br>5'-GGGTAGGGTAAATCAGTAAGAGGTGTT-3' | (SEQ ID NO: 423)<br>(SEQ ID NO: 1532)<br>(SEQ ID NO: 2641) |
| βc-3585 Target: | 5'-AGGGUAAAUCAGUAAGAGGUGUUat-3'<br>3'-CAUCCCAUUUAGUCAUUCUCCACAUA-5'<br>5'-GTAGGGTAAATCAGTAAGAGGTGTTAT-3' | (SEQ ID NO: 424)<br>(SEQ ID NO: 1533)<br>(SEQ ID NO: 2642) |
| βc-3587 Target: | 5'-GGUAAAUCAGUAAGAGGUGUUAUtt-3'<br>3'-UCCCAUUUAGUCAUUCUCCACAAUAAA-5'<br>5'-AGGGTAAATCAGTAAGAGGTGTTATTT-3' | (SEQ ID NO: 425)<br>(SEQ ID NO: 1534)<br>(SEQ ID NO: 2643) |
| βc-3589 Target: | 5'-UAAAUCAGUAAGAGGUGUUAUUUgg-3'<br>3'-CCAUUUAGUCAUUCUCCACAAUAAACC-5'<br>5'-GGTAAATCAGTAAGAGGTGTTATTTGG-3' | (SEQ ID NO: 426)<br>(SEQ ID NO: 1535)<br>(SEQ ID NO: 2644) |
| βc-3591 Target: | 5'-AAUCAGUAAGAGGUGUUAUUUGGaa-3'<br>3'-AUUUAGUCAUUCUCCACAAUAAACCUU-5'<br>5'-TAAATCAGTAAGAGGTGTTATTTGGAA-3' | (SEQ ID NO: 427)<br>(SEQ ID NO: 1536)<br>(SEQ ID NO: 2645) |
| βc-3593 Target: | 5'-UCAGUAAGAGGUGUUAUUUGGAAcc-3'<br>3'-UUAGUCAUUCUCCACAAUAAACCUUGG-5'<br>5'-AATCAGTAAGAGGTGTTATTTGGAACC-3' | (SEQ ID NO: 428)<br>(SEQ ID NO: 1537)<br>(SEQ ID NO: 2646) |
| βc-3633 Target: | 5'-UACCAGUUGCCUUUUAUCCCAAAgt-3'<br>3'-AAAUGGUCAACGGAAAAUAGGGUUUCA-5'<br>5'-TTTACCAGTTGCCTTTTATCCCAAAGT-3' | (SEQ ID NO: 429)<br>(SEQ ID NO: 1538)<br>(SEQ ID NO: 2647) |
| βc-3635 Target: | 5'-CCAGUUGCCUUUUAUCCCAAAGUtg-3'<br>3'-AUGGUCAACGGAAAAUAGGGUUUCAAC-5'<br>5'-TACCAGTTGCCTTTTATCCCAAAGTTG-3' | (SEQ ID NO: 430)<br>(SEQ ID NO: 1539)<br>(SEQ ID NO: 2648) |
| βc-3637 Target: | 5'-AGUUGCCUUUUAUCCCAAAGUUGtt-3'<br>3'-GGUCAACGGAAAAUAGGGUUUCAACAA-5'<br>5'-CCAGTTGCCTTTTATCCCAAAGTTGTT-3' | (SEQ ID NO: 431)<br>(SEQ ID NO: 1540)<br>(SEQ ID NO: 2649) |
| βc-3639 Target: | 5'-UUGCCUUUUAUCCCAAAGUUGUUgt-3'<br>3'-UCAACGGAAAAUAGGGUUUCAACAACA-5'<br>5'-AGTTGCCTTTTATCCCAAAGTTGTTGT-3' | (SEQ ID NO: 432)<br>(SEQ ID NO: 1541)<br>(SEQ ID NO: 2650) |
| βc-3641 Target: | 5'-GCCUUUUAUCCCAAAGUUGUUGUaa-3'<br>3'-AACGGAAAAUAGGGUUUCAACAACAUU-5'<br>5'-TTGCCTTTTATCCCAAAGTTGTTGTAA-3' | (SEQ ID NO: 433)<br>(SEQ ID NO: 1542)<br>(SEQ ID NO: 2651) |
| βc-3643 Target: | 5'-CUUUUAUCCCAAAGUUGUUGUAAcc-3'<br>3'-CGGAAAAUAGGGUUUCAACAACAUUGG-5'<br>5'-GCCTTTTATCCCAAAGTTGTTGTAACC-3' | (SEQ ID NO: 434)<br>(SEQ ID NO: 1543)<br>(SEQ ID NO: 2652) |
| βc-3645 Target: | 5'-UUUAUCCCAAAGUUGUUGUAACCtg-3'<br>3'-GAAAAUAGGGUUUCAACAACAUUGGAC-5'<br>5'-CTTTTATCCCAAAGTTGTTGTAACCTG-3' | (SEQ ID NO: 435)<br>(SEQ ID NO: 1544)<br>(SEQ ID NO: 2653) |
| βc-3647 Target: | 5'-UAUCCCAAAGUUGUUGUAACCUGct-3'<br>3'-AAAUAGGGUUUCAACAACAUUGGACGA-5'<br>5'-TTTATCCCAAAGTTGTTGTAACCTGCT-3' | (SEQ ID NO: 436)<br>(SEQ ID NO: 1545)<br>(SEQ ID NO: 2654) |
| βc-3649 Target: | 5'-UCCCAAAGUUGUUGUAACCUGCUgt-3'<br>3'-AUAGGGUUUCAACAACAUUGGACGACA-5'<br>5'-TATCCCAAAGTTGTTGTAACCTGCTGT-3' | (SEQ ID NO: 437)<br>(SEQ ID NO: 1546)<br>(SEQ ID NO: 2655) |

TABLE 3-continued

Selected Anti-β-catenin DsiRNAs, Duplexes Targeting Both Human and Mouse Sequences

| | | |
|---|---|---|
| | 5'-CCAAAGUUGUUGUAACCUGCUGUGa-3' | (SEQ ID NO: 438) |
| | 3'-AGGGUUUCAACAACAUUGGACGACACU-5' | (SEQ ID NO: 1547) |
| βc-3651 Target: | 5'-TCCCAAAGTTGTTGTAACCTGCTGTGA-3' | (SEQ ID NO: 2656) |
| | 5'-AAAGUUGUUGUAACCUGCUGUGAta-3' | (SEQ ID NO: 439) |
| | 3'-GGUUUCAACAACAUUGGACGACACUAU-5' | (SEQ ID NO: 1548) |
| βc-3653 Target: | 5'-CCAAAGTTGTTGTAACCTGCTGTGATA-3' | (SEQ ID NO: 2657) |
| | 5'-AGUUGUUGUAACCUGCUGUGAUAcg-3' | (SEQ ID NO: 440) |
| | 3'-UUUCAACAACAUUGGACGACACUAUGC-5' | (SEQ ID NO: 1549) |
| βc-3655 Target: | 5'-AAAGTTGTTGTAACCTGCTGTGATACG-3' | (SEQ ID NO: 2658) |
| | 5'-UUGUUGUAACCUGCUGUGAUACGat-3' | (SEQ ID NO: 441) |
| | 3'-UCAACAACAUUGGACGACACUAUGCUA-5' | (SEQ ID NO: 1550) |
| βc-3657 Target: | 5'-AGTTGTTGTAACCTGCTGTGATACGAT-3' | (SEQ ID NO: 2659) |
| | 5'-GUUGUAACCUGCUGUGAUACGAUgc-3' | (SEQ ID NO: 442) |
| | 3'-AACAACAUUGGACGACACUAUGCUACG-5' | (SEQ ID NO: 1551) |
| βc-3659 Target: | 5'-TTGTTGTAACCTGCTGTGATACGATGC-3' | (SEQ ID NO: 2660) |
| | 5'-AAAUGGUUCAGAAUUAAACUUUUaa-3' | (SEQ ID NO: 443) |
| | 3'-UUUUUACCAAGUCUUAAUUUGAAAAUU-5' | (SEQ ID NO: 1552) |
| βc-3708 Target: | 5'-AAAAATGGTTCAGAATTAAACTTTTAA-3' | (SEQ ID NO: 2661) |
| | 5'-AUGGUUCAGAAUUAAACUUUUAAtt-3' | (SEQ ID NO: 444) |
| | 3'-UUUACCAAGUCUUAAUUUGAAAAUUAA-5' | (SEQ ID NO: 1553) |
| βc-3710 Target: | 5'-AAATGGTTCAGAATTAAACTTTTAATT-3' | (SEQ ID NO: 2662) |
| | 5'-GGUUCAGAAUUAAACUUUUAAUUca-3' | (SEQ ID NO: 445) |
| | 3'-UACCAAGUCUUAAUUUGAAAAUUAAGU-5' | (SEQ ID NO: 1554) |
| βc-3712 Target: | 5'-ATGGTTCAGAATTAAACTTTTAATTCA-3' | (SEQ ID NO: 2663) |
| | 5'-UUCAGAAUUAAACUUUUAAUUCAtt-3' | (SEQ ID NO: 446) |
| | 3'-CCAAGUCUUAAUUUGAAAAUUAAGUAA-5' | (SEQ ID NO: 1555) |
| βc-3714 Target: | 5'-GGTTCAGAATTAAACTTTTAATTCATT-3' | (SEQ ID NO: 2664) |
| | 5'-CAGAAUUAAACUUUUAAUUCAUUcg-3' | (SEQ ID NO: 447) |
| | 3'-AAGUCUUAAUUUGAAAAUUAAGUAAGC-5' | (SEQ ID NO: 1556) |
| βc-3716 Target: | 5'-TTCAGAATTAAACTTTTAATTCATTCG-3' | (SEQ ID NO: 2665) |

TABLE 4

Selected Anti-β-catenin DsiRNAs, *Mus musculus* Unique Duplexes

| | | |
|---|---|---|
| | 5'-GCAGCAGUCUUACUUGGAUUCUGga-3' | (SEQ ID NO: 448) |
| | 3'-GUCGUCGUCAGAAUGAACCUAAGACCU-5' | (SEQ ID NO: 1557) |
| βc-m314 Target: | 5'-CAGCAGCAGTCTTACTTGGATTCTGGA-3' | (SEQ ID NO: 2666) |
| | 5'-ACUUGGAUUCUGGAAUCCAUUCUgg-3' | (SEQ ID NO: 449) |
| | 3'-AAUGAACCUAAGACCUUAGGUAAGACC-5' | (SEQ ID NO: 1558) |
| βc-m325 Target: | 5'-TTACTTGGATTCTGGAATCCATTCTGG-3' | (SEQ ID NO: 2667) |
| | 5'-GACACCUCCCAAGUCCUUUAUGAat-3' | (SEQ ID NO: 450) |
| | 3'-AACUGUGGAGGGUUCAGGAAAUACUUA-5' | (SEQ ID NO: 1559) |
| βc-m408 Target: | 5'-TTGACACCTCCCAAGTCCTTTATGAAT-3' | (SEQ ID NO: 2668) |
| | 5'-CGCAAGAGCAAGUAGCUGAUAUUga-3' | (SEQ ID NO: 451) |
| | 3'-GUGCGUUCUCGUUCAUCGACUAUAACU-5' | (SEQ ID NO: 1560) |
| βc-m460 Target: | 5'-CACGCAAGAGCAAGTAGCTGATATTGA-3' | (SEQ ID NO: 2669) |
| | 5'-CCAUGUUCCCUGAGACGCUAGAUga-3' | (SEQ ID NO: 452) |
| | 3'-ACGGUACAAGGGACUCUGCGAUCUACU-5' | (SEQ ID NO: 1561) |
| βc-m526 Target: | 5'-TGCCATGTTCCCTGAGACGCTAGATGA-3' | (SEQ ID NO: 2670) |
| | 5'-UGAAACAUGCAGUUGUCAAUUUGat-3' | (SEQ ID NO: 453) |
| | 3'-CAACUUUGUACGUCAACAGUUAAACUA-5' | (SEQ ID NO: 1562) |
| βc-m631 Target: | 5'-GTTGAAACATGCAGTTGTCAATTTGAT-3' | (SEQ ID NO: 2671) |
| | 5'-CAUGCAGUUGUCAAUUUGAUUAAct-3' | (SEQ ID NO: 454) |
| | 3'-UUGUACGUCAACAGUUAAACUAAUUGA-5' | (SEQ ID NO: 1563) |
| βc-m636 Target: | 5'-AACATGCAGTTGTCAATTTGATTAACT-3' | (SEQ ID NO: 2672) |

TABLE 4-continued

Selected Anti-β-catenin DsiRNAs, *Mus musculus* Unique Duplexes

| | | |
|---|---|---|
| βc-m642 Target: | 5'-GUUGUCAAUUUGAUUAACUAUCAgg-3'<br>3'-GUCAACAGUUAAACUAAUUGAUAGUCC-5'<br>5'-CAGTTGTCAATTTGATTAACTATCAGG-3' | (SEQ ID NO: 455)<br>(SEQ ID NO: 1564)<br>(SEQ ID NO: 2673) |
| βc-m723 Target: | 5'-GAGGACCAGGUGGUAGUUAAUAAag-3'<br>3'-UACUCCUGGUCCACCAUCAAUUAUUUC-5'<br>5'-ATGAGGACCAGGTGGTAGTTAATAAAG-3' | (SEQ ID NO: 456)<br>(SEQ ID NO: 1565)<br>(SEQ ID NO: 2674) |
| βc-m970 Target: | 5'-GGUCACCAGUGGAUUCUGUACUGtt-3'<br>3'-ACCCAGUGGUCACCUAAGACAUGACAA-5'<br>5'-TGGGTCACCAGTGGATTCTGTACTGTT-3' | (SEQ ID NO: 457)<br>(SEQ ID NO: 1566)<br>(SEQ ID NO: 2675) |
| βc-m976 Target: | 5'-CAGUGGAUUCUGUACUGUUCUACgc-3'<br>3'-UGGUCACCUAAGACAUGACAAGAUGCG-5'<br>5'-ACCAGTGGATTCTGTACTGTTCTACGC-3' | (SEQ ID NO: 458)<br>(SEQ ID NO: 1567)<br>(SEQ ID NO: 2676) |
| βc-m981 Target: | 5'-GAUUCUGUACUGUUCUACGCCAUca-3'<br>3'-ACCUAAGACAUGACAAGAUGCGGUAGU-5'<br>5'-TGGATTCTGTACTGTTCTACGCCATCA-3' | (SEQ ID NO: 459)<br>(SEQ ID NO: 1568)<br>(SEQ ID NO: 2677) |
| βc-m1066 Target: | 5'-GUGGACUGCAGAAAAUGGUUGCUtt-3'<br>3'-ACCACCUGACGUCUUUUACCAACGAAA-5'<br>5'-TGGTGGACTGCAGAAAATGGTTGCTTT-3' | (SEQ ID NO: 460)<br>(SEQ ID NO: 1569)<br>(SEQ ID NO: 2678) |
| βc-m1106 Target: | 5'-CGUGAAAUUCUUGGCUAUUACAAca-3'<br>3'-UUGCACUUUAAGAACCGAUAAUGUUGU-5'<br>5'-AACGTGAAATTCTTGGCTATTACAACA-3' | (SEQ ID NO: 461)<br>(SEQ ID NO: 1570)<br>(SEQ ID NO: 2679) |
| βc-m1354 Target: | 5'-CAAGUCAGCGACUUGUUCAAAACtg-3'<br>3'-GGGUUCAGUCGCUGAACAAGUUUUGAC-5'<br>5'-CCCAAGTCAGCGACTTGTTCAAAACTG-3' | (SEQ ID NO: 462)<br>(SEQ ID NO: 1571)<br>(SEQ ID NO: 2680) |
| βc-m1363 Target: | 5'-GACUUGUUCAAAACUGUCUUUGGac-3'<br>3'-CGCUGAACAAGUUUUGACAGAAACCUG-5'<br>5'-GCGACTTGTTCAAAACTGTCTTTGGAC-3' | (SEQ ID NO: 463)<br>(SEQ ID NO: 1572)<br>(SEQ ID NO: 2681) |
| βc-m1373 Target: | 5'-AAACUGUCUUUGGACUCUCAGAAac-3'<br>3'-GUUUUGACAGAAACCUGAGAGUCUUUG-5'<br>5'-CAAAACTGTCTTTGGACTCTCAGAAAC-3' | (SEQ ID NO: 464)<br>(SEQ ID NO: 1573)<br>(SEQ ID NO: 2682) |
| βc-m1508 Target: | 5'-CUCUAACCUCACUUGCAAUAAUUac-3'<br>3'-GAGAGAUUGGAGUGAACGUUAUUAAUG-5'<br>5'-CTCTCTAACCTCACTTGCAATAATTAC-3' | (SEQ ID NO: 465)<br>(SEQ ID NO: 1574)<br>(SEQ ID NO: 2683) |
| βc-m1515 Target: | 5'-CUCACUUGCAAUAAUUACAAAAAca-3'<br>3'-UGGAGUGAACGUUAUUAAUGUUUUUGU-5'<br>5'-ACCTCACTTGCAATAATTACAAAAACA-3' | (SEQ ID NO: 466)<br>(SEQ ID NO: 1575)<br>(SEQ ID NO: 2684) |
| βc-m1682 Target: | 5'-GAAUGCCGUUCGCCUUCAUUAUGga-3'<br>3'-GUCUUACGGCAAGCGGAAGUAAUACCU-5'<br>5'-CAGAATGCCGTTCGCCTTCATTATGGA-3' | (SEQ ID NO: 467)<br>(SEQ ID NO: 1576)<br>(SEQ ID NO: 2685) |
| βc-m1693 Target: | 5'-GCCUUCAUUAUGGACUGCCUGUUgt-3'<br>3'-AGCGGAAGUAAUACCUGACGGACAACA-5'<br>5'-TCGCCTTCATTATGGACTGCCTGTTGT-3' | (SEQ ID NO: 468)<br>(SEQ ID NO: 1577)<br>(SEQ ID NO: 2686) |
| βc-m1698 Target: | 5'-CAUUAUGGACUGCCUGUUGUGGUta-3'<br>3'-AAGUAAUACCUGACGGACAACACCAAU-5'<br>5'-TTCATTATGGACTGCCTGTTGTGGTTA-3' | (SEQ ID NO: 469)<br>(SEQ ID NO: 1578)<br>(SEQ ID NO: 2687) |
| βc-m1705 Target: | 5'-GACUGCCUGUUGUGGUUAAACUCct-3'<br>3'-ACCUGACGGACAACACCAAUUUGAGGA-5'<br>5'-TGGACTGCCTGTTGTGGTTAAACTCCT-3' | (SEQ ID NO: 470)<br>(SEQ ID NO: 1579)<br>(SEQ ID NO: 2688) |
| βc-m1763 Target: | 5'-AACUGUUGGAUUGAUUCGAAACCtt-3'<br>3'-CGUUGACAACCUAACUAAGCUUUGGAA-5'<br>5'-GCAACTGTTGGATTGATTCGAAACCTT-3' | (SEQ ID NO: 471)<br>(SEQ ID NO: 1580)<br>(SEQ ID NO: 2689) |
| βc-m2008 Target: | 5'-GAGGACUCAAUACCAUUCCAUUGtt-3'<br>3'-GGCUCCUGAGUUAUGGUAAGGUAACAA-5'<br>5'-CCGAGGACTCAATACCATTCCATTGTT-3' | (SEQ ID NO: 472)<br>(SEQ ID NO: 1581)<br>(SEQ ID NO: 2690) |
| βc-m2226 Target: | 5'-GAGGACAAGCCACAGGAUUACAAga-3'<br>3'-GACUCCUGUUCGGUGUCCUAAUGUUCU-5'<br>5'-CTGAGGACAAGCCACAGGATTACAAGA-3' | (SEQ ID NO: 473)<br>(SEQ ID NO: 1582)<br>(SEQ ID NO: 2691) |

TABLE 4-continued

Selected Anti-β-catenin DsiRNAs, *Mus musculus* Unique Duplexes

|  |  |  |
|---|---|---|
| βc-m2427 | 5'-AUGGACCCUAUGAUGGAGCAUGAga-3'<br>3'-CCUACCUGGGAUACUACCUCGUACUCU-5'<br>Target: 5'-GGATGGACCCTATGATGGAGCATGAGA-3' | (SEQ ID NO: 474)<br>(SEQ ID NO: 1583)<br>(SEQ ID NO: 2692) |
| βc-m2568 | 5'-GAUACUGACCUGUAAAUCGUCCUtt-3'<br>3'-AACUAUGACUGGACAUUUAGCAGGAAA-5'<br>Target: 5'-TTGATACTGACCTGTAAATCGTCCTTT-3' | (SEQ ID NO: 475)<br>(SEQ ID NO: 1584)<br>(SEQ ID NO: 2693) |
| βc-m2614 | 5'-CCAGUGUGGGUGAAUACUUUACUct-3'<br>3'-UCGGUCACACCCACUUAUGAAAUGAGA-5'<br>Target: 5'-AGCCAGTGTGGGTGAATACTTTACTCT-3' | (SEQ ID NO: 476)<br>(SEQ ID NO: 1585)<br>(SEQ ID NO: 2694) |
| βc-m2770 | 5'-CCACAGCUUUUGCAGCGUUAUACUc-3'<br>3'-ACGGUGUCGAAAACGUCGCAAUAUGAG-5'<br>Target: 5'-TGCCACAGCTTTTGCAGCGTTATACTC-3' | (SEQ ID NO: 477)<br>(SEQ ID NO: 1586)<br>(SEQ ID NO: 2695) |
| βc-m2777 | 5'-UUUUGCAGCGUUAUACUCAGAUGag-3'<br>3'-CGAAAACGUCGCAAUAUGAGUCUACUC-5'<br>Target: 5'-GCTTTTGCAGCGTTATACTCAGATGAG-3' | (SEQ ID NO: 478)<br>(SEQ ID NO: 1587)<br>(SEQ ID NO: 2696) |
| βc-m2784 | 5'-GCGUUAUACUCAGAUGAGUAACAtt-3'<br>3'-GUCGCAAUAUGAGUCUACUCAUUGUAA-5'<br>Target: 5'-CAGCGTTATACTCAGATGAGTAACATT-3' | (SEQ ID NO: 479)<br>(SEQ ID NO: 1588)<br>(SEQ ID NO: 2697) |
| βc-m2806 | 5'-AUUUGCUGUUUUCAACAUUAAUAgc-3'<br>3'-UGUAAACGACAAAAGUUGUAAUUAUCG-5'<br>Target: 5'-ACATTTGCTGTTTTCAACATTAATAGC-3' | (SEQ ID NO: 480)<br>(SEQ ID NO: 1589)<br>(SEQ ID NO: 2698) |
| βc-m2850 | 5'-CUGUAGUGUCUGAACGUGCAUUGtg-3'<br>3'-UCGACAUCACAGACUUGCACGUAACAC-5'<br>Target: 5'-AGCTGTAGTGTCTGAACGTGCATTGTG-3' | (SEQ ID NO: 481)<br>(SEQ ID NO: 1590)<br>(SEQ ID NO: 2699) |
| βc-m2965 | 5'-GAACAGUCGAAGUACGCUUUUUGtt-3'<br>3'-CCCUUGUCAGCUUCAUGCGAAAAACAA-5'<br>Target: 5'-GGGAACAGTCGAAGTACGCTTTTTGTT-3' | (SEQ ID NO: 482)<br>(SEQ ID NO: 1591)<br>(SEQ ID NO: 2700) |
| βc-m2970 | 5'-GUCGAAGUACGCUUUUUGUUCUGgt-3'<br>3'-GUCAGCUUCAUGCGAAAAACAAGACCA-5'<br>Target: 5'-CAGTCGAAGTACGCTTTTTGTTCTGGT-3' | (SEQ ID NO: 483)<br>(SEQ ID NO: 1592)<br>(SEQ ID NO: 2701) |
| βc-m2976 | 5'-GUACGCUUUUUGUUCUGGUCCUtt-3'<br>3'-UUCAUGCGAAAAACAAGACCAGGAAAA-5'<br>Target: 5'-AAGTACGCTTTTTGTTCTGGTCCTTTT-3' | (SEQ ID NO: 484)<br>(SEQ ID NO: 1593)<br>(SEQ ID NO: 2702) |
| βc-m3092 | 5'-CCUAGCCUUGCUUGUUCUUUGUUtt-3'<br>3'-UGGGAUCGGAACGAACAAGAAACAAAA-5'<br>Target: 5'-ACCCTAGCCTTGCTTGTTCTTTGTTTT-3' | (SEQ ID NO: 485)<br>(SEQ ID NO: 1594)<br>(SEQ ID NO: 2703) |
| βc-m3097 | 5'-CCUUGCUUGUUCUUUGUUUUAAUat-3'<br>3'-UCGGAACGAACAAGAAACAAAAUUAUA-5'<br>Target: 5'-AGCCTTGCTTGTTCTTTGTTTTAATAT-3' | (SEQ ID NO: 486)<br>(SEQ ID NO: 1595)<br>(SEQ ID NO: 2704) |
| βc-m3198 | 5'-AACCUGCUACAGCAAUUUCUGAUtt-3'<br>3'-ACUUGGACGAUGUCGUUAAAGACUAAA-5'<br>Target: 5'-TGAACCTGCTACAGCAATTTCTGATTT-3' | (SEQ ID NO: 487)<br>(SEQ ID NO: 1596)<br>(SEQ ID NO: 2705) |
| βc-m3207 | 5'-CAGCAAUUUCUGAUUUCUAAGAcc-3'<br>3'-AUGUCGUUAAAGACUAAAGAUUCUUGG-5'<br>Target: 5'-TACAGCAATTTCTGATTTCTAAGAACC-3' | (SEQ ID NO: 488)<br>(SEQ ID NO: 1597)<br>(SEQ ID NO: 2706) |
| βc-m3433 | 5'-GUAAGAGGUGUUAUUUGAGCCUUgt-3'<br>3'-GUCAUUCUCCACAAUAAACUCGGAACA-5'<br>Target: 5'-CAGTAAGAGGTGTTATTTGAGCCTTGT-3' | (SEQ ID NO: 489)<br>(SEQ ID NO: 1598)<br>(SEQ ID NO: 2707) |
| βc-m3439 | 5'-GGUGUUAUUUGAGCCUUGUUUUGga-3'<br>3'-CUCCACAAUAAACUCGGAACAAAACCU-5'<br>Target: 5'-GAGGTGTTATTTGAGCCTTGTTTTGGA-3' | (SEQ ID NO: 490)<br>(SEQ ID NO: 1599)<br>(SEQ ID NO: 2708) |
| βc-m3444 | 5'-UAUUUGAGCCUUGUUUUGGACAGta-3'<br>3'-CAAUAAACUCGGAACAAAACCUGUCAU-5'<br>Target: 5'-GTTATTTGAGCCTTGTTTTGGACAGTA-3' | (SEQ ID NO: 491)<br>(SEQ ID NO: 1600)<br>(SEQ ID NO: 2709) |
| βc-m3449 | 5'-GAGCCUUGUUUUGGACAGUAUACca-3'<br>3'-AACUCGGAACAAAACCUGUCAUAUGGU-5'<br>Target: 5'-TTGAGCCTTGTTTTGGACAGTATACCA-3' | (SEQ ID NO: 492)<br>(SEQ ID NO: 1601)<br>(SEQ ID NO: 2710) |

TABLE 4-continued

Selected Anti-β-catenin DsiRNAs, *Mus musculus* Unique Duplexes

```
              5'-CAACAGAUGCGGUUAUAGAAAUGgt-3'    (SEQ ID NO: 493)
              3'-AAGUUGUCUACGCCAAUAUCUUUACCA-5'  (SEQ ID NO: 1602)
βc-m3522 Target: 5'-TTCAACAGATGCGGTTATAGAAATGGT-3' (SEQ ID NO: 2711)

5'-GUUAUAGAAAUGGUUCAGAAUUAaa-3'    (SEQ ID NO: 494)
              3'-GCCAAUAUCUUUACCAAGUCUUAAUUU-5'  (SEQ ID NO: 1603)
βc-m3533 Target: 5'-CGGTTATAGAAATGGTTCAGAATTAAA-3' (SEQ ID NO: 2712)

5'-AGAAAUGGUUCAGAAUUAAACUUtt-3'    (SEQ ID NO: 495)
              3'-UAUCUUUACCAAGUCUUAAUUUGAAAA-5'  (SEQ ID NO: 1604)
βc-m3538 Target: 5'-ATAGAAATGGTTCAGAATTAAACTTTT-3' (SEQ ID NO: 2713)
```

Projected 21 nucleotide target sequences for each DsiRNA of Tables 2-4 above and of Tables 6-8 below are presented in Table 5.

TABLE 5

21 Nucleotide Target Sequences of Selected DsiRNAs

| DsiRNA | | Target Sequence | SEQ ID NO |
|---|---|---|---|
| βc-240 | 21 nt Target: | 5'-CCCTGAGGGTATTTGAAGTAT-3' | (SEQ ID NO: 4444) |
| βc-244 | 21 nt Target: | 5'-GAGGGTATTTGAAGTATACCA-3' | (SEQ ID NO: 4445) |
| βc-253 | 21 nt Target: | 5'-TGAAGTATACCATACAACTGT-3' | (SEQ ID NO: 4446) |
| βc-259 | 21 nt Target: | 5'-ATACCATACAACTGTTTTGAA-3' | (SEQ ID NO: 4447) |
| βc-264 | 21 nt Target: | 5'-ATACAACTGTTTTGAAAATCC-3' | (SEQ ID NO: 4448) |
| βc-496 | 21 nt Target: | 5'-CAGGGATTTTCTCAGTCCTTC-3' | (SEQ ID NO: 4449) |
| βc-516 | 21 nt Target: | 5'-CACTCAAGAACAAGTAGCTGA-3' | (SEQ ID NO: 4450) |
| βc-522 | 21 nt Target: | 5'-AGAACAAGTAGCTGATATTGA-3' | (SEQ ID NO: 4451) |
| βc-524 | 21 nt Target: | 5'-AACAAGTAGCTGATATTGATG-3' | (SEQ ID NO: 4452) |
| βc-540 | 21 nt Target: | 5'-TGATGGACAGTATGCAATGAC-3' | (SEQ ID NO: 4453) |
| βc-582 | 21 nt Target: | 5'-TGCTATGTTCCCTGAGACATT-3' | (SEQ ID NO: 4454) |
| βc-686 | 21 nt Target: | 5'-TGCTGAAACATGCAGTTGTAA-3' | (SEQ ID NO: 4455) |
| βc-692 | 21 nt Target: | 5'-AACATGCAGTTGTAAACTTGA-3' | (SEQ ID NO: 4456) |
| βc-697 | 21 nt Target: | 5'-GCAGTTGTAAACTTGATTAAC-3' | (SEQ ID NO: 4457) |
| βc-707 | 21 nt Target: | 5'-ACTTGATTAACTATCAAGATG-3' | (SEQ ID NO: 4458) |
| βc-753 | 21 nt Target: | 5'-CCCTGAACTGACAAAACTGCT-3' | (SEQ ID NO: 4459) |
| βc-870 | 21 nt Target: | 5'-TCAGATGGTGTCTGCTATTGT-3' | (SEQ ID NO: 4460) |
| βc-889 | 21 nt Target: | 5'-GTACGTACCATGCAGAATACA-3' | (SEQ ID NO: 4461) |
| βc-1060 | 21 nt Target: | 5'-ATTACAACTCTCCACAACCTT-3' | (SEQ ID NO: 4462) |
| βc-1065 | 21 nt Target: | 5'-AACTCTCCACAACCTTTTATT-3' | (SEQ ID NO: 4463) |
| βc-1070 | 21 nt Target: | 5'-TCCACAACCTTTTATTACATC-3' | (SEQ ID NO: 4464) |
| βc-1076 | 21 nt Target: | 5'-ACCTTTTATTACATCAAGAAG-3' | (SEQ ID NO: 4465) |
| βc-1154 | 21 nt Target: | 5'-ACAAAACAAATGTTAAATTCT-3' | (SEQ ID NO: 4466) |
| βc-1180 | 21 nt Target: | 5'-ATTACGACAGACTGCCTTCAA-3' | (SEQ ID NO: 4467) |
| βc-1185 | 21 nt Target: | 5'-GACAGACTGCCTTCAAATTTT-3' | (SEQ ID NO: 4468) |
| βc-1260 | 21 nt Target: | 5'-AGCTTTAGTAAATATAATGAG-3' | (SEQ ID NO: 4469) |
| βc-1294 | 21 nt Target: | 5'-GAAAAACTACTGTGGACCACA-3' | (SEQ ID NO: 4470) |

TABLE 5-continued

21 Nucleotide Target Sequences of Selected DsiRNAs

| | | |
|---|---|---|
| βc-1412 21 nt Target: | 5'-CAAGTCAACGTCTTGTTCAGA-3' | (SEQ ID NO: 4471) |
| βc-1418 21 nt Target: | 5'-AACGTCTTGTTCAGAACTGTC-3' | (SEQ ID NO: 4472) |
| βc-1423 21 nt Target: | 5'-CTTGTTCAGAACTGTCTTTGG-3' | (SEQ ID NO: 4473) |
| βc-1520 21 nt Target: | 5'-TGGGTTCAGATGATATAAATG-3' | (SEQ ID NO: 4474) |
| βc-1561 21 nt Target: | 5'-ATTCTTTCTAACCTCACTTGC-3' | (SEQ ID NO: 4475) |
| βc-1571 21 nt Target: | 5'-ACCTCACTTGCAATAATTATA-3' | (SEQ ID NO: 4476) |
| βc-1579 21 nt Target: | 5'-TGCAATAATTATAAGAACAAG-3' | (SEQ ID NO: 4477) |
| βc-1620 21 nt Target: | 5'-TGGTATAGAGGCTCTTGTGCG-3' | (SEQ ID NO: 4478) |
| βc-1816 21 nt Target: | 5'-AAGGCTACTGTTGGATTGATT-3' | (SEQ ID NO: 4479) |
| βc-1987 21 nt Target: | 5'-CGCATGGAAGAAATAGTTGAA-3' | (SEQ ID NO: 4480) |
| βc-1989 21 nt Target: | 5'-CATGGAAGAAATAGTTGAAGG-3' | (SEQ ID NO: 4481) |
| βc-2111 21 nt Target: | 5'-CCATTGAAAACATCCAAAGAG-3' | (SEQ ID NO: 4482) |
| βc-2282 21 nt Target: | 5'-CTGAGGACAAGCCACAAGATT-3' | (SEQ ID NO: 4483) |
| βc-2624 21 nt Target: | 5'-TTGATACTGACCTGTAAATCA-3' | (SEQ ID NO: 4484) |
| βc-2647 21 nt Target: | 5'-CTTTAGGTAAGAAGTTTTAAA-3' | (SEQ ID NO: 4485) |
| βc-2770 21 nt Target: | 5'-AACAGGTATATACTTTGAAAG-3' | (SEQ ID NO: 4486) |
| βc-2848 21 nt Target: | 5'-TGGAAGTTATTAACTTTAATG-3' | (SEQ ID NO: 4487) |
| βc-2874 21 nt Target: | 5'-TGCCACAGCTTTTGCAACTTA-3' | (SEQ ID NO: 4488) |
| βc-2909 21 nt Target: | 5'-AACATTTGCTGTTTTAAACAT-3' | (SEQ ID NO: 4489) |
| βc-3074 21 nt Target: | 5'-AACAATTGAAGTAAACTTTTT-3' | (SEQ ID NO: 4490) |
| βc-3197 21 nt Target: | 5'-AAACCCTAGCCTTGCTTGTTA-3' | (SEQ ID NO: 4491) |
| βc-3203 21 nt Target: | 5'-TAGCCTTGCTTGTTAAATTTT-3' | (SEQ ID NO: 4492) |
| βc-3273 21 nt Target: | 5'-TTGAAGTAGCTCTTTTTTTTT-3' | (SEQ ID NO: 4493) |
| βc-3333 21 nt Target: | 5'-TCGTAGTGTTAAGTTATAGTG-3' | (SEQ ID NO: 4494) |
| βc-3349 21 nt Target: | 5'-TAGTGAATACTGCTACAGCAA-3' | (SEQ ID NO: 4495) |
| βc-3354 21 nt Target: | 5'-AATACTGCTACAGCAATTTCT-3' | (SEQ ID NO: 4496) |
| βc-3371 21 nt Target: | 5'-TTCTAATTTTTAAGAATTGAG-3' | (SEQ ID NO: 4497) |
| βc-3376 21 nt Target: | 5'-ATTTTTAAGAATTGAGTAATG-3' | (SEQ ID NO: 4498) |
| βc-3411 21 nt Target: | 5'-TTCATAATCACTCTAATTAAT-3' | (SEQ ID NO: 4499) |
| βc-3426 21 nt Target: | 5'-ATTAATTGTAATCTGAATAAA-3' | (SEQ ID NO: 4500) |
| βc-3431 21 nt Target: | 5'-TTGTAATCTGAATAAAGTGTA-3' | (SEQ ID NO: 4501) |
| βc-3437 21 nt Target: | 5'-TCTGAATAAAGTGTAACAATT-3' | (SEQ ID NO: 4502) |
| βc-3458 21 nt Target: | 5'-GTGTAGCCTTTTGTATAAAA-3' | (SEQ ID NO: 4503) |
| βc-3468 21 nt Target: | 5'-TTTGTATAAAATAGACAAATA-3' | (SEQ ID NO: 4504) |
| βc-3488 21 nt Target: | 5'-AGAAAATGGTCCAATTAGTTT-3' | (SEQ ID NO: 4505) |
| βc-3496 21 nt Target: | 5'-GTCCAATTAGTTTCCTTTTTA-3' | (SEQ ID NO: 4506) |
| βc-3552 21 nt Target: | 5'-TTTTTGATCAAAAACTATTTG-3' | (SEQ ID NO: 4507) |
| βc-3600 21 nt Target: | 5'-AAGAGGTGTTATTTGGAACCT-3' | (SEQ ID NO: 4508) |
| βc-3605 21 nt Target: | 5'-GTGTTATTTGGAACCTTGTTT-3' | (SEQ ID NO: 4509) |

TABLE 5-continued

21 Nucleotide Target Sequences of Selected DsiRNAs

| | | |
|---|---|---|
| βc-3615 21 nt Target: | 5'-GAACCTTGTTTTGGACAGTTT-3' | (SEQ ID NO: 4510) |
| βc-3674 21 nt Target: | 5'-GTGATACGATGCTTCAAGAGA-3' | (SEQ ID NO: 4511) |
| βc-3686 21 nt Target: | 5'-TTCAAGAGAAAATGCGGTTAT-3' | (SEQ ID NO: 4512) |
| βc-3691 21 nt Target: | 5'-GAGAAAATGCGGTTATAAAAA-3' | (SEQ ID NO: 4513) |
| βc-3700 21 nt Target: | 5'-CGGTTATAAAAAATGGTTCAG-3' | (SEQ ID NO: 4514) |
| βc-3707 21 nt Target: | 5'-AAAAAATGGTTCAGAATTAAA-3' | (SEQ ID NO: 4515) |
| βc-284 21 nt Target: | 5'-CAGCGTGGACAATGGCTACTC-3' | (SEQ ID NO: 4516) |
| βc-285 21 nt Target: | 5'-AGCGTGGACAATGGCTACTCA-3' | (SEQ ID NO: 4517) |
| βc-286 21 nt Target: | 5'-GCGTGGACAATGGCTACTCAA-3' | (SEQ ID NO: 4518) |
| βc-287 21 nt Target: | 5'-CGTGGACAATGGCTACTCAAG-3' | (SEQ ID NO: 4519) |
| βc-288 21 nt Target: | 5'-GTGGACAATGGCTACTCAAGC-3' | (SEQ ID NO: 4520) |
| βc-289 21 nt Target: | 5'-TGGACAATGGCTACTCAAGCT-3' | (SEQ ID NO: 4521) |
| βc-290 21 nt Target: | 5'-GGACAATGGCTACTCAAGCTG-3' | (SEQ ID NO: 4522) |
| βc-291 21 nt Target: | 5'-GACAATGGCTACTCAAGCTGA-3' | (SEQ ID NO: 4523) |
| βc-312 21 nt Target: | 5'-TTTGATGGAGTTGGACATGGC-3' | (SEQ ID NO: 4524) |
| βc-313 21 nt Target: | 5'-TTGATGGAGTTGGACATGGCC-3' | (SEQ ID NO: 4525) |
| βc-314 21 nt Target: | 5'-TGATGGAGTTGGACATGGCCA-3' | (SEQ ID NO: 4526) |
| βc-315 21 nt Target: | 5'-GATGGAGTTGGACATGGCCAT-3' | (SEQ ID NO: 4527) |
| βc-316 21 nt Target: | 5'-ATGGAGTTGGACATGGCCATG-3' | (SEQ ID NO: 4528) |
| βc-317 21 nt Target: | 5'-TGGAGTTGGACATGGCCATGG-3' | (SEQ ID NO: 4529) |
| βc-318 21 nt Target: | 5'-GGAGTTGGACATGGCCATGGA-3' | (SEQ ID NO: 4530) |
| βc-389 21 nt Target: | 5'-ACTCTGGAATCCATTCTGGTG-3' | (SEQ ID NO: 4531) |
| βc-390 21 nt Target: | 5'-CTCTGGAATCCATTCTGGTGC-3' | (SEQ ID NO: 4532) |
| βc-391 21 nt Target: | 5'-TCTGGAATCCATTCTGGTGCC-3' | (SEQ ID NO: 4533) |
| βc-392 21 nt Target: | 5'-CTGGAATCCATTCTGGTGCCA-3' | (SEQ ID NO: 4534) |
| βc-393 21 nt Target: | 5'-TGGAATCCATTCTGGTGCCAC-3' | (SEQ ID NO: 4535) |
| βc-600 21 nt Target: | 5'-ATTAGATGAGGGCATGCAGAT-3' | (SEQ ID NO: 4536) |
| βc-601 21 nt Target: | 5'-TTAGATGAGGGCATGCAGATC-3' | (SEQ ID NO: 4537) |
| βc-602 21 nt Target: | 5'-TAGATGAGGGCATGCAGATCC-3' | (SEQ ID NO: 4538) |
| βc-603 21 nt Target: | 5'-AGATGAGGGCATGCAGATCCC-3' | (SEQ ID NO: 4539) |
| βc-604 21 nt Target: | 5'-GATGAGGGCATGCAGATCCCA-3' | (SEQ ID NO: 4540) |
| βc-605 21 nt Target: | 5'-ATGAGGGCATGCAGATCCCAT-3' | (SEQ ID NO: 4541) |
| βc-638 21 nt Target: | 5'-ATGCTGCTCATCCCACTAATG-3' | (SEQ ID NO: 4542) |
| βc-639 21 nt Target: | 5'-TGCTGCTCATCCCACTAATGT-3' | (SEQ ID NO: 4543) |
| βc-640 21 nt Target: | 5'-GCTGCTCATCCCACTAATGTC-3' | (SEQ ID NO: 4544) |
| βc-641 21 nt Target: | 5'-CTGCTCATCCCACTAATGTCC-3' | (SEQ ID NO: 4545) |
| βc-642 21 nt Target: | 5'-TGCTCATCCCACTAATGTCCA-3' | (SEQ ID NO: 4546) |
| βc-643 21 nt Target: | 5'-GCTCATCCCACTAATGTCCAG-3' | (SEQ ID NO: 4547) |
| βc-644 21 nt Target: | 5'-CTCATCCCACTAATGTCCAGC-3' | (SEQ ID NO: 4548) |

TABLE 5-continued

| 21 Nucleotide Target Sequences of Selected DsiRNAs | | |
|---|---|---|
| βc-645 21 nt Target: | 5'-TCATCCCACTAATGTCCAGCG-3' | (SEQ ID NO: 4549) |
| βc-665 21 nt Target: | 5'-GTTTGGCTGAACCATCACAGA-3' | (SEQ ID NO: 4550) |
| βc-666 21 nt Target: | 5'-TTTGGCTGAACCATCACAGAT-3' | (SEQ ID NO: 4551) |
| βc-667 21 nt Target: | 5'-TTGGCTGAACCATCACAGATG-3' | (SEQ ID NO: 4552) |
| βc-731 21 nt Target: | 5'-CAGAACTTGCCACACGTGCAA-3' | (SEQ ID NO: 4553) |
| βc-732 21 nt Target: | 5'-AGAACTTGCCACACGTGCAAT-3' | (SEQ ID NO: 4554) |
| βc-809 21 nt Target: | 5'-CAGTTATGGTCCATCAGCTTT-3' | (SEQ ID NO: 4555) |
| βc-810 21 nt Target: | 5'-AGTTATGGTCCATCAGCTTTC-3' | (SEQ ID NO: 4556) |
| βc-830 21 nt Target: | 5'-CTAAAAAGGAAGCTTCCAGAC-3' | (SEQ ID NO: 4557) |
| βc-831 21 nt Target: | 5'-TAAAAAGGAAGCTTCCAGACA-3' | (SEQ ID NO: 4558) |
| βc-893 21 nt Target: | 5'-GTACCATGCAGAATACAAATG-3' | (SEQ ID NO: 4559) |
| βc-894 21 nt Target: | 5'-TACCATGCAGAATACAAATGA-3' | (SEQ ID NO: 4560) |
| βc-895 21 nt Target: | 5'-ACCATGCAGAATACAAATGAT-3' | (SEQ ID NO: 4561) |
| βc-896 21 nt Target: | 5'-CCATGCAGAATACAAATGATG-3' | (SEQ ID NO: 4562) |
| βc-897 21 nt Target: | 5'-CATGCAGAATACAAATGATGT-3' | (SEQ ID NO: 4563) |
| βc-898 21 nt Target: | 5'-ATGCAGAATACAAATGATGTA-3' | (SEQ ID NO: 4564) |
| βc-899 21 nt Target: | 5'-TGCAGAATACAAATGATGTAG-3' | (SEQ ID NO: 4565) |
| βc-900 21 nt Target: | 5'-GCAGAATACAAATGATGTAGA-3' | (SEQ ID NO: 4566) |
| βc-977 21 nt Target: | 5'-TACTGGCCATCTTTAAGTCTG-3' | (SEQ ID NO: 4567) |
| βc-978 21 nt Target: | 5'-ACTGGCCATCTTTAAGTCTGG-3' | (SEQ ID NO: 4568) |
| βc-1091 21 nt Target: | 5'-AAGAAGGAGCTAAAATGGCAG-3' | (SEQ ID NO: 4569) |
| βc-1092 21 nt Target: | 5'-AGAAGGAGCTAAAATGGCAGT-3' | (SEQ ID NO: 4570) |
| βc-1093 21 nt Target: | 5'-GAAGGAGCTAAAATGGCAGTG-3' | (SEQ ID NO: 4571) |
| βc-1094 21 nt Target: | 5'-AAGGAGCTAAAATGGCAGTGC-3' | (SEQ ID NO: 4572) |
| βc-1095 21 nt Target: | 5'-AGGAGCTAAAATGGCAGTGCG-3' | (SEQ ID NO: 4573) |
| βc-1301 21 nt Target: | 5'-TACTGTGGACCACAAGCAGAG-3' | (SEQ ID NO: 4574) |
| βc-1302 21 nt Target: | 5'-ACTGTGGACCACAAGCAGAGT-3' | (SEQ ID NO: 4575) |
| βc-1303 21 nt Target: | 5'-CTGTGGACCACAAGCAGAGTG-3' | (SEQ ID NO: 4576) |
| βc-1304 21 nt Target: | 5'-TGTGGACCACAAGCAGAGTGC-3' | (SEQ ID NO: 4577) |
| βc-1305 21 nt Target: | 5'-GTGGACCACAAGCAGAGTGCT-3' | (SEQ ID NO: 4578) |
| βc-1306 21 nt Target: | 5'-TGGACCACAAGCAGAGTGCTG-3' | (SEQ ID NO: 4579) |
| βc-1307 21 nt Target: | 5'-GGACCACAAGCAGAGTGCTGA-3' | (SEQ ID NO: 4580) |
| βc-1308 21 nt Target: | 5'-GACCACAAGCAGAGTGCTGAA-3' | (SEQ ID NO: 4581) |
| βc-1309 21 nt Target: | 5'-ACCACAAGCAGAGTGCTGAAG-3' | (SEQ ID NO: 4582) |
| βc-1310 21 nt Target: | 5'-CCACAAGCAGAGTGCTGAAGG-3' | (SEQ ID NO: 4583) |
| βc-1311 21 nt Target: | 5'-CACAAGCAGAGTGCTGAAGGT-3' | (SEQ ID NO: 4584) |
| βc-1312 21 nt Target: | 5'-ACAAGCAGAGTGCTGAAGGTG-3' | (SEQ ID NO: 4585) |
| βc-1313 21 nt Target: | 5'-CAAGCAGAGTGCTGAAGGTGC-3' | (SEQ ID NO: 4586) |
| βc-1314 21 nt Target: | 5'-AAGCAGAGTGCTGAAGGTGCT-3' | (SEQ ID NO: 4587) |

TABLE 5-continued

21 Nucleotide Target Sequences of Selected DsiRNAs

| | | |
|---|---|---|
| βc-1430 21 nt Target: | 5'-AGAACTGTCTTTGGACTCTCA-3' | (SEQ ID NO: 4588) |
| βc-1431 21 nt Target: | 5'-GAACTGTCTTTGGACTCTCAG-3' | (SEQ ID NO: 4589) |
| βc-1526 21 nt Target: | 5'-CAGATGATATAAATGTGGTCA-3' | (SEQ ID NO: 4590) |
| βc-1527 21 nt Target: | 5'-AGATGATATAAATGTGGTCAC-3' | (SEQ ID NO: 4591) |
| βc-1528 21 nt Target: | 5'-GATGATATAAATGTGGTCACC-3' | (SEQ ID NO: 4592) |
| βc-1529 21 nt Target: | 5'-ATGATATAAATGTGGTCACCT-3' | (SEQ ID NO: 4593) |
| βc-1530 21 nt Target: | 5'-TGATATAAATGTGGTCACCTG-3' | (SEQ ID NO: 4594) |
| βc-1531 21 nt Target: | 5'-GATATAAATGTGGTCACCTGT-3' | (SEQ ID NO: 4595) |
| βc-1532 21 nt Target: | 5'-ATATAAATGTGGTCACCTGTG-3' | (SEQ ID NO: 4596) |
| βc-1533 21 nt Target: | 5'-TATAAATGTGGTCACCTGTGC-3' | (SEQ ID NO: 4597) |
| βc-1534 21 nt Target: | 5'-ATAAATGTGGTCACCTGTGCA-3' | (SEQ ID NO: 4598) |
| βc-1535 21 nt Target: | 5'-TAAATGTGGTCACCTGTGCAG-3' | (SEQ ID NO: 4599) |
| βc-1536 21 nt Target: | 5'-AAATGTGGTCACCTGTGCAGC-3' | (SEQ ID NO: 4600) |
| βc-1537 21 nt Target: | 5'-AATGTGGTCACCTGTGCAGCT-3' | (SEQ ID NO: 4601) |
| βc-1538 21 nt Target: | 5'-ATGTGGTCACCTGTGCAGCTG-3' | (SEQ ID NO: 4602) |
| βc-1539 21 nt Target: | 5'-TGTGGTCACCTGTGCAGCTGG-3' | (SEQ ID NO: 4603) |
| βc-1540 21 nt Target: | 5'-GTGGTCACCTGTGCAGCTGGA-3' | (SEQ ID NO: 4604) |
| βc-1541 21 nt Target: | 5'-TGGTCACCTGTGCAGCTGGAA-3' | (SEQ ID NO: 4605) |
| βc-1542 21 nt Target: | 5'-GGTCACCTGTGCAGCTGGAAT-3' | (SEQ ID NO: 4606) |
| βc-1543 21 nt Target: | 5'-GTCACCTGTGCAGCTGGAATT-3' | (SEQ ID NO: 4607) |
| βc-1544 21 nt Target: | 5'-TCACCTGTGCAGCTGGAATTC-3' | (SEQ ID NO: 4608) |
| βc-1545 21 nt Target: | 5'-CACCTGTGCAGCTGGAATTCT-3' | (SEQ ID NO: 4609) |
| βc-1565 21 nt Target: | 5'-TTTCTAACCTCACTTGCAATA-3' | (SEQ ID NO: 4610) |
| βc-1566 21 nt Target: | 5'-TTCTAACCTCACTTGCAATAA-3' | (SEQ ID NO: 4611) |
| βc-1567 21 nt Target: | 5'-TCTAACCTCACTTGCAATAAT-3' | (SEQ ID NO: 4612) |
| βc-1568 21 nt Target: | 5'-CTAACCTCACTTGCAATAATT-3' | (SEQ ID NO: 4613) |
| βc-1569 21 nt Target: | 5'-TAACCTCACTTGCAATAATTA-3' | (SEQ ID NO: 4614) |
| βc-1652 21 nt Target: | 5'-GGGCTGGTGACAGGGAAGACA-3' | (SEQ ID NO: 4615) |
| βc-1653 21 nt Target: | 5'-GGCTGGTGACAGGGAAGACAT-3' | (SEQ ID NO: 4616) |
| βc-1654 21 nt Target: | 5'-GCTGGTGACAGGGAAGACATC-3' | (SEQ ID NO: 4617) |
| βc-1655 21 nt Target: | 5'-CTGGTGACAGGGAAGACATCA-3' | (SEQ ID NO: 4618) |
| βc-1656 21 nt Target: | 5'-TGGTGACAGGGAAGACATCAC-3' | (SEQ ID NO: 4619) |
| βc-1657 21 nt Target: | 5'-GGTGACAGGGAAGACATCACT-3' | (SEQ ID NO: 4620) |
| βc-1658 21 nt Target: | 5'-GTGACAGGGAAGACATCACTG-3' | (SEQ ID NO: 4621) |
| βc-1659 21 nt Target: | 5'-TGACAGGGAAGACATCACTGA-3' | (SEQ ID NO: 4622) |
| βc-1660 21 nt Target: | 5'-GACAGGGAAGACATCACTGAG-3' | (SEQ ID NO: 4623) |
| βc-1661 21 nt Target: | 5'-ACAGGGAAGACATCACTGAGC-3' | (SEQ ID NO: 4624) |
| βc-1662 21 nt Target: | 5'-CAGGGAAGACATCACTGAGCC-3' | (SEQ ID NO: 4625) |
| βc-1663 21 nt Target: | 5'-AGGGAAGACATCACTGAGCCT-3' | (SEQ ID NO: 4626) |

TABLE 5-continued

21 Nucleotide Target Sequences of Selected DsiRNAs

| | | | |
|---|---|---|---|
| βc-1664 21 nt Target: | 5'-GGGAAGACATCACTGAGCCTG-3' | (SEQ ID NO: 4627) |
| βc-1665 21 nt Target: | 5'-GGAAGACATCACTGAGCCTGC-3' | (SEQ ID NO: 4628) |
| βc-1666 21 nt Target: | 5'-GAAGACATCACTGAGCCTGCC-3' | (SEQ ID NO: 4629) |
| βc-1667 21 nt Target: | 5'-AAGACATCACTGAGCCTGCCA-3' | (SEQ ID NO: 4630) |
| βc-1668 21 nt Target: | 5'-AGACATCACTGAGCCTGCCAT-3' | (SEQ ID NO: 4631) |
| βc-1669 21 nt Target: | 5'-GACATCACTGAGCCTGCCATC-3' | (SEQ ID NO: 4632) |
| βc-1670 21 nt Target: | 5'-ACATCACTGAGCCTGCCATCT-3' | (SEQ ID NO: 4633) |
| βc-1671 21 nt Target: | 5'-CATCACTGAGCCTGCCATCTG-3' | (SEQ ID NO: 4634) |
| βc-1672 21 nt Target: | 5'-ATCACTGAGCCTGCCATCTGT-3' | (SEQ ID NO: 4635) |
| βc-1673 21 nt Target: | 5'-TCACTGAGCCTGCCATCTGTG-3' | (SEQ ID NO: 4636) |
| βc-1674 21 nt Target: | 5'-CACTGAGCCTGCCATCTGTGC-3' | (SEQ ID NO: 4637) |
| βc-1675 21 nt Target: | 5'-ACTGAGCCTGCCATCTGTGCT-3' | (SEQ ID NO: 4638) |
| βc-1676 21 nt Target: | 5'-CTGAGCCTGCCATCTGTGCTC-3' | (SEQ ID NO: 4639) |
| βc-1677 21 nt Target: | 5'-TGAGCCTGCCATCTGTGCTCT-3' | (SEQ ID NO: 4640) |
| βc-1678 21 nt Target: | 5'-GAGCCTGCCATCTGTGCTCTT-3' | (SEQ ID NO: 4641) |
| βc-1679 21 nt Target: | 5'-AGCCTGCCATCTGTGCTCTTC-3' | (SEQ ID NO: 4642) |
| βc-1680 21 nt Target: | 5'-GCCTGCCATCTGTGCTCTTCG-3' | (SEQ ID NO: 4643) |
| βc-1681 21 nt Target: | 5'-CCTGCCATCTGTGCTCTTCGT-3' | (SEQ ID NO: 4644) |
| βc-1682 21 nt Target: | 5'-CTGCCATCTGTGCTCTTCGTC-3' | (SEQ ID NO: 4645) |
| βc-1683 21 nt Target: | 5'-TGCCATCTGTGCTCTTCGTCA-3' | (SEQ ID NO: 4646) |
| βc-1684 21 nt Target: | 5'-GCCATCTGTGCTCTTCGTCAT-3' | (SEQ ID NO: 4647) |
| βc-1685 21 nt Target: | 5'-CCATCTGTGCTCTTCGTCATC-3' | (SEQ ID NO: 4648) |
| βc-1686 21 nt Target: | 5'-CATCTGTGCTCTTCGTCATCT-3' | (SEQ ID NO: 4649) |
| βc-1687 21 nt Target: | 5'-ATCTGTGCTCTTCGTCATCTG-3' | (SEQ ID NO: 4650) |
| βc-1688 21 nt Target: | 5'-TCTGTGCTCTTCGTCATCTGA-3' | (SEQ ID NO: 4651) |
| βc-1689 21 nt Target: | 5'-CTGTGCTCTTCGTCATCTGAC-3' | (SEQ ID NO: 4652) |
| βc-1690 21 nt Target: | 5'-TGTGCTCTTCGTCATCTGACC-3' | (SEQ ID NO: 4653) |
| βc-1691 21 nt Target: | 5'-GTGCTCTTCGTCATCTGACCA-3' | (SEQ ID NO: 4654) |
| βc-1692 21 nt Target: | 5'-TGCTCTTCGTCATCTGACCAG-3' | (SEQ ID NO: 4655) |
| βc-1693 21 nt Target: | 5'-GCTCTTCGTCATCTGACCAGC-3' | (SEQ ID NO: 4656) |
| βc-1694 21 nt Target: | 5'-CTCTTCGTCATCTGACCAGCC-3' | (SEQ ID NO: 4657) |
| βc-1695 21 nt Target: | 5'-TCTTCGTCATCTGACCAGCCG-3' | (SEQ ID NO: 4658) |
| βc-1787 21 nt Target: | 5'-TACACCCACCATCCCACTGGC-3' | (SEQ ID NO: 4659) |
| βc-1788 21 nt Target: | 5'-ACACCCACCATCCCACTGGCC-3' | (SEQ ID NO: 4660) |
| βc-1789 21 nt Target: | 5'-CACCCACCATCCCACTGGCCT-3' | (SEQ ID NO: 4661) |
| βc-1790 21 nt Target: | 5'-ACCCACCATCCCACTGGCCTC-3' | (SEQ ID NO: 4662) |
| βc-1791 21 nt Target: | 5'-CCCACCATCCCACTGGCCTCT-3' | (SEQ ID NO: 4663) |
| βc-1792 21 nt Target: | 5'-CCACCATCCCACTGGCCTCTG-3' | (SEQ ID NO: 4664) |
| βc-1793 21 nt Target: | 5'-CACCATCCCACTGGCCTCTGA-3' | (SEQ ID NO: 4665) |

TABLE 5-continued

21 Nucleotide Target Sequences of Selected DsiRNAs

| | | |
|---|---|---|
| βc-1794 21 nt Target: | 5'-ACCATCCCACTGGCCTCTGAT-3' | (SEQ ID NO: 4666) |
| βc-1795 21 nt Target: | 5'-CCATCCCACTGGCCTCTGATA-3' | (SEQ ID NO: 4667) |
| βc-1796 21 nt Target: | 5'-CATCCCACTGGCCTCTGATAA-3' | (SEQ ID NO: 4668) |
| βc-1797 21 nt Target: | 5'-ATCCCACTGGCCTCTGATAAA-3' | (SEQ ID NO: 4669) |
| βc-1798 21 nt Target: | 5'-TCCCACTGGCCTCTGATAAAG-3' | (SEQ ID NO: 4670) |
| βc-1799 21 nt Target: | 5'-CCCACTGGCCTCTGATAAAGG-3' | (SEQ ID NO: 4671) |
| βc-1800 21 nt Target: | 5'-CCACTGGCCTCTGATAAAGGC-3' | (SEQ ID NO: 4672) |
| βc-1820 21 nt Target: | 5'-CTACTGTTGGATTGATTCGAA-3' | (SEQ ID NO: 4673) |
| βc-1821 21 nt Target: | 5'-TACTGTTGGATTGATTCGAAA-3' | (SEQ ID NO: 4674) |
| βc-2072 21 nt Target: | 5'-TAAATACCATTCCATTGTTTG-3' | (SEQ ID NO: 4675) |
| βc-2073 21 nt Target: | 5'-AAATACCATTCCATTGTTTGT-3' | (SEQ ID NO: 4676) |
| βc-2074 21 nt Target: | 5'-AATACCATTCCATTGTTTGTG-3' | (SEQ ID NO: 4677) |
| βc-2075 21 nt Target: | 5'-ATACCATTCCATTGTTTGTGC-3' | (SEQ ID NO: 4678) |
| βc-2076 21 nt Target: | 5'-TACCATTCCATTGTTTGTGCA-3' | (SEQ ID NO: 4679) |
| βc-2077 21 nt Target: | 5'-ACCATTCCATTGTTTGTGCAG-3' | (SEQ ID NO: 4680) |
| βc-2097 21 nt Target: | 5'-GCTGCTTTATTCTCCCATTGA-3' | (SEQ ID NO: 4681) |
| βc-2098 21 nt Target: | 5'-CTGCTTTATTCTCCCATTGAA-3' | (SEQ ID NO: 4682) |
| βc-2099 21 nt Target: | 5'-TGCTTTATTCTCCCATTGAAA-3' | (SEQ ID NO: 4683) |
| βc-2100 21 nt Target: | 5'-GCTTTATTCTCCCATTGAAAA-3' | (SEQ ID NO: 4684) |
| βc-2141 21 nt Target: | 5'-GGGTCCTCTGTGAACTTGCTC-3' | (SEQ ID NO: 4685) |
| βc-2142 21 nt Target: | 5'-GGTCCTCTGTGAACTTGCTCA-3' | (SEQ ID NO: 4686) |
| βc-2143 21 nt Target: | 5'-GTCCTCTGTGAACTTGCTCAG-3' | (SEQ ID NO: 4687) |
| βc-2144 21 nt Target: | 5'-TCCTCTGTGAACTTGCTCAGG-3' | (SEQ ID NO: 4688) |
| βc-2145 21 nt Target: | 5'-CCTCTGTGAACTTGCTCAGGA-3' | (SEQ ID NO: 4689) |
| βc-2146 21 nt Target: | 5'-CTCTGTGAACTTGCTCAGGAC-3' | (SEQ ID NO: 4690) |
| βc-2147 21 nt Target: | 5'-TCTGTGAACTTGCTCAGGACA-3' | (SEQ ID NO: 4691) |
| βc-2148 21 nt Target: | 5'-CTGTGAACTTGCTCAGGACAA-3' | (SEQ ID NO: 4692) |
| βc-2149 21 nt Target: | 5'-TGTGAACTTGCTCAGGACAAG-3' | (SEQ ID NO: 4693) |
| βc-2150 21 nt Target: | 5'-GTGAACTTGCTCAGGACAAGG-3' | (SEQ ID NO: 4694) |
| βc-2151 21 nt Target: | 5'-TGAACTTGCTCAGGACAAGGA-3' | (SEQ ID NO: 4695) |
| βc-2183 21 nt Target: | 5'-CTATTGAAGCTGAGGGAGCCA-3' | (SEQ ID NO: 4696) |
| βc-2184 21 nt Target: | 5'-TATTGAAGCTGAGGGAGCCAC-3' | (SEQ ID NO: 4697) |
| βc-2185 21 nt Target: | 5'-ATTGAAGCTGAGGGAGCCACA-3' | (SEQ ID NO: 4698) |
| βc-2270 21 nt Target: | 5'-TGTTCCGAATGTCTGAGGACA-3' | (SEQ ID NO: 4699) |
| βc-2271 21 nt Target: | 5'-GTTCCGAATGTCTGAGGACAA-3' | (SEQ ID NO: 4700) |
| βc-2272 21 nt Target: | 5'-TTCCGAATGTCTGAGGACAAG-3' | (SEQ ID NO: 4701) |
| βc-2273 21 nt Target: | 5'-TCCGAATGTCTGAGGACAAGC-3' | (SEQ ID NO: 4702) |
| βc-2274 21 nt Target: | 5'-CCGAATGTCTGAGGACAAGCC-3' | (SEQ ID NO: 4703) |
| βc-2275 21 nt Target: | 5'-CGAATGTCTGAGGACAAGCCA-3' | (SEQ ID NO: 4704) |

TABLE 5-continued

21 Nucleotide Target Sequences of Selected DsiRNAs

| | | | |
|---|---|---|---|
| βc-2276 21 nt Target: | 5'-GAATGTCTGAGGACAAGCCAC-3' | (SEQ ID NO: 4705) |
| βc-2277 21 nt Target: | 5'-AATGTCTGAGGACAAGCCACA-3' | (SEQ ID NO: 4706) |
| βc-2345 21 nt Target: | 5'-GAACAGAGCCAATGGCTTGGA-3' | (SEQ ID NO: 4707) |
| βc-2346 21 nt Target: | 5'-AACAGAGCCAATGGCTTGGAA-3' | (SEQ ID NO: 4708) |
| βc-2347 21 nt Target: | 5'-ACAGAGCCAATGGCTTGGAAT-3' | (SEQ ID NO: 4709) |
| βc-2348 21 nt Target: | 5'-CAGAGCCAATGGCTTGGAATG-3' | (SEQ ID NO: 4710) |
| βc-2349 21 nt Target: | 5'-AGAGCCAATGGCTTGGAATGA-3' | (SEQ ID NO: 4711) |
| βc-2350 21 nt Target: | 5'-GAGCCAATGGCTTGGAATGAG-3' | (SEQ ID NO: 4712) |
| βc-2351 21 nt Target: | 5'-AGCCAATGGCTTGGAATGAGA-3' | (SEQ ID NO: 4713) |
| βc-2352 21 nt Target: | 5'-GCCAATGGCTTGGAATGAGAC-3' | (SEQ ID NO: 4714) |
| βc-2353 21 nt Target: | 5'-CCAATGGCTTGGAATGAGACT-3' | (SEQ ID NO: 4715) |
| βc-2354 21 nt Target: | 5'-CAATGGCTTGGAATGAGACTG-3' | (SEQ ID NO: 4716) |
| βc-2355 21 nt Target: | 5'-AATGGCTTGGAATGAGACTGC-3' | (SEQ ID NO: 4717) |
| βc-2411 21 nt Target: | 5'-CCCTTGGATATCGCCAGGATG-3' | (SEQ ID NO: 4718) |
| βc-2412 21 nt Target: | 5'-CCTTGGATATCGCCAGGATGA-3' | (SEQ ID NO: 4719) |
| βc-2413 21 nt Target: | 5'-CTTGGATATCGCCAGGATGAT-3' | (SEQ ID NO: 4720) |
| βc-2414 21 nt Target: | 5'-TTGGATATCGCCAGGATGATC-3' | (SEQ ID NO: 4721) |
| βc-2415 21 nt Target: | 5'-TGGATATCGCCAGGATGATCC-3' | (SEQ ID NO: 4722) |
| βc-2441 21 nt Target: | 5'-ATCGTTCTTTTCACTCTGGTG-3' | (SEQ ID NO: 4723) |
| βc-2442 21 nt Target: | 5'-TCGTTCTTTTCACTCTGGTGG-3' | (SEQ ID NO: 4724) |
| βc-2443 21 nt Target: | 5'-CGTTCTTTTCACTCTGGTGGA-3' | (SEQ ID NO: 4725) |
| βc-2444 21 nt Target: | 5'-GTTCTTTTCACTCTGGTGGAT-3' | (SEQ ID NO: 4726) |
| βc-2445 21 nt Target: | 5'-TTCTTTTCACTCTGGTGGATA-3' | (SEQ ID NO: 4727) |
| βc-2501 21 nt Target: | 5'-AACATGAGATGGGTGGCCACC-3' | (SEQ ID NO: 4728) |
| βc-2502 21 nt Target: | 5'-ACATGAGATGGGTGGCCACCA-3' | (SEQ ID NO: 4729) |
| βc-2503 21 nt Target: | 5'-CATGAGATGGGTGGCCACCAC-3' | (SEQ ID NO: 4730) |
| βc-2504 21 nt Target: | 5'-ATGAGATGGGTGGCCACCACC-3' | (SEQ ID NO: 4731) |
| βc-2505 21 nt Target: | 5'-TGAGATGGGTGGCCACCACCC-3' | (SEQ ID NO: 4732) |
| βc-2506 21 nt Target: | 5'-GAGATGGGTGGCCACCACCCT-3' | (SEQ ID NO: 4733) |
| βc-2507 21 nt Target: | 5'-AGATGGGTGGCCACCACCCTG-3' | (SEQ ID NO: 4734) |
| βc-2508 21 nt Target: | 5'-GATGGGTGGCCACCACCCTGG-3' | (SEQ ID NO: 4735) |
| βc-2509 21 nt Target: | 5'-ATGGGTGGCCACCACCCTGGT-3' | (SEQ ID NO: 4736) |
| βc-2510 21 nt Target: | 5'-TGGGTGGCCACCACCCTGGTG-3' | (SEQ ID NO: 4737) |
| βc-2511 21 nt Target: | 5'-GGGTGGCCACCACCCTGGTGC-3' | (SEQ ID NO: 4738) |
| βc-2512 21 nt Target: | 5'-GGTGGCCACCACCCTGGTGCT-3' | (SEQ ID NO: 4739) |
| βc-2513 21 nt Target: | 5'-GTGGCCACCACCCTGGTGCTG-3' | (SEQ ID NO: 4740) |
| βc-2514 21 nt Target: | 5'-TGGCCACCACCCTGGTGCTGA-3' | (SEQ ID NO: 4741) |
| βc-2515 21 nt Target: | 5'-GGCCACCACCCTGGTGCTGAC-3' | (SEQ ID NO: 4742) |
| βc-2516 21 nt Target: | 5'-GCCACCACCCTGGTGCTGACT-3' | (SEQ ID NO: 4743) |

TABLE 5-continued

21 Nucleotide Target Sequences of Selected DsiRNAs

| βc-2517 21 nt Target: | 5'-CCACCACCCTGGTGCTGACTA-3' | (SEQ ID NO: 4744) |
| βc-2518 21 nt Target: | 5'-CACCACCCTGGTGCTGACTAT-3' | (SEQ ID NO: 4745) |
| βc-2519 21 nt Target: | 5'-ACCACCCTGGTGCTGACTATC-3' | (SEQ ID NO: 4746) |
| βc-2520 21 nt Target: | 5'-CCACCCTGGTGCTGACTATCC-3' | (SEQ ID NO: 4747) |
| βc-2521 21 nt Target: | 5'-CACCCTGGTGCTGACTATCCA-3' | (SEQ ID NO: 4748) |
| βc-2522 21 nt Target: | 5'-ACCCTGGTGCTGACTATCCAG-3' | (SEQ ID NO: 4749) |
| βc-2523 21 nt Target: | 5'-CCCTGGTGCTGACTATCCAGT-3' | (SEQ ID NO: 4750) |
| βc-2524 21 nt Target: | 5'-CCTGGTGCTGACTATCCAGTT-3' | (SEQ ID NO: 4751) |
| βc-2525 21 nt Target: | 5'-CTGGTGCTGACTATCCAGTTG-3' | (SEQ ID NO: 4752) |
| βc-2526 21 nt Target: | 5'-TGGTGCTGACTATCCAGTTGA-3' | (SEQ ID NO: 4753) |
| βc-2527 21 nt Target: | 5'-GGTGCTGACTATCCAGTTGAT-3' | (SEQ ID NO: 4754) |
| βc-2528 21 nt Target: | 5'-GTGCTGACTATCCAGTTGATG-3' | (SEQ ID NO: 4755) |
| βc-2529 21 nt Target: | 5'-TGCTGACTATCCAGTTGATGG-3' | (SEQ ID NO: 4756) |
| βc-2530 21 nt Target: | 5'-GCTGACTATCCAGTTGATGGG-3' | (SEQ ID NO: 4757) |
| βc-2531 21 nt Target: | 5'-CTGACTATCCAGTTGATGGGC-3' | (SEQ ID NO: 4758) |
| βc-2532 21 nt Target: | 5'-TGACTATCCAGTTGATGGGCT-3' | (SEQ ID NO: 4759) |
| βc-2533 21 nt Target: | 5'-GACTATCCAGTTGATGGGCTG-3' | (SEQ ID NO: 4760) |
| βc-2534 21 nt Target: | 5'-ACTATCCAGTTGATGGGCTGC-3' | (SEQ ID NO: 4761) |
| βc-2535 21 nt Target: | 5'-CTATCCAGTTGATGGGCTGCC-3' | (SEQ ID NO: 4762) |
| βc-2567 21 nt Target: | 5'-ATGCCCAGGACCTCATGGATG-3' | (SEQ ID NO: 4763) |
| βc-2568 21 nt Target: | 5'-TGCCCAGGACCTCATGGATGG-3' | (SEQ ID NO: 4764) |
| βc-2569 21 nt Target: | 5'-GCCCAGGACCTCATGGATGGG-3' | (SEQ ID NO: 4765) |
| βc-2603 21 nt Target: | 5'-ACAGCAATCAGCTGGCCTGGT-3' | (SEQ ID NO: 4766) |
| βc-2604 21 nt Target: | 5'-CAGCAATCAGCTGGCCTGGTT-3' | (SEQ ID NO: 4767) |
| βc-2605 21 nt Target: | 5'-AGCAATCAGCTGGCCTGGTTT-3' | (SEQ ID NO: 4768) |
| βc-2606 21 nt Target: | 5'-GCAATCAGCTGGCCTGGTTTG-3' | (SEQ ID NO: 4769) |
| βc-2607 21 nt Target: | 5'-CAATCAGCTGGCCTGGTTTGA-3' | (SEQ ID NO: 4770) |
| βc-2608 21 nt Target: | 5'-AATCAGCTGGCCTGGTTTGAT-3' | (SEQ ID NO: 4771) |
| βc-2609 21 nt Target: | 5'-ATCAGCTGGCCTGGTTTGATA-3' | (SEQ ID NO: 4772) |
| βc-2610 21 nt Target: | 5'-TCAGCTGGCCTGGTTTGATAC-3' | (SEQ ID NO: 4773) |
| βc-2611 21 nt Target: | 5'-CAGCTGGCCTGGTTTGATACT-3' | (SEQ ID NO: 4774) |
| βc-2612 21 nt Target: | 5'-AGCTGGCCTGGTTTGATACTG-3' | (SEQ ID NO: 4775) |
| βc-2613 21 nt Target: | 5'-GCTGGCCTGGTTTGATACTGA-3' | (SEQ ID NO: 4776) |
| βc-2614 21 nt Target: | 5'-CTGGCCTGGTTTGATACTGAC-3' | (SEQ ID NO: 4777) |
| βc-2615 21 nt Target: | 5'-TGGCCTGGTTTGATACTGACC-3' | (SEQ ID NO: 4778) |
| βc-2616 21 nt Target: | 5'-GGCCTGGTTTGATACTGACCT-3' | (SEQ ID NO: 4779) |
| βc-2617 21 nt Target: | 5'-GCCTGGTTTGATACTGACCTG-3' | (SEQ ID NO: 4780) |
| βc-2618 21 nt Target: | 5'-CCTGGTTTGATACTGACCTGT-3' | (SEQ ID NO: 4781) |
| βc-2619 21 nt Target: | 5'-CTGGTTTGATACTGACCTGTA-3' | (SEQ ID NO: 4782) |

TABLE 5-continued

| 21 Nucleotide Target Sequences of Selected DsiRNAs |
|---|
| βc-2620 21 nt Target: 5'-TGGTTTGATACTGACCTGTAA-3' (SEQ ID NO: 4783) |
| βc-2621 21 nt Target: 5'-GGTTTGATACTGACCTGTAAA-3' (SEQ ID NO: 4784) |
| βc-2622 21 nt Target: 5'-GTTTGATACTGACCTGTAAAT-3' (SEQ ID NO: 4785) |
| βc-2623 21 nt Target: 5'-TTTGATACTGACCTGTAAATC-3' (SEQ ID NO: 4786) |
| βc-2869 21 nt Target: 5'-TTTTTTGCCACAGCTTTTGCA-3' (SEQ ID NO: 4787) |
| βc-2902 21 nt Target: 5'-AATGAGTAACATTTGCTGTTT-3' (SEQ ID NO: 4788) |
| βc-2923 21 nt Target: 5'-TAAACATTAATAGCAGCCTTT-3' (SEQ ID NO: 4789) |
| βc-2925 21 nt Target: 5'-AACATTAATAGCAGCCTTTCT-3' (SEQ ID NO: 4790) |
| βc-2927 21 nt Target: 5'-CATTAATAGCAGCCTTTCTCT-3' (SEQ ID NO: 4791) |
| βc-2929 21 nt Target: 5'-TTAATAGCAGCCTTTCTCTCT-3' (SEQ ID NO: 4792) |
| βc-2973 21 nt Target: 5'-TTGCATTGTGATTGGCCTGTA-3' (SEQ ID NO: 4793) |
| βc-2975 21 nt Target: 5'-GCATTGTGATTGGCCTGTAGA-3' (SEQ ID NO: 4794) |
| βc-2977 21 nt Target: 5'-ATTGTGATTGGCCTGTAGAGT-3' (SEQ ID NO: 4795) |
| βc-2979 21 nt Target: 5'-TGTGATTGGCCTGTAGAGTTG-3' (SEQ ID NO: 4796) |
| βc-2981 21 nt Target: 5'-TGATTGGCCTGTAGAGTTGCT-3' (SEQ ID NO: 4797) |
| βc-2983 21 nt Target: 5'-ATTGGCCTGTAGAGTTGCTGA-3' (SEQ ID NO: 4798) |
| βc-2985 21 nt Target: 5'-TGGCCTGTAGAGTTGCTGAGA-3' (SEQ ID NO: 4799) |
| βc-2987 21 nt Target: 5'-GCCTGTAGAGTTGCTGAGAGG-3' (SEQ ID NO: 4800) |
| βc-2989 21 nt Target: 5'-CTGTAGAGTTGCTGAGAGGGC-3' (SEQ ID NO: 4801) |
| βc-3015 21 nt Target: 5'-GGGTGGGCTGGTATCTCAGAA-3' (SEQ ID NO: 4802) |
| βc-3017 21 nt Target: 5'-GTGGGCTGGTATCTCAGAAAG-3' (SEQ ID NO: 4803) |
| βc-3019 21 nt Target: 5'-GGGCTGGTATCTCAGAAAGTG-3' (SEQ ID NO: 4804) |
| βc-3021 21 nt Target: 5'-GCTGGTATCTCAGAAAGTGCC-3' (SEQ ID NO: 4805) |
| βc-3046 21 nt Target: 5'-ACACTAACCAAGCTGAGTTTC-3' (SEQ ID NO: 4806) |
| βc-3048 21 nt Target: 5'-ACTAACCAAGCTGAGTTTCCT-3' (SEQ ID NO: 4807) |
| βc-3050 21 nt Target: 5'-TAACCAAGCTGAGTTTCCTAT-3' (SEQ ID NO: 4808) |
| βc-3052 21 nt Target: 5'-ACCAAGCTGAGTTTCCTATGG-3' (SEQ ID NO: 4809) |
| βc-3054 21 nt Target: 5'-CAAGCTGAGTTTCCTATGGGA-3' (SEQ ID NO: 4810) |
| βc-3056 21 nt Target: 5'-AGCTGAGTTTCCTATGGGAAC-3' (SEQ ID NO: 4811) |
| βc-3087 21 nt Target: 5'-AACTTTTTGTTCTGGTCCTTT-3' (SEQ ID NO: 4812) |
| βc-3089 21 nt Target: 5'-CTTTTTGTTCTGGTCCTTTTT-3' (SEQ ID NO: 4813) |
| βc-3091 21 nt Target: 5'-TTTTGTTCTGGTCCTTTTTGG-3' (SEQ ID NO: 4814) |
| βc-3093 21 nt Target: 5'-TTGTTCTGGTCCTTTTTGGTC-3' (SEQ ID NO: 4815) |
| βc-3095 21 nt Target: 5'-GTTCTGGTCCTTTTTGGTCGA-3' (SEQ ID NO: 4816) |
| βc-3097 21 nt Target: 5'-TCTGGTCCTTTTTGGTCGAGG-3' (SEQ ID NO: 4817) |
| βc-3099 21 nt Target: 5'-TGGTCCTTTTTGGTCGAGGAG-3' (SEQ ID NO: 4818) |
| βc-3101 21 nt Target: 5'-GTCCTTTTTGGTCGAGGAGTA-3' (SEQ ID NO: 4819) |
| βc-3103 21 nt Target: 5'-CCTTTTTGGTCGAGGAGTAAC-3' (SEQ ID NO: 4820) |
| βc-3105 21 nt Target: 5'-TTTTTGGTCGAGGAGTAACAA-3' (SEQ ID NO: 4821) |

TABLE 5-continued

| 21 Nucleotide Target Sequences of Selected DsiRNAs |
|---|

βc-3107 21 nt Target:   5'-TTTGGTCGAGGAGTAACAATA-3'   (SEQ ID NO: 4822)

βc-3109 21 nt Target:   5'-TGGTCGAGGAGTAACAATACA-3'   (SEQ ID NO: 4823)

βc-3111 21 nt Target:   5'-GTCGAGGAGTAACAATACAAA-3'   (SEQ ID NO: 4824)

βc-3113 21 nt Target:   5'-CGAGGAGTAACAATACAAATG-3'   (SEQ ID NO: 4825)

βc-3115 21 nt Target:   5'-AGGAGTAACAATACAAATGGA-3'   (SEQ ID NO: 4826)

βc-3191 21 nt Target:   5'-TTTATCAAACCCTAGCCTTGC-3'   (SEQ ID NO: 4827)

βc-3193 21 nt Target:   5'-TATCAAACCCTAGCCTTGCTT-3'   (SEQ ID NO: 4828)

βc-3195 21 nt Target:   5'-TCAAACCCTAGCCTTGCTTGT-3'   (SEQ ID NO: 4829)

βc-3387 21 nt Target:   5'-TTGAGTAATGGTGTAGAACAC-3'   (SEQ ID NO: 4830)

βc-3389 21 nt Target:   5'-GAGTAATGGTGTAGAACACTA-3'   (SEQ ID NO: 4831)

βc-3391 21 nt Target:   5'-GTAATGGTGTAGAACACTAAT-3'   (SEQ ID NO: 4832)

βc-3393 21 nt Target:   5'-AATGGTGTAGAACACTAATTC-3'   (SEQ ID NO: 4833)

βc-3395 21 nt Target:   5'-TGGTGTAGAACACTAATTCAT-3'   (SEQ ID NO: 4834)

βc-3397 21 nt Target:   5'-GTGTAGAACACTAATTCATAA-3'   (SEQ ID NO: 4835)

βc-3399 21 nt Target:   5'-GTAGAACACTAATTCATAATC-3'   (SEQ ID NO: 4836)

βc-3401 21 nt Target:   5'-AGAACACTAATTCATAATCAC-3'   (SEQ ID NO: 4837)

βc-3500 21 nt Target:   5'-AATTAGTTTCCTTTTTAATAT-3'   (SEQ ID NO: 4838)

βc-3502 21 nt Target:   5'-TTAGTTTCCTTTTTAATATGC-3'   (SEQ ID NO: 4839)

βc-3504 21 nt Target:   5'-AGTTTCCTTTTTAATATGCTT-3'   (SEQ ID NO: 4840)

βc-3506 21 nt Target:   5'-TTTCCTTTTTAATATGCTTAA-3'   (SEQ ID NO: 4841)

βc-3508 21 nt Target:   5'-TCCTTTTTAATATGCTTAAAA-3'   (SEQ ID NO: 4842)

βc-3509 21 nt Target:   5'-CCTTTTTAATATGCTTAAAAT-3'   (SEQ ID NO: 4843)

βc-3510 21 nt Target:   5'-CTTTTTAATATGCTTAAAATA-3'   (SEQ ID NO: 4844)

βc-3512 21 nt Target:   5'-TTTTAATATGCTTAAAATAAG-3'   (SEQ ID NO: 4845)

βc-3514 21 nt Target:   5'-TTAATATGCTTAAAATAAGCA-3'   (SEQ ID NO: 4846)

βc-3516 21 nt Target:   5'-AATATGCTTAAAATAAGCAGG-3'   (SEQ ID NO: 4847)

βc-3518 21 nt Target:   5'-TATGCTTAAAATAAGCAGGTG-3'   (SEQ ID NO: 4848)

βc-3520 21 nt Target:   5'-TGCTTAAAATAAGCAGGTGGA-3'   (SEQ ID NO: 4849)

βc-3522 21 nt Target:   5'-CTTAAAATAAGCAGGTGGATC-3'   (SEQ ID NO: 4850)

βc-3524 21 nt Target:   5'-TAAAATAAGCAGGTGGATCTA-3'   (SEQ ID NO: 4851)

βc-3526 21 nt Target:   5'-AAATAAGCAGGTGGATCTATT-3'   (SEQ ID NO: 4852)

βc-3528 21 nt Target:   5'-ATAAGCAGGTGGATCTATTTC-3'   (SEQ ID NO: 4853)

βc-3530 21 nt Target:   5'-AAGCAGGTGGATCTATTTCAT-3'   (SEQ ID NO: 4854)

βc-3532 21 nt Target:   5'-GCAGGTGGATCTATTTCATGT-3'   (SEQ ID NO: 4855)

βc-3534 21 nt Target:   5'-AGGTGGATCTATTTCATGTTT-3'   (SEQ ID NO: 4856)

βc-3536 21 nt Target:   5'-GTGGATCTATTTCATGTTTTT-3'   (SEQ ID NO: 4857)

βc-3538 21 nt Target:   5'-GGATCTATTTCATGTTTTTGA-3'   (SEQ ID NO: 4858)

βc-3583 21 nt Target:   5'-GGGTAGGGTAAATCAGTAAGA-3'   (SEQ ID NO: 4859)

βc-3585 21 nt Target:   5'-GTAGGGTAAATCAGTAAGAGG-3'   (SEQ ID NO: 4860)

TABLE 5-continued

21 Nucleotide Target Sequences of Selected DsiRNAs

| | | |
|---|---|---|
| βc-3587 21 nt Target: | 5'-AGGGTAAATCAGTAAGAGGTG-3' | (SEQ ID NO: 4861) |
| βc-3589 21 nt Target: | 5'-GGTAAATCAGTAAGAGGTGTT-3' | (SEQ ID NO: 4862) |
| βc-3591 21 nt Target: | 5'-TAAATCAGTAAGAGGTGTTAT-3' | (SEQ ID NO: 4863) |
| βc-3593 21 nt Target: | 5'-AATCAGTAAGAGGTGTTATTT-3' | (SEQ ID NO: 4864) |
| βc-3633 21 nt Target: | 5'-TTTACCAGTTGCCTTTTATCC-3' | (SEQ ID NO: 4865) |
| βc-3635 21 nt Target: | 5'-TACCAGTTGCCTTTTATCCCA-3' | (SEQ ID NO: 4866) |
| βc-3637 21 nt Target: | 5'-CCAGTTGCCTTTTATCCCAAA-3' | (SEQ ID NO: 4867) |
| βc-3639 21 nt Target: | 5'-AGTTGCCTTTTATCCCAAAGT-3' | (SEQ ID NO: 4868) |
| βc-3641 21 nt Target: | 5'-TTGCCTTTTATCCCAAAGTTG-3' | (SEQ ID NO: 4869) |
| βc-3643 21 nt Target: | 5'-GCCTTTTATCCCAAAGTTGTT-3' | (SEQ ID NO: 4870) |
| βc-3645 21 nt Target: | 5'-CTTTTATCCCAAAGTTGTTGT-3' | (SEQ ID NO: 4871) |
| βc-3647 21 nt Target: | 5'-TTTATCCCAAAGTTGTTGTAA-3' | (SEQ ID NO: 4872) |
| βc-3649 21 nt Target: | 5'-TATCCCAAAGTTGTTGTAACC-3' | (SEQ ID NO: 4873) |
| βc-3651 21 nt Target: | 5'-TCCCAAAGTTGTTGTAACCTG-3' | (SEQ ID NO: 4874) |
| βc-3653 21 nt Target: | 5'-CCAAAGTTGTTGTAACCTGCT-3' | (SEQ ID NO: 4875) |
| βc-3655 21 nt Target: | 5'-AAAGTTGTTGTAACCTGCTGT-3' | (SEQ ID NO: 4876) |
| βc-3657 21 nt Target: | 5'-AGTTGTTGTAACCTGCTGTGA-3' | (SEQ ID NO: 4877) |
| βc-3659 21 nt Target: | 5'-TTGTTGTAACCTGCTGTGATA-3' | (SEQ ID NO: 4878) |
| βc-3708 21 nt Target: | 5'-AAAAATGGTTCAGAATTAAAC-3' | (SEQ ID NO: 4879) |
| βc-3710 21 nt Target: | 5'-AAATGGTTCAGAATTAAACTT-3' | (SEQ ID NO: 4880) |
| βc-3712 21 nt Target: | 5'-ATGGTTCAGAATTAAACTTTT-3' | (SEQ ID NO: 4881) |
| βc-3714 21 nt Target: | 5'-GGTTCAGAATTAAACTTTTAA-3' | (SEQ ID NO: 4882) |
| βc-3716 21 nt Target: | 5'-TTCAGAATTAAACTTTTAATT-3' | (SEQ ID NO: 4883) |
| βc-m314 21 nt Target: | 5'-CAGCAGCAGTCTTACTTGGAT-3' | (SEQ ID NO: 4884) |
| βc-m325 21 nt Target: | 5'-TTACTTGGATTCTGGAATCCA-3' | (SEQ ID NO: 4885) |
| βc-m408 21 nt Target: | 5'-TTGACACCTCCCAAGTCCTTT-3' | (SEQ ID NO: 4886) |
| βc-m460 21 nt Target: | 5'-CACGCAAGAGCAAGTAGCTGA-3' | (SEQ ID NO: 4887) |
| βc-m526 21 nt Target: | 5'-TGCCATGTTCCCTGAGACGCT-3' | (SEQ ID NO: 4888) |
| βc-m631 21 nt Target: | 5'-GTTGAAACATGCAGTTGTCAA-3' | (SEQ ID NO: 4889) |
| βc-m636 21 nt Target: | 5'-AACATGCAGTTGTCAATTTGA-3' | (SEQ ID NO: 4890) |
| βc-m642 21 nt Target: | 5'-CAGTTGTCAATTTGATTAACT-3' | (SEQ ID NO: 4891) |
| βc-m723 21 nt Target: | 5'-ATGAGGACCAGGTGGTAGTTA-3' | (SEQ ID NO: 4892) |
| βc-m970 21 nt Target: | 5'-TGGGTCACCAGTGGATTCTGT-3' | (SEQ ID NO: 4893) |
| βc-m976 21 nt Target: | 5'-ACCAGTGGATTCTGTACTGTT-3' | (SEQ ID NO: 4894) |
| βc-m981 21 nt Target: | 5'-TGGATTCTGTACTGTTCTACG-3' | (SEQ ID NO: 4895) |
| βc-m1066 21 nt Target: | 5'-TGGTGGACTGCAGAAAATGGT-3' | (SEQ ID NO: 4896) |
| βc-m1106 21 nt Target: | 5'-AACGTGAAATTCTTGGCTATT-3' | (SEQ ID NO: 4897) |
| βc-m1354 21 nt Target: | 5'-CCCAAGTCAGCGACTTGTTCA-3' | (SEQ ID NO: 4898) |
| βc-m1363 21 nt Target: | 5'-GCGACTTGTTCAAAACTGTCT-3' | (SEQ ID NO: 4899) |

TABLE 5-continued

21 Nucleotide Target Sequences of Selected DsiRNAs

| βc-m1373 21 nt Target: | 5'-CAAAACTGTCTTTGGACTCTC-3' | (SEQ ID NO: 4900) |
| βc-m1508 21 nt Target: | 5'-CTCTCTAACCTCACTTGCAAT-3' | (SEQ ID NO: 4901) |
| βc-m1515 21 nt Target: | 5'-ACCTCACTTGCAATAATTACA-3' | (SEQ ID NO: 4902) |
| βc-m1682 21 nt Target: | 5'-CAGAATGCCGTTCGCCTTCAT-3' | (SEQ ID NO: 4903) |
| βc-m1693 21 nt Target: | 5'-TCGCCTTCATTATGGACTGCC-3' | (SEQ ID NO: 4904) |
| βc-m1698 21 nt Target: | 5'-TTCATTATGGACTGCCTGTTG-3' | (SEQ ID NO: 4905) |
| βc-m1705 21 nt Target: | 5'-TGGACTGCCTGTTGTGGTTAA-3' | (SEQ ID NO: 4906) |
| βc-m1763 21 nt Target: | 5'-GCAACTGTTGGATTGATTCGA-3' | (SEQ ID NO: 4907) |
| βc-m2008 21 nt Target: | 5'-CCGAGGACTCAATACCATTCC-3' | (SEQ ID NO: 4908) |
| βc-m2226 21 nt Target: | 5'-CTGAGGACAAGCCACAGGATT-3' | (SEQ ID NO: 4909) |
| βc-m2427 21 nt Target: | 5'-GGATGGACCCTATGATGGAGC-3' | (SEQ ID NO: 4910) |
| βc-m2568 21 nt Target: | 5'-TTGATACTGACCTGTAAATCG-3' | (SEQ ID NO: 4911) |
| βc-m2614 21 nt Target: | 5'-AGCCAGTGTGGGTGAATACTT-3' | (SEQ ID NO: 4912) |
| βc-m2770 21 nt Target: | 5'-TGCCACAGCTTTTGCAGCGTT-3' | (SEQ ID NO: 4913) |
| βc-m2777 21 nt Target: | 5'-GCTTTTGCAGCGTTATACTCA-3' | (SEQ ID NO: 4914) |
| βc-m2784 21 nt Target: | 5'-CAGCGTTATACTCAGATGAGT-3' | (SEQ ID NO: 4915) |
| βc-m2806 21 nt Target: | 5'-ACATTTGCTGTTTTCAACATT-3' | (SEQ ID NO: 4916) |
| βc-m2850 21 nt Target: | 5'-AGCTGTAGTGTCTGAACGTGC-3' | (SEQ ID NO: 4917) |
| βc-m2965 21 nt Target: | 5'-GGGAACAGTCGAAGTACGCTT-3' | (SEQ ID NO: 4918) |
| βc-m2970 21 nt Target: | 5'-CAGTCGAAGTACGCTTTTTGT-3' | (SEQ ID NO: 4919) |
| βc-m2976 21 nt Target: | 5'-AAGTACGCTTTTTGTTCTGGT-3' | (SEQ ID NO: 4920) |
| βc-m3092 21 nt Target: | 5'-ACCCTAGCCTTGCTTGTTCTT-3' | (SEQ ID NO: 4921) |
| βc-m3097 21 nt Target: | 5'-AGCCTTGCTTGTTCTTTGTTT-3' | (SEQ ID NO: 4922) |
| βc-m3198 21 nt Target: | 5'-TGAACCTGCTACAGCAATTTC-3' | (SEQ ID NO: 4923) |
| βc-m3207 21 nt Target: | 5'-TACAGCAATTTCTGATTTCTA-3' | (SEQ ID NO: 4924) |
| βc-m3433 21 nt Target: | 5'-CAGTAAGAGGTGTTATTTGAG-3' | (SEQ ID NO: 4925) |
| βc-m3439 21 nt Target: | 5'-GAGGTGTTATTTGAGCCTTGT-3' | (SEQ ID NO: 4926) |
| βc-m3444 21 nt Target: | 5'-GTTATTTGAGCCTTGTTTTGG-3' | (SEQ ID NO: 4927) |
| βc-m3449 21 nt Target: | 5'-TTGAGCCTTGTTTTGGACAGT-3' | (SEQ ID NO: 4928) |
| βc-m3522 21 nt Target: | 5'-TTCAACAGATGCGGTTATAGA-3' | (SEQ ID NO: 4929) |
| βc-m3533 21 nt Target: | 5'-CGGTTATAGAAATGGTTCAGA-3' | (SEQ ID NO: 4930) |
| βc-m3538 21 nt Target: | 5'-ATAGAAATGGTTCAGAATTAA-3' | (SEQ ID NO: 4931) |

TABLE 6

Selected Anti-β-catenin DsiRNA Agents, Unmodified Duplexes

| | 5'-CUGAGGGUAUUUGAAGUAUACCAUA-3' | (SEQ ID NO: 3335) |
| | 3'-GGGACUCCCAUAAACUUCAUAUGGUAU-5' | (SEQ ID NO: 1117) |
| βc-240 Target: | 5'-CCCTGAGGGTATTTGAAGTATACCATA-3' | (SEQ ID NO: 2226) |
| | 5'-GGGUAUUUGAAGUAUACCAUACAAC-3' | (SEQ ID NO: 3336) |
| | 3'-CUCCCAUAAACUUCAUAUGGUAUGUUG-5' | (SEQ ID NO: 1118) |
| βc-244 Target: | 5'-GAGGGTATTTGAAGTATACCATACAAC-3' | (SEQ ID NO: 2227) |

TABLE 6-continued

Selected Anti-β-catenin DsiRNA Agents, Unmodified Duplexes

|  |  |  |  |
|---|---|---|---|
|  | 5'-AAGUAUACCAUACAACUGUUUUGAA-3' | (SEQ ID NO: 3337) |  |
|  | 3'-ACUUCAUAUGGUAUGUUGACAAAACUU-5' | (SEQ ID NO: 1119) |  |
| βc-253 Target: | 5'-TGAAGTATACCATACAACTGTTTTGAA-3' | (SEQ ID NO: 2228) |  |
|  | 5'-ACCAUACAACUGUUUUGAAAAUCCA-3' | (SEQ ID NO: 3338) |  |
|  | 3'-UAUGGUAUGUUGACAAAACUUUUAGGU-5' | (SEQ ID NO: 1120) |  |
| βc-259 Target: | 5'-ATACCATACAACTGTTTTGAAAATCCA-3' | (SEQ ID NO: 2229) |  |
|  | 5'-ACAACUGUUUUGAAAAUCCAGCGUG-3' | (SEQ ID NO: 3339) |  |
|  | 3'-UAUGUUGACAAAACUUUUAGGUCGCAC-5' | (SEQ ID NO: 1121) |  |
| βc-264 Target: | 5'-ATACAACTGTTTTGAAAATCCAGCGTG-3' | (SEQ ID NO: 2230) |  |
|  | 5'-GGGAUUUUCUCAGUCCUUCACUCAA-3' | (SEQ ID NO: 3340) |  |
|  | 3'-GUCCCUAAAAGAGUCAGGAAGUGAGUU-5' | (SEQ ID NO: 1122) |  |
| βc-496 Target: | 5'-CAGGGATTTTCTCAGTCCTTCACTCAA-3' | (SEQ ID NO: 2231) |  |
|  | 5'-CUCAAGAACAAGUAGCUGAUAUUGA-3' | (SEQ ID NO: 3341) |  |
|  | 3'-GUGAGUUCUUGUUCAUCGACUAUAACU-5' | (SEQ ID NO: 1123) |  |
| βc-516 Target: | 5'-CACTCAAGAACAAGTAGCTGATATTGA-3' | (SEQ ID NO: 2232) |  |
|  | 5'-AACAAGUAGCUGAUAUUGAUGGACA-3' | (SEQ ID NO: 3342) |  |
|  | 3'-UCUUGUUCAUCGACUAUAACUACCUGU-5' | (SEQ ID NO: 1124) |  |
| βc-522 Target: | 5'-AGAACAAGTAGCTGATATTGATGGACA-3' | (SEQ ID NO: 2233) |  |
|  | 5'-CAAGUAGCUGAUAUUGAUGGACAGU-3' | (SEQ ID NO: 3343) |  |
|  | 3'-UUGUUCAUCGACUAUAACUACCUGUCA-5' | (SEQ ID NO: 1125) |  |
| βc-524 Target: | 5'-AACAAGTAGCTGATATTGATGGACAGT-3' | (SEQ ID NO: 2234) |  |
|  | 5'-AUGGACAGUAUGCAAUGACUCGAGC-3' | (SEQ ID NO: 3344) |  |
|  | 3'-ACUACCUGUCAUACGUUACUGAGCUCG-5' | (SEQ ID NO: 1126) |  |
| βc-540 Target: | 5'-TGATGGACAGTATGCAATGACTCGAGC-3' | (SEQ ID NO: 2235) |  |
|  | 5'-CUAUGUUCCCUGAGACAUUAGAUGA-3' | (SEQ ID NO: 3345) |  |
|  | 3'-ACGAUACAAGGGACUCUGUAAUCUACU-5' | (SEQ ID NO: 1127) |  |
| βc-582 Target: | 5'-TGCTATGTTCCCTGAGACATTAGATGA-3' | (SEQ ID NO: 2236) |  |
|  | 5'-CUGAAACAUGCAGUUGUAAACUUGA-3' | (SEQ ID NO: 3346) |  |
|  | 3'-ACGACUUUGUACGUCAACAUUUGAACU-5' | (SEQ ID NO: 1128) |  |
| βc-686 Target: | 5'-TGCTGAAACATGCAGTTGTAAACTTGA-3' | (SEQ ID NO: 2237) |  |
|  | 5'-CAUGCAGUUGUAAACUUGAUUAACU-3' | (SEQ ID NO: 3347) |  |
|  | 3'-UUGUACGUCAACAUUUGAACUAAUUGA-5' | (SEQ ID NO: 1129) |  |
| βc-692 Target: | 5'-AACATGCAGTTGTAAACTTGATTAACT-3' | (SEQ ID NO: 2238) |  |
|  | 5'-AGUUGUAAACUUGAUUAACUAUCAA-3' | (SEQ ID NO: 3348) |  |
|  | 3'-CGUCAACAUUUGAACUAAUUGAUAGUU-5' | (SEQ ID NO: 1130) |  |
| βc-697 Target: | 5'-GCAGTTGTAAACTTGATTAACTATCAA-3' | (SEQ ID NO: 2239) |  |
|  | 5'-UUGAUUAACUAUCAAGAUGAUGCAG-3' | (SEQ ID NO: 3349) |  |
|  | 3'-UGAACUAAUUGAUAGUUCUACUACGUC-5' | (SEQ ID NO: 1131) |  |
| βc-707 Target: | 5'-ACTTGATTAACTATCAAGATGATGCAG-3' | (SEQ ID NO: 2240) |  |
|  | 5'-CUGAACUGACAAAACUGCUAAAUGA-3' | (SEQ ID NO: 3350) |  |
|  | 3'-GGGACUUGACUGUUUUGACGAUUUACU-5' | (SEQ ID NO: 1132) |  |
| βc-753 Target: | 5'-CCCTGAACTGACAAAACTGCTAAATGA-3' | (SEQ ID NO: 2241) |  |
|  | 5'-AGAUGGUGUCUGCUAUUGUACGUAC-3' | (SEQ ID NO: 3351) |  |
|  | 3'-AGUCUACCACAGACGAUAACAUGCAUG-5' | (SEQ ID NO: 1133) |  |
| βc-870 Target: | 5'-TCAGATGGTGTCTGCTATTGTACGTAC-3' | (SEQ ID NO: 2242) |  |
|  | 5'-ACGUACCAUGCAGAAUACAAAUGAU-3' | (SEQ ID NO: 3352) |  |
|  | 3'-CAUGCAUGGUACGUCUUAUGUUUACUA-5' | (SEQ ID NO: 1134) |  |
| βc-889 Target: | 5'-GTACGTACCATGCAGAATACAAATGAT-3' | (SEQ ID NO: 2243) |  |
|  | 5'-UACAACUCUCCACAACCUUUUAUUA-3' | (SEQ ID NO: 3353) |  |
|  | 3'-UAAUGUUGAGAGGUGUUGGAAAAUAAU-5' | (SEQ ID NO: 1135) |  |
| βc-1060 Target: | 5'-ATTACAACTCTCCACAACCTTTTATTA-3' | (SEQ ID NO: 2244) |  |
|  | 5'-CUCUCCACAACCUUUUAUUACAUCA-3' | (SEQ ID NO: 3354) |  |
|  | 3'-UUGAGAGGUGUUGGAAAAUAAUGUAGU-5' | (SEQ ID NO: 1136) |  |
| βc-1065 Target: | 5'-AACTCTCCACAACCTTTTATTACATCA-3' | (SEQ ID NO: 2245) |  |
|  | 5'-CACAACCUUUUAUUACAUCAAGAAG-3' | (SEQ ID NO: 3355) |  |
|  | 3'-AGGUGUUGGAAAAUAAUGUAGUUCUUC-5' | (SEQ ID NO: 1137) |  |
| βc-1070 Target: | 5'-TCCACAACCTTTTATTACATCAAGAAG-3' | (SEQ ID NO: 2246) |  |

TABLE 6-continued

Selected Anti-β-catenin DsiRNA Agents, Unmodified Duplexes

| | | |
|---|---|---|
| βc-1076 Target: | 5'-CUUUUAUUACAUCAAGAAGGAGCUA-3'<br>3'-UGGAAAAUAAUGUAGUUCUUCCUCGAU-5'<br>5'-ACCTTTTATTACATCAAGAAGGAGCTA-3' | (SEQ ID NO: 3356)<br>(SEQ ID NO: 1138)<br>(SEQ ID NO: 2247) |
| βc-1154 Target: | 5'-AAAACAAAUGUUAAAUUCUUGGCUA-3'<br>3'-UGUUUUGUUUACAAUUUAAGAACCGAU-5'<br>5'-ACAAAACAAATGTTAAATTCTTGGCTA-3' | (SEQ ID NO: 3357)<br>(SEQ ID NO: 1139)<br>(SEQ ID NO: 2248) |
| βc-1180 Target: | 5'-UACGACAGACUGCCUUCAAAUUUUA-3'<br>3'-UAAUGCUGUCUGACGGAAGUUUAAAAU-5'<br>5'-ATTACGACAGACTGCCTTCAAATTTTA-3' | (SEQ ID NO: 3358)<br>(SEQ ID NO: 1140)<br>(SEQ ID NO: 2249) |
| βc-1185 Target: | 5'-CAGACUGCCUUCAAAUUUUAGCUUA-3'<br>3'-CUGUCUGACGGAAGUUUAAAAUCGAAU-5'<br>5'-GACAGACTGCCTTCAAATTTTAGCTTA-3' | (SEQ ID NO: 3359)<br>(SEQ ID NO: 1141)<br>(SEQ ID NO: 2250) |
| βc-1260 Target: | 5'-CUUUAGUAAAUAUAAUGAGGACCUA-3'<br>3'-UCGAAAUCAUUUAUAUUACUCCUGGAU-5'<br>5'-AGCTTTAGTAAATATAATGAGGACCTA-3' | (SEQ ID NO: 3360)<br>(SEQ ID NO: 1142)<br>(SEQ ID NO: 2251) |
| βc-1294 Target: | 5'-AAAACUACUGUGGACCACAAGCAGA-3'<br>3'-CUUUUUGAUGACACCUGGUGUUCGUCU-5'<br>5'-GAAAAACTACTGTGGACCACAAGCAGA-3' | (SEQ ID NO: 3361)<br>(SEQ ID NO: 1143)<br>(SEQ ID NO: 2252) |
| βc-1412 Target: | 5'-AGUCAACGUCUUGUUCAGAACUGUC-3'<br>3'-GUUCAGUUGCAGAACAAGUCUUGACAG-5'<br>5'-CAAGTCAACGTCTTGTTCAGAACTGTC-3' | (SEQ ID NO: 3362)<br>(SEQ ID NO: 1144)<br>(SEQ ID NO: 2253) |
| βc-1418 Target: | 5'-CGUCUUGUUCAGAACUGUCUUUGGA-3'<br>3'-UUGCAGAACAAGUCUUGACAGAAACCU-5'<br>5'-AACGTCTTGTTCAGAACTGTCTTTGGA-3' | (SEQ ID NO: 3363)<br>(SEQ ID NO: 1145)<br>(SEQ ID NO: 2254) |
| βc-1423 Target: | 5'-UGUUCAGAACUGUCUUUGGACUCUC-3'<br>3'-GAACAAGUCUUGACAGAAACCUGAGAG-5'<br>5'-CTTGTTCAGAACTGTCTTTGGACTCTC-3' | (SEQ ID NO: 3364)<br>(SEQ ID NO: 1146)<br>(SEQ ID NO: 2255) |
| βc-1520 Target: | 5'-GGUUCAGAUGAUAUAAAUGUGGUCA-3'<br>3'-ACCCAAGUCUACUAUAUUUACACCAGU-5'<br>5'-TGGGTTCAGATGATATAAATGTGGTCA-3' | (SEQ ID NO: 3365)<br>(SEQ ID NO: 1147)<br>(SEQ ID NO: 2256) |
| βc-1561 Target: | 5'-UCUUUCUAACCUCACUUGCAAUAAU-3'<br>3'-UAAGAAAGAUUGGAGUGAACGUUAUUA-5'<br>5'-ATTCTTTCTAACCTCACTTGCAATAAT-3' | (SEQ ID NO: 3366)<br>(SEQ ID NO: 1148)<br>(SEQ ID NO: 2257) |
| βc-1571 Target: | 5'-CUCACUUGCAAUAAUUAUAAGAACA-3'<br>3'-UGGAGUGAACGUUAUUAAUAUUCUUGU-5'<br>5'-ACCTCACTTGCAATAATTATAAGAACA-3' | (SEQ ID NO: 3367)<br>(SEQ ID NO: 1149)<br>(SEQ ID NO: 2258) |
| βc-1579 Target: | 5'-CAAUAAUUAUAAGAACAAGAUGAUG-3'<br>3'-ACGUUAUUAAUAUUCUUGUUCUACUAC-5'<br>5'-TGCAATAATTATAAGAACAAGATGATG-3' | (SEQ ID NO: 3368)<br>(SEQ ID NO: 1150)<br>(SEQ ID NO: 2259) |
| βc-1620 Target: | 5'-GUAUAGAGGCUCUUGUGCGUACUGU-3'<br>3'-ACCAUAUCUCCGAGAACACGCAUGACA-5'<br>5'-TGGTATAGAGGCTCTTGTGCGTACTGT-3' | (SEQ ID NO: 3369)<br>(SEQ ID NO: 1151)<br>(SEQ ID NO: 2260) |
| βc-1816 Target: | 5'-GGCUACUGUUGGAUUGAUUCGAAAU-3'<br>3'-UUCCGAUGACAACCUAACUAAGCUUUA-5'<br>5'-AAGGCTACTGTTGGATTGATTCGAAAT-3' | (SEQ ID NO: 3370)<br>(SEQ ID NO: 1152)<br>(SEQ ID NO: 2261) |
| βc-1987 Target: | 5'-CAUGGAAGAAAUAGUUGAAGGUUGU-3'<br>3'-GCGUACCUUCUUUAUCAACUUCCAACA-5'<br>5'-CGCATGGAAGAAATAGTTGAAGGTTGT-3' | (SEQ ID NO: 3371)<br>(SEQ ID NO: 1153)<br>(SEQ ID NO: 2262) |
| βc-1989 Target: | 5'-UGGAAGAAAUAGUUGAAGGUUGUAC-3'<br>3'-GUACCUUCUUUAUCAACUUCCAACAUG-5'<br>5'-CATGGAAGAAATAGTTGAAGGTTGTAC-3' | (SEQ ID NO: 3372)<br>(SEQ ID NO: 1154)<br>(SEQ ID NO: 2263) |
| βc-2111 Target: | 5'-AUUGAAAACAUCCAAAGAGUAGCUG-3'<br>3'-GGUAACUUUUGUAGGUUUCUCAUCGAC-5'<br>5'-CCATTGAAAACATCCAAAGAGTAGCTG-3' | (SEQ ID NO: 3373)<br>(SEQ ID NO: 1155)<br>(SEQ ID NO: 2264) |
| βc-2282 Target: | 5'-GAGGACAAGCCACAAGAUUACAAGA-3'<br>3'-GACUCCUGUUCGGUGUUCUAAUGUUCU-5'<br>5'-CTGAGGACAAGCCACAAGATTACAAGA-3' | (SEQ ID NO: 3374)<br>(SEQ ID NO: 1156)<br>(SEQ ID NO: 2265) |

TABLE 6-continued

Selected Anti-β-catenin DsiRNA Agents, Unmodified Duplexes

| | | |
|---|---|---|
| βc-2624 Target: | 5'-GAUACUGACCUGUAAAUCAUCCUUU-3'<br>3'-AACUAUGACUGGACAUUUAGUAGGAAA-5'<br>5'-TTGATACTGACCTGTAAATCATCCTTT-3' | (SEQ ID NO: 3375)<br>(SEQ ID NO: 1157)<br>(SEQ ID NO: 2266) |
| βc-2647 Target: | 5'-UUAGGUAAGAAGUUUUAAAAAGCCA-3'<br>3'-GAAAUCCAUUCUUCAAAAUUUUUCGGU-5'<br>5'-CTTTAGGTAAGAAGTTTTAAAAAGCCA-3' | (SEQ ID NO: 3376)<br>(SEQ ID NO: 1158)<br>(SEQ ID NO: 2267) |
| βc-2770 Target: | 5'-CAGGUAUAUACUUUGAAAGGAGAUG-3'<br>3'-UUGUCCAUAUAUGAAACUUUCCUCUAC-5'<br>5'-AACAGGTATATACTTTGAAAGGAGATG-3' | (SEQ ID NO: 3377)<br>(SEQ ID NO: 1159)<br>(SEQ ID NO: 2268) |
| βc-2848 Target: | 5'-GAAGUUAUUAACUUUAAUGUUUUUU-3'<br>3'-ACCUUCAAUAAUUGAAAUUACAAAAAA-5'<br>5'-TGGAAGTTATTAACTTTAATGTTTTTT-3' | (SEQ ID NO: 3378)<br>(SEQ ID NO: 1160)<br>(SEQ ID NO: 2269) |
| βc-2874 Target: | 5'-CCACAGCUUUUGCAACUUAAUACUC-3'<br>3'-ACGGUGUCGAAAACGUUGAAUUAUGAG-5'<br>5'-TGCCACAGCTTTTGCAACTTAATACTC-3' | (SEQ ID NO: 3379)<br>(SEQ ID NO: 1161)<br>(SEQ ID NO: 2270) |
| βc-2909 Target: | 5'-CAUUUGCUGUUUUAAACAUUAAUAG-3'<br>3'-UUGUAAACGACAAAAUUUGUAAUUAUC-5'<br>5'-AACATTTGCTGTTTTAAACATTAATAG-3' | (SEQ ID NO: 3380)<br>(SEQ ID NO: 1162)<br>(SEQ ID NO: 2271) |
| βc-3074 Target: | 5'-CAAUUGAAGUAAACUUUUUGUUCUG-3'<br>3'-UUGUUAACUUCAUUUGAAAAACAAGAC-5'<br>5'-AACAATTGAAGTAAACTTTTGTTCTG-3' | (SEQ ID NO: 3381)<br>(SEQ ID NO: 1163)<br>(SEQ ID NO: 2272) |
| βc-3197 Target: | 5'-ACCCUAGCCUUGCUUGUUAAAUUUU-3'<br>3'-UUUGGGAUCGGAACGAACAAUUUAAAA-5'<br>5'-AAACCCTAGCCTTGCTTGTTAAATTTT-3' | (SEQ ID NO: 3382)<br>(SEQ ID NO: 1164)<br>(SEQ ID NO: 2273) |
| βc-3203 Target: | 5'-GCCUUGCUUGUUAAAUUUUUUUUU-3'<br>3'-AUCGGAACGAACAAUUUAAAAAAAAAA-5'<br>5'-TAGCCTTGCTTGTTAAATTTTTTTTT-3' | (SEQ ID NO: 3383)<br>(SEQ ID NO: 1165)<br>(SEQ ID NO: 2274) |
| βc-3273 Target: | 5'-GAAGUAGCUCUUUUUUUUUUUUUU-3'<br>3'-AACUUCAUCGAGAAAAAAAAAAAAAA-5'<br>5'-TTGAAGTAGCTCTTTTTTTTTTTTT-3' | (SEQ ID NO: 3384)<br>(SEQ ID NO: 1166)<br>(SEQ ID NO: 2275) |
| βc-3333 Target: | 5'-GUAGUGUUAAGUUAUAGUGAAUACU-3'<br>3'-AGCAUCACAAUUCAAUAUCACUUAUGA-5'<br>5'-TCGTAGTGTTAAGTTATAGTGAATACT-3' | (SEQ ID NO: 3385)<br>(SEQ ID NO: 1167)<br>(SEQ ID NO: 2276) |
| βc-3349 Target: | 5'-GUGAAUACUGCUACAGCAAUUUCUA-3'<br>3'-AUCACUUAUGACGAUGUCGUUAAAGAU-5'<br>5'-TAGTGAATACTGCTACAGCAATTTCTA-3' | (SEQ ID NO: 3386)<br>(SEQ ID NO: 1168)<br>(SEQ ID NO: 2277) |
| βc-3354 Target: | 5'-UACUGCUACAGCAAUUUCUAAUUUU-3'<br>3'-UUAUGACGAUGUCGUUAAAGAUUAAAA-5'<br>5'-AATACTGCTACAGCAATTTCTAATTTT-3' | (SEQ ID NO: 3387)<br>(SEQ ID NO: 1169)<br>(SEQ ID NO: 2278) |
| βc-3371 Target: | 5'-CUAAUUUUUAAGAAUUGAGUAAUGG-3'<br>3'-AAGAUUAAAAAUUCUUAACUCAUUACC-5'<br>5'-TTCTAATTTTTAAGAATTGAGTAATGG-3' | (SEQ ID NO: 3388)<br>(SEQ ID NO: 1170)<br>(SEQ ID NO: 2279) |
| βc-3376 Target: | 5'-UUUUAAGAAUUGAGUAAUGGUGUAG-3'<br>3'-UAAAAUUCUUAACUCAUUACCACAUC-5'<br>5'-ATTTTTAAGAATTGAGTAATGGTGTAG-3' | (SEQ ID NO: 3389)<br>(SEQ ID NO: 1171)<br>(SEQ ID NO: 2280) |
| βc-3411 Target: | 5'-CAUAAUCACUCUAAUUAAUUGUAAU-3'<br>3'-AAGUAUUAGUGAGAUUAAUUAACAUUA-5'<br>5'-TTCATAATCACTCTAATTAATTGTAAT-3' | (SEQ ID NO: 3390)<br>(SEQ ID NO: 1172)<br>(SEQ ID NO: 2281) |
| βc-3426 Target: | 5'-UAAUUGUAAUCUGAAUAAAGUGUAA-3'<br>3'-UAAUUAACAUUAGACUUAUUUCACAUU-5'<br>5'-ATTAATTGTAATCTGAATAAAGTGTAA-3' | (SEQ ID NO: 3391)<br>(SEQ ID NO: 1173)<br>(SEQ ID NO: 2282) |
| βc-3431 Target: | 5'-GUAAUCUGAAUAAAGUGUAACAAUU-3'<br>3'-AACAUUAGACUUAUUUCACAUUGUUAA-5'<br>5'-TTGTAATCTGAATAAAGTGTAACAATT-3' | (SEQ ID NO: 3392)<br>(SEQ ID NO: 1174)<br>(SEQ ID NO: 2283) |
| βc-3437 Target: | 5'-UGAAUAAAGUGUAACAAUUGUGUAG-3'<br>3'-AGACUUAUUUCACAUUGUUAACACAUC-5'<br>5'-TCTGAATAAAGTGTAACAATTGTGTAG-3' | (SEQ ID NO: 3393)<br>(SEQ ID NO: 1175)<br>(SEQ ID NO: 2284) |

TABLE 6-continued

Selected Anti-β-catenin DsiRNA Agents, Unmodified Duplexes

|  |  |  |
|---|---|---|
|  | 5'-GUAGCCUUUUGUAUAAAAUAGACA-3' | (SEQ ID NO: 3394) |
|  | 3'-CACAUCGGAAAAACAUAUUUUAUCUGU-5' | (SEQ ID NO: 1176) |
| βc-3458 Target: | 5'-GTGTAGCCTTTTGTATAAAATAGACA-3' | (SEQ ID NO: 2285) |
|  | 5'-UGUAUAAAAUAGACAAAUAGAAAAU-3' | (SEQ ID NO: 3395) |
|  | 3'-AAACAUAUUUUAUCUGUUUAUCUUUUA-5' | (SEQ ID NO: 1177) |
| βc-3468 Target: | 5'-TTTGTATAAAATAGACAAATAGAAAAT-3' | (SEQ ID NO: 2286) |
|  | 5'-AAAAUGGUCCAAUUAGUUUCCUUUU-3' | (SEQ ID NO: 3396) |
|  | 3'-UCUUUUACCAGGUUAAUCAAAGGAAAA-5' | (SEQ ID NO: 1178) |
| βc-3488 Target: | 5'-AGAAAATGGTCCAATTAGTTTCCTTTT-3' | (SEQ ID NO: 2287) |
|  | 5'-CCAAUUAGUUUCCUUUUAAUAUGC-3' | (SEQ ID NO: 3397) |
|  | 3'-CAGGUUAAUCAAAGGAAAAAUUAUACG-5' | (SEQ ID NO: 1179) |
| βc-3496 Target: | 5'-GTCCAATTAGTTTCCTTTTAATATGC-3' | (SEQ ID NO: 2288) |
|  | 5'-UUUGAUCAAAACUAUUUGGGAUAU-3' | (SEQ ID NO: 3398) |
|  | 3'-AAAAACUAGUUUUGAUAAACCCUAUA-5' | (SEQ ID NO: 1180) |
| βc-3552 Target: | 5'-TTTTTGATCAAAACTATTTGGGATAT-3' | (SEQ ID NO: 2289) |
|  | 5'-GAGGUGUUAUUUGGAACCUUGUUUU-3' | (SEQ ID NO: 3399) |
|  | 3'-UUCUCCACAAUAAACCUUGGAACAAAA-5' | (SEQ ID NO: 1181) |
| βc-3600 Target: | 5'-AAGAGGTGTTATTTGGAACCTTGTTTT-3' | (SEQ ID NO: 2290) |
|  | 5'-GUUAUUUGGAACCUUGUUUUGGACA-3' | (SEQ ID NO: 3400) |
|  | 3'-CACAAUAAACCUUGGAACAAAACCUGU-5' | (SEQ ID NO: 1182) |
| βc-3605 Target: | 5'-GTGTTATTTGGAACCTTGTTTTGGACA-3' | (SEQ ID NO: 2291) |
|  | 5'-ACCUUGUUUUGGACAGUUUACCAGU-3' | (SEQ ID NO: 3401) |
|  | 3'-CUUGGAACAAAACCUGUCAAAUGGUCA-5' | (SEQ ID NO: 1183) |
| βc-3615 Target: | 5'-GAACCTTGTTTTGGACAGTTTACCAGT-3' | (SEQ ID NO: 2292) |
|  | 5'-GAUACGAUGCUUCAAGAGAAAAUGC-3' | (SEQ ID NO: 3402) |
|  | 3'-CACUAUGCUACGAAGUUCUCUUUUACG-5' | (SEQ ID NO: 1184) |
| βc-3674 Target: | 5'-GTGATACGATGCTTCAAGAGAAAATGC-3' | (SEQ ID NO: 2293) |
|  | 5'-CAAGAGAAAAUGCGGUUAUAAAAAA-3' | (SEQ ID NO: 3403) |
|  | 3'-AAGUUCUCUUUUACGCCAAUAUUUUUU-5' | (SEQ ID NO: 1185) |
| βc-3686 Target: | 5'-TTCAAGAGAAAATGCGGTTATAAAAAA-3' | (SEQ ID NO: 2294) |
|  | 5'-GAAAAUGCGGUUAUAAAAAAUGGUU-3' | (SEQ ID NO: 3404) |
|  | 3'-CUCUUUUACGCCAAUAUUUUUUACCAA-5' | (SEQ ID NO: 1186) |
| βc-3691 Target: | 5'-GAGAAAATGCGGTTATAAAAAATGGTT-3' | (SEQ ID NO: 2295) |
|  | 5'-GUUAUAAAAAAUGGUUCAGAAUUAA-3' | (SEQ ID NO: 3405) |
|  | 3'-GCCAAUAUUUUUUACCAAGUCUUAAUU-5' | (SEQ ID NO: 1187) |
| βc-3700 Target: | 5'-CGGTTATAAAAAATGGTTCAGAATTAA-3' | (SEQ ID NO: 2296) |
|  | 5'-AAAAUGGUUCAGAAUUAAACUUUUA-3' | (SEQ ID NO: 3406) |
|  | 3'-UUUUUUACCAAGUCUUAAUUUGAAAAU-5' | (SEQ ID NO: 1188) |
| βc-3707 Target: | 5'-AAAAAATGGTTCAGAATTAAACTTTTA-3' | (SEQ ID NO: 2297) |
|  | 5'-GCGUGGACAAUGGCUACUCAAGCUG-3' | (SEQ ID NO: 3407) |
|  | 3'-GUCGCACCUGUUACCGAUGAGUUCGAC-5' | (SEQ ID NO: 1189) |
| βc-284 Target: | 5'-CAGCGTGGACAATGGCTACTCAAGCTG-3' | (SEQ ID NO: 2298) |
|  | 5'-CGUGGACAAUGGCUACUCAAGCUGA-3' | (SEQ ID NO: 3408) |
|  | 3'-UCGCACCUGUUACCGAUGAGUUCGACU-5' | (SEQ ID NO: 1190) |
| βc-285 Target: | 5'-AGCGTGGACAATGGCTACTCAAGCTGA-3' | (SEQ ID NO: 2299) |
|  | 5'-GUGGACAAUGGCUACUCAAGCUGAU-3' | (SEQ ID NO: 3409) |
|  | 3'-CGCACCUGUUACCGAUGAGUUCGACUA-5' | (SEQ ID NO: 1191) |
| βc-286 Target: | 5'-GCGTGGACAATGGCTACTCAAGCTGAT-3' | (SEQ ID NO: 2300) |
|  | 5'-UGGACAAUGGCUACUCAAGCUGAUU-3' | (SEQ ID NO: 3410) |
|  | 3'-GCACCUGUUACCGAUGAGUUCGACUAA-5' | (SEQ ID NO: 1192) |
| βc-287 Target: | 5'-CGTGGACAATGGCTACTCAAGCTGATT-3' | (SEQ ID NO: 2301) |
|  | 5'-GGACAAUGGCUACUCAAGCUGAUUU-3' | (SEQ ID NO: 3411) |
|  | 3'-CACCUGUUACCGAUGAGUUCGACUAAA-5' | (SEQ ID NO: 1193) |
| βc-288 Target: | 5'-GTGGACAATGGCTACTCAAGCTGATTT-3' | (SEQ ID NO: 2302) |
|  | 5'-GACAAUGGCUACUCAAGCUGAUUUG-3' | (SEQ ID NO: 3412) |
|  | 3'-ACCUGUUACCGAUGAGUUCGACUAAAC-5' | (SEQ ID NO: 1194) |
| βc-289 Target: | 5'-TGGACAATGGCTACTCAAGCTGATTTG-3' | (SEQ ID NO: 2303) |

TABLE 6-continued

Selected Anti-β-catenin DsiRNA Agents, Unmodified Duplexes

| | | |
|---|---|---|
| βc-290 Target: | 5'-ACAAUGGCUACUCAAGCUGAUUUGA-3'<br>3'-CCUGUUACCGAUGAGUUCGACUAAACU-5'<br>5'-GGACAATGGCTACTCAAGCTGATTTGA-3' | (SEQ ID NO: 3413)<br>(SEQ ID NO: 1195)<br>(SEQ ID NO: 2304) |
| βc-291 Target: | 5'-CAAUGGCUACUCAAGCUGAUUUGAU-3'<br>3'-CUGUUACCGAUGAGUUCGACUAAACUA-5'<br>5'-GACAATGGCTACTCAAGCTGATTTGAT-3' | (SEQ ID NO: 3414)<br>(SEQ ID NO: 1196)<br>(SEQ ID NO: 2305) |
| βc-312 Target: | 5'-UGAUGGAGUUGGACAUGGCCAUGGA-3'<br>3'-AAACUACCUCAACCUGUACCGGUACCU-5'<br>5'-TTTGATGGAGTTGGACATGGCCATGGA-3' | (SEQ ID NO: 3415)<br>(SEQ ID NO: 1197)<br>(SEQ ID NO: 2306) |
| βc-313 Target: | 5'-GAUGGAGUUGGACAUGGCCAUGGAA-3'<br>3'-AACUACCUCAACCUGUACCGGUACCUU-5'<br>5'-TTGATGGAGTTGGACATGGCCATGGAA-3' | (SEQ ID NO: 3416)<br>(SEQ ID NO: 1198)<br>(SEQ ID NO: 2307) |
| βc-314 Target: | 5'-AUGGAGUUGGACAUGGCCAUGGAAC-3'<br>3'-ACUACCUCAACCUGUACCGGUACCUUG-5'<br>5'-TGATGGAGTTGGACATGGCCATGGAAC-3' | (SEQ ID NO: 3417)<br>(SEQ ID NO: 1199)<br>(SEQ ID NO: 2308) |
| βc-315 Target: | 5'-UGGAGUUGGACAUGGCCAUGGAACC-3'<br>3'-CUACCUCAACCUGUACCGGUACCUUGG-5'<br>5'-GATGGAGTTGGACATGGCCATGGAACC-3' | (SEQ ID NO: 3418)<br>(SEQ ID NO: 1200)<br>(SEQ ID NO: 2309) |
| βc-316 Target: | 5'-GGAGUUGGACAUGGCCAUGGAACCA-3'<br>3'-UACCUCAACCUGUACCGGUACCUUGGU-5'<br>5'-ATGGAGTTGGACATGGCCATGGAACCA-3' | (SEQ ID NO: 3419)<br>(SEQ ID NO: 1201)<br>(SEQ ID NO: 2310) |
| βc-317 Target: | 5'-GAGUUGGACAUGGCCAUGGAACCAG-3'<br>3'-ACCUCAACCUGUACCGGUACCUUGGUC-5'<br>5'-TGGAGTTGGACATGGCCATGGAACCAG-3' | (SEQ ID NO: 3420)<br>(SEQ ID NO: 1202)<br>(SEQ ID NO: 2311) |
| βc-318 Target: | 5'-AGUUGGACAUGGCCAUGGAACCAGA-3'<br>3'-CCUCAACCUGUACCGGUACCUUGGUCU-5'<br>5'-GGAGTTGGACATGGCCATGGAACCAGA-3' | (SEQ ID NO: 3421)<br>(SEQ ID NO: 1203)<br>(SEQ ID NO: 2312) |
| βc-389 Target: | 5'-UCUGGAAUCCAUUCUGGUGCCACUA-3'<br>3'-UGAGACCUUAGGUAAGACCACGGUGAU-5'<br>5'-ACTCTGGAATCCATTCTGGTGCCACTA-3' | (SEQ ID NO: 3422)<br>(SEQ ID NO: 1204)<br>(SEQ ID NO: 2313) |
| βc-390 Target: | 5'-CUGGAAUCCAUUCUGGUGCCACUAC-3'<br>3'-GAGACCUUAGGUAAGACCACGGUGAUG-5'<br>5'-CTCTGGAATCCATTCTGGTGCCACTAC-3' | (SEQ ID NO: 3423)<br>(SEQ ID NO: 1205)<br>(SEQ ID NO: 2314) |
| βc-391 Target: | 5'-UGGAAUCCAUUCUGGUGCCACUACC-3'<br>3'-AGACCUUAGGUAAGACCACGGUGAUGG-5'<br>5'-TCTGGAATCCATTCTGGTGCCACTACC-3' | (SEQ ID NO: 3424)<br>(SEQ ID NO: 1206)<br>(SEQ ID NO: 2315) |
| βc-392 Target: | 5'-GGAAUCCAUUCUGGUGCCACUACCA-3'<br>3'-GACCUUAGGUAAGACCACGGUGAUGGU-5'<br>5'-CTGGAATCCATTCTGGTGCCACTACCA-3' | (SEQ ID NO: 3425)<br>(SEQ ID NO: 1207)<br>(SEQ ID NO: 2316) |
| βc-393 Target: | 5'-GAAUCCAUUCUGGUGCCACUACCAC-3'<br>3'-ACCUUAGGUAAGACCACGGUGAUGGUG-5'<br>5'-TGGAATCCATTCTGGTGCCACTACCAC-3' | (SEQ ID NO: 3426)<br>(SEQ ID NO: 1208)<br>(SEQ ID NO: 2317) |
| βc-600 Target: | 5'-UAGAUGAGGGCAUGCAGAUCCCAUC-3'<br>3'-UAAUCUACUCCCGUACGUCUAGGGUAG-5'<br>5'-ATTAGATGAGGGCATGCAGATCCCATC-3' | (SEQ ID NO: 3427)<br>(SEQ ID NO: 1209)<br>(SEQ ID NO: 2318) |
| βc-601 Target: | 5'-AGAUGAGGGCAUGCAGAUCCCAUCU-3'<br>3'-AAUCUACUCCCGUACGUCUAGGGUAGA-5'<br>5'-TTAGATGAGGGCATGCAGATCCCATCT-3' | (SEQ ID NO: 3428)<br>(SEQ ID NO: 1210)<br>(SEQ ID NO: 2319) |
| βc-602 Target: | 5'-GAUGAGGGCAUGCAGAUCCCAUCUA-3'<br>3'-AUCUACUCCCGUACGUCUAGGGUAGAU-5'<br>5'-TAGATGAGGGCATGCAGATCCCATCTA-3' | (SEQ ID NO: 3429)<br>(SEQ ID NO: 1211)<br>(SEQ ID NO: 2320) |
| βc-603 Target: | 5'-AUGAGGGCAUGCAGAUCCCAUCUAC-3'<br>3'-UCUACUCCCGUACGUCUAGGGUAGAUG-5'<br>5'-AGATGAGGGCATGCAGATCCCATCTAC-3' | (SEQ ID NO: 3430)<br>(SEQ ID NO: 1212)<br>(SEQ ID NO: 2321) |
| βc-604 Target: | 5'-UGAGGGCAUGCAGAUCCCAUCUACA-3'<br>3'-CUACUCCCGUACGUCUAGGGUAGAUGU-5'<br>5'-GATGAGGGCATGCAGATCCCATCTACA-3' | (SEQ ID NO: 3431)<br>(SEQ ID NO: 1213)<br>(SEQ ID NO: 2322) |

TABLE 6-continued

Selected Anti-β-catenin DsiRNA Agents, Unmodified Duplexes

|  |  |  |
|---|---|---|
|  | 5'-GAGGGCAUGCAGAUCCCAUCUACAC-3' | (SEQ ID NO: 3432) |
|  | 3'-UACUCCCGUACGUCUAGGGUAGAUGUG-5' | (SEQ ID NO: 1214) |
| βc-605 Target: | 5'-ATGAGGGCATGCAGATCCCATCTACAC-3' | (SEQ ID NO: 2323) |
|  | 5'-GCUGCUCAUCCCACUAAUGUCCAGC-3' | (SEQ ID NO: 3433) |
|  | 3'-UACGACGAGUAGGGUGAUUACAGGUCG-5' | (SEQ ID NO: 1215) |
| βc-638 Target: | 5'-ATGCTGCTCATCCCACTAATGTCCAGC-3' | (SEQ ID NO: 2324) |
|  | 5'-CUGCUCAUCCCACUAAUGUCCAGCG-3' | (SEQ ID NO: 3434) |
|  | 3'-ACGACGAGUAGGGUGAUUACAGGUCGC-5' | (SEQ ID NO: 1216) |
| βc-639 Target: | 5'-TGCTGCTCATCCCACTAATGTCCAGCG-3' | (SEQ ID NO: 2325) |
|  | 5'-UGCUCAUCCCACUAAUGUCCAGCGU-3' | (SEQ ID NO: 3435) |
|  | 3'-CGACGAGUAGGGUGAUUACAGGUCGCA-5' | (SEQ ID NO: 1217) |
| βc-640 Target: | 5'-GCTGCTCATCCCACTAATGTCCAGCGT-3' | (SEQ ID NO: 2326) |
|  | 5'-GCUCAUCCCACUAAUGUCCAGCGUU-3' | (SEQ ID NO: 3436) |
|  | 3'-GACGAGUAGGGUGAUUACAGGUCGCAA-5' | (SEQ ID NO: 1218) |
| βc-641 Target: | 5'-CTGCTCATCCCACTAATGTCCAGCGTT-3' | (SEQ ID NO: 2327) |
|  | 5'-CUCAUCCCACUAAUGUCCAGCGUUU-3' | (SEQ ID NO: 3437) |
|  | 3'-ACGAGUAGGGUGAUUACAGGUCGCAAA-5' | (SEQ ID NO: 1219) |
| βc-642 Target: | 5'-TGCTCATCCCACTAATGTCCAGCGTTT-3' | (SEQ ID NO: 2328) |
|  | 5'-UCAUCCCACUAAUGUCCAGCGUUUG-3' | (SEQ ID NO: 3438) |
|  | 3'-CGAGUAGGGUGAUUACAGGUCGCAAAC-5' | (SEQ ID NO: 1220) |
| βc-643 Target: | 5'-GCTCATCCCACTAATGTCCAGCGTTTG-3' | (SEQ ID NO: 2329) |
|  | 5'-CAUCCCACUAAUGUCCAGCGUUUGG-3' | (SEQ ID NO: 3439) |
|  | 3'-GAGUAGGGUGAUUACAGGUCGCAAACC-5' | (SEQ ID NO: 1221) |
| βc-644 Target: | 5'-CTCATCCCACTAATGTCCAGCGTTTGG-3' | (SEQ ID NO: 2330) |
|  | 5'-AUCCCACUAAUGUCCAGCGUUUGGC-3' | (SEQ ID NO: 3440) |
|  | 3'-AGUAGGGUGAUUACAGGUCGCAAACCG-5' | (SEQ ID NO: 1222) |
| βc-645 Target: | 5'-TCATCCCACTAATGTCCAGCGTTTGGC-3' | (SEQ ID NO: 2331) |
|  | 5'-UUGGCUGAACCAUCACAGAUGCUGA-3' | (SEQ ID NO: 3441) |
|  | 3'-CAAACCGACUUGGUAGUGUCUACGACU-5' | (SEQ ID NO: 1223) |
| βc-665 Target: | 5'-GTTTGGCTGAACCATCACAGATGCTGA-3' | (SEQ ID NO: 2332) |
|  | 5'-UGGCUGAACCAUCACAGAUGCUGAA-3' | (SEQ ID NO: 3442) |
|  | 3'-AAACCGACUUGGUAGUGUCUACGACUU-5' | (SEQ ID NO: 1224) |
| βc-666 Target: | 5'-TTTGGCTGAACCATCACAGATGCTGAA-3' | (SEQ ID NO: 2333) |
|  | 5'-GGCUGAACCAUCACAGAUGCUGAAA-3' | (SEQ ID NO: 3443) |
|  | 3'-AACCGACUUGGUAGUGUCUACGACUUU-5' | (SEQ ID NO: 1225) |
| βc-667 Target: | 5'-TTGGCTGAACCATCACAGATGCTGAAA-3' | (SEQ ID NO: 2334) |
|  | 5'-GAACUUGCCACACGUGCAAUCCCUG-3' | (SEQ ID NO: 3444) |
|  | 3'-GUCUUGAACGGUGUGCACGUUAGGGAC-5' | (SEQ ID NO: 1226) |
| βc-731 Target: | 5'-CAGAACTTGCCACACGTGCAATCCCTG-3' | (SEQ ID NO: 2335) |
|  | 5'-AACUUGCCACACGUGCAAUCCCUGA-3' | (SEQ ID NO: 3445) |
|  | 3'-UCUUGAACGGUGUGCACGUUAGGGACU-5' | (SEQ ID NO: 1227) |
| βc-732 Target: | 5'-AGAACTTGCCACACGTGCAATCCCTGA-3' | (SEQ ID NO: 2336) |
|  | 5'-GUUAUGGUCCAUCAGCUUUCUAAAA-3' | (SEQ ID NO: 3446) |
|  | 3'-GUCAAUACCAGGUAGUCGAAAGAUUUU-5' | (SEQ ID NO: 1228) |
| βc-809 Target: | 5'-CAGTTATGGTCCATCAGCTTTCTAAAA-3' | (SEQ ID NO: 2337) |
|  | 5'-UUAUGGUCCAUCAGCUUUCUAAAAA-3' | (SEQ ID NO: 3447) |
|  | 3'-UCAAUACCAGGUAGUCGAAAGAUUUUU-5' | (SEQ ID NO: 1229) |
| βc-810 Target: | 5'-AGTTATGGTCCATCAGCTTTCTAAAAA-3' | (SEQ ID NO: 2338) |
|  | 5'-AAAAAGGAAGCUUCCAGACACGCUA-3' | (SEQ ID NO: 3448) |
|  | 3'-GAUUUUUCCUUCGAAGGUCUGUGCGAU-5' | (SEQ ID NO: 1230) |
| βc-830 Target: | 5'-CTAAAAAGGAAGCTTCCAGACACGCTA-3' | (SEQ ID NO: 2339) |
|  | 5'-AAAAGGAAGCUUCCAGACACGCUAU-3' | (SEQ ID NO: 3449) |
|  | 3'-AUUUUUCCUUCGAAGGUCUGUGCGAUA-5' | (SEQ ID NO: 1231) |
| βc-831 Target: | 5'-TAAAAAGGAAGCTTCCAGACACGCTAT-3' | (SEQ ID NO: 2340) |
|  | 5'-ACCAUGCAGAAUACAAAUGAUGUAG-3' | (SEQ ID NO: 3450) |
|  | 3'-CAUGGUACGUCUUAUGUUUACUACAUC-5' | (SEQ ID NO: 1232) |
| βc-893 Target: | 5'-GTACCATGCAGAATACAAATGATGTAG-3' | (SEQ ID NO: 2341) |

TABLE 6-continued

Selected Anti-β-catenin DsiRNA Agents, Unmodified Duplexes

|  |  |  |  |
|---|---|---|---|
| βc-894 Target: | 5'-CCAUGCAGAAUACAAAUGAUGUAGA-3'<br>3'-AUGGUACGUCUUAUGUUUACUACAUCU-5'<br>5'-TACCATGCAGAATACAAATGATGTAGA-3' | (SEQ ID NO: 3451)<br>(SEQ ID NO: 1233)<br>(SEQ ID NO: 2342) |  |
| βc-895 Target: | 5'-CAUGCAGAAUACAAAUGAUGUAGAA-3'<br>3'-UGGUACGUCUUAUGUUUACUACAUCUU-5'<br>5'-ACCATGCAGAATACAAATGATGTAGAA-3' | (SEQ ID NO: 3452)<br>(SEQ ID NO: 1234)<br>(SEQ ID NO: 2343) |  |
| βc-896 Target: | 5'-AUGCAGAAUACAAAUGAUGUAGAAA-3'<br>3'-GGUACGUCUUAUGUUUACUACAUCUUU-5'<br>5'-CCATGCAGAATACAAATGATGTAGAAA-3' | (SEQ ID NO: 3453)<br>(SEQ ID NO: 1235)<br>(SEQ ID NO: 2344) |  |
| βc-897 Target: | 5'-UGCAGAAUACAAAUGAUGUAGAAAC-3'<br>3'-GUACGUCUUAUGUUUACUACAUCUUUG-5'<br>5'-CATGCAGAATACAAATGATGTAGAAAC-3' | (SEQ ID NO: 3454)<br>(SEQ ID NO: 1236)<br>(SEQ ID NO: 2345) |  |
| βc-898 Target: | 5'-GCAGAAUACAAAUGAUGUAGAAACA-3'<br>3'-UACGUCUUAUGUUUACUACAUCUUUGU-5'<br>5'-ATGCAGAATACAAATGATGTAGAAACA-3' | (SEQ ID NO: 3455)<br>(SEQ ID NO: 1237)<br>(SEQ ID NO: 2346) |  |
| βc-899 Target: | 5'-CAGAAUACAAAUGAUGUAGAAACAG-3'<br>3'-ACGUCUUAUGUUUACUACAUCUUUGUC-5'<br>5'-TGCAGAATACAAATGATGTAGAAACAG-3' | (SEQ ID NO: 3456)<br>(SEQ ID NO: 1238)<br>(SEQ ID NO: 2347) |  |
| βc-900 Target: | 5'-AGAAUACAAAUGAUGUAGAAACAGC-3'<br>3'-CGUCUUAUGUUUACUACAUCUUUGUCG-5'<br>5'-GCAGAATACAAATGATGTAGAAACAGC-3' | (SEQ ID NO: 3457)<br>(SEQ ID NO: 1239)<br>(SEQ ID NO: 2348) |  |
| βc-977 Target: | 5'-CUGGCCAUCUUUAAGUCUGGAGGCA-3'<br>3'-AUGACCGGUAGAAAUUCAGACCUCCGU-5'<br>5'-TACTGGCCATCTTTAAGTCTGGAGGCA-3' | (SEQ ID NO: 3458)<br>(SEQ ID NO: 1240)<br>(SEQ ID NO: 2349) |  |
| βc-978 Target: | 5'-UGGCCAUCUUUAAGUCUGGAGGCAU-3'<br>3'-UGACCGGUAGAAAUUCAGACCUCCGUA-5'<br>5'-ACTGGCCATCTTTAAGTCTGGAGGC-3' | (SEQ ID NO: 3459)<br>(SEQ ID NO: 1241)<br>(SEQ ID NO: 2350) |  |
| βc-1091 Target: | 5'-GAAGGAGCUAAAAUGGCAGUGCGUU-3'<br>3'-UUCUUCCUCGAUUUUACCGUCACGCAA-5'<br>5'-AAGAAGGAGCTAAAATGGCAGTGCGTT-3' | (SEQ ID NO: 3460)<br>(SEQ ID NO: 1242)<br>(SEQ ID NO: 2351) |  |
| βc-1092 Target: | 5'-AAGGAGCUAAAAUGGCAGUGCGUUU-3'<br>3'-UCUUCCUCGAUUUUACCGUCACGCAAA-5'<br>5'-AGAAGGAGCTAAAATGGCAGTGCGTTT-3' | (SEQ ID NO: 3461)<br>(SEQ ID NO: 1243)<br>(SEQ ID NO: 2352) |  |
| βc-1093 Target: | 5'-AGGAGCUAAAAUGGCAGUGCGUUUA-3'<br>3'-CUUCCUCGAUUUUACCGUCACGCAAAU-5'<br>5'-GAAGGAGCTAAAATGGCAGTGCGTTTA-3' | (SEQ ID NO: 3462)<br>(SEQ ID NO: 1244)<br>(SEQ ID NO: 2353) |  |
| βc-1094 Target: | 5'-GGAGCUAAAAUGGCAGUGCGUUUAG-3'<br>3'-UUCCUCGAUUUUACCGUCACGCAAAUC-5'<br>5'-AAGGAGCTAAAATGGCAGTGCGTTTAG-3' | (SEQ ID NO: 3463)<br>(SEQ ID NO: 1245)<br>(SEQ ID NO: 2354) |  |
| βc-1095 Target: | 5'-GAGCUAAAAUGGCAGUGCGUUUAGC-3'<br>3'-UCCUCGAUUUUACCGUCACGCAAAUCG-5'<br>5'-AGGAGCTAAAATGGCAGTGCGTTTAGC-3' | (SEQ ID NO: 3464)<br>(SEQ ID NO: 1246)<br>(SEQ ID NO: 2355) |  |
| βc-1301 Target: | 5'-CUGUGGACCACAAGCAGAGUGCUGA-3'<br>3'-AUGACACCUGGUGUUCGUCUCACGACU-5'<br>5'-TACTGTGGACCACAAGCAGAGTGCTGA-3' | (SEQ ID NO: 3465)<br>(SEQ ID NO: 1247)<br>(SEQ ID NO: 2356) |  |
| βc-1302 Target: | 5'-UGUGGACCACAAGCAGAGUGCUGAA-3'<br>3'-UGACACCUGGUGUUCGUCUCACGACUU-5'<br>5'-ACTGTGGACCACAAGCAGAGTGCTGAA-3' | (SEQ ID NO: 3466)<br>(SEQ ID NO: 1248)<br>(SEQ ID NO: 2357) |  |
| βc-1303 Target: | 5'-GUGGACCACAAGCAGAGUGCUGAAG-3'<br>3'-GACACCUGGUGUUCGUCUCACGACUUC-5'<br>5'-CTGTGGACCACAAGCAGAGTGCTGAAG-3' | (SEQ ID NO: 3467)<br>(SEQ ID NO: 1249)<br>(SEQ ID NO: 2358) |  |
| βc-1304 Target: | 5'-UGGACCACAAGCAGAGUGCUGAAGG-3'<br>3'-ACACCUGGUGUUCGUCUCACGACUUCC-5'<br>5'-TGTGGACCACAAGCAGAGTGCTGAAGG-3' | (SEQ ID NO: 3468)<br>(SEQ ID NO: 1250)<br>(SEQ ID NO: 2359) |  |
| βc-1305 Target: | 5'-GGACCACAAGCAGAGUGCUGAAGGU-3'<br>3'-CACCUGGUGUUCGUCUCACGACUUCCA-5'<br>5'-GTGGACCACAAGCAGAGTGCTGAAGGT-3' | (SEQ ID NO: 3469)<br>(SEQ ID NO: 1251)<br>(SEQ ID NO: 2360) |  |

TABLE 6-continued

Selected Anti-β-catenin DsiRNA Agents, Unmodified Duplexes

| | | |
|---|---|---|
| | 5'-GACCACAAGCAGAGUGCUGAAGGUG-3' | (SEQ ID NO: 3470) |
| | 3'-ACCUGGUGUUCGUCUCACGACUUCCAC-5' | (SEQ ID NO: 1252) |
| βc-1306 Target: | 5'-TGGACCACAAGCAGAGTGCTGAAGGTG-3' | (SEQ ID NO: 2361) |
| | 5'-ACCACAAGCAGAGUGCUGAAGGUGC-3' | (SEQ ID NO: 3471) |
| | 3'-CCUGGUGUUCGUCUCACGACUUCCACG-5' | (SEQ ID NO: 1253) |
| βc-1307 Target: | 5'-GGACCACAAGCAGAGTGCTGAAGGTGC-3' | (SEQ ID NO: 2362) |
| | 5'-CCACAAGCAGAGUGCUGAAGGUGCU-3' | (SEQ ID NO: 3472) |
| | 3'-CUGGUGUUCGUCUCACGACUUCCACGA-5' | (SEQ ID NO: 1254) |
| βc-1308 Target: | 5'-GACCACAAGCAGAGTGCTGAAGGTGCT-3' | (SEQ ID NO: 2363) |
| | 5'-CACAAGCAGAGUGCUGAAGGUGCUA-3' | (SEQ ID NO: 3473) |
| | 3'-UGGUGUUCGUCUCACGACUUCCACGAU-5' | (SEQ ID NO: 1255) |
| βc-1309 Target: | 5'-ACCACAAGCAGAGTGCTGAAGGTGCTA-3' | (SEQ ID NO: 2364) |
| | 5'-ACAAGCAGAGUGCUGAAGGUGCUAU-3' | (SEQ ID NO: 3474) |
| | 3'-GGUGUUCGUCUCACGACUUCCACGAUA-5' | (SEQ ID NO: 1256) |
| βc-1310 Target: | 5'-CCACAAGCAGAGTGCTGAAGGTGCTAT-3' | (SEQ ID NO: 2365) |
| | 5'-CAAGCAGAGUGCUGAAGGUGCUAUC-3' | (SEQ ID NO: 3475) |
| | 3'-GUGUUCGUCUCACGACUUCCACGAUAG-5' | (SEQ ID NO: 1257) |
| βc-1311 Target: | 5'-CACAAGCAGAGTGCTGAAGGTGCTATC-3' | (SEQ ID NO: 2366) |
| | 5'-AAGCAGAGUGCUGAAGGUGCUAUCU-3' | (SEQ ID NO: 3476) |
| | 3'-UGUUCGUCUCACGACUUCCACGAUAGA-5' | (SEQ ID NO: 1258) |
| βc-1312 Target: | 5'-ACAAGCAGAGTGCTGAAGGTGCTATCT-3' | (SEQ ID NO: 2367) |
| | 5'-AGCAGAGUGCUGAAGGUGCUAUCUG-3' | (SEQ ID NO: 3477) |
| | 3'-GUUCGUCUCACGACUUCCACGAUAGAC-5' | (SEQ ID NO: 1259) |
| βc-1313 Target: | 5'-CAAGCAGAGTGCTGAAGGTGCTATCTG-3' | (SEQ ID NO: 2368) |
| | 5'-GCAGAGUGCUGAAGGUGCUAUCUGU-3' | (SEQ ID NO: 3478) |
| | 3'-UUCGUCUCACGACUUCCACGAUAGACA-5' | (SEQ ID NO: 1260) |
| βc-1314 Target: | 5'-AAGCAGAGTGCTGAAGGTGCTATCTGT-3' | (SEQ ID NO: 2369) |
| | 5'-AACUGUCUUUGGACUCUCAGGAAUC-3' | (SEQ ID NO: 3479) |
| | 3'-UCUUGACAGAAACCUGAGAGUCCUUAG-5' | (SEQ ID NO: 1261) |
| βc-1430 Target: | 5'-AGAACTGTCTTTGGACTCTCAGGAATC-3' | (SEQ ID NO: 2370) |
| | 5'-ACUGUCUUUGGACUCUCAGGAAUCU-3' | (SEQ ID NO: 3480) |
| | 3'-CUUGACAGAAACCUGAGAGUCCUUAGA-5' | (SEQ ID NO: 1262) |
| βc-1431 Target: | 5'-GAACTGTCTTTGGACTCTCAGGAATCT-3' | (SEQ ID NO: 2371) |
| | 5'-GAUGAUAUAAAUGUGGUCACCUGUG-3' | (SEQ ID NO: 3481) |
| | 3'-GUCUACUAUAUUUACACCAGUGGACAC-5' | (SEQ ID NO: 1263) |
| βc-1526 Target: | 5'-CAGATGATATAAATGTGGTCACCTGTG-3' | (SEQ ID NO: 2372) |
| | 5'-AUGAUAUAAAUGUGGUCACCUGUGC-3' | (SEQ ID NO: 3482) |
| | 3'-UCUACUAUAUUUACACCAGUGGACACG-5' | (SEQ ID NO: 1264) |
| βc-1527 Target: | 5'-AGATGATATAAATGTGGTCACCTGTGC-3' | (SEQ ID NO: 2373) |
| | 5'-UGAUAUAAAUGUGGUCACCUGUGCA-3' | (SEQ ID NO: 3483) |
| | 3'-CUACUAUAUUUACACCAGUGGACACGU-5' | (SEQ ID NO: 1265) |
| βc-1528 Target: | 5'-GATGATATAAATGTGGTCACCTGTGCA-3' | (SEQ ID NO: 2374) |
| | 5'-GAUAUAAAUGUGGUCACCUGUGCAG-3' | (SEQ ID NO: 3484) |
| | 3'-UACUAUAUUUACACCAGUGGACACGUC-5' | (SEQ ID NO: 1266) |
| βc-1529 Target: | 5'-ATGATATAAATGTGGTCACCTGTGCAG-3' | (SEQ ID NO: 2375) |
| | 5'-AUAUAAAUGUGGUCACCUGUGCAGC-3' | (SEQ ID NO: 3485) |
| | 3'-ACUAUAUUUACACCAGUGGACACGUCG-5' | (SEQ ID NO: 1267) |
| βc-1530 Target: | 5'-TGATATAAATGTGGTCACCTGTGCAGC-3' | (SEQ ID NO: 2376) |
| | 5'-UAUAAAUGUGGUCACCUGUGCAGCU-3' | (SEQ ID NO: 3486) |
| | 3'-CUAUAUUUACACCAGUGGACACGUCGA-5' | (SEQ ID NO: 1268) |
| βc-1531 Target: | 5'-GATATAAATGTGGTCACCTGTGCAGCT-3' | (SEQ ID NO: 2377) |
| | 5'-AUAAAUGUGGUCACCUGUGCAGCUG-3' | (SEQ ID NO: 3487) |
| | 3'-UAUAUUUACACCAGUGGACACGUCGAC-5' | (SEQ ID NO: 1269) |
| βc-1532 Target: | 5'-ATATAAATGTGGTCACCTGTGCAGCTG-3' | (SEQ ID NO: 2378) |
| | 5'-UAAAUGUGGUCACCUGUGCAGCUGG-3' | (SEQ ID NO: 3488) |
| | 3'-AUAUUUACACCAGUGGACACGUCGACC-5' | (SEQ ID NO: 1270) |
| βc-1533 Target: | 5'-TATAAATGTGGTCACCTGTGCAGCTGG-3' | (SEQ ID NO: 2379) |

TABLE 6-continued

Selected Anti-β-catenin DsiRNA Agents, Unmodified Duplexes

| | | |
|---|---|---|
| βc-1534 Target: | 5'-AAAUGUGGUCACCUGUGCAGCUGGA-3'<br>3'-UAUUUACACCAGUGGACACGUCGACCU-5'<br>5'-ATAAATGTGGTCACCTGTGCAGCTGGA-3' | (SEQ ID NO: 3489)<br>(SEQ ID NO: 1271)<br>(SEQ ID NO: 2380) |
| βc-1535 Target: | 5'-AAUGUGGUCACCUGUGCAGCUGGAA-3'<br>3'-AUUUACACCAGUGGACACGUCGACCUU-5'<br>5'-TAAATGTGGTCACCTGTGCAGCTGGAA-3' | (SEQ ID NO: 3490)<br>(SEQ ID NO: 1272)<br>(SEQ ID NO: 2381) |
| βc-1536 Target: | 5'-AUGUGGUCACCUGUGCAGCUGGAAU-3'<br>3'-UUUACACCAGUGGACACGUCGACCUUA-5'<br>5'-AAATGTGGTCACCTGTGCAGCTGGAAT-3' | (SEQ ID NO: 3491)<br>(SEQ ID NO: 1273)<br>(SEQ ID NO: 2382) |
| βc-1537 Target: | 5'-UGUGGUCACCUGUGCAGCUGGAAUU-3'<br>3'-UUACACCAGUGGACACGUCGACCUUAA-5'<br>5'-AATGTGGTCACCTGTGCAGCTGGAATT-3' | (SEQ ID NO: 3492)<br>(SEQ ID NO: 1274)<br>(SEQ ID NO: 2383) |
| βc-1538 Target: | 5'-GUGGUCACCUGUGCAGCUGGAAUUC-3'<br>3'-UACACCAGUGGACACGUCGACCUUAAG-5'<br>5'-ATGTGGTCACCTGTGCAGCTGGAATTC-3' | (SEQ ID NO: 3493)<br>(SEQ ID NO: 1275)<br>(SEQ ID NO: 2384) |
| βc-1539 Target: | 5'-UGGUCACCUGUGCAGCUGGAAUUCU-3'<br>3'-ACACCAGUGGACACGUCGACCUUAAGA-5'<br>5'-TGTGGTCACCTGTGCAGCTGGAATTCT-3' | (SEQ ID NO: 3494)<br>(SEQ ID NO: 1276)<br>(SEQ ID NO: 2385) |
| βc-1540 Target: | 5'-GGUCACCUGUGCAGCUGGAAUUCUU-3'<br>3'-CACCAGUGGACACGUCGACCUUAAGAA-5'<br>5'-GTGGTCACCTGTGCAGCTGGAATTCTT-3' | (SEQ ID NO: 3495)<br>(SEQ ID NO: 1277)<br>(SEQ ID NO: 2386) |
| βc-1541 Target: | 5'-GUCACCUGUGCAGCUGGAAUUCUUU-3'<br>3'-ACCAGUGGACACGUCGACCUUAAGAAA-5'<br>5'-TGGTCACCTGTGCAGCTGGAATTCTTT-3' | (SEQ ID NO: 3496)<br>(SEQ ID NO: 1278)<br>(SEQ ID NO: 2387) |
| βc-1542 Target: | 5'-UCACCUGUGCAGCUGGAAUUCUUUC-3'<br>3'-CCAGUGGACACGUCGACCUUAAGAAAG-5'<br>5'-GGTCACCTGTGCAGCTGGAATTCTTTC-3' | (SEQ ID NO: 3497)<br>(SEQ ID NO: 1279)<br>(SEQ ID NO: 2388) |
| βc-1543 Target: | 5'-CACCUGUGCAGCUGGAAUUCUUUCU-3'<br>3'-CAGUGGACACGUCGACCUUAAGAAAGA-5'<br>5'-GTCACCTGTGCAGCTGGAATTCTTTCT-3' | (SEQ ID NO: 3498)<br>(SEQ ID NO: 1280)<br>(SEQ ID NO: 2389) |
| βc-1544 Target: | 5'-ACCUGUGCAGCUGGAAUUCUUUCUA-3'<br>3'-AGUGGACACGUCGACCUUAAGAAAGAU-5'<br>5'-TCACCTGTGCAGCTGGAATTCTTTCTA-3' | (SEQ ID NO: 3499)<br>(SEQ ID NO: 1281)<br>(SEQ ID NO: 2390) |
| βc-1545 Target: | 5'-CCUGUGCAGCUGGAAUUCUUUCUAA-3'<br>3'-GUGGACACGUCGACCUUAAGAAAGAUU-5'<br>5'-CACCTGTGCAGCTGGAATTCTTTCTAA-3' | (SEQ ID NO: 3500)<br>(SEQ ID NO: 1282)<br>(SEQ ID NO: 2391) |
| βc-1565 Target: | 5'-UCUAACCUCACUUGCAAUAAUUAUA-3'<br>3'-AAAGAUUGGAGUGAACGUUAUUAAUAU-5'<br>5'-TTTCTAACCTCACTTGCAATAATTATA-3' | (SEQ ID NO: 3501)<br>(SEQ ID NO: 1283)<br>(SEQ ID NO: 2392) |
| βc-1566 Target: | 5'-CUAACCUCACUUGCAAUAAUUAUAA-3'<br>3'-AAGAUUGGAGUGAACGUUAUUAAUAUU-5'<br>5'-TTCTAACCTCACTTGCAATAATTATAA-3' | (SEQ ID NO: 3502)<br>(SEQ ID NO: 1284)<br>(SEQ ID NO: 2393) |
| βc-1567 Target: | 5'-UAACCUCACUUGCAAUAAUUAUAAG-3'<br>3'-AGAUUGGAGUGAACGUUAUUAAUAUUC-5'<br>5'-TCTAACCTCACTTGCAATAATTATAAG-3' | (SEQ ID NO: 3503)<br>(SEQ ID NO: 1285)<br>(SEQ ID NO: 2394) |
| βc-1568 Target: | 5'-AACCUCACUUGCAAUAAUUAUAAGA-3'<br>3'-GAUUGGAGUGAACGUUAUUAAUAUUCU-5'<br>5'-CTAACCTCACTTGCAATAATTATAAGA-3' | (SEQ ID NO: 3504)<br>(SEQ ID NO: 1286)<br>(SEQ ID NO: 2395) |
| βc-1569 Target: | 5'-ACCUCACUUGCAAUAAUUAUAAGAA-3'<br>3'-AUUGGAGUGAACGUUAUUAAUAUUCUU-5'<br>5'-TAACCTCACTTGCAATAATTATAAGAA-3' | (SEQ ID NO: 3505)<br>(SEQ ID NO: 1287)<br>(SEQ ID NO: 2396) |
| βc-1652 Target: | 5'-GCUGGUGACAGGGAAGACAUCACUG-3'<br>3'-CCCGACCACUGUCCCUUCUGUAGUGAC-5'<br>5'-GGGCTGGTGACAGGGAAGACATCACTG-3' | (SEQ ID NO: 3506)<br>(SEQ ID NO: 1288)<br>(SEQ ID NO: 2397) |
| βc-1653 Target: | 5'-CUGGUGACAGGGAAGACAUCACUGA-3'<br>3'-CCGACCACUGUCCCUUCUGUAGUGACU-5'<br>5'-GGCTGGTGACAGGGAAGACATCACTGA-3' | (SEQ ID NO: 3507)<br>(SEQ ID NO: 1289)<br>(SEQ ID NO: 2398) |

TABLE 6-continued

Selected Anti-β-catenin DsiRNA Agents, Unmodified Duplexes

|  |  |  |
|---|---|---|
|  | 5'-UGGUGACAGGGAAGACAUCACUGAG-3' | (SEQ ID NO: 3508) |
|  | 3'-CGACCACUGUCCCUUCUGUAGUGACUC-5' | (SEQ ID NO: 1290) |
| βc-1654 Target: | 5'-GCTGGTGACAGGGAAGACATCACTGAG-3' | (SEQ ID NO: 2399) |
|  | 5'-GGUGACAGGGAAGACAUCACUGAGC-3' | (SEQ ID NO: 3509) |
|  | 3'-GACCACUGUCCCUUCUGUAGUGACUCG-5' | (SEQ ID NO: 1291) |
| βc-1655 Target: | 5'-CTGGTGACAGGGAAGACATCACTGAGC-3' | (SEQ ID NO: 2400) |
|  | 5'-GUGACAGGGAAGACAUCACUGAGCC-3' | (SEQ ID NO: 3510) |
|  | 3'-ACCACUGUCCCUUCUGUAGUGACUCGG-5' | (SEQ ID NO: 1292) |
| βc-1656 Target: | 5'-TGGTGACAGGGAAGACATCACTGAGCC-3' | (SEQ ID NO: 2401) |
|  | 5'-UGACAGGGAAGACAUCACUGAGCCU-3' | (SEQ ID NO: 3511) |
|  | 3'-CCACUGUCCCUUCUGUAGUGACUCGGA-5' | (SEQ ID NO: 1293) |
| βc-1657 Target: | 5'-GGTGACAGGGAAGACATCACTGAGCCT-3' | (SEQ ID NO: 2402) |
|  | 5'-GACAGGGAAGACAUCACUGAGCCUG-3' | (SEQ ID NO: 3512) |
|  | 3'-CACUGUCCCUUCUGUAGUGACUCGGAC-5' | (SEQ ID NO: 1294) |
| βc-1658 Target: | 5'-GTGACAGGGAAGACATCACTGAGCCTG-3' | (SEQ ID NO: 2403) |
|  | 5'-ACAGGGAAGACAUCACUGAGCCUGC-3' | (SEQ ID NO: 3513) |
|  | 3'-ACUGUCCCUUCUGUAGUGACUCGGACG-5' | (SEQ ID NO: 1295) |
| βc-1659 Target: | 5'-TGACAGGGAAGACATCACTGAGCCTGC-3' | (SEQ ID NO: 2404) |
|  | 5'-CAGGGAAGACAUCACUGAGCCUGCC-3' | (SEQ ID NO: 3514) |
|  | 3'-CUGUCCCUUCUGUAGUGACUCGGACGG-5' | (SEQ ID NO: 1296) |
| βc-1660 Target: | 5'-GACAGGGAAGACATCACTGAGCCTGCC-3' | (SEQ ID NO: 2405) |
|  | 5'-AGGGAAGACAUCACUGAGCCUGCCA-3' | (SEQ ID NO: 3515) |
|  | 3'-UGUCCCUUCUGUAGUGACUCGGACGGU-5' | (SEQ ID NO: 1297) |
| βc-1661 Target: | 5'-ACAGGGAAGACATCACTGAGCCTGCCA-3' | (SEQ ID NO: 2406) |
|  | 5'-GGGAAGACAUCACUGAGCCUGCCAU-3' | (SEQ ID NO: 3516) |
|  | 3'-GUCCCUUCUGUAGUGACUCGGACGGUA-5' | (SEQ ID NO: 1298) |
| βc-1662 Target: | 5'-CAGGGAAGACATCACTGAGCCTGCC-3' | (SEQ ID NO: 2407) |
|  | 5'-GGAAGACAUCACUGAGCCUGCCAUC-3' | (SEQ ID NO: 3517) |
|  | 3'-UCCCUUCUGUAGUGACUCGGACGGUAG-5' | (SEQ ID NO: 1299) |
| βc-1663 Target: | 5'-AGGGAAGACATCACTGAGCCTGCCATC-3' | (SEQ ID NO: 2408) |
|  | 5'-GAAGACAUCACUGAGCCUGCCAUCU-3' | (SEQ ID NO: 3518) |
|  | 3'-CCCUUCUGUAGUGACUCGGACGGUAGA-5' | (SEQ ID NO: 1300) |
| βc-1664 Target: | 5'-GGGAAGACATCACTGAGCCTGCCATCT-3' | (SEQ ID NO: 2409) |
|  | 5'-AAGACAUCACUGAGCCUGCCAUCUG-3' | (SEQ ID NO: 3519) |
|  | 3'-CCUUCUGUAGUGACUCGGACGGUAGAC-5' | (SEQ ID NO: 1301) |
| βc-1665 Target: | 5'-GGAAGACATCACTGAGCCTGCCATCTG-3' | (SEQ ID NO: 2410) |
|  | 5'-AGACAUCACUGAGCCUGCCAUCUGU-3' | (SEQ ID NO: 3520) |
|  | 3'-CUUCUGUAGUGACUCGGACGGUAGACA-5' | (SEQ ID NO: 1302) |
| βc-1666 Target: | 5'-GAAGACATCACTGAGCCTGCCATCTGT-3' | (SEQ ID NO: 2411) |
|  | 5'-GACAUCACUGAGCCUGCCAUCUGUG-3' | (SEQ ID NO: 3521) |
|  | 3'-UUCUGUAGUGACUCGGACGGUAGACAC-5' | (SEQ ID NO: 1303) |
| βc-1667 Target: | 5'-AAGACATCACTGAGCCTGCCATCTGTG-3' | (SEQ ID NO: 2412) |
|  | 5'-ACAUCACUGAGCCUGCCAUCUGUGC-3' | (SEQ ID NO: 3522) |
|  | 3'-UCUGUAGUGACUCGGACGGUAGACACG-5' | (SEQ ID NO: 1304) |
| βc-1668 Target: | 5'-AGACATCACTGAGCCTGCCATCTGTGC-3' | (SEQ ID NO: 2413) |
|  | 5'-CAUCACUGAGCCUGCCAUCUGUGCU-3' | (SEQ ID NO: 3523) |
|  | 3'-CUGUAGUGACUCGGACGGUAGACACGA-5' | (SEQ ID NO: 1305) |
| βc-1669 Target: | 5'-GACATCACTGAGCCTGCCATCTGTGCT-3' | (SEQ ID NO: 2414) |
|  | 5'-AUCACUGAGCCUGCCAUCUGUGCUC-3' | (SEQ ID NO: 3524) |
|  | 3'-UGUAGUGACUCGGACGGUAGACACGAG-5' | (SEQ ID NO: 1306) |
| βc-1670 Target: | 5'-ACATCACTGAGCCTGCCATCTGTGCTC-3' | (SEQ ID NO: 2415) |
|  | 5'-UCACUGAGCCUGCCAUCUGUGCUCU-3' | (SEQ ID NO: 3525) |
|  | 3'-GUAGUGACUCGGACGGUAGACACGAGA-5' | (SEQ ID NO: 1307) |
| βc-1671 Target: | 5'-CATCACTGAGCCTGCCATCTGTGCTCT-3' | (SEQ ID NO: 2416) |
|  | 5'-CACUGAGCCUGCCAUCUGUGCUCUU-3' | (SEQ ID NO: 3526) |
|  | 3'-UAGUGACUCGGACGGUAGACACGAGAA-5' | (SEQ ID NO: 1308) |
| βc-1672 Target: | 5'-ATCACTGAGCCTGCCATCTGTGCTCTT-3' | (SEQ ID NO: 2417) |

TABLE 6-continued

Selected Anti-β-catenin DsiRNA Agents, Unmodified Duplexes

| | | |
|---|---|---|
| βc-1673 Target: | 5'-ACUGAGCCUGCCAUCUGUGCUCUUC-3'<br>3'-AGUGACUCGGACGGUAGACACGAGAAG-5'<br>5'-TCACTGAGCCTGCCATCTGTGCTCTTC-3' | (SEQ ID NO: 3527)<br>(SEQ ID NO: 1309)<br>(SEQ ID NO: 2418) |
| βc-1674 Target: | 5'-CUGAGCCUGCCAUCUGUGCUCUUCG-3'<br>3'-GUGACUCGGACGGUAGACACGAGAAGC-5'<br>5'-CACTGAGCCTGCCATCTGTGCTCTTCG-3' | (SEQ ID NO: 3528)<br>(SEQ ID NO: 1310)<br>(SEQ ID NO: 2419) |
| βc-1675 Target: | 5'-UGAGCCUGCCAUCUGUGCUCUUCGU-3'<br>3'-UGACUCGGACGGUAGACACGAGAAGCA-5'<br>5'-ACTGAGCCTGCCATCTGTGCTCTTCGT-3' | (SEQ ID NO: 3529)<br>(SEQ ID NO: 1311)<br>(SEQ ID NO: 2420) |
| βc-1676 Target: | 5'-GAGCCUGCCAUCUGUGCUCUUCGUC-3'<br>3'-GACUCGGACGGUAGACACGAGAAGCAG-5'<br>5'-CTGAGCCTGCCATCTGTGCTCTTCGTC-3' | (SEQ ID NO: 3530)<br>(SEQ ID NO: 1312)<br>(SEQ ID NO: 2421) |
| βc-1677 Target: | 5'-AGCCUGCCAUCUGUGCUCUUCGUCA-3'<br>3'-ACUCGGACGGUAGACACGAGAAGCAGU-5'<br>5'-TGAGCCTGCCATCTGTGCTCTTCGTCA-3' | (SEQ ID NO: 3531)<br>(SEQ ID NO: 1313)<br>(SEQ ID NO: 2422) |
| βc-1678 Target: | 5'-GCCUGCCAUCUGUGCUCUUCGUCAU-3'<br>3'-CUCGGACGGUAGACACGAGAAGCAGUA-5'<br>5'-GAGCCTGCCATCTGTGCTCTTCGTC-3' | (SEQ ID NO: 3532)<br>(SEQ ID NO: 1314)<br>(SEQ ID NO: 2423) |
| βc-1679 Target: | 5'-CCUGCCAUCUGUGCUCUUCGUCAUC-3'<br>3'-UCGGACGGUAGACACGAGAAGCAGUAG-5'<br>5'-AGCCTGCCATCTGTGCTCTTCGTCATC-3' | (SEQ ID NO: 3533)<br>(SEQ ID NO: 1315)<br>(SEQ ID NO: 2424) |
| βc-1680 Target: | 5'-CUGCCAUCUGUGCUCUUCGUCAUCU-3'<br>3'-CGGACGGUAGACACGAGAAGCAGUAGA-5'<br>5'-GCCTGCCATCTGTGCTCTTCGTCATCT-3' | (SEQ ID NO: 3534)<br>(SEQ ID NO: 1316)<br>(SEQ ID NO: 2425) |
| βc-1681 Target: | 5'-UGCCAUCUGUGCUCUUCGUCAUCUG-3'<br>3'-GGACGGUAGACACGAGAAGCAGUAGAC-5'<br>5'-CCTGCCATCTGTGCTCTTCGTCATCTG-3' | (SEQ ID NO: 3535)<br>(SEQ ID NO: 1317)<br>(SEQ ID NO: 2426) |
| βc-1682 Target: | 5'-GCCAUCUGUGCUCUUCGUCAUCUGA-3'<br>3'-GACGGUAGACACGAGAAGCAGUAGACU-5'<br>5'-CTGCCATCTGTGCTCTTCGTCATCTGA-3' | (SEQ ID NO: 3536)<br>(SEQ ID NO: 1318)<br>(SEQ ID NO: 2427) |
| βc-1683 Target: | 5'-CCAUCUGUGCUCUUCGUCAUCUGAC-3'<br>3'-ACGGUAGACACGAGAAGCAGUAGACUG-5'<br>5'-TGCCATCTGTGCTCTTCGTCATCTGAC-3' | (SEQ ID NO: 3537)<br>(SEQ ID NO: 1319)<br>(SEQ ID NO: 2428) |
| βc-1684 Target: | 5'-CAUCUGUGCUCUUCGUCAUCUGACC-3'<br>3'-CGGUAGACACGAGAAGCAGUAGACUGG-5'<br>5'-GCCATCTGTGCTCTTCGTCATCTGACC-3' | (SEQ ID NO: 3538)<br>(SEQ ID NO: 1320)<br>(SEQ ID NO: 2429) |
| βc-1685 Target: | 5'-AUCUGUGCUCUUCGUCAUCUGACCA-3'<br>3'-GGUAGACACGAGAAGCAGUAGACUGGU-5'<br>5'-CCATCTGTGCTCTTCGTCATCTGACCA-3' | (SEQ ID NO: 3539)<br>(SEQ ID NO: 1321)<br>(SEQ ID NO: 2430) |
| βc-1686 Target: | 5'-UCUGUGCUCUUCGUCAUCUGACCAG-3'<br>3'-GUAGACACGAGAAGCAGUAGACUGGUC-5'<br>5'-CATCTGTGCTCTTCGTCATCTGACCAG-3' | (SEQ ID NO: 3540)<br>(SEQ ID NO: 1322)<br>(SEQ ID NO: 2431) |
| βc-1687 Target: | 5'-CUGUGCUCUUCGUCAUCUGACCAGC-3'<br>3'-UAGACACGAGAAGCAGUAGACUGGUCG-5'<br>5'-ATCTGTGCTCTTCGTCATCTGACCAGC-3' | (SEQ ID NO: 3541)<br>(SEQ ID NO: 1323)<br>(SEQ ID NO: 2432) |
| βc-1688 Target: | 5'-UGUGCUCUUCGUCAUCUGACCAGCC-3'<br>3'-AGACACGAGAAGCAGUAGACUGGUCGG-5'<br>5'-TCTGTGCTCTTCGTCATCTGACCAGCC-3' | (SEQ ID NO: 3542)<br>(SEQ ID NO: 1324)<br>(SEQ ID NO: 2433) |
| βc-1689 Target: | 5'-GUGCUCUUCGUCAUCUGACCAGCCG-3'<br>3'-GACACGAGAAGCAGUAGACUGGUCGGC-5'<br>5'-CTGTGCTCTTCGTCATCTGACCAGCCG-3' | (SEQ ID NO: 3543)<br>(SEQ ID NO: 1325)<br>(SEQ ID NO: 2434) |
| βc-1690 Target: | 5'-UGCUCUUCGUCAUCUGACCAGCCGA-3'<br>3'-ACACGAGAAGCAGUAGACUGGUCGGCU-5'<br>5'-TGTGCTCTTCGTCATCTGACCAGCCGA-3' | (SEQ ID NO: 3544)<br>(SEQ ID NO: 1326)<br>(SEQ ID NO: 2435) |
| βc-1691 Target: | 5'-GCUCUUCGUCAUCUGACCAGCCGAC-3'<br>3'-CACGAGAAGCAGUAGACUGGUCGGCUG-5'<br>5'-GTGCTCTTCGTCATCTGACCAGCCGAC-3' | (SEQ ID NO: 3545)<br>(SEQ ID NO: 1327)<br>(SEQ ID NO: 2436) |

TABLE 6-continued

Selected Anti-β-catenin DsiRNA Agents, Unmodified Duplexes

| | | |
|---|---|---|
| βc-1692 Target: | 5'-CUCUUCGUCAUCUGACCAGCCGACA-3'<br>3'-ACGAGAAGCAGUAGACUGGUCGGCUGU-5'<br>5'-TGCTCTTCGTCATCTGACCAGCCGACA-3' | (SEQ ID NO: 3546)<br>(SEQ ID NO: 1328)<br>(SEQ ID NO: 2437) |
| βc-1693 Target: | 5'-UCUUCGUCAUCUGACCAGCCGACAC-3'<br>3'-CGAGAAGCAGUAGACUGGUCGGCUGUG-5'<br>5'-GCTCTTCGTCATCTGACCAGCCGACAC-3' | (SEQ ID NO: 3547)<br>(SEQ ID NO: 1329)<br>(SEQ ID NO: 2438) |
| βc-1694 Target: | 5'-CUUCGUCAUCUGACCAGCCGACACC-3'<br>3'-GAGAAGCAGUAGACUGGUCGGCUGUGG-5'<br>5'-CTCTTCGTCATCTGACCAGCCGACACC-3' | (SEQ ID NO: 3548)<br>(SEQ ID NO: 1330)<br>(SEQ ID NO: 2439) |
| βc-1695 Target: | 5'-UUCGUCAUCUGACCAGCCGACACCA-3'<br>3'-AGAAGCAGUAGACUGGUCGGCUGUGGU-5'<br>5'-TCTTCGTCATCTGACCAGCCGACACCA-3' | (SEQ ID NO: 3549)<br>(SEQ ID NO: 1331)<br>(SEQ ID NO: 2440) |
| βc-1787 Target: | 5'-CACCCACCAUCCCACUGGCCUCUGA-3'<br>3'-AUGUGGGUGGUAGGGUGACCGGAGACU-5'<br>5'-TACACCCACCATCCCACTGGCCTCTGA-3' | (SEQ ID NO: 3550)<br>(SEQ ID NO: 1332)<br>(SEQ ID NO: 2441) |
| βc-1788 Target: | 5'-ACCCACCAUCCCACUGGCCUCUGAU-3'<br>3'-UGUGGGUGGUAGGGUGACCGGAGACUA-5'<br>5'-ACACCCACCATCCCACTGGCCTCTGAT-3' | (SEQ ID NO: 3551)<br>(SEQ ID NO: 1333)<br>(SEQ ID NO: 2442) |
| βc-1789 Target: | 5'-CCCACCAUCCCACUGGCCUCUGAUA-3'<br>3'-GUGGGUGGUAGGGUGACCGGAGACUAU-5'<br>5'-CACCCACCATCCCACTGGCCTCTGATA-3' | (SEQ ID NO: 3552)<br>(SEQ ID NO: 1334)<br>(SEQ ID NO: 2443) |
| βc-1790 Target: | 5'-CCACCAUCCCACUGGCCUCUGAUAA-3'<br>3'-UGGGUGGUAGGGUGACCGGAGACUAUU-5'<br>5'-ACCCACCATCCCACTGGCCTCTGATAA-3' | (SEQ ID NO: 3553)<br>(SEQ ID NO: 1335)<br>(SEQ ID NO: 2444) |
| βc-1791 Target: | 5'-CACCAUCCCACUGGCCUCUGAUAAA-3'<br>3'-GGGUGGUAGGGUGACCGGAGACUAUUU-5'<br>5'-CCCACCATCCCACTGGCCTCTGATAAA-3' | (SEQ ID NO: 3554)<br>(SEQ ID NO: 1336)<br>(SEQ ID NO: 2445) |
| βc-1792 Target: | 5'-ACCAUCCCACUGGCCUCUGAUAAAG-3'<br>3'-GGUGGUAGGGUGACCGGAGACUAUUUC-5'<br>5'-CCACCATCCCACTGGCCTCTGATAAAG-3' | (SEQ ID NO: 3555)<br>(SEQ ID NO: 1337)<br>(SEQ ID NO: 2446) |
| βc-1793 Target: | 5'-CCAUCCCACUGGCCUCUGAUAAAGG-3'<br>3'-GUGGUAGGGUGACCGGAGACUAUUUCC-5'<br>5'-CACCATCCCACTGGCCTCTGATAAAGG-3' | (SEQ ID NO: 3556)<br>(SEQ ID NO: 1338)<br>(SEQ ID NO: 2447) |
| βc-1794 Target: | 5'-CAUCCCACUGGCCUCUGAUAAAGGC-3'<br>3'-UGGUAGGGUGACCGGAGACUAUUUCCG-5'<br>5'-ACCATCCCACTGGCCTCTGATAAAGGC-3' | (SEQ ID NO: 3557)<br>(SEQ ID NO: 1339)<br>(SEQ ID NO: 2448) |
| βc-1795 Target: | 5'-AUCCCACUGGCCUCUGAUAAAGGCU-3'<br>3'-GGUAGGGUGACCGGAGACUAUUUCCGA-5'<br>5'-CCATCCCACTGGCCTCTGATAAAGGCT-3' | (SEQ ID NO: 3558)<br>(SEQ ID NO: 1340)<br>(SEQ ID NO: 2449) |
| βc-1796 Target: | 5'-UCCCACUGGCCUCUGAUAAAGGCUA-3'<br>3'-GUAGGGUGACCGGAGACUAUUUCCGAU-5'<br>5'-CATCCCACTGGCCTCTGATAAAGGCTA-3' | (SEQ ID NO: 3559)<br>(SEQ ID NO: 1341)<br>(SEQ ID NO: 2450) |
| βc-1797 Target: | 5'-CCCACUGGCCUCUGAUAAAGGCUAC-3'<br>3'-UAGGGUGACCGGAGACUAUUUCCGAUG-5'<br>5'-ATCCCACTGGCCTCTGATAAAGGCTAC-3' | (SEQ ID NO: 3560)<br>(SEQ ID NO: 1342)<br>(SEQ ID NO: 2451) |
| βc-1798 Target: | 5'-CCACUGGCCUCUGAUAAAGGCUACU-3'<br>3'-AGGGUGACCGGAGACUAUUUCCGAUGA-5'<br>5'-TCCCACTGGCCTCTGATAAAGGCTACT-3' | (SEQ ID NO: 3561)<br>(SEQ ID NO: 1343)<br>(SEQ ID NO: 2452) |
| βc-1799 Target: | 5'-CACUGGCCUCUGAUAAAGGCUACUG-3'<br>3'-GGGUGACCGGAGACUAUUUCCGAUGAC-5'<br>5'-CCCACTGGCCTCTGATAAAGGCTACTG-3' | (SEQ ID NO: 3562)<br>(SEQ ID NO: 1344)<br>(SEQ ID NO: 2453) |
| βc-1800 Target: | 5'-ACUGGCCUCUGAUAAAGGCUACUGU-3'<br>3'-GGUGACCGGAGACUAUUUCCGAUGACA-5'<br>5'-CCACTGGCCTCTGATAAAGGCTACTGT-3' | (SEQ ID NO: 3563)<br>(SEQ ID NO: 1345)<br>(SEQ ID NO: 2454) |
| βc-1820 Target: | 5'-ACUGUUGGAUUGAUUCGAAAUCUUG-3'<br>3'-GAUGACAACCUAACUAAGCUUUAGAAC-5'<br>5'-CTACTGTTGGATTGATTCGAAATCTTG-3' | (SEQ ID NO: 3564)<br>(SEQ ID NO: 1346)<br>(SEQ ID NO: 2455) |

TABLE 6-continued

Selected Anti-β-catenin DsiRNA Agents, Unmodified Duplexes

|  |  |  |  |
|---|---|---|---|
| βc-1821 Target: | 5'-CUGUUGGAUUGAUUCGAAAUCUUGC-3'<br>3'-AUGACAACCUAACUAAGCUUUAGAACG-5'<br>5'-TACTGTTGGATTGATTCGAAATCTTGC-3' | (SEQ ID NO: 3565)<br>(SEQ ID NO: 1347)<br>(SEQ ID NO: 2456) |
| βc-2072 Target: | 5'-AAUACCAUUCCAUUGUUUGUGCAGC-3'<br>3'-AUUUAUGGUAAGGUAACAAACACGUCG-5'<br>5'-TAAATACCATTCCATTGTTTGTGCAGC-3' | (SEQ ID NO: 3566)<br>(SEQ ID NO: 1348)<br>(SEQ ID NO: 2457) |
| βc-2073 Target: | 5'-AUACCAUUCCAUUGUUUGUGCAGCU-3'<br>3'-UUUAUGGUAAGGUAACAAACACGUCGA-5'<br>5'-AAATACCATTCCATTGTTTGTGCAGCT-3' | (SEQ ID NO: 3567)<br>(SEQ ID NO: 1349)<br>(SEQ ID NO: 2458) |
| βc-2074 Target: | 5'-UACCAUUCCAUUGUUUGUGCAGCUG-3'<br>3'-UUAUGGUAAGGUAACAAACACGUCGAC-5'<br>5'-AATACCATTCCATTGTTTGTGCAGCTG-3' | (SEQ ID NO: 3568)<br>(SEQ ID NO: 1350)<br>(SEQ ID NO: 2459) |
| βc-2075 Target: | 5'-ACCAUUCCAUUGUUUGUGCAGCUGC-3'<br>3'-UAUGGUAAGGUAACAAACACGUCGACG-5'<br>5'-ATACCATTCCATTGTTTGTGCAGCTGC-3' | (SEQ ID NO: 3569)<br>(SEQ ID NO: 1351)<br>(SEQ ID NO: 2460) |
| βc-2076 Target: | 5'-CCAUUCCAUUGUUUGUGCAGCUGCU-3'<br>3'-AUGGUAAGGUAACAAACACGUCGACGA-5'<br>5'-TACCATTCCATTGTTTGTGCAGCTGCT-3' | (SEQ ID NO: 3570)<br>(SEQ ID NO: 1352)<br>(SEQ ID NO: 2461) |
| βc-2077 Target: | 5'-CAUUCCAUUGUUUGUGCAGCUGCUU-3'<br>3'-UGGUAAGGUAACAAACACGUCGACGAA-5'<br>5'-ACCATTCCATTGTTTGTGCAGCTGCTT-3' | (SEQ ID NO: 3571)<br>(SEQ ID NO: 1353)<br>(SEQ ID NO: 2462) |
| βc-2097 Target: | 5'-UGCUUUAUUCUCCCAUUGAAAACAU-3'<br>3'-CGACGAAAUAAGAGGGUAACUUUUGUA-5'<br>5'-GCTGCTTTATTCTCCCATTGAAAAC-3' | (SEQ ID NO: 3572)<br>(SEQ ID NO: 1354)<br>(SEQ ID NO: 2463) |
| βc-2098 Target: | 5'-GCUUUAUUCUCCCAUUGAAAACAUC-3'<br>3'-GACGAAAUAAGAGGGUAACUUUUGUAG-5'<br>5'-CTGCTTTATTCTCCCATTGAAAACATC-3' | (SEQ ID NO: 3573)<br>(SEQ ID NO: 1355)<br>(SEQ ID NO: 2464) |
| βc-2099 Target: | 5'-CUUUAUUCUCCCAUUGAAAACAUCC-3'<br>3'-ACGAAAUAAGAGGGUAACUUUUGUAGG-5'<br>5'-TGCTTTATTCTCCCATTGAAAACATCC-3' | (SEQ ID NO: 3574)<br>(SEQ ID NO: 1356)<br>(SEQ ID NO: 2465) |
| βc-2100 Target: | 5'-UUUAUUCUCCCAUUGAAAACAUCCA-3'<br>3'-CGAAAUAAGAGGGUAACUUUUGUAGGU-5'<br>5'-GCTTTATTCTCCCATTGAAAACATCCA-3' | (SEQ ID NO: 3575)<br>(SEQ ID NO: 1357)<br>(SEQ ID NO: 2466) |
| βc-2141 Target: | 5'-GUCCUCUGUGAACUUGCUCAGGACA-3'<br>3'-CCCAGGAGACACUUGAACGAGUCCUGU-5'<br>5'-GGGTCCTCTGTGAACTTGCTCAGGACA-3' | (SEQ ID NO: 3576)<br>(SEQ ID NO: 1358)<br>(SEQ ID NO: 2467) |
| βc-2142 Target: | 5'-UCCUCUGUGAACUUGCUCAGGACAA-3'<br>3'-CCAGGAGACACUUGAACGAGUCCUGUU-5'<br>5'-GGTCCTCTGTGAACTTGCTCAGGACAA-3' | (SEQ ID NO: 3577)<br>(SEQ ID NO: 1359)<br>(SEQ ID NO: 2468) |
| βc-2143 Target: | 5'-CCUCUGUGAACUUGCUCAGGACAAG-3'<br>3'-CAGGAGACACUUGAACGAGUCCUGUUC-5'<br>5'-GTCCTCTGTGAACTTGCTCAGGACAAG-3' | (SEQ ID NO: 3578)<br>(SEQ ID NO: 1360)<br>(SEQ ID NO: 2469) |
| βc-2144 Target: | 5'-CUCUGUGAACUUGCUCAGGACAAGG-3'<br>3'-AGGAGACACUUGAACGAGUCCUGUUCC-5'<br>5'-TCCTCTGTGAACTTGCTCAGGACAAGG-3' | (SEQ ID NO: 3579)<br>(SEQ ID NO: 1361)<br>(SEQ ID NO: 2470) |
| βc-2145 Target: | 5'-UCUGUGAACUUGCUCAGGACAAGGA-3'<br>3'-GGAGACACUUGAACGAGUCCUGUUCCU-5'<br>5'-CCTCTGTGAACTTGCTCAGGACAAGGA-3' | (SEQ ID NO: 3580)<br>(SEQ ID NO: 1362)<br>(SEQ ID NO: 2471) |
| βc-2146 Target: | 5'-CUGUGAACUUGCUCAGGACAAGGAA-3'<br>3'-GAGACACUUGAACGAGUCCUGUUCCUU-5'<br>5'-CTCTGTGAACTTGCTCAGGACAAGGAA-3' | (SEQ ID NO: 3581)<br>(SEQ ID NO: 1363)<br>(SEQ ID NO: 2472) |
| βc-2147 Target: | 5'-UGUGAACUUGCUCAGGACAAGGAAG-3'<br>3'-AGACACUUGAACGAGUCCUGUUCCUUC-5'<br>5'-TCTGTGAACTTGCTCAGGACAAGGAAG-3' | (SEQ ID NO: 3582)<br>(SEQ ID NO: 1364)<br>(SEQ ID NO: 2473) |
| βc-2148 Target: | 5'-GUGAACUUGCUCAGGACAAGGAAGC-3'<br>3'-GACACUUGAACGAGUCCUGUUCCUUCG-5'<br>5'-CTGTGAACTTGCTCAGGACAAGGAAGC-3' | (SEQ ID NO: 3583)<br>(SEQ ID NO: 1365)<br>(SEQ ID NO: 2474) |

TABLE 6-continued

Selected Anti-β-catenin DsiRNA Agents, Unmodified Duplexes

|  |  |  |  |
|---|---|---|---|
| βc-2149 | Target: | 5'-UGAACUUGCUCAGGACAAGGAAGCU-3'<br>3'-ACACUUGAACGAGUCCUGUUCCUUCGA-5'<br>5'-TGTGAACTTGCTCAGGACAAGGAAGCT-3' | (SEQ ID NO: 3584)<br>(SEQ ID NO: 1366)<br>(SEQ ID NO: 2475) |
| βc-2150 | Target: | 5'-GAACUUGCUCAGGACAAGGAAGCUG-3'<br>3'-CACUUGAACGAGUCCUGUUCCUUCGAC-5'<br>5'-GTGAACTTGCTCAGGACAAGGAAGCTG-3' | (SEQ ID NO: 3585)<br>(SEQ ID NO: 1367)<br>(SEQ ID NO: 2476) |
| βc-2151 | Target: | 5'-AACUUGCUCAGGACAAGGAAGCUGC-3'<br>3'-ACUUGAACGAGUCCUGUUCCUUCGACG-5'<br>5'-TGAACTTGCTCAGGACAAGGAAGCTGC-3' | (SEQ ID NO: 3586)<br>(SEQ ID NO: 1368)<br>(SEQ ID NO: 2477) |
| βc-2183 | Target: | 5'-AUUGAAGCUGAGGGAGCCACAGCUC-3'<br>3'-GAUAACUUCGACUCCCUCGGUGUCGAG-5'<br>5'-CTATTGAAGCTGAGGGAGCCACAGCTC-3' | (SEQ ID NO: 3587)<br>(SEQ ID NO: 1369)<br>(SEQ ID NO: 2478) |
| βc-2184 | Target: | 5'-UUGAAGCUGAGGGAGCCACAGCUCC-3'<br>3'-AUAACUUCGACUCCCUCGGUGUCGAGG-5'<br>5'-TATTGAAGCTGAGGGAGCCACAGCTCC-3' | (SEQ ID NO: 3588)<br>(SEQ ID NO: 1370)<br>(SEQ ID NO: 2479) |
| βc-2185 | Target: | 5'-UGAAGCUGAGGGAGCCACAGCUCCU-3'<br>3'-UAACUUCGACUCCCUCGGUGUCGAGGA-5'<br>5'-ATTGAAGCTGAGGGAGCCACAGCTCCT-3' | (SEQ ID NO: 3589)<br>(SEQ ID NO: 1371)<br>(SEQ ID NO: 2480) |
| βc-2270 | Target: | 5'-UUCCGAAUGUCUGAGGACAAGCCAC-3'<br>3'-ACAAGGCUUACAGACUCCUGUUCGGUG-5'<br>5'-TGTTCCGAATGTCTGAGGACAAGCCAC-3' | (SEQ ID NO: 3590)<br>(SEQ ID NO: 1372)<br>(SEQ ID NO: 2481) |
| βc-2271 | Target: | 5'-UCCGAAUGUCUGAGGACAAGCCACA-3'<br>3'-CAAGGCUUACAGACUCCUGUUCGGUGU-5'<br>5'-GTTCCGAATGTCTGAGGACAAGCCACA-3' | (SEQ ID NO: 3591)<br>(SEQ ID NO: 1373)<br>(SEQ ID NO: 2482) |
| βc-2272 | Target: | 5'-CCGAAUGUCUGAGGACAAGCCACAA-3'<br>3'-AAGGCUUACAGACUCCUGUUCGGUGUU-5'<br>5'-TTCCGAATGTCTGAGGACAAGCCACAA-3' | (SEQ ID NO: 3592)<br>(SEQ ID NO: 1374)<br>(SEQ ID NO: 2483) |
| βc-2273 | Target: | 5'-CGAAUGUCUGAGGACAAGCCACAAG-3'<br>3'-AGGCUUACAGACUCCUGUUCGGUGUUC-5'<br>5'-TCCGAATGTCTGAGGACAAGCCACAAG-3' | (SEQ ID NO: 3593)<br>(SEQ ID NO: 1375)<br>(SEQ ID NO: 2484) |
| βc-2274 | Target: | 5'-GAAUGUCUGAGGACAAGCCACAAGA-3'<br>3'-GGCUUACAGACUCCUGUUCGGUGUUCU-5'<br>5'-CCGAATGTCTGAGGACAAGCCACAAGA-3' | (SEQ ID NO: 3594)<br>(SEQ ID NO: 1376)<br>(SEQ ID NO: 2485) |
| βc-2275 | Target: | 5'-AAUGUCUGAGGACAAGCCACAAGAU-3'<br>3'-GCUUACAGACUCCUGUUCGGUGUUCUA-5'<br>5'-CGAATGTCTGAGGACAAGCCACAAGAT-3' | (SEQ ID NO: 3595)<br>(SEQ ID NO: 1377)<br>(SEQ ID NO: 2486) |
| βc-2276 | Target: | 5'-AUGUCUGAGGACAAGCCACAAGAUU-3'<br>3'-CUUACAGACUCCUGUUCGGUGUUCUAA-5'<br>5'-GAATGTCTGAGGACAAGCCACAAGATT-3' | (SEQ ID NO: 3596)<br>(SEQ ID NO: 1378)<br>(SEQ ID NO: 2487) |
| βc-2277 | Target: | 5'-UGUCUGAGGACAAGCCACAAGAUUA-3'<br>3'-UUACAGACUCCUGUUCGGUGUUCUAAU-5'<br>5'-AATGTCTGAGGACAAGCCACAAGATTA-3' | (SEQ ID NO: 3597)<br>(SEQ ID NO: 1379)<br>(SEQ ID NO: 2488) |
| βc-2345 | Target: | 5'-ACAGAGCCAAUGGCUUGGAAUGAGA-3'<br>3'-CUUGUCUCGGUUACCGAACCUUACUCU-5'<br>5'-GAACAGAGCCAATGGCTTGGAATGAGA-3' | (SEQ ID NO: 3598)<br>(SEQ ID NO: 1380)<br>(SEQ ID NO: 2489) |
| βc-2346 | Target: | 5'-CAGAGCCAAUGGCUUGGAAUGAGAC-3'<br>3'-UUGUCUCGGUUACCGAACCUUACUCUG-5'<br>5'-AACAGAGCCAATGGCTTGGAATGAGAC-3' | (SEQ ID NO: 3599)<br>(SEQ ID NO: 1381)<br>(SEQ ID NO: 2490) |
| βc-2347 | Target: | 5'-AGAGCCAAUGGCUUGGAAUGAGACU-3'<br>3'-UGUCUCGGUUACCGAACCUUACUCUGA-5'<br>5'-ACAGAGCCAATGGCTTGGAATGAGACT-3' | (SEQ ID NO: 3600)<br>(SEQ ID NO: 1382)<br>(SEQ ID NO: 2491) |
| βc-2348 | Target: | 5'-GAGCCAAUGGCUUGGAAUGAGACUG-3'<br>3'-GUCUCGGUUACCGAACCUUACUCUGAC-5'<br>5'-CAGAGCCAATGGCTTGGAATGAGACTG-3' | (SEQ ID NO: 3601)<br>(SEQ ID NO: 1383)<br>(SEQ ID NO: 2492) |
| βc-2349 | Target: | 5'-AGCCAAUGGCUUGGAAUGAGACUGC-3'<br>3'-UCUCGGUUACCGAACCUUACUCUGACG-5'<br>5'-AGAGCCAATGGCTTGGAATGAGACTGC-3' | (SEQ ID NO: 3602)<br>(SEQ ID NO: 1384)<br>(SEQ ID NO: 2493) |

TABLE 6-continued

Selected Anti-β-catenin DsiRNA Agents, Unmodified Duplexes

| | | |
|---|---|---|
| βc-2350 Target: | 5'-GCCAAUGGCUUGGAAUGAGACUGCU-3'<br>3'-CUCGGUUACCGAACCUUACUCUGACGA-5'<br>5'-GAGCCAATGGCTTGGAATGAGACTGCT-3' | (SEQ ID NO: 3603)<br>(SEQ ID NO: 1385)<br>(SEQ ID NO: 2494) |
| βc-2351 Target: | 5'-CCAAUGGCUUGGAAUGAGACUGCUG-3'<br>3'-UCGGUUACCGAACCUUACUCUGACGAC-5'<br>5'-AGCCAATGGCTTGGAATGAGACTGCTG-3' | (SEQ ID NO: 3604)<br>(SEQ ID NO: 1386)<br>(SEQ ID NO: 2495) |
| βc-2352 Target: | 5'-CAAUGGCUUGGAAUGAGACUGCUGA-3'<br>3'-CGGUUACCGAACCUUACUCUGACGACU-5'<br>5'-GCCAATGGCTTGGAATGAGACTGCTGA-3' | (SEQ ID NO: 3605)<br>(SEQ ID NO: 1387)<br>(SEQ ID NO: 2496) |
| βc-2353 Target: | 5'-AAUGGCUUGGAAUGAGACUGCUGAU-3'<br>3'-GGUUACCGAACCUUACUCUGACGACUA-5'<br>5'-CCAATGGCTTGGAATGAGACTGCTGAT-3' | (SEQ ID NO: 3606)<br>(SEQ ID NO: 1388)<br>(SEQ ID NO: 2497) |
| βc-2354 Target: | 5'-AUGGCUUGGAAUGAGACUGCUGAUC-3'<br>3'-GUUACCGAACCUUACUCUGACGACUAG-5'<br>5'-CAATGGCTTGGAATGAGACTGCTGATC-3' | (SEQ ID NO: 3607)<br>(SEQ ID NO: 1389)<br>(SEQ ID NO: 2498) |
| βc-2355 Target: | 5'-UGGCUUGGAAUGAGACUGCUGAUCU-3'<br>3'-UUACCGAACCUUACUCUGACGACUAGA-5'<br>5'-AATGGCTTGGAATGAGACTGCTGATCT-3' | (SEQ ID NO: 3608)<br>(SEQ ID NO: 1390)<br>(SEQ ID NO: 2499) |
| βc-2411 Target: | 5'-CUUGGAUAUCGCCAGGAUGAUCCUA-3'<br>3'-GGGAACCUAUAGCGGUCCUACUAGGAU-5'<br>5'-CCCTTGGATATCGCCAGGATGATCCTA-3' | (SEQ ID NO: 3609)<br>(SEQ ID NO: 1391)<br>(SEQ ID NO: 2500) |
| βc-2412 Target: | 5'-UUGGAUAUCGCCAGGAUGAUCCUAG-3'<br>3'-GGAACCUAUAGCGGUCCUACUAGGAUC-5'<br>5'-CCTTGGATATCGCCAGGATGATCCTAG-3' | (SEQ ID NO: 3610)<br>(SEQ ID NO: 1392)<br>(SEQ ID NO: 2501) |
| βc-2413 Target: | 5'-UGGAUAUCGCCAGGAUGAUCCUAGC-3'<br>3'-GAACCUAUAGCGGUCCUACUAGGAUCG-5'<br>5'-CTTGGATATCGCCAGGATGATCCTAGC-3' | (SEQ ID NO: 3611)<br>(SEQ ID NO: 1393)<br>(SEQ ID NO: 2502) |
| βc-2414 Target: | 5'-GGAUAUCGCCAGGAUGAUCCUAGCU-3'<br>3'-AACCUAUAGCGGUCCUACUAGGAUCGA-5'<br>5'-TTGGATATCGCCAGGATGATCCTAGCT-3' | (SEQ ID NO: 3612)<br>(SEQ ID NO: 1394)<br>(SEQ ID NO: 2503) |
| βc-2415 Target: | 5'-GAUAUCGCCAGGAUGAUCCUAGCUA-3'<br>3'-ACCUAUAGCGGUCCUACUAGGAUCGAU-5'<br>5'-TGGATATCGCCAGGATGATCCTAGCTA-3' | (SEQ ID NO: 3613)<br>(SEQ ID NO: 1395)<br>(SEQ ID NO: 2504) |
| βc-2441 Target: | 5'-CGUUCUUUUCACUCUGGUGGAUAUG-3'<br>3'-UAGCAAGAAAAGUGAGACCACCUAUAC-5'<br>5'-ATCGTTCTTTTCACTCTGGTGGATATG-3' | (SEQ ID NO: 3614)<br>(SEQ ID NO: 1396)<br>(SEQ ID NO: 2505) |
| βc-2442 Target: | 5'-GUUCUUUUCACUCUGGUGGAUAUGG-3'<br>3'-AGCAAGAAAAGUGAGACCACCUAUACC-5'<br>5'-TCGTTCTTTTCACTCTGGTGGATATGG-3' | (SEQ ID NO: 3615)<br>(SEQ ID NO: 1397)<br>(SEQ ID NO: 2506) |
| βc-2443 Target: | 5'-UUCUUUUCACUCUGGUGGAUAUGGC-3'<br>3'-GCAAGAAAAGUGAGACCACCUAUACCG-5'<br>5'-CGTTCTTTTCACTCTGGTGGATATGGC-3' | (SEQ ID NO: 3616)<br>(SEQ ID NO: 1398)<br>(SEQ ID NO: 2507) |
| βc-2444 Target: | 5'-UCUUUUCACUCUGGUGGAUAUGGCC-3'<br>3'-CAAGAAAAGUGAGACCACCUAUACCGG-5'<br>5'-GTTCTTTTCACTCTGGTGGATATGGCC-3' | (SEQ ID NO: 3617)<br>(SEQ ID NO: 1399)<br>(SEQ ID NO: 2508) |
| βc-2445 Target: | 5'-CUUUUCACUCUGGUGGAUAUGGCCA-3'<br>3'-AAGAAAAGUGAGACCACCUAUACCGGU-5'<br>5'-TTCTTTTCACTCTGGTGGATATGGCCA-3' | (SEQ ID NO: 3618)<br>(SEQ ID NO: 1400)<br>(SEQ ID NO: 2509) |
| βc-2501 Target: | 5'-CAUGAGAUGGGUGGCCACCACCCUG-3'<br>3'-UUGUACUCUACCCACCGGUGGUGGGAC-5'<br>5'-AACATGAGATGGGTGGCCACCACCCTG-3' | (SEQ ID NO: 3619)<br>(SEQ ID NO: 1401)<br>(SEQ ID NO: 2510) |
| βc-2502 Target: | 5'-AUGAGAUGGGUGGCCACCACCCUGG-3'<br>3'-UGUACUCUACCCACCGGUGGUGGGACC-5'<br>5'-ACATGAGATGGGTGGCCACCACCCTGG-3' | (SEQ ID NO: 3620)<br>(SEQ ID NO: 1402)<br>(SEQ ID NO: 2511) |
| βc-2503 Target: | 5'-UGAGAUGGGUGGCCACCACCCUGGU-3'<br>3'-GUACUCUACCCACCGGUGGUGGGACCA-5'<br>5'-CATGAGATGGGTGGCCACCACCCTGGT-3' | (SEQ ID NO: 3621)<br>(SEQ ID NO: 1403)<br>(SEQ ID NO: 2512) |

TABLE 6-continued

Selected Anti-β-catenin DsiRNA Agents, Unmodified Duplexes

|  |  |  |  |
|---|---|---|---|
| βc-2504 Target: | 5'-GAGAUGGGUGGCCACCACCCUGGUG-3'<br>3'-UACUCUACCCACCGGUGGUGGGACCAC-5'<br>5'-ATGAGATGGGTGGCCACCACCCTGGTG-3' | (SEQ ID NO: 3622)<br>(SEQ ID NO: 1404)<br>(SEQ ID NO: 2513) |  |
| βc-2505 Target: | 5'-AGAUGGGUGGCCACCACCCUGGUGC-3'<br>3'-ACUCUACCCACCGGUGGUGGGACCACG-5'<br>5'-TGAGATGGGTGGCCACCACCCTGGTGC-3' | (SEQ ID NO: 3623)<br>(SEQ ID NO: 1405)<br>(SEQ ID NO: 2514) |  |
| βc-2506 Target: | 5'-GAUGGGUGGCCACCACCCUGGUGCU-3'<br>3'-CUCUACCCACCGGUGGUGGGACCACGA-5'<br>5'-GAGATGGGTGGCCACCACCCTGGTGCT-3' | (SEQ ID NO: 3624)<br>(SEQ ID NO: 1406)<br>(SEQ ID NO: 2515) |  |
| βc-2507 Target: | 5'-AUGGGUGGCCACCACCCUGGUGCUG-3'<br>3'-UCUACCCACCGGUGGUGGGACCACGAC-5'<br>5'-AGATGGGTGGCCACCACCCTGGTGCTG-3' | (SEQ ID NO: 3625)<br>(SEQ ID NO: 1407)<br>(SEQ ID NO: 2516) |  |
| βc-2508 Target: | 5'-UGGGUGGCCACCACCCUGGUGCUGA-3'<br>3'-CUACCCACCGGUGGUGGGACCACGACU-5'<br>5'-GATGGGTGGCCACCACCCTGGTGCTGA-3' | (SEQ ID NO: 3626)<br>(SEQ ID NO: 1408)<br>(SEQ ID NO: 2517) |  |
| βc-2509 Target: | 5'-GGGUGGCCACCACCCUGGUGCUGAC-3'<br>3'-UACCCACCGGUGGUGGGACCACGACUG-5'<br>5'-ATGGGTGGCCACCACCCTGGTGCTGAC-3' | (SEQ ID NO: 3627)<br>(SEQ ID NO: 1409)<br>(SEQ ID NO: 2518) |  |
| βc-2510 Target: | 5'-GGUGGCCACCACCCUGGUGCUGACU-3'<br>3'-ACCCACCGGUGGUGGGACCACGACUGA-5'<br>5'-TGGGTGGCCACCACCCTGGTGCTGACT-3' | (SEQ ID NO: 3628)<br>(SEQ ID NO: 1410)<br>(SEQ ID NO: 2519) |  |
| βc-2511 Target: | 5'-GUGGCCACCACCCUGGUGCUGACUA-3'<br>3'-CCCACCGGUGGUGGGACCACGACUGAU-5'<br>5'-GGGTGGCCACCACCCTGGTGCTGACTA-3' | (SEQ ID NO: 3629)<br>(SEQ ID NO: 1411)<br>(SEQ ID NO: 2520) |  |
| βc-2512 Target: | 5'-UGGCCACCACCCUGGUGCUGACUAU-3'<br>3'-CCACCGGUGGUGGGACCACGACUGAUA-5'<br>5'-GGTGGCCACCACCCTGGTGCTGACTAT-3' | (SEQ ID NO: 3630)<br>(SEQ ID NO: 1412)<br>(SEQ ID NO: 2521) |  |
| βc-2513 Target: | 5'-GGCCACCACCCUGGUGCUGACUAUC-3'<br>3'-CACCGGUGGUGGGACCACGACUGAUAG-5'<br>5'-GTGGCCACCACCCTGGTGCTGACTATC-3' | (SEQ ID NO: 3631)<br>(SEQ ID NO: 1413)<br>(SEQ ID NO: 2522) |  |
| βc-2514 Target: | 5'-GCCACCACCCUGGUGCUGACUAUCC-3'<br>3'-ACCGGUGGUGGGACCACGACUGAUAGG-5'<br>5'-TGGCCACCACCCTGGTGCTGACTATCC-3' | (SEQ ID NO: 3632)<br>(SEQ ID NO: 1414)<br>(SEQ ID NO: 2523) |  |
| βc-2515 Target: | 5'-CCACCACCCUGGUGCUGACUAUCCA-3'<br>3'-CCGGUGGUGGGACCACGACUGAUAGGU-5'<br>5'-GGCCACCACCCTGGTGCTGACTATCCA-3' | (SEQ ID NO: 3633)<br>(SEQ ID NO: 1415)<br>(SEQ ID NO: 2524) |  |
| βc-2516 Target: | 5'-CACCACCCUGGUGCUGACUAUCCAG-3'<br>3'-CGGUGGUGGGACCACGACUGAUAGGUC-5'<br>5'-GCCACCACCCTGGTGCTGACTATCCAG-3' | (SEQ ID NO: 3634)<br>(SEQ ID NO: 1416)<br>(SEQ ID NO: 2525) |  |
| βc-2517 Target: | 5'-ACCACCCUGGUGCUGACUAUCCAGU-3'<br>3'-GGUGGUGGGACCACGACUGAUAGGUCA-5'<br>5'-CCACCACCCTGGTGCTGACTATCCAGT-3' | (SEQ ID NO: 3635)<br>(SEQ ID NO: 1417)<br>(SEQ ID NO: 2526) |  |
| βc-2518 Target: | 5'-CCACCCUGGUGCUGACUAUCCAGUU-3'<br>3'-GUGGUGGGACCACGACUGAUAGGUCAA-5'<br>5'-CACCACCCTGGTGCTGACTATCCAGTT-3' | (SEQ ID NO: 3636)<br>(SEQ ID NO: 1418)<br>(SEQ ID NO: 2527) |  |
| βc-2519 Target: | 5'-CACCCUGGUGCUGACUAUCCAGUUG-3'<br>3'-UGGUGGGACCACGACUGAUAGGUCAAC-5'<br>5'-ACCACCCTGGTGCTGACTATCCAGTTG-3' | (SEQ ID NO: 3637)<br>(SEQ ID NO: 1419)<br>(SEQ ID NO: 2528) |  |
| βc-2520 Target: | 5'-ACCCUGGUGCUGACUAUCCAGUUGA-3'<br>3'-GGUGGGACCACGACUGAUAGGUCAACU-5'<br>5'-CCACCCTGGTGCTGACTATCCAGTTGA-3' | (SEQ ID NO: 3638)<br>(SEQ ID NO: 1420)<br>(SEQ ID NO: 2529) |  |
| βc-2521 Target: | 5'-CCCUGGUGCUGACUAUCCAGUUGAU-3'<br>3'-GUGGGACCACGACUGAUAGGUCAACUA-5'<br>5'-CACCCTGGTGCTGACTATCCAGTTGAT-3' | (SEQ ID NO: 3639)<br>(SEQ ID NO: 1421)<br>(SEQ ID NO: 2530) |  |
| βc-2522 Target: | 5'-CCUGGUGCUGACUAUCCAGUUGAUG-3'<br>3'-UGGGACCACGACUGAUAGGUCAACUAC-5'<br>5'-ACCCTGGTGCTGACTATCCAGTTGATG-3' | (SEQ ID NO: 3640)<br>(SEQ ID NO: 1422)<br>(SEQ ID NO: 2531) |  |

TABLE 6-continued

Selected Anti-β-catenin DsiRNA Agents, Unmodified Duplexes

|  |  |  |  |
|---|---|---|---|
| βc-2523 Target: | 5'-CUGGUGCUGACUAUCCAGUUGAUGG-3'<br>3'-GGGACCACGACUGAUAGGUCAACUACC-5'<br>5'-CCCTGGTGCTGACTATCCAGTTGATGG-3' | (SEQ ID NO: 3641)<br>(SEQ ID NO: 1423)<br>(SEQ ID NO: 2532) |  |
| βc-2524 Target: | 5'-UGGUGCUGACUAUCCAGUUGAUGGG-3'<br>3'-GGACCACGACUGAUAGGUCAACUACCC-5'<br>5'-CCTGGTGCTGACTATCCAGTTGATGGG-3' | (SEQ ID NO: 3642)<br>(SEQ ID NO: 1424)<br>(SEQ ID NO: 2533) |  |
| βc-2525 Target: | 5'-GGUGCUGACUAUCCAGUUGAUGGGC-3'<br>3'-GACCACGACUGAUAGGUCAACUACCCG-5'<br>5'-CTGGTGCTGACTATCCAGTTGATGGGC-3' | (SEQ ID NO: 3643)<br>(SEQ ID NO: 1425)<br>(SEQ ID NO: 2534) |  |
| βc-2526 Target: | 5'-GUGCUGACUAUCCAGUUGAUGGGCU-3'<br>3'-ACCACGACUGAUAGGUCAACUACCCGA-5'<br>5'-TGGTGCTGACTATCCAGTTGATGGGCT-3' | (SEQ ID NO: 3644)<br>(SEQ ID NO: 1426)<br>(SEQ ID NO: 2535) |  |
| βc-2527 Target: | 5'-UGCUGACUAUCCAGUUGAUGGGCUG-3'<br>3'-CCACGACUGAUAGGUCAACUACCCGAC-5'<br>5'-GGTGCTGACTATCCAGTTGATGGGCTG-3' | (SEQ ID NO: 3645)<br>(SEQ ID NO: 1427)<br>(SEQ ID NO: 2536) |  |
| βc-2528 Target: | 5'-GCUGACUAUCCAGUUGAUGGGCUGC-3'<br>3'-CACGACUGAUAGGUCAACUACCCGACG-5'<br>5'-GTGCTGACTATCCAGTTGATGGGCTGC-3' | (SEQ ID NO: 3646)<br>(SEQ ID NO: 1428)<br>(SEQ ID NO: 2537) |  |
| βc-2529 Target: | 5'-CUGACUAUCCAGUUGAUGGGCUGCC-3'<br>3'-ACGACUGAUAGGUCAACUACCCGACGG-5'<br>5'-TGCTGACTATCCAGTTGATGGGCTGCC-3' | (SEQ ID NO: 3647)<br>(SEQ ID NO: 1429)<br>(SEQ ID NO: 2538) |  |
| βc-2530 Target: | 5'-UGACUAUCCAGUUGAUGGGCUGCCA-3'<br>3'-CGACUGAUAGGUCAACUACCCGACGGU-5'<br>5'-GCTGACTATCCAGTTGATGGGCTGCCA-3' | (SEQ ID NO: 3648)<br>(SEQ ID NO: 1430)<br>(SEQ ID NO: 2539) |  |
| βc-2531 Target: | 5'-GACUAUCCAGUUGAUGGGCUGCCAG-3'<br>3'-GACUGAUAGGUCAACUACCCGACGGUC-5'<br>5'-CTGACTATCCAGTTGATGGGCTGCCAG-3' | (SEQ ID NO: 3649)<br>(SEQ ID NO: 1431)<br>(SEQ ID NO: 2540) |  |
| βc-2532 Target: | 5'-ACUAUCCAGUUGAUGGGCUGCCAGA-3'<br>3'-ACUGAUAGGUCAACUACCCGACGGUCU-5'<br>5'-TGACTATCCAGTTGATGGGCTGCCAGA-3' | (SEQ ID NO: 3650)<br>(SEQ ID NO: 1432)<br>(SEQ ID NO: 2541) |  |
| βc-2533 Target: | 5'-CUAUCCAGUUGAUGGGCUGCCAGAU-3'<br>3'-CUGAUAGGUCAACUACCCGACGGUCUA-5'<br>5'-GACTATCCAGTTGATGGGCTGCCAGAT-3' | (SEQ ID NO: 3651)<br>(SEQ ID NO: 1433)<br>(SEQ ID NO: 2542) |  |
| βc-2534 Target: | 5'-UAUCCAGUUGAUGGGCUGCCAGAUC-3'<br>3'-UGAUAGGUCAACUACCCGACGGUCUAG-5'<br>5'-ACTATCCAGTTGATGGGCTGCCAGATC-3' | (SEQ ID NO: 3652)<br>(SEQ ID NO: 1434)<br>(SEQ ID NO: 2543) |  |
| βc-2535 Target: | 5'-AUCCAGUUGAUGGGCUGCCAGAUCU-3'<br>3'-GAUAGGUCAACUACCCGACGGUCUAGA-5'<br>5'-CTATCCAGTTGATGGGCTGCCAGATCT-3' | (SEQ ID NO: 3653)<br>(SEQ ID NO: 1435)<br>(SEQ ID NO: 2544) |  |
| βc-2567 Target: | 5'-GCCCAGGACCUCAUGGAUGGGCUGC-3'<br>3'-UACGGGUCCUGGAGUACCUACCCGACG-5'<br>5'-ATGCCCAGGACCTCATGGATGGGCTGC-3' | (SEQ ID NO: 3654)<br>(SEQ ID NO: 1436)<br>(SEQ ID NO: 2545) |  |
| βc-2568 Target: | 5'-CCCAGGACCUCAUGGAUGGGCUGCC-3'<br>3'-ACGGGUCCUGGAGUACCUACCCGACGG-5'<br>5'-TGCCCAGGACCTCATGGATGGGCTGCC-3' | (SEQ ID NO: 3655)<br>(SEQ ID NO: 1437)<br>(SEQ ID NO: 2546) |  |
| βc-2569 Target: | 5'-CCAGGACCUCAUGGAUGGGCUGCCU-3'<br>3'-CGGGUCCUGGAGUACCUACCCGACGGA-5'<br>5'-GCCCAGGACCTCATGGATGGGCTGCCT-3' | (SEQ ID NO: 3656)<br>(SEQ ID NO: 1438)<br>(SEQ ID NO: 2547) |  |
| βc-2603 Target: | 5'-AGCAAUCAGCUGGCCUGGUUUGAUA-3'<br>3'-UGUCGUUAGUCGACCGGACCAAACUAU-5'<br>5'-ACAGCAATCAGCTGGCCTGGTTTGATA-3' | (SEQ ID NO: 3657)<br>(SEQ ID NO: 1439)<br>(SEQ ID NO: 2548) |  |
| βc-2604 Target: | 5'-GCAAUCAGCUGGCCUGGUUUGAUAC-3'<br>3'-GUCGUUAGUCGACCGGACCAAACUAUG-5'<br>5'-CAGCAATCAGCTGGCCTGGTTTGATAC-3' | (SEQ ID NO: 3658)<br>(SEQ ID NO: 1440)<br>(SEQ ID NO: 2549) |  |
| βc-2605 Target: | 5'-CAAUCAGCUGGCCUGGUUUGAUACU-3'<br>3'-UCGUUAGUCGACCGGACCAAACUAUGA-5'<br>5'-AGCAATCAGCTGGCCTGGTTTGATACT-3' | (SEQ ID NO: 3659)<br>(SEQ ID NO: 1441)<br>(SEQ ID NO: 2550) |  |

TABLE 6-continued

Selected Anti-β-catenin DsiRNA Agents, Unmodified Duplexes

|  |  |  |
|---|---|---|
|  | 5'-AAUCAGCUGGCCUGGUUUGAUACUG-3' | (SEQ ID NO: 3660) |
|  | 3'-CGUUAGUCGACCGGACCAAACUAUGAC-5' | (SEQ ID NO: 1442) |
| βc-2606 Target: | 5'-GCAATCAGCTGGCCTGGTTTGATACTG-3' | (SEQ ID NO: 2551) |
|  | 5'-AUCAGCUGGCCUGGUUUGAUACUGA-3' | (SEQ ID NO: 3661) |
|  | 3'-GUUAGUCGACCGGACCAAACUAUGACU-5' | (SEQ ID NO: 1443) |
| βc-2607 Target: | 5'-CAATCAGCTGGCCTGGTTTGATACTGA-3' | (SEQ ID NO: 2552) |
|  | 5'-UCAGCUGGCCUGGUUUGAUACUGAC-3' | (SEQ ID NO: 3662) |
|  | 3'-UUAGUCGACCGGACCAAACUAUGACUG-5' | (SEQ ID NO: 1444) |
| βc-2608 Target: | 5'-AATCAGCTGGCCTGGTTTGATACTGAC-3' | (SEQ ID NO: 2553) |
|  | 5'-CAGCUGGCCUGGUUUGAUACUGACC-3' | (SEQ ID NO: 3663) |
|  | 3'-UAGUCGACCGGACCAAACUAUGACUGG-5' | (SEQ ID NO: 1445) |
| βc-2609 Target: | 5'-ATCAGCTGGCCTGGTTTGATACTGACC-3' | (SEQ ID NO: 2554) |
|  | 5'-AGCUGGCCUGGUUUGAUACUGACCU-3' | (SEQ ID NO: 3664) |
|  | 3'-AGUCGACCGGACCAAACUAUGACUGGA-5' | (SEQ ID NO: 1446) |
| βc-2610 Target: | 5'-TCAGCTGGCCTGGTTTGATACTGACCT-3' | (SEQ ID NO: 2555) |
|  | 5'-GCUGGCCUGGUUUGAUACUGACCUG-3' | (SEQ ID NO: 3665) |
|  | 3'-GUCGACCGGACCAAACUAUGACUGGAC-5' | (SEQ ID NO: 1447) |
| βc-2611 Target: | 5'-CAGCTGGCCTGGTTTGATACTGACCTG-3' | (SEQ ID NO: 2556) |
|  | 5'-CUGGCCUGGUUUGAUACUGACCUGU-3' | (SEQ ID NO: 3666) |
|  | 3'-UCGACCGGACCAAACUAUGACUGGACA-5' | (SEQ ID NO: 1448) |
| βc-2612 Target: | 5'-AGCTGGCCTGGTTTGATACTGACCTGT-3' | (SEQ ID NO: 2557) |
|  | 5'-UGGCCUGGUUUGAUACUGACCUGUA-3' | (SEQ ID NO: 3667) |
|  | 3'-CGACCGGACCAAACUAUGACUGGACAU-5' | (SEQ ID NO: 1449) |
| βc-2613 Target: | 5'-GCTGGCCTGGTTTGATACTGACCTGTA-3' | (SEQ ID NO: 2558) |
|  | 5'-GGCCUGGUUUGAUACUGACCUGUAA-3' | (SEQ ID NO: 3668) |
|  | 3'-GACCGGACCAAACUAUGACUGGACAUU-5' | (SEQ ID NO: 1450) |
| βc-2614 Target: | 5'-CTGGCCTGGTTTGATACTGACCTGTAA-3' | (SEQ ID NO: 2559) |
|  | 5'-GCCUGGUUUGAUACUGACCUGUAAA-3' | (SEQ ID NO: 3669) |
|  | 3'-ACCGGACCAAACUAUGACUGGACAUUU-5' | (SEQ ID NO: 1451) |
| βc-2615 Target: | 5'-TGGCCTGGTTTGATACTGACCTGTAAA-3' | (SEQ ID NO: 2560) |
|  | 5'-CCUGGUUUGAUACUGACCUGUAAAU-3' | (SEQ ID NO: 3670) |
|  | 3'-CCGGACCAAACUAUGACUGGACAUUUA-5' | (SEQ ID NO: 1452) |
| βc-2616 Target: | 5'-GGCCTGGTTTGATACTGACCTGTAAAT-3' | (SEQ ID NO: 2561) |
|  | 5'-CUGGUUUGAUACUGACCUGUAAAUC-3' | (SEQ ID NO: 3671) |
|  | 3'-CGGACCAAACUAUGACUGGACAUUUAG-5' | (SEQ ID NO: 1453) |
| βc-2617 Target: | 5'-GCCTGGTTTGATACTGACCTGTAAATC-3' | (SEQ ID NO: 2562) |
|  | 5'-UGGUUUGAUACUGACCUGUAAAUCA-3' | (SEQ ID NO: 3672) |
|  | 3'-GGACCAAACUAUGACUGGACAUUUAGU-5' | (SEQ ID NO: 1454) |
| βc-2618 Target: | 5'-CCTGGTTTGATACTGACCTGTAAATCA-3' | (SEQ ID NO: 2563) |
|  | 5'-GGUUUGAUACUGACCUGUAAAUCAU-3' | (SEQ ID NO: 3673) |
|  | 3'-GACCAAACUAUGACUGGACAUUUAGUA-5' | (SEQ ID NO: 1455) |
| βc-2619 Target: | 5'-CTGGTTTGATACTGACCTGTAAATC-3' | (SEQ ID NO: 2564) |
|  | 5'-GUUUGAUACUGACCUGUAAAUCAUC-3' | (SEQ ID NO: 3674) |
|  | 3'-ACCAAACUAUGACUGGACAUUUAGUAG-5' | (SEQ ID NO: 1456) |
| βc-2620 Target: | 5'-TGGTTTGATACTGACCTGTAAATCATC-3' | (SEQ ID NO: 2565) |
|  | 5'-UUUGAUACUGACCUGUAAAUCAUCC-3' | (SEQ ID NO: 3675) |
|  | 3'-CCAAACUAUGACUGGACAUUUAGUAGG-5' | (SEQ ID NO: 1457) |
| βc-2621 Target: | 5'-GGTTTGATACTGACCTGTAAATCATCC-3' | (SEQ ID NO: 2566) |
|  | 5'-UUGAUACUGACCUGUAAAUCAUCCU-3' | (SEQ ID NO: 3676) |
|  | 3'-CAAACUAUGACUGGACAUUUAGUAGGA-5' | (SEQ ID NO: 1458) |
| βc-2622 Target: | 5'-GTTTGATACTGACCTGTAAATCATCCT-3' | (SEQ ID NO: 2567) |
|  | 5'-UGAUACUGACCUGUAAAUCAUCCUU-3' | (SEQ ID NO: 3677) |
|  | 3'-AAACUAUGACUGGACAUUUAGUAGGAA-5' | (SEQ ID NO: 1459) |
| βc-2623 Target: | 5'-TTTGATACTGACCTGTAAATCATCCTT-3' | (SEQ ID NO: 2568) |
|  | 5'-UUUUGCCACAGCUUUUGCAACUUAA-3' | (SEQ ID NO: 3678) |
|  | 3'-AAAAAACGGUGUCGAAAACGUUGAAUU-5' | (SEQ ID NO: 1460) |
| βc-2869 Target: | 5'-TTTTTTGCCACAGCTTTTGCAACTTAA-3' | (SEQ ID NO: 2569) |

TABLE 6-continued

Selected Anti-β-catenin DsiRNA Agents, Unmodified Duplexes

| | | |
|---|---|---|
| βc-2902 Target: | 5'-UGAGUAACAUUUGCUGUUUUAAACA-3'<br>3'-UUACUCAUUGUAAACGACAAAAUUUGU-5'<br>5'-AATGAGTAACATTTGCTGTTTTAAACA-3' | (SEQ ID NO: 3679)<br>(SEQ ID NO: 1461)<br>(SEQ ID NO: 2570) |
| βc-2923 Target: | 5'-AACAUUAAUAGCAGCCUUUCUCUCU-3'<br>3'-AUUUGUAAUUAUCGUCGGAAAGAGAGA-5'<br>5'-TAAACATTAATAGCAGCCTTTCTCTCT-3' | (SEQ ID NO: 3680)<br>(SEQ ID NO: 1462)<br>(SEQ ID NO: 2571) |
| βc-2925 Target: | 5'-CAUUAAUAGCAGCCUUUCUCUCUUU-3'<br>3'-UUGUAAUUAUCGUCGGAAAGAGAGAAA-5'<br>5'-AACATTAATAGCAGCCTTTCTCTCTTT-3' | (SEQ ID NO: 3681)<br>(SEQ ID NO: 1463)<br>(SEQ ID NO: 2572) |
| βc-2927 Target: | 5'-UUAAUAGCAGCCUUUCUCUCUUUAU-3'<br>3'-GUAAUUAUCGUCGGAAAGAGAGAAAUA-5'<br>5'-CATTAATAGCAGCCTTTCTCTCTTTAT-3' | (SEQ ID NO: 3682)<br>(SEQ ID NO: 1464)<br>(SEQ ID NO: 2573) |
| βc-2929 Target: | 5'-AAUAGCAGCCUUUCUCUCUUUAUAC-3'<br>3'-AAUUAUCGUCGGAAAGAGAGAAAUAUG-5'<br>5'-TTAATAGCAGCCTTTCTCTCTTTATAC-3' | (SEQ ID NO: 3683)<br>(SEQ ID NO: 1465)<br>(SEQ ID NO: 2574) |
| βc-2973 Target: | 5'-GCAUUGUGAUUGGCCUGUAGAGUUG-3'<br>3'-AACGUAACACUAACCGGACAUCUCAAC-5'<br>5'-TTGCATTGTGATTGGCCTGTAGAGTTG-3' | (SEQ ID NO: 3684)<br>(SEQ ID NO: 1466)<br>(SEQ ID NO: 2575) |
| βc-2975 Target: | 5'-AUUGUGAUUGGCCUGUAGAGUUGCU-3'<br>3'-CGUAACACUAACCGGACAUCUCAACGA-5'<br>5'-GCATTGTGATTGGCCTGTAGAGTTGCT-3' | (SEQ ID NO: 3685)<br>(SEQ ID NO: 1467)<br>(SEQ ID NO: 2576) |
| βc-2977 Target: | 5'-UGUGAUUGGCCUGUAGAGUUGCUGA-3'<br>3'-UAACACUAACCGGACAUCUCAACGACU-5'<br>5'-ATTGTGATTGGCCTGTAGAGTTGCTGA-3' | (SEQ ID NO: 3686)<br>(SEQ ID NO: 1468)<br>(SEQ ID NO: 2577) |
| βc-2979 Target: | 5'-UGAUUGGCCUGUAGAGUUGCUGAGA-3'<br>3'-ACACUAACCGGACAUCUCAACGACUCU-5'<br>5'-TGTGATTGGCCTGTAGAGTTGCTGAGA-3' | (SEQ ID NO: 3687)<br>(SEQ ID NO: 1469)<br>(SEQ ID NO: 2578) |
| βc-2981 Target: | 5'-AUUGGCCUGUAGAGUUGCUGAGAGG-3'<br>3'-ACUAACCGGACAUCUCAACGACUCUCC-5'<br>5'-TGATTGGCCTGTAGAGTTGCTGAGAGG-3' | (SEQ ID NO: 3688)<br>(SEQ ID NO: 1470)<br>(SEQ ID NO: 2579) |
| βc-2983 Target: | 5'-UGGCCUGUAGAGUUGCUGAGAGGGC-3'<br>3'-UAACCGGACAUCUCAACGACUCUCCCG-5'<br>5'-ATTGGCCTGTAGAGTTGCTGAGAGGGC-3' | (SEQ ID NO: 3689)<br>(SEQ ID NO: 1471)<br>(SEQ ID NO: 2580) |
| βc-2985 Target: | 5'-GCCUGUAGAGUUGCUGAGAGGGCUC-3'<br>3'-ACCGGACAUCUCAACGACUCUCCCGAG-5'<br>5'-TGGCCTGTAGAGTTGCTGAGAGGGCTC-3' | (SEQ ID NO: 3690)<br>(SEQ ID NO: 1472)<br>(SEQ ID NO: 2581) |
| βc-2987 Target: | 5'-CUGUAGAGUUGCUGAGAGGGCUCGA-3'<br>3'-CGGACAUCUCAACGACUCUCCCGAGCU-5'<br>5'-GCCTGTAGAGTTGCTGAGAGGGCTCGA-3' | (SEQ ID NO: 3691)<br>(SEQ ID NO: 1473)<br>(SEQ ID NO: 2582) |
| βc-2989 Target: | 5'-GUAGAGUUGCUGAGAGGGCUCGAGG-3'<br>3'-GACAUCUCAACGACUCUCCCGAGCUCC-5'<br>5'-CTGTAGAGTTGCTGAGAGGGCTCGAGG-3' | (SEQ ID NO: 3692)<br>(SEQ ID NO: 1474)<br>(SEQ ID NO: 2583) |
| βc-3015 Target: | 5'-GUGGGCUGGUAUCUCAGAAAGUGCC-3'<br>3'-CCCACCCGACCAUAGAGUCUUUCACGG-5'<br>5'-GGGTGGGCTGGTATCTCAGAAAGTGCC-3' | (SEQ ID NO: 3693)<br>(SEQ ID NO: 1475)<br>(SEQ ID NO: 2584) |
| βc-3017 Target: | 5'-GGGCUGGUAUCUCAGAAAGUGCCUG-3'<br>3'-CACCCGACCAUAGAGUCUUUCACGGAC-5'<br>5'-GTGGGCTGGTATCTCAGAAAGTGCCTG-3' | (SEQ ID NO: 3694)<br>(SEQ ID NO: 1476)<br>(SEQ ID NO: 2585) |
| βc-3019 Target: | 5'-GCUGGUAUCUCAGAAAGUGCCUGAC-3'<br>3'-CCCGACCAUAGAGUCUUUCACGGACUG-5'<br>5'-GGGCTGGTATCTCAGAAAGTGCCTGAC-3' | (SEQ ID NO: 3695)<br>(SEQ ID NO: 1477)<br>(SEQ ID NO: 2586) |
| βc-3021 Target: | 5'-UGGUAUCUCAGAAAGUGCCUGACAC-3'<br>3'-CGACCAUAGAGUCUUUCACGGACUGUG-5'<br>5'-GCTGGTATCTCAGAAAGTGCCTGACAC-3' | (SEQ ID NO: 3696)<br>(SEQ ID NO: 1478)<br>(SEQ ID NO: 2587) |
| βc-3046 Target: | 5'-ACUAACCAAGCUGAGUUUCCUAUGG-3'<br>3'-UGUGAUUGGUUCGACUCAAAGGAUACC-5'<br>5'-ACACTAACCAAGCTGAGTTTCCTATGG-3' | (SEQ ID NO: 3697)<br>(SEQ ID NO: 1479)<br>(SEQ ID NO: 2588) |

TABLE 6-continued

Selected Anti-β-catenin DsiRNA Agents, Unmodified Duplexes

| | | |
|---|---|---|
| βc-3048 Target: | 5'-UAACCAAGCUGAGUUUCCUAUGGGA-3'<br>3'-UGAUUGGUUCGACUCAAAGGAUACCCU-5'<br>5'-ACTAACCAAGCTGAGTTTCCTATGGGA-3' | (SEQ ID NO: 3698)<br>(SEQ ID NO: 1480)<br>(SEQ ID NO: 2589) |
| βc-3050 Target: | 5'-ACCAAGCUGAGUUUCCUAUGGGAAC-3'<br>3'-AUUGGUUCGACUCAAAGGAUACCCUUG-5'<br>5'-TAACCAAGCTGAGTTTCCTATGGGAAC-3' | (SEQ ID NO: 3699)<br>(SEQ ID NO: 1481)<br>(SEQ ID NO: 2590) |
| βc-3052 Target: | 5'-CAAGCUGAGUUUCCUAUGGGAACAA-3'<br>3'-UGGUUCGACUCAAAGGAUACCCUUGUU-5'<br>5'-ACCAAGCTGAGTTTCCTATGGGAACAA-3' | (SEQ ID NO: 3700)<br>(SEQ ID NO: 1482)<br>(SEQ ID NO: 2591) |
| βc-3054 Target: | 5'-AGCUGAGUUUCCUAUGGGAACAAUU-3'<br>3'-GUUCGACUCAAAGGAUACCCUUGUUAA-5'<br>5'-CAAGCTGAGTTTCCTATGGGAACAATT-3' | (SEQ ID NO: 3701)<br>(SEQ ID NO: 1483)<br>(SEQ ID NO: 2592) |
| βc-3056 Target: | 5'-CUGAGUUUCCUAUGGGAACAAUUGA-3'<br>3'-UCGACUCAAAGGAUACCCUUGUUAACU-5'<br>5'-AGCTGAGTTTCCTATGGGAACAATTGA-3' | (SEQ ID NO: 3702)<br>(SEQ ID NO: 1484)<br>(SEQ ID NO: 2593) |
| βc-3087 Target: | 5'-CUUUUUGUUCUGGUCCUUUUUGGUC-3'<br>3'-UUGAAAAACAAGACCAGGAAAAACCAG-5'<br>5'-AACTTTTGTTCTGGTCCTTTTTGGTC-3' | (SEQ ID NO: 3703)<br>(SEQ ID NO: 1485)<br>(SEQ ID NO: 2594) |
| βc-3089 Target: | 5'-UUUUGUUCUGGUCCUUUUUGGUCGA-3'<br>3'-GAAAAACAAGACCAGGAAAAACCAGCU-5'<br>5'-CTTTTGTTCTGGTCCTTTTTGGTCGA-3' | (SEQ ID NO: 3704)<br>(SEQ ID NO: 1486)<br>(SEQ ID NO: 2595) |
| βc-3091 Target: | 5'-UUGUUCUGGUCCUUUUUGGUCGAGG-3'<br>3'-AAAACAAGACCAGGAAAAACCAGCUCC-5'<br>5'-TTTTGTTCTGGTCCTTTTTGGTCGAGG-3' | (SEQ ID NO: 3705)<br>(SEQ ID NO: 1487)<br>(SEQ ID NO: 2596) |
| βc-3093 Target: | 5'-GUUCUGGUCCUUUUUGGUCGAGGAG-3'<br>3'-AACAAGACCAGGAAAAACCAGCUCCUC-5'<br>5'-TTGTTCTGGTCCTTTTTGGTCGAGGAG-3' | (SEQ ID NO: 3706)<br>(SEQ ID NO: 1488)<br>(SEQ ID NO: 2597) |
| βc-3095 Target: | 5'-UCUGGUCCUUUUUGGUCGAGGAGUA-3'<br>3'-CAAGACCAGGAAAAACCAGCUCCUCAU-5'<br>5'-GTTCTGGTCCTTTTTGGTCGAGGAGTA-3' | (SEQ ID NO: 3707)<br>(SEQ ID NO: 1489)<br>(SEQ ID NO: 2598) |
| βc-3097 Target: | 5'-UGGUCCUUUUUGGUCGAGGAGUAAC-3'<br>3'-AGACCAGGAAAAACCAGCUCCUCAUUG-5'<br>5'-TCTGGTCCTTTTTGGTCGAGGAGTAAC-3' | (SEQ ID NO: 3708)<br>(SEQ ID NO: 1490)<br>(SEQ ID NO: 2599) |
| βc-3099 Target: | 5'-GUCCUUUUUGGUCGAGGAGUAACAA-3'<br>3'-ACCAGGAAAAACCAGCUCCUCAUUGUU-5'<br>5'-TGGTCCTTTTTGGTCGAGGAGTAACAA-3' | (SEQ ID NO: 3709)<br>(SEQ ID NO: 1491)<br>(SEQ ID NO: 2600) |
| βc-3101 Target: | 5'-CCUUUUUGGUCGAGGAGUAACAAUA-3'<br>3'-CAGGAAAAACCAGCUCCUCAUUGUUAU-5'<br>5'-GTCCTTTTTGGTCGAGGAGTAACAATA-3' | (SEQ ID NO: 3710)<br>(SEQ ID NO: 1492)<br>(SEQ ID NO: 2601) |
| βc-3103 Target: | 5'-UUUUUGGUCGAGGAGUAACAAUACA-3'<br>3'-GGAAAAACCAGCUCCUCAUUGUUAUGU-5'<br>5'-CCTTTTTGGTCGAGGAGTAACAATACA-3' | (SEQ ID NO: 3711)<br>(SEQ ID NO: 1493)<br>(SEQ ID NO: 2602) |
| βc-3105 Target: | 5'-UUUGGUCGAGGAGUAACAAUACAAA-3'<br>3'-AAAAACCAGCUCCUCAUUGUUAUGUUU-5'<br>5'-TTTTTGGTCGAGGAGTAACAATACAAA-3' | (SEQ ID NO: 3712)<br>(SEQ ID NO: 1494)<br>(SEQ ID NO: 2603) |
| βc-3107 Target: | 5'-UGGUCGAGGAGUAACAAUACAAAUG-3'<br>3'-AAACCAGCUCCUCAUUGUUAUGUUUAC-5'<br>5'-TTTGGTCGAGGAGTAACAATACAAATG-3' | (SEQ ID NO: 3713)<br>(SEQ ID NO: 1495)<br>(SEQ ID NO: 2604) |
| βc-3109 Target: | 5'-GUCGAGGAGUAACAAUACAAAUGGA-3'<br>3'-ACCAGCUCCUCAUUGUUAUGUUUACCU-5'<br>5'-TGGTCGAGGAGTAACAATACAAATGGA-3' | (SEQ ID NO: 3714)<br>(SEQ ID NO: 1496)<br>(SEQ ID NO: 2605) |
| βc-3111 Target: | 5'-CGAGGAGUAACAAUACAAAUGGAUU-3'<br>3'-CAGCUCCUCAUUGUUAUGUUUACCUAA-5'<br>5'-GTCGAGGAGTAACAATACAAATGGATT-3' | (SEQ ID NO: 3715)<br>(SEQ ID NO: 1497)<br>(SEQ ID NO: 2606) |
| βc-3113 Target: | 5'-AGGAGUAACAAUACAAAUGGAUUUU-3'<br>3'-GCUCCUCAUUGUUAUGUUUACCUAAAA-5'<br>5'-CGAGGAGTAACAATACAAATGGATTTT-3' | (SEQ ID NO: 3716)<br>(SEQ ID NO: 1498)<br>(SEQ ID NO: 2607) |

TABLE 6-continued

Selected Anti-β-catenin DsiRNA Agents, Unmodified Duplexes

| | | |
|---|---|---|
| βc-3115 Target: | 5'-GAGUAACAAUACAAAUGGAUUUUGG-3'<br>3'-UCCUCAUUGUUAUGUUUACCUAAAACC-5'<br>5'-AGGAGTAACAATACAAATGGATTTTGG-3' | (SEQ ID NO: 3717)<br>(SEQ ID NO: 1499)<br>(SEQ ID NO: 2608) |
| βc-3191 Target: | 5'-UAUCAAACCCUAGCCUUGCUUGUUA-3'<br>3'-AAAUAGUUUGGGAUCGGAACGAACAAU-5'<br>5'-TTTATCAAACCCTAGCCTTGCTTGTTA-3' | (SEQ ID NO: 3718)<br>(SEQ ID NO: 1500)<br>(SEQ ID NO: 2609) |
| βc-3193 Target: | 5'-UCAAACCCUAGCCUUGCUUGUUAAA-3'<br>3'-AUAGUUUGGGAUCGGAACGAACAAUUU-5'<br>5'-TATCAAACCCTAGCCTTGCTTGTTAAA-3' | (SEQ ID NO: 3719)<br>(SEQ ID NO: 1501)<br>(SEQ ID NO: 2610) |
| βc-3195 Target: | 5'-AAACCCUAGCCUUGCUUGUUAAAUU-3'<br>3'-AGUUUGGGAUCGGAACGAACAAUUUAA-5'<br>5'-TCAAACCCTAGCCTTGCTTGTTAAATT-3' | (SEQ ID NO: 3720)<br>(SEQ ID NO: 1502)<br>(SEQ ID NO: 2611) |
| βc-3387 Target: | 5'-GAGUAAUGGUGUAGAACACUAAUUC-3'<br>3'-AACUCAUUACCACAUCUUGUGAUUAAG-5'<br>5'-TTGAGTAATGGTGTAGAACACTAATTC-3' | (SEQ ID NO: 3721)<br>(SEQ ID NO: 1503)<br>(SEQ ID NO: 2612) |
| βc-3389 Target: | 5'-GUAAUGGUGUAGAACACUAAUUCAU-3'<br>3'-CUCAUUACCACAUCUUGUGAUUAAGUA-5'<br>5'-GAGTAATGGTGTAGAACACTAATTC-3' | (SEQ ID NO: 3722)<br>(SEQ ID NO: 1504)<br>(SEQ ID NO: 2613) |
| βc-3391 Target: | 5'-AAUGGUGUAGAACACUAAUUCAUAA-3'<br>3'-CAUUACCACAUCUUGUGAUUAAGUAUU-5'<br>5'-GTAATGGTGTAGAACACTAATTCATAA-3' | (SEQ ID NO: 3723)<br>(SEQ ID NO: 1505)<br>(SEQ ID NO: 2614) |
| βc-3393 Target: | 5'-UGGUGUAGAACACUAAUUCAUAAUC-3'<br>3'-UUACCACAUCUUGUGAUUAAGUAUUAG-5'<br>5'-AATGGTGTAGAACACTAATTCATAATC-3' | (SEQ ID NO: 3724)<br>(SEQ ID NO: 1506)<br>(SEQ ID NO: 2615) |
| βc-3395 Target: | 5'-GUGUAGAACACUAAUUCAUAAUCAC-3'<br>3'-ACCACAUCUUGUGAUUAAGUAUUAGUG-5'<br>5'-TGGTGTAGAACACTAATTCATAATCAC-3' | (SEQ ID NO: 3725)<br>(SEQ ID NO: 1507)<br>(SEQ ID NO: 2616) |
| βc-3397 Target: | 5'-GUAGAACACUAAUUCAUAAUCACUC-3'<br>3'-CACAUCUUGUGAUUAAGUAUUAGUGAG-5'<br>5'-GTGTAGAACACTAATTCATAATCACTC-3' | (SEQ ID NO: 3726)<br>(SEQ ID NO: 1508)<br>(SEQ ID NO: 2617) |
| βc-3399 Target: | 5'-AGAACACUAAUUCAUAAUCACUCUA-3'<br>3'-CAUCUUGUGAUUAAGUAUUAGUGAGAU-5'<br>5'-GTAGAACACTAATTCATAATCACTCTA-3' | (SEQ ID NO: 3727)<br>(SEQ ID NO: 1509)<br>(SEQ ID NO: 2618) |
| βc-3401 Target: | 5'-AACACUAAUUCAUAAUCACUCUAAU-3'<br>3'-UCUUGUGAUUAAGUAUUAGUGAGAUUA-5'<br>5'-AGAACACTAATTCATAATCACTCTAAT-3' | (SEQ ID NO: 3728)<br>(SEQ ID NO: 1510)<br>(SEQ ID NO: 2619) |
| βc-3500 Target: | 5'-UUAGUUUCCUUUUUAAUAUGCUUAA-3'<br>3'-UUAAUCAAAGGAAAAAUUAUACGAAUU-5'<br>5'-AATTAGTTTCCTTTTTAATATGCTTAA-3' | (SEQ ID NO: 3729)<br>(SEQ ID NO: 1511)<br>(SEQ ID NO: 2620) |
| βc-3502 Target: | 5'-AGUUUCCUUUUUAAUAUGCUUAAAA-3'<br>3'-AAUCAAAGGAAAAAUUAUACGAAUUUU-5'<br>5'-TTAGTTTCCTTTTTAATATGCTTAAAA-3' | (SEQ ID NO: 3730)<br>(SEQ ID NO: 1512)<br>(SEQ ID NO: 2621) |
| βc-3504 Target: | 5'-UUUCCUUUUUAAUAUGCUUAAAAUA-3'<br>3'-UCAAAGGAAAAAUUAUACGAAUUUUAU-5'<br>5'-AGTTTCCTTTTTAATATGCTTAAAATA-3' | (SEQ ID NO: 3731)<br>(SEQ ID NO: 1513)<br>(SEQ ID NO: 2622) |
| βc-3506 Target: | 5'-UCCUUUUUAAUAUGCUUAAAAUAAG-3'<br>3'-AAAGGAAAAAUUAUACGAAUUUUAUUC-5'<br>5'-TTTCCTTTTTAATATGCTTAAAATAAG-3' | (SEQ ID NO: 3732)<br>(SEQ ID NO: 1514)<br>(SEQ ID NO: 2623) |
| βc-3508 Target: | 5'-CUUUUUAAUAUGCUUAAAAUAAGCA-3'<br>3'-AGGAAAAAUUAUACGAAUUUUAUUCGU-5'<br>5'-TCCTTTTTAATATGCTTAAAATAAGCA-3' | (SEQ ID NO: 3733)<br>(SEQ ID NO: 1515)<br>(SEQ ID NO: 2624) |
| βc-3509 Target: | 5'-UUUUUAAUAUGCUUAAAAUAAGCAG-3'<br>3'-GGAAAAAUUAUACGAAUUUUAUUCGUC-5'<br>5'-CCTTTTTAATATGCTTAAAATAAGCAG-3' | (SEQ ID NO: 3734)<br>(SEQ ID NO: 1516)<br>(SEQ ID NO: 2625) |
| βc-3510 Target: | 5'-UUUUAAUAUGCUUAAAAUAAGCAGG-3'<br>3'-GAAAAAUUAUACGAAUUUUAUUCGUCC-5'<br>5'-CTTTTTAATATGCTTAAAATAAGCAGG-3' | (SEQ ID NO: 3735)<br>(SEQ ID NO: 1517)<br>(SEQ ID NO: 2626) |

TABLE 6-continued

Selected Anti-β-catenin DsiRNA Agents, Unmodified Duplexes

| | | |
|---|---|---|
| | 5'-UUAAUAUGCUUAAAAUAAGCAGGUG-3' | (SEQ ID NO: 3736) |
| | 3'-AAAAUUAUACGAAUUUUAUUCGUCCAC-5' | (SEQ ID NO: 1518) |
| βc-3512 Target: | 5'-TTTTAATATGCTTAAAATAAGCAGGTG-3' | (SEQ ID NO: 2627) |
| | 5'-AAUAUGCUUAAAAUAAGCAGGUGGA-3' | (SEQ ID NO: 3737) |
| | 3'-AAUUAUACGAAUUUUAUUCGUCCACCU-5' | (SEQ ID NO: 1519) |
| βc-3514 Target: | 5'-TTAATATGCTTAAAATAAGCAGGTGGA-3' | (SEQ ID NO: 2628) |
| | 5'-UAUGCUUAAAAUAAGCAGGUGGAUC-3' | (SEQ ID NO: 3738) |
| | 3'-UUAUACGAAUUUUAUUCGUCCACCUAG-5' | (SEQ ID NO: 1520) |
| βc-3516 Target: | 5'-AATATGCTTAAAATAAGCAGGTGGATC-3' | (SEQ ID NO: 2629) |
| | 5'-UGCUUAAAAUAAGCAGGUGGAUCUA-3' | (SEQ ID NO: 3739) |
| | 3'-AUACGAAUUUUAUUCGUCCACCUAGAU-5' | (SEQ ID NO: 1521) |
| βc-3518 Target: | 5'-TATGCTTAAAATAAGCAGGTGGATCTA-3' | (SEQ ID NO: 2630) |
| | 5'-CUUAAAAUAAGCAGGUGGAUCUAUU-3' | (SEQ ID NO: 3740) |
| | 3'-ACGAAUUUUAUUCGUCCACCUAGAUAA-5' | (SEQ ID NO: 1522) |
| βc-3520 Target: | 5'-TGCTTAAAATAAGCAGGTGGATCTATT-3' | (SEQ ID NO: 2631) |
| | 5'-UAAAAUAAGCAGGUGGAUCUAUUUC-3' | (SEQ ID NO: 3741) |
| | 3'-GAAUUUUAUUCGUCCACCUAGAUAAAG-5' | (SEQ ID NO: 1523) |
| βc-3522 Target: | 5'-CTTAAAATAAGCAGGTGGATCTATTTC-3' | (SEQ ID NO: 2632) |
| | 5'-AAAUAAGCAGGUGGAUCUAUUUCAU-3' | (SEQ ID NO: 3742) |
| | 3'-AUUUUAUUCGUCCACCUAGAUAAAGUA-5' | (SEQ ID NO: 1524) |
| βc-3524 Target: | 5'-TAAAATAAGCAGGTGGATCTATTTC-3' | (SEQ ID NO: 2633) |
| | 5'-AUAAGCAGGUGGAUCUAUUUCAUGU-3' | (SEQ ID NO: 3743) |
| | 3'-UUUAUUCGUCCACCUAGAUAAAGUACA-5' | (SEQ ID NO: 1525) |
| βc-3526 Target: | 5'-AAATAAGCAGGTGGATCTATTTCATGT-3' | (SEQ ID NO: 2634) |
| | 5'-AAGCAGGUGGAUCUAUUUCAUGUUU-3' | (SEQ ID NO: 3744) |
| | 3'-UAUUCGUCCACCUAGAUAAAGUACAAA-5' | (SEQ ID NO: 1526) |
| βc-3528 Target: | 5'-ATAAGCAGGTGGATCTATTTCATGTTT-3' | (SEQ ID NO: 2635) |
| | 5'-GCAGGUGGAUCUAUUUCAUGUUUUU-3' | (SEQ ID NO: 3745) |
| | 3'-UUCGUCCACCUAGAUAAAGUACAAAAA-5' | (SEQ ID NO: 1527) |
| βc-3530 Target: | 5'-AAGCAGGTGGATCTATTTCATGTTTTT-3' | (SEQ ID NO: 2636) |
| | 5'-AGGUGGAUCUAUUUCAUGUUUUUGA-3' | (SEQ ID NO: 3746) |
| | 3'-CGUCCACCUAGAUAAAGUACAAAAACU-5' | (SEQ ID NO: 1528) |
| βc-3532 Target: | 5'-GCAGGTGGATCTATTTCATGTTTTGA-3' | (SEQ ID NO: 2637) |
| | 5'-GUGGAUCUAUUUCAUGUUUUUGAUC-3' | (SEQ ID NO: 3747) |
| | 3'-UCCACCUAGAUAAAGUACAAAAACUAG-5' | (SEQ ID NO: 1529) |
| βc-3534 Target: | 5'-AGGTGGATCTATTTCATGTTTTGATC-3' | (SEQ ID NO: 2638) |
| | 5'-GGAUCUAUUUCAUGUUUUUGAUCAA-3' | (SEQ ID NO: 3748) |
| | 3'-CACCUAGAUAAAGUACAAAAACUAGUU-5' | (SEQ ID NO: 1530) |
| βc-3536 Target: | 5'-GTGGATCTATTTCATGTTTTGATCAA-3' | (SEQ ID NO: 2639) |
| | 5'-AUCUAUUUCAUGUUUUUGAUCAAAA-3' | (SEQ ID NO: 3749) |
| | 3'-CCUAGAUAAAGUACAAAAACUAGUUUU-5' | (SEQ ID NO: 1531) |
| βc-3538 Target: | 5'-GGATCTATTTCATGTTTTGATCAAAA-3' | (SEQ ID NO: 2640) |
| | 5'-GUAGGGUAAAUCAGUAAGAGGUGUU-3' | (SEQ ID NO: 3750) |
| | 3'-CCCAUCCCAUUUAGUCAUUCUCCACAA-5' | (SEQ ID NO: 1532) |
| βc-3583 Target: | 5'-GGGTAGGGTAAATCAGTAAGAGGTGTT-3' | (SEQ ID NO: 2641) |
| | 5'-AGGGUAAAUCAGUAAGAGGUGUUAU-3' | (SEQ ID NO: 3751) |
| | 3'-CAUCCCAUUUAGUCAUUCUCCACAAUA-5' | (SEQ ID NO: 1533) |
| βc-3585 Target: | 5'-GTAGGGTAAATCAGTAAGAGGTGTTAT-3' | (SEQ ID NO: 2642) |
| | 5'-GGUAAAUCAGUAAGAGGUGUUAUUU-3' | (SEQ ID NO: 3752) |
| | 3'-UCCCAUUUAGUCAUUCUCCACAAUAAA-5' | (SEQ ID NO: 1534) |
| βc-3587 Target: | 5'-AGGGTAAATCAGTAAGAGGTGTTATTT-3' | (SEQ ID NO: 2643) |
| | 5'-UAAAUCAGUAAGAGGUGUUAUUUGG-3' | (SEQ ID NO: 3753) |
| | 3'-CCAUUUAGUCAUUCUCCACAAUAAACC-5' | (SEQ ID NO: 1535) |
| βc-3589 Target: | 5'-GGTAAATCAGTAAGAGGTGTTATTTGG-3' | (SEQ ID NO: 2644) |
| | 5'-AAUCAGUAAGAGGUGUUAUUUGGAA-3' | (SEQ ID NO: 3754) |
| | 3'-AUUUAGUCAUUCUCCACAAUAAACCUU-5' | (SEQ ID NO: 1536) |
| βc-3591 Target: | 5'-TAAATCAGTAAGAGGTGTTATTTGGAA-3' | (SEQ ID NO: 2645) |

TABLE 6-continued

Selected Anti-β-catenin DsiRNA Agents, Unmodified Duplexes

| | | |
|---|---|---|
| βc-3593 Target: | 5'-UCAGUAAGAGGUGUUAUUUGGAACC-3'<br>3'-UUAGUCAUUCUCCACAAUAAACCUUGG-5'<br>5'-AATCAGTAAGAGGTGTTATTTGGAACC-3' | (SEQ ID NO: 3755)<br>(SEQ ID NO: 1537)<br>(SEQ ID NO: 2646) |
| βc-3633 Target: | 5'-UACCAGUUGCCUUUUAUCCCAAAGU-3'<br>3'-AAAUGGUCAACGGAAAAUAGGGUUUCA-5'<br>5'-TTTACCAGTTGCCTTTTATCCCAAAGT-3' | (SEQ ID NO: 3756)<br>(SEQ ID NO: 1538)<br>(SEQ ID NO: 2647) |
| βc-3635 Target: | 5'-CCAGUUGCCUUUUAUCCCAAAGUUG-3'<br>3'-AUGGUCAACGGAAAAUAGGGUUUCAAC-5'<br>5'-TACCAGTTGCCTTTTATCCCAAAGTTG-3' | (SEQ ID NO: 3757)<br>(SEQ ID NO: 1539)<br>(SEQ ID NO: 2648) |
| βc-3637 Target: | 5'-AGUUGCCUUUUAUCCCAAAGUUGUU-3'<br>3'-GGUCAACGGAAAAUAGGGUUUCAACAA-5'<br>5'-CCAGTTGCCTTTTATCCCAAAGTTGTT-3' | (SEQ ID NO: 3758)<br>(SEQ ID NO: 1540)<br>(SEQ ID NO: 2649) |
| βc-3639 Target: | 5'-UUGCCUUUUAUCCCAAAGUUGUUGU-3'<br>3'-UCAACGGAAAAUAGGGUUUCAACAACA-5'<br>5'-AGTTGCCTTTTATCCCAAAGTTGTTGT-3' | (SEQ ID NO: 3759)<br>(SEQ ID NO: 1541)<br>(SEQ ID NO: 2650) |
| βc-3641 Target: | 5'-GCCUUUUAUCCCAAAGUUGUUGUAA-3'<br>3'-AACGGAAAAUAGGGUUUCAACAACAUU-5'<br>5'-TTGCCTTTTATCCCAAAGTTGTTGTAA-3' | (SEQ ID NO: 3760)<br>(SEQ ID NO: 1542)<br>(SEQ ID NO: 2651) |
| βc-3643 Target: | 5'-CUUUUAUCCCAAAGUUGUUGUAACC-3'<br>3'-CGGAAAAUAGGGUUUCAACAACAUUGG-5'<br>5'-GCCTTTTATCCCAAAGTTGTTGTAACC-3' | (SEQ ID NO: 3761)<br>(SEQ ID NO: 1543)<br>(SEQ ID NO: 2652) |
| βc-3645 Target: | 5'-UUUAUCCCAAAGUUGUUGUAACCUG-3'<br>3'-GAAAAUAGGGUUUCAACAACAUUGGAC-5'<br>5'-CTTTTATCCCAAAGTTGTTGTAACCTG-3' | (SEQ ID NO: 3762)<br>(SEQ ID NO: 1544)<br>(SEQ ID NO: 2653) |
| βc-3647 Target: | 5'-UAUCCCAAAGUUGUUGUAACCUGCU-3'<br>3'-AAAUAGGGUUUCAACAACAUUGGACGA-5'<br>5'-TTTATCCCAAAGTTGTTGTAACCTGCT-3' | (SEQ ID NO: 3763)<br>(SEQ ID NO: 1545)<br>(SEQ ID NO: 2654) |
| βc-3649 Target: | 5'-UCCCAAAGUUGUUGUAACCUGCUGU-3'<br>3'-AUAGGGUUUCAACAACAUUGGACGACA-5'<br>5'-TATCCCAAAGTTGTTGTAACCTGCTGT-3' | (SEQ ID NO: 3764)<br>(SEQ ID NO: 1546)<br>(SEQ ID NO: 2655) |
| βc-3651 Target: | 5'-CCAAAGUUGUUGUAACCUGCUGUGA-3'<br>3'-AGGGUUUCAACAACAUUGGACGACACU-5'<br>5'-TCCCAAAGTTGTTGTAACCTGCTGTGA-3' | (SEQ ID NO: 3765)<br>(SEQ ID NO: 1547)<br>(SEQ ID NO: 2656) |
| βc-3653 Target: | 5'-AAAGUUGUUGUAACCUGCUGUGAUA-3'<br>3'-GGUUUCAACAACAUUGGACGACACUAU-5'<br>5'-CCAAAGTTGTTGTAACCTGCTGTGATA-3' | (SEQ ID NO: 3766)<br>(SEQ ID NO: 1548)<br>(SEQ ID NO: 2657) |
| βc-3655 Target: | 5'-AGUUGUUGUAACCUGCUGUGAUACG-3'<br>3'-UUUCAACAACAUUGGACGACACUAUGC-5'<br>5'-AAAGTTGTTGTAACCTGCTGTGATACG-3' | (SEQ ID NO: 3767)<br>(SEQ ID NO: 1549)<br>(SEQ ID NO: 2658) |
| βc-3657 Target: | 5'-UUGUUGUAACCUGCUGUGAUACGAU-3'<br>3'-UCAACAACAUUGGACGACACUAUGCUA-5'<br>5'-AGTTGTTGTAACCTGCTGTGATACGAT-3' | (SEQ ID NO: 3768)<br>(SEQ ID NO: 1550)<br>(SEQ ID NO: 2659) |
| βc-3659 Target: | 5'-GUUGUAACCUGCUGUGAUACGAUGC-3'<br>3'-AACAACAUUGGACGACACUAUGCUACG-5'<br>5'-TTGTTGTAACCTGCTGTGATACGATGC-3' | (SEQ ID NO: 3769)<br>(SEQ ID NO: 1551)<br>(SEQ ID NO: 2660) |
| βc-3708 Target: | 5'-AAAUGGUUCAGAAUUAAACUUUUAA-3'<br>3'-UUUUUACCAAGUCUUAAUUUGAAAAUU-5'<br>5'-AAAAATGGTTCAGAATTAAACTTTTAA-3' | (SEQ ID NO: 3770)<br>(SEQ ID NO: 1552)<br>(SEQ ID NO: 2661) |
| βc-3710 Target: | 5'-AUGGUUCAGAAUUAAACUUUUAAUU-3'<br>3'-UUUACCAAGUCUUAAUUUGAAAAUUAA-5'<br>5'-AAATGGTTCAGAATTAAACTTTTAATT-3' | (SEQ ID NO: 3771)<br>(SEQ ID NO: 1553)<br>(SEQ ID NO: 2662) |
| βc-3712 Target: | 5'-GGUUCAGAAUUAAACUUUUAAUUCA-3'<br>3'-UACCAAGUCUUAAUUUGAAAAUUAAGU-5'<br>5'-ATGGTTCAGAATTAAACTTTTAATTCA-3' | (SEQ ID NO: 3772)<br>(SEQ ID NO: 1554)<br>(SEQ ID NO: 2663) |
| βc-3714 Target: | 5'-UUCAGAAUUAAACUUUUAAUUCAUU-3'<br>3'-CCAAGUCUUAAUUUGAAAAUUAAGUAA-5'<br>5'-GGTTCAGAATTAAACTTTTAATTCATT-3' | (SEQ ID NO: 3773)<br>(SEQ ID NO: 1555)<br>(SEQ ID NO: 2664) |

TABLE 6-continued

Selected Anti-β-catenin DsiRNA Agents, Unmodified Duplexes

|  |  |  |
|---|---|---|
|  | 5'-CAGAAUUAAACUUUUAAUUCAUUCG-3' | (SEQ ID NO: 3774) |
|  | 3'-AAGUCUUAAUUUGAAAAUUAAGUAAGC-5' | (SEQ ID NO: 1556) |
| βc-3716 Target: | 5'-TTCAGAATTAAACTTTTAATTCATTCG-3' | (SEQ ID NO: 2665) |
|  | 5'-GCAGCAGUCUUACUUGGAUUCUGGA-3' | (SEQ ID NO: 3775) |
|  | 3'-GUCGUCGUCAGAAUGAACCUAAGACCU-5' | (SEQ ID NO: 1557) |
| βc-m314 Target: | 5'-CAGCAGCAGTCTTACTTGGATTCTGGA-3' | (SEQ ID NO: 2666) |
|  | 5'-ACUUGGAUUCUGGAAUCCAUUCUGG-3' | (SEQ ID NO: 3776) |
|  | 3'-AAUGAACCUAAGACCUUAGGUAAGACC-5' | (SEQ ID NO: 1558) |
| βc-m325 Target: | 5'-TTACTTGGATTCTGGAATCCATTCTGG-3' | (SEQ ID NO: 2667) |
|  | 5'-GACACCUCCCAAGUCCUUUAUGAAU-3' | (SEQ ID NO: 3777) |
|  | 3'-AACUGUGGAGGGUUCAGGAAAUACUUA-5' | (SEQ ID NO: 1559) |
| βc-m408 Target: | 5'-TTGACACCTCCCAAGTCCTTTATGAAT-3' | (SEQ ID NO: 2668) |
|  | 5'-CGCAAGAGCAAGUAGCUGAUAUUGA-3' | (SEQ ID NO: 3778) |
|  | 3'-GUGCGUUCUCGUUCAUCGACUAUAACU-5' | (SEQ ID NO: 1560) |
| βc-m460 Target: | 5'-CACGCAAGAGCAAGTAGCTGATATTGA-3' | (SEQ ID NO: 2669) |
|  | 5'-CCAUGUUCCCUGAGACGCUAGAUGA-3' | (SEQ ID NO: 3779) |
|  | 3'-ACGGUACAAGGGACUCUGCGAUCUACU-5' | (SEQ ID NO: 1561) |
| βc-m526 Target: | 5'-TGCCATGTTCCCTGAGACGCTAGATGA-3' | (SEQ ID NO: 2670) |
|  | 5'-UGAAACAUGCAGUUGUCAAUUUGAU-3' | (SEQ ID NO: 3780) |
|  | 3'-CAACUUUGUACGUCAACAGUUAAACUA-5' | (SEQ ID NO: 1562) |
| βc-m631 Target: | 5'-GTTGAAACATGCAGTTGTCAATTTGAT-3' | (SEQ ID NO: 2671) |
|  | 5'-CAUGCAGUUGUCAAUUUGAUUAACU-3' | (SEQ ID NO: 3781) |
|  | 3'-UUGUACGUCAACAGUUAAACUAAUUGA-5' | (SEQ ID NO: 1563) |
| βc-m636 Target: | 5'-AACATGCAGTTGTCAATTTGATTAACT-3' | (SEQ ID NO: 2672) |
|  | 5'-GUUGUCAAUUUGAUUAACUAUCAGG-3' | (SEQ ID NO: 3782) |
|  | 3'-GUCAACAGUUAAACUAAUUGAUAGUCC-5' | (SEQ ID NO: 1564) |
| βc-m642 Target: | 5'-CAGTTGTCAATTTGATTAACTATCAGG-3' | (SEQ ID NO: 2673) |
|  | 5'-GAGGACCAGGUGGUAGUUAAUAAAG-3' | (SEQ ID NO: 3783) |
|  | 3'-UACUCCUGGUCCACCAUCAAUUAUUUC-5' | (SEQ ID NO: 1565) |
| βc-m723 Target: | 5'-ATGAGGACCAGGTGGTAGTTAATAAAG-3' | (SEQ ID NO: 2674) |
|  | 5'-GGUCACCAGUGGAUUCUGUACUGUU-3' | (SEQ ID NO: 3784) |
|  | 3'-ACCCAGUGGUCACCUAAGACAUGACAA-5' | (SEQ ID NO: 1566) |
| βc-m970 Target: | 5'-TGGGTCACCAGTGGATTCTGTACTGTT-3' | (SEQ ID NO: 2675) |
|  | 5'-CAGUGGAUUCUGUACUGUUCUACGC-3' | (SEQ ID NO: 3785) |
|  | 3'-UGGUCACCUAAGACAUGACAAGAUGCG-5' | (SEQ ID NO: 1567) |
| βc-m976 Target: | 5'-ACCAGTGGATTCTGTACTGTTCTACGC-3' | (SEQ ID NO: 2676) |
|  | 5'-GAUUCUGUACUGUUCUACGCCAUCA-3' | (SEQ ID NO: 3786) |
|  | 3'-ACCUAAGACAUGACAAGAUGCGGUAGU-5' | (SEQ ID NO: 1568) |
| βc-m981 Target: | 5'-TGGATTCTGTACTGTTCTACGCCATCA-3' | (SEQ ID NO: 2677) |
|  | 5'-GUGGACUGCAGAAAAUGGUUGCUUU-3' | (SEQ ID NO: 3787) |
|  | 3'-ACCACCUGACGUCUUUUACCAACGAAA-5' | (SEQ ID NO: 1569) |
| βc-m1066 Target: | 5'-TGGTGGACTGCAGAAAATGGTTGCTTT-3' | (SEQ ID NO: 2678) |
|  | 5'-CGUGAAAUUCUUGGCUAUUACAACA-3' | (SEQ ID NO: 3788) |
|  | 3'-UUGCACUUUAAGAACCGAUAAUGUUGU-5' | (SEQ ID NO: 1570) |
| βc-m1106 Target: | 5'-AACGTGAAATTCTTGGCTATTACAACA-3' | (SEQ ID NO: 2679) |
|  | 5'-CAAGUCAGCGACUUGUUCAAAACUG-3' | (SEQ ID NO: 3789) |
|  | 3'-GGGUUCAGUCGCUGAACAAGUUUUGAC-5' | (SEQ ID NO: 1571) |
| βc-m1354 Target: | 5'-CCCAAGTCAGCGACTTGTTCAAAACTG-3' | (SEQ ID NO: 2680) |
|  | 5'-GACUUGUUCAAAACUGUCUUUGGAC-3' | (SEQ ID NO: 3790) |
|  | 3'-CGCUGAACAAGUUUUGACAGAAACCUG-5' | (SEQ ID NO: 1572) |
| βc-m1363 Target: | 5'-GCGACTTGTTCAAAACTGTCTTTGGAC-3' | (SEQ ID NO: 2681) |
|  | 5'-AAACUGUCUUUGGACUCUCAGAAAC-3' | (SEQ ID NO: 3791) |
|  | 3'-GUUUUGACAGAAACCUGAGAGUCUUUG-5' | (SEQ ID NO: 1573) |
| βc-m1373 Target: | 5'-CAAAACTGTCTTTGGACTCTCAGAAAC-3' | (SEQ ID NO: 2682) |
|  | 5'-CUCUAACCUCACUUGCAAUAAUUAC-3' | (SEQ ID NO: 3792) |
|  | 3'-GAGAGAUUGGAGUGAACGUUAUUAAUG-5' | (SEQ ID NO: 1574) |
| βc-m1508 Target: | 5'-CTCTCTAACCTCACTTGCAATAATTAC-3' | (SEQ ID NO: 2683) |

TABLE 6-continued

Selected Anti-β-catenin DsiRNA Agents, Unmodified Duplexes

```
                         5'-CUCACUUGCAAUAAUUACAAAAACA-3'     (SEQ ID NO: 3793)
                         3'-UGGAGUGAACGUUAUUAAUGUUUUUGU-5'   (SEQ ID NO: 1575)
βc-m1515 Target:         5'-ACCTCACTTGCAATAATTACAAAAACA-3'   (SEQ ID NO: 2684)

5'-GAAUGCCGUUCGCCUUCAUUAUGGA-3'     (SEQ ID NO: 3794)
                         3'-GUCUUACGGCAAGCGGAAGUAAUACCU-5'   (SEQ ID NO: 1576)
βc-m1682 Target:         5'-CAGAATGCCGTTCGCCTTCATTATGGA-3'   (SEQ ID NO: 2685)

5'-GCCUUCAUUAUGGACUGCCUGUUGU-3'     (SEQ ID NO: 3795)
                         3'-AGCGGAAGUAAUACCUGACGGACAACA-5'   (SEQ ID NO: 1577)
βc-m1693 Target:         5'-TCGCCTTCATTATGGACTGCCTGTTGT-3'   (SEQ ID NO: 2686)

5'-CAUUAUGGACUGCCUGUUGUGGUUA-3'     (SEQ ID NO: 3796)
                         3'-AAGUAAUACCUGACGGACAACACCAAU-5'   (SEQ ID NO: 1578)
βc-m1698 Target:         5'-TTCATTATGGACTGCCTGTTGTGGTTA-3'   (SEQ ID NO: 2687)

5'-GACUGCCUGUUGUGGUUAAACUCCU-3'     (SEQ ID NO: 3797)
                         3'-ACCUGACGGACAACACCAAUUUGAGGA-5'   (SEQ ID NO: 1579)
βc-m1705 Target:         5'-TGGACTGCCTGTTGTGGTTAAACTCCT-3'   (SEQ ID NO: 2688)

5'-AACUGUUGGAUUGAUUCGAAACCUU-3'     (SEQ ID NO: 3798)
                         3'-CGUUGACAACCUAACUAAGCUUUGGAA-5'   (SEQ ID NO: 1580)
βc-m1763 Target:         5'-GCAACTGTTGGATTGATTCGAAACCTT-3'   (SEQ ID NO: 2689)

5'-GAGGACUCAAUACCAUUCCAUUGUU-3'     (SEQ ID NO: 3799)
                         3'-GGCUCCUGAGUUAUGGUAAGGUAACAA-5'   (SEQ ID NO: 1581)
βc-m2008 Target:         5'-CCGAGGACTCAATACCATTCCATTGTT-3'   (SEQ ID NO: 2690)

5'-GAGGACAAGCCACAGGAUUACAAGA-3'     (SEQ ID NO: 3800)
                         3'-GACUCCUGUUCGGUGUCCUAAUGUUCU-5'   (SEQ ID NO: 1582)
βc-m2226 Target:         5'-CTGAGGACAAGCCACAGGATTACAAGA-3'   (SEQ ID NO: 2691)

5'-AUGGACCCUAUGAUGGAGCAUGAGA-3'     (SEQ ID NO: 3801)
                         3'-CCUACCUGGGAUACUACCUCGUACUCU-5'   (SEQ ID NO: 1583)
βc-m2427 Target:         5'-GGATGGACCCTATGATGGAGCATGAGA-3'   (SEQ ID NO: 2692)

5'-GAUACUGACCUGUAAAUCGUCCUUU-3'     (SEQ ID NO: 3802)
                         3'-AACUAUGACUGGACAUUUAGCAGGAAA-5'   (SEQ ID NO: 1584)
βc-m2568 Target:         5'-TTGATACTGACCTGTAAATCGTCCTTT-3'   (SEQ ID NO: 2693)

5'-CCAGUGUGGGUGAAUACUUUACUCU-3'     (SEQ ID NO: 3803)
                         3'-UCGGUCACACCCACUUAUGAAAUGAGA-5'   (SEQ ID NO: 1585)
βc-m2614 Target:         5'-AGCCAGTGTGGGTGAATACTTTACTCT-3'   (SEQ ID NO: 2694)

5'-CCACAGCUUUUGCAGCGUUAUACUC-3'     (SEQ ID NO: 3804)
                         3'-ACGGUGUCGAAAACGUCGCAAUAUGAG-5'   (SEQ ID NO: 1586)
βc-m2770 Target:         5'-TGCCACAGCTTTTGCAGCGTTATACTC-3'   (SEQ ID NO: 2695)

5'-UUUUGCAGCGUUAUACUCAGAUGAG-3'     (SEQ ID NO: 3805)
                         3'-CGAAAACGUCGCAAUAUGAGUCUACUC-5'   (SEQ ID NO: 1587)
βc-m2777 Target:         5'-GCTTTTGCAGCGTTATACTCAGATGAG-3'   (SEQ ID NO: 2696)

5'-GCGUUAUACUCAGAUGAGUAACAUU-3'     (SEQ ID NO: 3806)
                         3'-GUCGCAAUAUGAGUCUACUCAUUGUAA-5'   (SEQ ID NO: 1588)
βc-m2784 Target:         5'-CAGCGTTATACTCAGATGAGTAACATT-3'   (SEQ ID NO: 2697)

5'-AUUUGCUGUUUUCAACAUUAAUAGC-3'     (SEQ ID NO: 3807)
                         3'-UGUAAACGACAAAAGUUGUAAUUAUCG-5'   (SEQ ID NO: 1589)
βc-m2806 Target:         5'-ACATTTGCTGTTTTCAACATTAATAGC-3'   (SEQ ID NO: 2698)

5'-CUGUAGUGUCUGAACGUGCAUUGUG-3'     (SEQ ID NO: 3808)
                         3'-UCGACAUCACAGACUUGCACGUAACAC-5'   (SEQ ID NO: 1590)
βc-m2850 Target:         5'-AGCTGTAGTGTCTGAACGTGCATTGTG-3'   (SEQ ID NO: 2699)

5'-GAACAGUCGAAGUACGCUUUUUGUU-3'     (SEQ ID NO: 3809)
                         3'-CCCUUGUCAGCUUCAUGCGAAAAACAA-5'   (SEQ ID NO: 1591)
βc-m2965 Target:         5'-GGGAACAGTCGAAGTACGCTTTTTGTT-3'   (SEQ ID NO: 2700)

5'-GUCGAAGUACGCUUUUUGUUCUGGU-3'     (SEQ ID NO: 3810)
                         3'-GUCAGCUUCAUGCGAAAAACAAGACCA-5'   (SEQ ID NO: 1592)
βc-m2970 Target:         5'-CAGTCGAAGTACGCTTTTTGTTCTGGT-3'   (SEQ ID NO: 2701)

5'-GUACGCUUUUUGUUCUGGUCCUUUU-3'     (SEQ ID NO: 3811)
                         3'-UUCAUGCGAAAAACAAGACCAGGAAAA-5'   (SEQ ID NO: 1593)
βc-m2976 Target:         5'-AAGTACGCTTTTTGTTCTGGTCCTTTT-3'   (SEQ ID NO: 2702)
```

TABLE 6-continued

Selected Anti-β-catenin DsiRNA Agents, Unmodified Duplexes

```
                5'-CCUAGCCUUGCUUGUUCUUUGUUUU-3'    (SEQ ID NO: 3812)
                3'-UGGGAUCGGAACGAACAAGAAACAAAA-5'  (SEQ ID NO: 1594)
βc-m3092 Target: 5'-ACCCTAGCCTTGCTTGTTCTTTGTTTT-3'  (SEQ ID NO: 2703)

5'-CCUUGCUUGUUCUUUGUUUUAAUAU-3'    (SEQ ID NO: 3813)
                3'-UCGGAACGAACAAGAAACAAAAUUAUA-5'  (SEQ ID NO: 1595)
βc-m3097 Target: 5'-AGCCTTGCTTGTTCTTTGTTTTAATAT-3'  (SEQ ID NO: 2704)

5'-AACCUGCUACAGCAAUUUCUGAUUU-3'    (SEQ ID NO: 3814)
                3'-ACUUGGACGAUGUCGUUAAAGACUAAA-5'  (SEQ ID NO: 1596)
βc-m3198 Target: 5'-TGAACCTGCTACAGCAATTTCTGATTT-3'  (SEQ ID NO: 2705)

5'-CAGCAAUUUCUGAUUUCUAAGAACC-3'    (SEQ ID NO: 3815)
                3'-AUGUCGUUAAAGACUAAAGAUUCUUGG-5'  (SEQ ID NO: 1597)
βc-m3207 Target: 5'-TACAGCAATTTCTGATTTCTAAGAACC-3'  (SEQ ID NO: 2706)

5'-GUAAGAGGUGUUAUUUGAGCCUUGU-3'    (SEQ ID NO: 3816)
                3'-GUCAUUCUCCACAAUAAACUCGGAACA-5'  (SEQ ID NO: 1598)
βc-m3433 Target: 5'-CAGTAAGAGGTGTTATTTGAGCCTTGT-3'  (SEQ ID NO: 2707)

5'-GGUGUUAUUUGAGCCUUGUUUUGGA-3'    (SEQ ID NO: 3817)
                3'-CUCCACAAUAAACUCGGAACAAAACCU-5'  (SEQ ID NO: 1599)
βc-m3439 Target: 5'-GAGGTGTTATTTGAGCCTTGTTTTGGA-3'  (SEQ ID NO: 2708)

5'-UAUUUGAGCCUUGUUUUGGACAGUA-3'    (SEQ ID NO: 3818)
                3'-CAAUAAACUCGGAACAAAACCUGUCAU-5'  (SEQ ID NO: 1600)
βc-m3444 Target: 5'-GTTATTTGAGCCTTGTTTTGGACAGTA-3'  (SEQ ID NO: 2709)

5'-GAGCCUUGUUUUGGACAGUAUACCA-3'    (SEQ ID NO: 3819)
                3'-AACUCGGAACAAAACCUGUCAUAUGGU-5'  (SEQ ID NO: 1601)
βc-m3449 Target: 5'-TTGAGCCTTGTTTTGGACAGTATACCA-3'  (SEQ ID NO: 2710)

5'-CAACAGAUGCGGUUAUAGAAAUGGU-3'    (SEQ ID NO: 3820)
                3'-AAGUUGUCUACGCCAAUAUCUUUACCA-5'  (SEQ ID NO: 1602)
βc-m3522 Target: 5'-TTCAACAGATGCGGTTATAGAAATGGT-3'  (SEQ ID NO: 2711)

5'-GUUAUAGAAAUGGUUCAGAAUUAAA-3'    (SEQ ID NO: 3821)
                3'-GCCAAUAUCUUUACCAAGUCUUAAUUU-5'  (SEQ ID NO: 1603)
βc-m3533 Target: 5'-CGGTTATAGAAATGGTTCAGAATTAAA-3'  (SEQ ID NO: 2712)

5'-AGAAAUGGUUCAGAAUUAAACUUUU-3'    (SEQ ID NO: 3822)
                3'-UAUCUUUACCAAGUCUUAAUUUGAAAA-5'  (SEQ ID NO: 1604)
βc-m3538 Target: 5'-ATAGAAATGGTTCAGAATTAAACTTTT-3'  (SEQ ID NO: 2713)
```

TABLE 7

Selected Anti-β-catenin DsiRNA Agents, Blunt/Frayed Duplexes

```
              5'-CCCUGAGGGUAUUUGAAGUAUACCA$^{CC-3'}$    (SEQ ID NO: 5553)
              3'-GGGACUCCCAUAAACUUCAUAUGGU$_{AU-5'}$    (SEQ ID NO: 1117)
βc-240 Target: 5'-CCCTGAGGGTATTTGAAGTATACCATA-3'       (SEQ ID NO: 2226)

5'-GAGGGUAUUUGAAGUAUACCAUACA$^{CA-3'}$    (SEQ ID NO: 5554)
              3'-CUCCCAUAAACUUCAUAUGGUAUGU$_{UG-5'}$    (SEQ ID NO: 1118)
βc-244 Target: 5'-GAGGGTATTTGAAGTATACCATACAAC-3'       (SEQ ID NO: 2227)

5'-UGAAGUAUACCAUACAACUGUUUUG$^{CC-3'}$    (SEQ ID NO: 5555)
              3'-ACUUCAUAUGGUAUGUUGACAAAAC$_{UU-5'}$    (SEQ ID NO: 1119)
βc-253 Target: 5'-TGAAGTATACCATACAACTGTTTTGAA-3'       (SEQ ID NO: 2228)

5'-AUACCAUACAACUGUUUUGAAAAUC$^{AC-3'}$    (SEQ ID NO: 5556)
              3'-UAUGGUAUGUUGACAAAACUUUUAG$_{GU-5'}$    (SEQ ID NO: 1120)
βc-259 Target: 5'-ATACCATACAACTGTTTTGAAAATCCA-3'       (SEQ ID NO: 2229)

5'-AUACAACUGUUUUGAAAAUCCAGCG$^{CA-3'}$    (SEQ ID NO: 5557)
              3'-UAUGUUGACAAAACUUUUAGGUCGCG$_{AC-5'}$   (SEQ ID NO: 1121)
βc-264 Target: 5'-ATACAACTGTTTTGAAAATCCAGCGTG-3'       (SEQ ID NO: 2230)
```

TABLE 7-continued

Selected Anti-β-catenin DsiRNA Agents, Blunt/Frayed Duplexes

```
              5'-CAGGGAUUUCUCAGUCCUUCACUCcC-3'     (SEQ ID NO: 5558)
              3'-GUCCCUAAAAGAGUCAGGAAGUGAGuU-5'    (SEQ ID NO: 1122)
βc-496 Target: 5'-CAGGGATTTTCTCAGTCCTTCACTCAA-3'   (SEQ ID NO: 2231)

5'-CACUCAAGAACAAGUAGCUGAUAUUaC-3'    (SEQ ID NO: 5559)
              3'-GUGAGUUCUUGUUCAUCGACUAUAAcU-5'    (SEQ ID NO: 1123)
βc-516 Target: 5'-CACTCAAGAACAAGTAGCTGATATTGA-3'   (SEQ ID NO: 2232)

5'-AGAACAAGUAGCUGAUAUUGAUGGAaC-3'    (SEQ ID NO: 5560)
              3'-UCUUGUUCAUCGACUAUAACUACCUgU-5'    (SEQ ID NO: 1124)
βc-522 Target: 5'-AGAACAAGTAGCTGATATTGATGGACA-3'   (SEQ ID NO: 2233)

5'-AACAAGUAGCUGAUAUUGAUGGACAaC-3'    (SEQ ID NO: 5561)
              3'-UUGUUCAUCGACUAUAACUACCUGUcA-5'    (SEQ ID NO: 1125)
βc-524 Target: 5'-AACAAGTAGCTGATATTGATGGACAGT-3'   (SEQ ID NO: 2234)

5'-UGAUGGACAGUAUGCAAUGACUCGAaA-3'    (SEQ ID NO: 5562)
              3'-ACUACCUGUCAUACGUUACUGAGCUcG-5'    (SEQ ID NO: 1126)
βc-540 Target: 5'-TGATGGACAGTATGCAATGACTCGAGC-3'   (SEQ ID NO: 2235)

5'-UGCUAUGUUCCCUGAGACAUUAGAUaC-3'    (SEQ ID NO: 5563)
              3'-ACGAUACAAGGGACUCUGUAAUCUAcU-5'    (SEQ ID NO: 1127)
βc-582 Target: 5'-TGCTATGTTCCCTGAGACATTAGATGA-3'   (SEQ ID NO: 2236)

5'-UGCUGAAACAUGCAGUUGUAAACUUaC-3'    (SEQ ID NO: 5564)
              3'-ACGACUUUGUACGUCAACAUUUGAAcU-5'    (SEQ ID NO: 1128)
βc-686 Target: 5'-TGCTGAAACATGCAGTTGTAAACTTGA-3'   (SEQ ID NO: 2237)

5'-AACAUGCAGUUGUAAACUUGAUUAAaC-3'    (SEQ ID NO: 5565)
              3'-UUGUACGUCAACAUUUGAACUAAUUgA-5'    (SEQ ID NO: 1129)
βc-692 Target: 5'-AACATGCAGTTGTAAACTTGATTAACT-3'   (SEQ ID NO: 2238)

5'-GCAGUUGUAAACUUGAUUAACUAUCcC-3'    (SEQ ID NO: 5566)
              3'-CGUCAACAUUUGAACUAAUUGAUAGuU-5'    (SEQ ID NO: 1130)
βc-697 Target: 5'-GCAGTTGTAAACTTGATTAACTATCAA-3'   (SEQ ID NO: 2239)

5'-ACUUGAUUAACUAUCAAGAUGAUGCcA-3'    (SEQ ID NO: 5567)
              3'-UGAACUAAUUGAUAGUUCUACUACGuC-5'    (SEQ ID NO: 1131)
βc-707 Target: 5'-ACTTGATTAACTATCAAGATGATGCAG-3'   (SEQ ID NO: 2240)

5'-CCCUGAACUGACAAAACUGCUAAAUaC-3'    (SEQ ID NO: 5568)
              3'-GGGACUUGACUGUUUUGACGAUUUAcU-5'    (SEQ ID NO: 1132)
βc-753 Target: 5'-CCCTGAACTGACAAAACTGCTAAATGA-3'   (SEQ ID NO: 2241)

5'-UCAGAUGGUGUCUGCUAUUGUACGUcA-3'    (SEQ ID NO: 5569)
              3'-AGUCUACCACAGACGAUAACAUGCAuG-5'    (SEQ ID NO: 1133)
βc-870 Target: 5'-TCAGATGGTGTCTGCTATTGTACGTAC-3'   (SEQ ID NO: 2242)

5'-GUACGUACCAUGCAGAAUACAAAUGcC-3'    (SEQ ID NO: 5570)
              3'-CAUGCAUGGUACGUCUUAUGUUUACuA-5'    (SEQ ID NO: 1134)
βc-889 Target: 5'-GTACGTACCATGCAGAATACAAATGAT-3'   (SEQ ID NO: 2243)
```

TABLE 7-continued

Selected Anti-β-catenin DsiRNA Agents, Blunt/Frayed Duplexes

```
         5'-AUUACAACUCUCCACAACCUUUUAU^(CC-3')  (SEQ ID NO: 5571)
         3'-UAAUGUUGAGAGGUGUUGGAAAAUA_(AU-5')  (SEQ ID NO: 1135)
βc-1060 Target: 5'-ATTACAACTCTCCACAACCTTTTATTA-3'  (SEQ ID NO: 2244)

5'-AACUCUCCACAACCUUUUAUUACAU^(AC-3')  (SEQ ID NO: 5572)
         3'-UUGAGAGGUGUUGGAAAAUAAUGUA_(GU-5')  (SEQ ID NO: 1136)
βc-1065 Target: 5'-AACTCTCCACAACCTTTTATTACATCA-3'  (SEQ ID NO: 2245)

5'-UCCACAACCUUUUAUUACAUCAAGA^(CA-3')  (SEQ ID NO: 5573)
         3'-AGGUGUUGGAAAAUAAUGUAGUUCU_(UC-5')  (SEQ ID NO: 1137)
βc-1070 Target: 5'-TCCACAACCTTTTATTACATCAAGAAG-3'  (SEQ ID NO: 2246)

5'-ACCUUUUAUUACAUCAAGAAGGAGC^(CC-3')  (SEQ ID NO: 5574)
         3'-UGGAAAAUAAUGUAGUUCUUCCUCG_(AU-5')  (SEQ ID NO: 1138)
βc-1076 Target: 5'-ACCTTTTATTACATCAAGAAGGAGCTA-3'  (SEQ ID NO: 2247)

5'-ACAAAACAAAUGUUAAAUUCUUGGC^(CC-3')  (SEQ ID NO: 5575)
         3'-UGUUUUGUUUACAAUUUAAGAACCG_(AU-5')  (SEQ ID NO: 1139)
βc-1154 Target: 5'-ACAAAACAAATGTTAAATTCTTGGCTA-3'  (SEQ ID NO: 2248)

5'-AUUACGACAGACUGCCUUCAAAUUU^(CC-3')  (SEQ ID NO: 5576)
         3'-UAAUGCUGUCUGACGGAAGUUUAAA_(AU-5')  (SEQ ID NO: 1140)
βc-1180 Target: 5'-ATTACGACAGACTGCCTTCAAATTTTA-3'  (SEQ ID NO: 2249)

5'-GACAGACUGCCUUCAAAUUUUAGCU^(CC-3')  (SEQ ID NO: 5577)
         3'-CUGUCUGACGGAAGUUUAAAAUCGA_(AU-5')  (SEQ ID NO: 1141)
βc-1185 Target: 5'-GACAGACTGCCTTCAAATTTTAGCTTA-3'  (SEQ ID NO: 2250)

5'-AGCUUUAGUAAAUAUAAUGAGGACC^(CC-3')  (SEQ ID NO: 5578)
         3'-UCGAAAUCAUUUAUAUUACUCCUGG_(AU-5')  (SEQ ID NO: 1142)
βc-1260 Target: 5'-AGCTTTAGTAAATATAATGAGGACCTA-3'  (SEQ ID NO: 2251)

5'-GAAAAACUACUGUGGACCACAAGCA^(AC-3')  (SEQ ID NO: 5579)
         3'-CUUUUUGAUGACACCUGGUGUUCGU_(CU-5')  (SEQ ID NO: 1143)
βc-1294 Target: 5'-GAAAAACTACTGTGGACCACAAGCAGA-3'  (SEQ ID NO: 2252)

5'-CAAGUCAACGUCUUGUUCAGAACUG^(CA-3')  (SEQ ID NO: 5580)
         3'-GUUCAGUUGCAGAACAAGUCUUGAC_(AG-5')  (SEQ ID NO: 1144)
βc-1412 Target: 5'-CAAGTCAACGTCTTGTTCAGAACTGTC-3'  (SEQ ID NO: 2253)

5'-AACGUCUUGUUCAGAACUGUCUUUG^(AC-3')  (SEQ ID NO: 5581)
         3'-UUGCAGAACAAGUCUUGACAGAAAC_(CU-5')  (SEQ ID NO: 1145)
βc-1418 Target: 5'-AACGTCTTGTTCAGAACTGTCTTTGGA-3'  (SEQ ID NO: 2254)

5'-CUUGUUCAGAACUGUCUUUGGACUC^(CA-3')  (SEQ ID NO: 5582)
         3'-GAACAAGUCUUGACAGAAACCUGAG_(AG-5')  (SEQ ID NO: 1146)
βc-1423 Target: 5'-CTTGTTCAGAACTGTCTTTGGACTCTC-3'  (SEQ ID NO: 2255)

5'-UGGGUUCAGAUGAUAUAAAUGUGGU^(AC-3')  (SEQ ID NO: 5583)
         3'-ACCCAAGUCUACUAUAUUUACACCA_(GU-5')  (SEQ ID NO: 1147)
βc-1520 Target: 5'-TGGGTTCAGATGATATAAATGTGGTCA-3'  (SEQ ID NO: 2256)

5'-AUUCUUUCUAACCUCACUUGCAAUA^(CC-3')  (SEQ ID NO: 5584)
         3'-UAAGAAAGAUUGGAGUGAACGUUAU_(UA-5')  (SEQ ID NO: 1148)
βc-1561 Target: 5'-ATTCTTTCTAACCTCACTTGCAATAAT-3'  (SEQ ID NO: 2257)
```

TABLE 7-continued

Selected Anti-β-catenin DsiRNA Agents, Blunt/Frayed Duplexes

```
                  5'-ACCUCACUUGCAAUAAUUAUAAGAA^AC-3'     (SEQ ID NO: 5585)
                  3'-UGGAGUGAACGUUAUUAAUAUUCUU_GU-5'     (SEQ ID NO: 1149)
βc-1571 Target:   5'-ACCTCACTTGCAATAATTATAAGAACA-3'      (SEQ ID NO: 2258)

5'-UGCAAUAAUUAUAAGAACAAGAUGA^CA-3'     (SEQ ID NO: 5586)
                  3'-ACGUUAUUAAUAUUCUUGUUCUACU_AC-5'     (SEQ ID NO: 1150)
βc-1579 Target:   5'-TGCAATAATTATAAGAACAAGATGATG-3'      (SEQ ID NO: 2259)

5'-UGGUAUAGAGGCUCUUGUGCGUACU^AC-3'     (SEQ ID NO: 5587)
                  3'-ACCAUAUCUCCGAGAACACGCAUGA_CA-5'     (SEQ ID NO: 1151)
βc-1620 Target:   5'-TGGTATAGAGGCTCTTGTGCGTACTGT-3'      (SEQ ID NO: 2260)

5'-AAGGCUACUGUUGGAUUGAUUCGAA^CC-3'     (SEQ ID NO: 5588)
                  3'-UUCCGAUGACAACCUAACUAAGCUU_UA-5'     (SEQ ID NO: 1152)
βc-1816 Target:   5'-AAGGCTACTGTTGGATTGATTCGAAAT-3'      (SEQ ID NO: 2261)

5'-CGCAUGGAAGAAAUAGUUGAAGGUU^AC-3'     (SEQ ID NO: 5589)
                  3'-GCGUACCUUCUUUAUCAACUUCCAA_CA-5'     (SEQ ID NO: 1153)
βc-1987 Target:   5'-CGCATGGAAGAAATAGTTGAAGGTTGT-3'      (SEQ ID NO: 2262)

5'-CAUGGAAGAAAUAGUUGAAGGUUGU^CA-3'     (SEQ ID NO: 5590)
                  3'-CUACCUUCUUUAUCAACUUCCAACA_UG-5'     (SEQ ID NO: 1154)
βc-1989 Target:   5'-CATGGAAGAAATAGTTGAAGGTTGTAC-3'      (SEQ ID NO: 2263)

5'-CCAUUGAAAACAUCCAAAGAGUAGC^CA-3'     (SEQ ID NO: 5591)
                  3'-GGUAACUUUUGUAGGUUUCUCAUCG_AC-5'     (SEQ ID NO: 1155)
βc-2111 Target:   5'-CCATTGAAAACATCCAAAGAGTAGCTG-3'      (SEQ ID NO: 2264)

5'-CUGAGGACAAGCCACAAGAUUACAA^AC-3'     (SEQ ID NO: 5592)
                  3'-GACUCCUGUUCGGUGUUCUAAUGUU_CU-5'     (SEQ ID NO: 1156)
βc-2282 Target:   5'-CTGAGGACAAGCCACAAGATTACAAGA-3'      (SEQ ID NO: 2265)

5'-UUGAUACUGACCUGUAAAUCAUCCU^CC-3'     (SEQ ID NO: 5593)
                  3'-AACUAUGACUGGACAUUUAGUAGGA_AA-5'     (SEQ ID NO: 1157)
βc-2624 Target:   5'-TTGATACTGACCTGTAAATCATCCTTT-3'      (SEQ ID NO: 2266)

5'-CUUUAGGUAAGAAGUUUUAAAAAGC^AC-3'     (SEQ ID NO: 5594)
                  3'-GAAAUCCAUUCUUCAAAAUUUUUCG_GU-5'     (SEQ ID NO: 1158)
βc-2647 Target:   5'-CTTTAGGTAAGAAGTTTTAAAAAGCCA-3'      (SEQ ID NO: 2267)

5'-AACAGGUAUAUACUUUGAAAGGAGA^CA-3'     (SEQ ID NO: 5595)
                  3'-UUGUCCAUAUAUGAAACUUUCCUCU_AC-5'     (SEQ ID NO: 1159)
βc-2770 Target:   5'-AACAGGTATATACTTTGAAAGGAGATG-3'      (SEQ ID NO: 2268)

5'-UGGAAGUUAUUAACUUUAAUGUUUU^CC-3'     (SEQ ID NO: 5596)
                  3'-ACCUUCAAUAAUUGAAAUUACAAAA_AA-5'     (SEQ ID NO: 1160)
βc-2848 Target:   5'-TGGAAGTTATTAACTTTAATGTTTTTT-3'      (SEQ ID NO: 2269)

5'-UGCCACAGCUUUUGCAACUUAAUAC^CA-3'     (SEQ ID NO: 5597)
                  3'-ACGGUGUCGAAAACGUUGAAUUAUG_AG-5'     (SEQ ID NO: 1161)
βc-2874 Target:   5'-TGCCACAGCTTTTGCAACTTAATACTC-3'      (SEQ ID NO: 2270)
```

TABLE 7-continued

Selected Anti-β-catenin DsiRNA Agents, Blunt/Frayed Duplexes

```
            5'-AACAUUUGCUGUUUUAAACAUUAAU^(CA-3')  (SEQ ID NO: 5598)
            3'-UUGUAAACGACAAAAUUUGUAAUUA_(UC-5')  (SEQ ID NO: 1162)
βc-2909 Target: 5'-AACATTTGCTGTTTTAAACATTAATAG-3'  (SEQ ID NO: 2271)

5'-AACAAUUGAAGUAAACUUUUUGUUC^(CA-3')  (SEQ ID NO: 5599)
            3'-UUGUUAACUUCAUUUGAAAAACAAG_(AC-5')  (SEQ ID NO: 1163)
βc-3074 Target: 5'-AACAATTGAAGTAAACTTTTGTTCTG-3'  (SEQ ID NO: 2272)

5'-AAACCCUAGCCUUGCUUGUUAAAUU^(CC-3')  (SEQ ID NO: 5600)
            3'-UUUGGGAUCGGAACGAACAAUUUAA_(AA-5')  (SEQ ID NO: 1164)
βc-3197 Target: 5'-AAACCCTAGCCTTGCTTGTTAAATTTT-3'  (SEQ ID NO: 2273)

5'-UAGCCUUGCUUCUUAAAUUUUUUUU^(CC-3')  (SEQ ID NO: 5601)
            3'-AUCGGAACGAACAAUUUAAAAAAAA_(AA-5')  (SEQ ID NO: 1165)
βc-3203 Target: 5'-TAGCCTTGCTTGTTAAATTTTTTTTT-3'  (SEQ ID NO: 2274)

5'-UUGAAGUAGCUCUUUUUUUUUUUUU^(CC-3')  (SEQ ID NO: 5602)
            3'-AACUUCAUCGAGAAAAAAAAAAAAA_(AA-5')  (SEQ ID NO: 1166)
βc-3273 Target: 5'-TTGAAGTAGCTCTTTTTTTTTTTTT-3'  (SEQ ID NO: 2275)

5'-UCGUAGUGUUAAGUUAUAGUGAAUA^(AC-3')  (SEQ ID NO: 5603)
            3'-AGCAUCACAAUUCAAUAUCACUUAU_(GA-5')  (SEQ ID NO: 1167)
βc-3333 Target: 5'-TCGTAGTGTTAAGTTATAGTGAATACT-3'  (SEQ ID NO: 2276)

5'-UAGUGAAUACUGCUACAGCAAUUUC^(CC-3')  (SEQ ID NO: 5604)
            3'-AUCACUUAUGACGAUGUCGUUAAAG_(AU-5')  (SEQ ID NO: 1168)
βc-3349 Target: 5'-TAGTGAATACTGCTACAGCAATTTCTA-3'  (SEQ ID NO: 2277)

5'-AAUACUGCUACAGCAAUUUCUAAUU^(CC-3')  (SEQ ID NO: 5605)
            3'-UUAUGACGAUGUCGUUAAAGAUUAA_(AA-5')  (SEQ ID NO: 1169)
βc-3354 Target: 5'-AATACTGCTACAGCAATTTCTAATTTT-3'  (SEQ ID NO: 2278)

5'-UUCUAAUUUUUAAGAAUUGAGUAAU^(AA-3')  (SEQ ID NO: 5606)
            3'-AAGAUUAAAAAUUCUUAACUCAUUA_(CC-5')  (SEQ ID NO: 1170)
βc-3371 Target: 5'-TTCTAATTTTTAAGAATTGAGTAATGG-3'  (SEQ ID NO: 2279)

5'-AUUUUUAAGAAUUGAGUAAUGGUGU^(CA-3')  (SEQ ID NO: 5607)
            3'-UAAAAAUUCUUAACUCAUUACCACA_(UC-5')  (SEQ ID NO: 1171)
βc-3376 Target: 5'-ATTTTTAAGAATTGAGTAATGGTGTAG-3'  (SEQ ID NO: 2280)

5'-UUCAUAAUCACUCUAAUUAAUUGUA^(CC-3')  (SEQ ID NO: 5608)
            3'-AAGUAUUAGUGAGAUUAAUUAACAU_(UA-5')  (SEQ ID NO: 1172)
βc-3411 Target: 5'-TTCATAATCACTCTAATTAATTGTAAT-3'  (SEQ ID NO: 2281)

5'-AUUAAUUGUAAUCUGAAUAAAGUGU^(CC-3')  (SEQ ID NO: 5609)
            3'-UAAUUAACAUUAGACUUAUUUCACA_(UU-5')  (SEQ ID NO: 1173)
βc-3426 Target: 5'-ATTAATTGTAATCTGAATAAAGTGTAA-3'  (SEQ ID NO: 2282)

5'-UUGUAAUCUGAAUAAAGUGUAACAA^(CC-3')  (SEQ ID NO: 5610)
            3'-AACAUUAGACUUAUUUCACAUUGUU_(AA-5')  (SEQ ID NO: 1174)
βc-3431 Target: 5'-TTGTAATCTGAATAAAGTGTAACAATT-3'  (SEQ ID NO: 2283)

5'-UCUGAAUAAAGUGUAACAAUUGUGU^(CA-3')  (SEQ ID NO: 5611)
            3'-AGACUUAUUUCACAUUGUUAACACA_(UC-5')  (SEQ ID NO: 1175)
βc-3437 Target: 5'-TCTGAATAAAGTGTAACAATTGTGTAG-3'  (SEQ ID NO: 2284)
```

TABLE 7-continued

Selected Anti-β-catenin DsiRNA Agents, Blunt/Frayed Duplexes

```
            5'-GUGUAGCCUUUUUGUAUAAAAUAGA^AC-3'    (SEQ ID NO: 5612)
            3'-CACAUCGGAAAAACAUAUUUUAUCU_GU-5'   (SEQ ID NO: 1176)
βc-3458 Target: 5'-GTGTAGCCTTTTTGTATAAAATAGACA-3' (SEQ ID NO: 2285)

5'-UUUGUAUAAAAUAGACAAAUAGAAA^CC-3'    (SEQ ID NO: 5613)
            3'-AAACAUAUUUUAUCUGUUUAUCUUU_UA-5'   (SEQ ID NO: 1177)
βc-3468 Target: 5'-TTTGTATAAAATAGACAAATAGAAAT-3' (SEQ ID NO: 2286)

5'-AGAAAAUGGUCCAAUUAGUUUCCUU^CC-3'    (SEQ ID NO: 5614)
            3'-UCUUUUACCAGGUUAAUCAAAGGAA_AA-5'   (SEQ ID NO: 1178)
βc-3488 Target: 5'-AGAAAATGGTCCAATTAGTTTCCTTTT-3' (SEQ ID NO: 2287)

5'-GUCCAAUUAGUUUCCUUUUUAAUAU^AA-3'    (SEQ ID NO: 5615)
            3'-CAGGUUAAUCAAAGGAAAAAUUAUA_CG-5'   (SEQ ID NO: 1179)
βc-3496 Target: 5'-GTCCAATTAGTTTCCTTTTTAATATGC-3' (SEQ ID NO: 2288)

5'-UUUUUGAUCAAAAACUAUUUGGGAU^CC-3'    (SEQ ID NO: 5616)
            3'-AAAAACUAGUUUUUGAUAAACCCUA_UA-5'   (SEQ ID NO: 1180)
βc-3552 Target: 5'-TTTTTGATCAAAAACTATTTGGGATAT-3' (SEQ ID NO: 2289)

5'-AAGAGGUGUUAUUUGGAACCUUGUU^CC-3'    (SEQ ID NO: 5617)
            3'-UUCUCCACAAUAAACCUUGGAACAA_AA-5'   (SEQ ID NO: 1181)
βc-3600 Target: 5'-AAGAGGTGTTATTTGGAACCTTGTTTT-3' (SEQ ID NO: 2290)

5'-GUGUUAUUUGGAACCUUGUUUUGGA^AC-3'    (SEQ ID NO: 5618)
            3'-CACAAUAAACCUUGGAACAAAACCU_GU-5'   (SEQ ID NO: 1182)
βc-3605 Target: 5'-GTGTTATTTGGAACCTTGTTTTGGACA-3' (SEQ ID NO: 2291)

5'-GAACCUUGUUUUGGACAGUUUACCA^AC-3'    (SEQ ID NO: 5619)
            3'-CUUGGAACAAAACCUGUCAAAUGGU_CA-5'   (SEQ ID NO: 1183)
βc-3615 Target: 5'-GAACCTTGTTTTGGACAGTTTACCAGT-3' (SEQ ID NO: 2292)

5'-GUGAUACGAUGCUUCAAGAGAAAAU^AA-3'    (SEQ ID NO: 5620)
            3'-CACUAUGCUACGAAGUUCUCUUUUA_CG-5'   (SEQ ID NO: 1184)
βc-3674 Target: 5'-GTGATACGATGCTTCAAGAGAAAATGC-3' (SEQ ID NO: 2293)

5'-UUCAAGAGAAAAUGCGGUUAUAAAA^CC-3'    (SEQ ID NO: 5621)
            3'-AAGUUCUCUUUUACGCCAAUAUUUU_UU-5'   (SEQ ID NO: 1185)
βc-3686 Target: 5'-TTCAAGAGAAAATGCGGTTATAAAAA-3' (SEQ ID NO: 2294)

5'-GAGAAAAUGCGGUUAUAAAAAAUGG^CC-3'    (SEQ ID NO: 5622)
            3'-CUCUUUUACGCCAAUAUUUUUUACC_AA-5'   (SEQ ID NO: 1186)
βc-3691 Target: 5'-GAGAAAATGCGGTTATAAAAAATGGTT-3' (SEQ ID NO: 2295)

5'-CGGUUAUAAAAAAUGGUUCAGAAUU^CC-3'    (SEQ ID NO: 5623)
            3'-GCCAAUAUUUUUUACCAAGUCUUAA_UU-5'   (SEQ ID NO: 1187)
βc-3700 Target: 5'-CGGTTATAAAAAATGGTTCAGAATTAA-3' (SEQ ID NO: 2296)

5'-AAAAAAUGGUUCAGAAUUAAACUUU^CC-3'    (SEQ ID NO: 5624)
            3'-UUUUUUACCAAGUCUUAAUUUGAAA_AU-5'   (SEQ ID NO: 1188)
βc-3707 Target: 5'-AAAAAATGGTTCAGAATTAAACTTTTA-3' (SEQ ID NO: 2297)

5'-CAGCGUGGACAAUGGCUACUCAAGC^CA-3'    (SEQ ID NO: 5625)
            3'-GUCGCACCUGUUACCGAUGAGUUCG_AC-5'   (SEQ ID NO: 1189)
βc-284 Target: 5'-CAGCGTGGACAATGGCTACTCAAGCTG-3'  (SEQ ID NO: 2298)
```

TABLE 7-continued

Selected Anti-β-catenin DsiRNA Agents, Blunt/Frayed Duplexes

```
           5'-AGCGUGGACAAUGGCUACUCAAGCU^(AC-3')      (SEQ ID NO: 5626)
           3'-UCGCACCUGUUACCGAUGAGUUCGA_(CU-5')     (SEQ ID NO: 1190)
βc-285 Target: 5'-AGCGTGGACAATGGCTACTCAAGCTGA-3'     (SEQ ID NO: 2299)

5'-GCGUGGACAAUGGCUACUCAAGCUG^(CC-3')      (SEQ ID NO: 5627)
           3'-CGCACCUGUUACCGAUGAGUUCGAC_(UA-5')     (SEQ ID NO: 1191)
βc-286 Target: 5'-GCGTGGACAATGGCTACTCAAGCTGAT-3'     (SEQ ID NO: 2300)

5'-CGUGGACAAUGGCUACUCAAGCUGA^(CC-3')      (SEQ ID NO: 5628)
           3'-GCACCUGUUACCGAUGAGUUCGACU_(AA-5')     (SEQ ID NO: 1192)
βc-287 Target: 5'-CGTGGACAATGGCTACTCAAGCTGATT-3'     (SEQ ID NO: 2301)

5'-GUGGACAAUGGCUACUCAAGCUGAU^(CC-3')      (SEQ ID NO: 5629)
           3'-CACCUGUUACCGAUGAGUUCGACUA_(AA-5')     (SEQ ID NO: 1193)
βc-288 Target: 5'-GTGGACAATGGCTACTCAAGCTGATTT-3'     (SEQ ID NO: 2302)

5'-UGGACAAUGGCUACUCAAGCUGAUU^(CA-3')      (SEQ ID NO: 5630)
           3'-ACCUGUUACCGAUGAGUUCGACUAA_(AC-5')     (SEQ ID NO: 1194)
βc-289 Target: 5'-TGGACAATGGCTACTCAAGCTGATTTG-3'     (SEQ ID NO: 2303)

5'-GGACAAUGGCUACUCAAGCUGAUUU^(AC-3')      (SEQ ID NO: 5631)
           3'-CCUGUUACCGAUGAGUUCGACUAAA_(CU-5')     (SEQ ID NO: 1195)
βc-290 Target: 5'-GGACAATGGCTACTCAAGCTGATTTGA-3'     (SEQ ID NO: 2304)

5'-GACAAUGGCUACUCAAGCUGAUUUG^(CC-3')      (SEQ ID NO: 5632)
           3'-CUGUUACCGAUGAGUUCGACUAAAC_(UA-5')     (SEQ ID NO: 1196)
βc-291 Target: 5'-GACAATGGCTACTCAAGCTGATTTGAT-3'     (SEQ ID NO: 2305)

5'-UUUGAUGGAGUUGGACAUGGCCAUGA^(AC-3')      (SEQ ID NO: 5633)
           3'-AAACUACCUCAACCUGUACCGGUAC_(CU-5')     (SEQ ID NO: 1197)
βc-312 Target: 5'-TTTGATGGAGTTGGACATGGCCATGGA-3'     (SEQ ID NO: 2306)

5'-UUGAUGGAGUUGGACAUGGCCAUGG^(CC-3')      (SEQ ID NO: 5634)
           3'-AACUACCUCAACCUGUACCGGUACC_(UU-5')     (SEQ ID NO: 1198)
βc-313 Target: 5'-TTGATGGAGTTGGACATGGCCATGGAA-3'     (SEQ ID NO: 2307)

5'-UGAUGGAGUUGGACAUGGCCAUGGA^(CA-3')      (SEQ ID NO: 5635)
           3'-ACUACCUCAACCUGUACCGGUACCU_(UG-5')     (SEQ ID NO: 1199)
βc-314 Target: 5'-TGATGGAGTTGGACATGGCCATGGAAC-3'     (SEQ ID NO: 2308)

5'-GAUGGAGUUGGACAUGGCCAUGGAA^(AA-3')      (SEQ ID NO: 5636)
           3'-CUACCUCAACCUGUACCGGUACCUU_(GG-5')     (SEQ ID NO: 1200)
βc-315 Target: 5'-GATGGAGTTGGACATGGCCATGGAACC-3'     (SEQ ID NO: 2309)

5'-AUGGAGUUGGACAUGGCCAUGGAAC^(AC-3')      (SEQ ID NO: 5637)
           3'-UACCUCAACCUGUACCGGUACCUUG_(GU-5')     (SEQ ID NO: 1201)
βc-316 Target: 5'-ATGGAGTTGGACATGGCCATGGAACCA-3'     (SEQ ID NO: 2310)

5'-UGGAGUUGGACAUGGCCAUGGAACC^(CA-3')      (SEQ ID NO: 5638)
           3'-ACCUCAACCUGUACCGGUACCUUGG_(UC-5')     (SEQ ID NO: 1202)
βc-317 Target: 5'-TGGAGTTGGACATGGCCATGGAACCAG-3'     (SEQ ID NO: 2311)

5'-GGAGUUGGACAUGGCCAUGGAACCA^(AC-3')      (SEQ ID NO: 5639)
           3'-CCUCAACCUGUACCGGUACCUUGGU_(CU-5')     (SEQ ID NO: 1203)
βc-318 Target: 5'-GGAGTTGGACATGGCCATGGAACCAGA-3'     (SEQ ID NO: 2312)
```

TABLE 7-continued

Selected Anti-β-catenin DsiRNA Agents, Blunt/Frayed Duplexes

```
              5'-ACUCUGGAAUCCAUUCUGGUGCCACC^CC-3'   (SEQ ID NO: 5640)
              3'-UGAGACCUUAGGUAAGACCACGGUG_AU-5'    (SEQ ID NO: 1204)
βc-389 Target: 5'-ACTCTGGAATCCATTCTGGTGCCACTA-3'   (SEQ ID NO: 2313)

5'-CUCUGGAAUCCAUUCUGGUGCCACU^CA-3'    (SEQ ID NO: 5641)
              3'-GAGACCUUAGGUAAGACCACGGUGA_UG-5'    (SEQ ID NO: 1205)
βc-390 Target: 5'-CTCTGGAATCCATTCTGGTGCCACTAC-3'   (SEQ ID NO: 2314)

5'-UCUGGAAUCCAUUCUGGUGCCACUA^AA-3'    (SEQ ID NO: 5642)
              3'-AGACCUUAGGUAAGACCACGGUGAU_GG-5'    (SEQ ID NO: 1206)
βc-391 Target: 5'-TCTGGAATCCATTCTGGTGCCACTACC-3'   (SEQ ID NO: 2315)

5'-CUGGAAUCCAUUCUGGUGCCACUAC^AC-3'    (SEQ ID NO: 5643)
              3'-GACCUUAGGUAAGACCACGGUGAUG_GU-5'    (SEQ ID NO: 1207)
βc-392 Target: 5'-CTGGAATCCATTCTGGTGCCACTACCA-3'   (SEQ ID NO: 2316)

5'-UGGAAUCCAUUCUGGUGCCACUACC^CA-3'    (SEQ ID NO: 5644)
              3'-ACCUUAGGUAAGACCACGGUGAUGG_UG-5'    (SEQ ID NO: 1208)
βc-393 Target: 5'-TGGAATCCATTCTGGTGCCACTACCAC-3'   (SEQ ID NO: 2317)

5'-AUUAGAUGAGGGCAUGCAGAUCCCA^CA-3'    (SEQ ID NO: 5645)
              3'-UAAUCUACUCCCGUACGUCUAGGGU_AG-5'    (SEQ ID NO: 1209)
βc-600 Target: 5'-ATTAGATGAGGGCATGCAGATCCCATC-3'   (SEQ ID NO: 2318)

5'-UUAGAUGAGGGCAUGCAGAUCCCAU^AC-3'    (SEQ ID NO: 5646)
              3'-AAUCUACUCCCGUACGUCUAGGGUA_GA-5'    (SEQ ID NO: 1210)
βc-601 Target: 5'-TTAGATGAGGGCATGCAGATCCCATCT-3'   (SEQ ID NO: 2319)

5'-UAGAUGAGGGCAUGCAGAUCCCAUC^CC-3'    (SEQ ID NO: 5647)
              3'-AUCUACUCCCGUACGUCUAGGGUAG_AU-5'    (SEQ ID NO: 1211)
βc-602 Target: 5'-TAGATGAGGGCATGCAGATCCCATCTA-3'   (SEQ ID NO: 2320)

5'-AGAUGAGGGCAUGCAGAUCCCAUCU^CA-3'    (SEQ ID NO: 5648)
              3'-UCUACUCCCGUACGUCUAGGGUAGA_UG-5'    (SEQ ID NO: 1212)
βc-603 Target: 5'-AGATGAGGGCATGCAGATCCCATCTAC-3'   (SEQ ID NO: 2321)

5'-GAUGAGGGCAUGCAGAUCCCAUCUA^AC-3'    (SEQ ID NO: 5649)
              3'-CUACUCCCGUACGUCUAGGGUAGAU_GU-5'    (SEQ ID NO: 1213)
βc-604 Target: 5'-GATGAGGGCATGCAGATCCCATCTACA-3'   (SEQ ID NO: 2322)

5'-AUGAGGGCAUGCAGAUCCCAUCUAC^CA-3'    (SEQ ID NO: 5650)
              3'-UACUCCCGUACGUCUAGGGUAGAUG_UG-5'    (SEQ ID NO: 1214)
βc-605 Target: 5'-ATGAGGGCATGCAGATCCCATCTACAC-3'   (SEQ ID NO: 2323)

5'-AUGCUGCUCAUCCCACUAAUGUCCA^AA-3'    (SEQ ID NO: 5651)
              3'-UACGACGAGUAGGGUGAUUACAGGU_CG-5'    (SEQ ID NO: 1215)
βc-638 Target: 5'-ATGCTGCTCATCCCACTAATGTCCAGC-3'   (SEQ ID NO: 2324)

5'-UGCUGCUCAUCCCACUAAUGUCCAG^AA-3'    (SEQ ID NO: 5652)
              3'-ACGACGAGUAGGGUGAUUACAGGUC_GC-5'    (SEQ ID NO: 1216)
βc-639 Target: 5'-TGCTGCTCATCCCACTAATGTCCAGCG-3'   (SEQ ID NO: 2325)

5'-GCUGCUCAUCCCACUAAUGUCCAGC^AC-3'    (SEQ ID NO: 5653)
              3'-CGACGAGUAGGGUGAUUACAGGUCG_CA-5'    (SEQ ID NO: 1217)
βc-640 Target: 5'-GCTGCTCATCCCACTAATGTCCAGCGT-3'   (SEQ ID NO: 2326)
```

TABLE 7-continued

Selected Anti-β-catenin DsiRNA Agents, Blunt/Frayed Duplexes

```
         5'-CUGCUCAUCCCACUAAUGUCCAGCG^(CC-3')     (SEQ ID NO: 5654)
         3'-GACGAGUAGGGUGAUUACAGGUCGC_(AA-5')     (SEQ ID NO: 1218)
βc-641 Target:  5'-CTGCTCATCCCACTAATGTCCAGCGTT-3'  (SEQ ID NO: 2327)

5'-UGCUCAUCCCACUAAUGUCCAGCGU^(CC-3')     (SEQ ID NO: 5655)
         3'-ACGAGUAGGGUGAUUACAGGUCGCA_(AA-5')     (SEQ ID NO: 1219)
βc-642 Target:  5'-TGCTCATCCCACTAATGTCCAGCGTTT-3' (SEQ ID NO: 2328)

5'-GCUCAUCCCACUAAUGUCCAGCGUU^(CA-3')     (SEQ ID NO: 5656)
         3'-CGAGUAGGGUGAUUACAGGUCGCAA_(AC-5')     (SEQ ID NO: 1220)
βc-643 Target:  5'-GCTCATCCCACTAATGTCCAGCGTTTG-3' (SEQ ID NO: 2329)

5'-CUCAUCCCACUAAUGUCCAGCGUUU^(AA-3')     (SEQ ID NO: 5657)
         3'-GAGUAGGGUGAUUACAGGUCGCAAA_(CC-5')     (SEQ ID NO: 1221)
βc-644 Target:  5'-CTCATCCCACTAATGTCCAGCGTTTGG-3' (SEQ ID NO: 2330)

5'-UCAUCCCACUAAUGUCCAGCGUUUG^(AA-3')     (SEQ ID NO: 5658)
         3'-AGUAGGGUGAUUACAGGUCGCAAAC_(CG-5')     (SEQ ID NO: 1222)
βc-645 Target:  5'-TCATCCCACTAATGTCCAGCGTTTGGC-3' (SEQ ID NO: 2331)

5'-GUUUGGCUGAACCAUCACAGAUGCU^(AC-3')     (SEQ ID NO: 5659)
         3'-CAAACCGACUUGGUAGUGUCUACGA_(CU-5')     (SEQ ID NO: 1223)
βc-665 Target:  5'-GTTTGGCTGAACCATCACAGATGCTGA-3' (SEQ ID NO: 2332)

5'-UUUGGCUGAACCAUCACAGAUGCUG^(CC-3')     (SEQ ID NO: 5660)
         3'-AAACCGACUUGGUAGUGUCUACGAC_(UU-5')     (SEQ ID NO: 1224)
βc-666 Target:  5'-TTTGGCTGAACCATCACAGATGCTGAA-3' (SEQ ID NO: 2333)

5'-UUGGCUGAACCAUCACAGAUGCUGA^(CC-3')     (SEQ ID NO: 5661)
         3'-AACCGACUUGGUAGUGUCUACGACU_(UU-5')     (SEQ ID NO: 1225)
βc-667 Target:  5'-TTGGCTGAACCATCACAGATGCTGAAA-3' (SEQ ID NO: 2334)

5'-CAGAACUUGCCACACGUGCAAUCCC^(CA-3')     (SEQ ID NO: 5662)
         3'-GUCUUGAACGGUGUGCACGUUAGGG_(AC-5')     (SEQ ID NO: 1226)
βc-731 Target:  5'-CAGAACTTGCCACACGTGCAATCCCTG-3' (SEQ ID NO: 2335)

5'-AGAACUUGCCACACGUGCAAUCCCU^(AC-3')     (SEQ ID NO: 5663)
         3'-UCUUGAACGGUGUGCACGUUAGGGA_(CU-5')     (SEQ ID NO: 1227)
βc-732 Target:  5'-AGAACTTGCCACACGTGCAATCCCTGA-3' (SEQ ID NO: 2336)

5'-CAGUUAUGGUCCAUCAGCUUUCUAA^(CC-3')     (SEQ ID NO: 5664)
         3'-GUCAAUACCAGGUAGUCGAAAGAUU_(UU-5')     (SEQ ID NO: 1228)
βc-809 Target:  5'-CAGTTATGGTCCATCAGCTTTCTAAAA-3' (SEQ ID NO: 2337)

5'-AGUUAUGGUCCAUCAGCUUUCUAAA^(CC-3')     (SEQ ID NO: 5665)
         3'-UCAAUACCAGGUAGUCGAAAGAUUU_(UU-5')     (SEQ ID NO: 1229)
βc-810 Target:  5'-AGTTATGGTCCATCAGCTTTCTAAAAA-3' (SEQ ID NO: 2338)

5'-CUAAAAAGGAAGCUUCCAGACACGC^(CC-3')     (SEQ ID NO: 5666)
         3'-GAUUUUUCCUUCGAAGGUCUGUGCG_(AU-5')     (SEQ ID NO: 1230)
βc-830 Target:  5'-CTAAAAAGGAAGCTTCCAGACACGCTA-3' (SEQ ID NO: 2339)
```

TABLE 7-continued

Selected Anti-β-catenin DsiRNA Agents, Blunt/Frayed Duplexes

```
         5'-UAAAAAGGAAGCUUCCAGACACGCU^(CC-3')  (SEQ ID NO: 5667)
         3'-AUUUUUCCUUCGAAGGUCUGUGCGA_(UA-5')  (SEQ ID NO: 1231)
βc-831 Target: 5'-TAAAAAGGAAGCTTCCAGACACGCTAT-3' (SEQ ID NO: 2340)

5'-GUACCAUGCAGAAUACAAAUGAUGU^(CA-3')  (SEQ ID NO: 5668)
         3'-CAUGGUACGUCUUAUGUUUACUACA_(UC-5')  (SEQ ID NO: 1232)
βc-893 Target: 5'-GTACCATGCAGAATACAAATGATGTAG-3' (SEQ ID NO: 2341)

5'-UACCAUGCAGAAUACAAAUGAUGUA^(AC-3')  (SEQ ID NO: 5669)
         3'-AUGGUACGUCUUAUGUUUACUACAU_(CU-5')  (SEQ ID NO: 1233)
βc-894 Target: 5'-TACCATGCAGAATACAAATGATGTAGA-3' (SEQ ID NO: 2342)

5'-ACCAUGCAGAAUACAAAUGAUGUAG^(CC-3')  (SEQ ID NO: 5670)
         3'-UGGUACGUCUUAUGUUUACUACAUC_(UU-5')  (SEQ ID NO: 1234)
βc-895 Target: 5'-ACCATGCAGAATACAAATGATGTAGAA-3' (SEQ ID NO: 2343)

5'-CCAUGCAGAAUACAAAUGAUGUAGA^(CC-3')  (SEQ ID NO: 5671)
         3'-GGUACGUCUUAUGUUUACUACAUCU_(UU-5')  (SEQ ID NO: 1235)
βc-896 Target: 5'-CCATGCAGAATACAAATGATGTAGAAA-3' (SEQ ID NO: 2344)

5'-CAUGCAGAAUACAAAUGAUGUAGAA^(CA-3')  (SEQ ID NO: 5672)
         3'-GUACGUCUUAUGUUUACUACAUCUU_(UG-5')  (SEQ ID NO: 1236)
βc-897 Target: 5'-CATGCAGAATACAAATGATGTAGAAAC-3' (SEQ ID NO: 2345)

5'-AUGCAGAAUACAAAUGAUGUAGAAA^(AC-3')  (SEQ ID NO: 5673)
         3'-UACGUCUUAUGUUUACUACAUCUUU_(GU-5')  (SEQ ID NO: 1237)
βc-898 Target: 5'-ATGCAGAATACAAATGATGTAGAAACA-3' (SEQ ID NO: 2346)

5'-UGCAGAAUACAAAUGAUGUAGAAAC^(CA-3')  (SEQ ID NO: 5674)
         3'-ACGUCUUAUGUUUACUACAUCUUUG_(UC-5')  (SEQ ID NO: 1238)
βc-899 Target: 5'-TGCAGAATACAAATGATGTAGAAACAG-3' (SEQ ID NO: 2347)

5'-GCAGAAUACAAAUGAUGUAGAAACA^(AA-3')  (SEQ ID NO: 5675)
         3'-CGUCUUAUGUUUACUACAUCUUUGU_(CG-5')  (SEQ ID NO: 1239)
βc-900 Target: 5'-GCAGAATACAAATGATGTAGAAACAGC-3' (SEQ ID NO: 2348)

5'-UACUGGCCAUCUUUAAGUCUGGAGG^(AC-3')  (SEQ ID NO: 5676)
         3'-AUGACCGGUAGAAAUUCAGACCUCC_(GU-5')  (SEQ ID NO: 1240)
βc-977 Target: 5'-TACTGGCCATCTTTAAGTCTGGAGGCA-3' (SEQ ID NO: 2349)

5'-ACUGGCCAUCUUUAAGUCUGGAGGC^(CC-3')  (SEQ ID NO: 5677)
         3'-UGACCGGUAGAAAUUCAGACCUCCG_(UA-5')  (SEQ ID NO: 1241)
βc-978 Target: 5'-ACTGGCCATCTTTAAGTCTGGAGGC-3' (SEQ ID NO: 2350)

5'-AAGAAGGAGCUAAAAUGGCAGUGCG^(CC-3')  (SEQ ID NO: 5678)
         3'-UUCUUCCUCGAUUUUACCGUCACGC_(AA-5')  (SEQ ID NO: 1242)
βc-1091 Target: 5'-AAGAAGGAGCTAAAATGGCAGTGCGTT-3' (SEQ ID NO: 2351)

5'-AGAAGGAGCUAAAAUGGCAGUGCGU^(CC-3')  (SEQ ID NO: 5679)
         3'-UCUUCCUCGAUUUUACCGUCACGCA_(AA-5')  (SEQ ID NO: 1243)
βc-1092 Target: 5'-AGAAGGAGCTAAAATGGCAGTGCGTTT-3' (SEQ ID NO: 2352)

5'-GAAGGAGCUAAAAUGGCAGUGCGUU^(CC-3')  (SEQ ID NO: 5680)
         3'-CUUCCUCGAUUUUACCGUCACGCAA_(AU-5')  (SEQ ID NO: 1244)
βc-1093 Target: 5'-GAAGGAGCTAAAATGGCAGTGCGTTTA-3' (SEQ ID NO: 2353)
```

TABLE 7-continued

Selected Anti-β-catenin DsiRNA Agents, Blunt/Frayed Duplexes

```
         5'-AAGGAGCUAAAAUGGCAGUGCGUUU^CA-3'    (SEQ ID NO: 5681)
         3'-UUCCUCGAUUUUACCGUCACGCAAA_UC-5'   (SEQ ID NO: 1245)
βc-1094 Target: 5'-AAGGAGCTAAAATGGCAGTGCGTTTAG-3'  (SEQ ID NO: 2354)

5'-AGGAGCUAAAAUGGCAGUGCGUUUA^AA-3'   (SEQ ID NO: 5682)
         3'-UCCUCGAUUUUACCGUCACGCAAAU_CG-5'   (SEQ ID NO: 1246)
βc-1095 Target: 5'-AGGAGCTAAAATGGCAGTGCGTTTAGC-3' (SEQ ID NO: 2355)

5'-UACUGUGGACCACAAGCAGAGUGCU^AC-3'   (SEQ ID NO: 5683)
         3'-AUGACACCUGGUGUUCGUCUCACGA_CU-5'   (SEQ ID NO: 1247)
βc-1301 Target: 5'-TACTGTGGACCACAAGCAGAGTGCTGA-3' (SEQ ID NO: 2356)

5'-ACUGUGGACCACAAGCAGAGUGCUG^CC-3'   (SEQ ID NO: 5684)
         3'-UGACACCUGGUGUUCGUCUCACGAC_UU-5'   (SEQ ID NO: 1248)
βc-1302 Target: 5'-ACTGTGGACCACAAGCAGAGTGCTGAA-3' (SEQ ID NO: 2357)

5'-CUGUGGACCACAAGCAGAGUGCUGA^CA-3'   (SEQ ID NO: 5685)
         3'-GACACCUGGUGUUCGUCUCACGACU_UC-5'   (SEQ ID NO: 1249)
βc-1303 Target: 5'-CTGTGGACCACAAGCAGAGTGCTGAAG-3' (SEQ ID NO: 2358)

5'-UGUGGACCACAAGCAGAGUGCUGAA^AA-3'   (SEQ ID NO: 5686)
         3'-ACACCUGGUGUUCGUCUCACGACUU_CC-5'   (SEQ ID NO: 1250)
βc-1304 Target: 5'-TGTGGACCACAAGCAGAGTGCTGAAGG-3' (SEQ ID NO: 2359)

5'-GUGGACCACAAGCAGAGUGCUGAAGA^AC-3'  (SEQ ID NO: 5687)
         3'-CACCUGGUGUUCGUCUCACGACUUC_CA-5'   (SEQ ID NO: 1251)
βc-1305 Target: 5'-GTGGACCACAAGCAGAGTGCTGAAGGT-3' (SEQ ID NO: 2360)

5'-UGGACCACAAGCAGAGUGCUGAAGG^CA-3'   (SEQ ID NO: 5688)
         3'-ACCUGGUGUUCGUCUCACGACUUCC_AC-5'   (SEQ ID NO: 1252)
βc-1306 Target: 5'-TGGACCACAAGCAGAGTGCTGAAGGTG-3' (SEQ ID NO: 2361)

5'-GGACCACAAGCAGAGUGCUGAAGGU^AA-3'   (SEQ ID NO: 5689)
         3'-CCUGGUGUUCGUCUCACGACUUCCA_CG-5'   (SEQ ID NO: 1253)
βc-1307 Target: 5'-GGACCACAAGCAGAGTGCTGAAGGTGC-3' (SEQ ID NO: 2362)

5'-GACCACAAGCAGAGUGCUGAAGGUG^AC-3'   (SEQ ID NO: 5690)
         3'-CUGGUGUUCGUCUCACGACUUCCAC_GA-5'   (SEQ ID NO: 1254)
βc-1308 Target: 5'-GACCACAAGCAGAGTGCTGAAGGTGCT-3' (SEQ ID NO: 2363)

5'-ACCACAAGCAGAGUGCUGAAGGUGC^CC-3'   (SEQ ID NO: 5691)
         3'-UGGUGUUCGUCUCACGACUUCCACG_AU-5'   (SEQ ID NO: 1255)
βc-1309 Target: 5'-ACCACAAGCAGAGTGCTGAAGGTGCTA-3' (SEQ ID NO: 2364)

5'-CCACAAGCAGAGUGCUGAAGGUGCU^CC-3'   (SEQ ID NO: 5692)
         3'-GGUGUUCGUCUCACGACUUCCACGA_UA-5'   (SEQ ID NO: 1256)
βc-1310 Target: 5'-CCACAAGCAGAGTGCTGAAGGTGCTAT-3' (SEQ ID NO: 2365)

5'-CACAAGCAGAGUGCUGAAGGUGCUA^CA-3'   (SEQ ID NO: 5693)
         3'-GUGUUCGUCUCACGACUUCCACGAU_AG-5'   (SEQ ID NO: 1257)
βc-1311 Target: 5'-CACAAGCAGAGTGCTGAAGGTGCTATC-3' (SEQ ID NO: 2366)

5'-ACAAGCAGAGUGCUGAAGGUGCUAU^AC-3'   (SEQ ID NO: 5694)
         3'-UGUUCGUCUCACGACUUCCACGAUA_GA-5'   (SEQ ID NO: 1258)
βc-1312 Target: 5'-ACAAGCAGAGTGCTGAAGGTGCTATCT-3' (SEQ ID NO: 2367)
```

TABLE 7-continued

Selected Anti-β-catenin DsiRNA Agents, Blunt/Frayed Duplexes

```
            5'-CAAGCAGAGUGCUGAAGGUGCUAUC^(CA)-3'   (SEQ ID NO: 5695)
            3'-GUUCGUCUCACGACUUCCACGAUAG_(AC)-5'  (SEQ ID NO: 1259)
βc-1313 Target: 5'-CAAGCAGAGTGCTGAAGGTGCTATCTG-3'  (SEQ ID NO: 2368)

5'-AAGCAGAGUGCUGAAGGUGCUAUCU^(AC)-3'  (SEQ ID NO: 5696)
            3'-UUCGUCUCACGACUUCCACGAUAGA_(CA)-5'  (SEQ ID NO: 1260)
βc-1314 Target: 5'-AAGCAGAGTGCTGAAGGTGCTATCTGT-3'  (SEQ ID NO: 2369)

5'-AGAACUGUCUUUGGACUCUCAGGAA^(CA)-3'  (SEQ ID NO: 5697)
            3'-UCUUGACAGAAACCUGAGAGUCCUU_(AG)-5'  (SEQ ID NO: 1261)
βc-1430 Target: 5'-AGAACTGTCTTTGGACTCTCAGGAATC-3'  (SEQ ID NO: 2370)

5'-GAACUGUCUUUGGACUCUCAGGAAU^(AC)-3'  (SEQ ID NO: 5698)
            3'-CUUGACAGAAACCUGAGAGUCCUUA_(GA)-5'  (SEQ ID NO: 1262)
βc-1431 Target: 5'-GAACTGTCTTTGGACTCTCAGGAATCT-3'  (SEQ ID NO: 2371)

5'-CAGAUGAUAUAAAUGUGGUCACCUG^(CA)-3'  (SEQ ID NO: 5699)
            3'-GUCUACUAUAUUUACACCAGUGGAC_(AC)-5'  (SEQ ID NO: 1263)
βc-1526 Target: 5'-CAGATGATATAAATGTGGTCACCTGTG-3'  (SEQ ID NO: 2372)

5'-AGAUGAUAUAAAUGUGGUCACCUGU^(AA)-3'  (SEQ ID NO: 5700)
            3'-UCUACUAUAUUUACACCAGUGGACA_(CG)-5'  (SEQ ID NO: 1264)
βc-1527 Target: 5'-AGATGATATAAATGTGGTCACCTGTGC-3'  (SEQ ID NO: 2373)

5'-GAUGAUAUAAAUGUGGUCACCUGUG^(AC)-3'  (SEQ ID NO: 5701)
            3'-CUACUAUAUUUACACCAGUGGACAC_(GU)-5'  (SEQ ID NO: 1265)
βc-1528 Target: 5'-GATGATATAAATGTGGTCACCTGTGCA-3'  (SEQ ID NO: 2374)

5'-AUGAUAUAAAUGUGGUCACCUGUCG^(CA)-3'  (SEQ ID NO: 5702)
            3'-UACUAUAUUUACACCAGUGGACACG_(UC)-5'  (SEQ ID NO: 1266)
βc-1529 Target: 5'-ATGATATAAATGTGGTCACCTGTGCAG-3'  (SEQ ID NO: 2375)

5'-UGAUAUAAAUGUGGUCACCUGUGCA^(AA)-3'  (SEQ ID NO: 5703)
            3'-ACUAUAUUUACACCAGUGGACACGU_(CG)-5'  (SEQ ID NO: 1267)
βc-1530 Target: 5'-TGATATAAATGTGGTCACCTGTGCAGC-3'  (SEQ ID NO: 2376)

5'-GAUAUAAAUGUGGUCACCUGUGCAG^(AC)-3'  (SEQ ID NO: 5704)
            3'-CUAUAUUUACACCAGUGGACACGUC_(GA)-5'  (SEQ ID NO: 1268)
βc-1531 Target: 5'-GATATAAATGTGGTCACCTGTGCAGCT-3'  (SEQ ID NO: 2377)

5'-AUAUAAAUGUGGUCACCUGUGCAGC^(CA)-3'  (SEQ ID NO: 5705)
            3'-UAUAUUUACACCAGUGGACACGUCG_(AC)-5'  (SEQ ID NO: 1269)
βc-1532 Target: 5'-ATATAAATGTGGTCACCTGTGCAGCTG-3'  (SEQ ID NO: 2378)

5'-UAUAAAUGUGGUCACCUGUGCAGCU^(AA)-3'  (SEQ ID NO: 5706)
            3'-AUAUUUACACCAGUGGACACGUCGA_(CC)-5'  (SEQ ID NO: 1270)
βc-1533 Target: 5'-TATAAATGTGGTCACCTGTGCAGCTGG-3'  (SEQ ID NO: 2379)

5'-AUAAAUGUGGUCACCUGUGCAGCUG^(AC)-3'  (SEQ ID NO: 5707)
            3'-UAUUUACACCAGUGGACACGUCGAC_(CU)-5'  (SEQ ID NO: 1271)
βc-1534 Target: 5'-ATAAATGTGGTCACCTGTGCAGCTGGA-3'  (SEQ ID NO: 2380)
```

TABLE 7-continued

Selected Anti-β-catenin DsiRNA Agents, Blunt/Frayed Duplexes

```
          5'-UAAAUGUGGUCACCUGUGCAGCUGG^CC-3'   (SEQ ID NO: 5708)
          3'-AUUUACACCAGUGGACACGUCGACC_UU-5'  (SEQ ID NO: 1272)

βc-1535 Target: 5'-TAAATGTGGTCACCTGTGCAGCTGGAA-3'  (SEQ ID NO: 2381)

5'-AAAUGUGGUCACCUGUGCAGCUGGA^CC-3'   (SEQ ID NO: 5709)
          3'-UUUACACCAGUGGACACGUCGACCU_UA-5'  (SEQ ID NO: 1273)

βc-1536 Target: 5'-AAATGTGGTCACCTGTGCAGCTGGAAT-3'  (SEQ ID NO: 2382)

5'-AAUGUGGUCACCUGUGCAGCUGGAA^CC-3'   (SEQ ID NO: 5710)
          3'-UUACACCAGUGGACACGUCGACCUU_AA-5'  (SEQ ID NO: 1274)

βc-1537 Target: 5'-AATGTGGTCACCTGTGCAGCTGGAATT-3'  (SEQ ID NO: 2383)

5'-AUGUGGUCACCUGUGCAGCUGGAAU^CA-3'   (SEQ ID NO: 5711)
          3'-UACACCAGUGGACACGUCGACCUUA_AG-5'  (SEQ ID NO: 1275)

βc-1538 Target: 5'-ATGTGGTCACCTGTGCAGCTGGAATTC-3'  (SEQ ID NO: 2384)

5'-UGUGGUCACCUGUGCAGCUGGAAUU^AC-3'   (SEQ ID NO: 5712)
          3'-ACACCAGUGGACACGUCGACCUUAA_GA-5'  (SEQ ID NO: 1276)

βc-1539 Target: 5'-TGTGGTCACCTGTGCAGCTGGAATTCT-3'  (SEQ ID NO: 2385)

5'-GUGGUCACCUGUGCAGCUGGAAUUC^CC-3'   (SEQ ID NO: 5713)
          3'-CACCAGUGGACACGUCGACCUUAAG_AA-5'  (SEQ ID NO: 1277)

βc-1540 Target: 5'-GTGGTCACCTGTGCAGCTGGAATTCTT-3'  (SEQ ID NO: 2386)

5'-UGGUCACCUGUGCAGCUGGAAUUCU^CC-3'   (SEQ ID NO: 5714)
          3'-ACCAGUGGACACGUCGACCUUAAGA_AA-5'  (SEQ ID NO: 1278)

βc-1541 Target: 5'-TGGTCACCTGTGCAGCTGGAATTCTTT-3'  (SEQ ID NO: 2387)

5'-GGUCACCUGUGCAGCUGGAAUUCUU^CA-3'   (SEQ ID NO: 5715)
          3'-CCAGUGGACACGUCGACCUUAAGAA_AG-5'  (SEQ ID NO: 1279)

βc-1542 Target: 5'-GGTCACCTGTGCAGCTGGAATTCTTTC-3'  (SEQ ID NO: 2388)

5'-GUCACCUGUGCAGCUGGAAUUCUUU^AC-3'   (SEQ ID NO: 5716)
          3'-CAGUGGACACGUCGACCUUAAGAAA_GA-5'  (SEQ ID NO: 1280)

βc-1543 Target: 5'-GTCACCTGTGCAGCTGGAATTCTTTCT-3'  (SEQ ID NO: 2389)

5'-UCACCUGUGCAGCUGGAAUUCUUUC^CC-3'   (SEQ ID NO: 5717)
          3'-AGUGGACACGUCGACCUUAAGAAAG_AU-5'  (SEQ ID NO: 1281)

βc-1544 Target: 5'-TCACCTGTGCAGCTGGAATTCTTTCTA-3'  (SEQ ID NO: 2390)

5'-CACCUGUGCAGCUGGAAUUCUUUCU^CC-3'   (SEQ ID NO: 5718)
          3'-GUGGACACGUCGACCUUAAGAAAGA_UU-5'  (SEQ ID NO: 1282)

βc-1545 Target: 5'-CACCTGTGCAGCTGGAATTCTTTCTAA-3'  (SEQ ID NO: 2391)

5'-UUUCUAACCUCACUUGCAAUAAUUA^CC-3'   (SEQ ID NO: 5719)
          3'-AAAGAUUGGAGUGAACGUUAUUAAU_AU-5'  (SEQ ID NO: 1283)

βc-1565 Target: 5'-TTTCTAACCTCACTTGCAATAATTATA-3'  (SEQ ID NO: 2392)

5'-UUCUAACCUCACUUGCAAUAAUUAU^CC-3'   (SEQ ID NO: 5720)
          3'-AAGAUUGGAGUGAACGUUAUUAAUA_UU-5'  (SEQ ID NO: 1284)

βc-1566 Target: 5'-TTCTAACCTCACTTGCAATAATTATAA-3'  (SEQ ID NO: 2393)
```

TABLE 7-continued

Selected Anti-β-catenin DsiRNA Agents, Blunt/Frayed Duplexes

```
            5'-UCUAACCUCACUUGCAAUAAUUAUA^(CA-3')  (SEQ ID NO: 5721)
            3'-AGAUUGGAGUGAACGUUAUUAAUAU_(UC-5')  (SEQ ID NO: 1285)
βc-1567 Target: 5'-TCTAACCTCACTTGCAATAATTATAAG-3'  (SEQ ID NO: 2394)

5'-CUAACCUCACUUGCAAUAAUUAUAA^(AC-3')  (SEQ ID NO: 5722)
            3'-GAUUGGAGUGAACGUUAUUAAUAUU_(CU-5')  (SEQ ID NO: 1286)
βc-1568 Target: 5'-CTAACCTCACTTGCAATAATTATAAGA-3'  (SEQ ID NO: 2395)

5'-UAACCUCACUUGCAAUAAUUAUAAG^(CC-3')  (SEQ ID NO: 5723)
            3'-AUUGGAGUGAACGUUAUUAAUAUUC_(UU-5')  (SEQ ID NO: 1287)
βc-1569 Target: 5'-TAACCTCACTTGCAATAATTATAAGAA-3'  (SEQ ID NO: 2396)

5'-GGGCUGGUGACAGGGAAGACAUCAC^(CA-3')  (SEQ ID NO: 5724)
            3'-CCCGACCACUGUCCCUUCUGUAGUG_(AC-5')  (SEQ ID NO: 1288)
βc-1652 Target: 5'-GGGCTGGTGACAGGGAAGACATCACTG-3'  (SEQ ID NO: 2397)

5'-GGCUGGUGACAGGGAAGACAUCACU^(AC-3')  (SEQ ID NO: 5725)
            3'-CCGACCACUGUCCCUUCUGUAGUGA_(CU-5')  (SEQ ID NO: 1289)
βc-1653 Target: 5'-GGCTGGTGACAGGGAAGACATCACTGA-3'  (SEQ ID NO: 2398)

5'-GCUGGUGACAGGGAAGACAUCACUG^(CA-3')  (SEQ ID NO: 5726)
            3'-CGACCACUGUCCCUUCUGUAGUGAC_(UC-5')  (SEQ ID NO: 1290)
βc-1654 Target: 5'-GCTGGTGACAGGGAAGACATCACTGAG-3'  (SEQ ID NO: 2399)

5'-CUGGUGACAGGGAAGACAUCACUGA^(AA-3')  (SEQ ID NO: 5727)
            3'-GACCACUGUCCCUUCUGUAGUGACU_(CG-5')  (SEQ ID NO: 1291)
βc-1655 Target: 5'-CTGGTGACAGGGAAGACATCACTGAGC-3'  (SEQ ID NO: 2400)

5'-UGGUGACAGGGAAGACAUCACUGAG^(AA-3')  (SEQ ID NO: 5728)
            3'-ACCACUGUCCCUUCUGUAGUGACUC_(GG-5')  (SEQ ID NO: 1292)
βc-1656 Target: 5'-TGGTGACAGGGAAGACATCACTGAGCC-3'  (SEQ ID NO: 2401)

5'-GGUGACAGGGAAGACAUCACUGAGC^(AC-3')  (SEQ ID NO: 5729)
            3'-CCACUGUCCCUUCUGUAGUGACUCG_(GA-5')  (SEQ ID NO: 1293)
βc-1657 Target: 5'-GGTGACAGGGAAGACATCACTGAGCCT-3'  (SEQ ID NO: 2402)

5'-GUGACAGGGAAGACAUCACUGAGCC^(CA-3')  (SEQ ID NO: 5730)
            3'-CACUGUCCCUUCUGUAGUGACUCGG_(AC-5')  (SEQ ID NO: 1294)
βc-1658 Target: 5'-GTGACAGGGAAGACATCACTGAGCCTG-3'  (SEQ ID NO: 2403)

5'-UGACAGGGAAGACAUCACUGAGCCU^(AA-3')  (SEQ ID NO: 5731)
            3'-ACUGUCCCUUCUGUAGUGACUCGGA_(CG-5')  (SEQ ID NO: 1295)
βc-1659 Target: 5'-TGACAGGGAAGACATCACTGAGCCTGC-3'  (SEQ ID NO: 2404)

5'-GACAGGGAAGACAUCACUGAGCCUG^(AA-3')  (SEQ ID NO: 5732)
            3'-CUGUCCCUUCUGUAGUGACUCGGAC_(GG-5')  (SEQ ID NO: 1296)
βc-1660 Target: 5'-GACAGGGAAGACATCACTGAGCCTGCC-3'  (SEQ ID NO: 2405)

5'-ACAGGGAAGACAUCACUGAGCCUGC^(AC-3')  (SEQ ID NO: 5733)
            3'-UGUCCCUUCUGUAGUGACUCGGACG_(GU-5')  (SEQ ID NO: 1297)
βc-1661 Target: 5'-ACAGGGAAGACATCACTGAGCCTGCCA-3'  (SEQ ID NO: 2406)

5'-CAGGGAAGACAUCACUGAGCCUGCC^(CC-3')  (SEQ ID NO: 5734)
            3'-GUCCCUUCUGUAGUGACUCGGACGG_(UA-5')  (SEQ ID NO: 1298)
βc-1662 Target: 5'-CAGGGAAGACATCACTGAGCCTGCC-3'  (SEQ ID NO: 2407)
```

TABLE 7-continued

Selected Anti-β-catenin DsiRNA Agents, Blunt/Frayed Duplexes

```
            5'-AGGGAAGACAUCACUGAGCCUGCCA^CA-3'  (SEQ ID NO: 5735)
            3'-UCCCUUCUGUAGUGACUCGGACGGU_AG-5'  (SEQ ID NO: 1299)
βc-1663 Target: 5'-AGGGAAGACATCACTGAGCCTGCCATC-3'  (SEQ ID NO: 2408)

5'-GGGAAGACAUCACUGAGCCUGCCAU^AC-3'  (SEQ ID NO: 5736)
            3'-CCCUUCUGUAGUGACUCGGACGGUA_GA-5'  (SEQ ID NO: 1300)
βc-1664 Target: 5'-GGGAAGACATCACTGAGCCTGCCATCT-3'  (SEQ ID NO: 2409)

5'-GGAAGACAUCACUGAGCCUGCCAUC^CA-3'  (SEQ ID NO: 5737)
            3'-CCUUCUGUAGUGACUCGGACGGUAG_AC-5'  (SEQ ID NO: 1301)
βc-1665 Target: 5'-GGAAGACATCACTGAGCCTGCCATCTG-3'  (SEQ ID NO: 2410)

5'-GAAGACAUCACUGAGCCUGCCAUCU^AC-3'  (SEQ ID NO: 5738)
            3'-CUUCUGUAGUGACUCGGACGGUAGA_CA-5'  (SEQ ID NO: 1302)
βc-1666 Target: 5'-GAAGACATCACTGAGCCTGCCATCTGT-3'  (SEQ ID NO: 2411)

5'-AAGACAUCACUGAGCCUGCCAUCUG^CA-3'  (SEQ ID NO: 5739)
            3'-UUCUGUAGUGACUCGGACGGUAGAC_AC-5'  (SEQ ID NO: 1303)
βc-1667 Target: 5'-AAGACATCACTGAGCCTGCCATCTGTG-3'  (SEQ ID NO: 2412)

5'-AGACAUCACUGAGCCUGCCAUCUGU^AA-3'  (SEQ ID NO: 5740)
            3'-UCUGUAGUGACUCGGACGGUAGACA_CG-5'  (SEQ ID NO: 1304)
βc-1668 Target: 5'-AGACATCACTGAGCCTGCCATCTGTGC-3'  (SEQ ID NO: 2413)

5'-GACAUCACUGAGCCUGCCAUCUGUG^AC-3'  (SEQ ID NO: 5741)
            3'-CUGUAGUGACUCGGACGGUAGACAC_GA-5'  (SEQ ID NO: 1305)
βc-1669 Target: 5'-GACATCACTGAGCCTGCCATCTGTGCT-3'  (SEQ ID NO: 2414)

5'-ACAUCACUGAGCCUGCCAUCUGUGC^CA-3'  (SEQ ID NO: 5742)
            3'-UGUAGUGACUCGGACGGUAGACACG_AG-5'  (SEQ ID NO: 1306)
βc-1670 Target: 5'-ACATCACTGAGCCTGCCATCTGTGCTC-3'  (SEQ ID NO: 2415)

5'-CAUCACUGAGCCUGCCAUCUGUGCU^AC-3'  (SEQ ID NO: 5743)
            3'-GUAGUGACUCGGACGGUAGACACGA_GA-5'  (SEQ ID NO: 1307)
βc-1671 Target: 5'-CATCACTGAGCCTGCCATCTGTGCTCT-3'  (SEQ ID NO: 2416)

5'-AUCACUGAGCCUGCCAUCUGUGCUC^CC-3'  (SEQ ID NO: 5744)
            3'-UAGUGACUCGGACGGUAGACACGAG_AA-5'  (SEQ ID NO: 1308)
βc-1672 Target: 5'-ATCACTGAGCCTGCCATCTGTGCTCTT-3'  (SEQ ID NO: 2417)

5'-UCACUGAGCCUGCCAUCUGUGCUCU^CA-3'  (SEQ ID NO: 5745)
            3'-AGUGACUCGGACGGUAGACACGAGA_AG-5'  (SEQ ID NO: 1309)
βc-1673 Target: 5'-TCACTGAGCCTGCCATCTGTGCTCTTC-3'  (SEQ ID NO: 2418)

5'-CACUGAGCCUGCCAUCUGUGCUCUU^AA-3'  (SEQ ID NO: 5746)
            3'-GUGACUCGGACGGUAGACACGAGAA_GC-5'  (SEQ ID NO: 1310)
βc-1674 Target: 5'-CACTGAGCCTGCCATCTGTGCTCTTCG-3'  (SEQ ID NO: 2419)

5'-ACUGAGCCUGCCAUCUGUGCUCUUC^AC-3'  (SEQ ID NO: 5747)
            3'-UGACUCGGACGGUAGACACGAGAAG_CA-5'  (SEQ ID NO: 1311)
βc-1675 Target: 5'-ACTGAGCCTGCCATCTGTGCTCTTCGT-3'  (SEQ ID NO: 2420)

5'-CUGAGCCUGCCAUCUGUGCUCUUCG^CA-3'  (SEQ ID NO: 5748)
            3'-GACUCGGACGGUAGACACGAGAAGC_AG-5'  (SEQ ID NO: 1312)
βc-1676 Target: 5'-CTGAGCCTGCCATCTGTGCTCTTCGTC-3'  (SEQ ID NO: 2421)
```

TABLE 7-continued

Selected Anti-β-catenin DsiRNA Agents, Blunt/Frayed Duplexes

```
         5'-UGAGCCUGCCAUCUGUGCUCUUCGUAC-3'   (SEQ ID NO: 5749)
         3'-ACUCGGACGGUAGACACGAGAAGCAGU-5'   (SEQ ID NO: 1313)
βc-1677 Target: 5'-TGAGCCTGCCATCTGTGCTCTTCGTCA-3'  (SEQ ID NO: 2422)

5'-GAGCCUGCCAUCUGUGCUCUUCGUCCC-3'   (SEQ ID NO: 5750)
         3'-CUCGGACGGUAGACACGAGAAGCAGUA-5'   (SEQ ID NO: 1314)
βc-1678 Target: 5'-GAGCCTGCCATCTGTGCTCTTCGTC-3'   (SEQ ID NO: 2423)

5'-AGCCUGCCAUCUGUGCUCUUCGUCACA-3'   (SEQ ID NO: 5751)
         3'-UCGGACGGUAGACACGAGAAGCAGUAG-5'   (SEQ ID NO: 1315)
βc-1679 Target: 5'-AGCCTGCCATCTGTGCTCTTCGTCATC-3' (SEQ ID NO: 2424)

5'-GCCUGCCAUCUGUGCUCUUCGUCAUAC-3'   (SEQ ID NO: 5752)
         3'-CGGACGGUAGACACGAGAAGCAGUAGA-5'   (SEQ ID NO: 1316)
βc-1680 Target: 5'-GCCTGCCATCTGTGCTCTTCGTCATCT-3' (SEQ ID NO: 2425)

5'-CCUGCCAUCUGUGCUCUUCGUCAUCCA-3'   (SEQ ID NO: 5753)
         3'-GGACGGUAGACACGAGAAGCAGUAGAC-5'   (SEQ ID NO: 1317)
βc-1681 Target: 5'-CCTGCCATCTGTGCTCTTCGTCATCTG-3' (SEQ ID NO: 2426)

5'-CUGCCAUCUGUGCUCUUCGUCAUCUAC-3'   (SEQ ID NO: 5754)
         3'-GACGGUAGACACGAGAAGCAGUAGACU-5'   (SEQ ID NO: 1318)
βc-1682 Target: 5'-CTGCCATCTGTGCTCTTCGTCATCTGA-3' (SEQ ID NO: 2427)

5'-UGCCAUCUGUGCUCUUCGUCAUCUGCA-3'   (SEQ ID NO: 5755)
         3'-ACGGUAGACACGAGAAGCAGUAGACUG-5'   (SEQ ID NO: 1319)
βc-1683 Target: 5'-TGCCATCTGTGCTCTTCGTCATCTGAC-3' (SEQ ID NO: 2428)

5'-GCCAUCUGUGCUCUUCGUCAUCUGAAA-3'   (SEQ ID NO: 5756)
         3'-CGGUAGACACGAGAAGCAGUAGACUGG-5'   (SEQ ID NO: 1320)
βc-1684 Target: 5'-GCCATCTGTGCTCTTCGTCATCTGACC-3' (SEQ ID NO: 2429)

5'-CCAUCUGUGCUCUUCGUCAUCUGACAC-3'   (SEQ ID NO: 5757)
         3'-GGUAGACACGAGAAGCAGUAGACUGGU-5'   (SEQ ID NO: 1321)
βc-1685 Target: 5'-CCATCTGTGCTCTTCGTCATCTGACCA-3' (SEQ ID NO: 2430)

5'-CAUCUGUGCUCUUCGUCAUCUGACCCA-3'   (SEQ ID NO: 5758)
         3'-GUAGACACGAGAAGCAGUAGACUGGUC-5'   (SEQ ID NO: 1322)
βc-1686 Target: 5'-CATCTGTGCTCTTCGTCATCTGACCAG-3' (SEQ ID NO: 2431)

5'-AUCUGUGCUCUUCGUCAUCUGACCAAA-3'   (SEQ ID NO: 5759)
         3'-UAGACACGAGAAGCAGUAGACUGGUCG-5'   (SEQ ID NO: 1323)
βc-1687 Target: 5'-ATCTGTGCTCTTCGTCATCTGACCAGC-3' (SEQ ID NO: 2432)

5'-UCUGUGCUCUUCGUCAUCUGACCAGAA-3'   (SEQ ID NO: 5760)
         3'-AGACACGAGAAGCAGUAGACUGGUCG-5'    (SEQ ID NO: 1324)
βc-1688 Target: 5'-TCTGTGCTCTTCGTCATCTGACCAGCC-3' (SEQ ID NO: 2433)

5'-CUGUGCUCUUCGUCAUCUGACCAGCAA-3'   (SEQ ID NO: 5761)
         3'-GACACGAGAAGCAGUAGACUGGUCGGC-5'   (SEQ ID NO: 1325)
βc-1689 Target: 5'-CTGTGCTCTTCGTCATCTGACCAGCCG-3' (SEQ ID NO: 2434)
```

TABLE 7-continued

Selected Anti-β-catenin DsiRNA Agents, Blunt/Frayed Duplexes

5'-UGUGCUCUUCGUCAUCUGACCAGCC$^{AC}$-3' (SEQ ID NO: 5762)
3'-ACACGAGAAGCAGUAGACUGGUCGG$_{CU}$-5' (SEQ ID NO: 1326)
βc-1690 Target: 5'-TGTGCTCTTCGTCATCTGACCAGCCGA-3' (SEQ ID NO: 2435)

5'-GUGCUCUUCGUCAUCUGACCAGCCG$^{CA}$-3' (SEQ ID NO: 5763)
3'-CACGAGAAGCAGUAGACUGGUCGGC$_{UG}$-5' (SEQ ID NO: 1327)
βc-1691 Target: 5'-GTGCTCTTCGTCATCTGACCAGCCGAC-3' (SEQ ID NO: 2436)

5'-UGCUCUUCGUCAUCUGACCAGCCGA$^{AC}$-3' (SEQ ID NO: 5764)
3'-ACGAGAAGCAGUAGACUGGUCGGCU$_{GU}$-5' (SEQ ID NO: 1328)
βc-1692 Target: 5'-TGCTCTTCGTCATCTGACCAGCCGACA-3' (SEQ ID NO: 2437)

5'-GCUCUUCGUCAUCUGACCAGCCGAC$^{CA}$-3' (SEQ ID NO: 5765)
3'-CGAGAAGCAGUAGACUGGUCGGCUG$_{UG}$-5' (SEQ ID NO: 1329)
βc-1693 Target: 5'-GCTCTTCGTCATCTGACCAGCCGACAC-3' (SEQ ID NO: 2438)

5'-CUCUUCGUCAUCUGACCAGCCGACA$^{AA}$-3' (SEQ ID NO: 5766)
3'-GAGAAGCAGUAGACUGGUCGGCUGU$_{GG}$-5' (SEQ ID NO: 1330)
βc-1694 Target: 5'-CTCTTCGTCATCTGACCAGCCGACACC-3' (SEQ ID NO: 2439)

5'-UCUUCGUCAUCUGACCAGCCGACAC$^{AC}$-3' (SEQ ID NO: 5767)
3'-AGAAGCAGUAGACUGGUCGGCUGUG$_{GU}$-5' (SEQ ID NO: 1331)
βc-1695 Target: 5'-TCTTCGTCATCTGACCAGCCGACACCA-3' (SEQ ID NO: 2440)

5'-UACACCCACCAUCCCACUGGCCUCU$^{AC}$-3' (SEQ ID NO: 5768)
3'-AUGUGGGUGGUAGGGUGACCGGAGA$_{CU}$-5' (SEQ ID NO: 1332)
βc-1787 Target: 5'-TACACCCACCATCCCACTGGCCTCTGA-3' (SEQ ID NO: 2441)

5'-ACACCCACCAUCCCACUGGCCUCUG$^{CC}$-3' (SEQ ID NO: 5769)
3'-UGUGGGUGGUAGGGUGACCGGAGAC$_{UA}$-5' (SEQ ID NO: 1333)
βc-1788 Target: 5'-ACACCCACCATCCCACTGGCCTCTGAT-3' (SEQ ID NO: 2442)

5'-CACCCACCAUCCCACUGGCCUCUGA$^{CC}$-3' (SEQ ID NO: 5770)
3'-GUGGGUGGUAGGGUGACCGGAGACU$_{AU}$-5' (SEQ ID NO: 1334)
βc-1789 Target: 5'-CACCCACCATCCCACTGGCCTCTGATA-3' (SEQ ID NO: 2443)

5'-ACCCACCAUCCCACUGGCCUCUGAU$^{CC}$-3' (SEQ ID NO: 5771)
3'-UGGGUGGUAGGGUGACCGGAGACUA$_{UU}$-5' (SEQ ID NO: 1335)
βc-1790 Target: 5'-ACCCACCATCCCACTGGCCTCTGATAA-3' (SEQ ID NO: 2444)

5'-CCCACCAUCCCACUGGCCUCUGAUA$^{CC}$-3' (SEQ ID NO: 5772)
3'-GGGUGGUAGGGUGACCGGAGACUAU$_{UU}$-5' (SEQ ID NO: 1336)
βc-1791 Target: 5'-CCCACCATCCCACTGGCCTCTGATAAA-3' (SEQ ID NO: 2445)

5'-CCACCAUCCCACUGGCCUCUGAUAA$^{CA}$-3' (SEQ ID NO: 5773)
3'-GGUGGUAGGGUGACCGGAGACUAUU$_{UC}$-5' (SEQ ID NO: 1337)
βc-1792 Target: 5'-CCACCATCCCACTGGCCTCTGATAAAG-3' (SEQ ID NO: 2446)

5'-CACCAUCCCACUGGCCUCUGAUAAA$^{AA}$-3' (SEQ ID NO: 5774)
3'-GUGGUAGGGUGACCGGAGACUAUUU$_{CC}$-5' (SEQ ID NO: 1338)
βc-1793 Target: 5'-CACCATCCCACTGGCCTCTGATAAAGG-3' (SEQ ID NO: 2447)

5'-ACCAUCCCACUGGCCUCUGAUAAAG$^{AA}$-3' (SEQ ID NO: 5775)
3'-UGGUAGGGUGACCGGAGACUAUUUC$_{CG}$-5' (SEQ ID NO: 1339)
βc-1794 Target: 5'-ACCATCCCACTGGCCTCTGATAAAGGC-3' (SEQ ID NO: 2448)

TABLE 7-continued

Selected Anti-β-catenin DsiRNA Agents, Blunt/Frayed Duplexes

```
              5'-CCAUCCCACUGGCCUCUGAUAAAGG^(AC-3')      (SEQ ID NO: 5776)
              3'-GGUAGGGUGACCGGAGACUAUUUCC_(A-5')      (SEQ ID NO: 1340)
                                            G
βc-1795 Target: 5'-CCATCCCACTGGCCTCTGATAAAGGCT-3'      (SEQ ID NO: 2449)

5'-CAUCCCACUGGCCUCUGAUAAAGGC^(CC-3')     (SEQ ID NO: 5777)
              3'-GUAGGGUGACCGGAGACUAUUUCCG_(U-5')     (SEQ ID NO: 1341)
                                            A
βc-1796 Target: 5'-CATCCCACTGGCCTCTGATAAAGGCTA-3'     (SEQ ID NO: 2450)

5'-AUCCCACUGGCCUCUGAUAAAGGCU^(CA-3')     (SEQ ID NO: 5778)
              3'-UAGGGUGACCGGAGACUAUUUCCGA_(G-5')     (SEQ ID NO: 1342)
                                             U
βc-1797 Target: 5'-ATCCCACTGGCCTCTGATAAAGGCTAC-3'     (SEQ ID NO: 2451)

5'-UCCCACUGGCCUCUGAUAAAGGCUA^(AC-3')     (SEQ ID NO: 5779)
              3'-AGGGUGACCGGAGACUAUUUCCGAU_(A-5')     (SEQ ID NO: 1343)
                                             G
βc-1798 Target: 5'-TCCCACTGGCCTCTGATAAAGGCTACT-3'     (SEQ ID NO: 2452)

5'-CCCACUGGCCUCUGAUAAAGGCUAC^(CA-3')     (SEQ ID NO: 5780)
              3'-GGGUGACCGGAGACUAUUUCCGAUG_(C-5')     (SEQ ID NO: 1344)
                                             A
βc-1799 Target: 5'-CCCACTGGCCTCTGATAAAGGCTACTG-3'     (SEQ ID NO: 2453)

5'-CCACUGGCCUCUGAUAAAGGCUACU^(AC-3')     (SEQ ID NO: 5781)
              3'-GGUGACCGGAGACUAUUUCCGAUGA_(A-5')     (SEQ ID NO: 1345)
                                             C
βc-1800 Target: 5'-CCACTGGCCTCTGATAAAGGCTACTGT-3'     (SEQ ID NO: 2454)

5'-CUACUGUUGGAUUGAUUCGAAAUCU^(CA-3')     (SEQ ID NO: 5782)
              3'-GAUGACAACCUAACUAAGCUUUAGA_(C-5')     (SEQ ID NO: 1346)
                                             A
βc-1820 Target: 5'-CTACTGTTGGATTGATTCGAAATCTTG-3'     (SEQ ID NO: 2455)

5'-UACUGUUGGAUUGAUUCGAAAUCUU^(AA-3')     (SEQ ID NO: 5783)
              3'-AUGACAACCUAACUAAGCUUUAGAA_(G-5')     (SEQ ID NO: 1347)
                                             C
βc-1821 Target: 5'-TACTGTTGGATTGATTCGAAATCTTGC-3'     (SEQ ID NO: 2456)

5'-UAAAUACCAUUCCAUUGUUUGUGCA^(AA-3')     (SEQ ID NO: 5784)
              3'-AUUUAUGGUAAGGUAACAAACACGU_(G-5')     (SEQ ID NO: 1348)
                                             C
βc-2072 Target: 5'-TAAATACCATTCCATTGTTTGTGCAGC-3'     (SEQ ID NO: 2457)

5'-AAAUACCAUUCCAUUGUUUGUGCAG^(AC-3')     (SEQ ID NO: 5785)
              3'-UUUAUGGUAAGGUAACAAACACGUC_(A-5')     (SEQ ID NO: 1349)
                                             G
βc-2073 Target: 5'-AAATACCATTCCATTGTTTGTGCAGCT-3'     (SEQ ID NO: 2458)

5'-AAUACCAUUCCAUUGUUUGUGCAGC^(CA-3')     (SEQ ID NO: 5786)
              3'-UUAUGGUAAGGUAACAAACACGUCG_(C-5')     (SEQ ID NO: 1350)
                                             A
βc-2074 Target: 5'-AATACCATTCCATTGTTTGTGCAGCTG-3'     (SEQ ID NO: 2459)

5'-AUACCAUUCCAUUGUUUGUGCAGCU^(AA-3')     (SEQ ID NO: 5787)
              3'-UAUGGUAAGGUAACAAACACGUCGA_(G-5')     (SEQ ID NO: 1351)
                                             C
βc-2075 Target: 5'-ATACCATTCCATTGTTTGTGCAGCTGC-3'     (SEQ ID NO: 2460)

5'-UACCAUUCCAUUGUUUGUGCAGCUG^(AC-3')     (SEQ ID NO: 5788)
              3'-AUGGUAAGGUAACAAACACGUCGAC_(A-5')     (SEQ ID NO: 1352)
                                             G
βc-2076 Target: 5'-TACCATTCCATTGTTTGTGCAGCTGCT-3'     (SEQ ID NO: 2461)
```

TABLE 7-continued

Selected Anti-β-catenin DsiRNA Agents, Blunt/Frayed Duplexes

```
         5'-ACCAUUCCAUUGUUUGUGCAGCUGC^(CC-3')   (SEQ ID NO: 5789)
         3'-UGGUAAGGUAACAAACACGUCGACG_(AA-5')  (SEQ ID NO: 1353)
βc-2077 Target: 5'-ACCATTCCATTGTTTGTGCAGCTGCTT-3' (SEQ ID NO: 2462)

5'-GCUGCUUUAUUCUCCCAUUGAAAAC^(CC-3')   (SEQ ID NO: 5790)
         3'-CGACGAAAUAAGAGGGUAACUUUUG_(UA-5')  (SEQ ID NO: 1354)
βc-2097 Target: 5'-GCTGCTTTATTCTCCCATTGAAAAC-3' (SEQ ID NO: 2463)

5'-CUGCUUUAUUCUCCCAUUGAAAACA^(CA-3')   (SEQ ID NO: 5791)
         3'-GACGAAAUAAGAGGGUAACUUUUGU_(AG-5')  (SEQ ID NO: 1355)
βc-2098 Target: 5'-CTGCTTTATTCTCCCATTGAAAACATC-3' (SEQ ID NO: 2464)

5'-UGCUUUAUUCUCCCAUUGAAAACAU^(AA-3')   (SEQ ID NO: 5792)
         3'-ACGAAAUAAGAGGGUAACUUUUGUA_(GG-5')  (SEQ ID NO: 1356)
βc-2099 Target: 5'-TGCTTTATTCTCCCATTGAAAACATCC-3' (SEQ ID NO: 2465)

5'-GCUUUAUUCUCCCAUUGAAAACAUC^(AC-3')   (SEQ ID NO: 5793)
         3'-CGAAAUAAGAGGGUAACUUUUGUAG_(GU-5')  (SEQ ID NO: 1357)
βc-2100 Target: 5'-GCTTTATTCTCCCATTGAAAACATCCA-3' (SEQ ID NO: 2466)

5'-GGGUCCUCUGUGAACUUGCUCAGGA^(AC-3')   (SEQ ID NO: 5794)
         3'-CCCAGGAGACACUUGAACGAGUCCU_(GU-5')  (SEQ ID NO: 1358)
βc-2141 Target: 5'-GGGTCCTCTGTGAACTTGCTCAGGACA-3' (SEQ ID NO: 2467)

5'-GGUCCUCUGUGAACUUGCUCAGGAC^(CC-3')   (SEQ ID NO: 5795)
         3'-CCAGGAGACACUUGAACGAGUCCUG_(UU-5')  (SEQ ID NO: 1359)
βc-2142 Target: 5'-GGTCCTCTGTGAACTTGCTCAGGACAA-3' (SEQ ID NO: 2468)

5'-GUCCUCUGUGAACUUGCUCAGGACA^(CA-3')   (SEQ ID NO: 5796)
         3'-CAGGAGACACUUGAACGAGUCCUGU_(UC-5')  (SEQ ID NO: 1360)
βc-2143 Target: 5'-GTCCTCTGTGAACTTGCTCAGGACAAG-3' (SEQ ID NO: 2469)

5'-UCCUCUGUGAACUUGCUCAGGACAA^(AA-3')   (SEQ ID NO: 5797)
         3'-AGGAGACACUUGAACGAGUCCUGUU_(CC-5')  (SEQ ID NO: 1361)
βc-2144 Target: 5'-TCCTCTGTGAACTTGCTCAGGACAAGG-3' (SEQ ID NO: 2470)

5'-CCUCUGUGAACUUGCUCAGGACAAG^(AC-3')   (SEQ ID NO: 5798)
         3'-GGAGACACUUGAACGAGUCCUGUUC_(CU-5')  (SEQ ID NO: 1362)
βc-2145 Target: 5'-CCTCTGTGAACTTGCTCAGGACAAGGA-3' (SEQ ID NO: 2471)

5'-CUCUGUGAACUUGCUCAGGACAAGG^(CC-3')   (SEQ ID NO: 5799)
         3'-GAGACACUUGAACGAGUCCUGUUCC_(UU-5')  (SEQ ID NO: 1363)
βc-2146 Target: 5'-CTCTGTGAACTTGCTCAGGACAAGGAA-3' (SEQ ID NO: 2472)

5'-UCUGUGAACUUGCUCAGGACAAGGA^(CA-3')   (SEQ ID NO: 5800)
         3'-AGACACUUGAACGAGUCCUGUUCCU_(UC-5')  (SEQ ID NO: 1364)
βc-2147 Target: 5'-TCTGTGAACTTGCTCAGGACAAGGAAG-3' (SEQ ID NO: 2473)

5'-CUGUGAACUUGCUCAGGACAAGGAA^(AA-3')   (SEQ ID NO: 5801)
         3'-GACACUUGAACGAGUCCUGUUCCUU_(CG-5')  (SEQ ID NO: 1365)
βc-2148 Target: 5'-CTGTGAACTTGCTCAGGACAAGGAAGC-3' (SEQ ID NO: 2474)

5'-UGUGAACUUGCUCAGGACAAGGAAG^(AC-3')   (SEQ ID NO: 5802)
         3'-ACACUUGAACGAGUCCUGUUCCUUC_(GA-5')  (SEQ ID NO: 1366)
βc-2149 Target: 5'-TGTGAACTTGCTCAGGACAAGGAAGCT-3' (SEQ ID NO: 2475)
```

TABLE 7-continued

Selected Anti-β-catenin DsiRNA Agents, Blunt/Frayed Duplexes

```
            5'-GUGAACUUGCUCAGGACAAGGAAGC^CA-3'    (SEQ ID NO: 5803)
            3'-CACUUGAACGAGUCCUGUUCCUUCG_AC-5'   (SEQ ID NO: 1367)
βc-2150 Target: 5'-GTGAACTTGCTCAGGACAAGGAAGCTG-3' (SEQ ID NO: 2476)

5'-UGAACUUGCUCAGGACAAGGAAGCU^AA-3'   (SEQ ID NO: 5804)
            3'-ACUUGAACGAGUCCUGUUCCUUCGA_CG-5'   (SEQ ID NO: 1368)
βc-2151 Target: 5'-TGAACTTGCTCAGGACAAGGAAGCTGC-3' (SEQ ID NO: 2477)

5'-CUAUUGAAGCUGAGGGAGCCACAGC^CA-3'   (SEQ ID NO: 5805)
            3'-GAUAACUUCGACUCCCUCGGUGUCG_AG-5'   (SEQ ID NO: 1369)
βc-2183 Target: 5'-CTATTGAAGCTGAGGGAGCCACAGCTC-3' (SEQ ID NO: 2478)

5'-UAUUGAAGCUGAGGGAGCCACAGCU^AA-3'   (SEQ ID NO: 5806)
            3'-AUAACUUCGACUCCCUCGGUGUCGA_GG-5'   (SEQ ID NO: 1370)
βc-2184 Target: 5'-TATTGAAGCTGAGGGAGCCACAGCTCC-3' (SEQ ID NO: 2479)

5'-AUUGAAGCUGAGGGAGCCACAGCUC^AC-3'   (SEQ ID NO: 5807)
            3'-UAACUUCGACUCCCUCGGUGUCGAG_GA-5'   (SEQ ID NO: 1371)
βc-2185 Target: 5'-ATTGAAGCTGAGGGAGCCACAGCTCCT-3' (SEQ ID NO: 2480)

5'-UGUUCCGAAUGUCUGAGGACAAGCC^CA-3'   (SEQ ID NO: 5808)
            3'-ACAAGGCUUACAGACUCCUGUUCGG_UG-5'   (SEQ ID NO: 1372)
βc-2270 Target: 5'-TGTTCCGAATGTCTGAGGACAAGCCAC-3' (SEQ ID NO: 2481)

5'-GUUCCGAAUGUCUGAGGACAAGCCA^AC-3'   (SEQ ID NO: 5809)
            3'-CAAGGCUUACAGACUCCUGUUCGGU_GU-5'   (SEQ ID NO: 1373)
βc-2271 Target: 5'-GTTCCGAATGTCTGAGGACAAGCCACA-3' (SEQ ID NO: 2482)

5'-UUCCGAAUGUCUGAGGACAAGCCAC^CC-3'   (SEQ ID NO: 5810)
            3'-AAGGCUUACAGACUCCUGUUCGGUG_UU-5'   (SEQ ID NO: 1374)
βc-2272 Target: 5'-TTCCGAATGTCTGAGGACAAGCCACAA-3' (SEQ ID NO: 2483)

5'-UCCGAAUGUCUGAGGACAAGCCACA^CA-3'   (SEQ ID NO: 5811)
            3'-AGGCUUACAGACUCCUGUUCGGUGU_UC-5'   (SEQ ID NO: 1375)
βc-2273 Target: 5'-TCCGAATGTCTGAGGACAAGCCACAAG-3' (SEQ ID NO: 2484)

5'-CCGAAUGUCUGAGGACAAGCCACAA^AC-3'   (SEQ ID NO: 5812)
            3'-GGCUUACAGACUCCUGUUCGGUGUU_CU-5'   (SEQ ID NO: 1376)
βc-2274 Target: 5'-CCGAATGTCTGAGGACAAGCCACAAGA-3' (SEQ ID NO: 2485)

5'-CGAAUGUCUGAGGACAAGCCACAAG^CC-3'   (SEQ ID NO: 5813)
            3'-GCUUACAGACUCCUGUUCGGUGUUC_UA-5'   (SEQ ID NO: 1377)
βc-2275 Target: 5'-CGAATGTCTGAGGACAAGCCACAAGAT-3' (SEQ ID NO: 2486)

5'-GAAUGUCUGAGGACAAGCCACAAGA^CC-3'   (SEQ ID NO: 5814)
            3'-CUUACAGACUCCUGUUCGGUGUUCU_AA-5'   (SEQ ID NO: 1378)
βc-2276 Target: 5'-GAATGTCTGAGGACAAGCCACAAGATT-3' (SEQ ID NO: 2487)

5'-AAUGUCUGAGGACAAGCCACAAGAU^CC-3'   (SEQ ID NO: 5815)
            3'-UUACAGACUCCUGUUCGGUGUUCUA_AU-5'   (SEQ ID NO: 1379)
βc-2277 Target: 5'-AATGTCTGAGGACAAGCCACAAGATTA-3' (SEQ ID NO: 2488)

5'-GAACAGAGCCAAUGGCUUGGAAUGA^AC-3'   (SEQ ID NO: 5816)
            3'-CUUGUCUCGGUUACCGAACCUUACU_CU-5'   (SEQ ID NO: 1380)
βc-2345 Target: 5'-GAACAGAGCCAATGGCTTGGAATGAGA-3' (SEQ ID NO: 2489)
```

TABLE 7-continued

Selected Anti-β-catenin DsiRNA Agents, Blunt/Frayed Duplexes

```
              5'-AACAGAGCCAAUGGCUUGGAAUGAG^CA-3'    (SEQ ID NO: 5817)
              3'-UUGUCUCGGUUACCGAACCUUACUC_UG-5'   (SEQ ID NO: 1381)
βc-2346 Target: 5'-AACAGAGCCAATGGCTTGGAATGAGAC-3'  (SEQ ID NO: 2490)

5'-ACAGAGCCAAUGGCUUGGAAUGAGA^AC-3'   (SEQ ID NO: 5818)
              3'-UGUCUCGGUUACCGAACCUUACUCU_GA-5'  (SEQ ID NO: 1382)
βc-2347 Target: 5'-ACAGAGCCAATGGCTTGGAATGAGACT-3' (SEQ ID NO: 2491)

5'-CAGAGCCAAUGGCUUGGAAUGAGAC^CA-3'   (SEQ ID NO: 5819)
              3'-GUCUCGGUUACCGAACCUUACUCUG_AC-5'  (SEQ ID NO: 1383)
βc-2348 Target: 5'-CAGAGCCAATGGCTTGGAATGAGACTG-3' (SEQ ID NO: 2492)

5'-AGAGCCAAUGGCUUGGAAUGAGACU^AA-3'   (SEQ ID NO: 5820)
              3'-UCUCGGUUACCGAACCUUACUCUGA_CG-5'  (SEQ ID NO: 1384)
βc-2349 Target: 5'-AGAGCCAATGGCTTGGAATGAGACTGC-3' (SEQ ID NO: 2493)

5'-GAGCCAAUGGCUUGGAAUGAGACUG^AC-3'   (SEQ ID NO: 5821)
              3'-CUCGGUUACCGAACCUUACUCUGAC_GA-5'  (SEQ ID NO: 1385)
βc-2350 Target: 5'-GAGCCAATGGCTTGGAATGAGACTGCT-3' (SEQ ID NO: 2494)

5'-AGCCAAUGGCUUGGAAUGAGACUGC^CA-3'   (SEQ ID NO: 5822)
              3'-UCGGUUACCGAACCUUACUCUGACG_AC-5'  (SEQ ID NO: 1386)
βc-2351 Target: 5'-AGCCAATGGCTTGGAATGAGACTGCTG-3' (SEQ ID NO: 2495)

5'-GCCAAUGGCUUGGAAUGAGACUGCU^AC-3'   (SEQ ID NO: 5823)
              3'-CGGUUACCGAACCUUACUCUGACGA_CU-5'  (SEQ ID NO: 1387)
βc-2352 Target: 5'-GCCAATGGCTTGGAATGAGACTGCTGA-3' (SEQ ID NO: 2496)

5'-CCAAUGGCUUGGAAUGAGACUGCUG^CC-3'   (SEQ ID NO: 5824)
              3'-GGUUACCGAACCUUACUCUGACGAC_UA-5'  (SEQ ID NO: 1388)
βc-2353 Target: 5'-CCAATGGCTTGGAATGAGACTGCTGAT-3' (SEQ ID NO: 2497)

5'-CAAUGGCUUGGAAUGAGACUGCUGA^CA-3'   (SEQ ID NO: 5825)
              3'-GUUACCGAACCUUACUCUGACGACU_AG-5'  (SEQ ID NO: 1389)
βc-2354 Target: 5'-CAATGGCTTGGAATGAGACTGCTGATC-3' (SEQ ID NO: 2498)

5'-AAUGGCUUGGAAUGAGACUGCUGAU^AC-3'   (SEQ ID NO: 5826)
              3'-UUACCGAACCUUACUCUGACGACUA_GA-5'  (SEQ ID NO: 1390)
βc-2355 Target: 5'-AATGGCTTGGAATGAGACTGCTGATCT-3' (SEQ ID NO: 2499)

5'-CCCUUGGAUAUCGCCAGGAUGAUCC^CC-3'   (SEQ ID NO: 5827)
              3'-GGGAACCUAUAGCGGUCCUACUAGG_AU-5'  (SEQ ID NO: 1391)
βc-2411 Target: 5'-CCCTTGGATATCGCCAGGATGATCCTA-3' (SEQ ID NO: 2500)

5'-CCUUGGAUAUCGCCAGGAUGAUCCU^CA-3'   (SEQ ID NO: 5828)
              3'-GGAACCUAUAGCGGUCCUACUAGGA_UC-5'  (SEQ ID NO: 1392)
βc-2412 Target: 5'-CCTTGGATATCGCCAGGATGATCCTAG-3' (SEQ ID NO: 2501)

5'-CUUGGAUAUCGCCAGGAUGAUCCUA^AA-3'   (SEQ ID NO: 5829)
              3'-GAACCUAUAGCGGUCCUACUAGGAU_CG-5'  (SEQ ID NO: 1393)
βc-2413 Target: 5'-CTTGGATATCGCCAGGATGATCCTAGC-3' (SEQ ID NO: 2502)

5'-UUGGAUAUCGCCAGGAUGAUCCUAG^AC-3'   (SEQ ID NO: 5830)
              3'-AACCUAUAGCGGUCCUACUAGGAUC_GA-5'  (SEQ ID NO: 1394)
βc-2414 Target: 5'-TTGGATATCGCCAGGATGATCCTAGCT-3' (SEQ ID NO: 2503)
```

TABLE 7-continued

Selected Anti-β-catenin DsiRNA Agents, Blunt/Frayed Duplexes

5'-UGGAUAUCGCCAGGAUGAUCCUAGC$^{CC}$-3' (SEQ ID NO: 5831)
3'-ACCUAUAGCGGUCCUACUAGGAUCG$_{AU}$-5' (SEQ ID NO: 1395)
βc-2415 Target: 5'-TGGATATCGCCAGGATGATCCTAGCTA-3' (SEQ ID NO: 2504)

5'-AUCGUUCUUUUCACUCUGGUGGAUA$^{CA}$-3' (SEQ ID NO: 5832)
3'-UAGCAAGAAAAGUGAGACCACCUAU$_{AC}$-5' (SEQ ID NO: 1396)
βc-2441 Target: 5'-ATCGTTCTTTTCACTCTGGTGGATATG-3' (SEQ ID NO: 2505)

5'-UCGUUCUUUUCACUCUGGUGGAUAU$^{AA}$-3' (SEQ ID NO: 5833)
3'-AGCAAGAAAAGUGAGACCACCUAUA$_{CC}$-5' (SEQ ID NO: 1397)
βc-2442 Target: 5'-TCGTTCTTTTCACTCTGGTGGATATGG-3' (SEQ ID NO: 2506)

5'-CGUUCUUUUCACUCUGGUGGAUAUG$^{AA}$-3' (SEQ ID NO: 5834)
3'-GCAAGAAAAGUGAGACCACCUAUAC$_{CG}$-5' (SEQ ID NO: 1398)
βc-2443 Target: 5'-CGTTCTTTTCACTCTGGTGGATATGGC-3' (SEQ ID NO: 2507)

5'-GUUCUUUUCACUCUGGUGGAUAUGG$^{AA}$-3' (SEQ ID NO: 5835)
3'-CAAGAAAAGUGAGACCACCUAUACC$_{GG}$-5' (SEQ ID NO: 1399)
βc-2444 Target: 5'-GTTCTTTTCACTCTGGTGGATATGGCC-3' (SEQ ID NO: 2508)

5'-UUCUUUUCACUCUGGUGGAUAUGGC$^{AC}$-3' (SEQ ID NO: 5836)
3'-AAGAAAAGUGAGACCACCUAUACCG$_{GU}$-5' (SEQ ID NO: 1400)
βc-2445 Target: 5'-TTCTTTTCACTCTGGTGGATATGGCCA-3' (SEQ ID NO: 2509)

5'-AACAUGAGAUGGGUGGCCACCACCC$^{CA}$-3' (SEQ ID NO: 5837)
3'-UUGUACUCUACCCACCGGUGGUGGG$_{AC}$-5' (SEQ ID NO: 1401)
βc-2501 Target: 5'-AACATGAGATGGGTGGCCACCACCCTG-3' (SEQ ID NO: 2510)

5'-ACAUGAGAUGGGUGGCCACCACCCU$^{AA}$-3' (SEQ ID NO: 5838)
3'-UGUACUCUACCCACCGGUGGUGGGA$_{CC}$-5' (SEQ ID NO: 1402)
βc-2502 Target: 5'-ACATGAGATGGGTGGCCACCACCCTGG-3' (SEQ ID NO: 2511)

5'-CAUGAGAUGGGUGGCCACCACCCUGA$^{C}$-3' (SEQ ID NO: 5839)
3'-GUACUCUACCCACCGGUGGUGGGAC$_{CA}$-5' (SEQ ID NO: 1403)
βc-2503 Target: 5'-CATGAGATGGGTGGCCACCACCCTGGT-3' (SEQ ID NO: 2512)

5'-AUGAGAUGGGUGGCCACCACCCUGG$^{CA}$-3' (SEQ ID NO: 5840)
3'-UACUCUACCCACCGGUGGUGGGACC$_{AC}$-5' (SEQ ID NO: 1404)
βc-2504 Target: 5'-ATGAGATGGGTGGCCACCACCCTGGTG-3' (SEQ ID NO: 2513)

5'-UGAGAUGGGUGGCCACCACCCUGGU$^{AA}$-3' (SEQ ID NO: 5841)
3'-ACUCUACCCACCGGUGGUGGGACCA$_{CG}$-5' (SEQ ID NO: 1405)
βc-2505 Target: 5'-TGAGATGGGTGGCCACCACCCTGGTGC-3' (SEQ ID NO: 2514)

5'-GAGAUGGGUGGCCACCACCCUGGUG$^{AC}$-3' (SEQ ID NO: 5842)
3'-CUCUACCCACCGGUGGUGGGACCAC$_{GA}$-5' (SEQ ID NO: 1406)
βc-2506 Target: 5'-GAGATGGGTGGCCACCACCCTGGTGCT-3' (SEQ ID NO: 2515)

5'-AGAUGGGUGGCCACCACCCUGGUGC$^{CA}$-3' (SEQ ID NO: 5843)
3'-UCUACCCACCGGUGGUGGGACCACG$_{AC}$-5' (SEQ ID NO: 1407)
βc-2507 Target: 5'-AGATGGGTGGCCACCACCCTGGTGCTG-3' (SEQ ID NO: 2516)

5'-GAUGGGUGGCCACCACCCUGGUGCU$^{AC}$-3' (SEQ ID NO: 5844)
3'-CUACCCACCGGUGGUGGGACCACGA$_{CU}$-5' (SEQ ID NO: 1408)
βc-2508 Target: 5'-GATGGGTGGCCACCACCCTGGTGCTGA-3' (SEQ ID NO: 2517)

TABLE 7-continued

Selected Anti-β-catenin DsiRNA Agents, Blunt/Frayed Duplexes

```
              5'-AUGGGUGGCCACCACCCUGGUGCUG^(CA-3')  (SEQ ID NO: 5845)
              3'-UACCCACCGGUGGUGGGACCACGAC_(UG-5') (SEQ ID NO: 1409)
βc-2509 Target: 5'-ATGGGTGGCCACCACCCTGGTGCTGAC-3'  (SEQ ID NO: 2518)

5'-UGGGUGGCCACCACCCUGGUGCUGA^(AC-3')  (SEQ ID NO: 5846)
              3'-ACCCACCGGUGGUGGGACCACGACU_(GA-5') (SEQ ID NO: 1410)
βc-2510 Target: 5'-TGGGTGGCCACCACCCTGGTGCTGACT-3'  (SEQ ID NO: 2519)

5'-GGGUGGCCACCACCCUGGUGCUGAC^(CC-3')  (SEQ ID NO: 5847)
              3'-CCCACCGGUGGUGGGACCACGACUG_(AU-5') (SEQ ID NO: 1411)
βc-2511 Target: 5'-GGGTGGCCACCACCCTGGTGCTGACTA-3' (SEQ ID NO: 2520)

5'-GGUGGCCACCACCCUGGUGCUGACU^(CC-3')  (SEQ ID NO: 5848)
              3'-CCACCGGUGGUGGGACCACGACUGA_(UA-5') (SEQ ID NO: 1412)
βc-2512 Target: 5'-GGTGGCCACCACCCTGGTGCTGACTAT-3' (SEQ ID NO: 2521)

5'-GUGGCCACCACCCUGGUGCUGACUA^(CA-3')  (SEQ ID NO: 5849)
              3'-CACCGGUGGUGGGACCACGACUGAU_(AG-5') (SEQ ID NO: 1413)
βc-2513 Target: 5'-GTGGCCACCACCCTGGTGCTGACTATC-3' (SEQ ID NO: 2522)

5'-UGGCCACCACCCUGGUGCUGACUAU^(AA-3')  (SEQ ID NO: 5850)
              3'-ACCGGUGGUGGGACCACGACUGAUA_(GG-5') (SEQ ID NO: 1414)
βc-2514 Target: 5'-TGGCCACCACCCTGGTGCTGACTATCC-3' (SEQ ID NO: 2523)

5'-GGCCACCACCCUGGUGCUGACUAUC^(AC-3')  (SEQ ID NO: 5851)
              3'-CCGGUGGUGGGACCACGACUGAUAG_(GU-5') (SEQ ID NO: 1415)
βc-2515 Target: 5'-GGCCACCACCCTGGTGCTGACTATCCA-3' (SEQ ID NO: 2524)

5'-GCCACCACCCUGGUGCUGACUAUCC^(CA-3')  (SEQ ID NO: 5852)
              3'-CGGUGGUGGGACCACGACUGAUAGG_(UC-5') (SEQ ID NO: 1416)
βc-2516 Target: 5'-GCCACCACCCTGGTGCTGACTATCCAG-3' (SEQ ID NO: 2525)

5'-CCACCACCCUGGUGCUGACUAUCCA^(AC-3')  (SEQ ID NO: 5853)
              3'-GGUGGUGGGACCACGACUGAUAGGU_(CA-5') (SEQ ID NO: 1417)
βc-2517 Target: 5'-CCACCACCCTGGTGCTGACTATCCAGT-3' (SEQ ID NO: 2526)

5'-CACCACCCUGGUGCUGACUAUCCAG^(CC-3')  (SEQ ID NO: 5854)
              3'-GUGGUGGGACCACGACUGAUAGGUC_(AA-5') (SEQ ID NO: 1418)
βc-2518 Target: 5'-CACCACCCTGGTGCTGACTATCCAGTT-3' (SEQ ID NO: 2527)

5'-ACCACCCUGGUGCUGACUAUCCAGU^(CA-3')  (SEQ ID NO: 5855)
              3'-UGGUGGGACCACGACUGAUAGGUCA_(AC-5') (SEQ ID NO: 1419)
βc-2519 Target: 5'-ACCACCCTGGTGCTGACTATCCAGTTG-3' (SEQ ID NO: 2528)

5'-CCACCCUGGUGCUGACUAUCCAGUU^(AC-3')  (SEQ ID NO: 5856)
              3'-GGUGGGACCACGACUGAUAGGUCAA_(CU-5') (SEQ ID NO: 1420)
βc-2520 Target: 5'-CCACCCTGGTGCTGACTATCCAGTTGA-3' (SEQ ID NO: 2529)

5'-CACCCUGGUGCUGACUAUCCAGUUG^(CC-3')  (SEQ ID NO: 5857)
              3'-GUGGGACCACGACUGAUAGGUCAAC_(UA-5') (SEQ ID NO: 1421)
βc-2521 Target: 5'-CACCCTGGTGCTGACTATCCAGTTGAT-3' (SEQ ID NO: 2530)
```

TABLE 7-continued

Selected Anti-β-catenin DsiRNA Agents, Blunt/Frayed Duplexes

5'-ACCCUGGUGCUGACUAUCCAGUUGA$^{CA}$-3' (SEQ ID NO: 5858)
3'-UGGGACCACGACUGAUAGGUCAACU$_{AC}$-5' (SEQ ID NO: 1422)
βc-2522 Target: 5'-ACCCTGGTGCTGACTATCCAGTTGATG-3' (SEQ ID NO: 2531)

5'-CCCUGGUGCUGACUAUCCAGUUGAU$^{AA}$-3' (SEQ ID NO: 5859)
3'-GGGACCACGACUGAUAGGUCAACUA$_{CC}$-5' (SEQ ID NO: 1423)
βc-2523 Target: 5'-CCCTGGTGCTGACTATCCAGTTGATGG-3' (SEQ ID NO: 2532)

5'-CCUGGUGCUGACUAUCCAGUUGAUG$^{AA}$-3' (SEQ ID NO: 5860)
3'-GGACCACGACUGAUAGGUCAACUAC$_{CC}$-5' (SEQ ID NO: 1424)
βc-2524 Target: 5'-CCTGGTGCTGACTATCCAGTTGATGGG-3' (SEQ ID NO: 2533)

5'-CUGGUGCUGACUAUCCAGUUGAUGG$^{AA}$-3' (SEQ ID NO: 5861)
3'-GACCACGACUGAUAGGUCAACUACC$_{CG}$-5' (SEQ ID NO: 1425)
βc-2525 Target: 5'-CTGGTGCTGACTATCCAGTTGATGGGC-3' (SEQ ID NO: 2534)

5'-UGGUGCUGACUAUCCAGUUGAUGGG$^{AC}$-3' (SEQ ID NO: 5862)
3'-ACCACGACUGAUAGGUCAACUACCC$_{GA}$-5' (SEQ ID NO: 1426)
βc-2526 Target: 5'-TGGTGCTGACTATCCAGTTGATGGGCT-3' (SEQ ID NO: 2535)

5'-GGUGCUGACUAUCCAGUUGAUGGGC$^{CA}$-3' (SEQ ID NO: 5863)
3'-CCACGACUGAUAGGUCAACUACCCG$_{AC}$-5' (SEQ ID NO: 1427)
βc-2527 Target: 5'-GGTGCTGACTATCCAGTTGATGGGCTG-3' (SEQ ID NO: 2536)

5'-GUGCUGACUAUCCAGUUGAUGGGCU$^{AA}$-3' (SEQ ID NO: 5864)
3'-CACGACUGAUAGGUCAACUACCCGA$_{CG}$-5' (SEQ ID NO: 1428)
βc-2528 Target: 5'-GTGCTGACTATCCAGTTGATGGGCTGC-3' (SEQ ID NO: 2537)

5'-UGCUGACUAUCCAGUUGAUGGGCUG$^{AA}$-3' (SEQ ID NO: 5865)
3'-ACGACUGAUAGGUCAACUACCCGAC$_{GG}$-5' (SEQ ID NO: 1429)
βc-2529 Target: 5'-TGCTGACTATCCAGTTGATGGGCTGCC-3' (SEQ ID NO: 2538)

5'-GCUGACUAUCCAGUUGAUGGGCUGC$^{AC}$-3' (SEQ ID NO: 5866)
3'-CGACUGAUAGGUCAACUACCCGACG$_{GU}$-5' (SEQ ID NO: 1430)
βc-2530 Target: 5'-GCTGACTATCCAGTTGATGGGCTGCCA-3' (SEQ ID NO: 2539)

5'-CUGACUAUCCAGUUGAUGGGCUGCC$^{CA}$-3' (SEQ ID NO: 5867)
3'-GACUGAUAGGUCAACUACCCGACGG$_{UC}$-5' (SEQ ID NO: 1431)
βc-2531 Target: 5'-CTGACTATCCAGTTGATGGGCTGCCAG-3' (SEQ ID NO: 2540)

5'-UGACUAUCCAGUUGAUGGGCUGCCA$^{AC}$-3' (SEQ ID NO: 5868)
3'-ACUGAUAGGUCAACUACCCGACGGU$_{CU}$-5' (SEQ ID NO: 1432)
βc-2532 Target: 5'-TGACTATCCAGTTGATGGGCTGCCAGA-3' (SEQ ID NO: 2541)

5'-GACUAUCCAGUUGAUGGGCUGCCAG$^{CC}$-3' (SEQ ID NO: 5869)
3'-CUGAUAGGUCAACUACCCGACGGUC$_{UA}$-5' (SEQ ID NO: 1433)
βc-2533 Target: 5'-GACTATCCAGTTGATGGGCTGCCAGAT-3' (SEQ ID NO: 2542)

5'-ACUAUCCAGUUGAUGGGCUGCCAGA$^{CA}$-3' (SEQ ID NO: 5870)
3'-UGAUAGGUCAACUACCCGACGGUCU$_{AG}$-5' (SEQ ID NO: 1434)
βc-2534 Target: 5'-ACTATCCAGTTGATGGGCTGCCAGATC-3' (SEQ ID NO: 2543)

5'-CUAUCCAGUUGAUGGGCUGCCAGAU$^{AC}$-3' (SEQ ID NO: 5871)
3'-GAUAGGUCAACUACCCGACGGUCUA$_{GA}$-5' (SEQ ID NO: 1435)
βc-2535 Target: 5'-CTATCCAGTTGATGGGCTGCCAGATCT-3' (SEQ ID NO: 2544)

TABLE 7-continued

Selected Anti-β-catenin DsiRNA Agents, Blunt/Frayed Duplexes

```
                5'-AUGCCCAGGACCUCAUGGAUGGGCU^AA-3'   (SEQ ID NO: 5872)
                3'-UACGGGUCCUGGAGUACCUACCCGA_CG-5'   (SEQ ID NO: 1436)
βc-2567 Target: 5'-ATGCCCAGGACCTCATGGATGGGCTGC-3'   (SEQ ID NO: 2545)

5'-UGCCCAGGACCUCAUGGAUGGGCUG^AA-3'   (SEQ ID NO: 5873)
                3'-ACGGGUCCUGGAGUACCUACCCGAC_GG-5'   (SEQ ID NO: 1437)
βc-2568 Target: 5'-TGCCCAGGACCTCATGGATGGGCTGCC-3'   (SEQ ID NO: 2546)

5'-GCCCAGGACCUCAUGGAUGGGCUGC^AC-3'   (SEQ ID NO: 5874)
                3'-CGGGUCCUGGAGUACCUACCCGACG_GA-5'   (SEQ ID NO: 1438)
βc-2569 Target: 5'-GCCCAGGACCTCATGGATGGGCTGCCT-3'   (SEQ ID NO: 2547)

5'-ACAGCAAUCAGCUGGCCUGGUUUGA^CC-3'   (SEQ ID NO: 5875)
                3'-UGUCGUUAGUCGACCGGACCAAACU_AU-5'   (SEQ ID NO: 1439)
βc-2603 Target: 5'-ACAGCAATCAGCTGGCCTGGTTTGATA-3'   (SEQ ID NO: 2548)

5'-CAGCAAUCAGCUGGCCUGGUUUGAU^CA-3'   (SEQ ID NO: 5876)
                3'-GUCGUUAGUCGACCGGACCAAACUA_UG-5'   (SEQ ID NO: 1440)
βc-2604 Target: 5'-CAGCAATCAGCTGGCCTGGTTTGATAC-3'   (SEQ ID NO: 2549)

5'-AGCAAUCAGCUGGCCUGGUUUGAUA^AC-3'   (SEQ ID NO: 5877)
                3'-UCGUUAGUCGACCGGACCAAACUAU_GA-5'   (SEQ ID NO: 1441)
βc-2605 Target: 5'-AGCAATCAGCTGGCCTGGTTTGATACT-3'   (SEQ ID NO: 2550)

5'-GCAAUCAGCUGGCCUGGUUUGAUAC^CA-3'   (SEQ ID NO: 5878)
                3'-CGUUAGUCGACCGGACCAAACUAUG_AC-5'   (SEQ ID NO: 1442)
βc-2606 Target: 5'-GCAATCAGCTGGCCTGGTTTGATACTG-3'   (SEQ ID NO: 2551)

5'-CAAUCAGCUGGCCUGGUUUGAUACU^AC-3'   (SEQ ID NO: 5879)
                3'-CUUAGUCGACCGGACCAAACUAUGA_CU-5'   (SEQ ID NO: 1443)
βc-2607 Target: 5'-CAATCAGCTGGCCTGGTTTGATACTGA-3'   (SEQ ID NO: 2552)

5'-AAUCAGCUGGCCUGGUUUGAUACUG^CA-3'   (SEQ ID NO: 5880)
                3'-UUAGUCGACCGGACCAAACUAUGAC_UG-5'   (SEQ ID NO: 1444)
βc-2608 Target: 5'-AATCAGCTGGCCTGGTTTGATACTGAC-3'   (SEQ ID NO: 2553)

5'-AUCAGCUGGCCUGGUUUGAUACUGA^AA-3'   (SEQ ID NO: 5881)
                3'-UAGUCGACCGGACCAAACUAUGACU_GG-5'   (SEQ ID NO: 1445)
βc-2609 Target: 5'-ATCAGCTGGCCTGGTTTGATACTGACC-3'   (SEQ ID NO: 2554)

5'-UCAGCUGGCCUGGUUUGAUACUGAC^AC-3'   (SEQ ID NO: 5882)
                3'-AGUCGACCGGACCAAACUAUGACUG_GA-5'   (SEQ ID NO: 1446)
βc-2610 Target: 5'-TCAGCTGGCCTGGTTTGATACTGACCT-3'   (SEQ ID NO: 2555)

5'-CAGCUGGCCUGGUUUGAUACUGACC^CA-3'   (SEQ ID NO: 5883)
                3'-GUCGACCGGACCAAACUAUGACUGG_AC-5'   (SEQ ID NO: 1447)
βc-2611 Target: 5'-CAGCTGGCCTGGTTTGATACTGACCTG-3'   (SEQ ID NO: 2556)

5'-AGCUGGCCUGGUUUGAUACUGACCU^AC-3'   (SEQ ID NO: 5884)
                3'-UCGACCGGACCAAACUAUGACUGGA_CA-5'   (SEQ ID NO: 1448)
βc-2612 Target: 5'-AGCTGGCCTGGTTTGATACTGACCTGT-3'   (SEQ ID NO: 2557)

5'-GCUGGCCUGGUUUGAUACUGACCUG^CC-3'   (SEQ ID NO: 5885)
                3'-CGACCGGACCAAACUAUGACUGGAC_AU-5'   (SEQ ID NO: 1449)
βc-2613 Target: 5'-GCTGGCCTGGTTTGATACTGACCTGTA-3'   (SEQ ID NO: 2558)
```

TABLE 7-continued

Selected Anti-β-catenin DsiRNA Agents, Blunt/Frayed Duplexes

```
         5'-CUGGCCUGGUUUGAUACUGACCUGU^CC-3'  (SEQ ID NO: 5886)
         3'-GACCGGACCAAACUAUGACUGGACA_UU-5'  (SEQ ID NO: 1450)
βc-2614 Target: 5'-CTGGCCTGGTTTGATACTGACCTGTAA-3'  (SEQ ID NO: 2559)

5'-UGGCCUGGUUUGAUACUGACCUGUA^CC-3'  (SEQ ID NO: 5887)
         3'-ACCGGACCAAACUAUGACUGGACAU_UU-5'  (SEQ ID NO: 1451)
βc-2615 Target: 5'-TGGCCTGGTTTGATACTGACCTGTAAA-3'  (SEQ ID NO: 2560)

5'-GGCCUGGUUUGAUACUGACCUGUAA^CC-3'  (SEQ ID NO: 5888)
         3'-CCGGACCAAACUAUGACUGGACAUU_UA-5'  (SEQ ID NO: 1452)
βc-2616 Target: 5'-GGCCTGGTTTGATACTGACCTGTAAAT-3'  (SEQ ID NO: 2561)

5'-GCCUGGUUUGAUACUGACCUGUAAA^CA-3'  (SEQ ID NO: 5889)
         3'-CGGACCAAACUAUGACUGGACAUUU_AG-5'  (SEQ ID NO: 1453)
βc-2617 Target: 5'-GCCTGGTTTGATACTGACCTGTAAATC-3'  (SEQ ID NO: 2562)

5'-CCUGGUUUGAUACUGACCUGUAAAU^AC-3'  (SEQ ID NO: 5890)
         3'-GGACCAAACUAUGACUGGACAUUUA_GU-5'  (SEQ ID NO: 1454)
βc-2618 Target: 5'-CCTGGTTTGATACTGACCTGTAAATCA-3'  (SEQ ID NO: 2563)

5'-CUGGUUUGAUACUGACCUGUAAAUC^CC-3'  (SEQ ID NO: 5891)
         3'-GACCAAACUAUGACUGGACAUUUAG_UA-5'  (SEQ ID NO: 1455)
βc-2619 Target: 5'-CTGGTTTGATACTGACCTGTAAATC-3'  (SEQ ID NO: 2564)

5'-UGGUUUGAUACUGACCUGUAAAUCA^CA-3'  (SEQ ID NO: 5892)
         3'-ACCAAACUAUGACUGGACAUUUAGU_AG-5'  (SEQ ID NO: 1456)
βc-2620 Target: 5'-TGGTTTGATACTGACCTGTAAATCATC-3'  (SEQ ID NO: 2565)

5'-GGUUUGAUACUGACCUGUAAAUCAU^AA-3'  (SEQ ID NO: 5893)
         3'-CCAAACUAUGACUGGACAUUUAGUA_GG-5'  (SEQ ID NO: 1457)
βc-2621 Target: 5'-GGTTTGATACTGACCTGTAAATCATCC-3'  (SEQ ID NO: 2566)

5'-GUUUGAUACUGACCUGUAAAUCAUC^AC-3'  (SEQ ID NO: 5894)
         3'-CAAACUAUGACUGGACAUUUAGUAG_GA-5'  (SEQ ID NO: 1458)
βc-2622 Target: 5'-GTTTGATACTGACCTGTAAATCATCCT-3'  (SEQ ID NO: 2567)

5'-UUUGAUACUGACCUGUAAAUCAUCC^CC-3'  (SEQ ID NO: 5895)
         3'-AAACUAUGACUGGACAUUUAGUAGG_AA-5'  (SEQ ID NO: 1459)
βc-2623 Target: 5'-TTTGATACTGACCTGTAAATCATCCTT-3'  (SEQ ID NO: 2568)

5'-UUUUUUGCCACAGCUUUUGCAACUU^CC-3'  (SEQ ID NO: 5896)
         3'-AAAAAACGGUGUCGAAAACGUUGAA_UU-5'  (SEQ ID NO: 1460)
βc-2869 Target: 5'-TTTTTTGCCACAGCTTTTGCAACTTAA-3'  (SEQ ID NO: 2569)

5'-AAUGAGUAACAUUUGCUGUUUUAAA^AC-3'  (SEQ ID NO: 5897)
         3'-UUACUCAUUGUAAACGACAAAAUUU_GU-5'  (SEQ ID NO: 1461)
βc-2902 Target: 5'-AATGAGTAACATTTGCTGTTTTAAACA-3'  (SEQ ID NO: 2570)

5'-UAAACAUUAAUAGCAGCCUUUCUCU^AC-3'  (SEQ ID NO: 5898)
         3'-AUUUGUAAUUAUCGUCGGAAAGAGA_GA-5'  (SEQ ID NO: 1462)
βc-2923 Target: 5'-TAAACATTAATAGCAGCCTTTCTCT-3'  (SEQ ID NO: 2571)
```

TABLE 7-continued

Selected Anti-β-catenin DsiRNA Agents, Blunt/Frayed Duplexes

```
               5'-AACAUUAAUAGCAGCCUUUCUCUCU^CC-3'  (SEQ ID NO: 5899)
               3'-UUGUAAUUAUCGUCGGAAAGAGAGA_AA-5'  (SEQ ID NO: 1463)
βc-2925 Target: 5'-AACATTAATAGCAGCCTTTCTCTCTTT-3'  (SEQ ID NO: 2572)

5'-CAUUAAUAGCAGCCUUUCUCUCUUU^CC-3'  (SEQ ID NO: 5900)
               3'-GUAAUUAUCGUCGGAAAGAGAGAAA_UA-5'  (SEQ ID NO: 1464)
βc-2927 Target: 5'-CATTAATAGCAGCCTTTCTCTCTTTAT-3'  (SEQ ID NO: 2573)

5'-UUAAUAGCAGCCUUUCUCUCUUUAU^CA-3'  (SEQ ID NO: 5901)
               3'-AAUUAUCGUCGGAAAGAGAGAAAUA_UG-5'  (SEQ ID NO: 1465)
βc-2929 Target: 5'-TTAATAGCAGCCTTTCTCTCTTTATAC-3'  (SEQ ID NO: 2574)

5'-UUGCAUUGUGAUUGGCCUGUAGAGU^CA-3'  (SEQ ID NO: 5902)
               3'-AACGUAACACUAACCGGACAUCUCA_AC-5'  (SEQ ID NO: 1466)
βc-2973 Target: 5'-TTGCATTGTGATTGGCCTGTAGAGTTG-3'  (SEQ ID NO: 2575)

5'-GCAUUGUGAUUGGCCUGUAGAGUUG^AC-3'  (SEQ ID NO: 5903)
               3'-CGUAACACUAACCGGACAUCUCAAC_GA-5'  (SEQ ID NO: 1467)
βc-2975 Target: 5'-GCATTGTGATTGGCCTGTAGAGTTGCT-3'  (SEQ ID NO: 2576)

5'-AUUGUGAUUGGCCUGUAGAGUUGCU^AC-3'  (SEQ ID NO: 5904)
               3'-UAACACUAACCGGACAUCUCAACGA_CU-5'  (SEQ ID NO: 1468)
βc-2977 Target: 5'-ATTGTGATTGGCCTGTAGAGTTGCTGA-3'  (SEQ ID NO: 2577)

5'-UGUGAUUGGCCUGUAGAGUUGCUGA^AC-3'  (SEQ ID NO: 5905)
               3'-ACACUAACCGGACAUCUCAACGACU_CU-5'  (SEQ ID NO: 1469)
βc-2979 Target: 5'-TGTGATTGGCCTGTAGAGTTGCTGAGA-3'  (SEQ ID NO: 2578)

5'-UGAUUGGCCUGUAGAGUUGCUGAGA^AA-3'  (SEQ ID NO: 5906)
               3'-ACUAACCGGACAUCUCAACGACUCU_CC-5'  (SEQ ID NO: 1470)
βc-2981 Target: 5'-TGATTGGCCTGTAGAGTTGCTGAGAGG-3'  (SEQ ID NO: 2579)

5'-AUUGGCCUGUAGAGUUGCUGAGAGG^AA-3'  (SEQ ID NO: 5907)
               3'-UAACCGGACAUCUCAACGACUCUCC_CG-5'  (SEQ ID NO: 1471)
βc-2983 Target: 5'-ATTGGCCTGTAGAGTTGCTGAGAGGGC-3'  (SEQ ID NO: 2580)

5'-UGGCCUGUAGAGUUGCUGAGAGGGC^CA-3'  (SEQ ID NO: 5908)
               3'-ACCGGACAUCUCAACGACUCUCCCG_AG-5'  (SEQ ID NO: 1472)
βc-2985 Target: 5'-TGGCCTGTAGAGTTGCTGAGAGGGCTC-3'  (SEQ ID NO: 2581)

5'-GCCUGUAGAGUUGCUGAGAGGGCUC^AC-3'  (SEQ ID NO: 5909)
               3'-CGGACAUCUCAACGACUCUCCCGAG_CU-5'  (SEQ ID NO: 1473)
βc-2987 Target: 5'-GCCTGTAGAGTTGCTGAGAGGGCTCGA-3'  (SEQ ID NO: 2582)

5'-CUGUAGAGUUGCUGAGAGGGCUCGA^AA-3'  (SEQ ID NO: 5910)
               3'-GACAUCUCAACGACUCUCCCGAGCU_CC-5'  (SEQ ID NO: 1474)
βc-2989 Target: 5'-CTGTAGAGTTGCTGAGAGGGCTCGAGG-3'  (SEQ ID NO: 2583)

5'-GGGUGGGCUGGUAUCUCAGAAAGUG^AA-3'  (SEQ ID NO: 5911)
               3'-CCCACCCGACCAUAGAGUCUUUCAC_GG-5'  (SEQ ID NO: 1475)
βc-3015 Target: 5'-GGGTGGGCTGGTATCTCAGAAAGTGCC-3'  (SEQ ID NO: 2584)

5'-GUGGGCUGGUAUCUCAGAAAGUGCC^CA-3'  (SEQ ID NO: 5912)
               3'-CACCCGACCAUAGAGUCUUUCACGG_AC-5'  (SEQ ID NO: 1476)
βc-3017 Target: 5'-GTGGGCTGGTATCTCAGAAAGTGCCTG-3'  (SEQ ID NO: 2585)
```

TABLE 7-continued

Selected Anti-β-catenin DsiRNA Agents, Blunt/Frayed Duplexes

```
        5'-GGGCUGGUAUCUCAGAAAGUGCCUG^(CA-3')  (SEQ ID NO: 5913)
        3'-CCCGACCAUAGAGUCUUUCACGGAC_(UG-5')  (SEQ ID NO: 1477)
βc-3019 Target: 5'-GGGCTGGTATCTCAGAAAGTGCCTGAC-3'  (SEQ ID NO: 2586)

5'-GCUGGUAUCUCAGAAAGUGCCUGAC^(CA-3')  (SEQ ID NO: 5914)
        3'-CGACCAUAGAGUCUUUCACGGACUG_(UG-5')  (SEQ ID NO: 1478)
βc-3021 Target: 5'-GCTGGTATCTCAGAAAGTGCCTGACAC-3'  (SEQ ID NO: 2587)

5'-ACACUAACCAAGCUGAGUUUCCUAU^(AA-3')  (SEQ ID NO: 5915)
        3'-UGUGAUUGGUUCGACUCAAAGGAUA_(CC-5')  (SEQ ID NO: 1479)
βc-3046 Target: 5'-ACACTAACCAAGCTGAGTTTCCTATGG-3'  (SEQ ID NO: 2588)

5'-ACUAACCAAGCUGAGUUUCCUAUGG^(AC-3')  (SEQ ID NO: 5916)
        3'-UGAUUGGUUCGACUCAAAGGAUACC_(CU-5')  (SEQ ID NO: 1480)
βc-3048 Target: 5'-ACTAACCAAGCTGAGTTTCCTATGGGA-3'  (SEQ ID NO: 2589)

5'-UAACCAAGCUGAGUUUCCUAUGGGA^(CA-3')  (SEQ ID NO: 5917)
        3'-AUUGGUUCGACUCAAAGGAUACCCU_(UG-5')  (SEQ ID NO: 1481)
βc-3050 Target: 5'-TAACCAAGCTGAGTTTCCTATGGGAAC-3'  (SEQ ID NO: 2590)

5'-ACCAAGCUGAGUUUCCUAUGGGAAC^(CC-3')  (SEQ ID NO: 5918)
        3'-UGGUUCGACUCAAAGGAUACCCUUG_(UU-5')  (SEQ ID NO: 1482)
βc-3052 Target: 5'-ACCAAGCTGAGTTTCCTATGGGAACAA-3'  (SEQ ID NO: 2591)

5'-CAAGCUGAGUUUCCUAUGGGAACAA^(CC-3')  (SEQ ID NO: 5919)
        3'-GUUCGACUCAAAGGAUACCCUUGUU_(AA-5')  (SEQ ID NO: 1483)
βc-3054 Target: 5'-CAAGCTGAGTTTCCTATGGGAACAATT-3'  (SEQ ID NO: 2592)

5'-AGCUGAGUUUCCUAUGGGAACAAUU^(AC-3')  (SEQ ID NO: 5920)
        3'-UCGACUCAAAGGAUACCCUUGUUAA_(CU-5')  (SEQ ID NO: 1484)
βc-3056 Target: 5'-AGCTGAGTTTCCTATGGGAACAATTGA-3'  (SEQ ID NO: 2593)

5'-AACUUUUUGUUCUGGUCCUUUUUGG^(CA-3')  (SEQ ID NO: 5921)
        3'-UUGAAAAACAAGACCAGGAAAAACC_(AG-5')  (SEQ ID NO: 1485)
βc-3087 Target: 5'-AACTTTTTGTTCTGGTCCTTTTTGGTC-3'  (SEQ ID NO: 2594)

5'-CUUUUUGUUCUGGUCCUUUUUGGUC^(AC-3')  (SEQ ID NO: 5922)
        3'-GAAAAACAAGACCAGGAAAAACCAG_(CU-5')  (SEQ ID NO: 1486)
βc-3089 Target: 5'-CTTTTTGTTCTGGTCCTTTTTGGTCGA-3'  (SEQ ID NO: 2595)

5'-UUUUGUUCUGGUCCUUUUUGGUCGA^(AA-3')  (SEQ ID NO: 5923)
        3'-AAAACAAGACCAGGAAAAACCAGCU_(CC-5')  (SEQ ID NO: 1487)
βc-3091 Target: 5'-TTTTGTTCTGGTCCTTTTTGGTCGAGG-3'  (SEQ ID NO: 2596)

5'-UUGUUCUGGUCCUUUUUGGUCGAGG^(CA-3')  (SEQ ID NO: 5924)
        3'-AACAAGACCAGGAAAAACCAGCUCC_(UC-5')  (SEQ ID NO: 1488)
βc-3093 Target: 5'-TTGTTCTGGTCCTTTTTGGTCGAGGAG-3'  (SEQ ID NO: 2597)

5'-GUUCUGGUCCUUUUUGGUCGAGGAG^(CC-3')  (SEQ ID NO: 5925)
        3'-CAAGACCAGGAAAAACCAGCUCCUC_(AU-5')  (SEQ ID NO: 1489)
βc-3095 Target: 5'-GTTCTGGTCCTTTTTGGTCGAGGAGTA-3'  (SEQ ID NO: 2598)

5'-UCUGGUCCUUUUUGGUCGAGGAGUA^(CA-3')  (SEQ ID NO: 5926)
        3'-AGACCAGGAAAAACCAGCUCCUCAU_(UG-5')  (SEQ ID NO: 1490)
βc-3097 Target: 5'-TCTGGTCCTTTTTGGTCGAGGAGTAAC-3'  (SEQ ID NO: 2599)
```

TABLE 7-continued

Selected Anti-β-catenin DsiRNA Agents, Blunt/Frayed Duplexes

```
          5'-UGGUCCUUUUUGGUCGAGGAGUAACCC-3'    (SEQ ID NO: 5927)
          3'-ACCAGGAAAAACCAGCUCCUCAUUGUU-5'    (SEQ ID NO: 1491)
βc-3099 Target: 5'-TGGTCCTTTTTGGTCGAGGAGTAACAA-3' (SEQ ID NO: 2600)

5'-GUCCUUUUUGGUCGAGGAGUAACAACC-3'    (SEQ ID NO: 5928)
          3'-CAGGAAAAACCAGCUCCUCAUUGUUAU-5'    (SEQ ID NO: 1492)
βc-3101 Target: 5'-GTCCTTTTTGGTCGAGGAGTAACAATA-3' (SEQ ID NO: 2601)

5'-CCUUUUUGGUCGAGGAGUAACAAUAAC-3'    (SEQ ID NO: 5929)
          3'-GGAAAAACCAGCUCCUCAUUGUUAUGU-5'    (SEQ ID NO: 1493)
βc-3103 Target: 5'-CCTTTTTGGTCGAGGAGTAACAATACA-3' (SEQ ID NO: 2602)

5'-UUUUUGGUCGAGGAGUAACAAUACACC-3'    (SEQ ID NO: 5930)
          3'-AAAAACCAGCUCCUCAUUGUUAUGUUU-5'    (SEQ ID NO: 1494)
βc-3105 Target: 5'-TTTTTGGTCGAGGAGTAACAATACAAA-3' (SEQ ID NO: 2603)

5'-UUUGGUCGAGGAGUAACAAUACAAACA-3'    (SEQ ID NO: 5931)
          3'-AAACCAGCUCCUCAUUGUUAUGUUUAC-5'    (SEQ ID NO: 1495)
βc-3107 Target: 5'-TTTGGTCGAGGAGTAACAATACAAATG-3' (SEQ ID NO: 2604)

5'-UGGUCGAGGAGUAACAAUACAAAUGAC-3'    (SEQ ID NO: 5932)
          3'-ACCAGCUCCUCAUUGUUAUGUUUACCU-5'    (SEQ ID NO: 1496)
βc-3109 Target: 5'-TGGTCGAGGAGTAACAATACAAATGGA-3' (SEQ ID NO: 2605)

5'-GUCGAGGAGUAACAAUACAAAUGGACC-3'    (SEQ ID NO: 5933)
          3'-CAGCUCCUCAUUGUUAUGUUUACCUAA-5'    (SEQ ID NO: 1497)
βc-3111 Target: 5'-GTCGAGGAGTAACAATACAAATGGATT-3' (SEQ ID NO: 2606)

5'-CGAGGAGUAACAAUACAAAUGGAUUCC-3'    (SEQ ID NO: 5934)
          3'-GCUCCUCAUUGUUAUGUUUACCUAAAA-5'    (SEQ ID NO: 1498)
βc-3113 Target: 5'-CGAGGAGTAACAATACAAATGGATTTT-3' (SEQ ID NO: 2607)

5'-AGGAGUAACAAUACAAAUGGAUUUUAA-3'    (SEQ ID NO: 5935)
          3'-UCCUCAUUGUUAUGUUUACCUAAAACC-5'    (SEQ ID NO: 1499)
βc-3115 Target: 5'-AGGAGTAACAATACAAATGGATTTTGG-3' (SEQ ID NO: 2608)

5'-UUUAUCAAACCCUAGCCUUGCUUGUCC-3'    (SEQ ID NO: 5936)
          3'-AAAUAGUUUGGGAUCGGAACGAACAAU-5'    (SEQ ID NO: 1500)
βc-3191 Target: 5'-TTTATCAAACCCTAGCCTTGCTTGTTA-3' (SEQ ID NO: 2609)

5'-UAUCAAACCCUAGCCUUGCUUGUUACC-3'    (SEQ ID NO: 5937)
          3'-AUAGUUUGGGAUCGGAACGAACAAUUU-5'    (SEQ ID NO: 1501)
βc-3193 Target: 5'-TATCAAACCCTAGCCTTGCTTGTTAAA-3' (SEQ ID NO: 2610)

5'-UCAAACCCUAGCCUUGCUUGUUAAACC-3'    (SEQ ID NO: 5938)
          3'-AGUUUGGGAUCGGAACGAACAAUUUAA-5'    (SEQ ID NO: 1502)
βc-3195 Target: 5'-TCAAACCCTAGCCTTGCTTGTTAAATT-3' (SEQ ID NO: 2611)

5'-UUGAGUAAUGGUGUAGAACACUAAUCA-3'    (SEQ ID NO: 5939)
          3'-AACUCAUUACCACAUCUUGUGAUUAAG-5'    (SEQ ID NO: 1503)
βc-3387 Target: 5'-TTGAGTAATGGTGTAGAACACTAATTC-3' (SEQ ID NO: 2612)

5'-GAGUAAUGGUGUAGAACACUAAUUCCC-3'    (SEQ ID NO: 5940)
          3'-CUCAUUACCACAUCUUGUGAUUAAGUA-5'    (SEQ ID NO: 1504)
βc-3389 Target: 5'-GAGTAATGGTGTAGAACACTAATTC-3' (SEQ ID NO: 2613)
```

TABLE 7-continued

Selected Anti-β-catenin DsiRNA Agents, Blunt/Frayed Duplexes

```
         5'-GUAAUGGUGUAGAACACUAAUUCAU^(CC-3')   (SEQ ID NO: 5941)
         3'-CAUUACCACAUCUUGUGAUUAAGUA_(U U-5')  (SEQ ID NO: 1505)
βc-3391 Target: 5'-GTAATGGTGTAGAACACTAATTCATAA-3'  (SEQ ID NO: 2614)

5'-AAUGGUGUAGAACACUAAUUCAUAA^(CA-3')   (SEQ ID NO: 5942)
         3'-UUACCACAUCUUGUGAUUAAGUAUU_(AG-5')   (SEQ ID NO: 1506)
βc-3393 Target: 5'-AATGGTGTAGAACACTAATTCATAATC-3'  (SEQ ID NO: 2615)

5'-UGGUGUAGAACACUAAUUCAUAAUC^(CA-3')   (SEQ ID NO: 5943)
         3'-ACCACAUCUUGUGAUUAAGUAUUAG_(UG-5')   (SEQ ID NO: 1507)
βc-3395 Target: 5'-TGGTGTAGAACACTAATTCATAATCAC-3'  (SEQ ID NO: 2616)

5'-GUGUAGAACACUAAUUGAUAAUCAC^(CA-3')   (SEQ ID NO: 5944)
         3'-CACAUCUUGUGAUUAAGUAUUAGUG_(AG-5')   (SEQ ID NO: 1508)
βc-3397 Target: 5'-GTGTAGAACACTAATTCATAATCACTC-3'  (SEQ ID NO: 2617)

5'-GUAGAACACUAAUUCAUAAUCACUC^(CC-3')   (SEQ ID NO: 5945)
         3'-CAUCUUGUGAUUAAGUAUUAGUGAG_(AU-5')   (SEQ ID NO: 1509)
βc-3399 Target: 5'-GTAGAACACTAATTCATAATCACTCTA-3'  (SEQ ID NO: 2618)

5'-AGAACACUAAUUCAUAAUCACUCUA^(CC-3')   (SEQ ID NO: 5946)
         3'-UCUUGUGAUUAAGUAUUAGUGAGAU_(UA-5')   (SEQ ID NO: 1510)
βc-3401 Target: 5'-AGAACACTAATTCATAATCACTCTAAT-3'  (SEQ ID NO: 2619)

5'-AAUUAGUUUCCUUUUUAAUAUGCUU^(CC-3')   (SEQ ID NO: 5947)
         3'-UUAAUCAAAGGAAAAAUUAUACGAA_(UU-5')   (SEQ ID NO: 1511)
βc-3500 Target: 5'-AATTAGTTTCCTTTTTAATATGCTTAA-3'  (SEQ ID NO: 2620)

5'-UUAGUUUCCUUUUUAAUAUGCUUAA^(CC-3')   (SEQ ID NO: 5948)
         3'-AAUCAAAGGAAAAAUUAUACGAAUU_(UU-5')   (SEQ ID NO: 1512)
βc-3502 Target: 5'-TTAGTTTCCTTTTTAATATGCTTAAAA-3'  (SEQ ID NO: 2621)

5'-AGUUUCCUUUUUAAUAUGCUUAAAA^(CC-3')   (SEQ ID NO: 5949)
         3'-UCAAAGGAAAAAUUAUACGAAUUUU_(AU-5')   (SEQ ID NO: 1513)
βc-3504 Target: 5'-AGTTTCCTTTTTAATATGCTTAAAATA-3'  (SEQ ID NO: 2622)

5'-UUUCCUUUUUAAUAUGCUUAAAAUA^(CA-3')   (SEQ ID NO: 5950)
         3'-AAAGGAAAAAUUAUACGAAUUUUAU_(UC-5')   (SEQ ID NO: 1514)
βc-3506 Target: 5'-TTTCCTTTTTAATATGCTTAAAATAAG-3'  (SEQ ID NO: 2623)

5'-UCCUUUUUAAUAUGCUUAAAAUAAG^(AC-3')   (SEQ ID NO: 5951)
         3'-AGGAAAAAUUAUACGAAUUUUAUUC_(GU-5')   (SEQ ID NO: 1515)
βc-3508 Target: 5'-TCCTTTTTAATATGCTTAAAATAAGCA-3'  (SEQ ID NO: 2624)

5'-CCUUUUUAAUAUGCUUAAAAUAAGC^(CA-3')   (SEQ ID NO: 5952)
         3'-GGAAAAAUUAUACGAAUUUUAUUCG_(UC-5')   (SEQ ID NO: 1516)
βc-3509 Target: 5'-CCTTTTTAATATGCTTAAAATAAGCAG-3'  (SEQ ID NO: 2625)

5'-CUUUUUAAUAUGCUUAAAAUAAGCA^(AA-3')   (SEQ ID NO: 5953)
         3'-GAAAAAUUAUACGAAUUUUAUUCGU_(CC-5')   (SEQ ID NO: 1517)
βc-3510 Target: 5'-CTTTTTAATATGCTTAAAATAAGCAGG-3'  (SEQ ID NO: 2626)
```

TABLE 7-continued

Selected Anti-β-catenin DsiRNA Agents, Blunt/Frayed Duplexes

```
             5'-UUUUAAUAUGCUUAAAAUAAGCAGG(CA)-3'  (SEQ ID NO: 5954)
             3'-AAAAUUAUACGAAUUUUAUUCGUCC(AC)-5'  (SEQ ID NO: 1518)
βc-3512 Target: 5'-TTTTAATATGCTTAAAATAAGCAGGTG-3'   (SEQ ID NO: 2627)

5'-UUAAUAUGCUUAAAAUAAGCAGGUG(AC)-3'  (SEQ ID NO: 5955)
             3'-AAUUAUACGAAUUUUAUUCGUCCAC(CU)-5'  (SEQ ID NO: 1519)
βc-3514 Target: 5'-TTAATATGCTTAAAATAAGCAGGTGGA-3'   (SEQ ID NO: 2628)

5'-AAUAUGCUUAAAAUAAGCAGGUGGA(CA)-3'  (SEQ ID NO: 5956)
             3'-UUAUACGAAUUUUAUUCGUCCACCU(AG)-5'  (SEQ ID NO: 1520)
βc-3516 Target: 5'-AATATGCTTAAAATAAGCAGGTGGATC-3'   (SEQ ID NO: 2629)

5'-UAUGCUUAAAAUAAGCAGGUGGAUC(CC)-3'  (SEQ ID NO: 5957)
             3'-AUACGAAUUUUAUUCGUCCACCUAG(AU)-5'  (SEQ ID NO: 1521)
βc-3518 Target: 5'-TATGCTTAAAATAAGCAGGTGGATCTA-3'   (SEQ ID NO: 2630)

5'-UGCUUAAAAUAAGCAGGUGGAUCUA(CC)-3'  (SEQ ID NO: 5958)
             3'-ACGAAUUUUAUUCGUCCACCUAGAU(AA)-5'  (SEQ ID NO: 1522)
βc-3520 Target: 5'-TGCTTAAAATAAGCAGGTGGATCTATT-3'   (SEQ ID NO: 2631)

5'-CUUAAAAUAAGCAGGUGGAUCUAUU(CA)-3'  (SEQ ID NO: 5959)
             3'-GAAUUUUAUUCGUCCACCUAGAUAA(AG)-5'  (SEQ ID NO: 1523)
βc-3522 Target: 5'-CTTAAAATAAGCAGGTGGATCTATTTC-3'   (SEQ ID NO: 2632)

5'-UAAAAUAAGCAGGUGGAUCUAUUUC(CC)-3'  (SEQ ID NO: 5960)
             3'-AUUUUAUUCGUCCACCUAGAUAAAG(UA)-5'  (SEQ ID NO: 1524)
βc-3524 Target: 5'-TAAAATAAGCAGGTGGATCTATTTC-3'     (SEQ ID NO: 2633)

5'-AAAUAAGCAGGUGGAUCUAUUUCAU(AC)-3'  (SEQ ID NO: 5961)
             3'-UUUAUUCGUCCACCUAGAUAAAGUA(CA)-5'  (SEQ ID NO: 1525)
βc-3526 Target: 5'-AAATAAGCAGGTGGATCTATTTCATGT-3'   (SEQ ID NO: 2634)

5'-AUAAGCAGGUGGAUCUAUUUCAUGU(CC)-3'  (SEQ ID NO: 5962)
             3'-UAUUCGUCCACCUAGAUAAAGUACA(AA)-5'  (SEQ ID NO: 1526)
βc-3528 Target: 5'-ATAAGCAGGTGGATCTATTTCATGTTT-3'   (SEQ ID NO: 2635)

5'-AAGCAGGUGGAUCUAUUUCAUGUUU(CC)-3'  (SEQ ID NO: 5963)
             3'-UUCGUCCACCUAGAUAAAGUACAAA(AA)-5'  (SEQ ID NO: 1527)
βc-3530 Target: 5'-AAGCAGGTGGATCTATTTCATGTTTTT-3'   (SEQ ID NO: 2636)

5'-GCAGGUGGAUCUAUUUCAUGUUUUU(AC)-3'  (SEQ ID NO: 5964)
             3'-CGUCCACCUAGAUAAAGUACAAAAA(CU)-5'  (SEQ ID NO: 1528)
βc-3532 Target: 5'-GCAGGTGGATCTATTTCATGTTTTTGA-3'   (SEQ ID NO: 2637)

5'-AGGUGGAUCUAUUUCAUGUUUUUGA(CA)-3'  (SEQ ID NO: 5965)
             3'-UCCACCUAGAUAAAGUACAAAAACU(AG)-5'  (SEQ ID NO: 1529)
βc-3534 Target: 5'-AGGTGGATCTATTTCATGTTTTTGATC-3'   (SEQ ID NO: 2638)

5'-GUGGAUCUAUUUCAUGUUUUUGAUC(CC)-3'  (SEQ ID NO: 5966)
             3'-CACCUAGAUAAAGUACAAAAACUAG(UU)-5'  (SEQ ID NO: 1530)
βc-3536 Target: 5'-GTGGATCTATTTCATGTTTTTGATCAA-3'   (SEQ ID NO: 2639)

5'-GGAUCUAUUUCAUGUUUUUGAUCAA(CC)-3'  (SEQ ID NO: 5967)
             3'-CCUAGAUAAAGUACAAAAACUAGUU(UU)-5'  (SEQ ID NO: 1531)
βc-3538 Target: 5'-GGATCTATTTCATGTTTTTGATCAAAA-3'   (SEQ ID NO: 2640)
```

TABLE 7-continued

Selected Anti-β-catenin DsiRNA Agents, Blunt/Frayed Duplexes

5'-GGGUAGGGUAAAUCAGUAAGAGGUG$^{CC}$-3' (SEQ ID NO: 5968)
3'-CCCAUCCCAUUUAGUCAUUCUCCAC$_{AA}$-5' (SEQ ID NO: 1532)
βc-3583 Target: 5'-GGGTAGGGTAAATCAGTAAGAGGTGTT-3' (SEQ ID NO: 2641)

5'-GUAGGGUAAAUCAGUAAGAGGUGUU$^{CC}$-3' (SEQ ID NO: 5969)
3'-CAUCCCAUUUAGUCAUUCUCCACAA$_{U}$-5' (SEQ ID NO: 1533)
βc-3585 Target: 5'-GTAGGGTAAATCAGTAAGAGGTGTTAT-3' (SEQ ID NO: 2642)

5'-AGGGUAAAUCAGUAAGAGGUGUUAU$^{CC}$-3' (SEQ ID NO: 5970)
3'-UCCCAUUUAGUCAUUCUCCACAAUA$_{A}$-5' (SEQ ID NO: 1534)
βc-3587 Target: 5'-AGGGTAAATCAGTAAGAGGTGTTATTT-3' (SEQ ID NO: 2643)

5'-GGUAAAUCAGUAAGAGGUGUUAUUU$^{AA}$-3' (SEQ ID NO: 5971)
3'-CCAUUUAGUCAUUCUCCACAAUAAA$_{CC}$-5' (SEQ ID NO: 1535)
βc-3589 Target: 5'-GGTAAATCAGTAAGAGGTGTTATTTGG-3' (SEQ ID NO: 2644)

5'-UAAAUCAGUAAGAGGUGUUAUUUGG$^{CC}$-3' (SEQ ID NO: 5972)
3'-AUUUAGUCAUUCUCCACAAUAAACC$_{UU}$-5' (SEQ ID NO: 1536)
βc-3591 Target: 5'-TAAATCAGTAAGAGGTGTTATTTGGAA-3' (SEQ ID NO: 2645)

5'-AAUCAGUAAGAGGUGUUAUUUGGAA$^{A}$-3' (SEQ ID NO: 5973)
3'-UUAGUCAUUCUCCACAAUAAACCUU$_{GG}$-5' (SEQ ID NO: 1537)
βc-3593 Target: 5'-AATCAGTAAGAGGTGTTATTTGGAACC-3' (SEQ ID NO: 2646)

5'-UUUACCAGUUGCCUUUUAUCCCAAA$^{AC}$-3' (SEQ ID NO: 5974)
3'-AAAUGGUCAACGGAAAAUAGGGUUU$_{CA}$-5' (SEQ ID NO: 1538)
βc-3633 Target: 5'-TTTACCAGTTGCCTTTTATCCCAAAGT-3' (SEQ ID NO: 2647)

5'-UACCAGUUGCCUUUUAUCCCAAAGU$^{CA}$-3' (SEQ ID NO: 5975)
3'-AUGGUCAACGGAAAAUAGGGUUUCA$_{AC}$-5' (SEQ ID NO: 1539)
βc-3635 Target: 5'-TACCAGTTGCCTTTTATCCCAAAGTTG-3' (SEQ ID NO: 2648)

5'-CCAGUUGCCUUUUAUCCCAAAGUUG$^{CC}$-3' (SEQ ID NO: 5976)
3'-GGUCAACGGAAAAUAGGGUUUCAAC$_{AA}$-5' (SEQ ID NO: 1540)
βc-3637 Target: 5'-CCAGTTGCCTTTTATCCCAAAGTTGTT-3' (SEQ ID NO: 2649)

5'-AGUUGCCUUUUAUCCCAAAGUUGUU$^{AC}$-3' (SEQ ID NO: 5977)
3'-UCAACGGAAAAUAGGGUUUCAACAA$_{CA}$-5' (SEQ ID NO: 1541)
βc-3639 Target: 5'-AGTTGCCTTTTATCCCAAAGTTGTTGT-3' (SEQ ID NO: 2650)

5'-UUGCCUUUUAUCCCAAAGUUGUUGU$^{CC}$-3' (SEQ ID NO: 5978)
3'-AACGGAAAAUAGGGUUUCAACAACA$_{UU}$-5' (SEQ ID NO: 1542)
βc-3641 Target: 5'-TTGCCTTTTATCCCAAAGTTGTTGTAA-3' (SEQ ID NO: 2651)

5'-GCCUUUUAUCCCAAAGUUGUUGUAA$^{AA}$-3' (SEQ ID NO: 5979)
3'-CGGAAAAUAGGGUUUCAACAACAUU$_{GG}$-5' (SEQ ID NO: 1543)
βc-3643 Target: 5'-GCCTTTTATCCCAAAGTTGTTGTAACC-3' (SEQ ID NO: 2652)

5'-CUUUUAUCCCAAAGUUGUUGUAACC$^{CA}$-3' (SEQ ID NO: 5980)
3'-GAAAAUAGGGUUUCAACAACAUUGG$_{AC}$-5' (SEQ ID NO: 1544)
βc-3645 Target: 5'-CTTTTATCCCAAAGTTGTTGTAACCTG-3' (SEQ ID NO: 2653)

TABLE 7-continued

Selected Anti-β-catenin DsiRNA Agents, Blunt/Frayed Duplexes

```
            5'-UUUAUCCCAAAGUUGUUGUAACCUGA^(AC-3')     (SEQ ID NO: 5981)
            3'-AAAUAGGGUUUCAACAACAUUGGAC_(GA-5')     (SEQ ID NO: 1545)
βc-3647 Target: 5'-TTTATCCCAAAGTTGTTGTAACCTGCT-3'   (SEQ ID NO: 2654)

5'-UAUCCCAAAGUUGUUGUAACCUGCU^(AC-3')     (SEQ ID NO: 5982)
            3'-AUAGGGUUUCAACAACAUUGGACGA_(CA-5')     (SEQ ID NO: 1546)
βc-3649 Target: 5'-TATCCCAAAGTTGTTGTAACCTGCTGT-3'   (SEQ ID NO: 2655)

5'-UCCCAAAGUUGUUGUAACCUGCUGU^(AC-3')     (SEQ ID NO: 5983)
            3'-AGGGUUUCAACAACAUUGGACGACA_(CU-5')     (SEQ ID NO: 1547)
βc-3651 Target: 5'-TCCCAAAGTTGTTGTAACCTGCTGTGA-3'   (SEQ ID NO: 2656)

5'-CCAAAGUUGUUGUAACCUGCUGUGA^(CC-3')     (SEQ ID NO: 5984)
            3'-GGUUUCAACAACAUUGGACGACACU_(AU-5')     (SEQ ID NO: 1548)
βc-3653 Target: 5'-CCAAAGTTGTTGTAACCTGCTGTGATA-3'   (SEQ ID NO: 2657)

5'-AAAGUUGUUGUAACCUGCUGUGAUA^(AA-3')     (SEQ ID NO: 5985)
            3'-UUUCAACAACAUUGGACGACACUAU_(GC-5')     (SEQ ID NO: 1549)
βc-3655 Target: 5'-AAAGTTGTTGTAACCTGCTGTGATACG-3'   (SEQ ID NO: 2658)

5'-AGUUGUUGUAACCUGCUGUGAUACG^(CC-3')     (SEQ ID NO: 5986)
            3'-UCAACAACAUUGGACGACACUAUGC_(UA-5')     (SEQ ID NO: 1550)
βc-3657 Target: 5'-AGTTGTTGTAACCTGCTGTGATACGAT-3'   (SEQ ID NO: 2659)

5'-UUGUUGUAACCUGCUGUGAUACGAU^(AA-3')     (SEQ ID NO: 5987)
            3'-AACAACAUUGGACGACACUAUGCUA_(CG-5')     (SEQ ID NO: 1551)
βc-3659 Target: 5'-TTGTTGTAACCTGCTGTGATACGATGC-3'   (SEQ ID NO: 2660)

5'-AAAAAUGGUUCAGAAUUAAACUUUU^(CC-3')     (SEQ ID NO: 5988)
            3'-UUUUUACCAAGUCUUAAUUUGAAAA_(UU-5')     (SEQ ID NO: 1552)
βc-3708 Target: 5'-AAAAATGGTTCAGAATTAAACTTTTAA-3'   (SEQ ID NO: 2661)

5'-AAAUGGUUCAGAAUUAAACUUUUAA^(CC-3')     (SEQ ID NO: 5989)
            3'-UUUUACCAAGUCUUAAUUUGAAAAUU_(AA-5')    (SEQ ID NO: 1553)
βc-3710 Target: 5'-AAATGGTTCAGAATTAAACTTTTAATT-3'   (SEQ ID NO: 2662)

5'-AUGGUUCAGAAUUAAACUUUUAAUU^(AC-3')     (SEQ ID NO: 5990)
            3'-UACCAAGUCUUAAUUUGAAAAUUAA_(GU-5')     (SEQ ID NO: 1554)
βc-3712 Target: 5'-ATGGTTCAGAATTAAACTTTTAATTCA-3'   (SEQ ID NO: 2663)

5'-GGUUCAGAAUUAAACUUUUAAUUCA^(CC-3')     (SEQ ID NO: 5991)
            3'-CCAAGUCUUAAUUUGAAAAUUAAGU_(AA-5')     (SEQ ID NO: 1555)
βc-3714 Target: 5'-GGTTCAGAATTAAACTTTTAATTCATT-3'   (SEQ ID NO: 2664)

5'-UUCAGAAUUAAACUUUUAAUUCAUU^(AA-3')     (SEQ ID NO: 5992)
            3'-AAGUCUUAAUUUGAAAAUUAAGUAA_(GC-5')     (SEQ ID NO: 1556)
βc-3716 Target: 5'-TTCAGAATTAAACTTTTAATTCATTCG-3'   (SEQ ID NO: 2665)

5'-CAGCAGCAGUCUUACUUGGAUUCUGA^(AC-3')    (SEQ ID NO: 5993)
            3'-GUCGUCGUCAGAAUGAACCUAAGAC_(CU-5')     (SEQ ID NO: 1557)
βc-m314 Target: 5'-CAGCAGCAGTCTTACTTGGATTCTGGA-3'   (SEQ ID NO: 2666)

5'-UUACUUGGAUUCUGGAAUCCAUUCU^(AA-3')     (SEQ ID NO: 5994)
            3'-AAUGAACCUAAGACCUUAGGUAAGA_(CC-5')     (SEQ ID NO: 1558)
βc-m325 Target: 5'-TTACTTGGATTCTGGAATCCATTCTGG-3'   (SEQ ID NO: 2667)
```

TABLE 7-continued

Selected Anti-β-catenin DsiRNA Agents, Blunt/Frayed Duplexes

5'-UUGACACCUCCCAAGUCCUUUAUGA$^{CC}$-3' (SEQ ID NO: 5995)
3'-AACUGUGGAGGGUUCAGGAAAUACU$_{UA}$-5' (SEQ ID NO: 1559)
βc-m408 Target: 5'-TTGACACCTCCCAAGTCCTTTATGAAT-3' (SEQ ID NO: 2668)

5'-CACGCAAGAGCAAGUAGCUGAUAUU$^{AC}$-3' (SEQ ID NO: 5996)
3'-GUGCGUUCUCGUUCAUCGACUAUAA$_{CU}$-5' (SEQ ID NO: 1560)
βc-m460 Target: 5'-CACGCAAGAGCAAGTAGCTGATATTGA-3' (SEQ ID NO: 2669)

5'-UGCCAUGUUCCCUGAGACGCUAGAU$^{AC}$-3' (SEQ ID NO: 5997)
3'-ACGGUACAAGGGACUCUGCGAUCUA$_{CU}$-5' (SEQ ID NO: 1561)
βc-m526 Target: 5'-TGCCATGTTCCCTGAGACGCTAGATGA-3' (SEQ ID NO: 2670)

5'-GUUGAAACAUGCAGUUGUCAAUUUG$^{CC}$-3' (SEQ ID NO: 5998)
3'-CAACUUUGUACGUCAACAGUUAAAC$_{UA}$-5' (SEQ ID NO: 1562)
βc-m631 Target: 5'-GTTGAAACATGCAGTTGTCAATTTGAT-3' (SEQ ID NO: 2671)

5'-AACAUGCAGUUGUCAAUUUGAUUAA$^{AC}$-3' (SEQ ID NO: 5999)
3'-UUGUACGUCAACAGUUAAACUAAUU$_{GA}$-5' (SEQ ID NO: 1563)
βc-m636 Target: 5'-AACATGCAGTTGTCAATTTGATTAACT-3' (SEQ ID NO: 2672)

5'-CAGUUGUCAAUUUGAUUAACUAUCA$^{AA}$-3' (SEQ ID NO: 6000)
3'-GUCAACAGUUAAACUAAUUGAUAGU$_{CC}$-5' (SEQ ID NO: 1564)
βc-m642 Target: 5'-CAGTTGTCAATTTGATTAACTATCAGG-3' (SEQ ID NO: 2673)

5'-AUGAGGACCAGGUGGUAGUUAAUAA$^{CA}$-3' (SEQ ID NO: 6001)
3'-UACUCCUGGUCCACCAUCAAUUAUU$_{UC}$-5' (SEQ ID NO: 1565)
βc-m723 Target: 5'-ATGAGGACCAGGTGGTAGTTAATAAAG-3' (SEQ ID NO: 2674)

5'-UGGGUCACCAGUGGAUUCUGUACUG$^{CC}$-3' (SEQ ID NO: 6002)
3'-ACCCAGUGGUCACCUAAGACAUGAC$_{AA}$-5' (SEQ ID NO: 1566)
βc-m970 Target: 5'-TGGGTCACCAGTGGATTCTGTACTGTT-3' (SEQ ID NO: 2675)

5'-ACCAGUGGAUUCUGUACUGUUCUAC$^{AA}$-3' (SEQ ID NO: 6003)
3'-UGGUCACCUAAGACAUGACAAGAUG$_{CG}$-5' (SEQ ID NO: 1567)
βc-m976 Target: 5'-ACCAGTGGATTCTGTACTGTTCTACGC-3' (SEQ ID NO: 2676)

5'-UGGAUUCUGUACUGUUCUACGCCAU$^{AC}$-3' (SEQ ID NO: 6004)
3'-ACCUAAGACAUGACAAGAUGCGGUA$_{GU}$-5' (SEQ ID NO: 1568)
βc-m981 Target: 5'-TGGATTCTGTACTGTTCTACGCCATCA-3' (SEQ ID NO: 2677)

5'-UGGUGGACUGCAGAAAAUGGUUGCU$^{CC}$-3' (SEQ ID NO: 6005)
3'-ACCACCUGACGUCUUUUACCAACGA$_{AA}$-5' (SEQ ID NO: 1569)
βc-m1066 Target: 5'-TGGTGGACTGCAGAAAATGGTTGCTTT-3' (SEQ ID NO: 2678)

5'-AACGUGAAAUUCUUGGCUAUUACAA$^{AC}$-3' (SEQ ID NO: 6006)
3'-UUGCACUUUAAGAACCGAUAAUGUU$_{GU}$-5' (SEQ ID NO: 1570)
βc-m1106 Target: 5'-AACGTGAAATTCTTGGCTATTACAACA-3' (SEQ ID NO: 2679)

5'-CCCAAGUCAGCGACUUGUUCAAAAC$^{CA}$-3' (SEQ ID NO: 6007)
3'-GGGUUCAGUCGCUGAACAAGUUUUG$_{AC}$-5' (SEQ ID NO: 1571)
βc-m1354 Target: 5'-CCCAAGTCAGCGACTTGTTCAAAACTG-3' (SEQ ID NO: 2680)

TABLE 7-continued

Selected Anti-β-catenin DsiRNA Agents, Blunt/Frayed Duplexes

```
         5'-GCGACUUGUUCAAAACUGUCUUUGG^CA-3'  (SEQ ID NO: 6008)
         3'-CGCUGAACAAGUUUUGACAGAAACC_UG-5'  (SEQ ID NO: 1572)
βc-m1363 Target: 5'-GCGACTTGTTCAAAACTGTCTTTGGAC-3'  (SEQ ID NO: 2681)

5'-CAAAACUGUCUUUGGACUCUCAGAA^CA-3'  (SEQ ID NO: 6009)
         3'-GUUUUGACAGAAACCUGAGAGUCUU_UG-5'  (SEQ ID NO: 1573)
βc-m1373 Target: 5'-CAAAACTGTCTTTGGACTCTCAGAAAC-3'  (SEQ ID NO: 2682)

5'-CUCUCUAACCUCACUUGCAAUAAUU^CA-3'  (SEQ ID NO: 6010)
         3'-GAGAGAUUGGAGUGAACGUUAUUAA_UG-5'  (SEQ ID NO: 1574)
βc-m1508 Target: 5'-CTCTCTAACCTCACTTGCAATAATTAC-3'  (SEQ ID NO: 2683)

5'-ACCUCACUUGCAAUAAUUACAAAAA^AC-3'  (SEQ ID NO: 6011)
         3'-UGGAGUGAACGUUAUUAAUGUUUUU_GU-5'  (SEQ ID NO: 1575)
βc-m1515 Target: 5'-ACCTCACTTGCAATAATTACAAAAACA-3'  (SEQ ID NO: 2684)

5'-CAGAAUGCCGUUCGCCUUCAUUAUG^AC-3'  (SEQ ID NO: 6012)
         3'-GUCUUACGGCAAGCGGAAGUAAUAC_CU-5'  (SEQ ID NO: 1576)
βc-m1682 Target: 5'-CAGAATGCCGTTCGCCTTCATTATGGA-3'  (SEQ ID NO: 2685)

5'-UCGCCUUCAUUAUGGACUGCCUGUU^AC-3'  (SEQ ID NO: 6013)
         3'-AGCGGAAGUAAUACCUGACGGACAA_CA-5'  (SEQ ID NO: 1577)
βc-m1693 Target: 5'-TCGCCTTCATTATGGACTGCCTGTTGT-3'  (SEQ ID NO: 2686)

5'-UUCAUUAUGGACUGCCUGUUGUGGU^CC-3'  (SEQ ID NO: 6014)
         3'-AAGUAAUACCUGACGGACAACACCA_AU-5'  (SEQ ID NO: 1578)
βc-m1698 Target: 5'-TTCATTATGGACTGCCTGTTGTGGTTA-3'  (SEQ ID NO: 2687)

5'-UGGACUGCCUGUUGUGGUUAAACUC^AC-3'  (SEQ ID NO: 6015)
         3'-ACCUGACGGACAACACCAAUUUGAG_GA-5'  (SEQ ID NO: 1579)
βc-m1705 Target: 5'-TGGACTGCCTGTTGTGGTTAAACTCCT-3'  (SEQ ID NO: 2688)

5'-GCAACUGUUGGAUUGAUUCGAAACC^CC-3'  (SEQ ID NO: 6016)
         3'-CGUUGACAACCUAACUAAGCUUUGG_AA-5'  (SEQ ID NO: 1580)
βc-m1763 Target: 5'-GCAACTGTTGGATTGATTCGAAACCTT-3'  (SEQ ID NO: 2689)

5'-CCGAGGACUCAAUACCAUUCCAUUG^CC-3'  (SEQ ID NO: 6017)
         3'-GGCUCCUGAGUUAUGGUAAGGUAAC_AA-5'  (SEQ ID NO: 1581)
βc-m2008 Target: 5'-CCGAGGACTCAATACCATTCCATTGTT-3'  (SEQ ID NO: 2690)

5'-CUGAGGACAAGCCACAGGAUUACAA^AC-3'  (SEQ ID NO: 6018)
         3'-GACUCCUGUUCGGUGUCCUAAUGUU_CU-5'  (SEQ ID NO: 1582)
βc-m2226 Target: 5'-CTGAGGACAAGCCACAGGATTACAAGA-3'  (SEQ ID NO: 2691)

5'-GGAUGGACCCUAUGAUGGAGCAUGA^AC-3'  (SEQ ID NO: 6019)
         3'-CCUACCUGGGAUACUACCUCGUACU_CU-5'  (SEQ ID NO: 1583)
βc-m2427 Target: 5'-GGATGGACCCTATGATGGAGCATGAGA-3'  (SEQ ID NO: 2692)

5'-UUGAUACUGACCUGUAAAUCGUCCU^CC-3'  (SEQ ID NO: 6020)
         3'-AACUAUGACUGGACAUUUAGCAGGA_AA-5'  (SEQ ID NO: 1584)
βc-m2568 Target: 5'-TTGATACTGACCTGTAAATCGTCCTTT-3'  (SEQ ID NO: 2693)

5'-AGCCAGUGUGGGUGAAUACUUUACU^AC-3'  (SEQ ID NO: 6021)
         3'-UCGGUCACACCCACUUAUGAAAUGA_GA-5'  (SEQ ID NO: 1585)
βc-m2614 Target: 5'-AGCCAGTGTGGGTGAATACTTTACTCT-3'  (SEQ ID NO: 2694)
```

TABLE 7-continued

Selected Anti-β-catenin DsiRNA Agents, Blunt/Frayed Duplexes

```
              5'-UGCCACAGCUUUUGCAGCGUUAUACC^CA-3'  (SEQ ID NO: 6022)
              3'-ACGGUGUCGAAAACGUCGCAAUAUG_AG-5'  (SEQ ID NO: 1586)
βc-m2770 Target: 5'-TGCCACAGCTTTTGCAGCGTTATACTC-3' (SEQ ID NO: 2695)

5'-GCUUUUGCAGCGUUAUACUCAGAUG^CA-3'  (SEQ ID NO: 6023)
              3'-CGAAAACGUCGCAAUAUGAGUCUAC_UC-5'  (SEQ ID NO: 1587)
βc-m2777 Target: 5'-GCTTTTGCAGCGTTATACTCAGATGAG-3' (SEQ ID NO: 2696)

5'-CAGCGUUAUACUCAGAUGAGUAACA^CC-3'  (SEQ ID NO: 6024)
              3'-GUCGCAAUAUGAGUCUACUCAUUGU_AA-5'  (SEQ ID NO: 1588)
βc-m2784 Target: 5'-CAGCGTTATACTCAGATGAGTAACATT-3' (SEQ ID NO: 2697)

5'-ACAUUUGCUGUUUUCAACAUUAAUA^AA-3'  (SEQ ID NO: 6025)
              3'-UGUAAACGACAAAAGUUGUAAUUAU_CG-5'  (SEQ ID NO: 1589)
βc-m2806 Target: 5'-ACATTTGCTGTTTTCAACATTAATAGC-3' (SEQ ID NO: 2698)

5'-AGCUGUAGUGUCUGAACGUGCAUUG^CA-3'  (SEQ ID NO: 6026)
              3'-UCGACAUCACAGACUUGCACGUAAC_AC-5'  (SEQ ID NO: 1590)
βc-m2850 Target: 5'-AGCTGTAGTGTCTGAACGTGCATTGTG-3' (SEQ ID NO: 2699)

5'-GGGAACAGUCGAAGUACGCUUUUUG^CC-3'  (SEQ ID NO: 6027)
              3'-CCCUUGUCAGCUUCAUGCGAAAAAC_AA-5'  (SEQ ID NO: 1591)
βc-m2965 Target: 5'-GGGAACAGTCGAAGTACGCTTTTTGTT-3' (SEQ ID NO: 2700)

5'-CAGUCGAAGUACGCUUUUUGUUCUGA^C-3'  (SEQ ID NO: 6028)
              3'-GUCAGCUUCAUGCGAAAAACAAGAC_CA-5'  (SEQ ID NO: 1592)
βc-m2970 Target: 5'-CAGTCGAAGTACGCTTTTTGTTCTGGT-3' (SEQ ID NO: 2701)

5'-AAGUACGCUUUUUGUUCUGGUCCUU^CC-3'  (SEQ ID NO: 6029)
              3'-UUCAUGCGAAAAACAAGACCAGGAA_AA-5'  (SEQ ID NO: 1593)
βc-m2976 Target: 5'-AAGTACGCTTTTTGTTCTGGTCCTTTT-3' (SEQ ID NO: 2702)

5'-ACCCUAGCCUUGCUUGUUCUUUGUU^CC-3'  (SEQ ID NO: 6030)
              3'-UGGGAUCGGAACGAACAAGAAACAA_AA-5'  (SEQ ID NO: 1594)
βc-m3092 Target: 5'-ACCCTAGCCTTGCTTGTTCTTTGTTTT-3' (SEQ ID NO: 2703)

5'-AGCCUUGCUUGUUCUUUGUUUUAAU^CC-3'  (SEQ ID NO: 6031)
              3'-UCGGAACGAACAAGAAACAAAAUUA_UA-5'  (SEQ ID NO: 1595)
βc-m3097 Target: 5'-AGCCTTGCTTGTTCTTTGTTTTAATAT-3' (SEQ ID NO: 2704)

5'-UGAACCUGCUACAGCAAUUUCUGAU^CC-3'  (SEQ ID NO: 6032)
              3'-ACUUGGACGAUGUCGUUAAAGACUA_AA-5'  (SEQ ID NO: 1596)
βc-m3198 Target: 5'-TGAACCTGCTACAGCAATTTCTGATTT-3' (SEQ ID NO: 2705)

5'-UACAGCAAUUUCUGAUUUCUAAGAA^AA-3'  (SEQ ID NO: 6033)
              3'-AUGUCGUUAAAGACUAAAGAUUCUU_GG-5'  (SEQ ID NO: 1597)
βc-m3207 Target: 5'-TACAGCAATTTCTGATTTCTAAGAACC-3' (SEQ ID NO: 2706)

5'-CAGUAAGAGGUGUUAUUUGAGCCUU^AC-3'  (SEQ ID NO: 6034)
              3'-GUCAUUCUCCACAAUAAACUCGGAA_CA-5'  (SEQ ID NO: 1598)
βc-m3433 Target: 5'-CAGTAAGAGGTGTTATTTGAGCCTTGT-3' (SEQ ID NO: 2707)

5'-GAGGUGUUAUUUGAGCCUUGUUUUG^AC-3'  (SEQ ID NO: 6035)
              3'-CUCCACAAUAAACUCGGAACAAAAC_CU-5'  (SEQ ID NO: 1599)
βc-m3439 Target: 5'-GAGGTGTTATTTGAGCCTTGTTTTGGA-3' (SEQ ID NO: 2708)
```

TABLE 7-continued

Selected Anti-β-catenin DsiRNA Agents, Blunt/Frayed Duplexes

```
                  5'-GUUAUUUGAGCCUUGUUUUGGACAGCC-3'     (SEQ ID NO: 6036)
                  3'-CAAUAAACUCGGAACAAAACCUGUCAU-5'     (SEQ ID NO: 1600)
βc-m3444 Target:  5'-GTTATTTGAGCCTTGTTTTGGACAGTA-3'     (SEQ ID NO: 2709)

5'-UUGAGCCUUGUUUUGGACAGUAUACAC-3'     (SEQ ID NO: 6037)
                  3'-AACUCGGAACAAAACCUGUCAUAUGGU-5'     (SEQ ID NO: 1601)
βc-m3449 Target:  5'-TTGAGCCTTGTTTTGGACAGTATACCA-3'     (SEQ ID NO: 2710)

5'-UUCAACAGAUGCGGUUAUAGAAAUGAC-3'     (SEQ ID NO: 6038)
                  3'-AAGUUGUCUACGCCAAUAUCUUUACCA-5'     (SEQ ID NO: 1602)
βc-m3522 Target:  5'-TTCAACAGATGCGGTTATAGAAATGGT-3'     (SEQ ID NO: 2711)

5'-CGGUUAUAGAAAUGGUUCAGAAUUACC-3'     (SEQ ID NO: 6039)
                  3'-GCCAAUAUCUUUACCAAGUCUUAAUUU-5'     (SEQ ID NO: 1603)
βc-m3533 Target:  5'-CGGTTATAGAAATGGTTCAGAATTAAA-3'     (SEQ ID NO: 2712)

5'-AUAGAAAUGGUUCAGAAUUAAACUUCC-3'     (SEQ ID NO: 6040)
                  3'-UAUCUUUACCAAGUCUUAAUUUGAAAA-5'     (SEQ ID NO: 1604)
βc-m3538 Target:  5'-ATAGAAATGGTTCAGAATTAAACTTTT-3'     (SEQ ID NO: 2713)
```

TABLE 8

Selected Anti-β-catenin DsiRNA Agents, Blunt Duplexes

```
                5'-CCCUGAGGGUAUUUGAAGUAUACCAUA-3'     (SEQ ID NO: 6662)
                3'-GGGACUCCCAUAAACUUCAUAUGGUAU-5'     (SEQ ID NO: 1117)
βc-240 Target:  5'-CCCTGAGGGTATTTGAAGTATACCATA-3'     (SEQ ID NO: 2226)

5'-GAGGGUAUUUGAAGUAUACCAUACAAC-3'     (SEQ ID NO: 6663)
                3'-CUCCCAUAAACUUCAUAUGGUAUGUUG-5'     (SEQ ID NO: 1118)
βc-244 Target:  5'-GAGGGTATTTGAAGTATACCATACAAC-3'     (SEQ ID NO: 2227)

5'-UGAAGUAUACCAUACAACUGUUUUGAA-3'     (SEQ ID NO: 6664)
                3'-ACUUCAUAUGGUAUGUUGACAAAACUU-5'     (SEQ ID NO: 1119)
βc-253 Target:  5'-TGAAGTATACCATACAACTGTTTTGAA-3'     (SEQ ID NO: 2228)

5'-AUACCAUACAACUGUUUUGAAAAUCCA-3'     (SEQ ID NO: 6665)
                3'-UAUGGUAUGUUGACAAAACUUUUAGGU-5'     (SEQ ID NO: 1120)
βc-259 Target:  5'-ATACCATACAACTGTTTTGAAAATCCA-3'     (SEQ ID NO: 2229)

5'-AUACAACUGUUUUGAAAAUCCAGCGUG-3'     (SEQ ID NO: 6666)
                3'-UAUGUUGACAAAACUUUUAGGUCGCAC-5'     (SEQ ID NO: 1121)
βc-264 Target:  5'-ATACAACTGTTTTGAAAATCCAGCGTG-3'     (SEQ ID NO: 2230)

5'-CAGGGAUUUUCUCAGUCCUUCACUCAA-3'     (SEQ ID NO: 6667)
                3'-GUCCCUAAAAGAGUCAGGAAGUGAGUU-5'     (SEQ ID NO: 1122)
βc-496 Target:  5'-CAGGGATTTTCTCAGTCCTTCACTCAA-3'     (SEQ ID NO: 2231)

5'-CACUCAAGAACAAGUAGCUGAUAUUGA-3'     (SEQ ID NO: 6668)
                3'-GUGAGUUCUUGUUCAUCGACUAUAACU-5'     (SEQ ID NO: 1123)
βc-516 Target:  5'-CACTCAAGAACAAGTAGCTGATATTGA-3'     (SEQ ID NO: 2232)

5'-AGAACAAGUAGCUGAUAUUGAUGGACA-3'     (SEQ ID NO: 6669)
                3'-UCUUGUUCAUCGACUAUAACUACCUGU-5'     (SEQ ID NO: 1124)
βc-522 Target:  5'-AGAACAAGTAGCTGATATTGATGGACA-3'     (SEQ ID NO: 2233)

5'-AACAAGUAGCUGAUAUUGAUGGACAGU-3'     (SEQ ID NO: 6670)
                3'-UUGUUCAUCGACUAUAACUACCUGUCA-5'     (SEQ ID NO: 1125)
βc-524 Target:  5'-AACAAGTAGCTGATATTGATGGACAGT-3'     (SEQ ID NO: 2234)

5'-UGAUGGACAGUAUGCAAUGACUCGAGC-3'     (SEQ ID NO: 6671)
                3'-ACUACCUGUCAUACGUUACUGAGCUCG-5'     (SEQ ID NO: 1126)
βc-540 Target:  5'-TGATGGACAGTATGCAATGACTCGAGC-3'     (SEQ ID NO: 2235)
```

TABLE 8-continued

Selected Anti-β-catenin DsiRNA Agents, Blunt Duplexes

| | | |
|---|---|---|
| | 5'-UGCUAUGUUCCCUGAGACAUUAGAUGA-3' | (SEQ ID NO: 6672) |
| | 3'-ACGAUACAAGGGACUCUGUAAUCUACU-5' | (SEQ ID NO: 1127) |
| βc-582 Target: | 5'-TGCTATGTTCCCTGAGACATTAGATGA-3' | (SEQ ID NO: 2236) |
| | 5'-UGCUGAAACAUGCAGUUGUAAACUUGA-3' | (SEQ ID NO: 6673) |
| | 3'-ACGACUUUGUACGUCAACAUUUGAACU-5' | (SEQ ID NO: 1128) |
| βc-686 Target: | 5'-TGCTGAAACATGCAGTTGTAAACTTGA-3' | (SEQ ID NO: 2237) |
| | 5'-AACAUGCAGUUGUAAACUUGAUUAACU-3' | (SEQ ID NO: 6674) |
| | 3'-UUGUACGUCAACAUUUGAACUAAUUGA-5' | (SEQ ID NO: 1129) |
| βc-692 Target: | 5'-AACATGCAGTTGTAAACTTGATTAACT-3' | (SEQ ID NO: 2238) |
| | 5'-GCAGUUGUAAACUUGAUUAACUAUCAA-3' | (SEQ ID NO: 6675) |
| | 3'-CGUCAACAUUUGAACUAAUUGAUAGUU-5' | (SEQ ID NO: 1130) |
| βc-697 Target: | 5'-GCAGTTGTAAACTTGATTAACTATCAA-3' | (SEQ ID NO: 2239) |
| | 5'-ACUUGAUUAACUAUCAAGAUGAUGCAG-3' | (SEQ ID NO: 6676) |
| | 3'-UGAACUAAUUGAUAGUUCUACUACGUC-5' | (SEQ ID NO: 1131) |
| βc-707 Target: | 5'-ACTTGATTAACTATCAAGATGATGCAG-3' | (SEQ ID NO: 2240) |
| | 5'-CCCUGAACUGACAAAACUGCUAAAUGA-3' | (SEQ ID NO: 6677) |
| | 3'-GGGACUUGACUGUUUUGACGAUUUACU-5' | (SEQ ID NO: 1132) |
| βc-753 Target: | 5'-CCCTGAACTGACAAAACTGCTAAATGA-3' | (SEQ ID NO: 2241) |
| | 5'-UCAGAUGGUGUCUGCUAUUGUACGUAC-3' | (SEQ ID NO: 6678) |
| | 3'-AGUCUACCACAGACGAUAACAUGCAUG-5' | (SEQ ID NO: 1133) |
| βc-870 Target: | 5'-TCAGATGGTGTCTGCTATTGTACGTAC-3' | (SEQ ID NO: 2242) |
| | 5'-GUACGUACCAUGCAGAAUACAAAUGAU-3' | (SEQ ID NO: 6679) |
| | 3'-CAUGCAUGGUACGUCUUAUGUUUACUA-5' | (SEQ ID NO: 1134) |
| βc-889 Target: | 5'-GTACGTACCATGCAGAATACAAATGAT-3' | (SEQ ID NO: 2243) |
| | 5'-AUUACAACUCUCCACAACCUUUUAUUA-3' | (SEQ ID NO: 6680) |
| | 3'-UAAUGUUGAGAGGUGUUGGAAAAUAAU-5' | (SEQ ID NO: 1135) |
| βc-1060 Target: | 5'-ATTACAACTCTCCACAACCTTTTATTA-3' | (SEQ ID NO: 2244) |
| | 5'-AACUCUCCACAACCUUUUAUUACAUCA-3' | (SEQ ID NO: 6681) |
| | 3'-UUGAGAGGUGUUGGAAAAUAAUGUAGU-5' | (SEQ ID NO: 1136) |
| βc-1065 Target: | 5'-AACTCTCCACAACCTTTTATTACATCA-3' | (SEQ ID NO: 2245) |
| | 5'-UCCACAACCUUUUAUUACAUCAAGAAG-3' | (SEQ ID NO: 6682) |
| | 3'-AGGUGUUGGAAAAUAAUGUAGUUCUUC-5' | (SEQ ID NO: 1137) |
| βc-1070 Target: | 5'-TCCACAACCTTTTATTACATCAAGAAG-3' | (SEQ ID NO: 2246) |
| | 5'-ACCUUUUAUUACAUCAAGAAGGAGCUA-3' | (SEQ ID NO: 6683) |
| | 3'-UGGAAAAUAAUGUAGUUCUUCCUCGAU-5' | (SEQ ID NO: 1138) |
| βc-1076 Target: | 5'-ACCTTTTATTACATCAAGAAGGAGCTA-3' | (SEQ ID NO: 2247) |
| | 5'-ACAAAACAAAUGUUAAAUUCUUGGCUA-3' | (SEQ ID NO: 6684) |
| | 3'-UGUUUUGUUUACAAUUUAAGAACCGAU-5' | (SEQ ID NO: 1139) |
| βc-1154 Target: | 5'-ACAAAACAAATGTTAAATTCTTGGCTA-3' | (SEQ ID NO: 2248) |
| | 5'-AUUACGACAGACUGCCUUCAAAUUUUA-3' | (SEQ ID NO: 6685) |
| | 3'-UAAUGCUGUCUGACGGAAGUUUAAAAU-5' | (SEQ ID NO: 1140) |
| βc-1180 Target: | 5'-ATTACGACAGACTGCCTTCAAATTTTA-3' | (SEQ ID NO: 2249) |
| | 5'-GACAGACUGCCUUCAAAUUUUAGCUUA-3' | (SEQ ID NO: 6686) |
| | 3'-CUGUCUGACGGAAGUUUAAAAUCGAAU-5' | (SEQ ID NO: 1141) |
| βc-1185 Target: | 5'-GACAGACTGCCTTCAAATTTTAGCTTA-3' | (SEQ ID NO: 2250) |
| | 5'-AGCUUUAGUAAAUAUAAUGAGGACCUA-3' | (SEQ ID NO: 6687) |
| | 3'-UCGAAAUCAUUUAUAUUACUCCUGGAU-5' | (SEQ ID NO: 1142) |
| βc-1260 Target: | 5'-AGCTTTAGTAAATATAATGAGGACCTA-3' | (SEQ ID NO: 2251) |
| | 5'-GAAAACUACUGUGGACCACAAGCAGA-3' | (SEQ ID NO: 6688) |
| | 3'-CUUUUUGAUGACACCUGGUGUUCGUCU-5' | (SEQ ID NO: 1143) |
| βc-1294 Target: | 5'-GAAAAACTACTGTGGACCACAAGCAGA-3' | (SEQ ID NO: 2252) |
| | 5'-CAAGUCAACGUCUUGUUCAGAACUGUC-3' | (SEQ ID NO: 6689) |
| | 3'-GUUCAGUUGCAGAACAAGUCUUGACAG-5' | (SEQ ID NO: 1144) |
| βc-1412 Target: | 5'-CAAGTCAACGTCTTGTTCAGAACTGTC-3' | (SEQ ID NO: 2253) |
| | 5'-AACGUCUUGUUCAGAACUGUCUUUGGA-3' | (SEQ ID NO: 6690) |
| | 3'-UUGCAGAACAAGUCUUGACAGAAACCU-5' | (SEQ ID NO: 1145) |
| βc-1418 Target: | 5'-AACGTCTTGTTCAGAACTGTCTTTGGA-3' | (SEQ ID NO: 2254) |

TABLE 8-continued

Selected Anti-β-catenin DsiRNA Agents, Blunt Duplexes

| | | |
|---|---|---|
| βc-1423 Target: | 5'-CUUGUUCAGAACUGUCUUUGGACUCUC-3'<br>3'-GAACAAGUCUUGACAGAAACCUGAGAG-5'<br>5'-CTTGTTCAGAACTGTCTTTGGACTCTC-3' | (SEQ ID NO: 6691)<br>(SEQ ID NO: 1146)<br>(SEQ ID NO: 2255) |
| βc-1520 Target: | 5'-UGGGUUCAGAUGAUAUAAAUGUGGUCA-3'<br>3'-ACCCAAGUCUACUAUAUUUACACCAGU-5'<br>5'-TGGGTTCAGATGATATAAATGTGGTCA-3' | (SEQ ID NO: 6692)<br>(SEQ ID NO: 1147)<br>(SEQ ID NO: 2256) |
| βc-1561 Target: | 5'-AUUCUUUCUAACCUCACUUGCAAUAAU-3'<br>3'-UAAGAAAGAUUGGAGUGAACGUUAUUA-5'<br>5'-ATTCTTTCTAACCTCACTTGCAATAAT-3' | (SEQ ID NO: 6693)<br>(SEQ ID NO: 1148)<br>(SEQ ID NO: 2257) |
| βc-1571 Target: | 5'-ACCUCACUUGCAAUAAUUAUAAGAACA-3'<br>3'-UGGAGUGAACGUUAUUAAUAUUCUUGU-5'<br>5'-ACCTCACTTGCAATAATTATAAGAACA-3' | (SEQ ID NO: 6694)<br>(SEQ ID NO: 1149)<br>(SEQ ID NO: 2258) |
| βc-1579 Target: | 5'-UGCAAUAAUUAUAAGAACAAGAUGAUG-3'<br>3'-ACGUUAUUAAUAUUCUUGUUCUACUAC-5'<br>5'-TGCAATAATTATAAGAACAAGATGATG-3' | (SEQ ID NO: 6695)<br>(SEQ ID NO: 1150)<br>(SEQ ID NO: 2259) |
| βc-1620 Target: | 5'-UGGUAUAGAGGCUCUUGUGCGUACUGU-3'<br>3'-ACCAUAUCUCCGAGAACACGCAUGACA-5'<br>5'-TGGTATAGAGGCTCTTGTGCGTACTGT-3' | (SEQ ID NO: 6696)<br>(SEQ ID NO: 1151)<br>(SEQ ID NO: 2260) |
| βc-1816 Target: | 5'-AAGGCUACUGUUGGAUUGAUUCGAAAU-3'<br>3'-UUCCGAUGACAACCUAACUAAGCUUUA-5'<br>5'-AAGGCTACTGTTGGATTGATTCGAAAT-3' | (SEQ ID NO: 6697)<br>(SEQ ID NO: 1152)<br>(SEQ ID NO: 2261) |
| βc-1987 Target: | 5'-CGCAUGGAAGAAAUAGUUGAAGGUUGU-3'<br>3'-GCGUACCUUCUUUAUCAACUUCCAACA-5'<br>5'-CGCATGGAAGAAATAGTTGAAGGTTGT-3' | (SEQ ID NO: 6698)<br>(SEQ ID NO: 1153)<br>(SEQ ID NO: 2262) |
| βc-1989 Target: | 5'-CAUGGAAGAAAUAGUUGAAGGUUGUAC-3'<br>3'-GUACCUUCUUUAUCAACUUCCAACAUG-5'<br>5'-CATGGAAGAAATAGTTGAAGGTTGTAC-3' | (SEQ ID NO: 6699)<br>(SEQ ID NO: 1154)<br>(SEQ ID NO: 2263) |
| βc-2111 Target: | 5'-CCAUUGAAAACAUCCAAAGAGUAGCUG-3'<br>3'-GGUAACUUUUGUAGGUUUCUCAUCGAC-5'<br>5'-CCATTGAAAACATCCAAAGAGTAGCTG-3' | (SEQ ID NO: 6700)<br>(SEQ ID NO: 1155)<br>(SEQ ID NO: 2264) |
| βc-2282 Target: | 5'-CUGAGGACAAGCCACAAGAUUACAAGA-3'<br>3'-GACUCCUGUUCGGUGUUCUAAUGUUCU-5'<br>5'-CTGAGGACAAGCCACAAGATTACAAGA-3' | (SEQ ID NO: 6701)<br>(SEQ ID NO: 1156)<br>(SEQ ID NO: 2265) |
| βc-2624 Target: | 5'-UUGAUACUGACCUGUAAAUCAUCCUUU-3'<br>3'-AACUAUGACUGGACAUUUAGUAGGAAA-5'<br>5'-TTGATACTGACCTGTAAATCATCCTTT-3' | (SEQ ID NO: 6702)<br>(SEQ ID NO: 1157)<br>(SEQ ID NO: 2266) |
| βc-2647 Target: | 5'-CUUUAGGUAAGAAGUUUUAAAAAGCCA-3'<br>3'-GAAAUCCAUUCUUCAAAAUUUUUCGGU-5'<br>5'-CTTTAGGTAAGAAGTTTTAAAAAGCCA-3' | (SEQ ID NO: 6703)<br>(SEQ ID NO: 1158)<br>(SEQ ID NO: 2267) |
| βc-2770 Target: | 5'-AACAGGUAUAUACUUUGAAAGGAGAUG-3'<br>3'-UUGUCCAUAUAUGAAACUUUCCUCUAC-5'<br>5'-AACAGGTATATACTTTGAAAGGAGATG-3' | (SEQ ID NO: 6704)<br>(SEQ ID NO: 1159)<br>(SEQ ID NO: 2268) |
| βc-2848 Target: | 5'-UGGAAGUUAUUAACUUUAAUGUUUUUU-3'<br>3'-ACCUUCAAUAAUUGAAAUUACAAAAAA-5'<br>5'-TGGAAGTTATTAACTTTAATGTTTTTT-3' | (SEQ ID NO: 6705)<br>(SEQ ID NO: 1160)<br>(SEQ ID NO: 2269) |
| βc-2874 Target: | 5'-UGCCACAGCUUUUGCAACUUAAUACUC-3'<br>3'-ACGGUGUCGAAAACGUUGAAUUAUGAG-5'<br>5'-TGCCACAGCTTTTGCAACTTAATACTC-3' | (SEQ ID NO: 6706)<br>(SEQ ID NO: 1161)<br>(SEQ ID NO: 2270) |
| βc-2909 Target: | 5'-AACAUUUGCUGUUUUAAACAUUAAUAG-3'<br>3'-UUGUAAACGACAAAAUUUGUAAUUAUC-5'<br>5'-AACATTTGCTGTTTTAAACATTAATAG-3' | (SEQ ID NO: 6707)<br>(SEQ ID NO: 1162)<br>(SEQ ID NO: 2271) |
| βc-3074 Target: | 5'-AACAAUUGAAGUAAACUUUUUGUUCUG-3'<br>3'-UUGUUAACUUCAUUUGAAAAACAAGAC-5'<br>5'-AACAATTGAAGTAAACTTTTTGTTCTG-3' | (SEQ ID NO: 6708)<br>(SEQ ID NO: 1163)<br>(SEQ ID NO: 2272) |
| βc-3197 Target: | 5'-AAACCCUAGCCUUGCUUGUUAAAUUUU-3'<br>3'-UUUGGGAUCGGAACGAACAAUUUAAAA-5'<br>5'-AAACCCTAGCCTTGCTTGTTAAATTTT-3' | (SEQ ID NO: 6709)<br>(SEQ ID NO: 1164)<br>(SEQ ID NO: 2273) |

TABLE 8-continued

Selected Anti-β-catenin DsiRNA Agents, Blunt Duplexes

| | | |
|---|---|---|
| βc-3203 Target: | 5'-UAGCCUUGCUUGUUAAAUUUUUUUUU-3'<br>3'-AUCGGAACGAACAAUUUAAAAAAAAA-5'<br>5'-TAGCCTTGCTTGTTAAATTTTTTTTT-3' | (SEQ ID NO: 6710)<br>(SEQ ID NO: 1165)<br>(SEQ ID NO: 2274) |
| βc-3273 Target: | 5'-UUGAAGUAGCUCUUUUUUUUUUUUUU-3'<br>3'-AACUUCAUCGAGAAAAAAAAAAAAAA-5'<br>5'-TTGAAGTAGCTCTTTTTTTTTTTTTT-3' | (SEQ ID NO: 6711)<br>(SEQ ID NO: 1166)<br>(SEQ ID NO: 2275) |
| βc-3333 Target: | 5'-UCGUAGUGUUAAGUUAUAGUGAAUACU-3'<br>3'-AGCAUCACAAUUCAAUAUCACUUAUGA-5'<br>5'-TCGTAGTGTTAAGTTATAGTGAATACT-3' | (SEQ ID NO: 6712)<br>(SEQ ID NO: 1167)<br>(SEQ ID NO: 2276) |
| βc-3349 Target: | 5'-UAGUGAAUACUGCUACAGCAAUUUCUA-3'<br>3'-AUCACUUAUGACGAUGUCGUUAAAGAU-5'<br>5'-TAGTGAATACTGCTACAGCAATTTCTA-3' | (SEQ ID NO: 6713)<br>(SEQ ID NO: 1168)<br>(SEQ ID NO: 2277) |
| βc-3354 Target: | 5'-AAUACUGCUACAGCAAUUUCUAAUUUU-3'<br>3'-UUAUGACGAUGUCGUUAAAGAUUAAAA-5'<br>5'-AATACTGCTACAGCAATTTCTAATTTT-3' | (SEQ ID NO: 6714)<br>(SEQ ID NO: 1169)<br>(SEQ ID NO: 2278) |
| βc-3371 Target: | 5'-UUCUAAUUUUUAAGAAUUGAGUAAUGG-3'<br>3'-AAGAUUAAAAAUUCUUAACUCAUUACC-5'<br>5'-TTCTAATTTTTAAGAATTGAGTAATGG-3' | (SEQ ID NO: 6715)<br>(SEQ ID NO: 1170)<br>(SEQ ID NO: 2279) |
| βc-3376 Target: | 5'-AUUUUUAAGAAUUGAGUAAUGGUGUAG-3'<br>3'-UAAAAAUUCUUAACUCAUUACCACAUC-5'<br>5'-ATTTTTAAGAATTGAGTAATGGTGTAG-3' | (SEQ ID NO: 6716)<br>(SEQ ID NO: 1171)<br>(SEQ ID NO: 2280) |
| βc-3411 Target: | 5'-UUCAUAAUCACUCUAAUUAAUUGUAAU-3'<br>3'-AAGUAUUAGUGAGAUUAAUUAACAUUA-5'<br>5'-TTCATAATCACTCTAATTAATTGTAAT-3' | (SEQ ID NO: 6717)<br>(SEQ ID NO: 1172)<br>(SEQ ID NO: 2281) |
| βc-3426 Target: | 5'-AUUAAUUGUAAUCUGAAUAAAGUGUAA-3'<br>3'-UAAUUAACAUUAGACUUAUUUCACAUU-5'<br>5'-ATTAATTGTAATCTGAATAAAGTGTAA-3' | (SEQ ID NO: 6718)<br>(SEQ ID NO: 1173)<br>(SEQ ID NO: 2282) |
| βc-3431 Target: | 5'-UUGUAAUCUGAAUAAAGUGUAACAAUU-3'<br>3'-AACAUUAGACUUAUUUCACAUUGUUAA-5'<br>5'-TTGTAATCTGAATAAAGTGTAACAATT-3' | (SEQ ID NO: 6719)<br>(SEQ ID NO: 1174)<br>(SEQ ID NO: 2283) |
| βc-3437 Target: | 5'-UCUGAAUAAAGUGUAACAAUUGUGUAG-3'<br>3'-AGACUUAUUUCACAUUGUUAACACAUC-5'<br>5'-TCTGAATAAAGTGTAACAATTGTGTAG-3' | (SEQ ID NO: 6720)<br>(SEQ ID NO: 1175)<br>(SEQ ID NO: 2284) |
| βc-3458 Target: | 5'-GUGUAGCCUUUUUGUAUAAAAUAGACA-3'<br>3'-CACAUCGGAAAAACAUAUUUUAUCUGU-5'<br>5'-GTGTAGCCTTTTGTATAAAATAGACA-3' | (SEQ ID NO: 6721)<br>(SEQ ID NO: 1176)<br>(SEQ ID NO: 2285) |
| βc-3468 Target: | 5'-UUUGUAUAAAAUAGACAAAUAGAAAAU-3'<br>3'-AAACAUAUUUUAUCUGUUUAUCUUUUA-5'<br>5'-TTTGTATAAAATAGACAAATAGAAAAT-3' | (SEQ ID NO: 6722)<br>(SEQ ID NO: 1177)<br>(SEQ ID NO: 2286) |
| βc-3488 Target: | 5'-AGAAAAUGGUCCAAUUAGUUUCCUUUU-3'<br>3'-UCUUUUACCAGGUUAAUCAAAGGAAAA-5'<br>5'-AGAAAATGGTCCAATTAGTTTCCTTTT-3' | (SEQ ID NO: 6723)<br>(SEQ ID NO: 1178)<br>(SEQ ID NO: 2287) |
| βc-3496 Target: | 5'-GUCCAAUUAGUUUCCUUUUAAUAUGC-3'<br>3'-CAGGUUAAUCAAAGGAAAAUUAUACG-5'<br>5'-GTCCAATTAGTTTCCTTTTAATATGC-3' | (SEQ ID NO: 6724)<br>(SEQ ID NO: 1179)<br>(SEQ ID NO: 2288) |
| βc-3552 Target: | 5'-UUUUUGAUCAAAACUAUUUGGGAUAU-3'<br>3'-AAAAACUAGUUUUUGAUAAACCCUAUA-5'<br>5'-TTTTTGATCAAAACTATTTGGGATAT-3' | (SEQ ID NO: 6725)<br>(SEQ ID NO: 1180)<br>(SEQ ID NO: 2289) |
| βc-3600 Target: | 5'-AAGAGGUGUUAUUUGGAACCUUGUUUU-3'<br>3'-UUCUCCACAAUAAACCUUGGAACAAAA-5'<br>5'-AAGAGGTGTTATTTGGAACCTTGTTTT-3' | (SEQ ID NO: 6726)<br>(SEQ ID NO: 1181)<br>(SEQ ID NO: 2290) |
| βc-3605 Target: | 5'-GUGUUAUUUGGAACCUUGUUUUGGACA-3'<br>3'-CACAAUAAACCUUGGAACAAAACCUGU-5'<br>5'-GTGTTATTTGGAACCTTGTTTTGGACA-3' | (SEQ ID NO: 6727)<br>(SEQ ID NO: 1182)<br>(SEQ ID NO: 2291) |
| βc-3615 Target: | 5'-GAACCUUGUUUUGGACAGUUUACCAGU-3'<br>3'-CUUGGAACAAAACCUGUCAAAUGGUCA-5'<br>5'-GAACCTTGTTTTGGACAGTTTACCAGT-3' | (SEQ ID NO: 6728)<br>(SEQ ID NO: 1183)<br>(SEQ ID NO: 2292) |

TABLE 8-continued

Selected Anti-β-catenin DsiRNA Agents, Blunt Duplexes

| | | |
|---|---|---|
| βc-3674 Target: | 5'-GUGAUACGAUGCUUCAAGAGAAAAUGC-3'<br>3'-CACUAUGCUACGAAGUUCUCUUUUACG-5'<br>5'-GTGATACGATGCTTCAAGAGAAAATGC-3' | (SEQ ID NO: 6729)<br>(SEQ ID NO: 1184)<br>(SEQ ID NO: 2293) |
| βc-3686 Target: | 5'-UUCAAGAGAAAAUGCGGUUAUAAAAAA-3'<br>3'-AAGUUCUCUUUUACGCCAAUAUUUUUU-5'<br>5'-TTCAAGAGAAAATGCGGTTATAAAAAA-3' | (SEQ ID NO: 6730)<br>(SEQ ID NO: 1185)<br>(SEQ ID NO: 2294) |
| βc-3691 Target: | 5'-GAGAAAAUGCGGUUAUAAAAAAUGGUU-3'<br>3'-CUCUUUUACGCCAAUAUUUUUUACCAA-5'<br>5'-GAGAAAATGCGGTTATAAAAAATGGTT-3' | (SEQ ID NO: 6731)<br>(SEQ ID NO: 1186)<br>(SEQ ID NO: 2295) |
| βc-3700 Target: | 5'-CGGUUAUAAAAAAUGGUUCAGAAUUAA-3'<br>3'-GCCAAUAUUUUUUACCAAGUCUUAAUU-5'<br>5'-CGGTTATAAAAAATGGTTCAGAATTAA-3' | (SEQ ID NO: 6732)<br>(SEQ ID NO: 1187)<br>(SEQ ID NO: 2296) |
| βc-3707 Target: | 5'-AAAAAAUGGUUCAGAAUUAAACUUUUA-3'<br>3'-UUUUUUACCAAGUCUUAAUUUGAAAAU-5'<br>5'-AAAAAATGGTTCAGAATTAAACTTTTA-3' | (SEQ ID NO: 6733)<br>(SEQ ID NO: 1188)<br>(SEQ ID NO: 2297) |
| βc-284 Target: | 5'-CAGCGUGGACAAUGGCUACUCAAGCUG-3'<br>3'-GUCGCACCUGUUACCGAUGAGUUCGAC-5'<br>5'-CAGCGTGGACAATGGCTACTCAAGCTG-3' | (SEQ ID NO: 6734)<br>(SEQ ID NO: 1189)<br>(SEQ ID NO: 2298) |
| βc-285 Target: | 5'-AGCGUGGACAAUGGCUACUCAAGCUGA-3'<br>3'-UCGCACCUGUUACCGAUGAGUUCGACU-5'<br>5'-AGCGTGGACAATGGCTACTCAAGCTGA-3' | (SEQ ID NO: 6735)<br>(SEQ ID NO: 1190)<br>(SEQ ID NO: 2299) |
| βc-286 Target: | 5'-GCGUGGACAAUGGCUACUCAAGCUGAU-3'<br>3'-CGCACCUGUUACCGAUGAGUUCGACUA-5'<br>5'-GCGTGGACAATGGCTACTCAAGCTGAT-3' | (SEQ ID NO: 6736)<br>(SEQ ID NO: 1191)<br>(SEQ ID NO: 2300) |
| βc-287 Target: | 5'-CGUGGACAAUGGCUACUCAAGCUGAUU-3'<br>3'-GCACCUGUUACCGAUGAGUUCGACUAA-5'<br>5'-CGTGGACAATGGCTACTCAAGCTGATT-3' | (SEQ ID NO: 6737)<br>(SEQ ID NO: 1192)<br>(SEQ ID NO: 2301) |
| βc-288 Target: | 5'-GUGGACAAUGGCUACUCAAGCUGAUUU-3'<br>3'-CACCUGUUACCGAUGAGUUCGACUAAA-5'<br>5'-GTGGACAATGGCTACTCAAGCTGATTT-3' | (SEQ ID NO: 6738)<br>(SEQ ID NO: 1193)<br>(SEQ ID NO: 2302) |
| βc-289 Target: | 5'-UGGACAAUGGCUACUCAAGCUGAUUUG-3'<br>3'-ACCUGUUACCGAUGAGUUCGACUAAAC-5'<br>5'-TGGACAATGGCTACTCAAGCTGATTTG-3' | (SEQ ID NO: 6739)<br>(SEQ ID NO: 1194)<br>(SEQ ID NO: 2303) |
| βc-290 Target: | 5'-GGACAAUGGCUACUCAAGCUGAUUUGA-3'<br>3'-CCUGUUACCGAUGAGUUCGACUAAACU-5'<br>5'-GGACAATGGCTACTCAAGCTGATTTGA-3' | (SEQ ID NO: 6740)<br>(SEQ ID NO: 1195)<br>(SEQ ID NO: 2304) |
| βc-291 Target: | 5'-GACAAUGGCUACUCAAGCUGAUUUGAU-3'<br>3'-CUGUUACCGAUGAGUUCGACUAAACUA-5'<br>5'-GACAATGGCTACTCAAGCTGATTTGAT-3' | (SEQ ID NO: 6741)<br>(SEQ ID NO: 1196)<br>(SEQ ID NO: 2305) |
| βc-312 Target: | 5'-UUUGAUGGAGUUGGACAUGGCCAUGGA-3'<br>3'-AAACUACCUCAACCUGUACCGGUACCU-5'<br>5'-TTTGATGGAGTTGGACATGGCCATGGA-3' | (SEQ ID NO: 6742)<br>(SEQ ID NO: 1197)<br>(SEQ ID NO: 2306) |
| βc-313 Target: | 5'-UUGAUGGAGUUGGACAUGGCCAUGGAA-3'<br>3'-AACUACCUCAACCUGUACCGGUACCUU-5'<br>5'-TTGATGGAGTTGGACATGGCCATGGAA-3' | (SEQ ID NO: 6743)<br>(SEQ ID NO: 1198)<br>(SEQ ID NO: 2307) |
| βc-314 Target: | 5'-UGAUGGAGUUGGACAUGGCCAUGGAAC-3'<br>3'-ACUACCUCAACCUGUACCGGUACCUUG-5'<br>5'-TGATGGAGTTGGACATGGCCATGGAAC-3' | (SEQ ID NO: 6744)<br>(SEQ ID NO: 1199)<br>(SEQ ID NO: 2308) |
| βc-315 Target: | 5'-GAUGGAGUUGGACAUGGCCAUGGAACC-3'<br>3'-CUACCUCAACCUGUACCGGUACCUUGG-5'<br>5'-GATGGAGTTGGACATGGCCATGGAACC-3' | (SEQ ID NO: 6745)<br>(SEQ ID NO: 1200)<br>(SEQ ID NO: 2309) |
| βc-316 Target: | 5'-AUGGAGUUGGACAUGGCCAUGGAACCA-3'<br>3'-UACCUCAACCUGUACCGGUACCUUGGU-5'<br>5'-ATGGAGTTGGACATGGCCATGGAACCA-3' | (SEQ ID NO: 6746)<br>(SEQ ID NO: 1201)<br>(SEQ ID NO: 2310) |
| βc-317 Target: | 5'-UGGAGUUGGACAUGGCCAUGGAACCAG-3'<br>3'-ACCUCAACCUGUACCGGUACCUUGGUC-5'<br>5'-TGGAGTTGGACATGGCCATGGAACCAG-3' | (SEQ ID NO: 6747)<br>(SEQ ID NO: 1202)<br>(SEQ ID NO: 2311) |

TABLE 8-continued

Selected Anti-β-catenin DsiRNA Agents, Blunt Duplexes

| | | |
|---|---|---|
| βc-318 Target: | 5'-GGAGUUGGACAUGGCCAUGGAACCAGA-3'<br>3'-CCUCAACCUGUACCGGUACCUUGGUCU-5'<br>5'-GGAGTTGGACATGGCCATGGAACCAGA-3' | (SEQ ID NO: 6748)<br>(SEQ ID NO: 1203)<br>(SEQ ID NO: 2312) |
| βc-389 Target: | 5'-ACUCUGGAAUCCAUUCUGGUGCCACUA-3'<br>3'-UGAGACCUUAGGUAAGACCACGGUGAU-5'<br>5'-ACTCTGGAATCCATTCTGGTGCCACTA-3' | (SEQ ID NO: 6749)<br>(SEQ ID NO: 1204)<br>(SEQ ID NO: 2313) |
| βc-390 Target: | 5'-CUCUGGAAUCCAUUCUGGUGCCACUAC-3'<br>3'-GAGACCUUAGGUAAGACCACGGUGAUG-5'<br>5'-CTCTGGAATCCATTCTGGTGCCACTAC-3' | (SEQ ID NO: 6750)<br>(SEQ ID NO: 1205)<br>(SEQ ID NO: 2314) |
| βc-391 Target: | 5'-UCUGGAAUCCAUUCUGGUGCCACUACC-3'<br>3'-AGACCUUAGGUAAGACCACGGUGAUGG-5'<br>5'-TCTGGAATCCATTCTGGTGCCACTACC-3' | (SEQ ID NO: 6751)<br>(SEQ ID NO: 1206)<br>(SEQ ID NO: 2315) |
| βc-392 Target: | 5'-CUGGAAUCCAUUCUGGUGCCACUACCA-3'<br>3'-GACCUUAGGUAAGACCACGGUGAUGGU-5'<br>5'-CTGGAATCCATTCTGGTGCCACTACCA-3' | (SEQ ID NO: 6752)<br>(SEQ ID NO: 1207)<br>(SEQ ID NO: 2316) |
| βc-393 Target: | 5'-UGGAAUCCAUUCUGGUGCCACUACCAC-3'<br>3'-ACCUUAGGUAAGACCACGGUGAUGGUG-5'<br>5'-TGGAATCCATTCTGGTGCCACTACCAC-3' | (SEQ ID NO: 6753)<br>(SEQ ID NO: 1208)<br>(SEQ ID NO: 2317) |
| βc-600 Target: | 5'-AUUAGAUGAGGGCAUGCAGAUCCCAUC-3'<br>3'-UAAUCUACUCCCGUACGUCUAGGGUAG-5'<br>5'-ATTAGATGAGGGCATGCAGATCCCATC-3' | (SEQ ID NO: 6754)<br>(SEQ ID NO: 1209)<br>(SEQ ID NO: 2318) |
| βc-601 Target: | 5'-UUAGAUGAGGGCAUGCAGAUCCCAUCU-3'<br>3'-AAUCUACUCCCGUACGUCUAGGGUAGA-5'<br>5'-TTAGATGAGGGCATGCAGATCCCATCT-3' | (SEQ ID NO: 6755)<br>(SEQ ID NO: 1210)<br>(SEQ ID NO: 2319) |
| βc-602 Target: | 5'-UAGAUGAGGGCAUGCAGAUCCCAUCUA-3'<br>3'-AUCUACUCCCGUACGUCUAGGGUAGAU-5'<br>5'-TAGATGAGGGCATGCAGATCCCATCTA-3' | (SEQ ID NO: 6756)<br>(SEQ ID NO: 1211)<br>(SEQ ID NO: 2320) |
| βc-603 Target: | 5'-AGAUGAGGGCAUGCAGAUCCCAUCUAC-3'<br>3'-UCUACUCCCGUACGUCUAGGGUAGAUG-5'<br>5'-AGATGAGGGCATGCAGATCCCATCTAC-3' | (SEQ ID NO: 6757)<br>(SEQ ID NO: 1212)<br>(SEQ ID NO: 2321) |
| βc-604 Target: | 5'-GAUGAGGGCAUGCAGAUCCCAUCUACA-3'<br>3'-CUACUCCCGUACGUCUAGGGUAGAUGU-5'<br>5'-GATGAGGGCATGCAGATCCCATCTACA-3' | (SEQ ID NO: 6758)<br>(SEQ ID NO: 1213)<br>(SEQ ID NO: 2322) |
| βc-605 Target: | 5'-AUGAGGGCAUGCAGAUCCCAUCUACAC-3'<br>3'-UACUCCCGUACGUCUAGGGUAGAUGUG-5'<br>5'-ATGAGGGCATGCAGATCCCATCTACAC-3' | (SEQ ID NO: 6759)<br>(SEQ ID NO: 1214)<br>(SEQ ID NO: 2323) |
| βc-638 Target: | 5'-AUGCUGCUCAUCCCACUAAUGUCCAGC-3'<br>3'-UACGACGAGUAGGGUGAUUACAGGUCG-5'<br>5'-ATGCTGCTCATCCCACTAATGTCCAGC-3' | (SEQ ID NO: 6760)<br>(SEQ ID NO: 1215)<br>(SEQ ID NO: 2324) |
| βc-639 Target: | 5'-UGCUGCUCAUCCCACUAAUGUCCAGCG-3'<br>3'-ACGACGAGUAGGGUGAUUACAGGUCGC-5'<br>5'-TGCTGCTCATCCCACTAATGTCCAGCG-3' | (SEQ ID NO: 6761)<br>(SEQ ID NO: 1216)<br>(SEQ ID NO: 2325) |
| βc-640 Target: | 5'-GCUGCUCAUCCCACUAAUGUCCAGCGU-3'<br>3'-CGACGAGUAGGGUGAUUACAGGUCGCA-5'<br>5'-GCTGCTCATCCCACTAATGTCCAGCGT-3' | (SEQ ID NO: 6762)<br>(SEQ ID NO: 1217)<br>(SEQ ID NO: 2326) |
| βc-641 Target: | 5'-CUGCUCAUCCCACUAAUGUCCAGCGUU-3'<br>3'-GACGAGUAGGGUGAUUACAGGUCGCAA-5'<br>5'-CTGCTCATCCCACTAATGTCCAGCGTT-3' | (SEQ ID NO: 6763)<br>(SEQ ID NO: 1218)<br>(SEQ ID NO: 2327) |
| βc-642 Target: | 5'-UGCUCAUCCCACUAAUGUCCAGCGUUU-3'<br>3'-ACGAGUAGGGUGAUUACAGGUCGCAAA-5'<br>5'-TGCTCATCCCACTAATGTCCAGCGTTT-3' | (SEQ ID NO: 6764)<br>(SEQ ID NO: 1219)<br>(SEQ ID NO: 2328) |
| βc-643 Target: | 5'-GCUCAUCCCACUAAUGUCCAGCGUUUG-3'<br>3'-CGAGUAGGGUGAUUACAGGUCGCAAAC-5'<br>5'-GCTCATCCCACTAATGTCCAGCGTTTG-3' | (SEQ ID NO: 6765)<br>(SEQ ID NO: 1220)<br>(SEQ ID NO: 2329) |
| βc-644 Target: | 5'-CUCAUCCCACUAAUGUCCAGCGUUUGG-3'<br>3'-GAGUAGGGUGAUUACAGGUCGCAAACC-5'<br>5'-CTCATCCCACTAATGTCCAGCGTTTGG-3' | (SEQ ID NO: 6766)<br>(SEQ ID NO: 1221)<br>(SEQ ID NO: 2330) |

TABLE 8-continued

Selected Anti-β-catenin DsiRNA Agents, Blunt Duplexes

| | | |
|---|---|---|
| | 5'-UCAUCCCACUAAUGUCCAGCGUUUGGC-3' | (SEQ ID NO: 6767) |
| | 3'-AGUAGGGUGAUUACAGGUCGCAAACCG-5' | (SEQ ID NO: 1222) |
| βc-645 Target: | 5'-TCATCCCACTAATGTCCAGCGTTTGGC-3' | (SEQ ID NO: 2331) |
| | 5'-GUUUGGCUGAACCAUCACAGAUGCUGA-3' | (SEQ ID NO: 6768) |
| | 3'-CAAACCGACUUGGUAGUGUCUACGACU-5' | (SEQ ID NO: 1223) |
| βc-665 Target: | 5'-GTTTGGCTGAACCATCACAGATGCTGA-3' | (SEQ ID NO: 2332) |
| | 5'-UUUGGCUGAACCAUCACAGAUGCUGAA-3' | (SEQ ID NO: 6769) |
| | 3'-AAACCGACUUGGUAGUGUCUACGACUU-5' | (SEQ ID NO: 1224) |
| βc-666 Target: | 5'-TTTGGCTGAACCATCACAGATGCTGAA-3' | (SEQ ID NO: 2333) |
| | 5'-UUGGCUGAACCAUCACAGAUGCUGAAA-3' | (SEQ ID NO: 6770) |
| | 3'-AACCGACUUGGUAGUGUCUACGACUUU-5' | (SEQ ID NO: 1225) |
| βc-667 Target: | 5'-TTGGCTGAACCATCACAGATGCTGAAA-3' | (SEQ ID NO: 2334) |
| | 5'-CAGAACUUGCCACACGUGCAAUCCCUG-3' | (SEQ ID NO: 6771) |
| | 3'-GUCUUGAACGGUGUGCACGUUAGGGAC-5' | (SEQ ID NO: 1226) |
| βc-731 Target: | 5'-CAGAACTTGCCACACGTGCAATCCCTG-3' | (SEQ ID NO: 2335) |
| | 5'-AGAACUUGCCACACGUGCAAUCCCUGA-3' | (SEQ ID NO: 6772) |
| | 3'-UCUUGAACGGUGUGCACGUUAGGGACU-5' | (SEQ ID NO: 1227) |
| βc-732 Target: | 5'-AGAACTTGCCACACGTGCAATCCCTGA-3' | (SEQ ID NO: 2336) |
| | 5'-CAGUUAUGGUCCAUCAGCUUUCUAAAA-3' | (SEQ ID NO: 6773) |
| | 3'-GUCAAUACCAGGUAGUCGAAAGAUUUU-5' | (SEQ ID NO: 1228) |
| βc-809 Target: | 5'-CAGTTATGGTCCATCAGCTTTCTAAAA-3' | (SEQ ID NO: 2337) |
| | 5'-AGUUAUGGUCCAUCAGCUUUCUAAAAA-3' | (SEQ ID NO: 6774) |
| | 3'-UCAAUACCAGGUAGUCGAAAGAUUUUU-5' | (SEQ ID NO: 1229) |
| βc-810 Target: | 5'-AGTTATGGTCCATCAGCTTTCTAAAAA-3' | (SEQ ID NO: 2338) |
| | 5'-CUAAAAAGGAAGCUUCCAGACACGCUA-3' | (SEQ ID NO: 6775) |
| | 3'-GAUUUUUCCUUCGAAGGUCUGUGCGAU-5' | (SEQ ID NO: 1230) |
| βc-830 Target: | 5'-CTAAAAAGGAAGCTTCCAGACACGCTA-3' | (SEQ ID NO: 2339) |
| | 5'-UAAAAAGGAAGCUUCCAGACACGCUAU-3' | (SEQ ID NO: 6776) |
| | 3'-AUUUUUCCUUCGAAGGUCUGUGCGAUA-5' | (SEQ ID NO: 1231) |
| βc-831 Target: | 5'-TAAAAAGGAAGCTTCCAGACACGCTAT-3' | (SEQ ID NO: 2340) |
| | 5'-GUACCAUGCAGAAUACAAAUGAUGUAG-3' | (SEQ ID NO: 6777) |
| | 3'-CAUGGUACGUCUUAUGUUUACUACAUC-5' | (SEQ ID NO: 1232) |
| βc-893 Target: | 5'-GTACCATGCAGAATACAAATGATGTAG-3' | (SEQ ID NO: 2341) |
| | 5'-UACCAUGCAGAAUACAAAUGAUGUAGA-3' | (SEQ ID NO: 6778) |
| | 3'-AUGGUACGUCUUAUGUUUACUACAUCU-5' | (SEQ ID NO: 1233) |
| βc-894 Target: | 5'-TACCATGCAGAATACAAATGATGTAGA-3' | (SEQ ID NO: 2342) |
| | 5'-ACCAUGCAGAAUACAAAUGAUGUAGAA-3' | (SEQ ID NO: 6779) |
| | 3'-UGGUACGUCUUAUGUUUACUACAUCUU-5' | (SEQ ID NO: 1234) |
| βc-895 Target: | 5'-ACCATGCAGAATACAAATGATGTAGAA-3' | (SEQ ID NO: 2343) |
| | 5'-CCAUGCAGAAUACAAAUGAUGUAGAAA-3' | (SEQ ID NO: 6780) |
| | 3'-GGUACGUCUUAUGUUUACUACAUCUUU-5' | (SEQ ID NO: 1235) |
| βc-896 Target: | 5'-CCATGCAGAATACAAATGATGTAGAAA-3' | (SEQ ID NO: 2344) |
| | 5'-CAUGCAGAAUACAAAUGAUGUAGAAAC-3' | (SEQ ID NO: 6781) |
| | 3'-GUACGUCUUAUGUUUACUACAUCUUUG-5' | (SEQ ID NO: 1236) |
| βc-897 Target: | 5'-CATGCAGAATACAAATGATGTAGAAAC-3' | (SEQ ID NO: 2345) |
| | 5'-AUGCAGAAUACAAAUGAUGUAGAAACA-3' | (SEQ ID NO: 6782) |
| | 3'-UACGUCUUAUGUUUACUACAUCUUUGU-5' | (SEQ ID NO: 1237) |
| βc-898 Target: | 5'-ATGCAGAATACAAATGATGTAGAAACA-3' | (SEQ ID NO: 2346) |
| | 5'-UGCAGAAUACAAAUGAUGUAGAAACAG-3' | (SEQ ID NO: 6783) |
| | 3'-ACGUCUUAUGUUUACUACAUCUUUGUC-5' | (SEQ ID NO: 1238) |
| βc-899 Target: | 5'-TGCAGAATACAAATGATGTAGAAACAG-3' | (SEQ ID NO: 2347) |
| | 5'-GCAGAAUACAAAUGAUGUAGAAACAGC-3' | (SEQ ID NO: 6784) |
| | 3'-CGUCUUAUGUUUACUACAUCUUUGUCG-5' | (SEQ ID NO: 1239) |
| βc-900 Target: | 5'-GCAGAATACAAATGATGTAGAAACAGC-3' | (SEQ ID NO: 2348) |
| | 5'-UACUGGCCAUCUUUAAGUCUGGAGGCA-3' | (SEQ ID NO: 6785) |
| | 3'-AUGACCGGUAGAAAUUCAGACCUCCGU-5' | (SEQ ID NO: 1240) |
| βc-977 Target: | 5'-TACTGGCCATCTTTAAGTCTGGAGGCA-3' | (SEQ ID NO: 2349) |

TABLE 8-continued

Selected Anti-β-catenin DsiRNA Agents, Blunt Duplexes

|  |  |  |
|---|---|---|
| βc-978 Target: | 5'-ACUGGCCAUCUUUAAGUCUGGAGGCAU-3'<br>3'-UGACCGGUAGAAAUUCAGACCUCCGUA-5'<br>5'-ACTGGCCATCTTTAAGTCTGGAGGC-3' | (SEQ ID NO: 6786)<br>(SEQ ID NO: 1241)<br>(SEQ ID NO: 2350) |
| βc-1091 Target: | 5'-AAGAAGGAGCUAAAAUGGCAGUGCGUU-3'<br>3'-UUCUUCCUCGAUUUUACCGUCACGCAA-5'<br>5'-AAGAAGGAGCTAAAATGGCAGTGCGTT-3' | (SEQ ID NO: 6787)<br>(SEQ ID NO: 1242)<br>(SEQ ID NO: 2351) |
| βc-1092 Target: | 5'-AGAAGGAGCUAAAAUGGCAGUGCGUUU-3'<br>3'-UCUUCCUCGAUUUUACCGUCACGCAAA-5'<br>5'-AGAAGGAGCTAAAATGGCAGTGCGTTT-3' | (SEQ ID NO: 6788)<br>(SEQ ID NO: 1243)<br>(SEQ ID NO: 2352) |
| βc-1093 Target: | 5'-GAAGGAGCUAAAAUGGCAGUGCGUUUA-3'<br>3'-CUUCCUCGAUUUUACCGUCACGCAAAU-5'<br>5'-GAAGGAGCTAAAATGGCAGTGCGTTTA-3' | (SEQ ID NO: 6789)<br>(SEQ ID NO: 1244)<br>(SEQ ID NO: 2353) |
| βc-1094 Target: | 5'-AAGGAGCUAAAAUGGCAGUGCGUUUAG-3'<br>3'-UUCCUCGAUUUUACCGUCACGCAAAUC-5'<br>5'-AAGGAGCTAAAATGGCAGTGCGTTTAG-3' | (SEQ ID NO: 6790)<br>(SEQ ID NO: 1245)<br>(SEQ ID NO: 2354) |
| βc-1095 Target: | 5'-AGGAGCUAAAAUGGCAGUGCGUUUAGC-3'<br>3'-UCCUCGAUUUUACCGUCACGCAAAUCG-5'<br>5'-AGGAGCTAAAATGGCAGTGCGTTTAGC-3' | (SEQ ID NO: 6791)<br>(SEQ ID NO: 1246)<br>(SEQ ID NO: 2355) |
| βc-1301 Target: | 5'-UACUGUGGACCACAAGCAGAGUGCUGA-3'<br>3'-AUGACACCUGGUGUUCGUCUCACGACU-5'<br>5'-TACTGTGGACCACAAGCAGAGTGCTGA-3' | (SEQ ID NO: 6792)<br>(SEQ ID NO: 1247)<br>(SEQ ID NO: 2356) |
| βc-1302 Target: | 5'-ACUGUGGACCACAAGCAGAGUGCUGAA-3'<br>3'-UGACACCUGGUGUUCGUCUCACGACUU-5'<br>5'-ACTGTGGACCACAAGCAGAGTGCTGAA-3' | (SEQ ID NO: 6793)<br>(SEQ ID NO: 1248)<br>(SEQ ID NO: 2357) |
| βc-1303 Target: | 5'-CUGUGGACCACAAGCAGAGUGCUGAAG-3'<br>3'-GACACCUGGUGUUCGUCUCACGACUUC-5'<br>5'-CTGTGGACCACAAGCAGAGTGCTGAAG-3' | (SEQ ID NO: 6794)<br>(SEQ ID NO: 1249)<br>(SEQ ID NO: 2358) |
| βc-1304 Target: | 5'-UGUGGACCACAAGCAGAGUGCUGAAGG-3'<br>3'-ACACCUGGUGUUCGUCUCACGACUUCC-5'<br>5'-TGTGGACCACAAGCAGAGTGCTGAAGG-3' | (SEQ ID NO: 6795)<br>(SEQ ID NO: 1250)<br>(SEQ ID NO: 2359) |
| βc-1305 Target: | 5'-GUGGACCACAAGCAGAGUGCUGAAGGU-3'<br>3'-CACCUGGUGUUCGUCUCACGACUUCCA-5'<br>5'-GTGGACCACAAGCAGAGTGCTGAAGGT-3' | (SEQ ID NO: 6796)<br>(SEQ ID NO: 1251)<br>(SEQ ID NO: 2360) |
| βc-1306 Target: | 5'-UGGACCACAAGCAGAGUGCUGAAGGUG-3'<br>3'-ACCUGGUGUUCGUCUCACGACUUCCAC-5'<br>5'-TGGACCACAAGCAGAGTGCTGAAGGTG-3' | (SEQ ID NO: 6797)<br>(SEQ ID NO: 1252)<br>(SEQ ID NO: 2361) |
| βc-1307 Target: | 5'-GGACCACAAGCAGAGUGCUGAAGGUGC-3'<br>3'-CCUGGUGUUCGUCUCACGACUUCCACG-5'<br>5'-GGACCACAAGCAGAGTGCTGAAGGTGC-3' | (SEQ ID NO: 6798)<br>(SEQ ID NO: 1253)<br>(SEQ ID NO: 2362) |
| βc-1308 Target: | 5'-GACCACAAGCAGAGUGCUGAAGGUGCU-3'<br>3'-CUGGUGUUCGUCUCACGACUUCCACGA-5'<br>5'-GACCACAAGCAGAGTGCTGAAGGTGCT-3' | (SEQ ID NO: 6799)<br>(SEQ ID NO: 1254)<br>(SEQ ID NO: 2363) |
| βc-1309 Target: | 5'-ACCACAAGCAGAGUGCUGAAGGUGCUA-3'<br>3'-UGGUGUUCGUCUCACGACUUCCACGAU-5'<br>5'-ACCACAAGCAGAGTGCTGAAGGTGCTA-3' | (SEQ ID NO: 6800)<br>(SEQ ID NO: 1255)<br>(SEQ ID NO: 2364) |
| βc-1310 Target: | 5'-CCACAAGCAGAGUGCUGAAGGUGCUAU-3'<br>3'-GGUGUUCGUCUCACGACUUCCACGAUA-5'<br>5'-CCACAAGCAGAGTGCTGAAGGTGCTAT-3' | (SEQ ID NO: 6801)<br>(SEQ ID NO: 1256)<br>(SEQ ID NO: 2365) |
| βc-1311 Target: | 5'-CACAAGCAGAGUGCUGAAGGUGCUAUC-3'<br>3'-GUGUUCGUCUCACGACUUCCACGAUAG-5'<br>5'-CACAAGCAGAGTGCTGAAGGTGCTATC-3' | (SEQ ID NO: 6802)<br>(SEQ ID NO: 1257)<br>(SEQ ID NO: 2366) |
| βc-1312 Target: | 5'-ACAAGCAGAGUGCUGAAGGUGCUAUCU-3'<br>3'-UGUUCGUCUCACGACUUCCACGAUAGA-5'<br>5'-ACAAGCAGAGTGCTGAAGGTGCTATCT-3' | (SEQ ID NO: 6803)<br>(SEQ ID NO: 1258)<br>(SEQ ID NO: 2367) |
| βc-1313 Target: | 5'-CAAGCAGAGUGCUGAAGGUGCUAUCUG-3'<br>3'-GUUCGUCUCACGACUUCCACGAUAGAC-5'<br>5'-CAAGCAGAGTGCTGAAGGTGCTATCTG-3' | (SEQ ID NO: 6804)<br>(SEQ ID NO: 1259)<br>(SEQ ID NO: 2368) |

TABLE 8-continued

Selected Anti-β-catenin DsiRNA Agents, Blunt Duplexes

|  |  |  |  |
|---|---|---|---|
| βc-1314 | Target: | 5'-AAGCAGAGUGCUGAAGGUGCUAUCUGU-3'<br>3'-UUCGUCUCACGACUUCCACGAUAGACA-5'<br>5'-AAGCAGAGTGCTGAAGGTGCTATCTGT-3' | (SEQ ID NO: 6805)<br>(SEQ ID NO: 1260)<br>(SEQ ID NO: 2369) |
| βc-1430 | Target: | 5'-AGAACUGUCUUUGGACUCUCAGGAAUC-3'<br>3'-UCUUGACAGAAACCUGAGAGUCCUUAG-5'<br>5'-AGAACTGTCTTTGGACTCTCAGGAATC-3' | (SEQ ID NO: 6806)<br>(SEQ ID NO: 1261)<br>(SEQ ID NO: 2370) |
| βc-1431 | Target: | 5'-GAACUGUCUUUGGACUCUCAGGAAUCU-3'<br>3'-CUUGACAGAAACCUGAGAGUCCUUAGA-5'<br>5'-GAACTGTCTTTGGACTCTCAGGAATCT-3' | (SEQ ID NO: 6807)<br>(SEQ ID NO: 1262)<br>(SEQ ID NO: 2371) |
| βc-1526 | Target: | 5'-CAGAUGAUAUAAAUGUGGUCACCUGUG-3'<br>3'-GUCUACUAUAUUUACACCAGUGGACAC-5'<br>5'-CAGATGATATAAATGTGGTCACCTGTG-3' | (SEQ ID NO: 6808)<br>(SEQ ID NO: 1263)<br>(SEQ ID NO: 2372) |
| βc-1527 | Target: | 5'-AGAUGAUAUAAAUGUGGUCACCUGUGC-3'<br>3'-UCUACUAUAUUUACACCAGUGGACACG-5'<br>5'-AGATGATATAAATGTGGTCACCTGTGC-3' | (SEQ ID NO: 6809)<br>(SEQ ID NO: 1264)<br>(SEQ ID NO: 2373) |
| βc-1528 | Target: | 5'-GAUGAUAUAAAUGUGGUCACCUGUGCA-3'<br>3'-CUACUAUAUUUACACCAGUGGACACGU-5'<br>5'-GATGATATAAATGTGGTCACCTGTGCA-3' | (SEQ ID NO: 6810)<br>(SEQ ID NO: 1265)<br>(SEQ ID NO: 2374) |
| βc-1529 | Target: | 5'-AUGAUAUAAAUGUGGUCACCUGUGCAG-3'<br>3'-UACUAUAUUUACACCAGUGGACACGUC-5'<br>5'-ATGATATAAATGTGGTCACCTGTGCAG-3' | (SEQ ID NO: 6811)<br>(SEQ ID NO: 1266)<br>(SEQ ID NO: 2375) |
| βc-1530 | Target: | 5'-UGAUAUAAAUGUGGUCACCUGUGCAGC-3'<br>3'-ACUAUAUUUACACCAGUGGACACGUCG-5'<br>5'-TGATATAAATGTGGTCACCTGTGCAGC-3' | (SEQ ID NO: 6812)<br>(SEQ ID NO: 1267)<br>(SEQ ID NO: 2376) |
| βc-1531 | Target: | 5'-GAUAUAAAUGUGGUCACCUGUGCAGCU-3'<br>3'-CUAUAUUUACACCAGUGGACACGUCGA-5'<br>5'-GATATAAATGTGGTCACCTGTGCAGCT-3' | (SEQ ID NO: 6813)<br>(SEQ ID NO: 1268)<br>(SEQ ID NO: 2377) |
| βc-1532 | Target: | 5'-AUAUAAAUGUGGUCACCUGUGCAGCUG-3'<br>3'-UAUAUUUACACCAGUGGACACGUCGAC-5'<br>5'-ATATAAATGTGGTCACCTGTGCAGCTG-3' | (SEQ ID NO: 6814)<br>(SEQ ID NO: 1269)<br>(SEQ ID NO: 2378) |
| βc-1533 | Target: | 5'-UAUAAAUGUGGUCACCUGUGCAGCUGG-3'<br>3'-AUAUUUACACCAGUGGACACGUCGACC-5'<br>5'-TATAAATGTGGTCACCTGTGCAGCTGG-3' | (SEQ ID NO: 6815)<br>(SEQ ID NO: 1270)<br>(SEQ ID NO: 2379) |
| βc-1534 | Target: | 5'-AUAAAUGUGGUCACCUGUGCAGCUGGA-3'<br>3'-UAUUUACACCAGUGGACACGUCGACCU-5'<br>5'-ATAAATGTGGTCACCTGTGCAGCTGGA-3' | (SEQ ID NO: 6816)<br>(SEQ ID NO: 1271)<br>(SEQ ID NO: 2380) |
| βc-1535 | Target: | 5'-UAAAUGUGGUCACCUGUGCAGCUGGAA-3'<br>3'-AUUUACACCAGUGGACACGUCGACCUU-5'<br>5'-TAAATGTGGTCACCTGTGCAGCTGGAA-3' | (SEQ ID NO: 6817)<br>(SEQ ID NO: 1272)<br>(SEQ ID NO: 2381) |
| βc-1536 | Target: | 5'-AAAUGUGGUCACCUGUGCAGCUGGAAU-3'<br>3'-UUUACACCAGUGGACACGUCGACCUUA-5'<br>5'-AAATGTGGTCACCTGTGCAGCTGGAAT-3' | (SEQ ID NO: 6818)<br>(SEQ ID NO: 1273)<br>(SEQ ID NO: 2382) |
| βc-1537 | Target: | 5'-AAUGUGGUCACCUGUGCAGCUGGAAUU-3'<br>3'-UUACACCAGUGGACACGUCGACCUUAA-5'<br>5'-AATGTGGTCACCTGTGCAGCTGGAATT-3' | (SEQ ID NO: 6819)<br>(SEQ ID NO: 1274)<br>(SEQ ID NO: 2383) |
| βc-1538 | Target: | 5'-AUGUGGUCACCUGUGCAGCUGGAAUUC-3'<br>3'-UACACCAGUGGACACGUCGACCUUAAG-5'<br>5'-ATGTGGTCACCTGTGCAGCTGGAATTC-3' | (SEQ ID NO: 6820)<br>(SEQ ID NO: 1275)<br>(SEQ ID NO: 2384) |
| βc-1539 | Target: | 5'-UGUGGUCACCUGUGCAGCUGGAAUUCU-3'<br>3'-ACACCAGUGGACACGUCGACCUUAAGA-5'<br>5'-TGTGGTCACCTGTGCAGCTGGAATTCT-3' | (SEQ ID NO: 6821)<br>(SEQ ID NO: 1276)<br>(SEQ ID NO: 2385) |
| βc-1540 | Target: | 5'-GUGGUCACCUGUGCAGCUGGAAUUCUU-3'<br>3'-CACCAGUGGACACGUCGACCUUAAGAA-5'<br>5'-GTGGTCACCTGTGCAGCTGGAATTCTT-3' | (SEQ ID NO: 6822)<br>(SEQ ID NO: 1277)<br>(SEQ ID NO: 2386) |
| βc-1541 | Target: | 5'-UGGUCACCUGUGCAGCUGGAAUUCUUU-3'<br>3'-ACCAGUGGACACGUCGACCUUAAGAAA-5'<br>5'-TGGTCACCTGTGCAGCTGGAATTCTTT-3' | (SEQ ID NO: 6823)<br>(SEQ ID NO: 1278)<br>(SEQ ID NO: 2387) |

TABLE 8-continued

Selected Anti-β-catenin DsiRNA Agents, Blunt Duplexes

|  |  |  |  |
|---|---|---|---|
| | 5'-GGUCACCUGUGCAGCUGGAAUUCUUUC-3' | (SEQ ID NO: 6824) |
| | 3'-CCAGUGGACACGUCGACCUUAAGAAAG-5' | (SEQ ID NO: 1279) |
| βc-1542 Target: | 5'-GGTCACCTGTGCAGCTGGAATTCTTTC-3' | (SEQ ID NO: 2388) |
| | 5'-GUCACCUGUGCAGCUGGAAUUCUUUCU-3' | (SEQ ID NO: 6825) |
| | 3'-CAGUGGACACGUCGACCUUAAGAAAGA-5' | (SEQ ID NO: 1280) |
| βc-1543 Target: | 5'-GTCACCTGTGCAGCTGGAATTCTTTCT-3' | (SEQ ID NO: 2389) |
| | 5'-UCACCUGUGCAGCUGGAAUUCUUUCUA-3' | (SEQ ID NO: 6826) |
| | 3'-AGUGGACACGUCGACCUUAAGAAAGAU-5' | (SEQ ID NO: 1281) |
| βc-1544 Target: | 5'-TCACCTGTGCAGCTGGAATTCTTTCTA-3' | (SEQ ID NO: 2390) |
| | 5'-CACCUGUGCAGCUGGAAUUCUUUCUAA-3' | (SEQ ID NO: 6827) |
| | 3'-GUGGACACGUCGACCUUAAGAAAGAUU-5' | (SEQ ID NO: 1282) |
| βc-1545 Target: | 5'-CACCTGTGCAGCTGGAATTCTTTCTAA-3' | (SEQ ID NO: 2391) |
| | 5'-UUUCUAACCUCACUUGCAAUAAUUAUA-3' | (SEQ ID NO: 6828) |
| | 3'-AAAGAUUGGAGUGAACGUUAUUAAUAU-5' | (SEQ ID NO: 1283) |
| βc-1565 Target: | 5'-TTTCTAACCTCACTTGCAATAATTATA-3' | (SEQ ID NO: 2392) |
| | 5'-UUCUAACCUCACUUGCAAUAAUUAUAA-3' | (SEQ ID NO: 6829) |
| | 3'-AAGAUUGGAGUGAACGUUAUUAAUAUU-5' | (SEQ ID NO: 1284) |
| βc-1566 Target: | 5'-TTCTAACCTCACTTGCAATAATTATAA-3' | (SEQ ID NO: 2393) |
| | 5'-UCUAACCUCACUUGCAAUAAUUAUAAG-3' | (SEQ ID NO: 6830) |
| | 3'-AGAUUGGAGUGAACGUUAUUAAUAUUC-5' | (SEQ ID NO: 1285) |
| βc-1567 Target: | 5'-TCTAACCTCACTTGCAATAATTATAAG-3' | (SEQ ID NO: 2394) |
| | 5'-CUAACCUCACUUGCAAUAAUUAUAAGA-3' | (SEQ ID NO: 6831) |
| | 3'-GAUUGGAGUGAACGUUAUUAAUAUUCU-5' | (SEQ ID NO: 1286) |
| βc-1568 Target: | 5'-CTAACCTCACTTGCAATAATTATAAGA-3' | (SEQ ID NO: 2395) |
| | 5'-UAACCUCACUUGCAAUAAUUAUAAGAA-3' | (SEQ ID NO: 6832) |
| | 3'-AUUGGAGUGAACGUUAUUAAUAUUCUU-5' | (SEQ ID NO: 1287) |
| βc-1569 Target: | 5'-TAACCTCACTTGCAATAATTATAAGAA-3' | (SEQ ID NO: 2396) |
| | 5'-GGGCUGGUGACAGGGAAGACAUCACUG-3' | (SEQ ID NO: 6833) |
| | 3'-CCCGACCACUGUCCCUUCUGUAGUGAC-5' | (SEQ ID NO: 1288) |
| βc-1652 Target: | 5'-GGGCTGGTGACAGGGAAGACATCACTG-3' | (SEQ ID NO: 2397) |
| | 5'-GGCUGGUGACAGGGAAGACAUCACUGA-3' | (SEQ ID NO: 6834) |
| | 3'-CCGACCACUGUCCCUUCUGUAGUGACU-5' | (SEQ ID NO: 1289) |
| βc-1653 Target: | 5'-GGCTGGTGACAGGGAAGACATCACTGA-3' | (SEQ ID NO: 2398) |
| | 5'-GCUGGUGACAGGGAAGACAUCACUGAG-3' | (SEQ ID NO: 6835) |
| | 3'-CGACCACUGUCCCUUCUGUAGUGACUC-5' | (SEQ ID NO: 1290) |
| βc-1654 Target: | 5'-GCTGGTGACAGGGAAGACATCACTGAG-3' | (SEQ ID NO: 2399) |
| | 5'-CUGGUGACAGGGAAGACAUCACUGAGC-3' | (SEQ ID NO: 6836) |
| | 3'-GACCACUGUCCCUUCUGUAGUGACUCG-5' | (SEQ ID NO: 1291) |
| βc-1655 Target: | 5'-CTGGTGACAGGGAAGACATCACTGAGC-3' | (SEQ ID NO: 2400) |
| | 5'-UGGUGACAGGGAAGACAUCACUGAGCC-3' | (SEQ ID NO: 6837) |
| | 3'-ACCACUGUCCCUUCUGUAGUGACUCGG-5' | (SEQ ID NO: 1292) |
| βc-1656 Target: | 5'-TGGTGACAGGGAAGACATCACTGAGCC-3' | (SEQ ID NO: 2401) |
| | 5'-GGUGACAGGGAAGACAUCACUGAGCCU-3' | (SEQ ID NO: 6838) |
| | 3'-CCACUGUCCCUUCUGUAGUGACUCGGA-5' | (SEQ ID NO: 1293) |
| βc-1657 Target: | 5'-GGTGACAGGGAAGACATCACTGAGCCT-3' | (SEQ ID NO: 2402) |
| | 5'-GUGACAGGGAAGACAUCACUGAGCCUG-3' | (SEQ ID NO: 6839) |
| | 3'-CACUGUCCCUUCUGUAGUGACUCGGAC-5' | (SEQ ID NO: 1294) |
| βc-1658 Target: | 5'-GTGACAGGGAAGACATCACTGAGCCTG-3' | (SEQ ID NO: 2403) |
| | 5'-UGACAGGGAAGACAUCACUGAGCCUGC-3' | (SEQ ID NO: 6840) |
| | 3'-ACUGUCCCUUCUGUAGUGACUCGGACG-5' | (SEQ ID NO: 1295) |
| βc-1659 Target: | 5'-TGACAGGGAAGACATCACTGAGCCTGC-3' | (SEQ ID NO: 2404) |
| | 5'-GACAGGGAAGACAUCACUGAGCCUGCC-3' | (SEQ ID NO: 6841) |
| | 3'-CUGUCCCUUCUGUAGUGACUCGGACGG-5' | (SEQ ID NO: 1296) |
| βc-1660 Target: | 5'-GACAGGGAAGACATCACTGAGCCTGCC-3' | (SEQ ID NO: 2405) |
| | 5'-ACAGGGAAGACAUCACUGAGCCUGCCA-3' | (SEQ ID NO: 6842) |
| | 3'-UGUCCCUUCUGUAGUGACUCGGACGGU-5' | (SEQ ID NO: 1297) |
| βc-1661 Target: | 5'-ACAGGGAAGACATCACTGAGCCTGCCA-3' | (SEQ ID NO: 2406) |

TABLE 8-continued

Selected Anti-β-catenin DsiRNA Agents, Blunt Duplexes

|  |  |  |  |
|---|---|---|---|
| βc-1662 | Target: | 5'-CAGGGAAGACAUCACUGAGCCUGCCAU-3'<br>3'-GUCCCUUCUGUAGUGACUCGGACGGUA-5'<br>5'-CAGGGAAGACATCACTGAGCCTGCC-3' | (SEQ ID NO: 6843)<br>(SEQ ID NO: 1298)<br>(SEQ ID NO: 2407) |
| βc-1663 | Target: | 5'-AGGGAAGACAUCACUGAGCCUGCCAUC-3'<br>3'-UCCCUUCUGUAGUGACUCGGACGGUAG-5'<br>5'-AGGGAAGACATCACTGAGCCTGCCATC-3' | (SEQ ID NO: 6844)<br>(SEQ ID NO: 1299)<br>(SEQ ID NO: 2408) |
| βc-1664 | Target: | 5'-GGGAAGACAUCACUGAGCCUGCCAUCU-3'<br>3'-CCCUUCUGUAGUGACUCGGACGGUAGA-5'<br>5'-GGGAAGACATCACTGAGCCTGCCATCT-3' | (SEQ ID NO: 6845)<br>(SEQ ID NO: 1300)<br>(SEQ ID NO: 2409) |
| βc-1665 | Target: | 5'-GGAAGACAUCACUGAGCCUGCCAUCUG-3'<br>3'-CCUUCUGUAGUGACUCGGACGGUAGAC-5'<br>5'-GGAAGACATCACTGAGCCTGCCATCTG-3' | (SEQ ID NO: 6846)<br>(SEQ ID NO: 1301)<br>(SEQ ID NO: 2410) |
| βc-1666 | Target: | 5'-GAAGACAUCACUGAGCCUGCCAUCUGU-3'<br>3'-CUUCUGUAGUGACUCGGACGGUAGACA-5'<br>5'-GAAGACATCACTGAGCCTGCCATCTGT-3' | (SEQ ID NO: 6847)<br>(SEQ ID NO: 1302)<br>(SEQ ID NO: 2411) |
| βc-1667 | Target: | 5'-AAGACAUCACUGAGCCUGCCAUCUGUG-3'<br>3'-UUCUGUAGUGACUCGGACGGUAGACAC-5'<br>5'-AAGACATCACTGAGCCTGCCATCTGTG-3' | (SEQ ID NO: 6848)<br>(SEQ ID NO: 1303)<br>(SEQ ID NO: 2412) |
| βc-1668 | Target: | 5'-AGACAUCACUGAGCCUGCCAUCUGUGC-3'<br>3'-UCUGUAGUGACUCGGACGGUAGACACG-5'<br>5'-AGACATCACTGAGCCTGCCATCTGTGC-3' | (SEQ ID NO: 6849)<br>(SEQ ID NO: 1304)<br>(SEQ ID NO: 2413) |
| βc-1669 | Target: | 5'-GACAUCACUGAGCCUGCCAUCUGUGCU-3'<br>3'-CUGUAGUGACUCGGACGGUAGACACGA-5'<br>5'-GACATCACTGAGCCTGCCATCTGTGCT-3' | (SEQ ID NO: 6850)<br>(SEQ ID NO: 1305)<br>(SEQ ID NO: 2414) |
| βc-1670 | Target: | 5'-ACAUCACUGAGCCUGCCAUCUGUGCUC-3'<br>3'-UGUAGUGACUCGGACGGUAGACACGAG-5'<br>5'-ACATCACTGAGCCTGCCATCTGTGCTC-3' | (SEQ ID NO: 6851)<br>(SEQ ID NO: 1306)<br>(SEQ ID NO: 2415) |
| βc-1671 | Target: | 5'-CAUCACUGAGCCUGCCAUCUGUGCUCU-3'<br>3'-GUAGUGACUCGGACGGUAGACACGAGA-5'<br>5'-CATCACTGAGCCTGCCATCTGTGCTCT-3' | (SEQ ID NO: 6852)<br>(SEQ ID NO: 1307)<br>(SEQ ID NO: 2416) |
| βc-1672 | Target: | 5'-AUCACUGAGCCUGCCAUCUGUGCUCUU-3'<br>3'-UAGUGACUCGGACGGUAGACACGAGAA-5'<br>5'-ATCACTGAGCCTGCCATCTGTGCTCTT-3' | (SEQ ID NO: 6853)<br>(SEQ ID NO: 1308)<br>(SEQ ID NO: 2417) |
| βc-1673 | Target: | 5'-UCACUGAGCCUGCCAUCUGUGCUCUUC-3'<br>3'-AGUGACUCGGACGGUAGACACGAGAAG-5'<br>5'-TCACTGAGCCTGCCATCTGTGCTCTTC-3' | (SEQ ID NO: 6854)<br>(SEQ ID NO: 1309)<br>(SEQ ID NO: 2418) |
| βc-1674 | Target: | 5'-CACUGAGCCUGCCAUCUGUGCUCUUCG-3'<br>3'-GUGACUCGGACGGUAGACACGAGAAGC-5'<br>5'-CACTGAGCCTGCCATCTGTGCTCTTCG-3' | (SEQ ID NO: 6855)<br>(SEQ ID NO: 1310)<br>(SEQ ID NO: 2419) |
| βc-1675 | Target: | 5'-ACUGAGCCUGCCAUCUGUGCUCUUCGU-3'<br>3'-UGACUCGGACGGUAGACACGAGAAGCA-5'<br>5'-ACTGAGCCTGCCATCTGTGCTCTTCGT-3' | (SEQ ID NO: 6856)<br>(SEQ ID NO: 1311)<br>(SEQ ID NO: 2420) |
| βc-1676 | Target: | 5'-CUGAGCCUGCCAUCUGUGCUCUUCGUC-3'<br>3'-GACUCGGACGGUAGACACGAGAAGCAG-5'<br>5'-CTGAGCCTGCCATCTGTGCTCTTCGTC-3' | (SEQ ID NO: 6857)<br>(SEQ ID NO: 1312)<br>(SEQ ID NO: 2421) |
| βc-1677 | Target: | 5'-UGAGCCUGCCAUCUGUGCUCUUCGUCA-3'<br>3'-ACUCGGACGGUAGACACGAGAAGCAGU-5'<br>5'-TGAGCCTGCCATCTGTGCTCTTCGTCA-3' | (SEQ ID NO: 6858)<br>(SEQ ID NO: 1313)<br>(SEQ ID NO: 2422) |
| βc-1678 | Target: | 5'-GAGCCUGCCAUCUGUGCUCUUCGUCAU-3'<br>3'-CUCGGACGGUAGACACGAGAAGCAGUA-5'<br>5'-GAGCCTGCCATCTGTGCTCTTCGTC-3' | (SEQ ID NO: 6859)<br>(SEQ ID NO: 1314)<br>(SEQ ID NO: 2423) |
| βc-1679 | Target: | 5'-AGCCUGCCAUCUGUGCUCUUCGUCAUC-3'<br>3'-UCGGACGGUAGACACGAGAAGCAGUAG-5'<br>5'-AGCCTGCCATCTGTGCTCTTCGTCATC-3' | (SEQ ID NO: 6860)<br>(SEQ ID NO: 1315)<br>(SEQ ID NO: 2424) |
| βc-1680 | Target: | 5'-GCCUGCCAUCUGUGCUCUUCGUCAUCU-3'<br>3'-CGGACGGUAGACACGAGAAGCAGUAGA-5'<br>5'-GCCTGCCATCTGTGCTCTTCGTCATCT-3' | (SEQ ID NO: 6861)<br>(SEQ ID NO: 1316)<br>(SEQ ID NO: 2425) |

TABLE 8-continued

Selected Anti-β-catenin DsiRNA Agents, Blunt Duplexes

| | | |
|---|---|---|
| βc-1681 Target: | 5'-CCUGCCAUCUGUGCUCUUCGUCAUCUG-3'<br>3'-GGACGGUAGACACGAGAAGCAGUAGAC-5'<br>5'-CCTGCCATCTGTGCTCTTCGTCATCTG-3' | (SEQ ID NO: 6862)<br>(SEQ ID NO: 1317)<br>(SEQ ID NO: 2426) |
| βc-1682 Target: | 5'-CUGCCAUCUGUGCUCUUCGUCAUCUGA-3'<br>3'-GACGGUAGACACGAGAAGCAGUAGACU-5'<br>5'-CTGCCATCTGTGCTCTTCGTCATCTGA-3' | (SEQ ID NO: 6863)<br>(SEQ ID NO: 1318)<br>(SEQ ID NO: 2427) |
| βc-1683 Target: | 5'-UGCCAUCUGUGCUCUUCGUCAUCUGAC-3'<br>3'-ACGGUAGACACGAGAAGCAGUAGACUG-5'<br>5'-TGCCATCTGTGCTCTTCGTCATCTGAC-3' | (SEQ ID NO: 6864)<br>(SEQ ID NO: 1319)<br>(SEQ ID NO: 2428) |
| βc-1684 Target: | 5'-GCCAUCUGUGCUCUUCGUCAUCUGACC-3'<br>3'-CGGUAGACACGAGAAGCAGUAGACUGG-5'<br>5'-GCCATCTGTGCTCTTCGTCATCTGACC-3' | (SEQ ID NO: 6865)<br>(SEQ ID NO: 1320)<br>(SEQ ID NO: 2429) |
| βc-1685 Target: | 5'-CCAUCUGUGCUCUUCGUCAUCUGACCA-3'<br>3'-GGUAGACACGAGAAGCAGUAGACUGGU-5'<br>5'-CCATCTGTGCTCTTCGTCATCTGACCA-3' | (SEQ ID NO: 6866)<br>(SEQ ID NO: 1321)<br>(SEQ ID NO: 2430) |
| βc-1686 Target: | 5'-CAUCUGUGCUCUUCGUCAUCUGACCAG-3'<br>3'-GUAGACACGAGAAGCAGUAGACUGGUC-5'<br>5'-CATCTGTGCTCTTCGTCATCTGACCAG-3' | (SEQ ID NO: 6867)<br>(SEQ ID NO: 1322)<br>(SEQ ID NO: 2431) |
| βc-1687 Target: | 5'-AUCUGUGCUCUUCGUCAUCUGACCAGC-3'<br>3'-UAGACACGAGAAGCAGUAGACUGGUCG-5'<br>5'-ATCTGTGCTCTTCGTCATCTGACCAGC-3' | (SEQ ID NO: 6868)<br>(SEQ ID NO: 1323)<br>(SEQ ID NO: 2432) |
| βc-1688 Target: | 5'-UCUGUGCUCUUCGUCAUCUGACCAGCC-3'<br>3'-AGACACGAGAAGCAGUAGACUGGUCGG-5'<br>5'-TCTGTGCTCTTCGTCATCTGACCAGCC-3' | (SEQ ID NO: 6869)<br>(SEQ ID NO: 1324)<br>(SEQ ID NO: 2433) |
| βc-1689 Target: | 5'-CUGUGCUCUUCGUCAUCUGACCAGCCG-3'<br>3'-GACACGAGAAGCAGUAGACUGGUCGGC-5'<br>5'-CTGTGCTCTTCGTCATCTGACCAGCCG-3' | (SEQ ID NO: 6870)<br>(SEQ ID NO: 1325)<br>(SEQ ID NO: 2434) |
| βc-1690 Target: | 5'-UGUGCUCUUCGUCAUCUGACCAGCCGA-3'<br>3'-ACACGAGAAGCAGUAGACUGGUCGGCU-5'<br>5'-TGTGCTCTTCGTCATCTGACCAGCCGA-3' | (SEQ ID NO: 6871)<br>(SEQ ID NO: 1326)<br>(SEQ ID NO: 2435) |
| βc-1691 Target: | 5'-GUGCUCUUCGUCAUCUGACCAGCCGAC-3'<br>3'-CACGAGAAGCAGUAGACUGGUCGGCUG-5'<br>5'-GTGCTCTTCGTCATCTGACCAGCCGAC-3' | (SEQ ID NO: 6872)<br>(SEQ ID NO: 1327)<br>(SEQ ID NO: 2436) |
| βc-1692 Target: | 5'-UGCUCUUCGUCAUCUGACCAGCCGACA-3'<br>3'-ACGAGAAGCAGUAGACUGGUCGGCUGU-5'<br>5'-TGCTCTTCGTCATCTGACCAGCCGACA-3' | (SEQ ID NO: 6873)<br>(SEQ ID NO: 1328)<br>(SEQ ID NO: 2437) |
| βc-1693 Target: | 5'-GCUCUUCGUCAUCUGACCAGCCGACAC-3'<br>3'-CGAGAAGCAGUAGACUGGUCGGCUGUG-5'<br>5'-GCTCTTCGTCATCTGACCAGCCGACAC-3' | (SEQ ID NO: 6874)<br>(SEQ ID NO: 1329)<br>(SEQ ID NO: 2438) |
| βc-1694 Target: | 5'-CUCUUCGUCAUCUGACCAGCCGACACC-3'<br>3'-GAGAAGCAGUAGACUGGUCGGCUGUGG-5'<br>5'-CTCTTCGTCATCTGACCAGCCGACACC-3' | (SEQ ID NO: 6875)<br>(SEQ ID NO: 1330)<br>(SEQ ID NO: 2439) |
| βc-1695 Target: | 5'-UCUUCGUCAUCUGACCAGCCGACACCA-3'<br>3'-AGAAGCAGUAGACUGGUCGGCUGUGGU-5'<br>5'-TCTTCGTCATCTGACCAGCCGACACCA-3' | (SEQ ID NO: 6876)<br>(SEQ ID NO: 1331)<br>(SEQ ID NO: 2440) |
| βc-1787 Target: | 5'-UACACCCACCAUCCCACUGGCCUCUGA-3'<br>3'-AUGUGGGUGGUAGGGUGACCGGAGACU-5'<br>5'-TACACCCACCATCCCACTGGCCTCTGA-3' | (SEQ ID NO: 6877)<br>(SEQ ID NO: 1332)<br>(SEQ ID NO: 2441) |
| βc-1788 Target: | 5'-ACACCCACCAUCCCACUGGCCUCUGAU-3'<br>3'-UGUGGGUGGUAGGGUGACCGGAGACUA-5'<br>5'-ACACCCACCATCCCACTGGCCTCTGAT-3' | (SEQ ID NO: 6878)<br>(SEQ ID NO: 1333)<br>(SEQ ID NO: 2442) |
| βc-1789 Target: | 5'-CACCCACCAUCCCACUGGCCUCUGAUA-3'<br>3'-GUGGGUGGUAGGGUGACCGGAGACUAU-5'<br>5'-CACCCACCATCCCACTGGCCTCTGATA-3' | (SEQ ID NO: 6879)<br>(SEQ ID NO: 1334)<br>(SEQ ID NO: 2443) |
| βc-1790 Target: | 5'-ACCCACCAUCCCACUGGCCUCUGAUAA-3'<br>3'-UGGGUGGUAGGGUGACCGGAGACUAUU-5'<br>5'-ACCCACCATCCCACTGGCCTCTGATAA-3' | (SEQ ID NO: 6880)<br>(SEQ ID NO: 1335)<br>(SEQ ID NO: 2444) |

TABLE 8-continued

Selected Anti-β-catenin DsiRNA Agents, Blunt Duplexes

|  |  |  |
|---|---|---|
| βc-1791 Target: | 5'-CCCACCAUCCCACUGGCCUCUGAUAAA-3'<br>3'-GGGUGGUAGGGUGACCGGAGACUAUUU-5'<br>5'-CCCACCATCCCACTGGCCTCTGATAAA-3' | (SEQ ID NO: 6881)<br>(SEQ ID NO: 1336)<br>(SEQ ID NO: 2445) |
| βc-1792 Target: | 5'-CCACCAUCCCACUGGCCUCUGAUAAAG-3'<br>3'-GGUGGUAGGGUGACCGGAGACUAUUUC-5'<br>5'-CCACCATCCCACTGGCCTCTGATAAAG-3' | (SEQ ID NO: 6882)<br>(SEQ ID NO: 1337)<br>(SEQ ID NO: 2446) |
| βc-1793 Target: | 5'-CACCAUCCCACUGGCCUCUGAUAAAGG-3'<br>3'-GUGGUAGGGUGACCGGAGACUAUUUCC-5'<br>5'-CACCATCCCACTGGCCTCTGATAAAGG-3' | (SEQ ID NO: 6883)<br>(SEQ ID NO: 1338)<br>(SEQ ID NO: 2447) |
| βc-1794 Target: | 5'-ACCAUCCCACUGGCCUCUGAUAAAGGC-3'<br>3'-UGGUAGGGUGACCGGAGACUAUUUCCG-5'<br>5'-ACCATCCCACTGGCCTCTGATAAAGGC-3' | (SEQ ID NO: 6884)<br>(SEQ ID NO: 1339)<br>(SEQ ID NO: 2448) |
| βc-1795 Target: | 5'-CCAUCCCACUGGCCUCUGAUAAAGGCU-3'<br>3'-GGUAGGGUGACCGGAGACUAUUUCCGA-5'<br>5'-CCATCCCACTGGCCTCTGATAAAGGCT-3' | (SEQ ID NO: 6885)<br>(SEQ ID NO: 1340)<br>(SEQ ID NO: 2449) |
| βc-1796 Target: | 5'-CAUCCCACUGGCCUCUGAUAAAGGCUA-3'<br>3'-GUAGGGUGACCGGAGACUAUUUCCGAU-5'<br>5'-CATCCCACTGGCCTCTGATAAAGGCTA-3' | (SEQ ID NO: 6886)<br>(SEQ ID NO: 1341)<br>(SEQ ID NO: 2450) |
| βc-1797 Target: | 5'-AUCCCACUGGCCUCUGAUAAAGGCUAC-3'<br>3'-UAGGGUGACCGGAGACUAUUUCCGAUG-5'<br>5'-ATCCCACTGGCCTCTGATAAAGGCTAC-3' | (SEQ ID NO: 6887)<br>(SEQ ID NO: 1342)<br>(SEQ ID NO: 2451) |
| βc-1798 Target: | 5'-UCCCACUGGCCUCUGAUAAAGGCUACU-3'<br>3'-AGGGUGACCGGAGACUAUUUCCGAUGA-5'<br>5'-TCCCACTGGCCTCTGATAAAGGCTACT-3' | (SEQ ID NO: 6888)<br>(SEQ ID NO: 1343)<br>(SEQ ID NO: 2452) |
| βc-1799 Target: | 5'-CCCACUGGCCUCUGAUAAAGGCUACUG-3'<br>3'-GGGUGACCGGAGACUAUUUCCGAUGAC-5'<br>5'-CCCACTGGCCTCTGATAAAGGCTACTG-3' | (SEQ ID NO: 6889)<br>(SEQ ID NO: 1344)<br>(SEQ ID NO: 2453) |
| βc-1800 Target: | 5'-CCACUGGCCUCUGAUAAAGGCUACUGU-3'<br>3'-GGUGACCGGAGACUAUUUCCGAUGACA-5'<br>5'-CCACTGGCCTCTGATAAAGGCTACTGT-3' | (SEQ ID NO: 6890)<br>(SEQ ID NO: 1345)<br>(SEQ ID NO: 2454) |
| βc-1820 Target: | 5'-CUACUGUUGGAUUGAUUCGAAAUCUUG-3'<br>3'-GAUGACAACCUAACUAAGCUUUAGAAC-5'<br>5'-CTACTGTTGGATTGATTCGAAATCTTG-3' | (SEQ ID NO: 6891)<br>(SEQ ID NO: 1346)<br>(SEQ ID NO: 2455) |
| βc-1821 Target: | 5'-UACUGUUGGAUUGAUUCGAAAUCUUGC-3'<br>3'-AUGACAACCUAACUAAGCUUUAGAACG-5'<br>5'-TACTGTTGGATTGATTCGAAATCTTGC-3' | (SEQ ID NO: 6892)<br>(SEQ ID NO: 1347)<br>(SEQ ID NO: 2456) |
| βc-2072 Target: | 5'-UAAAUACCAUUCCAUUGUUUGUGCAGC-3'<br>3'-AUUUAUGGUAAGGUAACAAACACGUCG-5'<br>5'-TAAATACCATTCCATTGTTTGTGCAGC-3' | (SEQ ID NO: 6893)<br>(SEQ ID NO: 1348)<br>(SEQ ID NO: 2457) |
| βc-2073 Target: | 5'-AAAUACCAUUCCAUUGUUUGUGCAGCU-3'<br>3'-UUUAUGGUAAGGUAACAAACACGUCGA-5'<br>5'-AAATACCATTCCATTGTTTGTGCAGCT-3' | (SEQ ID NO: 6894)<br>(SEQ ID NO: 1349)<br>(SEQ ID NO: 2458) |
| βc-2074 Target: | 5'-AAUACCAUUCCAUUGUUUGUGCAGCUG-3'<br>3'-UUAUGGUAAGGUAACAAACACGUCGAC-5'<br>5'-AATACCATTCCATTGTTTGTGCAGCTG-3' | (SEQ ID NO: 6895)<br>(SEQ ID NO: 1350)<br>(SEQ ID NO: 2459) |
| βc-2075 Target: | 5'-AUACCAUUCCAUUGUUUGUGCAGCUGC-3'<br>3'-UAUGGUAAGGUAACAAACACGUCGACG-5'<br>5'-ATACCATTCCATTGTTTGTGCAGCTGC-3' | (SEQ ID NO: 6896)<br>(SEQ ID NO: 1351)<br>(SEQ ID NO: 2460) |
| βc-2076 Target: | 5'-UACCAUUCCAUUGUUUGUGCAGCUGCU-3'<br>3'-AUGGUAAGGUAACAAACACGUCGACGA-5'<br>5'-TACCATTCCATTGTTTGTGCAGCTGCT-3' | (SEQ ID NO: 6897)<br>(SEQ ID NO: 1352)<br>(SEQ ID NO: 2461) |
| βc-2077 Target: | 5'-ACCAUUCCAUUGUUUGUGCAGCUGCUU-3'<br>3'-UGGUAAGGUAACAAACACGUCGACGAA-5'<br>5'-ACCATTCCATTGTTTGTGCAGCTGCTT-3' | (SEQ ID NO: 6898)<br>(SEQ ID NO: 1353)<br>(SEQ ID NO: 2462) |
| βc-2097 Target: | 5'-GCUGCUUUAUUCUCCCAUUGAAAACAU-3'<br>3'-CGACGAAAUAAGAGGGUAACUUUUGUA-5'<br>5'-GCTGCTTTATTCTCCCATTGAAAAC-3' | (SEQ ID NO: 6899)<br>(SEQ ID NO: 1354)<br>(SEQ ID NO: 2463) |

TABLE 8-continued

Selected Anti-β-catenin DsiRNA Agents, Blunt Duplexes

| | | | |
|---|---|---|---|
| βc-2098 Target: | 5'-CUGCUUUAUUCUCCCAUUGAAAACAUC-3'<br>3'-GACGAAAUAAGAGGGUAACUUUUGUAG-5'<br>5'-CTGCTTTATTCTCCCATTGAAAACATC-3' | (SEQ ID NO: 6900)<br>(SEQ ID NO: 1355)<br>(SEQ ID NO: 2464) |
| βc-2099 Target: | 5'-UGCUUUAUUCUCCCAUUGAAAACAUCC-3'<br>3'-ACGAAAUAAGAGGGUAACUUUUGUAGG-5'<br>5'-TGCTTTATTCTCCCATTGAAAACATCC-3' | (SEQ ID NO: 6901)<br>(SEQ ID NO: 1356)<br>(SEQ ID NO: 2465) |
| βc-2100 Target: | 5'-GCUUUAUUCUCCCAUUGAAAACAUCCA-3'<br>3'-CGAAAUAAGAGGGUAACUUUUGUAGGU-5'<br>5'-GCTTTATTCTCCCATTGAAAACATCCA-3' | (SEQ ID NO: 6902)<br>(SEQ ID NO: 1357)<br>(SEQ ID NO: 2466) |
| βc-2141 Target: | 5'-GGGUCCUCUGUGAACUUGCUCAGGACA-3'<br>3'-CCCAGGAGACACUUGAACGAGUCCUGU-5'<br>5'-GGGTCCTCTGTGAACTTGCTCAGGACA-3' | (SEQ ID NO: 6903)<br>(SEQ ID NO: 1358)<br>(SEQ ID NO: 2467) |
| βc-2142 Target: | 5'-GGUCCUCUGUGAACUUGCUCAGGACAA-3'<br>3'-CCAGGAGACACUUGAACGAGUCCUGUU-5'<br>5'-GGTCCTCTGTGAACTTGCTCAGGACAA-3' | (SEQ ID NO: 6904)<br>(SEQ ID NO: 1359)<br>(SEQ ID NO: 2468) |
| βc-2143 Target: | 5'-GUCCUCUGUGAACUUGCUCAGGACAAG-3'<br>3'-CAGGAGACACUUGAACGAGUCCUGUUC-5'<br>5'-GTCCTCTGTGAACTTGCTCAGGACAAG-3' | (SEQ ID NO: 6905)<br>(SEQ ID NO: 1360)<br>(SEQ ID NO: 2469) |
| βc-2144 Target: | 5'-UCCUCUGUGAACUUGCUCAGGACAAGG-3'<br>3'-AGGAGACACUUGAACGAGUCCUGUUCC-5'<br>5'-TCCTCTGTGAACTTGCTCAGGACAAGG-3' | (SEQ ID NO: 6906)<br>(SEQ ID NO: 1361)<br>(SEQ ID NO: 2470) |
| βc-2145 Target: | 5'-CCUCUGUGAACUUGCUCAGGACAAGGA-3'<br>3'-GGAGACACUUGAACGAGUCCUGUUCCU-5'<br>5'-CCTCTGTGAACTTGCTCAGGACAAGGA-3' | (SEQ ID NO: 6907)<br>(SEQ ID NO: 1362)<br>(SEQ ID NO: 2471) |
| βc-2146 Target: | 5'-CUCUGUGAACUUGCUCAGGACAAGGAA-3'<br>3'-GAGACACUUGAACGAGUCCUGUUCCUU-5'<br>5'-CTCTGTGAACTTGCTCAGGACAAGGAA-3' | (SEQ ID NO: 6908)<br>(SEQ ID NO: 1363)<br>(SEQ ID NO: 2472) |
| βc-2147 Target: | 5'-UCUGUGAACUUGCUCAGGACAAGGAAG-3'<br>3'-AGACACUUGAACGAGUCCUGUUCCUUC-5'<br>5'-TCTGTGAACTTGCTCAGGACAAGGAAG-3' | (SEQ ID NO: 6909)<br>(SEQ ID NO: 1364)<br>(SEQ ID NO: 2473) |
| βc-2148 Target: | 5'-CUGUGAACUUGCUCAGGACAAGGAAGC-3'<br>3'-GACACUUGAACGAGUCCUGUUCCUUCG-5'<br>5'-CTGTGAACTTGCTCAGGACAAGGAAGC-3' | (SEQ ID NO: 6910)<br>(SEQ ID NO: 1365)<br>(SEQ ID NO: 2474) |
| βc-2149 Target: | 5'-UGUGAACUUGCUCAGGACAAGGAAGCU-3'<br>3'-ACACUUGAACGAGUCCUGUUCCUUCGA-5'<br>5'-TGTGAACTTGCTCAGGACAAGGAAGCT-3' | (SEQ ID NO: 6911)<br>(SEQ ID NO: 1366)<br>(SEQ ID NO: 2475) |
| βc-2150 Target: | 5'-GUGAACUUGCUCAGGACAAGGAAGCUG-3'<br>3'-CACUUGAACGAGUCCUGUUCCUUCGAC-5'<br>5'-GTGAACTTGCTCAGGACAAGGAAGCTG-3' | (SEQ ID NO: 6912)<br>(SEQ ID NO: 1367)<br>(SEQ ID NO: 2476) |
| βc-2151 Target: | 5'-UGAACUUGCUCAGGACAAGGAAGCUGC-3'<br>3'-ACUUGAACGAGUCCUGUUCCUUCGACG-5'<br>5'-TGAACTTGCTCAGGACAAGGAAGCTGC-3' | (SEQ ID NO: 6913)<br>(SEQ ID NO: 1368)<br>(SEQ ID NO: 2477) |
| βc-2183 Target: | 5'-CUAUUGAAGCUGAGGGAGCCACAGCUC-3'<br>3'-GAUAACUUCGACUCCCUCGGUGUCGAG-5'<br>5'-CTATTGAAGCTGAGGGAGCCACAGCTC-3' | (SEQ ID NO: 6914)<br>(SEQ ID NO: 1369)<br>(SEQ ID NO: 2478) |
| βc-2184 Target: | 5'-UAUUGAAGCUGAGGGAGCCACAGCUCC-3'<br>3'-AUAACUUCGACUCCCUCGGUGUCGAGG-5'<br>5'-TATTGAAGCTGAGGGAGCCACAGCTCC-3' | (SEQ ID NO: 6915)<br>(SEQ ID NO: 1370)<br>(SEQ ID NO: 2479) |
| βc-2185 Target: | 5'-AUUGAAGCUGAGGGAGCCACAGCUCCU-3'<br>3'-UAACUUCGACUCCCUCGGUGUCGAGGA-5'<br>5'-ATTGAAGCTGAGGGAGCCACAGCTCCT-3' | (SEQ ID NO: 6916)<br>(SEQ ID NO: 1371)<br>(SEQ ID NO: 2480) |
| βc-2270 Target: | 5'-UGUUCCGAAUGUCUGAGGACAAGCCAC-3'<br>3'-ACAAGGCUUACAGACUCCUGUUCGGUG-5'<br>5'-TGTTCCGAATGTCTGAGGACAAGCCAC-3' | (SEQ ID NO: 6917)<br>(SEQ ID NO: 1372)<br>(SEQ ID NO: 2481) |
| βc-2271 Target: | 5'-GUUCCGAAUGUCUGAGGACAAGCCACA-3'<br>3'-CAAGGCUUACAGACUCCUGUUCGGUGU-5'<br>5'-GTTCCGAATGTCTGAGGACAAGCCACA-3' | (SEQ ID NO: 6918)<br>(SEQ ID NO: 1373)<br>(SEQ ID NO: 2482) |

TABLE 8-continued

Selected Anti-β-catenin DsiRNA Agents, Blunt Duplexes

|  |  |  |
|---|---|---|
| | 5'-UUCCGAAUGUCUGAGGACAAGCCACAA-3' | (SEQ ID NO: 6919) |
| | 3'-AAGGCUUACAGACUCCUGUUCGGUGUU-5' | (SEQ ID NO: 1374) |
| βc-2272 Target: | 5'-TTCCGAATGTCTGAGGACAAGCCACAA-3' | (SEQ ID NO: 2483) |
| | 5'-UCCGAAUGUCUGAGGACAAGCCACAAG-3' | (SEQ ID NO: 6920) |
| | 3'-AGGCUUACAGACUCCUGUUCGGUGUUC-5' | (SEQ ID NO: 1375) |
| βc-2273 Target: | 5'-TCCGAATGTCTGAGGACAAGCCACAAG-3' | (SEQ ID NO: 2484) |
| | 5'-CCGAAUGUCUGAGGACAAGCCACAAGA-3' | (SEQ ID NO: 6921) |
| | 3'-GGCUUACAGACUCCUGUUCGGUGUUCU-5' | (SEQ ID NO: 1376) |
| βc-2274 Target: | 5'-CCGAATGTCTGAGGACAAGCCACAAGA-3' | (SEQ ID NO: 2485) |
| | 5'-CGAAUGUCUGAGGACAAGCCACAAGAU-3' | (SEQ ID NO: 6922) |
| | 3'-GCUUACAGACUCCUGUUCGGUGUUCUA-5' | (SEQ ID NO: 1377) |
| βc-2275 Target: | 5'-CGAATGTCTGAGGACAAGCCACAAGAT-3' | (SEQ ID NO: 2486) |
| | 5'-GAAUGUCUGAGGACAAGCCACAAGAUU-3' | (SEQ ID NO: 6923) |
| | 3'-CUUACAGACUCCUGUUCGGUGUUCUAA-5' | (SEQ ID NO: 1378) |
| βc-2276 Target: | 5'-GAATGTCTGAGGACAAGCCACAAGATT-3' | (SEQ ID NO: 2487) |
| | 5'-AAUGUCUGAGGACAAGCCACAAGAUUA-3' | (SEQ ID NO: 6924) |
| | 3'-UUACAGACUCCUGUUCGGUGUUCUAAU-5' | (SEQ ID NO: 1379) |
| βc-2277 Target: | 5'-AATGTCTGAGGACAAGCCACAAGATTA-3' | (SEQ ID NO: 2488) |
| | 5'-GAACAGAGCCAAUGGCUUGGAAUGAGA-3' | (SEQ ID NO: 6925) |
| | 3'-CUUGUCUCGGUUACCGAACCUUACUCU-5' | (SEQ ID NO: 1380) |
| βc-2345 Target: | 5'-GAACAGAGCCAATGGCTTGGAATGAGA-3' | (SEQ ID NO: 2489) |
| | 5'-AACAGAGCCAAUGGCUUGGAAUGAGAC-3' | (SEQ ID NO: 6926) |
| | 3'-UUGUCUCGGUUACCGAACCUUACUCUG-5' | (SEQ ID NO: 1381) |
| βc-2346 Target: | 5'-AACAGAGCCAATGGCTTGGAATGAGAC-3' | (SEQ ID NO: 2490) |
| | 5'-ACAGAGCCAAUGGCUUGGAAUGAGACU-3' | (SEQ ID NO: 6927) |
| | 3'-UGUCUCGGUUACCGAACCUUACUCUGA-5' | (SEQ ID NO: 1382) |
| βc-2347 Target: | 5'-ACAGAGCCAATGGCTTGGAATGAGACT-3' | (SEQ ID NO: 2491) |
| | 5'-CAGAGCCAAUGGCUUGGAAUGAGACUG-3' | (SEQ ID NO: 6928) |
| | 3'-GUCUCGGUUACCGAACCUUACUCUGAC-5' | (SEQ ID NO: 1383) |
| βc-2348 Target: | 5'-CAGAGCCAATGGCTTGGAATGAGACTG-3' | (SEQ ID NO: 2492) |
| | 5'-AGAGCCAAUGGCUUGGAAUGAGACUGC-3' | (SEQ ID NO: 6929) |
| | 3'-UCUCGGUUACCGAACCUUACUCUGACG-5' | (SEQ ID NO: 1384) |
| βc-2349 Target: | 5'-AGAGCCAATGGCTTGGAATGAGACTGC-3' | (SEQ ID NO: 2493) |
| | 5'-GAGCCAAUGGCUUGGAAUGAGACUGCU-3' | (SEQ ID NO: 6930) |
| | 3'-CUCGGUUACCGAACCUUACUCUGACGA-5' | (SEQ ID NO: 1385) |
| βc-2350 Target: | 5'-GAGCCAATGGCTTGGAATGAGACTGCT-3' | (SEQ ID NO: 2494) |
| | 5'-AGCCAAUGGCUUGGAAUGAGACUGCUG-3' | (SEQ ID NO: 6931) |
| | 3'-UCGGUUACCGAACCUUACUCUGACGAC-5' | (SEQ ID NO: 1386) |
| βc-2351 Target: | 5'-AGCCAATGGCTTGGAATGAGACTGCTG-3' | (SEQ ID NO: 2495) |
| | 5'-GCCAAUGGCUUGGAAUGAGACUGCUGA-3' | (SEQ ID NO: 6932) |
| | 3'-CGGUUACCGAACCUUACUCUGACGACU-5' | (SEQ ID NO: 1387) |
| βc-2352 Target: | 5'-GCCAATGGCTTGGAATGAGACTGCTGA-3' | (SEQ ID NO: 2496) |
| | 5'-CCAAUGGCUUGGAAUGAGACUGCUGAU-3' | (SEQ ID NO: 6933) |
| | 3'-GGUUACCGAACCUUACUCUGACGACUA-5' | (SEQ ID NO: 1388) |
| βc-2353 Target: | 5'-CCAATGGCTTGGAATGAGACTGCTGAT-3' | (SEQ ID NO: 2497) |
| | 5'-CAAUGGCUUGGAAUGAGACUGCUGAUC-3' | (SEQ ID NO: 6934) |
| | 3'-GUUACCGAACCUUACUCUGACGACUAG-5' | (SEQ ID NO: 1389) |
| βc-2354 Target: | 5'-CAATGGCTTGGAATGAGACTGCTGATC-3' | (SEQ ID NO: 2498) |
| | 5'-AAUGGCUUGGAAUGAGACUGCUGAUCU-3' | (SEQ ID NO: 6935) |
| | 3'-UUACCGAACCUUACUCUGACGACUAGA-5' | (SEQ ID NO: 1390) |
| βc-2355 Target: | 5'-AATGGCTTGGAATGAGACTGCTGATCT-3' | (SEQ ID NO: 2499) |
| | 5'-CCCUUGGAUAUCGCCAGGAUGAUCCUA-3' | (SEQ ID NO: 6936) |
| | 3'-GGGAACCUAUAGCGGUCCUACUAGGAU-5' | (SEQ ID NO: 1391) |
| βc-2411 Target: | 5'-CCCTTGGATATCGCCAGGATGATCCTA-3' | (SEQ ID NO: 2500) |
| | 5'-CCUUGGAUAUCGCCAGGAUGAUCCUAG-3' | (SEQ ID NO: 6937) |
| | 3'-GGAACCUAUAGCGGUCCUACUAGGAUC-5' | (SEQ ID NO: 1392) |
| βc-2412 Target: | 5'-CCTTGGATATCGCCAGGATGATCCTAG-3' | (SEQ ID NO: 2501) |

TABLE 8-continued

Selected Anti-β-catenin DsiRNA Agents, Blunt Duplexes

| | | | |
|---|---|---|---|
| βc-2413 Target: | 5'-CUUGGAUAUCGCCAGGAUGAUCCUAGC-3'<br>3'-GAACCUAUAGCGGUCCUACUAGGAUCG-5'<br>5'-CTTGGATATCGCCAGGATGATCCTAGC-3' | (SEQ ID NO: 6938)<br>(SEQ ID NO: 1393)<br>(SEQ ID NO: 2502) | |
| βc-2414 Target: | 5'-UUGGAUAUCGCCAGGAUGAUCCUAGCU-3'<br>3'-AACCUAUAGCGGUCCUACUAGGAUCGA-5'<br>5'-TTGGATATCGCCAGGATGATCCTAGCT-3' | (SEQ ID NO: 6939)<br>(SEQ ID NO: 1394)<br>(SEQ ID NO: 2503) | |
| βc-2415 Target: | 5'-UGGAUAUCGCCAGGAUGAUCCUAGCUA-3'<br>3'-ACCUAUAGCGGUCCUACUAGGAUCGAU-5'<br>5'-TGGATATCGCCAGGATGATCCTAGCTA-3' | (SEQ ID NO: 6940)<br>(SEQ ID NO: 1395)<br>(SEQ ID NO: 2504) | |
| βc-2441 Target: | 5'-AUCGUUCUUUUCACUCUGGUGGAUAUG-3'<br>3'-UAGCAAGAAAAGUGAGACCACCUAUAC-5'<br>5'-ATCGTTCTTTTCACTCTGGTGGATATG-3' | (SEQ ID NO: 6941)<br>(SEQ ID NO: 1396)<br>(SEQ ID NO: 2505) | |
| βc-2442 Target: | 5'-UCGUUCUUUUCACUCUGGUGGAUAUGG-3'<br>3'-AGCAAGAAAAGUGAGACCACCUAUACC-5'<br>5'-TCGTTCTTTTCACTCTGGTGGATATGG-3' | (SEQ ID NO: 6942)<br>(SEQ ID NO: 1397)<br>(SEQ ID NO: 2506) | |
| βc-2443 Target: | 5'-CGUUCUUUUCACUCUGGUGGAUAUGGC-3'<br>3'-GCAAGAAAAGUGAGACCACCUAUACCG-5'<br>5'-CGTTCTTTTCACTCTGGTGGATATGGC-3' | (SEQ ID NO: 6943)<br>(SEQ ID NO: 1398)<br>(SEQ ID NO: 2507) | |
| βc-2444 Target: | 5'-GUUCUUUUCACUCUGGUGGAUAUGGCC-3'<br>3'-CAAGAAAAGUGAGACCACCUAUACCGG-5'<br>5'-GTTCTTTTCACTCTGGTGGATATGGCC-3' | (SEQ ID NO: 6944)<br>(SEQ ID NO: 1399)<br>(SEQ ID NO: 2508) | |
| βc-2445 Target: | 5'-UUCUUUUCACUCUGGUGGAUAUGGCCA-3'<br>3'-AAGAAAAGUGAGACCACCUAUACCGGU-5'<br>5'-TTCTTTTCACTCTGGTGGATATGGCCA-3' | (SEQ ID NO: 6945)<br>(SEQ ID NO: 1400)<br>(SEQ ID NO: 2509) | |
| βc-2501 Target: | 5'-AACAUGAGAUGGGUGGCCACCACCCUG-3'<br>3'-UUGUACUCUACCCACCGGUGGUGGGAC-5'<br>5'-AACATGAGATGGGTGGCCACCACCCTG-3' | (SEQ ID NO: 6946)<br>(SEQ ID NO: 1401)<br>(SEQ ID NO: 2510) | |
| βc-2502 Target: | 5'-ACAUGAGAUGGGUGGCCACCACCCUGG-3'<br>3'-UGUACUCUACCCACCGGUGGUGGGACC-5'<br>5'-ACATGAGATGGGTGGCCACCACCCTGG-3' | (SEQ ID NO: 6947)<br>(SEQ ID NO: 1402)<br>(SEQ ID NO: 2511) | |
| βc-2503 Target: | 5'-CAUGAGAUGGGUGGCCACCACCCUGGU-3'<br>3'-GUACUCUACCCACCGGUGGUGGGACCA-5'<br>5'-CATGAGATGGGTGGCCACCACCCTGGT-3' | (SEQ ID NO: 6948)<br>(SEQ ID NO: 1403)<br>(SEQ ID NO: 2512) | |
| βc-2504 Target: | 5'-AUGAGAUGGGUGGCCACCACCCUGGUG-3'<br>3'-UACUCUACCCACCGGUGGUGGGACCAC-5'<br>5'-ATGAGATGGGTGGCCACCACCCTGGTG-3' | (SEQ ID NO: 6949)<br>(SEQ ID NO: 1404)<br>(SEQ ID NO: 2513) | |
| βc-2505 Target: | 5'-UGAGAUGGGUGGCCACCACCCUGGUGC-3'<br>3'-ACUCUACCCACCGGUGGUGGGACCACG-5'<br>5'-TGAGATGGGTGGCCACCACCCTGGTGC-3' | (SEQ ID NO: 6950)<br>(SEQ ID NO: 1405)<br>(SEQ ID NO: 2514) | |
| βc-2506 Target: | 5'-GAGAUGGGUGGCCACCACCCUGGUGCU-3'<br>3'-CUCUACCCACCGGUGGUGGGACCACGA-5'<br>5'-GAGATGGGTGGCCACCACCCTGGTGCT-3' | (SEQ ID NO: 6951)<br>(SEQ ID NO: 1406)<br>(SEQ ID NO: 2515) | |
| βc-2507 Target: | 5'-AGAUGGGUGGCCACCACCCUGGUGCUG-3'<br>3'-UCUACCCACCGGUGGUGGGACCACGAC-5'<br>5'-AGATGGGTGGCCACCACCCTGGTGCTG-3' | (SEQ ID NO: 6952)<br>(SEQ ID NO: 1407)<br>(SEQ ID NO: 2516) | |
| βc-2508 Target: | 5'-GAUGGGUGGCCACCACCCUGGUGCUGA-3'<br>3'-CUACCCACCGGUGGUGGGACCACGACU-5'<br>5'-GATGGGTGGCCACCACCCTGGTGCTGA-3' | (SEQ ID NO: 6953)<br>(SEQ ID NO: 1408)<br>(SEQ ID NO: 2517) | |
| βc-2509 Target: | 5'-AUGGGUGGCCACCACCCUGGUGCUGAC-3'<br>3'-UACCCACCGGUGGUGGGACCACGACUG-5'<br>5'-ATGGGTGGCCACCACCCTGGTGCTGAC-3' | (SEQ ID NO: 6954)<br>(SEQ ID NO: 1409)<br>(SEQ ID NO: 2518) | |
| βc-2510 Target: | 5'-UGGGUGGCCACCACCCUGGUGCUGACU-3'<br>3'-ACCCACCGGUGGUGGGACCACGACUGA-5'<br>5'-TGGGTGGCCACCACCCTGGTGCTGACT-3' | (SEQ ID NO: 6955)<br>(SEQ ID NO: 1410)<br>(SEQ ID NO: 2519) | |
| βc-2511 Target: | 5'-GGGUGGCCACCACCCUGGUGCUGACUA-3'<br>3'-CCCACCGGUGGUGGGACCACGACUGAU-5'<br>5'-GGGTGGCCACCACCCTGGTGCTGACTA-3' | (SEQ ID NO: 6956)<br>(SEQ ID NO: 1411)<br>(SEQ ID NO: 2520) | |

TABLE 8-continued

Selected Anti-β-catenin DsiRNA Agents, Blunt Duplexes

| | | | |
|---|---|---|---|
| | 5'-GGUGGCCACCACCCUGGUGCUGACUAU-3' | (SEQ ID NO: 6957) |
| | 3'-CCACCGGUGGUGGGACCACGACUGAUA-5' | (SEQ ID NO: 1412) |
| βc-2512 Target: | 5'-GGTGGCCACCACCCTGGTGCTGACTAT-3' | (SEQ ID NO: 2521) |
| | 5'-GUGGCCACCACCCUGGUGCUGACUAUC-3' | (SEQ ID NO: 6958) |
| | 3'-CACCGGUGGUGGGACCACGACUGAUAG-5' | (SEQ ID NO: 1413) |
| βc-2513 Target: | 5'-GTGGCCACCACCCTGGTGCTGACTATC-3' | (SEQ ID NO: 2522) |
| | 5'-UGGCCACCACCCUGGUGCUGACUAUCC-3' | (SEQ ID NO: 6959) |
| | 3'-ACCGGUGGUGGGACCACGACUGAUAGG-5' | (SEQ ID NO: 1414) |
| βc-2514 Target: | 5'-TGGCCACCACCCTGGTGCTGACTATCC-3' | (SEQ ID NO: 2523) |
| | 5'-GGCCACCACCCUGGUGCUGACUAUCCA-3' | (SEQ ID NO: 6960) |
| | 3'-CCGGUGGUGGGACCACGACUGAUAGGU-5' | (SEQ ID NO: 1415) |
| βc-2515 Target: | 5'-GGCCACCACCCTGGTGCTGACTATCCA-3' | (SEQ ID NO: 2524) |
| | 5'-GCCACCACCCUGGUGCUGACUAUCCAG-3' | (SEQ ID NO: 6961) |
| | 3'-CGGUGGUGGGACCACGACUGAUAGGUC-5' | (SEQ ID NO: 1416) |
| βc-2516 Target: | 5'-GCCACCACCCTGGTGCTGACTATCCAG-3' | (SEQ ID NO: 2525) |
| | 5'-CCACCACCCUGGUGCUGACUAUCCAGU-3' | (SEQ ID NO: 6962) |
| | 3'-GGUGGUGGGACCACGACUGAUAGGUCA-5' | (SEQ ID NO: 1417) |
| βc-2517 Target: | 5'-CCACCACCCTGGTGCTGACTATCCAGT-3' | (SEQ ID NO: 2526) |
| | 5'-CACCACCCUGGUGCUGACUAUCCAGUU-3' | (SEQ ID NO: 6963) |
| | 3'-GUGGUGGGACCACGACUGAUAGGUCAA-5' | (SEQ ID NO: 1418) |
| βc-2518 Target: | 5'-CACCACCCTGGTGCTGACTATCCAGTT-3' | (SEQ ID NO: 2527) |
| | 5'-ACCACCCUGGUGCUGACUAUCCAGUUG-3' | (SEQ ID NO: 6964) |
| | 3'-UGGUGGGACCACGACUGAUAGGUCAAC-5' | (SEQ ID NO: 1419) |
| βc-2519 Target: | 5'-ACCACCCTGGTGCTGACTATCCAGTTG-3' | (SEQ ID NO: 2528) |
| | 5'-CCACCCUGGUGCUGACUAUCCAGUUGA-3' | (SEQ ID NO: 6965) |
| | 3'-GGUGGGACCACGACUGAUAGGUCAACU-5' | (SEQ ID NO: 1420) |
| βc-2520 Target: | 5'-CCACCCTGGTGCTGACTATCCAGTTGA-3' | (SEQ ID NO: 2529) |
| | 5'-CACCCUGGUGCUGACUAUCCAGUUGAU-3' | (SEQ ID NO: 6966) |
| | 3'-GUGGGACCACGACUGAUAGGUCAACUA-5' | (SEQ ID NO: 1421) |
| βc-2521 Target: | 5'-CACCCTGGTGCTGACTATCCAGTTGAT-3' | (SEQ ID NO: 2530) |
| | 5'-ACCCUGGUGCUGACUAUCCAGUUGAUG-3' | (SEQ ID NO: 6967) |
| | 3'-UGGGACCACGACUGAUAGGUCAACUAC-5' | (SEQ ID NO: 1422) |
| βc-2522 Target: | 5'-ACCCTGGTGCTGACTATCCAGTTGATG-3' | (SEQ ID NO: 2531) |
| | 5'-CCCUGGUGCUGACUAUCCAGUUGAUGG-3' | (SEQ ID NO: 6968) |
| | 3'-GGGACCACGACUGAUAGGUCAACUACC-5' | (SEQ ID NO: 1423) |
| βc-2523 Target: | 5'-CCCTGGTGCTGACTATCCAGTTGATGG-3' | (SEQ ID NO: 2532) |
| | 5'-CCUGGUGCUGACUAUCCAGUUGAUGGG-3' | (SEQ ID NO: 6969) |
| | 3'-GGACCACGACUGAUAGGUCAACUACCC-5' | (SEQ ID NO: 1424) |
| βc-2524 Target: | 5'-CCTGGTGCTGACTATCCAGTTGATGGG-3' | (SEQ ID NO: 2533) |
| | 5'-CUGGUGCUGACUAUCCAGUUGAUGGGC-3' | (SEQ ID NO: 6970) |
| | 3'-GACCACGACUGAUAGGUCAACUACCCG-5' | (SEQ ID NO: 1425) |
| βc-2525 Target: | 5'-CTGGTGCTGACTATCCAGTTGATGGGC-3' | (SEQ ID NO: 2534) |
| | 5'-UGGUGCUGACUAUCCAGUUGAUGGGCU-3' | (SEQ ID NO: 6971) |
| | 3'-ACCACGACUGAUAGGUCAACUACCCGA-5' | (SEQ ID NO: 1426) |
| βc-2526 Target: | 5'-TGGTGCTGACTATCCAGTTGATGGGCT-3' | (SEQ ID NO: 2535) |
| | 5'-GGUGCUGACUAUCCAGUUGAUGGGCUG-3' | (SEQ ID NO: 6972) |
| | 3'-CCACGACUGAUAGGUCAACUACCCGAC-5' | (SEQ ID NO: 1427) |
| βc-2527 Target: | 5'-GGTGCTGACTATCCAGTTGATGGGCTG-3' | (SEQ ID NO: 2536) |
| | 5'-GUGCUGACUAUCCAGUUGAUGGGCUGC-3' | (SEQ ID NO: 6973) |
| | 3'-CACGACUGAUAGGUCAACUACCCGACG-5' | (SEQ ID NO: 1428) |
| βc-2528 Target: | 5'-GTGCTGACTATCCAGTTGATGGGCTGC-3' | (SEQ ID NO: 2537) |
| | 5'-UGCUGACUAUCCAGUUGAUGGGCUGCC-3' | (SEQ ID NO: 6974) |
| | 3'-ACGACUGAUAGGUCAACUACCCGACGG-5' | (SEQ ID NO: 1429) |
| βc-2529 Target: | 5'-TGCTGACTATCCAGTTGATGGGCTGCC-3' | (SEQ ID NO: 2538) |
| | 5'-GCUGACUAUCCAGUUGAUGGGCUGCCA-3' | (SEQ ID NO: 6975) |
| | 3'-CGACUGAUAGGUCAACUACCCGACGGU-5' | (SEQ ID NO: 1430) |
| βc-2530 Target: | 5'-GCTGACTATCCAGTTGATGGGCTGCCA-3' | (SEQ ID NO: 2539) |

TABLE 8-continued

Selected Anti-β-catenin DsiRNA Agents, Blunt Duplexes

|  |  |  |
|---|---|---|
| βc-2531 Target: | 5'-CUGACUAUCCAGUUGAUGGGCUGCCAG-3'<br>3'-GACUGAUAGGUCAACUACCCGACGGUC-5'<br>5'-CTGACTATCCAGTTGATGGGCTGCCAG-3' | (SEQ ID NO: 6976)<br>(SEQ ID NO: 1431)<br>(SEQ ID NO: 2540) |
| βc-2532 Target: | 5'-UGACUAUCCAGUUGAUGGGCUGCCAGA-3'<br>3'-ACUGAUAGGUCAACUACCCGACGGUCU-5'<br>5'-TGACTATCCAGTTGATGGGCTGCCAGA-3' | (SEQ ID NO: 6977)<br>(SEQ ID NO: 1432)<br>(SEQ ID NO: 2541) |
| βc-2533 Target: | 5'-GACUAUCCAGUUGAUGGGCUGCCAGAU-3'<br>3'-CUGAUAGGUCAACUACCCGACGGUCUA-5'<br>5'-GACTATCCAGTTGATGGGCTGCCAGAT-3' | (SEQ ID NO: 6978)<br>(SEQ ID NO: 1433)<br>(SEQ ID NO: 2542) |
| βc-2534 Target: | 5'-ACUAUCCAGUUGAUGGGCUGCCAGAUC-3'<br>3'-UGAUAGGUCAACUACCCGACGGUCUAG-5'<br>5'-ACTATCCAGTTGATGGGCTGCCAGATC-3' | (SEQ ID NO: 6979)<br>(SEQ ID NO: 1434)<br>(SEQ ID NO: 2543) |
| βc-2535 Target: | 5'-CUAUCCAGUUGAUGGGCUGCCAGAUCU-3'<br>3'-GAUAGGUCAACUACCCGACGGUCUAGA-5'<br>5'-CTATCCAGTTGATGGGCTGCCAGATCT-3' | (SEQ ID NO: 6980)<br>(SEQ ID NO: 1435)<br>(SEQ ID NO: 2544) |
| βc-2567 Target: | 5'-AUGCCCAGGACCUCAUGGAUGGGCUGC-3'<br>3'-UACGGGUCCUGGAGUACCUACCCGACG-5'<br>5'-ATGCCCAGGACCTCATGGATGGGCTGC-3' | (SEQ ID NO: 6981)<br>(SEQ ID NO: 1436)<br>(SEQ ID NO: 2545) |
| βc-2568 Target: | 5'-UGCCCAGGACCUCAUGGAUGGGCUGCC-3'<br>3'-ACGGGUCCUGGAGUACCUACCCGACGG-5'<br>5'-TGCCCAGGACCTCATGGATGGGCTGCC-3' | (SEQ ID NO: 6982)<br>(SEQ ID NO: 1437)<br>(SEQ ID NO: 2546) |
| βc-2569 Target: | 5'-GCCCAGGACCUCAUGGAUGGGCUGCCU-3'<br>3'-CGGGUCCUGGAGUACCUACCCGACGGA-5'<br>5'-GCCCAGGACCTCATGGATGGGCTGCCT-3' | (SEQ ID NO: 6983)<br>(SEQ ID NO: 1438)<br>(SEQ ID NO: 2547) |
| βc-2603 Target: | 5'-ACAGCAAUCAGCUGGCCUGGUUUGAUA-3'<br>3'-UGUCGUUAGUCGACCGGACCAAACUAU-5'<br>5'-ACAGCAATCAGCTGGCCTGGTTTGATA-3' | (SEQ ID NO: 6984)<br>(SEQ ID NO: 1439)<br>(SEQ ID NO: 2548) |
| βc-2604 Target: | 5'-CAGCAAUCAGCUGGCCUGGUUUGAUAC-3'<br>3'-GUCGUUAGUCGACCGGACCAAACUAUG-5'<br>5'-CAGCAATCAGCTGGCCTGGTTTGATAC-3' | (SEQ ID NO: 6985)<br>(SEQ ID NO: 1440)<br>(SEQ ID NO: 2549) |
| βc-2605 Target: | 5'-AGCAAUCAGCUGGCCUGGUUUGAUACU-3'<br>3'-UCGUUAGUCGACCGGACCAAACUAUGA-5'<br>5'-AGCAATCAGCTGGCCTGGTTTGATACT-3' | (SEQ ID NO: 6986)<br>(SEQ ID NO: 1441)<br>(SEQ ID NO: 2550) |
| βc-2606 Target: | 5'-GCAAUCAGCUGGCCUGGUUUGAUACUG-3'<br>3'-CGUUAGUCGACCGGACCAAACUAUGAC-5'<br>5'-GCAATCAGCTGGCCTGGTTTGATACTG-3' | (SEQ ID NO: 6987)<br>(SEQ ID NO: 1442)<br>(SEQ ID NO: 2551) |
| βc-2607 Target: | 5'-CAAUCAGCUGGCCUGGUUUGAUACUGA-3'<br>3'-GUUAGUCGACCGGACCAAACUAUGACU-5'<br>5'-CAATCAGCTGGCCTGGTTTGATACTGA-3' | (SEQ ID NO: 6988)<br>(SEQ ID NO: 1443)<br>(SEQ ID NO: 2552) |
| βc-2608 Target: | 5'-AAUCAGCUGGCCUGGUUUGAUACUGAC-3'<br>3'-UUAGUCGACCGGACCAAACUAUGACUG-5'<br>5'-AATCAGCTGGCCTGGTTTGATACTGAC-3' | (SEQ ID NO: 6989)<br>(SEQ ID NO: 1444)<br>(SEQ ID NO: 2553) |
| βc-2609 Target: | 5'-AUCAGCUGGCCUGGUUUGAUACUGACC-3'<br>3'-UAGUCGACCGGACCAAACUAUGACUGG-5'<br>5'-ATCAGCTGGCCTGGTTTGATACTGACC-3' | (SEQ ID NO: 6990)<br>(SEQ ID NO: 1445)<br>(SEQ ID NO: 2554) |
| βc-2610 Target: | 5'-UCAGCUGGCCUGGUUUGAUACUGACCU-3'<br>3'-AGUCGACCGGACCAAACUAUGACUGGA-5'<br>5'-TCAGCTGGCCTGGTTTGATACTGACCT-3' | (SEQ ID NO: 6991)<br>(SEQ ID NO: 1446)<br>(SEQ ID NO: 2555) |
| βc-2611 Target: | 5'-CAGCUGGCCUGGUUUGAUACUGACCUG-3'<br>3'-GUCGACCGGACCAAACUAUGACUGGAC-5'<br>5'-CAGCTGGCCTGGTTTGATACTGACCTG-3' | (SEQ ID NO: 6992)<br>(SEQ ID NO: 1447)<br>(SEQ ID NO: 2556) |
| βc-2612 Target: | 5'-AGCUGGCCUGGUUUGAUACUGACCUGU-3'<br>3'-UCGACCGGACCAAACUAUGACUGGACA-5'<br>5'-AGCTGGCCTGGTTTGATACTGACCTGT-3' | (SEQ ID NO: 6993)<br>(SEQ ID NO: 1448)<br>(SEQ ID NO: 2557) |
| βc-2613 Target: | 5'-GCUGGCCUGGUUUGAUACUGACCUGUA-3'<br>3'-CGACCGGACCAAACUAUGACUGGACAU-5'<br>5'-GCTGGCCTGGTTTGATACTGACCTGTA-3' | (SEQ ID NO: 6994)<br>(SEQ ID NO: 1449)<br>(SEQ ID NO: 2558) |

TABLE 8-continued

Selected Anti-β-catenin DsiRNA Agents, Blunt Duplexes

|  |  |  |  |
|---|---|---|---|
| βc-2614 Target: | 5'-CUGGCCUGGUUUGAUACUGACCUGUAA-3'<br>3'-GACCGGACCAAACUAUGACUGGACAUU-5'<br>5'-CTGGCCTGGTTTGATACTGACCTGTAA-3' | (SEQ ID NO: 6995)<br>(SEQ ID NO: 1450)<br>(SEQ ID NO: 2559) |
| βc-2615 Target: | 5'-UGGCCUGGUUUGAUACUGACCUGUAAA-3'<br>3'-ACCGGACCAAACUAUGACUGGACAUUU-5'<br>5'-TGGCCTGGTTTGATACTGACCTGTAAA-3' | (SEQ ID NO: 6996)<br>(SEQ ID NO: 1451)<br>(SEQ ID NO: 2560) |
| βc-2616 Target: | 5'-GGCCUGGUUUGAUACUGACCUGUAAAU-3'<br>3'-CCGGACCAAACUAUGACUGGACAUUUA-5'<br>5'-GGCCTGGTTTGATACTGACCTGTAAAT-3' | (SEQ ID NO: 6997)<br>(SEQ ID NO: 1452)<br>(SEQ ID NO: 2561) |
| βc-2617 Target: | 5'-GCCUGGUUUGAUACUGACCUGUAAAUC-3'<br>3'-CGGACCAAACUAUGACUGGACAUUUAG-5'<br>5'-GCCTGGTTTGATACTGACCTGTAAATC-3' | (SEQ ID NO: 6998)<br>(SEQ ID NO: 1453)<br>(SEQ ID NO: 2562) |
| βc-2618 Target: | 5'-CCUGGUUUGAUACUGACCUGUAAAUCA-3'<br>3'-GGACCAAACUAUGACUGGACAUUUAGU-5'<br>5'-CCTGGTTTGATACTGACCTGTAAATCA-3' | (SEQ ID NO: 6999)<br>(SEQ ID NO: 1454)<br>(SEQ ID NO: 2563) |
| βc-2619 Target: | 5'-CUGGUUUGAUACUGACCUGUAAAUCAU-3'<br>3'-GACCAAACUAUGACUGGACAUUUAGUA-5'<br>5'-CTGGTTTGATACTGACCTGTAAATC-3' | (SEQ ID NO: 7000)<br>(SEQ ID NO: 1455)<br>(SEQ ID NO: 2564) |
| βc-2620 Target: | 5'-UGGUUUGAUACUGACCUGUAAAUCAUC-3'<br>3'-ACCAAACUAUGACUGGACAUUUAGUAG-5'<br>5'-TGGTTTGATACTGACCTGTAAATCATC-3' | (SEQ ID NO: 7001)<br>(SEQ ID NO: 1456)<br>(SEQ ID NO: 2565) |
| βc-2621 Target: | 5'-GGUUUGAUACUGACCUGUAAAUCAUCC-3'<br>3'-CCAAACUAUGACUGGACAUUUAGUAGG-5'<br>5'-GGTTTGATACTGACCTGTAAATCATCC-3' | (SEQ ID NO: 7002)<br>(SEQ ID NO: 1457)<br>(SEQ ID NO: 2566) |
| βc-2622 Target: | 5'-GUUUGAUACUGACCUGUAAAUCAUCCU-3'<br>3'-CAAACUAUGACUGGACAUUUAGUAGGA-5'<br>5'-GTTTGATACTGACCTGTAAATCATCCT-3' | (SEQ ID NO: 7003)<br>(SEQ ID NO: 1458)<br>(SEQ ID NO: 2567) |
| βc-2623 Target: | 5'-UUUGAUACUGACCUGUAAAUCAUCCUU-3'<br>3'-AAACUAUGACUGGACAUUUAGUAGGAA-5'<br>5'-TTTGATACTGACCTGTAAATCATCCTT-3' | (SEQ ID NO: 7004)<br>(SEQ ID NO: 1459)<br>(SEQ ID NO: 2568) |
| βc-2869 Target: | 5'-UUUUUUGCCACAGCUUUUGCAACUUAA-3'<br>3'-AAAAAACGGUGUCGAAAACGUUGAAUU-5'<br>5'-TTTTTTGCCACAGCTTTTGCAACTTAA-3' | (SEQ ID NO: 7005)<br>(SEQ ID NO: 1460)<br>(SEQ ID NO: 2569) |
| βc-2902 Target: | 5'-AAUGAGUAACAUUUGCUGUUUUAAACA-3'<br>3'-UUACUCAUUGUAAACGACAAAAUUUGU-5'<br>5'-AATGAGTAACATTTGCTGTTTTAAACA-3' | (SEQ ID NO: 7006)<br>(SEQ ID NO: 1461)<br>(SEQ ID NO: 2570) |
| βc-2923 Target: | 5'-UAAACAUUAAUAGCAGCCUUUCUCUCU-3'<br>3'-AUUUGUAAUUAUCGUCGGAAAGAGAGA-5'<br>5'-TAAACATTAATAGCAGCCTTTCTCTCT-3' | (SEQ ID NO: 7007)<br>(SEQ ID NO: 1462)<br>(SEQ ID NO: 2571) |
| βc-2925 Target: | 5'-AACAUUAAUAGCAGCCUUUCUCUCUUU-3'<br>3'-UUGUAAUUAUCGUCGGAAAGAGAGAAA-5'<br>5'-AACATTAATAGCAGCCTTTCTCTCTTT-3' | (SEQ ID NO: 7008)<br>(SEQ ID NO: 1463)<br>(SEQ ID NO: 2572) |
| βc-2927 Target: | 5'-CAUUAAUAGCAGCCUUUCUCUCUUUAU-3'<br>3'-GUAAUUAUCGUCGGAAAGAGAGAAAUA-5'<br>5'-CATTAATAGCAGCCTTTCTCTCTTTAT-3' | (SEQ ID NO: 7009)<br>(SEQ ID NO: 1464)<br>(SEQ ID NO: 2573) |
| βc-2929 Target: | 5'-UUAAUAGCAGCCUUUCUCUCUUUAUAC-3'<br>3'-AAUUAUCGUCGGAAAGAGAGAAAUAUG-5'<br>5'-TTAATAGCAGCCTTTCTCTCTTTATAC-3' | (SEQ ID NO: 7010)<br>(SEQ ID NO: 1465)<br>(SEQ ID NO: 2574) |
| βc-2973 Target: | 5'-UUGCAUUGUGAUUGGCCUGUAGAGUUG-3'<br>3'-AACGUAACACUAACCGGACAUCUCAAC-5'<br>5'-TTGCATTGTGATTGGCCTGTAGAGTTG-3' | (SEQ ID NO: 7011)<br>(SEQ ID NO: 1466)<br>(SEQ ID NO: 2575) |
| βc-2975 Target: | 5'-GCAUUGUGAUUGGCCUGUAGAGUUGCU-3'<br>3'-CGUAACACUAACCGGACAUCUCAACGA-5'<br>5'-GCATTGTGATTGGCCTGTAGAGTTGCT-3' | (SEQ ID NO: 7012)<br>(SEQ ID NO: 1467)<br>(SEQ ID NO: 2576) |
| βc-2977 Target: | 5'-AUUGUGAUUGGCCUGUAGAGUUGCUGA-3'<br>3'-UAACACUAACCGGACAUCUCAACGACU-5'<br>5'-ATTGTGATTGGCCTGTAGAGTTGCTGA-3' | (SEQ ID NO: 7013)<br>(SEQ ID NO: 1468)<br>(SEQ ID NO: 2577) |

TABLE 8-continued

Selected Anti-β-catenin DsiRNA Agents, Blunt Duplexes

| | | |
|---|---|---|
| | 5'-UGUGAUUGGCCUGUAGAGUUGCUGAGA-3' | (SEQ ID NO: 7014) |
| | 3'-ACACUAACCGGACAUCUCAACGACUCU-5' | (SEQ ID NO: 1469) |
| βc-2979 Target: | 5'-TGTGATTGGCCTGTAGAGTTGCTGAGA-3' | (SEQ ID NO: 2578) |
| | 5'-UGAUUGGCCUGUAGAGUUGCUGAGAGG-3' | (SEQ ID NO: 7015) |
| | 3'-ACUAACCGGACAUCUCAACGACUCUCC-5' | (SEQ ID NO: 1470) |
| βc-2981 Target: | 5'-TGATTGGCCTGTAGAGTTGCTGAGAGG-3' | (SEQ ID NO: 2579) |
| | 5'-AUUGGCCUGUAGAGUUGCUGAGAGGGC-3' | (SEQ ID NO: 7016) |
| | 3'-UAACCGGACAUCUCAACGACUCUCCCG-5' | (SEQ ID NO: 1471) |
| βc-2983 Target: | 5'-ATTGGCCTGTAGAGTTGCTGAGAGGGC-3' | (SEQ ID NO: 2580) |
| | 5'-UGGCCUGUAGAGUUGCUGAGAGGGCUC-3' | (SEQ ID NO: 7017) |
| | 3'-ACCGGACAUCUCAACGACUCUCCCGAG-5' | (SEQ ID NO: 1472) |
| βc-2985 Target: | 5'-TGGCCTGTAGAGTTGCTGAGAGGGCTC-3' | (SEQ ID NO: 2581) |
| | 5'-GCCUGUAGAGUUGCUGAGAGGGCUCGA-3' | (SEQ ID NO: 7018) |
| | 3'-CGGACAUCUCAACGACUCUCCCGAGCU-5' | (SEQ ID NO: 1473) |
| βc-2987 Target: | 5'-GCCTGTAGAGTTGCTGAGAGGGCTCGA-3' | (SEQ ID NO: 2582) |
| | 5'-CUGUAGAGUUGCUGAGAGGGCUCGAGG-3' | (SEQ ID NO: 7019) |
| | 3'-GACAUCUCAACGACUCUCCCGAGCUCC-5' | (SEQ ID NO: 1474) |
| βc-2989 Target: | 5'-CTGTAGAGTTGCTGAGAGGGCTCGAGG-3' | (SEQ ID NO: 2583) |
| | 5'-GGGUGGGCUGGUAUCUCAGAAAGUGCC-3' | (SEQ ID NO: 7020) |
| | 3'-CCCACCCGACCAUAGAGUCUUUCACGG-5' | (SEQ ID NO: 1475) |
| βc-3015 Target: | 5'-GGGTGGGCTGGTATCTCAGAAAGTGCC-3' | (SEQ ID NO: 2584) |
| | 5'-GUGGGCUGGUAUCUCAGAAAGUGCCUG-3' | (SEQ ID NO: 7021) |
| | 3'-CACCCGACCAUAGAGUCUUUCACGGAC-5' | (SEQ ID NO: 1476) |
| βc-3017 Target: | 5'-GTGGGCTGGTATCTCAGAAAGTGCCTG-3' | (SEQ ID NO: 2585) |
| | 5'-GGGCUGGUAUCUCAGAAAGUGCCUGAC-3' | (SEQ ID NO: 7022) |
| | 3'-CCCGACCAUAGAGUCUUUCACGGACUG-5' | (SEQ ID NO: 1477) |
| βc-3019 Target: | 5'-GGGCTGGTATCTCAGAAAGTGCCTGAC-3' | (SEQ ID NO: 2586) |
| | 5'-GCUGGUAUCUCAGAAAGUGCCUGACAC-3' | (SEQ ID NO: 7023) |
| | 3'-CGACCAUAGAGUCUUUCACGGACUGUG-5' | (SEQ ID NO: 1478) |
| βc-3021 Target: | 5'-GCTGGTATCTCAGAAAGTGCCTGACAC-3' | (SEQ ID NO: 2587) |
| | 5'-ACACUAACCAAGCUGAGUUUCCUAUGG-3' | (SEQ ID NO: 7024) |
| | 3'-UGUGAUUGGUUCGACUCAAAGGAUACC-5' | (SEQ ID NO: 1479) |
| βc-3046 Target: | 5'-ACACTAACCAAGCTGAGTTTCCTATGG-3' | (SEQ ID NO: 2588) |
| | 5'-ACUAACCAAGCUGAGUUUCCUAUGGGA-3' | (SEQ ID NO: 7025) |
| | 3'-UGAUUGGUUCGACUCAAAGGAUACCCU-5' | (SEQ ID NO: 1480) |
| βc-3048 Target: | 5'-ACTAACCAAGCTGAGTTTCCTATGGGA-3' | (SEQ ID NO: 2589) |
| | 5'-UAACCAAGCUGAGUUUCCUAUGGGAAC-3' | (SEQ ID NO: 7026) |
| | 3'-AUUGGUUCGACUCAAAGGAUACCCUUG-5' | (SEQ ID NO: 1481) |
| βc-3050 Target: | 5'-TAACCAAGCTGAGTTTCCTATGGGAAC-3' | (SEQ ID NO: 2590) |
| | 5'-ACCAAGCUGAGUUUCCUAUGGGAACAA-3' | (SEQ ID NO: 7027) |
| | 3'-UGGUUCGACUCAAAGGAUACCCUUGUU-5' | (SEQ ID NO: 1482) |
| βc-3052 Target: | 5'-ACCAAGCTGAGTTTCCTATGGGAACAA-3' | (SEQ ID NO: 2591) |
| | 5'-CAAGCUGAGUUUCCUAUGGGAACAAUU-3' | (SEQ ID NO: 7028) |
| | 3'-GUUCGACUCAAAGGAUACCCUUGUUAA-5' | (SEQ ID NO: 1483) |
| βc-3054 Target: | 5'-CAAGCTGAGTTTCCTATGGGAACAATT-3' | (SEQ ID NO: 2592) |
| | 5'-AGCUGAGUUUCCUAUGGGAACAAUUGA-3' | (SEQ ID NO: 7029) |
| | 3'-UCGACUCAAAGGAUACCCUUGUUAACU-5' | (SEQ ID NO: 1484) |
| βc-3056 Target: | 5'-AGCTGAGTTTCCTATGGGAACAATTGA-3' | (SEQ ID NO: 2593) |
| | 5'-AACUUUUGUUCUGGUCCUUUUUGGUC-3' | (SEQ ID NO: 7030) |
| | 3'-UUGAAAACAAGACCAGGAAAAACCAG-5' | (SEQ ID NO: 1485) |
| βc-3087 Target: | 5'-AACTTTTGTTCTGGTCCTTTTTGGTC-3' | (SEQ ID NO: 2594) |
| | 5'-CUUUUGUUCUGGUCCUUUUUGGUCGA-3' | (SEQ ID NO: 7031) |
| | 3'-GAAAACAAGACCAGGAAAAACCAGCU-5' | (SEQ ID NO: 1486) |
| βc-3089 Target: | 5'-CTTTTGTTCTGGTCCTTTTTGGTCGA-3' | (SEQ ID NO: 2595) |
| | 5'-UUUUGUUCUGGUCCUUUUUGGUCGAGG-3' | (SEQ ID NO: 7032) |
| | 3'-AAAACAAGACCAGGAAAAACCAGCUCC-5' | (SEQ ID NO: 1487) |
| βc-3091 Target: | 5'-TTTTGTTCTGGTCCTTTTTGGTCGAGG-3' | (SEQ ID NO: 2596) |

TABLE 8-continued

Selected Anti-β-catenin DsiRNA Agents, Blunt Duplexes

| | | |
|---|---|---|
| βc-3093 Target: | 5'-UUGUUCUGGUCCUUUUUGGUCGAGGAG-3'<br>3'-AACAAGACCAGGAAAAACCAGCUCCUC-5'<br>5'-TTGTTCTGGTCCTTTTTGGTCGAGGAG-3' | (SEQ ID NO: 7033)<br>(SEQ ID NO: 1488)<br>(SEQ ID NO: 2597) |
| βc-3095 Target: | 5'-GUUCUGGUCCUUUUUGGUCGAGGAGUA-3'<br>3'-CAAGACCAGGAAAAACCAGCUCCUCAU-5'<br>5'-GTTCTGGTCCTTTTTGGTCGAGGAGTA-3' | (SEQ ID NO: 7034)<br>(SEQ ID NO: 1489)<br>(SEQ ID NO: 2598) |
| βc-3097 Target: | 5'-UCUGGUCCUUUUUGGUCGAGGAGUAAC-3'<br>3'-AGACCAGGAAAAACCAGCUCCUCAUUG-5'<br>5'-TCTGGTCCTTTTTGGTCGAGGAGTAAC-3' | (SEQ ID NO: 7035)<br>(SEQ ID NO: 1490)<br>(SEQ ID NO: 2599) |
| βc-3099 Target: | 5'-UGGUCCUUUUUGGUCGAGGAGUAACAA-3'<br>3'-ACCAGGAAAAACCAGCUCCUCAUUGUU-5'<br>5'-TGGTCCTTTTTGGTCGAGGAGTAACAA-3' | (SEQ ID NO: 7036)<br>(SEQ ID NO: 1491)<br>(SEQ ID NO: 2600) |
| βc-3101 Target: | 5'-GUCCUUUUUGGUCGAGGAGUAACAAUA-3'<br>3'-CAGGAAAAACCAGCUCCUCAUUGUUAU-5'<br>5'-GTCCTTTTTGGTCGAGGAGTAACAATA-3' | (SEQ ID NO: 7037)<br>(SEQ ID NO: 1492)<br>(SEQ ID NO: 2601) |
| βc-3103 Target: | 5'-CCUUUUUGGUCGAGGAGUAACAAUACA-3'<br>3'-GGAAAAACCAGCUCCUCAUUGUUAUGU-5'<br>5'-CCTTTTTGGTCGAGGAGTAACAATACA-3' | (SEQ ID NO: 7038)<br>(SEQ ID NO: 1493)<br>(SEQ ID NO: 2602) |
| βc-3105 Target: | 5'-UUUUUGGUCGAGGAGUAACAAUACAAA-3'<br>3'-AAAAACCAGCUCCUCAUUGUUAUGUUU-5'<br>5'-TTTTTGGTCGAGGAGTAACAATACAAA-3' | (SEQ ID NO: 7039)<br>(SEQ ID NO: 1494)<br>(SEQ ID NO: 2603) |
| βc-3107 Target: | 5'-UUUGGUCGAGGAGUAACAAUACAAAUG-3'<br>3'-AAACCAGCUCCUCAUUGUUAUGUUUAC-5'<br>5'-TTTGGTCGAGGAGTAACAATACAAATG-3' | (SEQ ID NO: 7040)<br>(SEQ ID NO: 1495)<br>(SEQ ID NO: 2604) |
| βc-3109 Target: | 5'-UGGUCGAGGAGUAACAAUACAAAUGGA-3'<br>3'-ACCAGCUCCUCAUUGUUAUGUUUACCU-5'<br>5'-TGGTCGAGGAGTAACAATACAAATGGA-3' | (SEQ ID NO: 7041)<br>(SEQ ID NO: 1496)<br>(SEQ ID NO: 2605) |
| βc-3111 Target: | 5'-GUCGAGGAGUAACAAUACAAAUGGAUU-3'<br>3'-CAGCUCCUCAUUGUUAUGUUUACCUAA-5'<br>5'-GTCGAGGAGTAACAATACAAATGGATT-3' | (SEQ ID NO: 7042)<br>(SEQ ID NO: 1497)<br>(SEQ ID NO: 2606) |
| βc-3113 Target: | 5'-CGAGGAGUAACAAUACAAAUGGAUUUU-3'<br>3'-GCUCCUCAUUGUUAUGUUUACCUAAAA-5'<br>5'-CGAGGAGTAACAATACAAATGGATTTT-3' | (SEQ ID NO: 7043)<br>(SEQ ID NO: 1498)<br>(SEQ ID NO: 2607) |
| βc-3115 Target: | 5'-AGGAGUAACAAUACAAAUGGAUUUUGG-3'<br>3'-UCCUCAUUGUUAUGUUUACCUAAAACC-5'<br>5'-AGGAGTAACAATACAAATGGATTTTGG-3' | (SEQ ID NO: 7044)<br>(SEQ ID NO: 1499)<br>(SEQ ID NO: 2608) |
| βc-3191 Target: | 5'-UUUAUCAAACCCUAGCCUUGCUUGUUA-3'<br>3'-AAAUAGUUUGGGAUCGGAACGAACAAU-5'<br>5'-TTTATCAAACCCTAGCCTTGCTTGTTA-3' | (SEQ ID NO: 7045)<br>(SEQ ID NO: 1500)<br>(SEQ ID NO: 2609) |
| βc-3193 Target: | 5'-UAUCAAACCCUAGCCUUGCUUGUUAAA-3'<br>3'-AUAGUUUGGGAUCGGAACGAACAAUUU-5'<br>5'-TATCAAACCCTAGCCTTGCTTGTTAAA-3' | (SEQ ID NO: 7046)<br>(SEQ ID NO: 1501)<br>(SEQ ID NO: 2610) |
| βc-3195 Target: | 5'-UCAAACCCUAGCCUUGCUUGUUAAAUU-3'<br>3'-AGUUUGGGAUCGGAACGAACAAUUUAA-5'<br>5'-TCAAACCCTAGCCTTGCTTGTTAAATT-3' | (SEQ ID NO: 7047)<br>(SEQ ID NO: 1502)<br>(SEQ ID NO: 2611) |
| βc-3387 Target: | 5'-UUGAGUAAUGGUGUAGAACACUAAUUC-3'<br>3'-AACUCAUUACCACAUCUUGUGAUUAAG-5'<br>5'-TTGAGTAATGGTGTAGAACACTAATTC-3' | (SEQ ID NO: 7048)<br>(SEQ ID NO: 1503)<br>(SEQ ID NO: 2612) |
| βc-3389 Target: | 5'-GAGUAAUGGUGUAGAACACUAAUUCAU-3'<br>3'-CUCAUUACCACAUCUUGUGAUUAAGUA-5'<br>5'-GAGTAATGGTGTAGAACACTAATTC-3' | (SEQ ID NO: 7049)<br>(SEQ ID NO: 1504)<br>(SEQ ID NO: 2613) |
| βc-3391 Target: | 5'-GUAAUGGUGUAGAACACUAAUUCAUAA-3'<br>3'-CAUUACCACAUCUUGUGAUUAAGUAUU-5'<br>5'-GTAATGGTGTAGAACACTAATTCATAA-3' | (SEQ ID NO: 7050)<br>(SEQ ID NO: 1505)<br>(SEQ ID NO: 2614) |
| βc-3393 Target: | 5'-AAUGGUGUAGAACACUAAUUCAUAAUC-3'<br>3'-UUACCACAUCUUGUGAUUAAGUAUUAG-5'<br>5'-AATGGTGTAGAACACTAATTCATAATC-3' | (SEQ ID NO: 7051)<br>(SEQ ID NO: 1506)<br>(SEQ ID NO: 2615) |

TABLE 8-continued

Selected Anti-β-catenin DsiRNA Agents, Blunt Duplexes

|  |  |  |  |
|---|---|---|---|
|  | 5'-UGGUGUAGAACACUAAUUCAUAAUCAC-3' | (SEQ ID NO: 7052) |
|  | 3'-ACCACAUCUUGUGAUUAAGUAUUAGUG-5' | (SEQ ID NO: 1507) |
| βc-3395 Target: | 5'-TGGTGTAGAACACTAATTCATAATCAC-3' | (SEQ ID NO: 2616) |
|  | 5'-GUGUAGAACACUAAUUCAUAAUCACUC-3' | (SEQ ID NO: 7053) |
|  | 3'-CACAUCUUGUGAUUAAGUAUUAGUGAG-5' | (SEQ ID NO: 1508) |
| βc-3397 Target: | 5'-GTGTAGAACACTAATTCATAATCACTC-3' | (SEQ ID NO: 2617) |
|  | 5'-GUAGAACACUAAUUCAUAAUCACUCUA-3' | (SEQ ID NO: 7054) |
|  | 3'-CAUCUUGUGAUUAAGUAUUAGUGAGAU-5' | (SEQ ID NO: 1509) |
| βc-3399 Target: | 5'-GTAGAACACTAATTCATAATCACTCTA-3' | (SEQ ID NO: 2618) |
|  | 5'-AGAACACUAAUUCAUAAUCACUCUAAU-3' | (SEQ ID NO: 7055) |
|  | 3'-UCUUGUGAUUAAGUAUUAGUGAGAUUA-5' | (SEQ ID NO: 1510) |
| βc-3401 Target: | 5'-AGAACACTAATTCATAATCACTCTAAT-3' | (SEQ ID NO: 2619) |
|  | 5'-AAUUAGUUUCCUUUUUAAUAUGCUUAA-3' | (SEQ ID NO: 7056) |
|  | 3'-UUAAUCAAAGGAAAAAUUAUACGAAUU-5' | (SEQ ID NO: 1511) |
| βc-3500 Target: | 5'-AATTAGTTTCCTTTTTAATATGCTTAA-3' | (SEQ ID NO: 2620) |
|  | 5'-UUAGUUUCCUUUUUAAUAUGCUUAAAA-3' | (SEQ ID NO: 7057) |
|  | 3'-AAUCAAAGGAAAAAUUAUACGAAUUUU-5' | (SEQ ID NO: 1512) |
| βc-3502 Target: | 5'-TTAGTTTCCTTTTTAATATGCTTAAAA-3' | (SEQ ID NO: 2621) |
|  | 5'-AGUUUCCUUUUUAAUAUGCUUAAAAUA-3' | (SEQ ID NO: 7058) |
|  | 3'-UCAAAGGAAAAAUUAUACGAAUUUUAU-5' | (SEQ ID NO: 1513) |
| βc-3504 Target: | 5'-AGTTTCCTTTTTAATATGCTTAAAATA-3' | (SEQ ID NO: 2622) |
|  | 5'-UUUCCUUUUUAAUAUGCUUAAAAUAAG-3' | (SEQ ID NO: 7059) |
|  | 3'-AAAGGAAAAAUUAUACGAAUUUUAUUC-5' | (SEQ ID NO: 1514) |
| βc-3506 Target: | 5'-TTTCCTTTTTAATATGCTTAAAATAAG-3' | (SEQ ID NO: 2623) |
|  | 5'-UCCUUUUUAAUAUGCUUAAAAUAAGCA-3' | (SEQ ID NO: 7060) |
|  | 3'-AGGAAAAAUUAUACGAAUUUUAUUCGU-5' | (SEQ ID NO: 1515) |
| βc-3508 Target: | 5'-TCCTTTTTAATATGCTTAAAATAAGCA-3' | (SEQ ID NO: 2624) |
|  | 5'-CCUUUUUAAUAUGCUUAAAAUAAGCAG-3' | (SEQ ID NO: 7061) |
|  | 3'-GGAAAAAUUAUACGAAUUUUAUUCGUC-5' | (SEQ ID NO: 1516) |
| βc-3509 Target: | 5'-CCTTTTTAATATGCTTAAAATAAGCAG-3' | (SEQ ID NO: 2625) |
|  | 5'-CUUUUUAAUAUGCUUAAAAUAAGCAGG-3' | (SEQ ID NO: 7062) |
|  | 3'-GAAAAAUUAUACGAAUUUUAUUCGUCC-5' | (SEQ ID NO: 1517) |
| βc-3510 Target: | 5'-CTTTTTAATATGCTTAAAATAAGCAGG-3' | (SEQ ID NO: 2626) |
|  | 5'-UUUUAAUAUGCUUAAAAUAAGCAGGUG-3' | (SEQ ID NO: 7063) |
|  | 3'-AAAAUUAUACGAAUUUUAUUCGUCCAC-5' | (SEQ ID NO: 1518) |
| βc-3512 Target: | 5'-TTTTAATATGCTTAAAATAAGCAGGTG-3' | (SEQ ID NO: 2627) |
|  | 5'-UUAAUAUGCUUAAAAUAAGCAGGUGGA-3' | (SEQ ID NO: 7064) |
|  | 3'-AAUUAUACGAAUUUUAUUCGUCCACCU-5' | (SEQ ID NO: 1519) |
| βc-3514 Target: | 5'-TTAATATGCTTAAAATAAGCAGGTGGA-3' | (SEQ ID NO: 2628) |
|  | 5'-AAUAUGCUUAAAAUAAGCAGGUGGAUC-3' | (SEQ ID NO: 7065) |
|  | 3'-UUUAUACGAAUUUUAUUCGUCCACCUAG-5' | (SEQ ID NO: 1520) |
| βc-3516 Target: | 5'-AATATGCTTAAAATAAGCAGGTGGATC-3' | (SEQ ID NO: 2629) |
|  | 5'-UAUGCUUAAAAUAAGCAGGUGGAUCUA-3' | (SEQ ID NO: 7066) |
|  | 3'-AUACGAAUUUUAUUCGUCCACCUAGAU-5' | (SEQ ID NO: 1521) |
| βc-3518 Target: | 5'-TATGCTTAAAATAAGCAGGTGGATCTA-3' | (SEQ ID NO: 2630) |
|  | 5'-UGCUUAAAAUAAGCAGGUGGAUCUAUU-3' | (SEQ ID NO: 7067) |
|  | 3'-ACGAAUUUUAUUCGUCCACCUAGAUAA-5' | (SEQ ID NO: 1522) |
| βc-3520 Target: | 5'-TGCTTAAAATAAGCAGGTGGATCTATT-3' | (SEQ ID NO: 2631) |
|  | 5'-CUUAAAAUAAGCAGGUGGAUCUAUUUC-3' | (SEQ ID NO: 7068) |
|  | 3'-GAAUUUUAUUCGUCCACCUAGAUAAAG-5' | (SEQ ID NO: 1523) |
| βc-3522 Target: | 5'-CTTAAAATAAGCAGGTGGATCTATTTC-3' | (SEQ ID NO: 2632) |
|  | 5'-UAAAAUAAGCAGGUGGAUCUAUUUCAU-3' | (SEQ ID NO: 7069) |
|  | 3'-AUUUUAUUCGUCCACCUAGAUAAAGUA-5' | (SEQ ID NO: 1524) |
| βc-3524 Target: | 5'-TAAAATAAGCAGGTGGATCTATTTC-3' | (SEQ ID NO: 2633) |
|  | 5'-AAAUAAGCAGGUGGAUCUAUUUCAUGU-3' | (SEQ ID NO: 7070) |
|  | 3'-UUUAUUCGUCCACCUAGAUAAAGUACA-5' | (SEQ ID NO: 1525) |
| βc-3526 Target: | 5'-AAATAAGCAGGTGGATCTATTTCATGT-3' | (SEQ ID NO: 2634) |

TABLE 8-continued

Selected Anti-β-catenin DsiRNA Agents, Blunt Duplexes

|  |  |  |  |
|---|---|---|---|
| βc-3528 | Target: | 5'-AUAAGCAGGUGGAUCUAUUUCAUGUUU-3'<br>3'-UAUUCGUCCACCUAGAUAAAGUACAAA-5'<br>5'-ATAAGCAGGTGGATCTATTTCATGTTT-3' | (SEQ ID NO: 7071)<br>(SEQ ID NO: 1526)<br>(SEQ ID NO: 2635) |
| βc-3530 | Target: | 5'-AAGCAGGUGGAUCUAUUUCAUGUUUUU-3'<br>3'-UUCGUCCACCUAGAUAAAGUACAAAAA-5'<br>5'-AAGCAGGTGGATCTATTTCATGTTTTT-3' | (SEQ ID NO: 7072)<br>(SEQ ID NO: 1527)<br>(SEQ ID NO: 2636) |
| βc-3532 | Target: | 5'-GCAGGUGGAUCUAUUUCAUGUUUUUGA-3'<br>3'-CGUCCACCUAGAUAAAGUACAAAAACU-5'<br>5'-GCAGGTGGATCTATTTCATGTTTTTGA-3' | (SEQ ID NO: 7073)<br>(SEQ ID NO: 1528)<br>(SEQ ID NO: 2637) |
| βc-3534 | Target: | 5'-AGGUGGAUCUAUUUCAUGUUUUUGAUC-3'<br>3'-UCCACCUAGAUAAAGUACAAAAACUAG-5'<br>5'-AGGTGGATCTATTTCATGTTTTTGATC-3' | (SEQ ID NO: 7074)<br>(SEQ ID NO: 1529)<br>(SEQ ID NO: 2638) |
| βc-3536 | Target: | 5'-GUGGAUCUAUUUCAUGUUUUUGAUCAA-3'<br>3'-CACCUAGAUAAAGUACAAAAACUAGUU-5'<br>5'-GTGGATCTATTTCATGTTTTTGATCAA-3' | (SEQ ID NO: 7075)<br>(SEQ ID NO: 1530)<br>(SEQ ID NO: 2639) |
| βc-3538 | Target: | 5'-GGAUCUAUUUCAUGUUUUUGAUCAAAA-3'<br>3'-CCUAGAUAAAGUACAAAAACUAGUUUU-5'<br>5'-GGATCTATTTCATGTTTTTGATCAAAA-3' | (SEQ ID NO: 7076)<br>(SEQ ID NO: 1531)<br>(SEQ ID NO: 2640) |
| βc-3583 | Target: | 5'-GGGUAGGGUAAAUCAGUAAGAGGUGUU-3'<br>3'-CCCAUCCCAUUUAGUCAUUCUCCACAA-5'<br>5'-GGGTAGGGTAAATCAGTAAGAGGTGTT-3' | (SEQ ID NO: 7077)<br>(SEQ ID NO: 1532)<br>(SEQ ID NO: 2641) |
| βc-3585 | Target: | 5'-GUAGGGUAAAUCAGUAAGAGGUGUUAU-3'<br>3'-CAUCCCAUUUAGUCAUUCUCCACAAUA-5'<br>5'-GTAGGGTAAATCAGTAAGAGGTGTTAT-3' | (SEQ ID NO: 7078)<br>(SEQ ID NO: 1533)<br>(SEQ ID NO: 2642) |
| βc-3587 | Target: | 5'-AGGGUAAAUCAGUAAGAGGUGUUAUUU-3'<br>3'-UCCCAUUUAGUCAUUCUCCACAAUAAA-5'<br>5'-AGGGTAAATCAGTAAGAGGTGTTATTT-3' | (SEQ ID NO: 7079)<br>(SEQ ID NO: 1534)<br>(SEQ ID NO: 2643) |
| βc-3589 | Target: | 5'-GGUAAAUCAGUAAGAGGUGUUAUUUGG-3'<br>3'-CCAUUUAGUCAUUCUCCACAAUAAACC-5'<br>5'-GGTAAATCAGTAAGAGGTGTTATTTGG-3' | (SEQ ID NO: 7080)<br>(SEQ ID NO: 1535)<br>(SEQ ID NO: 2644) |
| βc-3591 | Target: | 5'-UAAAUCAGUAAGAGGUGUUAUUUGGAA-3'<br>3'-AUUUAGUCAUUCUCCACAAUAAACCUU-5'<br>5'-TAAATCAGTAAGAGGTGTTATTTGGAA-3' | (SEQ ID NO: 7081)<br>(SEQ ID NO: 1536)<br>(SEQ ID NO: 2645) |
| βc-3593 | Target: | 5'-AAUCAGUAAGAGGUGUUAUUUGGAACC-3'<br>3'-UUAGUCAUUCUCCACAAUAAACCUUGG-5'<br>5'-AATCAGTAAGAGGTGTTATTTGGAACC-3' | (SEQ ID NO: 7082)<br>(SEQ ID NO: 1537)<br>(SEQ ID NO: 2646) |
| βc-3633 | Target: | 5'-UUUACCAGUUGCCUUUUAUCCCAAAGU-3'<br>3'-AAAUGGUCAACGGAAAAUAGGGUUUCA-5'<br>5'-TTTACCAGTTGCCTTTTATCCCAAAGT-3' | (SEQ ID NO: 7083)<br>(SEQ ID NO: 1538)<br>(SEQ ID NO: 2647) |
| βc-3635 | Target: | 5'-UACCAGUUGCCUUUUAUCCCAAAGUUG-3'<br>3'-AUGGUCAACGGAAAAUAGGGUUUCAAC-5'<br>5'-TACCAGTTGCCTTTTATCCCAAAGTTG-3' | (SEQ ID NO: 7084)<br>(SEQ ID NO: 1539)<br>(SEQ ID NO: 2648) |
| βc-3637 | Target: | 5'-CCAGUUGCCUUUUAUCCCAAAGUUGUU-3'<br>3'-GGUCAACGGAAAAUAGGGUUUCAACAA-5'<br>5'-CCAGTTGCCTTTTATCCCAAAGTTGTT-3' | (SEQ ID NO: 7085)<br>(SEQ ID NO: 1540)<br>(SEQ ID NO: 2649) |
| βc-3639 | Target: | 5'-AGUUGCCUUUUAUCCCAAAGUUGUUGU-3'<br>3'-UCAACGGAAAAUAGGGUUUCAACAACA-5'<br>5'-AGTTGCCTTTTATCCCAAAGTTGTTGT-3' | (SEQ ID NO: 7086)<br>(SEQ ID NO: 1541)<br>(SEQ ID NO: 2650) |
| βc-3641 | Target: | 5'-UUGCCUUUUAUCCCAAAGUUGUUGUAA-3'<br>3'-AACGGAAAAUAGGGUUUCAACAACAUU-5'<br>5'-TTGCCTTTTATCCCAAAGTTGTTGTAA-3' | (SEQ ID NO: 7087)<br>(SEQ ID NO: 1542)<br>(SEQ ID NO: 2651) |
| βc-3643 | Target: | 5'-GCCUUUUAUCCCAAAGUUGUUGUAACC-3'<br>3'-CGGAAAAUAGGGUUUCAACAACAUUGG-5'<br>5'-GCCTTTTATCCCAAAGTTGTTGTAACC-3' | (SEQ ID NO: 7088)<br>(SEQ ID NO: 1543)<br>(SEQ ID NO: 2652) |
| βc-3645 | Target: | 5'-CUUUUAUCCCAAAGUUGUUGUAACCUG-3'<br>3'-GAAAAUAGGGUUUCAACAACAUUGGAC-5'<br>5'-CTTTTATCCCAAAGTTGTTGTAACCTG-3' | (SEQ ID NO: 7089)<br>(SEQ ID NO: 1544)<br>(SEQ ID NO: 2653) |

TABLE 8-continued

Selected Anti-β-catenin DsiRNA Agents, Blunt Duplexes

| | | |
|---|---|---|
| βc-3647 Target: | 5'-UUUAUCCCAAAGUUGUUGUAACCUGCU-3'<br>3'-AAAUAGGGUUUCAACAACAUUGGACGA-5'<br>5'-TTTATCCCAAAGTTGTTGTAACCTGCT-3' | (SEQ ID NO: 7090)<br>(SEQ ID NO: 1545)<br>(SEQ ID NO: 2654) |
| βc-3649 Target: | 5'-UAUCCCAAAGUUGUUGUAACCUGCUGU-3'<br>3'-AUAGGGUUUCAACAACAUUGGACGACA-5'<br>5'-TATCCCAAAGTTGTTGTAACCTGCTGT-3' | (SEQ ID NO: 7091)<br>(SEQ ID NO: 1546)<br>(SEQ ID NO: 2655) |
| βc-3651 Target: | 5'-UCCCAAAGUUGUUGUAACCUGCUGUGA-3'<br>3'-AGGGUUUCAACAACAUUGGACGACACU-5'<br>5'-TCCCAAAGTTGTTGTAACCTGCTGTGA-3' | (SEQ ID NO: 7092)<br>(SEQ ID NO: 1547)<br>(SEQ ID NO: 2656) |
| βc-3653 Target: | 5'-CCAAAGUUGUUGUAACCUGCUGUGAUA-3'<br>3'-GGUUUCAACAACAUUGGACGACACUAU-5'<br>5'-CCAAAGTTGTTGTAACCTGCTGTGATA-3' | (SEQ ID NO: 7093)<br>(SEQ ID NO: 1548)<br>(SEQ ID NO: 2657) |
| βc-3655 Target: | 5'-AAAGUUGUUGUAACCUGCUGUGAUACG-3'<br>3'-UUUCAACAACAUUGGACGACACUAUGC-5'<br>5'-AAAGTTGTTGTAACCTGCTGTGATACG-3' | (SEQ ID NO: 7094)<br>(SEQ ID NO: 1549)<br>(SEQ ID NO: 2658) |
| βc-3657 Target: | 5'-AGUUGUUGUAACCUGCUGUGAUACGAU-3'<br>3'-UCAACAACAUUGGACGACACUAUGCUA-5'<br>5'-AGTTGTTGTAACCTGCTGTGATACGAT-3' | (SEQ ID NO: 7095)<br>(SEQ ID NO: 1550)<br>(SEQ ID NO: 2659) |
| βc-3659 Target: | 5'-UUGUUGUAACCUGCUGUGAUACGAUGC-3'<br>3'-AACAACAUUGGACGACACUAUGCUACG-5'<br>5'-TTGTTGTAACCTGCTGTGATACGATGC-3' | (SEQ ID NO: 7096)<br>(SEQ ID NO: 1551)<br>(SEQ ID NO: 2660) |
| βc-3708 Target: | 5'-AAAAAUGGUUCAGAAUUAAACUUUUAA-3'<br>3'-UUUUUACCAAGUCUUAAUUUGAAAAUU-5'<br>5'-AAAAATGGTTCAGAATTAAACTTTTAA-3' | (SEQ ID NO: 7097)<br>(SEQ ID NO: 1552)<br>(SEQ ID NO: 2661) |
| βc-3710 Target: | 5'-AAAUGGUUCAGAAUUAAACUUUUAAUU-3'<br>3'-UUUACCAAGUCUUAAUUUGAAAAUUAA-5'<br>5'-AAATGGTTCAGAATTAAACTTTTAATT-3' | (SEQ ID NO: 7098)<br>(SEQ ID NO: 1553)<br>(SEQ ID NO: 2662) |
| βc-3712 Target: | 5'-AUGGUUCAGAAUUAAACUUUUAAUUCA-3'<br>3'-UACCAAGUCUUAAUUUGAAAAUUAAGU-5'<br>5'-ATGGTTCAGAATTAAACTTTTAATTCA-3' | (SEQ ID NO: 7099)<br>(SEQ ID NO: 1554)<br>(SEQ ID NO: 2663) |
| βc-3714 Target: | 5'-GGUUCAGAAUUAAACUUUUAAUUCAUU-3'<br>3'-CCAAGUCUUAAUUUGAAAAUUAAGUAA-5'<br>5'-GGTTCAGAATTAAACTTTTAATTCATT-3' | (SEQ ID NO: 7100)<br>(SEQ ID NO: 1555)<br>(SEQ ID NO: 2664) |
| βc-3716 Target: | 5'-UUCAGAAUUAAACUUUUAAUUCAUUCG-3'<br>3'-AAGUCUUAAUUUGAAAAUUAAGUAAGC-5'<br>5'-TTCAGAATTAAACTTTTAATTCATTCG-3' | (SEQ ID NO: 7101)<br>(SEQ ID NO: 1556)<br>(SEQ ID NO: 2665) |
| βc-m314 Target: | 5'-CAGCAGCAGUCUUACUUGGAUUCUGGA-3'<br>3'-GUCGUCGUCAGAAUGAACCUAAGACCU-5'<br>5'-CAGCAGCAGTCTTACTTGGATTCTGGA-3' | (SEQ ID NO: 7102)<br>(SEQ ID NO: 1557)<br>(SEQ ID NO: 2666) |
| βc-m325 Target: | 5'-UUACUUGGAUUCUGGAAUCCAUUCUGG-3'<br>3'-AAUGAACCUAAGACCUUAGGUAAGACC-5'<br>5'-TTACTTGGATTCTGGAATCCATTCTGG-3' | (SEQ ID NO: 7103)<br>(SEQ ID NO: 1558)<br>(SEQ ID NO: 2667) |
| βc-m408 Target: | 5'-UUGACACCUCCCAAGUCCUUUAUGAAU-3'<br>3'-AACUGUGGAGGGUUCAGGAAAUACUUA-5'<br>5'-TTGACACCTCCCAAGTCCTTTATGAAT-3' | (SEQ ID NO: 7104)<br>(SEQ ID NO: 1559)<br>(SEQ ID NO: 2668) |
| βc-m460 Target: | 5'-CACGCAAGAGCAAGUAGCUGAUAUUGA-3'<br>3'-GUGCGUUCUCGUUCAUCGACUAUAACU-5'<br>5'-CACGCAAGAGCAAGTAGCTGATATTGA-3' | (SEQ ID NO: 7105)<br>(SEQ ID NO: 1560)<br>(SEQ ID NO: 2669) |
| βc-m526 Target: | 5'-UGCCAUGUUCCCUGAGACGCUAGAUGA-3'<br>3'-ACGGUACAAGGGACUCUGCGAUCUACU-5'<br>5'-TGCCATGTTCCCTGAGACGCTAGATGA-3' | (SEQ ID NO: 7106)<br>(SEQ ID NO: 1561)<br>(SEQ ID NO: 2670) |
| βc-m631 Target: | 5'-GUUGAAACAUGCAGUUGUCAAUUUGAU-3'<br>3'-CAACUUUGUACGUCAACAGUUAAACUA-5'<br>5'-GTTGAAACATGCAGTTGTCAATTTGAT-3' | (SEQ ID NO: 7107)<br>(SEQ ID NO: 1562)<br>(SEQ ID NO: 2671) |
| βc-m636 Target: | 5'-AACAUGCAGUUGUCAAUUUGAUUAACU-3'<br>3'-UUGUACGUCAACAGUUAAACUAAUUGA-5'<br>5'-AACATGCAGTTGTCAATTTGATTAACT-3' | (SEQ ID NO: 7108)<br>(SEQ ID NO: 1563)<br>(SEQ ID NO: 2672) |

TABLE 8-continued

Selected Anti-β-catenin DsiRNA Agents, Blunt Duplexes

| | | | |
|---|---|---|---|
| | 5'-CAGUUGUCAAUUUGAUUAACUAUCAGG-3' | (SEQ ID NO: 7109) |
| | 3'-GUCAACAGUUAAACUAAUUGAUAGUCC-5' | (SEQ ID NO: 1564) |
| βc-m642 Target: | 5'-CAGTTGTCAATTTGATTAACTATCAGG-3' | (SEQ ID NO: 2673) |
| | 5'-AUGAGGACCAGGUGGUAGUUAAUAAAG-3' | (SEQ ID NO: 7110) |
| | 3'-UACUCCUGGUCCACCAUCAAUUAUUUC-5' | (SEQ ID NO: 1565) |
| βc-m723 Target: | 5'-ATGAGGACCAGGTGGTAGTTAATAAAG-3' | (SEQ ID NO: 2674) |
| | 5'-UGGGUCACCAGUGGAUUCUGUACUGUU-3' | (SEQ ID NO: 7111) |
| | 3'-ACCCAGUGGUCACCUAAGACAUGACAA-5' | (SEQ ID NO: 1566) |
| βc-m970 Target: | 5'-TGGGTCACCAGTGGATTCTGTACTGTT-3' | (SEQ ID NO: 2675) |
| | 5'-ACCAGUGGAUUCUGUACUGUUCUACGC-3' | (SEQ ID NO: 7112) |
| | 3'-UGGUCACCUAAGACAUGACAAGAUGCG-5' | (SEQ ID NO: 1567) |
| βc-m976 Target: | 5'-ACCAGTGGATTCTGTACTGTTCTACGC-3' | (SEQ ID NO: 2676) |
| | 5'-UGGAUUCUGUACUGUUCUACGCCAUCA-3' | (SEQ ID NO: 7113) |
| | 3'-ACCUAAGACAUGACAAGAUGCGGUAGU-5' | (SEQ ID NO: 1568) |
| βc-m981 Target: | 5'-TGGATTCTGTACTGTTCTACGCCATCA-3' | (SEQ ID NO: 2677) |
| | 5'-UGGUGGACUGCAGAAAAUGGUUGCUUU-3' | (SEQ ID NO: 7114) |
| | 3'-ACCACCUGACGUCUUUUACCAACGAAA-5' | (SEQ ID NO: 1569) |
| βc-m1066 Target: | 5'-TGGTGGACTGCAGAAAATGGTTGCTTT-3' | (SEQ ID NO: 2678) |
| | 5'-AACGUGAAAUUCUUGGCUAUUACAACA-3' | (SEQ ID NO: 7115) |
| | 3'-UUGCACUUUAAGAACCGAUAAUGUUGU-5' | (SEQ ID NO: 1570) |
| βc-m1106 Target: | 5'-AACGTGAAATTCTTGGCTATTACAACA-3' | (SEQ ID NO: 2679) |
| | 5'-CCCAAGUCAGCGACUUGUUCAAAACUG-3' | (SEQ ID NO: 7116) |
| | 3'-GGGUUCAGUCGCUGAACAAGUUUUGAC-5' | (SEQ ID NO: 1571) |
| βc-m1354 Target: | 5'-CCCAAGTCAGCGACTTGTTCAAAACTG-3' | (SEQ ID NO: 2680) |
| | 5'-GCGACUUGUUCAAAACUGUCUUUGGAC-3' | (SEQ ID NO: 7117) |
| | 3'-CGCUGAACAAGUUUUGACAGAAACCUG-5' | (SEQ ID NO: 1572) |
| βc-m1363 Target: | 5'-GCGACTTGTTCAAAACTGTCTTTGGAC-3' | (SEQ ID NO: 2681) |
| | 5'-CAAAACUGUCUUUGGACUCUCAGAAAC-3' | (SEQ ID NO: 7118) |
| | 3'-GUUUUGACAGAAACCUGAGAGUCUUUG-5' | (SEQ ID NO: 1573) |
| βc-m1373 Target: | 5'-CAAAACTGTCTTTGGACTCTCAGAAAC-3' | (SEQ ID NO: 2682) |
| | 5'-CUCUCUAACCUCACUUGCAAUAAUUAC-3' | (SEQ ID NO: 7119) |
| | 3'-GAGAGAUUGGAGUGAACGUUAUUAAUG-5' | (SEQ ID NO: 1574) |
| βc-m1508 Target: | 5'-CTCTCTAACCTCACTTGCAATAATTAC-3' | (SEQ ID NO: 2683) |
| | 5'-ACCUCACUUGCAAUAAUUACAAAAACA-3' | (SEQ ID NO: 7120) |
| | 3'-UGGAGUGAACGUUAUUAAUGUUUUUGU-5' | (SEQ ID NO: 1575) |
| βc-m1515 Target: | 5'-ACCTCACTTGCAATAATTACAAAAACA-3' | (SEQ ID NO: 2684) |
| | 5'-CAGAAUGCCGUUCGCCUUCAUUAUGGA-3' | (SEQ ID NO: 7121) |
| | 3'-GUCUUACGGCAAGCGGAAGUAAUACCU-5' | (SEQ ID NO: 1576) |
| βc-m1682 Target: | 5'-CAGAATGCCGTTCGCCTTCATTATGGA-3' | (SEQ ID NO: 2685) |
| | 5'-UCGCCUUCAUUAUGGACUGCCUGUUGU-3' | (SEQ ID NO: 7122) |
| | 3'-AGCGGAAGUAAUACCUGACGGACAACA-5' | (SEQ ID NO: 1577) |
| βc-m1693 Target: | 5'-TCGCCTTCATTATGGACTGCCTGTTGT-3' | (SEQ ID NO: 2686) |
| | 5'-UUCAUUAUGGACUGCCUGUUGUGGUUA-3' | (SEQ ID NO: 7123) |
| | 3'-AAGUAAUACCUGACGGACAACACCAAU-5' | (SEQ ID NO: 1578) |
| βc-m1698 Target: | 5'-TTCATTATGGACTGCCTGTTGTGGTTA-3' | (SEQ ID NO: 2687) |
| | 5'-UGGACUGCCUGUUGUGGUUAAACUCCU-3' | (SEQ ID NO: 7124) |
| | 3'-ACCUGACGGACAACACCAAUUUGAGGA-5' | (SEQ ID NO: 1579) |
| βc-m1705 Target: | 5'-TGGACTGCCTGTTGTGGTTAAACTCCT-3' | (SEQ ID NO: 2688) |
| | 5'-GCAACUGUUGGAUUGAUUCGAAACCUU-3' | (SEQ ID NO: 7125) |
| | 3'-CGUUGACAACCUAACUAAGCUUUGGAA-5' | (SEQ ID NO: 1580) |
| βc-m1763 Target: | 5'-GCAACTGTTGGATTGATTCGAAACCTT-3' | (SEQ ID NO: 2689) |
| | 5'-CCGAGGACUCAAUACCAUUCCAUUGUU-3' | (SEQ ID NO: 7126) |
| | 3'-GGCUCCUGAGUUAUGGUAAGGUAACAA-5' | (SEQ ID NO: 1581) |
| βc-m2008 Target: | 5'-CCGAGGACTCAATACCATTCCATTGTT-3' | (SEQ ID NO: 2690) |
| | 5'-CUGAGGACAAGCCACAGGAUUACAAGA-3' | (SEQ ID NO: 7127) |
| | 3'-GACUCCUGUUCGGUGUCCUAAUGUUCU-5' | (SEQ ID NO: 1582) |
| βc-m2226 Target: | 5'-CTGAGGACAAGCCACAGGATTACAAGA-3' | (SEQ ID NO: 2691) |

TABLE 8-continued

Selected Anti-β-catenin DsiRNA Agents, Blunt Duplexes

```
                5'-GGAUGGACCCUAUGAUGGAGCAUGAGA-3'   (SEQ ID NO: 7128)
                3'-CCUACCUGGGAUACUACCUCGUACUCU-5'   (SEQ ID NO: 1583)
βc-m2427 Target: 5'-GGATGGACCCTATGATGGAGCATGAGA-3'  (SEQ ID NO: 2692)

5'-UUGAUACUGACCUGUAAAUCGUCCUUU-3'   (SEQ ID NO: 7129)
                3'-AACUAUGACUGGACAUUUAGCAGGAAA-5'   (SEQ ID NO: 1584)
βc-m2568 Target: 5'-TTGATACTGACCTGTAAATCGTCCTTT-3'  (SEQ ID NO: 2693)

5'-AGCCAGUGUGGGUGAAUACUUUACUCU-3'   (SEQ ID NO: 7130)
                3'-UCGGUCACACCCACUUAUGAAAUGAGA-5'   (SEQ ID NO: 1585)
βc-m2614 Target: 5'-AGCCAGTGTGGGTGAATACTTTACTCT-3'  (SEQ ID NO: 2694)

5'-UGCCACAGCUUUUGCAGCGUUAUACUC-3'   (SEQ ID NO: 7131)
                3'-ACGGUGUCGAAAACGUCGCAAUAUGAG-5'   (SEQ ID NO: 1586)
βc-m2770 Target: 5'-TGCCACAGCTTTTGCAGCGTTATACTC-3'  (SEQ ID NO: 2695)

5'-GCUUUUGCAGCGUUAUACUCAGAUGAG-3'   (SEQ ID NO: 7132)
                3'-CGAAAACGUCGCAAUAUGAGUCUACUC-5'   (SEQ ID NO: 1587)
βc-m2777 Target: 5'-GCTTTTGCAGCGTTATACTCAGATGAG-3'  (SEQ ID NO: 2696)

5'-CAGCGUUAUACUCAGAUGAGUAACAUU-3'   (SEQ ID NO: 7133)
                3'-GUCGCAAUAUGAGUCUACUCAUUGUAA-5'   (SEQ ID NO: 1588)
βc-m2784 Target: 5'-CAGCGTTATACTCAGATGAGTAACATT-3'  (SEQ ID NO: 2697)

5'-ACAUUUGCUGUUUUCAACAUUAAUAGC-3'   (SEQ ID NO: 7134)
                3'-UGUAAACGACAAAAGUUGUAAUUAUCG-5'   (SEQ ID NO: 1589)
βc-m2806 Target: 5'-ACATTTGCTGTTTTCAACATTAATAGC-3'  (SEQ ID NO: 2698)

5'-AGCUGUAGUGUCUGAACGUGCAUUGUG-3'   (SEQ ID NO: 7135)
                3'-UCGACAUCACAGACUUGCACGUAACAC-5'   (SEQ ID NO: 1590)
βc-m2850 Target: 5'-AGCTGTAGTGTCTGAACGTGCATTGTG-3'  (SEQ ID NO: 2699)

5'-GGGAACAGUCGAAGUACGCUUUUUGUU-3'   (SEQ ID NO: 7136)
                3'-CCCUUGUCAGCUUCAUGCGAAAAACAA-5'   (SEQ ID NO: 1591)
βc-m2965 Target: 5'-GGGAACAGTCGAAGTACGCTTTTTGTT-3'  (SEQ ID NO: 2700)

5'-CAGUCGAAGUACGCUUUUUGUUCUGGU-3'   (SEQ ID NO: 7137)
                3'-GUCAGCUUCAUGCGAAAAACAAGACCA-5'   (SEQ ID NO: 1592)
βc-m2970 Target: 5'-CAGTCGAAGTACGCTTTTTGTTCTGGT-3'  (SEQ ID NO: 2701)

5'-AAGUACGCUUUUUGUUCUGGUCCUUUU-3'   (SEQ ID NO: 7138)
                3'-UUCAUGCGAAAAACAAGACCAGGAAAA-5'   (SEQ ID NO: 1593)
βc-m2976 Target: 5'-AAGTACGCTTTTTGTTCTGGTCCTTTT-3'  (SEQ ID NO: 2702)

5'-ACCCUAGCCUUGCUUGUUCUUUGUUUU-3'   (SEQ ID NO: 7139)
                3'-UGGGAUCGGAACGAACAAGAAACAAAA-5'   (SEQ ID NO: 1594)
βc-m3092 Target: 5'-ACCCTAGCCTTGCTTGTTCTTTGTTTT-3'  (SEQ ID NO: 2703)

5'-AGCCUUGCUUGUUCUUUGUUUUAAUAU-3'   (SEQ ID NO: 7140)
                3'-UCGGAACGAACAAGAAACAAAAUUAUA-5'   (SEQ ID NO: 1595)
βc-m3097 Target: 5'-AGCCTTGCTTGTTCTTTGTTTTAATAT-3'  (SEQ ID NO: 2704)

5'-UGAACCUGCUACAGCAAUUUCUGAUUU-3'   (SEQ ID NO: 7141)
                3'-ACUUGGACGAUGUCGUUAAAGACUAAA-5'   (SEQ ID NO: 1596)
βc-m3198 Target: 5'-TGAACCTGCTACAGCAATTTCTGATTT-3'  (SEQ ID NO: 2705)

5'-UACAGCAAUUUCUGAUUUCUAAGAACC-3'   (SEQ ID NO: 7142)
                3'-AUGUCGUUAAAGACUAAAGAUUCUUGG-5'   (SEQ ID NO: 1597)
βc-m3207 Target: 5'-TACAGCAATTTCTGATTTCTAAGAACC-3'  (SEQ ID NO: 2706)

5'-CAGUAAGAGGUGUUAUUUGAGCCUUGU-3'   (SEQ ID NO: 7143)
                3'-GUCAUUCUCCACAAUAAACUCGGAACA-5'   (SEQ ID NO: 1598)
βc-m3433 Target: 5'-CAGTAAGAGGTGTTATTTGAGCCTTGT-3'  (SEQ ID NO: 2707)

5'-GAGGUGUUAUUUGAGCCUUGUUUUGGA-3'   (SEQ ID NO: 7144)
                3'-CUCCACAAUAAACUCGGAACAAAACCU-5'   (SEQ ID NO: 1599)
βc-m3439 Target: 5'-GAGGTGTTATTTGAGCCTTGTTTTGGA-3'  (SEQ ID NO: 2708)

5'-GUUAUUUGAGCCUUGUUUUGGACAGUA-3'   (SEQ ID NO: 7145)
                3'-CAAUAAACUCGGAACAAAACCUGUCAU-5'   (SEQ ID NO: 1600)
βc-m3444 Target: 5'-GTTATTTGAGCCTTGTTTTGGACAGTA-3'  (SEQ ID NO: 2709)

5'-UUGAGCCUUGUUUUGGACAGUAUACCA-3'   (SEQ ID NO: 7146)
                3'-AACUCGGAACAAAACCUGUCAUAUGGU-5'   (SEQ ID NO: 1601)
βc-m3449 Target: 5'-TTGAGCCTTGTTTTGGACAGTATACCA-3'  (SEQ ID NO: 2710)
```

TABLE 8-continued

Selected Anti-β-catenin DsiRNA Agents, Blunt Duplexes

|  |  |  |
| --- | --- | --- |
| βc-m3522 Target: | 5'-UUCAACAGAUGCGGUUAUAGAAAUGGU-3'<br>3'-AAGUUGUCUACGCCAAUAUCUUUACCA-5'<br>5'-TTCAACAGATGCGGTTATAGAAATGGT-3' | (SEQ ID NO: 7147)<br>(SEQ ID NO: 1602)<br>(SEQ ID NO: 2711) |
| βc-m3533 Target: | 5'-CGGUUAUAGAAAUGGUUCAGAAUUAAA-3'<br>3'-GCCAAUAUCUUUACCAAGUCUUAAUUU-5'<br>5'-CGGTTATAGAAATGGTTCAGAATTAAA-3' | (SEQ ID NO: 7148)<br>(SEQ ID NO: 1603)<br>(SEQ ID NO: 2712) |
| βc-m3538 Target: | 5'-AUAGAAAUGGUUCAGAAUUAAACUUUU-3'<br>3'-UAUCUUUACCAAGUCUUAAUUUGAAAA-5'<br>5'-ATAGAAATGGTTCAGAATTAAACTTTT-3' | (SEQ ID NO: 7149)<br>(SEQ ID NO: 1604)<br>(SEQ ID NO: 2713) |

TABLE 9

Additional Selected Anti-β-catenin DsiRNAs, 25/27mer Duplexes

|  |  |  |
| --- | --- | --- |
| βc-244 Target: | 5'-UGUAUGGUAUACUUCAAAUACCCtc-3'<br>3'-CAACAUACCAUAUGAAGUUUAUGGGAG-5'<br>5'-GTTGTATGGTATACTTCAAATACCCTC-3' | (SEQ ID NO: 496)<br>(SEQ ID NO: 1605)<br>(SEQ ID NO: 2714) |
| βc-251 Target: | 5'-AAACAGUUGUAUGGUAUACUUCAaa-3'<br>3'-GUUUUGUCAACAUACCAUAUGAAGUUU-5'<br>5'-CAAAACAGTTGTATGGTATACTTCAAA-3' | (SEQ ID NO: 497)<br>(SEQ ID NO: 1606)<br>(SEQ ID NO: 2715) |
| βc-252 Target: | 5'-AAAACAGUUGUAUGGUAUACUUCaa-3'<br>3'-AGUUUUGUCAACAUACCAUAUGAAGUU-5'<br>5'-TCAAAACAGTTGTATGGTATACTTCAA-3' | (SEQ ID NO: 498)<br>(SEQ ID NO: 1607)<br>(SEQ ID NO: 2716) |
| βc-254 Target: | 5'-UCAAAACAGUUGUAUGGUAUACUtc-3'<br>3'-AAAGUUUUGUCAACAUACCAUAUGAAG-5'<br>5'-TTTCAAAACAGTTGTATGGTATACTTC-3' | (SEQ ID NO: 499)<br>(SEQ ID NO: 1608)<br>(SEQ ID NO: 2717) |
| βc-255 Target: | 5'-UUCAAAACAGUUGUAUGGUAUACtt-3'<br>3'-AAAAGUUUUGUCAACAUACCAUAUGAA-5'<br>5'-TTTTCAAAACAGTTGTATGGTATACTT-3' | (SEQ ID NO: 500)<br>(SEQ ID NO: 1609)<br>(SEQ ID NO: 2718) |
| βc-256 Target: | 5'-UUUCAAAACAGUUGUAUGGUAUAct-3'<br>3'-UAAAAGUUUUGUCAACAUACCAUAUGA-5'<br>5'-ATTTTCAAAACAGTTGTATGGTATACT-3' | (SEQ ID NO: 501)<br>(SEQ ID NO: 1610)<br>(SEQ ID NO: 2719) |
| βc-269 Target: | 5'-GUCCACGCUGGAUUUUCAAAACAgt-3'<br>3'-AACAGGUGCGACCUAAAAGUUUUGUCA-5'<br>5'-TTGTCCACGCTGGATTTTCAAAACAGT-3' | (SEQ ID NO: 502)<br>(SEQ ID NO: 1611)<br>(SEQ ID NO: 2720) |
| βc-270 Target: | 5'-UGUCCACGCUGGAUUUUCAAAACag-3'<br>3'-UAACAGGUGCGACCUAAAAGUUUUGUC-5'<br>5'-ATTGTCCACGCTGGATTTTCAAAACAG-3' | (SEQ ID NO: 503)<br>(SEQ ID NO: 1612)<br>(SEQ ID NO: 2721) |
| βc-293 Target: | 5'-AUCAAAUCAGCUUGAGUAGCCAUtg-3'<br>3'-GGUAGUUUAGUCGAACUCAUCGGUAAC-5'<br>5'-CCATCAAATCAGCTTGAGTAGCCATTG-3' | (SEQ ID NO: 504)<br>(SEQ ID NO: 1613)<br>(SEQ ID NO: 2722) |
| βc-302 Target: | 5'-UCCAACUCCAUCAAAUCAGCUUGag-3'<br>3'-ACAGGUUGAGGUAGUUUAGUCGAACUC-5'<br>5'-TGTCCAACTCCATCAAATCAGCTTGAG-3' | (SEQ ID NO: 505)<br>(SEQ ID NO: 1614)<br>(SEQ ID NO: 2723) |
| βc-431 Target: | 5'-UCCUCAGGAUUGCCUUUACCACUca-3'<br>3'-GAAGGAGUCCUAACGGAAAUGGUGAGU-5'<br>5'-CTTCCTCAGGATTGCCTTTACCACTCA-3' | (SEQ ID NO: 506)<br>(SEQ ID NO: 1615)<br>(SEQ ID NO: 2724) |
| βc-432 Target: | 5'-UUCCUCAGGAUUGCCUUUACCACtc-3'<br>3'-AGAAGGAGUCCUAACGGAAAUGGUGAG-5'<br>5'-TCTTCCTCAGGATTGCCTTTACCACTC-3' | (SEQ ID NO: 507)<br>(SEQ ID NO: 1616)<br>(SEQ ID NO: 2725) |
| βc-518 Target: | 5'-UCAAUAUCAGCUACUUGUUCUUGag-3'<br>3'-GUAGUUAUAGUCGAUGAACAAGAACUC-5'<br>5'-CATCAATATCAGCTACTTGTTCTTGAG-3' | (SEQ ID NO: 508)<br>(SEQ ID NO: 1617)<br>(SEQ ID NO: 2726) |
| βc-519 Target: | 5'-AUCAAUAUCAGCUACUUGUUCUUga-3'<br>3'-GGUAGUUAUAGUCGAUGAACAAGAACU-5'<br>5'-CCATCAATATCAGCTACTTGTTCTTGA-3' | (SEQ ID NO: 509)<br>(SEQ ID NO: 1618)<br>(SEQ ID NO: 2727) |
| βc-524 Target: | 5'-UGUCCAUCAAUAUCAGCUACUUGtt-3'<br>3'-UGACAGGUAGUUAUAGUCGAUGAACAA-5'<br>5'-ACTGTCCATCAATATCAGCTACTTGTT-3' | (SEQ ID NO: 510)<br>(SEQ ID NO: 1619)<br>(SEQ ID NO: 2728) |

TABLE 9-continued

Additional Selected Anti-β-catenin DsiRNAs, 25/27mer Duplexes

|  |  |  |
|---|---|---|
| βc-531 Target: | 5'-UGCAUACUGUCCAUCAAUAUCAGct-3'<br>3'-UAACGUAUGACAGGUAGUUAUAGUCGA-5'<br>5'-ATTGCATACTGTCCATCAATATCAGCT-3' | (SEQ ID NO: 511)<br>(SEQ ID NO: 1620)<br>(SEQ ID NO: 2729) |
| βc-537 Target: | 5'-AGUCAUUGCAUACUGUCCAUCAAta-3'<br>3'-GCUCAGUAACGUAUGACAGGUAGUUAU-5'<br>5'-CGAGTCATTGCATACTGTCCATCAATA-3' | (SEQ ID NO: 512)<br>(SEQ ID NO: 1621)<br>(SEQ ID NO: 2730) |
| βc-584 Target: | 5'-UCAUCUAAUGUCUCAGGGAACAUag-3'<br>3'-GGAGUAGAUUACAGAGUCCCUUGUAUC-5'<br>5'-CCTCATCTAATGTCTCAGGGAACATAG-3' | (SEQ ID NO: 513)<br>(SEQ ID NO: 1622)<br>(SEQ ID NO: 2731) |
| βc-680 Target: | 5'-ACAACUGCAUGUUUCAGCAUCUGtg-3'<br>3'-AAUGUUGACGUACAAAGUCGUAGACAC-5'<br>5'-TTACAACTGCATGTTTCAGCATCTGTG-3' | (SEQ ID NO: 514)<br>(SEQ ID NO: 1623)<br>(SEQ ID NO: 2732) |
| βc-682 Target: | 5'-UUACAACUGCAUGUUUCAGCAUCtg-3'<br>3'-CAAAUGUUGACGUACAAAGUCGUAGAC-5'<br>5'-GTTTACAACTGCATGTTTCAGCATCTG-3' | (SEQ ID NO: 515)<br>(SEQ ID NO: 1624)<br>(SEQ ID NO: 2733) |
| βc-692 Target: | 5'-UUAAUCAAGUUUACAACUGCAUGtt-3'<br>3'-UCAAUUAGUUCAAAUGUUGACGUACAA-5'<br>5'-AGTTAATCAAGTTTACAACTGCATGTT-3' | (SEQ ID NO: 516)<br>(SEQ ID NO: 1625)<br>(SEQ ID NO: 2734) |
| βc-698 Target: | 5'-UGAUAGUUAAUCAAGUUUACAACtg-3'<br>3'-GAACUAUCAAUUAGUUCAAAUGUUGAC-5'<br>5'-CTTGATAGTTAATCAAGTTTACAACTG-3' | (SEQ ID NO: 517)<br>(SEQ ID NO: 1626)<br>(SEQ ID NO: 2735) |
| βc-707 Target: | 5'-GCAUCAUCUUGAUAGUUAAUCAAgt-3'<br>3'-GACGUAGUAGAACUAUCAAUUAGUUCA-5'<br>5'-CTGCATCATCTTGATAGTTAATCAAGT-3' | (SEQ ID NO: 518)<br>(SEQ ID NO: 1627)<br>(SEQ ID NO: 2736) |
| βc-708 Target: | 5'-UGCAUCAUCUUGAUAGUUAAUCAag-3'<br>3'-AGACGUAGUAGAACUAUCAAUUAGUUC-5'<br>5'-TCTGCATCATCTTGATAGTTAATCAAG-3' | (SEQ ID NO: 519)<br>(SEQ ID NO: 1628)<br>(SEQ ID NO: 2737) |
| βc-763 Target: | 5'-GGUCCUCGUCAUUUAGCAGUUUGt-3'<br>3'-GACCAGGAGCAGUAAAUCGUCAAAACA-5'<br>5'-CTGGTCCTCGTCATTTAGCAGTTTTGT-3' | (SEQ ID NO: 520)<br>(SEQ ID NO: 1629)<br>(SEQ ID NO: 2738) |
| βc-790 Target: | 5'-UAACUGCAGCCUUAUUAACCACCac-3'<br>3'-GUAUUGACGUCGGAAUAAUUGGUGGUG-5'<br>5'-CATAACTGCAGCCTTATTAACCACCAC-3' | (SEQ ID NO: 521)<br>(SEQ ID NO: 1630)<br>(SEQ ID NO: 2739) |
| βc-791 Target: | 5'-AUAACUGCAGCCUUAUUAACCACca-3'<br>3'-GGUAUUGACGUCGGAAUAAUUGGUGGU-5'<br>5'-CCATAACTGCAGCCTTATTAACCACCA-3' | (SEQ ID NO: 522)<br>(SEQ ID NO: 1631)<br>(SEQ ID NO: 2740) |
| βc-794 Target: | 5'-ACCAUAACUGCAGCCUUAUUAACca-3'<br>3'-CCUGGUAUUGACGUCGGAAUAAUUGGU-5'<br>5'-GGACCATAACTGCAGCCTTATTAACCA-3' | (SEQ ID NO: 523)<br>(SEQ ID NO: 1632)<br>(SEQ ID NO: 2741) |
| βc-812 Target: | 5'-UUUUUAGAAAGCUGAUGGACCAUaa-3'<br>3'-GGAAAAAUCUUUCGACUACCUGGUAUU-5'<br>5'-CCTTTTTAGAAAGCTGATGGACCATAA-3' | (SEQ ID NO: 524)<br>(SEQ ID NO: 1633)<br>(SEQ ID NO: 2742) |
| βc-873 Target: | 5'-GGUACGUACAAUAGCAGACACCAtc-3'<br>3'-UACCAUGCAUGUUAUCGUCUGUGGUAG-5'<br>5'-ATGGTACGTACAATAGCAGACACCATC-3' | (SEQ ID NO: 525)<br>(SEQ ID NO: 1634)<br>(SEQ ID NO: 2743) |
| βc-890 Target: | 5'-UCAUUUGUAUUCUGCAUGGUACGta-3'<br>3'-GUAGUAAACAUAAGACGUACCAUGCAU-5'<br>5'-CATCATTTGTATTCTGCATGGTACGTA-3' | (SEQ ID NO: 526)<br>(SEQ ID NO: 1635)<br>(SEQ ID NO: 2744) |
| βc-899 Target: | 5'-GUUUCUACAUCAUUUGUAUUCUGca-3'<br>3'-GACAAAGAUGUAGUAAACAUAAGACGU-5'<br>5'-CTGTTTCTACATCATTTGTATTCTGCA-3' | (SEQ ID NO: 527)<br>(SEQ ID NO: 1636)<br>(SEQ ID NO: 2745) |
| βc-900 Target: | 5'-UGUUUCUACAUCAUUUGUAUUCUgc-3'<br>3'-CGACAAAGAUGUAGUAAACAUAAGACG-5'<br>5'-GCTGTTTCTACATCATTTGTATTCTGC-3' | (SEQ ID NO: 528)<br>(SEQ ID NO: 1637)<br>(SEQ ID NO: 2746) |
| βc-909 Target: | 5'-ACAACGAGCUGUUUCUACAUCAUtt-3'<br>3'-CAUGUUGCUCGACAAAGAUGUAGUAAA-5'<br>5'-GTACAACGAGCTGTTTCTACATCATTT-3' | (SEQ ID NO: 529)<br>(SEQ ID NO: 1638)<br>(SEQ ID NO: 2747) |

TABLE 9-continued

Additional Selected Anti-β-catenin DsiRNAs, 25/27mer Duplexes

|  |  |  |
|---|---|---|
| βc-911 Target: | 5'-GUACAACGAGCUGUUUCUACAUCat-3'<br>3'-GCCAUGUUGCUCGACAAAGAUGUAGUA-5'<br>5'-CGGTACAACGAGCTGTTTCTACATC-3' | (SEQ ID NO: 530)<br>(SEQ ID NO: 1639)<br>(SEQ ID NO: 2748) |
| βc-912 Target: | 5'-GGUACAACGAGCUGUUUCUACAUca-3'<br>3'-CGCCAUGUUGCUCGACAAAGAUGUAGU-5'<br>5'-GCGGTACAACGAGCTGTTTCTACATCA-3' | (SEQ ID NO: 531)<br>(SEQ ID NO: 1640)<br>(SEQ ID NO: 2749) |
| βc-1032 Target: | 5'-AUAAAACAACACAGAAUCCACUGgt-3'<br>3'-CGUAUUUUGUUGUGUCUUAGGUGACCA-5'<br>5'-GCATAAAACAACACAGAATCCACTGGT-3' | (SEQ ID NO: 532)<br>(SEQ ID NO: 1641)<br>(SEQ ID NO: 2750) |
| βc-1034 Target: | 5'-GCAUAAAACAACACAGAAUCCACtg-3'<br>3'-ACCGUAUUUUGUUGUGUCUUAGGUGAC-5'<br>5'-TGGCATAAAACAACACAGAATCCACTG-3' | (SEQ ID NO: 533)<br>(SEQ ID NO: 1642)<br>(SEQ ID NO: 2751) |
| βc-1035 Target: | 5'-GGCAUAAAACAACACAGAAUCCAct-3'<br>3'-UACCGUAUUUUGUUGUGUCUUAGGUGA-5'<br>5'-ATGGCATAAAACAACACAGAATCCACT-3' | (SEQ ID NO: 534)<br>(SEQ ID NO: 1643)<br>(SEQ ID NO: 2752) |
| βc-1076 Target: | 5'-GCUCCUUCUUGAUGUAAUAAAAGgt-3'<br>3'-AUCGAGGAAGAACUACAUUAUUUCCA-5'<br>5'-TAGCTCCTTCTTGATGTAATAAAAGGT-3' | (SEQ ID NO: 535)<br>(SEQ ID NO: 1644)<br>(SEQ ID NO: 2753) |
| βc-1077 Target: | 5'-AGCUCCUUCUUGAUGUAAUAAAAgg-3'<br>3'-AAUCGAGGAAGAACUACAUUAUUUCC-5'<br>5'-TTAGCTCCTTCTTGATGTAATAAAAGG-3' | (SEQ ID NO: 536)<br>(SEQ ID NO: 1645)<br>(SEQ ID NO: 2754) |
| βc-1144 Target: | 5'-UAACAUUUGUUUUGUUGAGCAAGgc-3'<br>3'-AAAUUGUAAACAAAACAACUCGUUCCG-5'<br>5'-TTTAACATTTGTTTTGTTGAGCAAGGC-3' | (SEQ ID NO: 537)<br>(SEQ ID NO: 1646)<br>(SEQ ID NO: 2755) |
| βc-1154 Target: | 5'-GCCAAGAAUUUAACAUUUGUUUUgt-3'<br>3'-AUCGGUUCUUAAAUUGUAAACAAAACA-5'<br>5'-TAGCCAAGAATTTAACATTTGTTTTGT-3' | (SEQ ID NO: 538)<br>(SEQ ID NO: 1647)<br>(SEQ ID NO: 2756) |
| βc-1159 Target: | 5'-UAAUAGCCAAGAAUUUAACAUUUgt-3'<br>3'-GCAUUAUCGGUUCUUAAAUUGUAAACA-5'<br>5'-CGTAATAGCCAAGAATTTAACATTTGT-3' | (SEQ ID NO: 539)<br>(SEQ ID NO: 1648)<br>(SEQ ID NO: 2757) |
| βc-1160 Target: | 5'-GUAAUAGCCAAGAAUUUAACAUUtg-3'<br>3'-AGCAUUAUCGGUUCUUAAAUUGUAAAC-5'<br>5'-TCGTAATAGCCAAGAATTTAACATTTG-3' | (SEQ ID NO: 540)<br>(SEQ ID NO: 1649)<br>(SEQ ID NO: 2758) |
| βc-1185 Target: | 5'-AGCUAAAAUUUGAAGGCAGUCUGtc-3'<br>3'-AUUCGAUUUUAAACUUCCGUCAGACAG-5'<br>5'-TAAGCTAAAATTTGAAGGCAGTCTGTC-3' | (SEQ ID NO: 541)<br>(SEQ ID NO: 1650)<br>(SEQ ID NO: 2759) |
| βc-1260 Target: | 5'-GGUCCUCAUUAUAUUUACUAAAGct-3'<br>3'-AUCCAGGAGUAAUAUAAAUGAUUUCGA-5'<br>5'-TAGGTCCTCATTATATTTACTAAAGCT-3' | (SEQ ID NO: 542)<br>(SEQ ID NO: 1651)<br>(SEQ ID NO: 2760) |
| βc-1265 Target: | 5'-GUAUAGGUCCUCAUUAUAUUUACta-3'<br>3'-UUCAUAUCCAGGAGUAAUAUAAAUGAU-5'<br>5'-AAGTATAGGTCCTCATTATATTTACTA-3' | (SEQ ID NO: 543)<br>(SEQ ID NO: 1652)<br>(SEQ ID NO: 2761) |
| βc-1266 Target: | 5'-AGUAUAGGUCCUCAUUAUAUUUAct-3'<br>3'-AUUCAUAUCCAGGAGUAAUAUAAAUGA-5'<br>5'-TAAGTATAGGTCCTCATTATATTTACT-3' | (SEQ ID NO: 544)<br>(SEQ ID NO: 1653)<br>(SEQ ID NO: 2762) |
| βc-1274 Target: | 5'-UUUUCGUAAGUAUAGGUCCUCAUta-3'<br>3'-CAAAAAGCAUUCAUAUCCAGGAGUAAU-5'<br>5'-GTTTTTCGTAAGTATAGGTCCTCATTA-3' | (SEQ ID NO: 545)<br>(SEQ ID NO: 1654)<br>(SEQ ID NO: 2763) |
| βc-1275 Target: | 5'-UUUUUCGUAAGUAUAGGUCCUCAtt-3'<br>3'-UCAAAAAGCAUUCAUAUCCAGGAGUAA-5'<br>5'-AGTTTTTCGTAAGTATAGGTCCTCATT-3' | (SEQ ID NO: 546)<br>(SEQ ID NO: 1655)<br>(SEQ ID NO: 2764) |
| βc-1276 Target: | 5'-GUUUUUCGUAAGUAUAGGUCCUCat-3'<br>3'-AUCAAAAAGCAUUCAUAUCCAGGAGUA-5'<br>5'-TAGTTTTTCGTAAGTATAGGTCCTC-3' | (SEQ ID NO: 547)<br>(SEQ ID NO: 1656)<br>(SEQ ID NO: 2765) |
| βc-1277 Target: | 5'-AGUUUUUCGUAAGUAUAGGUCCUca-3'<br>3'-CAUCAAAAAGCAUUCAUAUCCAGGAGU-5'<br>5'-GTAGTTTTTCGTAAGTATAGGTCCTCA-3' | (SEQ ID NO: 548)<br>(SEQ ID NO: 1657)<br>(SEQ ID NO: 2766) |

TABLE 9-continued

Additional Selected Anti-β-catenin DsiRNAs, 25/27mer Duplexes

| | | |
|---|---|---|
| βc-1287 Target: | 5'-GGUCCACAGUAGUUUUUCGUAAGta-3'<br>3'-CACCAGGUGUCAUCAAAAAGCAUUCAU-5'<br>5'-GTGGTCCACAGTAGTTTTTCGTAAGTA-3' | (SEQ ID NO: 549)<br>(SEQ ID NO: 1658)<br>(SEQ ID NO: 2767) |
| βc-1344 Target: | 5'-UACAAUAGCCGGCUUAUUACUAGag-3'<br>3'-AGAUGUUAUCGGCCGAAUAAUGAUCUC-5'<br>5'-TCTACAATAGCCGGCTTATTACTAGAG-3' | (SEQ ID NO: 550)<br>(SEQ ID NO: 1659)<br>(SEQ ID NO: 2768) |
| βc-1346 Target: | 5'-UCUACAAUAGCCGGCUUAUUACUag-3'<br>3'-GAAGAUGUUAUCGGCCGAAUAAUGAUC-5'<br>5'-CTTCTACAATAGCCGGCTTATTACTAG-3' | (SEQ ID NO: 551)<br>(SEQ ID NO: 1660)<br>(SEQ ID NO: 2769) |
| βc-1371 Target: | 5'-UCCUAAAGCUUGCAUUCCACCAGct-3'<br>3'-UCAGGAUUUCGAACGUAAGGUGGUCGA-5'<br>5'-AGTCCTAAAGCTTGCATTCCACCAGCT-3' | (SEQ ID NO: 552)<br>(SEQ ID NO: 1661)<br>(SEQ ID NO: 2770) |
| βc-1372 Target: | 5'-GUCCUAAAGCUUGCAUUCCACCAgc-3'<br>3'-UUCAGGAUUUCGAACGUAAGGUGGUCG-5'<br>5'-AAGTCCTAAAGCTTGCATTCCACCAGC-3' | (SEQ ID NO: 553)<br>(SEQ ID NO: 1662)<br>(SEQ ID NO: 2771) |
| βc-1373 Target: | 5'-AGUCCUAAAGCUUGCAUUCCACCag-3'<br>3'-CUUCAGGAUUUCGAACGUAAGGUGGUC-5'<br>5'-GAAGTCCTAAAGCTTGCATTCCACCAG-3' | (SEQ ID NO: 554)<br>(SEQ ID NO: 1663)<br>(SEQ ID NO: 2772) |
| βc-1410 Target: | 5'-GUUCUGAACAAGACGUUGACUUGga-3'<br>3'-GUCAAGACUUGUUCUGCAACUGAACCU-5'<br>5'-CAGTTCTGAACAAGACGTTGACTTGGA-3' | (SEQ ID NO: 555)<br>(SEQ ID NO: 1664)<br>(SEQ ID NO: 2773) |
| βc-1411 Target: | 5'-AGUUCUGAACAAGACGUUGACUUgg-3'<br>3'-UGUCAAGACUUGUUCUGCAACUGAACC-5'<br>5'-ACAGTTCTGAACAAGACGTTGACTTGG-3' | (SEQ ID NO: 556)<br>(SEQ ID NO: 1665)<br>(SEQ ID NO: 2774) |
| βc-1421 Target: | 5'-GUCCAAAGACAGUUCUGAACAAGac-3'<br>3'-CUCAGGUUUCUGUCAAGACUUGUUCUG-5'<br>5'-GAGTCCAAAGACAGTTCTGAACAAGAC-3' | (SEQ ID NO: 557)<br>(SEQ ID NO: 1666)<br>(SEQ ID NO: 2775) |
| βc-1458 Target: | 5'-UUCCUGUUUAGUUGCAGCAUCUGaa-3'<br>3'-GGAAGGACAAAUCAACGUCGUAGACUU-5'<br>5'-CCTTCCTGTTTAGTTGCAGCATCTGAA-3' | (SEQ ID NO: 558)<br>(SEQ ID NO: 1667)<br>(SEQ ID NO: 2776) |
| βc-1517 Target: | 5'-ACAUUUAUAUCAUCUGAACCCAGaa-3'<br>3'-GGUGUAAAUAUAGUAGACUUGGGUCUU-5'<br>5'-CCACATTTATATCATCTGAACCCAGAA-3' | (SEQ ID NO: 559)<br>(SEQ ID NO: 1668)<br>(SEQ ID NO: 2777) |
| βc-1520 Target: | 5'-ACCACAUUUAUAUCAUCUGAACCca-3'<br>3'-ACUGGUGUAAAUAUAGUAGACUUGGGU-5'<br>5'-TGACCACATTTATATCATCTGAACCCA-3' | (SEQ ID NO: 560)<br>(SEQ ID NO: 1669)<br>(SEQ ID NO: 2778) |
| βc-1529 Target: | 5'-GCACAGGUGACCACAUUUAUAUCat-3'<br>3'-GACGUGUCCACUGGUGUAAAUAUAGUA-5'<br>5'-CTGCACAGGTGACCACATTTATATC-3' | (SEQ ID NO: 561)<br>(SEQ ID NO: 1670)<br>(SEQ ID NO: 2779) |
| βc-1530 Target: | 5'-UGCACAGGUGACCACAUUUAUAUca-3'<br>3'-CGACGUGUCCACUGGUGUAAAUAUAGU-5'<br>5'-GCTGCACAGGTGACCACATTTATATCA-3' | (SEQ ID NO: 562)<br>(SEQ ID NO: 1671)<br>(SEQ ID NO: 2780) |
| βc-1558 Target: | 5'-UGCAAGUGAGGUUAGAAAGAAUUcc-3'<br>3'-UAACGUUCACUCCAAUCUUUCUUAAGG-5'<br>5'-ATTGCAAGTGAGGTTAGAAAGAATTCC-3' | (SEQ ID NO: 563)<br>(SEQ ID NO: 1672)<br>(SEQ ID NO: 2781) |
| βc-1566 Target: | 5'-AUAAUUAUUGCAAGUGAGGUUAGaa-3'<br>3'-AAUAUUAAUAACGUUCACUCCAAUCUU-5'<br>5'-TTATAATTATTGCAAGTGAGGTTAGAA-3' | (SEQ ID NO: 564)<br>(SEQ ID NO: 1673)<br>(SEQ ID NO: 2782) |
| βc-1579 Target: | 5'-UCAUCUUGUUCUUAUAAUUAUUGca-3'<br>3'-GUAGUAGAACAAGAAUAUUAAUAACGU-5'<br>5'-CATCATCTTGTTCTTATAATTATTGCA-3' | (SEQ ID NO: 565)<br>(SEQ ID NO: 1674)<br>(SEQ ID NO: 2783) |
| βc-1580 Target: | 5'-AUCAUCUUGUUCUUAUAAUUAUUgc-3'<br>3'-GGUAGUAGAACAAGAAUAUUAAUAACG-5'<br>5'-CCATCATCTTGTTCTTATAATTATTGC-3' | (SEQ ID NO: 566)<br>(SEQ ID NO: 1675)<br>(SEQ ID NO: 2784) |
| βc-1583 Target: | 5'-ACCAUCAUCUUGUUCUUAUAAUUat-3'<br>3'-UCUGGUAGUAGAACAAGAAUAUUAAUA-5'<br>5'-AGACCATCATCTTGTTCTTATAATTAT-3' | (SEQ ID NO: 567)<br>(SEQ ID NO: 1676)<br>(SEQ ID NO: 2785) |

TABLE 9-continued

Additional Selected Anti-β-catenin DsiRNAs, 25/27mer Duplexes

| | | | |
|---|---|---|---|
| βc-1585 Target: | 5'-AGACCAUCAUCUUGUUCUUAUAAtt-3'<br>3'-CGUCUGGUAGUAGAACAAGAAUAUUAA-5'<br>5'-GCAGACCATCATCTTGTTCTTATAATT-3' | (SEQ ID NO: 568)<br>(SEQ ID NO: 1677)<br>(SEQ ID NO: 2786) | |
| βc-1808 Target: | 5'-AAUCCAACAGUAGCCUUUAUCAGag-3'<br>3'-AGUUAGGUUGUCAUCGGAAAUAGUCUC-5'<br>5'-TCAATCCAACAGTAGCCTTTATCAGAG-3' | (SEQ ID NO: 569)<br>(SEQ ID NO: 1678)<br>(SEQ ID NO: 2787) | |
| βc-1813 Target: | 5'-GAAUCAAUCCAACAGUAGCCUUUat-3'<br>3'-AGCUUAGUUAGGUUGUCAUCGGAAAUA-5'<br>5'-TCGAATCAATCCAACAGTAGCCTTTAT-3' | (SEQ ID NO: 570)<br>(SEQ ID NO: 1679)<br>(SEQ ID NO: 2788) | |
| βc-1955 Target: | 5'-UCCACAAAUUGCUGCUGUGUCCCac-3'<br>3'-GGAGGUGUUUAACGACGACACAGGGUG-5'<br>5'-CCTCCACAAATTGCTGCTGTGTCCCAC-3' | (SEQ ID NO: 571)<br>(SEQ ID NO: 1680)<br>(SEQ ID NO: 2789) | |
| βc-1989 Target: | 5'-ACAACCUUCAACUAUUUCUUCCAtg-3'<br>3'-CAUGUUGGAAGUUGAUAAAGAAGGUAC-5'<br>5'-GTACAACCTTCAACTATTTCTTCCATG-3' | (SEQ ID NO: 572)<br>(SEQ ID NO: 1681)<br>(SEQ ID NO: 2790) | |
| βc-1990 Target: | 5'-UACAACCUUCAACUAUUUCUUCCat-3'<br>3'-CCAUGUUGGAAGUUGAUAAAGAAGGUA-5'<br>5'-GGTACAACCTTCAACTATTTCTTCC-3' | (SEQ ID NO: 573)<br>(SEQ ID NO: 1682)<br>(SEQ ID NO: 2791) | |
| βc-1991 Target: | 5'-GUACAACCUUCAACUAUUUCUUCca-3'<br>3'-GCCAUGUUGGAAGUUGAUAAAGAAGGU-5'<br>5'-CGGTACAACCTTCAACTATTTCTTCCA-3' | (SEQ ID NO: 574)<br>(SEQ ID NO: 1683)<br>(SEQ ID NO: 2792) | |
| βc-1992 Target: | 5'-GGUACAACCUUCAACUAUUUCUUcc-3'<br>3'-GGCCAUGUUGGAAGUUGAUAAAGAAGG-5'<br>5'-CCGGTACAACCTTCAACTATTTCTTCC-3' | (SEQ ID NO: 575)<br>(SEQ ID NO: 1684)<br>(SEQ ID NO: 2793) | |
| βc-1997 Target: | 5'-GCUCCGGUACAACCUUCAACUAUtt-3'<br>3'-CCCGAGGCCAUGUUGGAAGUUGAUAAA-5'<br>5'-GGGCTCCGGTACAACCTTCAACTATTT-3' | (SEQ ID NO: 576)<br>(SEQ ID NO: 1685)<br>(SEQ ID NO: 2794) | |
| βc-2036 Target: | 5'-ACAAUUCGGUUGUGAACAUCCCGag-3'<br>3'-AUUGUUAAGCCAACACUUGUAGGGCUC-5'<br>5'-TAACAATTCGGTTGTGAACATCCCGAG-3' | (SEQ ID NO: 577)<br>(SEQ ID NO: 1686)<br>(SEQ ID NO: 2795) | |
| βc-2037 Target: | 5'-AACAAUUCGGUUGUGAACAUCCCga-3'<br>3'-UAUUGUUAAGCCAACACUUGUAGGGCU-5'<br>5'-ATAACAATTCGGTTGTGAACATCCCGA-3' | (SEQ ID NO: 578)<br>(SEQ ID NO: 1687)<br>(SEQ ID NO: 2796) | |
| βc-2038 Target: | 5'-UAACAAUUCGGUUGUGAACAUCCcg-3'<br>3'-CUAUUGUUAAGCCAACACUUGUAGGGC-5'<br>5'-GATAACAATTCGGTTGTGAACATCCCG-3' | (SEQ ID NO: 579)<br>(SEQ ID NO: 1688)<br>(SEQ ID NO: 2797) | |
| βc-2039 Target: | 5'-AUAACAAUUCGGUUGUGAACAUCcc-3'<br>3'-ACUAUUGUUAAGCCAACACUUGUAGGG-5'<br>5'-TGATAACAATTCGGTTGTGAACATCCC-3' | (SEQ ID NO: 580)<br>(SEQ ID NO: 1689)<br>(SEQ ID NO: 2798) | |
| βc-2040 Target: | 5'-GAUAACAAUUCGGUUGUGAACAUcc-3'<br>3'-GACUAUUGUUAAGCCAACACUUGUAGG-5'<br>5'-CTGATAACAATTCGGTTGTGAACATCC-3' | (SEQ ID NO: 581)<br>(SEQ ID NO: 1690)<br>(SEQ ID NO: 2799) | |
| βc-2041 Target: | 5'-UGAUAACAAUUCGGUUGUGAACAtc-3'<br>3'-AGACUAUUGUUAAGCCAACACUUGUAG-5'<br>5'-TCTGATAACAATTCGGTTGTGAACATC-3' | (SEQ ID NO: 582)<br>(SEQ ID NO: 1691)<br>(SEQ ID NO: 2800) | |
| βc-2052 Target: | 5'-AUUUAGUCCUCUGAUAACAAUUCgg-3'<br>3'-CAUAAAUCAGGAGACUAUUGUUAAGCC-5'<br>5'-GTATTTAGTCCTCTGATAACAATTCGG-3' | (SEQ ID NO: 583)<br>(SEQ ID NO: 1692)<br>(SEQ ID NO: 2801) | |
| βc-2053 Target: | 5'-UAUUUAGUCCUCUGAUAACAAUUcg-3'<br>3'-CCAUAAAUCAGGAGACUAUUGUUAAGC-5'<br>5'-GGTATTTAGTCCTCTGATAACAATTCG-3' | (SEQ ID NO: 584)<br>(SEQ ID NO: 1693)<br>(SEQ ID NO: 2802) | |
| βc-2054 Target: | 5'-GUAUUUAGUCCUCUGAUAACAAUtc-3'<br>3'-ACCAUAAAUCAGGAGACUAUUGUUAAG-5'<br>5'-TGGTATTTAGTCCTCTGATAACAATTC-3' | (SEQ ID NO: 585)<br>(SEQ ID NO: 1694)<br>(SEQ ID NO: 2803) | |
| βc-2055 Target: | 5'-GGUAUUUAGUCCUCUGAUAACAAtt-3'<br>3'-UACCAUAAAUCAGGAGACUAUUGUUAA-5'<br>5'-ATGGTATTTAGTCCTCTGATAACAATT-3' | (SEQ ID NO: 586)<br>(SEQ ID NO: 1695)<br>(SEQ ID NO: 2804) | |

TABLE 9-continued

Additional Selected Anti-β-catenin DsiRNAs, 25/27mer Duplexes

| | | |
|---|---|---|
| βc-2065 Target: | 5'-ACAAUGGAAUGGUAUUUAGUCCUct-3'<br>3'-UUUGUUACCUUACCAUAAAUCAGGAGA-5'<br>5'-AAACAATGGAATGGTATTTAGTCCTCT-3' | (SEQ ID NO: 587)<br>(SEQ ID NO: 1696)<br>(SEQ ID NO: 2805) |
| βc-2069 Target: | 5'-ACAAACAAUGGAAUGGUAUUUAGtc-3'<br>3'-CGUGUUUGUUACCUUACCAUAAAUCAG-5'<br>5'-GCACAAACAATGGAATGGTATTTAGTC-3' | (SEQ ID NO: 588)<br>(SEQ ID NO: 1697)<br>(SEQ ID NO: 2806) |
| βc-2071 Target: | 5'-GCACAAACAAUGGAAUGGUAUUUag-3'<br>3'-GACGUGUUUGUUACCUUACCAUAAAUC-5'<br>5'-CTGCACAAACAATGGAATGGTATTTAG-3' | (SEQ ID NO: 589)<br>(SEQ ID NO: 1698)<br>(SEQ ID NO: 2807) |
| βc-2072 Target: | 5'-UGCACAAACAAUGGAAUGGUAUUta-3'<br>3'-CGACGUGUUUGUUACCUUACCAUAAAU-5'<br>5'-GCTGCACAAACAATGGAATGGTATTTA-3' | (SEQ ID NO: 590)<br>(SEQ ID NO: 1699)<br>(SEQ ID NO: 2808) |
| βc-2111 Target: | 5'-GCUACUCUUUGGAUGUUUUCAAUgg-3'<br>3'-GUCGAUGAGAAACCUACAAAAGUUACC-5'<br>5'-CAGCTACTCTTTGGATGTTTTCAATGG-3' | (SEQ ID NO: 591)<br>(SEQ ID NO: 1700)<br>(SEQ ID NO: 2809) |
| βc-2112 Target: | 5'-AGCUACUCUUUGGAUGUUUUCAAtg-3'<br>3'-CGUCGAUGAGAAACCUACAAAAGUUAC-5'<br>5'-GCAGCTACTCTTTGGATGTTTTCAATG-3' | (SEQ ID NO: 592)<br>(SEQ ID NO: 1701)<br>(SEQ ID NO: 2810) |
| βc-2168 Target: | 5'-GCUUCAAUAGCUUCUGCAGCUUCct-3'<br>3'-GUCGAAGUUAUCGAAGACGUCGAAGGA-5'<br>5'-CAGCTTCAATAGCTTCTGCAGCTTCCT-3' | (SEQ ID NO: 593)<br>(SEQ ID NO: 1702)<br>(SEQ ID NO: 2811) |
| βc-2175 Target: | 5'-UCCCUCAGCUUCAAUAGCUUCUGca-3'<br>3'-CGAGGGAGUCGAAGUUAUCGAAGACGU-5'<br>5'-GCTCCCTCAGCTTCAATAGCTTCTGCA-3' | (SEQ ID NO: 594)<br>(SEQ ID NO: 1703)<br>(SEQ ID NO: 2812) |
| βc-2177 Target: | 5'-GCUCCCUCAGCUUCAAUAGCUUCtg-3'<br>3'-ACCGAGGGAGUCGAAGUUAUCGAAGAC-5'<br>5'-TGGCTCCCTCAGCTTCAATAGCTTCTG-3' | (SEQ ID NO: 595)<br>(SEQ ID NO: 1704)<br>(SEQ ID NO: 2813) |
| βc-2214 Target: | 5'-AUUCCUAGAGUGAAGUAACUCUGtc-3'<br>3'-AGUAAGGAUCUCACUUCAUUGAGACAG-5'<br>5'-TCATTCCTAGAGTGAAGTAACTCTGTC-3' | (SEQ ID NO: 596)<br>(SEQ ID NO: 1705)<br>(SEQ ID NO: 2814) |
| βc-2216 Target: | 5'-UCAUUCCUAGAGUGAAGUAACUCtg-3'<br>3'-GAAGUAAGGAUCUCACUUCAUUGAGAC-5'<br>5'-CTTCATTCCTAGAGTGAAGTAACTCTG-3' | (SEQ ID NO: 597)<br>(SEQ ID NO: 1706)<br>(SEQ ID NO: 2815) |
| βc-2217 Target: | 5'-UUCAUUCCUAGAGUGAAGUAACUct-3'<br>3'-GGAAGUAAGGAUCUCACUUCAUUGAGA-5'<br>5'-CCTTCATTCCTAGAGTGAAGTAACTCT-3' | (SEQ ID NO: 598)<br>(SEQ ID NO: 1707)<br>(SEQ ID NO: 2816) |
| βc-2264 Target: | 5'-UCCUCAGACAUUCGGAACAAAACag-3'<br>3'-ACAGGAGUCUGUAAGCCUUGUUUUGUC-5'<br>5'-TGTCCTCAGACATTCGGAACAAAACAG-3' | (SEQ ID NO: 599)<br>(SEQ ID NO: 1708)<br>(SEQ ID NO: 2817) |
| βc-2266 Target: | 5'-UGUCCUCAGACAUUCGGAACAAAac-3'<br>3'-GAACAGGAGUCUGUAAGCCUUGUUUUG-5'<br>5'-CTTGTCCTCAGACATTCGGAACAAAAC-3' | (SEQ ID NO: 600)<br>(SEQ ID NO: 1709)<br>(SEQ ID NO: 2818) |
| βc-2287 Target: | 5'-GUUUCUUGUAAUCUUGUGGCUUGtc-3'<br>3'-GGCAAAGAACAUUAGAACACCGAACAG-5'<br>5'-CCGTTTCTTGTAATCTTGTGGCTTGTC-3' | (SEQ ID NO: 601)<br>(SEQ ID NO: 1710)<br>(SEQ ID NO: 2819) |
| βc-2295 Target: | 5'-UGAAAGCCGUUUCUUGUAAUCUUgt-3'<br>3'-UGACUUUCGGCAAAGAACAUUAGAACA-5'<br>5'-ACTGAAAGCCGTTTCTTGTAATCTTGT-3' | (SEQ ID NO: 602)<br>(SEQ ID NO: 1711)<br>(SEQ ID NO: 2820) |
| βc-2302 Target: | 5'-GCUCAACUGAAAGCCGUUUCUUGta-3'<br>3'-GUCGAGUUGACUUUCGGCAAAGAACAU-5'<br>5'-CAGCTCAACTGAAAGCCGTTTCTTGTA-3' | (SEQ ID NO: 603)<br>(SEQ ID NO: 1712)<br>(SEQ ID NO: 2821) |
| βc-2363 Target: | 5'-AGUCCAAGAUCAGCAGUCUCAUUcc-3'<br>3'-GUUCAGGUUCUAGUCGUCAGAGUAAGG-5'<br>5'-CAAGTCCAAGATCAGCAGTCTCATTCC-3' | (SEQ ID NO: 604)<br>(SEQ ID NO: 1713)<br>(SEQ ID NO: 2822) |
| βc-2373 Target: | 5'-ACCAAUAUCAAGUCCAAGAUCAGca-3'<br>3'-CGUGGUUAUAGUUCAGGUUCUAGUCGU-5'<br>5'-GCACCAATATCAAGTCCAAGATCAGCA-3' | (SEQ ID NO: 605)<br>(SEQ ID NO: 1714)<br>(SEQ ID NO: 2823) |

TABLE 9-continued

Additional Selected Anti-β-catenin DsiRNAs, 25/27mer Duplexes

|  |  |  |  |
|---|---|---|---|
| βc-2424 | Target: | 5'-AGAACGAUAGCUAGGAUCAUCCUgg-3'<br>3'-UUUCUUGCUAUCGAUCCUAGUAGGACC-5'<br>5'-AAAGAACGATAGCTAGGATCATCCTGG-3' | (SEQ ID NO: 606)<br>(SEQ ID NO: 1715)<br>(SEQ ID NO: 2824) |
| βc-2441 | Target: | 5'-UAUCCACCAGAGUGAAAAGAACGat-3'<br>3'-GUAUAGGUGGUCUCACUUUUCUUGCUA-5'<br>5'-CATATCCACCAGAGTGAAAAGAACGAT-3' | (SEQ ID NO: 607)<br>(SEQ ID NO: 1716)<br>(SEQ ID NO: 2825) |
| βc-2618 | Target: | 5'-AUUUACAGGUCAGUAUCAAACCAgg-3'<br>3'-ACUAAAUGUCCAGUCAUAGUUUGGUCC-5'<br>5'-TGATTTACAGGTCAGTATCAAACCAGG-3' | (SEQ ID NO: 608)<br>(SEQ ID NO: 1717)<br>(SEQ ID NO: 2826) |
| βc-2619 | Target: | 5'-GAUUUACAGGUCAGUAUCAAACCag-3'<br>3'-UACUAAAUGUCCAGUCAUAGUUUGGUC-5'<br>5'-ATGATTTACAGGTCAGTATCAAACCAG-3' | (SEQ ID NO: 609)<br>(SEQ ID NO: 1718)<br>(SEQ ID NO: 2827) |
| βc-2620 | Target: | 5'-UGAUUUACAGGUCAGUAUCAAACca-3'<br>3'-CUACUAAAUGUCCAGUCAUAGUUUGGU-5'<br>5'-GATGATTTACAGGTCAGTATCAAACCA-3' | (SEQ ID NO: 610)<br>(SEQ ID NO: 1719)<br>(SEQ ID NO: 2828) |
| βc-2634 | Target: | 5'-UCUUACCUAAAGGAUGAUUUACAgg-3'<br>3'-GAAGAAUGGAUUUCCUACUAAAUGUCC-5'<br>5'-CTTCTTACCTAAAGGATGATTTACAGG-3' | (SEQ ID NO: 611)<br>(SEQ ID NO: 1720)<br>(SEQ ID NO: 2829) |
| βc-2635 | Target: | 5'-UUCUUACCUAAAGGAUGAUUUACag-3'<br>3'-UGAAGAAUGGAUUUCCUACUAAAUGUC-5'<br>5'-ACTTCTTACCTAAAGGATGATTTACAG-3' | (SEQ ID NO: 612)<br>(SEQ ID NO: 1721)<br>(SEQ ID NO: 2830) |
| βc-2637 | Target: | 5'-ACUUCUUACCUAAAGGAUGAUUUac-3'<br>3'-UUUGAAGAAUGGAUUUCCUACUAAAUG-5'<br>5'-AAACTTCTTACCTAAAGGATGATTTAC-3' | (SEQ ID NO: 613)<br>(SEQ ID NO: 1722)<br>(SEQ ID NO: 2831) |
| βc-2645 | Target: | 5'-UUUUUAAAACUUCUUACCUAAAGga-3'<br>3'-CGAAAAAUUUUGAAGAAUGGAUUUCCU-5'<br>5'-GCTTTTTAAAACTTCTTACCTAAAGGA-3' | (SEQ ID NO: 614)<br>(SEQ ID NO: 1723)<br>(SEQ ID NO: 2832) |
| βc-2647 | Target: | 5'-GCUUUUUAAAACUUCUUACCUAAag-3'<br>3'-ACCGAAAAAUUUUGAAGAAUGGAUUUC-5'<br>5'-TGGCTTTTTAAAACTTCTTACCTAAAG-3' | (SEQ ID NO: 615)<br>(SEQ ID NO: 1724)<br>(SEQ ID NO: 2833) |
| βc-2653 | Target: | 5'-AAACUGGCUUUUUAAAACUUCUUac-3'<br>3'-GGUUUGACCGAAAAAUUUUGAAGAAUG-5'<br>5'-CCAAACTGGCTTTTTAAAACTTCTTAC-3' | (SEQ ID NO: 616)<br>(SEQ ID NO: 1725)<br>(SEQ ID NO: 2834) |
| βc-2657 | Target: | 5'-ACCCAAACUGGCUUUUUAAAACUtc-3'<br>3'-AAUGGGUUUGACCGAAAAAUUUUGAAG-5'<br>5'-TTACCCAAACTGGCTTTTTAAAACTTC-3' | (SEQ ID NO: 617)<br>(SEQ ID NO: 1726)<br>(SEQ ID NO: 2835) |
| βc-2658 | Target: | 5'-UACCCAAACUGGCUUUUUAAAACtt-3'<br>3'-AAAUGGGUUUGACCGAAAAAUUUUGAA-5'<br>5'-TTTACCCAAACTGGCTTTTTAAAACTT-3' | (SEQ ID NO: 618)<br>(SEQ ID NO: 1727)<br>(SEQ ID NO: 2836) |
| βc-2659 | Target: | 5'-UUACCCAAACUGGCUUUUUAAAAct-3'<br>3'-AAAAUGGGUUUGACCGAAAAAUUUUGA-5'<br>5'-TTTTACCCAAACTGGCTTTTTAAAACT-3' | (SEQ ID NO: 619)<br>(SEQ ID NO: 1728)<br>(SEQ ID NO: 2837) |
| βc-2660 | Target: | 5'-UUUACCCAAACUGGCUUUUUAAAac-3'<br>3'-UAAAAUGGGUUUGACCGAAAAAUUUUG-5'<br>5'-ATTTTACCCAAACTGGCTTTTTAAAAC-3' | (SEQ ID NO: 620)<br>(SEQ ID NO: 1729)<br>(SEQ ID NO: 2838) |
| βc-2701 | Target: | 5'-AACCAAGUCUUUCUGAAGUUCUGta-3'<br>3'-GGUUGGUUCAGAAAGACUUCAAGACAU-5'<br>5'-CCAACCAAGTCTTTCTGAAGTTCTGTA-3' | (SEQ ID NO: 621)<br>(SEQ ID NO: 1730)<br>(SEQ ID NO: 2839) |
| βc-2709 | Target: | 5'-ACCCUACCAACCAAGUCUUUCUGaa-3'<br>3'-GGUGGGAUGGUUGGUUCAGAAAGACUU-5'<br>5'-CCACCCTACCAACCAAGTCTTTCTGAA-3' | (SEQ ID NO: 622)<br>(SEQ ID NO: 1731)<br>(SEQ ID NO: 2840) |
| βc-2733 | Target: | 5'-UUACAAAUAGCCUAAACCACUCCca-3'<br>3'-UAAAUGUUUAUCGGAUUUGGUGAGGGU-5'<br>5'-ATTTACAAATAGCCTAAACCACTCCCA-3' | (SEQ ID NO: 623)<br>(SEQ ID NO: 1732)<br>(SEQ ID NO: 2841) |
| βc-2734 | Target: | 5'-UUUACAAAUAGCCUAAACCACUCcc-3'<br>3'-CUAAAUGUUUAUCGGAUUUGGUGAGGG-5'<br>5'-GATTTACAAATAGCCTAAACCACTCCC-3' | (SEQ ID NO: 624)<br>(SEQ ID NO: 1733)<br>(SEQ ID NO: 2842) |

TABLE 9-continued

Additional Selected Anti-β-catenin DsiRNAs, 25/27mer Duplexes

| | | |
|---|---|---|
| βc-2735 Target: | 5'-AUUUACAAAUAGCCUAAACCACUcc-3'<br>3'-UCUAAAUGUUUAUCGGAUUUGGUGAGG-5'<br>5'-AGATTTACAAATAGCCTAAACCACTCC-3' | (SEQ ID NO: 625)<br>(SEQ ID NO: 1734)<br>(SEQ ID NO: 2843) |
| βc-2736 Target: | 5'-GAUUUACAAAUAGCCUAAACCACUc-3'<br>3'-GUCUAAAUGUUUAUCGGAUUUGGUGAG-5'<br>5'-CAGATTTACAAATAGCCTAAACCACTC-3' | (SEQ ID NO: 626)<br>(SEQ ID NO: 1735)<br>(SEQ ID NO: 2844) |
| βc-2747 Target: | 5'-UUUUUGUGGCAGAUUUACAAAUAgc-3'<br>3'-ACAAAAACACCGUCUAAAUGUUUAUCG-5'<br>5'-TGTTTTTGTGGCAGATTTACAAATAGC-3' | (SEQ ID NO: 627)<br>(SEQ ID NO: 1736)<br>(SEQ ID NO: 2845) |
| βc-2748 Target: | 5'-GUUUUUGUGGCAGAUUUACAAAUag-3'<br>3'-GACAAAAACACCGUCUAAAUGUUUAUC-5'<br>5'-CTGTTTTTGTGGCAGATTTACAAATAG-3' | (SEQ ID NO: 628)<br>(SEQ ID NO: 1737)<br>(SEQ ID NO: 2846) |
| βc-2749 Target: | 5'-UGUUUUUGUGGCAGAUUUACAAAta-3'<br>3'-GGACAAAAACACCGUCUAAAUGUUUAU-5'<br>5'-CCTGTTTTTGTGGCAGATTTACAAATA-3' | (SEQ ID NO: 629)<br>(SEQ ID NO: 1738)<br>(SEQ ID NO: 2847) |
| βc-2754 Target: | 5'-AUACCUGUUUUUGUGGCAGAUUUac-3'<br>3'-UAUAUGGACAAAAACACCGUCUAAAUG-5'<br>5'-ATATACCTGTTTTTGTGGCAGATTTAC-3' | (SEQ ID NO: 630)<br>(SEQ ID NO: 1739)<br>(SEQ ID NO: 2848) |
| βc-2764 Target: | 5'-UUCAAAGUAUAUACCUGUUUUUGtg-3'<br>3'-GAAAGUUUCAUAUAUGGACAAAAACAC-5'<br>5'-CTTTCAAAGTATATACCTGTTTTTGTG-3' | (SEQ ID NO: 631)<br>(SEQ ID NO: 1740)<br>(SEQ ID NO: 2849) |
| βc-2770 Target: | 5'-UCUCCUUUCAAAGUAUAUACCUGtt-3'<br>3'-GUAGAGGAAAGUUUCAUAUAUGGACAA-5'<br>5'-CATCTCCTTTCAAAGTATATACCTGTT-3' | (SEQ ID NO: 632)<br>(SEQ ID NO: 1741)<br>(SEQ ID NO: 2850) |
| βc-2771 Target: | 5'-AUCUCCUUUCAAAGUAUAUACCUgt-3'<br>3'-UGUAGAGGAAAGUUUCAUAUAUGGACA-5'<br>5'-ACATCTCCTTTCAAAGTATATACCTGT-3' | (SEQ ID NO: 633)<br>(SEQ ID NO: 1742)<br>(SEQ ID NO: 2851) |
| βc-2773 Target: | 5'-ACAUCUCCUUUCAAAGUAUAUACct-3'<br>3'-UCUGUAGAGGAAAGUUUCAUAUAUGGA-5'<br>5'-AGACATCTCCTTTCAAAGTATATACCT-3' | (SEQ ID NO: 634)<br>(SEQ ID NO: 1743)<br>(SEQ ID NO: 2852) |
| βc-2774 Target: | 5'-GACAUCUCCUUUCAAAGUAUAUAcc-3'<br>3'-UUCUGUAGAGGAAAGUUUCAUAUAUGG-5'<br>5'-AAGACATCTCCTTTCAAAGTATATACC-3' | (SEQ ID NO: 635)<br>(SEQ ID NO: 1744)<br>(SEQ ID NO: 2853) |
| βc-2775 Target: | 5'-AGACAUCUCCUUUCAAAGUAUAUac-3'<br>3'-GUUCUGUAGAGGAAAGUUUCAUAUAUG-5'<br>5'-CAAGACATCTCCTTTCAAAGTATATAC-3' | (SEQ ID NO: 636)<br>(SEQ ID NO: 1745)<br>(SEQ ID NO: 2854) |
| βc-2780 Target: | 5'-UUCCAAGACAUCUCCUUUCAAAGta-3'<br>3'-ACAAGGUUCUGUAGAGGAAAGUUUCAU-5'<br>5'-TGTTCCAAGACATCTCCTTTCAAAGTA-3' | (SEQ ID NO: 637)<br>(SEQ ID NO: 1746)<br>(SEQ ID NO: 2855) |
| βc-2788 Target: | 5'-UUCCAAUGUUCCAAGACAUCUCCtt-3'<br>3'-GUAAGGUUACAAGGUUCUGUAGAGGAA-5'<br>5'-CATTCCAATGTTCCAAGACATCTCCTT-3' | (SEQ ID NO: 638)<br>(SEQ ID NO: 1747)<br>(SEQ ID NO: 2856) |
| βc-2789 Target: | 5'-AUUCCAAUGUUCCAAGACAUCUCct-3'<br>3'-UGUAAGGUUACAAGGUUCUGUAGAGGA-5'<br>5'-ACATTCCAATGTTCCAAGACATCTCCT-3' | (SEQ ID NO: 639)<br>(SEQ ID NO: 1748)<br>(SEQ ID NO: 2857) |
| βc-2791 Target: | 5'-ACAUUCCAAUGUUCCAAGACAUCtc-3'<br>3'-CUUGUAAGGUUACAAGGUUCUGUAGAG-5'<br>5'-GAACATTCCAATGTTCCAAGACATCTC-3' | (SEQ ID NO: 640)<br>(SEQ ID NO: 1749)<br>(SEQ ID NO: 2858) |
| βc-2803 Target: | 5'-AGAAAUCUGAGAACAUUCCAAUGtt-3'<br>3'-GGUCUUUAGACUCUUGUAAGGUUACAA-5'<br>5'-CCAGAAATCTGAGAACATTCCAATGTT-3' | (SEQ ID NO: 641)<br>(SEQ ID NO: 1750)<br>(SEQ ID NO: 2859) |
| βc-2807 Target: | 5'-AACCAGAAAUCUGAGAACAUUCCaa-3'<br>3'-UGUUGGUCUUUAGACUCUUGUAAGGUU-5'<br>5'-ACAACCAGAAATCTGAGAACATTCCAA-3' | (SEQ ID NO: 642)<br>(SEQ ID NO: 1751)<br>(SEQ ID NO: 2860) |
| βc-2809 Target: | 5'-ACAACCAGAAAUCUGAGAACAUUcc-3'<br>3'-AUUGUUGGUCUUUAGACUCUUGUAAGG-5'<br>5'-TAACAACCAGAAATCTGAGAACATTCC-3' | (SEQ ID NO: 643)<br>(SEQ ID NO: 1752)<br>(SEQ ID NO: 2861) |

TABLE 9-continued

Additional Selected Anti-β-catenin DsiRNAs, 25/27mer Duplexes

| | | | |
|---|---|---|---|
| βc-2810 Target: | 5'-AACAACCAGAAAUCUGAGAACAUtc-3'<br>3'-UAUUGUUGGUCUUUAGACUCUUGUAAG-5'<br>5'-ATAACAACCAGAAATCTGAGAACATTC-3' | (SEQ ID NO: 644)<br>(SEQ ID NO: 1753)<br>(SEQ ID NO: 2862) | |
| βc-2811 Target: | 5'-UAACAACCAGAAAUCUGAGAACAtt-3'<br>3'-GUAUUGUUGGUCUUUAGACUCUUGUAA-5'<br>5'-CATAACAACCAGAAATCTGAGAACATT-3' | (SEQ ID NO: 645)<br>(SEQ ID NO: 1754)<br>(SEQ ID NO: 2863) | |
| βc-2817 Target: | 5'-AUCACAUAACAACCAGAAAUCUGag-3'<br>3'-ACUAGUGUAUUGUUGGUCUUUAGACUC-5'<br>5'-TGATCACATAACAACCAGAAATCTGAG-3' | (SEQ ID NO: 646)<br>(SEQ ID NO: 1755)<br>(SEQ ID NO: 2864) | |
| βc-2818 Target: | 5'-GAUCACAUAACAACCAGAAAUCUga-3'<br>3'-UACUAGUGUAUUGUUGGUCUUUAGACU-5'<br>5'-ATGATCACATAACAACCAGAAATCTGA-3' | (SEQ ID NO: 647)<br>(SEQ ID NO: 1756)<br>(SEQ ID NO: 2865) | |
| βc-2824 Target: | 5'-ACACAUGAUCACAUAACAACCAGaa-3'<br>3'-GGUGUGUACUAGUGUAUUGUUGGUCUU-5'<br>5'-CCACACATGATCACATAACAACCAGAA-3' | (SEQ ID NO: 648)<br>(SEQ ID NO: 1757)<br>(SEQ ID NO: 2866) | |
| βc-2827 Target: | 5'-UCCACACAUGAUCACAUAACAACCa-3'<br>3'-GAAGGUGUGUACUAGUGUAUUGUUGGU-5'<br>5'-CTTCCACACATGATCACATAACAACCA-3' | (SEQ ID NO: 649)<br>(SEQ ID NO: 1758)<br>(SEQ ID NO: 2867) | |
| βc-2832 Target: | 5'-UAACUUCCACACAUGAUCACAUAac-3'<br>3'-UUAUUGAAGGUGUGUACUAGUGUAUUG-5'<br>5'-AATAACTTCCACACATGATCACATAAC-3' | (SEQ ID NO: 650)<br>(SEQ ID NO: 1759)<br>(SEQ ID NO: 2868) | |
| βc-2833 Target: | 5'-AUAACUUCCACACAUGAUCACAUaa-3'<br>3'-AUUAUUGAAGGUGUGUACUAGUGUAUU-5'<br>5'-TAATAACTTCCACACATGATCACATAA-3' | (SEQ ID NO: 651)<br>(SEQ ID NO: 1760)<br>(SEQ ID NO: 2869) | |
| βc-2834 Target: | 5'-AAUAACUUCCACACAUGAUCACAta-3'<br>3'-AAUUAUUGAAGGUGUGUACUAGUGUAU-5'<br>5'-TTAATAACTTCCACACATGATCACATA-3' | (SEQ ID NO: 652)<br>(SEQ ID NO: 1761)<br>(SEQ ID NO: 2870) | |
| βc-2835 Target: | 5'-UAAUAACUUCCACACAUGAUCACat-3'<br>3'-CAAUUAUUGAAGGUGUGUACUAGUGUA-5'<br>5'-GTTAATAACTTCCACACATGATCAC-3' | (SEQ ID NO: 653)<br>(SEQ ID NO: 1762)<br>(SEQ ID NO: 2871) | |
| βc-2842 Target: | 5'-UUAAAGUUAAUAACUUCCACACAtg-3'<br>3'-GUAAUUUCAAUUAUUGAAGGUGUGUAC-5'<br>5'-CATTAAAGTTAATAACTTCCACACATG-3' | (SEQ ID NO: 654)<br>(SEQ ID NO: 1763)<br>(SEQ ID NO: 2872) | |
| βc-2843 Target: | 5'-AUUAAAGUUAAUAACUUCCACACat-3'<br>3'-UGUAAUUUCAAUUAUUGAAGGUGUGUA-5'<br>5'-ACATTAAAGTTAATAACTTCCACAC-3' | (SEQ ID NO: 655)<br>(SEQ ID NO: 1764)<br>(SEQ ID NO: 2873) | |
| βc-2845 Target: | 5'-ACAUUAAAGUUAAUAACUUCCACac-3'<br>3'-UUUGUAAUUUCAAUUAUUGAAGGUGUG-5'<br>5'-AAACATTAAAGTTAATAACTTCCACAC-3' | (SEQ ID NO: 656)<br>(SEQ ID NO: 1765)<br>(SEQ ID NO: 2874) | |
| βc-2846 Target: | 5'-AACAUUAAAGUUAAUAACUUCCAca-3'<br>3'-UUUUGUAAUUUCAAUUAUUGAAGGUGU-5'<br>5'-AAAACATTAAAGTTAATAACTTCCACA-3' | (SEQ ID NO: 657)<br>(SEQ ID NO: 1766)<br>(SEQ ID NO: 2875) | |
| βc-2847 Target: | 5'-AAACAUUAAAGUUAAUAACUUCCac-3'<br>3'-UUUUUGUAAUUUCAAUUAUUGAAGGUG-5'<br>5'-AAAAACATTAAAGTTAATAACTTCCAC-3' | (SEQ ID NO: 658)<br>(SEQ ID NO: 1767)<br>(SEQ ID NO: 2876) | |
| βc-2848 Target: | 5'-AAAACAUUAAAGUUAAUAACUUCca-3'<br>3'-UUUUUUGUAAUUUCAAUUAUUGAAGGU-5'<br>5'-AAAAAACATTAAAGTTAATAACTTCCA-3' | (SEQ ID NO: 659)<br>(SEQ ID NO: 1768)<br>(SEQ ID NO: 2877) | |
| βc-2849 Target: | 5'-AAAAACAUUAAAGUUAAUAACUUcc-3'<br>3'-GUUUUUUGUAAUUUCAAUUAUUGAAGG-5'<br>5'-CAAAAAACATTAAAGTTAATAACTTCC-3' | (SEQ ID NO: 660)<br>(SEQ ID NO: 1769)<br>(SEQ ID NO: 2878) | |
| βc-2850 Target: | 5'-AAAAAACAUUAAAGUUAAUAACUtc-3'<br>3'-CGUUUUUUGUAAUUUCAAUUAUUGAAG-5'<br>5'-GCAAAAAACATTAAAGTTAATAACTTC-3' | (SEQ ID NO: 661)<br>(SEQ ID NO: 1770)<br>(SEQ ID NO: 2879) | |
| βc-2852 Target: | 5'-GCAAAAAACAUUAAAGUUAAUAAct-3'<br>3'-ACCGUUUUUUGUAAUUUCAAUUAUUGA-5'<br>5'-TGGCAAAAAACATTAAAGTTAATAACT-3' | (SEQ ID NO: 662)<br>(SEQ ID NO: 1771)<br>(SEQ ID NO: 2880) | |

TABLE 9-continued

Additional Selected Anti-β-catenin DsiRNAs, 25/27mer Duplexes

| | | |
|---|---|---|
| βc-2853 Target: | 5'-GGCAAAAAACAUUAAGUUAAUAac-3'<br>3'-CACCGUUUUUGUAAUUUCAAUUAUUG-5'<br>5'-GTGGCAAAAAACATTAAAGTTAATAAC-3' | (SEQ ID NO: 663)<br>(SEQ ID NO: 1772)<br>(SEQ ID NO: 2881) |
| βc-2864 Target: | 5'-GCAAAAGCUGUGGCAAAAAACAUta-3'<br>3'-AACGUUUUCGACACCGUUUUUGUAAU-5'<br>5'-TTGCAAAAGCTGTGGCAAAAAACATTA-3' | (SEQ ID NO: 664)<br>(SEQ ID NO: 1773)<br>(SEQ ID NO: 2882) |
| βc-2865 Target: | 5'-UGCAAAAGCUGUGGCAAAAAACAtt-3'<br>3'-CAACGUUUUCGACACCGUUUUUGUAA-5'<br>5'-GTTGCAAAAGCTGTGGCAAAAAACATT-3' | (SEQ ID NO: 665)<br>(SEQ ID NO: 1774)<br>(SEQ ID NO: 2883) |
| βc-2882 Target: | 5'-UCAUUUGAGUAUUAAGUUGCAAAag-3'<br>3'-UGAGUAAACUCAUAAUUCAACGUUUUC-5'<br>5'-ACTCATTTGAGTATTAAGTTGCAAAAG-3' | (SEQ ID NO: 666)<br>(SEQ ID NO: 1775)<br>(SEQ ID NO: 2884) |
| βc-2899 Target: | 5'-AAAACAGCAAAUGUUACUCAUUUga-3'<br>3'-AAUUUUGUCGUUUACAAUGAGUAAACU-5'<br>5'-TTAAAACAGCAAATGTTACTCATTTGA-3' | (SEQ ID NO: 667)<br>(SEQ ID NO: 1776)<br>(SEQ ID NO: 2885) |
| βc-2900 Target: | 5'-UAAAACAGCAAAUGUUACUCAUUtg-3'<br>3'-AAAUUUUGUCGUUUACAAUGAGUAAAC-5'<br>5'-TTTAAAACAGCAAATGTTACTCATTTG-3' | (SEQ ID NO: 668)<br>(SEQ ID NO: 1777)<br>(SEQ ID NO: 2886) |
| βc-2901 Target: | 5'-UUAAAACAGCAAAUGUUACUCAUtt-3'<br>3'-CAAAUUUUGUCGUUUACAAUGAGUAAA-5'<br>5'-GTTTAAAACAGCAAATGTTACTCATTT-3' | (SEQ ID NO: 669)<br>(SEQ ID NO: 1778)<br>(SEQ ID NO: 2887) |
| βc-2902 Target: | 5'-UUUAAAACAGCAAAUGUUACUCAtt-3'<br>3'-ACAAAUUUUGUCGUUUACAAUGAGUAA-5'<br>5'-TGTTTAAAACAGCAAATGTTACTCATT-3' | (SEQ ID NO: 670)<br>(SEQ ID NO: 1779)<br>(SEQ ID NO: 2888) |
| βc-2903 Target: | 5'-GUUUAAAACAGCAAAUGUUACUCat-3'<br>3'-UACAAAUUUUGUCGUUUACAAUGAGUA-5'<br>5'-ATGTTTAAAACAGCAAATGTTACTC-3' | (SEQ ID NO: 671)<br>(SEQ ID NO: 1780)<br>(SEQ ID NO: 2889) |
| βc-2904 Target: | 5'-UGUUUAAAACAGCAAAUGUUACUca-3'<br>3'-UUACAAAUUUUGUCGUUUACAAUGAGU-5'<br>5'-AATGTTTAAAACAGCAAATGTTACTCA-3' | (SEQ ID NO: 672)<br>(SEQ ID NO: 1781)<br>(SEQ ID NO: 2890) |
| βc-2909 Target: | 5'-AUUAAUGUUUAAAACAGCAAAUGtt-3'<br>3'-GAUAAUUACAAAUUUUGUCGUUUACAA-5'<br>5'-CTATTAATGTTTAAAACAGCAAATGTT-3' | (SEQ ID NO: 673)<br>(SEQ ID NO: 1782)<br>(SEQ ID NO: 2891) |
| βc-2921 Target: | 5'-AGAAAGGCUGCUAUUAAUGUUUAaa-3'<br>3'-UCUCUUUCCGACGAUAAUUACAAAUUU-5'<br>5'-AGAGAAAGGCTGCTATTAATGTTTAAA-3' | (SEQ ID NO: 674)<br>(SEQ ID NO: 1783)<br>(SEQ ID NO: 2892) |
| βc-2949 Target: | 5'-AGUUCAGACAAUACAGCUGUAUAaa-3'<br>3'-GUUCAAGUCUGUUAUGUCGACAUAUUU-5'<br>5'-CAAGTTCAGACAATACAGCTGTATAAA-3' | (SEQ ID NO: 675)<br>(SEQ ID NO: 1784)<br>(SEQ ID NO: 2893) |
| βc-2957 Target: | 5'-ACAAUGCAAGUUCAGACAAUACAgc-3'<br>3'-AGUGUUACGUUCAAGUCUGUUAUGUCG-5'<br>5'-TCACAATGCAAGTTCAGACAATACAGC-3' | (SEQ ID NO: 676)<br>(SEQ ID NO: 1785)<br>(SEQ ID NO: 2894) |
| βc-2959 Target: | 5'-UCACAAUGCAAGUUCAGACAAUAca-3'<br>3'-UUAGUGUUACGUUCAAGUCUGUUAUGU-5'<br>5'-AATCACAATGCAAGTTCAGACAATACA-3' | (SEQ ID NO: 677)<br>(SEQ ID NO: 1786)<br>(SEQ ID NO: 2895) |
| βc-2961 Target: | 5'-AAUCACAAUGCAAGUUCAGACAAta-3'<br>3'-GGUUAGUGUUACGUUCAAGUCUGUUAU-5'<br>5'-CCAATCACAATGCAAGTTCAGACAATA-3' | (SEQ ID NO: 678)<br>(SEQ ID NO: 1787)<br>(SEQ ID NO: 2896) |
| βc-2965 Target: | 5'-GGCCAAUCACAAUGCAAGUUCAGac-3'<br>3'-GUCCGGUUAGUGUUACGUUCAAGUCUG-5'<br>5'-CAGGCCAATCACAATGCAAGTTCAGAC-3' | (SEQ ID NO: 679)<br>(SEQ ID NO: 1788)<br>(SEQ ID NO: 2897) |
| βc-3052 Target: | 5'-GUUCCAUAGGAAACUCAGCUUGgt-3'<br>3'-AACAAGGGUAUCCUUUGAGUCGAACCA-5'<br>5'-TTGTTCCCATAGGAAACTCAGCTTGGT-3' | (SEQ ID NO: 680)<br>(SEQ ID NO: 1789)<br>(SEQ ID NO: 2898) |
| βc-3058 Target: | 5'-UCAAUUGUUCCCAUAGGAAACUCag-3'<br>3'-GAAGUUAACAAGGGUAUCCUUUGAGUC-5'<br>5'-CTTCAATTGTTCCCATAGGAAACTCAG-3' | (SEQ ID NO: 681)<br>(SEQ ID NO: 1790)<br>(SEQ ID NO: 2899) |

TABLE 9-continued

Additional Selected Anti-β-catenin DsiRNAs, 25/27mer Duplexes

```
                      5'-UUCAAUUGUUCCCAUAGGAAACUca-3'    (SEQ ID NO: 682)
                      3'-UGAAGUUAACAAGGGUAUCCUUUGAGU-5'  (SEQ ID NO: 1791)
βc-3059  Target:      5'-ACTTCAATTGTTCCCATAGGAAACTCA-3'  (SEQ ID NO: 2900)

5'-GUUUACUUCAAUUGUUCCCAUAGga-3'    (SEQ ID NO: 683)
                      3'-UUCAAAUGAAGUUAACAAGGGUAUCCU-5'  (SEQ ID NO: 1792)
βc-3065  Target:      5'-AAGTTTACTTCAATTGTTCCCATAGGA-3'  (SEQ ID NO: 2901)

5'-AGUUUACUUCAAUUGUUCCCAUAgg-3'    (SEQ ID NO: 684)
                      3'-UUUCAAAUGAAGUUAACAAGGGUAUCC-5'  (SEQ ID NO: 1793)
βc-3066  Target:      5'-AAAGTTTACTTCAATTGTTCCCATAGG-3'  (SEQ ID NO: 2902)

5'-AAAAGUUUACUUCAAUUGUUCCCca-3'    (SEQ ID NO: 685)
                      3'-UGUUUUUCAAAUGAAGUUAACAAGGGU-5'  (SEQ ID NO: 1794)
βc-3070  Target:      5'-ACAAAAGTTTACTTCAATTGTTCCCA-3'   (SEQ ID NO: 2903)

5'-GAACAAAAGUUUACUUCAAUUGtt-3'     (SEQ ID NO: 686)
                      3'-GUCUUGUUUUUCAAAUGAAGUUAACAA-5'  (SEQ ID NO: 1795)
βc-3074  Target:      5'-CAGAACAAAAGTTTACTTCAATTGTT-3'   (SEQ ID NO: 2904)

5'-GACCAGAACAAAAAGUUUACUUCaa-3'    (SEQ ID NO: 687)
                      3'-UCCUGGUCUUGUUUUUCAAAUGAAGUU-5'  (SEQ ID NO: 1796)
βc-3079  Target:      5'-AGGACCAGAACAAAAAGTTTACTTCAA-3'  (SEQ ID NO: 2905)

5'-GGACCAGAACAAAAAGUUUACUUca-3'    (SEQ ID NO: 688)
                      3'-UUCCUGGUCUUGUUUUUCAAAUGAAGU-5'  (SEQ ID NO: 1797)
βc-3080  Target:      5'-AAGGACCAGAACAAAAAGTTTACTTCA-3'  (SEQ ID NO: 2906)

5'-ACCAAAAAGGACCAGAACAAAAAgt-3'    (SEQ ID NO: 689)
                      3'-GCUGGUUUUUCCUGGUCUUGUUUUUCA-5'  (SEQ ID NO: 1798)
βc-3088  Target:      5'-CGACCAAAAAGGACCAGAACAAAAAGT-3'  (SEQ ID NO: 2907)

5'-GACCAAAAAGGACCAGAACAAAAag-3'    (SEQ ID NO: 690)
                      3'-AGCUGGUUUUUCCUGGUCUUGUUUUUC-5'  (SEQ ID NO: 1799)
βc-3089  Target:      5'-TCGACCAAAAAGGACCAGAACAAAAAG-3'  (SEQ ID NO: 2908)

5'-ACUCCUCGACCAAAAAGGACCAGaa-3'    (SEQ ID NO: 691)
                      3'-AAUGAGGAGCUGGUUUUUCCUGGUCUU-5'  (SEQ ID NO: 1800)
βc-3096  Target:      5'-TTACTCCTCGACCAAAAAGGACCAGAA-3'  (SEQ ID NO: 2909)

5'-UCCAUUUGUAUUGUUACUCCUCGac-3'    (SEQ ID NO: 692)
                      3'-UUAGGUAAACAUAACAAUGAGGAGCUG-5'  (SEQ ID NO: 1801)
βc-3111  Target:      5'-AATCCATTTGTATTGTTACTCCTCGAC-3'  (SEQ ID NO: 2910)

5'-AUCCAUUUGUAUUGUUACUCCUCga-3'    (SEQ ID NO: 693)
                      3'-UUUAGGUAAACAUAACAAUGAGGAGCU-5'  (SEQ ID NO: 1802)
βc-3112  Target:      5'-AAATCCATTTGTATTGTTACTCCTCGA-3'  (SEQ ID NO: 2911)

5'-AAUCCAUUUGUAUUGUUACUCCUcg-3'    (SEQ ID NO: 694)
                      3'-UUUUAGGUAAACAUAACAAUGAGGAGC-5'  (SEQ ID NO: 1803)
βc-3113  Target:      5'-AAAATCCATTTGTATTGTTACTCCTCG-3'  (SEQ ID NO: 2912)

5'-AAAUCCAUUUGUAUUGUUACUCCtc-3'    (SEQ ID NO: 695)
                      3'-GUUUUAGGUAAACAUAACAAUGAGGAG-5'  (SEQ ID NO: 1804)
βc-3114  Target:      5'-CAAAATCCATTTGTATTGTTACTCCTC-3'  (SEQ ID NO: 2913)

5'-AAAAUCCAUUUGUAUUGUUACUCct-3'    (SEQ ID NO: 696)
                      3'-GGUUUUAGGUAAACAUAACAAUGAGGA-5'  (SEQ ID NO: 1805)
βc-3115  Target:      5'-CCAAAATCCATTTGTATTGTTACTCCT-3'  (SEQ ID NO: 2914)

5'-ACUCCCAAAAUCCAUUUGUAUUGtt-3'    (SEQ ID NO: 697)
                      3'-AGUGAGGGUUUUAGGUAAACAUAACAA-5'  (SEQ ID NO: 1806)
βc-3121  Target:      5'-TCACTCCCAAAATCCATTTGTATTGTT-3'  (SEQ ID NO: 2915)

5'-UUCACUUCUUGAGUCACUCCCAAaa-3'    (SEQ ID NO: 698)
                      3'-AGAAGUGAAGAACUCAGUGAGGGUUUU-5'  (SEQ ID NO: 1807)
βc-3136  Target:      5'-TCTTCACTTCTTGAGTCACTCCCAAAA-3'  (SEQ ID NO: 2916)

5'-UCUUCACUUCUUGAGUCACUCCCaa-3'    (SEQ ID NO: 699)
                      3'-UAAGAAGUGAAGAACUCAGUGAGGGUU-5'  (SEQ ID NO: 1808)
βc-3138  Target:      5'-ATTCTTCACTTCTTGAGTCACTCCCAA-3'  (SEQ ID NO: 2917)

5'-UUCUUCACUUCUUGAGUCACUCCca-3'    (SEQ ID NO: 700)
                      3'-GUAAGAAGUGAAGAACUCAGUGAGGGU-5'  (SEQ ID NO: 1809)
βc-3139  Target:      5'-CATTCTTCACTTCTTGAGTCACTCCCA-3'  (SEQ ID NO: 2918)
```

TABLE 9-continued

Additional Selected Anti-β-catenin DsiRNAs, 25/27mer Duplexes

| | | | |
|---|---|---|---|
| βc-3140 Target: | 5'-AUUCUUCACUUCUUGAGUCACUCcc-3'<br>3'-CGUAAGAAGUGAAGAACUCAGUGAGGG-5'<br>5'-GCATTCTTCACTTCTTGAGTCACTCCC-3' | (SEQ ID NO: 701)<br>(SEQ ID NO: 1810)<br>(SEQ ID NO: 2919) | |
| βc-3142 Target: | 5'-GCAUUCUUCACUUCUUGAGUCACtc-3'<br>3'-CACGUAAGAAGUGAAGAACUCAGUGAG-5'<br>5'-GTGCATTCTTCACTTCTTGAGTCACTC-3' | (SEQ ID NO: 702)<br>(SEQ ID NO: 1811)<br>(SEQ ID NO: 2920) | |
| βc-3150 Target: | 5'-AUUCUUGUGCAUUCUUCACUUCUg-3'<br>3'-GGUAAGAACACGUAAGAAGUGAAGAAC-5'<br>5'-CCATTCTTGTGCATTCTTCACTTCTTG-3' | (SEQ ID NO: 703)<br>(SEQ ID NO: 1812)<br>(SEQ ID NO: 2921) | |
| βc-3153 Target: | 5'-UCCAUUCUUGUGCAUUCUUCACUtc-3'<br>3'-CUAGGUAAGAACACGUAAGAAGUGAAG-5'<br>5'-GATCCATTCTTGTGCATTCTTCACTTC-3' | (SEQ ID NO: 704)<br>(SEQ ID NO: 1813)<br>(SEQ ID NO: 2922) | |
| βc-3154 Target: | 5'-AUCCAUUCUUGUGCAUUCUUCACtt-3'<br>3'-ACUAGGUAAGAACACGUAAGAAGUGAA-5'<br>5'-TGATCCATTCTTGTGCATTCTTCACTT-3' | (SEQ ID NO: 705)<br>(SEQ ID NO: 1814)<br>(SEQ ID NO: 2923) | |
| βc-3155 Target: | 5'-GAUCCAUUCUUGUGCAUUCUUCAct-3'<br>3'-CACUAGGUAAGAACACGUAAGAAGUGA-5'<br>5'-GTGATCCATTCTTGTGCATTCTTCACT-3' | (SEQ ID NO: 706)<br>(SEQ ID NO: 1815)<br>(SEQ ID NO: 2924) | |
| βc-3168 Target: | 5'-AAUUCCAUCUUGUGAUCCAUUCUtg-3'<br>3'-AUUUAAGGUAGAACACUAGGUAAGAAC-5'<br>5'-TAAATTCCATCTTGTGATCCATTCTTG-3' | (SEQ ID NO: 707)<br>(SEQ ID NO: 1816)<br>(SEQ ID NO: 2925) | |
| βc-3170 Target: | 5'-UAAAUUCCAUCUUGUGAUCCAUUct-3'<br>3'-CUAUUUAAGGUAGAACACUAGGUAAGA-5'<br>5'-GATAAATTCCATCTTGTGATCCATTCT-3' | (SEQ ID NO: 708)<br>(SEQ ID NO: 1817)<br>(SEQ ID NO: 2926) | |
| βc-3171 Target: | 5'-AUAAAUUCCAUCUUGUGAUCCAUtc-3'<br>3'-ACUAUUUAAGGUAGAACACUAGGUAAG-5'<br>5'-TGATAAATTCCATCTTGTGATCCATTC-3' | (SEQ ID NO: 709)<br>(SEQ ID NO: 1818)<br>(SEQ ID NO: 2927) | |
| βc-3172 Target: | 5'-GAUAAAUUCCAUCUUGUGAUCCAtt-3'<br>3'-AACUAUUUAAGGUAGAACACUAGGUAA-5'<br>5'-TTGATAAATTCCATCTTGTGATCCATT-3' | (SEQ ID NO: 710)<br>(SEQ ID NO: 1819)<br>(SEQ ID NO: 2928) | |
| βc-3173 Target: | 5'-UGAUAAAUUCCAUCUUGUGAUCCat-3'<br>3'-AAACUAUUUAAGGUAGAACACUAGGUA-5'<br>5'-TTTGATAAATTCCATCTTGTGATCC-3' | (SEQ ID NO: 711)<br>(SEQ ID NO: 1820)<br>(SEQ ID NO: 2929) | |
| βc-3183 Target: | 5'-GGCUAGGGUUUGAUAAAUUCCAUct-3'<br>3'-UUCCGAUCCCAAACUAUUUAAGGUAGA-5'<br>5'-AAGGCTAGGGTTTGATAAATTCCATCT-3' | (SEQ ID NO: 712)<br>(SEQ ID NO: 1821)<br>(SEQ ID NO: 2930) | |
| βc-3200 Target: | 5'-AAAAAUUUAACAAGCAAGGCUAGgg-3'<br>3'-UUUUUUUAAAUUGUUCGUUCCGAUCCC-5'<br>5'-AAAAAATTTAACAAGCAAGGCTAGGG-3' | (SEQ ID NO: 713)<br>(SEQ ID NO: 1822)<br>(SEQ ID NO: 2931) | |
| βc-3209 Target: | 5'-AAAAAAAAAAAAAUUUAACAAGca-3'<br>3'-UUUUUUUUUUUUUUUAAAUUGUUCGU-5'<br>5'-AAAAAAAAAAAAAATTTAACAAGCA-3' | (SEQ ID NO: 714)<br>(SEQ ID NO: 1823)<br>(SEQ ID NO: 2932) | |
| βc-3210 Target: | 5'-AAAAAAAAAAAAAAUUUAACAAgc-3'<br>3'-UUUUUUUUUUUUUUUUAAAUUGUUCG-5'<br>5'-AAAAAAAAAAAAAAATTTAACAAGC-3' | (SEQ ID NO: 715)<br>(SEQ ID NO: 1824)<br>(SEQ ID NO: 2933) | |
| βc-3211 Target: | 5'-AAAAAAAAAAAAAAAUUUAACAag-3'<br>3'-UUUUUUUUUUUUUUUUUAAAUUGUUC-5'<br>5'-AAAAAAAAAAAAAAAATTTAACAAG-3' | (SEQ ID NO: 716)<br>(SEQ ID NO: 1825)<br>(SEQ ID NO: 2934) | |
| βc-3212 Target: | 5'-AAAAAAAAAAAAAAAAUUUAACaa-3'<br>3'-UUUUUUUUUUUUUUUUUUAAAUUGUU-5'<br>5'-AAAAAAAAAAAAAAAAATTTAACAA-3' | (SEQ ID NO: 717)<br>(SEQ ID NO: 1826)<br>(SEQ ID NO: 2935) | |
| βc-3213 Target: | 5'-AAAAAAAAAAAAAAAAAUUUAAca-3'<br>3'-AUUUUUUUUUUUUUUUUUUAAAUUGU-5'<br>5'-TAAAAAAAAAAAAAAAAAATTTAACA-3' | (SEQ ID NO: 718)<br>(SEQ ID NO: 1827)<br>(SEQ ID NO: 2936) | |
| βc-3214 Target: | 5'-AAAAAAAAAAAAAAAAAAUUUAac-3'<br>3'-AAUUUUUUUUUUUUUUUUUUUAAAUUG-5'<br>5'-TTAAAAAAAAAAAAAAAAAAATTTAAC-3' | (SEQ ID NO: 719)<br>(SEQ ID NO: 1828)<br>(SEQ ID NO: 2937) | |

TABLE 9-continued

Additional Selected Anti-β-catenin DsiRNAs, 25/27mer Duplexes

| | | |
|---|---|---|
| βc-3215 Target: | 5'-UAAAAAAAAAAAAAAAAAAAUUUaa-3'<br>3'-GAAUUUUUUUUUUUUUUUUUAAAUU-5'<br>5'-CTTAAAAAAAAAAAAAAAAAATTTAA-3' | (SEQ ID NO: 720)<br>(SEQ ID NO: 1829)<br>(SEQ ID NO: 2938) |
| βc-3216 Target: | 5'-UUAAAAAAAAAAAAAAAAAAAUUta-3'<br>3'-AGAAUUUUUUUUUUUUUUUUAAAU-5'<br>5'-TCTTAAAAAAAAAAAAAAAAAATTTA-3' | (SEQ ID NO: 721)<br>(SEQ ID NO: 1830)<br>(SEQ ID NO: 2939) |
| βc-3218 Target: | 5'-UCUUAAAAAAAAAAAAAAAAAAAtt-3'<br>3'-UAAGAAUUUUUUUUUUUUUUUUAA-5'<br>5'-ATTCTTAAAAAAAAAAAAAAAAAATT-3' | (SEQ ID NO: 722)<br>(SEQ ID NO: 1831)<br>(SEQ ID NO: 2940) |
| βc-3219 Target: | 5'-UUCUUAAAAAAAAAAAAAAAAAAat-3'<br>3'-AUAAGAAUUUUUUUUUUUUUUUUA-5'<br>5'-TATTCTTAAAAAAAAAAAAAAAAAAT-3' | (SEQ ID NO: 723)<br>(SEQ ID NO: 1832)<br>(SEQ ID NO: 2941) |
| βc-3220 Target: | 5'-AUUCUUAAAAAAAAAAAAAAAAAaa-3'<br>3'-UAUAAGAAUUUUUUUUUUUUUUUU-5'<br>5'-ATATTCTTAAAAAAAAAAAAAAAAA-3' | (SEQ ID NO: 724)<br>(SEQ ID NO: 1833)<br>(SEQ ID NO: 2942) |
| βc-3221 Target: | 5'-UAUUCUUAAAAAAAAAAAAAAAAaa-3'<br>3'-CUAUAAGAAUUUUUUUUUUUUUUU-5'<br>5'-GATATTCTTAAAAAAAAAAAAAAAA-3' | (SEQ ID NO: 725)<br>(SEQ ID NO: 1834)<br>(SEQ ID NO: 2943) |
| βc-3222 Target: | 5'-AUAUUCUUAAAAAAAAAAAAAAAaa-3'<br>3'-UCUAUAAGAAUUUUUUUUUUUUUU-5'<br>5'-AGATATTCTTAAAAAAAAAAAAAAA-3' | (SEQ ID NO: 726)<br>(SEQ ID NO: 1835)<br>(SEQ ID NO: 2944) |
| βc-3223 Target: | 5'-GAUAUUCUUAAAAAAAAAAAAAAaa-3'<br>3'-GUCUAUAAGAAUUUUUUUUUUUUU-5'<br>5'-CAGATATTCTTAAAAAAAAAAAAAA-3' | (SEQ ID NO: 727)<br>(SEQ ID NO: 1836)<br>(SEQ ID NO: 2945) |
| βc-3224 Target: | 5'-AGAUAUUCUUAAAAAAAAAAAAAaa-3'<br>3'-UGUCUAUAAGAAUUUUUUUUUUUU-5'<br>5'-ACAGATATTCTTAAAAAAAAAAAAA-3' | (SEQ ID NO: 728)<br>(SEQ ID NO: 1837)<br>(SEQ ID NO: 2946) |
| βc-3228 Target: | 5'-UUACAGAUAUUCUUAAAAAAAAAaa-3'<br>3'-GUAAUGUCUAUAAGAAUUUUUUUU-5'<br>5'-CATTACAGATATTCTTAAAAAAAAA-3' | (SEQ ID NO: 729)<br>(SEQ ID NO: 1838)<br>(SEQ ID NO: 2947) |
| βc-3229 Target: | 5'-AUUACAGAUAUUCUUAAAAAAAAaa-3'<br>3'-GGUAAUGUCUAUAAGAAUUUUUUU-5'<br>5'-CCATTACAGATATTCTTAAAAAAAA-3' | (SEQ ID NO: 730)<br>(SEQ ID NO: 1839)<br>(SEQ ID NO: 2948) |
| βc-3233 Target: | 5'-UACCAUUACAGAUAUUCUUAAAAaa-3'<br>3'-UCAUGGUAAUGUCUAUAAGAAUUUUU-5'<br>5'-AGTACCATTACAGATATTCTTAAAAAA-3' | (SEQ ID NO: 731)<br>(SEQ ID NO: 1840)<br>(SEQ ID NO: 2949) |
| βc-3234 Target: | 5'-GUACCAUUACAGAUAUUCUUAAaa-3'<br>3'-GUCAUGGUAAUGUCUAUAAGAAUUUUU-5'<br>5'-CAGTACCATTACAGATATTCTTAAAAA-3' | (SEQ ID NO: 732)<br>(SEQ ID NO: 1841)<br>(SEQ ID NO: 2950) |
| βc-3235 Target: | 5'-AGUACCAUUACAGAUAUUCUUAAaa-3'<br>3'-AGUCAUGGUAAUGUCUAUAAGAAUUUU-5'<br>5'-TCAGTACCATTACAGATATTCTTAAAA-3' | (SEQ ID NO: 733)<br>(SEQ ID NO: 1842)<br>(SEQ ID NO: 2951) |
| βc-3239 Target: | 5'-AGUCAGUACCAUUACAGAUAUUCtt-3'<br>3'-UUUCAGUCAUGGUAAUGUCUAUAAGAA-5'<br>5'-AAAGTCAGTACCATTACAGATATTCTT-3' | (SEQ ID NO: 734)<br>(SEQ ID NO: 1843)<br>(SEQ ID NO: 2952) |
| βc-3256 Target: | 5'-UACUUCAAAGCAAGCAAAGUCAGta-3'<br>3'-CGAUGAAGUUUCGUUCGUUUCAGUCAU-5'<br>5'-GCTACTTCAAAGCAAGCAAAGTCAGTA-3' | (SEQ ID NO: 735)<br>(SEQ ID NO: 1844)<br>(SEQ ID NO: 2953) |
| βc-3265 Target: | 5'-AAAAAGAGCUACUUCAAAGCAAGca-3'<br>3'-UUUUUUUCUCGAUGAAGUUUCGUUCGU-5'<br>5'-AAAAAAAGAGCTACTTCAAAGCAAGCA-3' | (SEQ ID NO: 736)<br>(SEQ ID NO: 1845)<br>(SEQ ID NO: 2954) |
| βc-3270 Target: | 5'-AAAAAAAAAAGAGCUACUUCAAAgc-3'<br>3'-UUUUUUUUUUUCUCGAUGAAGUUUCG-5'<br>5'-AAAAAAAAAAAGAGCTACTTCAAAGC-3' | (SEQ ID NO: 737)<br>(SEQ ID NO: 1846)<br>(SEQ ID NO: 2955) |
| βc-3271 Target: | 5'-AAAAAAAAAAAGAGCUACUUCAAag-3'<br>3'-UUUUUUUUUUUUCUCGAUGAAGUUUC-5'<br>5'-AAAAAAAAAAAAGAGCTACTTCAAAG-3' | (SEQ ID NO: 738)<br>(SEQ ID NO: 1847)<br>(SEQ ID NO: 2956) |

TABLE 9-continued

Additional Selected Anti-β-catenin DsiRNAs, 25/27mer Duplexes

|  |  |  |  |
|---|---|---|---|
| βc-3273 | Target: | 5'-AAAAAAAAAAAAAGAGCUACUUCaa-3'<br>3'-UUUUUUUUUUUUUUCUCGAUGAAGUU-5'<br>5'-AAAAAAAAAAAAAAGAGCTACTTCAA-3' | (SEQ ID NO: 739)<br>(SEQ ID NO: 1848)<br>(SEQ ID NO: 2957) |
| βc-3274 | Target: | 5'-AAAAAAAAAAAAAGAGCUACUUca-3'<br>3'-UUUUUUUUUUUUUUCUCGAUGAAGU-5'<br>5'-AAAAAAAAAAAAAAGAGCTACTTCA-3' | (SEQ ID NO: 740)<br>(SEQ ID NO: 1849)<br>(SEQ ID NO: 2958) |
| βc-3275 | Target: | 5'-AAAAAAAAAAAAAGAGCUACUtc-3'<br>3'-UUUUUUUUUUUUUUUCUCGAUGAAG-5'<br>5'-AAAAAAAAAAAAAAGAGCTACTTC-3' | (SEQ ID NO: 741)<br>(SEQ ID NO: 1850)<br>(SEQ ID NO: 2959) |
| βc-3276 | Target: | 5'-AAAAAAAAAAAAAGAGCUACtt-3'<br>3'-UUUUUUUUUUUUUUUUCUCGAUGAA-5'<br>5'-AAAAAAAAAAAAAAAGAGCTACTT-3' | (SEQ ID NO: 742)<br>(SEQ ID NO: 1851)<br>(SEQ ID NO: 2960) |
| βc-3282 | Target: | 5'-AAAAAAAAAAAAAAAAAAAGag-3'<br>3'-UUUUUUUUUUUUUUUUUUUUUCUC-5'<br>5'-AAAAAAAAAAAAAAAAAAAAAGAG-3' | (SEQ ID NO: 743)<br>(SEQ ID NO: 1852)<br>(SEQ ID NO: 2961) |
| βc-3283 | Target: | 5'-AAAAAAAAAAAAAAAAAAAAga-3'<br>3'-UUUUUUUUUUUUUUUUUUUUUUCU-5'<br>5'-AAAAAAAAAAAAAAAAAAAAAAGA-3' | (SEQ ID NO: 744)<br>(SEQ ID NO: 1853)<br>(SEQ ID NO: 2962) |
| βc-3284 | Target: | 5'-AAAAAAAAAAAAAAAAAAAAag-3'<br>3'-GUUUUUUUUUUUUUUUUUUUUUUC-5'<br>5'-CAAAAAAAAAAAAAAAAAAAAAAG-3' | (SEQ ID NO: 745)<br>(SEQ ID NO: 1854)<br>(SEQ ID NO: 2963) |
| βc-3285 | Target: | 5'-AAAAAAAAAAAAAAAAAAAAaa-3'<br>3'-CGUUUUUUUUUUUUUUUUUUUUUU-5'<br>5'-GCAAAAAAAAAAAAAAAAAAAAAA-3' | (SEQ ID NO: 746)<br>(SEQ ID NO: 1855)<br>(SEQ ID NO: 2964) |
| βc-3287 | Target: | 5'-GCAAAAAAAAAAAAAAAAAAAAaa-3'<br>3'-GACGUUUUUUUUUUUUUUUUUUUU-5'<br>5'-CTGCAAAAAAAAAAAAAAAAAAAA-3' | (SEQ ID NO: 747)<br>(SEQ ID NO: 1856)<br>(SEQ ID NO: 2965) |
| βc-3288 | Target: | 5'-UGCAAAAAAAAAAAAAAAAAAAaa-3'<br>3'-UGACGUUUUUUUUUUUUUUUUUUU-5'<br>5'-ACTGCAAAAAAAAAAAAAAAAAAA-3' | (SEQ ID NO: 748)<br>(SEQ ID NO: 1857)<br>(SEQ ID NO: 2966) |
| βc-3292 | Target: | 5'-UUACUGCAAAAAAAAAAAAAAAaa-3'<br>3'-UCAAUGACGUUUUUUUUUUUUUUU-5'<br>5'-AGTTACTGCAAAAAAAAAAAAAAA-3' | (SEQ ID NO: 749)<br>(SEQ ID NO: 1858)<br>(SEQ ID NO: 2967) |
| βc-3293 | Target: | 5'-GUUACUGCAAAAAAAAAAAAAAaa-3'<br>3'-GUCAAUGACGUUUUUUUUUUUUUU-5'<br>5'-CAGTTACTGCAAAAAAAAAAAAAA-3' | (SEQ ID NO: 750)<br>(SEQ ID NO: 1859)<br>(SEQ ID NO: 2968) |
| βc-3294 | Target: | 5'-AGUUACUGCAAAAAAAAAAAAAaa-3'<br>3'-UGUCAAUGACGUUUUUUUUUUUUU-5'<br>5'-ACAGTTACTGCAAAAAAAAAAAAA-3' | (SEQ ID NO: 751)<br>(SEQ ID NO: 1860)<br>(SEQ ID NO: 2969) |
| βc-3298 | Target: | 5'-AAACAGUUACUGCAAAAAAAAAaa-3'<br>3'-UUUUUGUCAAUGACGUUUUUUUUU-5'<br>5'-AAAAACAGTTACTGCAAAAAAAAA-3' | (SEQ ID NO: 752)<br>(SEQ ID NO: 1861)<br>(SEQ ID NO: 2970) |
| βc-3299 | Target: | 5'-AAAACAGUUACUGCAAAAAAAAaa-3'<br>3'-UUUUUUGUCAAUGACGUUUUUUUU-5'<br>5'-AAAAAACAGTTACTGCAAAAAAAA-3' | (SEQ ID NO: 753)<br>(SEQ ID NO: 1862)<br>(SEQ ID NO: 2971) |
| βc-3300 | Target: | 5'-AAAACAGUUACUGCAAAAAAAaa-3'<br>3'-AUUUUUUGUCAAUGACGUUUUUUU-5'<br>5'-TAAAAAACAGTTACTGCAAAAAAA-3' | (SEQ ID NO: 754)<br>(SEQ ID NO: 1863)<br>(SEQ ID NO: 2972) |
| βc-3302 | Target: | 5'-UAAAAACAGUUACUGCAAAAAAaa-3'<br>3'-GAAUUUUUUGUCAAUGACGUUUUU-5'<br>5'-CTTAAAAAACAGTTACTGCAAAAA-3' | (SEQ ID NO: 755)<br>(SEQ ID NO: 1864)<br>(SEQ ID NO: 2973) |
| βc-3303 | Target: | 5'-UUAAAAACAGUUACUGCAAAAAaa-3'<br>3'-UGAAUUUUUUGUCAAUGACGUUUU-5'<br>5'-ACTTAAAAAACAGTTACTGCAAAA-3' | (SEQ ID NO: 756)<br>(SEQ ID NO: 1865)<br>(SEQ ID NO: 2974) |
| βc-3305 | Target: | 5'-ACUUAAAAACAGUUACUGCAAAaa-3'<br>3'-UCUGAAUUUUUUGUCAAUGACGUUUU-5'<br>5'-AGACTTAAAAAACAGTTACTGCAAAAA-3' | (SEQ ID NO: 757)<br>(SEQ ID NO: 1866)<br>(SEQ ID NO: 2975) |

TABLE 9-continued

Additional Selected Anti-β-catenin DsiRNAs, 25/27mer Duplexes

| | | |
|---|---|---|
| βc-3315 Target: | 5'-ACUACGAGAGACUUAAAAAACAGtt-3'<br>3'-UGUGAUGCUCUCUGAAUUUUUGUCAA-5'<br>5'-ACACTACGAGAGACTTAAAAAACAGTT-3' | (SEQ ID NO: 758)<br>(SEQ ID NO: 1867)<br>(SEQ ID NO: 2976) |
| βc-3317 Target: | 5'-ACACUACGAGAGACUUAAAAAACag-3'<br>3'-AUUGUGAUGCUCUCUGAAUUUUUGUC-5'<br>5'-TAACACTACGAGAGACTTAAAAAACAG-3' | (SEQ ID NO: 759)<br>(SEQ ID NO: 1868)<br>(SEQ ID NO: 2977) |
| βc-3318 Target: | 5'-AACACUACGAGAGACUUAAAAAAca-3'<br>3'-AAUUGUGAUGCUCUCUGAAUUUUUGU-5'<br>5'-TTAACACTACGAGAGACTTAAAAAACA-3' | (SEQ ID NO: 760)<br>(SEQ ID NO: 1869)<br>(SEQ ID NO: 2978) |
| βc-3320 Target: | 5'-UUAACACUACGAGAGACUUAAAAaa-3'<br>3'-UGAAUUGUGAUGCUCUCUGAAUUUUUU-5'<br>5'-ACTTAACACTACGAGAGACTTAAAAAA-3' | (SEQ ID NO: 761)<br>(SEQ ID NO: 1870)<br>(SEQ ID NO: 2979) |
| βc-3323 Target: | 5'-AACUUAACACUACGAGAGACUUAaa-3'<br>3'-UAUUGAAUUGUGAUGCUCUCUGAAUUU-5'<br>5'-ATAACTTAACACTACGAGAGACTTAAA-3' | (SEQ ID NO: 762)<br>(SEQ ID NO: 1871)<br>(SEQ ID NO: 2980) |
| βc-3324 Target: | 5'-UAACUUAACACUACGAGAGACUUaa-3'<br>3'-AUAUUGAAUUGUGAUGCUCUCUGAAUU-5'<br>5'-TATAACTTAACACTACGAGAGACTTAA-3' | (SEQ ID NO: 763)<br>(SEQ ID NO: 1872)<br>(SEQ ID NO: 2981) |
| βc-3332 Target: | 5'-AUUCACUAUAACUUAACACUACGag-3'<br>3'-CAUAAGUGAUAUUGAAUUGUGAUGCUC-5'<br>5'-GTATTCACTATAACTTAACACTACGAG-3' | (SEQ ID NO: 764)<br>(SEQ ID NO: 1873)<br>(SEQ ID NO: 2982) |
| βc-3333 Target: | 5'-UAUUCACUAUAACUUAACACUACga-3'<br>3'-UCAUAAGUGAUAUUGAAUUGUGAUGCU-5'<br>5'-AGTATTCACTATAACTTAACACTACGA-3' | (SEQ ID NO: 765)<br>(SEQ ID NO: 1874)<br>(SEQ ID NO: 2983) |
| βc-3334 Target: | 5'-GUAUUCACUAUAACUUAACACUAcg-3'<br>3'-GUCAUAAGUGAUAUUGAAUUGUGAUGC-5'<br>5'-CAGTATTCACTATAACTTAACACTACG-3' | (SEQ ID NO: 766)<br>(SEQ ID NO: 1875)<br>(SEQ ID NO: 2984) |
| βc-3335 Target: | 5'-AGUAUUCACUAUAACUUAACACUac-3'<br>3'-CGUCAUAAGUGAUAUUGAAUUGUGAUG-5'<br>5'-GCAGTATTCACTATAACTTAACACTAC-3' | (SEQ ID NO: 767)<br>(SEQ ID NO: 1876)<br>(SEQ ID NO: 2985) |
| βc-3348 Target: | 5'-AAAUUGCUGUAGCAGUAUUCACUat-3'<br>3'-UCUUUAACGACAUCGUCAUAAGUGAUA-5'<br>5'-AGAAATTGCTGTAGCAGTATTCACTAT-3' | (SEQ ID NO: 768)<br>(SEQ ID NO: 1877)<br>(SEQ ID NO: 2986) |
| βc-3349 Target: | 5'-GAAAUUGCUGUAGCAGUAUUCACta-3'<br>3'-AUCUUUAACGACAUCGUCAUAAGUGAU-5'<br>5'-TAGAAATTGCTGTAGCAGTATTCACTA-3' | (SEQ ID NO: 769)<br>(SEQ ID NO: 1878)<br>(SEQ ID NO: 2987) |
| βc-3350 Target: | 5'-AGAAAUUGCUGUAGCAGUAUUCAct-3'<br>3'-AAUCUUUAACGACAUCGUCAUAAGUGA-5'<br>5'-TTAGAAATTGCTGTAGCAGTATTCACT-3' | (SEQ ID NO: 770)<br>(SEQ ID NO: 1879)<br>(SEQ ID NO: 2988) |
| βc-3366 Target: | 5'-UCAAUUCUUAAAAAUUAGAAAUUgc-3'<br>3'-UGAGUUAAGAAUUUUUAAUCUUUAACG-5'<br>5'-ACTCAATTCTTAAAAATTAGAAATTGC-3' | (SEQ ID NO: 771)<br>(SEQ ID NO: 1880)<br>(SEQ ID NO: 2989) |
| βc-3371 Target: | 5'-AUUACUCAAUUCUUAAAAAUUAGaa-3'<br>3'-GGUAAUGAGUUAAGAAUUUUUAAUCUU-5'<br>5'-CCATTACTCAATTCTTAAAAATTAGAA-3' | (SEQ ID NO: 772)<br>(SEQ ID NO: 1881)<br>(SEQ ID NO: 2990) |
| βc-3374 Target: | 5'-ACCAUUACUCAAUUCUUAAAAAUta-3'<br>3'-UGUGGUAAUGAGUUAAGAAUUUUUAAU-5'<br>5'-ACACCATTACTCAATTCTTAAAAATTA-3' | (SEQ ID NO: 773)<br>(SEQ ID NO: 1882)<br>(SEQ ID NO: 2991) |
| βc-3376 Target: | 5'-ACACCAUUACUCAAUUCUUAAAAat-3'<br>3'-GAUGUGGUAAUGAGUUAAGAAUUUUUA-5'<br>5'-CTACACCATTACTCAATTCTTAAAAAT-3' | (SEQ ID NO: 774)<br>(SEQ ID NO: 1883)<br>(SEQ ID NO: 2992) |
| βc-3377 Target: | 5'-UACACCAUUACUCAAUUCUUAAAaa-3'<br>3'-AGAUGUGGUAAUGAGUUAAGAAUUUUU-5'<br>5'-TCTACACCATTACTCAATTCTTAAAAA-3' | (SEQ ID NO: 775)<br>(SEQ ID NO: 1884)<br>(SEQ ID NO: 2993) |
| βc-3379 Target: | 5'-UCUACACCAUUACUCAAUUCUUAaa-3'<br>3'-CAAGAUGUGGUAAUGAGUUAAGAAUUU-5'<br>5'-GTTCTACACCATTACTCAATTCTTAAA-3' | (SEQ ID NO: 776)<br>(SEQ ID NO: 1885)<br>(SEQ ID NO: 2994) |

TABLE 9-continued

Additional Selected Anti-β-catenin DsiRNAs, 25/27mer Duplexes

| | | |
|---|---|---|
| βc-3381 Target: | 5'-GUUCUACACCAUUACUCAAUUCUta-3'<br>3'-CACAAGAUGUGGUAAUGAGUUAAGAAU-5'<br>5'-GTGTTCTACACCATTACTCAATTCTTA-3' | (SEQ ID NO: 777)<br>(SEQ ID NO: 1886)<br>(SEQ ID NO: 2995) |
| βc-3389 Target: | 5'-GAAUUAGUGUUCUACACCAUUACtc-3'<br>3'-UACUUAAUCACAAGAUGUGGUAAUGAG-5'<br>5'-ATGAATTAGTGTTCTACACCATTACTC-3' | (SEQ ID NO: 778)<br>(SEQ ID NO: 1887)<br>(SEQ ID NO: 2996) |
| βc-3394 Target: | 5'-AUUAUGAAUUAGUGUUCUACACCat-3'<br>3'-ACUAAUACUUAAUCACAAGAUGUGGUA-5'<br>5'-TGATTATGAATTAGTGTTCTACACC-3' | (SEQ ID NO: 779)<br>(SEQ ID NO: 1888)<br>(SEQ ID NO: 2997) |
| βc-3395 Target: | 5'-GAUUAUGAAUUAGUGUUCUACACCca-3'<br>3'-CACUAAUACUUAAUCACAAGAUGUGGU-5'<br>5'-GTGATTATGAATTAGTGTTCTACACCA-3' | (SEQ ID NO: 780)<br>(SEQ ID NO: 1889)<br>(SEQ ID NO: 2998) |
| βc-3396 Target: | 5'-UGAUUAUGAAUUAGUGUUCUACAcc-3'<br>3'-UCACUAAUACUUAAUCACAAGAUGUGG-5'<br>5'-AGTGATTATGAATTAGTGTTCTACACC-3' | (SEQ ID NO: 781)<br>(SEQ ID NO: 1890)<br>(SEQ ID NO: 2999) |
| βc-3405 Target: | 5'-UAAUUAGAGUGAUUAUGAAUUAGtg-3'<br>3'-UAAUUAAUCUCACUAAUACUUAAUCAC-5'<br>5'-ATTAATTAGAGTGATTATGAATTAGTG-3' | (SEQ ID NO: 782)<br>(SEQ ID NO: 1891)<br>(SEQ ID NO: 3000) |
| βc-3406 Target: | 5'-UUAAUUAGAGUGAUUAUGAAUUAgt-3'<br>3'-UUAAUUAAUCUCACUAAUACUUAAUCA-5'<br>5'-AATTAATTAGAGTGATTATGAATTAGT-3' | (SEQ ID NO: 783)<br>(SEQ ID NO: 1892)<br>(SEQ ID NO: 3001) |
| βc-3407 Target: | 5'-AUUAAUUAGAGUGAUUAUGAAUUag-3'<br>3'-GUUAAUUAAUCUCACUAAUACUUAAUC-5'<br>5'-CAATTAATTAGAGTGATTATGAATTAG-3' | (SEQ ID NO: 784)<br>(SEQ ID NO: 1893)<br>(SEQ ID NO: 3002) |
| βc-3411 Target: | 5'-UACAAUUAAUUAGAGUGAUUAUGaa-3'<br>3'-UAAUGUUAAUUAAUCUCACUAAUACUU-5'<br>5'-ATTACAATTAATTAGAGTGATTATGAA-3' | (SEQ ID NO: 785)<br>(SEQ ID NO: 1894)<br>(SEQ ID NO: 3003) |
| βc-3412 Target: | 5'-UUACAAUUAAUUAGAGUGAUUAUga-3'<br>3'-CUAAUGUUAAUUAAUCUCACUAAUACU-5'<br>5'-GATTACAATTAATTAGAGTGATTATGA-3' | (SEQ ID NO: 786)<br>(SEQ ID NO: 1895)<br>(SEQ ID NO: 3004) |
| βc-3413 Target: | 5'-AUUACAAUUAAUUAGAGUGAUUAtg-3'<br>3'-UCUAAUGUUAAUUAAUCUCACUAAUAC-5'<br>5'-AGATTACAATTAATTAGAGTGATTATG-3' | (SEQ ID NO: 787)<br>(SEQ ID NO: 1896)<br>(SEQ ID NO: 3005) |
| βc-3421 Target: | 5'-UUAUUCAGAUUACAAUUAAUUAGag-3'<br>3'-GAAAUAAGUCUAAUGUUAAUUAAUCUC-5'<br>5'-CTTTATTCAGATTACAATTAATTAGAG-3' | (SEQ ID NO: 788)<br>(SEQ ID NO: 1897)<br>(SEQ ID NO: 3006) |
| βc-3422 Target: | 5'-UUUAUUCAGAUUACAAUUAAUUAga-3'<br>3'-UGAAAUAAGUCUAAUGUUAAUUAAUCU-5'<br>5'-ACTTTATTCAGATTACAATTAATTAGA-3' | (SEQ ID NO: 789)<br>(SEQ ID NO: 1898)<br>(SEQ ID NO: 3007) |
| βc-3426 Target: | 5'-ACACUUUAUUCAGAUUACAAUUAat-3'<br>3'-AAUGUGAAAUAAGUCUAAUGUUAAUUA-5'<br>5'-TTACACTTTATTCAGATTACAATTAAT-3' | (SEQ ID NO: 790)<br>(SEQ ID NO: 1899)<br>(SEQ ID NO: 3008) |
| βc-3427 Target: | 5'-UACACUUUAUUCAGAUUACAAUUaa-3'<br>3'-CAAUGUGAAAUAAGUCUAAUGUUAAUU-5'<br>5'-GTTACACTTTATTCAGATTACAATTAA-3' | (SEQ ID NO: 791)<br>(SEQ ID NO: 1900)<br>(SEQ ID NO: 3009) |
| βc-3428 Target: | 5'-UUACACUUUAUUCAGAUUACAAUta-3'<br>3'-ACAAUGUGAAAUAAGUCUAAUGUUAAU-5'<br>5'-TGTTACACTTTATTCAGATTACAATTA-3' | (SEQ ID NO: 792)<br>(SEQ ID NO: 1901)<br>(SEQ ID NO: 3010) |
| βc-3429 Target: | 5'-GUUACACUUUAUUCAGAUUACAAtt-3'<br>3'-AACAAUGUGAAAUAAGUCUAAUGUUAA-5'<br>5'-TTGTTACACTTTATTCAGATTACAATT-3' | (SEQ ID NO: 793)<br>(SEQ ID NO: 1902)<br>(SEQ ID NO: 3011) |
| βc-3430 Target: | 5'-UGUUACACUUUAUUCAGAUUACAat-3'<br>3'-UAACAAUGUGAAAUAAGUCUAAUGUUA-5'<br>5'-ATTGTTACACTTTATTCAGATTACAAT-3' | (SEQ ID NO: 794)<br>(SEQ ID NO: 1903)<br>(SEQ ID NO: 3012) |
| βc-3437 Target: | 5'-ACACAAUUGUUACACUUUAUUCAga-3'<br>3'-GAUGUGUUAACAAUGUGAAAUAAGUCU-5'<br>5'-CTACACAATTGTTACACTTTATTCAGA-3' | (SEQ ID NO: 795)<br>(SEQ ID NO: 1904)<br>(SEQ ID NO: 3013) |

TABLE 9-continued

Additional Selected Anti-β-catenin DsiRNAs, 25/27mer Duplexes

| | | |
|---|---|---|
| βc-3441 Target: | 5'-GGCUACACAAUUGUUACACUUUAtt-3'<br>3'-UUCCGAUGUGUUAACAAUGUGAAAUAA-5'<br>5'-AAGGCTACACAATTGTTACACTTTATT-3' | (SEQ ID NO: 796)<br>(SEQ ID NO: 1905)<br>(SEQ ID NO: 3014) |
| βc-3446 Target: | 5'-AAAAAGGCUACACAAUUGUUACAct-3'<br>3'-UGUUUUUCCGAUGUGUUAACAAUGUGA-5'<br>5'-ACAAAAAGGCTACACAATTGTTACACT-3' | (SEQ ID NO: 797)<br>(SEQ ID NO: 1906)<br>(SEQ ID NO: 3015) |
| βc-3452 Target: | 5'-UUUAUACAAAAGGCUACACAAUUgt-3'<br>3'-AAAAUAUGUUUUUCCGAUGUGUUAACA-5'<br>5'-TTTTATACAAAAGGCTACACAATTGT-3' | (SEQ ID NO: 798)<br>(SEQ ID NO: 1907)<br>(SEQ ID NO: 3016) |
| βc-3453 Target: | 5'-UUUUAUACAAAAGGCUACACAAUtg-3'<br>3'-UAAAAUAUGUUUUUCCGAUGUGUUAAC-5'<br>5'-ATTTTATACAAAAGGCTACACAATTG-3' | (SEQ ID NO: 799)<br>(SEQ ID NO: 1908)<br>(SEQ ID NO: 3017) |
| βc-3455 Target: | 5'-AUUUUAUACAAAAGGCUACACAat-3'<br>3'-GAUAAAAUAUGUUUUUCCGAUGUGUUA-5'<br>5'-CTATTTTATACAAAAGGCTACACAAT-3' | (SEQ ID NO: 800)<br>(SEQ ID NO: 1909)<br>(SEQ ID NO: 3018) |
| βc-3456 Target: | 5'-UAUUUUAUACAAAAGGCUACACaa-3'<br>3'-AGAUAAAAUAUGUUUUUCCGAUGUGUU-5'<br>5'-TCTATTTTATACAAAAGGCTACACAA-3' | (SEQ ID NO: 801)<br>(SEQ ID NO: 1910)<br>(SEQ ID NO: 3019) |
| βc-3458 Target: | 5'-UCUAUUUUAUACAAAAGGCUACac-3'<br>3'-ACAGAUAAAAUAUGUUUUUCCGAUGUG-5'<br>5'-TGTCTATTTTATACAAAAGGCTACAC-3' | (SEQ ID NO: 802)<br>(SEQ ID NO: 1911)<br>(SEQ ID NO: 3020) |
| βc-3464 Target: | 5'-UAUUUGUCUAUUUUAUACAAAAgg-3'<br>3'-AGAUAAACAGAUAAAAUAUGUUUUUCC-5'<br>5'-TCTATTTGTCTATTTTATACAAAAGG-3' | (SEQ ID NO: 803)<br>(SEQ ID NO: 1912)<br>(SEQ ID NO: 3021) |
| βc-3466 Target: | 5'-UCUAUUUGUCUAUUUUAUACAAAaa-3'<br>3'-AAAGAUAAACAGAUAAAAUAUGUUUUU-5'<br>5'-TTTCTATTTGTCTATTTTATACAAAAA-3' | (SEQ ID NO: 804)<br>(SEQ ID NO: 1913)<br>(SEQ ID NO: 3022) |
| βc-3467 Target: | 5'-UUCUAUUUGUCUAUUUUAUACAAaa-3'<br>3'-AAAAGAUAAACAGAUAAAAUAUGUUUU-5'<br>5'-TTTTCTATTTGTCTATTTTATACAAAA-3' | (SEQ ID NO: 805)<br>(SEQ ID NO: 1914)<br>(SEQ ID NO: 3023) |
| βc-3468 Target: | 5'-UUUCUAUUUGUCUAUUUUAUACAaa-3'<br>3'-UAAAAGAUAAACAGAUAAAAUAUGUUU-5'<br>5'-ATTTTCTATTTGTCTATTTTATACAAA-3' | (SEQ ID NO: 806)<br>(SEQ ID NO: 1915)<br>(SEQ ID NO: 3024) |
| βc-3469 Target: | 5'-UUUUCUAUUUGUCUAUUUUAUACaa-3'<br>3'-GUAAAAGAUAAACAGAUAAAAUAUGUU-5'<br>5'-CATTTTCTATTTGTCTATTTTATACAA-3' | (SEQ ID NO: 807)<br>(SEQ ID NO: 1916)<br>(SEQ ID NO: 3025) |
| βc-3470 Target: | 5'-AUUUUCUAUUUGUCUAUUUUAUAca-3'<br>3'-GGUAAAAGAUAAACAGAUAAAAUAUGU-5'<br>5'-CCATTTTCTATTTGTCTATTTTATACA-3' | (SEQ ID NO: 808)<br>(SEQ ID NO: 1917)<br>(SEQ ID NO: 3026) |
| βc-3473 Target: | 5'-ACCAUUUUCUAUUUGUCUAUUUUat-3'<br>3'-CCUGGUAAAAGAUAAACAGAUAAAAUA-5'<br>5'-GGACCATTTTCTATTTGTCTATTTTAT-3' | (SEQ ID NO: 809)<br>(SEQ ID NO: 1918)<br>(SEQ ID NO: 3027) |
| βc-3474 Target: | 5'-GACCAUUUUCUAUUUGUCUAUUUta-3'<br>3'-ACCUGGUAAAAGAUAAACAGAUAAAAU-5'<br>5'-TGGACCATTTTCTATTTGTCTATTTTA-3' | (SEQ ID NO: 810)<br>(SEQ ID NO: 1919)<br>(SEQ ID NO: 3028) |
| βc-3475 Target: | 5'-GGACCAUUUUCUAUUUGUCUAUUtt-3'<br>3'-AACCUGGUAAAAGAUAAACAGAUAAAA-5'<br>5'-TTGGACCATTTTCTATTTGTCTATTTT-3' | (SEQ ID NO: 811)<br>(SEQ ID NO: 1920)<br>(SEQ ID NO: 3029) |
| βc-3482 Target: | 5'-ACUAUUGGACCAUUUUCUAUUUgt-3'<br>3'-UUUGAUUAACCUGGUAAAAGAUAAACA-5'<br>5'-AAACTAATTGGACCATTTTCTATTTGT-3' | (SEQ ID NO: 812)<br>(SEQ ID NO: 1921)<br>(SEQ ID NO: 3030) |
| βc-3483 Target: | 5'-AACUAUUGGACCAUUUUCUAUUtg-3'<br>3'-CUUUGAUUAACCUGGUAAAAGAUAAAC-5'<br>5'-GAAACTAATTGGACCATTTTCTATTTG-3' | (SEQ ID NO: 813)<br>(SEQ ID NO: 1922)<br>(SEQ ID NO: 3031) |
| βc-3484 Target: | 5'-AAACUAAUUGGACCAUUUUCUAUtt-3'<br>3'-CCUUUGAUUAACCUGGUAAAAGAUAAA-5'<br>5'-GGAAACTAATTGGACCATTTTCTATTT-3' | (SEQ ID NO: 814)<br>(SEQ ID NO: 1923)<br>(SEQ ID NO: 3032) |

TABLE 9-continued

Additional Selected Anti-β-catenin DsiRNAs, 25/27mer Duplexes

| | | |
|---|---|---|
| βc-3485 Target: | 5'-GAAACUAAUUGGACCAUUUUCUAtt-3'<br>3'-UCCUUUGAUUAACCUGGUAAAAGAUAA-5'<br>5'-AGGAAACTAATTGGACCATTTTCTATT-3' | (SEQ ID NO: 815)<br>(SEQ ID NO: 1924)<br>(SEQ ID NO: 3033) |
| βc-3491 Target: | 5'-AAAAAGGAAACUAAUUGGACCAUtt-3'<br>3'-AAUUUUCCUUUGAUUAACCUGGUAAA-5'<br>5'-TTAAAAAGGAAACTAATTGGACCATTT-3' | (SEQ ID NO: 816)<br>(SEQ ID NO: 1925)<br>(SEQ ID NO: 3034) |
| βc-3492 Target: | 5'-UAAAAAGGAAACUAAUUGGACCAtt-3'<br>3'-UAAUUUUCCUUUGAUUAACCUGGUAA-5'<br>5'-ATTAAAAAGGAAACTAATTGGACCATT-3' | (SEQ ID NO: 817)<br>(SEQ ID NO: 1926)<br>(SEQ ID NO: 3035) |
| βc-3498 Target: | 5'-GCAUAUUAAAAGGAAACUAAUUgg-3'<br>3'-UUCGUAUAAUUUUCCUUUGAUUAACC-5'<br>5'-AAGCATATTAAAAGGAAACTAATTGG-3' | (SEQ ID NO: 818)<br>(SEQ ID NO: 1927)<br>(SEQ ID NO: 3036) |
| βc-3499 Target: | 5'-AGCAUAUUAAAAAGGAAACUAAUtg-3'<br>3'-AUUCGUAUAAUUUUUCCUUUGAUUAAC-5'<br>5'-TAAGCATATTAAAAAGGAAACTAATTG-3' | (SEQ ID NO: 819)<br>(SEQ ID NO: 1928)<br>(SEQ ID NO: 3037) |
| βc-3503 Target: | 5'-UUUAAGCAUAUUAAAAGGAAACta-3'<br>3'-UAAAAUUCGUAUAAUUUUUCCUUUGAU-5'<br>5'-ATTTTAAGCATATTAAAAAGGAAACTA-3' | (SEQ ID NO: 820)<br>(SEQ ID NO: 1929)<br>(SEQ ID NO: 3038) |
| βc-3509 Target: | 5'-GCUUAUUUUAAGCAUAUUAAAAgg-3'<br>3'-GACGAAUAAAAUUCGUAUAAUUUUUCC-5'<br>5'-CTGCTTATTTTAAGCATATTAAAAGG-3' | (SEQ ID NO: 821)<br>(SEQ ID NO: 1930)<br>(SEQ ID NO: 3039) |
| βc-3510 Target: | 5'-UGCUUAUUUUAAGCAUAUUAAAAag-3'<br>3'-GGACGAAUAAAAUUCGUAUAAUUUUUC-5'<br>5'-CCTGCTTATTTTAAGCATATTAAAAAG-3' | (SEQ ID NO: 822)<br>(SEQ ID NO: 1931)<br>(SEQ ID NO: 3040) |
| βc-3516 Target: | 5'-UCCACCUGCUUAUUUUAAGCAUAtt-3'<br>3'-CUAGGUGGACGAAUAAAAUUCGUAUAA-5'<br>5'-GATCCACCTGCTTATTTTAAGCATATT-3' | (SEQ ID NO: 823)<br>(SEQ ID NO: 1932)<br>(SEQ ID NO: 3041) |
| βc-3531 Target: | 5'-AAAACAUGAAAUAGAUCCACCUGct-3'<br>3'-GUUUUUGUACUUUAUCUAGGUGGACGA-5'<br>5'-CAAAAACATGAAATAGATCCACCTGCT-3' | (SEQ ID NO: 824)<br>(SEQ ID NO: 1933)<br>(SEQ ID NO: 3042) |
| βc-3532 Target: | 5'-AAAAACAUGAAAUAGAUCCACCUgc-3'<br>3'-AGUUUUUGUACUUUAUCUAGGUGGACG-5'<br>5'-TCAAAAACATGAAATAGATCCACCTGC-3' | (SEQ ID NO: 825)<br>(SEQ ID NO: 1934)<br>(SEQ ID NO: 3043) |
| βc-3534 Target: | 5'-UCAAAACAUGAAAUAGAUCCACct-3'<br>3'-CUAGUUUUUGUACUUUAUCUAGGUGGA-5'<br>5'-GATCAAAAACATGAAATAGATCCACCT-3' | (SEQ ID NO: 826)<br>(SEQ ID NO: 1935)<br>(SEQ ID NO: 3044) |
| βc-3535 Target: | 5'-AUCAAAAACAUGAAAUAGAUCCAcc-3'<br>3'-ACUAGUUUUUGUACUUUAUCUAGGUGG-5'<br>5'-TGATCAAAAACATGAAATAGATCCACC-3' | (SEQ ID NO: 827)<br>(SEQ ID NO: 1936)<br>(SEQ ID NO: 3045) |
| βc-3536 Target: | 5'-GAUCAAAAACAUGAAAUAGAUCCac-3'<br>3'-AACUAGUUUUUGUACUUUAUCUAGGUG-5'<br>5'-TTGATCAAAAACATGAAATAGATCCAC-3' | (SEQ ID NO: 828)<br>(SEQ ID NO: 1937)<br>(SEQ ID NO: 3046) |
| βc-3541 Target: | 5'-UUUUUGAUCAAAAACAUGAAAUAga-3'<br>3'-UCAAAAACUAGUUUUUGUACUUUAUCU-5'<br>5'-AGTTTTTGATCAAAAACATGAAATAGA-3' | (SEQ ID NO: 829)<br>(SEQ ID NO: 1938)<br>(SEQ ID NO: 3047) |
| βc-3547 Target: | 5'-AAAUAGUUUUUGAUCAAAAACAUga-3'<br>3'-GGUUUAUCAAAAACUAGUUUUUGUACU-5'<br>5'-CCAAATAGTTTTTGATCAAAAACATGA-3' | (SEQ ID NO: 830)<br>(SEQ ID NO: 1939)<br>(SEQ ID NO: 3048) |
| βc-3551 Target: | 5'-UCCCAAAUAGUUUUUGAUCAAAAac-3'<br>3'-AUAGGGUUUAUCAAAAACUAGUUUUUG-5'<br>5'-TATCCCAAATAGTTTTTGATCAAAAAC-3' | (SEQ ID NO: 831)<br>(SEQ ID NO: 1940)<br>(SEQ ID NO: 3049) |
| βc-3552 Target: | 5'-AUCCCAAAUAGUUUUUGAUCAAAaa-3'<br>3'-UAUAGGGUUUAUCAAAAACUAGUUUUU-5'<br>5'-ATATCCCAAATAGTTTTTGATCAAAAA-3' | (SEQ ID NO: 832)<br>(SEQ ID NO: 1941)<br>(SEQ ID NO: 3050) |
| βc-3553 Target: | 5'-UAUCCCAAAUAGUUUUUGAUCAAaa-3'<br>3'-GUAUAGGGUUUAUCAAAAACUAGUUUU-5'<br>5'-CATATCCCAAATAGTTTTTGATCAAAA-3' | (SEQ ID NO: 833)<br>(SEQ ID NO: 1942)<br>(SEQ ID NO: 3051) |

TABLE 9-continued

Additional Selected Anti-β-catenin DsiRNAs, 25/27mer Duplexes

| | | |
|---|---|---|
| βc-3554 Target: | 5'-AUAUCCCAAAUAGUUUUUGAUCAaa-3'<br>3'-UGUAUAGGGUUUAUCAAAAACUAGUUU-5'<br>5'-ACATATCCCAAATAGTTTTTGATCAAA-3' | (SEQ ID NO: 834)<br>(SEQ ID NO: 1943)<br>(SEQ ID NO: 3052) |
| βc-3558 Target: | 5'-AUACAUAUCCCAAAUAGUUUUUGat-3'<br>3'-GGUAUGUAUAGGGUUUAUCAAAAACUA-5'<br>5'-CCATACATATCCCAAATAGTTTTTGAT-3' | (SEQ ID NO: 835)<br>(SEQ ID NO: 1944)<br>(SEQ ID NO: 3053) |
| βc-3567 Target: | 5'-ACCCUACCCAUACAUAUCCCAAAta-3'<br>3'-AAUGGGAUGGGUAUGUAUAGGGUUUAU-5'<br>5'-TTACCCTACCCATACATATCCCAAATA-3' | (SEQ ID NO: 836)<br>(SEQ ID NO: 1945)<br>(SEQ ID NO: 3054) |
| βc-3568 Target: | 5'-UACCCUACCCAUACAUAUCCCAAat-3'<br>3'-AAAUGGGAUGGGUAUGUAUAGGGUUUA-5'<br>5'-TTTACCCTACCCATACATATCCCAAAT-3' | (SEQ ID NO: 837)<br>(SEQ ID NO: 1946)<br>(SEQ ID NO: 3055) |
| βc-3569 Target: | 5'-UUACCCUACCCAUACAUAUCCCAaa-3'<br>3'-UAAAUGGGAUGGGUAUGUAUAGGGUUU-5'<br>5'-ATTTACCCTACCCATACATATCCCAAA-3' | (SEQ ID NO: 838)<br>(SEQ ID NO: 1947)<br>(SEQ ID NO: 3056) |
| βc-3582 Target: | 5'-ACCUCUUACUGAUUUACCCUACCca-3'<br>3'-UGUGGAGAAUGACUAAAUGGGAUGGGU-5'<br>5'-ACACCTCTTACTGATTTACCCTACCCA-3' | (SEQ ID NO: 839)<br>(SEQ ID NO: 1948)<br>(SEQ ID NO: 3057) |
| βc-3584 Target: | 5'-ACACCUCUUACUGAUUUACCCUAcc-3'<br>3'-AUUGUGGAGAAUGACUAAAUGGGAUGG-5'<br>5'-TAACACCTCTTACTGATTTACCCTACC-3' | (SEQ ID NO: 840)<br>(SEQ ID NO: 1949)<br>(SEQ ID NO: 3058) |
| βc-3585 Target: | 5'-AACACCUCUUACUGAUUUACCCUac-3'<br>3'-UAUUGUGGAGAAUGACUAAAUGGGAUG-5'<br>5'-ATAACACCTCTTACTGATTTACCCTAC-3' | (SEQ ID NO: 841)<br>(SEQ ID NO: 1950)<br>(SEQ ID NO: 3059) |
| βc-3586 Target: | 5'-UAACACCUCUUACUGAUUUACCCta-3'<br>3'-UUAUUGUGGAGAAUGACUAAAUGGGAU-5'<br>5'-AATAACACCTCTTACTGATTTACCCTA-3' | (SEQ ID NO: 842)<br>(SEQ ID NO: 1951)<br>(SEQ ID NO: 3060) |
| βc-3587 Target: | 5'-AUAACACCUCUUACUGAUUUACCct-3'<br>3'-UUUAUUGUGGAGAAUGACUAAAUGGGA-5'<br>5'-AAATAACACCTCTTACTGATTTACCCT-3' | (SEQ ID NO: 843)<br>(SEQ ID NO: 1952)<br>(SEQ ID NO: 3061) |
| βc-3588 Target: | 5'-AAUAACACCUCUUACUGAUUUACcc-3'<br>3'-GUUUAUUGUGGAGAAUGACUAAAUGGG-5'<br>5'-CAAATAACACCTCTTACTGATTTACCC-3' | (SEQ ID NO: 844)<br>(SEQ ID NO: 1953)<br>(SEQ ID NO: 3062) |
| βc-3594 Target: | 5'-GUUCCAAAUAACACCUCUUACUGat-3'<br>3'-UCCAAGGUUUAUUGUGGAGAAUGACUA-5'<br>5'-AGGTTCCAAATAACACCTCTTACTGAT-3' | (SEQ ID NO: 845)<br>(SEQ ID NO: 1954)<br>(SEQ ID NO: 3063) |
| βc-3600 Target: | 5'-AACAAGGUUCCAAAUAACACCUCtt-3'<br>3'-UUUUGUUCCAAGGUUUAUUGUGGAGAA-5'<br>5'-AAAACAAGGTTCCAAATAACACCTCTT-3' | (SEQ ID NO: 846)<br>(SEQ ID NO: 1955)<br>(SEQ ID NO: 3064) |
| βc-3601 Target: | 5'-AAACAAGGUUCCAAAUAACACCUct-3'<br>3'-GUUUUGUUCCAAGGUUUAUUGUGGAGA-5'<br>5'-CAAAACAAGGTTCCAAATAACACCTCT-3' | (SEQ ID NO: 847)<br>(SEQ ID NO: 1956)<br>(SEQ ID NO: 3065) |
| βc-3602 Target: | 5'-AAAACAAGGUUCCAAAUAACACCtc-3'<br>3'-GGUUUUGUUCCAAGGUUUAUUGUGGAG-5'<br>5'-CCAAAACAAGGTTCCAAATAACACCTC-3' | (SEQ ID NO: 848)<br>(SEQ ID NO: 1957)<br>(SEQ ID NO: 3066) |
| βc-3607 Target: | 5'-UGUCCAAAACAAGGUUCCAAAUAac-3'<br>3'-UGACAGGUUUUGUUCCAAGGUUUAUUG-5'<br>5'-ACTGTCCAAAACAAGGTTCCAAATAAC-3' | (SEQ ID NO: 849)<br>(SEQ ID NO: 1958)<br>(SEQ ID NO: 3067) |
| βc-3611 Target: | 5'-AAACUGUCCAAAACAAGGUUCCAaa-3'<br>3'-CAUUUGACAGGUUUUGUUCCAAGGUUU-5'<br>5'-GTAAACTGTCCAAAACAAGGTTCCAAA-3' | (SEQ ID NO: 850)<br>(SEQ ID NO: 1959)<br>(SEQ ID NO: 3068) |
| βc-3612 Target: | 5'-UAAACUGUCCAAAACAAGGUUCCaa-3'<br>3'-CCAUUUGACAGGUUUUGUUCCAAGGUU-5'<br>5'-GGTAAACTGTCCAAAACAAGGTTCCAA-3' | (SEQ ID NO: 851)<br>(SEQ ID NO: 1960)<br>(SEQ ID NO: 3069) |
| βc-3620 Target: | 5'-GCAACUGGUAAACUGUCCAAAACaa-3'<br>3'-UCCGUUGACCAUUUGACAGGUUUUGUU-5'<br>5'-AGGCAACTGGTAAACTGTCCAAAACA-3' | (SEQ ID NO: 852)<br>(SEQ ID NO: 1961)<br>(SEQ ID NO: 3070) |

TABLE 9-continued

Additional Selected Anti-β-catenin DsiRNAs, 25/27mer Duplexes

| | | |
|---|---|---|
| βc-3628 Target: | 5'-GAUAAAAGGCAACUGGUAAACUGtc-3'<br>3'-CCCUAUUUUCCGUUGACCAUUUGACAG-5'<br>5'-GGGATAAAAGGCAACTGGTAAACTGTC-3' | (SEQ ID NO: 853)<br>(SEQ ID NO: 1962)<br>(SEQ ID NO: 3071) |
| βc-3629 Target: | 5'-GGAUAAAAGGCAACUGGUAAACUgt-3'<br>3'-ACCCUAUUUUCCGUUGACCAUUUGACA-5'<br>5'-TGGGATAAAAGGCAACTGGTAAACTGT-3' | (SEQ ID NO: 854)<br>(SEQ ID NO: 1963)<br>(SEQ ID NO: 3072) |
| βc-3636 Target: | 5'-AACUUUGGGAUAAAAGGCAACUGgt-3'<br>3'-UGUUGAAACCCUAUUUUCCGUUGACCA-5'<br>5'-ACAACTTTGGGATAAAAGGCAACTGGT-3' | (SEQ ID NO: 855)<br>(SEQ ID NO: 1964)<br>(SEQ ID NO: 3073) |
| βc-3638 Target: | 5'-ACAACUUUGGGAUAAAAGGCAACtg-3'<br>3'-GUUGUUGAAACCCUAUUUUCCGUUGAC-5'<br>5'-CAACAACTTTGGGATAAAAGGCAACTG-3' | (SEQ ID NO: 856)<br>(SEQ ID NO: 1965)<br>(SEQ ID NO: 3074) |
| βc-3643 Target: | 5'-UUACAACAACUUUGGGAUAAAAGgc-3'<br>3'-CCAAUGUUGUUGAAACCCUAUUUUCCG-5'<br>5'-GGTTACAACAACTTTGGGATAAAAGGC-3' | (SEQ ID NO: 857)<br>(SEQ ID NO: 1966)<br>(SEQ ID NO: 3075) |
| βc-3644 Target: | 5'-GUUACAACAACUUUGGGAUAAAAgg-3'<br>3'-UCCAAUGUUGUUGAAACCCUAUUUUCC-5'<br>5'-AGGTTACAACAACTTTGGGATAAAAGG-3' | (SEQ ID NO: 858)<br>(SEQ ID NO: 1967)<br>(SEQ ID NO: 3076) |
| βc-3645 Target: | 5'-GGUUACAACAACUUUGGGAUAAAag-3'<br>3'-GUCCAAUGUUGUUGAAACCCUAUUUUC-5'<br>5'-CAGGTTACAACAACTTTGGGATAAAAG-3' | (SEQ ID NO: 859)<br>(SEQ ID NO: 1968)<br>(SEQ ID NO: 3077) |
| βc-3653 Target: | 5'-UCACAGCAGGUUACAACAACUUUgg-3'<br>3'-AUAGUGUCGUCCAAUGUUGUUGAAACC-5'<br>5'-TATCACAGCAGGTTACAACAACTTTGG-3' | (SEQ ID NO: 860)<br>(SEQ ID NO: 1969)<br>(SEQ ID NO: 3078) |
| βc-3654 Target: | 5'-AUCACAGCAGGUUACAACAACUUtg-3'<br>3'-CAUAGUGUCGUCCAAUGUUGUUGAAAC-5'<br>5'-GTATCACAGCAGGTTACAACAACTTTG-3' | (SEQ ID NO: 861)<br>(SEQ ID NO: 1970)<br>(SEQ ID NO: 3079) |
| βc-3656 Target: | 5'-GUAUCACAGCAGGUUACAACAACtt-3'<br>3'-AGCAUAGUGUCGUCCAAUGUUGUUGAA-5'<br>5'-TCGTATCACAGCAGGTTACAACAACTT-3' | (SEQ ID NO: 862)<br>(SEQ ID NO: 1971)<br>(SEQ ID NO: 3080) |
| βc-3670 Target: | 5'-UCUCUUGAAGCAUCGUAUCACAGca-3'<br>3'-AAAGAGAACUUCGUAGCAUAGUGUCGU-5'<br>5'-TTTCTCTTGAAGCATCGTATCACAGCA-3' | (SEQ ID NO: 863)<br>(SEQ ID NO: 1972)<br>(SEQ ID NO: 3081) |
| βc-3671 Target: | 5'-UUCUCUUGAAGCAUCGUAUCACAgc-3'<br>3'-AAAAGAGAACUUCGUAGCAUAGUGUCG-5'<br>5'-TTTTCTCTTGAAGCATCGTATCACAGC-3' | (SEQ ID NO: 864)<br>(SEQ ID NO: 1973)<br>(SEQ ID NO: 3082) |
| βc-3673 Target: | 5'-UUUUCUCUUGAAGCAUCGUAUCAca-3'<br>3'-GUAAAAGAGAACUUCGUAGCAUAGUGU-5'<br>5'-CATTTTCTCTTGAAGCATCGTATCACA-3' | (SEQ ID NO: 865)<br>(SEQ ID NO: 1974)<br>(SEQ ID NO: 3083) |
| βc-3686 Target: | 5'-UUUUAUAACCGCAUUUUCUCUUGaa-3'<br>3'-AAAAAAUAUUGGCGUAAAAGAGAACUU-5'<br>5'-TTTTTTATAACCGCATTTTCTCTTGAA-3' | (SEQ ID NO: 866)<br>(SEQ ID NO: 1975)<br>(SEQ ID NO: 3084) |
| βc-3687 Target: | 5'-UUUUUAUAACCGCAUUUUCUCUUga-3'<br>3'-UAAAAAAUAUUGGCGUAAAAGAGAACU-5'<br>5'-ATTTTTTATAACCGCATTTTCTCTTGA-3' | (SEQ ID NO: 867)<br>(SEQ ID NO: 1976)<br>(SEQ ID NO: 3085) |
| βc-3688 Target: | 5'-UUUUUUAUAACCGCAUUUUCUCUtg-3'<br>3'-GUAAAAAAUAUUGGCGUAAAAGAGAAC-5'<br>5'-CATTTTTTATAACCGCATTTTCTCTTG-3' | (SEQ ID NO: 868)<br>(SEQ ID NO: 1977)<br>(SEQ ID NO: 3086) |
| βc-3689 Target: | 5'-AUUUUUUAUAACCGCAUUUUCUCtt-3'<br>3'-GGUAAAAAAUAUUGGCGUAAAAGAGAA-5'<br>5'-CCATTTTTTATAACCGCATTTTCTCTT-3' | (SEQ ID NO: 869)<br>(SEQ ID NO: 1978)<br>(SEQ ID NO: 3087) |
| βc-3694 Target: | 5'-GAACCAUUUUUUAUAACCGCAUUtt-3'<br>3'-GACUUGGUAAAAAAUAUUGGCGUAAAA-5'<br>5'-CTGAACCATTTTTTATAACCGCATTTT-3' | (SEQ ID NO: 870)<br>(SEQ ID NO: 1979)<br>(SEQ ID NO: 3088) |
| βc-3699 Target: | 5'-AUUCUGAACCAUUUUUUAUAACCgc-3'<br>3'-AUUAAGACUUGGUAAAAAAUAUUGGCG-5'<br>5'-TAATTCTGAACCATTTTTTATAACCGC-3' | (SEQ ID NO: 871)<br>(SEQ ID NO: 1980)<br>(SEQ ID NO: 3089) |

TABLE 9-continued

Additional Selected Anti-β-catenin DsiRNAs, 25/27mer Duplexes

| | | |
|---|---|---|
| βc-3700 Target: | 5'-AAUUCUGAACCAUUUUUUAUAACcg-3'<br>3'-AAUUAAGACUUGGUAAAAAAUAUUGGC-5'<br>5'-TTAATTCTGAACCATTTTTTATAACCG-3' | (SEQ ID NO: 872)<br>(SEQ ID NO: 1981)<br>(SEQ ID NO: 3090) |
| βc-3701 Target: | 5'-UAAUUCUGAACCAUUUUUUAUAAcc-3'<br>3'-AAAUUAAGACUUGGUAAAAAAUAUUGG-5'<br>5'-TTTAATTCTGAACCATTTTTTATAACC-3' | (SEQ ID NO: 873)<br>(SEQ ID NO: 1982)<br>(SEQ ID NO: 3091) |
| βc-3702 Target: | 5'-UUAAUUCUGAACCAUUUUUUAUac-3'<br>3'-CAAAUUAAGACUUGGUAAAAAAUAUUG-5'<br>5'-GTTTAATTCTGAACCATTTTTTATAAC-3' | (SEQ ID NO: 874)<br>(SEQ ID NO: 1983)<br>(SEQ ID NO: 3092) |
| βc-3703 Target: | 5'-UUUAAUUCUGAACCAUUUUUUAUaa-3'<br>3'-UCAAAUUAAGACUUGGUAAAAAAUAUU-5'<br>5'-AGTTTAATTCTGAACCATTTTTTATAA-3' | (SEQ ID NO: 875)<br>(SEQ ID NO: 1984)<br>(SEQ ID NO: 3093) |
| βc-3704 Target: | 5'-GUUUAAUUCUGAACCAUUUUUUAta-3'<br>3'-UUCAAAUUAAGACUUGGUAAAAAAUAU-5'<br>5'-AAGTTTAATTCTGAACCATTTTTTATA-3' | (SEQ ID NO: 876)<br>(SEQ ID NO: 1985)<br>(SEQ ID NO: 3094) |
| βc-3709 Target: | 5'-UAAAAGUUUAAUUCUGAACCAUUtt-3'<br>3'-UAAUUUUCAAAUUAAGACUUGGUAAAA-5'<br>5'-ATTAAAAGTTTAATTCTGAACCATTTT-3' | (SEQ ID NO: 877)<br>(SEQ ID NO: 1986)<br>(SEQ ID NO: 3095) |
| βc-3710 Target: | 5'-UUAAAAGUUUAAUUCUGAACCAUtt-3'<br>3'-UUAAUUUUCAAAUUAAGACUUGGUAAA-5'<br>5'-AATTAAAAGTTTAATTCTGAACCATTT-3' | (SEQ ID NO: 878)<br>(SEQ ID NO: 1987)<br>(SEQ ID NO: 3096) |
| βc-3712 Target: | 5'-AAUUAAAAGUUUAAUUCUGAACCat-3'<br>3'-ACUUAAUUUUCAAAUUAAGACUUGGUA-5'<br>5'-TGAATTAAAAGTTTAATTCTGAACC-3' | (SEQ ID NO: 879)<br>(SEQ ID NO: 1988)<br>(SEQ ID NO: 3097) |
| βc-2634t2 Target: | 5'-AUACAGCUAAAGGAUGAUUUACAgg-3'<br>3'-GUUAUGUCGAUUUCCUACUAAAUGUCC-5'<br>5'-CAATACAGCTAAAGGATGATTTACAGG-3' | (SEQ ID NO: 880)<br>(SEQ ID NO: 1989)<br>(SEQ ID NO: 3098) |
| βc-2635t2 Target: | 5'-AAUACAGCUAAAGGAUGAUUUACag-3'<br>3'-UGUUAUGUCGAUUUCCUACUAAAUGUC-5'<br>5'-ACAATACAGCTAAAGGATGATTTACAG-3' | (SEQ ID NO: 881)<br>(SEQ ID NO: 1990)<br>(SEQ ID NO: 3099) |
| βc-2637t2 Target: | 5'-ACAAUACAGCUAAAGGAUGAUUUac-3'<br>3'-UCUGUUAUGUCGAUUUCCUACUAAAUG-5'<br>5'-AGACAATACAGCTAAAGGATGATTTAC-3' | (SEQ ID NO: 882)<br>(SEQ ID NO: 1991)<br>(SEQ ID NO: 3100) |
| βc-2633t3 Target: | 5'-UACUCCUAAAGGAUGAUUUACAgt-3'<br>3'-CAAUGAGGAUUUCCUACUAAAUGUCCA-5'<br>5'-GTTACTCCTAAAGGATGATTTACAGGT-3' | (SEQ ID NO: 883)<br>(SEQ ID NO: 1992)<br>(SEQ ID NO: 3101) |
| βc-2634t3 Target: | 5'-UUACUCCUAAAGGAUGAUUUACAgg-3'<br>3'-ACAAUGAGGAUUUCCUACUAAAUGUCC-5'<br>5'-TGTTACTCCTAAAGGATGATTTACAGG-3' | (SEQ ID NO: 884)<br>(SEQ ID NO: 1993)<br>(SEQ ID NO: 3102) |
| βc-2635t3 Target: | 5'-GUUACUCCUAAAGGAUGAUUUACag-3'<br>3'-AACAAUGAGGAUUUCCUACUAAAUGUC-5'<br>5'-TTGTTACTCCTAAAGGATGATTTACAG-3' | (SEQ ID NO: 885)<br>(SEQ ID NO: 1994)<br>(SEQ ID NO: 3103) |
| βc-2636t3 Target: | 5'-UGUUACUCCUAAAGGAUGAUUUACa-3'<br>3'-UAACAAUGAGGAUUUCCUACUAAAUGU-5'<br>5'-ATTGTTACTCCTAAAGGATGATTTACA-3' | (SEQ ID NO: 886)<br>(SEQ ID NO: 1995)<br>(SEQ ID NO: 3104) |
| βc-m318 Target: | 5'-AUUCCAGAAUCCAAGUAAGACUGct-3'<br>3'-CCUAAGGUCUUAGGUUCAUUCUGACGA-5'<br>5'-GGATTCCAGAATCCAAGTAAGACTGCT-3' | (SEQ ID NO: 887)<br>(SEQ ID NO: 1996)<br>(SEQ ID NO: 3105) |
| βc-m417 Target: | 5'-UGCUCCCAUUCAUAAAGGACUUGgg-3'<br>3'-GAACGAGGGUAAGUAUUUCCUGAACCC-5'<br>5'-CTTGCTCCCATTCATAAAGGACTTGGG-3' | (SEQ ID NO: 888)<br>(SEQ ID NO: 1997)<br>(SEQ ID NO: 3106) |
| βc-m462 Target: | 5'-UCAAUAUCAGCUACUUGCUCUUGcg-3'<br>3'-GCAGUUAUAGUCGAUGAACGAGAACGC-5'<br>5'-CGTCAATATCAGCTACTTGCTCTTGCG-3' | (SEQ ID NO: 889)<br>(SEQ ID NO: 1998)<br>(SEQ ID NO: 3107) |
| βc-m463 Target: | 5'-GUCAAUAUCAGCUACUUGCUCUUgc-3'<br>3'-GGCAGUUAUAGUCGAUGAACGAGAACG-5'<br>5'-CCGTCAATATCAGCTACTTGCTCTTGC-3' | (SEQ ID NO: 890)<br>(SEQ ID NO: 1999)<br>(SEQ ID NO: 3108) |

TABLE 9-continued

Additional Selected Anti-β-catenin DsiRNAs, 25/27mer Duplexes

| | | |
|---|---|---|
| βc-m468 Target: | 5'-UGCCCGUCAAUAUCAGCUACUUGct-3'<br>3'-UGACGGGCAGUUAUAGUCGAUGAACGA-5'<br>5'-ACTGCCCGTCAATATCAGCTACTTGCT-3' | (SEQ ID NO: 891)<br>(SEQ ID NO: 2000)<br>(SEQ ID NO: 3109) |
| βc-m613 Target: | 5'-UUUCAACAUCUGUGAUGGUUCAGcc-3'<br>3'-ACAAAGUUGUAGACACUACCAAGUCGG-5'<br>5'-TGTTTCAACATCTGTGATGGTTCAGCC-3' | (SEQ ID NO: 892)<br>(SEQ ID NO: 2001)<br>(SEQ ID NO: 3110) |
| βc-m614 Target: | 5'-GUUUCAACAUCUGUGAUGGUUCAgc-3'<br>3'-UACAAAGUUGUAGACACUACCAAGUCG-5'<br>5'-ATGTTTCAACATCTGTGATGGTTCAGC-3' | (SEQ ID NO: 893)<br>(SEQ ID NO: 2002)<br>(SEQ ID NO: 3111) |
| βc-m624 Target: | 5'-ACAACUGCAUGUUUCAACAUCUGtg-3'<br>3'-ACUGUUGACGUACAAAGUUGUAGACAC-5'<br>5'-TGACAACTGCATGTTTCAACATCTGTG-3' | (SEQ ID NO: 894)<br>(SEQ ID NO: 2003)<br>(SEQ ID NO: 3112) |
| βc-m626 Target: | 5'-UGACAACUGCAUGUUUCAACAUCtg-3'<br>3'-UAACUGUUGACGUACAAAGUUGUAGAC-5'<br>5'-ATTGACAACTGCATGTTTCAACATCTG-3' | (SEQ ID NO: 895)<br>(SEQ ID NO: 2004)<br>(SEQ ID NO: 3113) |
| βc-m630 Target: | 5'-AAAUUGACAACUGCAUGUUUCAAca-3'<br>3'-AGUUUAACUGUUGACGUACAAAGUUGU-5'<br>5'-TCAAATTGACAACTGCATGTTTCAACA-3' | (SEQ ID NO: 896)<br>(SEQ ID NO: 2005)<br>(SEQ ID NO: 3114) |
| βc-m636 Target: | 5'-UUAAUCAAAUUGACAACUGCAUGtt-3'<br>3'-UCAAUUAGUUUAACUGUUGACGUACAA-5'<br>5'-AGTTAATCAAATTGACAACTGCATGTT-3' | (SEQ ID NO: 897)<br>(SEQ ID NO: 2006)<br>(SEQ ID NO: 3115) |
| βc-m642 Target: | 5'-UGAUAGUUAAUCAAAUUGACAACtg-3'<br>3'-GGACUAUCAAUUAGUUUAACUGUUGAC-5'<br>5'-CCTGATAGTTAATCAAATTGACAACTG-3' | (SEQ ID NO: 898)<br>(SEQ ID NO: 2007)<br>(SEQ ID NO: 3116) |
| βc-m648 Target: | 5'-UCAUCCUGAUAGUUAAUCAAAUUga-3'<br>3'-GCAGUAGGACUAUCAAUUAGUUUAACU-5'<br>5'-CGTCATCCTGATAGTTAATCAAATTGA-3' | (SEQ ID NO: 899)<br>(SEQ ID NO: 2008)<br>(SEQ ID NO: 3117) |
| βc-m649 Target: | 5'-GUCAUCCUGAUAGUUAAUCAAAUtg-3'<br>3'-CGCAGUAGGACUAUCAAUUAGUUUAAC-5'<br>5'-GCGTCATCCTGATAGTTAATCAAATTG-3' | (SEQ ID NO: 900)<br>(SEQ ID NO: 2009)<br>(SEQ ID NO: 3118) |
| βc-m702 Target: | 5'-UCAUCGUUUAGCAGUUUUGUCAGct-3'<br>3'-GGAGUAGCAAAUCGUCAAAACAGUCGA-5'<br>5'-CCTCATCGTTTAGCAGTTTTGTCAGCT-3' | (SEQ ID NO: 901)<br>(SEQ ID NO: 2010)<br>(SEQ ID NO: 3119) |
| βc-m707 Target: | 5'-GGUCCUCAUCGUUUAGCAGUUUUgt-3'<br>3'-GACCAGGAGUAGCAAAUCGUCAAAACA-5'<br>5'-CTGGTCCTCATCGTTTAGCAGTTTTGT-3' | (SEQ ID NO: 902)<br>(SEQ ID NO: 2011)<br>(SEQ ID NO: 3120) |
| βc-m734 Target: | 5'-UAACAGCAGCUUUAUUAACUACCac-3'<br>3'-GUAUUGUCGUCGAAAUAAUUGAUGGUG-5'<br>5'-CATAACAGCAGCTTTATTAACTACCAC-3' | (SEQ ID NO: 903)<br>(SEQ ID NO: 2012)<br>(SEQ ID NO: 3121) |
| βc-m735 Target: | 5'-AUAACAGCAGCUUUAUUAACUACca-3'<br>3'-GGUAUUGUCGUCGAAAUAAUUGAUGGU-5'<br>5'-CCATAACAGCAGCTTTATTAACTACCA-3' | (SEQ ID NO: 904)<br>(SEQ ID NO: 2013)<br>(SEQ ID NO: 3122) |
| βc-m738 Target: | 5'-ACCAUAACAGCAGCUUUAUUAACta-3'<br>3'-CCUGGUAUUGUCGUCGAAAUAAUUGAU-5'<br>5'-GGACCATAACAGCAGCTTTATTAACTA-3' | (SEQ ID NO: 905)<br>(SEQ ID NO: 2014)<br>(SEQ ID NO: 3123) |
| βc-m739 Target: | 5'-GACCAUAACAGCAGCUUUAUUAAct-3'<br>3'-ACCUGGUAUUGUCGUCGAAAUAAUUGA-5'<br>5'-TGGACCATAACAGCAGCTTTATTAACT-3' | (SEQ ID NO: 906)<br>(SEQ ID NO: 2015)<br>(SEQ ID NO: 3124) |
| βc-m843 Target: | 5'-GUCUCUACAUCAUUUGUAUUCUGca-3'<br>3'-GACAGAGAUGUAGUAAACAUAAGACGU-5'<br>5'-CTGTCTCTACATCATTTGTATTCTGCA-3' | (SEQ ID NO: 907)<br>(SEQ ID NO: 2016)<br>(SEQ ID NO: 3125) |
| βc-m844 Target: | 5'-UGUCUCUACAUCAUUUGUAUUCUgc-3'<br>3'-CGACAGAGAUGUAGUAAACAUAAGACG-5'<br>5'-GCTGTCTCTACATCATTTGTATTCTGC-3' | (SEQ ID NO: 908)<br>(SEQ ID NO: 2017)<br>(SEQ ID NO: 3126) |
| βc-m1063 Target: | 5'-AACCAUUUUCUGCAGUCCACCAGct-3'<br>3'-CGUUGGUAAAAGACGUCAGGUGGUCGA-5'<br>5'-GCAACCATTTTCTGCAGTCCACCAGCT-3' | (SEQ ID NO: 909)<br>(SEQ ID NO: 2018)<br>(SEQ ID NO: 3127) |

TABLE 9-continued

Additional Selected Anti-β-catenin DsiRNAs, 25/27mer Duplexes

| | | |
|---|---|---|
| βc-m1065 Target: | 5'-GCAACCAUUUCUGCAGUCCACCag-3'<br>3'-UUCGUUGGUAAAAGACGUCAGGUGGUC-5'<br>5'-AAGCAACCATTTTCTGCAGTCCACCAG-3' | (SEQ ID NO: 910)<br>(SEQ ID NO: 2019)<br>(SEQ ID NO: 3128) |
| βc-m1080 Target: | 5'-GUUUUGUUGAGCAAAGCAACCAUtt-3'<br>3'-AACAAAACAACUCGUUUCGUUGGUAAA-5'<br>5'-TTGTTTTGTTGAGCAAAGCAACCATTT-3' | (SEQ ID NO: 911)<br>(SEQ ID NO: 2020)<br>(SEQ ID NO: 3129) |
| βc-m1081 Target: | 5'-UGUUUUGUUGAGCAAAGCAACCAtt-3'<br>3'-AAACAAAACAACUCGUUUCGUUGGUAA-5'<br>5'-TTTGTTTTGTTGAGCAAAGCAACCATT-3' | (SEQ ID NO: 912)<br>(SEQ ID NO: 2021)<br>(SEQ ID NO: 3130) |
| βc-m1098 Target: | 5'-GCCAAGAAUUUCACGUUUGUUUUgt-3'<br>3'-AUCGGUUCUUAAAGUGCAAACAAAACA-5'<br>5'-TAGCCAAGAATTTCACGTTTGTTTTGT-3' | (SEQ ID NO: 913)<br>(SEQ ID NO: 2022)<br>(SEQ ID NO: 3131) |
| βc-m1140 Target: | 5'-UGAUUGCCAUAAGCUAAGAUCUGaa-3'<br>3'-GAACUAACGGUAUUCGAUUCUAGACUU-5'<br>5'-CTTGATTGCCATAAGCTAAGATCTGAA-3' | (SEQ ID NO: 914)<br>(SEQ ID NO: 2023)<br>(SEQ ID NO: 3132) |
| βc-m1145 Target: | 5'-UCUCUUGAUUGCCAUAAGCUAAGat-3'<br>3'-CGAGAGAACUAACGGUAUUCGAUUCUA-5'<br>5'-GCTCTCTTGATTGCCATAAGCTAAGAT-3' | (SEQ ID NO: 915)<br>(SEQ ID NO: 2024)<br>(SEQ ID NO: 3133) |
| βc-m1217 Target: | 5'-UCUCAUAAGUGUAGGUCCUCAUUat-3'<br>3'-GAAGAGUAUUCACAUCCAGGAGUAAUA-5'<br>5'-CTTCTCATAAGTGTAGGTCCTCATTAT-3' | (SEQ ID NO: 916)<br>(SEQ ID NO: 2025)<br>(SEQ ID NO: 3134) |
| βc-m1218 Target: | 5'-UUCUCAUAAGUGUAGGUCCUCAUta-3'<br>3'-CGAAGAGUAUUCACAUCCAGGAGUAAU-5'<br>5'-GCTTCTCATAAGTGTAGGTCCTCATTA-3' | (SEQ ID NO: 917)<br>(SEQ ID NO: 2026)<br>(SEQ ID NO: 3135) |
| βc-m1220 Target: | 5'-GCUUCUCAUAAGUGUAGGUCCUCat-3'<br>3'-UUCGAAGAGUAUUCACAUCCAGGAGUA-5'<br>5'-AAGCTTCTCATAAGTGTAGGTCCTC-3' | (SEQ ID NO: 918)<br>(SEQ ID NO: 2027)<br>(SEQ ID NO: 3136) |
| βc-m1221 Target: | 5'-AGCUUCUCAUAAGUGUAGGUCCUca-3'<br>3'-CUUCGAAGAGUAUUCACAUCCAGGAGU-5'<br>5'-GAAGCTTCTCATAAGTGTAGGTCCTCA-3' | (SEQ ID NO: 919)<br>(SEQ ID NO: 2028)<br>(SEQ ID NO: 3137) |
| βc-m1365 Target: | 5'-GUCCAAAGACAGUUUUGAACAAGtc-3'<br>3'-CUCAGGUUUCUGUCAAAACUUGUUCAG-5'<br>5'-GAGTCCAAAGACAGTTTTGAACAAGTC-3' | (SEQ ID NO: 920)<br>(SEQ ID NO: 2029)<br>(SEQ ID NO: 3138) |
| βc-m1366 Target: | 5'-AGUCCAAAGACAGUUUUGAACAAgt-3'<br>3'-UCUCAGGUUUCUGUCAAAACUUGUUCA-5'<br>5'-AGAGTCCAAAGACAGTTTTGAACAAGT-3' | (SEQ ID NO: 921)<br>(SEQ ID NO: 2030)<br>(SEQ ID NO: 3139) |
| βc-m1461 Target: | 5'-ACAUUUAUAUCAUCGGAACCCAGaa-3'<br>3'-GGUGUAAAUAUAGUAGCCUUGGGUCUU-5'<br>5'-CCACATTTATATCATCGGAACCCAGAA-3' | (SEQ ID NO: 922)<br>(SEQ ID NO: 2031)<br>(SEQ ID NO: 3140) |
| βc-m1464 Target: | 5'-ACCACAUUUAUAUCAUCGGAACCca-3'<br>3'-ACUGGUGUAAAUAUAGUAGCCUUGGGU-5'<br>5'-TGACCACATTTATATCATCGGAACCCA-3' | (SEQ ID NO: 923)<br>(SEQ ID NO: 2032)<br>(SEQ ID NO: 3141) |
| βc-m1473 Target: | 5'-GCACAGGUGACCACAUUUAUAUCat-3'<br>3'-GACGUGUCCACUGGUGUAAAUAUAGUA-5'<br>5'-CTGCACAGGTGACCACATTTATATC-3' | (SEQ ID NO: 924)<br>(SEQ ID NO: 2033)<br>(SEQ ID NO: 3142) |
| βc-m1474 Target: | 5'-UGCACAGGUGACCACAUUUAUAUca-3'<br>3'-CGACGUGUCCACUGGUGUAAAUAUAGU-5'<br>5'-GCTGCACAGGTGACCACATTTATATCA-3' | (SEQ ID NO: 925)<br>(SEQ ID NO: 2034)<br>(SEQ ID NO: 3143) |
| βc-m1510 Target: | 5'-GUAAUUAUUGCAAGUGAGGUUAGag-3'<br>3'-AACAUUAAUAACGUUCACUCCAAUCUC-5'<br>5'-TTGTAATTATTGCAAGTGAGGTTAGAG-3' | (SEQ ID NO: 926)<br>(SEQ ID NO: 2035)<br>(SEQ ID NO: 3144) |
| βc-m1523 Target: | 5'-UCAUCUUGUUUUUGUAAUUAUUGca-3'<br>3'-GUAGUAGAACAAAAACAUUAAUAACGU-5'<br>5'-CATCATCTTGTTTTTGTAATTATTGCA-3' | (SEQ ID NO: 927)<br>(SEQ ID NO: 2036)<br>(SEQ ID NO: 3145) |
| βc-m1524 Target: | 5'-AUCAUCUUGUUUUUGUAAUUAUUgc-3'<br>3'-GGUAGUAGAACAAAAACAUUAAUAACG-5'<br>5'-CCATCATCTTGTTTTTGTAATTATTGC-3' | (SEQ ID NO: 928)<br>(SEQ ID NO: 2037)<br>(SEQ ID NO: 3146) |

TABLE 9-continued

Additional Selected Anti-β-catenin DsiRNAs, 25/27mer Duplexes

|  |  |  |
| --- | --- | --- |
| βc-m1527 Target: | 5'-ACCAUCAUCUUGUUUUUGUAAUUat-3'<br>3'-UGUGGUAGUAGAACAAAAACAUUAAUA-5'<br>5'-ACACCATCATCTTGTTTTTGTAATTAT-3' | (SEQ ID NO: 929)<br>(SEQ ID NO: 2038)<br>(SEQ ID NO: 3147) |
| βc-m1532 Target: | 5'-GGCACACCAUCAUCUUGUUUUUGta-3'<br>3'-AACCGUGUGGUAGUAGAACAAAAACAU-5'<br>5'-TTGGCACACCATCATCTTGTTTTTGTA-3' | (SEQ ID NO: 930)<br>(SEQ ID NO: 2039)<br>(SEQ ID NO: 3148) |
| βc-m1752 Target: | 5'-AAUCCAACAGUUGCCUUUAUCAGag-3'<br>3'-AGUUAGGUUGUCAACGGAAAUAGUCUC-5'<br>5'-TCAATCCAACAGTTGCCTTTATCAGAG-3' | (SEQ ID NO: 931)<br>(SEQ ID NO: 2040)<br>(SEQ ID NO: 3149) |
| βc-m1757 Target: | 5'-GAAUCAAUCCAACAGUUGCCUUUat-3'<br>3'-AGCUUAGUUAGGUUGUCAACGGAAAUA-5'<br>5'-TCGAATCAATCCAACAGTTGCCTTTAT-3' | (SEQ ID NO: 932)<br>(SEQ ID NO: 2041)<br>(SEQ ID NO: 3150) |
| βc-m1827 Target: | 5'-UGAACUAGUCGUGGAAUAGCACCct-3'<br>3'-CGACUUGAUCAGCACCUUAUCGUGGGA-5'<br>5'-GCTGAACTAGTCGTGGAATAGCACCCT-3' | (SEQ ID NO: 933)<br>(SEQ ID NO: 2042)<br>(SEQ ID NO: 3151) |
| βc-m1934 Target: | 5'-UACACCCUUCUACUAUCUCCUCCat-3'<br>3'-UCAUGUGGGAAGAUGAUAGAGGAGGUA-5'<br>5'-AGTACACCCTTCTACTATCTCCTCC-3' | (SEQ ID NO: 934)<br>(SEQ ID NO: 2043)<br>(SEQ ID NO: 3152) |
| βc-m1935 Target: | 5'-GUACACCCUUCUACUAUCUCCUCca-3'<br>3'-GUCAUGUGGGAAGAUGAUAGAGGAGGU-5'<br>5'-CAGTACACCCTTCTACTATCTCCTCCA-3' | (SEQ ID NO: 935)<br>(SEQ ID NO: 2044)<br>(SEQ ID NO: 3153) |
| βc-m1936 Target: | 5'-AGUACACCCUUCUACUAUCUCCUcc-3'<br>3'-GGUCAUGUGGGAAGAUGAUAGAGGAGG-5'<br>5'-CCAGTACACCCTTCTACTATCTCCTCC-3' | (SEQ ID NO: 936)<br>(SEQ ID NO: 2045)<br>(SEQ ID NO: 3154) |
| βc-m1941 Target: | 5'-GCUCCAGUACACCCUUCUACUAUct-3'<br>3'-CUCGAGGUCAUGUGGGAAGAUGAUAGA-5'<br>5'-GAGCTCCAGTACACCCTTCTACTATCT-3' | (SEQ ID NO: 937)<br>(SEQ ID NO: 2046)<br>(SEQ ID NO: 3155) |
| βc-m2009 Target: | 5'-ACAAUGGAAUGGUAUUGAGUCCUcg-3'<br>3'-UUUGUUACCUUACCAUAACUCAGGAGC-5'<br>5'-AAACAATGGAATGGTATTGAGTCCTCG-3' | (SEQ ID NO: 938)<br>(SEQ ID NO: 2047)<br>(SEQ ID NO: 3156) |
| βc-m2015 Target: | 5'-GCACAAACAAUGGAAUGGUAUUGag-3'<br>3'-GACGUGUUUGUUACCUUACCAUAACUC-5'<br>5'-CTGCACAAACAATGGAATGGTATTGAG-3' | (SEQ ID NO: 939)<br>(SEQ ID NO: 2048)<br>(SEQ ID NO: 3157) |
| βc-m2016 Target: | 5'-UGCACAAACAAUGGAAUGGUAUUga-3'<br>3'-UGACGUGUUUGUUACCUUACCAUAACU-5'<br>5'-ACTGCACAAACAATGGAATGGTATTGA-3' | (SEQ ID NO: 940)<br>(SEQ ID NO: 2049)<br>(SEQ ID NO: 3158) |
| βc-m2021 Target: | 5'-GCAACUGCACAAACAAUGGAAUGgt-3'<br>3'-UUCGUUGACGUGUUUGUUACCUUACCA-5'<br>5'-AAGCAACTGCACAAACAATGGAATGGT-3' | (SEQ ID NO: 941)<br>(SEQ ID NO: 2050)<br>(SEQ ID NO: 3159) |
| βc-m2028 Target: | 5'-GAAUAAAGCAACUGCACAAACAAtg-3'<br>3'-CUCUUAUUUCGUUGACGUGUUUGUUAC-5'<br>5'-GAGAATAAAGCAACTGCACAAACAATG-3' | (SEQ ID NO: 942)<br>(SEQ ID NO: 2051)<br>(SEQ ID NO: 3160) |
| βc-m2037 Target: | 5'-UCAAUGGGAGAAUAAAGCAACUGca-3'<br>3'-AAAGUUACCCUCUUAUUUCGUUGACGU-5'<br>5'-TTTCAATGGGAGAATAAAGCAACTGCA-3' | (SEQ ID NO: 943)<br>(SEQ ID NO: 2052)<br>(SEQ ID NO: 3161) |
| βc-m2038 Target: | 5'-UUCAAUGGGAGAAUAAAGCAACUgc-3'<br>3'-AAAAGUUACCCUCUUAUUUCGUUGACG-5'<br>5'-TTTTCAATGGGAGAATAAAGCAACTGC-3' | (SEQ ID NO: 944)<br>(SEQ ID NO: 2053)<br>(SEQ ID NO: 3162) |
| βc-m2039 Target: | 5'-UUUCAAUGGGAGAAUAAAGCAACtg-3'<br>3'-UAAAAGUUACCCUCUUAUUUCGUUGAC-5'<br>5'-ATTTTCAATGGGAGAATAAAGCAACTG-3' | (SEQ ID NO: 945)<br>(SEQ ID NO: 2054)<br>(SEQ ID NO: 3163) |
| βc-m2043 Target: | 5'-AUAUUUUCAAUGGGAGAAUAAAGca-3'<br>3'-CCUAUAAAAGUUACCCUCUUAUUUCGU-5'<br>5'-GGATATTTTCAATGGGAGAATAAAGCA-3' | (SEQ ID NO: 946)<br>(SEQ ID NO: 2055)<br>(SEQ ID NO: 3164) |
| βc-m2044 Target: | 5'-GAUAUUUUCAAUGGGAGAAUAAAgc-3'<br>3'-ACCUAUAAAAGUUACCCUCUUAUUUCG-5'<br>5'-TGGATATTTTCAATGGGAGAATAAAGC-3' | (SEQ ID NO: 947)<br>(SEQ ID NO: 2056)<br>(SEQ ID NO: 3165) |

TABLE 9-continued

Additional Selected Anti-β-catenin DsiRNAs, 25/27mer Duplexes

|  |  |  |
| --- | --- | --- |
| βc-m2045 Target: | 5'-GGAUAUUUCAAUGGGAGAAUAAag-3'<br>3'-AACCUAUAAAAGUUACCCUCUUAUUUC-5'<br>5'-TTGGATATTTTCAATGGGAGAATAAAG-3' | (SEQ ID NO: 948)<br>(SEQ ID NO: 2057)<br>(SEQ ID NO: 3166) |
| βc-m2055 Target: | 5'-GCUACUCUUUGGAUAUUUUCAAUgg-3'<br>3'-GUCGAUGAGAAACCUAUAAAAGUUACC-5'<br>5'-CAGCTACTCTTTGGATATTTTCAATGG-3' | (SEQ ID NO: 949)<br>(SEQ ID NO: 2058)<br>(SEQ ID NO: 3167) |
| βc-m2056 Target: | 5'-AGCUACUCUUUGGAUAUUUUCAAtg-3'<br>3'-CGUCGAUGAGAAACCUAUAAAAGUUAC-5'<br>5'-GCAGCTACTCTTTGGATATTTTCAATG-3' | (SEQ ID NO: 950)<br>(SEQ ID NO: 2059)<br>(SEQ ID NO: 3168) |
| βc-m2231 Target: | 5'-GCUUCUUGUAAUCCUGUGGCUUGtc-3'<br>3'-GGCGAAGAACAUUAGGACACCGAACAG-5'<br>5'-CCGCTTCTTGTAATCCTGTGGCTTGTC-3' | (SEQ ID NO: 951)<br>(SEQ ID NO: 2060)<br>(SEQ ID NO: 3169) |
| βc-m2307 Target: | 5'-AGUCCAAGAUCUGCAGUCUCAUUcc-3'<br>3'-GGUCAGGUUCUAGACGUCAGAGUAAGG-5'<br>5'-CCAGTCCAAGATCTGCAGTCTCATTCC-3' | (SEQ ID NO: 952)<br>(SEQ ID NO: 2061)<br>(SEQ ID NO: 3170) |
| βc-m2385 Target: | 5'-UAUCCACCAGAGUGAAAAGAACGgt-3'<br>3'-GCAUAGGUGGUCUCACUUUUCUUGCCA-5'<br>5'-CGTATCCACCAGAGTGAAAAGAACGGT-3' | (SEQ ID NO: 953)<br>(SEQ ID NO: 2062)<br>(SEQ ID NO: 3171) |
| βc-m2539 Target: | 5'-GGCCAGCUGAUUGCUAUCACCUGgg-3'<br>3'-GUCCGGUCGACUAACGAUAGUGGACCC-5'<br>5'-CAGGCCAGCTGATTGCTATCACCTGGG-3' | (SEQ ID NO: 954)<br>(SEQ ID NO: 2063)<br>(SEQ ID NO: 3172) |
| βc-m2562 Target: | 5'-AUUUACAGGUCAGUAUCAAACCAgg-3'<br>3'-GCUAAAUGUCCAGUCAUAGUUUGGUCC-5'<br>5'-CGATTTACAGGTCAGTATCAAACCAGG-3' | (SEQ ID NO: 955)<br>(SEQ ID NO: 2064)<br>(SEQ ID NO: 3173) |
| βc-m2563 Target: | 5'-GAUUUACAGGUCAGUAUCAAACCag-3'<br>3'-UGCUAAAUGUCCAGUCAUAGUUUGGUC-5'<br>5'-ACGATTTACAGGTCAGTATCAAACCAG-3' | (SEQ ID NO: 956)<br>(SEQ ID NO: 2065)<br>(SEQ ID NO: 3174) |
| βc-m2578 Target: | 5'-UCUUACCUAAAGGACGAUUUACAgg-3'<br>3'-AAAGAAUGGAUUUCCUGCUAAAUGUCC-5'<br>5'-TTTCTTACCTAAAGGACGATTTACAGG-3' | (SEQ ID NO: 957)<br>(SEQ ID NO: 2066)<br>(SEQ ID NO: 3175) |
| βc-m2580 Target: | 5'-UUUCUUACCUAAAGGACGAUUUAca-3'<br>3'-CGAAAGAAUGGAUUUCCUGCUAAAUGU-5'<br>5'-GCTTTCTTACCTAAAGGACGATTTACA-3' | (SEQ ID NO: 958)<br>(SEQ ID NO: 2067)<br>(SEQ ID NO: 3176) |
| βc-m2589 Target: | 5'-UUUAUAAGCUUUCUUACCUAAAGga-3'<br>3'-GAAAAUAUUCGAAAGAAUGGAUUUCCU-5'<br>5'-CTTTTATAAGCTTTCTTACCTAAAGGA-3' | (SEQ ID NO: 959)<br>(SEQ ID NO: 2068)<br>(SEQ ID NO: 3177) |
| βc-m2590 Target: | 5'-UUUUAUAAGCUUUCUUACCUAAAgg-3'<br>3'-CGAAAAUAUUCGAAAGAAUGGAUUUCC-5'<br>5'-GCTTTTATAAGCTTTCTTACCTAAAGG-3' | (SEQ ID NO: 960)<br>(SEQ ID NO: 2069)<br>(SEQ ID NO: 3178) |
| βc-m2593 Target: | 5'-GGCUUUUAUAAGCUUUCUUACCUaa-3'<br>3'-GACCGAAAAUAUUCGAAAGAAUGGAUU-5'<br>5'-CTGGCTTTTATAAGCTTTCTTACCTAA-3' | (SEQ ID NO: 961)<br>(SEQ ID NO: 2070)<br>(SEQ ID NO: 3179) |
| βc-m2598 Target: | 5'-ACACUGGCUUUUAUAAGCUUUCUta-3'<br>3'-GGUGUGACCGAAAAUAUUCGAAAGAAU-5'<br>5'-CCACACTGGCTTTTATAAGCTTTCTTA-3' | (SEQ ID NO: 962)<br>(SEQ ID NO: 2071)<br>(SEQ ID NO: 3180) |
| βc-m2604 Target: | 5'-UCACCCACACUGGCUUUUAUAAGct-3'<br>3'-UAAGUGGGUGUGACCGAAAAUAUUCGA-5'<br>5'-ATTCACCCACACTGGCTTTTATAAGCT-3' | (SEQ ID NO: 963)<br>(SEQ ID NO: 2072)<br>(SEQ ID NO: 3181) |
| βc-m2644 Target: | 5'-UACCAAGUCUUUCUGGAGUUCUGca-3'<br>3'-GGAUGGUUCAGAAAGACCUCAAGACGU-5'<br>5'-CCTACCAAGTCTTTCTGGAGTTCTGCA-3' | (SEQ ID NO: 964)<br>(SEQ ID NO: 2073)<br>(SEQ ID NO: 3182) |
| βc-m2674 Target: | 5'-UUACAAACAGGCCUAAAACCAUUcc-3'<br>3'-UAAAUGUUUGUCCGGAUUUUGGUAAGG-5'<br>5'-ATTTACAAACAGGCCTAAAACCATTCC-3' | (SEQ ID NO: 965)<br>(SEQ ID NO: 2074)<br>(SEQ ID NO: 3183) |
| βc-m2675 Target: | 5'-UUUACAAACAGGCCUAAAACCAUtc-3'<br>3'-CUAAAUGUUUGUCCGGAUUUUGGUAAG-5'<br>5'-GATTTACAAACAGGCCTAAAACCATTC-3' | (SEQ ID NO: 966)<br>(SEQ ID NO: 2075)<br>(SEQ ID NO: 3184) |

TABLE 9-continued

Additional Selected Anti-β-catenin DsiRNAs, 25/27mer Duplexes

| | | |
|---|---|---|
| βc-m2676 Target: | 5'-AUUUACAAACAGGCCUAAAACCAtt-3'<br>3'-UCUAAAUGUUUGUCCGGAUUUUGGUAA-5'<br>5'-AGATTTACAAACAGGCCTAAAACCATT-3' | (SEQ ID NO: 967)<br>(SEQ ID NO: 2076)<br>(SEQ ID NO: 3185) |
| βc-m2710 Target: | 5'-UCUCCUUCCAAGGUAUGUAUCUGtt-3'<br>3'-GUAGAGGAAGGUUCCAUACAUAGACAA-5'<br>5'-CATCTCCTTCCAAGGTATGTATCTGTT-3' | (SEQ ID NO: 968)<br>(SEQ ID NO: 2077)<br>(SEQ ID NO: 3186) |
| βc-m2711 Target: | 5'-AUCUCCUUCCAAGGUAUGUAUCUgt-3'<br>3'-UGUAGAGGAAGGUUCCAUACAUAGACA-5'<br>5'-ACATCTCCTTCCAAGGTATGTATCTGT-3' | (SEQ ID NO: 969)<br>(SEQ ID NO: 2078)<br>(SEQ ID NO: 3187) |
| βc-m2725 Target: | 5'-UUCCACACAUGAACAUCUCCUUCca-3'<br>3'-UGAAGGUGUGUACUUGUAGAGGAAGGU-5'<br>5'-ACTTCCACACATGAACATCTCCTTCCA-3' | (SEQ ID NO: 970)<br>(SEQ ID NO: 2079)<br>(SEQ ID NO: 3188) |
| βc-m2728 Target: | 5'-AACUUCCACACAUGAACAUCUCCtt-3'<br>3'-CUUUGAAGGUGUGUACUUGUAGAGGAA-5'<br>5'-GAAACTTCCACACATGAACATCTCCTT-3' | (SEQ ID NO: 971)<br>(SEQ ID NO: 2080)<br>(SEQ ID NO: 3189) |
| βc-m2729 Target: | 5'-AAACUUCCACACAUGAACAUCUCct-3'<br>3'-UCUUUGAAGGUGUGUACUUGUAGAGGA-5'<br>5'-AGAAACTTCCACACATGAACATCTCCT-3' | (SEQ ID NO: 972)<br>(SEQ ID NO: 2081)<br>(SEQ ID NO: 3190) |
| βc-m2730 Target: | 5'-GAAACUUCCACACAUGAACAUCUcc-3'<br>3'-CUCUUUGAAGGUGUGUACUUGUAGAGG-5'<br>5'-GAGAAACTTCCACACATGAACATCTCC-3' | (SEQ ID NO: 973)<br>(SEQ ID NO: 2082)<br>(SEQ ID NO: 3191) |
| βc-m2731 Target: | 5'-AGAAACUUCCACACAUGAACAUCtc-3'<br>3'-ACUCUUUGAAGGUGUGUACUUGUAGAG-5'<br>5'-TGAGAAACTTCCACACATGAACATCTC-3' | (SEQ ID NO: 974)<br>(SEQ ID NO: 2083)<br>(SEQ ID NO: 3192) |
| βc-m2739 Target: | 5'-UCAACGUGAGAAACUUCCACACAtg-3'<br>3'-GUAGUUGCACUCUUUGAAGGUGUGUAC-5'<br>5'-CATCAACGTGAGAAACTTCCACACATG-3' | (SEQ ID NO: 975)<br>(SEQ ID NO: 2084)<br>(SEQ ID NO: 3193) |
| βc-m2742 Target: | 5'-ACAUCAACGUGAGAAACUUCCACac-3'<br>3'-UUUGUAGUUGCACUCUUUGAAGGUGUG-5'<br>5'-AAACATCAACGTGAGAAACTTCCACAC-3' | (SEQ ID NO: 976)<br>(SEQ ID NO: 2085)<br>(SEQ ID NO: 3194) |
| βc-m2743 Target: | 5'-AACAUCAACGUGAGAAACUUCCAca-3'<br>3'-UUUUGUAGUUGCACUCUUUGAAGGUGU-5'<br>5'-AAAACATCAACGTGAGAAACTTCCACA-3' | (SEQ ID NO: 977)<br>(SEQ ID NO: 2086)<br>(SEQ ID NO: 3195) |
| βc-m2744 Target: | 5'-AAACAUCAACGUGAGAAACUUCCac-3'<br>3'-UUUUUGUAGUUGCACUCUUUGAAGGUG-5'<br>5'-AAAAACATCAACGTGAGAAACTTCCAC-3' | (SEQ ID NO: 978)<br>(SEQ ID NO: 2087)<br>(SEQ ID NO: 3196) |
| βc-m2745 Target: | 5'-AAAACAUCAACGUGAGAAACUUCca-3'<br>3'-GUUUUUGUAGUUGCACUCUUUGAAGGU-5'<br>5'-CAAAAACATCAACGTGAGAAACTTCCA-3' | (SEQ ID NO: 979)<br>(SEQ ID NO: 2088)<br>(SEQ ID NO: 3197) |
| βc-m2746 Target: | 5'-AAAAACAUCAACGUGAGAAACUUcc-3'<br>3'-CGUUUUUGUAGUUGCACUCUUUGAAGG-5'<br>5'-GCAAAAACATCAACGTGAGAAACTTCC-3' | (SEQ ID NO: 980)<br>(SEQ ID NO: 2089)<br>(SEQ ID NO: 3198) |
| βc-m2748 Target: | 5'-GCAAAAACAUCAACGUGAGAAACtt-3'<br>3'-ACCGUUUUUGUAGUUGCACUCUUUGAA-5'<br>5'-TGGCAAAAACATCAACGTGAGAAACTT-3' | (SEQ ID NO: 981)<br>(SEQ ID NO: 2090)<br>(SEQ ID NO: 3199) |
| βc-m2760 Target: | 5'-GCAAAAGCUGUGGCAAAAACAUCaa-3'<br>3'-GACGUUUUCGACACCGUUUUUGUAGUU-5'<br>5'-CTGCAAAAGCTGTGGCAAAAACATCAA-3' | (SEQ ID NO: 982)<br>(SEQ ID NO: 2091)<br>(SEQ ID NO: 3200) |
| βc-m2761 Target: | 5'-UGCAAAAGCUGUGGCAAAAACAUca-3'<br>3'-CGACGUUUUCGACACCGUUUUUGUAGU-5'<br>5'-GCTGCAAAAGCTGTGGCAAAAACATCA-3' | (SEQ ID NO: 983)<br>(SEQ ID NO: 2092)<br>(SEQ ID NO: 3201) |
| βc-m2778 Target: | 5'-UCAUCUGAGUAUAACGCUGCAAAag-3'<br>3'-UGAGUAGACUCAUAUUGCGACGUUUUC-5'<br>5'-ACTCATCTGAGTATAACGCTGCAAAAG-3' | (SEQ ID NO: 984)<br>(SEQ ID NO: 2093)<br>(SEQ ID NO: 3202) |
| βc-m2795 Target: | 5'-AAAACAGCAAAUGUUACUCAUCUga-3'<br>3'-ACUUUUGUCGUUUACAAUGAGUAGACU-5'<br>5'-TGAAAACAGCAAATGTTACTCATCTGA-3' | (SEQ ID NO: 985)<br>(SEQ ID NO: 2094)<br>(SEQ ID NO: 3203) |

TABLE 9-continued

Additional Selected Anti-β-catenin DsiRNAs, 25/27mer Duplexes

| | | |
|---|---|---|
| βc-m2796 | 5'-GAAAACAGCAAAUGUUACUCAUCtg-3'<br>3'-AACUUUUGUCGUUUACAAUGAGUAGAC-5'<br>Target: 5'-TTGAAAACAGCAAATGTTACTCATCTG-3' | (SEQ ID NO: 986)<br>(SEQ ID NO: 2095)<br>(SEQ ID NO: 3204) |
| βc-m2797 | 5'-UGAAAACAGCAAAUGUUACUCAUct-3'<br>3'-CAACUUUUGUCGUUUACAAUGAGUAGA-5'<br>Target: 5'-GTTGAAAACAGCAAATGTTACTCATCT-3' | (SEQ ID NO: 987)<br>(SEQ ID NO: 2096)<br>(SEQ ID NO: 3205) |
| βc-m2805 | 5'-AUUAAUGUUGAAAACAGCAAAUGtt-3'<br>3'-GAUAAUUACAACUUUUGUCGUUUACAA-5'<br>Target: 5'-CTATTAATGTTGAAAACAGCAAATGTT-3' | (SEQ ID NO: 988)<br>(SEQ ID NO: 2097)<br>(SEQ ID NO: 3206) |
| βc-m2834 | 5'-ACUACAGCUGUAUAGAGAGAAAGgc-3'<br>3'-UGUGAUGUCGACAUAUCUCUCUUUCCG-5'<br>Target: 5'-ACACTACAGCTGTATAGAGAGAAAGGC-3' | (SEQ ID NO: 989)<br>(SEQ ID NO: 2098)<br>(SEQ ID NO: 3207) |
| βc-m2859 | 5'-GGCCAAUCACAAUGCACGUUCAGac-3'<br>3'-GUCCGGUUAGUGUUACGUGCAAGUCUG-5'<br>Target: 5'-CAGGCCAATCACAATGCACGTTCAGAC-3' | (SEQ ID NO: 990)<br>(SEQ ID NO: 2099)<br>(SEQ ID NO: 3208) |
| βc-m2946 | 5'-GUUCCCAUAGGAAACUCAGCUUGgt-3'<br>3'-GACAAGGGUAUCCUUUGAGUCGAACCA-5'<br>Target: 5'-CTGTTCCCATAGGAAACTCAGCTTGGT-3' | (SEQ ID NO: 991)<br>(SEQ ID NO: 2100)<br>(SEQ ID NO: 3209) |
| βc-m2968 | 5'-GAACAAAAAGCGUACUUCGACUGtt-3'<br>3'-GUCUUGUUUUUCGCAUGAAGCUGACAA-5'<br>Target: 5'-CAGAACAAAAAGCGTACTTCGACTGTT-3' | (SEQ ID NO: 992)<br>(SEQ ID NO: 2101)<br>(SEQ ID NO: 3210) |
| βc-m2974 | 5'-GGACCAGAACAAAAAGCGUACUUcg-3'<br>3'-UUCCUGGUCUUGUUUUUCGCAUGAAGC-5'<br>Target: 5'-AAGGACCAGAACAAAAAGCGTACTTCG-3' | (SEQ ID NO: 993)<br>(SEQ ID NO: 2102)<br>(SEQ ID NO: 3211) |
| βc-m2982 | 5'-ACCAAAAAGGACCAGAACAAAAAgc-3'<br>3'-GCUGGUUUUUCCUGGUCUUGUUUUUCG-5'<br>Target: 5'-CGACCAAAAAGGACCAGAACAAAAAGC-3' | (SEQ ID NO: 994)<br>(SEQ ID NO: 2103)<br>(SEQ ID NO: 3212) |
| βc-m2983 | 5'-GACCAAAAAGGACCAGAACAAAAag-3'<br>3'-AGCUGGUUUUUCCUGGUCUUGUUUUUC-5'<br>Target: 5'-TCGACCAAAAAGGACCAGAACAAAAAG-3' | (SEQ ID NO: 995)<br>(SEQ ID NO: 2104)<br>(SEQ ID NO: 3213) |
| βc-m2990 | 5'-ACUCCUCGACCAAAAAGGACCAGaa-3'<br>3'-AAUGAGGAGCUGGUUUUUCCUGGUCUU-5'<br>Target: 5'-TTACTCCTCGACCAAAAAGGACCAGAA-3' | (SEQ ID NO: 996)<br>(SEQ ID NO: 2105)<br>(SEQ ID NO: 3214) |
| βc-m3005 | 5'-UCCAUUUGUAUUGUUACUCCUCGac-3'<br>3'-UUAGGUAAACAUAACAAUGAGGAGCUG-5'<br>Target: 5'-AATCCATTTGTATTGTTACTCCTCGAC-3' | (SEQ ID NO: 997)<br>(SEQ ID NO: 2106)<br>(SEQ ID NO: 3215) |
| βc-m3006 | 5'-AUCCAUUUGUAUUGUUACUCCUCga-3'<br>3'-UUUAGGUAAACAUAACAAUGAGGAGCU-5'<br>Target: 5'-AAATCCATTTGTATTGTTACTCCTCGA-3' | (SEQ ID NO: 998)<br>(SEQ ID NO: 2107)<br>(SEQ ID NO: 3216) |
| βc-m3007 | 5'-AAUCCAUUUGUAUUGUUACUCCUcg-3'<br>3'-GUUUAGGUAAACAUAACAAUGAGGAGC-5'<br>Target: 5'-CAAATCCATTTGTATTGTTACTCCTCG-3' | (SEQ ID NO: 999)<br>(SEQ ID NO: 2108)<br>(SEQ ID NO: 3217) |
| βc-m3008 | 5'-AAAUCCAUUUGUAUUGUUACUCCtc-3'<br>3'-GGUUUAGGUAAACAUAACAAUGAGGAG-5'<br>Target: 5'-CCAAATCCATTTGTATTGTTACTCCTC-3' | (SEQ ID NO: 1000)<br>(SEQ ID NO: 2109)<br>(SEQ ID NO: 3218) |
| βc-m3015 | 5'-ACUCCCCAAAUCCAUUUGUAUUGtt-3'<br>3'-AGUGAGGGGUUUAGGUAAACAUAACAA-5'<br>Target: 5'-TCACTCCCCAAATCCATTTGTATTGTT-3' | (SEQ ID NO: 1001)<br>(SEQ ID NO: 2110)<br>(SEQ ID NO: 3219) |
| βc-m3047 | 5'-UCCAUUCGUGUGCAUUCUUCACUgc-3'<br>3'-CUAGGUAAGCACACGUAAGAAGUGACG-5'<br>Target: 5'-GATCCATTCGTGTGCATTCTTCACTGC-3' | (SEQ ID NO: 1002)<br>(SEQ ID NO: 2111)<br>(SEQ ID NO: 3220) |
| βc-m3048 | 5'-AUCCAUUCGUGUGCAUUCUUCACtg-3'<br>3'-ACUAGGUAAGCACACGUAAGAAGUGAC-5'<br>Target: 5'-TGATCCATTCGTGTGCATTCTTCACTG-3' | (SEQ ID NO: 1003)<br>(SEQ ID NO: 2112)<br>(SEQ ID NO: 3221) |
| βc-m3049 | 5'-GAUCCAUUCGUGUGCAUUCUUCAct-3'<br>3'-CACUAGGUAAGCACACGUAAGAAGUGA-5'<br>Target: 5'-GTGATCCATTCGTGTGCATTCTTCACT-3' | (SEQ ID NO: 1004)<br>(SEQ ID NO: 2113)<br>(SEQ ID NO: 3222) |

TABLE 9-continued

Additional Selected Anti-β-catenin DsiRNAs, 25/27mer Duplexes

| | | |
|---|---|---|
| βc-m3093 Target: | 5'-AAACAAAGAACAAGCAAGGCUAGgg-3'<br>3'-AUUUUGUUUCUUGUUCGUUCCGAUCCC-5'<br>5'-TAAAACAAAGAACAAGCAAGGCTAGGG-3' | (SEQ ID NO: 1005)<br>(SEQ ID NO: 2114)<br>(SEQ ID NO: 3223) |
| βc-m3109 Target: | 5'-ACCACUACAGAUAUUAAAACAAAga-3'<br>3'-CGUGGUGAUGUCUAUAAUUUUGUUUCU-5'<br>5'-GCACCACTACAGATATTAAAACAAAGA-3' | (SEQ ID NO: 1006)<br>(SEQ ID NO: 2115)<br>(SEQ ID NO: 3224) |
| βc-m3111 Target: | 5'-GCACCACUACAGAUAUUAAAACAaa-3'<br>3'-GUCGUGGUGAUGUCUAUAAUUUUGUUU-5'<br>5'-CAGCACCACTACAGATATTAAAACAAA-3' | (SEQ ID NO: 1007)<br>(SEQ ID NO: 2116)<br>(SEQ ID NO: 3225) |
| βc-m3112 Target: | 5'-AGCACCACUACAGAUAUUAAAACaa-3'<br>3'-AGUCGUGGUGAUGUCUAUAAUUUUGUU-5'<br>5'-TCAGCACCACTACAGATATTAAAACAA-3' | (SEQ ID NO: 1008)<br>(SEQ ID NO: 2117)<br>(SEQ ID NO: 3226) |
| βc-m3133 Target: | 5'-AAAAUAAAAGCAAGCAAAGUCAGca-3'<br>3'-UUUUUUAUUUUCGUUCGUUUCAGUCGU-5'<br>5'-AAAAAATAAAAGCAAGCAAAGTCAGCA-3' | (SEQ ID NO: 1009)<br>(SEQ ID NO: 2118)<br>(SEQ ID NO: 3227) |
| βc-m3137 Target: | 5'-GCAAAAAAUAAAAGCAAGCAAAGtc-3'<br>3'-GACGUUUUUUAUUUUCGUUCGUUUCAG-5'<br>5'-CTGCAAAAAATAAAAGCAAGCAAAGTC-3' | (SEQ ID NO: 1010)<br>(SEQ ID NO: 2119)<br>(SEQ ID NO: 3228) |
| βc-m3142 Target: | 5'-UUACUGCAAAAAAUAAAAGCAAGca-3'<br>3'-UCAAUGACGUUUUUUAUUUUCGUUCGU-5'<br>5'-AGTTACTGCAAAAAATAAAAGCAAGCA-3' | (SEQ ID NO: 1011)<br>(SEQ ID NO: 2120)<br>(SEQ ID NO: 3229) |
| βc-m3148 Target: | 5'-UAACAGUUACUGCAAAAAAUAAAag-3'<br>3'-UGAUUGUCAAUGACGUUUUUUAUUUUC-5'<br>5'-ACTAACAGTTACTGCAAAAAATAAAG-3' | (SEQ ID NO: 1012)<br>(SEQ ID NO: 2121)<br>(SEQ ID NO: 3230) |
| βc-m3150 Target: | 5'-ACUAACAGUUACUGCAAAAAAUAaa-3'<br>3'-UUUGAUUGUCAAUGACGUUUUUUAUUU-5'<br>5'-AAACTAACAGTTACTGCAAAAAATAAA-3' | (SEQ ID NO: 1013)<br>(SEQ ID NO: 2122)<br>(SEQ ID NO: 3231) |
| βc-m3152 Target: | 5'-AAACUAACAGUUACUGCAAAAAAta-3'<br>3'-UUUUUGAUUGUCAAUGACGUUUUUUAU-5'<br>5'-AAAAACTAACAGTTACTGCAAAAAATA-3' | (SEQ ID NO: 1014)<br>(SEQ ID NO: 2123)<br>(SEQ ID NO: 3232) |
| βc-m3153 Target: | 5'-AAAACUAACAGUUACUGCAAAAAat-3'<br>3'-AUUUUUGAUUGUCAAUGACGUUUUUUA-5'<br>5'-TAAAAACTAACAGTTACTGCAAAAAAT-3' | (SEQ ID NO: 1015)<br>(SEQ ID NO: 2124)<br>(SEQ ID NO: 3233) |
| βc-m3155 Target: | 5'-UAAAACUAACAGUUACUGCAAAaa-3'<br>3'-GAAUUUUUGAUUGUCAAUGACGUUUUU-5'<br>5'-CTTAAAAACTAACAGTTACTGCAAAAA-3' | (SEQ ID NO: 1016)<br>(SEQ ID NO: 2125)<br>(SEQ ID NO: 3234) |
| βc-m3159 Target: | 5'-UACUUAAAAACUAACAGUUACUGca-3'<br>3'-UGAUGAAUUUUUGAUUGUCAAUGACGU-5'<br>5'-ACTACTTAAAAACTAACAGTTACTGCA-3' | (SEQ ID NO: 1017)<br>(SEQ ID NO: 2126)<br>(SEQ ID NO: 3235) |
| βc-m3161 Target: | 5'-ACUACUUAAAAACUAACAGUUACtg-3'<br>3'-UGUGAUGAAUUUUUGAUUGUCAAUGAC-5'<br>5'-ACACTACTTAAAAACTAACAGTTACTG-3' | (SEQ ID NO: 1018)<br>(SEQ ID NO: 2127)<br>(SEQ ID NO: 3236) |
| βc-m3165 Target: | 5'-UAACACUACUUAAAAACUAACAGtt-3'<br>3'-GUAUUGUGAUGAAUUUUUGAUUGUCAA-5'<br>5'-CATAACACTACTTAAAAACTAACAGTT-3' | (SEQ ID NO: 1019)<br>(SEQ ID NO: 2128)<br>(SEQ ID NO: 3237) |
| βc-m3166 Target: | 5'-AUAACACUACUUAAAAACUAACAgt-3'<br>3'-UGUAUUGUGAUGAAUUUUUGAUUGUCA-5'<br>5'-ACATAACACTACTTAAAAACTAACAGT-3' | (SEQ ID NO: 1020)<br>(SEQ ID NO: 2129)<br>(SEQ ID NO: 3238) |
| βc-m3168 Target: | 5'-ACAUAACACUACUUAAAAACUAAca-3'<br>3'-CUUGUAUUGUGAUGAAUUUUUGAUUGU-5'<br>5'-GAACATAACACTACTTAAAAACTAACA-3' | (SEQ ID NO: 1021)<br>(SEQ ID NO: 2130)<br>(SEQ ID NO: 3239) |
| βc-m3169 Target: | 5'-AACAUAACACUACUUAAAAACUAac-3'<br>3'-UCUUGUAUUGUGAUGAAUUUUUGAUUG-5'<br>5'-AGAACATAACACTACTTAAAAACTAAC-3' | (SEQ ID NO: 1022)<br>(SEQ ID NO: 2131)<br>(SEQ ID NO: 3240) |
| βc-m3170 Target: | 5'-GAACAUAACACUACUUAAAAACUaa-3'<br>3'-AUCUUGUAUUGUGAUGAAUUUUUGAUU-5'<br>5'-TAGAACATAACACTACTTAAAAACTAA-3' | (SEQ ID NO: 1023)<br>(SEQ ID NO: 2132)<br>(SEQ ID NO: 3241) |

TABLE 9-continued

Additional Selected Anti-β-catenin DsiRNAs, 25/27mer Duplexes

| | | |
|---|---|---|
| βc-m3171 Target: | 5'-AGAACAUAACACUACUUAAAAACta-3'<br>3'-GAUCUUGUAUUGUGAUGAAUUUUUGAU-5'<br>5'-CTAGAACATAACACTACTTAAAAACTA-3' | (SEQ ID NO: 1024)<br>(SEQ ID NO: 2133)<br>(SEQ ID NO: 3242) |
| βc-m3176 Target: | 5'-UCACUAGAACAUAACACUACUUAaa-3'<br>3'-CAAGUGAUCUUGUAUUGUGAUGAAUUU-5'<br>5'-GTTCACTAGAACATAACACTACTTAAA-3' | (SEQ ID NO: 1025)<br>(SEQ ID NO: 2134)<br>(SEQ ID NO: 3243) |
| βc-m3178 Target: | 5'-GUUCACUAGAACAUAACACUACUta-3'<br>3'-UCCAAGUGAUCUUGUAUUGUGAUGAAU-5'<br>5'-AGGTTCACTAGAACATAACACTACTTA-3' | (SEQ ID NO: 1026)<br>(SEQ ID NO: 2135)<br>(SEQ ID NO: 3244) |
| βc-m3179 Target: | 5'-GGUUCACUAGAACAUAACACUACUtt-3'<br>3'-GUCCAAGUGAUCUUGUAUUGUGAUGAA-5'<br>5'-CAGGTTCACTAGAACATAACACTACTT-3' | (SEQ ID NO: 1027)<br>(SEQ ID NO: 2136)<br>(SEQ ID NO: 3245) |
| βc-m3216 Target: | 5'-AUUACUCGGUUCUUAGAAAUCAGaa-3'<br>3'-GGUAAUGAGCCAAGAAUCUUUAGUCUU-5'<br>5'-CCATTACTCGGTTCTTAGAAATCAGAA-3' | (SEQ ID NO: 1028)<br>(SEQ ID NO: 2137)<br>(SEQ ID NO: 3246) |
| βc-m3219 Target: | 5'-ACCAUUACUCGGUUCUUAGAAAUca-3'<br>3'-UGUGGUAAUGAGCCAAGAAUCUUUAGU-5'<br>5'-ACACCATTACTCGGTTCTTAGAAATCA-3' | (SEQ ID NO: 1029)<br>(SEQ ID NO: 2138)<br>(SEQ ID NO: 3247) |
| βc-m3224 Target: | 5'-UCUACACCAUUACUCGGUUCUUAga-3'<br>3'-CAAGAUGUGGUAAUGAGCCAAGAAUCU-5'<br>5'-GTTCTACACCATTACTCGGTTCTTAGA-3' | (SEQ ID NO: 1030)<br>(SEQ ID NO: 2139)<br>(SEQ ID NO: 3248) |
| βc-m3234 Target: | 5'-GAAUUAGUGUUCUACACCAUUACtc-3'<br>3'-UACUUAAUCACAAGAUGUGGUAAUGAG-5'<br>5'-ATGAATTAGTGTTCTACACCATTACTC-3' | (SEQ ID NO: 1031)<br>(SEQ ID NO: 2140)<br>(SEQ ID NO: 3249) |
| βc-m3239 Target: | 5'-AUUAUGAAUUAGUGUUCUACACCat-3'<br>3'-ACUAAUACUUAAUCACAAGAUGUGGUA-5'<br>5'-TGATTATGAATTAGTGTTCTACACC-3' | (SEQ ID NO: 1032)<br>(SEQ ID NO: 2141)<br>(SEQ ID NO: 3250) |
| βc-m3240 Target: | 5'-GAUUAUGAAUUAGUGUUCUACACca-3'<br>3'-CACUAAUACUUAAUCACAAGAUGUGGU-5'<br>5'-GTGATTATGAATTAGTGTTCTACACCA-3' | (SEQ ID NO: 1033)<br>(SEQ ID NO: 2142)<br>(SEQ ID NO: 3251) |
| βc-m3241 Target: | 5'-UGAUUAUGAAUUAGUGUUCUACAcc-3'<br>3'-GCACUAAUACUUAAUCACAAGAUGUGG-5'<br>5'-CGTGATTATGAATTAGTGTTCTACACC-3' | (SEQ ID NO: 1034)<br>(SEQ ID NO: 2143)<br>(SEQ ID NO: 3252) |
| βc-m3251 Target: | 5'-ACAAUUAGCGUGAUUAUGAAUUAgt-3'<br>3'-AAUGUUAAUCGCACUAAUACUUAAUCA-5'<br>5'-TTACAATTAGCGTGATTATGAATTAGT-3' | (SEQ ID NO: 1035)<br>(SEQ ID NO: 2144)<br>(SEQ ID NO: 3253) |
| βc-m3252 Target: | 5'-UACAAUUAGCGUGAUUAUGAAUUag-3'<br>3'-UAAUGUUAAUCGCACUAAUACUUAAUC-5'<br>5'-ATTACAATTAGCGTGATTATGAATTAG-3' | (SEQ ID NO: 1036)<br>(SEQ ID NO: 2145)<br>(SEQ ID NO: 3254) |
| βc-m3256 Target: | 5'-AGAUUACAAUUAGCGUGAUUAUGaa-3'<br>3'-GGUCUAAUGUUAAUCGCACUAAUACUU-5'<br>5'-CCAGATTACAATTAGCGTGATTATGAA-3' | (SEQ ID NO: 1037)<br>(SEQ ID NO: 2146)<br>(SEQ ID NO: 3255) |
| βc-m3267 Target: | 5'-UACACGUCUCCAGAUUACAAUUAgc-3'<br>3'-CAAUGUGCAGAGGUCUAAUGUUAAUCG-5'<br>5'-GTTACACGTCTCCAGATTACAATTAGC-3' | (SEQ ID NO: 1038)<br>(SEQ ID NO: 2147)<br>(SEQ ID NO: 3256) |
| βc-m3269 Target: | 5'-GUUACACGUCUCCAGAUUACAAUta-3'<br>3'-UACAAUGUGCAGAGGUCUAAUGUUAAU-5'<br>5'-ATGTTACACGTCTCCAGATTACAATTA-3' | (SEQ ID NO: 1039)<br>(SEQ ID NO: 2148)<br>(SEQ ID NO: 3257) |
| βc-m3277 Target: | 5'-UACACAAUGUUACACGUCUCCAGat-3'<br>3'-CGAUGUGUUACAAUGUGCAGAGGUCUA-5'<br>5'-GCTACACAATGTTACACGTCTCCAGAT-3' | (SEQ ID NO: 1040)<br>(SEQ ID NO: 2149)<br>(SEQ ID NO: 3258) |
| βc-m3279 Target: | 5'-GCUACACAAUGUUACACGUCUCCag-3'<br>3'-UCCGAUGUGUUACAAUGUGCAGAGGUC-5'<br>5'-AGGCTACACAATGTTACACGTCTCCAG-3' | (SEQ ID NO: 1041)<br>(SEQ ID NO: 2150)<br>(SEQ ID NO: 3259) |
| βc-m3286 Target: | 5'-ACAAAAGGCUACACAAUGUUACAcg-3'<br>3'-UAUGUUUUCCGAUGUGUUACAAUGUGC-5'<br>5'-ATACAAAAGGCTACACAATGTTACACG-3' | (SEQ ID NO: 1042)<br>(SEQ ID NO: 2151)<br>(SEQ ID NO: 3260) |

TABLE 9-continued

Additional Selected Anti-β-catenin DsiRNAs, 25/27mer Duplexes

|  |  |  |
| --- | --- | --- |
| βc-m3287 Target: | 5'-UACAAAAGGCUACACAAUGUUACac-3'<br>3'-AUAUGUUUUCCGAUGUGUUACAAUGUG-5'<br>5'-TATACAAAAGGCTACACAATGTTACAC-3' | (SEQ ID NO: 1043)<br>(SEQ ID NO: 2152)<br>(SEQ ID NO: 3261) |
| βc-m3291 Target: | 5'-UUUAUACAAAAGGCUACACAAUGtt-3'<br>3'-AUAAAUAUGUUUUCCGAUGUGUUACAA-5'<br>5'-TATTTATACAAAAGGCTACACAATGTT-3' | (SEQ ID NO: 1044)<br>(SEQ ID NO: 2153)<br>(SEQ ID NO: 3262) |
| βc-m3292 Target: | 5'-AUUUAUACAAAAGGCUACACAAUgt-3'<br>3'-GAUAAAUAUGUUUUCCGAUGUGUUACA-5'<br>5'-CTATTTATACAAAAGGCTACACAATGT-3' | (SEQ ID NO: 1045)<br>(SEQ ID NO: 2154)<br>(SEQ ID NO: 3263) |
| βc-m3295 Target: | 5'-UCUAUUUAUACAAAAGGCUACACaa-3'<br>3'-ACAGAUAAAUAUGUUUUCCGAUGUGUU-5'<br>5'-TGTCTATTTATACAAAAGGCTACACAA-3' | (SEQ ID NO: 1046)<br>(SEQ ID NO: 2155)<br>(SEQ ID NO: 3264) |
| βc-m3296 Target: | 5'-GUCUAUUUAUACAAAAGGCUACAca-3'<br>3'-GACAGAUAAAUAUGUUUUCCGAUGUGU-5'<br>5'-CTGTCTATTTATACAAAAGGCTACACA-3' | (SEQ ID NO: 1047)<br>(SEQ ID NO: 2156)<br>(SEQ ID NO: 3265) |
| βc-m3297 Target: | 5'-UGUCUAUUUAUACAAAAGGCUACac-3'<br>3'-AGACAGAUAAAUAUGUUUUCCGAUGUG-5'<br>5'-TCTGTCTATTTATACAAAAGGCTACAC-3' | (SEQ ID NO: 1048)<br>(SEQ ID NO: 2157)<br>(SEQ ID NO: 3266) |
| βc-m3303 Target: | 5'-UCUAUCUGUCUAUUUAUACAAAAgg-3'<br>3'-AAAGAUAGACAGAUAAAUAUGUUUUCC-5'<br>5'-TTTCTATCTGTCTATTTATACAAAAGG-3' | (SEQ ID NO: 1049)<br>(SEQ ID NO: 2158)<br>(SEQ ID NO: 3267) |
| βc-m3304 Target: | 5'-UUCUAUCUGUCUAUUUAUACAAAag-3'<br>3'-UAAAGAUAGACAGAUAAAUAUGUUUUC-5'<br>5'-ATTTCTATCTGTCTATTTATACAAAAG-3' | (SEQ ID NO: 1050)<br>(SEQ ID NO: 2159)<br>(SEQ ID NO: 3268) |
| βc-m3305 Target: | 5'-UUUCUAUCUGUCUAUUUAUACAAaa-3'<br>3'-GUAAAGAUAGACAGAUAAAUAUGUUUU-5'<br>5'-CATTTCTATCTGTCTATTTATACAAAA-3' | (SEQ ID NO: 1051)<br>(SEQ ID NO: 2160)<br>(SEQ ID NO: 3269) |
| βc-m3306 Target: | 5'-AUUUCUAUCUGUCUAUUUAUACAaa-3'<br>3'-GGUAAAGAUAGACAGAUAAAUAUGUUU-5'<br>5'-CCATTTCTATCTGTCTATTTATACAAA-3' | (SEQ ID NO: 1052)<br>(SEQ ID NO: 2161)<br>(SEQ ID NO: 3270) |
| βc-m3310 Target: | 5'-GACCAUUUCUAUCUGUCUAUUUAta-3'<br>3'-GCCUGGUAAAGAUAGACAGAUAAAUAU-5'<br>5'-CGGACCATTTCTATCTGTCTATTTATA-3' | (SEQ ID NO: 1053)<br>(SEQ ID NO: 2162)<br>(SEQ ID NO: 3271) |
| βc-m3311 Target: | 5'-GGACCAUUUCUAUCUGUCUAUUUat-3'<br>3'-AGCCUGGUAAAGAUAGACAGAUAAAUA-5'<br>5'-TCGGACCATTTCTATCTGTCTATTTAT-3' | (SEQ ID NO: 1054)<br>(SEQ ID NO: 2163)<br>(SEQ ID NO: 3272) |
| βc-m3318 Target: | 5'-ACUAAUCGGACCAUUUCUAUCUGtc-3'<br>3'-UUUGAUUAGCCUGGUAAAGAUAGACAG-5'<br>5'-AAACTAATCGGACCATTTCTATCTGTC-3' | (SEQ ID NO: 1055)<br>(SEQ ID NO: 2164)<br>(SEQ ID NO: 3273) |
| βc-m3319 Target: | 5'-AACUAAUCGGACCAUUUCUAUCUgt-3'<br>3'-CUUUGAUUAGCCUGGUAAAGAUAGACA-5'<br>5'-GAAACTAATCGGACCATTTCTATCTGT-3' | (SEQ ID NO: 1056)<br>(SEQ ID NO: 2165)<br>(SEQ ID NO: 3274) |
| βc-m3320 Target: | 5'-AAACUAAUCGGACCAUUUCUAUCtg-3'<br>3'-CCUUUGAUUAGCCUGGUAAAGAUAGAC-5'<br>5'-GGAAACTAATCGGACCATTTCTATCTG-3' | (SEQ ID NO: 1057)<br>(SEQ ID NO: 2166)<br>(SEQ ID NO: 3275) |
| βc-m3321 Target: | 5'-GAAACUAAUCGGACCAUUUCUAUct-3'<br>3'-UCCUUUGAUUAGCCUGGUAAAGAUAGA-5'<br>5'-AGGAAACTAATCGGACCATTTCTATCT-3' | (SEQ ID NO: 1058)<br>(SEQ ID NO: 2167)<br>(SEQ ID NO: 3276) |
| βc-m3328 Target: | 5'-UAAAAGGAAACUAAUCGGACCAtt-3'<br>3'-UAAUUUUCCUUUGAUUAGCCUGGUAA-5'<br>5'-ATTAAAAGGAAACTAATCGGACCATT-3' | (SEQ ID NO: 1059)<br>(SEQ ID NO: 2168)<br>(SEQ ID NO: 3277) |
| βc-m3334 Target: | 5'-GCAUAUUAAAAGGAAACUAAUCgg-3'<br>3'-UUCGUAUAAUUUUCCUUUGAUUAGCC-5'<br>5'-AAGCATATTAAAAGGAAACTAATCGG-3' | (SEQ ID NO: 1060)<br>(SEQ ID NO: 2169)<br>(SEQ ID NO: 3278) |
| βc-m3335 Target: | 5'-AGCAUAUUAAAAGGAAACUAAUcg-3'<br>3'-AUUCGUAUAAUUUUCCUUUGAUUAGC-5'<br>5'-TAAGCATATTAAAAGGAAACTAATCG-3' | (SEQ ID NO: 1061)<br>(SEQ ID NO: 2170)<br>(SEQ ID NO: 3279) |

TABLE 9-continued

Additional Selected Anti-β-catenin DsiRNAs, 25/27mer Duplexes

| | | |
|---|---|---|
| βc-m3339 Target: | 5'-UUUAAGCAUAUUAAAAAGGAAACta-3'<br>3'-UAAAAUUCGUAUAAUUUUUCCUUUGAU-5'<br>5'-ATTTTAAGCATATTAAAAAGGAAACTA-3' | (SEQ ID NO: 1062)<br>(SEQ ID NO: 2171)<br>(SEQ ID NO: 3280) |
| βc-m3345 Target: | 5'-GCUUAUUUUAAGCAUAUUAAAAgg-3'<br>3'-GACGAAUAAAAUUCGUAUAAUUUUUCC-5'<br>5'-CTGCTTATTTTAAGCATATTAAAAAGG-3' | (SEQ ID NO: 1063)<br>(SEQ ID NO: 2172)<br>(SEQ ID NO: 3281) |
| βc-m3346 Target: | 5'-UGCUUAUUUUAAGCAUAUUAAAAag-3'<br>3'-GGACGAAUAAAAUUCGUAUAAUUUUUC-5'<br>5'-CCTGCTTATTTTAAGCATATTAAAAAG-3' | (SEQ ID NO: 1064)<br>(SEQ ID NO: 2173)<br>(SEQ ID NO: 3282) |
| βc-m3352 Target: | 5'-UCCACCUGCUUAUUUUAAGCAUAtt-3'<br>3'-CUAGGUGGACGAAUAAAAUUCGUAUAA-5'<br>5'-GATCCACCTGCTTATTTTAAGCATATT-3' | (SEQ ID NO: 1065)<br>(SEQ ID NO: 2174)<br>(SEQ ID NO: 3283) |
| βc-m3367 Target: | 5'-AAAACAUGAAAUAGAUCCACCUGct-3'<br>3'-GUUUUUGUACUUUAUCUAGGUGGACGA-5'<br>5'-CAAAAACATGAAATAGATCCACCTGCT-3' | (SEQ ID NO: 1066)<br>(SEQ ID NO: 2175)<br>(SEQ ID NO: 3284) |
| βc-m3368 Target: | 5'-AAAACAUGAAAUAGAUCCACCUgc-3'<br>3'-AGUUUUUGUACUUUAUCUAGGUGGACG-5'<br>5'-TCAAAAACATGAAATAGATCCACCTGC-3' | (SEQ ID NO: 1067)<br>(SEQ ID NO: 2176)<br>(SEQ ID NO: 3285) |
| βc-m3370 Target: | 5'-UCAAAAACAUGAAAUAGAUCCACct-3'<br>3'-CAAGUUUUUGUACUUUAUCUAGGUGGA-5'<br>5'-GTTCAAAAACATGAAATAGATCCACCT-3' | (SEQ ID NO: 1068)<br>(SEQ ID NO: 2177)<br>(SEQ ID NO: 3286) |
| βc-m3371 Target: | 5'-UUCAAAAACAUGAAAUAGAUCCAcc-3'<br>3'-ACAAGUUUUUGUACUUUAUCUAGGUGG-5'<br>5'-TGTTCAAAAACATGAAATAGATCCACC-3' | (SEQ ID NO: 1069)<br>(SEQ ID NO: 2178)<br>(SEQ ID NO: 3287) |
| βc-m3372 Target: | 5'-GUUCAAAAACAUGAAAUAGAUCCac-3'<br>3'-AACAAGUUUUUGUACUUUAUCUAGGUG-5'<br>5'-TTGTTCAAAAACATGAAATAGATCCAC-3' | (SEQ ID NO: 1070)<br>(SEQ ID NO: 2179)<br>(SEQ ID NO: 3288) |
| βc-m3377 Target: | 5'-UUUUUGUUCAAAAACAUGAAAUAga-3'<br>3'-UCAAAAACAAGUUUUUGUACUUUAUCU-5'<br>5'-AGTTTTTGTTCAAAAACATGAAATAGA-3' | (SEQ ID NO: 1071)<br>(SEQ ID NO: 2180)<br>(SEQ ID NO: 3289) |
| βc-m3383 Target: | 5'-AUAAAGUUUUUGUUCAAAAACAUga-3'<br>3'-GCUAUUUCAAAAACAAGUUUUUGUACU-5'<br>5'-CGATAAAGTTTTTGTTCAAAAACATGA-3' | (SEQ ID NO: 1072)<br>(SEQ ID NO: 2181)<br>(SEQ ID NO: 3290) |
| βc-m3389 Target: | 5'-UCCCCGAUAAAGUUUUUGUUCAAaa-3'<br>3'-AUAGGGGCUAUUUCAAAAACAAGUUUU-5'<br>5'-TATCCCCGATAAAGTTTTTGTTCAAAA-3' | (SEQ ID NO: 1073)<br>(SEQ ID NO: 2182)<br>(SEQ ID NO: 3291) |
| βc-m3390 Target: | 5'-AUCCCCGAUAAAGUUUUUGUUCAaa-3'<br>3'-CAUAGGGGCUAUUUCAAAAACAAGUUU-5'<br>5'-GTATCCCCGATAAAGTTTTTGTTCAAA-3' | (SEQ ID NO: 1074)<br>(SEQ ID NO: 2183)<br>(SEQ ID NO: 3292) |
| βc-m3419 Target: | 5'-ACCUCUUACUGAUUUACCCUACCgc-3'<br>3'-UGUGGAGAAUGACUAAAUGGGAUGGCG-5'<br>5'-ACACCTCTTACTGATTTACCCTACCGC-3' | (SEQ ID NO: 1075)<br>(SEQ ID NO: 2184)<br>(SEQ ID NO: 3293) |
| βc-m3421 Target: | 5'-ACACCUCUUACUGAUUUACCCUAcc-3'<br>3'-AUUGUGGAGAAUGACUAAAUGGGAUGG-5'<br>5'-TAACACCTCTTACTGATTTACCCTACC-3' | (SEQ ID NO: 1076)<br>(SEQ ID NO: 2185)<br>(SEQ ID NO: 3294) |
| βc-m3422 Target: | 5'-AACACCUCUUACUGAUUUACCCUac-3'<br>3'-UAUUGUGGAGAAUGACUAAAUGGGAUG-5'<br>5'-ATAACACCTCTTACTGATTTACCCTAC-3' | (SEQ ID NO: 1077)<br>(SEQ ID NO: 2186)<br>(SEQ ID NO: 3295) |
| βc-m3423 Target: | 5'-UAACACCUCUUACUGAUUUACCCta-3'<br>3'-UUAUUGUGGAGAAUGACUAAAUGGGAU-5'<br>5'-AATAACACCCTCTTACTGATTTACCCTA-3' | (SEQ ID NO: 1078)<br>(SEQ ID NO: 2187)<br>(SEQ ID NO: 3296) |
| βc-m3424 Target: | 5'-AUAACACCUCUUACUGAUUUACCct-3'<br>3'-UUUAUUGUGGAGAAUGACUAAAUGGGA-5'<br>5'-AAATAACACCTCTTACTGATTTACCCT-3' | (SEQ ID NO: 1079)<br>(SEQ ID NO: 2188)<br>(SEQ ID NO: 3297) |
| βc-m3425 Target: | 5'-AAUAACACCUCUUACUGAUUUACcc-3'<br>3'-GUUUAUUGUGGAGAAUGACUAAAUGGG-5'<br>5'-CAAATAACACCTCTTACTGATTTACCC-3' | (SEQ ID NO: 1080)<br>(SEQ ID NO: 2189)<br>(SEQ ID NO: 3298) |

TABLE 9-continued

Additional Selected Anti-β-catenin DsiRNAs, 25/27mer Duplexes

| | | |
|---|---|---|
| | 5'-GGCUCAAAUAACACCUCUUACUGat-3' | (SEQ ID NO: 1081) |
| | 3'-UUCCGAGUUUAUUGUGGAGAAUGACUA-5' | (SEQ ID NO: 2190) |
| βc-m3431 Target: | 5'-AAGGCTCAAATAACACCTCTTACTGAT-3' | (SEQ ID NO: 3299) |
| | 5'-AACAAGGCUCAAAUAACACCUCUta-3' | (SEQ ID NO: 1082) |
| | 3'-UUUUGUUCCGAGUUUAUUGUGGAGAAU-5' | (SEQ ID NO: 2191) |
| βc-m3436 Target: | 5'-AAAACAAGGCTCAAATAACACCTCTTA-3' | (SEQ ID NO: 3300) |
| | 5'-AAACAAGGCUCAAAUAACACCUCtt-3' | (SEQ ID NO: 1083) |
| | 3'-GUUUUGUUCCGAGUUUAUUGUGGAGAA-5' | (SEQ ID NO: 2192) |
| βc-m3437 Target: | 5'-CAAAACAAGGCTCAAATAACACCTCTT-3' | (SEQ ID NO: 3301) |
| | 5'-AAAACAAGGCUCAAAUAACACCUct-3' | (SEQ ID NO: 1084) |
| | 3'-GGUUUUGUUCCGAGUUUAUUGUGGAGA-5' | (SEQ ID NO: 2193) |
| βc-m3438 Target: | 5'-CCAAAACAAGGCTCAAATAACACCTCT-3' | (SEQ ID NO: 3302) |
| | 5'-UCCAAAACAAGGCUCAAAUAACAcc-3' | (SEQ ID NO: 1085) |
| | 3'-ACAGGUUUUGUUCCGAGUUUAUUGUGG-5' | (SEQ ID NO: 2194) |
| βc-m3441 Target: | 5'-TGTCCAAAACAAGGCTCAAATAACACC-3' | (SEQ ID NO: 3303) |
| | 5'-UGUCCAAAACAAGGCUCAAAUAAca-3' | (SEQ ID NO: 1086) |
| | 3'-UGACAGGUUUUGUUCCGAGUUUAUUGU-5' | (SEQ ID NO: 2195) |
| βc-m3443 Target: | 5'-ACTGTCCAAAACAAGGCTCAAATAACA-3' | (SEQ ID NO: 3304) |
| | 5'-UAUACUGUCCAAAACAAGGCUCAaa-3' | (SEQ ID NO: 1087) |
| | 3'-CCAUAUGACAGGUUUUGUUCCGAGUUU-5' | (SEQ ID NO: 2196) |
| βc-m3448 Target: | 5'-GGTATACTGTCCAAAACAAGGCTCAAA-3' | (SEQ ID NO: 3305) |
| | 5'-GCAACUGGUAUACUGUCCAAAACaa-3' | (SEQ ID NO: 1088) |
| | 3'-UCCGUUGACCAUAUGACAGGUUUUGUU-5' | (SEQ ID NO: 2197) |
| βc-m3456 Target: | 5'-AGGCAACTGGTATACTGTCCAAAACAA-3' | (SEQ ID NO: 3306) |
| | 5'-GAUAAAAGGCAACUGGUAUACUGtc-3' | (SEQ ID NO: 1089) |
| | 3'-CCCUAUUUUCCGUUGACCAUAUGACAG-5' | (SEQ ID NO: 2198) |
| βc-m3464 Target: | 5'-GGGATAAAAGGCAACTGGTATACTGTC-3' | (SEQ ID NO: 3307) |
| | 5'-GGAUAAAAGGCAACUGGUAUACUgt-3' | (SEQ ID NO: 1090) |
| | 3'-ACCCUAUUUUCCGUUGACCAUAUGACA-5' | (SEQ ID NO: 2199) |
| βc-m3465 Target: | 5'-TGGGATAAAAGGCAACTGGTATACTGT-3' | (SEQ ID NO: 3308) |
| | 5'-AACUUUGGGAUAAAAGGCAACUGgt-3' | (SEQ ID NO: 1091) |
| | 3'-UGUUGAAACCCUAUUUUCCGUUGACCA-5' | (SEQ ID NO: 2200) |
| βc-m3472 Target: | 5'-ACAACTTTGGGATAAAAGGCAACTGGT-3' | (SEQ ID NO: 3309) |
| | 5'-ACAACUUUGGGAUAAAAGGCAACtg-3' | (SEQ ID NO: 1092) |
| | 3'-GUUGUUGAAACCCUAUUUUCCGUUGAC-5' | (SEQ ID NO: 2201) |
| βc-m3474 Target: | 5'-CAACAACTTTGGGATAAAAGGCAACTG-3' | (SEQ ID NO: 3310) |
| | 5'-UUACAACAACUUUGGGAUAAAAGgc-3' | (SEQ ID NO: 1093) |
| | 3'-CCAAUGUUGUUGAAACCCUAUUUUCCG-5' | (SEQ ID NO: 2202) |
| βc-m3479 Target: | 5'-GGTTACAACAACTTTGGGATAAAAGGC-3' | (SEQ ID NO: 3311) |
| | 5'-GUUACAACAACUUUGGGAUAAAAgg-3' | (SEQ ID NO: 1094) |
| | 3'-UCCAAUGUUGUUGAAACCCUAUUUUCC-5' | (SEQ ID NO: 2203) |
| βc-m3480 Target: | 5'-AGGTTACAACAACTTTGGGATAAAAGG-3' | (SEQ ID NO: 3312) |
| | 5'-GGUUACAACAACUUUGGGAUAAAag-3' | (SEQ ID NO: 1095) |
| | 3'-GUCCAAUGUUGUUGAAACCCUAUUUUC-5' | (SEQ ID NO: 2204) |
| βc-m3481 Target: | 5'-CAGGTTACAACAACTTTGGGATAAAAG-3' | (SEQ ID NO: 3313) |
| | 5'-UCACAGCAGGUUACAACAACUUUgg-3' | (SEQ ID NO: 1096) |
| | 3'-AUAGUGUCGUCCAAUGUUGUUGAAACC-5' | (SEQ ID NO: 2205) |
| βc-m3489 Target: | 5'-TATCACAGCAGGTTACAACAACTTTGG-3' | (SEQ ID NO: 3314) |
| | 5'-AUCACAGCAGGUUACAACAACUUtg-3' | (SEQ ID NO: 1097) |
| | 3'-CAUAGUGUCGUCCAAUGUUGUUGAAAC-5' | (SEQ ID NO: 2206) |
| βc-m3490 Target: | 5'-GTATCACAGCAGGTTACAACAACTTTG-3' | (SEQ ID NO: 3315) |
| | 5'-GUAUCACAGCAGGUUACAACAACtt-3' | (SEQ ID NO: 1098) |
| | 3'-AACAUAGUGUCGUCCAAUGUUGUUGAA-5' | (SEQ ID NO: 2207) |
| βc-m3492 Target: | 5'-TTGTATCACAGCAGGTTACAACAACTT-3' | (SEQ ID NO: 3316) |
| | 5'-GCAUCUGUUGAAGCAUUGUAUCAca-3' | (SEQ ID NO: 1099) |
| | 3'-GGCGUAGACAACUUCGUAACAUAGUGU-5' | (SEQ ID NO: 2208) |
| βc-m3509 Target: | 5'-CCGCATCTGTTGAAGCATTGTATCACA-3' | (SEQ ID NO: 3317) |

TABLE 9-continued

Additional Selected Anti-β-catenin DsiRNAs, 25/27mer Duplexes

|  |  |  |
|---|---|---|
| βc-m3527 Target: | 5'-UGAACCAUUUCUAUAACCGCAUCtg-3'<br>3'-AGACUUGGUAAAGAUAUUGGCGUAGAC-5'<br>5'-TCTGAACCATTTCTATAACCGCATCTG-3' | (SEQ ID NO: 1100)<br>(SEQ ID NO: 2209)<br>(SEQ ID NO: 3318) |
| βc-m3531 Target: | 5'-AUUCUGAACCAUUUCUAUAACCGca-3'<br>3'-AUUAAGACUUGGUAAAGAUAUUGGCGU-5'<br>5'-TAATTCTGAACCATTTCTATAACCGCA-3' | (SEQ ID NO: 1101)<br>(SEQ ID NO: 2210)<br>(SEQ ID NO: 3319) |
| βc-m3533 Target: | 5'-UAAUUCUGAACCAUUUCUAUAACcg-3'<br>3'-AAAUUAAGACUUGGUAAAGAUAUUGGC-5'<br>5'-TTTAATTCTGAACCATTTCTATAACCG-3' | (SEQ ID NO: 1102)<br>(SEQ ID NO: 2211)<br>(SEQ ID NO: 3320) |
| βc-m3534 Target: | 5'-UUAAUUCUGAACCAUUUCUAUAcc-3'<br>3'-CAAAUUAAGACUUGGUAAAGAUAUUGG-5'<br>5'-GTTTAATTCTGAACCATTTCTATAACC-3' | (SEQ ID NO: 1103)<br>(SEQ ID NO: 2212)<br>(SEQ ID NO: 3321) |
| βc-m3535 Target: | 5'-UUUAAUUCUGAACCAUUUCUAUAac-3'<br>3'-UCAAAUUAAGACUUGGUAAAGAUAUUG-5'<br>5'-AGTTTAATTCTGAACCATTTCTATAAC-3' | (SEQ ID NO: 1104)<br>(SEQ ID NO: 2213)<br>(SEQ ID NO: 3322) |
| βc-m3536 Target: | 5'-GUUUAAUUCUGAACCAUUUCUAUaa-3'<br>3'-UUCAAAUUAAGACUUGGUAAAGAUAUU-5'<br>5'-AAGTTTAATTCTGAACCATTTCTATAA-3' | (SEQ ID NO: 1105)<br>(SEQ ID NO: 2214)<br>(SEQ ID NO: 3323) |
| βc-m3541 Target: | 5'-UAAAGUUUAAUUCUGAACCAUUtc-3'<br>3'-UAAUUUUCAAAUUAAGACUUGGUAAAG-5'<br>5'-ATTAAAAGTTTAATTCTGAACCATTTC-3' | (SEQ ID NO: 1106)<br>(SEQ ID NO: 2215)<br>(SEQ ID NO: 3324) |
| βc-m3542 Target: | 5'-UUAAAGUUUAAUUCUGAACCAUtt-3'<br>3'-UUAAUUUUCAAAUUAAGACUUGGUAAA-5'<br>5'-AATTAAAAGTTTAATTCTGAACCATTT-3' | (SEQ ID NO: 1107)<br>(SEQ ID NO: 2216)<br>(SEQ ID NO: 3325) |
| βc-m3544 Target: | 5'-AAUUAAAAGUUUAAUUCUGAACCat-3'<br>3'-ACUUAAUUUUCAAAUUAAGACUUGGUA-5'<br>5'-TGAATTAAAAGTTTAATTCTGAACC-3' | (SEQ ID NO: 1108)<br>(SEQ ID NO: 2217)<br>(SEQ ID NO: 3326) |
| βc-m3550 Target: | 5'-UGAAUGAAUUAAAAGUUUAAUUCtg-3'<br>3'-AAACUUACUUAAUUUUCAAAUUAAGAC-5'<br>5'-TTTGAATGAATTAAAAGTTTAATTCTG-3' | (SEQ ID NO: 1109)<br>(SEQ ID NO: 2218)<br>(SEQ ID NO: 3327) |
| βc-m3554 Target: | 5'-UUUUUGAAUGAAUUAAAAGUUUAat-3'<br>3'-AAAAAAACUUACUUAAUUUUCAAAUUA-5'<br>5'-TTTTTTTGAATGAATTAAAAGTTTAAT-3' | (SEQ ID NO: 1110)<br>(SEQ ID NO: 2219)<br>(SEQ ID NO: 3328) |
| βc-m3558 Target: | 5'-UUUUUUUUUGAAUGAAUUAAAAGtt-3'<br>3'-AAAAAAAAAACUUACUUAAUUUUCAA-5'<br>5'-TTTTTTTTTGAATGAATTAAAAGTT-3' | (SEQ ID NO: 1111)<br>(SEQ ID NO: 2220)<br>(SEQ ID NO: 3329) |
| βc-m3559 Target: | 5'-UUUUUUUUUUGAAUGAAUUAAAAgt-3'<br>3'-AAAAAAAAAAACUUACUUAAUUUUCA-5'<br>5'-TTTTTTTTTTGAATGAATTAAAAGT-3' | (SEQ ID NO: 1112)<br>(SEQ ID NO: 2221)<br>(SEQ ID NO: 3330) |
| βc-m3560 Target: | 5'-UUUUUUUUUUUGAAUGAAUUAAAag-3'<br>3'-AAAAAAAAAAAACUUACUUAAUUUUC-5'<br>5'-TTTTTTTTTTTGAATGAATTAAAAG-3' | (SEQ ID NO: 1113)<br>(SEQ ID NO: 2222)<br>(SEQ ID NO: 3331) |
| βc-m3561 Target: | 5'-UUUUUUUUUUUUGAAUGAAUUAAaa-3'<br>3'-AAAAAAAAAAAAACUUACUUAAUUUU-5'<br>5'-TTTTTTTTTTTTGAATGAATTAAAA-3' | (SEQ ID NO: 1114)<br>(SEQ ID NO: 2223)<br>(SEQ ID NO: 3332) |
| βc-m3562 Target: | 5'-UUUUUUUUUUUUUGAAUGAAUUAaa-3'<br>3'-AAAAAAAAAAAAAACUUACUUAAUUU-5'<br>5'-TTTTTTTTTTTTTGAATGAATTAAA-3' | (SEQ ID NO: 1115)<br>(SEQ ID NO: 2224)<br>(SEQ ID NO: 3333) |
| βc-m3563 Target: | 5'-UUUUUUUUUUUUUUGAAUGAAUUaa-3'<br>3'-AAAAAAAAAAAAAAACUUACUUAAUU-5'<br>5'-TTTTTTTTTTTTTTGAATGAATTAA-3' | (SEQ ID NO: 1116)<br>(SEQ ID NO: 2225)<br>(SEQ ID NO: 3334) |

Projected 21 nucleotide target sequences for each DsiRNA of Table 9 above and of Tables 11-13 below are presented in Table 10.

TABLE 10

21 Nucleotide Target Sequences of Additional Selected DsiRNAs

| | | |
|---|---|---|
| βc-244 21 nt Target: | 5'-GTTGTATGGTATACTTCAAAT-3' | (SEQ ID NO: 4932) |
| βc-251 21 nt Target: | 5'-CAAAACAGTTGTATGGTATAC-3' | (SEQ ID NO: 4933) |
| βc-252 21 nt Target: | 5'-TCAAAACAGTTGTATGGTATA-3' | (SEQ ID NO: 4934) |
| βc-254 21 nt Target: | 5'-TTTCAAAACAGTTGTATGGTA-3' | (SEQ ID NO: 4935) |
| βc-255 21 nt Target: | 5'-TTTTCAAAACAGTTGTATGGT-3' | (SEQ ID NO: 4936) |
| βc-256 21 nt Target: | 5'-ATTTTCAAAACAGTTGTATGG-3' | (SEQ ID NO: 4937) |
| βc-269 21 nt Target: | 5'-TTGTCCACGCTGGATTTTCAA-3' | (SEQ ID NO: 4938) |
| βc-270 21 nt Target: | 5'-ATTGTCCACGCTGGATTTTCA-3' | (SEQ ID NO: 4939) |
| βc-293 21 nt Target: | 5'-CCATCAAATCAGCTTGAGTAG-3' | (SEQ ID NO: 4940) |
| βc-302 21 nt Target: | 5'-TGTCCAACTCCATCAAATCAG-3' | (SEQ ID NO: 4941) |
| βc-431 21 nt Target: | 5'-CTTCCTCAGGATTGCCTTTAC-3' | (SEQ ID NO: 4942) |
| βc-432 21 nt Target: | 5'-TCTTCCTCAGGATTGCCTTTA-3' | (SEQ ID NO: 4943) |
| βc-518 21 nt Target: | 5'-CATCAATATCAGCTACTTGTT-3' | (SEQ ID NO: 4944) |
| βc-519 21 nt Target: | 5'-CCATCAATATCAGCTACTTGT-3' | (SEQ ID NO: 4945) |
| βc-524 21 nt Target: | 5'-ACTGTCCATCAATATCAGCTA-3' | (SEQ ID NO: 4946) |
| βc-531 21 nt Target: | 5'-ATTGCATACTGTCCATCAATA-3' | (SEQ ID NO: 4947) |
| βc-537 21 nt Target: | 5'-CGAGTCATTGCATACTGTCCA-3' | (SEQ ID NO: 4948) |
| βc-584 21 nt Target: | 5'-CCTCATCTAATGTCTCAGGGA-3' | (SEQ ID NO: 4949) |
| βc-680 21 nt Target: | 5'-TTACAACTGCATGTTTCAGCA-3' | (SEQ ID NO: 4950) |
| βc-682 21 nt Target: | 5'-GTTTACAACTGCATGTTTCAG-3' | (SEQ ID NO: 4951) |
| βc-692 21 nt Target: | 5'-AGTTAATCAAGTTTACAACTG-3' | (SEQ ID NO: 4952) |
| βc-698 21 nt Target: | 5'-CTTGATAGTTAATCAAGTTTA-3' | (SEQ ID NO: 4953) |
| βc-707 21 nt Target: | 5'-CTGCATCATCTTGATAGTTAA-3' | (SEQ ID NO: 4954) |
| βc-708 21 nt Target: | 5'-TCTGCATCATCTTGATAGTTA-3' | (SEQ ID NO: 4955) |
| βc-763 21 nt Target: | 5'-CTGGTCCTCGTCATTTAGCAG-3' | (SEQ ID NO: 4956) |
| βc-790 21 nt Target: | 5'-CATAACTGCAGCCTTATTAAC-3' | (SEQ ID NO: 4957) |
| βc-791 21 nt Target: | 5'-CCATAACTGCAGCCTTATTAA-3' | (SEQ ID NO: 4958) |
| βc-794 21 nt Target: | 5'-GGACCATAACTGCAGCCTTAT-3' | (SEQ ID NO: 4959) |
| βc-812 21 nt Target: | 5'-CCTTTTTAGAAAGCTGATGGA-3' | (SEQ ID NO: 4960) |
| βc-873 21 nt Target: | 5'-ATGGTACGTACAATAGCAGAC-3' | (SEQ ID NO: 4961) |
| βc-890 21 nt Target: | 5'-CATCATTTGTATTCTGCATGG-3' | (SEQ ID NO: 4962) |
| βc-899 21 nt Target: | 5'-CTGTTTCTACATCATTTGTAT-3' | (SEQ ID NO: 4963) |
| βc-900 21 nt Target: | 5'-GCTGTTTCTACATCATTTGTA-3' | (SEQ ID NO: 4964) |
| βc-909 21 nt Target: | 5'-GTACAACGAGCTGTTTCTACA-3' | (SEQ ID NO: 4965) |
| βc-911 21 nt Target: | 5'-CGGTACAACGAGCTGTTTCTA-3' | (SEQ ID NO: 4966) |
| βc-912 21 nt Target: | 5'-GCGGTACAACGAGCTGTTTCT-3' | (SEQ ID NO: 4967) |
| βc-1032 21 nt Target: | 5'-GCATAAAACAACACAGAATCC-3' | (SEQ ID NO: 4968) |

TABLE 10-continued

21 Nucleotide Target Sequences of Additional Selected DsiRNAs

| | | |
|---|---|---|
| βc-1034 21 nt Target: | 5'-TGGCATAAAACAACACAGAAT-3' | (SEQ ID NO: 4969) |
| βc-1035 21 nt Target: | 5'-ATGGCATAAAACAACACAGAA-3' | (SEQ ID NO: 4970) |
| βc-1076 21 nt Target: | 5'-TAGCTCCTTCTTGATGTAATA-3' | (SEQ ID NO: 4971) |
| βc-1077 21 nt Target: | 5'-TTAGCTCCTTCTTGATGTAAT-3' | (SEQ ID NO: 4972) |
| βc-1144 21 nt Target: | 5'-TTTAACATTTGTTTTGTTGAG-3' | (SEQ ID NO: 4973) |
| βc-1154 21 nt Target: | 5'-TAGCCAAGAATTTAACATTTG-3' | (SEQ ID NO: 4974) |
| βc-1159 21 nt Target: | 5'-CGTAATAGCCAAGAATTTAAC-3' | (SEQ ID NO: 4975) |
| βc-1160 21 nt Target: | 5'-TCGTAATAGCCAAGAATTTAA-3' | (SEQ ID NO: 4976) |
| βc-1185 21 nt Target: | 5'-TAAGCTAAAATTTGAAGGCAG-3' | (SEQ ID NO: 4977) |
| βc-1260 21 nt Target: | 5'-TAGGTCCTCATTATATTTACT-3' | (SEQ ID NO: 4978) |
| βc-1265 21 nt Target: | 5'-AAGTATAGGTCCTCATTATAT-3' | (SEQ ID NO: 4979) |
| βc-1266 21 nt Target: | 5'-TAAGTATAGGTCCTCATTATA-3' | (SEQ ID NO: 4980) |
| βc-1274 21 nt Target: | 5'-GTTTTTCGTAAGTATAGGTCC-3' | (SEQ ID NO: 4981) |
| βc-1275 21 nt Target: | 5'-AGTTTTTCGTAAGTATAGGTC-3' | (SEQ ID NO: 4982) |
| βc-1276 21 nt Target: | 5'-TAGTTTTTCGTAAGTATAGGT-3' | (SEQ ID NO: 4983) |
| βc-1277 21 nt Target: | 5'-GTAGTTTTTCGTAAGTATAGG-3' | (SEQ ID NO: 4984) |
| βc-1287 21 nt Target: | 5'-GTGGTCCACAGTAGTTTTTCG-3' | (SEQ ID NO: 4985) |
| βc-1344 21 nt Target: | 5'-TCTACAATAGCCGGCTTATTA-3' | (SEQ ID NO: 4986) |
| βc-1346 21 nt Target: | 5'-CTTCTACAATAGCCGGCTTAT-3' | (SEQ ID NO: 4987) |
| βc-1371 21 nt Target: | 5'-AGTCCTAAAGCTTGCATTCCA-3' | (SEQ ID NO: 4988) |
| βc-1372 21 nt Target: | 5'-AAGTCCTAAAGCTTGCATTCC-3' | (SEQ ID NO: 4989) |
| βc-1373 21 nt Target: | 5'-GAAGTCCTAAAGCTTGCATTC-3' | (SEQ ID NO: 4990) |
| βc-1410 21 nt Target: | 5'-CAGTTCTGAACAAGACGTTGA-3' | (SEQ ID NO: 4991) |
| βc-1411 21 nt Target: | 5'-ACAGTTCTGAACAAGACGTTG-3' | (SEQ ID NO: 4992) |
| βc-1421 21 nt Target: | 5'-GAGTCCAAAGACAGTTCTGAA-3' | (SEQ ID NO: 4993) |
| βc-1458 21 nt Target: | 5'-CCTTCCTGTTTAGTTGCAGCA-3' | (SEQ ID NO: 4994) |
| βc-1517 21 nt Target: | 5'-CCACATTTATATCATCTGAAC-3' | (SEQ ID NO: 4995) |
| βc-1520 21 nt Target: | 5'-TGACCACATTTATATCATCTG-3' | (SEQ ID NO: 4996) |
| βc-1529 21 nt Target: | 5'-CTGCACAGGTGACCACATTTA-3' | (SEQ ID NO: 4997) |
| βc-1530 21 nt Target: | 5'-GCTGCACAGGTGACCACATTT-3' | (SEQ ID NO: 4998) |
| βc-1558 21 nt Target: | 5'-ATTGCAAGTGAGGTTAGAAAG-3' | (SEQ ID NO: 4999) |
| βc-1566 21 nt Target: | 5'-TTATAATTATTGCAAGTGAGG-3' | (SEQ ID NO: 5000) |
| βc-1579 21 nt Target: | 5'-CATCATCTTGTTCTTATAATT-3' | (SEQ ID NO: 5001) |
| βc-1580 21 nt Target: | 5'-CCATCATCTTGTTCTTATAAT-3' | (SEQ ID NO: 5002) |
| βc-1583 21 nt Target: | 5'-AGACCATCATCTTGTTCTTAT-3' | (SEQ ID NO: 5003) |
| βc-1585 21 nt Target: | 5'-GCAGACCATCATCTTGTTCTT-3' | (SEQ ID NO: 5004) |
| βc-1808 21 nt Target: | 5'-TCAATCCAACAGTAGCCTTTA-3' | (SEQ ID NO: 5005) |
| βc-1813 21 nt Target: | 5'-TCGAATCAATCCAACAGTAGC-3' | (SEQ ID NO: 5006) |
| βc-1955 21 nt Target: | 5'-CCTCCACAAATTGCTGCTGTG-3' | (SEQ ID NO: 5007) |

TABLE 10-continued

21 Nucleotide Target Sequences of Additional Selected DsiRNAs

| | | |
|---|---|---|
| βc-1989 21 nt Target: | 5'-GTACAACCTTCAACTATTTCT-3' | (SEQ ID NO: 5008) |
| βc-1990 21 nt Target: | 5'-GGTACAACCTTCAACTATTTC-3' | (SEQ ID NO: 5009) |
| βc-1991 21 nt Target: | 5'-CGGTACAACCTTCAACTATTT-3' | (SEQ ID NO: 5010) |
| βc-1992 21 nt Target: | 5'-CCGGTACAACCTTCAACTATT-3' | (SEQ ID NO: 5011) |
| βc-1997 21 nt Target: | 5'-GGGCTCCGGTACAACCTTCAA-3' | (SEQ ID NO: 5012) |
| βc-2036 21 nt Target: | 5'-TAACAATTCGGTTGTGAACAT-3' | (SEQ ID NO: 5013) |
| βc-2037 21 nt Target: | 5'-ATAACAATTCGGTTGTGAACA-3' | (SEQ ID NO: 5014) |
| βc-2038 21 nt Target: | 5'-GATAACAATTCGGTTGTGAAC-3' | (SEQ ID NO: 5015) |
| βc-2039 21 nt Target: | 5'-TGATAACAATTCGGTTGTGAA-3' | (SEQ ID NO: 5016) |
| βc-2040 21 nt Target: | 5'-CTGATAACAATTCGGTTGTGA-3' | (SEQ ID NO: 5017) |
| βc-2041 21 nt Target: | 5'-TCTGATAACAATTCGGTTGTG-3' | (SEQ ID NO: 5018) |
| βc-2052 21 nt Target: | 5'-GTATTTAGTCCTCTGATAACA-3' | (SEQ ID NO: 5019) |
| βc-2053 21 nt Target: | 5'-GGTATTTAGTCCTCTGATAAC-3' | (SEQ ID NO: 5020) |
| βc-2054 21 nt Target: | 5'-TGGTATTTAGTCCTCTGATAA-3' | (SEQ ID NO: 5021) |
| βc-2055 21 nt Target: | 5'-ATGGTATTTAGTCCTCTGATA-3' | (SEQ ID NO: 5022) |
| βc-2065 21 nt Target: | 5'-AAACAATGGAATGGTATTTAG-3' | (SEQ ID NO: 5023) |
| βc-2069 21 nt Target: | 5'-GCACAAACAATGGAATGGTAT-3' | (SEQ ID NO: 5024) |
| βc-2071 21 nt Target: | 5'-CTGCACAAACAATGGAATGGT-3' | (SEQ ID NO: 5025) |
| βc-2072 21 nt Target: | 5'-GCTGCACAAACAATGGAATGG-3' | (SEQ ID NO: 5026) |
| βc-2111 21 nt Target: | 5'-CAGCTACTCTTTGGATGTTTT-3' | (SEQ ID NO: 5027) |
| βc-2112 21 nt Target: | 5'-GCAGCTACTCTTTGGATGTTT-3' | (SEQ ID NO: 5028) |
| βc-2168 21 nt Target: | 5'-CAGCTTCAATAGCTTCTGCAG-3' | (SEQ ID NO: 5029) |
| βc-2175 21 nt Target: | 5'-GCTCCCTCAGCTTCAATAGCT-3' | (SEQ ID NO: 5030) |
| βc-2177 21 nt Target: | 5'-TGGCTCCCTCAGCTTCAATAG-3' | (SEQ ID NO: 5031) |
| βc-2214 21 nt Target: | 5'-TCATTCCTAGAGTGAAGTAAC-3' | (SEQ ID NO: 5032) |
| βc-2216 21 nt Target: | 5'-CTTCATTCCTAGAGTGAAGTA-3' | (SEQ ID NO: 5033) |
| βc-2217 21 nt Target: | 5'-CCTTCATTCCTAGAGTGAAGT-3' | (SEQ ID NO: 5034) |
| βc-2264 21 nt Target: | 5'-TGTCCTCAGACATTCGGAACA-3' | (SEQ ID NO: 5035) |
| βc-2266 21 nt Target: | 5'-CTTGTCCTCAGACATTCGGAA-3' | (SEQ ID NO: 5036) |
| βc-2287 21 nt Target: | 5'-CCGTTTCTTGTAATCTTGTGG-3' | (SEQ ID NO: 5037) |
| βc-2295 21 nt Target: | 5'-ACTGAAAGCCGTTTCTTGTAA-3' | (SEQ ID NO: 5038) |
| βc-2302 21 nt Target: | 5'-CAGCTCAACTGAAAGCCGTTT-3' | (SEQ ID NO: 5039) |
| βc-2363 21 nt Target: | 5'-CAAGTCCAAGATCAGCAGTCT-3' | (SEQ ID NO: 5040) |
| βc-2373 21 nt Target: | 5'-GCACCAATATCAAGTCCAAGA-3' | (SEQ ID NO: 5041) |
| βc-2424 21 nt Target: | 5'-AAAGAACGATAGCTAGGATCA-3' | (SEQ ID NO: 5042) |
| βc-2441 21 nt Target: | 5'-CATATCCACCAGAGTGAAAAG-3' | (SEQ ID NO: 5043) |
| βc-2618 21 nt Target: | 5'-TGATTTACAGGTCAGTATCAA-3' | (SEQ ID NO: 5044) |
| βc-2619 21 nt Target: | 5'-ATGATTTACAGGTCAGTATCA-3' | (SEQ ID NO: 5045) |
| βc-2620 21 nt Target: | 5'-GATGATTTACAGGTCAGTATC-3' | (SEQ ID NO: 5046) |

TABLE 10-continued

21 Nucleotide Target Sequences of Additional Selected DsiRNAs

| | | |
|---|---|---|
| βc-2634 21 nt Target: | 5'-CTTCTTACCTAAAGGATGATT-3' | (SEQ ID NO: 5047) |
| βc-2635 21 nt Target: | 5'-ACTTCTTACCTAAAGGATGAT-3' | (SEQ ID NO: 5048) |
| βc-2637 21 nt Target: | 5'-AAACTTCTTACCTAAAGGATG-3' | (SEQ ID NO: 5049) |
| βc-2645 21 nt Target: | 5'-GCTTTTTAAAACTTCTTACCT-3' | (SEQ ID NO: 5050) |
| βc-2647 21 nt Target: | 5'-TGGCTTTTTAAAACTTCTTAC-3' | (SEQ ID NO: 5051) |
| βc-2653 21 nt Target: | 5'-CCAAACTGGCTTTTTAAAACT-3' | (SEQ ID NO: 5052) |
| βc-2657 21 nt Target: | 5'-TTACCCAAACTGGCTTTTTAA-3' | (SEQ ID NO: 5053) |
| βc-2658 21 nt Target: | 5'-TTTACCCAAACTGGCTTTTTA-3' | (SEQ ID NO: 5054) |
| βc-2659 21 nt Target: | 5'-TTTTACCCAAACTGGCTTTTT-3' | (SEQ ID NO: 5055) |
| βc-2660 21 nt Target: | 5'-ATTTTACCCAAACTGGCTTTT-3' | (SEQ ID NO: 5056) |
| βc-2701 21 nt Target: | 5'-CCAACCAAGTCTTTCTGAAGT-3' | (SEQ ID NO: 5057) |
| βc-2709 21 nt Target: | 5'-CCACCCTACCAACCAAGTCTT-3' | (SEQ ID NO: 5058) |
| βc-2733 21 nt Target: | 5'-ATTTACAAATAGCCTAAACCA-3' | (SEQ ID NO: 5059) |
| βc-2734 21 nt Target: | 5'-GATTTACAAATAGCCTAAACC-3' | (SEQ ID NO: 5060) |
| βc-2735 21 nt Target: | 5'-AGATTTACAAATAGCCTAAAC-3' | (SEQ ID NO: 5061) |
| βc-2736 21 nt Target: | 5'-CAGATTTACAAATAGCCTAAA-3' | (SEQ ID NO: 5062) |
| βc-2747 21 nt Target: | 5'-TGTTTTTGTGGCAGATTTACA-3' | (SEQ ID NO: 5063) |
| βc-2748 21 nt Target: | 5'-CTGTTTTTGTGGCAGATTTAC-3' | (SEQ ID NO: 5064) |
| βc-2749 21 nt Target: | 5'-CCTGTTTTTGTGGCAGATTTA-3' | (SEQ ID NO: 5065) |
| βc-2754 21 nt Target: | 5'-ATATACCTGTTTTTGTGGCAG-3' | (SEQ ID NO: 5066) |
| βc-2764 21 nt Target: | 5'-CTTTCAAAGTATATACCTGTT-3' | (SEQ ID NO: 5067) |
| βc-2770 21 nt Target: | 5'-CATCTCCTTTCAAAGTATATA-3' | (SEQ ID NO: 5068) |
| βc-2771 21 nt Target: | 5'-ACATCTCCTTTCAAAGTATAT-3' | (SEQ ID NO: 5069) |
| βc-2773 21 nt Target: | 5'-AGACATCTCCTTTCAAAGTAT-3' | (SEQ ID NO: 5070) |
| βc-2774 21 nt Target: | 5'-AAGACATCTCCTTTCAAAGTA-3' | (SEQ ID NO: 5071) |
| βc-2775 21 nt Target: | 5'-CAAGACATCTCCTTTCAAAGT-3' | (SEQ ID NO: 5072) |
| βc-2780 21 nt Target: | 5'-TGTTCCAAGACATCTCCTTTC-3' | (SEQ ID NO: 5073) |
| βc-2788 21 nt Target: | 5'-CATTCCAATGTTCCAAGACAT-3' | (SEQ ID NO: 5074) |
| βc-2789 21 nt Target: | 5'-ACATTCCAATGTTCCAAGACA-3' | (SEQ ID NO: 5075) |
| βc-2791 21 nt Target: | 5'-GAACATTCCAATGTTCCAAGA-3' | (SEQ ID NO: 5076) |
| βc-2803 21 nt Target: | 5'-CCAGAAATCTGAGAACATTCC-3' | (SEQ ID NO: 5077) |
| βc-2807 21 nt Target: | 5'-ACAACCAGAAATCTGAGAACA-3' | (SEQ ID NO: 5078) |
| βc-2809 21 nt Target: | 5'-TAACAACCAGAAATCTGAGAA-3' | (SEQ ID NO: 5079) |
| βc-2810 21 nt Target: | 5'-ATAACAACCAGAAATCTGAGA-3' | (SEQ ID NO: 5080) |
| βc-2811 21 nt Target: | 5'-CATAACAACCAGAAATCTGAG-3' | (SEQ ID NO: 5081) |
| βc-2817 21 nt Target: | 5'-TGATCACATAACAACCAGAAA-3' | (SEQ ID NO: 5082) |
| βc-2818 21 nt Target: | 5'-ATGATCACATAACAACCAGAA-3' | (SEQ ID NO: 5083) |
| βc-2824 21 nt Target: | 5'-CCACACATGATCACATAACAA-3' | (SEQ ID NO: 5084) |
| βc-2827 21 nt Target: | 5'-CTTCCACACATGATCACATAA-3' | (SEQ ID NO: 5085) |

TABLE 10-continued

21 Nucleotide Target Sequences of Additional Selected DsiRNAs

| | | |
|---|---|---|
| βc-2832 21 nt Target: | 5'-AATAACTTCCACACATGATCA-3' | (SEQ ID NO: 5086) |
| βc-2833 21 nt Target: | 5'-TAATAACTTCCACACATGATC-3' | (SEQ ID NO: 5087) |
| βc-2834 21 nt Target: | 5'-TTAATAACTTCCACACATGAT-3' | (SEQ ID NO: 5088) |
| βc-2835 21 nt Target: | 5'-GTTAATAACTTCCACACATGA-3' | (SEQ ID NO: 5089) |
| βc-2842 21 nt Target: | 5'-CATTAAAGTTAATAACTTCCA-3' | (SEQ ID NO: 5090) |
| βc-2843 21 nt Target: | 5'-ACATTAAAGTTAATAACTTCC-3' | (SEQ ID NO: 5091) |
| βc-2845 21 nt Target: | 5'-AAACATTAAAGTTAATAACTT-3' | (SEQ ID NO: 5092) |
| βc-2846 21 nt Target: | 5'-AAAACATTAAAGTTAATAACT-3' | (SEQ ID NO: 5093) |
| βc-2847 21 nt Target: | 5'-AAAAACATTAAAGTTAATAAC-3' | (SEQ ID NO: 5094) |
| βc-2848 21 nt Target: | 5'-AAAAAACATTAAAGTTAATAA-3' | (SEQ ID NO: 5095) |
| βc-2849 21 nt Target: | 5'-CAAAAAACATTAAAGTTAATA-3' | (SEQ ID NO: 5096) |
| βc-2850 21 nt Target: | 5'-GCAAAAAACATTAAAGTTAAT-3' | (SEQ ID NO: 5097) |
| βc-2852 21 nt Target: | 5'-TGGCAAAAAACATTAAAGTTA-3' | (SEQ ID NO: 5098) |
| βc-2853 21 nt Target: | 5'-GTGGCAAAAAACATTAAAGTT-3' | (SEQ ID NO: 5099) |
| βc-2864 21 nt Target: | 5'-TTGCAAAAGCTGTGGCAAAAA-3' | (SEQ ID NO: 5100) |
| βc-2865 21 nt Target: | 5'-GTTGCAAAAGCTGTGGCAAAA-3' | (SEQ ID NO: 5101) |
| βc-2882 21 nt Target: | 5'-ACTCATTTGAGTATTAAGTTG-3' | (SEQ ID NO: 5102) |
| βc-2899 21 nt Target: | 5'-TTAAAACAGCAAATGTTACTC-3' | (SEQ ID NO: 5103) |
| βc-2900 21 nt Target: | 5'-TTTAAAACAGCAAATGTTACT-3' | (SEQ ID NO: 5104) |
| βc-2901 21 nt Target: | 5'-GTTTAAAACAGCAAATGTTAC-3' | (SEQ ID NO: 5105) |
| βc-2902 21 nt Target: | 5'-TGTTTAAAACAGCAAATGTTA-3' | (SEQ ID NO: 5106) |
| βc-2903 21 nt Target: | 5'-ATGTTTAAAACAGCAAATGTT-3' | (SEQ ID NO: 5107) |
| βc-2904 21 nt Target: | 5'-AATGTTTAAAACAGCAAATGT-3' | (SEQ ID NO: 5108) |
| βc-2909 21 nt Target: | 5'-CTATTAATGTTTAAAACAGCA-3' | (SEQ ID NO: 5109) |
| βc-2921 21 nt Target: | 5'-AGAGAAAGGCTGCTATTAATG-3' | (SEQ ID NO: 5110) |
| βc-2949 21 nt Target: | 5'-CAAGTTCAGACAATACAGCTG-3' | (SEQ ID NO: 5111) |
| βc-2957 21 nt Target: | 5'-TCACAATGCAAGTTCAGACAA-3' | (SEQ ID NO: 5112) |
| βc-2959 21 nt Target: | 5'-AATCACAATGCAAGTTCAGAC-3' | (SEQ ID NO: 5113) |
| βc-2961 21 nt Target: | 5'-CCAATCACAATGCAAGTTCAG-3' | (SEQ ID NO: 5114) |
| βc-2965 21 nt Target: | 5'-CAGGCCAATCACAATGCAAGT-3' | (SEQ ID NO: 5115) |
| βc-3052 21 nt Target: | 5'-TTGTTCCCATAGGAAACTCAG-3' | (SEQ ID NO: 5116) |
| βc-3058 21 nt Target: | 5'-CTTCAATTGTTCCCATAGGAA-3' | (SEQ ID NO: 5117) |
| βc-3059 21 nt Target: | 5'-ACTTCAATTGTTCCCATAGGA-3' | (SEQ ID NO: 5118) |
| βc-3065 21 nt Target: | 5'-AAGTTTACTTCAATTGTTCCC-3' | (SEQ ID NO: 5119) |
| βc-3066 21 nt Target: | 5'-AAAGTTTACTTCAATTGTTCC-3' | (SEQ ID NO: 5120) |
| βc-3070 21 nt Target: | 5'-ACAAAAAGTTTACTTCAATTG-3' | (SEQ ID NO: 5121) |
| βc-3074 21 nt Target: | 5'-CAGAACAAAAAGTTTACTTCA-3' | (SEQ ID NO: 5122) |
| βc-3079 21 nt Target: | 5'-AGGACCAGAACAAAAAGTTTA-3' | (SEQ ID NO: 5123) |
| βc-3080 21 nt Target: | 5'-AAGGACCAGAACAAAAAGTTT-3' | (SEQ ID NO: 5124) |

TABLE 10-continued

21 Nucleotide Target Sequences of Additional Selected DsiRNAs

| | | |
|---|---|---|
| βc-3088 21 nt Target: | 5'-CGACCAAAAAGGACCAGAACA-3' | (SEQ ID NO: 5125) |
| βc-3089 21 nt Target: | 5'-TCGACCAAAAAGGACCAGAAC-3' | (SEQ ID NO: 5126) |
| βc-3096 21 nt Target: | 5'-TTACTCCTCGACCAAAAAGGA-3' | (SEQ ID NO: 5127) |
| βc-3111 21 nt Target: | 5'-AATCCATTTGTATTGTTACTC-3' | (SEQ ID NO: 5128) |
| βc-3112 21 nt Target: | 5'-AAATCCATTTGTATTGTTACT-3' | (SEQ ID NO: 5129) |
| βc-3113 21 nt Target: | 5'-AAAATCCATTTGTATTGTTAC-3' | (SEQ ID NO: 5130) |
| βc-3114 21 nt Target: | 5'-CAAAATCCATTTGTATTGTTA-3' | (SEQ ID NO: 5131) |
| βc-3115 21 nt Target: | 5'-CCAAAATCCATTTGTATTGTT-3' | (SEQ ID NO: 5132) |
| βc-3121 21 nt Target: | 5'-TCACTCCCAAAATCCATTTGT-3' | (SEQ ID NO: 5133) |
| βc-3136 21 nt Target: | 5'-TCTTCACTTCTTGAGTCACTC-3' | (SEQ ID NO: 5134) |
| βc-3138 21 nt Target: | 5'-ATTCTTCACTTCTTGAGTCAC-3' | (SEQ ID NO: 5135) |
| βc-3139 21 nt Target: | 5'-CATTCTTCACTTCTTGAGTCA-3' | (SEQ ID NO: 5136) |
| βc-3140 21 nt Target: | 5'-GCATTCTTCACTTCTTGAGTC-3' | (SEQ ID NO: 5137) |
| βc-3142 21 nt Target: | 5'-GTGCATTCTTCACTTCTTGAG-3' | (SEQ ID NO: 5138) |
| βc-3150 21 nt Target: | 5'-CCATTCTTGTGCATTCTTCAC-3' | (SEQ ID NO: 5139) |
| βc-3153 21 nt Target: | 5'-GATCCATTCTTGTGCATTCTT-3' | (SEQ ID NO: 5140) |
| βc-3154 21 nt Target: | 5'-TGATCCATTCTTGTGCATTCT-3' | (SEQ ID NO: 5141) |
| βc-3155 21 nt Target: | 5'-GTGATCCATTCTTGTGCATTC-3' | (SEQ ID NO: 5142) |
| βc-3168 21 nt Target: | 5'-TAAATTCCATCTTGTGATCCA-3' | (SEQ ID NO: 5143) |
| βc-3170 21 nt Target: | 5'-GATAAATTCCATCTTGTGATC-3' | (SEQ ID NO: 5144) |
| βc-3171 21 nt Target: | 5'-TGATAAATTCCATCTTGTGAT-3' | (SEQ ID NO: 5145) |
| βc-3172 21 nt Target: | 5'-TTGATAAATTCCATCTTGTGA-3' | (SEQ ID NO: 5146) |
| βc-3173 21 nt Target: | 5'-TTTGATAAATTCCATCTTGTG-3' | (SEQ ID NO: 5147) |
| βc-3183 21 nt Target: | 5'-AAGGCTAGGGTTTGATAAATT-3' | (SEQ ID NO: 5148) |
| βc-3200 21 nt Target: | 5'-AAAAAAATTTAACAAGCAAGG-3' | (SEQ ID NO: 5149) |
| βc-3209 21 nt Target: | 5'-AAAAAAAAAAAAAAATTTAA-3' | (SEQ ID NO: 5150) |
| βc-3210 21 nt Target: | 5'-AAAAAAAAAAAAAAAATTTA-3' | (SEQ ID NO: 5151) |
| βc-3211 21 nt Target: | 5'-AAAAAAAAAAAAAAAAATTT-3' | (SEQ ID NO: 5152) |
| βc-3212 21 nt Target: | 5'-AAAAAAAAAAAAAAAAAATT-3' | (SEQ ID NO: 5153) |
| βc-3213 21 nt Target: | 5'-TAAAAAAAAAAAAAAAAAAT-3' | (SEQ ID NO: 5154) |
| βc-3214 21 nt Target: | 5'-TTAAAAAAAAAAAAAAAAAA-3' | (SEQ ID NO: 5155) |
| βc-3215 21 nt Target: | 5'-CTTAAAAAAAAAAAAAAAAA-3' | (SEQ ID NO: 5156) |
| βc-3216 21 nt Target: | 5'-TCTTAAAAAAAAAAAAAAAA-3' | (SEQ ID NO: 5157) |
| βc-3218 21 nt Target: | 5'-ATTCTTAAAAAAAAAAAAAA-3' | (SEQ ID NO: 5158) |
| βc-3219 21 nt Target: | 5'-TATTCTTAAAAAAAAAAAAA-3' | (SEQ ID NO: 5159) |
| βc-3220 21 nt Target: | 5'-ATATTCTTAAAAAAAAAAAA-3' | (SEQ ID NO: 5160) |
| βc-3221 21 nt Target: | 5'-GATATTCTTAAAAAAAAAAA-3' | (SEQ ID NO: 5161) |
| βc-3222 21 nt Target: | 5'-AGATATTCTTAAAAAAAAAA-3' | (SEQ ID NO: 5162) |
| βc-3223 21 nt Target: | 5'-CAGATATTCTTAAAAAAAAA-3' | (SEQ ID NO: 5163) |

TABLE 10-continued

21 Nucleotide Target Sequences of Additional Selected DsiRNAs

| | | |
|---|---|---|
| βc-3224 21 nt Target: | 5'-ACAGATATTCTTAAAAAAAA-3' | (SEQ ID NO: 5164) |
| βc-3228 21 nt Target: | 5'-CATTACAGATATTCTTAAAAA-3' | (SEQ ID NO: 5165) |
| βc-3229 21 nt Target: | 5'-CCATTACAGATATTCTTAAAA-3' | (SEQ ID NO: 5166) |
| βc-3233 21 nt Target: | 5'-AGTACCATTACAGATATTCTT-3' | (SEQ ID NO: 5167) |
| βc-3234 21 nt Target: | 5'-CAGTACCATTACAGATATTCT-3' | (SEQ ID NO: 5168) |
| βc-3235 21 nt Target: | 5'-TCAGTACCATTACAGATATTC-3' | (SEQ ID NO: 5169) |
| βc-3239 21 nt Target: | 5'-AAAGTCAGTACCATTACAGAT-3' | (SEQ ID NO: 5170) |
| βc-3256 21 nt Target: | 5'-GCTACTTCAAAGCAAGCAAAG-3' | (SEQ ID NO: 5171) |
| βc-3265 21 nt Target: | 5'-AAAAAAAGAGCTACTTCAAAG-3' | (SEQ ID NO: 5172) |
| βc-3270 21 nt Target: | 5'-AAAAAAAAAAAAGAGCTACTT-3' | (SEQ ID NO: 5173) |
| βc-3271 21 nt Target: | 5'-AAAAAAAAAAAAAGAGCTACT-3' | (SEQ ID NO: 5174) |
| βc-3273 21 nt Target: | 5'-AAAAAAAAAAAAAAAGAGCTA-3' | (SEQ ID NO: 5175) |
| βc-3274 21 nt Target: | 5'-AAAAAAAAAAAAAAAAGAGCT-3' | (SEQ ID NO: 5176) |
| βc-3275 21 nt Target: | 5'-AAAAAAAAAAAAAAAAAGAGC-3' | (SEQ ID NO: 5177) |
| βc-3276 21 nt Target: | 5'-AAAAAAAAAAAAAAAAAAGAG-3' | (SEQ ID NO: 5178) |
| βc-3282 21 nt Target: | 5'-AAAAAAAAAAAAAAAAAAAAA-3' | (SEQ ID NO: 5179) |
| βc-3283 21 nt Target: | 5'-AAAAAAAAAAAAAAAAAAAAA-3' | (SEQ ID NO: 5180) |
| βc-3284 21 nt Target: | 5'-CAAAAAAAAAAAAAAAAAAAA-3' | (SEQ ID NO: 5181) |
| βc-3285 21 nt Target: | 5'-GCAAAAAAAAAAAAAAAAAAA-3' | (SEQ ID NO: 5182) |
| βc-3287 21 nt Target: | 5'-CTGCAAAAAAAAAAAAAAAAA-3' | (SEQ ID NO: 5183) |
| βc-3288 21 nt Target: | 5'-ACTGCAAAAAAAAAAAAAAAA-3' | (SEQ ID NO: 5184) |
| βc-3292 21 nt Target: | 5'-AGTTACTGCAAAAAAAAAAAA-3' | (SEQ ID NO: 5185) |
| βc-3293 21 nt Target: | 5'-CAGTTACTGCAAAAAAAAAAA-3' | (SEQ ID NO: 5186) |
| βc-3294 21 nt Target: | 5'-ACAGTTACTGCAAAAAAAAAA-3' | (SEQ ID NO: 5187) |
| βc-3298 21 nt Target: | 5'-AAAAACAGTTACTGCAAAAAA-3' | (SEQ ID NO: 5188) |
| βc-3299 21 nt Target: | 5'-AAAAAACAGTTACTGCAAAAA-3' | (SEQ ID NO: 5189) |
| βc-3300 21 nt Target: | 5'-TAAAAAACAGTTACTGCAAAA-3' | (SEQ ID NO: 5190) |
| βc-3302 21 nt Target: | 5'-CTTAAAAAACAGTTACTGCAA-3' | (SEQ ID NO: 5191) |
| βc-3303 21 nt Target: | 5'-ACTTAAAAAACAGTTACTGCA-3' | (SEQ ID NO: 5192) |
| βc-3305 21 nt Target: | 5'-AGACTTAAAAAACAGTTACTG-3' | (SEQ ID NO: 5193) |
| βc-3315 21 nt Target: | 5'-ACACTACGAGAGACTTAAAAA-3' | (SEQ ID NO: 5194) |
| βc-3317 21 nt Target: | 5'-TAACACTACGAGAGACTTAAA-3' | (SEQ ID NO: 5195) |
| βc-3318 21 nt Target: | 5'-TTAACACTACGAGAGACTTAA-3' | (SEQ ID NO: 5196) |
| βc-3320 21 nt Target: | 5'-ACTTAACACTACGAGAGACTT-3' | (SEQ ID NO: 5197) |
| βc-3323 21 nt Target: | 5'-ATAACTTAACACTACGAGAGA-3' | (SEQ ID NO: 5198) |
| βc-3324 21 nt Target: | 5'-TATAACTTAACACTACGAGAG-3' | (SEQ ID NO: 5199) |
| βc-3332 21 nt Target: | 5'-GTATTCACTATAACTTAACAC-3' | (SEQ ID NO: 5200) |
| βc-3333 21 nt Target: | 5'-AGTATTCACTATAACTTAACA-3' | (SEQ ID NO: 5201) |
| βc-3334 21 nt Target: | 5'-CAGTATTCACTATAACTTAAC-3' | (SEQ ID NO: 5202) |

TABLE 10-continued

21 Nucleotide Target Sequences of Additional Selected DsiRNAs

| | | |
|---|---|---|
| βc-3335 21 nt Target: | 5'-GCAGTATTCACTATAACTTAA-3' | (SEQ ID NO: 5203) |
| βc-3348 21 nt Target: | 5'-AGAAATTGCTGTAGCAGTATT-3' | (SEQ ID NO: 5204) |
| βc-3349 21 nt Target: | 5'-TAGAAATTGCTGTAGCAGTAT-3' | (SEQ ID NO: 5205) |
| βc-3350 21 nt Target: | 5'-TTAGAAATTGCTGTAGCAGTA-3' | (SEQ ID NO: 5206) |
| βc-3366 21 nt Target: | 5'-ACTCAATTCTTAAAAATTAGA-3' | (SEQ ID NO: 5207) |
| βc-3371 21 nt Target: | 5'-CCATTACTCAATTCTTAAAAA-3' | (SEQ ID NO: 5208) |
| βc-3374 21 nt Target: | 5'-ACACCATTACTCAATTCTTAA-3' | (SEQ ID NO: 5209) |
| βc-3376 21 nt Target: | 5'-CTACACCATTACTCAATTCTT-3' | (SEQ ID NO: 5210) |
| βc-3377 21 nt Target: | 5'-TCTACACCATTACTCAATTCT-3' | (SEQ ID NO: 5211) |
| βc-3379 21 nt Target: | 5'-GTTCTACACCATTACTCAATT-3' | (SEQ ID NO: 5212) |
| βc-3381 21 nt Target: | 5'-GTGTTCTACACCATTACTCAA-3' | (SEQ ID NO: 5213) |
| βc-3389 21 nt Target: | 5'-ATGAATTAGTGTTCTACACCA-3' | (SEQ ID NO: 5214) |
| βc-3394 21 nt Target: | 5'-TGATTATGAATTAGTGTTCTA-3' | (SEQ ID NO: 5215) |
| βc-3395 21 nt Target: | 5'-GTGATTATGAATTAGTGTTCT-3' | (SEQ ID NO: 5216) |
| βc-3396 21 nt Target: | 5'-AGTGATTATGAATTAGTGTTC-3' | (SEQ ID NO: 5217) |
| βc-3405 21 nt Target: | 5'-ATTAATTAGAGTGATTATGAA-3' | (SEQ ID NO: 5218) |
| βc-3406 21 nt Target: | 5'-AATTAATTAGAGTGATTATGA-3' | (SEQ ID NO: 5219) |
| βc-3407 21 nt Target: | 5'-CAATTAATTAGAGTGATTATG-3' | (SEQ ID NO: 5220) |
| βc-3411 21 nt Target: | 5'-ATTACAATTAATTAGAGTGAT-3' | (SEQ ID NO: 5221) |
| βc-3412 21 nt Target: | 5'-GATTACAATTAATTAGAGTGA-3' | (SEQ ID NO: 5222) |
| βc-3413 21 nt Target: | 5'-AGATTACAATTAATTAGAGTG-3' | (SEQ ID NO: 5223) |
| βc-3421 21 nt Target: | 5'-CTTTATTCAGATTACAATTAA-3' | (SEQ ID NO: 5224) |
| βc-3422 21 nt Target: | 5'-ACTTTATTCAGATTACAATTA-3' | (SEQ ID NO: 5225) |
| βc-3426 21 nt Target: | 5'-TTACACTTTATTCAGATTACA-3' | (SEQ ID NO: 5226) |
| βc-3427 21 nt Target: | 5'-GTTACACTTTATTCAGATTAC-3' | (SEQ ID NO: 5227) |
| βc-3428 21 nt Target: | 5'-TGTTACACTTTATTCAGATTA-3' | (SEQ ID NO: 5228) |
| βc-3429 21 nt Target: | 5'-TTGTTACACTTTATTCAGATT-3' | (SEQ ID NO: 5229) |
| βc-3430 21 nt Target: | 5'-ATTGTTACACTTTATTCAGAT-3' | (SEQ ID NO: 5230) |
| βc-3437 21 nt Target: | 5'-CTACACAATTGTTACACTTTA-3' | (SEQ ID NO: 5231) |
| βc-3441 21 nt Target: | 5'-AAGGCTACACAATTGTTACAC-3' | (SEQ ID NO: 5232) |
| βc-3446 21 nt Target: | 5'-ACAAAAGGCTACACAATTGT-3' | (SEQ ID NO: 5233) |
| βc-3452 21 nt Target: | 5'-TTTTATACAAAAGGCTACAC-3' | (SEQ ID NO: 5234) |
| βc-3453 21 nt Target: | 5'-ATTTTATACAAAAGGCTACA-3' | (SEQ ID NO: 5235) |
| βc-3455 21 nt Target: | 5'-CTATTTTATACAAAAGGCTA-3' | (SEQ ID NO: 5236) |
| βc-3456 21 nt Target: | 5'-TCTATTTTATACAAAAGGCT-3' | (SEQ ID NO: 5237) |
| βc-3458 21 nt Target: | 5'-TGTCTATTTTATACAAAAGG-3' | (SEQ ID NO: 5238) |
| βc-3464 21 nt Target: | 5'-TCTATTTGTCTATTTTATACA-3' | (SEQ ID NO: 5239) |
| βc-3466 21 nt Target: | 5'-TTTCTATTTGTCTATTTTATA-3' | (SEQ ID NO: 5240) |
| βc-3467 21 nt Target: | 5'-TTTTCTATTTGTCTATTTTAT-3' | (SEQ ID NO: 5241) |

TABLE 10-continued

21 Nucleotide Target Sequences of Additional Selected DsiRNAs

| | | |
|---|---|---|
| βc-3468 21 nt Target: | 5'-ATTTTCTATTTGTCTATTTTA-3' | (SEQ ID NO: 5242) |
| βc-3469 21 nt Target: | 5'-CATTTTCTATTTGTCTATTTT-3' | (SEQ ID NO: 5243) |
| βc-3470 21 nt Target: | 5'-CCATTTTCTATTTGTCTATTT-3' | (SEQ ID NO: 5244) |
| βc-3473 21 nt Target: | 5'-GGACCATTTTCTATTTGTCTA-3' | (SEQ ID NO: 5245) |
| βc-3474 21 nt Target: | 5'-TGGACCATTTTCTATTTGTCT-3' | (SEQ ID NO: 5246) |
| βc-3475 21 nt Target: | 5'-TTGGACCATTTTCTATTTGTC-3' | (SEQ ID NO: 5247) |
| βc-3482 21 nt Target: | 5'-AAACTAATTGGACCATTTTCT-3' | (SEQ ID NO: 5248) |
| βc-3483 21 nt Target: | 5'-GAAACTAATTGGACCATTTTC-3' | (SEQ ID NO: 5249) |
| βc-3484 21 nt Target: | 5'-GGAAACTAATTGGACCATTTT-3' | (SEQ ID NO: 5250) |
| βc-3485 21 nt Target: | 5'-AGGAAACTAATTGGACCATTT-3' | (SEQ ID NO: 5251) |
| βc-3491 21 nt Target: | 5'-TTAAAAAGGAAACTAATTGGA-3' | (SEQ ID NO: 5252) |
| βc-3492 21 nt Target: | 5'-ATTAAAAAGGAAACTAATTGG-3' | (SEQ ID NO: 5253) |
| βc-3498 21 nt Target: | 5'-AAGCATATTAAAAAGGAAACT-3' | (SEQ ID NO: 5254) |
| βc-3499 21 nt Target: | 5'-TAAGCATATTAAAAAGGAAAC-3' | (SEQ ID NO: 5255) |
| βc-3503 21 nt Target: | 5'-ATTTTAAGCATATTAAAAAGG-3' | (SEQ ID NO: 5256) |
| βc-3509 21 nt Target: | 5'-CTGCTTATTTTAAGCATATTA-3' | (SEQ ID NO: 5257) |
| βc-3510 21 nt Target: | 5'-CCTGCTTATTTTAAGCATATT-3' | (SEQ ID NO: 5258) |
| βc-3516 21 nt Target: | 5'-GATCCACCTGCTTATTTTAAG-3' | (SEQ ID NO: 5259) |
| βc-3531 21 nt Target: | 5'-CAAAAACATGAAATAGATCCA-3' | (SEQ ID NO: 5260) |
| βc-3532 21 nt Target: | 5'-TCAAAAACATGAAATAGATCC-3' | (SEQ ID NO: 5261) |
| βc-3534 21 nt Target: | 5'-GATCAAAAACATGAAATAGAT-3' | (SEQ ID NO: 5262) |
| βc-3535 21 nt Target: | 5'-TGATCAAAAACATGAAATAGA-3' | (SEQ ID NO: 5263) |
| βc-3536 21 nt Target: | 5'-TTGATCAAAAACATGAAATAG-3' | (SEQ ID NO: 5264) |
| βc-3541 21 nt Target: | 5'-AGTTTTTGATCAAAAACATGA-3' | (SEQ ID NO: 5265) |
| βc-3547 21 nt Target: | 5'-CCAAATAGTTTTTGATCAAAA-3' | (SEQ ID NO: 5266) |
| βc-3551 21 nt Target: | 5'-TATCCCAAATAGTTTTTGATC-3' | (SEQ ID NO: 5267) |
| βc-3552 21 nt Target: | 5'-ATATCCCAAATAGTTTTTGAT-3' | (SEQ ID NO: 5268) |
| βc-3553 21 nt Target: | 5'-CATATCCCAAATAGTTTTTGA-3' | (SEQ ID NO: 5269) |
| βc-3554 21 nt Target: | 5'-ACATATCCCAAATAGTTTTTG-3' | (SEQ ID NO: 5270) |
| βc-3558 21 nt Target: | 5'-CCATACATATCCCAAATAGTT-3' | (SEQ ID NO: 5271) |
| βc-3567 21 nt Target: | 5'-TTACCCTACCCATACATATCC-3' | (SEQ ID NO: 5272) |
| βc-3568 21 nt Target: | 5'-TTTACCCTACCCATACATATC-3' | (SEQ ID NO: 5273) |
| βc-3569 21 nt Target: | 5'-ATTTACCCTACCCATACATAT-3' | (SEQ ID NO: 5274) |
| βc-3582 21 nt Target: | 5'-ACACCTCTTACTGATTTACCC-3' | (SEQ ID NO: 5275) |
| βc-3584 21 nt Target: | 5'-TAACACCTCTTACTGATTTAC-3' | (SEQ ID NO: 5276) |
| βc-3585 21 nt Target: | 5'-ATAACACCTCTTACTGATTTA-3' | (SEQ ID NO: 5277) |
| βc-3586 21 nt Target: | 5'-AATAACACCTCTTACTGATTT-3' | (SEQ ID NO: 5278) |
| βc-3587 21 nt Target: | 5'-AAATAACACCTCTTACTGATT-3' | (SEQ ID NO: 5279) |
| βc-3588 21 nt Target: | 5'-CAAATAACACCTCTTACTGAT-3' | (SEQ ID NO: 5280) |

TABLE 10-continued

21 Nucleotide Target Sequences of Additional Selected DsiRNAs

| βc-3594 21 nt Target: | 5'-AGGTTCCAAATAACACCTCTT-3' | (SEQ ID NO: 5281) |
| βc-3600 21 nt Target: | 5'-AAAACAAGGTTCCAAATAACA-3' | (SEQ ID NO: 5282) |
| βc-3601 21 nt Target: | 5'-CAAAACAAGGTTCCAAATAAC-3' | (SEQ ID NO: 5283) |
| βc-3602 21 nt Target: | 5'-CCAAAACAAGGTTCCAAATAA-3' | (SEQ ID NO: 5284) |
| βc-3607 21 nt Target: | 5'-ACTGTCCAAAACAAGGTTCCA-3' | (SEQ ID NO: 5285) |
| βc-3611 21 nt Target: | 5'-GTAAACTGTCCAAAACAAGGT-3' | (SEQ ID NO: 5286) |
| βc-3612 21 nt Target: | 5'-GGTAAACTGTCCAAAACAAGG-3' | (SEQ ID NO: 5287) |
| βc-3620 21 nt Target: | 5'-AGGCAACTGGTAAACTGTCCA-3' | (SEQ ID NO: 5288) |
| βc-3628 21 nt Target: | 5'-GGGATAAAAGGCAACTGGTAA-3' | (SEQ ID NO: 5289) |
| βc-3629 21 nt Target: | 5'-TGGGATAAAAGGCAACTGGTA-3' | (SEQ ID NO: 5290) |
| βc-3636 21 nt Target: | 5'-ACAACTTTGGGATAAAAGGCA-3' | (SEQ ID NO: 5291) |
| βc-3638 21 nt Target: | 5'-CAACAACTTTGGGATAAAAGG-3' | (SEQ ID NO: 5292) |
| βc-3643 21 nt Target: | 5'-GGTTACAACAACTTTGGGATA-3' | (SEQ ID NO: 5293) |
| βc-3644 21 nt Target: | 5'-AGGTTACAACAACTTTGGGAT-3' | (SEQ ID NO: 5294) |
| βc-3645 21 nt Target: | 5'-CAGGTTACAACAACTTTGGGA-3' | (SEQ ID NO: 5295) |
| βc-3653 21 nt Target: | 5'-TATCACAGCAGGTTACAACAA-3' | (SEQ ID NO: 5296) |
| βc-3654 21 nt Target: | 5'-GTATCACAGCAGGTTACAACA-3' | (SEQ ID NO: 5297) |
| βc-3656 21 nt Target: | 5'-TCGTATCACAGCAGGTTACAA-3' | (SEQ ID NO: 5298) |
| βc-3670 21 nt Target: | 5'-TTTCTCTTGAAGCATCGTATC-3' | (SEQ ID NO: 5299) |
| βc-3671 21 nt Target: | 5'-TTTTCTCTTGAAGCATCGTAT-3' | (SEQ ID NO: 5300) |
| βc-3673 21 nt Target: | 5'-CATTTTCTCTTGAAGCATCGT-3' | (SEQ ID NO: 5301) |
| βc-3686 21 nt Target: | 5'-TTTTTTATAACCGCATTTTCT-3' | (SEQ ID NO: 5302) |
| βc-3687 21 nt Target: | 5'-ATTTTTTATAACCGCATTTTC-3' | (SEQ ID NO: 5303) |
| βc-3688 21 nt Target: | 5'-CATTTTTTATAACCGCATTTT-3' | (SEQ ID NO: 5304) |
| βc-3689 21 nt Target: | 5'-CCATTTTTTATAACCGCATTT-3' | (SEQ ID NO: 5305) |
| βc-3694 21 nt Target: | 5'-CTGAACCATTTTTTATAACCG-3' | (SEQ ID NO: 5306) |
| βc-3699 21 nt Target: | 5'-TAATTCTGAACCATTTTTTAT-3' | (SEQ ID NO: 5307) |
| βc-3700 21 nt Target: | 5'-TTAATTCTGAACCATTTTTTA-3' | (SEQ ID NO: 5308) |
| βc-3701 21 nt Target: | 5'-TTTAATTCTGAACCATTTTTT-3' | (SEQ ID NO: 5309) |
| βc-3702 21 nt Target: | 5'-GTTTAATTCTGAACCATTTTT-3' | (SEQ ID NO: 5310) |
| βc-3703 21 nt Target: | 5'-AGTTTAATTCTGAACCATTTT-3' | (SEQ ID NO: 5311) |
| βc-3704 21 nt Target: | 5'-AAGTTTAATTCTGAACCATTT-3' | (SEQ ID NO: 5312) |
| βc-3709 21 nt Target: | 5'-ATTAAAAGTTTAATTCTGAAC-3' | (SEQ ID NO: 5313) |
| βc-3710 21 nt Target: | 5'-AATTAAAAGTTTAATTCTGAA-3' | (SEQ ID NO: 5314) |
| βc-3712 21 nt Target: | 5'-TGAATTAAAAGTTTAATTCTG-3' | (SEQ ID NO: 5315) |
| βc-2634t2 21 nt Target: | 5'-CAATACAGCTAAAGGATGATT-3' | (SEQ ID NO: 5316) |
| βc-2635t2 21 nt Target: | 5'-ACAATACAGCTAAAGGATGAT-3' | (SEQ ID NO: 5317) |
| βc-2637t2 21 nt Target: | 5'-AGACAATACAGCTAAAGGATG-3' | (SEQ ID NO: 5318) |
| βc-2633t3 21 nt Target: | 5'-GTTACTCCTAAAGGATGATTT-3' | (SEQ ID NO: 5319) |

TABLE 10-continued

21 Nucleotide Target Sequences of Additional Selected DsiRNAs

| | | |
|---|---|---|
| βc-2634t3 21 nt Target: | 5'-TGTTACTCCTAAAGGATGATT-3' | (SEQ ID NO: 5320) |
| βc-2635t3 21 nt Target: | 5'-TTGTTACTCCTAAAGGATGAT-3' | (SEQ ID NO: 5321) |
| βc-2636t3 21 nt Target: | 5'-ATTGTTACTCCTAAAGGATGA-3' | (SEQ ID NO: 5322) |
| βc-m318 21 nt Target: | 5'-GGATTCCAGAATCCAAGTAAG-3' | (SEQ ID NO: 5323) |
| βc-m417 21 nt Target: | 5'-CTTGCTCCCATTCATAAAGGA-3' | (SEQ ID NO: 5324) |
| βc-m462 21 nt Target: | 5'-CGTCAATATCAGCTACTTGCT-3' | (SEQ ID NO: 5325) |
| βc-m463 21 nt Target: | 5'-CCGTCAATATCAGCTACTTGC-3' | (SEQ ID NO: 5326) |
| βc-m468 21 nt Target: | 5'-ACTGCCCGTCAATATCAGCTA-3' | (SEQ ID NO: 5327) |
| βc-m613 21 nt Target: | 5'-TGTTTCAACATCTGTGATGGT-3' | (SEQ ID NO: 5328) |
| βc-m614 21 nt Target: | 5'-ATGTTTCAACATCTGTGATGG-3' | (SEQ ID NO: 5329) |
| βc-m624 21 nt Target: | 5'-TGACAACTGCATGTTTCAACA-3' | (SEQ ID NO: 5330) |
| βc-m626 21 nt Target: | 5'-ATTGACAACTGCATGTTTCAA-3' | (SEQ ID NO: 5331) |
| βc-m630 21 nt Target: | 5'-TCAAATTGACAACTGCATGTT-3' | (SEQ ID NO: 5332) |
| βc-m636 21 nt Target: | 5'-AGTTAATCAAATTGACAACTG-3' | (SEQ ID NO: 5333) |
| βc-m642 21 nt Target: | 5'-CCTGATAGTTAATCAAATTGA-3' | (SEQ ID NO: 5334) |
| βc-m648 21 nt Target: | 5'-CGTCATCCTGATAGTTAATCA-3' | (SEQ ID NO: 5335) |
| βc-m649 21 nt Target: | 5'-GCGTCATCCTGATAGTTAATC-3' | (SEQ ID NO: 5336) |
| βc-m702 21 nt Target: | 5'-CCTCATCGTTTAGCAGTTTTG-3' | (SEQ ID NO: 5337) |
| βc-m707 21 nt Target: | 5'-CTGGTCCTCATCGTTTAGCAG-3' | (SEQ ID NO: 5338) |
| βc-m734 21 nt Target: | 5'-CATAACAGCAGCTTTATTAAC-3' | (SEQ ID NO: 5339) |
| βc-m735 21 nt Target: | 5'-CCATAACAGCAGCTTTATTAA-3' | (SEQ ID NO: 5340) |
| βc-m738 21 nt Target: | 5'-GGACCATAACAGCAGCTTTAT-3' | (SEQ ID NO: 5341) |
| βc-m739 21 nt Target: | 5'-TGGACCATAACAGCAGCTTTA-3' | (SEQ ID NO: 5342) |
| βc-m843 21 nt Target: | 5'-CTGTCTCTACATCATTTGTAT-3' | (SEQ ID NO: 5343) |
| βc-m844 21 nt Target: | 5'-GCTGTCTCTACATCATTTGTA-3' | (SEQ ID NO: 5344) |
| βc-m1063 21 nt Target: | 5'-GCAACCATTTTCTGCAGTCCA-3' | (SEQ ID NO: 5345) |
| βc-m1065 21 nt Target: | 5'-AAGCAACCATTTTCTGCAGTC-3' | (SEQ ID NO: 5346) |
| βc-m1080 21 nt Target: | 5'-TTGTTTTGTTGAGCAAAGCAA-3' | (SEQ ID NO: 5347) |
| βc-m1081 21 nt Target: | 5'-TTTGTTTTGTTGAGCAAAGCA-3' | (SEQ ID NO: 5348) |
| βc-m1098 21 nt Target: | 5'-TAGCCAAGAATTTCACGTTTG-3' | (SEQ ID NO: 5349) |
| βc-m1140 21 nt Target: | 5'-CTTGATTGCCATAAGCTAAGA-3' | (SEQ ID NO: 5350) |
| βc-m1145 21 nt Target: | 5'-GCTCTCTTGATTGCCATAAGC-3' | (SEQ ID NO: 5351) |
| βc-m1217 21 nt Target: | 5'-CTTCTCATAAGTGTAGGTCCT-3' | (SEQ ID NO: 5352) |
| βc-m1218 21 nt Target: | 5'-GCTTCTCATAAGTGTAGGTCC-3' | (SEQ ID NO: 5353) |
| βc-m1220 21 nt Target: | 5'-AAGCTTCTCATAAGTGTAGGT-3' | (SEQ ID NO: 5354) |
| βc-m1221 21 nt Target: | 5'-GAAGCTTCTCATAAGTGTAGG-3' | (SEQ ID NO: 5355) |
| βc-m1365 21 nt Target: | 5'-GAGTCCAAAGACAGTTTTGAA-3' | (SEQ ID NO: 5356) |
| βc-m1366 21 nt Target: | 5'-AGAGTCCAAAGACAGTTTTGA-3' | (SEQ ID NO: 5357) |
| βc-m1461 21 nt Target: | 5'-CCACATTTATATCATCGGAAC-3' | (SEQ ID NO: 5358) |

TABLE 10-continued

21 Nucleotide Target Sequences of Additional Selected DsiRNAs

| βc-m1464 21 nt Target: | 5'-TGACCACATTTATATCATCGG-3' (SEQ ID NO: 5359) |
| βc-m1473 21 nt Target: | 5'-CTGCACAGGTGACCACATTTA-3' (SEQ ID NO: 5360) |
| βc-m1474 21 nt Target: | 5'-GCTGCACAGGTGACCACATTT-3' (SEQ ID NO: 5361) |
| βc-m1510 21 nt Target: | 5'-TTGTAATTATTGCAAGTGAGG-3' (SEQ ID NO: 5362) |
| βc-m1523 21 nt Target: | 5'-CATCATCTTGTTTTTGTAATT-3' (SEQ ID NO: 5363) |
| βc-m1524 21 nt Target: | 5'-CCATCATCTTGTTTTTGTAAT-3' (SEQ ID NO: 5364) |
| βc-m1527 21 nt Target: | 5'-ACACCATCATCTTGTTTTTGT-3' (SEQ ID NO: 5365) |
| βc-m1532 21 nt Target: | 5'-TTGGCACACCATCATCTTGTT-3' (SEQ ID NO: 5366) |
| βc-m1752 21 nt Target: | 5'-TCAATCCAACAGTTGCCTTTA-3' (SEQ ID NO: 5367) |
| βc-m1757 21 nt Target: | 5'-TCGAATCAATCCAACAGTTGC-3' (SEQ ID NO: 5368) |
| βc-m1827 21 nt Target: | 5'-GCTGAACTAGTCGTGGAATAG-3' (SEQ ID NO: 5369) |
| βc-m1934 21 nt Target: | 5'-AGTACACCCTTCTACTATCTC-3' (SEQ ID NO: 5370) |
| βc-m1935 21 nt Target: | 5'-CAGTACACCCTTCTACTATCT-3' (SEQ ID NO: 5371) |
| βc-m1936 21 nt Target: | 5'-CCAGTACACCCTTCTACTATC-3' (SEQ ID NO: 5372) |
| βc-m1941 21 nt Target: | 5'-GAGCTCCAGTACACCCTTCTA-3' (SEQ ID NO: 5373) |
| βc-m2009 21 nt Target: | 5'-AAACAATGGAATGGTATTGAG-3' (SEQ ID NO: 5374) |
| βc-m2015 21 nt Target: | 5'-CTGCACAAACAATGGAATGGT-3' (SEQ ID NO: 5375) |
| βc-m2016 21 nt Target: | 5'-ACTGCACAAACAATGGAATGG-3' (SEQ ID NO: 5376) |
| βc-m2021 21 nt Target: | 5'-AAGCAACTGCACAAACAATGG-3' (SEQ ID NO: 5377) |
| βc-m2028 21 nt Target: | 5'-GAGAATAAAGCAACTGCACAA-3' (SEQ ID NO: 5378) |
| βc-m2037 21 nt Target: | 5'-TTTCAATGGGAGAATAAAGCA-3' (SEQ ID NO: 5379) |
| βc-m2038 21 nt Target: | 5'-TTTTCAATGGGAGAATAAAGC-3' (SEQ ID NO: 5380) |
| βc-m2039 21 nt Target: | 5'-ATTTTCAATGGGAGAATAAAG-3' (SEQ ID NO: 5381) |
| βc-m2043 21 nt Target: | 5'-GGATATTTTCAATGGGAGAAT-3' (SEQ ID NO: 5382) |
| βc-m2044 21 nt Target: | 5'-TGGATATTTTCAATGGGAGAA-3' (SEQ ID NO: 5383) |
| βc-m2045 21 nt Target: | 5'-TTGGATATTTTCAATGGGAGA-3' (SEQ ID NO: 5384) |
| βc-m2055 21 nt Target: | 5'-CAGCTACTCTTTGGATATTTT-3' (SEQ ID NO: 5385) |
| βc-m2056 21 nt Target: | 5'-GCAGCTACTCTTTGGATATTT-3' (SEQ ID NO: 5386) |
| βc-m2231 21 nt Target: | 5'-CCGCTTCTTGTAATCCTGTGG-3' (SEQ ID NO: 5387) |
| βc-m2307 21 nt Target: | 5'-CCAGTCCAAGATCTGCAGTCT-3' (SEQ ID NO: 5388) |
| βc-m2385 21 nt Target: | 5'-CGTATCCACCAGAGTGAAAAG-3' (SEQ ID NO: 5389) |
| βc-m2539 21 nt Target: | 5'-CAGGCCAGCTGATTGCTATCA-3' (SEQ ID NO: 5390) |
| βc-m2562 21 nt Target: | 5'-CGATTTACAGGTCAGTATCAA-3' (SEQ ID NO: 5391) |
| βc-m2563 21 nt Target: | 5'-ACGATTTACAGGTCAGTATCA-3' (SEQ ID NO: 5392) |
| βc-m2578 21 nt Target: | 5'-TTTCTTACCTAAAGGACGATT-3' (SEQ ID NO: 5393) |
| βc-m2580 21 nt Target: | 5'-GCTTTCTTACCTAAAGGACGA-3' (SEQ ID NO: 5394) |
| βc-m2589 21 nt Target: | 5'-CTTTTATAAGCTTTCTTACCT-3' (SEQ ID NO: 5395) |
| βc-m2590 21 nt Target: | 5'-GCTTTTATAAGCTTTCTTACC-3' (SEQ ID NO: 5396) |
| βc-m2593 21 nt Target: | 5'-CTGGCTTTTATAAGCTTTCTT-3' (SEQ ID NO: 5397) |

TABLE 10-continued

21 Nucleotide Target Sequences of Additional Selected DsiRNAs

| βc-m2598 21 nt Target: | 5'-CCACACTGGCTTTTATAAGCT-3' | (SEQ ID NO: 5398) |
| βc-m2604 21 nt Target: | 5'-ATTCACCCACACTGGCTTTTA-3' | (SEQ ID NO: 5399) |
| βc-m2644 21 nt Target: | 5'-CCTACCAAGTCTTTCTGGAGT-3' | (SEQ ID NO: 5400) |
| βc-m2674 21 nt Target: | 5'-ATTTACAAACAGGCCTAAAAC-3' | (SEQ ID NO: 5401) |
| βc-m2675 21 nt Target: | 5'-GATTTACAAACAGGCCTAAAA-3' | (SEQ ID NO: 5402) |
| βc-m2676 21 nt Target: | 5'-AGATTTACAAACAGGCCTAAA-3' | (SEQ ID NO: 5403) |
| βc-m2710 21 nt Target: | 5'-CATCTCCTTCCAAGGTATGTA-3' | (SEQ ID NO: 5404) |
| βc-m2711 21 nt Target: | 5'-ACATCTCCTTCCAAGGTATGT-3' | (SEQ ID NO: 5405) |
| βc-m2725 21 nt Target: | 5'-ACTTCCACACATGAACATCTC-3' | (SEQ ID NO: 5406) |
| βc-m2728 21 nt Target: | 5'-GAAACTTCCACACATGAACAT-3' | (SEQ ID NO: 5407) |
| βc-m2729 21 nt Target: | 5'-AGAAACTTCCACACATGAACA-3' | (SEQ ID NO: 5408) |
| βc-m2730 21 nt Target: | 5'-GAGAAACTTCCACACATGAAC-3' | (SEQ ID NO: 5409) |
| βc-m2731 21 nt Target: | 5'-TGAGAAACTTCCACACATGAA-3' | (SEQ ID NO: 5410) |
| βc-m2739 21 nt Target: | 5'-CATCAACGTGAGAAACTTCCA-3' | (SEQ ID NO: 5411) |
| βc-m2742 21 nt Target: | 5'-AAACATCAACGTGAGAAACTT-3' | (SEQ ID NO: 5412) |
| βc-m2743 21 nt Target: | 5'-AAAACATCAACGTGAGAAACT-3' | (SEQ ID NO: 5413) |
| βc-m2744 21 nt Target: | 5'-AAAAACATCAACGTGAGAAAC-3' | (SEQ ID NO: 5414) |
| βc-m2745 21 nt Target: | 5'-CAAAAACATCAACGTGAGAAA-3' | (SEQ ID NO: 5415) |
| βc-m2746 21 nt Target: | 5'-GCAAAAACATCAACGTGAGAA-3' | (SEQ ID NO: 5416) |
| βc-m2748 21 nt Target: | 5'-TGGCAAAAACATCAACGTGAG-3' | (SEQ ID NO: 5417) |
| βc-m2760 21 nt Target: | 5'-CTGCAAAAGCTGTGGCAAAAA-3' | (SEQ ID NO: 5418) |
| βc-m2761 21 nt Target: | 5'-GCTGCAAAAGCTGTGGCAAAA-3' | (SEQ ID NO: 5419) |
| βc-m2778 21 nt Target: | 5'-ACTCATCTGAGTATAACGCTG-3' | (SEQ ID NO: 5420) |
| βc-m2795 21 nt Target: | 5'-TGAAAACAGCAAATGTTACTC-3' | (SEQ ID NO: 5421) |
| βc-m2796 21 nt Target: | 5'-TTGAAAACAGCAAATGTTACT-3' | (SEQ ID NO: 5422) |
| βc-m2797 21 nt Target: | 5'-GTTGAAAACAGCAAATGTTAC-3' | (SEQ ID NO: 5423) |
| βc-m2805 21 nt Target: | 5'-CTATTAATGTTGAAAACAGCA-3' | (SEQ ID NO: 5424) |
| βc-m2834 21 nt Target: | 5'-ACACTACAGCTGTATAGAGAG-3' | (SEQ ID NO: 5425) |
| βc-m2859 21 nt Target: | 5'-CAGGCCAATCACAATGCACGT-3' | (SEQ ID NO: 5426) |
| βc-m2946 21 nt Target: | 5'-CTGTTCCCATAGGAAACTCAG-3' | (SEQ ID NO: 5427) |
| βc-m2968 21 nt Target: | 5'-CAGAACAAAAGCGTACTTCG-3' | (SEQ ID NO: 5428) |
| βc-m2974 21 nt Target: | 5'-AAGGACCAGAACAAAAAGCGT-3' | (SEQ ID NO: 5429) |
| βc-m2982 21 nt Target: | 5'-CGACCAAAAAGGACCAGAACA-3' | (SEQ ID NO: 5430) |
| βc-m2983 21 nt Target: | 5'-TCGACCAAAAAGGACCAGAAC-3' | (SEQ ID NO: 5431) |
| βc-m2990 21 nt Target: | 5'-TTACTCCTCGACCAAAAAGGA-3' | (SEQ ID NO: 5432) |
| βc-m3005 21 nt Target: | 5'-AATCCATTTGTATTGTTACTC-3' | (SEQ ID NO: 5433) |
| βc-m3006 21 nt Target: | 5'-AAATCCATTTGTATTGTTACT-3' | (SEQ ID NO: 5434) |
| βc-m3007 21 nt Target: | 5'-CAAATCCATTTGTATTGTTAC-3' | (SEQ ID NO: 5435) |
| βc-m3008 21 nt Target: | 5'-CCAAATCCATTTGTATTGTTA-3' | (SEQ ID NO: 5436) |

TABLE 10-continued

21 Nucleotide Target Sequences of Additional Selected DsiRNAs

| | | |
|---|---|---|
| βc-m3015 21 nt Target: | 5'-TCACTCCCCAAATCCATTTGT-3' | (SEQ ID NO: 5437) |
| βc-m3047 21 nt Target: | 5'-GATCCATTCGTGTGCATTCTT-3' | (SEQ ID NO: 5438) |
| βc-m3048 21 nt Target: | 5'-TGATCCATTCGTGTGCATTCT-3' | (SEQ ID NO: 5439) |
| βc-m3049 21 nt Target: | 5'-GTGATCCATTCGTGTGCATTC-3' | (SEQ ID NO: 5440) |
| βc-m3093 21 nt Target: | 5'-TAAAACAAAGAACAAGCAAGG-3' | (SEQ ID NO: 5441) |
| βc-m3109 21 nt Target: | 5'-GCACCACTACAGATATTAAAA-3' | (SEQ ID NO: 5442) |
| βc-m3111 21 nt Target: | 5'-CAGCACCACTACAGATATTAA-3' | (SEQ ID NO: 5443) |
| βc-m3112 21 nt Target: | 5'-TCAGCACCACTACAGATATTA-3' | (SEQ ID NO: 5444) |
| βc-m3133 21 nt Target: | 5'-AAAAAATAAAGCAAGCAAAG-3' | (SEQ ID NO: 5445) |
| βc-m3137 21 nt Target: | 5'-CTGCAAAAAATAAAGCAAGC-3' | (SEQ ID NO: 5446) |
| βc-m3142 21 nt Target: | 5'-AGTTACTGCAAAAAATAAAG-3' | (SEQ ID NO: 5447) |
| βc-m3148 21 nt Target: | 5'-ACTAACAGTTACTGCAAAAAA-3' | (SEQ ID NO: 5448) |
| βc-m3150 21 nt Target: | 5'-AAACTAACAGTTACTGCAAAA-3' | (SEQ ID NO: 5449) |
| βc-m3152 21 nt Target: | 5'-AAAAACTAACAGTTACTGCAA-3' | (SEQ ID NO: 5450) |
| βc-m3153 21 nt Target: | 5'-TAAAAACTAACAGTTACTGCA-3' | (SEQ ID NO: 5451) |
| βc-m3155 21 nt Target: | 5'-CTTAAAAACTAACAGTTACTG-3' | (SEQ ID NO: 5452) |
| βc-m3159 21 nt Target: | 5'-ACTACTTAAAAACTAACAGTT-3' | (SEQ ID NO: 5453) |
| βc-m3161 21 nt Target: | 5'-ACACTACTTAAAAACTAACAG-3' | (SEQ ID NO: 5454) |
| βc-m3165 21 nt Target: | 5'-CATAACACTACTTAAAAACTA-3' | (SEQ ID NO: 5455) |
| βc-m3166 21 nt Target: | 5'-ACATAACACTACTTAAAAACT-3' | (SEQ ID NO: 5456) |
| βc-m3168 21 nt Target: | 5'-GAACATAACACTACTTAAAAA-3' | (SEQ ID NO: 5457) |
| βc-m3169 21 nt Target: | 5'-AGAACATAACACTACTTAAAA-3' | (SEQ ID NO: 5458) |
| βc-m3170 21 nt Target: | 5'-TAGAACATAACACTACTTAAA-3' | (SEQ ID NO: 5459) |
| βc-m3171 21 nt Target: | 5'-CTAGAACATAACACTACTTAA-3' | (SEQ ID NO: 5460) |
| βc-m3176 21 nt Target: | 5'-GTTCACTAGAACATAACACTA-3' | (SEQ ID NO: 5461) |
| βc-m3178 21 nt Target: | 5'-AGGTTCACTAGAACATAACAC-3' | (SEQ ID NO: 5462) |
| βc-m3179 21 nt Target: | 5'-CAGGTTCACTAGAACATAACA-3' | (SEQ ID NO: 5463) |
| βc-m3216 21 nt Target: | 5'-CCATTACTCGGTTCTTAGAAA-3' | (SEQ ID NO: 5464) |
| βc-m3219 21 nt Target: | 5'-ACACCATTACTCGGTTCTTAG-3' | (SEQ ID NO: 5465) |
| βc-m3224 21 nt Target: | 5'-GTTCTACACCATTACTCGGTT-3' | (SEQ ID NO: 5466) |
| βc-m3234 21 nt Target: | 5'-ATGAATTAGTGTTCTACACCA-3' | (SEQ ID NO: 5467) |
| βc-m3239 21 nt Target: | 5'-TGATTATGAATTAGTGTTCTA-3' | (SEQ ID NO: 5468) |
| βc-m3240 21 nt Target: | 5'-GTGATTATGAATTAGTGTTCT-3' | (SEQ ID NO: 5469) |
| βc-m3241 21 nt Target: | 5'-CGTGATTATGAATTAGTGTTC-3' | (SEQ ID NO: 5470) |
| βc-m3251 21 nt Target: | 5'-TTACAATTAGCGTGATTATGA-3' | (SEQ ID NO: 5471) |
| βc-m3252 21 nt Target: | 5'-ATTACAATTAGCGTGATTATG-3' | (SEQ ID NO: 5472) |
| βc-m3256 21 nt Target: | 5'-CCAGATTACAATTAGCGTGAT-3' | (SEQ ID NO: 5473) |
| βc-m3267 21 nt Target: | 5'-GTTACACGTCTCCAGATTACA-3' | (SEQ ID NO: 5474) |
| βc-m3269 21 nt Target: | 5'-ATGTTACACGTCTCCAGATTA-3' | (SEQ ID NO: 5475) |

TABLE 10-continued

21 Nucleotide Target Sequences of Additional Selected DsiRNAs

| | | |
|---|---|---|
| βc-m3277 21 nt Target: | 5'-GCTACACAATGTTACACGTCT-3' | (SEQ ID NO: 5476) |
| βc-m3279 21 nt Target: | 5'-AGGCTACACAATGTTACACGT-3' | (SEQ ID NO: 5477) |
| βc-m3286 21 nt Target: | 5'-ATACAAAAGGCTACACAATGT-3' | (SEQ ID NO: 5478) |
| βc-m3287 21 nt Target: | 5'-TATACAAAAGGCTACACAATG-3' | (SEQ ID NO: 5479) |
| βc-m3291 21 nt Target: | 5'-TATTTATACAAAAGGCTACAC-3' | (SEQ ID NO: 5480) |
| βc-m3292 21 nt Target: | 5'-CTATTTATACAAAAGGCTACA-3' | (SEQ ID NO: 5481) |
| βc-m3295 21 nt Target: | 5'-TGTCTATTTATACAAAAGGCT-3' | (SEQ ID NO: 5482) |
| βc-m3296 21 nt Target: | 5'-CTGTCTATTTATACAAAAGGC-3' | (SEQ ID NO: 5483) |
| βc-m3297 21 nt Target: | 5'-TCTGTCTATTTATACAAAAGG-3' | (SEQ ID NO: 5484) |
| βc-m3303 21 nt Target: | 5'-TTTCTATCTGTCTATTTATAC-3' | (SEQ ID NO: 5485) |
| βc-m3304 21 nt Target: | 5'-ATTTCTATCTGTCTATTTATA-3' | (SEQ ID NO: 5486) |
| βc-m3305 21 nt Target: | 5'-CATTTCTATCTGTCTATTTAT-3' | (SEQ ID NO: 5487) |
| βc-m3306 21 nt Target: | 5'-CCATTTCTATCTGTCTATTTA-3' | (SEQ ID NO: 5488) |
| βc-m3310 21 nt Target: | 5'-CGGACCATTTCTATCTGTCTA-3' | (SEQ ID NO: 5489) |
| βc-m3311 21 nt Target: | 5'-TCGGACCATTTCTATCTGTCT-3' | (SEQ ID NO: 5490) |
| βc-m3318 21 nt Target: | 5'-AAACTAATCGGACCATTTCTA-3' | (SEQ ID NO: 5491) |
| βc-m3319 21 nt Target: | 5'-GAAACTAATCGGACCATTTCT-3' | (SEQ ID NO: 5492) |
| βc-m3320 21 nt Target: | 5'-GGAAACTAATCGGACCATTTC-3' | (SEQ ID NO: 5493) |
| βc-m3321 21 nt Target: | 5'-AGGAAACTAATCGGACCATTT-3' | (SEQ ID NO: 5494) |
| βc-m3328 21 nt Target: | 5'-ATTAAAAAGGAAACTAATCGG-3' | (SEQ ID NO: 5495) |
| βc-m3334 21 nt Target: | 5'-AAGCATATTAAAAAGGAAACT-3' | (SEQ ID NO: 5496) |
| βc-m3335 21 nt Target: | 5'-TAAGCATATTAAAAAGGAAAC-3' | (SEQ ID NO: 5497) |
| βc-m3339 21 nt Target: | 5'-ATTTTAAGCATATTAAAAAGG-3' | (SEQ ID NO: 5498) |
| βc-m3345 21 nt Target: | 5'-CTGCTTATTTTAAGCATATTA-3' | (SEQ ID NO: 5499) |
| βc-m3346 21 nt Target: | 5'-CCTGCTTATTTTAAGCATATT-3' | (SEQ ID NO: 5500) |
| βc-m3352 21 nt Target: | 5'-GATCCACCTGCTTATTTTAAG-3' | (SEQ ID NO: 5501) |
| βc-m3367 21 nt Target: | 5'-CAAAAACATGAAATAGATCCA-3' | (SEQ ID NO: 5502) |
| βc-m3368 21 nt Target: | 5'-TCAAAAACATGAAATAGATCC-3' | (SEQ ID NO: 5503) |
| βc-m3370 21 nt Target: | 5'-GTTCAAAAACATGAAATAGAT-3' | (SEQ ID NO: 5504) |
| βc-m3371 21 nt Target: | 5'-TGTTCAAAAACATGAAATAGA-3' | (SEQ ID NO: 5505) |
| βc-m3372 21 nt Target: | 5'-TTGTTCAAAAACATGAAATAG-3' | (SEQ ID NO: 5506) |
| βc-m3377 21 nt Target: | 5'-AGTTTTTGTTCAAAAACATGA-3' | (SEQ ID NO: 5507) |
| βc-m3383 21 nt Target: | 5'-CGATAAAGTTTTTGTTCAAAA-3' | (SEQ ID NO: 5508) |
| βc-m3389 21 nt Target: | 5'-TATCCCCGATAAAGTTTTTGT-3' | (SEQ ID NO: 5509) |
| βc-m3390 21 nt Target: | 5'-GTATCCCCGATAAAGTTTTTG-3' | (SEQ ID NO: 5510) |
| βc-m3419 21 nt Target: | 5'-ACACCTCTTACTGATTTACCC-3' | (SEQ ID NO: 5511) |
| βc-m3421 21 nt Target: | 5'-TAACACCTCTTACTGATTTAC-3' | (SEQ ID NO: 5512) |
| βc-m3422 21 nt Target: | 5'-ATAACACCTCTTACTGATTTA-3' | (SEQ ID NO: 5513) |
| βc-m3423 21 nt Target: | 5'-AATAACACCTCTTACTGATTT-3' | (SEQ ID NO: 5514) |

TABLE 10-continued

21 Nucleotide Target Sequences of Additional Selected DsiRNAs

| | | |
|---|---|---|
| βc-m3424 21 nt Target: | 5'-AAATAACACCTCTTACTGATT-3' | (SEQ ID NO: 5515) |
| βc-m3425 21 nt Target: | 5'-CAAATAACACCTCTTACTGAT-3' | (SEQ ID NO: 5516) |
| βc-m3431 21 nt Target: | 5'-AAGGCTCAAATAACACCTCTT-3' | (SEQ ID NO: 5517) |
| βc-m3436 21 nt Target: | 5'-AAAACAAGGCTCAAATAACAC-3' | (SEQ ID NO: 5518) |
| βc-m3437 21 nt Target: | 5'-CAAAACAAGGCTCAAATAACA-3' | (SEQ ID NO: 5519) |
| βc-m3438 21 nt Target: | 5'-CCAAAACAAGGCTCAAATAAC-3' | (SEQ ID NO: 5520) |
| βc-m3441 21 nt Target: | 5'-TGTCCAAAACAAGGCTCAAAT-3' | (SEQ ID NO: 5521) |
| βc-m3443 21 nt Target: | 5'-ACTGTCCAAAACAAGGCTCAA-3' | (SEQ ID NO: 5522) |
| βc-m3448 21 nt Target: | 5'-GGTATACTGTCCAAAACAAGG-3' | (SEQ ID NO: 5523) |
| βc-m3456 21 nt Target: | 5'-AGGCAACTGGTATACTGTCCA-3' | (SEQ ID NO: 5524) |
| βc-m3464 21 nt Target: | 5'-GGGATAAAAGGCAACTGGTAT-3' | (SEQ ID NO: 5525) |
| βc-m3465 21 nt Target: | 5'-TGGGATAAAAGGCAACTGGTA-3' | (SEQ ID NO: 5526) |
| βc-m3472 21 nt Target: | 5'-ACAACTTTGGGATAAAAGGCA-3' | (SEQ ID NO: 5527) |
| βc-m3474 21 nt Target: | 5'-CAACAACTTTGGGATAAAAGG-3' | (SEQ ID NO: 5528) |
| βc-m3479 21 nt Target: | 5'-GGTTACAACAACTTTGGGATA-3' | (SEQ ID NO: 5529) |
| βc-m3480 21 nt Target: | 5'-AGGTTACAACAACTTTGGGAT-3' | (SEQ ID NO: 5530) |
| βc-m3481 21 nt Target: | 5'-CAGGTTACAACAACTTTGGGA-3' | (SEQ ID NO: 5531) |
| βc-m3489 21 nt Target: | 5'-TATCACAGCAGGTTACAACAA-3' | (SEQ ID NO: 5532) |
| βc-m3490 21 nt Target: | 5'-GTATCACAGCAGGTTACAACA-3' | (SEQ ID NO: 5533) |
| βc-m3492 21 nt Target: | 5'-TTGTATCACAGCAGGTTACAA-3' | (SEQ ID NO: 5534) |
| βc-m3509 21 nt Target: | 5'-CCGCATCTGTTGAAGCATTGT-3' | (SEQ ID NO: 5535) |
| βc-m3527 21 nt Target: | 5'-TCTGAACCATTTCTATAACCG-3' | (SEQ ID NO: 5536) |
| βc-m3531 21 nt Target: | 5'-TAATTCTGAACCATTTCTATA-3' | (SEQ ID NO: 5537) |
| βc-m3533 21 nt Target: | 5'-TTTAATTCTGAACCATTTCTA-3' | (SEQ ID NO: 5538) |
| βc-m3534 21 nt Target: | 5'-GTTTAATTCTGAACCATTTCT-3' | (SEQ ID NO: 5539) |
| βc-m3535 21 nt Target: | 5'-AGTTTAATTCTGAACCATTTC-3' | (SEQ ID NO: 5540) |
| βc-m3536 21 nt Target: | 5'-AAGTTTAATTCTGAACCATTT-3' | (SEQ ID NO: 5541) |
| βc-m3541 21 nt Target: | 5'-ATTAAAAGTTTAATTCTGAAC-3' | (SEQ ID NO: 5542) |
| βc-m3542 21 nt Target: | 5'-AATTAAAAGTTTAATTCTGAA-3' | (SEQ ID NO: 5543) |
| βc-m3544 21 nt Target: | 5'-TGAATTAAAAGTTTAATTCTG-3' | (SEQ ID NO: 5544) |
| βc-m3550 21 nt Target: | 5'-TTTGAATGAATTAAAAGTTTA-3' | (SEQ ID NO: 5545) |
| βc-m3554 21 nt Target: | 5'-TTTTTTTGAATGAATTAAAAG-3' | (SEQ ID NO: 5546) |
| βc-m3558 21 nt Target: | 5'-TTTTTTTTTTTGAATGAATTA-3' | (SEQ ID NO: 5547) |
| βc-m3559 21 nt Target: | 5'-TTTTTTTTTTTTGAATGAATT-3' | (SEQ ID NO: 5548) |
| βc-m3560 21 nt Target: | 5'-TTTTTTTTTTTTTGAATGAAT-3' | (SEQ ID NO: 5549) |
| βc-m3561 21 nt Target: | 5'-TTTTTTTTTTTTTTGAATGAA-3' | (SEQ ID NO: 5550) |
| βc-m3562 21 nt Target: | 5'-TTTTTTTTTTTTTTTGAATGA-3' | (SEQ ID NO: 5551) |
| βc-m3563 21 nt Target: | 5'-TTTTTTTTTTTTTTTTGAATG-3' | (SEQ ID NO: 5552) |

TABLE 11

Additional Selected Anti-β-catenin DsiRNAs, 25/27mer Duplexes, Unmodified

| | | |
|---|---|---|
| βc-244 Target: | 5'-UGUAUGGUAUACUUCAAAUACCCUC-3'<br>3'-CAACAUACCAUAUGAAGUUUAUGGGAG-5'<br>5'-GTTGTATGGTATACTTCAAATACCCTC-3' | (SEQ ID NO: 3823)<br>(SEQ ID NO: 1605)<br>(SEQ ID NO: 2714) |
| βc-251 Target: | 5'-AAACAGUUGUAUGGUAUACUUCAAA-3'<br>3'-GUUUUGUCAACAUACCAUAUGAAGUUU-5'<br>5'-CAAAACAGTTGTATGGTATACTTCAAA-3' | (SEQ ID NO: 3824)<br>(SEQ ID NO: 1606)<br>(SEQ ID NO: 2715) |
| βc-252 Target: | 5'-AAAACAGUUGUAUGGUAUACUUCAA-3'<br>3'-AGUUUUGUCAACAUACCAUAUGAAGUU-5'<br>5'-TCAAAACAGTTGTATGGTATACTTCAA-3' | (SEQ ID NO: 3825)<br>(SEQ ID NO: 1607)<br>(SEQ ID NO: 2716) |
| βc-254 Target: | 5'-UCAAAACAGUUGUAUGGUAUACUUC-3'<br>3'-AAAGUUUUGUCAACAUACCAUAUGAAG-5'<br>5'-TTTCAAAACAGTTGTATGGTATACTTC-3' | (SEQ ID NO: 3826)<br>(SEQ ID NO: 1608)<br>(SEQ ID NO: 2717) |
| βc-255 Target: | 5'-UUCAAAACAGUUGUAUGGUAUACUU-3'<br>3'-AAAAGUUUUGUCAACAUACCAUAUGAA-5'<br>5'-TTTTCAAAACAGTTGTATGGTATACTT-3' | (SEQ ID NO: 3827)<br>(SEQ ID NO: 1609)<br>(SEQ ID NO: 2718) |
| βc-256 Target: | 5'-UUUCAAAACAGUUGUAUGGUAUACU-3'<br>3'-UAAAAGUUUUGUCAACAUACCAUAUGA-5'<br>5'-ATTTTCAAAACAGTTGTATGGTATACT-3' | (SEQ ID NO: 3828)<br>(SEQ ID NO: 1610)<br>(SEQ ID NO: 2719) |
| βc-269 Target: | 5'-GUCCACGCUGGAUUUUCAAAACAGU-3'<br>3'-AACAGGUGCGACCUAAAAGUUUUGUCA-5'<br>5'-TTGTCCACGCTGGATTTTCAAAACAGT-3' | (SEQ ID NO: 3829)<br>(SEQ ID NO: 1611)<br>(SEQ ID NO: 2720) |
| βc-270 Target: | 5'-UGUCCACGCUGGAUUUUCAAAACAG-3'<br>3'-UAACAGGUGCGACCUAAAAGUUUUGUC-5'<br>5'-ATTGTCCACGCTGGATTTTCAAAACAG-3' | (SEQ ID NO: 3830)<br>(SEQ ID NO: 1612)<br>(SEQ ID NO: 2721) |
| βc-293 Target: | 5'-AUCAAAUCAGCUUGAGUAGCCAUUG-3'<br>3'-GGUAGUUUAGUCGAACUCAUCGGUAAC-5'<br>5'-CCATCAAATCAGCTTGAGTAGCCATTG-3' | (SEQ ID NO: 3831)<br>(SEQ ID NO: 1613)<br>(SEQ ID NO: 2722) |
| βc-302 Target: | 5'-UCCAACUCCAUCAAAUCAGCUUGAG-3'<br>3'-ACAGGUUGAGGUAGUUUAGUCGAACUC-5'<br>5'-TGTCCAACTCCATCAAATCAGCTTGAG-3' | (SEQ ID NO: 3832)<br>(SEQ ID NO: 1614)<br>(SEQ ID NO: 2723) |
| βc-431 Target: | 5'-UCCUCAGGAUUGCCUUUACCACUCA-3'<br>3'-GAAGGAGUCCUAACGGAAAUGGUGAGU-5'<br>5'-CTTCCTCAGGATTGCCTTTACCACTCA-3' | (SEQ ID NO: 3833)<br>(SEQ ID NO: 1615)<br>(SEQ ID NO: 2724) |
| βc-432 Target: | 5'-UUCCUCAGGAUUGCCUUUACCACUC-3'<br>3'-AGAAGGAGUCCUAACGGAAAUGGUGAG-5'<br>5'-TCTTCCTCAGGATTGCCTTTACCACTC-3' | (SEQ ID NO: 3834)<br>(SEQ ID NO: 1616)<br>(SEQ ID NO: 2725) |
| βc-518 Target: | 5'-UCAAUAUCAGCUACUUGUUCUUGAG-3'<br>3'-GUAGUUAUAGUCGAUGAACAAGAACUC-5'<br>5'-CATCAATATCAGCTACTTGTTCTTGAG-3' | (SEQ ID NO: 3835)<br>(SEQ ID NO: 1617)<br>(SEQ ID NO: 2726) |
| βc-519 Target: | 5'-AUCAAUAUCAGCUACUUGUUCUUGA-3'<br>3'-GGUAGUUAUAGUCGAUGAACAAGAACU-5'<br>5'-CCATCAATATCAGCTACTTGTTCTTGA-3' | (SEQ ID NO: 3836)<br>(SEQ ID NO: 1618)<br>(SEQ ID NO: 2727) |
| βc-524 Target: | 5'-UGUCCAUCAAUAUCAGCUACUUGUU-3'<br>3'-UGACAGGUAGUUAUAGUCGAUGAACAA-5'<br>5'-ACTGTCCATCAATATCAGCTACTTGTT-3' | (SEQ ID NO: 3837)<br>(SEQ ID NO: 1619)<br>(SEQ ID NO: 2728) |
| βc-531 Target: | 5'-UGCAUACUGUCCAUCAAUAUCAGCU-3'<br>3'-UAACGUAUGACAGGUAGUUAUAGUCGA-5'<br>5'-ATTGCATACTGTCCATCAATATCAGCT-3' | (SEQ ID NO: 3838)<br>(SEQ ID NO: 1620)<br>(SEQ ID NO: 2729) |
| βc-537 Target: | 5'-AGUCAUUGCAUACUGUCCAUCAAUA-3'<br>3'-GCUCAGUAACGUAUGACAGGUAGUUAU-5'<br>5'-CGAGTCATTGCATACTGTCCATCAATA-3' | (SEQ ID NO: 3839)<br>(SEQ ID NO: 1621)<br>(SEQ ID NO: 2730) |
| βc-584 Target: | 5'-UCAUCUAAUGUCUCAGGGAACAUAG-3'<br>3'-GGAGUAGAUUACAGAGUCCCUUGUAUC-5'<br>5'-CCTCATCTAATGTCTCAGGGAACATAG-3' | (SEQ ID NO: 3840)<br>(SEQ ID NO: 1622)<br>(SEQ ID NO: 2731) |
| βc-680 Target: | 5'-ACAACUGCAUGUUUCAGCAUCUGUG-3'<br>3'-AAUGUUGACGUACAAAGUCGUAGACAC-5'<br>5'-TTACAACTGCATGTTTCAGCATCTGTG-3' | (SEQ ID NO: 3841)<br>(SEQ ID NO: 1623)<br>(SEQ ID NO: 2732) |

TABLE 11-continued

Additional Selected Anti-β-catenin DsiRNAs, 25/27mer Duplexes, Unmodified

| | | |
|---|---|---|
| βc-682 Target: | 5'-UUACAACUGCAUGUUUCAGCAUCUG-3'<br>3'-CAAAUGUUGACGUACAAAGUCGUAGAC-5'<br>5'-GTTTACAACTGCATGTTTCAGCATCTG-3' | (SEQ ID NO: 3842)<br>(SEQ ID NO: 1624)<br>(SEQ ID NO: 2733) |
| βc-692 Target: | 5'-UUAAUCAAGUUUACAACUGCAUGUU-3'<br>3'-UCAAUUAGUUCAAAUGUUGACGUACAA-5'<br>5'-AGTTAATCAAGTTTACAACTGCATGTT-3' | (SEQ ID NO: 3843)<br>(SEQ ID NO: 1625)<br>(SEQ ID NO: 2734) |
| βc-698 Target: | 5'-UGAUAGUUAAUCAAGUUUACAACUG-3'<br>3'-GAACUAUCAAUUAGUUCAAAUGUUGAC-5'<br>5'-CTTGATAGTTAATCAAGTTTACAACTG-3' | (SEQ ID NO: 3844)<br>(SEQ ID NO: 1626)<br>(SEQ ID NO: 2735) |
| βc-707 Target: | 5'-GCAUCAUCUUGAUAGUUAAUCAAGU-3'<br>3'-GACGUAGUAGAACUAUCAAUUAGUUCA-5'<br>5'-CTGCATCATCTTGATAGTTAATCAAGT-3' | (SEQ ID NO: 3845)<br>(SEQ ID NO: 1627)<br>(SEQ ID NO: 2736) |
| βc-708 Target: | 5'-UGCAUCAUCUUGAUAGUUAAUCAAG-3'<br>3'-AGACGUAGUAGAACUAUCAAUUAGUUC-5'<br>5'-TCTGCATCATCTTGATAGTTAATCAAG-3' | (SEQ ID NO: 3846)<br>(SEQ ID NO: 1628)<br>(SEQ ID NO: 2737) |
| βc-763 Target: | 5'-GGUCCUCGUCAUUUAGCAGUUUUGU-3'<br>3'-GACCAGGAGCAGUAAAUCGUCAAAACA-5'<br>5'-CTGGTCCTCGTCATTTAGCAGTTTTGT-3' | (SEQ ID NO: 3847)<br>(SEQ ID NO: 1629)<br>(SEQ ID NO: 2738) |
| βc-790 Target: | 5'-UAACUGCAGCCUUAUUAACCACCAC-3'<br>3'-GUAUUGACGUCGGAAUAAUUGGUGGUG-5'<br>5'-CATAACTGCAGCCTTATTAACCACCAC-3' | (SEQ ID NO: 3848)<br>(SEQ ID NO: 1630)<br>(SEQ ID NO: 2739) |
| βc-791 Target: | 5'-AUAACUGCAGCCUUAUUAACCACCA-3'<br>3'-GGUAUUGACGUCGGAAUAAUUGGUGGU-5'<br>5'-CCATAACTGCAGCCTTATTAACCACCA-3' | (SEQ ID NO: 3849)<br>(SEQ ID NO: 1631)<br>(SEQ ID NO: 2740) |
| βc-794 Target: | 5'-ACCAUAACUGCAGCCUUAUUAACCA-3'<br>3'-CCUGGUAUUGACGUCGGAAUAAUUGGU-5'<br>5'-GGACCATAACTGCAGCCTTATTAACCA-3' | (SEQ ID NO: 3850)<br>(SEQ ID NO: 1632)<br>(SEQ ID NO: 2741) |
| βc-812 Target: | 5'-UUUUUAGAAAGCUGAUGGACCAUAA-3'<br>3'-GGAAAAAUCUUUCGACUACCUGGUAUU-5'<br>5'-CCTTTTTAGAAAGCTGATGGACCATAA-3' | (SEQ ID NO: 3851)<br>(SEQ ID NO: 1633)<br>(SEQ ID NO: 2742) |
| βc-873 Target: | 5'-GGUACGUACAAUAGCAGACACCAUC-3'<br>3'-UACCAUGCAUGUUAUCGUCUGUGGUAG-5'<br>5'-ATGGTACGTACAATAGCAGACACCATC-3' | (SEQ ID NO: 3852)<br>(SEQ ID NO: 1634)<br>(SEQ ID NO: 2743) |
| βc-890 Target: | 5'-UCAUUUGUAUUCUGCAUGGUACGUA-3'<br>3'-GUAGUAAACAUAAGACGUACCAUGCAU-5'<br>5'-CATCATTTGTATTCTGCATGGTACGTA-3' | (SEQ ID NO: 3853)<br>(SEQ ID NO: 1635)<br>(SEQ ID NO: 2744) |
| βc-899 Target: | 5'-GUUUCUACAUCAUUUGUAUUCUGCA-3'<br>3'-GACAAAGAUGUAGUAAACAUAAGACGU-5'<br>5'-CTGTTTCTACATCATTTGTATTCTGCA-3' | (SEQ ID NO: 3854)<br>(SEQ ID NO: 1636)<br>(SEQ ID NO: 2745) |
| βc-900 Target: | 5'-UGUUUCUACAUCAUUUGUAUUCUGC-3'<br>3'-CGACAAAGAUGUAGUAAACAUAAGACG-5'<br>5'-GCTGTTTCTACATCATTTGTATTCTGC-3' | (SEQ ID NO: 3855)<br>(SEQ ID NO: 1637)<br>(SEQ ID NO: 2746) |
| βc-909 Target: | 5'-ACAACGAGCUGUUUCUACAUCAUUU-3'<br>3'-CAUGUUGCUCGACAAAGAUGUAGUAAA-5'<br>5'-GTACAACGAGCTGTTTCTACATCATTT-3' | (SEQ ID NO: 3856)<br>(SEQ ID NO: 1638)<br>(SEQ ID NO: 2747) |
| βc-911 Target: | 5'-GUACAACGAGCUGUUUCUACAUCAU-3'<br>3'-GCCAUGUUGCUCGACAAAGAUGUAGUA-5'<br>5'-CGGTACAACGAGCTGTTTCTACATC-3' | (SEQ ID NO: 3857)<br>(SEQ ID NO: 1639)<br>(SEQ ID NO: 2748) |
| βc-912 Target: | 5'-GGUACAACGAGCUGUUUCUACAUCA-3'<br>3'-CGCCAUGUUGCUCGACAAAGAUGUAGU-5'<br>5'-GCGGTACAACGAGCTGTTTCTACATCA-3' | (SEQ ID NO: 3858)<br>(SEQ ID NO: 1640)<br>(SEQ ID NO: 2749) |
| βc-1032 Target: | 5'-AUAAAACAACACAGAAUCCACUGGU-3'<br>3'-CGUAUUUUGUUGUGUCUUAGGUGACCA-5'<br>5'-GCATAAAACAACACAGAATCCACTGGT-3' | (SEQ ID NO: 3859)<br>(SEQ ID NO: 1641)<br>(SEQ ID NO: 2750) |
| βc-1034 Target: | 5'-GCAUAAAACAACACAGAAUCCACUG-3'<br>3'-ACCGUAUUUUGUUGUGUCUUAGGUGAC-5'<br>5'-TGGCATAAAACAACACAGAATCCACTG-3' | (SEQ ID NO: 3860)<br>(SEQ ID NO: 1642)<br>(SEQ ID NO: 2751) |

TABLE 11-continued

Additional Selected Anti-β-catenin DsiRNAs, 25/27mer Duplexes, Unmodified

| | | |
|---|---|---|
| βc-1035 | 5'-GGCAUAAAACAACACAGAAUCCACU-3'<br>3'-UACCGUAUUUGUUGUGUCUUAGGUGA-5'<br>Target: 5'-ATGGCATAAAACAACACAGAATCCACT-3' | (SEQ ID NO: 3861)<br>(SEQ ID NO: 1643)<br>(SEQ ID NO: 2752) |
| βc-1076 | 5'-GCUCCUUCUUGAUGUAAUAAAAGGU-3'<br>3'-AUCGAGGAAGAACUACAUUAUUUUCCA-5'<br>Target: 5'-TAGCTCCTTCTTGATGTAATAAAAGGT-3' | (SEQ ID NO: 3862)<br>(SEQ ID NO: 1644)<br>(SEQ ID NO: 2753) |
| βc-1077 | 5'-AGCUCCUUCUUGAUGUAAUAAAAGG-3'<br>3'-AAUCGAGGAAGAACUACAUUAUUUUCC-5'<br>Target: 5'-TTAGCTCCTTCTTGATGTAATAAAAGG-3' | (SEQ ID NO: 3863)<br>(SEQ ID NO: 1645)<br>(SEQ ID NO: 2754) |
| βc-1144 | 5'-UAACAUUUGUUUUGUUGAGCAAGGC-3'<br>3'-AAAUUGUAAACAAAACAACUCGUUCCG-5'<br>Target: 5'-TTTAACATTTGTTTTGTTGAGCAAGGC-3' | (SEQ ID NO: 3864)<br>(SEQ ID NO: 1646)<br>(SEQ ID NO: 2755) |
| βc-1154 | 5'-GCCAAGAAUUUAACAUUUGUUUUGU-3'<br>3'-AUCGGUUCUUAAAUUGUAAACAAAACA-5'<br>Target: 5'-TAGCCAAGAATTTAACATTTGTTTTGT-3' | (SEQ ID NO: 3865)<br>(SEQ ID NO: 1647)<br>(SEQ ID NO: 2756) |
| βc-1159 | 5'-UAAUAGCCAAGAAUUUAACAUUUGU-3'<br>3'-GCAUUAUCGGUUCUUAAAUUGUAAACA-5'<br>Target: 5'-CGTAATAGCCAAGAATTTAACATTTGT-3' | (SEQ ID NO: 3866)<br>(SEQ ID NO: 1648)<br>(SEQ ID NO: 2757) |
| βc-1160 | 5'-GUAAUAGCCAAGAAUUUAACAUUUG-3'<br>3'-AGCAUUAUCGGUUCUUAAAUUGUAAAC-5'<br>Target: 5'-TCGTAATAGCCAAGAATTTAACATTTG-3' | (SEQ ID NO: 3867)<br>(SEQ ID NO: 1649)<br>(SEQ ID NO: 2758) |
| βc-1185 | 5'-AGCUAAAAUUUGAAGGCAGUCUGUC-3'<br>3'-AUUCGAUUUUAAACUUCCGUCAGACAG-5'<br>Target: 5'-TAAGCTAAAATTTGAAGGCAGTCTGTC-3' | (SEQ ID NO: 3868)<br>(SEQ ID NO: 1650)<br>(SEQ ID NO: 2759) |
| βc-1260 | 5'-GGUCCUCAUUAUAUUUACUAAAGCU-3'<br>3'-AUCCAGGAGUAAUAUAAAUGAUUUCGA-5'<br>Target: 5'-TAGGTCCTCATTATATTTACTAAAGCT-3' | (SEQ ID NO: 3869)<br>(SEQ ID NO: 1651)<br>(SEQ ID NO: 2760) |
| βc-1265 | 5'-GUAUAGGUCCUCAUUAUAUUUACUA-3'<br>3'-UUCAUAUCCAGGAGUAAUAUAAAUGAU-5'<br>Target: 5'-AAGTATAGGTCCTCATTATATTTACTA-3' | (SEQ ID NO: 3870)<br>(SEQ ID NO: 1652)<br>(SEQ ID NO: 2761) |
| βc-1266 | 5'-AGUAUAGGUCCUCAUUAUAUUUACU-3'<br>3'-AUUCAUAUCCAGGAGUAAUAUAAAUGA-5'<br>Target: 5'-TAAGTATAGGTCCTCATTATATTTACT-3' | (SEQ ID NO: 3871)<br>(SEQ ID NO: 1653)<br>(SEQ ID NO: 2762) |
| βc-1274 | 5'-UUUUCGUAAGUAUAGGUCCUCAUUA-3'<br>3'-CAAAAAGCAUUCAUAUCCAGGAGUAAU-5'<br>Target: 5'-GTTTTTCGTAAGTATAGGTCCTCATTA-3' | (SEQ ID NO: 3872)<br>(SEQ ID NO: 1654)<br>(SEQ ID NO: 2763) |
| βc-1275 | 5'-UUUUUCGUAAGUAUAGGUCCUCAUU-3'<br>3'-UCAAAAAGCAUUCAUAUCCAGGAGUAA-5'<br>Target: 5'-AGTTTTTCGTAAGTATAGGTCCTCATT-3' | (SEQ ID NO: 3873)<br>(SEQ ID NO: 1655)<br>(SEQ ID NO: 2764) |
| βc-1276 | 5'-GUUUUUCGUAAGUAUAGGUCCUCAU-3'<br>3'-AUCAAAAAGCAUUCAUAUCCAGGAGUA-5'<br>Target: 5'-TAGTTTTTCGTAAGTATAGGTCCTC-3' | (SEQ ID NO: 3874)<br>(SEQ ID NO: 1656)<br>(SEQ ID NO: 2765) |
| βc-1277 | 5'-AGUUUUUCGUAAGUAUAGGUCCUCA-3'<br>3'-CAUCAAAAAGCAUUCAUAUCCAGGAGU-5'<br>Target: 5'-GTAGTTTTTCGTAAGTATAGGTCCTCA-3' | (SEQ ID NO: 3875)<br>(SEQ ID NO: 1657)<br>(SEQ ID NO: 2766) |
| βc-1287 | 5'-GGUCCACAGUAGUUUUCGUAAGUA-3'<br>3'-CACCAGGUGUCAUCAAAAAGCAUUCAU-5'<br>Target: 5'-GTGGTCCACAGTAGTTTTCGTAAGTA-3' | (SEQ ID NO: 3876)<br>(SEQ ID NO: 1658)<br>(SEQ ID NO: 2767) |
| βc-1344 | 5'-UACAAUAGCCGGCUUAUUACUAGAG-3'<br>3'-AGAUGUUAUCGGCCGAAUAAUGAUCUC-5'<br>Target: 5'-TCTACAATAGCCGGCTTATTACTAGAG-3' | (SEQ ID NO: 3877)<br>(SEQ ID NO: 1659)<br>(SEQ ID NO: 2768) |
| βc-1346 | 5'-UCUACAAUAGCCGGCUUAUUACUAG-3'<br>3'-GAAGAUGUUAUCGGCCGAAUAAUGAUC-5'<br>Target: 5'-CTTCTACAATAGCCGGCTTATTACTAG-3' | (SEQ ID NO: 3878)<br>(SEQ ID NO: 1660)<br>(SEQ ID NO: 2769) |
| βc-1371 | 5'-UCCUAAAGCUUGCAUUCCACCAGCU-3'<br>3'-UCAGGAUUUCGAACGUAAGGUGGUCGA-5'<br>Target: 5'-AGTCCTAAAGCTTGCATTCCACCAGCT-3' | (SEQ ID NO: 3879)<br>(SEQ ID NO: 1661)<br>(SEQ ID NO: 2770) |

TABLE 11-continued

Additional Selected Anti-β-catenin DsiRNAs, 25/27mer Duplexes, Unmodified

| | | |
|---|---|---|
| βc-1372 Target: | 5'-GUCCUAAAGCUUGCAUUCCACCAGC-3'<br>3'-UUCAGGAUUUCGAACGUAAGGUGGUCG-5'<br>5'-AAGTCCTAAAGCTTGCATTCCACCAGC-3' | (SEQ ID NO: 3880)<br>(SEQ ID NO: 1662)<br>(SEQ ID NO: 2771) |
| βc-1373 Target: | 5'-AGUCCUAAAGCUUGCAUUCCACCAG-3'<br>3'-CUUCAGGAUUUCGAACGUAAGGUGGUC-5'<br>5'-GAAGTCCTAAAGCTTGCATTCCACCAG-3' | (SEQ ID NO: 3881)<br>(SEQ ID NO: 1663)<br>(SEQ ID NO: 2772) |
| βc-1410 Target: | 5'-GUUCUGAACAAGACGUUGACUUGGA-3'<br>3'-GUCAAGACUUGUUCUGCAACUGAACCU-5'<br>5'-CAGTTCTGAACAAGACGTTGACTTGGA-3' | (SEQ ID NO: 3882)<br>(SEQ ID NO: 1664)<br>(SEQ ID NO: 2773) |
| βc-1411 Target: | 5'-AGUUCUGAACAAGACGUUGACUUGG-3'<br>3'-UGUCAAGACUUGUUCUGCAACUGAACC-5'<br>5'-ACAGTTCTGAACAAGACGTTGACTTGG-3' | (SEQ ID NO: 3883)<br>(SEQ ID NO: 1665)<br>(SEQ ID NO: 2774) |
| βc-1421 Target: | 5'-GUCCAAAGACAGUUCUGAACAAGAC-3'<br>3'-CUCAGGUUUCUGUCAAGACUUGUUCUG-5'<br>5'-GAGTCCAAAGACAGTTCTGAACAAGAC-3' | (SEQ ID NO: 3884)<br>(SEQ ID NO: 1666)<br>(SEQ ID NO: 2775) |
| βc-1458 Target: | 5'-UUCCUGUUUAGUUGCAGCAUCUGAA-3'<br>3'-GGAAGGACAAAUCAACGUCGUAGACUU-5'<br>5'-CCTTCCTGTTTAGTTGCAGCATCTGAA-3' | (SEQ ID NO: 3885)<br>(SEQ ID NO: 1667)<br>(SEQ ID NO: 2776) |
| βc-1517 Target: | 5'-ACAUUUAUAUCAUCUGAACCCAGAA-3'<br>3'-GGUGUAAAUAUAGUAGACUUGGGUCUU-5'<br>5'-CCACATTTATATCATCTGAACCCAGAA-3' | (SEQ ID NO: 3886)<br>(SEQ ID NO: 1668)<br>(SEQ ID NO: 2777) |
| βc-1520 Target: | 5'-ACCACAUUUAUAUCAUCUGAACCCA-3'<br>3'-ACUGGUGUAAAUAUAGUAGACUUGGGU-5'<br>5'-TGACCACATTTATATCATCTGAACCCA-3' | (SEQ ID NO: 3887)<br>(SEQ ID NO: 1669)<br>(SEQ ID NO: 2778) |
| βc-1529 Target: | 5'-GCACAGGUGACCACAUUUAUAUCAU-3'<br>3'-GACGUGUCCACUGGUGUAAAUAUAGUA-5'<br>5'-CTGCACAGGTGACCACATTTATATC-3' | (SEQ ID NO: 3888)<br>(SEQ ID NO: 1670)<br>(SEQ ID NO: 2779) |
| βc-1530 Target: | 5'-UGCACAGGUGACCACAUUUAUAUCA-3'<br>3'-CGACGUGUCCACUGGUGUAAAUAUAGU-5'<br>5'-GCTGCACAGGTGACCACATTTATATCA-3' | (SEQ ID NO: 3889)<br>(SEQ ID NO: 1671)<br>(SEQ ID NO: 2780) |
| βc-1558 Target: | 5'-UGCAAGUGAGGUUAGAAAGAAUUCC-3'<br>3'-UAACGUUCACUCCAAUCUUUCUUAAGG-5'<br>5'-ATTGCAAGTGAGGTTAGAAAGAATTCC-3' | (SEQ ID NO: 3890)<br>(SEQ ID NO: 1672)<br>(SEQ ID NO: 2781) |
| βc-1566 Target: | 5'-AUAAUUAUUGCAAGUGAGGUUAGAA-3'<br>3'-AAUAUUAAUAACGUUCACUCCAAUCUU-5'<br>5'-TTATAATTATTGCAAGTGAGGTTAGAA-3' | (SEQ ID NO: 3891)<br>(SEQ ID NO: 1673)<br>(SEQ ID NO: 2782) |
| βc-1579 Target: | 5'-UCAUCUUGUUCUUAUAAUUAUUGCA-3'<br>3'-GUAGUAGAACAAGAAUAUUAAUAACGU-5'<br>5'-CATCATCTTGTTCTTATAATTATTGCA-3' | (SEQ ID NO: 3892)<br>(SEQ ID NO: 1674)<br>(SEQ ID NO: 2783) |
| βc-1580 Target: | 5'-AUCAUCUUGUUCUUAUAAUUAUUGC-3'<br>3'-GGUAGUAGAACAAGAAUAUUAAUAACG-5'<br>5'-CCATCATCTTGTTCTTATAATTATTGC-3' | (SEQ ID NO: 3893)<br>(SEQ ID NO: 1675)<br>(SEQ ID NO: 2784) |
| βc-1583 Target: | 5'-ACCAUCAUCUUGUUCUUAUAAUUAU-3'<br>3'-UCUGGUAGUAGAACAAGAAUAUUAAUA-5'<br>5'-AGACCATCATCTTGTTCTTATAATTAT-3' | (SEQ ID NO: 3894)<br>(SEQ ID NO: 1676)<br>(SEQ ID NO: 2785) |
| βc-1585 Target: | 5'-AGACCAUCAUCUUGUUCUUAUAAUU-3'<br>3'-CGUCUGGUAGUAGAACAAGAAUAUUAA-5'<br>5'-GCAGACCATCATCTTGTTCTTATAATT-3' | (SEQ ID NO: 3895)<br>(SEQ ID NO: 1677)<br>(SEQ ID NO: 2786) |
| βc-1808 Target: | 5'-AAUCCAACAGUAGCCUUUAUCAGAG-3'<br>3'-AGUUAGGUUGUCAUCGGAAAUAGUCUC-5'<br>5'-TCAATCCAACAGTAGCCTTTATCAGAG-3' | (SEQ ID NO: 3896)<br>(SEQ ID NO: 1678)<br>(SEQ ID NO: 2787) |
| βc-1813 Target: | 5'-GAAUCAAUCCAACAGUAGCCUUUAU-3'<br>3'-AGCUUAGUUAGGUUGUCAUCGGAAAUA-5'<br>5'-TCGAATCAATCCAACAGTAGCCTTTAT-3' | (SEQ ID NO: 3897)<br>(SEQ ID NO: 1679)<br>(SEQ ID NO: 2788) |
| βc-1955 Target: | 5'-UCCACAAAUUGCUGCUGUGUCCCAC-3'<br>3'-GGAGGUGUUUAACGACGACACAGGGUG-5'<br>5'-CCTCCACAAATTGCTGCTGTGTCCCAC-3' | (SEQ ID NO: 3898)<br>(SEQ ID NO: 1680)<br>(SEQ ID NO: 2789) |

TABLE 11-continued

Additional Selected Anti-β-catenin DsiRNAs, 25/27mer Duplexes, Unmodified

| | | |
|---|---|---|
| βc-1989 Target: | 5'-ACAACCUUCAACUAUUUCUUCCAUG-3'<br>3'-CAUGUUGGAAGUUGAUAAAGAAGGUAC-5'<br>5'-GTACAACCTTCAACTATTTCTTCCATG-3' | (SEQ ID NO: 3899)<br>(SEQ ID NO: 1681)<br>(SEQ ID NO: 2790) |
| βc-1990 Target: | 5'-UACAACCUUCAACUAUUUCUUCCAU-3'<br>3'-CCAUGUUGGAAGUUGAUAAAGAAGGUA-5'<br>5'-GGTACAACCTTCAACTATTTCTTCC-3' | (SEQ ID NO: 3900)<br>(SEQ ID NO: 1682)<br>(SEQ ID NO: 2791) |
| βc-1991 Target: | 5'-GUACAACCUUCAACUAUUUCUUCCA-3'<br>3'-GCCAUGUUGGAAGUUGAUAAAGAAGGU-5'<br>5'-CGGTACAACCTTCAACTATTTCTTCCA-3' | (SEQ ID NO: 3901)<br>(SEQ ID NO: 1683)<br>(SEQ ID NO: 2792) |
| βc-1992 Target: | 5'-GGUACAACCUUCAACUAUUUCUUCC-3'<br>3'-GGCCAUGUUGGAAGUUGAUAAAGAAGG-5'<br>5'-CCGGTACAACCTTCAACTATTTCTTCC-3' | (SEQ ID NO: 3902)<br>(SEQ ID NO: 1684)<br>(SEQ ID NO: 2793) |
| βc-1997 Target: | 5'-GCUCCGGUACAACCUUCAACUAUUU-3'<br>3'-CCCGAGGCCAUGUUGGAAGUUGAUAAA-5'<br>5'-GGGCTCCGGTACAACCTTCAACTATTT-3' | (SEQ ID NO: 3903)<br>(SEQ ID NO: 1685)<br>(SEQ ID NO: 2794) |
| βc-2036 Target: | 5'-ACAAUUCGGUUGUGAACAUCCCGAG-3'<br>3'-AUUGUUAAGCCAACACUUGUAGGGCUC-5'<br>5'-TAACAATTCGGTTGTGAACATCCCGAG-3' | (SEQ ID NO: 3904)<br>(SEQ ID NO: 1686)<br>(SEQ ID NO: 2795) |
| βc-2037 Target: | 5'-AACAAUUCGGUUGUGAACAUCCCGA-3'<br>3'-UAUUGUUAAGCCAACACUUGUAGGGCU-5'<br>5'-ATAACAATTCGGTTGTGAACATCCCGA-3' | (SEQ ID NO: 3905)<br>(SEQ ID NO: 1687)<br>(SEQ ID NO: 2796) |
| βc-2038 Target: | 5'-UAACAAUUCGGUUGUGAACAUCCCG-3'<br>3'-CUAUUGUUAAGCCAACACUUGUAGGGC-5'<br>5'-GATAACAATTCGGTTGTGAACATCCCG-3' | (SEQ ID NO: 3906)<br>(SEQ ID NO: 1688)<br>(SEQ ID NO: 2797) |
| βc-2039 Target: | 5'-AUAACAAUUCGGUUGUGAACAUCCC-3'<br>3'-ACUAUUGUUAAGCCAACACUUGUAGGG-5'<br>5'-TGATAACAATTCGGTTGTGAACATCCC-3' | (SEQ ID NO: 3907)<br>(SEQ ID NO: 1689)<br>(SEQ ID NO: 2798) |
| βc-2040 Target: | 5'-GAUAACAAUUCGGUUGUGAACAUCC-3'<br>3'-GACUAUUGUUAAGCCAACACUUGUAGG-5'<br>5'-CTGATAACAATTCGGTTGTGAACATCC-3' | (SEQ ID NO: 3908)<br>(SEQ ID NO: 1690)<br>(SEQ ID NO: 2799) |
| βc-2041 Target: | 5'-UGAUAACAAUUCGGUUGUGAACAUC-3'<br>3'-AGACUAUUGUUAAGCCAACACUUGUAG-5'<br>5'-TCTGATAACAATTCGGTTGTGAACATC-3' | (SEQ ID NO: 3909)<br>(SEQ ID NO: 1691)<br>(SEQ ID NO: 2800) |
| βc-2052 Target: | 5'-AUUUAGUCCUCUGAUAACAAUUCGG-3'<br>3'-CAUAAAUCAGGAGACUAUUGUUAAGCC-5'<br>5'-GTATTTAGTCCTCTGATAACAATTCGG-3' | (SEQ ID NO: 3910)<br>(SEQ ID NO: 1692)<br>(SEQ ID NO: 2801) |
| βc-2053 Target: | 5'-UAUUUAGUCCUCUGAUAACAAUUCG-3'<br>3'-CCAUAAAUCAGGAGACUAUUGUUAAGC-5'<br>5'-GGTATTTAGTCCTCTGATAACAATTCG-3' | (SEQ ID NO: 3911)<br>(SEQ ID NO: 1693)<br>(SEQ ID NO: 2802) |
| βc-2054 Target: | 5'-GUAUUUAGUCCUCUGAUAACAAUUC-3'<br>3'-ACCAUAAAUCAGGAGACUAUUGUUAAG-5'<br>5'-TGGTATTTAGTCCTCTGATAACAATTC-3' | (SEQ ID NO: 3912)<br>(SEQ ID NO: 1694)<br>(SEQ ID NO: 2803) |
| βc-2055 Target: | 5'-GGUAUUUAGUCCUCUGAUAACAAUU-3'<br>3'-UACCAUAAAUCAGGAGACUAUUGUUAA-5'<br>5'-ATGGTATTTAGTCCTCTGATAACAATT-3' | (SEQ ID NO: 3913)<br>(SEQ ID NO: 1695)<br>(SEQ ID NO: 2804) |
| βc-2065 Target: | 5'-ACAAUGGAAUGGUAUUUAGUCCUCU-3'<br>3'-UUUGUUACCUUACCAUAAAUCAGGAGA-5'<br>5'-AAACAATGGAATGGTATTTAGTCCTCT-3' | (SEQ ID NO: 3914)<br>(SEQ ID NO: 1696)<br>(SEQ ID NO: 2805) |
| βc-2069 Target: | 5'-ACAAACAAUGGAAUGGUAUUUAGUC-3'<br>3'-CGUGUUUGUUACCUUACCAUAAAUCAG-5'<br>5'-GCACAAACAATGGAATGGTATTTAGTC-3' | (SEQ ID NO: 3915)<br>(SEQ ID NO: 1697)<br>(SEQ ID NO: 2806) |
| βc-2071 Target: | 5'-GCACAAACAAUGGAAUGGUAUUUAG-3'<br>3'-GACGUGUUUGUUACCUUACCAUAAAUC-5'<br>5'-CTGCACAAACAATGGAATGGTATTTAG-3' | (SEQ ID NO: 3916)<br>(SEQ ID NO: 1698)<br>(SEQ ID NO: 2807) |
| βc-2072 Target: | 5'-UGCACAAACAAUGGAAUGGUAUUUA-3'<br>3'-CGACGUGUUUGUUACCUUACCAUAAAU-5'<br>5'-GCTGCACAAACAATGGAATGGTATTTA-3' | (SEQ ID NO: 3917)<br>(SEQ ID NO: 1699)<br>(SEQ ID NO: 2808) |

TABLE 11-continued

Additional Selected Anti-β-catenin DsiRNAs, 25/27mer Duplexes, Unmodified

| | | |
|---|---|---|
| βc-2111 Target: | 5'-GCUACUCUUUGGAUGUUUUCAAUGG-3'<br>3'-GUCGAUGAGAAACCUACAAAAGUUACC-5'<br>5'-CAGCTACTCTTTGGATGTTTTCAATGG-3' | (SEQ ID NO: 3918)<br>(SEQ ID NO: 1700)<br>(SEQ ID NO: 2809) |
| βc-2112 Target: | 5'-AGCUACUCUUUGGAUGUUUUCAAUG-3'<br>3'-CGUCGAUGAGAAACCUACAAAAGUUAC-5'<br>5'-GCAGCTACTCTTTGGATGTTTTCAATG-3' | (SEQ ID NO: 3919)<br>(SEQ ID NO: 1701)<br>(SEQ ID NO: 2810) |
| βc-2168 Target: | 5'-GCUUCAAUAGCUUCUGCAGCUUCCU-3'<br>3'-GUCGAAGUUAUCGAAGACGUCGAAGGA-5'<br>5'-CAGCTTCAATAGCTTCTGCAGCTTCCT-3' | (SEQ ID NO: 3920)<br>(SEQ ID NO: 1702)<br>(SEQ ID NO: 2811) |
| βc-2175 Target: | 5'-UCCCUCAGCUUCAAUAGCUUCUGCA-3'<br>3'-CGAGGGAGUCGAAGUUAUCGAAGACGU-5'<br>5'-GCTCCCTCAGCTTCAATAGCTTCTGCA-3' | (SEQ ID NO: 3921)<br>(SEQ ID NO: 1703)<br>(SEQ ID NO: 2812) |
| βc-2177 Target: | 5'-GCUCCCUCAGCUUCAAUAGCUUCUG-3'<br>3'-ACCGAGGGAGUCGAAGUUAUCGAAGAC-5'<br>5'-TGGCTCCCTCAGCTTCAATAGCTTCTG-3' | (SEQ ID NO: 3922)<br>(SEQ ID NO: 1704)<br>(SEQ ID NO: 2813) |
| βc-2214 Target: | 5'-AUUCCUAGAGUGAAGUAACUCUGUC-3'<br>3'-AGUAAGGAUCUCACUUCAUUGAGACAG-5'<br>5'-TCATTCCTAGAGTGAAGTAACTCTGTC-3' | (SEQ ID NO: 3923)<br>(SEQ ID NO: 1705)<br>(SEQ ID NO: 2814) |
| βc-2216 Target: | 5'-UCAUUCCUAGAGUGAAGUAACUCUG-3'<br>3'-GAAGUAAGGAUCUCACUUCAUUGAGAC-5'<br>5'-CTTCATTCCTAGAGTGAAGTAACTCTG-3' | (SEQ ID NO: 3924)<br>(SEQ ID NO: 1706)<br>(SEQ ID NO: 2815) |
| βc-2217 Target: | 5'-UUCAUUCCUAGAGUGAAGUAACUCU-3'<br>3'-GGAAGUAAGGAUCUCACUUCAUUGAGA-5'<br>5'-CCTTCATTCCTAGAGTGAAGTAACTCT-3' | (SEQ ID NO: 3925)<br>(SEQ ID NO: 1707)<br>(SEQ ID NO: 2816) |
| βc-2264 Target: | 5'-UCCUCAGACAUUCGGAACAAAACAG-3'<br>3'-ACAGGAGUCUGUAAGCCUUGUUUUGUC-5'<br>5'-TGTCCTCAGACATTCGGAACAAAACAG-3' | (SEQ ID NO: 3926)<br>(SEQ ID NO: 1708)<br>(SEQ ID NO: 2817) |
| βc-2266 Target: | 5'-UGUCCUCAGACAUUCGGAACAAAAC-3'<br>3'-GAACAGGAGUCUGUAAGCCUUGUUUUG-5'<br>5'-CTTGTCCTCAGACATTCGGAACAAAAC-3' | (SEQ ID NO: 3927)<br>(SEQ ID NO: 1709)<br>(SEQ ID NO: 2818) |
| βc-2287 Target: | 5'-GUUUCUUGUAAUCUUGUGGCUUGUC-3'<br>3'-GGCAAAGAACAUUAGAACACCGAACAG-5'<br>5'-CCGTTTCTTGTAATCTTGTGGCTTGTC-3' | (SEQ ID NO: 3928)<br>(SEQ ID NO: 1710)<br>(SEQ ID NO: 2819) |
| βc-2295 Target: | 5'-UGAAAGCCGUUUCUUGUAAUCUUGU-3'<br>3'-UGACUUUCGGCAAAGAACAUUAGAACA-5'<br>5'-ACTGAAAGCCGTTTCTTGTAATCTTGT-3' | (SEQ ID NO: 3929)<br>(SEQ ID NO: 1711)<br>(SEQ ID NO: 2820) |
| βc-2302 Target: | 5'-GCUCAACUGAAAGCCGUUUCUUGUA-3'<br>3'-GUCGAGUUGACUUUCGGCAAAGAACAU-5'<br>5'-CAGCTCAACTGAAAGCCGTTTCTTGTA-3' | (SEQ ID NO: 3930)<br>(SEQ ID NO: 1712)<br>(SEQ ID NO: 2821) |
| βc-2363 Target: | 5'-AGUCCAAGAUCAGCAGUCUCAUUCC-3'<br>3'-GUUCAGGUUCUAGUCGUCAGAGUAAGG-5'<br>5'-CAAGTCCAAGATCAGCAGTCTCATTCC-3' | (SEQ ID NO: 3931)<br>(SEQ ID NO: 1713)<br>(SEQ ID NO: 2822) |
| βc-2373 Target: | 5'-ACCAAUAUCAAGUCCAAGAUCAGCA-3'<br>3'-CGUGGUUAUAGUUCAGGUUCUAGUCGU-5'<br>5'-GCACCAATATCAAGTCCAAGATCAGCA-3' | (SEQ ID NO: 3932)<br>(SEQ ID NO: 1714)<br>(SEQ ID NO: 2823) |
| βc-2424 Target: | 5'-AGAACGAUAGCUAGGAUCAUCCUGG-3'<br>3'-UUUCUUGCUAUCGAUCCUAGUAGGACC-5'<br>5'-AAAGAACGATAGCTAGGATCATCCTGG-3' | (SEQ ID NO: 3933)<br>(SEQ ID NO: 1715)<br>(SEQ ID NO: 2824) |
| βc-2441 Target: | 5'-UAUCCACCAGAGUGAAAAGAACGAU-3'<br>3'-GUAUAGGUGGUCUCACUUUUCUUGCUA-5'<br>5'-CATATCCACCAGAGTGAAAAGAACGAT-3' | (SEQ ID NO: 3934)<br>(SEQ ID NO: 1716)<br>(SEQ ID NO: 2825) |
| βc-2618 Target: | 5'-AUUUACAGGUCAGUAUCAAACCAGG-3'<br>3'-ACUAAAUGUCCAGUCAUAGUUUGGUCC-5'<br>5'-TGATTTACAGGTCAGTATCAAACCAGG-3' | (SEQ ID NO: 3935)<br>(SEQ ID NO: 1717)<br>(SEQ ID NO: 2826) |
| βc-2619 Target: | 5'-GAUUUACAGGUCAGUAUCAAACCAG-3'<br>3'-UACUAAAUGUCCAGUCAUAGUUUGGUC-5'<br>5'-ATGATTTACAGGTCAGTATCAAACCAG-3' | (SEQ ID NO: 3936)<br>(SEQ ID NO: 1718)<br>(SEQ ID NO: 2827) |

TABLE 11-continued

Additional Selected Anti-β-catenin DsiRNAs, 25/27mer Duplexes, Unmodified

| | | |
|---|---|---|
| βc-2620 Target: | 5'-UGAUUUACAGGUCAGUAUCAAACCA-3'<br>3'-CUACUAAAUGUCCAGUCAUAGUUUGGU-5'<br>5'-GATGATTTACAGGTCAGTATCAAACCA-3' | (SEQ ID NO: 3937)<br>(SEQ ID NO: 1719)<br>(SEQ ID NO: 2828) |
| βc-2634 Target: | 5'-UCUUACCUAAAGGAUGAUUUACAGG-3'<br>3'-GAAGAAUGGAUUUCCUACUAAAUGUCC-5'<br>5'-CTTCTTACCTAAAGGATGATTTACAGG-3' | (SEQ ID NO: 3938)<br>(SEQ ID NO: 1720)<br>(SEQ ID NO: 2829) |
| βc-2635 Target: | 5'-UUCUUACCUAAAGGAUGAUUUACAG-3'<br>3'-UGAAGAAUGGAUUUCCUACUAAAUGUC-5'<br>5'-ACTTCTTACCTAAAGGATGATTTACAG-3' | (SEQ ID NO: 3939)<br>(SEQ ID NO: 1721)<br>(SEQ ID NO: 2830) |
| βc-2637 Target: | 5'-ACUUCUUACCUAAAGGAUGAUUUAC-3'<br>3'-UUUGAAGAAUGGAUUUCCUACUAAAUG-5'<br>5'-AAACTTCTTACCTAAAGGATGATTTAC-3' | (SEQ ID NO: 3940)<br>(SEQ ID NO: 1722)<br>(SEQ ID NO: 2831) |
| βc-2645 Target: | 5'-UUUUUAAAACUUCUUACCUAAAGGA-3'<br>3'-CGAAAAAUUUUGAAGAAUGGAUUUCCU-5'<br>5'-GCTTTTTAAAACTTCTTACCTAAAGGA-3' | (SEQ ID NO: 3941)<br>(SEQ ID NO: 1723)<br>(SEQ ID NO: 2832) |
| βc-2647 Target: | 5'-GCUUUUUAAAACUUCUUACCUAAAG-3'<br>3'-ACCGAAAAAUUUUGAAGAAUGGAUUUC-5'<br>5'-TGGCTTTTTAAAACTTCTTACCTAAAG-3' | (SEQ ID NO: 3942)<br>(SEQ ID NO: 1724)<br>(SEQ ID NO: 2833) |
| βc-2653 Target: | 5'-AAACUGGCUUUUUAAAACUUCUUAC-3'<br>3'-GGUUUGACCGAAAAAUUUUGAAGAAUG-5'<br>5'-CCAAACTGGCTTTTTAAAACTTCTTAC-3' | (SEQ ID NO: 3943)<br>(SEQ ID NO: 1725)<br>(SEQ ID NO: 2834) |
| βc-2657 Target: | 5'-ACCCAAACUGGCUUUUUAAAACUUC-3'<br>3'-AAUGGGUUUGACCGAAAAAUUUUGAAG-5'<br>5'-TTACCCAAACTGGCTTTTTAAAACTTC-3' | (SEQ ID NO: 3944)<br>(SEQ ID NO: 1726)<br>(SEQ ID NO: 2835) |
| βc-2658 Target: | 5'-UACCCAAACUGGCUUUUUAAAACUU-3'<br>3'-AAAUGGGUUUGACCGAAAAAUUUUGAA-5'<br>5'-TTTACCCAAACTGGCTTTTTAAAACTT-3' | (SEQ ID NO: 3945)<br>(SEQ ID NO: 1727)<br>(SEQ ID NO: 2836) |
| βc-2659 Target: | 5'-UUACCCAAACUGGCUUUUUAAAACU-3'<br>3'-AAAAUGGGUUUGACCGAAAAAUUUUGA-5'<br>5'-TTTTACCCAAACTGGCTTTTTAAAACT-3' | (SEQ ID NO: 3946)<br>(SEQ ID NO: 1728)<br>(SEQ ID NO: 2837) |
| βc-2660 Target: | 5'-UUUACCCAAACUGGCUUUUUAAAAC-3'<br>3'-UAAAAUGGGUUUGACCGAAAAAUUUUG-5'<br>5'-ATTTTACCCAAACTGGCTTTTTAAAAC-3' | (SEQ ID NO: 3947)<br>(SEQ ID NO: 1729)<br>(SEQ ID NO: 2838) |
| βc-2701 Target: | 5'-AACCAAGUCUUUCUGAAGUUCUGUA-3'<br>3'-GGUUGGUUCAGAAAGACUUCAAGACAU-5'<br>5'-CCAACCAAGTCTTTCTGAAGTTCTGTA-3' | (SEQ ID NO: 3948)<br>(SEQ ID NO: 1730)<br>(SEQ ID NO: 2839) |
| βc-2709 Target: | 5'-ACCCUACCAACCAAGUCUUUCUGAA-3'<br>3'-GGUGGGAUGGUUGGUUCAGAAAGACUU-5'<br>5'-CCACCCTACCAACCAAGTCTTTCTGAA-3' | (SEQ ID NO: 3949)<br>(SEQ ID NO: 1731)<br>(SEQ ID NO: 2840) |
| βc-2733 Target: | 5'-UUACAAAUAGCCUAAACCACUCCCA-3'<br>3'-UAAAUGUUUAUCGGAUUUGGUGAGGGU-5'<br>5'-ATTTACAAATAGCCTAAACCACTCCCA-3' | (SEQ ID NO: 3950)<br>(SEQ ID NO: 1732)<br>(SEQ ID NO: 2841) |
| βc-2734 Target: | 5'-UUUACAAAUAGCCUAAACCACUCCC-3'<br>3'-CUAAAUGUUUAUCGGAUUUGGUGAGGG-5'<br>5'-GATTTACAAATAGCCTAAACCACTCCC-3' | (SEQ ID NO: 3951)<br>(SEQ ID NO: 1733)<br>(SEQ ID NO: 2842) |
| βc-2735 Target: | 5'-AUUUACAAAUAGCCUAAACCACUCC-3'<br>3'-UCUAAAUGUUUAUCGGAUUUGGUGAGG-5'<br>5'-AGATTTACAAATAGCCTAAACCACTCC-3' | (SEQ ID NO: 3952)<br>(SEQ ID NO: 1734)<br>(SEQ ID NO: 2843) |
| βc-2736 Target: | 5'-GAUUUACAAAUAGCCUAAACCACUC-3'<br>3'-GUCUAAAUGUUUAUCGGAUUUGGUGAG-5'<br>5'-CAGATTTACAAATAGCCTAAACCACTC-3' | (SEQ ID NO: 3953)<br>(SEQ ID NO: 1735)<br>(SEQ ID NO: 2844) |
| βc-2747 Target: | 5'-UUUUUGUGGCAGAUUUACAAAUAGC-3'<br>3'-ACAAAAACACCGUCUAAAUGUUUAUCG-5'<br>5'-TGTTTTTGTGGCAGATTTACAAATAGC-3' | (SEQ ID NO: 3954)<br>(SEQ ID NO: 1736)<br>(SEQ ID NO: 2845) |
| βc-2748 Target: | 5'-GUUUUUGUGGCAGAUUUACAAAUAG-3'<br>3'-GACAAAAACACCGUCUAAAUGUUUAUC-5'<br>5'-CTGTTTTTGTGGCAGATTTACAAATAG-3' | (SEQ ID NO: 3955)<br>(SEQ ID NO: 1737)<br>(SEQ ID NO: 2846) |

TABLE 11-continued

Additional Selected Anti-β-catenin DsiRNAs, 25/27mer Duplexes, Unmodified

| | | |
|---|---|---|
| βc-2749 Target: | 5'-UGUUUUUGUGGCAGAUUUACAAAUA-3'<br>3'-GGACAAAAACACCGUCUAAAUGUUUAU-5'<br>5'-CCTGTTTTTGTGGCAGATTTACAAATA-3' | (SEQ ID NO: 3956)<br>(SEQ ID NO: 1738)<br>(SEQ ID NO: 2847) |
| βc-2754 Target: | 5'-AUACCUGUUUUUGUGGCAGAUUUAC-3'<br>3'-UAUAUGGACAAAAACACCGUCUAAAUG-5'<br>5'-ATATACCTGTTTTTGTGGCAGATTTAC-3' | (SEQ ID NO: 3957)<br>(SEQ ID NO: 1739)<br>(SEQ ID NO: 2848) |
| βc-2764 Target: | 5'-UUCAAAGUAUAUACCUGUUUUGUG-3'<br>3'-GAAAGUUUCAUAUAUGGACAAAAACAC-5'<br>5'-CTTTCAAAGTATATACCTGTTTTTGTG-3' | (SEQ ID NO: 3958)<br>(SEQ ID NO: 1740)<br>(SEQ ID NO: 2849) |
| βc-2770 Target: | 5'-UCUCCUUUCAAAGUAUAUACCUGUU-3'<br>3'-GUAGAGGAAAGUUUCAUAUAUGGACAA-5'<br>5'-CATCTCCTTTCAAAGTATATACCTGTT-3' | (SEQ ID NO: 3959)<br>(SEQ ID NO: 1741)<br>(SEQ ID NO: 2850) |
| βc-2771 Target: | 5'-AUCUCCUUUCAAAGUAUAUACCUGU-3'<br>3'-UGUAGAGGAAAGUUUCAUAUAUGGACA-5'<br>5'-ACATCTCCTTTCAAAGTATATACCTGT-3' | (SEQ ID NO: 3960)<br>(SEQ ID NO: 1742)<br>(SEQ ID NO: 2851) |
| βc-2773 Target: | 5'-ACAUCUCCUUUCAAAGUAUAUACCU-3'<br>3'-UCUGUAGAGGAAAGUUUCAUAUAUGGA-5'<br>5'-AGACATCTCCTTTCAAAGTATATACCT-3' | (SEQ ID NO: 3961)<br>(SEQ ID NO: 1743)<br>(SEQ ID NO: 2852) |
| βc-2774 Target: | 5'-GACAUCUCCUUUCAAAGUAUAUACC-3'<br>3'-UUCUGUAGAGGAAAGUUUCAUAUAUGG-5'<br>5'-AAGACATCTCCTTTCAAAGTATATACC-3' | (SEQ ID NO: 3962)<br>(SEQ ID NO: 1744)<br>(SEQ ID NO: 2853) |
| βc-2775 Target: | 5'-AGACAUCUCCUUUCAAAGUAUAUAC-3'<br>3'-GUUCUGUAGAGGAAAGUUUCAUAUAUG-5'<br>5'-CAAGACATCTCCTTTCAAAGTATATAC-3' | (SEQ ID NO: 3963)<br>(SEQ ID NO: 1745)<br>(SEQ ID NO: 2854) |
| βc-2780 Target: | 5'-UUCCAAGACAUCUCCUUUCAAAGUA-3'<br>3'-ACAAGGUUCUGUAGAGGAAAGUUUCAU-5'<br>5'-TGTTCAAGACATCTCCTTTCAAAGTA-3' | (SEQ ID NO: 3964)<br>(SEQ ID NO: 1746)<br>(SEQ ID NO: 2855) |
| βc-2788 Target: | 5'-UUCCAAUGUUCCAAGACAUCUCCUU-3'<br>3'-GUAAGGUUACAAGGUUCUGUAGAGGAA-5'<br>5'-CATTCCAATGTTCCAAGACATCTCCTT-3' | (SEQ ID NO: 3965)<br>(SEQ ID NO: 1747)<br>(SEQ ID NO: 2856) |
| βc-2789 Target: | 5'-AUUCCAAUGUUCCAAGACAUCUCCU-3'<br>3'-UGUAAGGUUACAAGGUUCUGUAGAGGA-5'<br>5'-ACATTCCAATGTTCCAAGACATCTCCT-3' | (SEQ ID NO: 3966)<br>(SEQ ID NO: 1748)<br>(SEQ ID NO: 2857) |
| βc-2791 Target: | 5'-ACAUUCCAAUGUUCCAAGACAUCUC-3'<br>3'-CUUGUAAGGUUACAAGGUUCUGUAGAG-5'<br>5'-GAACATTCCAATGTTCCAAGACATCTC-3' | (SEQ ID NO: 3967)<br>(SEQ ID NO: 1749)<br>(SEQ ID NO: 2858) |
| βc-2803 Target: | 5'-AGAAAUCUGAGAACAUUCCAAUGUU-3'<br>3'-GGUCUUUAGACUCUUGUAAGGUUACAA-5'<br>5'-CCAGAAATCTGAGAACATTCCAATGTT-3' | (SEQ ID NO: 3968)<br>(SEQ ID NO: 1750)<br>(SEQ ID NO: 2859) |
| βc-2807 Target: | 5'-AACCAGAAAUCUGAGAACAUUCCAA-3'<br>3'-UGUUGGUCUUUAGACUCUUGUAAGGUU-5'<br>5'-ACAACCAGAAATCTGAGAACATTCCAA-3' | (SEQ ID NO: 3969)<br>(SEQ ID NO: 1751)<br>(SEQ ID NO: 2860) |
| βc-2809 Target: | 5'-ACAACCAGAAAUCUGAGAACAUUCC-3'<br>3'-AUUGUUGGUCUUUAGACUCUUGUAAGG-5'<br>5'-TAACAACCAGAAATCTGAGAACATTCC-3' | (SEQ ID NO: 3970)<br>(SEQ ID NO: 1752)<br>(SEQ ID NO: 2861) |
| βc-2810 Target: | 5'-AACAACCAGAAAUCUGAGAACAUUC-3'<br>3'-UAUUGUUGGUCUUUAGACUCUUGUAAG-5'<br>5'-ATAACAACCAGAAATCTGAGAACATTC-3' | (SEQ ID NO: 3971)<br>(SEQ ID NO: 1753)<br>(SEQ ID NO: 2862) |
| βc-2811 Target: | 5'-UAACAACCAGAAAUCUGAGAACAUU-3'<br>3'-GUAUUGUUGGUCUUUAGACUCUUGUAA-5'<br>5'-CATAACAACCAGAAATCTGAGAACATT-3' | (SEQ ID NO: 3972)<br>(SEQ ID NO: 1754)<br>(SEQ ID NO: 2863) |
| βc-2817 Target: | 5'-AUCACAUAACAACCAGAAAUCUGAG-3'<br>3'-ACUAGUGUAUUGUUGGUCUUUAGACUC-5'<br>5'-TGATCACATAACAACCAGAAATCTGAG-3' | (SEQ ID NO: 3973)<br>(SEQ ID NO: 1755)<br>(SEQ ID NO: 2864) |
| βc-2818 Target: | 5'-GAUCACAUAACAACCAGAAAUCUGA-3'<br>3'-UACUAGUGUAUUGUUGGUCUUUAGACU-5'<br>5'-ATGATCACATAACAACCAGAAATCTGA-3' | (SEQ ID NO: 3974)<br>(SEQ ID NO: 1756)<br>(SEQ ID NO: 2865) |

TABLE 11-continued

Additional Selected Anti-β-catenin DsiRNAs, 25/27mer Duplexes, Unmodified

| | | |
|---|---|---|
| βc-2824 Target: | 5'-ACACAUGAUCACAUAACAACCAGAA-3'<br>3'-GGUGUGUACUAGUGUAUUGUUGGUCUU-5'<br>5'-CCACACATGATCACATAACAACCAGAA-3' | (SEQ ID NO: 3975)<br>(SEQ ID NO: 1757)<br>(SEQ ID NO: 2866) |
| βc-2827 Target: | 5'-UCCACACAUGAUCACAUAACAACCA-3'<br>3'-GAAGGUGUGUACUAGUGUAUUGUUGGU-5'<br>5'-CTTCCACACATGATCACATAACAACCA-3' | (SEQ ID NO: 3976)<br>(SEQ ID NO: 1758)<br>(SEQ ID NO: 2867) |
| βc-2832 Target: | 5'-UAACUUCCACACAUGAUCACAUAAC-3'<br>3'-UUAUUGAAGGUGUGUACUAGUGUAUUG-5'<br>5'-AATAACTTCCACACATGATCACATAAC-3' | (SEQ ID NO: 3977)<br>(SEQ ID NO: 1759)<br>(SEQ ID NO: 2868) |
| βc-2833 Target: | 5'-AUAACUUCCACACAUGAUCACAUAA-3'<br>3'-AUUAUUGAAGGUGUGUACUAGUGUAUU-5'<br>5'-TAATAACTTCCACACATGATCACATAA-3' | (SEQ ID NO: 3978)<br>(SEQ ID NO: 1760)<br>(SEQ ID NO: 2869) |
| βc-2834 Target: | 5'-AAUAACUUCCACACAUGAUCACAUA-3'<br>3'-AAUUAUUGAAGGUGUGUACUAGUGUAU-5'<br>5'-TTAATAACTTCCACACATGATCACATA-3' | (SEQ ID NO: 3979)<br>(SEQ ID NO: 1761)<br>(SEQ ID NO: 2870) |
| βc-2835 Target: | 5'-UAAUAACUUCCACACAUGAUCACAU-3'<br>3'-CAAUUAUUGAAGGUGUGUACUAGUGUA-5'<br>5'-GTTAATAACTTCCACACATGATCAC-3' | (SEQ ID NO: 3980)<br>(SEQ ID NO: 1762)<br>(SEQ ID NO: 2871) |
| βc-2842 Target: | 5'-UUAAAGUUAAUAACUUCCACACAUG-3'<br>3'-GUAAUUUCAAUUAUUGAAGGUGUGUAC-5'<br>5'-CATTAAAGTTAATAACTTCCACACATG-3' | (SEQ ID NO: 3981)<br>(SEQ ID NO: 1763)<br>(SEQ ID NO: 2872) |
| βc-2843 Target: | 5'-AUUAAAGUUAAUAACUUCCACACAU-3'<br>3'-UGUAAUUUCAAUUAUUGAAGGUGUGUA-5'<br>5'-ACATTAAAGTTAATAACTTCCACAC-3' | (SEQ ID NO: 3982)<br>(SEQ ID NO: 1764)<br>(SEQ ID NO: 2873) |
| βc-2845 Target: | 5'-ACAUUAAAGUUAAUAACUUCCACAC-3'<br>3'-UUUGUAAUUUCAAUUAUUGAAGGUGUG-5'<br>5'-AAACATTAAAGTTAATAACTTCCAC-3' | (SEQ ID NO: 3983)<br>(SEQ ID NO: 1765)<br>(SEQ ID NO: 2874) |
| βc-2846 Target: | 5'-AACAUUAAAGUUAAUAACUUCCACA-3'<br>3'-UUUUGUAAUUUCAAUUAUUGAAGGUGU-5'<br>5'-AAACATTAAAGTTAATAACTTCCACA-3' | (SEQ ID NO: 3984)<br>(SEQ ID NO: 1766)<br>(SEQ ID NO: 2875) |
| βc-2847 Target: | 5'-AAACAUUAAAGUUAAUAACUUCCAC-3'<br>3'-UUUUUGUAAUUUCAAUUAUUGAAGGUG-5'<br>5'-AAAACATTAAAGTTAATAACTTCCAC-3' | (SEQ ID NO: 3985)<br>(SEQ ID NO: 1767)<br>(SEQ ID NO: 2876) |
| βc-2848 Target: | 5'-AAAACAUUAAAGUUAAUAACUUCCA-3'<br>3'-UUUUUUGUAAUUUCAAUUAUUGAAGGU-5'<br>5'-AAAAACATTAAAGTTAATAACTTCCA-3' | (SEQ ID NO: 3986)<br>(SEQ ID NO: 1768)<br>(SEQ ID NO: 2877) |
| βc-2849 Target: | 5'-AAAACAUUAAAGUUAAUAACUUCC-3'<br>3'-GUUUUUUGUAAUUUCAAUUAUUGAAGG-5'<br>5'-CAAAAAACATTAAAGTTAATAACTTCC-3' | (SEQ ID NO: 3987)<br>(SEQ ID NO: 1769)<br>(SEQ ID NO: 2878) |
| βc-2850 Target: | 5'-AAAAACAUUAAAGUUAAUAACUUC-3'<br>3'-CGUUUUUUGUAAUUUCAAUUAUUGAAG-5'<br>5'-GCAAAAAACATTAAAGTTAATAACTTC-3' | (SEQ ID NO: 3988)<br>(SEQ ID NO: 1770)<br>(SEQ ID NO: 2879) |
| βc-2852 Target: | 5'-GCAAAAACAUUAAAGUUAAUAACU-3'<br>3'-ACCGUUUUUUGUAAUUUCAAUUAUUGA-5'<br>5'-TGGCAAAAAACATTAAAGTTAATAACT-3' | (SEQ ID NO: 3989)<br>(SEQ ID NO: 1771)<br>(SEQ ID NO: 2880) |
| βc-2853 Target: | 5'-GGCAAAAACAUUAAAGUUAAUAAC-3'<br>3'-CACCGUUUUUUGUAAUUUCAAUUAUUG-5'<br>5'-GTGGCAAAAAACATTAAAGTTAATAAC-3' | (SEQ ID NO: 3990)<br>(SEQ ID NO: 1772)<br>(SEQ ID NO: 2881) |
| βc-2864 Target: | 5'-GCAAAGCUGUGGCAAAAACAUUA-3'<br>3'-AACGUUUUCGACACCGUUUUUUGUAAU-5'<br>5'-TTGCAAAAGCTGTGGCAAAAAACATTA-3' | (SEQ ID NO: 3991)<br>(SEQ ID NO: 1773)<br>(SEQ ID NO: 2882) |
| βc-2865 Target: | 5'-UGCAAAAGCUGUGGCAAAAACAUU-3'<br>3'-CAACGUUUUCGACACCGUUUUUUGUAA-5'<br>5'-GTTGCAAAAGCTGTGGCAAAAAACATT-3' | (SEQ ID NO: 3992)<br>(SEQ ID NO: 1774)<br>(SEQ ID NO: 2883) |
| βc-2882 Target: | 5'-UCAUUUGAGUAUUAAGUUGCAAAAG-3'<br>3'-UGAGUAAACUCAUAAUUCAACGUUUUC-5'<br>5'-ACTCATTTGAGTATTAAGTTGCAAAAG-3' | (SEQ ID NO: 3993)<br>(SEQ ID NO: 1775)<br>(SEQ ID NO: 2884) |

TABLE 11-continued

Additional Selected Anti-β-catenin DsiRNAs, 25/27mer Duplexes, Unmodified

| | | |
|---|---|---|
| βc-2899 Target: | 5'-AAAACAGCAAAUGUUACUCAUUUGA-3'<br>3'-AAUUUUGUCGUUUACAAUGAGUAAACU-5'<br>5'-TTAAAACAGCAAATGTTACTCATTTGA-3' | (SEQ ID NO: 3994)<br>(SEQ ID NO: 1776)<br>(SEQ ID NO: 2885) |
| βc-2900 Target: | 5'-UAAAACAGCAAAUGUUACUCAUUUG-3'<br>3'-AAAUUUUGUCGUUUACAAUGAGUAAAC-5'<br>5'-TTTAAAACAGCAAATGTTACTCATTTG-3' | (SEQ ID NO: 3995)<br>(SEQ ID NO: 1777)<br>(SEQ ID NO: 2886) |
| βc-2901 Target: | 5'-UUAAAACAGCAAAUGUUACUCAUUU-3'<br>3'-CAAAUUUUGUCGUUUACAAUGAGUAAA-5'<br>5'-GTTTAAAACAGCAAATGTTACTCATTT-3' | (SEQ ID NO: 3996)<br>(SEQ ID NO: 1778)<br>(SEQ ID NO: 2887) |
| βc-2902 Target: | 5'-UUUAAAACAGCAAAUGUUACUCAUU-3'<br>3'-ACAAAUUUUGUCGUUUACAAUGAGUAA-5'<br>5'-TGTTTAAAACAGCAAATGTTACTCATT-3' | (SEQ ID NO: 3997)<br>(SEQ ID NO: 1779)<br>(SEQ ID NO: 2888) |
| βc-2903 Target: | 5'-GUUUAAAACAGCAAAUGUUACUCAU-3'<br>3'-UACAAAUUUUGUCGUUUACAAUGAGUA-5'<br>5'-ATGTTTAAAACAGCAAATGTTACTC-3' | (SEQ ID NO: 3998)<br>(SEQ ID NO: 1780)<br>(SEQ ID NO: 2889) |
| βc-2904 Target: | 5'-UGUUUAAAACAGCAAAUGUUACUCA-3'<br>3'-UUACAAAUUUUGUCGUUUACAAUGAGU-5'<br>5'-AATGTTTAAAACAGCAAATGTTACTCA-3' | (SEQ ID NO: 3999)<br>(SEQ ID NO: 1781)<br>(SEQ ID NO: 2890) |
| βc-2909 Target: | 5'-AUUAAUGUUUAAAACAGCAAAUGUU-3'<br>3'-GAUAAUUACAAAUUUUGUCGUUUACAA-5'<br>5'-CTATTAATGTTTAAAACAGCAAATGTT-3' | (SEQ ID NO: 4000)<br>(SEQ ID NO: 1782)<br>(SEQ ID NO: 2891) |
| βc-2921 Target: | 5'-AGAAAGGCUGCUAUUAAUGUUUAAA-3'<br>3'-UCUCUUUCCGACGAUAAUUACAAAUUU-5'<br>5'-AGAGAAAGGCTGCTATTAATGTTTAAA-3' | (SEQ ID NO: 4001)<br>(SEQ ID NO: 1783)<br>(SEQ ID NO: 2892) |
| βc-2949 Target: | 5'-AGUUCAGACAAUACAGCUGUAUAAA-3'<br>3'-GUUCAAGUCUGUUAUGUCGACAUAUUU-5'<br>5'-CAAGTTCAGACAATACAGCTGTATAAA-3' | (SEQ ID NO: 4002)<br>(SEQ ID NO: 1784)<br>(SEQ ID NO: 2893) |
| βc-2957 Target: | 5'-ACAAUGCAAGUUCAGACAAUACAGC-3'<br>3'-AGUGUUACGUUCAAGUCUGUUAUGUCG-5'<br>5'-TCACAATGCAAGTTCAGACAATACAGC-3' | (SEQ ID NO: 4003)<br>(SEQ ID NO: 1785)<br>(SEQ ID NO: 2894) |
| βc-2959 Target: | 5'-UCACAAUGCAAGUUCAGACAAUACA-3'<br>3'-UUAGUGUUACGUUCAAGUCUGUUAUGU-5'<br>5'-AATCACAATGCAAGTTCAGACAATACA-3' | (SEQ ID NO: 4004)<br>(SEQ ID NO: 1786)<br>(SEQ ID NO: 2895) |
| βc-2961 Target: | 5'-AAUCACAAUGCAAGUUCAGACAAUA-3'<br>3'-GGUUAGUGUUACGUUCAAGUCUGUUAU-5'<br>5'-CCAATCACAATGCAAGTTCAGACAATA-3' | (SEQ ID NO: 4005)<br>(SEQ ID NO: 1787)<br>(SEQ ID NO: 2896) |
| βc-2965 Target: | 5'-GGCCAAUCACAAUGCAAGUUCAGAC-3'<br>3'-GUCCGGUUAGUGUUACGUUCAAGUCUG-5'<br>5'-CAGGCCAATCACAATGCAAGTTCAGAC-3' | (SEQ ID NO: 4006)<br>(SEQ ID NO: 1788)<br>(SEQ ID NO: 2897) |
| βc-3052 Target: | 5'-GUUCCCAUAGGAAACUCAGCUUGGU-3'<br>3'-AACAAGGGUAUCCUUUGAGUCGAACCA-5'<br>5'-TTGTTCCCATAGGAAACTCAGCTTGGT-3' | (SEQ ID NO: 4007)<br>(SEQ ID NO: 1789)<br>(SEQ ID NO: 2898) |
| βc-3058 Target: | 5'-UCAAUUGUUCCCAUAGGAAACUCAG-3'<br>3'-GAAGUUAACAAGGGUAUCCUUUGAGUC-5'<br>5'-CTTCAATTGTTCCCATAGGAAACTCAG-3' | (SEQ ID NO: 4008)<br>(SEQ ID NO: 1790)<br>(SEQ ID NO: 2899) |
| βc-3059 Target: | 5'-UUCAAUUGUUCCCAUAGGAAACUCA-3'<br>3'-UGAAGUUAACAAGGGUAUCCUUUGAGU-5'<br>5'-ACTTCAATTGTTCCCATAGGAAACTCA-3' | (SEQ ID NO: 4009)<br>(SEQ ID NO: 1791)<br>(SEQ ID NO: 2900) |
| βc-3065 Target: | 5'-GUUUACUUCAAUUGUUCCCAUAGGA-3'<br>3'-UUCAAAUGAAGUUAACAAGGGUAUCCU-5'<br>5'-AAGTTTACTTCAATTGTTCCCATAGGA-3' | (SEQ ID NO: 4010)<br>(SEQ ID NO: 1792)<br>(SEQ ID NO: 2901) |
| βc-3066 Target: | 5'-AGUUUACUUCAAUUGUUCCCAUAGG-3'<br>3'-UUUCAAAUGAAGUUAACAAGGGUAUCC-5'<br>5'-AAAGTTTACTTCAATTGTTCCCATAGG-3' | (SEQ ID NO: 4011)<br>(SEQ ID NO: 1793)<br>(SEQ ID NO: 2902) |
| βc-3070 Target: | 5'-AAAAAGUUUACUUCAAUUGUUCCCA-3'<br>3'-UGUUUUUCAAAUGAAGUUAACAAGGGU-5'<br>5'-ACAAAAAGTTTACTTCAATTGTTCCCA-3' | (SEQ ID NO: 4012)<br>(SEQ ID NO: 1794)<br>(SEQ ID NO: 2903) |

TABLE 11-continued

Additional Selected Anti-β-catenin DsiRNAs, 25/27mer Duplexes, Unmodified

| | | |
|---|---|---|
| βc-3074 Target: | 5'-GAACAAAAGUUUACUUCAAUUGUU-3'<br>3'-GUCUUGUUUUUCAAAUGAAGUUAACAA-5'<br>5'-CAGAACAAAAAGTTTACTTCAATTGTT-3' | (SEQ ID NO: 4013)<br>(SEQ ID NO: 1795)<br>(SEQ ID NO: 2904) |
| βc-3079 Target: | 5'-GACCAGAACAAAAGUUUACUUCAA-3'<br>3'-UCCUGGUCUUGUUUUUCAAAUGAAGUU-5'<br>5'-AGGACCAGAACAAAAAGTTTACTTCAA-3' | (SEQ ID NO: 4014)<br>(SEQ ID NO: 1796)<br>(SEQ ID NO: 2905) |
| βc-3080 Target: | 5'-GGACCAGAACAAAAGUUUACUUCA-3'<br>3'-UUCCUGGUCUUGUUUUUCAAAUGAAGU-5'<br>5'-AAGGACCAGAACAAAAAGTTTACTTCA-3' | (SEQ ID NO: 4015)<br>(SEQ ID NO: 1797)<br>(SEQ ID NO: 2906) |
| βc-3088 Target: | 5'-ACCAAAAAGGACCAGAACAAAAAGU-3'<br>3'-GCUGGUUUUUCCUGGUCUUGUUUUUCA-5'<br>5'-CGACCAAAAAGGACCAGAACAAAAAGT-3' | (SEQ ID NO: 4016)<br>(SEQ ID NO: 1798)<br>(SEQ ID NO: 2907) |
| βc-3089 Target: | 5'-GACCAAAAAGGACCAGAACAAAAAG-3'<br>3'-AGCUGGUUUUUCCUGGUCUUGUUUUUC-5'<br>5'-TCGACCAAAAAGGACCAGAACAAAAAG-3' | (SEQ ID NO: 4017)<br>(SEQ ID NO: 1799)<br>(SEQ ID NO: 2908) |
| βc-3096 Target: | 5'-ACUCCUCGACCAAAAAGGACCAGAA-3'<br>3'-AAUGAGGAGCUGGUUUUUCCUGGUCUU-5'<br>5'-TTACTCCTCGACCAAAAAGGACCAGAA-3' | (SEQ ID NO: 4018)<br>(SEQ ID NO: 1800)<br>(SEQ ID NO: 2909) |
| βc-3111 Target: | 5'-UCCAUUUGUAUUGUUACUCCUCGAC-3'<br>3'-UUAGGUAAACAUAACAAUGAGGAGCUG-5'<br>5'-AATCCATTTGTATTGTTACTCCTCGAC-3' | (SEQ ID NO: 4019)<br>(SEQ ID NO: 1801)<br>(SEQ ID NO: 2910) |
| βc-3112 Target: | 5'-AUCCAUUUGUAUUGUUACUCCUCGA-3'<br>3'-UUUAGGUAAACAUAACAAUGAGGAGCU-5'<br>5'-AAATCCATTTGTATTGTTACTCCTCGA-3' | (SEQ ID NO: 4020)<br>(SEQ ID NO: 1802)<br>(SEQ ID NO: 2911) |
| βc-3113 Target: | 5'-AAUCCAUUUGUAUUGUUACUCCUCG-3'<br>3'-UUUUAGGUAAACAUAACAAUGAGGAGC-5'<br>5'-AAAATCCATTTGTATTGTTACTCCTCG-3' | (SEQ ID NO: 4021)<br>(SEQ ID NO: 1803)<br>(SEQ ID NO: 2912) |
| βc-3114 Target: | 5'-AAAUCCAUUUGUAUUGUUACUCCUC-3'<br>3'-GUUUUAGGUAAACAUAACAAUGAGGAG-5'<br>5'-CAAAATCCATTTGTATTGTTACTCCTC-3' | (SEQ ID NO: 4022)<br>(SEQ ID NO: 1804)<br>(SEQ ID NO: 2913) |
| βc-3115 Target: | 5'-AAAAUCCAUUUGUAUUGUUACUCCU-3'<br>3'-GGUUUUAGGUAAACAUAACAAUGAGGA-5'<br>5'-CCAAAATCCATTTGTATTGTTACTCCT-3' | (SEQ ID NO: 4023)<br>(SEQ ID NO: 1805)<br>(SEQ ID NO: 2914) |
| βc-3121 Target: | 5'-ACUCCCAAAAUCCAUUUGUAUUGUU-3'<br>3'-AGUGAGGGUUUUAGGUAAACAUAACAA-5'<br>5'-TCACTCCCAAAATCCATTTGTATTGTT-3' | (SEQ ID NO: 4024)<br>(SEQ ID NO: 1806)<br>(SEQ ID NO: 2915) |
| βc-3136 Target: | 5'-UUCACUUCUUGAGUCACUCCCAAAA-3'<br>3'-AGAAGUGAAGAACUCAGUGAGGGUUUU-5'<br>5'-TCTTCACTTCTTGAGTCACTCCCAAAA-3' | (SEQ ID NO: 4025)<br>(SEQ ID NO: 1807)<br>(SEQ ID NO: 2916) |
| βc-3138 Target: | 5'-UCUUCACUUCUUGAGUCACUCCCAA-3'<br>3'-UAAGAAGUGAAGAACUCAGUGAGGGUU-5'<br>5'-ATTCTTCACTTCTTGAGTCACTCCCAA-3' | (SEQ ID NO: 4026)<br>(SEQ ID NO: 1808)<br>(SEQ ID NO: 2917) |
| βc-3139 Target: | 5'-UUCUUCACUUCUUGAGUCACUCCCA-3'<br>3'-GUAAGAAGUGAAGAACUCAGUGAGGGU-5'<br>5'-CATTCTTCACTTCTTGAGTCACTCCCA-3' | (SEQ ID NO: 4027)<br>(SEQ ID NO: 1809)<br>(SEQ ID NO: 2918) |
| βc-3140 Target: | 5'-AUUCUUCACUUCUUGAGUCACUCCC-3'<br>3'-CGUAAGAAGUGAAGAACUCAGUGAGGG-5'<br>5'-GCATTCTTCACTTCTTGAGTCACTCCC-3' | (SEQ ID NO: 4028)<br>(SEQ ID NO: 1810)<br>(SEQ ID NO: 2919) |
| βc-3142 Target: | 5'-GCAUUCUUCACUUCUUGAGUCACUC-3'<br>3'-CACGUAAGAAGUGAAGAACUCAGUGAG-5'<br>5'-GTGCATTCTTCACTTCTTGAGTCACTC-3' | (SEQ ID NO: 4029)<br>(SEQ ID NO: 1811)<br>(SEQ ID NO: 2920) |
| βc-3150 Target: | 5'-AUUCUUGUGCAUUCUUCACUUCUUG-3'<br>3'-GGUAAGAACACGUAAGAAGUGAAGAAC-5'<br>5'-CCATTCTTGTGCATTCTTCACTTCTTG-3' | (SEQ ID NO: 4030)<br>(SEQ ID NO: 1812)<br>(SEQ ID NO: 2921) |
| βc-3153 Target: | 5'-UCCAUUCUUGUGCAUUCUUCACUUC-3'<br>3'-CUAGGUAAGAACACGUAAGAAGUGAAG-5'<br>5'-GATCCATTCTTGTGCATTCTTCACTTC-3' | (SEQ ID NO: 4031)<br>(SEQ ID NO: 1813)<br>(SEQ ID NO: 2922) |

TABLE 11-continued

Additional Selected Anti-β-catenin DsiRNAs, 25/27mer Duplexes, Unmodified

| | | | |
|---|---|---|---|
| βc-3154 | Target: | 5'-AUCCAUUCUUGUGCAUUCUUCACUU-3'<br>3'-ACUAGGUAAGAACACGUAAGAAGUGAA-5'<br>5'-TGATCCATTCTTGTGCATTCTTCACTT-3' | (SEQ ID NO: 4032)<br>(SEQ ID NO: 1814)<br>(SEQ ID NO: 2923) |
| βc-3155 | Target: | 5'-GAUCCAUUCUUGUGCAUUCUUCACU-3'<br>3'-CACUAGGUAAGAACACGUAAGAAGUGA-5'<br>5'-GTGATCCATTCTTGTGCATTCTTCACT-3' | (SEQ ID NO: 4033)<br>(SEQ ID NO: 1815)<br>(SEQ ID NO: 2924) |
| βc-3168 | Target: | 5'-AAUUCCAUCUUGUGAUCCAUUCUUG-3'<br>3'-AUUUAAGGUAGAACACUAGGUAAGAAC-5'<br>5'-TAAATTCCATCTTGTGATCCATTCTTG-3' | (SEQ ID NO: 4034)<br>(SEQ ID NO: 1816)<br>(SEQ ID NO: 2925) |
| βc-3170 | Target: | 5'-UAAAUUCCAUCUUGUGAUCCAUUCU-3'<br>3'-CUAUUUAAGGUAGAACACUAGGUAAGA-5'<br>5'-GATAAATTCCATCTTGTGATCCATTCT-3' | (SEQ ID NO: 4035)<br>(SEQ ID NO: 1817)<br>(SEQ ID NO: 2926) |
| βc-3171 | Target: | 5'-AUAAAUUCCAUCUUGUGAUCCAUUC-3'<br>3'-ACUAUUUAAGGUAGAACACUAGGUAAG-5'<br>5'-TGATAAATTCCATCTTGTGATCCATTC-3' | (SEQ ID NO: 4036)<br>(SEQ ID NO: 1818)<br>(SEQ ID NO: 2927) |
| βc-3172 | Target: | 5'-GAUAAAUUCCAUCUUGUGAUCCAUU-3'<br>3'-AACUAUUUAAGGUAGAACACUAGGUAA-5'<br>5'-TTGATAAATTCCATCTTGTGATCCATT-3' | (SEQ ID NO: 4037)<br>(SEQ ID NO: 1819)<br>(SEQ ID NO: 2928) |
| βc-3173 | Target: | 5'-UGAUAAAUUCCAUCUUGUGAUCCAU-3'<br>3'-AAACUAUUUAAGGUAGAACACUAGGUA-5'<br>5'-TTTGATAAATTCCATCTTGTGATCC-3' | (SEQ ID NO: 4038)<br>(SEQ ID NO: 1820)<br>(SEQ ID NO: 2929) |
| βc-3183 | Target: | 5'-GGCUAGGGUUUGAUAAAUUCCAUCU-3'<br>3'-UUCCGAUCCCAAACUAUUUAAGGUAGA-5'<br>5'-AAGGCTAGGGTTTGATAAATTCCATCT-3' | (SEQ ID NO: 4039)<br>(SEQ ID NO: 1821)<br>(SEQ ID NO: 2930) |
| βc-3200 | Target: | 5'-AAAAAUUUAACAAGCAAGGCUAGGG-3'<br>3'-UUUUUUUAAAUUGUUCGUUCCGAUCCC-5'<br>5'-AAAAAAATTTAACAAGCAAGGCTAGGG-3' | (SEQ ID NO: 4040)<br>(SEQ ID NO: 1822)<br>(SEQ ID NO: 2931) |
| βc-3209 | Target: | 5'-AAAAAAAAAAAAAAUUUAACAAGCA-3'<br>3'-UUUUUUUUUUUUUUUUAAAUUGUUCGU-5'<br>5'-AAAAAAAAAAAAAAATTTAACAAGCA-3' | (SEQ ID NO: 4041)<br>(SEQ ID NO: 1823)<br>(SEQ ID NO: 2932) |
| βc-3210 | Target: | 5'-AAAAAAAAAAAAAAAUUUAACAAGC-3'<br>3'-UUUUUUUUUUUUUUUUUAAAUUGUUCG-5'<br>5'-AAAAAAAAAAAAAAAATTTAACAAGC-3' | (SEQ ID NO: 4042)<br>(SEQ ID NO: 1824)<br>(SEQ ID NO: 2933) |
| βc-3211 | Target: | 5'-AAAAAAAAAAAAAAAAUUUAACAAG-3'<br>3'-UUUUUUUUUUUUUUUUUUAAAUUGUUC-5'<br>5'-AAAAAAAAAAAAAAAAATTTAACAAG-3' | (SEQ ID NO: 4043)<br>(SEQ ID NO: 1825)<br>(SEQ ID NO: 2934) |
| βc-3212 | Target: | 5'-AAAAAAAAAAAAAAAAAUUUAACAA-3'<br>3'-UUUUUUUUUUUUUUUUUUUAAAUUGUU-5'<br>5'-AAAAAAAAAAAAAAAAAATTTAACAA-3' | (SEQ ID NO: 4044)<br>(SEQ ID NO: 1826)<br>(SEQ ID NO: 2935) |
| βc-3213 | Target: | 5'-AAAAAAAAAAAAAAAAAAUUUAACA-3'<br>3'-AUUUUUUUUUUUUUUUUUUUAAAUUGU-5'<br>5'-TAAAAAAAAAAAAAAAAAAATTTAACA-3' | (SEQ ID NO: 4045)<br>(SEQ ID NO: 1827)<br>(SEQ ID NO: 2936) |
| βc-3214 | Target: | 5'-AAAAAAAAAAAAAAAAAAAUUUAAC-3'<br>3'-AAUUUUUUUUUUUUUUUUUUUUAAAUUG-5'<br>5'-TTAAAAAAAAAAAAAAAAAAATTTAAC-3' | (SEQ ID NO: 4046)<br>(SEQ ID NO: 1828)<br>(SEQ ID NO: 2937) |
| βc-3215 | Target: | 5'-UAAAAAAAAAAAAAAAAAAAUUUAA-3'<br>3'-GAAUUUUUUUUUUUUUUUUUUUUAAAUU-5'<br>5'-CTTAAAAAAAAAAAAAAAAAAAATTTAA-3' | (SEQ ID NO: 4047)<br>(SEQ ID NO: 1829)<br>(SEQ ID NO: 2938) |
| βc-3216 | Target: | 5'-UUAAAAAAAAAAAAAAAAAAAUUUA-3'<br>3'-AGAAUUUUUUUUUUUUUUUUUUUUUAAAU-5'<br>5'-TCTTAAAAAAAAAAAAAAAAAAAATTTA-3' | (SEQ ID NO: 4048)<br>(SEQ ID NO: 1830)<br>(SEQ ID NO: 2939) |
| βc-3218 | Target: | 5'-UCUUAAAAAAAAAAAAAAAAAAAUU-3'<br>3'-UAAGAAUUUUUUUUUUUUUUUUUUUUAA-5'<br>5'-ATTCTTAAAAAAAAAAAAAAAAAAAATT-3' | (SEQ ID NO: 4049)<br>(SEQ ID NO: 1831)<br>(SEQ ID NO: 2940) |
| βc-3219 | Target: | 5'-UUCUUAAAAAAAAAAAAAAAAAAAU-3'<br>3'-AUAAGAAUUUUUUUUUUUUUUUUUUUUA-5'<br>5'-TATTCTTAAAAAAAAAAAAAAAAAAAAT-3' | (SEQ ID NO: 4050)<br>(SEQ ID NO: 1832)<br>(SEQ ID NO: 2941) |

TABLE 11-continued

Additional Selected Anti-β-catenin DsiRNAs, 25/27mer Duplexes, Unmodified

| | | |
|---|---|---|
| βc-3220 Target: | 5'-AUUCUUAAAAAAAAAAAAAAAAA-3'<br>3'-UAUAAGAAUUUUUUUUUUUUUUUUU-5'<br>5'-ATATTCTTAAAAAAAAAAAAAAAAA-3' | (SEQ ID NO: 4051)<br>(SEQ ID NO: 1833)<br>(SEQ ID NO: 2942) |
| βc-3221 Target: | 5'-UAUUCUUAAAAAAAAAAAAAAAAA-3'<br>3'-CUAUAAGAAUUUUUUUUUUUUUUUU-5'<br>5'-GATATTCTTAAAAAAAAAAAAAAAA-3' | (SEQ ID NO: 4052)<br>(SEQ ID NO: 1834)<br>(SEQ ID NO: 2943) |
| βc-3222 Target: | 5'-AUAUUCUUAAAAAAAAAAAAAAAA-3'<br>3'-UCUAUAAGAAUUUUUUUUUUUUUUU-5'<br>5'-AGATATTCTTAAAAAAAAAAAAAAA-3' | (SEQ ID NO: 4053)<br>(SEQ ID NO: 1835)<br>(SEQ ID NO: 2944) |
| βc-3223 Target: | 5'-GAUAUUCUUAAAAAAAAAAAAAAA-3'<br>3'-GUCUAUAAGAAUUUUUUUUUUUUUU-5'<br>5'-CAGATATTCTTAAAAAAAAAAAAAA-3' | (SEQ ID NO: 4054)<br>(SEQ ID NO: 1836)<br>(SEQ ID NO: 2945) |
| βc-3224 Target: | 5'-AGAUAUUCUUAAAAAAAAAAAAAA-3'<br>3'-UGUCUAUAAGAAUUUUUUUUUUUUU-5'<br>5'-ACAGATATTCTTAAAAAAAAAAAAA-3' | (SEQ ID NO: 4055)<br>(SEQ ID NO: 1837)<br>(SEQ ID NO: 2946) |
| βc-3228 Target: | 5'-UUACAGAUAUUCUUAAAAAAAAAA-3'<br>3'-GUAAUGUCUAUAAGAAUUUUUUUUU-5'<br>5'-CATTACAGATATTCTTAAAAAAAAA-3' | (SEQ ID NO: 4056)<br>(SEQ ID NO: 1838)<br>(SEQ ID NO: 2947) |
| βc-3229 Target: | 5'-AUUACAGAUAUUCUUAAAAAAAAA-3'<br>3'-GGUAAUGUCUAUAAGAAUUUUUUUU-5'<br>5'-CCATTACAGATATTCTTAAAAAAAAA-3' | (SEQ ID NO: 4057)<br>(SEQ ID NO: 1839)<br>(SEQ ID NO: 2948) |
| βc-3233 Target: | 5'-UACCAUUACAGAUAUUCUUAAAAA-3'<br>3'-UCAUGGUAAUGUCUAUAAGAAUUUUU-5'<br>5'-AGTACCATTACAGATATTCTTAAAAA-3' | (SEQ ID NO: 4058)<br>(SEQ ID NO: 1840)<br>(SEQ ID NO: 2949) |
| βc-3234 Target: | 5'-GUACCAUUACAGAUAUUCUUAAAA-3'<br>3'-GUCAUGGUAAUGUCUAUAAGAAUUUUU-5'<br>5'-CAGTACCATTACAGATATTCTTAAAAA-3' | (SEQ ID NO: 4059)<br>(SEQ ID NO: 1841)<br>(SEQ ID NO: 2950) |
| βc-3235 Target: | 5'-AGUACCAUUACAGAUAUUCUUAAAA-3'<br>3'-AGUCAUGGUAAUGUCUAUAAGAAUUUU-5'<br>5'-TCAGTACCATTACAGATATTCTTAAAA-3' | (SEQ ID NO: 4060)<br>(SEQ ID NO: 1842)<br>(SEQ ID NO: 2951) |
| βc-3239 Target: | 5'-AGUCAGUACCAUUACAGAUAUUCUU-3'<br>3'-UUUCAGUCAUGGUAAUGUCUAUAAGAA-5'<br>5'-AAAGTCAGTACCATTACAGATATTCTT-3' | (SEQ ID NO: 4061)<br>(SEQ ID NO: 1843)<br>(SEQ ID NO: 2952) |
| βc-3256 Target: | 5'-UACUUCAAAGCAAGCAAAGUCAGUA-3'<br>3'-CGAUGAAGUUUCGUUCGUUUCAGUCAU-5'<br>5'-GCTACTTCAAAGCAAGCAAAGTCAGTA-3' | (SEQ ID NO: 4062)<br>(SEQ ID NO: 1844)<br>(SEQ ID NO: 2953) |
| βc-3265 Target: | 5'-AAAAAGAGCUACUUCAAAGCAAGCA-3'<br>3'-UUUUUUUCUCGAUGAAGUUUCGUUCGU-5'<br>5'-AAAAAAAGAGCTACTTCAAAGCAAGCA-3' | (SEQ ID NO: 4063)<br>(SEQ ID NO: 1845)<br>(SEQ ID NO: 2954) |
| βc-3270 Target: | 5'-AAAAAAAAAAGAGCUACUUCAAAGC-3'<br>3'-UUUUUUUUUUUCUCGAUGAAGUUUCG-5'<br>5'-AAAAAAAAAAAGAGCTACTTCAAAGC-3' | (SEQ ID NO: 4064)<br>(SEQ ID NO: 1846)<br>(SEQ ID NO: 2955) |
| βc-3271 Target: | 5'-AAAAAAAAAAAGAGCUACUUCAAAG-3'<br>3'-UUUUUUUUUUUUCUCGAUGAAGUUUC-5'<br>5'-AAAAAAAAAAAAGAGCTACTTCAAAG-3' | (SEQ ID NO: 4065)<br>(SEQ ID NO: 1847)<br>(SEQ ID NO: 2956) |
| βc-3273 Target: | 5'-AAAAAAAAAAAAAGAGCUACUUCAA-3'<br>3'-UUUUUUUUUUUUUUCUCGAUGAAGUU-5'<br>5'-AAAAAAAAAAAAAAGAGCTACTTCAA-3' | (SEQ ID NO: 4066)<br>(SEQ ID NO: 1848)<br>(SEQ ID NO: 2957) |
| βc-3274 Target: | 5'-AAAAAAAAAAAAAAGAGCUACUUCA-3'<br>3'-UUUUUUUUUUUUUUUCUCGAUGAAGU-5'<br>5'-AAAAAAAAAAAAAAAGAGCTACTTCA-3' | (SEQ ID NO: 4067)<br>(SEQ ID NO: 1849)<br>(SEQ ID NO: 2958) |
| βc-3275 Target: | 5'-AAAAAAAAAAAAAAAGAGCUACUUC-3'<br>3'-UUUUUUUUUUUUUUUUCUCGAUGAAG-5'<br>5'-AAAAAAAAAAAAAAAAGAGCTACTTC-3' | (SEQ ID NO: 4068)<br>(SEQ ID NO: 1850)<br>(SEQ ID NO: 2959) |
| βc-3276 Target: | 5'-AAAAAAAAAAAAAAAAGAGCUACUU-3'<br>3'-UUUUUUUUUUUUUUUUUCUCGAUGAA-5'<br>5'-AAAAAAAAAAAAAAAAAGAGCTACTT-3' | (SEQ ID NO: 4069)<br>(SEQ ID NO: 1851)<br>(SEQ ID NO: 2960) |

TABLE 11-continued

Additional Selected Anti-β-catenin DsiRNAs, 25/27mer Duplexes, Unmodified

| | | |
|---|---|---|
| βc-3282 Target: | 5'-AAAAAAAAAAAAAAAAAAAAAAGAG-3'<br>3'-UUUUUUUUUUUUUUUUUUUUUUCUC-5'<br>5'-AAAAAAAAAAAAAAAAAAAAAAAGAG-3' | (SEQ ID NO: 4070)<br>(SEQ ID NO: 1852)<br>(SEQ ID NO: 2961) |
| βc-3283 Target: | 5'-AAAAAAAAAAAAAAAAAAAAAAGA-3'<br>3'-UUUUUUUUUUUUUUUUUUUUUUUCU-5'<br>5'-AAAAAAAAAAAAAAAAAAAAAAAAGA-3' | (SEQ ID NO: 4071)<br>(SEQ ID NO: 1853)<br>(SEQ ID NO: 2962) |
| βc-3284 Target: | 5'-AAAAAAAAAAAAAAAAAAAAAAAG-3'<br>3'-GUUUUUUUUUUUUUUUUUUUUUUUC-5'<br>5'-CAAAAAAAAAAAAAAAAAAAAAAAAG-3' | (SEQ ID NO: 4072)<br>(SEQ ID NO: 1854)<br>(SEQ ID NO: 2963) |
| βc-3285 Target: | 5'-AAAAAAAAAAAAAAAAAAAAAAAA-3'<br>3'-CGUUUUUUUUUUUUUUUUUUUUUUU-5'<br>5'-GCAAAAAAAAAAAAAAAAAAAAAAAA-3' | (SEQ ID NO: 4073)<br>(SEQ ID NO: 1855)<br>(SEQ ID NO: 2964) |
| βc-3287 Target: | 5'-GCAAAAAAAAAAAAAAAAAAAAAA-3'<br>3'-GACGUUUUUUUUUUUUUUUUUUUUU-5'<br>5'-CTGCAAAAAAAAAAAAAAAAAAAAAA-3' | (SEQ ID NO: 4074)<br>(SEQ ID NO: 1856)<br>(SEQ ID NO: 2965) |
| βc-3288 Target: | 5'-UGCAAAAAAAAAAAAAAAAAAAAA-3'<br>3'-UGACGUUUUUUUUUUUUUUUUUUUU-5'<br>5'-ACTGCAAAAAAAAAAAAAAAAAAAAA-3' | (SEQ ID NO: 4075)<br>(SEQ ID NO: 1857)<br>(SEQ ID NO: 2966) |
| βc-3292 Target: | 5'-UUACUGCAAAAAAAAAAAAAAAAA-3'<br>3'-UCAAUGACGUUUUUUUUUUUUUUUU-5'<br>5'-AGTTACTGCAAAAAAAAAAAAAAAAA-3' | (SEQ ID NO: 4076)<br>(SEQ ID NO: 1858)<br>(SEQ ID NO: 2967) |
| βc-3293 Target: | 5'-GUUACUGCAAAAAAAAAAAAAAAA-3'<br>3'-GUCAAUGACGUUUUUUUUUUUUUUU-5'<br>5'-CAGTTACTGCAAAAAAAAAAAAAAAA-3' | (SEQ ID NO: 4077)<br>(SEQ ID NO: 1859)<br>(SEQ ID NO: 2968) |
| βc-3294 Target: | 5'-AGUUACUGCAAAAAAAAAAAAAAA-3'<br>3'-UGUCAAUGACGUUUUUUUUUUUUUU-5'<br>5'-ACAGTTACTGCAAAAAAAAAAAAAAA-3' | (SEQ ID NO: 4078)<br>(SEQ ID NO: 1860)<br>(SEQ ID NO: 2969) |
| βc-3298 Target: | 5'-AAACAGUUACUGCAAAAAAAAAAA-3'<br>3'-UUUUUGUCAAUGACGUUUUUUUUUU-5'<br>5'-AAAAACAGTTACTGCAAAAAAAAAAA-3' | (SEQ ID NO: 4079)<br>(SEQ ID NO: 1861)<br>(SEQ ID NO: 2970) |
| βc-3299 Target: | 5'-AAAACAGUUACUGCAAAAAAAAAA-3'<br>3'-UUUUUUGUCAAUGACGUUUUUUUUU-5'<br>5'-AAAAAACAGTTACTGCAAAAAAAAAA-3' | (SEQ ID NO: 4080)<br>(SEQ ID NO: 1862)<br>(SEQ ID NO: 2971) |
| βc-3300 Target: | 5'-AAAACAGUUACUGCAAAAAAAAAA-3'<br>3'-AUUUUUUGUCAAUGACGUUUUUUUU-5'<br>5'-TAAAAAACAGTTACTGCAAAAAAAAA-3' | (SEQ ID NO: 4081)<br>(SEQ ID NO: 1863)<br>(SEQ ID NO: 2972) |
| βc-3302 Target: | 5'-UAAAAAACAGUUACUGCAAAAAAA-3'<br>3'-GAAUUUUUUGUCAAUGACGUUUUUU-5'<br>5'-CTTAAAAAACAGTTACTGCAAAAAAAA-3' | (SEQ ID NO: 4082)<br>(SEQ ID NO: 1864)<br>(SEQ ID NO: 2973) |
| βc-3303 Target: | 5'-UUAAAAAACAGUUACUGCAAAAAA-3'<br>3'-UGAAUUUUUUGUCAAUGACGUUUUU-5'<br>5'-ACTTAAAAAACAGTTACTGCAAAAAAA-3' | (SEQ ID NO: 4083)<br>(SEQ ID NO: 1865)<br>(SEQ ID NO: 2974) |
| βc-3305 Target: | 5'-ACUUAAAAAACAGUUACUGCAAAAA-3'<br>3'-UCUGAAUUUUUUGUCAAUGACGUUUU-5'<br>5'-AGACTTAAAAAACAGTTACTGCAAAAA-3' | (SEQ ID NO: 4084)<br>(SEQ ID NO: 1866)<br>(SEQ ID NO: 2975) |
| βc-3315 Target: | 5'-ACUACGAGAGACUUAAAAAACAGUU-3'<br>3'-UGUGAUGCUCUCUGAAUUUUUUGUCAA-5'<br>5'-ACACTACGAGAGACTTAAAAAACAGTT-3' | (SEQ ID NO: 4085)<br>(SEQ ID NO: 1867)<br>(SEQ ID NO: 2976) |
| βc-3317 Target: | 5'-ACACUACGAGAGACUUAAAAAACAG-3'<br>3'-AUUGUGAUGCUCUCUGAAUUUUUUGUC-5'<br>5'-TAACACTACGAGAGACTTAAAAAACAG-3' | (SEQ ID NO: 4086)<br>(SEQ ID NO: 1868)<br>(SEQ ID NO: 2977) |
| βc-3318 Target: | 5'-AACACUACGAGAGACUUAAAAAACA-3'<br>3'-AAUUGUGAUGCUCUCUGAAUUUUUUGU-5'<br>5'-TTAACACTACGAGAGACTTAAAAAACA-3' | (SEQ ID NO: 4087)<br>(SEQ ID NO: 1869)<br>(SEQ ID NO: 2978) |
| βc-3320 Target: | 5'-UUAACACUACGAGAGACUUAAAAAA-3'<br>3'-UGAAUUGUGAUGCUCUCUGAAUUUUUU-5'<br>5'-ACTTAACACTACGAGAGACTTAAAAAA-3' | (SEQ ID NO: 4088)<br>(SEQ ID NO: 1870)<br>(SEQ ID NO: 2979) |

TABLE 11-continued

Additional Selected Anti-β-catenin DsiRNAs, 25/27mer Duplexes, Unmodified

| | | |
|---|---|---|
| βc-3323 Target: | 5'-AACUUAACACUACGAGAGACUUAAA-3'<br>3'-UAUUGAAUUGUGAUGCUCUCUGAAUUU-5'<br>5'-ATAACTTAACACTACGAGAGACTTAAA-3' | (SEQ ID NO: 4089)<br>(SEQ ID NO: 1871)<br>(SEQ ID NO: 2980) |
| βc-3324 Target: | 5'-UAACUUAACACUACGAGAGACUUAA-3'<br>3'-AUAUUGAAUUGUGAUGCUCUCUGAAUU-5'<br>5'-TATAACTTAACACTACGAGAGACTTAA-3' | (SEQ ID NO: 4090)<br>(SEQ ID NO: 1872)<br>(SEQ ID NO: 2981) |
| βc-3332 Target: | 5'-AUUCACUAUAACUUAACACUACGAG-3'<br>3'-CAUAAGUGAUAUUGAAUUGUGAUGCUC-5'<br>5'-GTATTCACTATAACTTAACACTACGAG-3' | (SEQ ID NO: 4091)<br>(SEQ ID NO: 1873)<br>(SEQ ID NO: 2982) |
| βc-3333 Target: | 5'-UAUUCACUAUAACUUAACACUACGA-3'<br>3'-UCAUAAGUGAUAUUGAAUUGUGAUGCU-5'<br>5'-AGTATTCACTATAACTTAACACTACGA-3' | (SEQ ID NO: 4092)<br>(SEQ ID NO: 1874)<br>(SEQ ID NO: 2983) |
| βc-3334 Target: | 5'-GUAUUCACUAUAACUUAACACUACG-3'<br>3'-GUCAUAAGUGAUAUUGAAUUGUGAUGC-5'<br>5'-CAGTATTCACTATAACTTAACACTACG-3' | (SEQ ID NO: 4093)<br>(SEQ ID NO: 1875)<br>(SEQ ID NO: 2984) |
| βc-3335 Target: | 5'-AGUAUUCACUAUAACUUAACACUAC-3'<br>3'-CGUCAUAAGUGAUAUUGAAUUGUGAUG-5'<br>5'-GCAGTATTCACTATAACTTAACACTAC-3' | (SEQ ID NO: 4094)<br>(SEQ ID NO: 1876)<br>(SEQ ID NO: 2985) |
| βc-3348 Target: | 5'-AAAUUGCUGUAGCAGUAUUCACUAU-3'<br>3'-UCUUUAACGACAUCGUCAUAAGUGAUA-5'<br>5'-AGAAATTGCTGTAGCAGTATTCACTAT-3' | (SEQ ID NO: 4095)<br>(SEQ ID NO: 1877)<br>(SEQ ID NO: 2986) |
| βc-3349 Target: | 5'-GAAAUUGCUGUAGCAGUAUUCACUA-3'<br>3'-AUCUUUAACGACAUCGUCAUAAGUGAU-5'<br>5'-TAGAAATTGCTGTAGCAGTATTCACTA-3' | (SEQ ID NO: 4096)<br>(SEQ ID NO: 1878)<br>(SEQ ID NO: 2987) |
| βc-3350 Target: | 5'-AGAAAUUGCUGUAGCAGUAUUCACU-3'<br>3'-AAUCUUUAACGACAUCGUCAUAAGUGA-5'<br>5'-TTAGAAATTGCTGTAGCAGTATTCACT-3' | (SEQ ID NO: 4097)<br>(SEQ ID NO: 1879)<br>(SEQ ID NO: 2988) |
| βc-3366 Target: | 5'-UCAAUUCUUAAAAAUUAGAAAUUGC-3'<br>3'-UGAGUUAAGAAUUUUUAAUCUUUAACG-5'<br>5'-ACTCAATTCTTAAAAATTAGAAATTGC-3' | (SEQ ID NO: 4098)<br>(SEQ ID NO: 1880)<br>(SEQ ID NO: 2989) |
| βc-3371 Target: | 5'-AUUACUCAAUUCUUAAAAAUUAGAA-3'<br>3'-GGUAAUGAGUUAAGAAUUUUUAAUCUU-5'<br>5'-CCATTACTCAATTCTTAAAAATTAGAA-3' | (SEQ ID NO: 4099)<br>(SEQ ID NO: 1881)<br>(SEQ ID NO: 2990) |
| βc-3374 Target: | 5'-ACCAUUACUCAAUUCUUAAAAAUUA-3'<br>3'-UGUGGUAAUGAGUUAAGAAUUUUUAAU-5'<br>5'-ACACCATTACTCAATTCTTAAAAATTA-3' | (SEQ ID NO: 4100)<br>(SEQ ID NO: 1882)<br>(SEQ ID NO: 2991) |
| βc-3376 Target: | 5'-ACACCAUUACUCAAUUCUUAAAAAU-3'<br>3'-GAUGUGGUAAUGAGUUAAGAAUUUUUA-5'<br>5'-CTACACCATTACTCAATTCTTAAAAAT-3' | (SEQ ID NO: 4101)<br>(SEQ ID NO: 1883)<br>(SEQ ID NO: 2992) |
| βc-3377 Target: | 5'-UACACCAUUACUCAAUUCUUAAAAA-3'<br>3'-AGAUGUGGUAAUGAGUUAAGAAUUUUU-5'<br>5'-TCTACACCATTACTCAATTCTTAAAAA-3' | (SEQ ID NO: 4102)<br>(SEQ ID NO: 1884)<br>(SEQ ID NO: 2993) |
| βc-3379 Target: | 5'-UCUACACCAUUACUCAAUUCUUAAA-3'<br>3'-CAAGAUGUGGUAAUGAGUUAAGAAUUU-5'<br>5'-GTTCTACACCATTACTCAATTCTTAAA-3' | (SEQ ID NO: 4103)<br>(SEQ ID NO: 1885)<br>(SEQ ID NO: 2994) |
| βc-3381 Target: | 5'-GUUCUACACCAUUACUCAAUUCUUA-3'<br>3'-CACAAGAUGUGGUAAUGAGUUAAGAAU-5'<br>5'-GTGTTCTACACCATTACTCAATTCTTA-3' | (SEQ ID NO: 4104)<br>(SEQ ID NO: 1886)<br>(SEQ ID NO: 2995) |
| βc-3389 Target: | 5'-GAAUUAGUGUUCUACACCAUUACUC-3'<br>3'-UACUUAAUCACAAGAUGUGGUAAUGAG-5'<br>5'-ATGAATTAGTGTTCTACACCATTACTC-3' | (SEQ ID NO: 4105)<br>(SEQ ID NO: 1887)<br>(SEQ ID NO: 2996) |
| βc-3394 Target: | 5'-AUUAUGAAUUAGUGUUCUACACCAU-3'<br>3'-ACUAAUACUUAAUCACAAGAUGUGGUA-5'<br>5'-TGATTATGAATTAGTGTTCTACACC-3' | (SEQ ID NO: 4106)<br>(SEQ ID NO: 1888)<br>(SEQ ID NO: 2997) |
| βc-3395 Target: | 5'-GAUUAUGAAUUAGUGUUCUACACCA-3'<br>3'-CACUAAUACUUAAUCACAAGAUGUGGU-5'<br>5'-GTGATTATGAATTAGTGTTCTACACCA-3' | (SEQ ID NO: 4107)<br>(SEQ ID NO: 1889)<br>(SEQ ID NO: 2998) |

TABLE 11-continued

Additional Selected Anti-β-catenin DsiRNAs, 25/27mer Duplexes, Unmodified

| | | |
|---|---|---|
| βc-3396 Target: | 5'-UGAUUAUGAAUUAGUGUUCUACACC-3'<br>3'-UCACUAAUACUUAAUCACAAGAUGUGG-5'<br>5'-AGTGATTATGAATTAGTGTTCTACACC-3' | (SEQ ID NO: 4108)<br>(SEQ ID NO: 1890)<br>(SEQ ID NO: 2999) |
| βc-3405 Target: | 5'-UAAUUAGAGUGAUUAUGAAUUAGUG-3'<br>3'-UAAUUAAUCUCACUAAUACUUAAUCAC-5'<br>5'-ATTAATTAGAGTGATTATGAATTAGTG-3' | (SEQ ID NO: 4109)<br>(SEQ ID NO: 1891)<br>(SEQ ID NO: 3000) |
| βc-3406 Target: | 5'-UUAAUUAGAGUGAUUAUGAAUUAGU-3'<br>3'-UUAAUUAAUCUCACUAAUACUUAAUCA-5'<br>5'-AATTAATTAGAGTGATTATGAATTAGT-3' | (SEQ ID NO: 4110)<br>(SEQ ID NO: 1892)<br>(SEQ ID NO: 3001) |
| βc-3407 Target: | 5'-AUUAAUUAGAGUGAUUAUGAAUUAG-3'<br>3'-GUUAAUUAAUCUCACUAAUACUUAAUC-5'<br>5'-CAATTAATTAGAGTGATTATGAATTAG-3' | (SEQ ID NO: 4111)<br>(SEQ ID NO: 1893)<br>(SEQ ID NO: 3002) |
| βc-3411 Target: | 5'-UACAAUUAAUUAGAGUGAUUAUGAA-3'<br>3'-UAAUGUUAAUUAAUCUCACUAAUACUU-5'<br>5'-ATTACAATTAATTAGAGTGATTATGAA-3' | (SEQ ID NO: 4112)<br>(SEQ ID NO: 1894)<br>(SEQ ID NO: 3003) |
| βc-3412 Target: | 5'-UUACAAUUAAUUAGAGUGAUUAUGA-3'<br>3'-CUAAUGUUAAUUAAUCUCACUAAUACU-5'<br>5'-GATTACAATTAATTAGAGTGATTATGA-3' | (SEQ ID NO: 4113)<br>(SEQ ID NO: 1895)<br>(SEQ ID NO: 3004) |
| βc-3413 Target: | 5'-AUUACAAUUAAUUAGAGUGAUUAUG-3'<br>3'-UCUAAUGUUAAUUAAUCUCACUAAUAC-5'<br>5'-AGATTACAATTAATTAGAGTGATTATG-3' | (SEQ ID NO: 4114)<br>(SEQ ID NO: 1896)<br>(SEQ ID NO: 3005) |
| βc-3421 Target: | 5'-UUAUUCAGAUUACAAUUAAUUAGAG-3'<br>3'-GAAAUAAGUCUAAUGUUAAUUAAUCUC-5'<br>5'-CTTTATTCAGATTACAATTAATTAGAG-3' | (SEQ ID NO: 4115)<br>(SEQ ID NO: 1897)<br>(SEQ ID NO: 3006) |
| βc-3422 Target: | 5'-UUUAUUCAGAUUACAAUUAAUUAGA-3'<br>3'-UGAAAUAAGUCUAAUGUUAAUUAAUCU-5'<br>5'-ACTTTATTCAGATTACAATTAATTAGA-3' | (SEQ ID NO: 4116)<br>(SEQ ID NO: 1898)<br>(SEQ ID NO: 3007) |
| βc-3426 Target: | 5'-ACACUUUAUUCAGAUUACAAUUAAU-3'<br>3'-AAUGUGAAAUAAGUCUAAUGUUAAUUA-5'<br>5'-TTACACTTTATTCAGATTACAATTAAT-3' | (SEQ ID NO: 4117)<br>(SEQ ID NO: 1899)<br>(SEQ ID NO: 3008) |
| βc-3427 Target: | 5'-UACACUUUAUUCAGAUUACAAUUAA-3'<br>3'-CAAUGUGAAAUAAGUCUAAUGUUAAUU-5'<br>5'-GTTACACTTTATTCAGATTACAATTAA-3' | (SEQ ID NO: 4118)<br>(SEQ ID NO: 1900)<br>(SEQ ID NO: 3009) |
| βc-3428 Target: | 5'-UUACACUUUAUUCAGAUUACAAUUA-3'<br>3'-ACAAUGUGAAAUAAGUCUAAUGUUAAU-5'<br>5'-TGTTACACTTTATTCAGATTACAATTA-3' | (SEQ ID NO: 4119)<br>(SEQ ID NO: 1901)<br>(SEQ ID NO: 3010) |
| βc-3429 Target: | 5'-GUUACACUUUAUUCAGAUUACAAUU-3'<br>3'-AACAAUGUGAAAUAAGUCUAAUGUUAA-5'<br>5'-TTGTTACACTTTATTCAGATTACAATT-3' | (SEQ ID NO: 4120)<br>(SEQ ID NO: 1902)<br>(SEQ ID NO: 3011) |
| βc-3430 Target: | 5'-UGUUACACUUUAUUCAGAUUACAAU-3'<br>3'-UAACAAUGUGAAAUAAGUCUAAUGUUA-5'<br>5'-ATTGTTACACTTTATTCAGATTACAAT-3' | (SEQ ID NO: 4121)<br>(SEQ ID NO: 1903)<br>(SEQ ID NO: 3012) |
| βc-3437 Target: | 5'-ACACAAUUGUUACACUUUAUUCAGA-3'<br>3'-GAUGUGUUAACAAUGUGAAAUAAGUCU-5'<br>5'-CTACACAATTGTTACACTTTATTCAGA-3' | (SEQ ID NO: 4122)<br>(SEQ ID NO: 1904)<br>(SEQ ID NO: 3013) |
| βc-3441 Target: | 5'-GGCUACACAAUUGUUACACUUUAUU-3'<br>3'-UUCCGAUGUGUUAACAAUGUGAAAUAA-5'<br>5'-AAGGCTACACAATTGTTACACTTTATT-3' | (SEQ ID NO: 4123)<br>(SEQ ID NO: 1905)<br>(SEQ ID NO: 3014) |
| βc-3446 Target: | 5'-AAAAAGGCUACACAAUUGUUACACU-3'<br>3'-UGUUUUUCCGAUGUGUUAACAAUGUGA-5'<br>5'-ACAAAAGGCTACACAATTGTTACACT-3' | (SEQ ID NO: 4124)<br>(SEQ ID NO: 1906)<br>(SEQ ID NO: 3015) |
| βc-3452 Target: | 5'-UUAUACAAAAGGCUACACAAUUGU-3'<br>3'-AAAAUAUGUUUUCCGAUGUGUUAACA-5'<br>5'-TTTTATACAAAAGGCTACACAATTGT-3' | (SEQ ID NO: 4125)<br>(SEQ ID NO: 1907)<br>(SEQ ID NO: 3016) |
| βc-3453 Target: | 5'-UUUAUACAAAAGGCUACACAAUUG-3'<br>3'-UAAAAUAUGUUUUCCGAUGUGUUAAC-5'<br>5'-ATTTTATACAAAAGGCTACACAATTG-3' | (SEQ ID NO: 4126)<br>(SEQ ID NO: 1908)<br>(SEQ ID NO: 3017) |

TABLE 11-continued

Additional Selected Anti-β-catenin DsiRNAs, 25/27mer Duplexes, Unmodified

| | | |
|---|---|---|
| βc-3455 Target: | 5'-AUUUUAUACAAAAAGGCUACACAAU-3'<br>3'-GAUAAAAUAUGUUUUUCCGAUGUGUUA-5'<br>5'-CTATTTTATACAAAAAGGCTACACAAT-3' | (SEQ ID NO: 4127)<br>(SEQ ID NO: 1909)<br>(SEQ ID NO: 3018) |
| βc-3456 Target: | 5'-UAUUUUAUACAAAAAGGCUACACAA-3'<br>3'-AGAUAAAAUAUGUUUUUCCGAUGUGUU-5'<br>5'-TCTATTTTATACAAAAAGGCTACACAA-3' | (SEQ ID NO: 4128)<br>(SEQ ID NO: 1910)<br>(SEQ ID NO: 3019) |
| βc-3458 Target: | 5'-UCUAUUUUAUACAAAAAGGCUACAC-3'<br>3'-ACAGAUAAAAUAUGUUUUUCCGAUGUG-5'<br>5'-TGTCTATTTTATACAAAAAGGCTACAC-3' | (SEQ ID NO: 4129)<br>(SEQ ID NO: 1911)<br>(SEQ ID NO: 3020) |
| βc-3464 Target: | 5'-UAUUUGUCUAUUUUAUACAAAAAGG-3'<br>3'-AGAUAAACAGAUAAAAUAUGUUUUUCC-5'<br>5'-TCTATTTGTCTATTTTATACAAAAAGG-3' | (SEQ ID NO: 4130)<br>(SEQ ID NO: 1912)<br>(SEQ ID NO: 3021) |
| βc-3466 Target: | 5'-UCUAUUUGUCUAUUUUAUACAAAAA-3'<br>3'-AAAGAUAAACAGAUAAAAUAUGUUUUU-5'<br>5'-TTTCTATTTGTCTATTTTATACAAAAA-3' | (SEQ ID NO: 4131)<br>(SEQ ID NO: 1913)<br>(SEQ ID NO: 3022) |
| βc-3467 Target: | 5'-UUCUAUUUGUCUAUUUUAUACAAAA-3'<br>3'-AAAAGAUAAACAGAUAAAAUAUGUUUU-5'<br>5'-TTTTCTATTTGTCTATTTTATACAAAA-3' | (SEQ ID NO: 4132)<br>(SEQ ID NO: 1914)<br>(SEQ ID NO: 3023) |
| βc-3468 Target: | 5'-UUUCUAUUUGUCUAUUUUAUACAAA-3'<br>3'-UAAAAGAUAAACAGAUAAAAUAUGUUU-5'<br>5'-ATTTTCTATTTGTCTATTTTATACAAA-3' | (SEQ ID NO: 4133)<br>(SEQ ID NO: 1915)<br>(SEQ ID NO: 3024) |
| βc-3469 Target: | 5'-UUUUCUAUUUGUCUAUUUUAUACAA-3'<br>3'-GUAAAAGAUAAACAGAUAAAAUAUGUU-5'<br>5'-CATTTTCTATTTGTCTATTTTATACAA-3' | (SEQ ID NO: 4134)<br>(SEQ ID NO: 1916)<br>(SEQ ID NO: 3025) |
| βc-3470 Target: | 5'-AUUUUCUAUUUGUCUAUUUUAUACA-3'<br>3'-GGUAAAAGAUAAACAGAUAAAAUAUGU-5'<br>5'-CCATTTTCTATTTGTCTATTTTATACA-3' | (SEQ ID NO: 4135)<br>(SEQ ID NO: 1917)<br>(SEQ ID NO: 3026) |
| βc-3473 Target: | 5'-ACCAUUUUCUAUUUGUCUAUUUUAU-3'<br>3'-CCUGGUAAAAGAUAAACAGAUAAAAUA-5'<br>5'-GGACCATTTTCTATTTGTCTATTTTAT-3' | (SEQ ID NO: 4136)<br>(SEQ ID NO: 1918)<br>(SEQ ID NO: 3027) |
| βc-3474 Target: | 5'-GACCAUUUUCUAUUUGUCUAUUUUA-3'<br>3'-ACCUGGUAAAAGAUAAACAGAUAAAAU-5'<br>5'-TGGACCATTTTCTATTTGTCTATTTTA-3' | (SEQ ID NO: 4137)<br>(SEQ ID NO: 1919)<br>(SEQ ID NO: 3028) |
| βc-3475 Target: | 5'-GGACCAUUUUCUAUUUGUCUAUUUU-3'<br>3'-AACCUGGUAAAAGAUAAACAGAUAAAA-5'<br>5'-TTGGACCATTTTCTATTTGTCTATTTT-3' | (SEQ ID NO: 4138)<br>(SEQ ID NO: 1920)<br>(SEQ ID NO: 3029) |
| βc-3482 Target: | 5'-ACUAAUUGGACCAUUUUCUAUUUGU-3'<br>3'-UUUGAUUAACCUGGUAAAAGAUAAACA-5'<br>5'-AAACTAATTGGACCATTTTCTATTTGT-3' | (SEQ ID NO: 4139)<br>(SEQ ID NO: 1921)<br>(SEQ ID NO: 3030) |
| βc-3483 Target: | 5'-AACUAAUUGGACCAUUUUCUAUUUG-3'<br>3'-CUUUGAUUAACCUGGUAAAAGAUAAAC-5'<br>5'-GAAACTAATTGGACCATTTTCTATTTG-3' | (SEQ ID NO: 4140)<br>(SEQ ID NO: 1922)<br>(SEQ ID NO: 3031) |
| βc-3484 Target: | 5'-AAACUAAUUGGACCAUUUUCUAUUU-3'<br>3'-CCUUUGAUUAACCUGGUAAAAGAUAAA-5'<br>5'-GGAAACTAATTGGACCATTTTCTATTT-3' | (SEQ ID NO: 4141)<br>(SEQ ID NO: 1923)<br>(SEQ ID NO: 3032) |
| βc-3485 Target: | 5'-GAAACUAAUUGGACCAUUUUCUAUU-3'<br>3'-UCCUUUGAUUAACCUGGUAAAAGAUAA-5'<br>5'-AGGAAACTAATTGGACCATTTTCTATT-3' | (SEQ ID NO: 4142)<br>(SEQ ID NO: 1924)<br>(SEQ ID NO: 3033) |
| βc-3491 Target: | 5'-AAAAAGGAAACUAAUUGGACCAUUU-3'<br>3'-AAUUUUUCCUUUGAUUAACCUGGUAAA-5'<br>5'-TTAAAAGGAAACTAATTGGACCATTT-3' | (SEQ ID NO: 4143)<br>(SEQ ID NO: 1925)<br>(SEQ ID NO: 3034) |
| βc-3492 Target: | 5'-UAAAAGGAAACUAAUUGGACCAUU-3'<br>3'-UAAUUUUUCCUUUGAUUAACCUGGUAA-5'<br>5'-ATTAAAAGGAAACTAATTGGACCATT-3' | (SEQ ID NO: 4144)<br>(SEQ ID NO: 1926)<br>(SEQ ID NO: 3035) |
| βc-3498 Target: | 5'-GCAUAUUAAAAGGAAACUAAUUGG-3'<br>3'-UUCGUAUAAUUUUCCUUUGAUUAACC-5'<br>5'-AAGCATATTAAAAGGAAACTAATTGG-3' | (SEQ ID NO: 4145)<br>(SEQ ID NO: 1927)<br>(SEQ ID NO: 3036) |

TABLE 11-continued

Additional Selected Anti-β-catenin DsiRNAs, 25/27mer Duplexes, Unmodified

| | | |
|---|---|---|
| βc-3499 Target: | 5'-AGCAUAUUAAAAAGGAAACUAAUUG-3'<br>3'-AUUCGUAUAAUUUUCCUUUGAUUAAC-5'<br>5'-TAAGCATATTAAAAAGGAAACTAATTG-3' | (SEQ ID NO: 4146)<br>(SEQ ID NO: 1928)<br>(SEQ ID NO: 3037) |
| βc-3503 Target: | 5'-UUUAAGCAUAUUAAAAAGGAAACUA-3'<br>3'-UAAAAUUCGUAUAAUUUUUCCUUUGAU-5'<br>5'-ATTTTAAGCATATTAAAAAGGAAACTA-3' | (SEQ ID NO: 4147)<br>(SEQ ID NO: 1929)<br>(SEQ ID NO: 3038) |
| βc-3509 Target: | 5'-GCUUAUUUUAAGCAUAUUAAAAAGG-3'<br>3'-GACGAAUAAAAUUCGUAUAAUUUUUCC-5'<br>5'-CTGCTTATTTTAAGCATATTAAAAGG-3' | (SEQ ID NO: 4148)<br>(SEQ ID NO: 1930)<br>(SEQ ID NO: 3039) |
| βc-3510 Target: | 5'-UGCUUAUUUUAAGCAUAUUAAAAAG-3'<br>3'-GGACGAAUAAAAUUCGUAUAAUUUUUC-5'<br>5'-CCTGCTTATTTTAAGCATATTAAAAG-3' | (SEQ ID NO: 4149)<br>(SEQ ID NO: 1931)<br>(SEQ ID NO: 3040) |
| βc-3516 Target: | 5'-UCCACCUGCUUAUUUUAAGCAUAUU-3'<br>3'-CUAGGUGGACGAAUAAAAUUCGUAUAA-5'<br>5'-GATCCACCTGCTTATTTTAAGCATATT-3' | (SEQ ID NO: 4150)<br>(SEQ ID NO: 1932)<br>(SEQ ID NO: 3041) |
| βc-3531 Target: | 5'-AAAACAUGAAAUAGAUCCACCUGCU-3'<br>3'-GUUUUUGUACUUUAUCUAGGUGGACGA-5'<br>5'-CAAAAACATGAAATAGATCCACCTGCT-3' | (SEQ ID NO: 4151)<br>(SEQ ID NO: 1933)<br>(SEQ ID NO: 3042) |
| βc-3532 Target: | 5'-AAAACAUGAAAUAGAUCCACCUGC-3'<br>3'-AGUUUUGUACUUUAUCUAGGUGGACG-5'<br>5'-TCAAAAACATGAAATAGATCCACCTGC-3' | (SEQ ID NO: 4152)<br>(SEQ ID NO: 1934)<br>(SEQ ID NO: 3043) |
| βc-3534 Target: | 5'-UCAAAAACAUGAAAUAGAUCCACCU-3'<br>3'-CUAGUUUUUGUACUUUAUCUAGGUGGA-5'<br>5'-GATCAAAAACATGAAATAGATCCACCT-3' | (SEQ ID NO: 4153)<br>(SEQ ID NO: 1935)<br>(SEQ ID NO: 3044) |
| βc-3535 Target: | 5'-AUCAAAAACAUGAAAUAGAUCCACC-3'<br>3'-ACUAGUUUUUGUACUUUAUCUAGGUGG-5'<br>5'-TGATCAAAAACATGAAATAGATCCACC-3' | (SEQ ID NO: 4154)<br>(SEQ ID NO: 1936)<br>(SEQ ID NO: 3045) |
| βc-3536 Target: | 5'-GAUCAAAAACAUGAAAUAGAUCCAC-3'<br>3'-AACUAGUUUUUGUACUUUAUCUAGGUG-5'<br>5'-TTGATCAAAAACATGAAATAGATCCAC-3' | (SEQ ID NO: 4155)<br>(SEQ ID NO: 1937)<br>(SEQ ID NO: 3046) |
| βc-3541 Target: | 5'-UUUUUGAUCAAAAACAUGAAAUAGA-3'<br>3'-UCAAAAACUAGUUUUUGUACUUUAUCU-5'<br>5'-AGTTTTTGATCAAAAACATGAAATAGA-3' | (SEQ ID NO: 4156)<br>(SEQ ID NO: 1938)<br>(SEQ ID NO: 3047) |
| βc-3547 Target: | 5'-AAAUAGUUUUUGAUCAAAAACAUGA-3'<br>3'-GGUUUAUCAAAAACUAGUUUUUGUACU-5'<br>5'-CCAAATAGTTTTTGATCAAAAACATGA-3' | (SEQ ID NO: 4157)<br>(SEQ ID NO: 1939)<br>(SEQ ID NO: 3048) |
| βc-3551 Target: | 5'-UCCCAAAUAGUUUUUGAUCAAAAC-3'<br>3'-AUAGGGUUUAUCAAAAACUAGUUUUUG-5'<br>5'-TATCCCAAATAGTTTTTGATCAAAAC-3' | (SEQ ID NO: 4158)<br>(SEQ ID NO: 1940)<br>(SEQ ID NO: 3049) |
| βc-3552 Target: | 5'-AUCCCAAAUAGUUUUUGAUCAAAAA-3'<br>3'-UAUAGGGUUUAUCAAAAACUAGUUUUU-5'<br>5'-ATATCCCAAATAGTTTTTGATCAAAAA-3' | (SEQ ID NO: 4159)<br>(SEQ ID NO: 1941)<br>(SEQ ID NO: 3050) |
| βc-3553 Target: | 5'-UAUCCCAAAUAGUUUUUGAUCAAAA-3'<br>3'-GUAUAGGGUUUAUCAAAAACUAGUUUU-5'<br>5'-CATATCCCAAATAGTTTTTGATCAAAA-3' | (SEQ ID NO: 4160)<br>(SEQ ID NO: 1942)<br>(SEQ ID NO: 3051) |
| βc-3554 Target: | 5'-AUAUCCCAAAUAGUUUUUGAUCAAA-3'<br>3'-UGUAUAGGGUUUAUCAAAAACUAGUUU-5'<br>5'-ACATATCCCAAATAGTTTTTGATCAAA-3' | (SEQ ID NO: 4161)<br>(SEQ ID NO: 1943)<br>(SEQ ID NO: 3052) |
| βc-3558 Target: | 5'-AUACAUAUCCCAAAUAGUUUUUGAU-3'<br>3'-GGUAUGUAUAGGGUUUAUCAAAAACUA-5'<br>5'-CCATACATATCCCAAATAGTTTTTGAT-3' | (SEQ ID NO: 4162)<br>(SEQ ID NO: 1944)<br>(SEQ ID NO: 3053) |
| βc-3567 Target: | 5'-ACCCUACCCAUACAUAUCCCAAAUA-3'<br>3'-AAUGGGAUGGGUAUGUAUAGGGUUUAU-5'<br>5'-TTACCCTACCCATACATATCCCAAATA-3' | (SEQ ID NO: 4163)<br>(SEQ ID NO: 1945)<br>(SEQ ID NO: 3054) |
| βc-3568 Target: | 5'-UACCCUACCCAUACAUAUCCCAAAU-3'<br>3'-AAAUGGGAUGGGUAUGUAUAGGGUUUA-5'<br>5'-TTTACCCTACCCATACATATCCCAAAT-3' | (SEQ ID NO: 4164)<br>(SEQ ID NO: 1946)<br>(SEQ ID NO: 3055) |

TABLE 11-continued

Additional Selected Anti-β-catenin DsiRNAs, 25/27mer Duplexes, Unmodified

| | | |
|---|---|---|
| βc-3569 Target: | 5'-UUACCCUACCCAUACAUAUCCCAAA-3'<br>3'-UAAAUGGGAUGGGUAUGUAUAGGGUUU-5'<br>5'-ATTTACCCTACCCATACATATCCCAAA-3' | (SEQ ID NO: 4165)<br>(SEQ ID NO: 1947)<br>(SEQ ID NO: 3056) |
| βc-3582 Target: | 5'-ACCUCUUACUGAUUUACCCUACCCA-3'<br>3'-UGUGGAGAAUGACUAAAUGGGAUGGGU-5'<br>5'-ACACCTCTTACTGATTTACCCTACCCA-3' | (SEQ ID NO: 4166)<br>(SEQ ID NO: 1948)<br>(SEQ ID NO: 3057) |
| βc-3584 Target: | 5'-ACACCUCUUACUGAUUUACCCUACC-3'<br>3'-AUUGUGGAGAAUGACUAAAUGGGAUGG-5'<br>5'-TAACACCTCTTACTGATTTACCCTACC-3' | (SEQ ID NO: 4167)<br>(SEQ ID NO: 1949)<br>(SEQ ID NO: 3058) |
| βc-3585 Target: | 5'-AACACCUCUUACUGAUUUACCCUAC-3'<br>3'-UAUUGUGGAGAAUGACUAAAUGGGAUG-5'<br>5'-ATAACACCTCTTACTGATTTACCCTAC-3' | (SEQ ID NO: 4168)<br>(SEQ ID NO: 1950)<br>(SEQ ID NO: 3059) |
| βc-3586 Target: | 5'-UAACACCUCUUACUGAUUUACCCUA-3'<br>3'-UUAUUGUGGAGAAUGACUAAAUGGGAU-5'<br>5'-AATAACACCTCTTACTGATTTACCCTA-3' | (SEQ ID NO: 4169)<br>(SEQ ID NO: 1951)<br>(SEQ ID NO: 3060) |
| βc-3587 Target: | 5'-AUAACACCUCUUACUGAUUUACCCU-3'<br>3'-UUUAUUGUGGAGAAUGACUAAAUGGGA-5'<br>5'-AAATAACACCTCTTACTGATTTACCCT-3' | (SEQ ID NO: 4170)<br>(SEQ ID NO: 1952)<br>(SEQ ID NO: 3061) |
| βc-3588 Target: | 5'-AAUAACACCUCUUACUGAUUUACCC-3'<br>3'-GUUUAUUGUGGAGAAUGACUAAAUGGG-5'<br>5'-CAAATAACACCTCTTACTGATTTACCC-3' | (SEQ ID NO: 4171)<br>(SEQ ID NO: 1953)<br>(SEQ ID NO: 3062) |
| βc-3594 Target: | 5'-GUUCCAAAUAACACCUCUUACUGAU-3'<br>3'-UCCAAGGUUUAUUGUGGAGAAUGACUA-5'<br>5'-AGGTTCCAAATAACACCTCTTACTGAT-3' | (SEQ ID NO: 4172)<br>(SEQ ID NO: 1954)<br>(SEQ ID NO: 3063) |
| βc-3600 Target: | 5'-AACAAGGUUCCAAAUAACACCUCUU-3'<br>3'-UUUUGUUCCAAGGUUUAUUGUGGAGAA-5'<br>5'-AAAACAAGGTTCCAAATAACACCTCTT-3' | (SEQ ID NO: 4173)<br>(SEQ ID NO: 1955)<br>(SEQ ID NO: 3064) |
| βc-3601 Target: | 5'-AAACAAGGUUCCAAAUAACACCUCU-3'<br>3'-GUUUUGUUCCAAGGUUUAUUGUGGAGA-5'<br>5'-CAAAACAAGGTTCCAAATAACACCTCT-3' | (SEQ ID NO: 4174)<br>(SEQ ID NO: 1956)<br>(SEQ ID NO: 3065) |
| βc-3602 Target: | 5'-AAAACAAGGUUCCAAAUAACACCUC-3'<br>3'-GGUUUUGUUCCAAGGUUUAUUGUGGAG-5'<br>5'-CCAAAACAAGGTTCCAAATAACACCTC-3' | (SEQ ID NO: 4175)<br>(SEQ ID NO: 1957)<br>(SEQ ID NO: 3066) |
| βc-3607 Target: | 5'-UGUCCAAAACAAGGUUCCAAAUAAC-3'<br>3'-UGACAGGUUUUGUUCCAAGGUUUAUUG-5'<br>5'-ACTGTCCAAAACAAGGTTCCAAATAAC-3' | (SEQ ID NO: 4176)<br>(SEQ ID NO: 1958)<br>(SEQ ID NO: 3067) |
| βc-3611 Target: | 5'-AAACUGUCCAAAACAAGGUUCCAAA-3'<br>3'-CAUUUGACAGGUUUUGUUCCAAGGUUU-5'<br>5'-GTAAACTGTCCAAAACAAGGTTCCAAA-3' | (SEQ ID NO: 4177)<br>(SEQ ID NO: 1959)<br>(SEQ ID NO: 3068) |
| βc-3612 Target: | 5'-UAAACUGUCCAAAACAAGGUUCCAA-3'<br>3'-CCAUUUGACAGGUUUUGUUCCAAGGUU-5'<br>5'-GGTAAACTGTCCAAAACAAGGTTCCAA-3' | (SEQ ID NO: 4178)<br>(SEQ ID NO: 1960)<br>(SEQ ID NO: 3069) |
| βc-3620 Target: | 5'-GCAACUGGUAAACUGUCCAAAACAA-3'<br>3'-UCCGUUGACCAUUUGACAGGUUUUGUU-5'<br>5'-AGGCAACTGGTAAACTGTCCAAAACAA-3' | (SEQ ID NO: 4179)<br>(SEQ ID NO: 1961)<br>(SEQ ID NO: 3070) |
| βc-3628 Target: | 5'-GAUAAAAGGCAACUGGUAAACUGUC-3'<br>3'-CCCUAUUUUCCGUUGACCAUUUGACAG-5'<br>5'-GGGATAAAAGGCAACTGGTAAACTGTC-3' | (SEQ ID NO: 4180)<br>(SEQ ID NO: 1962)<br>(SEQ ID NO: 3071) |
| βc-3629 Target: | 5'-GGAUAAAAGGCAACUGGUAAACUGU-3'<br>3'-ACCCUAUUUUCCGUUGACCAUUUGACA-5'<br>5'-TGGGATAAAAGGCAACTGGTAAACTGT-3' | (SEQ ID NO: 4181)<br>(SEQ ID NO: 1963)<br>(SEQ ID NO: 3072) |
| βc-3636 Target: | 5'-AACUUUGGGAUAAAAGGCAACUGGU-3'<br>3'-UGUUGAAACCCUAUUUUCCGUUGACCA-5'<br>5'-ACAACTTTGGGATAAAAGGCAACTGGT-3' | (SEQ ID NO: 4182)<br>(SEQ ID NO: 1964)<br>(SEQ ID NO: 3073) |
| βc-3638 Target: | 5'-ACAACUUUGGGAUAAAAGGCAACUG-3'<br>3'-GUUGUUGAAACCCUAUUUUCCGUUGAC-5'<br>5'-CAACAACTTTGGGATAAAAGGCAACTG-3' | (SEQ ID NO: 4183)<br>(SEQ ID NO: 1965)<br>(SEQ ID NO: 3074) |

TABLE 11-continued

Additional Selected Anti-β-catenin DsiRNAs, 25/27mer Duplexes, Unmodified

| | | |
|---|---|---|
| βc-3643 Target: | 5'-UUACAACAACUUUGGGAUAAAAGGC-3'<br>3'-CCAAUGUUGUUGAAACCCUAUUUUCCG-5'<br>5'-GGTTACAACAACTTTGGGATAAAAGGC-3' | (SEQ ID NO: 4184)<br>(SEQ ID NO: 1966)<br>(SEQ ID NO: 3075) |
| βc-3644 Target: | 5'-GUUACAACAACUUUGGGAUAAAAGG-3'<br>3'-UCCAAUGUUGUUGAAACCCUAUUUUCC-5'<br>5'-AGGTTACAACAACTTTGGGATAAAAGG-3' | (SEQ ID NO: 4185)<br>(SEQ ID NO: 1967)<br>(SEQ ID NO: 3076) |
| βc-3645 Target: | 5'-GGUUACAACAACUUUGGGAUAAAAG-3'<br>3'-GUCCAAUGUUGUUGAAACCCUAUUUUC-5'<br>5'-CAGGTTACAACAACTTTGGGATAAAAG-3' | (SEQ ID NO: 4186)<br>(SEQ ID NO: 1968)<br>(SEQ ID NO: 3077) |
| βc-3653 Target: | 5'-UCACAGCAGGUUACAACAACUUUGG-3'<br>3'-AUAGUGUCGUCCAAUGUUGUUGAAACC-5'<br>5'-TATCACAGCAGGTTACAACAACTTTGG-3' | (SEQ ID NO: 4187)<br>(SEQ ID NO: 1969)<br>(SEQ ID NO: 3078) |
| βc-3654 Target: | 5'-AUCACAGCAGGUUACAACAACUUUG-3'<br>3'-CAUAGUGUCGUCCAAUGUUGUUGAAAC-5'<br>5'-GTATCACAGCAGGTTACAACAACTTTG-3' | (SEQ ID NO: 4188)<br>(SEQ ID NO: 1970)<br>(SEQ ID NO: 3079) |
| βc-3656 Target: | 5'-GUAUCACAGCAGGUUACAACAACUU-3'<br>3'-AGCAUAGUGUCGUCCAAUGUUGUUGAA-5'<br>5'-TCGTATCACAGCAGGTTACAACAACTT-3' | (SEQ ID NO: 4189)<br>(SEQ ID NO: 1971)<br>(SEQ ID NO: 3080) |
| βc-3670 Target: | 5'-UCUCUUGAAGCAUCGUAUCACAGCA-3'<br>3'-AAAGAGAACUUCGUAGCAUAGUGUCGU-5'<br>5'-TTTCTCTTGAAGCATCGTATCACAGCA-3' | (SEQ ID NO: 4190)<br>(SEQ ID NO: 1972)<br>(SEQ ID NO: 3081) |
| βc-3671 Target: | 5'-UUCUCUUGAAGCAUCGUAUCACAGC-3'<br>3'-AAAAGAGAACUUCGUAGCAUAGUGUCG-5'<br>5'-TTTTCTCTTGAAGCATCGTATCACAGC-3' | (SEQ ID NO: 4191)<br>(SEQ ID NO: 1973)<br>(SEQ ID NO: 3082) |
| βc-3673 Target: | 5'-UUUUCUCUUGAAGCAUCGUAUCACA-3'<br>3'-GUAAAAGAGAACUUCGUAGCAUAGUGU-5'<br>5'-CATTTTCTCTTGAAGCATCGTATCACA-3' | (SEQ ID NO: 4192)<br>(SEQ ID NO: 1974)<br>(SEQ ID NO: 3083) |
| βc-3686 Target: | 5'-UUUUAUAACCGCAUUUUCUCUUGAA-3'<br>3'-AAAAAAUAUUGGCGUAAAAGAGAACUU-5'<br>5'-TTTTTTATAACCGCATTTTCTCTTGAA-3' | (SEQ ID NO: 4193)<br>(SEQ ID NO: 1975)<br>(SEQ ID NO: 3084) |
| βc-3687 Target: | 5'-UUUUUAUAACCGCAUUUUCUCUUGA-3'<br>3'-UAAAAAAUAUUGGCGUAAAAGAGAACU-5'<br>5'-ATTTTTTATAACCGCATTTTCTCTTGA-3' | (SEQ ID NO: 4194)<br>(SEQ ID NO: 1976)<br>(SEQ ID NO: 3085) |
| βc-3688 Target: | 5'-UUUUUUAUAACCGCAUUUUCUCUUG-3'<br>3'-GUAAAAAAUAUUGGCGUAAAAGAGAAC-5'<br>5'-CATTTTTTATAACCGCATTTTCTCTTG-3' | (SEQ ID NO: 4195)<br>(SEQ ID NO: 1977)<br>(SEQ ID NO: 3086) |
| βc-3689 Target: | 5'-AUUUUUUAUAACCGCAUUUUCUCUU-3'<br>3'-GGUAAAAAAUAUUGGCGUAAAAGAGAA-5'<br>5'-CCATTTTTTATAACCGCATTTTCTCTT-3' | (SEQ ID NO: 4196)<br>(SEQ ID NO: 1978)<br>(SEQ ID NO: 3087) |
| βc-3694 Target: | 5'-GAACCAUUUUUUAUAACCGCAUUUU-3'<br>3'-GACUUGGUAAAAAAUAUUGGCGUAAAA-5'<br>5'-CTGAACCATTTTTTATAACCGCATTTT-3' | (SEQ ID NO: 4197)<br>(SEQ ID NO: 1979)<br>(SEQ ID NO: 3088) |
| βc-3699 Target: | 5'-AUUCUGAACCAUUUUUUAUAACCGC-3'<br>3'-AUUAAGACUUGGUAAAAAAUAUUGGCG-5'<br>5'-TAATTCTGAACCATTTTTTATAACCGC-3' | (SEQ ID NO: 4198)<br>(SEQ ID NO: 1980)<br>(SEQ ID NO: 3089) |
| βc-3700 Target: | 5'-AAUUCUGAACCAUUUUUUAUAACCG-3'<br>3'-AAUUAAGACUUGGUAAAAAAUAUUGGC-5'<br>5'-TTAATTCTGAACCATTTTTTATAACCG-3' | (SEQ ID NO: 4199)<br>(SEQ ID NO: 1981)<br>(SEQ ID NO: 3090) |
| βc-3701 Target: | 5'-UAAUUCUGAACCAUUUUUUAUAACC-3'<br>3'-AAAUUAAGACUUGGUAAAAAAUAUUGG-5'<br>5'-TTTAATTCTGAACCATTTTTTATAACC-3' | (SEQ ID NO: 4200)<br>(SEQ ID NO: 1982)<br>(SEQ ID NO: 3091) |
| βc-3702 Target: | 5'-UUAAUUCUGAACCAUUUUUUAUAAC-3'<br>3'-CAAAUUAAGACUUGGUAAAAAAUAUUG-5'<br>5'-GTTTAATTCTGAACCATTTTTTATAAC-3' | (SEQ ID NO: 4201)<br>(SEQ ID NO: 1983)<br>(SEQ ID NO: 3092) |
| βc-3703 Target: | 5'-UUUAAUUCUGAACCAUUUUUUAUAA-3'<br>3'-UCAAAUUAAGACUUGGUAAAAAAUAUU-5'<br>5'-AGTTTAATTCTGAACCATTTTTTATAA-3' | (SEQ ID NO: 4202)<br>(SEQ ID NO: 1984)<br>(SEQ ID NO: 3093) |

TABLE 11-continued

Additional Selected Anti-β-catenin DsiRNAs, 25/27mer Duplexes, Unmodified

| | | |
|---|---|---|
| βc-3704 Target: | 5'-GUUUAAUUCUGAACCAUUUUUUAUA-3'<br>3'-UUCAAAUUAAGACUUGGUAAAAAAUAU-5'<br>5'-AAGTTTAATTCTGAACCATTTTTATA-3' | (SEQ ID NO: 4203)<br>(SEQ ID NO: 1985)<br>(SEQ ID NO: 3094) |
| βc-3709 Target: | 5'-UAAAAGUUUAAUUCUGAACCAUUUU-3'<br>3'-UAAUUUUCAAAUUAAGACUUGGUAAAA-5'<br>5'-ATTAAAAGTTTAATTCTGAACCATTTT-3' | (SEQ ID NO: 4204)<br>(SEQ ID NO: 1986)<br>(SEQ ID NO: 3095) |
| βc-3710 Target: | 5'-UUAAAAGUUUAAUUCUGAACCAUUU-3'<br>3'-UUAAUUUUCAAAUUAAGACUUGGUAAA-5'<br>5'-AATTAAAAGTTTAATTCTGAACCATTT-3' | (SEQ ID NO: 4205)<br>(SEQ ID NO: 1987)<br>(SEQ ID NO: 3096) |
| βc-3712 Target: | 5'-AAUUAAAAGUUUAAUUCUGAACCAU-3'<br>3'-ACUUAAUUUUCAAAUUAAGACUUGGUA-5'<br>5'-TGAATTAAAAGTTTAATTCTGAACC-3' | (SEQ ID NO: 4206)<br>(SEQ ID NO: 1988)<br>(SEQ ID NO: 3097) |
| βc-2634t2 Target: | 5'-AUACAGCUAAAGGAUGAUUUACAGG-3'<br>3'-GUUAUGUCGAUUUCCUACUAAAUGUCC-5'<br>5'-CAATACAGCTAAAGGATGATTTACAGG-3' | (SEQ ID NO: 4207)<br>(SEQ ID NO: 1989)<br>(SEQ ID NO: 3098) |
| βc-2635t2 Target: | 5'-AAUACAGCUAAAGGAUGAUUUACAG-3'<br>3'-UGUUAUGUCGAUUUCCUACUAAAUGUC-5'<br>5'-ACAATACAGCTAAAGGATGATTTACAG-3' | (SEQ ID NO: 4208)<br>(SEQ ID NO: 1990)<br>(SEQ ID NO: 3099) |
| βc-2637t2 Target: | 5'-ACAAUACAGCUAAAGGAUGAUUUAC-3'<br>3'-UCUGUUAUGUCGAUUUCCUACUAAAUG-5'<br>5'-AGACAATACAGCTAAAGGATGATTTAC-3' | (SEQ ID NO: 4209)<br>(SEQ ID NO: 1991)<br>(SEQ ID NO: 3100) |
| βc-2633t3 Target: | 5'-UACUCCUAAAGGAUGAUUUACAGGU-3'<br>3'-CAAUGAGGAUUUCCUACUAAAUGUCCA-5'<br>5'-GTTACTCCTAAAGGATGATTTACAGGT-3' | (SEQ ID NO: 4210)<br>(SEQ ID NO: 1992)<br>(SEQ ID NO: 3101) |
| βc-2634t3 Target: | 5'-UUACUCCUAAAGGAUGAUUUACAGG-3'<br>3'-ACAAUGAGGAUUUCCUACUAAAUGUCC-5'<br>5'-TGTTACTCCTAAAGGATGATTTACAGG-3' | (SEQ ID NO: 4211)<br>(SEQ ID NO: 1993)<br>(SEQ ID NO: 3102) |
| βc-2635t3 Target: | 5'-GUUACUCCUAAAGGAUGAUUUACAG-3'<br>3'-AACAAUGAGGAUUUCCUACUAAAUGUC-5'<br>5'-TTGTTACTCCTAAAGGATGATTTACAG-3' | (SEQ ID NO: 4212)<br>(SEQ ID NO: 1994)<br>(SEQ ID NO: 3103) |
| βc-2636t3 Target: | 5'-UGUUACUCCUAAAGGAUGAUUUACA-3'<br>3'-UAACAAUGAGGAUUUCCUACUAAAUGU-5'<br>5'-ATTGTTACTCCTAAAGGATGATTTACA-3' | (SEQ ID NO: 4213)<br>(SEQ ID NO: 1995)<br>(SEQ ID NO: 3104) |
| βc-m318 Target: | 5'-AUUCCAGAAUCCAAGUAAGACUGCU-3'<br>3'-CCUAAGGUCUUAGGUUCAUUCUGACGA-5'<br>5'-GGATTCCAGAATCCAAGTAAGACTGCT-3' | (SEQ ID NO: 4214)<br>(SEQ ID NO: 1996)<br>(SEQ ID NO: 3105) |
| βc-m417 Target: | 5'-UGCUCCCAUUCAUAAAGGACUUGGG-3'<br>3'-GAACGAGGGUAAGUAUUUCCUGAACCC-5'<br>5'-CTTGCTCCCATTCATAAAGGACTTGGG-3' | (SEQ ID NO: 4215)<br>(SEQ ID NO: 1997)<br>(SEQ ID NO: 3106) |
| βc-m462 Target: | 5'-UCAAUAUCAGCUACUUGCUCUUGCG-3'<br>3'-GCAGUUAUAGUCGAUGAACGAGAACGC-5'<br>5'-CGTCAATATCAGCTACTTGCTCTTGCG-3' | (SEQ ID NO: 4216)<br>(SEQ ID NO: 1998)<br>(SEQ ID NO: 3107) |
| βc-m463 Target: | 5'-GUCAAUAUCAGCUACUUGCUCUUGC-3'<br>3'-GGCAGUUAUAGUCGAUGAACGAGAACG-5'<br>5'-CCGTCAATATCAGCTACTTGCTCTTGC-3' | (SEQ ID NO: 4217)<br>(SEQ ID NO: 1999)<br>(SEQ ID NO: 3108) |
| βc-m468 Target: | 5'-UGCCCGUCAAUAUCAGCUACUUGCU-3'<br>3'-UGACGGGCAGUUAUAGUCGAUGAACGA-5'<br>5'-ACTGCCCGTCAATATCAGCTACTTGCT-3' | (SEQ ID NO: 4218)<br>(SEQ ID NO: 2000)<br>(SEQ ID NO: 3109) |
| βc-m613 Target: | 5'-UUUCAACAUCUGUGAUGGUUCAGCC-3'<br>3'-ACAAAGUUGUAGACACUACCAAGUCGG-5'<br>5'-TGTTTCAACATCTGTGATGGTTCAGCC-3' | (SEQ ID NO: 4219)<br>(SEQ ID NO: 2001)<br>(SEQ ID NO: 3110) |
| βc-m614 Target: | 5'-GUUUCAACAUCUGUGAUGGUUCAGC-3'<br>3'-UACAAAGUUGUAGACACUACCAAGUCG-5'<br>5'-ATGTTTCAACATCTGTGATGGTTCAGC-3' | (SEQ ID NO: 4220)<br>(SEQ ID NO: 2002)<br>(SEQ ID NO: 3111) |
| βc-m624 Target: | 5'-ACAACUGCAUGUUUCAACAUCUGUG-3'<br>3'-ACUGUUGACGUACAAAGUUGUAGACAC-5'<br>5'-TGACAACTGCATGTTTCAACATCTGTG-3' | (SEQ ID NO: 4221)<br>(SEQ ID NO: 2003)<br>(SEQ ID NO: 3112) |

TABLE 11-continued

Additional Selected Anti-β-catenin DsiRNAs, 25/27mer Duplexes, Unmodified

| | | |
|---|---|---|
| βc-m626 Target: | 5'-UGACAACUGCAUGUUUCAACAUCUG-3'<br>3'-UAACUGUUGACGUACAAAGUUGUAGAC-5'<br>5'-ATTGACAACTGCATGTTTCAACATCTG-3' | (SEQ ID NO: 4222)<br>(SEQ ID NO: 2004)<br>(SEQ ID NO: 3113) |
| βc-m630 Target: | 5'-AAAUUGACAACUGCAUGUUUCAACA-3'<br>3'-AGUUUAACUGUUGACGUACAAAGUUGU-5'<br>5'-TCAAATTGACAACTGCATGTTTCAACA-3' | (SEQ ID NO: 4223)<br>(SEQ ID NO: 2005)<br>(SEQ ID NO: 3114) |
| βc-m636 Target: | 5'-UUAAUCAAAUUGACAACUGCAUGUU-3'<br>3'-UCAAUUAGUUUAACUGUUGACGUACAA-5'<br>5'-AGTTAATCAAATTGACAACTGCATGTT-3' | (SEQ ID NO: 4224)<br>(SEQ ID NO: 2006)<br>(SEQ ID NO: 3115) |
| βc-m642 Target: | 5'-UGAUAGUUAAUCAAAUUGACAACUG-3'<br>3'-GGACUAUCAAUUAGUUUAACUGUUGAC-5'<br>5'-CCTGATAGTTAATCAAATTGACAACTG-3' | (SEQ ID NO: 4225)<br>(SEQ ID NO: 2007)<br>(SEQ ID NO: 3116) |
| βc-m648 Target: | 5'-UCAUCCUGAUAGUUAAUCAAAUUGA-3'<br>3'-GCAGUAGGACUAUCAAUUAGUUUAACU-5'<br>5'-CGTCATCCTGATAGTTAATCAAATTGA-3' | (SEQ ID NO: 4226)<br>(SEQ ID NO: 2008)<br>(SEQ ID NO: 3117) |
| βc-m649 Target: | 5'-GUCAUCCUGAUAGUUAAUCAAAUUG-3'<br>3'-CGCAGUAGGACUAUCAAUUAGUUUAAC-5'<br>5'-GCGTCATCCTGATAGTTAATCAAATTG-3' | (SEQ ID NO: 4227)<br>(SEQ ID NO: 2009)<br>(SEQ ID NO: 3118) |
| βc-m702 Target: | 5'-UCAUCGUUUAGCAGUUUUGUCAGCU-3'<br>3'-GGAGUAGCAAAUCGUCAAAACAGUCGA-5'<br>5'-CCTCATCGTTTAGCAGTTTTGTCAGCT-3' | (SEQ ID NO: 4228)<br>(SEQ ID NO: 2010)<br>(SEQ ID NO: 3119) |
| βc-m707 Target: | 5'-GGUCCUCAUCGUUUAGCAGUUUUGU-3'<br>3'-GACCAGGAGUAGCAAAUCGUCAAAACA-5'<br>5'-CTGGTCCTCATCGTTTAGCAGTTTTGT-3' | (SEQ ID NO: 4229)<br>(SEQ ID NO: 2011)<br>(SEQ ID NO: 3120) |
| βc-m734 Target: | 5'-UAACAGCAGCUUUAUUAACUACCAC-3'<br>3'-GUAUUGUCGUCGAAAUAAUUGAUGGUG-5'<br>5'-CATAACAGCAGCTTTATTAACTACCAC-3' | (SEQ ID NO: 4230)<br>(SEQ ID NO: 2012)<br>(SEQ ID NO: 3121) |
| βc-m735 Target: | 5'-AUAACAGCAGCUUUAUUAACUACCA-3'<br>3'-GGUAUUGUCGUCGAAAUAAUUGAUGGU-5'<br>5'-CCATAACAGCAGCTTTATTAACTACCA-3' | (SEQ ID NO: 4231)<br>(SEQ ID NO: 2013)<br>(SEQ ID NO: 3122) |
| βc-m738 Target: | 5'-ACCAUAACAGCAGCUUUAUUAACUA-3'<br>3'-CCUGGUAUUGUCGUCGAAAUAAUUGAU-5'<br>5'-GGACCATAACAGCAGCTTTATTAACTA-3' | (SEQ ID NO: 4232)<br>(SEQ ID NO: 2014)<br>(SEQ ID NO: 3123) |
| βc-m739 Target: | 5'-GACCAUAACAGCAGCUUUAUUAACU-3'<br>3'-ACCUGGUAUUGUCGUCGAAAUAAUUGA-5'<br>5'-TGGACCATAACAGCAGCTTTATTAACT-3' | (SEQ ID NO: 4233)<br>(SEQ ID NO: 2015)<br>(SEQ ID NO: 3124) |
| βc-m843 Target: | 5'-GUCUCUACAUCAUUUGUAUUCUGCA-3'<br>3'-GACAGAGAUGUAGUAAACAUAAGACGU-5'<br>5'-CTGTCTCTACATCATTTGTATTCTGCA-3' | (SEQ ID NO: 4234)<br>(SEQ ID NO: 2016)<br>(SEQ ID NO: 3125) |
| βc-m844 Target: | 5'-UGUCUCUACAUCAUUUGUAUUCUGC-3'<br>3'-CGACAGAGAUGUAGUAAACAUAAGACG-5'<br>5'-GCTGTCTCTACATCATTTGTATTCTGC-3' | (SEQ ID NO: 4235)<br>(SEQ ID NO: 2017)<br>(SEQ ID NO: 3126) |
| βc-m1063 Target: | 5'-AACCAUUUUCUGCAGUCCACCAGCU-3'<br>3'-CGUUGGUAAAAGACGUCAGGUGGUCGA-5'<br>5'-GCAACCATTTTCTGCAGTCCACCAGCT-3' | (SEQ ID NO: 4236)<br>(SEQ ID NO: 2018)<br>(SEQ ID NO: 3127) |
| βc-m1065 Target: | 5'-GCAACCAUUUUCUGCAGUCCACCAG-3'<br>3'-UUCGUUGGUAAAAGACGUCAGGUGGUC-5'<br>5'-AAGCAACCATTTTCTGCAGTCCACCAG-3' | (SEQ ID NO: 4237)<br>(SEQ ID NO: 2019)<br>(SEQ ID NO: 3128) |
| βc-m1080 Target: | 5'-GUUUUGUUGAGCAAAGCAACCAUUU-3'<br>3'-AACAAAACAACUCGUUUCGUUGGUAAA-5'<br>5'-TTGTTTTGTTGAGCAAAGCAACCATTT-3' | (SEQ ID NO: 4238)<br>(SEQ ID NO: 2020)<br>(SEQ ID NO: 3129) |
| βc-m1081 Target: | 5'-UGUUUUGUUGAGCAAAGCAACCAUU-3'<br>3'-AAACAAAACAACUCGUUUCGUUGGUAA-5'<br>5'-TTTGTTTTGTTGAGCAAAGCAACCATT-3' | (SEQ ID NO: 4239)<br>(SEQ ID NO: 2021)<br>(SEQ ID NO: 3130) |
| βc-m1098 Target: | 5'-GCCAAGAAUUUCACGUUUGUUUUGU-3'<br>3'-AUCGGUUCUUAAAGUGCAAACAAAACA-5'<br>5'-TAGCCAAGAATTTCACGTTTGTTTTGT-3' | (SEQ ID NO: 4240)<br>(SEQ ID NO: 2022)<br>(SEQ ID NO: 3131) |

TABLE 11-continued

Additional Selected Anti-β-catenin DsiRNAs, 25/27mer Duplexes, Unmodified

| | | |
|---|---|---|
| βc-m1140 Target: | 5'-UGAUUGCCAUAAGCUAAGAUCUGAA-3'<br>3'-GAACUAACGGUAUUCGAUUCUAGACUU-5'<br>5'-CTTGATTGCCATAAGCTAAGATCTGAA-3' | (SEQ ID NO: 4241)<br>(SEQ ID NO: 2023)<br>(SEQ ID NO: 3132) |
| βc-m1145 Target: | 5'-UCUCUUGAUUGCCAUAAGCUAAGAU-3'<br>3'-CGAGAGAACUAACGGUAUUCGAUUCUA-5'<br>5'-GCTCTCTTGATTGCCATAAGCTAAGAT-3' | (SEQ ID NO: 4242)<br>(SEQ ID NO: 2024)<br>(SEQ ID NO: 3133) |
| βc-m1217 Target: | 5'-UCUCAUAAGUGUAGGUCCUCAUUAU-3'<br>3'-GAAGAGUAUUCACAUCCAGGAGUAAUA-5'<br>5'-CTTCTCATAAGTGTAGGTCCTCATTAT-3' | (SEQ ID NO: 4243)<br>(SEQ ID NO: 2025)<br>(SEQ ID NO: 3134) |
| βc-m1218 Target: | 5'-UUCUCAUAAGUGUAGGUCCUCAUUA-3'<br>3'-CGAAGAGUAUUCACAUCCAGGAGUAAU-5'<br>5'-GCTTCTCATAAGTGTAGGTCCTCATTA-3' | (SEQ ID NO: 4244)<br>(SEQ ID NO: 2026)<br>(SEQ ID NO: 3135) |
| βc-m1220 Target: | 5'-GCUUCUCAUAAGUGUAGGUCCUCAU-3'<br>3'-UUCGAAGAGUAUUCACAUCCAGGAGUA-5'<br>5'-AAGCTTCTCATAAGTGTAGGTCCTC-3' | (SEQ ID NO: 4245)<br>(SEQ ID NO: 2027)<br>(SEQ ID NO: 3136) |
| βc-m1221 Target: | 5'-AGCUUCUCAUAAGUGUAGGUCCUCA-3'<br>3'-CUUCGAAGAGUAUUCACAUCCAGGAGU-5'<br>5'-GAAGCTTCTCATAAGTGTAGGTCCTCA-3' | (SEQ ID NO: 4246)<br>(SEQ ID NO: 2028)<br>(SEQ ID NO: 3137) |
| βc-m1365 Target: | 5'-GUCCAAAGACAGUUUUGAACAAGUC-3'<br>3'-CUCAGGUUUCUGUCAAAACUUGUUCAG-5'<br>5'-GAGTCCAAAGACAGTTTTGAACAAGTC-3' | (SEQ ID NO: 4247)<br>(SEQ ID NO: 2029)<br>(SEQ ID NO: 3138) |
| βc-m1366 Target: | 5'-AGUCCAAAGACAGUUUUGAACAAGU-3'<br>3'-UCUCAGGUUUCUGUCAAAACUUGUUCA-5'<br>5'-AGAGTCCAAAGACAGTTTTGAACAAGT-3' | (SEQ ID NO: 4248)<br>(SEQ ID NO: 2030)<br>(SEQ ID NO: 3139) |
| βc-m1461 Target: | 5'-ACAUUUAUAUCAUCGGAACCCAGAA-3'<br>3'-GGUGUAAAUAUAGUAGCCUUGGGUCUU-5'<br>5'-CCACATTTATATCATCGGAACCCAGAA-3' | (SEQ ID NO: 4249)<br>(SEQ ID NO: 2031)<br>(SEQ ID NO: 3140) |
| βc-m1464 Target: | 5'-ACCACAUUUAUAUCAUCGGAACCCA-3'<br>3'-ACUGGUGUAAAUAUAGUAGCCUUGGGU-5'<br>5'-TGACCACATTTATATCATCGGAACCCA-3' | (SEQ ID NO: 4250)<br>(SEQ ID NO: 2032)<br>(SEQ ID NO: 3141) |
| βc-m1473 Target: | 5'-GCACAGGUGACCACAUUUAUAUCAU-3'<br>3'-GACGUGUCCACUGGUGUAAAUAUAGUA-5'<br>5'-CTGCACAGGTGACCACATTTATATC-3' | (SEQ ID NO: 4251)<br>(SEQ ID NO: 2033)<br>(SEQ ID NO: 3142) |
| βc-m1474 Target: | 5'-UGCACAGGUGACCACAUUUAUAUCA-3'<br>3'-CGACGUGUCCACUGGUGUAAAUAUAGU-5'<br>5'-GCTGCACAGGTGACCACATTTATATCA-3' | (SEQ ID NO: 4252)<br>(SEQ ID NO: 2034)<br>(SEQ ID NO: 3143) |
| βc-m1510 Target: | 5'-GUAAUUAUUGCAAGUGAGGUUAGAG-3'<br>3'-AACAUUAAUAACGUUCACUCCAAUCUC-5'<br>5'-TTGTAATTATTGCAAGTGAGGTTAGAG-3' | (SEQ ID NO: 4253)<br>(SEQ ID NO: 2035)<br>(SEQ ID NO: 3144) |
| βc-m1523 Target: | 5'-UCAUCUUGUUUUUGUAAUUAUUGCA-3'<br>3'-GUAGUAGAACAAAAACAUUAAUAACGU-5'<br>5'-CATCATCTTGTTTTTGTAATTATTGCA-3' | (SEQ ID NO: 4254)<br>(SEQ ID NO: 2036)<br>(SEQ ID NO: 3145) |
| βc-m1524 Target: | 5'-AUCAUCUUGUUUUUGUAAUUAUUGC-3'<br>3'-GGUAGUAGAACAAAAACAUUAAUAACG-5'<br>5'-CCATCATCTTGTTTTTGTAATTATTGC-3' | (SEQ ID NO: 4255)<br>(SEQ ID NO: 2037)<br>(SEQ ID NO: 3146) |
| βc-m1527 Target: | 5'-ACCAUCAUCUUGUUUUUGUAAUUAU-3'<br>3'-UGUGGUAGUAGAACAAAAACAUUAAUA-5'<br>5'-ACACCATCATCTTGTTTTTGTAATTAT-3' | (SEQ ID NO: 4256)<br>(SEQ ID NO: 2038)<br>(SEQ ID NO: 3147) |
| βc-m1532 Target: | 5'-GGCACACCAUCAUCUUGUUUUUGUA-3'<br>3'-AACCGUGUGGUAGUAGAACAAAAACAU-5'<br>5'-TTGGCACACCATCATCTTGTTTTTGTA-3' | (SEQ ID NO: 4257)<br>(SEQ ID NO: 2039)<br>(SEQ ID NO: 3148) |
| βc-m1752 Target: | 5'-AAUCCAACAGUUGCCUUUAUCAGAG-3'<br>3'-AGUUAGGUUGUCAACGGAAAUAGUCUC-5'<br>5'-TCAATCCAACAGTTGCCTTTATCAGAG-3' | (SEQ ID NO: 4258)<br>(SEQ ID NO: 2040)<br>(SEQ ID NO: 3149) |
| βc-m1757 Target: | 5'-GAAUCAAUCCAACAGUUGCCUUUAU-3'<br>3'-AGCUUAGUUAGGUUGUCAACGGAAAUA-5'<br>5'-TCGAATCAATCCAACAGTTGCCTTTAT-3' | (SEQ ID NO: 4259)<br>(SEQ ID NO: 2041)<br>(SEQ ID NO: 3150) |

TABLE 11-continued

Additional Selected Anti-β-catenin DsiRNAs, 25/27mer Duplexes, Unmodified

| | | |
|---|---|---|
| βc-m1827 Target: | 5'-UGAACUAGUCGUGGAAUAGCACCCU-3'<br>3'-CGACUUGAUCAGCACCUUAUCGUGGGA-5'<br>5'-GCTGAACTAGTCGTGGAATAGCACCCT-3' | (SEQ ID NO: 4260)<br>(SEQ ID NO: 2042)<br>(SEQ ID NO: 3151) |
| βc-m1934 Target: | 5'-UACACCCUUCUACUAUCUCCUCCAU-3'<br>3'-UCAUGUGGGAAGAUGAUAGAGGAGGUA-5'<br>5'-AGTACACCCTTCTACTATCTCCTCC-3' | (SEQ ID NO: 4261)<br>(SEQ ID NO: 2043)<br>(SEQ ID NO: 3152) |
| βc-m1935 Target: | 5'-GUACACCCUUCUACUAUCUCCUCCA-3'<br>3'-GUCAUGUGGGAAGAUGAUAGAGGAGGU-5'<br>5'-CAGTACACCCTTCTACTATCTCCTCCA-3' | (SEQ ID NO: 4262)<br>(SEQ ID NO: 2044)<br>(SEQ ID NO: 3153) |
| βc-m1936 Target: | 5'-AGUACACCCUUCUACUAUCUCCUCC-3'<br>3'-GGUCAUGUGGGAAGAUGAUAGAGGAGG-5'<br>5'-CCAGTACACCCTTCTACTATCTCCTCC-3' | (SEQ ID NO: 4263)<br>(SEQ ID NO: 2045)<br>(SEQ ID NO: 3154) |
| βc-m1941 Target: | 5'-GCUCCAGUACACCCUUCUACUAUCU-3'<br>3'-CUCGAGGUCAUGUGGGAAGAUGAUAGA-5'<br>5'-GAGCTCCAGTACACCCTTCTACTATCT-3' | (SEQ ID NO: 4264)<br>(SEQ ID NO: 2046)<br>(SEQ ID NO: 3155) |
| βc-m2009 Target: | 5'-ACAAUGGAAUGGUAUUGAGUCCUCG-3'<br>3'-UUUGUUACCUUACCAUAACUCAGGAGC-5'<br>5'-AAACAATGGAATGGTATTGAGTCCTCG-3' | (SEQ ID NO: 4265)<br>(SEQ ID NO: 2047)<br>(SEQ ID NO: 3156) |
| βc-m2015 Target: | 5'-GCACAAACAAUGGAAUGGUAUUGAG-3'<br>3'-GACGUGUUUGUUACCUUACCAUAACUC-5'<br>5'-CTGCACAAACAATGGAATGGTATTGAG-3' | (SEQ ID NO: 4266)<br>(SEQ ID NO: 2048)<br>(SEQ ID NO: 3157) |
| βc-m2016 Target: | 5'-UGCACAAACAAUGGAAUGGUAUUGA-3'<br>3'-UGACGUGUUUGUUACCUUACCAUAACU-5'<br>5'-ACTGCACAAACAATGGAATGGTATTGA-3' | (SEQ ID NO: 4267)<br>(SEQ ID NO: 2049)<br>(SEQ ID NO: 3158) |
| βc-m2021 Target: | 5'-GCAACUGCACAAACAAUGGAAUGGU-3'<br>3'-UUCGUUGACGUGUUUGUUACCUUACCA-5'<br>5'-AAGCAACTGCACAAACAATGGAATGGT-3' | (SEQ ID NO: 4268)<br>(SEQ ID NO: 2050)<br>(SEQ ID NO: 3159) |
| βc-m2028 Target: | 5'-GAAUAAAGCAACUGCACAAACAAUG-3'<br>3'-CUCUUAUUUCGUUGACGUGUUUGUUAC-5'<br>5'-GAGAATAAAGCAACTGCACAAACAATG-3' | (SEQ ID NO: 4269)<br>(SEQ ID NO: 2051)<br>(SEQ ID NO: 3160) |
| βc-m2037 Target: | 5'-UCAAUGGGAGAAUAAAGCAACUGCA-3'<br>3'-AAAGUUACCCUCUUAUUUCGUUGACGU-5'<br>5'-TTTCAATGGGAGAATAAAGCAACTGCA-3' | (SEQ ID NO: 4270)<br>(SEQ ID NO: 2052)<br>(SEQ ID NO: 3161) |
| βc-m2038 Target: | 5'-UUCAAUGGGAGAAUAAAGCAACUGC-3'<br>3'-AAAAGUUACCCUCUUAUUUCGUUGACG-5'<br>5'-TTTTCAATGGGAGAATAAAGCAACTGC-3' | (SEQ ID NO: 4271)<br>(SEQ ID NO: 2053)<br>(SEQ ID NO: 3162) |
| βc-m2039 Target: | 5'-UUUCAAUGGGAGAAUAAAGCAACUG-3'<br>3'-UAAAAGUUACCCUCUUAUUUCGUUGAC-5'<br>5'-ATTTTCAATGGGAGAATAAAGCAACTG-3' | (SEQ ID NO: 4272)<br>(SEQ ID NO: 2054)<br>(SEQ ID NO: 3163) |
| βc-m2043 Target: | 5'-AUAUUUUCAAUGGGAGAAUAAAGCA-3'<br>3'-CCUAUAAAAGUUACCCUCUUAUUUCGU-5'<br>5'-GGATATTTTCAATGGGAGAATAAAGCA-3' | (SEQ ID NO: 4273)<br>(SEQ ID NO: 2055)<br>(SEQ ID NO: 3164) |
| βc-m2044 Target: | 5'-GAUAUUUUCAAUGGGAGAAUAAAGC-3'<br>3'-ACCUAUAAAAGUUACCCUCUUAUUUCG-5'<br>5'-TGGATATTTTCAATGGGAGAATAAAGC-3' | (SEQ ID NO: 4274)<br>(SEQ ID NO: 2056)<br>(SEQ ID NO: 3165) |
| βc-m2045 Target: | 5'-GGAUAUUUUCAAUGGGAGAAUAAAG-3'<br>3'-AACCUAUAAAAGUUACCCUCUUAUUUC-5'<br>5'-TTGGATATTTTCAATGGGAGAATAAAG-3' | (SEQ ID NO: 4275)<br>(SEQ ID NO: 2057)<br>(SEQ ID NO: 3166) |
| βc-m2055 Target: | 5'-GCUACUCUUUGGAUAUUUUCAAUGG-3'<br>3'-GUCGAUGAGAAACCUAUAAAAGUUACC-5'<br>5'-CAGCTACTCTTTGGATATTTTCAATGG-3' | (SEQ ID NO: 4276)<br>(SEQ ID NO: 2058)<br>(SEQ ID NO: 3167) |
| βc-m2056 Target: | 5'-AGCUACUCUUUGGAUAUUUUCAAUG-3'<br>3'-CGUCGAUGAGAAACCUAUAAAAGUUAC-5'<br>5'-GCAGCTACTCTTTGGATATTTTCAATG-3' | (SEQ ID NO: 4277)<br>(SEQ ID NO: 2059)<br>(SEQ ID NO: 3168) |
| βc-m2231 Target: | 5'-GCUUCUUGUAAUCCUGUGGCUUGUC-3'<br>3'-GGCGAAGAACAUUAGGACACCGAACAG-5'<br>5'-CCGCTTCTTGTAATCCTGTGGCTTGTC-3' | (SEQ ID NO: 4278)<br>(SEQ ID NO: 2060)<br>(SEQ ID NO: 3169) |

TABLE 11-continued

Additional Selected Anti-β-catenin DsiRNAs, 25/27mer Duplexes, Unmodified

| | | |
|---|---|---|
| | 5'-AGUCCAAGAUCUGCAGUCUCAUUCC-3' | (SEQ ID NO: 4279) |
| | 3'-GGUCAGGUUCUAGACGUCAGAGUAAGG-5' | (SEQ ID NO: 2061) |
| βc-m2307 Target: | 5'-CCAGTCCAAGATCTGCAGTCTCATTCC-3' | (SEQ ID NO: 3170) |
| | 5'-UAUCCACCAGAGUGAAAAGAACGGU-3' | (SEQ ID NO: 4280) |
| | 3'-GCAUAGGUGGUCUCACUUUUCUUGCCA-5' | (SEQ ID NO: 2062) |
| βc-m2385 Target: | 5'-CGTATCCACCAGAGTGAAAAGAACGGT-3' | (SEQ ID NO: 3171) |
| | 5'-GGCCAGCUGAUUGCUAUCACCUGGG-3' | (SEQ ID NO: 4281) |
| | 3'-GUCCGGUCGACUAACGAUAGUGGACCC-5' | (SEQ ID NO: 2063) |
| βc-m2539 Target: | 5'-CAGGCCAGCTGATTGCTATCACCTGGG-3' | (SEQ ID NO: 3172) |
| | 5'-AUUUACAGGUCAGUAUCAAACCAGG-3' | (SEQ ID NO: 4282) |
| | 3'-GCUAAAUGUCCAGUCAUAGUUUGGUCC-5' | (SEQ ID NO: 2064) |
| βc-m2562 Target: | 5'-CGATTTACAGGTCAGTATCAAACCAGG-3' | (SEQ ID NO: 3173) |
| | 5'-GAUUUACAGGUCAGUAUCAAACCAG-3' | (SEQ ID NO: 4283) |
| | 3'-UGCUAAAUGUCCAGUCAUAGUUUGGUC-5' | (SEQ ID NO: 2065) |
| βc-m2563 Target: | 5'-ACGATTTACAGGTCAGTATCAAACCAG-3' | (SEQ ID NO: 3174) |
| | 5'-UCUUACCUAAAGGACGAUUUACAGG-3' | (SEQ ID NO: 4284) |
| | 3'-AAAGAAUGGAUUUCCUGCUAAAUGUCC-5' | (SEQ ID NO: 2066) |
| βc-m2578 Target: | 5'-TTTCTTACCTAAAGGACGATTTACAGG-3' | (SEQ ID NO: 3175) |
| | 5'-UUUCUUACCUAAAGGACGAUUUACA-3' | (SEQ ID NO: 4285) |
| | 3'-CGAAAGAAUGGAUUUCCUGCUAAAUGU-5' | (SEQ ID NO: 2067) |
| βc-m2580 Target: | 5'-GCTTTCTTACCTAAAGGACGATTTACA-3' | (SEQ ID NO: 3176) |
| | 5'-UUUAUAAGCUUUCUUACCUAAAGGA-3' | (SEQ ID NO: 4286) |
| | 3'-GAAAAUAUUCGAAAGAAUGGAUUUCCU-5' | (SEQ ID NO: 2068) |
| βc-m2589 Target: | 5'-CTTTTATAAGCTTTCTTACCTAAAGGA-3' | (SEQ ID NO: 3177) |
| | 5'-UUUUAUAAGCUUUCUUACCUAAAGG-3' | (SEQ ID NO: 4287) |
| | 3'-CGAAAAUAUUCGAAAGAAUGGAUUUCC-5' | (SEQ ID NO: 2069) |
| βc-m2590 Target: | 5'-GCTTTTATAAGCTTTCTTACCTAAAGG-3' | (SEQ ID NO: 3178) |
| | 5'-GGCUUUUAUAAGCUUUCUUACCUAA-3' | (SEQ ID NO: 4288) |
| | 3'-GACCGAAAAUAUUCGAAAGAAUGGAUU-5' | (SEQ ID NO: 2070) |
| βc-m2593 Target: | 5'-CTGGCTTTTATAAGCTTTCTTACCTAA-3' | (SEQ ID NO: 3179) |
| | 5'-ACACUGGCUUUUAUAAGCUUUCUUA-3' | (SEQ ID NO: 4289) |
| | 3'-GGUGUGACCGAAAAUAUUCGAAAGAAU-5' | (SEQ ID NO: 2071) |
| βc-m2598 Target: | 5'-CCACACTGGCTTTTATAAGCTTTCTTA-3' | (SEQ ID NO: 3180) |
| | 5'-UCACCCACACUGGCUUUUAUAAGCU-3' | (SEQ ID NO: 4290) |
| | 3'-UAAGUGGGUGUGACCGAAAAUAUUCGA-5' | (SEQ ID NO: 2072) |
| βc-m2604 Target: | 5'-ATTCACCCACACTGGCTTTTATAAGCT-3' | (SEQ ID NO: 3181) |
| | 5'-UACCAAGUCUUUCUGGAGUUCUGCA-3' | (SEQ ID NO: 4291) |
| | 3'-GGAUGGUUCAGAAAGACCUCAAGACGU-5' | (SEQ ID NO: 2073) |
| βc-m2644 Target: | 5'-CCTACCAAGTCTTTCTGGAGTTCTGCA-3' | (SEQ ID NO: 3182) |
| | 5'-UUACAAACAGGCCUAAAACCAUUCC-3' | (SEQ ID NO: 4292) |
| | 3'-UAAAUGUUUGUCCGGAUUUUGGUAAGG-5' | (SEQ ID NO: 2074) |
| βc-m2674 Target: | 5'-ATTTACAAACAGGCCTAAAACCATTCC-3' | (SEQ ID NO: 3183) |
| | 5'-UUUACAAACAGGCCUAAAACCAUUC-3' | (SEQ ID NO: 4293) |
| | 3'-CUAAAUGUUUGUCCGGAUUUUGGUAAG-5' | (SEQ ID NO: 2075) |
| βc-m2675 Target: | 5'-GATTTACAAACAGGCCTAAAACCATTC-3' | (SEQ ID NO: 3184) |
| | 5'-AUUUACAAACAGGCCUAAAACCAUU-3' | (SEQ ID NO: 4294) |
| | 3'-UCUAAAUGUUUGUCCGGAUUUUGGUAA-5' | (SEQ ID NO: 2076) |
| βc-m2676 Target: | 5'-AGATTTACAAACAGGCCTAAAACCATT-3' | (SEQ ID NO: 3185) |
| | 5'-UCUCCUUCCAAGGUAUGUAUCUGUU-3' | (SEQ ID NO: 4295) |
| | 3'-GUAGAGGAAGGUUCCAUACAUAGACAA-5' | (SEQ ID NO: 2077) |
| βc-m2710 Target: | 5'-CATCTCCTTCCAAGGTATGTATCTGTT-3' | (SEQ ID NO: 3186) |
| | 5'-AUCUCCUUCCAAGGUAUGUAUCUGU-3' | (SEQ ID NO: 4296) |
| | 3'-UGUAGAGGAAGGUUCCAUACAUAGACA-5' | (SEQ ID NO: 2078) |
| βc-m2711 Target: | 5'-ACATCTCCTTCCAAGGTATGTATCTGT-3' | (SEQ ID NO: 3187) |
| | 5'-UUCCACACAUGAACAUCUCCUUCCA-3' | (SEQ ID NO: 4297) |
| | 3'-UGAAGGUGUGUACUUGUAGAGGAAGGU-5' | (SEQ ID NO: 2079) |
| βc-m2725 Target: | 5'-ACTTCCACACATGAACATCTCCTTCCA-3' | (SEQ ID NO: 3188) |

TABLE 11-continued

Additional Selected Anti-β-catenin DsiRNAs, 25/27mer Duplexes, Unmodified

| | | |
|---|---|---|
| βc-m2728 Target: | 5'-AACUUCCACACAUGAACAUCUCCUU-3'<br>3'-CUUUGAAGGUGUGUACUUGUAGAGGAA-5'<br>5'-GAAACTTCCACACATGAACATCTCCTT-3' | (SEQ ID NO: 4298)<br>(SEQ ID NO: 2080)<br>(SEQ ID NO: 3189) |
| βc-m2729 Target: | 5'-AAACUUCCACACAUGAACAUCUCCU-3'<br>3'-UCUUUGAAGGUGUGUACUUGUAGAGGA-5'<br>5'-AGAAACTTCCACACATGAACATCTCCT-3' | (SEQ ID NO: 4299)<br>(SEQ ID NO: 2081)<br>(SEQ ID NO: 3190) |
| βc-m2730 Target: | 5'-GAAACUUCCACACAUGAACAUCUCC-3'<br>3'-CUCUUUGAAGGUGUGUACUUGUAGAGG-5'<br>5'-GAGAAACTTCCACACATGAACATCTCC-3' | (SEQ ID NO: 4300)<br>(SEQ ID NO: 2082)<br>(SEQ ID NO: 3191) |
| βc-m2731 Target: | 5'-AGAAACUUCCACACAUGAACAUCUC-3'<br>3'-ACUCUUUGAAGGUGUGUACUUGUAGAG-5'<br>5'-TGAGAAACTTCCACACATGAACATCTC-3' | (SEQ ID NO: 4301)<br>(SEQ ID NO: 2083)<br>(SEQ ID NO: 3192) |
| βc-m2739 Target: | 5'-UCAACGUGAGAAACUUCCACACAUG-3'<br>3'-GUAGUUGCACUCUUUGAAGGUGUGUAC-5'<br>5'-CATCAACGTGAGAAACTTCCACACATG-3' | (SEQ ID NO: 4302)<br>(SEQ ID NO: 2084)<br>(SEQ ID NO: 3193) |
| βc-m2742 Target: | 5'-ACAUCAACGUGAGAAACUUCCACAC-3'<br>3'-UUUGUAGUUGCACUCUUUGAAGGUGUG-5'<br>5'-AAACATCAACGTGAGAAACTTCCACAC-3' | (SEQ ID NO: 4303)<br>(SEQ ID NO: 2085)<br>(SEQ ID NO: 3194) |
| βc-m2743 Target: | 5'-AACAUCAACGUGAGAAACUUCCACA-3'<br>3'-UUUUGUAGUUGCACUCUUUGAAGGUGU-5'<br>5'-AAAACATCAACGTGAGAAACTTCCACA-3' | (SEQ ID NO: 4304)<br>(SEQ ID NO: 2086)<br>(SEQ ID NO: 3195) |
| βc-m2744 Target: | 5'-AAACAUCAACGUGAGAAACUUCCAC-3'<br>3'-UUUUUGUAGUUGCACUCUUUGAAGGUG-5'<br>5'-AAAAACATCAACGTGAGAAACTTCCAC-3' | (SEQ ID NO: 4305)<br>(SEQ ID NO: 2087)<br>(SEQ ID NO: 3196) |
| βc-m2745 Target: | 5'-AAAACAUCAACGUGAGAAACUUCCA-3'<br>3'-GUUUUUGUAGUUGCACUCUUUGAAGGU-5'<br>5'-CAAAAACATCAACGTGAGAAACTTCCA-3' | (SEQ ID NO: 4306)<br>(SEQ ID NO: 2088)<br>(SEQ ID NO: 3197) |
| βc-m2746 Target: | 5'-AAAAACAUCAACGUGAGAAACUUCC-3'<br>3'-CGUUUUUGUAGUUGCACUCUUUGAAGG-5'<br>5'-GCAAAAACATCAACGTGAGAAACTTCC-3' | (SEQ ID NO: 4307)<br>(SEQ ID NO: 2089)<br>(SEQ ID NO: 3198) |
| βc-m2748 Target: | 5'-GCAAAAACAUCAACGUGAGAAACUU-3'<br>3'-ACCGUUUUUGUAGUUGCACUCUUUGAA-5'<br>5'-TGGCAAAAACATCAACGTGAGAAACTT-3' | (SEQ ID NO: 4308)<br>(SEQ ID NO: 2090)<br>(SEQ ID NO: 3199) |
| βc-m2760 Target: | 5'-GCAAAAGCUGUGGCAAAAACAUCAA-3'<br>3'-GACGUUUUCGACACCGUUUUUGUAGUU-5'<br>5'-CTGCAAAAGCTGTGGCAAAAACATCAA-3' | (SEQ ID NO: 4309)<br>(SEQ ID NO: 2091)<br>(SEQ ID NO: 3200) |
| βc-m2761 Target: | 5'-UGCAAAAGCUGUGGCAAAAACAUCA-3'<br>3'-CGACGUUUUCGACACCGUUUUUGUAGU-5'<br>5'-GCTGCAAAAGCTGTGGCAAAAACATCA-3' | (SEQ ID NO: 4310)<br>(SEQ ID NO: 2092)<br>(SEQ ID NO: 3201) |
| βc-m2778 Target: | 5'-UCAUCUGAGUAUAACGCUGCAAAAG-3'<br>3'-UGAGUAGACUCAUAUUGCGACGUUUUC-5'<br>5'-ACTCATCTGAGTATAACGCTGCAAAAG-3' | (SEQ ID NO: 4311)<br>(SEQ ID NO: 2093)<br>(SEQ ID NO: 3202) |
| βc-m2795 Target: | 5'-AAAACAGCAAAUGUUACUCAUCUGA-3'<br>3'-ACUUUUGUCGUUUACAAUGAGUAGACU-5'<br>5'-TGAAAACAGCAAATGTTACTCATCTGA-3' | (SEQ ID NO: 4312)<br>(SEQ ID NO: 2094)<br>(SEQ ID NO: 3203) |
| βc-m2796 Target: | 5'-GAAACAGCAAAUGUUACUCAUCUG-3'<br>3'-AACUUUUGUCGUUUACAAUGAGUAGAC-5'<br>5'-TTGAAAACAGCAAATGTTACTCATCTG-3' | (SEQ ID NO: 4313)<br>(SEQ ID NO: 2095)<br>(SEQ ID NO: 3204) |
| βc-m2797 Target: | 5'-UGAAAACAGCAAAUGUUACUCAUCU-3'<br>3'-CAACUUUUGUCGUUUACAAUGAGUAGA-5'<br>5'-GTTGAAAACAGCAAATGTTACTCATCT-3' | (SEQ ID NO: 4314)<br>(SEQ ID NO: 2096)<br>(SEQ ID NO: 3205) |
| βc-m2805 Target: | 5'-AUUAAUGUUGAAAACAGCAAAUGUU-3'<br>3'-GAUAAUUACAACUUUUGUCGUUUACAA-5'<br>5'-CTATTAATGTTGAAAACAGCAAATGTT-3' | (SEQ ID NO: 4315)<br>(SEQ ID NO: 2097)<br>(SEQ ID NO: 3206) |
| βc-m2834 Target: | 5'-ACUACAGCUGUAUAGAGAGAAAGGC-3'<br>3'-UGUGAUGUCGACAUAUCUCUCUUUCCG-5'<br>5'-ACACTACAGCTGTATAGAGAGAAAGGC-3' | (SEQ ID NO: 4316)<br>(SEQ ID NO: 2098)<br>(SEQ ID NO: 3207) |

TABLE 11-continued

Additional Selected Anti-β-catenin DsiRNAs, 25/27mer Duplexes, Unmodified

| | | |
|---|---|---|
| βc-m2859 Target: | 5'-GGCCAAUCACAAUGCACGUUCAGAC-3'<br>3'-GUCCGGUUAGUGUUACGUGCAAGUCUG-5'<br>5'-CAGGCCAATCACAATGCACGTTCAGAC-3' | (SEQ ID NO: 4317)<br>(SEQ ID NO: 2099)<br>(SEQ ID NO: 3208) |
| βc-m2946 Target: | 5'-GUUCCCAUAGGAAACUCAGCUUGGU-3'<br>3'-GACAAGGGUAUCCUUUGAGUCGAACCA-5'<br>5'-CTGTTCCCATAGGAAACTCAGCTTGGT-3' | (SEQ ID NO: 4318)<br>(SEQ ID NO: 2100)<br>(SEQ ID NO: 3209) |
| βc-m2968 Target: | 5'-GAACAAAAAGCGUACUUCGACUGUU-3'<br>3'-GUCUUGUUUUUCGCAUGAAGCUGACAA-5'<br>5'-CAGAACAAAAAGCGTACTTCGACTGTT-3' | (SEQ ID NO: 4319)<br>(SEQ ID NO: 2101)<br>(SEQ ID NO: 3210) |
| βc-m2974 Target: | 5'-GGACCAGAACAAAAAGCGUACUUCG-3'<br>3'-UUCCUGGUCUUGUUUUUCGCAUGAAGC-5'<br>5'-AAGGACCAGAACAAAAAGCGTACTTCG-3' | (SEQ ID NO: 4320)<br>(SEQ ID NO: 2102)<br>(SEQ ID NO: 3211) |
| βc-m2982 Target: | 5'-ACCAAAAAGGACCAGAACAAAAAGC-3'<br>3'-GCUGGUUUUUCCUGGUCUUGUUUUUCG-5'<br>5'-CGACCAAAAAGGACCAGAACAAAAAGC-3' | (SEQ ID NO: 4321)<br>(SEQ ID NO: 2103)<br>(SEQ ID NO: 3212) |
| βc-m2983 Target: | 5'-GACCAAAAAGGACCAGAACAAAAAG-3'<br>3'-AGCUGGUUUUUCCUGGUCUUGUUUUUC-5'<br>5'-TCGACCAAAAAGGACCAGAACAAAAAG-3' | (SEQ ID NO: 4322)<br>(SEQ ID NO: 2104)<br>(SEQ ID NO: 3213) |
| βc-m2990 Target: | 5'-ACUCCUCGACCAAAAAGGACCAGAA-3'<br>3'-AAUGAGGAGCUGGUUUUUCCUGGUCUU-5'<br>5'-TTACTCCTCGACCAAAAAGGACCAGAA-3' | (SEQ ID NO: 4323)<br>(SEQ ID NO: 2105)<br>(SEQ ID NO: 3214) |
| βc-m3005 Target: | 5'-UCCAUUUGUAUUGUUACUCCUCGAC-3'<br>3'-UUAGGUAAACAUAACAAUGAGGAGCUG-5'<br>5'-AATCCATTTGTATTGTTACTCCTCGAC-3' | (SEQ ID NO: 4324)<br>(SEQ ID NO: 2106)<br>(SEQ ID NO: 3215) |
| βc-m3006 Target: | 5'-AUCCAUUUGUAUUGUUACUCCUCGA-3'<br>3'-UUUAGGUAAACAUAACAAUGAGGAGCU-5'<br>5'-AAATCCATTTGTATTGTTACTCCTCGA-3' | (SEQ ID NO: 4325)<br>(SEQ ID NO: 2107)<br>(SEQ ID NO: 3216) |
| βc-m3007 Target: | 5'-AAUCCAUUUGUAUUGUUACUCCUCG-3'<br>3'-GUUUAGGUAAACAUAACAAUGAGGAGC-5'<br>5'-CAAATCCATTTGTATTGTTACTCCTCG-3' | (SEQ ID NO: 4326)<br>(SEQ ID NO: 2108)<br>(SEQ ID NO: 3217) |
| βc-m3008 Target: | 5'-AAAUCCAUUUGUAUUGUUACUCCUC-3'<br>3'-GGUUUAGGUAAACAUAACAAUGAGGAG-5'<br>5'-CCAAATCCATTTGTATTGTTACTCCTC-3' | (SEQ ID NO: 4327)<br>(SEQ ID NO: 2109)<br>(SEQ ID NO: 3218) |
| βc-m3015 Target: | 5'-ACUCCCCAAAUCCAUUUGUAUUGUU-3'<br>3'-AGUGAGGGGUUUAGGUAAACAUAACAA-5'<br>5'-TCACTCCCCAAATCCATTTGTATTGTT-3' | (SEQ ID NO: 4328)<br>(SEQ ID NO: 2110)<br>(SEQ ID NO: 3219) |
| βc-m3047 Target: | 5'-UCCAUUCGUGUGCAUUCUUCACUGC-3'<br>3'-CUAGGUAAGCACACGUAAGAAGUGACG-5'<br>5'-GATCCATTCGTGTGCATTCTTCACTGC-3' | (SEQ ID NO: 4329)<br>(SEQ ID NO: 2111)<br>(SEQ ID NO: 3220) |
| βc-m3048 Target: | 5'-AUCCAUUCGUGUGCAUUCUUCACUG-3'<br>3'-ACUAGGUAAGCACACGUAAGAAGUGAC-5'<br>5'-TGATCCATTCGTGTGCATTCTTCACTG-3' | (SEQ ID NO: 4330)<br>(SEQ ID NO: 2112)<br>(SEQ ID NO: 3221) |
| βc-m3049 Target: | 5'-GAUCCAUUCGUGUGCAUUCUUCACU-3'<br>3'-CACUAGGUAAGCACACGUAAGAAGUGA-5'<br>5'-GTGATCCATTCGTGTGCATTCTTCACT-3' | (SEQ ID NO: 4331)<br>(SEQ ID NO: 2113)<br>(SEQ ID NO: 3222) |
| βc-m3093 Target: | 5'-AAACAAAGAACAAGCAAGGCUAGGG-3'<br>3'-AUUUUGUUUCUUGUUCGUUCCGAUCCC-5'<br>5'-TAAAACAAAGAACAAGCAAGGCTAGGG-3' | (SEQ ID NO: 4332)<br>(SEQ ID NO: 2114)<br>(SEQ ID NO: 3223) |
| βc-m3109 Target: | 5'-ACCACUACAGAUAUUAAAACAAAGA-3'<br>3'-CGUGGUGAUGUCUAUAAUUUUGUUUCU-5'<br>5'-GCACCACTACAGATATTAAAACAAAGA-3' | (SEQ ID NO: 4333)<br>(SEQ ID NO: 2115)<br>(SEQ ID NO: 3224) |
| βc-m3111 Target: | 5'-GCACCACUACAGAUAUUAAAACAAA-3'<br>3'-GUCGUGGUGAUGUCUAUAAUUUUGUUU-5'<br>5'-CAGCACCACTACAGATATTAAAACAAA-3' | (SEQ ID NO: 4334)<br>(SEQ ID NO: 2116)<br>(SEQ ID NO: 3225) |
| βc-m3112 Target: | 5'-AGCACCACUACAGAUAUUAAAACAA-3'<br>3'-AGUCGUGGUGAUGUCUAUAAUUUUGUU-5'<br>5'-TCAGCACCACTACAGATATTAAAACAA-3' | (SEQ ID NO: 4335)<br>(SEQ ID NO: 2117)<br>(SEQ ID NO: 3226) |

TABLE 11-continued

Additional Selected Anti-β-catenin DsiRNAs, 25/27mer Duplexes, Unmodified

| | | |
|---|---|---|
| βc-m3133 Target: | 5'-AAAAUAAAAGCAAGCAAAGUCAGCA-3'<br>3'-UUUUUUAUUUUCGUUCGUUUCAGUCGU-5'<br>5'-AAAAAATAAAAGCAAGCAAAGTCAGCA-3' | (SEQ ID NO: 4336)<br>(SEQ ID NO: 2118)<br>(SEQ ID NO: 3227) |
| βc-m3137 Target: | 5'-GCAAAAAAUAAAAGCAAGCAAAGUC-3'<br>3'-GACGUUUUUUAUUUUCGUUCGUUUCAG-5'<br>5'-CTGCAAAAAATAAAAGCAAGCAAAGTC-3' | (SEQ ID NO: 4337)<br>(SEQ ID NO: 2119)<br>(SEQ ID NO: 3228) |
| βc-m3142 Target: | 5'-UUACUGCAAAAAAUAAAAGCAAGCA-3'<br>3'-UCAAUGACGUUUUUUAUUUUCGUUCGU-5'<br>5'-AGTTACTGCAAAAAATAAAAGCAAGCA-3' | (SEQ ID NO: 4338)<br>(SEQ ID NO: 2120)<br>(SEQ ID NO: 3229) |
| βc-m3148 Target: | 5'-UAACAGUUACUGCAAAAAAUAAAAG-3'<br>3'-UGAUUGUCAAUGACGUUUUUUAUUUUC-5'<br>5'-ACTAACAGTTACTGCAAAAAATAAAAG-3' | (SEQ ID NO: 4339)<br>(SEQ ID NO: 2121)<br>(SEQ ID NO: 3230) |
| βc-m3150 Target: | 5'-ACUAACAGUUACUGCAAAAAAUAAA-3'<br>3'-UUUGAUUGUCAAUGACGUUUUUUAUUU-5'<br>5'-AAACTAACAGTTACTGCAAAAAATAAA-3' | (SEQ ID NO: 4340)<br>(SEQ ID NO: 2122)<br>(SEQ ID NO: 3231) |
| βc-m3152 Target: | 5'-AAACUAACAGUUACUGCAAAAAAUA-3'<br>3'-UUUUUGAUUGUCAAUGACGUUUUUUAU-5'<br>5'-AAAAACTAACAGTTACTGCAAAAAATA-3' | (SEQ ID NO: 4341)<br>(SEQ ID NO: 2123)<br>(SEQ ID NO: 3232) |
| βc-m3153 Target: | 5'-AAAACUAACAGUUACUGCAAAAAAU-3'<br>3'-AUUUUUGAUUGUCAAUGACGUUUUUUA-5'<br>5'-TAAAAACTAACAGTTACTGCAAAAAAT-3' | (SEQ ID NO: 4342)<br>(SEQ ID NO: 2124)<br>(SEQ ID NO: 3233) |
| βc-m3155 Target: | 5'-UAAAAACUAACAGUUACUGCAAAAA-3'<br>3'-GAAUUUUUGAUUGUCAAUGACGUUUUU-5'<br>5'-CTTAAAAACTAACAGTTACTGCAAAAA-3' | (SEQ ID NO: 4343)<br>(SEQ ID NO: 2125)<br>(SEQ ID NO: 3234) |
| βc-m3159 Target: | 5'-UACUUAAAAACUAACAGUUACUGCA-3'<br>3'-UGAUGAAUUUUUGAUUGUCAAUGACGU-5'<br>5'-ACTACTTAAAAACTAACAGTTACTGCA-3' | (SEQ ID NO: 4344)<br>(SEQ ID NO: 2126)<br>(SEQ ID NO: 3235) |
| βc-m3161 Target: | 5'-ACUACUUAAAAACUAACAGUUACUG-3'<br>3'-UGUGAUGAAUUUUUGAUUGUCAAUGAC-5'<br>5'-ACACTACTTAAAAACTAACAGTTACTG-3' | (SEQ ID NO: 4345)<br>(SEQ ID NO: 2127)<br>(SEQ ID NO: 3236) |
| βc-m3165 Target: | 5'-UAACACUACUUAAAAACUAACAGUU-3'<br>3'-GUAUUGUGAUGAAUUUUUGAUUGUCAA-5'<br>5'-CATAACACTACTTAAAAACTAACAGTT-3' | (SEQ ID NO: 4346)<br>(SEQ ID NO: 2128)<br>(SEQ ID NO: 3237) |
| βc-m3166 Target: | 5'-AUAACACUACUUAAAAACUAACAGU-3'<br>3'-UGUAUUGUGAUGAAUUUUUGAUUGUCA-5'<br>5'-ACATAACACTACTTAAAAACTAACAGT-3' | (SEQ ID NO: 4347)<br>(SEQ ID NO: 2129)<br>(SEQ ID NO: 3238) |
| βc-m3168 Target: | 5'-ACAUAACACUACUUAAAAACUAACA-3'<br>3'-CUUGUAUUGUGAUGAAUUUUUGAUUGU-5'<br>5'-GAACATAACACTACTTAAAAACTAACA-3' | (SEQ ID NO: 4348)<br>(SEQ ID NO: 2130)<br>(SEQ ID NO: 3239) |
| βc-m3169 Target: | 5'-AACAUAACACUACUUAAAAACUAAC-3'<br>3'-UCUUGUAUUGUGAUGAAUUUUUGAUUG-5'<br>5'-AGAACATAACACTACTTAAAAACTAAC-3' | (SEQ ID NO: 4349)<br>(SEQ ID NO: 2131)<br>(SEQ ID NO: 3240) |
| βc-m3170 Target: | 5'-GAACAUAACACUACUUAAAAACUAA-3'<br>3'-AUCUUGUAUUGUGAUGAAUUUUUGAUU-5'<br>5'-TAGAACATAACACTACTTAAAAACTAA-3' | (SEQ ID NO: 4350)<br>(SEQ ID NO: 2132)<br>(SEQ ID NO: 3241) |
| βc-m3171 Target: | 5'-AGAACAUAACACUACUUAAAAACUA-3'<br>3'-GAUCUUGUAUUGUGAUGAAUUUUUGAU-5'<br>5'-CTAGAACATAACACTACTTAAAAACTA-3' | (SEQ ID NO: 4351)<br>(SEQ ID NO: 2133)<br>(SEQ ID NO: 3242) |
| βc-m3176 Target: | 5'-UCACUAGAACAUAACACUACUUAAA-3'<br>3'-CAAGUGAUCUUGUAUUGUGAUGAAUUU-5'<br>5'-GTTCACTAGAACATAACACTACTTAAA-3' | (SEQ ID NO: 4352)<br>(SEQ ID NO: 2134)<br>(SEQ ID NO: 3243) |
| βc-m3178 Target: | 5'-GUUCACUAGAACAUAACACUACUUA-3'<br>3'-UCCAAGUGAUCUUGUAUUGUGAUGAAU-5'<br>5'-AGGTTCACTAGAACATAACACTACTTA-3' | (SEQ ID NO: 4353)<br>(SEQ ID NO: 2135)<br>(SEQ ID NO: 3244) |
| βc-m3179 Target: | 5'-GGUUCACUAGAACAUAACACUACUU-3'<br>3'-GUCCAAGUGAUCUUGUAUUGUGAUGAA-5'<br>5'-CAGGTTCACTAGAACATAACACTACTT-3' | (SEQ ID NO: 4354)<br>(SEQ ID NO: 2136)<br>(SEQ ID NO: 3245) |

TABLE 11-continued

Additional Selected Anti-β-catenin DsiRNAs, 25/27mer Duplexes, Unmodified

| | | |
|---|---|---|
| βc-m3216 | 5'-AUUACUCGGUUCUUAGAAAUCAGAA-3'<br>3'-GGUAAUGAGCCAAGAAUCUUUAGUCUU-5'<br>Target: 5'-CCATTACTCGGTTCTTAGAAATCAGAA-3' | (SEQ ID NO: 4355)<br>(SEQ ID NO: 2137)<br>(SEQ ID NO: 3246) |
| βc-m3219 | 5'-ACCAUUACUCGGUUCUUAGAAAUCA-3'<br>3'-UGUGGUAAUGAGCCAAGAAUCUUUAGU-5'<br>Target: 5'-ACACCATTACTCGGTTCTTAGAAATCA-3' | (SEQ ID NO: 4356)<br>(SEQ ID NO: 2138)<br>(SEQ ID NO: 3247) |
| βc-m3224 | 5'-UCUACACCAUUACUCGGUUCUUAGA-3'<br>3'-CAAGAUGUGGUAAUGAGCCAAGAAUCU-5'<br>Target: 5'-GTTCTACACCATTACTCGGTTCTTAGA-3' | (SEQ ID NO: 4357)<br>(SEQ ID NO: 2139)<br>(SEQ ID NO: 3248) |
| βc-m3234 | 5'-GAAUUAGUGUUCUACACCAUUACUC-3'<br>3'-UACUUAAUCACAAGAUGUGGUAAUGAG-5'<br>Target: 5'-ATGAATTAGTGTTCTACACCATTACTC-3' | (SEQ ID NO: 4358)<br>(SEQ ID NO: 2140)<br>(SEQ ID NO: 3249) |
| βc-m3239 | 5'-AUUAUGAAUUAGUGUUCUACACCAU-3'<br>3'-ACUAAUACUUAAUCACAAGAUGUGGUA-5'<br>Target: 5'-TGATTATGAATTAGTGTTCTACACC-3' | (SEQ ID NO: 4359)<br>(SEQ ID NO: 2141)<br>(SEQ ID NO: 3250) |
| βc-m3240 | 5'-GAUUAUGAAUUAGUGUUCUACACCA-3'<br>3'-CACUAAUACUUAAUCACAAGAUGUGGU-5'<br>Target: 5'-GTGATTATGAATTAGTGTTCTACCA-3' | (SEQ ID NO: 4360)<br>(SEQ ID NO: 2142)<br>(SEQ ID NO: 3251) |
| βc-m3241 | 5'-UGAUUAUGAAUUAGUGUUCUACACC-3'<br>3'-GCACUAAUACUUAAUCACAAGAUGUGG-5'<br>Target: 5'-CGTGATTATGAATTAGTGTTCTACACC-3' | (SEQ ID NO: 4361)<br>(SEQ ID NO: 2143)<br>(SEQ ID NO: 3252) |
| βc-m3251 | 5'-ACAAUUAGCGUGAUUAUGAAUUAGU-3'<br>3'-AAUGUUAAUCGCACUAAUACUUAAUCA-5'<br>Target: 5'-TTACAATTAGCGTGATTATGAATTAGT-3' | (SEQ ID NO: 4362)<br>(SEQ ID NO: 2144)<br>(SEQ ID NO: 3253) |
| βc-m3252 | 5'-UACAAUUAGCGUGAUUAUGAAUUAG-3'<br>3'-UAAUGUUAAUCGCACUAAUACUUAAUC-5'<br>Target: 5'-ATTACAATTAGCGTGATTATGAATTAG-3' | (SEQ ID NO: 4363)<br>(SEQ ID NO: 2145)<br>(SEQ ID NO: 3254) |
| βc-m3256 | 5'-AGAUUACAAUUAGCGUGAUUAUGAA-3'<br>3'-GGUCUAAUGUUAAUCGCACUAAUACUU-5'<br>Target: 5'-CCAGATTACAATTAGCGTGATTATGAA-3' | (SEQ ID NO: 4364)<br>(SEQ ID NO: 2146)<br>(SEQ ID NO: 3255) |
| βc-m3267 | 5'-UACACGUCUCCAGAUUACAAUUAGC-3'<br>3'-CAAUGUGCAGAGGUCUAAUGUUAAUCG-5'<br>Target: 5'-GTTACACGTCTCCAGATTACAATTAGC-3' | (SEQ ID NO: 4365)<br>(SEQ ID NO: 2147)<br>(SEQ ID NO: 3256) |
| βc-m3269 | 5'-GUUACACGUCUCCAGAUUACAAUUA-3'<br>3'-UACAAUGUGCAGAGGUCUAAUGUUAAU-5'<br>Target: 5'-ATGTTACACGTCTCCAGATTACAATTA-3' | (SEQ ID NO: 4366)<br>(SEQ ID NO: 2148)<br>(SEQ ID NO: 3257) |
| βc-m3277 | 5'-UACACAAUGUUACACGUCUCCAGAU-3'<br>3'-CGAUGUGUUACAAUGUGCAGAGGUCUA-5'<br>Target: 5'-GCTACACAATGTTACACGTCTCCAGAT-3' | (SEQ ID NO: 4367)<br>(SEQ ID NO: 2149)<br>(SEQ ID NO: 3258) |
| βc-m3279 | 5'-GCUACACAAUGUUACACGUCUCCAG-3'<br>3'-UCCGAUGUGUUACAAUGUGCAGAGGUC-5'<br>Target: 5'-AGGCTACACAATGTTACACGTCTCCAG-3' | (SEQ ID NO: 4368)<br>(SEQ ID NO: 2150)<br>(SEQ ID NO: 3259) |
| βc-m3286 | 5'-ACAAAAGGCUACACAAUGUUACACG-3'<br>3'-UAUGUUUUCCGAUGUGUUACAAUGUGC-5'<br>Target: 5'-ATACAAAAGGCTACACAATGTTACACG-3' | (SEQ ID NO: 4369)<br>(SEQ ID NO: 2151)<br>(SEQ ID NO: 3260) |
| βc-m3287 | 5'-UACAAAAGGCUACACAAUGUUACAC-3'<br>3'-AUAUGUUUUCCGAUGUGUUACAAUGUG-5'<br>Target: 5'-TATACAAAAGGCTACACAATGTTACAC-3' | (SEQ ID NO: 4370)<br>(SEQ ID NO: 2152)<br>(SEQ ID NO: 3261) |
| βc-m3291 | 5'-UUUAUACAAAAGGCUACACAAUGUU-3'<br>3'-AUAAAUAUGUUUUCCGAUGUGUUACAA-5'<br>Target: 5'-TATTTATACAAAAGGCTACACAATGTT-3' | (SEQ ID NO: 4371)<br>(SEQ ID NO: 2153)<br>(SEQ ID NO: 3262) |
| βc-m3292 | 5'-AUUUAUACAAAAGGCUACACAAUGU-3'<br>3'-GAUAAAUAUGUUUUCCGAUGUGUUACA-5'<br>Target: 5'-CTATTTATACAAAAGGCTACACAATGT-3' | (SEQ ID NO: 4372)<br>(SEQ ID NO: 2154)<br>(SEQ ID NO: 3263) |
| βc-m3295 | 5'-UCUAUUUAUACAAAAGGCUACACAA-3'<br>3'-ACAGAUAAAUAUGUUUUCCGAUGUGUU-5'<br>Target: 5'-TGTCTATTTATACAAAAGGCTACACA-3' | (SEQ ID NO: 4373)<br>(SEQ ID NO: 2155)<br>(SEQ ID NO: 3264) |

TABLE 11-continued

Additional Selected Anti-β-catenin DsiRNAs, 25/27mer Duplexes, Unmodified

| | | |
|---|---|---|
| βc-m3296 Target: | 5'-GUCUAUUUAUACAAAAGGCUACACA-3'<br>3'-GACAGAUAAAUAUGUUUUCCGAUGUGU-5'<br>5'-CTGTCTATTTATACAAAAGGCTACACA-3' | (SEQ ID NO: 4374)<br>(SEQ ID NO: 2156)<br>(SEQ ID NO: 3265) |
| βc-m3297 Target: | 5'-UGUCUAUUUAUACAAAAGGCUACAC-3'<br>3'-AGACAGAUAAAUAUGUUUUCCGAUGUG-5'<br>5'-TCTGTCTATTTATACAAAAGGCTACAC-3' | (SEQ ID NO: 4375)<br>(SEQ ID NO: 2157)<br>(SEQ ID NO: 3266) |
| βc-m3303 Target: | 5'-UCUAUCUGUCUAUUUAUACAAAAGG-3'<br>3'-AAAGAUAGACAGAUAAAUAUGUUUUCC-5'<br>5'-TTTCTATCTGTCTATTTATACAAAAGG-3' | (SEQ ID NO: 4376)<br>(SEQ ID NO: 2158)<br>(SEQ ID NO: 3267) |
| βc-m3304 Target: | 5'-UUCUAUCUGUCUAUUUAUACAAAAG-3'<br>3'-UAAAGAUAGACAGAUAAAUAUGUUUUC-5'<br>5'-ATTTCTATCTGTCTATTTATACAAAAG-3' | (SEQ ID NO: 4377)<br>(SEQ ID NO: 2159)<br>(SEQ ID NO: 3268) |
| βc-m3305 Target: | 5'-UUUCUAUCUGUCUAUUUAUACAAAA-3'<br>3'-GUAAAGAUAGACAGAUAAAUAUGUUUU-5'<br>5'-CATTTCTATCTGTCTATTTATACAAAA-3' | (SEQ ID NO: 4378)<br>(SEQ ID NO: 2160)<br>(SEQ ID NO: 3269) |
| βc-m3306 Target: | 5'-AUUUCUAUCUGUCUAUUUAUACAAA-3'<br>3'-GGUAAAGAUAGACAGAUAAAUAUGUUU-5'<br>5'-CCATTTCTATCTGTCTATTTATACAAA-3' | (SEQ ID NO: 4379)<br>(SEQ ID NO: 2161)<br>(SEQ ID NO: 3270) |
| βc-m3310 Target: | 5'-GACCAUUUCUAUCUGUCUAUUUAUA-3'<br>3'-GCCUGGUAAAGAUAGACAGAUAAAUAU-5'<br>5'-CGGACCATTTCTATCTGTCTATTTATA-3' | (SEQ ID NO: 4380)<br>(SEQ ID NO: 2162)<br>(SEQ ID NO: 3271) |
| βc-m3311 Target: | 5'-GGACCAUUUCUAUCUGUCUAUUUAU-3'<br>3'-AGCCUGGUAAAGAUAGACAGAUAAAUA-5'<br>5'-TCGGACCATTTCTATCTGTCTATTTAT-3' | (SEQ ID NO: 4381)<br>(SEQ ID NO: 2163)<br>(SEQ ID NO: 3272) |
| βc-m3318 Target: | 5'-ACUAAUCGGACCAUUUCUAUCUGUC-3'<br>3'-UUUGAUUAGCCUGGUAAAGAUAGACAG-5'<br>5'-AAACTAATCGGACCATTTCTATCTGTC-3' | (SEQ ID NO: 4382)<br>(SEQ ID NO: 2164)<br>(SEQ ID NO: 3273) |
| βc-m3319 Target: | 5'-AACUAAUCGGACCAUUUCUAUCUGU-3'<br>3'-CUUUGAUUAGCCUGGUAAAGAUAGACA-5'<br>5'-GAAACTAATCGGACCATTTCTATCTGT-3' | (SEQ ID NO: 4383)<br>(SEQ ID NO: 2165)<br>(SEQ ID NO: 3274) |
| βc-m3320 Target: | 5'-AAACUAAUCGGACCAUUUCUAUCUG-3'<br>3'-CCUUUGAUUAGCCUGGUAAAGAUAGAC-5'<br>5'-GGAAACTAATCGGACCATTTCTATCTG-3' | (SEQ ID NO: 4384)<br>(SEQ ID NO: 2166)<br>(SEQ ID NO: 3275) |
| βc-m3321 Target: | 5'-GAAACUAAUCGGACCAUUUCUAUCU-3'<br>3'-UCCUUUGAUUAGCCUGGUAAAGAUAGA-5'<br>5'-AGGAAACTAATCGGACCATTTCTATCT-3' | (SEQ ID NO: 4385)<br>(SEQ ID NO: 2167)<br>(SEQ ID NO: 3276) |
| βc-m3328 Target: | 5'-UAAAAAGGAAACUAAUCGGACCAUU-3'<br>3'-UAAUUUUUCCUUUGAUUAGCCUGGUAA-5'<br>5'-ATTAAAAAGGAAACTAATCGGACCATT-3' | (SEQ ID NO: 4386)<br>(SEQ ID NO: 2168)<br>(SEQ ID NO: 3277) |
| βc-m3334 Target: | 5'-GCAUAUUAAAAAGGAAACUAAUCGG-3'<br>3'-UUCGUAUAAUUUUUCCUUUGAUUAGCC-5'<br>5'-AAGCATATTAAAAAGGAAACTAATCGG-3' | (SEQ ID NO: 4387)<br>(SEQ ID NO: 2169)<br>(SEQ ID NO: 3278) |
| βc-m3335 Target: | 5'-AGCAUAUUAAAAAGGAAACUAAUCG-3'<br>3'-AUUCGUAUAAUUUUUCCUUUGAUUAGC-5'<br>5'-TAAGCATATTAAAAAGGAAACTAATCG-3' | (SEQ ID NO: 4388)<br>(SEQ ID NO: 2170)<br>(SEQ ID NO: 3279) |
| βc-m3339 Target: | 5'-UUUAAGCAUAUUAAAAAGGAAACUA-3'<br>3'-UAAAAUUCGUAUAAUUUUUCCUUUGAU-5'<br>5'-ATTTTAAGCATATTAAAAAGGAAACTA-3' | (SEQ ID NO: 4389)<br>(SEQ ID NO: 2171)<br>(SEQ ID NO: 3280) |
| βc-m3345 Target: | 5'-GCUUAUUUUAAGCAUAUUAAAAAGG-3'<br>3'-GACGAAUAAAAUUCGUAUAAUUUUUCC-5'<br>5'-CTGCTTATTTTAAGCATATTAAAAAGG-3' | (SEQ ID NO: 4390)<br>(SEQ ID NO: 2172)<br>(SEQ ID NO: 3281) |
| βc-m3346 Target: | 5'-UGCUUAUUUUAAGCAUAUUAAAAAG-3'<br>3'-GGACGAAUAAAAUUCGUAUAAUUUUUC-5'<br>5'-CCTGCTTATTTTAAGCATATTAAAAAG-3' | (SEQ ID NO: 4391)<br>(SEQ ID NO: 2173)<br>(SEQ ID NO: 3282) |
| βc-m3352 Target: | 5'-UCCACCUGCUUAUUUUAAGCAUAUU-3'<br>3'-CUAGGUGGACGAAUAAAAUUCGUAUAA-5'<br>5'-GATCCACCTGCTTATTTTAAGCATATT-3' | (SEQ ID NO: 4392)<br>(SEQ ID NO: 2174)<br>(SEQ ID NO: 3283) |

TABLE 11-continued

Additional Selected Anti-β-catenin DsiRNAs, 25/27mer Duplexes, Unmodified

| | | |
|---|---|---|
| βc-m3367 Target: | 5'-AAAACAUGAAAUAGAUCCACCUGCU-3'<br>3'-GUUUUUGUACUUUAUCUAGGUGGACGA-5'<br>5'-CAAAAACATGAAATAGATCCACCTGCT-3' | (SEQ ID NO: 4393)<br>(SEQ ID NO: 2175)<br>(SEQ ID NO: 3284) |
| βc-m3368 Target: | 5'-AAAACAUGAAAUAGAUCCACCUGC-3'<br>3'-AGUUUUUGUACUUUAUCUAGGUGGACG-5'<br>5'-TCAAAAACATGAAATAGATCCACCTGC-3' | (SEQ ID NO: 4394)<br>(SEQ ID NO: 2176)<br>(SEQ ID NO: 3285) |
| βc-m3370 Target: | 5'-UCAAAAACAUGAAAUAGAUCCACCU-3'<br>3'-CAAGUUUUUGUACUUUAUCUAGGUGGA-5'<br>5'-GTTCAAAAACATGAAATAGATCCACCT-3' | (SEQ ID NO: 4395)<br>(SEQ ID NO: 2177)<br>(SEQ ID NO: 3286) |
| βc-m3371 Target: | 5'-UUCAAAAACAUGAAAUAGAUCCACC-3'<br>3'-ACAAGUUUUUGUACUUUAUCUAGGUGG-5'<br>5'-TGTTCAAAAACATGAAATAGATCCACC-3' | (SEQ ID NO: 4396)<br>(SEQ ID NO: 2178)<br>(SEQ ID NO: 3287) |
| βc-m3372 Target: | 5'-GUUCAAAAACAUGAAAUAGAUCCAC-3'<br>3'-AACAAGUUUUUGUACUUUAUCUAGGUG-5'<br>5'-TTGTTCAAAAACATGAAATAGATCCAC-3' | (SEQ ID NO: 4397)<br>(SEQ ID NO: 2179)<br>(SEQ ID NO: 3288) |
| βc-m3377 Target: | 5'-UUUUUGUUCAAAAACAUGAAAUAGA-3'<br>3'-UCAAAAACAAGUUUUUGUACUUUAUCU-5'<br>5'-AGTTTTTGTTCAAAAACATGAAATAGA-3' | (SEQ ID NO: 4398)<br>(SEQ ID NO: 2180)<br>(SEQ ID NO: 3289) |
| βc-m3383 Target: | 5'-AUAAAGUUUUUGUUCAAAAACAUGA-3'<br>3'-GCUAUUUCAAAAACAAGUUUUUGUACU-5'<br>5'-CGATAAAGTTTTTGTTCAAAAACATGA-3' | (SEQ ID NO: 4399)<br>(SEQ ID NO: 2181)<br>(SEQ ID NO: 3290) |
| βc-m3389 Target: | 5'-UCCCCGAUAAAGUUUUUGUUCAAAA-3'<br>3'-AUAGGGGCUAUUUCAAAAACAAGUUUU-5'<br>5'-TATCCCGATAAAGTTTTTGTTCAAAA-3' | (SEQ ID NO: 4400)<br>(SEQ ID NO: 2182)<br>(SEQ ID NO: 3291) |
| βc-m3390 Target: | 5'-AUCCCCGAUAAAGUUUUUGUUCAAA-3'<br>3'-CAUAGGGGCUAUUUCAAAAACAAGUUU-5'<br>5'-GTATCCCCGATAAAGTTTTTGTTCAAA-3' | (SEQ ID NO: 4401)<br>(SEQ ID NO: 2183)<br>(SEQ ID NO: 3292) |
| βc-m3419 Target: | 5'-ACCUCUUACUGAUUUACCCUACCGC-3'<br>3'-UGUGGAGAAUGACUAAAUGGGAUGGCG-5'<br>5'-ACACCTCTTACTGATTTACCCTACCGC-3' | (SEQ ID NO: 4402)<br>(SEQ ID NO: 2184)<br>(SEQ ID NO: 3293) |
| βc-m3421 Target: | 5'-ACACCUCUUACUGAUUUACCCUACC-3'<br>3'-AUUGUGGAGAAUGACUAAAUGGGAUGG-5'<br>5'-TAACACCTCTTACTGATTTACCCTACC-3' | (SEQ ID NO: 4403)<br>(SEQ ID NO: 2185)<br>(SEQ ID NO: 3294) |
| βc-m3422 Target: | 5'-AACACCUCUUACUGAUUUACCCUAC-3'<br>3'-UAUUGUGGAGAAUGACUAAAUGGGAUG-5'<br>5'-ATAACACCTCTTACTGATTTACCCTAC-3' | (SEQ ID NO: 4404)<br>(SEQ ID NO: 2186)<br>(SEQ ID NO: 3295) |
| βc-m3423 Target: | 5'-UAACACCUCUUACUGAUUUACCCUA-3'<br>3'-UUAUUGUGGAGAAUGACUAAAUGGGAU-5'<br>5'-AATAACACCTCTTACTGATTTACCCTA-3' | (SEQ ID NO: 4405)<br>(SEQ ID NO: 2187)<br>(SEQ ID NO: 3296) |
| βc-m3424 Target: | 5'-AUAACACCUCUUACUGAUUUACCCU-3'<br>3'-UUUAUUGUGGAGAAUGACUAAAUGGGA-5'<br>5'-AAATAACACCTCTTACTGATTTACCCT-3' | (SEQ ID NO: 4406)<br>(SEQ ID NO: 2188)<br>(SEQ ID NO: 3297) |
| βc-m3425 Target: | 5'-AAUAACACCUCUUACUGAUUUACCC-3'<br>3'-GUUUAUUGUGGAGAAUGACUAAAUGGG-5'<br>5'-CAAATAACACCTCTTACTGATTTACCC-3' | (SEQ ID NO: 4407)<br>(SEQ ID NO: 2189)<br>(SEQ ID NO: 3298) |
| βc-m3431 Target: | 5'-GGCUCAAAUAACACCUCUUACUGAU-3'<br>3'-UUCCGAGUUUAUUGUGGAGAAUGACUA-5'<br>5'-AAGGCTCAAATAACACCTCTTACTGAT-3' | (SEQ ID NO: 4408)<br>(SEQ ID NO: 2190)<br>(SEQ ID NO: 3299) |
| βc-m3436 Target: | 5'-AACAAGGCUCAAAUAACACCUCUUA-3'<br>3'-UUUUGUUCCGAGUUUAUUGUGGAGAAU-5'<br>5'-AAAACAAGGCTCAAATAACACCTCTTA-3' | (SEQ ID NO: 4409)<br>(SEQ ID NO: 2191)<br>(SEQ ID NO: 3300) |
| βc-m3437 Target: | 5'-AAACAAGGCUCAAAUAACACCUCUU-3'<br>3'-GUUUUGUUCCGAGUUUAUUGUGGAGAA-5'<br>5'-CAAAACAAGGCTCAAATAACACCTCTT-3' | (SEQ ID NO: 4410)<br>(SEQ ID NO: 2192)<br>(SEQ ID NO: 3301) |
| βc-m3438 Target: | 5'-AAAACAAGGCUCAAAUAACACCUCU-3'<br>3'-GGUUUUGUUCCGAGUUUAUUGUGGAGA-5'<br>5'-CCAAAACAAGGCTCAAATAACACCTCT-3' | (SEQ ID NO: 4411)<br>(SEQ ID NO: 2193)<br>(SEQ ID NO: 3302) |

TABLE 11-continued

Additional Selected Anti-β-catenin DsiRNAs, 25/27mer Duplexes, Unmodified

| | | |
|---|---|---|
| βc-m3441 Target: | 5'-UCCAAAACAAGGCUCAAAUAACACC-3'<br>3'-ACAGGUUUUGUUCCGAGUUUAUUGUGG-5'<br>5'-TGTCCAAAACAAGGCTCAAATAACACC-3' | (SEQ ID NO: 4412)<br>(SEQ ID NO: 2194)<br>(SEQ ID NO: 3303) |
| βc-m3443 Target: | 5'-UGUCCAAAACAAGGCUCAAAUAACA-3'<br>3'-UGACAGGUUUUGUUCCGAGUUUAUUGU-5'<br>5'-ACTGTCCAAAACAAGGCTCAAATAACA-3' | (SEQ ID NO: 4413)<br>(SEQ ID NO: 2195)<br>(SEQ ID NO: 3304) |
| βc-m3448 Target: | 5'-UAUACUGUCCAAAACAAGGCUCAAA-3'<br>3'-CCAUAUGACAGGUUUUGUUCCGAGUUU-5'<br>5'-GGTATACTGTCCAAAACAAGGCTCAAA-3' | (SEQ ID NO: 4414)<br>(SEQ ID NO: 2196)<br>(SEQ ID NO: 3305) |
| βc-m3456 Target: | 5'-GCAACUGGUAUACUGUCCAAAACAA-3'<br>3'-UCCGUUGACCAUAUGACAGGUUUUGUU-5'<br>5'-AGGCAACTGGTATACTGTCCAAAACAA-3' | (SEQ ID NO: 4415)<br>(SEQ ID NO: 2197)<br>(SEQ ID NO: 3306) |
| βc-m3464 Target: | 5'-GAUAAAAGGCAACUGGUAUACUGUC-3'<br>3'-CCCUAUUUUCCGUUGACCAUAUGACAG-5'<br>5'-GGGATAAAAGGCAACTGGTATACTGTC-3' | (SEQ ID NO: 4416)<br>(SEQ ID NO: 2198)<br>(SEQ ID NO: 3307) |
| βc-m3465 Target: | 5'-GGAUAAAAGGCAACUGGUAUACUGU-3'<br>3'-ACCCUAUUUUCCGUUGACCAUAUGACA-5'<br>5'-TGGGATAAAAGGCAACTGGTATACTGT-3' | (SEQ ID NO: 4417)<br>(SEQ ID NO: 2199)<br>(SEQ ID NO: 3308) |
| βc-m3472 Target: | 5'-AACUUUGGGAUAAAAGGCAACUGGU-3'<br>3'-UGUUGAAACCCUAUUUUCCGUUGACCA-5'<br>5'-ACAACTTTGGGATAAAAGGCAACTGGT-3' | (SEQ ID NO: 4418)<br>(SEQ ID NO: 2200)<br>(SEQ ID NO: 3309) |
| βc-m3474 Target: | 5'-ACAACUUUGGGAUAAAAGGCAACUG-3'<br>3'-GUUGUUGAAACCCUAUUUUCCGUUGAC-5'<br>5'-CAACAACTTTGGGATAAAAGGCAACTG-3' | (SEQ ID NO: 4419)<br>(SEQ ID NO: 2201)<br>(SEQ ID NO: 3310) |
| βc-m3479 Target: | 5'-UUACAACAACUUUGGGAUAAAAGGC-3'<br>3'-CCAAUGUUGUUGAAACCCUAUUUUCCG-5'<br>5'-GGTTACAACAACTTTGGGATAAAAGGC-3' | (SEQ ID NO: 4420)<br>(SEQ ID NO: 2202)<br>(SEQ ID NO: 3311) |
| βc-m3480 Target: | 5'-GUUACAACAACUUUGGGAUAAAAGG-3'<br>3'-UCCAAUGUUGUUGAAACCCUAUUUUCC-5'<br>5'-AGGTTACAACAACTTTGGGATAAAAGG-3' | (SEQ ID NO: 4421)<br>(SEQ ID NO: 2203)<br>(SEQ ID NO: 3312) |
| βc-m3481 Target: | 5'-GGUUACAACAACUUUGGGAUAAAAG-3'<br>3'-GUCCAAUGUUGUUGAAACCCUAUUUUC-5'<br>5'-CAGGTTACAACAACTTTGGGATAAAAG-3' | (SEQ ID NO: 4422)<br>(SEQ ID NO: 2204)<br>(SEQ ID NO: 3313) |
| βc-m3489 Target: | 5'-UCACAGCAGGUUACAACAACUUUGG-3'<br>3'-AUAGUGUCGUCCAAUGUUGUUGAAACC-5'<br>5'-TATCACAGCAGGTTACAACAACTTTGG-3' | (SEQ ID NO: 4423)<br>(SEQ ID NO: 2205)<br>(SEQ ID NO: 3314) |
| βc-m3490 Target: | 5'-AUCACAGCAGGUUACAACAACUUUG-3'<br>3'-CAUAGUGUCGUCCAAUGUUGUUGAAAC-5'<br>5'-GTATCACAGCAGGTTACAACAACTTTG-3' | (SEQ ID NO: 4424)<br>(SEQ ID NO: 2206)<br>(SEQ ID NO: 3315) |
| βc-m3492 Target: | 5'-GUAUCACAGCAGGUUACAACAACUU-3'<br>3'-AACAUAGUGUCGUCCAAUGUUGUUGAA-5'<br>5'-TTGTATCACAGCAGGTTACAACAACTT-3' | (SEQ ID NO: 4425)<br>(SEQ ID NO: 2207)<br>(SEQ ID NO: 3316) |
| βc-m3509 Target: | 5'-GCAUCUGUUGAAGCAUUGUAUCACA-3'<br>3'-GGCGUAGACAACUUCGUAACAUAGUGU-5'<br>5'-CCGCATCTGTTGAAGCATTGTATCACA-3' | (SEQ ID NO: 4426)<br>(SEQ ID NO: 2208)<br>(SEQ ID NO: 3317) |
| βc-m3527 Target: | 5'-UGAACCAUUUCUAUAACCGCAUCUG-3'<br>3'-AGACUUGGUAAAGAUAUUGGCGUAGAC-5'<br>5'-TCTGAACCATTTCTATAACCGCATCTG-3' | (SEQ ID NO: 4427)<br>(SEQ ID NO: 2209)<br>(SEQ ID NO: 3318) |
| βc-m3531 Target: | 5'-AUUCUGAACCAUUUCUAUAACCGCA-3'<br>3'-AUUAAGACUUGGUAAAGAUAUUGGCGU-5'<br>5'-TAATTCTGAACCATTTCTATAACCGCA-3' | (SEQ ID NO: 4428)<br>(SEQ ID NO: 2210)<br>(SEQ ID NO: 3319) |
| βc-m3533 Target: | 5'-UAAUUCUGAACCAUUUCUAUAACCG-3'<br>3'-AAAUUAAGACUUGGUAAAGAUAUUGGC-5'<br>5'-TTTAATTCTGAACCATTTCTATAACCG-3' | (SEQ ID NO: 4429)<br>(SEQ ID NO: 2211)<br>(SEQ ID NO: 3320) |
| βc-m3534 Target: | 5'-UUAAUUCUGAACCAUUUCUAUAACC-3'<br>3'-CAAAUUAAGACUUGGUAAAGAUAUUGG-5'<br>5'-GTTTAATTCTGAACCATTTCTATAACC-3' | (SEQ ID NO: 4430)<br>(SEQ ID NO: 2212)<br>(SEQ ID NO: 3321) |

TABLE 11-continued

Additional Selected Anti-β-catenin DsiRNAs, 25/27mer Duplexes, Unmodified

| | | |
|---|---|---|
| βc-m3535 Target: | 5'-UUUAAUUCUGAACCAUUUCUAUAAC-3'<br>3'-UCAAAUUAAGACUUGGUAAAGAUAUUG-5'<br>5'-AGTTTAATTCTGAACCATTTCTATAAC-3' | (SEQ ID NO: 4431)<br>(SEQ ID NO: 2213)<br>(SEQ ID NO: 3322) |
| βc-m3536 Target: | 5'-GUUUAAUUCUGAACCAUUUCUAUAA-3'<br>3'-UUCAAAUUAAGACUUGGUAAAGAUAUU-5'<br>5'-AAGTTTAATTCTGAACCATTTCTATAA-3' | (SEQ ID NO: 4432)<br>(SEQ ID NO: 2214)<br>(SEQ ID NO: 3323) |
| βc-m3541 Target: | 5'-UAAAAGUUUAAUUCUGAACCAUUUC-3'<br>3'-UAAUUUUCAAAUUAAGACUUGGUAAAG-5'<br>5'-ATTAAAAGTTTAATTCTGAACCATTTC-3' | (SEQ ID NO: 4433)<br>(SEQ ID NO: 2215)<br>(SEQ ID NO: 3324) |
| βc-m3542 Target: | 5'-UUAAAAGUUUAAUUCUGAACCAUUU-3'<br>3'-UUUAAUUUUCAAAUUAAGACUUGGUAAA-5'<br>5'-AATTAAAAGTTTAATTCTGAACCATTT-3' | (SEQ ID NO: 4434)<br>(SEQ ID NO: 2216)<br>(SEQ ID NO: 3325) |
| βc-m3544 Target: | 5'-AAUUAAAAGUUUAAUUCUGAACCAU-3'<br>3'-ACUUAAUUUUCAAAUUAAGACUUGGUA-5'<br>5'-TGAATTAAAAGTTTAATTCTGAACC-3' | (SEQ ID NO: 4435)<br>(SEQ ID NO: 2217)<br>(SEQ ID NO: 3326) |
| βc-m3550 Target: | 5'-UGAAUGAAUUAAAAGUUUAAUUCUG-3'<br>3'-AAACUUACUUAAUUUUCAAAUUAAGAC-5'<br>5'-TTTGAATGAATTAAAAGTTTAATTCTG-3' | (SEQ ID NO: 4436)<br>(SEQ ID NO: 2218)<br>(SEQ ID NO: 3327) |
| βc-m3554 Target: | 5'-UUUUUGAAUGAAUUAAAAGUUUAAU-3'<br>3'-AAAAAAACUUACUUAAUUUUCAAAUUA-5'<br>5'-TTTTTTTGAATGAATTAAAAGTTTAAT-3' | (SEQ ID NO: 4437)<br>(SEQ ID NO: 2219)<br>(SEQ ID NO: 3328) |
| βc-m3558 Target: | 5'-UUUUUUUUUGAAUGAAUUAAAAGUU-3'<br>3'-AAAAAAAAAAACUUACUUAAUUUUCAA-5'<br>5'-TTTTTTTTTTGAATGAATTAAAAGTT-3' | (SEQ ID NO: 4438)<br>(SEQ ID NO: 2220)<br>(SEQ ID NO: 3329) |
| βc-m3559 Target: | 5'-UUUUUUUUUUGAAUGAAUUAAAAGU-3'<br>3'-AAAAAAAAAAACUUACUUAAUUUUCA-5'<br>5'-TTTTTTTTTTTGAATGAATTAAAAGT-3' | (SEQ ID NO: 4439)<br>(SEQ ID NO: 2221)<br>(SEQ ID NO: 3330) |
| βc-m3560 Target: | 5'-UUUUUUUUUUUGAAUGAAUUAAAAG-3'<br>3'-AAAAAAAAAAAACUUACUUAAUUUUC-5'<br>5'-TTTTTTTTTTTTGAATGAATTAAAAG-3' | (SEQ ID NO: 4440)<br>(SEQ ID NO: 2222)<br>(SEQ ID NO: 3331) |
| βc-m3561 Target: | 5'-UUUUUUUUUUUUGAAUGAAUUAAAA-3'<br>3'-AAAAAAAAAAAAACUUACUUAAUUUU-5'<br>5'-TTTTTTTTTTTTTGAATGAATTAAAA-3' | (SEQ ID NO: 4441)<br>(SEQ ID NO: 2223)<br>(SEQ ID NO: 3332) |
| βc-m3562 Target: | 5'-UUUUUUUUUUUUUGAAUGAAUUAAA-3'<br>3'-AAAAAAAAAAAAAACUUACUUAAUUU-5'<br>5'-TTTTTTTTTTTTTTGAATGAATTAAA-3' | (SEQ ID NO: 4442)<br>(SEQ ID NO: 2224)<br>(SEQ ID NO: 3333) |
| βc-m3563 Target: | 5'-UUUUUUUUUUUUUUGAAUGAAUUAA-3'<br>3'-AAAAAAAAAAAAAAACUUACUUAAUU-5'<br>5'-TTTTTTTTTTTTTTTGAATGAATTAA-3' | (SEQ ID NO: 4443)<br>(SEQ ID NO: 2225)<br>(SEQ ID NO: 3334) |

TABLE 12

Additional Selected Anti-β-catenin DsiRNAs, Blunt/Frayed Duplexes

| | | |
|---|---|---|
| | 5'-GUUGUAUGGUAUACUUCAAAUACCC$^{CA-3'}$<br>3'-CAACAUACCAUAUGAAGUUUAUGGGA$_{G-5'}$ | (SEQ ID NO: 6041)<br>(SEQ ID NO: 1605) |
| βc-244 Target: | 5'-GTTGTATGGTATACTTCAAATACCCTC-3' | (SEQ ID NO: 2714) |
| | 5'-CAAAACAGUUGUAUGGUAUACUUCA$^{CC-3'}$<br>3'-GUUUUGUCAACAUACCAUAUGAAGU$_{U-5'}$ | (SEQ ID NO: 6042)<br>(SEQ ID NO: 1606) |
| βc-251 Target: | 5'-CAAAACAGTTGTATGGTATACTTCAAA-3' | (SEQ ID NO: 2715) |
| | 5'-UCAAAACAGUUGUAUGGUAUACUUC$^{CC-3'}$<br>3'-AGUUUUGUCAACAUACCAUAUGAAG$_{U-5'}$ | (SEQ ID NO: 6043)<br>(SEQ ID NO: 1607) |
| βc-252 Target: | 5'-TCAAAACAGTTGTATGGTATACTTCAA-3' | (SEQ ID NO: 2716) |

TABLE 12-continued

Additional Selected Anti-β-catenin DsiRNAs, Blunt/Frayed Duplexes

```
        5'-UUUCAAAACAGUUGUAUGGUAUACA^CA-3'  (SEQ ID NO: 6044)
        3'-AAAGUUUUGUCAACAUACCAUAUGA_AG-5'  (SEQ ID NO: 1608)
```

βc-254 Target: 5'-TTTCAAAACAGTTGTATGGTATACTTC-3' (SEQ ID NO: 2717)

```
        5'-UUUUCAAAACAGUUGUAUGGUAUAC^CC-3'  (SEQ ID NO: 6045)
        3'-AAAAGUUUUGUCAACAUACCAUAUG_AA-5'  (SEQ ID NO: 1609)
```

βc-255 Target: 5'-TTTTCAAAACAGTTGTATGGTATACTT-3' (SEQ ID NO: 2718)

```
        5'-AUUUUCAAAACAGUUGUAUGGUAUA^AC-3'  (SEQ ID NO: 6046)
        3'-UAAAAGUUUUGUCAACAUACCAUAU_GA-5'  (SEQ ID NO: 1610)
```

βc-256 Target: 5'-ATTTTCAAAACAGTTGTATGGTATACT-3' (SEQ ID NO: 2719)

```
        5'-UUGUCCACGCUGGAUUUUCAAAACA^AC-3'  (SEQ ID NO: 6047)
        3'-AACAGGUGCGACCUAAAAGUUUUGU_CA-5'  (SEQ ID NO: 1611)
```

βc-269 Target: 5'-TTGTCCACGCTGGATTTTCAAAACAGT-3' (SEQ ID NO: 2720)

```
        5'-AUUGUCCACGCUGGAUUUUCAAAAC^CA-3'  (SEQ ID NO: 6048)
        3'-UAACAGGUGCGACCUAAAAGUUUUG_UC-5'  (SEQ ID NO: 1612)
```

βc-270 Target: 5'-ATTGTCCACGCTGGATTTTCAAAACAG-3' (SEQ ID NO: 2721)

```
        5'-CCAUCAAAUCAGCUUGAGUAGCCAU^CA-3'  (SEQ ID NO: 6049)
        3'-GGUAGUUUAGUCGAACUCAUCGGUA_AC-5'  (SEQ ID NO: 1613)
```

βc-293 Target: 5'-CCATCAAATCAGCTTGAGTAGCCATTG-3' (SEQ ID NO: 2722)

```
        5'-UGUCCAACUCCAUCAAAUCAGCUUG^CA-3'  (SEQ ID NO: 6050)
        3'-ACAGGUUGAGGUAGUUUAGUCGAAC_UC-5'  (SEQ ID NO: 1614)
```

βc-302 Target: 5'-TGTCCAACTCCATCAAATCAGCTTGAG-3' (SEQ ID NO: 2723)

```
        5'-CUUCCUCAGGAUUGCCUUUACCACU^AC-3'  (SEQ ID NO: 6051)
        3'-GAAGGAGUCCUAACGGAAAUGGUGA_GU-5'  (SEQ ID NO: 1615)
```

βc-431 Target: 5'-CTTCCTCAGGATTGCCTTTACCACTCA-3' (SEQ ID NO: 2724)

```
        5'-UCUUCCUCAGGAUUGCCUUUACCAC^CA-3'  (SEQ ID NO: 6052)
        3'-AGAAGGAGUCCUAACGGAAAUGGUG_AG-5'  (SEQ ID NO: 1616)
```

βc-432 Target: 5'-TCTTCCTCAGGATTGCCTTTACCACTC-3' (SEQ ID NO: 2725)

```
        5'-CAUCAAUAUCAGCUACUUGUUCUUG^CA-3'  (SEQ ID NO: 6053)
        3'-GUAGUUAUAGUCGAUGAACAAGAAC_UC-5'  (SEQ ID NO: 1617)
```

βc-518 Target: 5'-CATCAATATCAGCTACTTGTTCTTGAG-3' (SEQ ID NO: 2726)

```
        5'-CCAUCAAUAUCAGCUACUUGUUCUU^AC-3'  (SEQ ID NO: 6054)
        3'-GGUAGUUAUAGUCGAUGAACAAGAA_CU-5'  (SEQ ID NO: 1618)
```

βc-519 Target: 5'-CCATCAATATCAGCTACTTGTTCTTGA-3' (SEQ ID NO: 2727)

```
        5'-ACUGUCCAUCAAUAUCAGCUACUUG^CC-3'  (SEQ ID NO: 6055)
        3'-UGACAGGUAGUUAUAGUCGAUGAAC_AA-5'  (SEQ ID NO: 1619)
```

βc-524 Target: 5'-ACTGTCCATCAATATCAGCTACTTGTT-3' (SEQ ID NO: 2728)

TABLE 12-continued

Additional Selected Anti-β-catenin DsiRNAs, Blunt/Frayed Duplexes

```
         5'-AUUGCAUACUGUCCAUCAAUAUCAG^AC-3'   (SEQ ID NO: 6056)
         3'-UAACGUAUGACAGGUAGUUAUAGUC_GA-5'   (SEQ ID NO: 1620)
```

βc-531 Target: 5'-ATTGCATACTGTCCATCAATATCAGCT-3' (SEQ ID NO: 2729)

```
         5'-CGAGUCAUUGCAUACUGUCCAUCAA^CC-3'   (SEQ ID NO: 6057)
         3'-GCUCAGUAACGUAUGACAGGUAGUU_AU-5'   (SEQ ID NO: 1621)
```

βc-537 Target: 5'-CGAGTCATTGCATACTGTCCATCAATA-3' (SEQ ID NO: 2730)

```
         5'-CCUCAUCUAAUGUCUCAGGGAACAU^CA-3'   (SEQ ID NO: 6058)
         3'-GGAGUAGAUUACAGAGUCCCUUGUA_UC-5'   (SEQ ID NO: 1622)
```

βc-584 Target: 5'-CCTCATCTAATGTCTCAGGGAACATAG-3' (SEQ ID NO: 2731)

```
         5'-UUACAACUGCAUGUUUCAGCAUCUG^CA-3'   (SEQ ID NO: 6059)
         3'-AAUGUUGACGUACAAAGUCGUAGAC_AC-5'   (SEQ ID NO: 1623)
```

βc-680 Target: 5'-TTACAACTGCATGTTTCAGCATCTGTG-3' (SEQ ID NO: 2732)

```
         5'-GUUUACAACUGCAUGUUUCAGCAUC^CA-3'   (SEQ ID NO: 6060)
         3'-CAAAUGUUGACGUACAAAGUCGUAG_AC-5'   (SEQ ID NO: 1624)
```

βc-682 Target: 5'-GTTTACAACTGCATGTTTCAGCATCTG-3' (SEQ ID NO: 2733)

```
         5'-AGUUAAUCAAGUUUACAACUGCAUG^CC-3'   (SEQ ID NO: 6061)
         3'-UCAAUUAGUUCAAAUGUUGACGUAC_AA-5'   (SEQ ID NO: 1625)
```

βc-692 Target: 5'-AGTTAATCAAGTTTACAACTGCATGTT-3' (SEQ ID NO: 2734)

```
         5'-CUUGAUAGUUAAUCAAGUUUACAAC^CA-3'   (SEQ ID NO: 6062)
         3'-GAACUAUCAAUUAGUUCAAAUGUUG_AC-5'   (SEQ ID NO: 1626)
```

βc-698 Target: 5'-CTTGATAGTTAATCAAGTTTACAACTG-3' (SEQ ID NO: 2735)

```
         5'-CUGCAUCAUCUUGAUAGUUAAUCAA^AC-3'   (SEQ ID NO: 6063)
         3'-GACGUAGUAGAACUAUCAAUUAGUU_CA-5'   (SEQ ID NO: 1627)
```

βc-707 Target: 5'-CTGCATCATCTTGATAGTTAATCAAGT-3' (SEQ ID NO: 2736)

```
         5'-UCUGCAUCAUCUUGAUAGUUAAUCA^CA-3'   (SEQ ID NO: 6064)
         3'-AGACGUAGUAGAACUAUCAAUUAGU_UC-5'   (SEQ ID NO: 1628)
```

βc-708 Target: 5'-TCTGCATCATCTTGATAGTTAATCAAG-3' (SEQ ID NO: 2737)

```
         5'-CUGGUCCUCGUCAUUUAGCAGUUUU^AC-3'   (SEQ ID NO: 6065)
         3'-GACCAGGAGCAGUAAAUCGUCAAAA_CA-5'   (SEQ ID NO: 1629)
```

βc-763 Target: 5'-CTGGTCCTCGTCATTTAGCAGTTTTGT-3' (SEQ ID NO: 2738)

```
         5'-CAUAACUGCAGCCUUAUUAACCACC^CA-3'   (SEQ ID NO: 6066)
         3'-GUAUUGACGUCGGAAUAAUUGGUGG_UG-5'   (SEQ ID NO: 1630)
```

βc-790 Target: 5'-CATAACTGCAGCCTTATTAACCACCAC-3' (SEQ ID NO: 2739)

```
         5'-CCAUAACUGCAGCCUUAUUAACCAC^AC-3'   (SEQ ID NO: 6067)
         3'-GGUAUUGACGUCGGAAUAAUUGGUG_GU-5'   (SEQ ID NO: 1631)
```

βc-791 Target: 5'-CCATAACTGCAGCCTTATTAACCACCA-3' (SEQ ID NO: 2740)

TABLE 12-continued

Additional Selected Anti-β-catenin DsiRNAs, Blunt/Frayed Duplexes

```
                5'-GGACCAUAACUGCAGCCUUAUUAACA^(AC-3')  (SEQ ID NO: 6068)
                3'-CCUGGUAUUGACGUCGGAAUAAUUG_(GU-5')   (SEQ ID NO: 1632)

βc-794 Target:  5'-GGACCATAACTGCAGCCTTATTAACCA-3'  (SEQ ID NO: 2741)

5'-CCUUUUUAGAAAGCUGAUGGACCAU^(CC-3')   (SEQ ID NO: 6069)
                3'-GGAAAAAUCUUUCGACUACCUGGUA_(UU-5')   (SEQ ID NO: 1633)

βc-812 Target:  5'-CCTTTTTAGAAAGCTGATGGACCATAA-3' (SEQ ID NO: 2742)

5'-AUGGUACGUACAAUAGCAGACACCA^(CA-3')   (SEQ ID NO: 6070)
                3'-UACCAUGCAUGUUAUCGUCUGUGGU_(AG-5')   (SEQ ID NO: 1634)

βc-873 Target:  5'-ATGGTACGTACAATAGCAGACACCATC-3' (SEQ ID NO: 2743)

5'-CAUCAUUUGUAUUCUGCAUGGUACG^(CC-3')   (SEQ ID NO: 6071)
                3'-GUAGUAAACAUAAGACGUACCAUGC_(AU-5')   (SEQ ID NO: 1635)

βc-890 Target:  5'-CATCATTTGTATTCTGCATGGTACGTA-3' (SEQ ID NO: 2744)

5'-CUGUUUCUACAUCAUUUGUAUUCUG^(AC-3')   (SEQ ID NO: 6072)
                3'-GACAAAGAUGUAGUAAACAUAAGAC_(GU-5')   (SEQ ID NO: 1636)

βc-899 Target:  5'-CTGTTTCTACATCATTTGTATTCTGCA-3' (SEQ ID NO: 2745)

5'-GCUGUUUCUACAUCAUUUGUAUUCU^(AA-3')   (SEQ ID NO: 6073)
                3'-CGACAAAGAUGUAGUAAACAUAAGA_(CG-5')   (SEQ ID NO: 1637)

βc-900 Target:  5'-GCTGTTTCTACATCATTTGTATTCTGC-3' (SEQ ID NO: 2746)

5'-GUACAACGAGCUGUUUCUACAUCAU^(CC-3')   (SEQ ID NO: 6074)
                3'-CAUGUUGCUCGACAAAGAUGUAGUA_(AA-5')   (SEQ ID NO: 1638)

βc-909 Target:  5'-GTACAACGAGCTGTTTCTACATCATTT-3' (SEQ ID NO: 2747)

5'-CGGUACAACGAGCUGUUUCUACAUC^(CC-3')   (SEQ ID NO: 6075)
                3'-GCCAUGUUGCUCGACAAAGAUGUAG_(UA-5')   (SEQ ID NO: 1639)

βc-911 Target:  5'-CGGTACAACGAGCTGTTTCTACATC-3' (SEQ ID NO: 2748)

5'-GCGGUACAACGAGCUGUUUCUACAU^(AC-3')   (SEQ ID NO: 6076)
                3'-CGCCAUGUUGCUCGACAAAGAUGUA_(GU-5')   (SEQ ID NO: 1640)

βc-912 Target:  5'-GCGGTACAACGAGCTGTTTCTACATCA-3' (SEQ ID NO: 2749)

5'-GCAUAAAACAACACAGAAUCCACUG^(AC-3')   (SEQ ID NO: 6077)
                3'-CGUAUUUUGUUGUGUCUUAGGUGAC_(CA-5')   (SEQ ID NO: 1641)

βc-1032 Target: 5'-GCATAAAACAACACAGAATCCACTGGT-3' (SEQ ID NO: 2750)

5'-UGGCAUAAAACAACACAGAAUCCAC^(CA-3')   (SEQ ID NO: 6078)
                3'-ACCGUAUUUUGUUGUGUCUUAGGUG_(AC-5')   (SEQ ID NO: 1642)

βc-1034 Target: 5'-TGGCATAAAACAACACAGAATCCACTG-3' (SEQ ID NO: 2751)

5'-AUGGCAUAAAACAACACAGAAUCCA^(AC-3')   (SEQ ID NO: 6079)
                3'-UACCGUAUUUUGUUGUGUCUUAGGU_(GA-5')   (SEQ ID NO: 1643)

βc-1035 Target: 5'-ATGGCATAAAACAACACAGAATCCACT-3' (SEQ ID NO: 2752)
```

TABLE 12-continued

Additional Selected Anti-β-catenin DsiRNAs, Blunt/Frayed Duplexes

```
        5'-UAGCUCCUUCUUGAUGUAAUAAAAG^AC-3'    (SEQ ID NO: 6080)
        3'-AUCGAGGAAGAACUACAUUAUUUC_CA-5'    (SEQ ID NO: 1644)

βc-1076 Target: 5'-TAGCTCCTTCTTGATGTAATAAAAGGT-3'  (SEQ ID NO: 2753)

5'-UUAGCUCCUUCUUGAUGUAAUAAAA^AA-3'    (SEQ ID NO: 6081)
        3'-AAUCGAGGAAGAACUACAUUAUUUU_CC-5'    (SEQ ID NO: 1645)

βc-1077 Target: 5'-TTAGCTCCTTCTTGATGTAATAAAAGG-3'  (SEQ ID NO: 2754)

5'-UUUAACAUUUGUUUUGUUGAGCAAG^AA-3'    (SEQ ID NO: 6082)
        3'-AAAUUGUAAACAAAACAACUCGUUC_CG-5'    (SEQ ID NO: 1646)

βc-1144 Target: 5'-TTTAACATTTGTTTTGTTGAGCAAGGC-3'  (SEQ ID NO: 2755)

5'-UAGCCAAGAAUUUAACAUUUGUUUU^AC-3'    (SEQ ID NO: 6083)
        3'-AUCGGUUCUUAAAUUGUAAACAAAA_CA-5'    (SEQ ID NO: 1647)

βc-1154 Target: 5'-TAGCCAAGAATTTAACATTTGTTTTGT-3'  (SEQ ID NO: 2756)

5'-CGUAAUAGCCAAGAAUUUAACAUUU^AC-3'    (SEQ ID NO: 6084)
        3'-GCAUUAUCGGUUCUUAAAUUGUAAA_CA-5'    (SEQ ID NO: 1648)

βc-1159 Target: 5'-CGTAATAGCCAAGAATTTAACATTTGT-3'  (SEQ ID NO: 2757)

5'-UCGUAAUAGCCAAGAAUUUAACAUU^CA-3'    (SEQ ID NO: 6085)
        3'-AGCAUUAUCGGUUCUUAAAUUGUAA_AC-5'    (SEQ ID NO: 1649)

βc-1160 Target: 5'-TCGTAATAGCCAAGAATTTAACATTTG-3'  (SEQ ID NO: 2758)

5'-UAAGCUAAAAUUUGAAGGCAGUCUG^CA-3'    (SEQ ID NO: 6086)
        3'-AUUCGAUUUUAAACUUCCGUCAGAC_AG-5'    (SEQ ID NO: 1650)

βc-1185 Target: 5'-TAAGCTAAAATTTGAAGGCAGTCTGTC-3'  (SEQ ID NO: 2759)

5'-UAGGUCCUCAUUAUAUUUACUAAAG^AC-3'    (SEQ ID NO: 6087)
        3'-AUCCAGGAGUAAUAUAAAUGAUUUC_GA-5'    (SEQ ID NO: 1651)

βc-1260 Target: 5'-TAGGTCCTCATTATATTTACTAAAGCT-3'  (SEQ ID NO: 2760)

5'-AAGUAUAGGUCCUCAUUAUAUUUAC^CC-3'    (SEQ ID NO: 6088)
        3'-UUCAUAUCCAGGAGUAAUAUAAAUG_AU-5'    (SEQ ID NO: 1652)

βc-1265 Target: 5'-AAGTATAGGTCCTCATTATATTTACTA-3'  (SEQ ID NO: 2761)

5'-UAAGUAUAGGUCCUCAUUAUAUUUA^AC-3'    (SEQ ID NO: 6089)
        3'-AUUCAUAUCCAGGAGUAAUAUAAAU_GA-5'    (SEQ ID NO: 1653)

βc-1266 Target: 5'-TAAGTATAGGTCCTCATTATATTTACT-3'  (SEQ ID NO: 2762)

5'-GUUUUUCGUAAGUAUAGGUCCUCAU^CC-3'    (SEQ ID NO: 6090)
        3'-CAAAAAGCAUUCAUAUCCAGGAGUA_AU-5'    (SEQ ID NO: 1654)

βc-1274 Target: 5'-GTTTTTCGTAAGTATAGGTCCTCATTA-3'  (SEQ ID NO: 2763)

5'-AGUUUUUCGUAAGUAUAGGUCCUCA^CC-3'    (SEQ ID NO: 6091)
        3'-UCAAAAAGCAUUCAUAUCCAGGAGU_AA-5'    (SEQ ID NO: 1655)

βc-1275 Target: 5'-AGTTTTTCGTAAGTATAGGTCCTCATT-3'  (SEQ ID NO: 2764)
```

TABLE 12-continued

Additional Selected Anti-β-catenin DsiRNAs, Blunt/Frayed Duplexes

```
      5'-UAGUUUUUCGUAAGUAUAGGUCCUC^CC-3'   (SEQ ID NO: 6092)
      3'-AUCAAAAAGCAUUCAUAUCCAGGAG_UA-5'   (SEQ ID NO: 1656)
```

βc-1276 Target: 5'-TAGTTTTTCGTAAGTATAGGTCCTC-3' (SEQ ID NO: 2765)

```
      5'-GUAGUUUUUCGUAAGUAUAGGUCCU^AC-3'   (SEQ ID NO: 6093)
      3'-CAUCAAAAAGCAUUCAUAUCCAGGA_GU-5'   (SEQ ID NO: 1657)
```

βc-1277 Target: 5'-GTAGTTTTTCGTAAGTATAGGTCCTCA-3' (SEQ ID NO: 2766)

```
      5'-GUGGUCCACAGUAGUUUUUCGUAAG^CC-3'   (SEQ ID NO: 6094)
      3'-CACCAGGUGUCAUCAAAAAGCAUUC_AU-5'   (SEQ ID NO: 1658)
```

βc-1287 Target: 5'-GTGGTCCACAGTAGTTTTTCGTAAGTA-3' (SEQ ID NO: 2767)

```
      5'-UCUACAAUAGCCGGCUUAUUACUAG^CA-3'   (SEQ ID NO: 6095)
      3'-AGAUGUUAUCGGCCGAAUAAUGAUC_UC-5'   (SEQ ID NO: 1659)
```

βc-1344 Target: 5'-TCTACAATAGCCGGCTTATTACTAGAG-3' (SEQ ID NO: 2768)

```
      5'-CUUCUACAAUAGCCGGCUUAUUACU^CA-3'   (SEQ ID NO: 6096)
      3'-GAAGAUGUUAUCGGCCGAAUAAUGA_UC-5'   (SEQ ID NO: 1660)
```

βc-1346 Target: 5'-CTTCTACAATAGCCGGCTTATTACTAG-3' (SEQ ID NO: 2769)

```
      5'-AGUCCUAAAGCUUGCAUUCCACCAG^AC-3'   (SEQ ID NO: 6097)
      3'-UCAGGAUUUCGAACGUAAGGUGGUC_GA-5'   (SEQ ID NO: 1661)
```

βc-1371 Target: 5'-AGTCCTAAAGCTTGCATTCCACCAGCT-3' (SEQ ID NO: 2770)

```
      5'-AAGUCCUAAAGCUUGCAUUCCACCA^AA-3'   (SEQ ID NO: 6098)
      3'-UUCAGGAUUUCGAACGUAAGGUGGU_CG-5'   (SEQ ID NO: 1662)
```

βc-1372 Target: 5'-AAGTCCTAAAGCTTGCATTCCACCAGC-3' (SEQ ID NO: 2771)

```
      5'-GAAGUCCUAAAGCUUGCAUUCCACC^CA-3'   (SEQ ID NO: 6099)
      3'-CUUCAGGAUUUCGAACGUAAGGUGG_UC-5'   (SEQ ID NO: 1663)
```

βc-1373 Target: 5'-GAAGTCCTAAAGCTTGCATTCCACCAG-3' (SEQ ID NO: 2772)

```
      5'-CAGUUCUGAACAAGACGUUGACUUG^AC-3'   (SEQ ID NO: 6100)
      3'-GUCAAGACUUGUUCUGCAACUGAAC_UC-5'   (SEQ ID NO: 1664)
```

βc-1410 Target: 5'-CAGTTCTGAACAAGACGTTGACTTGA-3' (SEQ ID NO: 2773)

```
      5'-ACAGUUCUGAACAAGACGUUGACUU^AA-3'   (SEQ ID NO: 6101)
      3'-UGUCAAGACUUGUUCUGCAACUGAA_CC-5'   (SEQ ID NO: 1665)
```

βc-1411 Target: 5'-ACAGTTCTGAACAAGACGTTGACTTGG-3' (SEQ ID NO: 2774)

```
      5'-GAGUCCAAAGACAGUUCUGAACAAG^CA-3'   (SEQ ID NO: 6102)
      3'-CUCAGGUUUCUGUCAAGACUUGUUC_UG-5'   (SEQ ID NO: 1666)
```

βc-1421 Target: 5'-GAGTCCAAAGACAGTTCTGAACAAGAC-3' (SEQ ID NO: 2775)

```
      5'-CCUUCCUGUUUAGUUGCAGCAUCUG^CC-3'   (SEQ ID NO: 6103)
      3'-GGAAGGACAAAUCAACGUCGUAGAC_UU-5'   (SEQ ID NO: 1667)
```

βc-1458 Target: 5'-CCTTCCTGTTTAGTTGCAGCATCTGAA-3' (SEQ ID NO: 2776)

TABLE 12-continued

Additional Selected Anti-β-catenin DsiRNAs, Blunt/Frayed Duplexes

```
5'-CCACAUUUAUAUCAUCUGAACCCAG^(CC-3')   (SEQ ID NO: 6104)
3'-GGUGUAAAUAUAGUAGACUUGGGUC_(UU-5')   (SEQ ID NO: 1668)
```

βc-1517 Target: 5'-CCACATTTATATCATCTGAACCCAGAA-3'  (SEQ ID NO: 2777)

```
5'-UGACCACAUUUAUAUCAUCUGAACC^(AC-3')   (SEQ ID NO: 6105)
3'-ACUGGUGUAAAUAUAGUAGACUUGG_(GU-5')   (SEQ ID NO: 1669)
```

βc-1520 Target: 5'-TGACCACATTTATATCATCTGAACCCA-3'  (SEQ ID NO: 2778)

```
5'-CUGCACAGGUGACCACAUUUAUAUC^(CC-3')   (SEQ ID NO: 6106)
3'-GACGUGUCCACUGGUGUAAAUAUAG_(UA-5')   (SEQ ID NO: 1670)
```

βc-1529 Target: 5'-CTGCACAGGTGACCACATTTATATC-3'  (SEQ ID NO: 2779)

```
5'-GCUGCACAGGUGACCACAUUUAUAU^(AC-3')   (SEQ ID NO: 6107)
3'-CGACGUGUCCACUGGUGUAAAUAUA_(GU-5')   (SEQ ID NO: 1671)
```

βc-1530 Target: 5'-GCTGCACAGGTGACCACATTTATATCA-3'  (SEQ ID NO: 2780)

```
5'-AUUGCAAGUGAGGUUAGAAAGAAUU^(AA-3')   (SEQ ID NO: 6108)
3'-UAACGUUCACUCCAAUCUUUCUUAA_(GG-5')   (SEQ ID NO: 1672)
```

βc-1558 Target: 5'-ATTGCAAGTGAGGTTAGAAAGAATTCC-3'  (SEQ ID NO: 2781)

```
5'-UUAUAAUUAUUGCAAGUGAGGUUAG^(CC-3')   (SEQ ID NO: 6109)
3'-AAUAUUAAUAACGUUCACUCCAAUC_(UU-5')   (SEQ ID NO: 1673)
```

βc-1566 Target: 5'-TTATAATTATTGCAAGTGAGGTTAGAA-3'  (SEQ ID NO: 2782)

```
5'-CAUCAUCUUGUUCUUAUAAUUAUUG^(AC-3')   (SEQ ID NO: 6110)
3'-GUAGUAGAACAAGAAUAUUAAUAAC_(GU-5')   (SEQ ID NO: 1674)
```

βc-1579 Target: 5'-CATCATCTTGTTCTTATAATTATTGCA-3'  (SEQ ID NO: 2783)

```
5'-CCAUCAUCUUGUUCUUAUAAUUAUU^(AA-3')   (SEQ ID NO: 6111)
3'-GGUAGUAGAACAAGAAUAUUAAUAA_(CG-5')   (SEQ ID NO: 1675)
```

βc-1580 Target: 5'-CCATCATCTTGTTCTTATAATTATTGC-3'  (SEQ ID NO: 2784)

```
5'-AGACCAUCAUCUUGUUCUUAUAAUU^(CC-3')   (SEQ ID NO: 6112)
3'-UCUGGUAGUAGAACAAGAAUAUUAA_(UA-5')   (SEQ ID NO: 1676)
```

βc-1583 Target: 5'-AGACCATCATCTTGTTCTTATAATTAT-3'  (SEQ ID NO: 2785)

```
5'-GCAGACCAUCAUCUUGUUCUUAUAA^(CC-3')   (SEQ ID NO: 6113)
3'-CGUCUGGUAGUAGAACAAGAAUAUU_(AA-5')   (SEQ ID NO: 1677)
```

βc-1585 Target: 5'-GCAGACCATCATCTTGTTCTTATAATT-3'  (SEQ ID NO: 2786)

```
5'-UCAAUCCAACAGUAGCCUUUAUCAG^(CA-3')   (SEQ ID NO: 6114)
3'-AGUUAGGUUGUCAUCGGAAAUAGUC_(UC-5')   (SEQ ID NO: 1678)
```

βc-1808 Target: 5'-TCAATCCAACAGTAGCCTTTATCAGAG-3'  (SEQ ID NO: 2787)

```
5'-UCGAAUCAAUCCAACAGUAGCCUUU^(CC-3')   (SEQ ID NO: 6115)
3'-AGCUUAGUUAGGUUGUCAUCGGAAA_(UA-5')   (SEQ ID NO: 1679)
```

βc-1813 Target: 5'-TCGAATCAATCCAACAGTAGCCTTTAT-3'  (SEQ ID NO: 2788)

TABLE 12-continued

Additional Selected Anti-β-catenin DsiRNAs, Blunt/Frayed Duplexes

```
        5'-CCUCCACAAAUUGCUGCUGUGUCCC^(CA-3')  (SEQ ID NO: 6116)
        3'-GGAGGUGUUUAACGACGACACAGGG_(UG-5')  (SEQ ID NO: 1680)
```

βc-1955 Target: 5'-CCTCCACAAATTGCTGCTGTGTCCCAC-3' (SEQ ID NO: 2789)

```
        5'-GUACAACCUUCAACUAUUUCUUCCA^(CA-3')  (SEQ ID NO: 6117)
        3'-CAUGUUGGAAGUUGAUAAAGAAGGU_(AC-5')  (SEQ ID NO: 1681)
```

βc-1989 Target: 5'-GTACAACCTTCAACTATTTCTTCCATG-3' (SEQ ID NO: 2790)

```
        5'-GGUACAACCUUCAACUAUUUCUUCC^(CC-3')  (SEQ ID NO: 6118)
        3'-CCAUGUUGGAAGUUGAUAAAGAAGG_(UA-5')  (SEQ ID NO: 1682)
```

βc-1990 Target: 5'-GGTACAACCTTCAACTATTTCTTCC-3' (SEQ ID NO: 2791)

```
        5'-CGGUACAACCUUCAACUAUUUCUUC^(AC-3')  (SEQ ID NO: 6119)
        3'-GCCAUGUUGGAAGUUGAUAAAGAAG_(GU-5')  (SEQ ID NO: 1683)
```

βc-1991 Target: 5'-CGGTACAACCTTCAACTATTTCTTCA-3' (SEQ ID NO: 2792)

```
        5'-CCGGUACAACCUUCAACUAUUUCUU^(AA-3')  (SEQ ID NO: 6120)
        3'-GGCCAUGUUGGAAGUUGAUAAAGAA_(GG-5')  (SEQ ID NO: 1684)
```

βc-1992 Target: 5'-CCGGTACAACCTTCAACTATTTCTTCC-3' (SEQ ID NO: 2793)

```
        5'-GGGCUCCGGUACAACCUUCAACUAU^(CC-3')  (SEQ ID NO: 6121)
        3'-CCCGAGGCCAUGUUGGAAGUUGAUA_(AA-5')  (SEQ ID NO: 1685)
```

βc-1997 Target: 5'-GGGCTCCGGTACAACCTTCAACTATTT-3' (SEQ ID NO: 2794)

```
        5'-UAACAAUUCGGUUGUGAACAUCCCG^(CA-3')  (SEQ ID NO: 6122)
        3'-AUUGUUAAGCCAACACUUGUAGGGC_(UC-5')  (SEQ ID NO: 1686)
```

βc-2036 Target: 5'-TAACAATTCGGTTGTGAACATCCCGAG-3' (SEQ ID NO: 2795)

```
        5'-AUAACAAUUCGGUUGUGAACAUCCC^(AC-3')  (SEQ ID NO: 6123)
        3'-UAUUGUUAAGCCAACACUUGUAGGG_(CU-5')  (SEQ ID NO: 1687)
```

βc-2037 Target: 5'-ATAACAATTCGGTTGTGAACATCCGA-3' (SEQ ID NO: 2796)

```
        5'-GAUAACAAUUCGGUUGUGAACAUCC^(AA-3')  (SEQ ID NO: 6124)
        3'-CUAUUGUUAAGCCAACACUUGUAGG_(GC-5')  (SEQ ID NO: 1688)
```

βc-2038 Target: 5'-GATAACAATTCGGTTGTGAACATCCCG-3' (SEQ ID NO: 2797)

```
        5'-UGAUAACAAUUCGGUUGUGAACAUC^(AA-3')  (SEQ ID NO: 6125)
        3'-ACUAUUGUUAAGCCAACACUUGUAG_(GG-5')  (SEQ ID NO: 1689)
```

βc-2039 Target: 5'-TGATAACAATTCGGTTGTGAACATCCC-3' (SEQ ID NO: 2798)

```
        5'-CUGAUAACAAUUCGGUUGUGAACAU^(AA-3')  (SEQ ID NO: 6126)
        3'-GACUAUUGUUAAGCCAACACUUGUA_(GG-5')  (SEQ ID NO: 1690)
```

βc-2040 Target: 5'-CTGATAACAATTCGGTTGTGAACATCC-3' (SEQ ID NO: 2799)

```
        5'-UCUGAUAACAAUUCGGUUGUGAACA^(CA-3')  (SEQ ID NO: 6127)
        3'-AGACUAUUGUUAAGCCAACACUUGU_(AG-5')  (SEQ ID NO: 1691)
```

βc-2041 Target: 5'-TCTGATAACAATTCGGTTGTGAACATC-3' (SEQ ID NO: 2800)

TABLE 12-continued

Additional Selected Anti-β-catenin DsiRNAs, Blunt/Frayed Duplexes

```
         5'-GUAUUUAGUCCUCUGAUAACAAUUC^(A A-3')   (SEQ ID NO: 6128)
         3'-CAUAAAUCAGGAGACUAUUGUUAAG_(C C-5')   (SEQ ID NO: 1692)
```

βc-2052 Target: 5'-GTATTTAGTCCTCTGATAACAATTCGG-3' (SEQ ID NO: 2801)

```
         5'-GGUAUUUAGUCCUCUGAUAACAAUU^(A A-3')   (SEQ ID NO: 6129)
         3'-CCAUAAAUCAGGAGACUAUUGUUAA_(G C-5')   (SEQ ID NO: 1693)
```

βc-2053 Target: 5'-GGTATTTAGTCCTCTGATAACAATTCG-3' (SEQ ID NO: 2802)

```
         5'-UGGUAUUUAGUCCUCUGAUAACAAU^(C A-3')   (SEQ ID NO: 6130)
         3'-ACCAUAAAUCAGGAGACUAUUGUUA_(A G-5')   (SEQ ID NO: 1694)
```

βc-2054 Target: 5'-TGGTATTTAGTCCTCTGATAACAATTC-3' (SEQ ID NO: 2803)

```
         5'-AUGGUAUUUAGUCCUCUGAUAACAA^(C C-3')   (SEQ ID NO: 6131)
         3'-UACCAUAAAUCAGGAGACUAUUGUU_(A A-5')   (SEQ ID NO: 1695)
```

βc-2055 Target: 5'-ATGGTATTTAGTCCTCTGATAACAATT-3' (SEQ ID NO: 2804)

```
         5'-AAACAAUGGAAUGGUAUUUAGUCCU^(A C-3')   (SEQ ID NO: 6132)
         3'-CAACAUACCAUAUGAAGUUUAUGGG_(A G-5')   (SEQ ID NO: 1696)
```

βc-2065 Target: 5'-AAACAATGGAATGGTATTTAGTCCTCT-3' (SEQ ID NO: 2805)

```
         5'-GCACAAACAAUGGAAUGGUAUUUAG^(C A-3')   (SEQ ID NO: 6133)
         3'-CGUGUUUGUUACCUUACCAUAAAUC_(A G-5')   (SEQ ID NO: 1697)
```

βc-2069 Target: 5'-GCACAAACAATGGAATGGTATTTAGTC-3' (SEQ ID NO: 2806)

```
         5'-CUGCACAAACAAUGGAAUGGUAUUU^(C A-3')   (SEQ ID NO: 6134)
         3'-GACGUGUUUGUUACCUUACCAUAAA_(U C-5')   (SEQ ID NO: 1698)
```

βc-2071 Target: 5'-CTGCACAAACAATGGAATGGTATTTAG-3' (SEQ ID NO: 2807)

```
         5'-GCUGCACAAACAAUGGAAUGGUAUU^(C C-3')   (SEQ ID NO: 6135)
         3'-CGACGUGUUUGUUACCUUACCAUAA_(A U-5')   (SEQ ID NO: 1699)
```

βc-2072 Target: 5'-GCTGCACAAACAATGGAATGGTATTTA-3' (SEQ ID NO: 2808)

```
         5'-CAGCUACUCUUUGGAUGUUUUCAAU^(A A-3')   (SEQ ID NO: 6136)
         3'-GUCGAUGAGAAACCUACAAAAGUUA_(C C-5')   (SEQ ID NO: 1700)
```

βc-2111 Target: 5'-CAGCTACTCTTTGGATGTTTTCAATGG-3' (SEQ ID NO: 2809)

```
         5'-GCAGCUACUCUUUGGAUGUUUUCAA^(C A-3')   (SEQ ID NO: 6137)
         3'-CGUCGAUGAGAAACCUACAAAAGUU_(A C-5')   (SEQ ID NO: 1701)
```

βc-2112 Target: 5'-GCAGCTACTCTTTGGATGTTTTCAATG-3' (SEQ ID NO: 2810)

```
         5'-CAGCUUCAAUAGCUUCUGCAGCUUC^(A C-3')   (SEQ ID NO: 6138)
         3'-GUCGAAGUUAUCGAAGACGUCGAAG_(G A-5')   (SEQ ID NO: 1702)
```

βc-2168 Target: 5'-CAGCTTCAATAGCTTCTGCAGCTTCCT-3' (SEQ ID NO: 2811)

```
         5'-GCUCCCUCAGCUUCAAUAGCUUCUG^(A C-3')   (SEQ ID NO: 6139)
         3'-CGAGGGAGUCGAAGUUAUCGAAGAC_(G U-5')   (SEQ ID NO: 1703)
```

βc-2175 Target: 5'-GCTCCCTCAGCTTCAATAGCTTCTGCA-3' (SEQ ID NO: 2812)

TABLE 12-continued

Additional Selected Anti-β-catenin DsiRNAs, Blunt/Frayed Duplexes

```
5'-UGGCUCCCUCAGCUUCAAUAGCUUC^(CA-3')  (SEQ ID NO: 6140)
3'-ACCGAGGGAGUCGAAGUUAUCGAAG_(AC-5')  (SEQ ID NO: 1704)
```

βc-2177 Target: 5'-TGGCTCCCTCAGCTTCAATAGCTTCTG-3' (SEQ ID NO: 2813)

```
5'-UCAUUCCUAGAGUGAAGUAACUCUG^(CA-3')  (SEQ ID NO: 6141)
3'-AGUAAGGAUCUCACUUCAUUGAGAC_(AG-5')  (SEQ ID NO: 1705)
```

βc-2214 Target: 5'-TCATTCCTAGAGTGAAGTAACTCTGTC-3' (SEQ ID NO: 2814)

```
5'-CUUCAUUCCUAGAGUGAAGUAACUC^(CA-3')  (SEQ ID NO: 6142)
3'-GAAGUAAGGAUCUCACUUCAUUGAG_(AC-5')  (SEQ ID NO: 1706)
```

βc-2216 Target: 5'-CTTCATTCCTAGAGTGAAGTAACTCTG-3' (SEQ ID NO: 2815)

```
5'-CCUUCAUUCCUAGAGUGAAGUAACU^(AC-3')  (SEQ ID NO: 6143)
3'-GGAAGUAAGGAUCUCACUUCAUUGA_(GA-5')  (SEQ ID NO: 1707)
```

βc-2217 Target: 5'-CCTTCATTCCTAGAGTGAAGTAACTCT-3' (SEQ ID NO: 2816)

```
5'-UGUCCUCAGACAUUCGGAACAAAAC^(CA-3')  (SEQ ID NO: 6144)
3'-ACAGGAGUCUGUAAGCCUUGUUUUG_(UC-5')  (SEQ ID NO: 1708)
```

βc-2264 Target: 5'-TGTCCTCAGACATTCGGAACAAAACAG-3' (SEQ ID NO: 2817)

```
5'-CUUGUCCUCAGACAUUCGGAACAAA^(CA-3')  (SEQ ID NO: 6145)
3'-GAACAGGAGUCUGUAAGCCUUGUUU_(UG-5')  (SEQ ID NO: 1709)
```

βc-2266 Target: 5'-CTTGTCCTCAGACATTCGGAACAAAC-3' (SEQ ID NO: 2818)

```
5'-CCGUUUCUUGUAAUCUUGUGGCUUG^(CA-3')  (SEQ ID NO: 6146)
3'-GGCAAAGAACAUUAGAACACCGAAC_(AG-5')  (SEQ ID NO: 1710)
```

βc-2287 Target: 5'-CCGTTTCTTGTAATCTTGTGGCTTGTC-3' (SEQ ID NO: 2819)

```
5'-ACUGAAAGCCGUUUCUUGUAAUCUU^(AC-3')  (SEQ ID NO: 6147)
3'-UGACUUUCGGCAAAGAACAUUAGAA_(CA-5')  (SEQ ID NO: 1711)
```

βc-2295 Target: 5'-ACTGAAAGCCGTTTCTTGTAATCTTGT-3' (SEQ ID NO: 2820)

```
5'-CAGCUCAACUGAAAGCCGUUUCUUG^(CC-3')  (SEQ ID NO: 6148)
3'-GUCGAGUUGACUUUCGGCAAAGAAC_(AU-5')  (SEQ ID NO: 1712)
```

βc-2302 Target: 5'-CAGCTCAACTGAAAGCCGTTTCTTGTA-3' (SEQ ID NO: 2821)

```
5'-CAAGUCCAAGAUCAGCAGUCUCAUU^(AA-3')  (SEQ ID NO: 6149)
3'-GUUCAGGUUCUAGUCGUCAGAGUAA_(G-5')   (SEQ ID NO: 1713)
```

βc-2363 Target: 5'-CAAGTCCAAGATCAGCAGTCTCATTCC-3' (SEQ ID NO: 2822)

```
5'-GCACCAAUAUCAAGUCCAAGAUCAG^(AC-3')  (SEQ ID NO: 6150)
3'-CGUGGUUAUAGUUCAGGUUCUAGUC_(GU-5')  (SEQ ID NO: 1714)
```

βc-2373 Target: 5'-GCACCAATATCAAGTCCAAGATCAGCA-3' (SEQ ID NO: 2823)

```
5'-AAAGAACGAUAGCUAGGAUCAUCCU^(AA-3')  (SEQ ID NO: 6151)
3'-UUUCUUGCUAUCGAUCCUAGUAGGA_(CC-5')  (SEQ ID NO: 1715)
```

βc-2424 Target: 5'-AAAGAACGATAGCTAGGATCATCCTGG-3' (SEQ ID NO: 2824)

TABLE 12-continued

Additional Selected Anti-β-catenin DsiRNAs, Blunt/Frayed Duplexes

```
            5'-CAUAUCCACCAGAGUGAAAAGAACG^CC-3'   (SEQ ID NO: 6152)
            3'-GUAUAGGUGGUCUCACUUUUCUUGC_UA-5'   (SEQ ID NO: 1716)

βc-2441 Target: 5'-CATATCCACCAGAGTGAAAAGAACGAT-3' (SEQ ID NO: 2825)

5'-UGAUUUACAGGUCAGUAUCAAACCA^AA-3'   (SEQ ID NO: 6153)
            3'-ACUAAAUGUCCAGUCAUAGUUUGGU_CC-5'   (SEQ ID NO: 1717)

βc-2618 Target: 5'-TGATTTACAGGTCAGTATCAAACCAGG-3' (SEQ ID NO: 2826)

5'-AUGAUUUACAGGUCAGUAUCAAACC^CA-3'   (SEQ ID NO: 6154)
            3'-UACUAAAUGUCCAGUCAUAGUUUGG_UC-5'   (SEQ ID NO: 1718)

βc-2619 Target: 5'-ATGATTTACAGGTCAGTATCAAACCAG-3' (SEQ ID NO: 2827)

5'-GAUGAUUUACAGGUCAGUAUCAAAC^AC-3'   (SEQ ID NO: 6155)
            3'-CUACUAAAUGUCCAGUCAUAGUUUG_GU-5'   (SEQ ID NO: 1719)

βc-2620 Target: 5'-GATGATTTACAGGTCAGTATCAAACCA-3' (SEQ ID NO: 2828)

5'-CUUCUUACCUAAAGGAUGAUUUACA^AA-3'   (SEQ ID NO: 6156)
            3'-GAAGAAUGGAUUUCCUACUAAAUGU_CC-5'   (SEQ ID NO: 1720)

βc-2634 Target: 5'-CTTCTTACCTAAAGGATGATTTACAGG-3' (SEQ ID NO: 2829)

5'-ACUUCUUACCUAAAGGAUGAUUUAC^CA-3'   (SEQ ID NO: 6157)
            3'-UGAAGAAUGGAUUUCCUACUAAAUG_UC-5'   (SEQ ID NO: 1721)

βc-2635 Target: 5'-ACTTCTTACCTAAAGGATGATTTACAG-3' (SEQ ID NO: 2830)

5'-AAACUUCUUACCUAAAGGAUGAUUU^CA-3'   (SEQ ID NO: 6158)
            3'-UUUGAAGAAUGGAUUUCCUACUAAA_UG-5'   (SEQ ID NO: 1722)

βc-2637 Target: 5'-AAACTTCTTACCTAAAGGATGATTTAC-3' (SEQ ID NO: 2831)

5'-GCUUUUUAAAACUUCUUACCUAAAG^AC-3'   (SEQ ID NO: 6159)
            3'-CGAAAAAUUUUGAAGAAUGGAUUUC_UU-5'   (SEQ ID NO: 1723)

βc-2645 Target: 5'-GCTTTTTAAAACTTCTTACCTAAGGA-3' (SEQ ID NO: 2832)

5'-UGGCUUUUUAAAACUUCUUACCUAA^CA-3'   (SEQ ID NO: 6160)
            3'-ACCGAAAAAUUUUGAAGAAUGGAUU_UC-5'   (SEQ ID NO: 1724)

βc-2647 Target: 5'-TGGCTTTTTAAAACTTCTTACCTAAAG-3' (SEQ ID NO: 2833)

5'-CCAAACUGGCUUUUUAAAACUUCUU^CA-3'   (SEQ ID NO: 6161)
            3'-GGUUUGACCGAAAAAUUUUGAAGAA_UG-5'   (SEQ ID NO: 1725)

βc-2653 Target: 5'-CCAAACTGGCTTTTTAAAACTTCTTAC-3' (SEQ ID NO: 2834)

5'-UUACCCAAACUGGCUUUUUAAAACU^CA-3'   (SEQ ID NO: 6162)
            3'-AAUGGGUUUGACCGAAAAAUUUUGA_AG-5'   (SEQ ID NO: 1726)

βc-2657 Target: 5'-TTACCCAAACTGGCTTTTTAAAACTTC-3' (SEQ ID NO: 2835)

5'-UUUACCCAAACUGGCUUUUUAAAAC^CC-3'   (SEQ ID NO: 6163)
            3'-AAAUGGGUUUGACCGAAAAAUUUUG_AA-5'   (SEQ ID NO: 1727)

βc-2658 Target: 5'-TTTACCCAAACTGGCTTTTTAAAACTT-3' (SEQ ID NO: 2836)
```

TABLE 12-continued

Additional Selected Anti-β-catenin DsiRNAs, Blunt/Frayed Duplexes

```
5'-UUUUACCCAAACUGGCUUUUUAAAA^(AC-3')      (SEQ ID NO: 6164)
3'-AAAAUGGGUUUGACCGAAAAAUUUU_(GA-5')      (SEQ ID NO: 1728)
```

βc-2659 Target: 5'-TTTTACCCAAACTGGCTTTTTAAAACT-3' (SEQ ID NO: 2837)

```
5'-AUUUUACCCAAACUGGCUUUUUAAA^(CA-3')      (SEQ ID NO: 6165)
3'-UAAAAUGGGUUUGACCGAAAAAUUU_(UG-5')      (SEQ ID NO: 1729)
```

βc-2660 Target: 5'-ATTTTACCCAAACTGGCTTTTTAAAAC-3' (SEQ ID NO: 2838)

```
5'-CCAACCAAGUCUUUCUGAAGUUCUG^(CC-3')      (SEQ ID NO: 6166)
3'-GGUUGGUUCAGAAAGACUUCAAGAC_(AU-5')      (SEQ ID NO: 1730)
```

βc-2701 Target: 5'-CCAACCAAGTCTTTCTGAAGTTCTGTA-3' (SEQ ID NO: 2839)

```
5'-CCACCCUACCAACCAAGUCUUUCUG^(CC-3')      (SEQ ID NO: 6167)
3'-GGUGGGAUGGUUGGUUCAGAAAGAC_(UU-5')      (SEQ ID NO: 1731)
```

βc-2709 Target: 5'-CCACCCTACCAACCAAGTCTTTCTGAA-3' (SEQ ID NO: 2840)

```
5'-AUUUACAAAUAGCCUAAACCACUCC^(AC-3')      (SEQ ID NO: 6168)
3'-UAAAUGUUUAUCGGAUUUGGUGAGG_(GU-5')      (SEQ ID NO: 1732)
```

βc-2733 Target: 5'-ATTTACAAATAGCCTAAACCACTCCCA-3' (SEQ ID NO: 2841)

```
5'-GAUUUACAAAUAGCCUAAACCACUC^(AA-3')      (SEQ ID NO: 6169)
3'-CUAAAUGUUUAUCGGAUUUGGUGAG_(GG-5')      (SEQ ID NO: 1733)
```

βc-2734 Target: 5'-GATTTACAAATAGCCTAAACCACTCCC-3' (SEQ ID NO: 2842)

```
5'-AGAUUUACAAAUAGCCUAAACCACU^(AA-3')      (SEQ ID NO: 6170)
3'-UCUAAAUGUUUAUCGGAUUUGGUGA_(GG-5')      (SEQ ID NO: 1734)
```

βc-2735 Target: 5'-AGATTTACAAATAGCCTAAACCACTCC-3' (SEQ ID NO: 2843)

```
5'-CAGAUUUACAAAUAGCCUAAACCAC^(CA-3')      (SEQ ID NO: 6171)
3'-GUCUAAAUGUUUAUCGGAUUUGGUG_(AG-5')      (SEQ ID NO: 1735)
```

βc-2736 Target: 5'-CAGATTTACAAATAGCCTAAACCACTC-3' (SEQ ID NO: 2844)

```
5'-UGUUUUUGUGGCAGAUUUACAAAUA^(AA-3')      (SEQ ID NO: 6172)
3'-ACAAAAACACCGUCUAAAUGUUUAU_(CG-5')      (SEQ ID NO: 1736)
```

βc-2747 Target: 5'-TGTTTTTGTGGCAGATTTACAAATAGC-3' (SEQ ID NO: 2845)

```
5'-CUGUUUUUGUGGCAGAUUUACAAAU^(CA-3')      (SEQ ID NO: 6173)
3'-GACAAAAACACCGUCUAAAUGUUUA_(UC-5')      (SEQ ID NO: 1737)
```

βc-2748 Target: 5'-CTGTTTTTGTGGCAGATTTACAAATAG-3' (SEQ ID NO: 2846)

```
5'-CCUGUUUUUGUGGCAGAUUUACAAA^(CC-3')      (SEQ ID NO: 6174)
3'-GGACAAAAACACCGUCUAAAUGUUU_(AU-5')      (SEQ ID NO: 1738)
```

βc-2749 Target: 5'-CCTGTTTTTGTGGCAGATTTACAAATA-3' (SEQ ID NO: 2847)

```
5'-AUAUACCUGUUUUUGUGGCAGAUUU^(CA-3')      (SEQ ID NO: 6175)
3'-UAUAUGGACAAAAACACCGUCUAAA_(UG-5')      (SEQ ID NO: 1739)
```

βc-2754 Target: 5'-ATATACCTGTTTTTGTGGCAGATTTAC-3' (SEQ ID NO: 2848)

TABLE 12-continued

Additional Selected Anti-β-catenin DsiRNAs, Blunt/Frayed Duplexes

```
          5'-CUUUCAAAGUAUAUACCUGUUUUUG^(CA-3')   (SEQ ID NO: 6176)
          3'-GAAAGUUUCAUAUAUGGACAAAAAC_(AC-5')   (SEQ ID NO: 1740)
```

βc-2764 Target: 5'-CTTTCAAAGTATATACCTGTTTTGTG-3' (SEQ ID NO: 2849)

```
          5'-CAUCUCCUUUCAAAGUAUAUACCUG^(CC-3')   (SEQ ID NO: 6177)
          3'-GUAGAGGAAAGUUUCAUAUAUGGAC_(AA-5')   (SEQ ID NO: 1741)
```

βc-2770 Target: 5'-CATCTCCTTTCAAAGTATATACCTGTT-3' (SEQ ID NO: 2850)

```
          5'-ACAUCUCCUUUCAAAGUAUAUACCU^(AC-3')   (SEQ ID NO: 6178)
          3'-UGUAGAGGAAAGUUUCAUAUAUGGA_(CA-5')   (SEQ ID NO: 1742)
```

βc-2771 Target: 5'-ACATCTCCTTTCAAAGTATATACCTGT-3' (SEQ ID NO: 2851)

```
          5'-AGACAUCUCCUUUCAAAGUAUAUAC^(AC-3')   (SEQ ID NO: 6179)
          3'-UCUGUAGAGGAAAGUUUCAUAUAUG_(GA-5')   (SEQ ID NO: 1743)
```

βc-2773 Target: 5'-AGACATCTCCTTTCAAAGTATATACCT-3' (SEQ ID NO: 2852)

```
          5'-AAGACAUCUCCUUUCAAAGUAUAUA^(AA-3')   (SEQ ID NO: 6180)
          3'-UUCUGUAGAGGAAAGUUUCAUAUAU_(GG-5')   (SEQ ID NO: 1744)
```

βc-2774 Target: 5'-AAGACATCTCCTTTCAAAGTATATACC-3' (SEQ ID NO: 2853)

```
          5'-CAAGACAUCUCCUUUCAAAGUAUAU^(CA-3')   (SEQ ID NO: 6181)
          3'-GUUCUGUAGAGGAAAGUUUCAUAUA_(UG-5')   (SEQ ID NO: 1745)
```

βc-2775 Target: 5'-CAAGACATCTCCTTTCAAAGTATATAC-3' (SEQ ID NO: 2854)

```
          5'-UGUUCCAAGACAUCUCCUUUCAAAG^(CC-3')   (SEQ ID NO: 6182)
          3'-ACAAGGUUCUGUAGAGGAAAGUUUC_(AU-5')   (SEQ ID NO: 1746)
```

βc-2780 Target: 5'-TGTTCCAAGACATCTCCTTTCAAAGTA-3' (SEQ ID NO: 2855)

```
          5'-CAUUCCAAUGUUCCAAGACAUCUCC^(CC-3')   (SEQ ID NO: 6183)
          3'-GUAAGGUUACAAGGUUCUGUAGAGG_(AA-5')   (SEQ ID NO: 1747)
```

βc-2788 Target: 5'-CATTCCAATGTTCCAAGACATCTCCTT-3' (SEQ ID NO: 2856)

```
          5'-ACAUUCCAAUGUUCCAAGACAUCUC^(AC-3')   (SEQ ID NO: 6184)
          3'-UGUAAGGUUACAAGGUUCUGUAGAG_(GA-5')   (SEQ ID NO: 1748)
```

βc-2789 Target: 5'-ACATTCCAATGTTCCAAGACATCTCCT-3' (SEQ ID NO: 2857)

```
          5'-GAACAUUCCAAUGUUCCAAGACAUC^(CA-3')   (SEQ ID NO: 6185)
          3'-CUUGUAAGGUUACAAGGUUCUGUAG_(AG-5')   (SEQ ID NO: 1749)
```

βc-2791 Target: 5'-GAACATTCCAATGTTCCAAGACATCTC-3' (SEQ ID NO: 2858)

```
          5'-CCAGAAAUCUGAGAACAUUCCAAUG^(CC-3')   (SEQ ID NO: 6186)
          3'-GGUCUUUAGACUCUUGUAAGGUUAC_(AA-5')   (SEQ ID NO: 1750)
```

βc-2803 Target: 5'-CCAGAAATCTGAGAACATTCCAATGTT-3' (SEQ ID NO: 2859)

```
          5'-ACAACCAGAAAUCUGAGAACAUUCC^(CC-3')   (SEQ ID NO: 6187)
          3'-UGUUGGUCUUUAGACUCUUGUAAGG_(UU-5')   (SEQ ID NO: 1751)
```

βc-2807 Target: 5'-ACAACCAGAAATCTGAGAACATTCCAA-3' (SEQ ID NO: 2860)

TABLE 12-continued

Additional Selected Anti-β-catenin DsiRNAs, Blunt/Frayed Duplexes

```
5'-UAACAACCAGAAAUCUGAGAACAUU^(A-3')     (SEQ ID NO: 6188)
3'-AUUGUUGGUCUUUAGACUCUUGUAA_(G-5')     (SEQ ID NO: 1752)
```

βc-2809 Target: 5'-TAACAACCAGAAATCTGAGAACATTCC-3'     (SEQ ID NO: 2861)

```
5'-AUAACAACCAGAAAUCUGAGAACAU^(C-3')     (SEQ ID NO: 6189)
3'-UAUUGUUGGUCUUUAGACUCUUGUA_(G-5')     (SEQ ID NO: 1753)
```

βc-2810 Target: 5'-ATAACAACCAGAAATCTGAGAACATTC-3'     (SEQ ID NO: 2862)

```
5'-CAUAACAACCAGAAAUCUGAGAACA^(C-3')     (SEQ ID NO: 6190)
3'-GUAUUGUUGGUCUUUAGACUCUUGU_(A-5')     (SEQ ID NO: 1754)
```

βc-2811 Target: 5'-CATAACAACCAGAAATCTGAGAACATT-3'     (SEQ ID NO: 2863)

```
5'-UGAUCACAUAACAACCAGAAAUCUG^(A-3')     (SEQ ID NO: 6191)
3'-ACUAGUGUAUUGUUGGUCUUUAGAC_(C-5')     (SEQ ID NO: 1755)
```

βc-2817 Target: 5'-TGATCACATAACAACCAGAAATCTGAG-3'     (SEQ ID NO: 2864)

```
5'-AUGAUCACAUAACAACCAGAAAUCU^(C-3')     (SEQ ID NO: 6192)
3'-UACUAGUGUAUUGUUGGUCUUUAGA_(U-5')     (SEQ ID NO: 1756)
```

βc-2818 Target: 5'-ATGATCACATAACAACCAGAAATCTGA-3'     (SEQ ID NO: 2865)

```
5'-CCACACAUGAUCACAUAACAACCAG^(C-3')     (SEQ ID NO: 6193)
3'-GGUGUGUACUAGUGUAUUGUUGGUC_(U-5')     (SEQ ID NO: 1757)
```

βc-2824 Target: 5'-CCACACATGATCACATAACAACCAGAA-3'     (SEQ ID NO: 2866)

```
5'-CUUCCACACAUGAUCACAUAACAAC^(C-3')     (SEQ ID NO: 6194)
3'-GAAGGUGUGUACUAGUGUAUUGUUG_(U-5')     (SEQ ID NO: 1758)
```

βc-2827 Target: 5'-CTTCCACACATGATCACATAACAACCA-3'     (SEQ ID NO: 2867)

```
5'-AAUAACUUCCACACAUGAUCACAUA^(A-3')     (SEQ ID NO: 6195)
3'-UUAUUGAAGGUGUGUACUAGUGUAU_(G-5')     (SEQ ID NO: 1759)
```

βc-2832 Target: 5'-AATAACTTCCACACATGATCACATAAC-3'     (SEQ ID NO: 2868)

```
5'-UAAUAACUUCCACACAUGAUCACAU^(C-3')     (SEQ ID NO: 6196)
3'-AUUAUUGAAGGUGUGUACUAGUGUA_(U-5')     (SEQ ID NO: 1760)
```

βc-2833 Target: 5'-TAATAACTTCCACACATGATCACATAA-3'     (SEQ ID NO: 2869)

```
5'-UUAAUAACUUCCACACAUGAUCACA^(C-3')     (SEQ ID NO: 6197)
3'-AAUUAUUGAAGGUGUGUACUAGUGU_(U-5')     (SEQ ID NO: 1761)
```

βc-2834 Target: 5'-TTAATAACTTCCACACATGATCACATA-3'     (SEQ ID NO: 2870)

```
5'-GUUAAUAACUUCCACACAUGAUCAC^(C-3')     (SEQ ID NO: 6198)
3'-CAAUUAUUGAAGGUGUGUACUAGUG_(A-5')     (SEQ ID NO: 1762)
```

βc-2835 Target: 5'-GTTAATAACTTCCACACATGATCAC-3'     (SEQ ID NO: 2871)

```
5'-CAUUAAAGUUAAUAACUUCCACACA^(A-3')     (SEQ ID NO: 6199)
3'-GUAAUUUCAAUUAUUGAAGGUGUGU_(C-5')     (SEQ ID NO: 1763)
```

βc-2842 Target: 5'-CATTAAAGTTAATAACTTCCACACATG-3'     (SEQ ID NO: 2872)

TABLE 12-continued

Additional Selected Anti-β-catenin DsiRNAs, Blunt/Frayed Duplexes

```
5'-ACAUUAAAGUUAAUAACUUCCACACCC-3'   (SEQ ID NO: 6200)
3'-UGUAAUUUCAAUUAUUGAAGGUGUGUA-5'   (SEQ ID NO: 1764)
```

βc-2843 Target: 5'-ACATTAAAGTTAATAACTTCCACAC-3' (SEQ ID NO: 2873)

```
5'-AAACAUUAAAGUUAAUAACUUCCACCA-3'   (SEQ ID NO: 6201)
3'-UUUGUAAUUUCAAUUAUUGAAGGUGUG-5'   (SEQ ID NO: 1765)
```

βc-2845 Target: 5'-AAACATTAAAGTTAATAACTTCCACAC-3' (SEQ ID NO: 2874)

```
5'-AAAACAUUAAAGUUAAUAACUUCCAAC-3'   (SEQ ID NO: 6202)
3'-UUUUGUAAUUUCAAUUAUUGAAGGUU-5'    (SEQ ID NO: 1766)
```

βc-2846 Target: 5'-AAAACATTAAAGTTAATAACTTCCACA-3' (SEQ ID NO: 2875)

```
5'-AAAAACAUUAAAGUUAAUAACUUCCCA-3'   (SEQ ID NO: 6203)
3'-UUUUUGUAAUUUCAAUUAUUGAAGGUG-5'   (SEQ ID NO: 1767)
```

βc-2847 Target: 5'-AAAAACATTAAAGTTAATAACTTCCAC-3' (SEQ ID NO: 2876)

```
5'-AAAAAACAUUAAAGUUAAUAACUUCAC-3'   (SEQ ID NO: 6204)
3'-UUUUUUGUAAUUUCAAUUAUUGAAGGU-5'   (SEQ ID NO: 1768)
```

βc-2848 Target: 5'-AAAAAACATTAAAGTTAATAACTTCCA-3' (SEQ ID NO: 2877)

```
5'-CAAAAAACAUUAAAGUUAAUAACUUAA-3'   (SEQ ID NO: 6205)
3'-GUUUUUUGUAAUUUCAAUUAUUGAAG-5'    (SEQ ID NO: 1769)
```

βc-2849 Target: 5'-CAAAAAACATTAAAGTTAATAACTTCC-3' (SEQ ID NO: 2878)

```
5'-GCAAAAAACAUUAAAGUUAAUAACUCA-3'   (SEQ ID NO: 6206)
3'-CGUUUUUUGUAAUUUCAAUUAUUGAA-5'    (SEQ ID NO: 1770)
```

βc-2850 Target: 5'-GCAAAAAACATTAAAGTTAATAACTTC-3' (SEQ ID NO: 2879)

```
5'-UGGCAAAAAACAUUAAAGUUAAUAAAC-3'   (SEQ ID NO: 6207)
3'-ACCGUUUUUUGUAAUUUCAAUUAUUG-5'    (SEQ ID NO: 1771)
```

βc-2852 Target: 5'-TGGCAAAAAACATTAAAGTTAATAACT-3' (SEQ ID NO: 2880)

```
5'-GUGGCAAAAAACAUUAAAGUUAAUACA-3'   (SEQ ID NO: 6208)
3'-CACCGUUUUUUGUAAUUUCAAUUAUU-5'    (SEQ ID NO: 1772)
```

βc-2853 Target: 5'-GTGGCAAAAAACATTAAAGTTAATAAC-3' (SEQ ID NO: 2881)

```
5'-UUGCAAAAGCUGUGGCAAAAAACAUCC-3'   (SEQ ID NO: 6209)
3'-AACGUUUUCGACACCGUUUUUUGUA-5'     (SEQ ID NO: 1773)
```

βc-2864 Target: 5'-TTGCAAAAGCTGTGGCAAAAAACATTA-3' (SEQ ID NO: 2882)

```
5'-GUUGCAAAAGCUGUGGCAAAAAACACC-3'   (SEQ ID NO: 6210)
3'-CAACGUUUUCGACACCGUUUUUUGU-5'     (SEQ ID NO: 1774)
```

βc-2865 Target: 5'-GTTGCAAAAGCTGTGGCAAAAAACATT-3' (SEQ ID NO: 2883)

```
5'-ACUCAUUUGAGUAUUAAGUUGCAAACA-3'   (SEQ ID NO: 6211)
3'-UGAGUAAACUCAUAAUUCAACGUUU-5'     (SEQ ID NO: 1775)
```

βc-2882 Target: 5'-ACTCATTTGAGTATTAAGTTGCAAAAG-3' (SEQ ID NO: 2884)

TABLE 12-continued

Additional Selected Anti-β-catenin DsiRNAs, Blunt/Frayed Duplexes

```
5'-UUAAAACAGCAAAUGUUACUCAUUU^AC-3'   (SEQ ID NO: 6212)
3'-AAUUUUGUCGUUUACAAUGAGUAAA_CU-5'   (SEQ ID NO: 1776)
```

βc-2899 Target: 5'-TTAAAACAGCAAATGTTACTCATTTGA-3' (SEQ ID NO: 2885)

```
5'-UUUAAAACAGCAAAUGUUACUCAUU^CA-3'   (SEQ ID NO: 6213)
3'-AAAUUUUGUCGUUUACAAUGAGUAA_AC-5'   (SEQ ID NO: 1777)
```

βc-2900 Target: 5'-TTTAAAACAGCAAATGTTACTCATTTG-3' (SEQ ID NO: 2886)

```
5'-GUUUAAAACAGCAAAUGUUACUCAU^CC-3'   (SEQ ID NO: 6214)
3'-CAAAUUUUGUCGUUUACAAUGAGUA_AA-5'   (SEQ ID NO: 1778)
```

βc-2901 Target: 5'-GTTTAAAACAGCAAATGTTACTCATTT-3' (SEQ ID NO: 2887)

```
5'-UGUUUAAAACAGCAAAUGUUACUCA^CC-3'   (SEQ ID NO: 6215)
3'-ACAAAUUUUGUCGUUUACAAUGAGU_AA-5'   (SEQ ID NO: 1779)
```

βc-2902 Target: 5'-TGTTTAAAACAGCAAATGTTACTCATT-3' (SEQ ID NO: 2888)

```
5'-AUGUUUAAAACAGCAAAUGUUACUC^CC-3'   (SEQ ID NO: 6216)
3'-UACAAAUUUUGUCGUUUACAAUGAG_UA-5'   (SEQ ID NO: 1780)
```

βc-2903 Target: 5'-ATGTTTAAAACAGCAAATGTTACTC-3' (SEQ ID NO: 2889)

```
5'-AAUGUUUAAAACAGCAAAUGUUACU^AC-3'   (SEQ ID NO: 6217)
3'-UUACAAAUUUUGUCGUUUACAAUGA_GU-5'   (SEQ ID NO: 1781)
```

βc-2904 Target: 5'-AATGTTTAAAACAGCAAATGTTACTCA-3' (SEQ ID NO: 2890)

```
5'-CUAUUAAUGUUUAAAACAGCAAAUG^CC-3'   (SEQ ID NO: 6218)
3'-GAUAAUUACAAAUUUUGUCGUUUAC_AA-5'   (SEQ ID NO: 1782)
```

βc-2909 Target: 5'-CTATTAATGTTTAAAACAGCAAATGTT-3' (SEQ ID NO: 2891)

```
5'-AGAGAAAGGCUGCUAUUAAUGUUUA^CC-3'   (SEQ ID NO: 6219)
3'-UCUCUUUCCGACGAUAAUUACAAAU_UU-5'   (SEQ ID NO: 1783)
```

βc-2921 Target: 5'-AGAGAAAGGCTGCTATTAATGTTTAAA-3' (SEQ ID NO: 2892)

```
5'-CAAGUUCAGACAAUACAGCUGUAUA^CC-3'   (SEQ ID NO: 6220)
3'-GUUCAAGUCUGUUAUGUCGACAUAU_UU-5'   (SEQ ID NO: 1784)
```

βc-2949 Target: 5'-CAAGTTCAGACAATACAGCTGTATAAA-3' (SEQ ID NO: 2893)

```
5'-UCACAAUGCAAGUUCAGACAAUACA^AA-3'   (SEQ ID NO: 6221)
3'-AGUGUUACGUUCAAGUCUGUUAUGU_CG-5'   (SEQ ID NO: 1785)
```

βc-2957 Target: 5'-TCACAATGCAAGTTCAGACAATACAGC-3' (SEQ ID NO: 2894)

```
5'-AAUCACAAUGCAAGUUCAGACAAUA^AC-3'   (SEQ ID NO: 6222)
3'-UUAGUGUUACGUUCAAGUCUGUUAU_GU-5'   (SEQ ID NO: 1786)
```

βc-2959 Target: 5'-AATCACAATGCAAGTTCAGACAATACA-3' (SEQ ID NO: 2895)

```
5'-CCAAUCACAAUGCAAGUUCAGACAA^CC-3'   (SEQ ID NO: 6223)
3'-GGUUAGUGUUACGUUCAAGUCUGUU_AU-5'   (SEQ ID NO: 1787)
```

βc-2961 Target: 5'-CCAATCACAATGCAAGTTCAGACAATA-3' (SEQ ID NO: 2896)

TABLE 12-continued

Additional Selected Anti-β-catenin DsiRNAs, Blunt/Frayed Duplexes

```
        5'-CAGGCCAAUCACAAUGCAAGUUCAG^CA-3'   (SEQ ID NO: 6224)
        3'-GUCCGGUUAGUGUUACGUUCAAGUC_UG-5'   (SEQ ID NO: 1788)

βc-2965 Target: 5'-CAGGCCAATCACAATGCAAGTTCAGAC-3'  (SEQ ID NO: 2897)

5'-UUGUUCCCAUAGGAAACUCAGCUUG^AC-3'   (SEQ ID NO: 6225)
        3'-AACAAGGGUAUCCUUUGAGUCGAAC_CA-5'   (SEQ ID NO: 1789)

βc-3052 Target: 5'-TTGTTCCCATAGGAAACTCAGCTTGGT-3'  (SEQ ID NO: 2898)

5'-CUUCAAUUGUUCCCAUAGGAAACUC^CA-3'   (SEQ ID NO: 6226)
        3'-GAAGUUAACAAGGGUAUCCUUUGAG_UC-5'   (SEQ ID NO: 1790)

βc-3058 Target: 5'-CTTCAATTGTTCCCATAGGAAACTCAG-3'  (SEQ ID NO: 2899)

5'-ACUUCAAUUGUUCCCAUAGGAAACU^AC-3'   (SEQ ID NO: 6227)
        3'-UGAAGUUAACAAGGGUAUCCUUUGA_GU-5'   (SEQ ID NO: 1791)

βc-3059 Target: 5'-ACTTCAATTGTTCCCATAGGAAACTCA-3'  (SEQ ID NO: 2900)

5'-AAGUUUACUUCAAUUGUUCCCAUAG^AC-3'   (SEQ ID NO: 6228)
        3'-UUCAAAUGAAGUUAACAAGGGUAUC_CU-5'   (SEQ ID NO: 1792)

βc-3065 Target: 5'-AAGTTTACTTCAATTGTTCCCATAGGA-3'  (SEQ ID NO: 2901)

5'-AAAGUUUACUUCAAUUGUUCCCAUA^AA-3'   (SEQ ID NO: 6229)
        3'-UUUCAAAUGAAGUUAACAAGGGUAU_CC-5'   (SEQ ID NO: 1793)

βc-3066 Target: 5'-AAAGTTTACTTCAATTGTTCCCATAGG-3'  (SEQ ID NO: 2902)

5'-ACAAAAGUUUACUUCAAUUGUUCC^AC-3'    (SEQ ID NO: 6230)
        3'-UGUUUUCAAAUGAAGUUAACAAGG_GU-5'    (SEQ ID NO: 1794)

βc-3070 Target: 5'-ACAAAAGTTTACTTCAATTGTTCCCA-3'   (SEQ ID NO: 2903)

5'-CAGAACAAAAGUUUACUUCAAUUG^CC-3'    (SEQ ID NO: 6231)
        3'-GUCUUGUUUUCAAAUGAAGUUAAC_AA-5'    (SEQ ID NO: 1795)

βc-3074 Target: 5'-CAGAACAAAAGTTTACTTCAATTGTT-3'   (SEQ ID NO: 2904)

5'-AGGACCAGAACAAAAGUUUACUUC^CC-3'    (SEQ ID NO: 6232)
        3'-UCCUGGUCUUGUUUUCAAAUGAAG_UU-5'    (SEQ ID NO: 1796)

βc-3079 Target: 5'-AGGACCAGAACAAAAGTTTACTTCAA-3'   (SEQ ID NO: 2905)

5'-AAGGACCAGAACAAAAGUUUACUU^AC-3'    (SEQ ID NO: 6233)
        3'-UUCCUGGUCUUGUUUUCAAAUGAA_GU-5'    (SEQ ID NO: 1797)

βc-3080 Target: 5'-AAGGACCAGAACAAAAGTTTACTTCA-3'   (SEQ ID NO: 2906)

5'-CGACCAAAAAGGACCAGAACAAAAA^AC-3'   (SEQ ID NO: 6234)
        3'-GCUGGUUUUUCCUGGUCUUGUUUUU_CA-5'   (SEQ ID NO: 1798)

βc-3088 Target: 5'-CGACCAAAAAGGACCAGAACAAAAAGT-3'  (SEQ ID NO: 2907)

5'-UCGACCAAAAAGGACCAGAACAAAA^CA-3'   (SEQ ID NO: 6235)
        3'-AGCUGGUUUUUCCUGGUCUUGUUUU_UC-5'   (SEQ ID NO: 1799)

βc-3089 Target: 5'-TCGACCAAAAAGGACCAGAACAAAAG-3'   (SEQ ID NO: 2908)
```

TABLE 12-continued

Additional Selected Anti-β-catenin DsiRNAs, Blunt/Frayed Duplexes

```
    5'-UUACUCCUCGACCAAAAAGGACCAG^(C C-3')   (SEQ ID NO: 6236)
    3'-AAUGAGGAGCUGGUUUUUCCUGGUC_(U U-5')   (SEQ ID NO: 1800)
```

βc-3096 Target: 5'-TTACTCCTCGACCAAAAAGGACCAGAA-3' (SEQ ID NO: 2909)

```
    5'-AAUCCAUUUGUAUUGUUACUCCUCG^(C A-3')   (SEQ ID NO: 6237)
    3'-UUAGGUAAACAUAACAAUGAGGAGC_(U G-5')   (SEQ ID NO: 1801)
```

βc-3111 Target: 5'-AATCCATTTGTATTGTTACTCCTCGAC-3' (SEQ ID NO: 2910)

```
    5'-AAAUCCAUUUGUAUUGUUACUCCUC^(A C-3')   (SEQ ID NO: 6238)
    3'-UUUAGGUAAACAUAACAAUGAGGAG_(C U-5')   (SEQ ID NO: 1802)
```

βc-3112 Target: 5'-AAATCCATTTGTATTGTTACTCCTCGA-3' (SEQ ID NO: 2911)

```
    5'-AAAAUCCAUUUGUAUUGUUACUCCU^(A A-3')   (SEQ ID NO: 6239)
    3'-UUUUAGGUAAACAUAACAAUGAGGA_(G C-5')   (SEQ ID NO: 1803)
```

βc-3113 Target: 5'-AAAATCCATTTGTATTGTTACTCCTCG-3' (SEQ ID NO: 2912)

```
    5'-CAAAAUCCAUUUGUAUUGUUACUCC^(C A-3')   (SEQ ID NO: 6240)
    3'-GUUUUAGGUAAACAUAACAAUGAGG_(A G-5')   (SEQ ID NO: 1804)
```

βc-3114 Target: 5'-CAAAATCCATTTGTATTGTTACTCCTC-3' (SEQ ID NO: 2913)

```
    5'-CCAAAAUCCAUUUGUAUUGUUACUC^(A C-3')   (SEQ ID NO: 6241)
    3'-GGUUUUAGGUAAACAUAACAAUGAG_(G A-5')   (SEQ ID NO: 1805)
```

βc-3115 Target: 5'-CCAAAATCCATTTGTATTGTTACTCCT-3' (SEQ ID NO: 2914)

```
    5'-UCACUCCCAAAAUCCAUUUGUAUUG^(C C-3')   (SEQ ID NO: 6242)
    3'-AGUGAGGGUUUUAGGUAAACAUAAC_(A A-5')   (SEQ ID NO: 1806)
```

βc-3121 Target: 5'-TCACTCCCAAAATCCATTTGTATTGTT-3' (SEQ ID NO: 2915)

```
    5'-UCUUCACUUCUUGAGUCACUCCCAA^(C C-3')   (SEQ ID NO: 6243)
    3'-AGAAGUGAAGAACUCAGUGAGGGUU_(U U-5')   (SEQ ID NO: 1807)
```

βc-3136 Target: 5'-TCTTCACTTCTTGAGTCACTCCCAAAA-3' (SEQ ID NO: 2916)

```
    5'-AUUCUUCACUUCUUGAGUCACUCCC^(C C-3')   (SEQ ID NO: 6244)
    3'-UAAGAAGUGAAGAACUCAGUGAGGG_(U U-5')   (SEQ ID NO: 1808)
```

βc-3138 Target: 5'-ATTCTTCACTTCTTGAGTCACTCCCAA-3' (SEQ ID NO: 2917)

```
    5'-CAUUCUUCACUUCUUGAGUCACUCC^(A C-3')   (SEQ ID NO: 6245)
    3'-GUAAGAAGUGAAGAACUCAGUGAGG_(G U-5')   (SEQ ID NO: 1809)
```

βc-3139 Target: 5'-CATTCTTCACTTCTTGAGTCACTCCCA-3' (SEQ ID NO: 2918)

```
    5'-GCAUUCUUCACUUCUUGAGUCACUC^(A A-3')   (SEQ ID NO: 6246)
    3'-CGUAAGAAGUGAAGAACUCAGUGAG_(G G-5')   (SEQ ID NO: 1810)
```

βc-3140 Target: 5'-GCATTCTTCACTTCTTGAGTCACTCCC-3' (SEQ ID NO: 2919)

```
    5'-GUGCAUUCUUCACUUCUUGAGUCAC^(C A-3')   (SEQ ID NO: 6247)
    3'-CACGUAAGAAGUGAAGAACUCAGUG_(A G-5')   (SEQ ID NO: 1811)
```

βc-3142 Target: 5'-GTGCATTCTTCACTTCTTGAGTCACTC-3' (SEQ ID NO: 2920)

TABLE 12-continued

Additional Selected Anti-β-catenin DsiRNAs, Blunt/Frayed Duplexes

```
        5'-CCAUUCUUGUGCAUUCUUCACUUCU^CA-3'   (SEQ ID NO: 6248)
        3'-GGUAAGAACACGUAAGAAGUGAAGA_AC-5'   (SEQ ID NO: 1812)
```

βc-3150 Target: 5'-CCATTCTTGTGCATTCTTCACTTCTTG-3' (SEQ ID NO: 2921)

```
        5'-GAUCCAUUCUUGUGCAUUCUUCACU^CA-3'   (SEQ ID NO: 6249)
        3'-CUAGGUAAGAACACGUAAGAAGUGA_AG-5'   (SEQ ID NO: 1813)
```

βc-3153 Target: 5'-GATCCATTCTTGTGCATTCTTCACTTC-3' (SEQ ID NO: 2922)

```
        5'-UGAUCCAUUCUUGUGCAUUCUUCAC^CC-3'   (SEQ ID NO: 6250)
        3'-ACUAGGUAAGAACACGUAAGAAGUG_AA-5'   (SEQ ID NO: 1814)
```

βc-3154 Target: 5'-TGATCCATTCTTGTGCATTCTTCACTT-3' (SEQ ID NO: 2923)

```
        5'-GUGAUCCAUUCUUGUGCAUUCUUCA^AC-3'   (SEQ ID NO: 6251)
        3'-CACUAGGUAAGAACACGUAAGAAGU_GA-5'   (SEQ ID NO: 1815)
```

βc-3155 Target: 5'-GTGATCCATTCTTGTGCATTCTTCACT-3' (SEQ ID NO: 2924)

```
        5'-UAAAUUCCAUCUUGUGAUCCAUUCU^CA-3'   (SEQ ID NO: 6252)
        3'-AUUUAAGGUAGAACACUAGGUAAGA_AC-5'   (SEQ ID NO: 1816)
```

βc-3168 Target: 5'-TAAATTCCATCTTGTGATCCATTCTTG-3' (SEQ ID NO: 2925)

```
        5'-GAUAAAUUCCAUCUUGUGAUCCAUU^AC-3'   (SEQ ID NO: 6253)
        3'-CUAUUUAAGGUAGAACACUAGGUAA_GA-5'   (SEQ ID NO: 1817)
```

βc-3170 Target: 5'-GATAAATTCCATCTTGTGATCCATTCT-3' (SEQ ID NO: 2926)

```
        5'-UGAUAAAUUCCAUCUUGUGAUCCAU^CA-3'   (SEQ ID NO: 6254)
        3'-ACUAUUUAAGGUAGAACACUAGGUA_AG-5'   (SEQ ID NO: 1818)
```

βc-3171 Target: 5'-TGATAAATTCCATCTTGTGATCCATTC-3' (SEQ ID NO: 2927)

```
        5'-UUGAUAAAUUCCAUCUUGUGAUCCA^CC-3'   (SEQ ID NO: 6255)
        3'-AACUAUUUAAGGUAGAACACUAGGU_AA-5'   (SEQ ID NO: 1819)
```

βc-3172 Target: 5'-TTGATAAATTCCATCTTGTGATCCATT-3' (SEQ ID NO: 2928)

```
        5'-UUUGAUAAAUUCCAUCUUGUGAUCC^CC-3'   (SEQ ID NO: 6256)
        3'-AAACUAUUUAAGGUAGAACACUAGG_UA-5'   (SEQ ID NO: 1820)
```

βc-3173 Target: 5'-TTTGATAAATTCCATCTTGTGATCC-3' (SEQ ID NO: 2929)

```
        5'-AAGGCUAGGGUUUGAUAAAUUCCAU^AC-3'   (SEQ ID NO: 6257)
        3'-UUCCGAUCCCAAACUAUUUAAGGUA_GA-5'   (SEQ ID NO: 1821)
```

βc-3183 Target: 5'-AAGGCTAGGGTTTGATAAATTCCATCT-3' (SEQ ID NO: 2930)

```
        5'-AAAAAAAUUUAACAAGCAAGGCUAG^AA-3'   (SEQ ID NO: 6258)
        3'-UUUUUUUAAAUUGUUCGUUCCGAUC_CC-5'   (SEQ ID NO: 1822)
```

βc-3200 Target: 5'-AAAAAAATTTAACAAGCAAGGCTAGGG-3' (SEQ ID NO: 2931)

```
        5'-AAAAAAAAAAAAAAAUUUAACAAG^AC-3'    (SEQ ID NO: 6259)
        3'-UUUUUUUUUUUUUUUUAAAUUGUUC_GU-5'   (SEQ ID NO: 1823)
```

βc-3209 Target: 5'-AAAAAAAAAAAAAAAATTTAACAAGCA-3' (SEQ ID NO: 2932)

TABLE 12-continued

Additional Selected Anti-β-catenin DsiRNAs, Blunt/Frayed Duplexes

```
        5'-AAAAAAAAAAAAAAAAAUUUAACAA^A A-3'    (SEQ ID NO: 6260)
        3'-UUUUUUUUUUUUUUUUUAAAUUGUU_G-5'     (SEQ ID NO: 1824)
```

βc-3210 Target: 5'-AAAAAAAAAAAAAAAATTTAACAAGC-3'  (SEQ ID NO: 2933)

```
        5'-AAAAAAAAAAAAAAAAAUUUAACA^C A-3'    (SEQ ID NO: 6261)
        3'-UUUUUUUUUUUUUUUUUUAAAUUGU_C-5'    (SEQ ID NO: 1825)
```

βc-3211 Target: 5'-AAAAAAAAAAAAAAAATTTAACAAG-3'  (SEQ ID NO: 2934)

```
        5'-AAAAAAAAAAAAAAAAAAUUUAAC^C C-3'    (SEQ ID NO: 6262)
        3'-UUUUUUUUUUUUUUUUUUUAAAUUG_U-5'    (SEQ ID NO: 1826)
```

βc-3212 Target: 5'-AAAAAAAAAAAAAAAAATTTAACAA-3'  (SEQ ID NO: 2935)

```
        5'-UAAAAAAAAAAAAAAAAAAUUUAA^A C-3'    (SEQ ID NO: 6263)
        3'-AUUUUUUUUUUUUUUUUUUUAAAUU_U-5'    (SEQ ID NO: 1827)
```

βc-3213 Target: 5'-TAAAAAAAAAAAAAAAAAATTTAACA-3'  (SEQ ID NO: 2936)

```
        5'-UUAAAAAAAAAAAAAAAAAAUUUA^C A-3'    (SEQ ID NO: 6264)
        3'-AAUUUUUUUUUUUUUUUUUUUAAAU_G-5'    (SEQ ID NO: 1828)
```

βc-3214 Target: 5'-TTAAAAAAAAAAAAAAAAAATTTAAC-3'  (SEQ ID NO: 2937)

```
        5'-CUUAAAAAAAAAAAAAAAAAAUUU^C C-3'    (SEQ ID NO: 6265)
        3'-GAAUUUUUUUUUUUUUUUUUUUAAA_U-5'    (SEQ ID NO: 1829)
```

βc-3215 Target: 5'-CTTAAAAAAAAAAAAAAAAAATTTAA-3'  (SEQ ID NO: 2938)

```
        5'-UCUUAAAAAAAAAAAAAAAAAAUU^C C-3'    (SEQ ID NO: 6266)
        3'-AGAAUUUUUUUUUUUUUUUUUUUAA_U-5'    (SEQ ID NO: 1830)
```

βc-3216 Target: 5'-TCTTAAAAAAAAAAAAAAAAAATTTA-3'  (SEQ ID NO: 2939)

```
        5'-AUUCUUAAAAAAAAAAAAAAAAAA^C C-3'    (SEQ ID NO: 6267)
        3'-UAAGAAUUUUUUUUUUUUUUUUUU_A-5'    (SEQ ID NO: 1831)
```

βc-3218 Target: 5'-ATTCTTAAAAAAAAAAAAAAAAAATT-3'  (SEQ ID NO: 2940)

```
        5'-UAUUCUUAAAAAAAAAAAAAAAAA^C C-3'    (SEQ ID NO: 6268)
        3'-AUAAGAAUUUUUUUUUUUUUUUUU_A-5'    (SEQ ID NO: 1832)
```

βc-3219 Target: 5'-TATTCTTAAAAAAAAAAAAAAAAAAT-3'  (SEQ ID NO: 2941)

```
        5'-AUAUUCUUAAAAAAAAAAAAAAAA^C C-3'    (SEQ ID NO: 6269)
        3'-UAUAAGAAUUUUUUUUUUUUUUUU_U-5'    (SEQ ID NO: 1833)
```

βc-3220 Target: 5'-ATATTCTTAAAAAAAAAAAAAAAAAA-3'  (SEQ ID NO: 2942)

```
        5'-GAUAUUCUUAAAAAAAAAAAAAAA^C C-3'    (SEQ ID NO: 6270)
        3'-CUAUAAGAAUUUUUUUUUUUUUUU_U-5'    (SEQ ID NO: 1834)
```

βc-3221 Target: 5'-GATATTCTTAAAAAAAAAAAAAAAA-3'  (SEQ ID NO: 2943)

```
        5'-AGAUAUUCUUAAAAAAAAAAAAAA^C C-3'    (SEQ ID NO: 6271)
        3'-UCUAUAAGAAUUUUUUUUUUUUUU_U-5'    (SEQ ID NO: 1835)
```

βc-3222 Target: 5'-AGATATTCTTAAAAAAAAAAAAAAA-3'  (SEQ ID NO: 2944)

TABLE 12-continued

Additional Selected Anti-β-catenin DsiRNAs, Blunt/Frayed Duplexes

```
5'-CAGAUAUUCUUAAAAAAAAAAAAAA^CC-3' (SEQ ID NO: 6272)
3'-GUCUAUAAGAAUUUUUUUUUUUUU_UU-5'  (SEQ ID NO: 1836)
```

βc-3223 Target: 5'-CAGATATTCTTAAAAAAAAAAAAAA-3' (SEQ ID NO: 2945)

```
5'-ACAGAUAUUCUUAAAAAAAAAAAAA^CC-3' (SEQ ID NO: 6273)
3'-UGUCUAUAAGAAUUUUUUUUUUUU_UU-5'  (SEQ ID NO: 1837)
```

βc-3224 Target: 5'-ACAGATATTCTTAAAAAAAAAAAAA-3' (SEQ ID NO: 2946)

```
5'-CAUUACAGAUAUUCUUAAAAAAAAA^CC-3' (SEQ ID NO: 6274)
3'-GUAAUGUCUAUAAGAAUUUUUUUU_UU-5'  (SEQ ID NO: 1838)
```

βc-3228 Target: 5'-CATTACAGATATTCTTAAAAAAAAA-3' (SEQ ID NO: 2947)

```
5'-CCAUUACAGAUAUUCUUAAAAAAAA^CC-3' (SEQ ID NO: 6275)
3'-GGUAAUGUCUAUAAGAAUUUUUUU_UU-5'  (SEQ ID NO: 1839)
```

βc-3229 Target: 5'-CCATTACAGATATTCTTAAAAAAAA-3' (SEQ ID NO: 2948)

```
5'-AGUACCAUUACAGAUAUUCUUAAAA^CC-3' (SEQ ID NO: 6276)
3'-UCAUGGUAAUGUCUAUAAGAAUUUU_UU-5' (SEQ ID NO: 1840)
```

βc-3233 Target: 5'-AGTACCATTACAGATATTCTTAAAAA-3' (SEQ ID NO: 2949)

```
5'-CAGUACCAUUACAGAUAUUCUUAAA^CC-3' (SEQ ID NO: 6277)
3'-GUCAUGGUAAUGUCUAUAAGAAUUU_UU-5' (SEQ ID NO: 1841)
```

βc-3234 Target: 5'-CAGTACCATTACAGATATTCTTAAAAA-3' (SEQ ID NO: 2950)

```
5'-UCAGUACCAUUACAGAUAUUCUUAA^CC-3' (SEQ ID NO: 6278)
3'-AGUCAUGGUAAUGUCUAUAAGAAUU_UU-5' (SEQ ID NO: 1842)
```

βc-3235 Target: 5'-TCAGTACCATTACAGATATTCTTAAA-3' (SEQ ID NO: 2951)

```
5'-AAAGUCAGUACCAUUACAGAUAUUC^CC-3' (SEQ ID NO: 6279)
3'-UUUCAGUCAUGGUAAUGUCUAUAAG_AA-5' (SEQ ID NO: 1843)
```

βc-3239 Target: 5'-AAAGTCAGTACCATTACAGATATTCTT-3' (SEQ ID NO: 2952)

```
5'-GCUACUUCAAAGCAAGCAAAGUCAG^CC-3' (SEQ ID NO: 6280)
3'-CGAUGAAGUUUCGUUCGUUUCAGUC_AU-5' (SEQ ID NO: 1844)
```

βc-3256 Target: 5'-GCTACTTCAAAGCAAGCAAAGTCAGTA-3' (SEQ ID NO: 2953)

```
5'-AAAAAAAGAGCUACUUCAAAGCAAG^AC-3' (SEQ ID NO: 6281)
3'-UUUUUUUCUCGAUGAAGUUUCGUUC_GU-5' (SEQ ID NO: 1845)
```

βc-3265 Target: 5'-AAAAAAAGAGCTACTTCAAAGCAAGCA-3' (SEQ ID NO: 2954)

```
5'-AAAAAAAAAAAGAGCUACUUCAAA^AA-3'  (SEQ ID NO: 6282)
3'-UUUUUUUUUUUUCUCGAUGAAGUUU_CG-5' (SEQ ID NO: 1846)
```

βc-3270 Target: 5'-AAAAAAAAAAAGAGCTACTTCAAAGC-3' (SEQ ID NO: 2955)

```
5'-AAAAAAAAAAAAGAGCUACUUCAA^CA-3'  (SEQ ID NO: 6283)
3'-UUUUUUUUUUUUUCUCGAUGAAGUU_UC-5' (SEQ ID NO: 1847)
```

βc-3271 Target: 5'-AAAAAAAAAAAAGAGCTACTTCAAAG-3' (SEQ ID NO: 2956)

TABLE 12-continued

Additional Selected Anti-β-catenin DsiRNAs, Blunt/Frayed Duplexes

```
         5'-AAAAAAAAAAAAAAAGAGCUACUUC^CC-3'  (SEQ ID NO: 6284)
         3'-UUUUUUUUUUUUUUUCUCGAUGAAG_UU-5'  (SEQ ID NO: 1848)
```

βc-3273 Target: 5'-AAAAAAAAAAAAAAAGAGCTACTTCAA-3' (SEQ ID NO: 2957)

```
         5'-AAAAAAAAAAAAAAAGAGCUACUUA^C-3'   (SEQ ID NO: 6285)
         3'-UUUUUUUUUUUUUUUCUCGAUGAA_GU-5'   (SEQ ID NO: 1849)
```

βc-3274 Target: 5'-AAAAAAAAAAAAAAAGAGCTACTTCA-3' (SEQ ID NO: 2958)

```
         5'-AAAAAAAAAAAAAAAGAGCUACU^CA-3'    (SEQ ID NO: 6286)
         3'-UUUUUUUUUUUUUUUCUCGAUGA_AG-5'    (SEQ ID NO: 1850)
```

βc-3275 Target: 5'-AAAAAAAAAAAAAAAGAGCTACTTC-3' (SEQ ID NO: 2959)

```
         5'-AAAAAAAAAAAAAAAGAGCUAC^CC-3'     (SEQ ID NO: 6287)
         3'-UUUUUUUUUUUUUUUUCUCGAUG_AA-5'    (SEQ ID NO: 1851)
```

βc-3276 Target: 5'-AAAAAAAAAAAAAAAAGAGCTACTT-3' (SEQ ID NO: 2960)

```
         5'-AAAAAAAAAAAAAAAAAAAAAG^CA-3'     (SEQ ID NO: 6288)
         3'-UUUUUUUUUUUUUUUUUUUUUC_UC-5'     (SEQ ID NO: 1852)
```

βc-3282 Target: 5'-AAAAAAAAAAAAAAAAAAAAAGAG-3' (SEQ ID NO: 2961)

```
         5'-AAAAAAAAAAAAAAAAAAAAAAA^C-3'     (SEQ ID NO: 6289)
         3'-UUUUUUUUUUUUUUUUUUUUUUU_CU-5'    (SEQ ID NO: 1853)
```

βc-3283 Target: 5'-AAAAAAAAAAAAAAAAAAAAAAAGA-3' (SEQ ID NO: 2962)

```
         5'-CAAAAAAAAAAAAAAAAAAAAAA^CA-3'    (SEQ ID NO: 6290)
         3'-GUUUUUUUUUUUUUUUUUUUUUU_UC-5'    (SEQ ID NO: 1854)
```

βc-3284 Target: 5'-CAAAAAAAAAAAAAAAAAAAAAAAG-3' (SEQ ID NO: 2963)

```
         5'-GCAAAAAAAAAAAAAAAAAAAAAA^CC-3'   (SEQ ID NO: 6291)
         3'-CGUUUUUUUUUUUUUUUUUUUUUU_UU-5'   (SEQ ID NO: 1855)
```

βc-3285 Target: 5'-GCAAAAAAAAAAAAAAAAAAAAAAA-3' (SEQ ID NO: 2964)

```
         5'-CUGCAAAAAAAAAAAAAAAAAAAAA^CC-3'  (SEQ ID NO: 6292)
         3'-GACGUUUUUUUUUUUUUUUUUUUUU_UU-5'  (SEQ ID NO: 1856)
```

βc-3287 Target: 5'-CTGCAAAAAAAAAAAAAAAAAAAAA-3' (SEQ ID NO: 2965)

```
         5'-ACUGCAAAAAAAAAAAAAAAAAAAA^CC-3'  (SEQ ID NO: 6293)
         3'-UGACGUUUUUUUUUUUUUUUUUUUU_UU-5'  (SEQ ID NO: 1857)
```

βc-3288 Target: 5'-ACTGCAAAAAAAAAAAAAAAAAAAA-3' (SEQ ID NO: 2966)

```
         5'-AGUUACUGCAAAAAAAAAAAAAAAA^CC-3'  (SEQ ID NO: 6294)
         3'-UCAAUGACGUUUUUUUUUUUUUUUU_UU-5'  (SEQ ID NO: 1858)
```

βc-3292 Target: 5'-AGTTACTGCAAAAAAAAAAAAAAAA-3' (SEQ ID NO: 2967)

```
         5'-CAGUUACUGCAAAAAAAAAAAAAAA^CC-3'  (SEQ ID NO: 6295)
         3'-GUCAAUGACGUUUUUUUUUUUUUUU_UU-5'  (SEQ ID NO: 1859)
```

βc-3293 Target: 5'-CAGTTACTGCAAAAAAAAAAAAAAA-3' (SEQ ID NO: 2968)

TABLE 12-continued

Additional Selected Anti-β-catenin DsiRNAs, Blunt/Frayed Duplexes

```
      5'-ACAGUUACUGCAAAAAAAAAAAAAA C-3'   (SEQ ID NO: 6296)
                                      C
      3'-UGUCAAUGACGUUUUUUUUUUUUU U-5'   (SEQ ID NO: 1860)
                                      U
```

βc-3294 Target: 5'-ACAGTTACTGCAAAAAAAAAAAAAA-3' (SEQ ID NO: 2969)

```
      5'-AAAAACAGUUACUGCAAAAAAAAAA C-3'   (SEQ ID NO: 6297)
                                      C
      3'-UUUUUGUCAAUGACGUUUUUUUUUU U-5'   (SEQ ID NO: 1861)
                                      U
```

βc-3298 Target: 5'-AAAAACAGTTACTGCAAAAAAAAAA-3' (SEQ ID NO: 2970)

```
      5'-AAAAAACAGUUACUGCAAAAAAAAA C-3'   (SEQ ID NO: 6298)
                                      C
      3'-UUUUUUGUCAAUGACGUUUUUUUUU U-5'   (SEQ ID NO: 1862)
                                      U
```

βc-3299 Target: 5'-AAAAAACAGTTACTGCAAAAAAAAA-3' (SEQ ID NO: 2971)

```
      5'-UAAAAAACAGUUACUGCAAAAAAAA C-3'   (SEQ ID NO: 6299)
                                      C
      3'-AUUUUUUGUCAAUGACGUUUUUUUU U-5'   (SEQ ID NO: 1863)
                                      U
```

βc-3300 Target: 5'-TAAAAAACAGTTACTGCAAAAAAAA-3' (SEQ ID NO: 2972)

```
      5'-CUUAAAAAACAGUUACUGCAAAAAA C-3'   (SEQ ID NO: 6300)
                                      C
      3'-GAAUUUUUUGUCAAUGACGUUUUUU U-5'   (SEQ ID NO: 1864)
                                      U
```

βc-3302 Target: 5'-CTTAAAAAACAGTTACTGCAAAAAA-3' (SEQ ID NO: 2973)

```
      5'-ACUUAAAAAACAGUUACUGCAAAAA C-3'   (SEQ ID NO: 6301)
                                      C
      3'-UGAAUUUUUUGUCAAUGACGUUUUU U-5'   (SEQ ID NO: 1865)
                                      U
```

βc-3303 Target: 5'-ACTTAAAAAACAGTTACTGCAAAAA-3' (SEQ ID NO: 2974)

```
      5'-AGACUUAAAAAACAGUUACUGCAAA C-3'   (SEQ ID NO: 6302)
                                      C
      3'-UCUGAAUUUUUUGUCAAUGACGUUU U-5'   (SEQ ID NO: 1866)
                                      U
```

βc-3305 Target: 5'-AGACTTAAAAAACAGTTACTGCAAA-3' (SEQ ID NO: 2975)

```
      5'-ACACUACGAGAGACUUAAAAAACAG C-3'   (SEQ ID NO: 6303)
                                      C
      3'-UGUGAUGCUCUCUGAAUUUUUUGUC A-5'   (SEQ ID NO: 1867)
                                      A
```

βc-3315 Target: 5'-ACACTACGAGAGACTTAAAAAACAGTT-3' (SEQ ID NO: 2976)

```
      5'-UAACACUACGAGAGACUUAAAAAAC A-3'   (SEQ ID NO: 6304)
                                      C
      3'-AUUGUGAUGCUCUCUGAAUUUUUUG U-5'   (SEQ ID NO: 1868)
                                      C
```

βc-3317 Target: 5'-TAACACTACGAGAGACTTAAAAAACAG-3' (SEQ ID NO: 2977)

```
      5'-UUAACACUACGAGAGACUUAAAAAA C-3'   (SEQ ID NO: 6305)
                                      C
      3'-AAUUGUGAUGCUCUCUGAAUUUUUU U-5'   (SEQ ID NO: 1869)
                                      G
```

βc-3318 Target: 5'-TTAACACTACGAGAGACTTAAAAACA-3' (SEQ ID NO: 2978)

```
      5'-ACUUAACACUACGAGAGACUUAAAA C-3'   (SEQ ID NO: 6306)
                                      C
      3'-UGAAUUGUGAUGCUCUCUGAAUUUU U-5'   (SEQ ID NO: 1870)
                                      U
```

βc-3320 Target: 5'-ACTTAACACTACGAGAGACTTAAAAA-3' (SEQ ID NO: 2979)

```
      5'-AUAACUUAACACUACGAGAGACUUA C-3'   (SEQ ID NO: 6307)
                                      C
      3'-UAUUGAAUUGUGAUGCUCUCUGAAU U-5'   (SEQ ID NO: 1871)
                                      U
```

βc-3323 Target: 5'-ATAACTTAACACTACGAGAGACTTAAA-3' (SEQ ID NO: 2980)

TABLE 12-continued

Additional Selected Anti-β-catenin DsiRNAs, Blunt/Frayed Duplexes

```
5'-UAUAACUUAACACUACGAGAGACUU^CC-3'     (SEQ ID NO: 6308)
3'-AUAUUGAAUUGUGAUGCUCUCUGAA_UU-5'     (SEQ ID NO: 1872)
```

βc-3324 Target: 5'-TATAACTTAACACTACGAGAGACTTAA-3'     (SEQ ID NO: 2981)

```
5'-GUAUUCACUAUAACUUAACACUACG^CA-3'     (SEQ ID NO: 6309)
3'-CAUAAGUGAUAUUGAAUUGUGAUGC_UC-5'     (SEQ ID NO: 1873)
```

βc-3332 Target: 5'-GTATTCACTATAACTTAACACTACGAG-3'     (SEQ ID NO: 2982)

```
5'-AGUAUUCACUAUAACUUAACACUAC^AC-3'     (SEQ ID NO: 6310)
3'-UCAUAAGUGAUAUUGAAUUGUGAUG_CU-5'     (SEQ ID NO: 1874)
```

βc-3333 Target: 5'-AGTATTCACTATAACTTAACACTACGA-3'     (SEQ ID NO: 2983)

```
5'-CAGUAUUCACUAUAACUUAACACUA^AA-3'     (SEQ ID NO: 6311)
3'-GUCAUAAGUGAUAUUGAAUUGUGAU_GC-5'     (SEQ ID NO: 1875)
```

βc-3334 Target: 5'-CAGTATTCACTATAACTTAACACTACG-3'     (SEQ ID NO: 2984)

```
5'-GCAGUAUUCACUAUAACUUAACACU^CA-3'     (SEQ ID NO: 6312)
3'-CGUCAUAAGUGAUAUUGAAUUGUGA_UG-5'     (SEQ ID NO: 1876)
```

βc-3335 Target: 5'-GCAGTATTCACTATAACTTAACACTAC-3'     (SEQ ID NO: 2985)

```
5'-AGAAAUUGCUGUAGCAGUAUUCACU^CC-3'     (SEQ ID NO: 6313)
3'-UCUUUAACGACAUCGUCAUAAGUGA_UA-5'     (SEQ ID NO: 1877)
```

βc-3348 Target: 5'-AGAAATTGCTGTAGCAGTATTCACTAT-3'     (SEQ ID NO: 2986)

```
5'-UAGAAAUUGCUGUAGCAGUAUUCAC^CC-3'     (SEQ ID NO: 6314)
3'-AUCUUUAACGACAUCGUCAUAAGUG_AU-5'     (SEQ ID NO: 1878)
```

βc-3349 Target: 5'-TAGAAATTGCTGTAGCAGTATTCACTA-3'     (SEQ ID NO: 2987)

```
5'-UUAGAAAUUGCUGUAGCAGUAUUCA^AC-3'     (SEQ ID NO: 6315)
3'-AAUCUUUAACGACAUCGUCAUAAGU_GA-5'     (SEQ ID NO: 1879)
```

βc-3350 Target: 5'-TTAGAAATTGCTGTAGCAGTATTCACT-3'     (SEQ ID NO: 2988)

```
5'-ACUCAAUUCUUAAAAAUUAGAAAUU^AA-3'     (SEQ ID NO: 6316)
3'-UGAGUUAAGAAUUUUUAAUCUUUAA_CG-5'     (SEQ ID NO: 1880)
```

βc-3366 Target: 5'-ACTCAATTCTTAAAAATTAGAAATTGC-3'     (SEQ ID NO: 2989)

```
5'-CCAUUACUCAAUUCUUAAAAAUUAG^CC-3'     (SEQ ID NO: 6317)
3'-GGUAAUGAGUUAAGAAUUUUUAAUC_UU-5'     (SEQ ID NO: 1881)
```

βc-3371 Target: 5'-CCATTACTCAATTCTTAAAAATTAGAA-3'     (SEQ ID NO: 2990)

```
5'-ACACCAUUACUCAAUUCUUAAAAAU^CC-3'     (SEQ ID NO: 6318)
3'-UGUGGUAAUGAGUUAAGAAUUUUUA_AU-5'     (SEQ ID NO: 1882)
```

βc-3374 Target: 5'-ACACCATTACTCAATTCTTAAAAATTA-3'     (SEQ ID NO: 2991)

```
5'-CUACACCAUUACUCAAUUCUUAAAA^CC-3'     (SEQ ID NO: 6319)
3'-GAUGUGGUAAUGAGUUAAGAAUUUU_AU-5'     (SEQ ID NO: 1883)
```

βc-3376 Target: 5'-CTACACCATTACTCAATTCTTAAAAAT-3'     (SEQ ID NO: 2992)

TABLE 12-continued

Additional Selected Anti-β-catenin DsiRNAs, Blunt/Frayed Duplexes

```
5'-UCUACACCAUUACUCAAUUCUUAAA^(CC-3')  (SEQ ID NO: 6320)
3'-AGAUGUGGUAAUGAGUUAAGAAUUU_(U-5')   (SEQ ID NO: 1884)
```

βc-3377 Target: 5'-TCTACACCATTACTCAATTCTTAAAAA-3' (SEQ ID NO: 2993)

```
5'-GUUCUACACCAUUACUCAAUUCUUA^(CC-3')  (SEQ ID NO: 6321)
3'-CAAGAUGUGGUAAUGAGUUAAGAAU_(U-5')   (SEQ ID NO: 1885)
```

βc-3379 Target: 5'-GTTCTACACCATTACTCAATTCTTAAA-3' (SEQ ID NO: 2994)

```
5'-GUGUUCUACACCAUUACUCAAUUCU^(CC-3')  (SEQ ID NO: 6322)
3'-CACAAGAUGUGGUAAUGAGUUAAGA_(AU-5')  (SEQ ID NO: 1886)
```

βc-3381 Target: 5'-GTGTTCTACACCATTACTCAATTCTTA-3' (SEQ ID NO: 2995)

```
5'-AUGAAUUAGUGUUCUACACCAUUAC^(CA-3')  (SEQ ID NO: 6323)
3'-UACUUAAUCACAAGAUGUGGUAAUG_(AG-5')  (SEQ ID NO: 1887)
```

βc-3389 Target: 5'-ATGAATTAGTGTTCTACACCATTACTC-3' (SEQ ID NO: 2996)

```
5'-UGAUUAUGAAUUAGUGUUCUACACC^(CC-3')  (SEQ ID NO: 6324)
3'-ACUAAUACUUAAUCACAAGAUGUGG_(UA-5')  (SEQ ID NO: 1888)
```

βc-3394 Target: 5'-TGATTATGAATTAGTGTTCTACACC-3' (SEQ ID NO: 2997)

```
5'-GUGAUUAUGAAUUAGUGUUCUACAC^(AC-3')  (SEQ ID NO: 6325)
3'-CACUAAUACUUAAUCACAAGAUGUG_(GU-5')  (SEQ ID NO: 1889)
```

βc-3395 Target: 5'-GTGATTATGAATTAGTGTTCTACACCA-3' (SEQ ID NO: 2998)

```
5'-AGUGAUUAUGAAUUAGUGUUCUACA^(AA-3')  (SEQ ID NO: 6326)
3'-UCACUAAUACUUAAUCACAAGAUGU_(GG-5')  (SEQ ID NO: 1890)
```

βc-3396 Target: 5'-AGTGATTATGAATTAGTGTTCTACACC-3' (SEQ ID NO: 2999)

```
5'-AUUAAUUAGAGUGAUUAUGAAUUAG^(CA-3')  (SEQ ID NO: 6327)
3'-UAAUUAAUCUCACUAAUACUUAAUC_(AC-5')  (SEQ ID NO: 1891)
```

βc-3405 Target: 5'-ATTAATTAGAGTGATTATGAATTAGTG-3' (SEQ ID NO: 3000)

```
5'-AAUUAAUUAGAGUGAUUAUGAAUUA^(AC-3')  (SEQ ID NO: 6328)
3'-UUAAUUAAUCUCACUAAUACUUAAU_(CA-5')  (SEQ ID NO: 1892)
```

βc-3406 Target: 5'-AATTAATTAGAGTGATTATGAATTAGT-3' (SEQ ID NO: 3001)

```
5'-CAAUUAAUUAGAGUGAUUAUGAAUU^(CA-3')  (SEQ ID NO: 6329)
3'-GUUAAUUAAUCUCACUAAUACUUAA_(UC-5')  (SEQ ID NO: 1893)
```

βc-3407 Target: 5'-CAATTAATTAGAGTGATTATGAATTAG-3' (SEQ ID NO: 3002)

```
5'-AUUACAAUUAAUUAGAGUGAUUAUG^(CC-3')  (SEQ ID NO: 6330)
3'-UAAUGUUAAUUAAUCUCACUAAUAC_(UU-5')  (SEQ ID NO: 1894)
```

βc-3411 Target: 5'-ATTACAATTAATTAGAGTGATTATGAA-3' (SEQ ID NO: 3003)

```
5'-GAUUACAAUUAAUUAGAGUGAUUAU^(AC-3')  (SEQ ID NO: 6331)
3'-CUAAUGUUAAUUAAUCUCACUAAUA_(CU-5')  (SEQ ID NO: 1895)
```

βc-3412 Target: 5'-GATTACAATTAATTAGAGTGATTATGA-3' (SEQ ID NO: 3004)

TABLE 12-continued

Additional Selected Anti-β-catenin DsiRNAs, Blunt/Frayed Duplexes

```
           5'-AGAUUACAAUUAAUUAGAGUGAUUA CA-3'   (SEQ ID NO: 6332)
           3'-UCUAAUGUUAAUUAAUCUCACUAAU AC-5'   (SEQ ID NO: 1896)

βc-3413 Target: 5'-AGATTACAATTAATTAGAGTGATTATG-3'   (SEQ ID NO: 3005)

5'-CUUUAUUCAGAUUACAAUUAAUUAG CA-3'   (SEQ ID NO: 6333)
           3'-GAAAUAAGUCUAAUGUUAAUUAAUC UC-5'   (SEQ ID NO: 1897)

βc-3421 Target: 5'-CTTTATTCAGATTACAATTAATTAGAG-3'   (SEQ ID NO: 3006)

5'-ACUUUAUUCAGAUUACAAUUAAUUA AC-3'   (SEQ ID NO: 6334)
           3'-UGAAAUAAGUCUAAUGUUAAUUAAU CU-5'   (SEQ ID NO: 1898)

βc-3422 Target: 5'-ACTTTATTCAGATTACAATTAATTAGA-3'   (SEQ ID NO: 3007)

5'-UUACACUUUAUUCAGAUUACAAUUA CC-3'   (SEQ ID NO: 6335)
           3'-AAUGUGAAAUAAGUCUAAUGUUAAU UA-5'   (SEQ ID NO: 1899)

βc-3426 Target: 5'-TTACACTTTATTCAGATTACAATTAAT-3'   (SEQ ID NO: 3008)

5'-GUUACACUUUAUUCAGAUUACAAUU CC-3'   (SEQ ID NO: 6336)
           3'-CAAUGUGAAAUAAGUCUAAUGUUAA UU-5'   (SEQ ID NO: 1900)

βc-3427 Target: 5'-GTTACACTTTATTCAGATTACAATTAA-3'   (SEQ ID NO: 3009)

5'-UGUUACACUUUAUUCAGAUUACAAU CC-3'   (SEQ ID NO: 6337)
           3'-ACAAUGUGAAAUAAGUCUAAUGUUA AU-5'   (SEQ ID NO: 1901)

βc-3428 Target: 5'-TGTTACACTTTATTCAGATTACAATTA-3'   (SEQ ID NO: 3010)

5'-UUGUUACACUUUAUUCAGAUUACAA CC-3'   (SEQ ID NO: 6338)
           3'-AACAAUGUGAAAUAAGUCUAAUGUU AA-5'   (SEQ ID NO: 1902)

βc-3429 Target: 5'-TTGTTACACTTTATTCAGATTACAATT-3'   (SEQ ID NO: 3011)

5'-AUUGUUACACUUUAUUCAGAUUACA CC-3'   (SEQ ID NO: 6339)
           3'-UAACAAUGUGAAAUAAGUCUAAUGU UA-5'   (SEQ ID NO: 1903)

βc-3430 Target: 5'-ATTGTTACACTTTATTCAGATTACAAT-3'   (SEQ ID NO: 3012)

5'-CUACACAAUUGUUACACUUUAUUCA AC-3'   (SEQ ID NO: 6340)
           3'-GAUGUGUUAACAAUGUGAAAUAAGU CU-5'   (SEQ ID NO: 1904)

βc-3437 Target: 5'-CTACACAATTGTTACACTTTATTCAGA-3'   (SEQ ID NO: 3013)

5'-AAGGCUACACAAUUGUUACACUUUA CC-3'   (SEQ ID NO: 6341)
           3'-UUCCGAUGUGUUAACAAUGUGAAAU AA-5'   (SEQ ID NO: 1905)

βc-3441 Target: 5'-AAGGCTACACAATTGTTACACTTTATT-3'   (SEQ ID NO: 3014)

5'-ACAAAAAGGCUACACAAUUGUUACA AC-3'   (SEQ ID NO: 6342)
           3'-UGUUUUUCCGAUGUGUUAACAAUGU GA-5'   (SEQ ID NO: 1906)

βc-3446 Target: 5'-ACAAAAAGGCTACACAATTGTTACACT-3'   (SEQ ID NO: 3015)

5'-UUUUAUACAAAAAGGCUACACAAUU AC-3'   (SEQ ID NO: 6343)
           3'-AAAAUAUGUUUUUCCGAUGUGUUAA CA-5'   (SEQ ID NO: 1907)

βc-3452 Target: 5'-TTTTATACAAAAAGGCTACACAATTGT-3'   (SEQ ID NO: 3016)
```

TABLE 12-continued

Additional Selected Anti-β-catenin DsiRNAs, Blunt/Frayed Duplexes

```
       5'-AUUUUAUACAAAAAGGCUACACAAU CA-3'      (SEQ ID NO: 6344)
       3'-UAAAAUAUGUUUUUCCGAUGUGUUA AC-5'     (SEQ ID NO: 1908)
```

βc-3453 Target: 5'-ATTTTATACAAAAGGCTACACAATTG-3'   (SEQ ID NO: 3017)

```
       5'-CUAUUUUAUACAAAAAGGCUACACA CC-3'      (SEQ ID NO: 6345)
       3'-GAUAAAAUAUGUUUUUCCGAUGUGU UA-5'     (SEQ ID NO: 1909)
```

βc-3455 Target: 5'-CTATTTTATACAAAAGGCTACACAAT-3'   (SEQ ID NO: 3018)

```
       5'-UCUAUUUUAUACAAAAAGGCUACAC CC-3'      (SEQ ID NO: 6346)
       3'-AGAUAAAAUAUGUUUUUCCGAUGUG UU-5'     (SEQ ID NO: 1910)
```

βc-3456 Target: 5'-TCTATTTTATACAAAAGGCTACACAA-3'   (SEQ ID NO: 3019)

```
       5'-UGUCUAUUUUAUACAAAAGGCUAC CA-3'       (SEQ ID NO: 6347)
       3'-ACAGAUAAAAUAUGUUUUUCCGAUG UG-5'     (SEQ ID NO: 1911)
```

βc-3458 Target: 5'-TGTCTATTTTATACAAAAGGCTACAC-3'   (SEQ ID NO: 3020)

```
       5'-UCUAUUUGUCUAUUUUAUACAAAAA AA-3'      (SEQ ID NO: 6348)
       3'-AGAUAAACAGAUAAAAUAUGUUUUU CC-5'     (SEQ ID NO: 1912)
```

βc-3464 Target: 5'-TCTATTTGTCTATTTTATACAAAAGG-3'   (SEQ ID NO: 3021)

```
       5'-UUUCUAUUUGUCUAUUUUAUACAAA CC-3'      (SEQ ID NO: 6349)
       3'-AAAGAUAAACAGAUAAAAUAUGUUU UU-5'     (SEQ ID NO: 1913)
```

βc-3466 Target: 5'-TTTCTATTTGTCTATTTTATACAAAA-3'   (SEQ ID NO: 3022)

```
       5'-UUUUCUAUUUGUCUAUUUUAUACAA CC-3'      (SEQ ID NO: 6350)
       3'-AAAAGAUAAACAGAUAAAAUAUGUU UU-5'     (SEQ ID NO: 1914)
```

βc-3467 Target: 5'-TTTTCTATTTGTCTATTTTATACAAA-3'   (SEQ ID NO: 3023)

```
       5'-AUUUUCUAUUUGUCUAUUUUAUACA CC-3'      (SEQ ID NO: 6351)
       3'-UAAAAGAUAAACAGAUAAAAUAUGU UU-5'     (SEQ ID NO: 1915)
```

βc-3468 Target: 5'-ATTTTCTATTTGTCTATTTTATACAAA-3'   (SEQ ID NO: 3024)

```
       5'-CAUUUUCUAUUUGUCUAUUUUAUAC CC-3'      (SEQ ID NO: 6352)
       3'-GUAAAAGAUAAACAGAUAAAAUAUG UU-5'     (SEQ ID NO: 1916)
```

βc-3469 Target: 5'-CATTTTCTATTTGTCTATTTTATACAA-3'   (SEQ ID NO: 3025)

```
       5'-CCAUUUUCUAUUUGUCUAUUUUAUA AC-3'      (SEQ ID NO: 6353)
       3'-GGUAAAAGAUAAACAGAUAAAAUAU GU-5'     (SEQ ID NO: 1917)
```

βc-3470 Target: 5'-CCATTTTCTATTTGTCTATTTTATACA-3'   (SEQ ID NO: 3026)

```
       5'-GGACCAUUUUCUAUUUGUCUAUUUU CC-3'      (SEQ ID NO: 6354)
       3'-CCUGGUAAAAGAUAAACAGAUAAAA UA-5'     (SEQ ID NO: 1918)
```

βc-3473 Target: 5'-GGACCATTTTCTATTTGTCTATTTTAT-3'   (SEQ ID NO: 3027)

```
       5'-UGGACCAUUUUCUAUUUGUCUAUUU CC-3'      (SEQ ID NO: 6355)
       3'-ACCUGGUAAAAGAUAAACAGAUAAA AU-5'     (SEQ ID NO: 1919)
```

βc-3474 Target: 5'-TGGACCATTTTCTATTTGTCTATTTTA-3'   (SEQ ID NO: 3028)

TABLE 12-continued

Additional Selected Anti-β-catenin DsiRNAs, Blunt/Frayed Duplexes

```
5'-UUGGACCAUUUUCUAUUUGUCUAUUᶜᶜ-3'    (SEQ ID NO: 6356)
3'-AACCUGGUAAAAGAUAAACAGAUAAₐ-5'      (SEQ ID NO: 1920)
```

βc-3475 Target: 5'-TTGGACCATTTTCTATTTGTCTATTTT-3' (SEQ ID NO: 3029)

```
5'-AAACUAAUUGGACCAUUUUCUAUUUᴬᶜ-3'    (SEQ ID NO: 6357)
3'-UUUGAUUAACCUGGUAAAAGAUAAAᴄ-ₐ-5'    (SEQ ID NO: 1921)
```

βc-3482 Target: 5'-AAACTAATTGGACCATTTTCTATTTGT-3' (SEQ ID NO: 3030)

```
5'-GAAACUAAUUGGACCAUUUUCUAUUᶜᴬ-3'    (SEQ ID NO: 6358)
3'-CUUUGAUUAACCUGGUAAAAGAUAAₐ-ᴄ-5'    (SEQ ID NO: 1922)
```

βc-3483 Target: 5'-GAAACTAATTGGACCATTTTCTATTTG-3' (SEQ ID NO: 3031)

```
5'-GGAAACUAAUUGGACCAUUUUCUAUᶜᶜ-3'    (SEQ ID NO: 6359)
3'-CCUUUGAUUAACCUGGUAAAAGAUAₐ-ₐ-5'    (SEQ ID NO: 1923)
```

βc-3484 Target: 5'-GGAAACTAATTGGACCATTTTCTATTT-3' (SEQ ID NO: 3032)

```
5'-AGGAAACUAAUUGGACCAUUUUCUAᶜᶜ-3'    (SEQ ID NO: 6360)
3'-UCCUUUGAUUAACCUGGUAAAAGAUₐ-ₐ-5'    (SEQ ID NO: 1924)
```

βc-3485 Target: 5'-AGGAAACTAATTGGACCATTTTCTATT-3' (SEQ ID NO: 3033)

```
5'-UUAAAAAGGAAACUAAUUGGACCAUᶜᶜ-3'    (SEQ ID NO: 6361)
3'-AAUUUUUCCUUUGAUUAACCUGGUAₐ-ₐ-5'    (SEQ ID NO: 1925)
```

βc-3491 Target: 5'-TTAAAAAGGAAACTAATTGGACCATTT-3' (SEQ ID NO: 3034)

```
5'-AUUAAAAAGGAAACUAAUUGGACCAᶜᶜ-3'    (SEQ ID NO: 6362)
3'-UAAUUUUUCCUUUGAUUAACCUGGUₐ-ₐ-5'    (SEQ ID NO: 1926)
```

βc-3492 Target: 5'-ATTAAAAAGGAAACTAATTGGACCATT-3' (SEQ ID NO: 3035)

```
5'-AAGCAUAUUAAAAGGAAACUAAUUᴬᴬ-3'     (SEQ ID NO: 6363)
3'-UUCGUAUAAUUUUUCCUUUGAUUAAᴄ-5'      (SEQ ID NO: 1927)
```

βc-3498 Target: 5'-AAGCATATTAAAAGGAAACTAATTGG-3' (SEQ ID NO: 3036)

```
5'-UAAGCAUAUUAAAAGGAAACUAAUᶜᴬ-3'     (SEQ ID NO: 6364)
3'-AUUCGUAUAAUUUUUCCUUUGAUUAₐ-ᴄ-5'    (SEQ ID NO: 1928)
```

βc-3499 Target: 5'-TAAGCATATTAAAAGGAAACTAATTG-3' (SEQ ID NO: 3037)

```
5'-AUUUUAAGCAUAUUAAAAGGAAACᶜᶜ-3'     (SEQ ID NO: 6365)
3'-UAAAAUUCGUAUAAUUUUUCCUUUGₐ-ᵤ-5'    (SEQ ID NO: 1929)
```

βc-3503 Target: 5'-ATTTTAAGCATATTAAAAGGAAACTA-3' (SEQ ID NO: 3038)

```
5'-CUGCUUAUUUUAAGCAUAUUAAAAAᴬ-3'     (SEQ ID NO: 6366)
3'-GACGAAUAAAAUUCGUAUAAUUUUUᴄ-5'      (SEQ ID NO: 1930)
```

βc-3509 Target: 5'-CTGCTTATTTTAAGCATATTAAAAGG-3' (SEQ ID NO: 3039)

```
5'-CCUGCUUAUUUUAAGCAUAUUAAAAᶜᴬ-3'    (SEQ ID NO: 6367)
3'-GGACGAAUAAAAUUCGUAUAAUUUUUᵤ-ᴄ-5'   (SEQ ID NO: 1931)
```

βc-3510 Target: 5'-CCTGCTTATTTTAAGCATATTAAAAG-3' (SEQ ID NO: 3040)

TABLE 12-continued

Additional Selected Anti-β-catenin DsiRNAs, Blunt/Frayed Duplexes

```
5'-GAUCCACCUGCUUAUUUUAAGCAUA^C C-3'   (SEQ ID NO: 6368)
3'-CUAGGUGGACGAAUAAAAUUCGUAU_A A-5'   (SEQ ID NO: 1932)
```

βc-3516 Target: 5'-GATCCACCTGCTTATTTTAAGCATATT-3'   (SEQ ID NO: 3041)

```
5'-CAAAAACAUGAAAUAGAUCCACCUG^A C-3'   (SEQ ID NO: 6369)
3'-GUUUUUGUACUUUAUCUAGGUGGAC_G A-5'   (SEQ ID NO: 1933)
```

βc-3531 Target: 5'-CAAAAACATGAAATAGATCCACCTGCT-3'   (SEQ ID NO: 3042)

```
5'-UCAAAAACAUGAAAUAGAUCCACCU^A A-3'   (SEQ ID NO: 6370)
3'-AGUUUUUGUACUUUAUCUAGGUGGA_C G-5'   (SEQ ID NO: 1934)
```

βc-3532 Target: 5'-TCAAAAACATGAAATAGATCCACCTGC-3'   (SEQ ID NO: 3043)

```
5'-GAUCAAAAACAUGAAAUAGAUCCAC^A C-3'   (SEQ ID NO: 6371)
3'-CUAGUUUUUGUACUUUAUCUAGGUG_G A-5'   (SEQ ID NO: 1935)
```

βc-3534 Target: 5'-GATCAAAAACATGAAATAGATCCACCT-3'   (SEQ ID NO: 3044)

```
5'-UGAUCAAAAACAUGAAAUAGAUCCA^A A-3'   (SEQ ID NO: 6372)
3'-ACUAGUUUUUGUACUUUAUCUAGGU_G G-5'   (SEQ ID NO: 1936)
```

βc-3535 Target: 5'-TGATCAAAAACATGAAATAGATCCACC-3'   (SEQ ID NO: 3045)

```
5'-UUGAUCAAAAACAUGAAAUAGAUCC^C A-3'   (SEQ ID NO: 6373)
3'-AACUAGUUUUUGUACUUUAUCUAGG_U G-5'   (SEQ ID NO: 1937)
```

βc-3536 Target: 5'-TTGATCAAAAACATGAAATAGATCCAC-3'   (SEQ ID NO: 3046)

```
5'-AGUUUUUGAUCAAAAACAUGAAAUA^A C-3'   (SEQ ID NO: 6374)
3'-UCAAAAACUAGUUUUUGUACUUUAU_C U-5'   (SEQ ID NO: 1938)
```

βc-3541 Target: 5'-AGTTTTTGATCAAAAACATGAAATAGA-3'   (SEQ ID NO: 3047)

```
5'-CCAAAUAGUUUUUGAUCAAAAACAU^A C-3'   (SEQ ID NO: 6375)
3'-GGUUUAUCAAAAACUAGUUUUUGUA_C U-5'   (SEQ ID NO: 1939)
```

βc-3547 Target: 5'-CCAAATAGTTTTTGATCAAAAACATGA-3'   (SEQ ID NO: 3048)

```
5'-UAUCCCAAAUAGUUUUUGAUCAAAAC^A-3'   (SEQ ID NO: 6376)
3'-AUAGGGUUUAUCAAAAACUAGUUUUU_G-5'   (SEQ ID NO: 1940)
```

βc-3551 Target: 5'-TATCCCAAATAGTTTTTGATCAAAAAC-3'   (SEQ ID NO: 3049)

```
5'-AUAUCCCAAAUAGUUUUUGAUCAAA^C C-3'   (SEQ ID NO: 6377)
3'-UAUAGGGUUUAUCAAAAACUAGUUU_U U-5'   (SEQ ID NO: 1941)
```

βc-3552 Target: 5'-ATATCCCAAATAGTTTTTGATCAAAAA-3'   (SEQ ID NO: 3050)

```
5'-CAUAUCCCAAAUAGUUUUUGAUCAA^C C-3'   (SEQ ID NO: 6378)
3'-GUAUAGGGUUUAUCAAAAACUAGUU_U U-5'   (SEQ ID NO: 1942)
```

βc-3553 Target: 5'-CATATCCCAAATAGTTTTTGATCAAAA-3'   (SEQ ID NO: 3051)

```
5'-ACAUAUCCCAAAUAGUUUUUGAUCA^C C-3'   (SEQ ID NO: 6379)
3'-UGUAUAGGGUUUAUCAAAAACUAGU_U U-5'   (SEQ ID NO: 1943)
```

βc-3554 Target: 5'-ACATATCCCAAATAGTTTTTGATCAAA-3'   (SEQ ID NO: 3052)

TABLE 12-continued

Additional Selected Anti-β-catenin DsiRNAs, Blunt/Frayed Duplexes

```
        5'-CCAUACAUAUCCCAAAUAGUUUUUGᶜᶜ⁻³'        (SEQ ID NO: 6380)
        3'-GGUAUGUAUAGGGUUUAUCAAAAACᵤₐ₋₅'        (SEQ ID NO: 1944)
```

βc-3558 Target: 5'-CCATACATATCCCAAATAGTTTTGAT-3' (SEQ ID NO: 3053)

```
        5'-UUACCCUACCCAUACAUAUCCCAAAᶜᶜ⁻³'        (SEQ ID NO: 6381)
        3'-AAUGGGAUGGGUAUGUAUAGGGUUUₐᵤ₋₅'        (SEQ ID NO: 1945)
```

βc-3567 Target: 5'-TTACCCTACCCATACATATCCCAATA-3' (SEQ ID NO: 3054)

```
        5'-UUUACCCUACCCAUACAUAUCCCAAᶜᶜ⁻³'        (SEQ ID NO: 6382)
        3'-AAAUGGGAUGGGUAUGUAUAGGGUUᵤₐ₋₅'        (SEQ ID NO: 1946)
```

βc-3568 Target: 5'-TTTACCCTACCCATACATATCCCAAT-3' (SEQ ID NO: 3055)

```
        5'-AUUUACCCUACCCAUACAUAUCCCAᶜᶜ⁻³'        (SEQ ID NO: 6383)
        3'-UAAAUGGGAUGGGUAUGUAUAGGGUᵤᵤ₋₅'        (SEQ ID NO: 1947)
```

βc-3569 Target: 5'-ATTTACCCTACCCATACATATCCCAAA-3' (SEQ ID NO: 3056)

```
        5'-ACACCUCUUACUGAUUUACCCUACCᴬᶜ⁻³'        (SEQ ID NO: 6384)
        3'-UGUGGAGAAUGACUAAAUGGGAUGGᵍᵤ₋₅'        (SEQ ID NO: 1948)
```

βc-3582 Target: 5'-ACACCTCTTACTGATTTACCCTACCCA-3' (SEQ ID NO: 3057)

```
        5'-UAACACCUCUUACUGAUUUACCCUAᴬᴬ⁻³'        (SEQ ID NO: 6385)
        3'-AUUGUGGAGAAUGACUAAAUGGGAUᵍᵍ₋₅'        (SEQ ID NO: 1949)
```

βc-3584 Target: 5'-TAACACCTCTTACTGATTTACCCTACC-3' (SEQ ID NO: 3058)

```
        5'-AUAACACCUCUUACUGAUUUACCCUᶜᴬ⁻³'        (SEQ ID NO: 6386)
        3'-UAUUGUGGAGAAUGACUAAAUGGGAᵤᵍ₋₅'        (SEQ ID NO: 1950)
```

βc-3585 Target: 5'-ATAACACCTCTTACTGATTTACCCTAC-3' (SEQ ID NO: 3059)

```
        5'-AAUAACACCUCUUACUGAUUUACCCᶜᶜ⁻³'        (SEQ ID NO: 6387)
        3'-UUAUUGUGGAGAAUGACUAAAUGGGₐᵤ₋₅'        (SEQ ID NO: 1951)
```

βc-3586 Target: 5'-AATAACACCTCTTACTGATTTACCCTA-3' (SEQ ID NO: 3060)

```
        5'-AAAUAACACCUCUUACUGAUUUACCᴬᶜ⁻³'        (SEQ ID NO: 6388)
        3'-UUUAUUGUGGAGAAUGACUAAAUGGᵍₐ₋₅'        (SEQ ID NO: 1952)
```

βc-3587 Target: 5'-AAATAACACCTCTTACTGATTTACCCT-3' (SEQ ID NO: 3061)

```
        5'-CAAAUAACACCUCUUACUGAUUUACᴬᴬ⁻³'        (SEQ ID NO: 6389)
        3'-GUUUAUUGUGGAGAAUGACUAAAUGᵍᵍ₋₅'        (SEQ ID NO: 1953)
```

βc-3588 Target: 5'-CAAATAACACCTCTTACTGATTTACCC-3' (SEQ ID NO: 3062)

```
        5'-AGGUUCCAAAUAACACCUCUUACUGᶜᶜ⁻³'        (SEQ ID NO: 6390)
        3'-UCCAAGGUUUAUUGUGGAGAAUGACᵤₐ₋₅'        (SEQ ID NO: 1954)
```

βc-3594 Target: 5'-AGGTTCCAAATAACACCTCTTACTGAT-3' (SEQ ID NO: 3063)

```
        5'-AAAACAAGGUUCCAAAUAACACCUCᶜᶜ⁻³'        (SEQ ID NO: 6391)
        3'-UUUUGUUCCAAGGUUUAUUGUGGAGₐₐ₋₅'        (SEQ ID NO: 1955)
```

βc-3600 Target: 5'-AAAACAAGGTTCCAAATAACACCTCTT-3' (SEQ ID NO: 3064)

TABLE 12-continued

Additional Selected Anti-β-catenin DsiRNAs, Blunt/Frayed Duplexes

```
       5'-CAAAACAAGGUUCCAAAUAACACCUA C-3'  (SEQ ID NO: 6392)
       3'-GUUUUGUUCCAAGGUUUAUUGUGGA G-A-5' (SEQ ID NO: 1956)
```

βc-3601 Target: 5'-CAAAACAAGGTTCCAAATAACACCTCT-3' (SEQ ID NO: 3065)

```
       5'-CCAAAACAAGGUUCCAAAUAACACC C-A-3'  (SEQ ID NO: 6393)
       3'-GGUUUUGUUCCAAGGUUUAUUGUGG A-G-5' (SEQ ID NO: 1957)
```

βc-3602 Target: 5'-CCAAAACAAGGTTCCAAATAACACCTC-3' (SEQ ID NO: 3066)

```
       5'-ACUGUCCAAAACAAGGUUCCAAAUA C-A-3'  (SEQ ID NO: 6394)
       3'-UGACAGGUUUUGUUCCAAGGUUUAU U-G-5' (SEQ ID NO: 1958)
```

βc-3607 Target: 5'-ACTGTCCAAAACAAGGTTCCAAATAAC-3' (SEQ ID NO: 3067)

```
       5'-GUAAACUGUCCAAAACAAGGUUCCA C-C-3'  (SEQ ID NO: 6395)
       3'-CAUUUGACAGGUUUUGUUCCAAGGU U-U-5' (SEQ ID NO: 1959)
```

βc-3611 Target: 5'-GTAAACTGTCCAAAACAAGGTTCCAAA-3' (SEQ ID NO: 3068)

```
       5'-GGUAAACUGUCCAAAACAAGGUUCC C-C-3'  (SEQ ID NO: 6396)
       3'-CCAUUUGACAGGUUUUGUUCCAAGG U-U-5' (SEQ ID NO: 1960)
```

βc-3612 Target: 5'-GGTAAACTGTCCAAAACAAGGTTCCAA-3' (SEQ ID NO: 3069)

```
       5'-AGGCAACUGGUAAACUGUCCAAAAC C-C-3'  (SEQ ID NO: 6397)
       3'-UCCGUUGACCAUUUGACAGGUUUUG U-U-5' (SEQ ID NO: 1961)
```

βc-3620 Target: 5'-AGGCAACTGGTAAACTGTCCAAAACAA-3' (SEQ ID NO: 3070)

```
       5'-GGGAUAAAAGGCAACUGGUAAACUG C-A-3'  (SEQ ID NO: 6398)
       3'-CCCUAUUUUCCGUUGACCAUUUGAC A-G-5' (SEQ ID NO: 1962)
```

βc-3628 Target: 5'-GGGATAAAAGGCAACTGGTAAACTGTC-3' (SEQ ID NO: 3071)

```
       5'-UGGGAUAAAAGGCAACUGGUAAACU A-C-3'  (SEQ ID NO: 6399)
       3'-ACCCUAUUUUCCGUUGACCAUUUGA C-A-5' (SEQ ID NO: 1963)
```

βc-3629 Target: 5'-TGGGATAAAAGGCAACTGGTAAACTGT-3' (SEQ ID NO: 3072)

```
       5'-ACAACUUUGGGAUAAAAGGCAACUG A-C-3'  (SEQ ID NO: 6400)
       3'-UGUUGAAACCCUAUUUUCCGUUGAC C-A-5' (SEQ ID NO: 1964)
```

βc-3636 Target: 5'-ACAACTTTGGGATAAAAGGCAACTGGT-3' (SEQ ID NO: 3073)

```
       5'-CAACAACUUUGGGAUAAAAGGCAAC C-A-3'  (SEQ ID NO: 6401)
       3'-GUUGUUGAAACCCUAUUUUCCGUUG A-C-5' (SEQ ID NO: 1965)
```

βc-3638 Target: 5'-CAACAACTTTGGGATAAAAGGCAACTG-3' (SEQ ID NO: 3074)

```
       5'-GGUUACAACAACUUUGGGAUAAAAG A-A-3'  (SEQ ID NO: 6402)
       3'-CCAAUGUUGUUGAAACCCUAUUUUC C-G-5' (SEQ ID NO: 1966)
```

βc-3643 Target: 5'-GGTTACAACAACTTTGGGATAAAAGGC-3' (SEQ ID NO: 3075)

```
       5'-AGGUUACAACAACUUUGGGAUAAAA A-A-3'  (SEQ ID NO: 6403)
       3'-UCCAAUGUUGUUGAAACCCUAUUUU C-C-5' (SEQ ID NO: 1967)
```

βc-3644 Target: 5'-AGGTTACAACAACTTTGGGATAAAAGG-3' (SEQ ID NO: 3076)

TABLE 12-continued

Additional Selected Anti-β-catenin DsiRNAs, Blunt/Frayed Duplexes

```
           5'-CAGGUUACAACAACUUUGGGAUAAA^(CA-3')       (SEQ ID NO: 6404)
           3'-GUCCAAUGUUGUUGAAACCCUAUUU_(UC-5')      (SEQ ID NO: 1968)

βc-3645 Target: 5'-CAGGTTACAACAACTTTGGGATAAAG-3'      (SEQ ID NO: 3077)

5'-UAUCACAGCAGGUUACAACAACUUU^(AA-3')       (SEQ ID NO: 6405)
           3'-AUAGUGUCGUCCAAUGUUGUUGAAA_(CC-5')      (SEQ ID NO: 1969)

βc-3653 Target: 5'-TATCACAGCAGGTTACAACAACTTTGG-3'     (SEQ ID NO: 3078)

5'-GUAUCACAGCAGGUUACAACAACUU^(CA-3')       (SEQ ID NO: 6406)
           3'-CAUAGUGUCGUCCAAUGUUGUUGAA_(AC-5')      (SEQ ID NO: 1970)

βc-3654 Target: 5'-GTATCACAGCAGGTTACAACAACTTTG-3'     (SEQ ID NO: 3079)

5'-UCGUAUCACAGCAGGUUACAACAAC^(CC-3')       (SEQ ID NO: 6407)
           3'-AGCAUAGUGUCGUCCAAUGUUGUUG_(AA-5')      (SEQ ID NO: 1971)

βc-3656 Target: 5'-TCGTATCACAGCAGGTTACAACAACTT-3'     (SEQ ID NO: 3080)

5'-UUUCUCUUGAAGCAUCGUAUCACAG^(AC-3')       (SEQ ID NO: 6408)
           3'-AAAGAGAACUUCGUAGCAUAGUGUC_(GU-5')      (SEQ ID NO: 1972)

βc-3670 Target: 5'-TTTCTCTTGAAGCATCGTATCACAGCA-3'     (SEQ ID NO: 3081)

5'-UUUUCUCUUGAAGCAUCGUAUCACA^(AA-3')       (SEQ ID NO: 6409)
           3'-AAAAGAGAACUUCGUAGCAUAGUGU_(CG-5')      (SEQ ID NO: 1973)

βc-3671 Target: 5'-TTTTCTCTTGAAGCATCGTATCACAGC-3'     (SEQ ID NO: 3082)

5'-CAUUUUCUCUUGAAGCAUCGUAUCA^(AC-3')       (SEQ ID NO: 6410)
           3'-GUAAAAGAGAACUUCGUAGCAUAGU_(GU-5')      (SEQ ID NO: 1974)

βc-3673 Target: 5'-CATTTTCTCTTGAAGCATCGTATCACA-3'     (SEQ ID NO: 3083)

5'-UUUUUUAUAACCGCAUUUUCUCUUG^(CC-3')       (SEQ ID NO: 6411)
           3'-AAAAAAUAUUGGCGUAAAAGAGAAC_(UU-5')      (SEQ ID NO: 1975)

βc-3686 Target: 5'-TTTTTTATAACCGCATTTTCTCTTGAA-3'     (SEQ ID NO: 3084)

5'-AUUUUUUAUAACCGCAUUUUCUCUU^(AC-3')       (SEQ ID NO: 6412)
           3'-UAAAAAAUAUUGGCGUAAAAGAGAA_(CU-5')      (SEQ ID NO: 1976)

βc-3687 Target: 5'-ATTTTTTATAACCGCATTTTCTCTTGA-3'     (SEQ ID NO: 3085)

5'-CAUUUUUUAUAACCGCAUUUUCUCU^(CA-3')       (SEQ ID NO: 6413)
           3'-GUAAAAAAUAUUGGCGUAAAAGAGA_(AC-5')      (SEQ ID NO: 1977)

βc-3688 Target: 5'-CATTTTTTATAACCGCATTTTCTCTTG-3'     (SEQ ID NO: 3086)

5'-CCAUUUUUUAUAACCGCAUUUUCUC^(CC-3')       (SEQ ID NO: 6414)
           3'-GGUAAAAAAUAUUGGCGUAAAAGAGA_(AA-5')     (SEQ ID NO: 1978)

βc-3689 Target: 5'-CCATTTTTTATAACCGCATTTTCTCTT-3'     (SEQ ID NO: 3087)

5'-CUGAACCAUUUUUUAUAACCGCAUU^(CC-3')       (SEQ ID NO: 6415)
           3'-GACUUGGUAAAAAAUAUUGGCGUAA_(AA-5')      (SEQ ID NO: 1979)

βc-3694 Target: 5'-CTGAACCATTTTTTATAACCGCATTTT-3'     (SEQ ID NO: 3088)
```

TABLE 12-continued

Additional Selected Anti-β-catenin DsiRNAs, Blunt/Frayed Duplexes

```
5'-UAAUUCUGAACCAUUUUUAUAACC^(A A-3')   (SEQ ID NO: 6416)
3'-AUUAAGACUUGGUAAAAAAUAUUGG_(C G-5')  (SEQ ID NO: 1980)
```

βc-3699 Target: 5'-TAATTCTGAACCATTTTTTATAACCGC-3'  (SEQ ID NO: 3089)

```
5'-UUAAUUCUGAACCAUUUUUUAUAAC^(A A-3')   (SEQ ID NO: 6417)
3'-AAUUAAGACUUGGUAAAAAAUAUUG_(G C-5')   (SEQ ID NO: 1981)
```

βc-3700 Target: 5'-TTAATTCTGAACCATTTTTTATAACCG-3'  (SEQ ID NO: 3090)

```
5'-UUUAAUUCUGAACCAUUUUUUAUAA^(A A-3')   (SEQ ID NO: 6418)
3'-AAAUUAAGACUUGGUAAAAAAUAUU_(G G-5')   (SEQ ID NO: 1982)
```

βc-3701 Target: 5'-TTTAATTCTGAACCATTTTTTATAACC-3'  (SEQ ID NO: 3091)

```
5'-GUUUAAUUCUGAACCAUUUUUUAUA^(C A-3')   (SEQ ID NO: 6419)
3'-CAAAUUAAGACUUGGUAAAAAAUAU_(U G-5')   (SEQ ID NO: 1983)
```

βc-3702 Target: 5'-GTTTAATTCTGAACCATTTTTTATAAC-3'  (SEQ ID NO: 3092)

```
5'-AGUUUAAUUCUGAACCAUUUUUUAU^(C C-3')   (SEQ ID NO: 6420)
3'-UCAAAUUAAGACUUGGUAAAAAAUA_(U U-5')   (SEQ ID NO: 1984)
```

βc-3703 Target: 5'-AGTTTAATTCTGAACCATTTTTTATAA-3'  (SEQ ID NO: 3093)

```
5'-AAGUUUAAUUCUGAACCAUUUUUUA^(C C-3')   (SEQ ID NO: 6421)
3'-UUCAAAUUAAGACUUGGUAAAAAAU_(A U-5')   (SEQ ID NO: 1985)
```

βc-3704 Target: 5'-AAGTTTAATTCTGAACCATTTTTTATA-3'  (SEQ ID NO: 3094)

```
5'-AUUAAAAGUUUAAUUCUGAACCAUU^(C C-3')   (SEQ ID NO: 6422)
3'-UAAUUUUCAAAUUAAGACUUGGUAA_(A A-5')   (SEQ ID NO: 1986)
```

βc-3709 Target: 5'-ATTAAAAGTTTAATTCTGAACCATTTT-3'  (SEQ ID NO: 3095)

```
5'-AAUUAAAAGUUUAAUUCUGAACCAU^(C C-3')   (SEQ ID NO: 6423)
3'-UUAAUUUUCAAAUUAAGACUUGGUA_(A A-5')   (SEQ ID NO: 1987)
```

βc-3710 Target: 5'-AATTAAAAGTTTAATTCTGAACCATTT-3'  (SEQ ID NO: 3096)

```
5'-UGAAUUAAAAGUUUAAUUCUGAACC^(C C-3')   (SEQ ID NO: 6424)
3'-ACUUAAUUUUCAAAUUAAGACUUGG_(U A-5')   (SEQ ID NO: 1988)
```

βc-3712 Target: 5'-TGAATTAAAAGTTTAATTCTGAACC-3'  (SEQ ID NO: 3097)

```
5'-CAAUACAGCUAAAGGAUGAUUUACA^(A A-3')   (SEQ ID NO: 6425)
3'-GUUAUGUCGAUUUCCUACUAAAUGU_(C C-5')   (SEQ ID NO: 1989)
```

βc-2634t2 Target: 5'-CAATACAGCTAAAGGATGATTTACAGG-3'  (SEQ ID NO: 3098)

```
5'-ACAAUACAGCUAAAGGAUGAUUUAC^(C A-3')   (SEQ ID NO: 6426)
3'-UGUUAUGUCGAUUUCCUACUAAAUG_(U C-5')   (SEQ ID NO: 1990)
```

βc-2635t2 Target: 5'-ACAATACAGCTAAAGGATGATTTACAG-3'  (SEQ ID NO: 3099)

```
5'-AGACAAUACAGCUAAAGGAUGAUUU^(C A-3')   (SEQ ID NO: 6427)
3'-UCUGUUAUGUCGAUUUCCUACUAAA_(U G-5')   (SEQ ID NO: 1991)
```

βc-2637t2 Target: 5'-AGACAATACAGCTAAAGGATGATTTAC-3'  (SEQ ID NO: 3100)

TABLE 12-continued

Additional Selected Anti-β-catenin DsiRNAs, Blunt/Frayed Duplexes

```
5'-GUUACUCCUAAAGGAUGAUUUACAGA^AC-3'  (SEQ ID NO: 6428)
3'-CAAUGAGGAUUUCCUACUAAAUGUC_CA-5'   (SEQ ID NO: 1992)
```

βc-2633t3 Target: 5'-GTTACTCCTAAAGGATGATTTACAGGT-3' (SEQ ID NO: 3101)

```
5'-UGUUACUCCUAAAGGAUGAUUUACA^AA-3'  (SEQ ID NO: 6429)
3'-ACAAUGAGGAUUUCCUACUAAAUGU_CC-5'   (SEQ ID NO: 1993)
```

βc-2634t3 Target: 5'-TGTTACTCCTAAAGGATGATTTACAGG-3' (SEQ ID NO: 3102)

```
5'-UUGUUACUCCUAAAGGAUGAUUUAC^CA-3'  (SEQ ID NO: 6430)
3'-AACAAUGAGGAUUUCCUACUAAAUG_UC-5'   (SEQ ID NO: 1994)
```

βc-2635t3 Target: 5'-TTGTTACTCCTAAAGGATGATTTACAG-3' (SEQ ID NO: 3103)

```
5'-AUUGUUACUCCUAAAGGAUGAUUUA^AC-3'  (SEQ ID NO: 6431)
3'-UAACAAUGAGGAUUUCCUACUAAAU_GU-5'   (SEQ ID NO: 1995)
```

βc-2636t3 Target: 5'-ATTGTTACTCCTAAAGGATGATTTACA-3' (SEQ ID NO: 3104)

```
5'-GGAUUCCAGAAUCCAAGUAAGACUG^AC-3'  (SEQ ID NO: 6432)
3'-CCUAAGGUCUUAGGUUCAUUCUGAC_GA-5'   (SEQ ID NO: 1996)
```

βc-m318 Target: 5'-GGATTCCAGAATCCAAGTAAGACTGCT-3' (SEQ ID NO: 3105)

```
5'-CUUGCUCCCAUUCAUAAAGGACUUG^AA-3'  (SEQ ID NO: 6433)
3'-GAACGAGGGUAAGUAUUUCCUGAAC_CC-5'   (SEQ ID NO: 1997)
```

βc-m417 Target: 5'-CTTGCTCCCATTCATAAAGGACTTGGG-3' (SEQ ID NO: 3106)

```
5'-CGUCAAUAUCAGCUACUUGCUCUUG^AA-3'  (SEQ ID NO: 6434)
3'-GCAGUUAUAGUCGAUGAACGAGAAC_GC-5'   (SEQ ID NO: 1998)
```

βc-m462 Target: 5'-CGTCAATATCAGCTACTTGCTCTTGCG-3' (SEQ ID NO: 3107)

```
5'-CCGUCAAUAUCAGCUACUUGCUCUU^AA-3'  (SEQ ID NO: 6435)
3'-GGCAGUUAUAGUCGAUGAACGAGAA_CG-5'   (SEQ ID NO: 1999)
```

βc-m463 Target: 5'-CCGTCAATATCAGCTACTTGCTCTTGC-3' (SEQ ID NO: 3108)

```
5'-ACUGCCCGUCAAUAUCAGCUACUUG^AC-3'  (SEQ ID NO: 6436)
3'-UGACGGGCAGUUAUAGUCGAUGAAC_GA-5'   (SEQ ID NO: 2000)
```

βc-m468 Target: 5'-ACTGCCCGTCAATATCAGCTACTTGCT-3' (SEQ ID NO: 3109)

```
5'-UGUUUCAACAUCUGUGAUGGUUCAG^AA-3'  (SEQ ID NO: 6437)
3'-ACAAAGUUGUAGACACUACCAAGUC_GG-5'   (SEQ ID NO: 2001)
```

βc-m613 Target: 5'-TGTTTCAACATCTGTGATGGTTCAGCC-3' (SEQ ID NO: 3110)

```
5'-AUGUUUCAACAUCUGUGAUGGUUCA^AA-3'  (SEQ ID NO: 6438)
3'-UACAAAGUUGUAGACACUACCAAGU_CG-5'   (SEQ ID NO: 2002)
```

βc-m614 Target: 5'-ATGTTTCAACATCTGTGATGGTTCAGC-3' (SEQ ID NO: 3111)

```
5'-UGACAACUGCAUGUUUCAACAUCUG^CA-3'  (SEQ ID NO: 6439)
3'-ACUGUUGACGUACAAAGUUGUAGAC_AC-5'   (SEQ ID NO: 2003)
```

βc-m624 Target: 5'-TGACAACTGCATGTTTCAACATCTGTG-3' (SEQ ID NO: 3112)

TABLE 12-continued

Additional Selected Anti-β-catenin DsiRNAs, Blunt/Frayed Duplexes

```
5'-AUUGACAACUGCAUGUUUCAACAUCCA-3'        (SEQ ID NO: 6440)
3'-UAACUGUUGACGUACAAAGUUGUAGAC-5'        (SEQ ID NO: 2004)
```

βc-m626 Target: 5'-ATTGACAACTGCATGTTTCAACATCTG-3' (SEQ ID NO: 3113)

```
5'-UCAAAUUGACAACUGCAUGUUUCAAAC-3'        (SEQ ID NO: 6441)
3'-AGUUUAACUGUUGACGUACAAAGUUGU-5'        (SEQ ID NO: 2005)
```

βc-m630 Target: 5'-TCAAATTGACAACTGCATGTTTCAACA-3' (SEQ ID NO: 3114)

```
5'-AGUUAAUCAAAUUGACAACUGCAUGCC-3'        (SEQ ID NO: 6442)
3'-UCAAUUAGUUUAACUGUUGACGUACAA-5'        (SEQ ID NO: 2006)
```

βc-m636 Target: 5'-AGTTAATCAAATTGACAACTGCATGTT-3' (SEQ ID NO: 3115)

```
5'-CCUGAUAGUUAAUCAAAUUGACAACCA-3'        (SEQ ID NO: 6443)
3'-GGACUAUCAAUUAGUUUAACUGUUGAC-5'        (SEQ ID NO: 2007)
```

βc-m642 Target: 5'-CCTGATAGTTAATCAAATTGACAACTG-3' (SEQ ID NO: 3116)

```
5'-CGUCAUCCUGAUAGUUAAUCAAAUUAC-3'        (SEQ ID NO: 6444)
3'-GCAGUAGGACUAUCAAUUAGUUUAACU-5'        (SEQ ID NO: 2008)
```

βc-m648 Target: 5'-CGTCATCCTGATAGTTAATCAAATTGA-3' (SEQ ID NO: 3117)

```
5'-GCGUCAUCCUGAUAGUUAAUCAAAUCA-3'        (SEQ ID NO: 6445)
3'-CGCAGUAGGACUAUCAAUUAGUUUAAC-5'        (SEQ ID NO: 2009)
```

βc-m649 Target: 5'-GCGTCATCCTGATAGTTAATCAAATTG-3' (SEQ ID NO: 3118)

```
5'-CCUCAUCGUUUAGCAGUUUUGUCAGA-3'         (SEQ ID NO: 6446)
3'-GGAGUAGCAAAUCGUCAAAACAGUCGA-5'        (SEQ ID NO: 2010)
```

βc-m702 Target: 5'-CCTCATCGTTTAGCAGTTTTGTCAGCT-3' (SEQ ID NO: 3119)

```
5'-CUGGUCCUCAUCGUUUAGCAGUUUUAC-3'        (SEQ ID NO: 6447)
3'-GACCAGGAGUAGCAAAUCGUCAAAACA-5'        (SEQ ID NO: 2011)
```

βc-m707 Target: 5'-CTGGTCCTCATCGTTTAGCAGTTTTGT-3' (SEQ ID NO: 3120)

```
5'-CAUAACAGCAGCUUUAUUAACUACCCA-3'        (SEQ ID NO: 6448)
3'-GUAUUGUCGUCGAAAUAAUUGAUGGUG-5'        (SEQ ID NO: 2012)
```

βc-m734 Target: 5'-CATAACAGCAGCTTTATTAACTACCAC-3' (SEQ ID NO: 3121)

```
5'-CCAUAACAGCAGCUUUAUUAACUACAC-3'        (SEQ ID NO: 6449)
3'-GGUAUUGUCGUCGAAAUAAUUGAUGGU-5'        (SEQ ID NO: 2013)
```

βc-m735 Target: 5'-CCATAACAGCAGCTTTATTAACTACCA-3' (SEQ ID NO: 3122)

```
5'-GGACCAUAACAGCAGCUUUAUUAACCC-3'        (SEQ ID NO: 6450)
3'-CCUGGUAUUGUCGUCGAAAUAAUUGAU-5'        (SEQ ID NO: 2014)
```

βc-m738 Target: 5'-GGACCATAACAGCAGCTTTATTAACTA-3' (SEQ ID NO: 3123)

```
5'-UGGACCAUAACAGCAGCUUUAUUAAAC-3'        (SEQ ID NO: 6451)
3'-ACCUGGUAUUGUCGUCGAAAUAAUUGA-5'        (SEQ ID NO: 2015)
```

βc-m739 Target: 5'-TGGACCATAACAGCAGCTTTATTAACT-3' (SEQ ID NO: 3124)

TABLE 12-continued

Additional Selected Anti-β-catenin DsiRNAs, Blunt/Frayed Duplexes

```
5'-CUGUCUCUACAUCAUUUGUAUUCUGAC-3'     (SEQ ID NO: 6452)
3'-GACAGAGAUGUAGUAAACAUAAGACGU-5'     (SEQ ID NO: 2016)
```

βc-m843 Target: 5'-CTGTCTCTACATCATTTGTATTCTGCA-3' (SEQ ID NO: 3125)

```
5'-GCUGUCUCUACAUCAUUUGUAUUCUAA-3'     (SEQ ID NO: 6453)
3'-CGACAGAGAUGUAGUAAAGAUAAGACG-5'     (SEQ ID NO: 2017)
```

βc-m844 Target: 5'-GCTGTCTCTACATCATTTGTATTCTGC-3' (SEQ ID NO: 3126)

```
5'-GCAACCAUUUUCUGCAGUCCACCAGAC-3'     (SEQ ID NO: 6454)
3'-CGUUGGUAAAAGACGUCAGGUGGUCGA-5'     (SEQ ID NO: 2018)
```

βc-m1063 Target: 5'-GCAACCATTTTCTGCAGTCCACCAGCT-3' (SEQ ID NO: 3127)

```
5'-AAGCAACCAUUUUCUGCAGUCCACCCA-3'     (SEQ ID NO: 6455)
3'-UUCGUUGGUAAAAGACGUCAGGUGGUC-5'     (SEQ ID NO: 2019)
```

βc-m1065 Target: 5'-AAGCAACCATTTTCTGCAGTCCACCAG-3' (SEQ ID NO: 3128)

```
5'-UUGUUUUGUUGAGCAAAGCAACCAUCC-3'     (SEQ ID NO: 6456)
3'-AACAAAACAACUCGUUUCGUUGGUAAA-5'     (SEQ ID NO: 2020)
```

βc-m1080 Target: 5'-TTGTTTTGTTGAGCAAAGCAACCATTT-3' (SEQ ID NO: 3129)

```
5'-UUUGUUUUGUUGAGCAAAGCAACCACC-3'     (SEQ ID NO: 6457)
3'-AAACAAAACAACUCGUUUCGUUGGUAA-5'     (SEQ ID NO: 2021)
```

βc-m1081 Target: 5'-TTTGTTTTGTTGAGCAAAGCAACCATT-3' (SEQ ID NO: 3130)

```
5'-UAGCCAAGAAUUUCACGUUUGUUUUAC-3'     (SEQ ID NO: 6458)
3'-AUCGGUUCUUAAAGUGCAAACAAAACA-5'     (SEQ ID NO: 2022)
```

βc-m1098 Target: 5'-TAGCCAAGAATTTCACGTTTGTTTTGT-3' (SEQ ID NO: 3131)

```
5'-CUUGAUUGCCAUAAGCUAAGAUCUGCC-3'     (SEQ ID NO: 6459)
3'-GAACUAACGGUAUUCGAUUCUAGACUU-5'     (SEQ ID NO: 2023)
```

βc-m1140 Target: 5'-CTTGATTGCCATAAGCTAAGATCTGAA-3' (SEQ ID NO: 3132)

```
5'-GCUCUCUUGAUUGCCAUAAGCUAAGCC-3'     (SEQ ID NO: 6460)
3'-CGAGAGAACUAACGGUAUUCGAUUCUA-5'     (SEQ ID NO: 2024)
```

βc-m1145 Target: 5'-GCTCTCTTGATTGCCATAAGCTAAGAT-3' (SEQ ID NO: 3133)

```
5'-CUUCUCAUAAGUGUAGGUCCUCAUUCC-3'     (SEQ ID NO: 6461)
3'-GAAGAGUAUUCACAUCCAGGAGUAAUA-5'     (SEQ ID NO: 2025)
```

βc-m1217 Target: 5'-CTTCTCATAAGTGTAGGTCCTCATTAT-3' (SEQ ID NO: 3134)

```
5'-GCUUCUCAUAAGUGUAGGUCCUCAUCC-3'     (SEQ ID NO: 6462)
3'-CGAAGAGUAUUCACAUCCAGGAGUAAU-5'     (SEQ ID NO: 2026)
```

βc-m1218 Target: 5'-GCTTCTCATAAGTGTAGGTCCTCATTA-3' (SEQ ID NO: 3135)

```
5'-AAGCUUCUCAUAAGUGUAGGUCCUCCC-3'     (SEQ ID NO: 6463)
3'-UUCGAAGAGUAUUCACAUCCAGGAGUA-5'     (SEQ ID NO: 2027)
```

βc-m1220 Target: 5'-AAGCTTCTCATAAGTGTAGGTCCTC-3' (SEQ ID NO: 3136)

TABLE 12-continued

Additional Selected Anti-β-catenin DsiRNAs, Blunt/Frayed Duplexes

```
        5'-GAAGCUUCUCAUAAGUGUAGGUCCUAC-3'   (SEQ ID NO: 6464)
        3'-CUUCGAAGAGUAUUCACAUCCAGGAGU-5'   (SEQ ID NO: 2028)

βc-m1221 Target: 5'-GAAGCTTCTCATAAGTGTAGGTCCTCA-3'  (SEQ ID NO: 3137)

5'-GAGUCCAAAGACAGUUUUGAACAAGCA-3'   (SEQ ID NO: 6465)
        3'-CUCAGGUUUCUGUCAAAACUUGUUCAG-5'   (SEQ ID NO: 2029)

βc-m1365 Target: 5'-GAGTCCAAAGACAGTTTTGAACAAGTC-3'  (SEQ ID NO: 3138)

5'-AGAGUCCAAAGACAGUUUUGAACAAAC-3'   (SEQ ID NO: 6466)
        3'-UCUCAGGUUUCUGUCAAAACUUGUUCA-5'   (SEQ ID NO: 2030)

βc-m1366 Target: 5'-AGAGTCCAAAGACAGTTTTGAACAAGT-3'  (SEQ ID NO: 3139)

5'-CCACAUUUAUAUCAUCGGAACCCAGCC-3'   (SEQ ID NO: 6467)
        3'-GGUGUAAAUAUAGUAGCCUUGGGUCUU-5'   (SEQ ID NO: 2031)

βc-m1461 Target: 5'-CCACATTTATATCATCGGAACCCAGAA-3'  (SEQ ID NO: 3140)

5'-UGACCACAUUUAUAUCAUCGGAACCAC-3'   (SEQ ID NO: 6468)
        3'-ACUGGUGUAAAUAUAGUAGCCUUGGGU-5'   (SEQ ID NO: 2032)

βc-m1464 Target: 5'-TGACCACATTTATATCATCGGAACCCA-3'  (SEQ ID NO: 3141)

5'-CUGCACAGGUGACCACAUUUAUAUCCC-3'   (SEQ ID NO: 6469)
        3'-GACGUGUCCACUGGUGUAAAUAUAGUA-5'   (SEQ ID NO: 2033)

βc-m1473 Target: 5'-CTGCACAGGTGACCACATTTATATC-3'    (SEQ ID NO: 3142)

5'-GCUGCACAGGUGACCACAUUUAUAUAC-3'   (SEQ ID NO: 6470)
        3'-CGACGUGUCCACUGGUGUAAAUAUAGU-5'   (SEQ ID NO: 2034)

βc-m1474 Target: 5'-GCTGCACAGGTGACCACATTTATATCA-3'  (SEQ ID NO: 3143)

5'-UUGUAAUUAUUGCAAGUGAGGUUAGCA-3'   (SEQ ID NO: 6471)
        3'-AACAUUAAUAACGUUCACUCCAAUCUC-5'   (SEQ ID NO: 2035)

βc-m1510 Target: 5'-TTGTAATTATTGCAAGTGAGGTTAGAG-3'  (SEQ ID NO: 3144)

5'-CAUCAUCUUGUUUUUGUAAUUAUUGAC-3'   (SEQ ID NO: 6472)
        3'-GUAGUAGAACAAAAACAUUAAUAACGU-5'   (SEQ ID NO: 2036)

βc-m1523 Target: 5'-CATCATCTTGTTTTGTAATTATTGCA-3'   (SEQ ID NO: 3145)

5'-CCAUCAUCUUGUUUUUGUAAUUAUUAA-3'   (SEQ ID NO: 6473)
        3'-GGUAGUAGAACAAAAACAUUAAUAACG-5'   (SEQ ID NO: 2037)

βc-m1524 Target: 5'-CCATCATCTTGTTTTTGTAATTATTGC-3'  (SEQ ID NO: 3146)

5'-ACACCAUCAUCUUGUUUUUGUAAUUCC-3'   (SEQ ID NO: 6474)
        3'-UGUGGUAGUAGAACAAAAACAUUAAUA-5'   (SEQ ID NO: 2038)

βc-m1527 Target: 5'-ACACCATCATCTTGTTTTTGTAATTAT-3'  (SEQ ID NO: 3147)

5'-UUGGCACACCAUCAUCUUGUUUUUGCC-3'   (SEQ ID NO: 6475)
        3'-AACCGUGUGGUAGUAGAACAAAAACAU-5'   (SEQ ID NO: 2039)

βc-m1532 Target: 5'-TTGGCACACCATCATCTTGTTTTTGTA-3'  (SEQ ID NO: 3148)
```

TABLE 12-continued

Additional Selected Anti-β-catenin DsiRNAs, Blunt/Frayed Duplexes

```
           5'-UCAAUCCAACAGUUGCCUUUAUCAG^(cA-3')     (SEQ ID NO: 6476)
           3'-AGUUAGGUUGUCAACGGAAAUAGUC_(UC-5')    (SEQ ID NO: 2040)
```

βc-m1752 Target: 5'-TCAATCCAACAGTTGCCTTTATCAGAG-3'  (SEQ ID NO: 3149)

```
           5'-UCGAAUCAAUCCAACAGUUGCCUUU^(cC-3')    (SEQ ID NO: 6477)
           3'-AGCUUAGUUAGGUUGUCAACGGAAA_(UA-5')    (SEQ ID NO: 2041)
```

βc-m1757 Target: 5'-TCGAATCAATCCAACAGTTGCCTTTAT-3'  (SEQ ID NO: 3150)

```
           5'-GCUGAACUAGUCGUGGAAUAGCACC^(AC-3')    (SEQ ID NO: 6478)
           3'-CGACUUGAUCAGCACCUUAUCGUGG_(GA-5')    (SEQ ID NO: 2042)
```

βc-m1827 Target: 5'-GCTGAACTAGTCGTGGAATAGCACCCT-3'  (SEQ ID NO: 3151)

```
           5'-AGUACACCCUUCUACUAUCUCCUCC^(cC-3')    (SEQ ID NO: 6479)
           3'-UCAUGUGGGAAGAUGAUAGAGGAGG_(UA-5')    (SEQ ID NO: 2043)
```

βc-m1934 Target: 5'-AGTACACCCTTCTACTATCTCCTCC-3'  (SEQ ID NO: 3152)

```
           5'-CAGUACACCCUUCUACUAUCUCCUC^(AC-3')    (SEQ ID NO: 6480)
           3'-GUCAUGUGGGAAGAUGAUAGAGGAG_(GU-5')    (SEQ ID NO: 2044)
```

βc-m1935 Target: 5'-CAGTACACCCTTCTACTATCTCCTCCA-3'  (SEQ ID NO: 3153)

```
           5'-CCAGUACACCCUUCUACUAUCUCCU^(AA-3')    (SEQ ID NO: 6481)
           3'-GGUCAUGUGGGAAGAUGAUAGAGGA_(GG-5')    (SEQ ID NO: 2045)
```

βc-m1936 Target: 5'-CCAGTACACCCTTCTACTATCTCCTCC-3'  (SEQ ID NO: 3154)

```
           5'-GAGCUCCAGUACACCCUUCUACUAU^(AC-3')    (SEQ ID NO: 6482)
           3'-CUCGAGGUCAUGUGGGAAGAUGAUA_(GA-5')    (SEQ ID NO: 2046)
```

βc-m1941 Target: 5'-GAGCTCCAGTACACCCTTCTACTATCT-3'  (SEQ ID NO: 3155)

```
           5'-AAACAAUGGAAUGGUAUUGAGUCCU^(AA-3')    (SEQ ID NO: 6483)
           3'-UUUGUUACCUUACCAUAACUCAGGA_(GC-5')    (SEQ ID NO: 2047)
```

βc-m2009 Target: 5'-AAACAATGGAATGGTATTGAGTCCTCG-3'  (SEQ ID NO: 3156)

```
           5'-CUGCACAAACAAUGGAAUGGUAUUG^(cA-3')    (SEQ ID NO: 6484)
           3'-GACGUGUUUGUUACCUUACCAUAAC_(UC-5')    (SEQ ID NO: 2048)
```

βc-m2015 Target: 5'-CTGCACAAACAATGGAATGGTATTGAG-3'  (SEQ ID NO: 3157)

```
           5'-ACUGCACAAACAAUGGAAUGGUAUU^(AC-3')    (SEQ ID NO: 6485)
           3'-UGACGUGUUUGUUACCUUACCAUAA_(CU-5')    (SEQ ID NO: 2049)
```

βc-m2016 Target: 5'-ACTGCACAAACAATGGAATGGTATTGA-3'  (SEQ ID NO: 3158)

```
           5'-AAGCAACUGCACAAACAAUGGAAUG^(AC-3')    (SEQ ID NO: 6486)
           3'-UUCGUUGACGUGUUUGUUACCUUAC_(CA-5')    (SEQ ID NO: 2050)
```

βc-m2021 Target: 5'-AAGCAACTGCACAAACAATGGAATGGT-3'  (SEQ ID NO: 3159)

```
           5'-GAGAAUAAAGCAACUGCACAAACAA^(cA-3')    (SEQ ID NO: 6487)
           3'-CUCUUAUUUCGUUGACGUGUUUGUU_(AC-5')    (SEQ ID NO: 2051)
```

βc-m2028 Target: 5'-GAGAATAAAGCAACTGCACAAACAATG-3'  (SEQ ID NO: 3160)

TABLE 12-continued

Additional Selected Anti-β-catenin DsiRNAs, Blunt/Frayed Duplexes

```
       5'-UUUCAAUGGGAGAAUAAAGCAACUG^AC-3'    (SEQ ID NO: 6488)
       3'-AAAGUUACCCUCUUAUUUCGUUGAC_GU-5'    (SEQ ID NO: 2052)
```

βc-m2037 Target: 5'-TTTCAATGGGAGAATAAAGCAACTGCA-3' (SEQ ID NO: 3161)

```
       5'-UUUUCAAUGGGAGAAUAAAGCAACU^AA-3'    (SEQ ID NO: 6489)
       3'-AAAAGUUACCCUCUUAUUUCGUUGA_CG-5'    (SEQ ID NO: 2053)
```

βc-m2038 Target: 5'-TTTTCAATGGGAGAATAAAGCAACTGC-3' (SEQ ID NO: 3162)

```
       5'-AUUUUCAAUGGGAGAAUAAAGCAAC^CA-3'    (SEQ ID NO: 6490)
       3'-UAAAAGUUACCCUCUUAUUUCGUUG_AC-5'    (SEQ ID NO: 2054)
```

βc-m2039 Target: 5'-ATTTTCAATGGGAGAATAAAGCAACTG-3' (SEQ ID NO: 3163)

```
       5'-GGAUAUUUUCAAUGGGAGAAUAAAG^AC-3'    (SEQ ID NO: 6491)
       3'-CCUAUAAAAGUUACCCUCUUAUUUC_GU-5'    (SEQ ID NO: 2055)
```

βc-m2043 Target: 5'-GGATATTTTCAATGGGAGAATAAAGCA-3' (SEQ ID NO: 3164)

```
       5'-UGGAUAUUUUCAAUGGGAGAAUAAA^AA-3'    (SEQ ID NO: 6492)
       3'-ACCUAUAAAAGUUACCCUCUUAUUU_CG-5'    (SEQ ID NO: 2056)
```

βc-m2044 Target: 5'-TGGATATTTTCAATGGGAGAATAAAGC-3' (SEQ ID NO: 3165)

```
       5'-UUGGAUAUUUUCAAUGGGAGAAUAA^CA-3'    (SEQ ID NO: 6493)
       3'-AACCUAUAAAAGUUACCCUCUUAUU_UC-5'    (SEQ ID NO: 2057)
```

βc-m2045 Target: 5'-TTGGATATTTTCAATGGGAGAATAAAG-3' (SEQ ID NO: 3166)

```
       5'-CAGCUACUCUUUGGAUAUUUUCAAU^AA-3'    (SEQ ID NO: 6494)
       3'-GUCGAUGAGAAACCUAUAAAAGUUA_CC-5'    (SEQ ID NO: 2058)
```

βc-m2055 Target: 5'-CAGCTACTCTTTGGATATTTTCAATGG-3' (SEQ ID NO: 3167)

```
       5'-GCAGCUACUCUUUGGAUAUUUUCAA^CA-3'    (SEQ ID NO: 6495)
       3'-CGUCGAUGAGAAACCUAUAAAAGUU_AC-5'    (SEQ ID NO: 2059)
```

βc-m2056 Target: 5'-GCAGCTACTCTTTGGATATTTTCAATG-3' (SEQ ID NO: 3168)

```
       5'-CCGCUUCUUGUAAUCCUGUGGCUUG^CA-3'    (SEQ ID NO: 6496)
       3'-GGCGAAGAACAUUAGGACACCGAAC_AG-5'    (SEQ ID NO: 2060)
```

βc-m2231 Target: 5'-CCGCTTCTTGTAATCCTGTGGCTTGTC-3' (SEQ ID NO: 3169)

```
       5'-CCAGUCCAAGAUCUGCAGUCUCAUU^AA-3'    (SEQ ID NO: 6497)
       3'-GGUCAGGUUCUAGACGUCAGAGUAA_GG-5'    (SEQ ID NO: 2061)
```

βc-m2307 Target: 5'-CCAGTCCAAGATCTGCAGTCTCATTCC-3' (SEQ ID NO: 3170)

```
       5'-CGUAUCCACCAGAGUGAAAAGAACG^AC-3'    (SEQ ID NO: 6498)
       3'-GCAUAGGUGGUCUCACUUUUCUUGC_CA-5'    (SEQ ID NO: 2062)
```

βc-m2385 Target: 5'-CGTATCCACCAGAGTGAAAAGAACGGT-3' (SEQ ID NO: 3171)

```
       5'-CAGGCCAGCUGAUUGCUAUCACCUG^AA-3'    (SEQ ID NO: 6499)
       3'-GUCCGGUCGACUAACGAUAGUGGAC_CC-5'    (SEQ ID NO: 2063)
```

βc-m2539 Target: 5'-CAGGCCAGCTGATTGCTATCACCTGGG-3' (SEQ ID NO: 3172)

TABLE 12-continued

Additional Selected Anti-β-catenin DsiRNAs, Blunt/Frayed Duplexes

```
            5'-CGAUUUACAGGUCAGUAUCAAACCA^AA-3'    (SEQ ID NO: 6500)
            3'-GCUAAAUGUCCAGUCAUAGUUUGGU_CC-5'    (SEQ ID NO: 2064)

βc-m2562 Target: 5'-CGATTTACAGGTCAGTATCAAACCAGG-3'  (SEQ ID NO: 3173)

5'-ACGAUUUACAGGUCAGUAUCAAACC^CA-3'    (SEQ ID NO: 6501)
            3'-UGCUAAAUGUCCAGUCAUAGUUUGG_UC-5'    (SEQ ID NO: 2065)

βc-m2563 Target: 5'-ACGATTTACAGGTCAGTATCAAACCAG-3'  (SEQ ID NO: 3174)

5'-UUUCUUACCUAAAGGACGAUUUACA^AA-3'    (SEQ ID NO: 6502)
            3'-AAAGAAUGGAUUUCCUGCUAAAUGU_CC-5'    (SEQ ID NO: 2066)

βc-m2578 Target: 5'-TTTCTTACCTAAAGGACGATTTACAGG-3'  (SEQ ID NO: 3175)

5'-GCUUUCUUACCUAAAGGACGAUUUA^AC-3'    (SEQ ID NO: 6503)
            3'-CGAAAGAAUGGAUUUCCUGCUAAAU_GU-5'    (SEQ ID NO: 2067)

βc-m2580 Target: 5'-GCTTTCTTACCTAAAGGACGATTTACA-3'  (SEQ ID NO: 3176)

5'-CUUUUAUAAGCUUUCUUACCUAAAG^AC-3'    (SEQ ID NO: 6504)
            3'-GAAAAUAUUCGAAAGAAUGGAUUUC_CU-5'    (SEQ ID NO: 2068)

βc-m2589 Target: 5'-CTTTTATAAGCTTTCTTACCTAAAGGA-3'  (SEQ ID NO: 3177)

5'-GCUUUUAUAAGCUUUCUUACCUAAA^AA-3'    (SEQ ID NO: 6505)
            3'-CGAAAAUAUUCGAAAGAAUGGAUUU_CC-5'    (SEQ ID NO: 2069)

βc-m2590 Target: 5'-GCTTTTATAAGCTTTCTTACCTAAAGG-3'  (SEQ ID NO: 3178)

5'-CUGGCUUUUAUAAGCUUUCUUACCU^CC-3'    (SEQ ID NO: 6506)
            3'-GACCGAAAAUAUUCGAAAGAAUGGA_UU-5'    (SEQ ID NO: 2070)

βc-m2593 Target: 5'-CTGGCTTTTATAAGCTTTCTTACCTAA-3'  (SEQ ID NO: 3179)

5'-CCACACUGGCUUUUAUAAGCUUUCU^CC-3'    (SEQ ID NO: 6507)
            3'-GGUGUGACCGAAAAUAUUCGAAAGA_AU-5'    (SEQ ID NO: 2071)

βc-m2598 Target: 5'-CCACACTGGCTTTTATAAGCTTTCTTA-3'  (SEQ ID NO: 3180)

5'-AUUCACCCACACUGGCUUUUAUAAG^AC-3'    (SEQ ID NO: 6508)
            3'-UAAGUGGGUGUGACCGAAAAUAUUC_GA-5'    (SEQ ID NO: 2072)

βc-m2604 Target: 5'-ATTCACCCACACTGGCTTTTATAAGCT-3'  (SEQ ID NO: 3181)

5'-CCUACCAAGUCUUUCUGGAGUUCUG^AC-3'    (SEQ ID NO: 6509)
            3'-GGAUGGUUCAGAAAGACCUCAAGAC_GU-5'    (SEQ ID NO: 2073)

βc-m2644 Target: 5'-CCTACCAAGTCTTTCTGGAGTTCTGCA-3'  (SEQ ID NO: 3182)

5'-AUUUACAAACAGGCCUAAAACCAUU^AA-3'    (SEQ ID NO: 6510)
            3'-UAAAUGUUUGUCCGGAUUUUGGUAA_GG-5'    (SEQ ID NO: 2074)

βc-m2674 Target: 5'-ATTTACAAACAGGCCTAAAACCATTCC-3'  (SEQ ID NO: 3183)

5'-GAUUUACAAACAGGCCUAAAACCAU^CA-3'    (SEQ ID NO: 6511)
            3'-CUAAAUGUUUGUCCGGAUUUUGGUA_AG-5'    (SEQ ID NO: 2075)

βc-m2675 Target: 5'-GATTTACAAACAGGCCTAAAACCATTC-3'  (SEQ ID NO: 3184)
```

TABLE 12-continued

Additional Selected Anti-β-catenin DsiRNAs, Blunt/Frayed Duplexes

```
          5'-AGAUUUACAAACAGGCCUAAAACCA^CC-3'  (SEQ ID NO: 6512)
          3'-UCUAAAUGUUUGUCCGGAUUUUGGU_AA-5'  (SEQ ID NO: 2076)
```

βc-m2676 Target: 5'-AGATTTACAAACAGGCCTAAAACCATT-3' (SEQ ID NO: 3185)

```
          5'-CAUCUCCUUCCAAGGUAUGUAUCUG^CC-3'  (SEQ ID NO: 6513)
          3'-GUAGAGGAAGGUUCCAUACAUAGAC_AA-5'  (SEQ ID NO: 2077)
```

βc-m2710 Target: 5'-CATCTCCTTCCAAGGTATGTATCTGTT-3' (SEQ ID NO: 3186)

```
          5'-ACAUCUCCUUCCAAGGUAUGUAUCU^AC-3'  (SEQ ID NO: 6514)
          3'-UGUAGAGGAAGGUUCCAUACAUAGA_CC-5'  (SEQ ID NO: 2078)
```

βc-m2711 Target: 5'-ACATCTCCTTCCAAGGTATGTATCTGT-3' (SEQ ID NO: 3187)

```
          5'-ACUUCCACACAUGAACAUCUCCUUC^AC-3'  (SEQ ID NO: 6515)
          3'-UGAAGGUGUGUACUUGUAGAGGAAG_GU-5'  (SEQ ID NO: 2079)
```

βc-m2725 Target: 5'-ACTTCCACACATGAACATCTCCTTCCA-3' (SEQ ID NO: 3188)

```
          5'-GAAACUUCCACACAUGAACAUCUCC^CC-3'  (SEQ ID NO: 6516)
          3'-CUUUGAAGGUGUGUACUUGUAGAGG_AA-5'  (SEQ ID NO: 2080)
```

βc-m2728 Target: 5'-GAAACTTCCACACATGAACATCTCCTT-3' (SEQ ID NO: 3189)

```
          5'-AGAAACUUCCACACAUGAACAUCUC^AC-3'  (SEQ ID NO: 6517)
          3'-UCUUUGAAGGUGUGUACUUGUAGAG_GA-5'  (SEQ ID NO: 2081)
```

βc-m2729 Target: 5'-AGAAACTTCCACACATGAACATCTCCT-3' (SEQ ID NO: 3190)

```
          5'-GAGAAACUUCCACACAUGAACAUCU^AA-3'  (SEQ ID NO: 6518)
          3'-CUCUUUGAAGGUGUGUACUUGUAGA_GG-5'  (SEQ ID NO: 2082)
```

βc-m2730 Target: 5'-GAGAAACTTCCACACATGAACATCTCC-3' (SEQ ID NO: 3191)

```
          5'-UGAGAAACUCCCACACAUGAACAUC^CA-3'  (SEQ ID NO: 6519)
          3'-ACUCUUUGAAGGUGUGUACUUGUAG_AG-5'  (SEQ ID NO: 2083)
```

βc-m2731 Target: 5'-TGAGAAACTTCCACACATGAACATCTC-3' (SEQ ID NO: 3192)

```
          5'-CAUCAACGUGAGAAACUUCCACACA^CA-3'  (SEQ ID NO: 6520)
          3'-GUAGUUGCACUCUUUGAAGGUGUGU_AC-5'  (SEQ ID NO: 2084)
```

βc-m2739 Target: 5'-CATCAACGTGAGAAACTTCCACACATG-3' (SEQ ID NO: 3193)

```
          5'-AAACAUCAACGUGAGAAACUUCCAC^CA-3'  (SEQ ID NO: 6521)
          3'-UUUGUAGUUGCACUCUUUGAAGGUG_UG-5'  (SEQ ID NO: 2085)
```

βc-m2742 Target: 5'-AAACATCAACGTGAGAAACTTCCACAC-3' (SEQ ID NO: 3194)

```
          5'-AAAACAUCAACGUGAGAAACUUCCA^AC-3'  (SEQ ID NO: 6522)
          3'-UUUUGUAGUUGCACUCUUUGAAGGU_GU-5'  (SEQ ID NO: 2086)
```

βc-m2743 Target: 5'-AAAACATCAACGTGAGAAACTTCCACA-3' (SEQ ID NO: 3195)

```
          5'-AAAAACAUCAACGUGAGAAACUUCC^CA-3'  (SEQ ID NO: 6523)
          3'-UUUUUGUAGUUGCACUCUUUGAAGG_UG-5'  (SEQ ID NO: 2087)
```

βc-m2744 Target: 5'-AAAAACATCAACGTGAGAAACTTCCAC-3' (SEQ ID NO: 3196)

TABLE 12-continued

Additional Selected Anti-β-catenin DsiRNAs, Blunt/Frayed Duplexes

```
          5'-CAAAAACAUCAACGUGAGAAACUUCᴬᶜ-3'    (SEQ ID NO: 6524)
          3'-GUUUUUGUAGUUGCACUCUUUGAAGᴳᵤ-5'    (SEQ ID NO: 2088)

βc-m2745 Target: 5'-CAAAAACATCAACGTGAGAAACTTCCA-3'  (SEQ ID NO: 3197)

5'-GCAAAAACAUCAACGUGAGAAACUUᴬᴬ-3'    (SEQ ID NO: 6525)
          3'-CGUUUUUGUAGUUGCACUCUUUGAAᴳ_G-5'   (SEQ ID NO: 2089)

βc-m2746 Target: 5'-GCAAAAACATCAACGTGAGAAACTTCC-3'  (SEQ ID NO: 3198)

5'-UGGCAAAAACAUCAACGUGAGAAACᶜᶜ-3'    (SEQ ID NO: 6526)
          3'-ACCGUUUUUGUAGUUGCACUCUUUGᴬᴬ-5'    (SEQ ID NO: 2090)

βc-m2748 Target: 5'-TGGCAAAAACATCAACGTGAGAAACTT-3'  (SEQ ID NO: 3199)

5'-CUGCAAAAGCUGUGGCAAAAACAUCᶜᶜ-3'    (SEQ ID NO: 6527)
          3'-GACGUUUUCGACACCGUUUUUGUAGᵤᵤ-5'    (SEQ ID NO: 2091)

βc-m2760 Target: 5'-CTGCAAAAGCTGTGGCAAAAACATCAA-3'  (SEQ ID NO: 3200)

5'-GCUGCAAAAGCUGUGGCAAAAACAUᴬᶜ-3'    (SEQ ID NO: 6528)
          3'-CGACGUUUUCGACACCGUUUUUGUAᴳᵤ-5'    (SEQ ID NO: 2092)

βc-m2761 Target: 5'-GCTGCAAAAGCTGTGGCAAAAACATCA-3'  (SEQ ID NO: 3201)

5'-ACUCAUCUGAGUAUAACGCUGCAAAᶜᴬ-3'    (SEQ ID NO: 6529)
          3'-UGAGUAGACUCAUAUUGCGACGUUUᵤᶜ-5'    (SEQ ID NO: 2093)

βc-m2778 Target: 5'-ACTCATCTGAGTATAACGCTGCAAAAG-3'  (SEQ ID NO: 3202)

5'-UGAAAACAGCAAAUGUUACUCAUCUᴬᶜ-3'    (SEQ ID NO: 6530)
          3'-ACUUUUGUCGUUUACAAUGAGUAGAᶜᵤ-5'    (SEQ ID NO: 2094)

βc-m2795 Target: 5'-TGAAAACAGCAAATGTTACTCATCTGA-3'  (SEQ ID NO: 3203)

5'-UUGAAAACAGCAAAUGUUACUCAUCᶜᴬ-3'    (SEQ ID NO: 6531)
          3'-AACUUUUGUCGUUUACAAUGAGUAGᴬᶜ-5'    (SEQ ID NO: 2095)

βc-m2796 Target: 5'-TTGAAAACAGCAAATGTTACTCATCTG-3'  (SEQ ID NO: 3204)

5'-GUUGAAAACAGCAAAUGUUACUCAUᴬᶜ-3'    (SEQ ID NO: 6532)
          3'-CAACUUUUGUCGUUUACAAUGAGUAᴳᴬ-5'    (SEQ ID NO: 2096)

βc-m2797 Target: 5'-GTTGAAAACAGCAAATGTTACTCATCT-3'  (SEQ ID NO: 3205)

5'-CUAUUAAUGUUGAAAACAGCAAAUGᶜᶜ-3'    (SEQ ID NO: 6533)
          3'-GAUAAUUACAACUUUUGUCGUUUACᴬᴬ-5'    (SEQ ID NO: 2097)

βc-m2805 Target: 5'-CTATTAATGTTGAAAACAGCAAATGTT-3'  (SEQ ID NO: 3206)

5'-ACACUACAGCUGUAUAGAGAGAAAGᴬᴬ-3'    (SEQ ID NO: 6534)
          3'-UGUGAUGUCGACAUAUCUCUCUUUCᶜᴳ-5'    (SEQ ID NO: 2098)

βc-m2834 Target: 5'-ACACTACAGCTGTATAGAGAGAAAGGC-3'  (SEQ ID NO: 3207)

5'-CAGGCCAAUCACAAUGCACGUUCAGᶜᴬ-3'    (SEQ ID NO: 6535)
          3'-GUCCGGUUAGUGUUACGUGCAAGUCᵤᴳ-5'    (SEQ ID NO: 2099)

βc-m2859 Target: 5'-CAGGCCAATCACAATGCACGTTCAGAC-3'  (SEQ ID NO: 3208)
```

TABLE 12-continued

Additional Selected Anti-β-catenin DsiRNAs, Blunt/Frayed Duplexes

```
              5'-CUGUUCCCAUAGGAAACUCAGCUUG A C-3'  (SEQ ID NO: 6536)
              3'-GACAAGGGUAUCCUUUGAGUCGAAC C A-5'  (SEQ ID NO: 2100)

βc-m2946  Target: 5'-CTGTTCCCATAGGAAACTCAGCTTGGT-3'  (SEQ ID NO: 3209)

5'-CAGAACAAAAAGCGUACUUCGACUG C C-3'  (SEQ ID NO: 6537)
              3'-GUCUUGUUUUUCGCAUGAAGCUGAC A A-5'  (SEQ ID NO: 2101)

βc-m2968  Target: 5'-CAGAACAAAAAGCGTACTTCGACTGTT-3'  (SEQ ID NO: 3210)

5'-AAGGACCAGAACAAAAAGCGUACUU A A-3'  (SEQ ID NO: 6538)
              3'-UUCCUGGUCUUGUUUUUCGCAUGAA G C-5'  (SEQ ID NO: 2102)

βc-m2974  Target: 5'-AAGGACCAGAACAAAAAGCGTACTTCG-3'  (SEQ ID NO: 3211)

5'-CGACCAAAAAGGACCAGAACAAAAA A A-3'  (SEQ ID NO: 6539)
              3'-GCUGGUUUUUCCUGGUCUUGUUUUU C G-5'  (SEQ ID NO: 2103)

βc-m2982  Target: 5'-CGACCAAAAAGGACCAGAACAAAAAGC-3'  (SEQ ID NO: 3212)

5'-UCGACCAAAAAGGACCAGAACAAAA C A-3'  (SEQ ID NO: 6540)
              3'-AGCUGGUUUUUCCUGGUCUUGUUUU U C-5'  (SEQ ID NO: 2104)

βc-m2983  Target: 5'-TCGACCAAAAAGGACCAGAACAAAAG-3'  (SEQ ID NO: 3213)

5'-UUACUCCUCGACCAAAAAGGACCAG C C-3'  (SEQ ID NO: 6541)
              3'-AAUGAGGAGCUGGUUUUUCCUGGUC U U-5'  (SEQ ID NO: 2105)

βc-m2990  Target: 5'-TTACTCCTCGACCAAAAAGGACCAGAA-3'  (SEQ ID NO: 3214)

5'-AAUCCAUUUGUAUUGUUACUCCUCG C A-3'  (SEQ ID NO: 6542)
              3'-UUAGGUAAACAUAACAAUGAGGAGC U G-5'  (SEQ ID NO: 2106)

βc-m3005  Target: 5'-AATCCATTTGTATTGTTACTCCTCGAC-3'  (SEQ ID NO: 3215)

5'-AAAUCCAUUUGUAUUGUUACUCCUC A C-3'  (SEQ ID NO: 6543)
              3'-UUUAGGUAAACAUAACAAUGAGGAG C U-5'  (SEQ ID NO: 2107)

βc-m3006  Target: 5'-AAATCCATTTGTATTGTTACTCCTCGA-3'  (SEQ ID NO: 3216)

5'-CAAAUCCAUUUGUAUUGUUACUCCU A A-3'  (SEQ ID NO: 6544)
              3'-GUUUAGGUAAACAUAACAAUGAGGA G C-5'  (SEQ ID NO: 2108)

βc-m3007  Target: 5'-CAAATCCATTTGTATTGTTACTCCTCG-3'  (SEQ ID NO: 3217)

5'-CCAAAUCCAUUUGUAUUGUUACUCC C A-3'  (SEQ ID NO: 6545)
              3'-GGUUUAGGUAAACAUAACAAUGAGG A G-5'  (SEQ ID NO: 2109)

βc-m3008  Target: 5'-CCAAATCCATTTGTATTGTTACTCCTC-3'  (SEQ ID NO: 3218)

5'-UCACUCCCCAAAUCCAUUUGUAUUG C C-3'  (SEQ ID NO: 6546)
              3'-AGUGAGGGGUUUAGGUAAACAUAAC A A-5'  (SEQ ID NO: 2110)

βc-m3015  Target: 5'-TCACTCCCCAAATCCATTTGTATTGTT-3'  (SEQ ID NO: 3219)

5'-GAUCCAUUGCUCUCCAUUCUUCACU A A-3'  (SEQ ID NO: 6547)
              3'-CUAGGUAACGACACGUAAGAAGUGA C G-5'  (SEQ ID NO: 2111)

βc-m3047  Target: 5'-GATCCATTCGTGTGCATTCTTCACTGC-3'  (SEQ ID NO: 3220)
```

TABLE 12-continued

Additional Selected Anti-β-catenin DsiRNAs, Blunt/Frayed Duplexes

```
        5'-UGAUCCAUUCGUGUGCAUUCUUCAC^(CA-3')  (SEQ ID NO: 6548)
        3'-ACUAGGUAAGCACACGUAAGAAGUG_(AC-5') (SEQ ID NO: 2112)
```

βc-m3048 Target: 5'-TGATCCATTCGTGTGCATTCTTCACTG-3' (SEQ ID NO: 3221)

```
        5'-GUGAUCCAUUCGUGUGCAUUCUUCA^(AC-3')  (SEQ ID NO: 6549)
        3'-CACUAGGUAAGCACACGUAAGAAGU_(GA-5') (SEQ ID NO: 2113)
```

βc-m3049 Target: 5'-GTGATCCATTCGTGTGCATTCTTCACT-3' (SEQ ID NO: 3222)

```
        5'-UAAAACAAAGAACAAGCAAGGCUAG^(AA-3')  (SEQ ID NO: 6550)
        3'-AUUUUGUUUCUUGUUCGUUCCGAUC_(CC-5') (SEQ ID NO: 2114)
```

βc-m3093 Target: 5'-TAAAACAAAGAACAAGCAAGGCTAGGG-3' (SEQ ID NO: 3223)

```
        5'-GCACCACUACAGAUAUUAAACAAA^(AC-3')   (SEQ ID NO: 6551)
        3'-CGUGGUGAUGUCUAUAAUUUGUUU_(CU-5')  (SEQ ID NO: 2115)
```

βc-m3109 Target: 5'-GCACCACTACAGATATTAAACAAAGA-3' (SEQ ID NO: 3224)

```
        5'-CAGCACCACUACAGAUAUUAAACA^(CC-3')   (SEQ ID NO: 6552)
        3'-GUCGUGGUGAUGUCUAUAAUUUGU_(UU-5')  (SEQ ID NO: 2116)
```

βc-m3111 Target: 5'-CAGCACCACTACAGATATTAAACAAA-3' (SEQ ID NO: 3225)

```
        5'-UCAGCACCACUACAGAUAUUAAAC^(CC-3')   (SEQ ID NO: 6553)
        3'-AGUCGUGGUGAUGUCUAUAAUUUG_(UU-5')  (SEQ ID NO: 2117)
```

βc-m3112 Target: 5'-TCAGCACCACTACAGATATTAAACAA-3' (SEQ ID NO: 3226)

```
        5'-AAAAAAUAAAAGCAAGCAAAGUCAG^(AC-3')  (SEQ ID NO: 6554)
        3'-UUUUUUAUUUUCGUUCGUUUCAGUC_(GU-5') (SEQ ID NO: 2118)
```

βc-m3133 Target: 5'-AAAAAATAAAAGCAAGCAAAGTCAGCA-3' (SEQ ID NO: 3227)

```
        5'-CUGCAAAAAAUAAAAGCAAGCAAAG^(CA-3')  (SEQ ID NO: 6555)
        3'-GACGUUUUUUAUUUUCGUUCGUUUC_(AG-5') (SEQ ID NO: 2119)
```

βc-m3137 Target: 5'-CTGCAAAAAATAAAAGCAAGCAAAGTC-3' (SEQ ID NO: 3228)

```
        5'-AGUUACUGCAAAAAAUAAAAGCAAG^(AC-3')  (SEQ ID NO: 6556)
        3'-UCAAUGACGUUUUUUAUUUUCGUUC_(GU-5') (SEQ ID NO: 2120)
```

βc-m3142 Target: 5'-AGTTACTGCAAAAAATAAAGCAAGCA-3' (SEQ ID NO: 3229)

```
        5'-ACUAACAGUUACUGCAAAAAAUAAA^(CA-3')  (SEQ ID NO: 6557)
        3'-UGAUUGUCAAUGACGUUUUUUAUUU_(UC-5') (SEQ ID NO: 2121)
```

βc-m3148 Target: 5'-ACTAACAGTTACTGCAAAAAATAAAG-3' (SEQ ID NO: 3230)

```
        5'-AAACUAACAGUUACUGCAAAAAAUA^(CC-3')  (SEQ ID NO: 6558)
        3'-UUUGAUUGUCAAUGACGUUUUUUAU_(UU-5') (SEQ ID NO: 2122)
```

βc-m3150 Target: 5'-AAACTAACAGTTACTGCAAAAAATAAA-3' (SEQ ID NO: 3231)

```
        5'-AAAAACUAACAGUUACUGCAAAAAA^(CC-3')  (SEQ ID NO: 6559)
        3'-UUUUUGAUUGUCAAUGACGUUUUUU_(AU-5') (SEQ ID NO: 2123)
```

βc-m3152 Target: 5'-AAAAACTAACAGTTACTGCAAAAAATA-3' (SEQ ID NO: 3232)

TABLE 12-continued

Additional Selected Anti-β-catenin DsiRNAs, Blunt/Frayed Duplexes

```
              5'-UAAAAACUAACAGUUACUGCAAAAA^CC-3'   (SEQ ID NO: 6560)
              3'-AUUUUUGAUUGUCAAUGACGUUUUU_UA-5'  (SEQ ID NO: 2124)

βc-m3153 Target: 5'-TAAAAACTAACAGTTACTGCAAAAAAT-3' (SEQ ID NO: 3233)

5'-CUUAAAAACUAACAGUUACUGCAAA^CC-3'  (SEQ ID NO: 6561)
              3'-GAAUUUUUGAUUGUCAAUGACGUUU_UU-5'  (SEQ ID NO: 2125)

βc-m3155 Target: 5'-CTTAAAAACTAACAGTTACTGCAAAA-3'  (SEQ ID NO: 3234)

5'-ACUACUUAAAAACUAACAGUUACUGA^C-3'  (SEQ ID NO: 6562)
              3'-UGAUGAAUUUUUGAUUGUCAAUGAC_GU-5'  (SEQ ID NO: 2126)

βc-m3159 Target: 5'-ACTACTTAAAAACTAACAGTTACTGCA-3' (SEQ ID NO: 3235)

5'-ACACUACUUAAAAACUAACAGUUAC^CA-3'  (SEQ ID NO: 6563)
              3'-UGUGAUGAAUUUUUGAUUGUCAAUG_AC-5'  (SEQ ID NO: 2127)

βc-m3161 Target: 5'-ACACTACTTAAAAACTAACAGTTACTG-3' (SEQ ID NO: 3236)

5'-CAUAACACUACUUAAAAACUAACAG^CC-3'  (SEQ ID NO: 6564)
              3'-GUAUUGUGAUGAAUUUUUGAUUGUC_AA-5'  (SEQ ID NO: 2128)

βc-m3165 Target: 5'-CATAACACTACTTAAAAACTAACAGTT-3' (SEQ ID NO: 3237)

5'-ACAUAACACUACUUAAAAACUAACA^AC-3'  (SEQ ID NO: 6565)
              3'-UGUAUUGUGAUGAAUUUUUGAUUGU_CA-5'  (SEQ ID NO: 2129)

βc-m3166 Target: 5'-ACATAACACTACTTAAAAACTAACAGT-3' (SEQ ID NO: 3238)

5'-GAACAUAACACUACUUAAAAACUAA^AC-3'  (SEQ ID NO: 6566)
              3'-CUUGUAUUGUGAUGAAUUUUUGAUU_GU-5'  (SEQ ID NO: 2130)

βc-m3168 Target: 5'-GAACATAACACTACTTAAAAACTAACA-3' (SEQ ID NO: 3239)

5'-AGAACAUAACACUACUUAAAAACUA^CA-3'  (SEQ ID NO: 6567)
              3'-UCUUGUAUUGUGAUGAAUUUUUGAU_UG-5'  (SEQ ID NO: 2131)

βc-m3169 Target: 5'-AGAACATAACACTACTTAAAAACTAAC-3' (SEQ ID NO: 3240)

5'-UAGAACAUAACACUACUUAAAAACU^CC-3'  (SEQ ID NO: 6568)
              3'-AUCUUGUAUUGUGAUGAAUUUUUGA_UU-5'  (SEQ ID NO: 2132)

βc-m3170 Target: 5'-TAGAACATAACACTACTTAAAAACTAA-3' (SEQ ID NO: 3241)

5'-CUAGAACAUAACACUACUUAAAAAC^CC-3'  (SEQ ID NO: 6569)
              3'-GAUCUUGUAUUGUGAUGAAUUUUUG_AU-5'  (SEQ ID NO: 2133)

βc-m3171 Target: 5'-CTAGAACATAACACTACTTAAAAACTA-3' (SEQ ID NO: 3242)

5'-GUUCACUAGAACAUAACACUACUUA^CC-3'  (SEQ ID NO: 6570)
              3'-CAAGUGAUCUUGUAUUGUGAUGAAU_UU-5'  (SEQ ID NO: 2134)

βc-m3176 Target: 5'-GTTCACTAGAACATAACACTACTTAAA-3' (SEQ ID NO: 3243)

5'-AGGUUCACUAGAACAUAACACUACU^CC-3'  (SEQ ID NO: 6571)
              3'-UCCAAGUGAUCUUGUAUUGUGAUGA_AU-5'  (SEQ ID NO: 2135)

βc-m3178 Target: 5'-AGGTTCACTAGAACATAACACTACTTA-3' (SEQ ID NO: 3244)
```

TABLE 12-continued

Additional Selected Anti-β-catenin DsiRNAs, Blunt/Frayed Duplexes

```
        5'-CAGGUUCACUAGAACAUAACACUAC^CC-3'  (SEQ ID NO: 6572)
        3'-GUCCAAGUGAUCUUGUAUUGUGAUG_AA-5'  (SEQ ID NO: 2136)
```

βc-m3179 Target: 5'-CAGGTTCACTAGAACATAACACTACTT-3' (SEQ ID NO: 3245)

```
        5'-CCAUUACUCGGUUCUUAGAAAUCAG^CC-3'  (SEQ ID NO: 6573)
        3'-GGUAAUGAGCCAAGAAUCUUUAGUC_UU-5'  (SEQ ID NO: 2137)
```

βc-m3216 Target: 5'-CCATTACTCGGTTCTTAGAAATCAGAA-3' (SEQ ID NO: 3246)

```
        5'-ACACCAUUACUCGGUUCUUAGAAAU^AC-3'  (SEQ ID NO: 6574)
        3'-UGUGGUAAUGAGCCAAGAAUCUUUA_GU-5'  (SEQ ID NO: 2138)
```

βc-m3219 Target: 5'-ACACCATTACTCGGTTCTTAGAAATCA-3' (SEQ ID NO: 3247)

```
        5'-GUUCUACACCAUUACUCGGUUCUUA^AC-3'  (SEQ ID NO: 6575)
        3'-CAAGAUGUGGUAAUGAGCCAAGAAU_CU-5'  (SEQ ID NO: 2139)
```

βc-m3224 Target: 5'-GTTCTACACCATTACTCGGTTCTTAGA-3' (SEQ ID NO: 3248)

```
        5'-AUGAAUUAGUGUUCUACACCAUUAC^CA-3'  (SEQ ID NO: 6576)
        3'-UACUUAAUCACAAGAUGUGGUAAUG_AG-5'  (SEQ ID NO: 2140)
```

βc-m3234 Target: 5'-ATGAATTAGTGTTCTACACCATTACTC-3' (SEQ ID NO: 3249)

```
        5'-UGAUUAUGAAUUAGUGUUCUACACC^CC-3'  (SEQ ID NO: 6577)
        3'-ACUAAUACUUAAUCACAAGAUGUGG_UA-5'  (SEQ ID NO: 2141)
```

βc-m3239 Target: 5'-TGATTATGAATTAGTGTTCTACACC-3' (SEQ ID NO: 3250)

```
        5'-GUGAUUAUGAAUUAGUGUUCUACAC^AC-3'  (SEQ ID NO: 6578)
        3'-CACUAAUACUUAAUCACAAGAUGUG_GU-5'  (SEQ ID NO: 2142)
```

βc-m3240 Target: 5'-GTGATTATGAATTAGTGTTCTACACCA-3' (SEQ ID NO: 3251)

```
        5'-CGUGAUUAUGAAUUAGUGUUCUACA^AA-3'  (SEQ ID NO: 6579)
        3'-GCACUAAUACUUAAUCACAAGAUGU_GG-5'  (SEQ ID NO: 2143)
```

βc-m3241 Target: 5'-CGTGATTATGAATTAGTGTTCTACACC-3' (SEQ ID NO: 3252)

```
        5'-UUACAAUUAGCGUGAUUAUGAAUUA^AC-3'  (SEQ ID NO: 6580)
        3'-AAUGUUAAUCGCACUAAUACUUAAU_CA-5'  (SEQ ID NO: 2144)
```

βc-m3251 Target: 5'-TTACAATTAGCGTGATTATGAATTAGT-3' (SEQ ID NO: 3253)

```
        5'-AUUACAAUUAGCGUGAUUAUGAAUU^CA-3'  (SEQ ID NO: 6581)
        3'-UAAUGUUAAUCGCACUAAUACUUAA_UC-5'  (SEQ ID NO: 2145)
```

βc-m3252 Target: 5'-ATTACAATTAGCGTGATTATGAATTAG-3' (SEQ ID NO: 3254)

```
        5'-CCAGAUUACAAUUAGCGUGAUUAUG^CC-3'  (SEQ ID NO: 6582)
        3'-GGUCUAAUGUUAAUCGCACUAAUAC_UU-5'  (SEQ ID NO: 2146)
```

βc-m3256 Target: 5'-CCAGATTACAATTAGCGTGATTATGAA-3' (SEQ ID NO: 3255)

```
        5'-GUUACACGUCUCCAGAUUACAAUUA^AA-3'  (SEQ ID NO: 6583)
        3'-CAAUGUGCAGAGGUCUAAUGUUAAU_CG-5'  (SEQ ID NO: 2147)
```

βc-m3267 Target: 5'-GTTACACGTCTCCAGATTACAATTAGC-3' (SEQ ID NO: 3256)

TABLE 12-continued

Additional Selected Anti-β-catenin DsiRNAs, Blunt/Frayed Duplexes

```
        5'-AUGUUACACGUCUCCAGAUUACAAU^CC-3'   (SEQ ID NO: 6584)
        3'-UACAAUGUGCAGAGGUCUAAUGUUA_AU-5'   (SEQ ID NO: 2148)
```

βc-m3269 Target: 5'-ATGTTACACGTCTCCAGATTACAATTA-3' (SEQ ID NO: 3257)

```
        5'-GCUACACAAUGUUACACGUCUCCAG^CC-3'   (SEQ ID NO: 6585)
        3'-CGAUGUGUUACAAUGUGCAGAGGUC_UA-5'   (SEQ ID NO: 2149)
```

βc-m3277 Target: 5'-GCTACACAATGTTACACGTCTCCAGAT-3' (SEQ ID NO: 3258)

```
        5'-AGGCUACACAAUGUUACACGUCUCC^CA-3'   (SEQ ID NO: 6586)
        3'-UCCGAUGUGUUACAAUGUGCAGAGG_UC-5'   (SEQ ID NO: 2150)
```

βc-m3279 Target: 5'-AGGCTACACAATGTTACACGTCTCCAG-3' (SEQ ID NO: 3259)

```
        5'-AUACAAAAGGCUACACAAUGUUACA^AA-3'   (SEQ ID NO: 6587)
        3'-UAUGUUUUCCGAUGUGUUACAAUGU_GC-5'   (SEQ ID NO: 2151)
```

βc-m3286 Target: 5'-ATACAAAAGGCTACACAATGTTACACG-3' (SEQ ID NO: 3260)

```
        5'-UAUACAAAAGGCUACACAAUGUUAC^CA-3'   (SEQ ID NO: 6588)
        3'-AUAUGUUUUCCGAUGUGUUACAAUG_UG-5'   (SEQ ID NO: 2152)
```

βc-m3287 Target: 5'-TATACAAAAGGCTACACAATGTTACAC-3' (SEQ ID NO: 3261)

```
        5'-UAUUUAUACAAAAGGCUACACAAUG^CC-3'   (SEQ ID NO: 6589)
        3'-AUAAAUAUGUUUUCCGAUGUGUUAC_AA-5'   (SEQ ID NO: 2153)
```

βc-m3291 Target: 5'-TATTTATACAAAAGGCTACACAATGTT-3' (SEQ ID NO: 3262)

```
        5'-CUAUUUAUACAAAAGGCUACACAAU^AC-3'   (SEQ ID NO: 6590)
        3'-GAUAAAUAUGUUUUCCGAUGUGUUA_CA-5'   (SEQ ID NO: 2154)
```

βc-m3292 Target: 5'-CTATTTATACAAAAGGCTACACAATGT-3' (SEQ ID NO: 3263)

```
        5'-UGUCUAUUUAUACAAAAGGCUACAC^CC-3'   (SEQ ID NO: 6591)
        3'-ACAGAUAAAUAUGUUUUCCGAUGUG_UU-5'   (SEQ ID NO: 2155)
```

βc-m3295 Target: 5'-TGTCTATTTATACAAAAGGCTACACAA-3' (SEQ ID NO: 3264)

```
        5'-CUGUCUAUUUAUACAAAAGGCUACA^AC-3'   (SEQ ID NO: 6592)
        3'-GACAGAUAAAUAUGUUUUCCGAUGU_GU-5'   (SEQ ID NO: 2156)
```

βc-m3296 Target: 5'-CTGTCTATTTATACAAAAGGCTACACA-3' (SEQ ID NO: 3265)

```
        5'-UCUGUCUAUUUAUACAAAAGGCUAC^CA-3'   (SEQ ID NO: 6593)
        3'-AGACAGAUAAAUAUGUUUUCCGAUG_UG-5'   (SEQ ID NO: 2157)
```

βc-m3297 Target: 5'-TCTGTCTATTTATACAAAAGGCTACAC-3' (SEQ ID NO: 3266)

```
        5'-UUUCUAUCUGUCUAUUUAUACAAAA^AA-3'   (SEQ ID NO: 6594)
        3'-AAAGAUAGACAGAUAAAUAUGUUUU_CC-5'   (SEQ ID NO: 2158)
```

βc-m3303 Target: 5'-TTTCTATCTGTCTATTTATACAAAAGG-3' (SEQ ID NO: 3267)

```
        5'-AUUUCUAUCUGUCUAUUUAUACAAA^CA-3'   (SEQ ID NO: 6595)
        3'-UAAAGAUAGACAGAUAAAUAUGUUU_UC-5'   (SEQ ID NO: 2159)
```

βc-m3304 Target: 5'-ATTTCTATCTGTCTATTTATACAAAAG-3' (SEQ ID NO: 3268)

TABLE 12-continued

Additional Selected Anti-β-catenin DsiRNAs, Blunt/Frayed Duplexes

```
5'-CAUUUCUAUCUGUCUAUUUAUACAA^CC-3'  (SEQ ID NO: 6596)
3'-GUAAAGAUAGACAGAUAAAUAUGUU_U-5'   (SEQ ID NO: 2160)
```

βc-m3305 Target: 5'-CATTTCTATCTGTCTATTTATACAAAA-3' (SEQ ID NO: 3269)

```
5'-CCAUUUCUAUCUGUCUAUUUAUACA^CC-3'  (SEQ ID NO: 6597)
3'-GGUAAAGAUAGACAGAUAAAUAUGU_U-5'   (SEQ ID NO: 2161)
```

βc-m3306 Target: 5'-CCATTTCTATCTGTCTATTTATACAAA-3' (SEQ ID NO: 3270)

```
5'-CGGACCAUUUCUAUCUGUCUAUUUA^CC-3'  (SEQ ID NO: 6598)
3'-GCCUGGUAAAGAUAGACAGAUAAAU_A-5'   (SEQ ID NO: 2162)
```

βc-m3310 Target: 5'-CGGACCATTTCTATCTGTCTATTTATA-3' (SEQ ID NO: 3271)

```
5'-UCGGACCAUUUCUAUCUGUCUAUUU^CC-3'  (SEQ ID NO: 6599)
3'-AGCCUGGUAAAGAUAGACAGAUAAA_U-5'   (SEQ ID NO: 2163)
```

βc-m3311 Target: 5'-TCGGACCATTTCTATCTGTCTATTTAT-3' (SEQ ID NO: 3272)

```
5'-AAACUAAUCGGACCAUUUCUAUCUG^CA-3'  (SEQ ID NO: 6600)
3'-UUUGAUUAGCCUGGUAAAGAUAGAC_G-5'   (SEQ ID NO: 2164)
```

βc-m3318 Target: 5'-AAACTAATCGGACCATTTCTATCTGTC-3' (SEQ ID NO: 3273)

```
5'-GAAACUAAUCGGACCAUUUCUAUCU^AC-3'  (SEQ ID NO: 6601)
3'-CUUUGAUUAGCCUGGUAAAGAUAGA_A-5'   (SEQ ID NO: 2165)
```

βc-m3319 Target: 5'-GAAACTAATCGGACCATTTCTATCTGT-3' (SEQ ID NO: 3274)

```
5'-GGAAACUAAUCGGACCAUUUCUAUC^CA-3'  (SEQ ID NO: 6602)
3'-CCUUUGAUUAGCCUGGUAAAGAUAG_C-5'   (SEQ ID NO: 2166)
```

βc-m3320 Target: 5'-GGAAACTAATCGGACCATTTCTATCTG-3' (SEQ ID NO: 3275)

```
5'-AGGAAACUAAUCGGACCAUUUCUAU^AC-3'  (SEQ ID NO: 6603)
3'-UCCUUUGAUUAGCCUGGUAAAGAUA_A-5'   (SEQ ID NO: 2167)
```

βc-m3321 Target: 5'-AGGAAACTAATCGGACCATTTCTATCT-3' (SEQ ID NO: 3276)

```
5'-AUUAAAAGGAAACUAAUCGGACCA^CC-3'   (SEQ ID NO: 6604)
3'-UAAUUUUCCUUUGAUUAGCCUGGU_A-5'    (SEQ ID NO: 2168)
```

βc-m3328 Target: 5'-ATTAAAAGGAAACTAATCGGACCATT-3' (SEQ ID NO: 3277)

```
5'-AAGCAUAUUAAAAGGAAACUAAUC^AA-3'   (SEQ ID NO: 6605)
3'-UUCGUAUAAUUUUCCUUUGAUUAG_C-5'    (SEQ ID NO: 2169)
```

βc-m3334 Target: 5'-AAGCATATTAAAAGGAAACTAATCGG-3' (SEQ ID NO: 3278)

```
5'-UAAGCAUAUUAAAAGGAAACUAAU^AA-3'   (SEQ ID NO: 6606)
3'-AUUCGUAUAAUUUUCCUUUGAUUA_C-5'    (SEQ ID NO: 2170)
```

βc-m3335 Target: 5'-TAAGCATATTAAAAGGAAACTAATCG-3' (SEQ ID NO: 3279)

```
5'-AUUUUAAGCAUAUUAAAAGGAAAC^CC-3'   (SEQ ID NO: 6607)
3'-UAAAAUUCGUAUAAUUUUCCUUUG_A-5'    (SEQ ID NO: 2171)
```

βc-m3339 Target: 5'-ATTTTAAGCATATTAAAAGGAAACTA-3' (SEQ ID NO: 3280)

TABLE 12-continued

Additional Selected Anti-β-catenin DsiRNAs, Blunt/Frayed Duplexes

```
        5'-CUGCUUAUUUUAAGCAUAUUAAAAA^AA-3'   (SEQ ID NO: 6608)
        3'-GACGAAUAAAAUUCGUAUAAUUUUU_CC-5'   (SEQ ID NO: 2172)
```

βc-m3345 Target: 5'-CTGCTTATTTTAAGCATATTAAAAAGG-3' (SEQ ID NO: 3281)

```
        5'-CCUGCUUAUUUUAAGCAUAUUAAAA^CA-3'   (SEQ ID NO: 6609)
        3'-GGACGAAUAAAAUUCGUAUAAUUUU_UC-5'   (SEQ ID NO: 2173)
```

βc-m3346 Target: 5'-CCTGCTTATTTTAAGCATATTAAAAG-3' (SEQ ID NO: 3282)

```
        5'-GAUCCACCUGCUUAUUUUAAGCAUA^CC-3'   (SEQ ID NO: 6610)
        3'-CUAGGUGGACGAAUAAAAUUCGUAU_AA-5'   (SEQ ID NO: 2174)
```

βc-m3352 Target: 5'-GATCCACCTGCTTATTTTAAGCATATT-3' (SEQ ID NO: 3283)

```
        5'-CAAAAACAUGAAAUAGAUCCACCUG^AC-3'   (SEQ ID NO: 6611)
        3'-GUUUUUGUACUUUAUCUAGGUGGAC_GA-5'   (SEQ ID NO: 2175)
```

βc-m3367 Target: 5'-CAAAAACATGAAATAGATCCACCTGCT-3' (SEQ ID NO: 3284)

```
        5'-UCAAAAACAUGAAAUAGAUCCACCU^AA-3'   (SEQ ID NO: 6612)
        3'-AGUUUUUGUACUUUAUCUAGGUGGA_CG-5'   (SEQ ID NO: 2176)
```

βc-m3368 Target: 5'-TCAAAAACATGAAATAGATCCACCTGC-3' (SEQ ID NO: 3285)

```
        5'-GUUCAAAAACAUGAAAUAGAUCCAC^AC-3'   (SEQ ID NO: 6613)
        3'-CAAGUUUUUGUACUUUAUCUAGGUG_GA-5'   (SEQ ID NO: 2177)
```

βc-m3370 Target: 5'-GTTCAAAAACATGAAATAGATCCACCT-3' (SEQ ID NO: 3286)

```
        5'-UGUUCAAAAACAUGAAAUAGAUCCA^AA-3'   (SEQ ID NO: 6614)
        3'-ACAAGUUUUUGUACUUUAUCUAGGU_GG-5'   (SEQ ID NO: 2178)
```

βc-m3371 Target: 5'-TGTTCAAAAACATGAAATAGATCCACC-3' (SEQ ID NO: 3287)

```
        5'-UUGUUCAAAAACAUGAAAUAGAUCC^CA-3'   (SEQ ID NO: 6615)
        3'-AACAAGUUUUUGUACUUUAUCUAGG_UG-5'   (SEQ ID NO: 2179)
```

βc-m3372 Target: 5'-TTGTTCAAAAACATGAAATAGATCCAC-3' (SEQ ID NO: 3288)

```
        5'-AGUUUUUGUUCAAAAACAUGAAAUA^AC-3'   (SEQ ID NO: 6616)
        3'-UCAAAAACAAGUUUUUGUACUUUAU_CU-5'   (SEQ ID NO: 2180)
```

βc-m3377 Target: 5'-AGTTTTTGTTCAAAAACATGAAATAGA-3' (SEQ ID NO: 3289)

```
        5'-CGAUAAAGUUUUUGUUCAAAAACAU^AC-3'   (SEQ ID NO: 6617)
        3'-GCUAUUUCAAAAACAAGUUUUUGUA_CU-5'   (SEQ ID NO: 2181)
```

βc-m3383 Target: 5'-CGATAAAGTTTTTGTTCAAAAACATGA-3' (SEQ ID NO: 3290)

```
        5'-UAUCCCCGAUAAAGUUUUUGUUCAA^CC-3'   (SEQ ID NO: 6618)
        3'-AUAGGGGCUAUUUCAAAAACAAGUU_UU-5'   (SEQ ID NO: 2182)
```

βc-m3389 Target: 5'-TATCCCCGATAAAGTTTTTGTTCAAAA-3' (SEQ ID NO: 3291)

```
        5'-GUAUCCCCGAUAAAGUUUUUGUUCA^CC-3'   (SEQ ID NO: 6619)
        3'-CAUAGGGGCUAUUUCAAAAACAAGU_UU-5'   (SEQ ID NO: 2183)
```

βc-m3390 Target: 5'-GTATCCCCGATAAAGTTTTTGTTCAAA-3' (SEQ ID NO: 3292)

TABLE 12-continued

Additional Selected Anti-β-catenin DsiRNAs, Blunt/Frayed Duplexes

```
           5'-ACACCUCUUACUGAUUUACCCUACC^(AA)-3'  (SEQ ID NO: 6620)
           3'-UGUGGAGAAUGACUAAAUGGGAUGG_(CG)-5'  (SEQ ID NO: 2184)

βc-m3419 Target: 5'-ACACCTCTTACTGATTTACCCTACCGC-3'  (SEQ ID NO: 3293)

5'-UAACACCUCUUACUGAUUUACCCUA^(AA)-3'  (SEQ ID NO: 6621)
           3'-AUUGUGGAGAAUGACUAAAUGGGAU_(CG)-5'  (SEQ ID NO: 2185)

βc-m3421 Target: 5'-TAACACCTCTTACTGATTTACCCTACC-3'  (SEQ ID NO: 3294)

5'-AUAACACCUCUUACUGAUUUACCCU^(CA)-3'  (SEQ ID NO: 6622)
           3'-UAUUGUGGAGAAUGACUAAAUGGGA_(UG)-5'  (SEQ ID NO: 2186)

βc-m3422 Target: 5'-ATAACACCTCTTACTGATTTACCCTAC-3'  (SEQ ID NO: 3295)

5'-AAUAACACCUCUUACUGAUUUACCC^(CC)-3'  (SEQ ID NO: 6623)
           3'-UUAUUGUGGAGAAUGACUAAAUGGG_(AU)-5'  (SEQ ID NO: 2187)

βc-m3423 Target: 5'-AATAACACCTCTTACTGATTTACCCTA-3'  (SEQ ID NO: 3296)

5'-AAAUAACACCUCUUACUGAUUUACC^(AC)-3'  (SEQ ID NO: 6624)
           3'-UUUAUUGUGGAGAAUGACUAAAUGG_(GA)-5'  (SEQ ID NO: 2188)

βc-m3424 Target: 5'-AAATAACACCTCTTACTGATTTACCCT-3'  (SEQ ID NO: 3297)

5'-CAAAUAACACCUCUUACUGAUUUAC^(AA)-3'  (SEQ ID NO: 6625)
           3'-GUUUAUUGUGGAGAAUGACUAAAUG_(CG)-5'  (SEQ ID NO: 2189)

βc-m3425 Target: 5'-CAAATAACACCTCTTACTGATTTACCC-3'  (SEQ ID NO: 3298)

5'-AAGGCUCAAAUAACACCUCUUACUG^(CC)-3'  (SEQ ID NO: 6626)
           3'-UUCCGAGUUUAUUGUGGAGAAUGAC_(UA)-5'  (SEQ ID NO: 2190)

βc-m3431 Target: 5'-AAGGCTCAAATAACACCTCTTACTGAT-3'  (SEQ ID NO: 3299)

5'-AAAACAAGGCUCAAAUAACACCUCU^(CC)-3'  (SEQ ID NO: 6627)
           3'-UUUUGUUCCGAGUUUAUUGUGGAGA_(AU)-5'  (SEQ ID NO: 2191)

βc-m3436 Target: 5'-AAAACAAGGCTCAAATAACACCTCTTA-3'  (SEQ ID NO: 3300)

5'-CAAAACAAGGCUCAAAUAACACCUC^(CC)-3'  (SEQ ID NO: 6628)
           3'-GUUUUGUUCCGAGUUUAUUGUGGAG_(AA)-5'  (SEQ ID NO: 2192)

βc-m3437 Target: 5'-CAAAACAAGGCTCAAATAACACCTCTT-3'  (SEQ ID NO: 3301)

5'-CCAAAACAAGGCUCAAAUAACACCU^(AC)-3'  (SEQ ID NO: 6629)
           3'-GGUUUUGUUCCGAGUUUAUUGUGGA_(GA)-5'  (SEQ ID NO: 2193)

βc-m3438 Target: 5'-CCAAAACAAGGCTCAAATAACACCTCT-3'  (SEQ ID NO: 3302)

5'-UGUCCAAAACAAGGCUCAAAUAACA^(AA)-3'  (SEQ ID NO: 6630)
           3'-ACAGGUUUUGUUCCGAGUUUAUUGU_(CG)-5'  (SEQ ID NO: 2194)

βc-m3441 Target: 5'-TGTCCAAAACAAGGCTCAAATAACACC-3'  (SEQ ID NO: 3303)

5'-ACUGUCCAAAACAAGGCUCAAAUAA^(AC)-3'  (SEQ ID NO: 6631)
           3'-UGACAGGUUUUGUUCCGAGUUUAUU_(UG)-5'  (SEQ ID NO: 2195)

βc-m3443 Target: 5'-ACTGTCCAAAACAAGGCTCAAATAACA-3'  (SEQ ID NO: 3304)
```

TABLE 12-continued

Additional Selected Anti-β-catenin DsiRNAs, Blunt/Frayed Duplexes

```
5'-GGUAUACUGUCCAAAACAAGGCUCA^CC-3'  (SEQ ID NO: 6632)
3'-CCAUAUGACAGGUUUUGUUCCGAGU_UU-5'  (SEQ ID NO: 2196)
```

βc-m3448 Target: 5'-GGTATACTGTCCAAAACAAGGCTCAAA-3' (SEQ ID NO: 3305)

```
5'-AGGCAACUGGUAUACUGUCCAAAAC^CC-3'  (SEQ ID NO: 6633)
3'-UCCGUUGACCAUAUGACAGGUUUUG_UU-5'  (SEQ ID NO: 2197)
```

βc-m3456 Target: 5'-AGGCAACTGGTATACTGTCCAAAACAA-3' (SEQ ID NO: 3306)

```
5'-GGGAUAAAAGGCAACUGGUAUACUG^CA-3'  (SEQ ID NO: 6634)
3'-CCCUAUUUUCCGUUGACCAUAUGAC_AG-5'  (SEQ ID NO: 2198)
```

βc-m3464 Target: 5'-GGGATAAAAGGCAACTGGTATACTGTC-3' (SEQ ID NO: 3307)

```
5'-UGGGAUAAAAGGCAACUGGUAUACU^AC-3'  (SEQ ID NO: 6635)
3'-ACCCUAUUUUCCGUUGACCAUAUGA_CA-5'  (SEQ ID NO: 2199)
```

βc-m3465 Target: 5'-TGGGATAAAAGGCAACTGGTATACTGT-3' (SEQ ID NO: 3308)

```
5'-ACAACUUUGGGAUAAAAGGCAACUG^AC-3'  (SEQ ID NO: 6636)
3'-UGUUGAAACCCUAUUUUCCGUUGAC_CA-5'  (SEQ ID NO: 2200)
```

βc-m3472 Target: 5'-ACAACTTTGGGATAAAAGGCAACTGGT-3' (SEQ ID NO: 3309)

```
5'-CAACAACUUUGGGAUAAAAGGCAAC^CA-3'  (SEQ ID NO: 6637)
3'-GUUGUUGAAACCCUAUUUUCCGUUG_AC-5'  (SEQ ID NO: 2201)
```

βc-m3474 Target: 5'-CAACAACTTTGGGATAAAAGGCAACTG-3' (SEQ ID NO: 3310)

```
5'-GGUUACAACAACUUUGGGAUAAAAG^AA-3'  (SEQ ID NO: 6638)
3'-CCAAUGUUGUUGAAACCCUAUUUUC_CG-5'  (SEQ ID NO: 2202)
```

βc-m3479 Target: 5'-GGTTACAACAACTTTGGGATAAAAGGC-3' (SEQ ID NO: 3311)

```
5'-AGGUUACAACAACUUUGGGAUAAAA^AA-3'  (SEQ ID NO: 6639)
3'-UCCAAUGUUGUUGAAACCCUAUUUU_CC-5'  (SEQ ID NO: 2203)
```

βc-m3480 Target: 5'-AGGTTACAACAACTTTGGGATAAAAGG-3' (SEQ ID NO: 3312)

```
5'-CAGGUUACAACAACUUUGGGAUAAA^CA-3'  (SEQ ID NO: 6640)
3'-GUCCAAUGUUGUUGAAACCCUAUUU_UC-5'  (SEQ ID NO: 2204)
```

βc-m3481 Target: 5'-CAGGTTACAACAACTTTGGGATAAAG-3' (SEQ ID NO: 3313)

```
5'-UAUCACAGCAGGUUACAACAACUUU^AA-3'  (SEQ ID NO: 6641)
3'-AUAGUGUCGUCCAAUGUUGUUGAAA_CC-5'  (SEQ ID NO: 2205)
```

βc-m3489 Target: 5'-TATCACAGCAGGTTACAACAACTTTGG-3' (SEQ ID NO: 3314)

```
5'-GUAUCACAGCAGGUUACAACAACUU^CA-3'  (SEQ ID NO: 6642)
3'-CAUAGUGUCGUCCAAUGUUGUUGAA_AC-5'  (SEQ ID NO: 2206)
```

βc-m3490 Target: 5'-GTATCACAGCAGGTTACAACAACTTTG-3' (SEQ ID NO: 3315)

```
5'-UUGUAUCACAGCAGGUUACAACAAC^CC-3'  (SEQ ID NO: 6643)
3'-AACAUAGUGUCGUCCAAUGUUGUUG_AA-5'  (SEQ ID NO: 2207)
```

βc-m3492 Target: 5'-TTGTATCACAGCAGGTTACAACAACTT-3' (SEQ ID NO: 3316)

TABLE 12-continued

Additional Selected Anti-β-catenin DsiRNAs, Blunt/Frayed Duplexes

```
          5'-CCGCAUCUGUUGAAGCAUUGUAUCA^(AC-3')    (SEQ ID NO: 6644)
          3'-GGCGUAGACAACUUCGUAACAUAGU_(GU-5')   (SEQ ID NO: 2208)
```

βc-m3509 Target: 5'-CCGCATCTGTTGAAGCATTGTATCACA-3' (SEQ ID NO: 3317)

```
          5'-UCUGAACCAUUUCUAUAACCGCAUC^(CA-3')    (SEQ ID NO: 6645)
          3'-AGACUUGGUAAAGAUAUUGGCGUAG_(AC-5')   (SEQ ID NO: 2209)
```

βc-m3527 Target: 5'-TCTGAACCATTTCTATAACCGCATCTG-3' (SEQ ID NO: 3318)

```
          5'-UAAUUCUGAACCAUUUCUAUAACCG^(AC-3')    (SEQ ID NO: 6646)
          3'-AUUAAGACUUGGUAAAGAUAUUGGC_(GU-5')   (SEQ ID NO: 2210)
```

βc-m3531 Target: 5'-TAATTCTGAACCATTTCTATAACCGCA-3' (SEQ ID NO: 3319)

```
          5'-UUUAAUUCUGAACCAUUUCUAUAAC^(AA-3')    (SEQ ID NO: 6647)
          3'-AAAUUAAGACUUGGUAAAGAUAUUG_(GC-5')   (SEQ ID NO: 2211)
```

βc-m3533 Target: 5'-TTTAATTCTGAACCATTTCTATAACCG-3' (SEQ ID NO: 3320)

```
          5'-GUUUAAUUCUGAACCAUUUCUAUAA^(AA-3')    (SEQ ID NO: 6648)
          3'-CAAAUUAAGACUUGGUAAAGAUAUU_(GG-5')   (SEQ ID NO: 2212)
```

βc-m3534 Target: 5'-GTTTAATTCTGAACCATTTCTATAACC-3' (SEQ ID NO: 3321)

```
          5'-AGUUUAAUUCUGAACCAUUUCUAUA^(CA-3')    (SEQ ID NO: 6649)
          3'-UCAAAUUAAGACUUGGUAAAGAUAU_(UG-5')   (SEQ ID NO: 2213)
```

βc-m3535 Target: 5'-AGTTTAATTCTGAACCATTTCTATAAC-3' (SEQ ID NO: 3322)

```
          5'-AAGUUUAAUUCUGAACCAUUUCUAU^(CC-3')    (SEQ ID NO: 6650)
          3'-UUCAAAUUAAGACUUGGUAAAGAUA_(UU-5')   (SEQ ID NO: 2214)
```

βc-m3536 Target: 5'-AAGTTTAATTCTGAACCATTTCTATAA-3' (SEQ ID NO: 3323)

```
          5'-AUUAAAAGUUUAAUUCUGAACCAUU^(CA-3')    (SEQ ID NO: 6651)
          3'-UAAUUUUCAAAUUAAGACUUGGUAA_(AG-5')   (SEQ ID NO: 2215)
```

βc-m3541 Target: 5'-ATTAAAAGTTTAATTCTGAACCATTTC-3' (SEQ ID NO: 3324)

```
          5'-AAUUAAAAGUUUAAUUCUGAACCAU^(CC-3')    (SEQ ID NO: 6652)
          3'-UUAAUUUUCAAAUUAAGACUUGGUA_(AA-5')   (SEQ ID NO: 2216)
```

βc-m3542 Target: 5'-AATTAAAAGTTTAATTCTGAACCATTT-3' (SEQ ID NO: 3325)

```
          5'-UGAAUUAAAAGUUUAAUUCUGAACC^(CC-3')    (SEQ ID NO: 6653)
          3'-ACUUAAUUUUCAAAUUAAGACUUGG_(UA-5')   (SEQ ID NO: 2217)
```

βc-m3544 Target: 5'-TGAATTAAAAGTTTAATTCTGAACC-3' (SEQ ID NO: 3326)

```
          5'-UUUGAAUGAAUUAAAAGUUUAAUUC^(CA-3')    (SEQ ID NO: 6654)
          3'-AAACUUACUUAAUUUUCAAAUUAAG_(AC-5')   (SEQ ID NO: 2218)
```

βc-m3550 Target: 5'-TTTGAATGAATTAAAAGTTTAATTCTG-3' (SEQ ID NO: 3327)

```
          5'-UUUUUUUGAAUGAAUUAAAAGUUUA^(CC-3')    (SEQ ID NO: 6655)
          3'-AAAAAAACUUACUUAAUUUUCAAAU_(UA-5')   (SEQ ID NO: 2219)
```

βc-m3554 Target: 5'-TTTTTTTGAATGAATTAAAAGTTTAAT-3' (SEQ ID NO: 3328)

TABLE 12-continued

Additional Selected Anti-β-catenin DsiRNAs, Blunt/Frayed Duplexes

```
              5'-UUUUUUUUUUUGAAUGAAUUAAAAG^CC-3'    (SEQ ID NO: 6656)
              3'-AAAAAAAAAAACUUACUUAAUUUUC_A A-5'   (SEQ ID NO: 2220)
```

βc-m3558 Target:  5'-TTTTTTTTTTTGAATGAATTAAAAGTT-3'  (SEQ ID NO: 3329)

```
              5'-UUUUUUUUUUUUGAAUGAAUUAAAA^AC-3'    (SEQ ID NO: 6657)
              3'-AAAAAAAAAAAACUUACUUAAUUUU_C A-5'   (SEQ ID NO: 2221)
```

βc-m3559 Target:  5'-TTTTTTTTTTTTGAATGAATTAAAAGT-3'  (SEQ ID NO: 3330)

```
              5'-UUUUUUUUUUUUUGAAUGAAUUAAA^CA-3'    (SEQ ID NO: 6658)
              3'-AAAAAAAAAAAAACUUACUUAAUUU_U C-5'   (SEQ ID NO: 2222)
```

βc-m3560 Target:  5'-TTTTTTTTTTTTTGAATGAATTAAAAG-3'  (SEQ ID NO: 3331)

```
              5'-UUUUUUUUUUUUUUGAAUGAAUUAA^CC-3'    (SEQ ID NO: 6659)
              3'-AAAAAAAAAAAAAACUUACUUAAUU_U U-5'   (SEQ ID NO: 2223)
```

βc-m3561 Target:  5'-TTTTTTTTTTTTTTGAATGAATTAAAA-3'  (SEQ ID NO: 3332)

```
              5'-UUUUUUUUUUUUUUUGAAUGAAUUA^CC-3'    (SEQ ID NO: 6660)
              3'-AAAAAAAAAAAAAAACUUACUUAAU_U U-5'   (SEQ ID NO: 2224)
```

βc-m3562 Target:  5'-TTTTTTTTTTTTTTTGAATGAATTAAA-3'  (SEQ ID NO: 3333)

```
              5'-UUUUUUUUUUUUUUUUGAAUGAAUU^CC-3'    (SEQ ID NO: 6661)
              3'-AAAAAAAAAAAAAAAACUUACUUAA_U U-5'   (SEQ ID NO: 2225)
```

βc-m3563 Target:  5'-TTTTTTTTTTTTTTTTGAATGAATTAA-3'  (SEQ ID NO: 3334)

TABLE 13

Additional Selected Anti-β-catenin DsiRNAs, Blunt, Unfrayed Duplexes

|  |  |  |
|---|---|---|
|  | 5'-GUUGUAUGGUAUACUUCAAAUACCCUC-3' | (SEQ ID NO: 7150) |
|  | 3'-CAACAUACCAUAUGAAGUUUAUGGGAG-5' | (SEQ ID NO: 1605) |
| βc-244 Target: | 5'-GTTGTATGGTATACTTCAAATACCCTC-3' | (SEQ ID NO: 2714) |
|  | 5'-CAAAACAGUUGUAUGGUAUACUUCAAA-3' | (SEQ ID NO: 7151) |
|  | 3'-GUUUUGUCAACAUACCAUAUGAAGUUU-5' | (SEQ ID NO: 1606) |
| βc-251 Target: | 5'-CAAAACAGTTGTATGGTATACTTCAAA-3' | (SEQ ID NO: 2715) |
|  | 5'-UCAAAACAGUUGUAUGGUAUACUUCAA-3' | (SEQ ID NO: 7152) |
|  | 3'-AGUUUUGUCAACAUACCAUAUGAAGUU-5' | (SEQ ID NO: 1607) |
| βc-252 Target: | 5'-TCAAAACAGTTGTATGGTATACTTCAA-3' | (SEQ ID NO: 2716) |
|  | 5'-UUUCAAAACAGUUGUAUGGUAUACUUC-3' | (SEQ ID NO: 7153) |
|  | 3'-AAAGUUUUGUCAACAUACCAUAUGAAG-5' | (SEQ ID NO: 1608) |
| βc-254 Target: | 5'-TTTCAAAACAGTTGTATGGTATACTTC-3' | (SEQ ID NO: 2717) |
|  | 5'-UUUUCAAAACAGUUGUAUGGUAUACUU-3' | (SEQ ID NO: 7154) |
|  | 3'-AAAAGUUUUGUCAACAUACCAUAUGAA-5' | (SEQ ID NO: 1609) |
| βc-255 Target: | 5'-TTTTCAAAACAGTTGTATGGTATACTT-3' | (SEQ ID NO: 2718) |
|  | 5'-AUUUUCAAAACAGUUGUAUGGUAUACU-3' | (SEQ ID NO: 7155) |
|  | 3'-UAAAAGUUUUGUCAACAUACCAUAUGA-5' | (SEQ ID NO: 1610) |
| βc-256 Target: | 5'-ATTTTCAAAACAGTTGTATGGTATACT-3' | (SEQ ID NO: 2719) |
|  | 5'-UUGUCCACGCUGGAUUUUCAAAACAGU-3' | (SEQ ID NO: 7156) |
|  | 3'-AACAGGUGCGACCUAAAAGUUUUGUCA-5' | (SEQ ID NO: 1611) |
| βc-269 Target: | 5'-TTGTCCACGCTGGATTTTCAAAACAGT-3' | (SEQ ID NO: 2720) |
|  | 5'-AUUGUCCACGCUGGAUUUUCAAAACAG-3' | (SEQ ID NO: 7157) |
|  | 3'-UAACAGGUGCGACCUAAAAGUUUUGUC-5' | (SEQ ID NO: 1612) |
| βc-270 Target: | 5'-ATTGTCCACGCTGGATTTTCAAAACAG-3' | (SEQ ID NO: 2721) |

TABLE 13-continued

Additional Selected Anti-β-catenin DsiRNAs, Blunt, Unfrayed Duplexes

| | | |
|---|---|---|
| βc-293 Target: | 5'-CCAUCAAAUCAGCUUGAGUAGCCAUUG-3'<br>3'-GGUAGUUUAGUCGAACUCAUCGGUAAC-5'<br>5'-CCATCAAATCAGCTTGAGTAGCCATTG-3' | (SEQ ID NO: 7158)<br>(SEQ ID NO: 1613)<br>(SEQ ID NO: 2722) |
| βc-302 Target: | 5'-UGUCCAACUCCAUCAAAUCAGCUUGAG-3'<br>3'-ACAGGUUGAGGUAGUUUAGUCGAACUC-5'<br>5'-TGTCCAACTCCATCAAATCAGCTTGAG-3' | (SEQ ID NO: 7159)<br>(SEQ ID NO: 1614)<br>(SEQ ID NO: 2723) |
| βc-431 Target: | 5'-CUUCCUCAGGAUUGCCUUUACCACUCA-3'<br>3'-GAAGGAGUCCUAACGGAAAUGGUGAGU-5'<br>5'-CTTCCTCAGGATTGCCTTTACCACTCA-3' | (SEQ ID NO: 7160)<br>(SEQ ID NO: 1615)<br>(SEQ ID NO: 2724) |
| βc-432 Target: | 5'-UCUUCCUCAGGAUUGCCUUUACCACUC-3'<br>3'-AGAAGGAGUCCUAACGGAAAUGGUGAG-5'<br>5'-TCTTCCTCAGGATTGCCTTTACCACTC-3' | (SEQ ID NO: 7161)<br>(SEQ ID NO: 1616)<br>(SEQ ID NO: 2725) |
| βc-518 Target: | 5'-CAUCAAUAUCAGCUACUUGUUCUUGAG-3'<br>3'-GUAGUUAUAGUCGAUGAACAAGAACUC-5'<br>5'-CATCAATATCAGCTACTTGTTCTTGAG-3' | (SEQ ID NO: 7162)<br>(SEQ ID NO: 1617)<br>(SEQ ID NO: 2726) |
| βc-519 Target: | 5'-CCAUCAAUAUCAGCUACUUGUUCUUGA-3'<br>3'-GGUAGUUAUAGUCGAUGAACAAGAACU-5'<br>5'-CCATCAATATCAGCTACTTGTTCTTGA-3' | (SEQ ID NO: 7163)<br>(SEQ ID NO: 1618)<br>(SEQ ID NO: 2727) |
| βc-524 Target: | 5'-ACUGUCCAUCAAUAUCAGCUACUUGUU-3'<br>3'-UGACAGGUAGUUAUAGUCGAUGAACAA-5'<br>5'-ACTGTCCATCAATATCAGCTACTTGTT-3' | (SEQ ID NO: 7164)<br>(SEQ ID NO: 1619)<br>(SEQ ID NO: 2728) |
| βc-531 Target: | 5'-AUUGCAUACUGUCCAUCAAUAUCAGCU-3'<br>3'-UAACGUAUGACAGGUAGUUAUAGUCGA-5'<br>5'-ATTGCATACTGTCCATCAATATCAGCT-3' | (SEQ ID NO: 7165)<br>(SEQ ID NO: 1620)<br>(SEQ ID NO: 2729) |
| βc-537 Target: | 5'-CGAGUCAUUGCAUACUGUCCAUCAAUA-3'<br>3'-GCUCAGUAACGUAUGACAGGUAGUUAU-5'<br>5'-CGAGTCATTGCATACTGTCCATCAATA-3' | (SEQ ID NO: 7166)<br>(SEQ ID NO: 1621)<br>(SEQ ID NO: 2730) |
| βc-584 Target: | 5'-CCUCAUCUAAUGUCUCAGGGAACAUAG-3'<br>3'-GGAGUAGAUUACAGAGUCCCUUGUAUC-5'<br>5'-CCTCATCTAATGTCTCAGGGAACATAG-3' | (SEQ ID NO: 7167)<br>(SEQ ID NO: 1622)<br>(SEQ ID NO: 2731) |
| βc-680 Target: | 5'-UUACAACUGCAUGUUUCAGCAUCUGUG-3'<br>3'-AAUGUUGACGUACAAAGUCGUAGACAC-5'<br>5'-TTACAACTGCATGTTTCAGCATCTGTG-3' | (SEQ ID NO: 7168)<br>(SEQ ID NO: 1623)<br>(SEQ ID NO: 2732) |
| βc-682 Target: | 5'-GUUUACAACUGCAUGUUUCAGCAUCUG-3'<br>3'-CAAAUGUUGACGUACAAAGUCGUAGAC-5'<br>5'-GTTTACAACTGCATGTTTCAGCATCTG-3' | (SEQ ID NO: 7169)<br>(SEQ ID NO: 1624)<br>(SEQ ID NO: 2733) |
| βc-692 Target: | 5'-AGUUAAUCAAGUUUACAACUGCAUGUU-3'<br>3'-UCAAUUAGUUCAAAUGUUGACGUACAA-5'<br>5'-AGTTAATCAAGTTTACAACTGCATGTT-3' | (SEQ ID NO: 7170)<br>(SEQ ID NO: 1625)<br>(SEQ ID NO: 2734) |
| βc-698 Target: | 5'-CUUGAUAGUUAAUCAAGUUUACAACUG-3'<br>3'-GAACUAUCAAUUAGUUCAAAUGUUGAC-5'<br>5'-CTTGATAGTTAATCAAGTTTACAACTG-3' | (SEQ ID NO: 7171)<br>(SEQ ID NO: 1626)<br>(SEQ ID NO: 2735) |
| βc-707 Target: | 5'-CUGCAUCAUCUUGAUAGUUAAUCAAGU-3'<br>3'-GACGUAGUAGAACUAUCAAUUAGUUCA-5'<br>5'-CTGCATCATCTTGATAGTTAATCAAGT-3' | (SEQ ID NO: 7172)<br>(SEQ ID NO: 1627)<br>(SEQ ID NO: 2736) |
| βc-708 Target: | 5'-UCUGCAUCAUCUUGAUAGUUAAUCAAG-3'<br>3'-AGACGUAGUAGAACUAUCAAUUAGUUC-5'<br>5'-TCTGCATCATCTTGATAGTTAATCAAG-3' | (SEQ ID NO: 7173)<br>(SEQ ID NO: 1628)<br>(SEQ ID NO: 2737) |
| βc-763 Target: | 5'-CUGGUCCUCGUCAUUUAGCAGUUUUGU-3'<br>3'-GACCAGGAGCAGUAAAUCGUCAAAACA-5'<br>5'-CTGGTCCTCGTCATTTAGCAGTTTTGT-3' | (SEQ ID NO: 7174)<br>(SEQ ID NO: 1629)<br>(SEQ ID NO: 2738) |
| βc-790 Target: | 5'-CAUAACUGCAGCCUUAUUAACCACCAC-3'<br>3'-GUAUUGACGUCGGAAUAAUUGGUGGUG-5'<br>5'-CATAACTGCAGCCTTATTAACCACCAC-3' | (SEQ ID NO: 7175)<br>(SEQ ID NO: 1630)<br>(SEQ ID NO: 2739) |
| βc-791 Target: | 5'-CCAUAACUGCAGCCUUAUUAACCACCA-3'<br>3'-GGUAUUGACGUCGGAAUAAUUGGUGGU-5'<br>5'-CCATAACTGCAGCCTTATTAACCACCA-3' | (SEQ ID NO: 7176)<br>(SEQ ID NO: 1631)<br>(SEQ ID NO: 2740) |

TABLE 13-continued

Additional Selected Anti-β-catenin DsiRNAs, Blunt, Unfrayed Duplexes

| | | |
|---|---|---|
| βc-794 Target: | 5'-GGACCAUAACUGCAGCCUUAUUAACCA-3'<br>3'-CCUGGUAUUGACGUCGGAAUAAUUGGU-5'<br>5'-GGACCATAACTGCAGCCTTATTAACCA-3' | (SEQ ID NO: 7177)<br>(SEQ ID NO: 1632)<br>(SEQ ID NO: 2741) |
| βc-812 Target: | 5'-CCUUUUUAGAAAGCUGAUGGACCAUAA-3'<br>3'-GGAAAAAUCUUUCGACUACCUGGUAUU-5'<br>5'-CCTTTTTAGAAAGCTGATGGACCATAA-3' | (SEQ ID NO: 7178)<br>(SEQ ID NO: 1633)<br>(SEQ ID NO: 2742) |
| βc-873 Target: | 5'-AUGGUACGUACAAUAGCAGACACCAUC-3'<br>3'-UACCAUGCAUGUUAUCGUCUGUGGUAG-5'<br>5'-ATGGTACGTACAATAGCAGACACCATC-3' | (SEQ ID NO: 7179)<br>(SEQ ID NO: 1634)<br>(SEQ ID NO: 2743) |
| βc-890 Target: | 5'-CAUCAUUUGUAUUCUGCAUGGUACGUA-3'<br>3'-GUAGUAAACAUAAGACGUACCAUGCAU-5'<br>5'-CATCATTTGTATTCTGCATGGTACGTA-3' | (SEQ ID NO: 7180)<br>(SEQ ID NO: 1635)<br>(SEQ ID NO: 2744) |
| βc-899 Target: | 5'-CUGUUUCUACAUCAUUUGUAUUCUGCA-3'<br>3'-GACAAAGAUGUAGUAAACAUAAGACGU-5'<br>5'-CTGTTTCTACATCATTTGTATTCTGCA-3' | (SEQ ID NO: 7181)<br>(SEQ ID NO: 1636)<br>(SEQ ID NO: 2745) |
| βc-900 Target: | 5'-GCUGUUUCUACAUCAUUUGUAUUCUGC-3'<br>3'-CGACAAAGAUGUAGUAAACAUAAGACG-5'<br>5'-GCTGTTTCTACATCATTTGTATTCTGC-3' | (SEQ ID NO: 7182)<br>(SEQ ID NO: 1637)<br>(SEQ ID NO: 2746) |
| βc-909 Target: | 5'-GUACAACGAGCUGUUUCUACAUCAUUU-3'<br>3'-CAUGUUGCUCGACAAAGAUGUAGUAAA-5'<br>5'-GTACAACGAGCTGTTTCTACATCATTT-3' | (SEQ ID NO: 7183)<br>(SEQ ID NO: 1638)<br>(SEQ ID NO: 2747) |
| βc-911 Target: | 5'-CGGUACAACGAGCUGUUUCUACAUCAU-3'<br>3'-GCCAUGUUGCUCGACAAAGAUGUAGUA-5'<br>5'-CGGTACAACGAGCTGTTTCTACATC-3' | (SEQ ID NO: 7184)<br>(SEQ ID NO: 1639)<br>(SEQ ID NO: 2748) |
| βc-912 Target: | 5'-GCGGUACAACGAGCUGUUUCUACAUCA-3'<br>3'-CGCCAUGUUGCUCGACAAAGAUGUAGU-5'<br>5'-GCGGTACAACGAGCTGTTTCTACATCA-3' | (SEQ ID NO: 7185)<br>(SEQ ID NO: 1640)<br>(SEQ ID NO: 2749) |
| βc-1032 Target: | 5'-GCAUAAAACAACACAGAAUCCACUGGU-3'<br>3'-CGUAUUUUGUUGUGUCUUAGGUGACCA-5'<br>5'-GCATAAAACAACACAGAATCCACTGGT-3' | (SEQ ID NO: 7186)<br>(SEQ ID NO: 1641)<br>(SEQ ID NO: 2750) |
| βc-1034 Target: | 5'-UGGCAUAAAACAACACAGAAUCCACUG-3'<br>3'-ACCGUAUUUUGUUGUGUCUUAGGUGAC-5'<br>5'-TGGCATAAAACAACACAGAATCCACTG-3' | (SEQ ID NO: 7187)<br>(SEQ ID NO: 1642)<br>(SEQ ID NO: 2751) |
| βc-1035 Target: | 5'-AUGGCAUAAAACAACACAGAAUCCACU-3'<br>3'-UACCGUAUUUUGUUGUGUCUUAGGUGA-5'<br>5'-ATGGCATAAAACAACACAGAATCCACT-3' | (SEQ ID NO: 7188)<br>(SEQ ID NO: 1643)<br>(SEQ ID NO: 2752) |
| βc-1076 Target: | 5'-UAGCUCCUUCUUGAUGUAAUAAAAGGU-3'<br>3'-AUCGAGGAAGAACUACAUUAUUUUCCA-5'<br>5'-TAGCTCCTTCTTGATGTAATAAAAGGT-3' | (SEQ ID NO: 7189)<br>(SEQ ID NO: 1644)<br>(SEQ ID NO: 2753) |
| βc-1077 Target: | 5'-UUAGCUCCUUCUUGAUGUAAUAAAAGG-3'<br>3'-AAUCGAGGAAGAACUACAUUAUUUUCC-5'<br>5'-TTAGCTCCTTCTTGATGTAATAAAAGG-3' | (SEQ ID NO: 7190)<br>(SEQ ID NO: 1645)<br>(SEQ ID NO: 2754) |
| βc-1144 Target: | 5'-UUUAACAUUUGUUUUGUUGAGCAAGGC-3'<br>3'-AAAUUGUAAACAAAACAACUCGUUCCG-5'<br>5'-TTTAACATTTGTTTTGTTGAGCAAGGC-3' | (SEQ ID NO: 7191)<br>(SEQ ID NO: 1646)<br>(SEQ ID NO: 2755) |
| βc-1154 Target: | 5'-UAGCCAAGAAUUUAACAUUUGUUUUGU-3'<br>3'-AUCGGUUCUUAAAUUGUAAACAAAACA-5'<br>5'-TAGCCAAGAATTTAACATTTGTTTTGT-3' | (SEQ ID NO: 7192)<br>(SEQ ID NO: 1647)<br>(SEQ ID NO: 2756) |
| βc-1159 Target: | 5'-CGUAAUAGCCAAGAAUUUAACAUUUGU-3'<br>3'-GCAUUAUCGGUUCUUAAAUUGUAAACA-5'<br>5'-CGTAATAGCCAAGAATTTAACATTTGT-3' | (SEQ ID NO: 7193)<br>(SEQ ID NO: 1648)<br>(SEQ ID NO: 2757) |
| βc-1160 Target: | 5'-UCGUAAUAGCCAAGAAUUUAACAUUUG-3'<br>3'-AGCAUUAUCGGUUCUUAAAUUGUAAAC-5'<br>5'-TCGTAATAGCCAAGAATTTAACATTTG-3' | (SEQ ID NO: 7194)<br>(SEQ ID NO: 1649)<br>(SEQ ID NO: 2758) |
| βc-1185 Target: | 5'-UAAGCUAAAAUUUGAAGGCAGUCUGUC-3'<br>3'-AUUCGAUUUUAAACUUCCGUCAGACAG-5'<br>5'-TAAGCTAAAATTTGAAGGCAGTCTGTC-3' | (SEQ ID NO: 7195)<br>(SEQ ID NO: 1650)<br>(SEQ ID NO: 2759) |

TABLE 13-continued

Additional Selected Anti-β-catenin DsiRNAs, Blunt, Unfrayed Duplexes

| | | |
|---|---|---|
| βc-1260 Target: | 5'-UAGGUCCUCAUUAUAUUUACUAAAGCU-3'<br>3'-AUCCAGGAGUAAUAUAAAUGAUUUCGA-5'<br>5'-TAGGTCCTCATTATATTTACTAAAGCT-3' | (SEQ ID NO: 7196)<br>(SEQ ID NO: 1651)<br>(SEQ ID NO: 2760) |
| βc-1265 Target: | 5'-AAGUAUAGGUCCUCAUUAUAUUUACUA-3'<br>3'-UUCAUAUCCAGGAGUAAUAUAAAUGAU-5'<br>5'-AAGTATAGGTCCTCATTATATTTACTA-3' | (SEQ ID NO: 7197)<br>(SEQ ID NO: 1652)<br>(SEQ ID NO: 2761) |
| βc-1266 Target: | 5'-UAAGUAUAGGUCCUCAUUAUAUUUACU-3'<br>3'-AUUCAUAUCCAGGAGUAAUAUAAAUGA-5'<br>5'-TAAGTATAGGTCCTCATTATATTTACT-3' | (SEQ ID NO: 7198)<br>(SEQ ID NO: 1653)<br>(SEQ ID NO: 2762) |
| βc-1274 Target: | 5'-GUUUUUCGUAAGUAUAGGUCCUCAUUA-3'<br>3'-CAAAAAGCAUUCAUAUCCAGGAGUAAU-5'<br>5'-GTTTTTCGTAAGTATAGGTCCTCATTA-3' | (SEQ ID NO: 7199)<br>(SEQ ID NO: 1654)<br>(SEQ ID NO: 2763) |
| βc-1275 Target: | 5'-AGUUUUUCGUAAGUAUAGGUCCUCAUU-3'<br>3'-UCAAAAAGCAUUCAUAUCCAGGAGUAA-5'<br>5'-AGTTTTTCGTAAGTATAGGTCCTCATT-3' | (SEQ ID NO: 7200)<br>(SEQ ID NO: 1655)<br>(SEQ ID NO: 2764) |
| βc-1276 Target: | 5'-UAGUUUUUCGUAAGUAUAGGUCCUCAU-3'<br>3'-AUCAAAAAGCAUUCAUAUCCAGGAGUA-5'<br>5'-TAGTTTTTCGTAAGTATAGGTCCTC-3' | (SEQ ID NO: 7201)<br>(SEQ ID NO: 1656)<br>(SEQ ID NO: 2765) |
| βc-1277 Target: | 5'-GUAGUUUUUCGUAAGUAUAGGUCCUCA-3'<br>3'-CAUCAAAAAGCAUUCAUAUCCAGGAGU-5'<br>5'-GTAGTTTTTCGTAAGTATAGGTCCTCA-3' | (SEQ ID NO: 7202)<br>(SEQ ID NO: 1657)<br>(SEQ ID NO: 2766) |
| βc-1287 Target: | 5'-GUGGUCCACAGUAGUUUUUCGUAAGUA-3'<br>3'-CACCAGGUGUCAUCAAAAAGCAUUCAU-5'<br>5'-GTGGTCCACAGTAGTTTTTCGTAAGTA-3' | (SEQ ID NO: 7203)<br>(SEQ ID NO: 1658)<br>(SEQ ID NO: 2767) |
| βc-1344 Target: | 5'-UCUACAAUAGCCGGCUUAUUACUAGAG-3'<br>3'-AGAUGUUAUCGGCCGAAUAAUGAUCUC-5'<br>5'-TCTACAATAGCCGGCTTATTACTAGAG-3' | (SEQ ID NO: 7204)<br>(SEQ ID NO: 1659)<br>(SEQ ID NO: 2768) |
| βc-1346 Target: | 5'-CUUCUACAAUAGCCGGCUUAUUACUAG-3'<br>3'-GAAGAUGUUAUCGGCCGAAUAAUGAUC-5'<br>5'-CTTCTACAATAGCCGGCTTATTACTAG-3' | (SEQ ID NO: 7205)<br>(SEQ ID NO: 1660)<br>(SEQ ID NO: 2769) |
| βc-1371 Target: | 5'-AGUCCUAAAGCUUGCAUUCCACCAGCU-3'<br>3'-UCAGGAUUUCGAACGUAAGGUGGUCGA-5'<br>5'-AGTCCTAAAGCTTGCATTCCACCAGCT-3' | (SEQ ID NO: 7206)<br>(SEQ ID NO: 1661)<br>(SEQ ID NO: 2770) |
| βc-1372 Target: | 5'-AAGUCCUAAAGCUUGCAUUCCACCAGC-3'<br>3'-UUCAGGAUUUCGAACGUAAGGUGGUCG-5'<br>5'-AAGTCCTAAAGCTTGCATTCCACCAGC-3' | (SEQ ID NO: 7207)<br>(SEQ ID NO: 1662)<br>(SEQ ID NO: 2771) |
| βc-1373 Target: | 5'-GAAGUCCUAAAGCUUGCAUUCCACCAG-3'<br>3'-CUUCAGGAUUUCGAACGUAAGGUGGUC-5'<br>5'-GAAGTCCTAAAGCTTGCATTCCACCAG-3' | (SEQ ID NO: 7208)<br>(SEQ ID NO: 1663)<br>(SEQ ID NO: 2772) |
| βc-1410 Target: | 5'-CAGUUCUGAACAAGACGUUGACUUGGA-3'<br>3'-GUCAAGACUUGUUCUGCAACUGAACCU-5'<br>5'-CAGTTCTGAACAAGACGTTGACTTGGA-3' | (SEQ ID NO: 7209)<br>(SEQ ID NO: 1664)<br>(SEQ ID NO: 2773) |
| βc-1411 Target: | 5'-ACAGUUCUGAACAAGACGUUGACUUGG-3'<br>3'-UGUCAAGACUUGUUCUGCAACUGAACC-5'<br>5'-ACAGTTCTGAACAAGACGTTGACTTGG-3' | (SEQ ID NO: 7210)<br>(SEQ ID NO: 1665)<br>(SEQ ID NO: 2774) |
| βc-1421 Target: | 5'-GAGUCCAAAGACAGUUCUGAACAAGAC-3'<br>3'-CUCAGGUUUCUGUCAAGACUUGUUCUG-5'<br>5'-GAGTCCAAAGACAGTTCTGAACAAGAC-3' | (SEQ ID NO: 7211)<br>(SEQ ID NO: 1666)<br>(SEQ ID NO: 2775) |
| βc-1458 Target: | 5'-CCUUCCUGUUUAGUUGCAGCAUCUGAA-3'<br>3'-GGAAGGACAAAUCAACGUCGUAGACUU-5'<br>5'-CCTTCCTGTTTAGTTGCAGCATCTGAA-3' | (SEQ ID NO: 7212)<br>(SEQ ID NO: 1667)<br>(SEQ ID NO: 2776) |
| βc-1517 Target: | 5'-CCACAUUUAUAUCAUCUGAACCCAGAA-3'<br>3'-GGUGUAAAUAUAGUAGACUUGGGUCUU-5'<br>5'-CCACATTTATATCATCTGAACCCAGAA-3' | (SEQ ID NO: 7213)<br>(SEQ ID NO: 1668)<br>(SEQ ID NO: 2777) |
| βc-1520 Target: | 5'-UGACCACAUUUAUAUCAUCUGAACCCA-3'<br>3'-ACUGGUGUAAAUAUAGUAGACUUGGGU-5'<br>5'-TGACCACATTTATATCATCTGAACCCA-3' | (SEQ ID NO: 7214)<br>(SEQ ID NO: 1669)<br>(SEQ ID NO: 2778) |

TABLE 13-continued

Additional Selected Anti-β-catenin DsiRNAs, Blunt, Unfrayed Duplexes

| | | |
|---|---|---|
| βc-1529 Target: | 5'-CUGCACAGGUGACCACAUUUAUAUCAU-3'<br>3'-GACGUGUCCACUGGUGUAAAUAUAGUA-5'<br>5'-CTGCACAGGTGACCACATTTATATC-3' | (SEQ ID NO: 7215)<br>(SEQ ID NO: 1670)<br>(SEQ ID NO: 2779) |
| βc-1530 Target: | 5'-GCUGCACAGGUGACCACAUUUAUAUCA-3'<br>3'-CGACGUGUCCACUGGUGUAAAUAUAGU-5'<br>5'-GCTGCACAGGTGACCACATTTATATCA-3' | (SEQ ID NO: 7216)<br>(SEQ ID NO: 1671)<br>(SEQ ID NO: 2780) |
| βc-1558 Target: | 5'-AUUGCAAGUGAGGUUAGAAAGAAUUCC-3'<br>3'-UAACGUUCACUCCAAUCUUUCUUAAGG-5'<br>5'-ATTGCAAGTGAGGTTAGAAAGAATTCC-3' | (SEQ ID NO: 7217)<br>(SEQ ID NO: 1672)<br>(SEQ ID NO: 2781) |
| βc-1566 Target: | 5'-UUAUAAUUAUUGCAAGUGAGGUUAGAA-3'<br>3'-AAUAUUAAUAACGUUCACUCCAAUCUU-5'<br>5'-TTATAATTATTGCAAGTGAGGTTAGAA-3' | (SEQ ID NO: 7218)<br>(SEQ ID NO: 1673)<br>(SEQ ID NO: 2782) |
| βc-1579 Target: | 5'-CAUCAUCUUGUUCUUAUAAUUAUUGCA-3'<br>3'-GUAGUAGAACAAGAAUAUUAAUAACGU-5'<br>5'-CATCATCTTGTTCTTATAATTATTGCA-3' | (SEQ ID NO: 7219)<br>(SEQ ID NO: 1674)<br>(SEQ ID NO: 2783) |
| βc-1580 Target: | 5'-CCAUCAUCUUGUUCUUAUAAUUAUUGC-3'<br>3'-GGUAGUAGAACAAGAAUAUUAAUAACG-5'<br>5'-CCATCATCTTGTTCTTATAATTATTGC-3' | (SEQ ID NO: 7220)<br>(SEQ ID NO: 1675)<br>(SEQ ID NO: 2784) |
| βc-1583 Target: | 5'-AGACCAUCAUCUUGUUCUUAUAAUUAU-3'<br>3'-UCUGGUAGUAGAACAAGAAUAUUAAUA-5'<br>5'-AGACCATCATCTTGTTCTTATAATTAT-3' | (SEQ ID NO: 7221)<br>(SEQ ID NO: 1676)<br>(SEQ ID NO: 2785) |
| βc-1585 Target: | 5'-GCAGACCAUCAUCUUGUUCUUAUAAUU-3'<br>3'-CGUCUGGUAGUAGAACAAGAAUAUUAA-5'<br>5'-GCAGACCATCATCTTGTTCTTATAATT-3' | (SEQ ID NO: 7222)<br>(SEQ ID NO: 1677)<br>(SEQ ID NO: 2786) |
| βc-1808 Target: | 5'-UCAAUCCAACAGUAGCCUUUAUCAGAG-3'<br>3'-AGUUAGGUUGUCAUCGGAAAUAGUCUC-5'<br>5'-TCAATCCAACAGTAGCCTTTATCAGAG-3' | (SEQ ID NO: 7223)<br>(SEQ ID NO: 1678)<br>(SEQ ID NO: 2787) |
| βc-1813 Target: | 5'-UCGAAUCAAUCCAACAGUAGCCUUUAU-3'<br>3'-AGCUUAGUUAGGUUGUCAUCGGAAAUA-5'<br>5'-TCGAATCAATCCAACAGTAGCCTTTAT-3' | (SEQ ID NO: 7224)<br>(SEQ ID NO: 1679)<br>(SEQ ID NO: 2788) |
| βc-1955 Target: | 5'-CCUCCACAAAUUGCUGCUGUGUCCCAC-3'<br>3'-GGAGGUGUUUAACGACGACACAGGGUG-5'<br>5'-CCTCCACAAATTGCTGCTGTGTCCCAC-3' | (SEQ ID NO: 7225)<br>(SEQ ID NO: 1680)<br>(SEQ ID NO: 2789) |
| βc-1989 Target: | 5'-GUACAACCUUCAACUAUUUCUUCCAUG-3'<br>3'-CAUGUUGGAAGUUGAUAAAGAAGGUAC-5'<br>5'-GTACAACCTTCAACTATTTCTTCCATG-3' | (SEQ ID NO: 7226)<br>(SEQ ID NO: 1681)<br>(SEQ ID NO: 2790) |
| βc-1990 Target: | 5'-GGUACAACCUUCAACUAUUUCUUCCAU-3'<br>3'-CCAUGUUGGAAGUUGAUAAAGAAGGUA-5'<br>5'-GGTACAACCTTCAACTATTTCTTCC-3' | (SEQ ID NO: 7227)<br>(SEQ ID NO: 1682)<br>(SEQ ID NO: 2791) |
| βc-1991 Target: | 5'-CGGUACAACCUUCAACUAUUUCUUCCA-3'<br>3'-GCCAUGUUGGAAGUUGAUAAAGAAGGU-5'<br>5'-CGGTACAACCTTCAACTATTTCTTCCA-3' | (SEQ ID NO: 7228)<br>(SEQ ID NO: 1683)<br>(SEQ ID NO: 2792) |
| βc-1992 Target: | 5'-CCGGUACAACCUUCAACUAUUUCUUCC-3'<br>3'-GGCCAUGUUGGAAGUUGAUAAAGAAGG-5'<br>5'-CCGGTACAACCTTCAACTATTTCTTCC-3' | (SEQ ID NO: 7229)<br>(SEQ ID NO: 1684)<br>(SEQ ID NO: 2793) |
| βc-1997 Target: | 5'-GGGCUCCGGUACAACCUUCAACUAUUU-3'<br>3'-CCCGAGGCCAUGUUGGAAGUUGAUAAA-5'<br>5'-GGGCTCCGGTACAACCTTCAACTATTT-3' | (SEQ ID NO: 7230)<br>(SEQ ID NO: 1685)<br>(SEQ ID NO: 2794) |
| βc-2036 Target: | 5'-UAACAAUUCGGUUGUGAACAUCCCGAG-3'<br>3'-AUUGUUAAGCCAACACUUGUAGGGCUC-5'<br>5'-TAACAATTCGGTTGTGAACATCCCGAG-3' | (SEQ ID NO: 7231)<br>(SEQ ID NO: 1686)<br>(SEQ ID NO: 2795) |
| βc-2037 Target: | 5'-AUAACAAUUCGGUUGUGAACAUCCCGA-3'<br>3'-UAUUGUUAAGCCAACACUUGUAGGGCU-5'<br>5'-ATAACAATTCGGTTGTGAACATCCCGA-3' | (SEQ ID NO: 7232)<br>(SEQ ID NO: 1687)<br>(SEQ ID NO: 2796) |
| βc-2038 Target: | 5'-GAUAACAAUUCGGUUGUGAACAUCCCG-3'<br>3'-CUAUUGUUAAGCCAACACUUGUAGGGC-5'<br>5'-GATAACAATTCGGTTGTGAACATCCCG-3' | (SEQ ID NO: 7233)<br>(SEQ ID NO: 1688)<br>(SEQ ID NO: 2797) |
| | 5'-UGAUAACAAUUCGGUUGUGAACAUCCC-3' | (SEQ ID NO: 7234) |

TABLE 13-continued

Additional Selected Anti-β-catenin DsiRNAs, Blunt, Unfrayed Duplexes

| | | |
|---|---|---|
| βc-2039 Target: | 3'-ACUAUUGUUAAGCCAACACUUGUAGGG-5'<br>5'-TGATAACAATTCGGTTGTGAACATCCC-3' | (SEQ ID NO: 1689)<br>(SEQ ID NO: 2798) |
| βc-2040 Target: | 5'-CUGAUAACAAUUCGGUUGUGAACAUCC-3'<br>3'-GACUAUUGUUAAGCCAACACUUGUAGG-5'<br>5'-CTGATAACAATTCGGTTGTGAACATCC-3' | (SEQ ID NO: 7235)<br>(SEQ ID NO: 1690)<br>(SEQ ID NO: 2799) |
| βc-2041 Target: | 5'-UCUGAUAACAAUUCGGUUGUGAACAUC-3'<br>3'-AGACUAUUGUUAAGCCAACACUUGUAG-5'<br>5'-TCTGATAACAATTCGGTTGTGAACATC-3' | (SEQ ID NO: 7236)<br>(SEQ ID NO: 1691)<br>(SEQ ID NO: 2800) |
| βc-2052 Target: | 5'-GUAUUUAGUCCUCUGAUAACAAUUCGG-3'<br>3'-CAUAAAUCAGGAGACUAUUGUUAAGCC-5'<br>5'-GTATTTAGTCCTCTGATAACAATTCGG-3' | (SEQ ID NO: 7237)<br>(SEQ ID NO: 1692)<br>(SEQ ID NO: 2801) |
| βc-2053 Target: | 5'-GGUAUUUAGUCCUCUGAUAACAAUUCG-3'<br>3'-CCAUAAAUCAGGAGACUAUUGUUAAGC-5'<br>5'-GGTATTTAGTCCTCTGATAACAATTCG-3' | (SEQ ID NO: 7238)<br>(SEQ ID NO: 1693)<br>(SEQ ID NO: 2802) |
| βc-2054 Target: | 5'-UGGUAUUUAGUCCUCUGAUAACAAUUC-3'<br>3'-ACCAUAAAUCAGGAGACUAUUGUUAAG-5'<br>5'-TGGTATTTAGTCCTCTGATAACAATTC-3' | (SEQ ID NO: 7239)<br>(SEQ ID NO: 1694)<br>(SEQ ID NO: 2803) |
| βc-2055 Target: | 5'-AUGGUAUUUAGUCCUCUGAUAACAAUU-3'<br>3'-UACCAUAAAUCAGGAGACUAUUGUUAA-5'<br>5'-ATGGTATTTAGTCCTCTGATAACAATT-3' | (SEQ ID NO: 7240)<br>(SEQ ID NO: 1695)<br>(SEQ ID NO: 2804) |
| βc-2065 Target: | 5'-AAACAAUGGAAUGGUAUUUAGUCCUCU-3'<br>3'-UUUGUUACCUUACCAUAAAUCAGGAGA-5'<br>5'-AAACAATGGAATGGTATTTAGTCCTCT-3' | (SEQ ID NO: 7241)<br>(SEQ ID NO: 1696)<br>(SEQ ID NO: 2805) |
| βc-2069 Target: | 5'-GCACAAACAAUGGAAUGGUAUUUAGUC-3'<br>3'-CGUGUUUGUUACCUUACCAUAAAUCAG-5'<br>5'-GCACAAACAATGGAATGGTATTTAGTC-3' | (SEQ ID NO: 7242)<br>(SEQ ID NO: 1697)<br>(SEQ ID NO: 2806) |
| βc-2071 Target: | 5'-CUGCACAAACAAUGGAAUGGUAUUUAG-3'<br>3'-GACGUGUUUGUUACCUUACCAUAAAUC-5'<br>5'-CTGCACAAACAATGGAATGGTATTTAG-3' | (SEQ ID NO: 7243)<br>(SEQ ID NO: 1698)<br>(SEQ ID NO: 2807) |
| βc-2072 Target: | 5'-GCUGCACAAACAAUGGAAUGGUAUUUA-3'<br>3'-CGACGUGUUUGUUACCUUACCAUAAAU-5'<br>5'-GCTGCACAAACAATGGAATGGTATTTA-3' | (SEQ ID NO: 7244)<br>(SEQ ID NO: 1699)<br>(SEQ ID NO: 2808) |
| βc-2111 Target: | 5'-CAGCUACUCUUUGGAUGUUUUCAAUGG-3'<br>3'-GUCGAUGAGAAACCUACAAAAGUUACC-5'<br>5'-CAGCTACTCTTTGGATGTTTTCAATGG-3' | (SEQ ID NO: 7245)<br>(SEQ ID NO: 1700)<br>(SEQ ID NO: 2809) |
| βc-2112 Target: | 5'-GCAGCUACUCUUUGGAUGUUUUCAAUG-3'<br>3'-CGUCGAUGAGAAACCUACAAAAGUUAC-5'<br>5'-GCAGCTACTCTTTGGATGTTTTCAATG-3' | (SEQ ID NO: 7246)<br>(SEQ ID NO: 1701)<br>(SEQ ID NO: 2810) |
| βc-2168 Target: | 5'-CAGCUUCAAUAGCUUCUGCAGCUUCCU-3'<br>3'-GUCGAAGUUAUCGAAGACGUCGAAGGA-5'<br>5'-CAGCTTCAATAGCTTCTGCAGCTTCCT-3' | (SEQ ID NO: 7247)<br>(SEQ ID NO: 1702)<br>(SEQ ID NO: 2811) |
| βc-2175 Target: | 5'-GCUCCCUCAGCUUCAAUAGCUUCUGCA-3'<br>3'-CGAGGGAGUCGAAGUUAUCGAAGACGU-5'<br>5'-GCTCCCTCAGCTTCAATAGCTTCTGCA-3' | (SEQ ID NO: 7248)<br>(SEQ ID NO: 1703)<br>(SEQ ID NO: 2812) |
| βc-2177 Target: | 5'-UGGCUCCCUCAGCUUCAAUAGCUUCUG-3'<br>3'-ACCGAGGGAGUCGAAGUUAUCGAAGAC-5'<br>5'-TGGCTCCCTCAGCTTCAATAGCTTCTG-3' | (SEQ ID NO: 7249)<br>(SEQ ID NO: 1704)<br>(SEQ ID NO: 2813) |
| βc-2214 Target: | 5'-UCAUUCCUAGAGUGAAGUAACUCUGUC-3'<br>3'-AGUAAGGAUCUCACUUCAUUGAGACAG-5'<br>5'-TCATTCCTAGAGTGAAGTAACTCTGTC-3' | (SEQ ID NO: 7250)<br>(SEQ ID NO: 1705)<br>(SEQ ID NO: 2814) |
| βc-2216 Target: | 5'-CUUCAUUCCUAGAGUGAAGUAACUCUG-3'<br>3'-GAAGUAAGGAUCUCACUUCAUUGAGAC-5'<br>5'-CTTCATTCCTAGAGTGAAGTAACTCTG-3' | (SEQ ID NO: 7251)<br>(SEQ ID NO: 1706)<br>(SEQ ID NO: 2815) |
| βc-2217 Target: | 5'-CCUUCAUUCCUAGAGUGAAGUAACUCU-3'<br>3'-GGAAGUAAGGAUCUCACUUCAUUGAGA-5'<br>5'-CCTTCATTCCTAGAGTGAAGTAACTCT-3' | (SEQ ID NO: 7252)<br>(SEQ ID NO: 1707)<br>(SEQ ID NO: 2816) |

TABLE 13-continued

Additional Selected Anti-β-catenin DsiRNAs, Blunt, Unfrayed Duplexes

| | | |
|---|---|---|
| βc-2264 Target: | 5'-UGUCCUCAGACAUUCGGAACAAAACAG-3'<br>3'-ACAGGAGUCUGUAAGCCUUGUUUUGUC-5'<br>5'-TGTCCTCAGACATTCGGAACAAAACAG-3' | (SEQ ID NO: 7253)<br>(SEQ ID NO: 1708)<br>(SEQ ID NO: 2817) |
| βc-2266 Target: | 5'-CUUGUCCUCAGACAUUCGGAACAAAAC-3'<br>3'-GAACAGGAGUCUGUAAGCCUUGUUUUG-5'<br>5'-CTTGTCCTCAGACATTCGGAACAAAAC-3' | (SEQ ID NO: 7254)<br>(SEQ ID NO: 1709)<br>(SEQ ID NO: 2818) |
| βc-2287 Target: | 5'-CCGUUUCUUGUAAUCUUGUGGCUUGUC-3'<br>3'-GGCAAAGAACAUUAGAACACCGAACAG-5'<br>5'-CCGTTTCTTGTAATCTTGTGGCTTGTC-3' | (SEQ ID NO: 7255)<br>(SEQ ID NO: 1710)<br>(SEQ ID NO: 2819) |
| βc-2295 Target: | 5'-ACUGAAAGCCGUUUCUUGUAAUCUUGU-3'<br>3'-UGACUUUCGGCAAAGAACAUUAGAACA-5'<br>5'-ACTGAAAGCCGTTTCTTGTAATCTTGT-3' | (SEQ ID NO: 7256)<br>(SEQ ID NO: 1711)<br>(SEQ ID NO: 2820) |
| βc-2302 Target: | 5'-CAGCUCAACUGAAAGCCGUUUCUUGUA-3'<br>3'-GUCGAGUUGACUUUCGGCAAAGAACAU-5'<br>5'-CAGCTCAACTGAAAGCCGTTTCTTGTA-3' | (SEQ ID NO: 7257)<br>(SEQ ID NO: 1712)<br>(SEQ ID NO: 2821) |
| βc-2363 Target: | 5'-CAAGUCCAAGAUCAGCAGUCUCAUUCC-3'<br>3'-GUUCAGGUUCUAGUCGUCAGAGUAAGG-5'<br>5'-CAAGTCCAAGATCAGCAGTCTCATTCC-3' | (SEQ ID NO: 7258)<br>(SEQ ID NO: 1713)<br>(SEQ ID NO: 2822) |
| βc-2373 Target: | 5'-GCACCAAUAUCAAGUCCAAGAUCAGCA-3'<br>3'-CGUGGUUAUAGUUCAGGUUCUAGUCGU-5'<br>5'-GCACCAATATCAAGTCCAAGATCAGCA-3' | (SEQ ID NO: 7259)<br>(SEQ ID NO: 1714)<br>(SEQ ID NO: 2823) |
| βc-2424 Target: | 5'-AAAGAACGAUAGCUAGGAUCAUCCUGG-3'<br>3'-UUUCUUGCUAUCGAUCCUAGUAGGACC-5'<br>5'-AAAGAACGATAGCTAGGATCATCCTGG-3' | (SEQ ID NO: 7260)<br>(SEQ ID NO: 1715)<br>(SEQ ID NO: 2824) |
| βc-2441 Target: | 5'-CAUAUCCACCAGAGUGAAAAGAACGAU-3'<br>3'-GUAUAGGUGGUCUCACUUUUCUUGCUA-5'<br>5'-CATATCCACCAGAGTGAAAAGAACGAT-3' | (SEQ ID NO: 7261)<br>(SEQ ID NO: 1716)<br>(SEQ ID NO: 2825) |
| βc-2618 Target: | 5'-UGAUUUACAGGUCAGUAUCAAACCAGG-3'<br>3'-ACUAAAUGUCCAGUCAUAGUUUGGUCC-5'<br>5'-TGATTTACAGGTCAGTATCAAACCAGG-3' | (SEQ ID NO: 7262)<br>(SEQ ID NO: 1717)<br>(SEQ ID NO: 2826) |
| βc-2619 Target: | 5'-AUGAUUUACAGGUCAGUAUCAAACCAG-3'<br>3'-UACUAAAUGUCCAGUCAUAGUUUGGUC-5'<br>5'-ATGATTTACAGGTCAGTATCAAACCAG-3' | (SEQ ID NO: 7263)<br>(SEQ ID NO: 1718)<br>(SEQ ID NO: 2827) |
| βc-2620 Target: | 5'-GAUGAUUUACAGGUCAGUAUCAAACCA-3'<br>3'-CUACUAAAUGUCCAGUCAUAGUUUGGU-5'<br>5'-GATGATTTACAGGTCAGTATCAAACCA-3' | (SEQ ID NO: 7264)<br>(SEQ ID NO: 1719)<br>(SEQ ID NO: 2828) |
| βc-2634 Target: | 5'-CUUCUUACCUAAAGGAUGAUUUACAGG-3'<br>3'-GAAGAAUGGAUUUCCUACUAAAUGUCC-5'<br>5'-CTTCTTACCTAAAGGATGATTTACAGG-3' | (SEQ ID NO: 7265)<br>(SEQ ID NO: 1720)<br>(SEQ ID NO: 2829) |
| βc-2635 Target: | 5'-ACUUCUUACCUAAAGGAUGAUUUACAG-3'<br>3'-UGAAGAAUGGAUUUCCUACUAAAUGUC-5'<br>5'-ACTTCTTACCTAAAGGATGATTTACAG-3' | (SEQ ID NO: 7266)<br>(SEQ ID NO: 1721)<br>(SEQ ID NO: 2830) |
| βc-2637 Target: | 5'-AAACUUCUUACCUAAAGGAUGAUUUAC-3'<br>3'-UUUGAAGAAUGGAUUUCCUACUAAAUG-5'<br>5'-AAACTTCTTACCTAAAGGATGATTTAC-3' | (SEQ ID NO: 7267)<br>(SEQ ID NO: 1722)<br>(SEQ ID NO: 2831) |
| βc-2645 Target: | 5'-GCUUUUUAAAACUUCUUACCUAAAGGA-3'<br>3'-CGAAAAAUUUUGAAGAAUGGAUUUCCU-5'<br>5'-GCTTTTTAAAACTTCTTACCTAAAGGA-3' | (SEQ ID NO: 7268)<br>(SEQ ID NO: 1723)<br>(SEQ ID NO: 2832) |
| βc-2647 Target: | 5'-UGGCUUUUUAAAACUUCUUACCUAAAG-3'<br>3'-ACCGAAAAAUUUUGAAGAAUGGAUUUC-5'<br>5'-TGGCTTTTTAAAACTTCTTACCTAAAG-3' | (SEQ ID NO: 7269)<br>(SEQ ID NO: 1724)<br>(SEQ ID NO: 2833) |
| βc-2653 Target: | 5'-CCAAACUGGCUUUUUAAAACUUCUUAC-3'<br>3'-GGUUUGACCGAAAAAUUUUGAAGAAUG-5'<br>5'-CCAAACTGGCTTTTTAAAACTTCTTAC-3' | (SEQ ID NO: 7270)<br>(SEQ ID NO: 1725)<br>(SEQ ID NO: 2834) |
| βc-2657 Target: | 5'-UUACCCAAACUGGCUUUUUAAAACUUC-3'<br>3'-AAUGGGUUUGACCGAAAAAUUUUGAAG-5'<br>5'-TTACCCAAACTGGCTTTTTAAAACTTC-3' | (SEQ ID NO: 7271)<br>(SEQ ID NO: 1726)<br>(SEQ ID NO: 2835) |

TABLE 13-continued

Additional Selected Anti-β-catenin DsiRNAs, Blunt, Unfrayed Duplexes

| | | |
|---|---|---|
| βc-2658 Target: | 5'-UUUACCCAAACUGGCUUUUUAAAACUU-3'<br>3'-AAAUGGGUUUGACCGAAAAAUUUUGAA-5'<br>5'-TTTACCCAAACTGGCTTTTTAAAACTT-3' | (SEQ ID NO: 7272)<br>(SEQ ID NO: 1727)<br>(SEQ ID NO: 2836) |
| βc-2659 Target: | 5'-UUUUACCCAAACUGGCUUUUUAAAACU-3'<br>3'-AAAAUGGGUUUGACCGAAAAAUUUUGA-5'<br>5'-TTTTACCCAAACTGGCTTTTTAAAACT-3' | (SEQ ID NO: 7273)<br>(SEQ ID NO: 1728)<br>(SEQ ID NO: 2837) |
| βc-2660 Target: | 5'-AUUUUACCCAAACUGGCUUUUUAAAAC-3'<br>3'-UAAAAUGGGUUUGACCGAAAAAUUUUG-5'<br>5'-ATTTTACCCAAACTGGCTTTTTAAAAC-3' | (SEQ ID NO: 7274)<br>(SEQ ID NO: 1729)<br>(SEQ ID NO: 2838) |
| βc-2701 Target: | 5'-CCAACCAAGUCUUUCUGAAGUUCUGUA-3'<br>3'-GGUUGGUUCAGAAAGACUUCAAGACAU-5'<br>5'-CCAACCAAGTCTTTCTGAAGTTCTGTA-3' | (SEQ ID NO: 7275)<br>(SEQ ID NO: 1730)<br>(SEQ ID NO: 2839) |
| βc-2709 Target: | 5'-CCACCCUACCAACCAAGUCUUUCUGAA-3'<br>3'-GGUGGGAUGGUUGGUUCAGAAAGACUU-5'<br>5'-CCACCCTACCAACCAAGTCTTTCTGAA-3' | (SEQ ID NO: 7276)<br>(SEQ ID NO: 1731)<br>(SEQ ID NO: 2840) |
| βc-2733 Target: | 5'-AUUUACAAAUAGCCUAAACCACUCCCA-3'<br>3'-UAAAUGUUUAUCGGAUUUGGUGAGGGU-5'<br>5'-ATTTACAAATAGCCTAAACCACTCCCA-3' | (SEQ ID NO: 7277)<br>(SEQ ID NO: 1732)<br>(SEQ ID NO: 2841) |
| βc-2734 Target: | 5'-GAUUUACAAAUAGCCUAAACCACUCCC-3'<br>3'-CUAAAUGUUUAUCGGAUUUGGUGAGGG-5'<br>5'-GATTTACAAATAGCCTAAACCACTCCC-3' | (SEQ ID NO: 7278)<br>(SEQ ID NO: 1733)<br>(SEQ ID NO: 2842) |
| βc-2735 Target: | 5'-AGAUUUACAAAUAGCCUAAACCACUCC-3'<br>3'-UCUAAAUGUUUAUCGGAUUUGGUGAGG-5'<br>5'-AGATTTACAAATAGCCTAAACCACTCC-3' | (SEQ ID NO: 7279)<br>(SEQ ID NO: 1734)<br>(SEQ ID NO: 2843) |
| βc-2736 Target: | 5'-CAGAUUUACAAAUAGCCUAAACCACUC-3'<br>3'-GUCUAAAUGUUUAUCGGAUUUGGUGAG-5'<br>5'-CAGATTTACAAATAGCCTAAACCACTC-3' | (SEQ ID NO: 7280)<br>(SEQ ID NO: 1735)<br>(SEQ ID NO: 2844) |
| βc-2747 Target: | 5'-UGUUUUUGUGGCAGAUUUACAAAUAGC-3'<br>3'-ACAAAAACACCGUCUAAAUGUUUAUCG-5'<br>5'-TGTTTTTGTGGCAGATTTACAAATAGC-3' | (SEQ ID NO: 7281)<br>(SEQ ID NO: 1736)<br>(SEQ ID NO: 2845) |
| βc-2748 Target: | 5'-CUGUUUUUGUGGCAGAUUUACAAAUAG-3'<br>3'-GACAAAAACACCGUCUAAAUGUUUAUC-5'<br>5'-CTGTTTTTGTGGCAGATTTACAAATAG-3' | (SEQ ID NO: 7282)<br>(SEQ ID NO: 1737)<br>(SEQ ID NO: 2846) |
| βc-2749 Target: | 5'-CCUGUUUUUGUGGCAGAUUUACAAAUA-3'<br>3'-GGACAAAAACACCGUCUAAAUGUUUAU-5'<br>5'-CCTGTTTTTGTGGCAGATTTACAAATA-3' | (SEQ ID NO: 7283)<br>(SEQ ID NO: 1738)<br>(SEQ ID NO: 2847) |
| βc-2754 Target: | 5'-AUAUACCUGUUUUUGUGGCAGAUUUAC-3'<br>3'-UAUAUGGACAAAAACACCGUCUAAAUG-5'<br>5'-ATATACCTGTTTTTGTGGCAGATTTAC-3' | (SEQ ID NO: 7284)<br>(SEQ ID NO: 1739)<br>(SEQ ID NO: 2848) |
| βc-2764 Target: | 5'-CUUUCAAAGUAUAUACCUGUUUUUGUG-3'<br>3'-GAAAGUUUCAUAUAUGGACAAAAACAC-5'<br>5'-CTTTCAAAGTATATACCTGTTTTTGTG-3' | (SEQ ID NO: 7285)<br>(SEQ ID NO: 1740)<br>(SEQ ID NO: 2849) |
| βc-2770 Target: | 5'-CAUCUCCUUUCAAAGUAUAUACCUGUU-3'<br>3'-GUAGAGGAAAGUUUCAUAUAUGGACAA-5'<br>5'-CATCTCCTTTCAAAGTATATACCTGTT-3' | (SEQ ID NO: 7286)<br>(SEQ ID NO: 1741)<br>(SEQ ID NO: 2850) |
| βc-2771 Target: | 5'-ACAUCUCCUUUCAAAGUAUAUACCUGU-3'<br>3'-UGUAGAGGAAAGUUUCAUAUAUGGACA-5'<br>5'-ACATCTCCTTTCAAAGTATATACCTGT-3' | (SEQ ID NO: 7287)<br>(SEQ ID NO: 1742)<br>(SEQ ID NO: 2851) |
| βc-2773 Target: | 5'-AGACAUCUCCUUUCAAAGUAUAUACCU-3'<br>3'-UCUGUAGAGGAAAGUUUCAUAUAUGGA-5'<br>5'-AGACATCTCCTTTCAAAGTATATACCT-3' | (SEQ ID NO: 7288)<br>(SEQ ID NO: 1743)<br>(SEQ ID NO: 2852) |
| βc-2774 Target: | 5'-AAGACAUCUCCUUUCAAAGUAUAUACC-3'<br>3'-UUCUGUAGAGGAAAGUUUCAUAUAUGG-5'<br>5'-AAGACATCTCCTTTCAAAGTATATACC-3' | (SEQ ID NO: 7289)<br>(SEQ ID NO: 1744)<br>(SEQ ID NO: 2853) |
| βc-2775 Target: | 5'-CAAGACAUCUCCUUUCAAAGUAUAUAC-3'<br>3'-GUUCUGUAGAGGAAAGUUUCAUAUAUG-5'<br>5'-CAAGACATCTCCTTTCAAAGTATATAC-3' | (SEQ ID NO: 7290)<br>(SEQ ID NO: 1745)<br>(SEQ ID NO: 2854) |

TABLE 13-continued

Additional Selected Anti-β-catenin DsiRNAs, Blunt, Unfrayed Duplexes

| | | |
|---|---|---|
| βc-2780 Target: | 5'-UGUUCCAAGACAUCUCCUUUCAAAGUA-3'<br>3'-ACAAGGUUCUGUAGAGGAAAGUUUCAU-5'<br>5'-TGTTCCAAGACATCTCCTTTCAAAGTA-3' | (SEQ ID NO: 7291)<br>(SEQ ID NO: 1746)<br>(SEQ ID NO: 2855) |
| βc-2788 Target: | 5'-CAUUCCAAUGUUCCAAGACAUCUCCUU-3'<br>3'-GUAAGGUUACAAGGUUCUGUAGAGGAA-5'<br>5'-CATTCCAATGTTCCAAGACATCTCCTT-3' | (SEQ ID NO: 7292)<br>(SEQ ID NO: 1747)<br>(SEQ ID NO: 2856) |
| βc-2789 Target: | 5'-ACAUUCCAAUGUUCCAAGACAUCUCCU-3'<br>3'-UGUAAGGUUACAAGGUUCUGUAGAGGA-5'<br>5'-ACATTCCAATGTTCCAAGACATCTCCT-3' | (SEQ ID NO: 7293)<br>(SEQ ID NO: 1748)<br>(SEQ ID NO: 2857) |
| βc-2791 Target: | 5'-GAACAUUCCAAUGUUCCAAGACAUCUC-3'<br>3'-CUUGUAAGGUUACAAGGUUCUGUAGAG-5'<br>5'-GAACATTCCAATGTTCCAAGACATCTC-3' | (SEQ ID NO: 7294)<br>(SEQ ID NO: 1749)<br>(SEQ ID NO: 2858) |
| βc-2803 Target: | 5'-CCAGAAAUCUGAGAACAUUCCAAUGUU-3'<br>3'-GGUCUUUAGACUCUUGUAAGGUUACAA-5'<br>5'-CCAGAAATCTGAGAACATTCCAATGTT-3' | (SEQ ID NO: 7295)<br>(SEQ ID NO: 1750)<br>(SEQ ID NO: 2859) |
| βc-2807 Target: | 5'-ACAACCAGAAAUCUGAGAACAUUCCAA-3'<br>3'-UGUUGGUCUUUAGACUCUUGUAAGGUU-5'<br>5'-ACAACCAGAAATCTGAGAACATTCCAA-3' | (SEQ ID NO: 7296)<br>(SEQ ID NO: 1751)<br>(SEQ ID NO: 2860) |
| βc-2809 Target: | 5'-UAACAACCAGAAAUCUGAGAACAUUCC-3'<br>3'-AUUGUUGGUCUUUAGACUCUUGUAAGG-5'<br>5'-TAACAACCAGAAATCTGAGAACATTCC-3' | (SEQ ID NO: 7297)<br>(SEQ ID NO: 1752)<br>(SEQ ID NO: 2861) |
| βc-2810 Target: | 5'-AUAACAACCAGAAAUCUGAGAACAUUC-3'<br>3'-UAUUGUUGGUCUUUAGACUCUUGUAAG-5'<br>5'-ATAACAACCAGAAATCTGAGAACATTC-3' | (SEQ ID NO: 7298)<br>(SEQ ID NO: 1753)<br>(SEQ ID NO: 2862) |
| βc-2811 Target: | 5'-CAUAACAACCAGAAAUCUGAGAACAUU-3'<br>3'-GUAUUGUUGGUCUUUAGACUCUUGUAA-5'<br>5'-CATAACAACCAGAAATCTGAGAACATT-3' | (SEQ ID NO: 7299)<br>(SEQ ID NO: 1754)<br>(SEQ ID NO: 2863) |
| βc-2817 Target: | 5'-UGAUCACAUAACAACCAGAAAUCUGAG-3'<br>3'-ACUAGUGUAUUGUUGGUCUUUAGACUC-5'<br>5'-TGATCACATAACAACCAGAAATCTGAG-3' | (SEQ ID NO: 7300)<br>(SEQ ID NO: 1755)<br>(SEQ ID NO: 2864) |
| βc-2818 Target: | 5'-AUGAUCACAUAACAACCAGAAAUCUGA-3'<br>3'-UACUAGUGUAUUGUUGGUCUUUAGACU-5'<br>5'-ATGATCACATAACAACCAGAAATCTGA-3' | (SEQ ID NO: 7301)<br>(SEQ ID NO: 1756)<br>(SEQ ID NO: 2865) |
| βc-2824 Target: | 5'-CCACACAUGAUCACAUAACAACCAGAA-3'<br>3'-GGUGUGUACUAGUGUAUUGUUGGUCUU-5'<br>5'-CCACACATGATCACATAACAACCAGAA-3' | (SEQ ID NO: 7302)<br>(SEQ ID NO: 1757)<br>(SEQ ID NO: 2866) |
| βc-2827 Target: | 5'-CUUCCACACAUGAUCACAUAACAACCA-3'<br>3'-GAAGGUGUGUACUAGUGUAUUGUUGGU-5'<br>5'-CTTCCACACATGATCACATAACAACCA-3' | (SEQ ID NO: 7303)<br>(SEQ ID NO: 1758)<br>(SEQ ID NO: 2867) |
| βc-2832 Target: | 5'-AAUAACUUCCACACAUGAUCACAUAAC-3'<br>3'-UUAUUGAAGGUGUGUACUAGUGUAUUG-5'<br>5'-AATAACTTCCACACATGATCACATAAC-3' | (SEQ ID NO: 7304)<br>(SEQ ID NO: 1759)<br>(SEQ ID NO: 2868) |
| βc-2833 Target: | 5'-UAAUAACUUCCACACAUGAUCACAUAA-3'<br>3'-AUUAUUGAAGGUGUGUACUAGUGUAUU-5'<br>5'-TAATAACTTCCACACATGATCACATAA-3' | (SEQ ID NO: 7305)<br>(SEQ ID NO: 1760)<br>(SEQ ID NO: 2869) |
| βc-2834 Target: | 5'-UUAAUAACUUCCACACAUGAUCACAUA-3'<br>3'-AAUUAUUGAAGGUGUGUACUAGUGUAU-5'<br>5'-TTAATAACTTCCACACATGATCACATA-3' | (SEQ ID NO: 7306)<br>(SEQ ID NO: 1761)<br>(SEQ ID NO: 2870) |
| βc-2835 Target: | 5'-GUUAAUAACUUCCACACAUGAUCACAU-3'<br>3'-CAAUUAUUGAAGGUGUGUACUAGUGUA-5'<br>5'-GTTAATAACTTCCACACATGATCAC-3' | (SEQ ID NO: 7307)<br>(SEQ ID NO: 1762)<br>(SEQ ID NO: 2871) |
| βc-2842 Target: | 5'-CAUUAAAGUUAAUAACUUCCACACAUG-3'<br>3'-GUAAUUUCAAUUAUUGAAGGUGUGUAC-5'<br>5'-CATTAAAGTTAATAACTTCCACACATG-3' | (SEQ ID NO: 7308)<br>(SEQ ID NO: 1763)<br>(SEQ ID NO: 2872) |
| βc-2843 Target: | 5'-ACAUUAAAGUUAAUAACUUCCACACAU-3'<br>3'-UGUAAUUUCAAUUAUUGAAGGUGUGUA-5'<br>5'-ACATTAAAGTTAATAACTTCCACAC-3' | (SEQ ID NO: 7309)<br>(SEQ ID NO: 1764)<br>(SEQ ID NO: 2873) |

TABLE 13-continued

Additional Selected Anti-β-catenin DsiRNAs, Blunt, Unfrayed Duplexes

| | | |
|---|---|---|
| βc-2845 Target: | 5'-AAACAUUAAAGUUAAUAACUUCCACAC-3'<br>3'-UUUGUAAUUUCAAUUAUUGAAGGUGUG-5'<br>5'-AAACATTAAAGTTAATAACTTCCACAC-3' | (SEQ ID NO: 7310)<br>(SEQ ID NO: 1765)<br>(SEQ ID NO: 2874) |
| βc-2846 Target: | 5'-AAAACAUUAAAGUUAAUAACUUCCACA-3'<br>3'-UUUUGUAAUUUCAAUUAUUGAAGGUGU-5'<br>5'-AAAACATTAAAGTTAATAACTTCCACA-3' | (SEQ ID NO: 7311)<br>(SEQ ID NO: 1766)<br>(SEQ ID NO: 2875) |
| βc-2847 Target: | 5'-AAAAACAUUAAAGUUAAUAACUUCCAC-3'<br>3'-UUUUUGUAAUUUCAAUUAUUGAAGGUG-5'<br>5'-AAAAACATTAAAGTTAATAACTTCCAC-3' | (SEQ ID NO: 7312)<br>(SEQ ID NO: 1767)<br>(SEQ ID NO: 2876) |
| βc-2848 Target: | 5'-AAAAAACAUUAAAGUUAAUAACUUCCA-3'<br>3'-UUUUUUGUAAUUUCAAUUAUUGAAGGU-5'<br>5'-AAAAAACATTAAAGTTAATAACTTCCA-3' | (SEQ ID NO: 7313)<br>(SEQ ID NO: 1768)<br>(SEQ ID NO: 2877) |
| βc-2849 Target: | 5'-CAAAAAACAUUAAAGUUAAUAACUUCC-3'<br>3'-GUUUUUUGUAAUUUCAAUUAUUGAAGG-5'<br>5'-CAAAAAACATTAAAGTTAATAACTTCC-3' | (SEQ ID NO: 7314)<br>(SEQ ID NO: 1769)<br>(SEQ ID NO: 2878) |
| βc-2850 Target: | 5'-GCAAAAAACAUUAAAGUUAAUAACUUC-3'<br>3'-CGUUUUUUGUAAUUUCAAUUAUUGAAG-5'<br>5'-GCAAAAAACATTAAAGTTAATAACTTC-3' | (SEQ ID NO: 7315)<br>(SEQ ID NO: 1770)<br>(SEQ ID NO: 2879) |
| βc-2852 Target: | 5'-UGGCAAAAAACAUUAAAGUUAAUAACU-3'<br>3'-ACCGUUUUUUGUAAUUUCAAUUAUUGA-5'<br>5'-TGGCAAAAAACATTAAAGTTAATAACT-3' | (SEQ ID NO: 7316)<br>(SEQ ID NO: 1771)<br>(SEQ ID NO: 2880) |
| βc-2853 Target: | 5'-GUGGCAAAAAACAUUAAAGUUAAUAAC-3'<br>3'-CACCGUUUUUUGUAAUUUCAAUUAUUG-5'<br>5'-GTGGCAAAAAACATTAAAGTTAATAAC-3' | (SEQ ID NO: 7317)<br>(SEQ ID NO: 1772)<br>(SEQ ID NO: 2881) |
| βc-2864 Target: | 5'-UUGCAAAAGCUGUGGCAAAAAACAUUA-3'<br>3'-AACGUUUUCGACACCGUUUUUUGUAAU-5'<br>5'-TTGCAAAAGCTGTGGCAAAAAACATTA-3' | (SEQ ID NO: 7318)<br>(SEQ ID NO: 1773)<br>(SEQ ID NO: 2882) |
| βc-2865 Target: | 5'-GUUGCAAAAGCUGUGGCAAAAAACAUU-3'<br>3'-CAACGUUUUCGACACCGUUUUUUGUAA-5'<br>5'-GTTGCAAAAGCTGTGGCAAAAAACATT-3' | (SEQ ID NO: 7319)<br>(SEQ ID NO: 1774)<br>(SEQ ID NO: 2883) |
| βc-2882 Target: | 5'-ACUCAUUUGAGUAUUAAGUUGCAAAAG-3'<br>3'-UGAGUAAACUCAUAAUUCAACGUUUUC-5'<br>5'-ACTCATTTGAGTATTAAGTTGCAAAAG-3' | (SEQ ID NO: 7320)<br>(SEQ ID NO: 1775)<br>(SEQ ID NO: 2884) |
| βc-2899 Target: | 5'-UUAAAACAGCAAAUGUUACUCAUUUGA-3'<br>3'-AAUUUUGUCGUUUACAAUGAGUAAACU-5'<br>5'-TTAAAACAGCAAATGTTACTCATTTGA-3' | (SEQ ID NO: 7321)<br>(SEQ ID NO: 1776)<br>(SEQ ID NO: 2885) |
| βc-2900 Target: | 5'-UUUAAAACAGCAAAUGUUACUCAUUUG-3'<br>3'-AAAUUUUGUCGUUUACAAUGAGUAAAC-5'<br>5'-TTTAAAACAGCAAATGTTACTCATTTG-3' | (SEQ ID NO: 7322)<br>(SEQ ID NO: 1777)<br>(SEQ ID NO: 2886) |
| βc-2901 Target: | 5'-GUUUAAAACAGCAAAUGUUACUCAUUU-3'<br>3'-CAAAUUUUGUCGUUUACAAUGAGUAAA-5'<br>5'-GTTTAAAACAGCAAATGTTACTCATTT-3' | (SEQ ID NO: 7323)<br>(SEQ ID NO: 1778)<br>(SEQ ID NO: 2887) |
| βc-2902 Target: | 5'-UGUUUAAAACAGCAAAUGUUACUCAUU-3'<br>3'-ACAAAUUUUGUCGUUUACAAUGAGUAA-5'<br>5'-TGTTTAAAACAGCAAATGTTACTCATT-3' | (SEQ ID NO: 7324)<br>(SEQ ID NO: 1779)<br>(SEQ ID NO: 2888) |
| βc-2903 Target: | 5'-AUGUUUAAAACAGCAAAUGUUACUCAU-3'<br>3'-UACAAAUUUUGUCGUUUACAAUGAGUA-5'<br>5'-ATGTTTAAAACAGCAAATGTTACTC-3' | (SEQ ID NO: 7325)<br>(SEQ ID NO: 1780)<br>(SEQ ID NO: 2889) |
| βc-2904 Target: | 5'-AAUGUUUAAAACAGCAAAUGUUACUCA-3'<br>3'-UUACAAAUUUUGUCGUUUACAAUGAGU-5'<br>5'-AATGTTTAAAACAGCAAATGTTACTCA-3' | (SEQ ID NO: 7326)<br>(SEQ ID NO: 1781)<br>(SEQ ID NO: 2890) |
| βc-2909 Target: | 5'-CUAUUAAUGUUUAAAACAGCAAAUGUU-3'<br>3'-GAUAAUUACAAAUUUUGUCGUUUACAA-5'<br>5'-CTATTAATGTTTAAAACAGCAAATGTT-3' | (SEQ ID NO: 7327)<br>(SEQ ID NO: 1782)<br>(SEQ ID NO: 2891) |
| βc-2921 Target: | 5'-AGAGAAAGGCUGCUAUUAAUGUUUAAA-3'<br>3'-UCUCUUUCCGACGAUAAUUACAAAUUU-5'<br>5'-AGAGAAAGGCTGCTATTAATGTTTAAA-3' | (SEQ ID NO: 7328)<br>(SEQ ID NO: 1783)<br>(SEQ ID NO: 2892) |

TABLE 13-continued

Additional Selected Anti-β-catenin DsiRNAs, Blunt, Unfrayed Duplexes

| | | |
|---|---|---|
| βc-2949 Target: | 5'-CAAGUUCAGACAAUACAGCUGUAUAAA-3'<br>3'-GUUCAAGUCUGUUAUGUCGACAUAUUU-5'<br>5'-CAAGTTCAGACAATACAGCTGTATAAA-3' | (SEQ ID NO: 7329)<br>(SEQ ID NO: 1784)<br>(SEQ ID NO: 2893) |
| βc-2957 Target: | 5'-UCACAAUGCAAGUUCAGACAAUACAGC-3'<br>3'-AGUGUUACGUUCAAGUCUGUUAUGUCG-5'<br>5'-TCACAATGCAAGTTCAGACAATACAGC-3' | (SEQ ID NO: 7330)<br>(SEQ ID NO: 1785)<br>(SEQ ID NO: 2894) |
| βc-2959 Target: | 5'-AAUCACAAUGCAAGUUCAGACAAUACA-3'<br>3'-UUAGUGUUACGUUCAAGUCUGUUAUGU-5'<br>5'-AATCACAATGCAAGTTCAGACAATACA-3' | (SEQ ID NO: 7331)<br>(SEQ ID NO: 1786)<br>(SEQ ID NO: 2895) |
| βc-2961 Target: | 5'-CCAAUCACAAUGCAAGUUCAGACAAUA-3'<br>3'-GGUUAGUGUUACGUUCAAGUCUGUUAU-5'<br>5'-CCAATCACAATGCAAGTTCAGACAATA-3' | (SEQ ID NO: 7332)<br>(SEQ ID NO: 1787)<br>(SEQ ID NO: 2896) |
| βc-2965 Target: | 5'-CAGGCCAAUCACAAUGCAAGUUCAGAC-3'<br>3'-GUCCGGUUAGUGUUACGUUCAAGUCUG-5'<br>5'-CAGGCCAATCACAATGCAAGTTCAGAC-3' | (SEQ ID NO: 7333)<br>(SEQ ID NO: 1788)<br>(SEQ ID NO: 2897) |
| βc-3052 Target: | 5'-UUGUUCCCAUAGGAAACUCAGCUUGGU-3'<br>3'-AACAAGGGUAUCCUUUGAGUCGAACCA-5'<br>5'-TTGTTCCCATAGGAAACTCAGCTTGGT-3' | (SEQ ID NO: 7334)<br>(SEQ ID NO: 1789)<br>(SEQ ID NO: 2898) |
| βc-3058 Target: | 5'-CUUCAAUUGUUCCCAUAGGAAACUCAG-3'<br>3'-GAAGUUAACAAGGGUAUCCUUUGAGUC-5'<br>5'-CTTCAATTGTTCCCATAGGAAACTCAG-3' | (SEQ ID NO: 7335)<br>(SEQ ID NO: 1790)<br>(SEQ ID NO: 2899) |
| βc-3059 Target: | 5'-ACUUCAAUUGUUCCCAUAGGAAACUCA-3'<br>3'-UGAAGUUAACAAGGGUAUCCUUUGAGU-5'<br>5'-ACTTCAATTGTTCCCATAGGAAACTCA-3' | (SEQ ID NO: 7336)<br>(SEQ ID NO: 1791)<br>(SEQ ID NO: 2900) |
| βc-3065 Target: | 5'-AAGUUUACUUCAAUUGUUCCCAUAGGA-3'<br>3'-UUCAAAUGAAGUUAACAAGGGUAUCCU-5'<br>5'-AAGTTTACTTCAATTGTTCCCATAGGA-3' | (SEQ ID NO: 7337)<br>(SEQ ID NO: 1792)<br>(SEQ ID NO: 2901) |
| βc-3066 Target: | 5'-AAAGUUUACUUCAAUUGUUCCCAUAGG-3'<br>3'-UUUCAAAUGAAGUUAACAAGGGUAUCC-5'<br>5'-AAAGTTTACTTCAATTGTTCCCATAGG-3' | (SEQ ID NO: 7338)<br>(SEQ ID NO: 1793)<br>(SEQ ID NO: 2902) |
| βc-3070 Target: | 5'-ACAAAAGUUUACUUCAAUUGUUCCCA-3'<br>3'-UGUUUUCAAAUGAAGUUAACAAGGGU-5'<br>5'-ACAAAAGTTTACTTCAATTGTTCCCA-3' | (SEQ ID NO: 7339)<br>(SEQ ID NO: 1794)<br>(SEQ ID NO: 2903) |
| βc-3074 Target: | 5'-CAGAACAAAAGUUUACUUCAAUUGUU-3'<br>3'-GUCUUGUUUUCAAAUGAAGUUAACAA-5'<br>5'-CAGAACAAAAGTTTACTTCAATTGTT-3' | (SEQ ID NO: 7340)<br>(SEQ ID NO: 1795)<br>(SEQ ID NO: 2904) |
| βc-3079 Target: | 5'-AGGACCAGAACAAAAGUUUACUUCAA-3'<br>3'-UCCUGGUCUUGUUUUCAAAUGAAGUU-5'<br>5'-AGGACCAGAACAAAAGTTTACTTCAA-3' | (SEQ ID NO: 7341)<br>(SEQ ID NO: 1796)<br>(SEQ ID NO: 2905) |
| βc-3080 Target: | 5'-AAGGACCAGAACAAAAGUUUACUUCA-3'<br>3'-UUCCUGGUCUUGUUUUCAAAUGAAGU-5'<br>5'-AAGGACCAGAACAAAAGTTTACTTCA-3' | (SEQ ID NO: 7342)<br>(SEQ ID NO: 1797)<br>(SEQ ID NO: 2906) |
| βc-3088 Target: | 5'-CGACCAAAAAGGACCAGAACAAAAGU-3'<br>3'-GCUGGUUUUUCCUGGUCUUGUUUUCA-5'<br>5'-CGACCAAAAAGGACCAGAACAAAAGT-3' | (SEQ ID NO: 7343)<br>(SEQ ID NO: 1798)<br>(SEQ ID NO: 2907) |
| βc-3089 Target: | 5'-UCGACCAAAAAGGACCAGAACAAAAG-3'<br>3'-AGCUGGUUUUUCCUGGUCUUGUUUUC-5'<br>5'-TCGACCAAAAAGGACCAGAACAAAAG-3' | (SEQ ID NO: 7344)<br>(SEQ ID NO: 1799)<br>(SEQ ID NO: 2908) |
| βc-3096 Target: | 5'-UUACUCCUCGACCAAAAAGGACCAGAA-3'<br>3'-AAUGAGGAGCUGGUUUUUCCUGGUCUU-5'<br>5'-TTACTCCTCGACCAAAAAGGACCAGAA-3' | (SEQ ID NO: 7345)<br>(SEQ ID NO: 1800)<br>(SEQ ID NO: 2909) |
| βc-3111 Target: | 5'-AAUCCAUUUGUAUUGUUACUCCUCGAC-3'<br>3'-UUUAGGUAAACAUAACAAUGAGGAGCUG-5'<br>5'-AATCCATTTGTATTGTTACTCCTCGAC-3' | (SEQ ID NO: 7346)<br>(SEQ ID NO: 1801)<br>(SEQ ID NO: 2910) |
| βc-3112 Target: | 5'-AAAUCCAUUUGUAUUGUUACUCCUCGA-3'<br>3'-UUUAGGUAAACAUAACAAUGAGGAGCU-5'<br>5'-AAATCCATTTGTATTGTTACTCCTCGA-3' | (SEQ ID NO: 7347)<br>(SEQ ID NO: 1802)<br>(SEQ ID NO: 2911) |

TABLE 13-continued

Additional Selected Anti-β-catenin DsiRNAs, Blunt, Unfrayed Duplexes

| | | | |
|---|---|---|---|
| βc-3113 Target: | 5'-AAAAUCCAUUUGUAUUGUUACUCCUCG-3'<br>3'-UUUUAGGUAAACAUAACAAUGAGGAGC-5'<br>5'-AAAATCCATTTGTATTGTTACTCCTCG-3' | (SEQ ID NO: 7348)<br>(SEQ ID NO: 1803)<br>(SEQ ID NO: 2912) | |
| βc-3114 Target: | 5'-CAAAAUCCAUUUGUAUUGUUACUCCUC-3'<br>3'-GUUUUAGGUAAACAUAACAAUGAGGAG-5'<br>5'-CAAAATCCATTTGTATTGTTACTCCTC-3' | (SEQ ID NO: 7349)<br>(SEQ ID NO: 1804)<br>(SEQ ID NO: 2913) | |
| βc-3115 Target: | 5'-CCAAAAUCCAUUUGUAUUGUUACUCCU-3'<br>3'-GGUUUUAGGUAAACAUAACAAUGAGGA-5'<br>5'-CCAAAATCCATTTGTATTGTTACTCCT-3' | (SEQ ID NO: 7350)<br>(SEQ ID NO: 1805)<br>(SEQ ID NO: 2914) | |
| βc-3121 Target: | 5'-UCACUCCCAAAAUCCAUUUGUAUUGUU-3'<br>3'-AGUGAGGGUUUUAGGUAAACAUAACAA-5'<br>5'-TCACTCCCAAAATCCATTTGTATTGTT-3' | (SEQ ID NO: 7351)<br>(SEQ ID NO: 1806)<br>(SEQ ID NO: 2915) | |
| βc-3136 Target: | 5'-UCUUCACUUCUUGAGUCACUCCCAAAA-3'<br>3'-AGAAGUGAAGAACUCAGUGAGGGUUUU-5'<br>5'-TCTTCACTTCTTGAGTCACTCCCAAAA-3' | (SEQ ID NO: 7352)<br>(SEQ ID NO: 1807)<br>(SEQ ID NO: 2916) | |
| βc-3138 Target: | 5'-AUUCUUCACUUCUUGAGUCACUCCCAA-3'<br>3'-UAAGAAGUGAAGAACUCAGUGAGGGUU-5'<br>5'-ATTCTTCACTTCTTGAGTCACTCCCAA-3' | (SEQ ID NO: 7353)<br>(SEQ ID NO: 1808)<br>(SEQ ID NO: 2917) | |
| βc-3139 Target: | 5'-CAUUCUUCACUUCUUGAGUCACUCCCA-3'<br>3'-GUAAGAAGUGAAGAACUCAGUGAGGGU-5'<br>5'-CATTCTTCACTTCTTGAGTCACTCCCA-3' | (SEQ ID NO: 7354)<br>(SEQ ID NO: 1809)<br>(SEQ ID NO: 2918) | |
| βc-3140 Target: | 5'-GCAUUCUUCACUUCUUGAGUCACUCCC-3'<br>3'-CGUAAGAAGUGAAGAACUCAGUGAGGG-5'<br>5'-GCATTCTTCACTTCTTGAGTCACTCCC-3' | (SEQ ID NO: 7355)<br>(SEQ ID NO: 1810)<br>(SEQ ID NO: 2919) | |
| βc-3142 Target: | 5'-GUGCAUUCUUCACUUCUUGAGUCACUC-3'<br>3'-CACGUAAGAAGUGAAGAACUCAGUGAG-5'<br>5'-GTGCATTCTTCACTTCTTGAGTCACTC-3' | (SEQ ID NO: 7356)<br>(SEQ ID NO: 1811)<br>(SEQ ID NO: 2920) | |
| βc-3150 Target: | 5'-CCAUUCUUGUGCAUUCUUCACUUCUUG-3'<br>3'-GGUAAGAACACGUAAGAAGUGAAGAAC-5'<br>5'-CCATTCTTGTGCATTCTTCACTTCTTG-3' | (SEQ ID NO: 7357)<br>(SEQ ID NO: 1812)<br>(SEQ ID NO: 2921) | |
| βc-3153 Target: | 5'-GAUCCAUUCUUGUGCAUUCUUCACUUC-3'<br>3'-CUAGGUAAGAACACGUAAGAAGUGAAG-5'<br>5'-GATCCATTCTTGTGCATTCTTCACTTC-3' | (SEQ ID NO: 7358)<br>(SEQ ID NO: 1813)<br>(SEQ ID NO: 2922) | |
| βc-3154 Target: | 5'-UGAUCCAUUCUUGUGCAUUCUUCACUU-3'<br>3'-ACUAGGUAAGAACACGUAAGAAGUGAA-5'<br>5'-TGATCCATTCTTGTGCATTCTTCACTT-3' | (SEQ ID NO: 7359)<br>(SEQ ID NO: 1814)<br>(SEQ ID NO: 2923) | |
| βc-3155 Target: | 5'-GUGAUCCAUUCUUGUGCAUUCUUCACU-3'<br>3'-CACUAGGUAAGAACACGUAAGAAGUGA-5'<br>5'-GTGATCCATTCTTGTGCATTCTTCACT-3' | (SEQ ID NO: 7360)<br>(SEQ ID NO: 1815)<br>(SEQ ID NO: 2924) | |
| βc-3168 Target: | 5'-UAAAUUCCAUCUUGUGAUCCAUUCUUG-3'<br>3'-AUUUAAGGUAGAACACUAGGUAAGAAC-5'<br>5'-TAAATTCCATCTTGTGATCCATTCTTG-3' | (SEQ ID NO: 7361)<br>(SEQ ID NO: 1816)<br>(SEQ ID NO: 2925) | |
| βc-3170 Target: | 5'-GAUAAAUUCCAUCUUGUGAUCCAUUCU-3'<br>3'-CUAUUUAAGGUAGAACACUAGGUAAGA-5'<br>5'-GATAAATTCCATCTTGTGATCCATTCT-3' | (SEQ ID NO: 7362)<br>(SEQ ID NO: 1817)<br>(SEQ ID NO: 2926) | |
| βc-3171 Target: | 5'-UGAUAAAUUCCAUCUUGUGAUCCAUUC-3'<br>3'-ACUAUUUAAGGUAGAACACUAGGUAAG-5'<br>5'-TGATAAATTCCATCTTGTGATCCATTC-3' | (SEQ ID NO: 7363)<br>(SEQ ID NO: 1818)<br>(SEQ ID NO: 2927) | |
| βc-3172 Target: | 5'-UUGAUAAAUUCCAUCUUGUGAUCCAUU-3'<br>3'-AACUAUUUAAGGUAGAACACUAGGUAA-5'<br>5'-TTGATAAATTCCATCTTGTGATCCATT-3' | (SEQ ID NO: 7364)<br>(SEQ ID NO: 1819)<br>(SEQ ID NO: 2928) | |
| βc-3173 Target: | 5'-UUUGAUAAAUUCCAUCUUGUGAUCCAU-3'<br>3'-AAACUAUUUAAGGUAGAACACUAGGUA-5'<br>5'-TTTGATAAATTCCATCTTGTGATCC-3' | (SEQ ID NO: 7365)<br>(SEQ ID NO: 1820)<br>(SEQ ID NO: 2929) | |
| βc-3183 Target: | 5'-AAGGCUAGGGUUUGAUAAAUUCCAUCU-3'<br>3'-UUCCGAUCCCAAACUAUUUAAGGUAGA-5'<br>5'-AAGGCTAGGGTTTGATAAATTCCATCT-3' | (SEQ ID NO: 7366)<br>(SEQ ID NO: 1821)<br>(SEQ ID NO: 2930) | |

TABLE 13-continued

Additional Selected Anti-β-catenin DsiRNAs, Blunt, Unfrayed Duplexes

| | | |
|---|---|---|
| βc-3200 Target: | 5'-AAAAAAAUUUAACAAGCAAGGCUAGGG-3'<br>3'-UUUUUUUAAAUUGUUCGUUCCGAUCCC-5'<br>5'-AAAAAAATTTAACAAGCAAGGCTAGGG-3' | (SEQ ID NO: 7367)<br>(SEQ ID NO: 1822)<br>(SEQ ID NO: 2931) |
| βc-3209 Target: | 5'-AAAAAAAAAAAAAAAUUUAACAAGCA-3'<br>3'-UUUUUUUUUUUUUUUAAAUUGUUCGU-5'<br>5'-AAAAAAAAAAAAAAATTTAACAAGCA-3' | (SEQ ID NO: 7368)<br>(SEQ ID NO: 1823)<br>(SEQ ID NO: 2932) |
| βc-3210 Target: | 5'-AAAAAAAAAAAAAAAAUUUAACAAGC-3'<br>3'-UUUUUUUUUUUUUUUUAAAUUGUUCG-5'<br>5'-AAAAAAAAAAAAAAAATTTAACAAGC-3' | (SEQ ID NO: 7369)<br>(SEQ ID NO: 1824)<br>(SEQ ID NO: 2933) |
| βc-3211 Target: | 5'-AAAAAAAAAAAAAAAAAUUUAACAAG-3'<br>3'-UUUUUUUUUUUUUUUUUAAAUUGUUC-5'<br>5'-AAAAAAAAAAAAAAAAATTTAACAAG-3' | (SEQ ID NO: 7370)<br>(SEQ ID NO: 1825)<br>(SEQ ID NO: 2934) |
| βc-3212 Target: | 5'-AAAAAAAAAAAAAAAAAAUUUAACAA-3'<br>3'-UUUUUUUUUUUUUUUUUUAAAUUGUU-5'<br>5'-AAAAAAAAAAAAAAAAAATTTAACAA-3' | (SEQ ID NO: 7371)<br>(SEQ ID NO: 1826)<br>(SEQ ID NO: 2935) |
| βc-3213 Target: | 5'-UAAAAAAAAAAAAAAAAAAAUUUAACA-3'<br>3'-AUUUUUUUUUUUUUUUUUUUAAAUUGU-5'<br>5'-TAAAAAAAAAAAAAAAAAAATTTAACA-3' | (SEQ ID NO: 7372)<br>(SEQ ID NO: 1827)<br>(SEQ ID NO: 2936) |
| βc-3214 Target: | 5'-UUAAAAAAAAAAAAAAAAAAUUUAAC-3'<br>3'-AAUUUUUUUUUUUUUUUUUUAAAUUG-5'<br>5'-TTAAAAAAAAAAAAAAAAAATTTAAC-3' | (SEQ ID NO: 7373)<br>(SEQ ID NO: 1828)<br>(SEQ ID NO: 2937) |
| βc-3215 Target: | 5'-CUUAAAAAAAAAAAAAAAAAAUUUAA-3'<br>3'-GAAUUUUUUUUUUUUUUUUUUAAAUU-5'<br>5'-CTTAAAAAAAAAAAAAAAAAATTTAA-3' | (SEQ ID NO: 7374)<br>(SEQ ID NO: 1829)<br>(SEQ ID NO: 2938) |
| βc-3216 Target: | 5'-UCUUAAAAAAAAAAAAAAAAAAUUUA-3'<br>3'-AGAAUUUUUUUUUUUUUUUUUUAAAU-5'<br>5'-TCTTAAAAAAAAAAAAAAAAAATTTA-3' | (SEQ ID NO: 7375)<br>(SEQ ID NO: 1830)<br>(SEQ ID NO: 2939) |
| βc-3218 Target: | 5'-AUUCUUAAAAAAAAAAAAAAAAAAUU-3'<br>3'-UAAGAAUUUUUUUUUUUUUUUUUUAA-5'<br>5'-ATTCTTAAAAAAAAAAAAAAAAAATT-3' | (SEQ ID NO: 7376)<br>(SEQ ID NO: 1831)<br>(SEQ ID NO: 2940) |
| βc-3219 Target: | 5'-UAUUCUUAAAAAAAAAAAAAAAAAAU-3'<br>3'-AUAAGAAUUUUUUUUUUUUUUUUUUA-5'<br>5'-TATTCTTAAAAAAAAAAAAAAAAAAT-3' | (SEQ ID NO: 7377)<br>(SEQ ID NO: 1832)<br>(SEQ ID NO: 2941) |
| βc-3220 Target: | 5'-AUAUUCUUAAAAAAAAAAAAAAAAAA-3'<br>3'-UAUAAGAAUUUUUUUUUUUUUUUUUU-5'<br>5'-ATATTCTTAAAAAAAAAAAAAAAAAA-3' | (SEQ ID NO: 7378)<br>(SEQ ID NO: 1833)<br>(SEQ ID NO: 2942) |
| βc-3221 Target: | 5'-GAUAUUCUUAAAAAAAAAAAAAAAAA-3'<br>3'-CUAUAAGAAUUUUUUUUUUUUUUUUU-5'<br>5'-GATATTCTTAAAAAAAAAAAAAAAAA-3' | (SEQ ID NO: 7379)<br>(SEQ ID NO: 1834)<br>(SEQ ID NO: 2943) |
| βc-3222 Target: | 5'-AGAUAUUCUUAAAAAAAAAAAAAAAA-3'<br>3'-UCUAUAAGAAUUUUUUUUUUUUUUUU-5'<br>5'-AGATATTCTTAAAAAAAAAAAAAAAA-3' | (SEQ ID NO: 7380)<br>(SEQ ID NO: 1835)<br>(SEQ ID NO: 2944) |
| βc-3223 Target: | 5'-CAGAUAUUCUUAAAAAAAAAAAAAAA-3'<br>3'-GUCUAUAAGAAUUUUUUUUUUUUUUU-5'<br>5'-CAGATATTCTTAAAAAAAAAAAAAAA-3' | (SEQ ID NO: 7381)<br>(SEQ ID NO: 1836)<br>(SEQ ID NO: 2945) |
| βc-3224 Target: | 5'-ACAGAUAUUCUUAAAAAAAAAAAAAA-3'<br>3'-UGUCUAUAAGAAUUUUUUUUUUUUUU-5'<br>5'-ACAGATATTCTTAAAAAAAAAAAAAA-3' | (SEQ ID NO: 7382)<br>(SEQ ID NO: 1837)<br>(SEQ ID NO: 2946) |
| βc-3228 Target: | 5'-CAUUACAGAUAUUCUUAAAAAAAAAA-3'<br>3'-GUAAUGUCUAUAAGAAUUUUUUUUUU-5'<br>5'-CATTACAGATATTCTTAAAAAAAAAA-3' | (SEQ ID NO: 7383)<br>(SEQ ID NO: 1838)<br>(SEQ ID NO: 2947) |
| βc-3229 Target: | 5'-CCAUUACAGAUAUUCUUAAAAAAAAA-3'<br>3'-GGUAAUGUCUAUAAGAAUUUUUUUUU-5'<br>5'-CCATTACAGATATTCTTAAAAAAAAA-3' | (SEQ ID NO: 7384)<br>(SEQ ID NO: 1839)<br>(SEQ ID NO: 2948) |
| βc-3233 Target: | 5'-AGUACCAUUACAGAUAUUCUUAAAAA-3'<br>3'-UCAUGGUAAUGUCUAUAAGAAUUUUU-5'<br>5'-AGTACCATTACAGATATTCTTAAAAA-3' | (SEQ ID NO: 7385)<br>(SEQ ID NO: 1840)<br>(SEQ ID NO: 2949) |

TABLE 13-continued

Additional Selected Anti-β-catenin DsiRNAs, Blunt, Unfrayed Duplexes

| | | |
|---|---|---|
| βc-3234 Target: | 5'-CAGUACCAUUACAGAUAUUCUUAAAAA-3'<br>3'-GUCAUGGUAAUGUCUAUAAGAAUUUUU-5'<br>5'-CAGTACCATTACAGATATTCTTAAAAA-3' | (SEQ ID NO: 7386)<br>(SEQ ID NO: 1841)<br>(SEQ ID NO: 2950) |
| βc-3235 Target: | 5'-UCAGUACCAUUACAGAUAUUCUUAAAA-3'<br>3'-AGUCAUGGUAAUGUCUAUAAGAAUUUU-5'<br>5'-TCAGTACCATTACAGATATTCTTAAAA-3' | (SEQ ID NO: 7387)<br>(SEQ ID NO: 1842)<br>(SEQ ID NO: 2951) |
| βc-3239 Target: | 5'-AAAGUCAGUACCAUUACAGAUAUUCUU-3'<br>3'-UUUCAGUCAUGGUAAUGUCUAUAAGAA-5'<br>5'-AAAGTCAGTACCATTACAGATATTCTT-3' | (SEQ ID NO: 7388)<br>(SEQ ID NO: 1843)<br>(SEQ ID NO: 2952) |
| βc-3256 Target: | 5'-GCUACUUCAAAGCAAGCAAAGUCAGUA-3'<br>3'-CGAUGAAGUUUCGUUCGUUUCAGUCAU-5'<br>5'-GCTACTTCAAAGCAAGCAAAGTCAGTA-3' | (SEQ ID NO: 7389)<br>(SEQ ID NO: 1844)<br>(SEQ ID NO: 2953) |
| βc-3265 Target: | 5'-AAAAAAAGAGCUACUUCAAAGCAAGCA-3'<br>3'-UUUUUUUCUCGAUGAAGUUUCGUUCGU-5'<br>5'-AAAAAAAGAGCTACTTCAAAGCAAGCA-3' | (SEQ ID NO: 7390)<br>(SEQ ID NO: 1845)<br>(SEQ ID NO: 2954) |
| βc-3270 Target: | 5'-AAAAAAAAAAAAGAGCUACUUCAAAGC-3'<br>3'-UUUUUUUUUUUUCUCGAUGAAGUUUCG-5'<br>5'-AAAAAAAAAAAAGAGCTACTTCAAAGC-3' | (SEQ ID NO: 7391)<br>(SEQ ID NO: 1846)<br>(SEQ ID NO: 2955) |
| βc-3271 Target: | 5'-AAAAAAAAAAAAAGAGCUACUUCAAAG-3'<br>3'-UUUUUUUUUUUUUCUCGAUGAAGUUUC-5'<br>5'-AAAAAAAAAAAAAGAGCTACTTCAAAG-3' | (SEQ ID NO: 7392)<br>(SEQ ID NO: 1847)<br>(SEQ ID NO: 2956) |
| βc-3273 Target: | 5'-AAAAAAAAAAAAAAAGAGCUACUUCAA-3'<br>3'-UUUUUUUUUUUUUUUCUCGAUGAAGUU-5'<br>5'-AAAAAAAAAAAAAAAGAGCTACTTCAA-3' | (SEQ ID NO: 7393)<br>(SEQ ID NO: 1848)<br>(SEQ ID NO: 2957) |
| βc-3274 Target: | 5'-AAAAAAAAAAAAAAAAGAGCUACUUCA-3'<br>3'-UUUUUUUUUUUUUUUUCUCGAUGAAGU-5'<br>5'-AAAAAAAAAAAAAAAAGAGCTACTTCA-3' | (SEQ ID NO: 7394)<br>(SEQ ID NO: 1849)<br>(SEQ ID NO: 2958) |
| βc-3275 Target: | 5'-AAAAAAAAAAAAAAAAAGAGCUACUUC-3'<br>3'-UUUUUUUUUUUUUUUUUCUCGAUGAAG-5'<br>5'-AAAAAAAAAAAAAAAAAGAGCTACTTC-3' | (SEQ ID NO: 7395)<br>(SEQ ID NO: 1850)<br>(SEQ ID NO: 2959) |
| βc-3276 Target: | 5'-AAAAAAAAAAAAAAAAAAGAGCUACUU-3'<br>3'-UUUUUUUUUUUUUUUUUUCUCGAUGAA-5'<br>5'-AAAAAAAAAAAAAAAAAAGAGCTACTT-3' | (SEQ ID NO: 7396)<br>(SEQ ID NO: 1851)<br>(SEQ ID NO: 2960) |
| βc-3282 Target: | 5'-AAAAAAAAAAAAAAAAAAAAAAAAGAG-3'<br>3'-UUUUUUUUUUUUUUUUUUUUUUUUCUC-5'<br>5'-AAAAAAAAAAAAAAAAAAAAAAAAGAG-3' | (SEQ ID NO: 7397)<br>(SEQ ID NO: 1852)<br>(SEQ ID NO: 2961) |
| βc-3283 Target: | 5'-AAAAAAAAAAAAAAAAAAAAAAAAAGA-3'<br>3'-UUUUUUUUUUUUUUUUUUUUUUUUUCU-5'<br>5'-AAAAAAAAAAAAAAAAAAAAAAAAAGA-3' | (SEQ ID NO: 7398)<br>(SEQ ID NO: 1853)<br>(SEQ ID NO: 2962) |
| βc-3284 Target: | 5'-CAAAAAAAAAAAAAAAAAAAAAAAAAG-3'<br>3'-GUUUUUUUUUUUUUUUUUUUUUUUUUC-5'<br>5'-CAAAAAAAAAAAAAAAAAAAAAAAAAG-3' | (SEQ ID NO: 7399)<br>(SEQ ID NO: 1854)<br>(SEQ ID NO: 2963) |
| βc-3285 Target: | 5'-GCAAAAAAAAAAAAAAAAAAAAAAAAA-3'<br>3'-CGUUUUUUUUUUUUUUUUUUUUUUUUU-5'<br>5'-GCAAAAAAAAAAAAAAAAAAAAAAAAA-3' | (SEQ ID NO: 7400)<br>(SEQ ID NO: 1855)<br>(SEQ ID NO: 2964) |
| βc-3287 Target: | 5'-CUGCAAAAAAAAAAAAAAAAAAAAAAA-3'<br>3'-GACGUUUUUUUUUUUUUUUUUUUUUUU-5'<br>5'-CTGCAAAAAAAAAAAAAAAAAAAAAAA-3' | (SEQ ID NO: 7401)<br>(SEQ ID NO: 1856)<br>(SEQ ID NO: 2965) |
| βc-3288 Target: | 5'-ACUGCAAAAAAAAAAAAAAAAAAAAAA-3'<br>3'-UGACGUUUUUUUUUUUUUUUUUUUUUU-5'<br>5'-ACTGCAAAAAAAAAAAAAAAAAAAAAA-3' | (SEQ ID NO: 7402)<br>(SEQ ID NO: 1857)<br>(SEQ ID NO: 2966) |
| βc-3292 Target: | 5'-AGUUACUGCAAAAAAAAAAAAAAAAAA-3'<br>3'-UCAAUGACGUUUUUUUUUUUUUUUUUU-5'<br>5'-AGTTACTGCAAAAAAAAAAAAAAAAAA-3' | (SEQ ID NO: 7403)<br>(SEQ ID NO: 1858)<br>(SEQ ID NO: 2967) |
| βc-3293 Target: | 5'-CAGUUACUGCAAAAAAAAAAAAAAAAA-3'<br>3'-GUCAAUGACGUUUUUUUUUUUUUUUUU-5'<br>5'-CAGTTACTGCAAAAAAAAAAAAAAAAA-3' | (SEQ ID NO: 7404)<br>(SEQ ID NO: 1859)<br>(SEQ ID NO: 2968) |

TABLE 13-continued

Additional Selected Anti-β-catenin DsiRNAs, Blunt, Unfrayed Duplexes

| | | |
|---|---|---|
| βc-3294 Target: | 5'-ACAGUUACUGCAAAAAAAAAAAAAAA-3'<br>3'-UGUCAAUGACGUUUUUUUUUUUUUUU-5'<br>5'-ACAGTTACTGCAAAAAAAAAAAAAAA-3' | (SEQ ID NO: 7405)<br>(SEQ ID NO: 1860)<br>(SEQ ID NO: 2969) |
| βc-3298 Target: | 5'-AAAAACAGUUACUGCAAAAAAAAAAAA-3'<br>3'-UUUUUGUCAAUGACGUUUUUUUUUUU-5'<br>5'-AAAAACAGTTACTGCAAAAAAAAAAAA-3' | (SEQ ID NO: 7406)<br>(SEQ ID NO: 1861)<br>(SEQ ID NO: 2970) |
| βc-3299 Target: | 5'-AAAAAACAGUUACUGCAAAAAAAAAAA-3'<br>3'-UUUUUUGUCAAUGACGUUUUUUUUUU-5'<br>5'-AAAAAACAGTTACTGCAAAAAAAAAAA-3' | (SEQ ID NO: 7407)<br>(SEQ ID NO: 1862)<br>(SEQ ID NO: 2971) |
| βc-3300 Target: | 5'-UAAAAAACAGUUACUGCAAAAAAAAAA-3'<br>3'-AUUUUUUGUCAAUGACGUUUUUUUUU-5'<br>5'-TAAAAAACAGTTACTGCAAAAAAAAAA-3' | (SEQ ID NO: 7408)<br>(SEQ ID NO: 1863)<br>(SEQ ID NO: 2972) |
| βc-3302 Target: | 5'-CUUAAAAAACAGUUACUGCAAAAAAAA-3'<br>3'-GAAUUUUUUGUCAAUGACGUUUUUUUU-5'<br>5'-CTTAAAAAACAGTTACTGCAAAAAAAA-3' | (SEQ ID NO: 7409)<br>(SEQ ID NO: 1864)<br>(SEQ ID NO: 2973) |
| βc-3303 Target: | 5'-ACUUAAAAAACAGUUACUGCAAAAAAA-3'<br>3'-UGAAUUUUUUGUCAAUGACGUUUUUUU-5'<br>5'-ACTTAAAAAACAGTTACTGCAAAAAAA-3' | (SEQ ID NO: 7410)<br>(SEQ ID NO: 1865)<br>(SEQ ID NO: 2974) |
| βc-3305 Target: | 5'-AGACUUAAAAAACAGUUACUGCAAAAA-3'<br>3'-UCUGAAUUUUUUGUCAAUGACGUUUUU-5'<br>5'-AGACTTAAAAAACAGTTACTGCAAAAA-3' | (SEQ ID NO: 7411)<br>(SEQ ID NO: 1866)<br>(SEQ ID NO: 2975) |
| βc-3315 Target: | 5'-ACACUACGAGAGACUUAAAAAACAGUU-3'<br>3'-UGUGAUGCUCUCUGAAUUUUUUGUCAA-5'<br>5'-ACACTACGAGAGACTTAAAAAACAGTT-3' | (SEQ ID NO: 7412)<br>(SEQ ID NO: 1867)<br>(SEQ ID NO: 2976) |
| βc-3317 Target: | 5'-UAACACUACGAGAGACUUAAAAAACAG-3'<br>3'-AUUGUGAUGCUCUCUGAAUUUUUUGUC-5'<br>5'-TAACACTACGAGAGACTTAAAAAACAG-3' | (SEQ ID NO: 7413)<br>(SEQ ID NO: 1868)<br>(SEQ ID NO: 2977) |
| βc-3318 Target: | 5'-UUAACACUACGAGAGACUUAAAAAACA-3'<br>3'-AAUUGUGAUGCUCUCUGAAUUUUUUGU-5'<br>5'-TTAACACTACGAGAGACTTAAAAAACA-3' | (SEQ ID NO: 7414)<br>(SEQ ID NO: 1869)<br>(SEQ ID NO: 2978) |
| βc-3320 Target: | 5'-ACUUAACACUACGAGAGACUUAAAAAA-3'<br>3'-UGAAUUGUGAUGCUCUCUGAAUUUUUU-5'<br>5'-ACTTAACACTACGAGAGACTTAAAAAA-3' | (SEQ ID NO: 7415)<br>(SEQ ID NO: 1870)<br>(SEQ ID NO: 2979) |
| βc-3323 Target: | 5'-AUAACUUAACACUACGAGAGACUUAAA-3'<br>3'-UAUUGAAUUGUGAUGCUCUCUGAAUUU-5'<br>5'-ATAACTTAACACTACGAGAGACTTAAA-3' | (SEQ ID NO: 7416)<br>(SEQ ID NO: 1871)<br>(SEQ ID NO: 2980) |
| βc-3324 Target: | 5'-UAUAACUUAACACUACGAGAGACUUAA-3'<br>3'-AUAUUGAAUUGUGAUGCUCUCUGAAUU-5'<br>5'-TATAACTTAACACTACGAGAGACTTAA-3' | (SEQ ID NO: 7417)<br>(SEQ ID NO: 1872)<br>(SEQ ID NO: 2981) |
| βc-3332 Target: | 5'-GUAUUCACUAUAACUUAACACUACGAG-3'<br>3'-CAUAAGUGAUAUUGAAUUGUGAUGCUC-5'<br>5'-GTATTCACTATAACTTAACACTACGAG-3' | (SEQ ID NO: 7418)<br>(SEQ ID NO: 1873)<br>(SEQ ID NO: 2982) |
| βc-3333 Target: | 5'-AGUAUUCACUAUAACUUAACACUACGA-3'<br>3'-UCAUAAGUGAUAUUGAAUUGUGAUGCU-5'<br>5'-AGTATTCACTATAACTTAACACTACGA-3' | (SEQ ID NO: 7419)<br>(SEQ ID NO: 1874)<br>(SEQ ID NO: 2983) |
| βc-3334 Target: | 5'-CAGUAUUCACUAUAACUUAACACUACG-3'<br>3'-GUCAUAAGUGAUAUUGAAUUGUGAUGC-5'<br>5'-CAGTATTCACTATAACTTAACACTACG-3' | (SEQ ID NO: 7420)<br>(SEQ ID NO: 1875)<br>(SEQ ID NO: 2984) |
| βc-3335 Target: | 5'-GCAGUAUUCACUAUAACUUAACACUAC-3'<br>3'-CGUCAUAAGUGAUAUUGAAUUGUGAUG-5'<br>5'-GCAGTATTCACTATAACTTAACACTAC-3' | (SEQ ID NO: 7421)<br>(SEQ ID NO: 1876)<br>(SEQ ID NO: 2985) |
| βc-3348 Target: | 5'-AGAAAUUGCUGUAGCAGUAUUCACUAU-3'<br>3'-UCUUUAACGACAUCGUCAUAAGUGAUA-5'<br>5'-AGAAATTGCTGTAGCAGTATTCACTAT-3' | (SEQ ID NO: 7422)<br>(SEQ ID NO: 1877)<br>(SEQ ID NO: 2986) |
| βc-3349 Target: | 5'-UAGAAAUUGCUGUAGCAGUAUUCACUA-3'<br>3'-AUCUUUAACGACAUCGUCAUAAGUGAU-5'<br>5'-TAGAAATTGCTGTAGCAGTATTCACTA-3' | (SEQ ID NO: 7423)<br>(SEQ ID NO: 1878)<br>(SEQ ID NO: 2987) |

TABLE 13-continued

Additional Selected Anti-β-catenin DsiRNAs, Blunt, Unfrayed Duplexes

| | | |
|---|---|---|
| βc-3350 Target: | 5'-UUAGAAAUUGCUGUAGCAGUAUUCACU-3'<br>3'-AAUCUUUAACGACAUCGUCAUAAGUGA-5'<br>5'-TTAGAAATTGCTGTAGCAGTATTCACT-3' | (SEQ ID NO: 7424)<br>(SEQ ID NO: 1879)<br>(SEQ ID NO: 2988) |
| βc-3366 Target: | 5'-ACUCAAUUCUUAAAAAUUAGAAAUUGC-3'<br>3'-UGAGUUAAGAAUUUUUAAUCUUUAACG-5'<br>5'-ACTCAATTCTTAAAAATTAGAAATTGC-3' | (SEQ ID NO: 7425)<br>(SEQ ID NO: 1880)<br>(SEQ ID NO: 2989) |
| βc-3371 Target: | 5'-CCAUUACUCAAUUCUUAAAAAUUAGAA-3'<br>3'-GGUAAUGAGUUAAGAAUUUUUAAUCUU-5'<br>5'-CCATTACTCAATTCTTAAAAATTAGAA-3' | (SEQ ID NO: 7426)<br>(SEQ ID NO: 1881)<br>(SEQ ID NO: 2990) |
| βc-3374 Target: | 5'-ACACCAUUACUCAAUUCUUAAAAAUUA-3'<br>3'-UGUGGUAAUGAGUUAAGAAUUUUUAAU-5'<br>5'-ACACCATTACTCAATTCTTAAAAATTA-3' | (SEQ ID NO: 7427)<br>(SEQ ID NO: 1882)<br>(SEQ ID NO: 2991) |
| βc-3376 Target: | 5'-CUACACCAUUACUCAAUUCUUAAAAAU-3'<br>3'-GAUGUGGUAAUGAGUUAAGAAUUUUUA-5'<br>5'-CTACACCATTACTCAATTCTTAAAAAT-3' | (SEQ ID NO: 7428)<br>(SEQ ID NO: 1883)<br>(SEQ ID NO: 2992) |
| βc-3377 Target: | 5'-UCUACACCAUUACUCAAUUCUUAAAAA-3'<br>3'-AGAUGUGGUAAUGAGUUAAGAAUUUUU-5'<br>5'-TCTACACCATTACTCAATTCTTAAAAA-3' | (SEQ ID NO: 7429)<br>(SEQ ID NO: 1884)<br>(SEQ ID NO: 2993) |
| βc-3379 Target: | 5'-GUUCUACACCAUUACUCAAUUCUUAAA-3'<br>3'-CAAGAUGUGGUAAUGAGUUAAGAAUUU-5'<br>5'-GTTCTACACCATTACTCAATTCTTAAA-3' | (SEQ ID NO: 7430)<br>(SEQ ID NO: 1885)<br>(SEQ ID NO: 2994) |
| βc-3381 Target: | 5'-GUGUUCUACACCAUUACUCAAUUCUUA-3'<br>3'-CACAAGAUGUGGUAAUGAGUUAAGAAU-5'<br>5'-GTGTTCTACACCATTACTCAATTCTTA-3' | (SEQ ID NO: 7431)<br>(SEQ ID NO: 1886)<br>(SEQ ID NO: 2995) |
| βc-3389 Target: | 5'-AUGAAUUAGUGUUCUACACCAUUACUC-3'<br>3'-UACUUAAUCACAAGAUGUGGUAAUGAG-5'<br>5'-ATGAATTAGTGTTCTACACCATTACTC-3' | (SEQ ID NO: 7432)<br>(SEQ ID NO: 1887)<br>(SEQ ID NO: 2996) |
| βc-3394 Target: | 5'-UGAUUAUGAAUUAGUGUUCUACACCAU-3'<br>3'-ACUAAUACUUAAUCACAAGAUGUGGUA-5'<br>5'-TGATTATGAATTAGTGTTCTACACC-3' | (SEQ ID NO: 7433)<br>(SEQ ID NO: 1888)<br>(SEQ ID NO: 2997) |
| βc-3395 Target: | 5'-GUGAUUAUGAAUUAGUGUUCUACACCA-3'<br>3'-CACUAAUACUUAAUCACAAGAUGUGGU-5'<br>5'-GTGATTATGAATTAGTGTTCTACACCA-3' | (SEQ ID NO: 7434)<br>(SEQ ID NO: 1889)<br>(SEQ ID NO: 2998) |
| βc-3396 Target: | 5'-AGUGAUUAUGAAUUAGUGUUCUACACC-3'<br>3'-UCACUAAUACUUAAUCACAAGAUGUGG-5'<br>5'-AGTGATTATGAATTAGTGTTCTACACC-3' | (SEQ ID NO: 7435)<br>(SEQ ID NO: 1890)<br>(SEQ ID NO: 2999) |
| βc-3405 Target: | 5'-AUUAAUUAGAGUGAUUAUGAAUUAGUG-3'<br>3'-UAAUUAAUCUCACUAAUACUUAAUCAC-5'<br>5'-ATTAATTAGAGTGATTATGAATTAGTG-3' | (SEQ ID NO: 7436)<br>(SEQ ID NO: 1891)<br>(SEQ ID NO: 3000) |
| βc-3406 Target: | 5'-AAUUAAUUAGAGUGAUUAUGAAUUAGU-3'<br>3'-UUAAUUAAUCUCACUAAUACUUAAUCA-5'<br>5'-AATTAATTAGAGTGATTATGAATTAGT-3' | (SEQ ID NO: 7437)<br>(SEQ ID NO: 1892)<br>(SEQ ID NO: 3001) |
| βc-3407 Target: | 5'-CAAUUAAUUAGAGUGAUUAUGAAUUAG-3'<br>3'-GUUAAUUAAUCUCACUAAUACUUAAUC-5'<br>5'-CAATTAATTAGAGTGATTATGAATTAG-3' | (SEQ ID NO: 7438)<br>(SEQ ID NO: 1893)<br>(SEQ ID NO: 3002) |
| βc-3411 Target: | 5'-AUUACAAUUAAUUAGAGUGAUUAUGAA-3'<br>3'-UAAUGUUAAUUAAUCUCACUAAUACUU-5'<br>5'-ATTACAATTAATTAGAGTGATTATGAA-3' | (SEQ ID NO: 7439)<br>(SEQ ID NO: 1894)<br>(SEQ ID NO: 3003) |
| βc-3412 Target: | 5'-GAUUACAAUUAAUUAGAGUGAUUAUGA-3'<br>3'-CUAAUGUUAAUUAAUCUCACUAAUACU-5'<br>5'-GATTACAATTAATTAGAGTGATTATGA-3' | (SEQ ID NO: 7440)<br>(SEQ ID NO: 1895)<br>(SEQ ID NO: 3004) |
| βc-3413 Target: | 5'-AGAUUACAAUUAAUUAGAGUGAUUAUG-3'<br>3'-UCUAAUGUUAAUUAAUCUCACUAAUAC-5'<br>5'-AGATTACAATTAATTAGAGTGATTATG-3' | (SEQ ID NO: 7441)<br>(SEQ ID NO: 1896)<br>(SEQ ID NO: 3005) |
| βc-3421 Target: | 5'-CUUUAUUCAGAUUACAAUUAAUUAGAG-3'<br>3'-GAAAUAAGUCUAAUGUUAAUUAAUCUC-5'<br>5'-CTTTATTCAGATTACAATTAATTAGAG-3' | (SEQ ID NO: 7442)<br>(SEQ ID NO: 1897)<br>(SEQ ID NO: 3006) |

TABLE 13-continued

Additional Selected Anti-β-catenin DsiRNAs, Blunt, Unfrayed Duplexes

| | | |
|---|---|---|
| βc-3422 Target: | 5'-ACUUUAUUCAGAUUACAAUUAAUUAGA-3'<br>3'-UGAAAUAAGUCUAAUGUUAAUUAAUCU-5'<br>5'-ACTTTATTCAGATTACAATTAATTAGA-3' | (SEQ ID NO: 7443)<br>(SEQ ID NO: 1898)<br>(SEQ ID NO: 3007) |
| βc-3426 Target: | 5'-UUACACUUUAUUCAGAUUACAAUUAAU-3'<br>3'-AAUGUGAAAUAAGUCUAAUGUUAAUUA-5'<br>5'-TTACACTTTATTCAGATTACAATTAAT-3' | (SEQ ID NO: 7444)<br>(SEQ ID NO: 1899)<br>(SEQ ID NO: 3008) |
| βc-3427 Target: | 5'-GUUACACUUUAUUCAGAUUACAAUUAA-3'<br>3'-CAAUGUGAAAUAAGUCUAAUGUUAAUU-5'<br>5'-GTTACACTTTATTCAGATTACAATTAA-3' | (SEQ ID NO: 7445)<br>(SEQ ID NO: 1900)<br>(SEQ ID NO: 3009) |
| βc-3428 Target: | 5'-UGUUACACUUUAUUCAGAUUACAAUUA-3'<br>3'-ACAAUGUGAAAUAAGUCUAAUGUUAAU-5'<br>5'-TGTTACACTTTATTCAGATTACAATTA-3' | (SEQ ID NO: 7446)<br>(SEQ ID NO: 1901)<br>(SEQ ID NO: 3010) |
| βc-3429 Target: | 5'-UUGUUACACUUUAUUCAGAUUACAAUU-3'<br>3'-AACAAUGUGAAAUAAGUCUAAUGUUAA-5'<br>5'-TTGTTACACTTTATTCAGATTACAATT-3' | (SEQ ID NO: 7447)<br>(SEQ ID NO: 1902)<br>(SEQ ID NO: 3011) |
| βc-3430 Target: | 5'-AUUGUUACACUUUAUUCAGAUUACAAU-3'<br>3'-UAACAAUGUGAAAUAAGUCUAAUGUUA-5'<br>5'-ATTGTTACACTTTATTCAGATTACAAT-3' | (SEQ ID NO: 7448)<br>(SEQ ID NO: 1903)<br>(SEQ ID NO: 3012) |
| βc-3437 Target: | 5'-CUACACAAUUGUUACACUUUAUUCAGA-3'<br>3'-GAUGUGUUAACAAUGUGAAAUAAGUCU-5'<br>5'-CTACACAATTGTTACACTTTATTCAGA-3' | (SEQ ID NO: 7449)<br>(SEQ ID NO: 1904)<br>(SEQ ID NO: 3013) |
| βc-3441 Target: | 5'-AAGGCUACACAAUUGUUACACUUUAUU-3'<br>3'-UUCCGAUGUGUUAACAAUGUGAAAUAA-5'<br>5'-AAGGCTACACAATTGTTACACTTTATT-3' | (SEQ ID NO: 7450)<br>(SEQ ID NO: 1905)<br>(SEQ ID NO: 3014) |
| βc-3446 Target: | 5'-ACAAAAGGCUACACAAUUGUUACACU-3'<br>3'-UGUUUUCCGAUGUGUUAACAAUGUGA-5'<br>5'-ACAAAAGGCTACACAATTGTTACACT-3' | (SEQ ID NO: 7451)<br>(SEQ ID NO: 1906)<br>(SEQ ID NO: 3015) |
| βc-3452 Target: | 5'-UUUUAUACAAAAGGCUACACAAUUGU-3'<br>3'-AAAAUAUGUUUUCCGAUGUGUUAACA-5'<br>5'-TTTTATACAAAAGGCTACACAATTGT-3' | (SEQ ID NO: 7452)<br>(SEQ ID NO: 1907)<br>(SEQ ID NO: 3016) |
| βc-3453 Target: | 5'-AUUUUAUACAAAAGGCUACACAAUUG-3'<br>3'-UAAAAUAUGUUUUCCGAUGUGUUAAC-5'<br>5'-ATTTTATACAAAAGGCTACACAATTG-3' | (SEQ ID NO: 7453)<br>(SEQ ID NO: 1908)<br>(SEQ ID NO: 3017) |
| βc-3455 Target: | 5'-CUAUUUUAUACAAAAGGCUACACAAU-3'<br>3'-GAUAAAAUAUGUUUUCCGAUGUGUUA-5'<br>5'-CTATTTTATACAAAAGGCTACACAAT-3' | (SEQ ID NO: 7454)<br>(SEQ ID NO: 1909)<br>(SEQ ID NO: 3018) |
| βc-3456 Target: | 5'-UCUAUUUUAUACAAAAGGCUACACAA-3'<br>3'-AGAUAAAAUAUGUUUUCCGAUGUGUU-5'<br>5'-TCTATTTTATACAAAAGGCTACACAA-3' | (SEQ ID NO: 7455)<br>(SEQ ID NO: 1910)<br>(SEQ ID NO: 3019) |
| βc-3458 Target: | 5'-UGUCUAUUUUAUACAAAAGGCUACAC-3'<br>3'-ACAGAUAAAAUAUGUUUUCCGAUGUG-5'<br>5'-TGTCTATTTTATACAAAAGGCTACAC-3' | (SEQ ID NO: 7456)<br>(SEQ ID NO: 1911)<br>(SEQ ID NO: 3020) |
| βc-3464 Target: | 5'-UCUAUUGUCUAUUUUAUACAAAAGG-3'<br>3'-AGAUAAACAGAUAAAAUAUGUUUUCC-5'<br>5'-TCTATTGTCTATTTTATACAAAAGG-3' | (SEQ ID NO: 7457)<br>(SEQ ID NO: 1912)<br>(SEQ ID NO: 3021) |
| βc-3466 Target: | 5'-UUUCUAUUGUCUAUUUUAUACAAAAA-3'<br>3'-AAAGAUAAACAGAUAAAAUAUGUUUUU-5'<br>5'-TTTCTATTGTCTATTTTATACAAAAA-3' | (SEQ ID NO: 7458)<br>(SEQ ID NO: 1913)<br>(SEQ ID NO: 3022) |
| βc-3467 Target: | 5'-UUUUCUAUUGUCUAUUUUAUACAAAA-3'<br>3'-AAAAGAUAAACAGAUAAAAUAUGUUUU-5'<br>5'-TTTTCTATTGTCTATTTTATACAAAA-3' | (SEQ ID NO: 7459)<br>(SEQ ID NO: 1914)<br>(SEQ ID NO: 3023) |
| βc-3468 Target: | 5'-AUUUUCUAUUGUCUAUUUUAUACAAA-3'<br>3'-UAAAAGAUAAACAGAUAAAAUAUGUUU-5'<br>5'-ATTTTCTATTGTCTATTTTATACAAA-3' | (SEQ ID NO: 7460)<br>(SEQ ID NO: 1915)<br>(SEQ ID NO: 3024) |
| βc-3469 Target: | 5'-CAUUUUCUAUUGUCUAUUUUAUACAA-3'<br>3'-GUAAAAGAUAAACAGAUAAAAUAUGUU-5'<br>5'-CATTTTCTATTGTCTATTTTATACAA-3' | (SEQ ID NO: 7461)<br>(SEQ ID NO: 1916)<br>(SEQ ID NO: 3025) |

TABLE 13-continued

Additional Selected Anti-β-catenin DsiRNAs, Blunt, Unfrayed Duplexes

| | | |
|---|---|---|
| βc-3470 Target: | 5'-CCAUUUUCUAUUUGUCUAUUUUAUACA-3'<br>3'-GGUAAAAGAUAAACAGAUAAAAUAUGU-5'<br>5'-CCATTTTCTATTTGTCTATTTTATACA-3' | (SEQ ID NO: 7462)<br>(SEQ ID NO: 1917)<br>(SEQ ID NO: 3026) |
| βc-3473 Target: | 5'-GGACCAUUUUCUAUUUGUCUAUUUUAU-3'<br>3'-CCUGGUAAAAGAUAAACAGAUAAAAUA-5'<br>5'-GGACCATTTTCTATTTGTCTATTTTAT-3' | (SEQ ID NO: 7463)<br>(SEQ ID NO: 1918)<br>(SEQ ID NO: 3027) |
| βc-3474 Target: | 5'-UGGACCAUUUUCUAUUUGUCUAUUUUA-3'<br>3'-ACCUGGUAAAAGAUAAACAGAUAAAAU-5'<br>5'-TGGACCATTTTCTATTTGTCTATTTTA-3' | (SEQ ID NO: 7464)<br>(SEQ ID NO: 1919)<br>(SEQ ID NO: 3028) |
| βc-3475 Target: | 5'-UUGGACCAUUUUCUAUUUGUCUAUUUU-3'<br>3'-AACCUGGUAAAAGAUAAACAGAUAAAA-5'<br>5'-TTGGACCATTTTCTATTTGTCTATTTT-3' | (SEQ ID NO: 7465)<br>(SEQ ID NO: 1920)<br>(SEQ ID NO: 3029) |
| βc-3482 Target: | 5'-AAACUAAUUGGACCAUUUUCUAUUUGU-3'<br>3'-UUUGAUUAACCUGGUAAAAGAUAAACA-5'<br>5'-AAACTAATTGGACCATTTTCTATTTGT-3' | (SEQ ID NO: 7466)<br>(SEQ ID NO: 1921)<br>(SEQ ID NO: 3030) |
| βc-3483 Target: | 5'-GAAACUAAUUGGACCAUUUUCUAUUUG-3'<br>3'-CUUUGAUUAACCUGGUAAAAGAUAAAC-5'<br>5'-GAAACTAATTGGACCATTTTCTATTTG-3' | (SEQ ID NO: 7467)<br>(SEQ ID NO: 1922)<br>(SEQ ID NO: 3031) |
| βc-3484 Target: | 5'-GGAAACUAAUUGGACCAUUUUCUAUUU-3'<br>3'-CCUUUGAUUAACCUGGUAAAAGAUAAA-5'<br>5'-GGAAACTAATTGGACCATTTTCTATTT-3' | (SEQ ID NO: 7468)<br>(SEQ ID NO: 1923)<br>(SEQ ID NO: 3032) |
| βc-3485 Target: | 5'-AGGAAACUAAUUGGACCAUUUUCUAUU-3'<br>3'-UCCUUUGAUUAACCUGGUAAAAGAUAA-5'<br>5'-AGGAAACTAATTGGACCATTTTCTATT-3' | (SEQ ID NO: 7469)<br>(SEQ ID NO: 1924)<br>(SEQ ID NO: 3033) |
| βc-3491 Target: | 5'-UUAAAAAGGAAACUAAUUGGACCAUUU-3'<br>3'-AAUUUUUCCUUUGAUUAACCUGGUAAA-5'<br>5'-TTAAAAAGGAAACTAATTGGACCATTT-3' | (SEQ ID NO: 7470)<br>(SEQ ID NO: 1925)<br>(SEQ ID NO: 3034) |
| βc-3492 Target: | 5'-AUUAAAAAGGAAACUAAUUGGACCAUU-3'<br>3'-UAAUUUUUCCUUUGAUUAACCUGGUAA-5'<br>5'-ATTAAAAAGGAAACTAATTGGACCATT-3' | (SEQ ID NO: 7471)<br>(SEQ ID NO: 1926)<br>(SEQ ID NO: 3035) |
| βc-3498 Target: | 5'-AAGCAUAUUAAAAGGAAACUAAUUGG-3'<br>3'-UUCGUAUAAUUUUUCCUUUGAUUAACC-5'<br>5'-AAGCATATTAAAAGGAAACTAATTGG-3' | (SEQ ID NO: 7472)<br>(SEQ ID NO: 1927)<br>(SEQ ID NO: 3036) |
| βc-3499 Target: | 5'-UAAGCAUAUUAAAAAGGAAACUAAUUG-3'<br>3'-AUUCGUAUAAUUUUUCCUUUGAUUAAC-5'<br>5'-TAAGCATATTAAAAAGGAAACTAATTG-3' | (SEQ ID NO: 7473)<br>(SEQ ID NO: 1928)<br>(SEQ ID NO: 3037) |
| βc-3503 Target: | 5'-AUUUUAAGCAUAUUAAAAGGAAACUA-3'<br>3'-UAAAAUUCGUAUAAUUUUUCCUUUGAU-5'<br>5'-ATTTTAAGCATATTAAAAGGAAACTA-3' | (SEQ ID NO: 7474)<br>(SEQ ID NO: 1929)<br>(SEQ ID NO: 3038) |
| βc-3509 Target: | 5'-CUGCUUAUUUUAAGCAUAUUAAAAAGG-3'<br>3'-GACGAAUAAAAUUCGUAUAAUUUUUCC-5'<br>5'-CTGCTTATTTTAAGCATATTAAAAAGG-3' | (SEQ ID NO: 7475)<br>(SEQ ID NO: 1930)<br>(SEQ ID NO: 3039) |
| βc-3510 Target: | 5'-CCUGCUUAUUUUAAGCAUAUUAAAAAG-3'<br>3'-GGACGAAUAAAAUUCGUAUAAUUUUUC-5'<br>5'-CCTGCTTATTTTAAGCATATTAAAAAG-3' | (SEQ ID NO: 7476)<br>(SEQ ID NO: 1931)<br>(SEQ ID NO: 3040) |
| βc-3516 Target: | 5'-GAUCCACCUGCUUAUUUUAAGCAUAUU-3'<br>3'-CUAGGUGGACGAAUAAAAUUCGUAUAA-5'<br>5'-GATCCACCTGCTTATTTTAAGCATATT-3' | (SEQ ID NO: 7477)<br>(SEQ ID NO: 1932)<br>(SEQ ID NO: 3041) |
| βc-3531 Target: | 5'-CAAAAACAUGAAAUAGAUCCACCUGCU-3'<br>3'-GUUUUUGUACUUUAUCUAGGUGGACGA-5'<br>5'-CAAAAACATGAAATAGATCCACCTGCT-3' | (SEQ ID NO: 7478)<br>(SEQ ID NO: 1933)<br>(SEQ ID NO: 3042) |
| βc-3532 Target: | 5'-UCAAAAACAUGAAAUAGAUCCACCUGC-3'<br>3'-AGUUUUUGUACUUUAUCUAGGUGGACG-5'<br>5'-TCAAAAACATGAAATAGATCCACCTGC-3' | (SEQ ID NO: 7479)<br>(SEQ ID NO: 1934)<br>(SEQ ID NO: 3043) |
| βc-3534 Target: | 5'-GAUCAAAAACAUGAAAUAGAUCCACCU-3'<br>3'-CUAGUUUUUGUACUUUAUCUAGGUGGA-5'<br>5'-GATCAAAAACATGAAATAGATCCACCT-3' | (SEQ ID NO: 7480)<br>(SEQ ID NO: 1935)<br>(SEQ ID NO: 3044) |

TABLE 13-continued

Additional Selected Anti-β-catenin DsiRNAs, Blunt, Unfrayed Duplexes

| | | |
|---|---|---|
| βc-3535 Target: | 5'-UGAUCAAAAACAUGAAAUAGAUCCACC-3'<br>3'-ACUAGUUUUUGUACUUUAUCUAGGUGG-5'<br>5'-TGATCAAAAACATGAAATAGATCCACC-3' | (SEQ ID NO: 7481)<br>(SEQ ID NO: 1936)<br>(SEQ ID NO: 3045) |
| βc-3536 Target: | 5'-UUGAUCAAAAACAUGAAAUAGAUCCAC-3'<br>3'-AACUAGUUUUUGUACUUUAUCUAGGUG-5'<br>5'-TTGATCAAAAACATGAAATAGATCCAC-3' | (SEQ ID NO: 7482)<br>(SEQ ID NO: 1937)<br>(SEQ ID NO: 3046) |
| βc-3541 Target: | 5'-AGUUUUUGAUCAAAAACAUGAAAUAGA-3'<br>3'-UCAAAAACUAGUUUUUGUACUUUAUCU-5'<br>5'-AGTTTTTGATCAAAAACATGAAATAGA-3' | (SEQ ID NO: 7483)<br>(SEQ ID NO: 1938)<br>(SEQ ID NO: 3047) |
| βc-3547 Target: | 5'-CCAAAUAGUUUUUGAUCAAAAACAUGA-3'<br>3'-GGUUUAUCAAAAACUAGUUUUUGUACU-5'<br>5'-CCAAATAGTTTTTGATCAAAAACATGA-3' | (SEQ ID NO: 7484)<br>(SEQ ID NO: 1939)<br>(SEQ ID NO: 3048) |
| βc-3551 Target: | 5'-UAUCCCAAAUAGUUUUUGAUCAAAAAC-3'<br>3'-AUAGGGUUUAUCAAAAACUAGUUUUUG-5'<br>5'-TATCCCAAATAGTTTTTGATCAAAAAC-3' | (SEQ ID NO: 7485)<br>(SEQ ID NO: 1940)<br>(SEQ ID NO: 3049) |
| βc-3552 Target: | 5'-AUAUCCCAAAUAGUUUUUGAUCAAAAA-3'<br>3'-UAUAGGGUUUAUCAAAAACUAGUUUUU-5'<br>5'-ATATCCCAAATAGTTTTTGATCAAAAA-3' | (SEQ ID NO: 7486)<br>(SEQ ID NO: 1941)<br>(SEQ ID NO: 3050) |
| βc-3553 Target: | 5'-CAUAUCCCAAAUAGUUUUUGAUCAAAA-3'<br>3'-GUAUAGGGUUUAUCAAAAACUAGUUUU-5'<br>5'-CATATCCCAAATAGTTTTTGATCAAAA-3' | (SEQ ID NO: 7487)<br>(SEQ ID NO: 1942)<br>(SEQ ID NO: 3051) |
| βc-3554 Target: | 5'-ACAUAUCCCAAAUAGUUUUUGAUCAAA-3'<br>3'-UGUAUAGGGUUUAUCAAAAACUAGUUU-5'<br>5'-ACATATCCCAAATAGTTTTTGATCAAA-3' | (SEQ ID NO: 7488)<br>(SEQ ID NO: 1943)<br>(SEQ ID NO: 3052) |
| βc-3558 Target: | 5'-CCAUACAUAUCCCAAAUAGUUUUUGAU-3'<br>3'-GGUAUGUAUAGGGUUUAUCAAAAACUA-5'<br>5'-CCATACATATCCCAAATAGTTTTTGAT-3' | (SEQ ID NO: 7489)<br>(SEQ ID NO: 1944)<br>(SEQ ID NO: 3053) |
| βc-3567 Target: | 5'-UUACCCUACCCAUACAUAUCCCAAAUA-3'<br>3'-AAUGGGAUGGGUAUGUAUAGGGUUUAU-5'<br>5'-TTACCCTACCCATACATATCCCAAATA-3' | (SEQ ID NO: 7490)<br>(SEQ ID NO: 1945)<br>(SEQ ID NO: 3054) |
| βc-3568 Target: | 5'-UUUACCCUACCCAUACAUAUCCCAAAU-3'<br>3'-AAAUGGGAUGGGUAUGUAUAGGGUUUA-5'<br>5'-TTTACCCTACCCATACATATCCCAAAT-3' | (SEQ ID NO: 7491)<br>(SEQ ID NO: 1946)<br>(SEQ ID NO: 3055) |
| βc-3569 Target: | 5'-AUUUACCCUACCCAUACAUAUCCCAAA-3'<br>3'-UAAAUGGGAUGGGUAUGUAUAGGGUUU-5'<br>5'-ATTTACCCTACCCATACATATCCCAAA-3' | (SEQ ID NO: 7492)<br>(SEQ ID NO: 1947)<br>(SEQ ID NO: 3056) |
| βc-3582 Target: | 5'-ACACCUCUUACUGAUUUACCCUACCCA-3'<br>3'-UGUGGAGAAUGACUAAAUGGGAUGGGU-5'<br>5'-ACACCTCTTACTGATTTACCCTACCCA-3' | (SEQ ID NO: 7493)<br>(SEQ ID NO: 1948)<br>(SEQ ID NO: 3057) |
| βc-3584 Target: | 5'-UAACACCUCUUACUGAUUUACCCUACC-3'<br>3'-AUUGUGGAGAAUGACUAAAUGGGAUGG-5'<br>5'-TAACACCTCTTACTGATTTACCCTACC-3' | (SEQ ID NO: 7494)<br>(SEQ ID NO: 1949)<br>(SEQ ID NO: 3058) |
| βc-3585 Target: | 5'-AUAACACCUCUUACUGAUUUACCCUAC-3'<br>3'-UAUUGUGGAGAAUGACUAAAUGGGAUG-5'<br>5'-ATAACACCTCTTACTGATTTACCCTAC-3' | (SEQ ID NO: 7495)<br>(SEQ ID NO: 1950)<br>(SEQ ID NO: 3059) |
| βc-3586 Target: | 5'-AAUAACACCUCUUACUGAUUUACCCUA-3'<br>3'-UUAUUGUGGAGAAUGACUAAAUGGGAU-5'<br>5'-AATAACACCTCTTACTGATTTACCCTA-3' | (SEQ ID NO: 7496)<br>(SEQ ID NO: 1951)<br>(SEQ ID NO: 3060) |
| βc-3587 Target: | 5'-AAAUAACACCUCUUACUGAUUUACCCU-3'<br>3'-UUUAUUGUGGAGAAUGACUAAAUGGGA-5'<br>5'-AAATAACACCTCTTACTGATTTACCCT-3' | (SEQ ID NO: 7497)<br>(SEQ ID NO: 1952)<br>(SEQ ID NO: 3061) |
| βc-3588 Target: | 5'-CAAAUAACACCUCUUACUGAUUUACCC-3'<br>3'-GUUUAUUGUGGAGAAUGACUAAAUGGG-5'<br>5'-CAAATAACACCTCTTACTGATTTACCC-3' | (SEQ ID NO: 7498)<br>(SEQ ID NO: 1953)<br>(SEQ ID NO: 3062) |
| βc-3594 Target: | 5'-AGGUUCCAAAUAACACCUCUUACUGAU-3'<br>3'-UCCAAGGUUUAUUGUGGAGAAUGACUA-5'<br>5'-AGGTTCCAAATAACACCTCTTACTGAT-3' | (SEQ ID NO: 7499)<br>(SEQ ID NO: 1954)<br>(SEQ ID NO: 3063) |

TABLE 13-continued

Additional Selected Anti-β-catenin DsiRNAs, Blunt, Unfrayed Duplexes

| | | |
|---|---|---|
| βc-3600 Target: | 5'-AAAACAAGGUUCCAAAUAACACCUCUU-3'<br>3'-UUUUGUUCCAAGGUUUAUUGUGGAGAA-5'<br>5'-AAAACAAGGTTCCAAATAACACCTCTT-3' | (SEQ ID NO: 7500)<br>(SEQ ID NO: 1955)<br>(SEQ ID NO: 3064) |
| βc-3601 Target: | 5'-CAAAACAAGGUUCCAAAUAACACCUCU-3'<br>3'-GUUUUGUUCCAAGGUUUAUUGUGGAGA-5'<br>5'-CAAAACAAGGTTCCAAATAACACCTCT-3' | (SEQ ID NO: 7501)<br>(SEQ ID NO: 1956)<br>(SEQ ID NO: 3065) |
| βc-3602 Target: | 5'-CCAAAACAAGGUUCCAAAUAACACCUC-3'<br>3'-GGUUUUGUUCCAAGGUUUAUUGUGGAG-5'<br>5'-CCAAAACAAGGTTCCAAATAACACCTC-3' | (SEQ ID NO: 7502)<br>(SEQ ID NO: 1957)<br>(SEQ ID NO: 3066) |
| βc-3607 Target: | 5'-ACUGUCCAAAACAAGGUUCCAAAUAAC-3'<br>3'-UGACAGGUUUUGUUCCAAGGUUUAUUG-5'<br>5'-ACTGTCCAAAACAAGGTTCCAAATAAC-3' | (SEQ ID NO: 7503)<br>(SEQ ID NO: 1958)<br>(SEQ ID NO: 3067) |
| βc-3611 Target: | 5'-GUAAACUGUCCAAAACAAGGUUCCAAA-3'<br>3'-CAUUUGACAGGUUUUGUUCCAAGGUUU-5'<br>5'-GTAAACTGTCCAAAACAAGGTTCCAAA-3' | (SEQ ID NO: 7504)<br>(SEQ ID NO: 1959)<br>(SEQ ID NO: 3068) |
| βc-3612 Target: | 5'-GGUAAACUGUCCAAAACAAGGUUCCAA-3'<br>3'-CCAUUUGACAGGUUUUGUUCCAAGGUU-5'<br>5'-GGTAAACTGTCCAAAACAAGGTTCCAA-3' | (SEQ ID NO: 7505)<br>(SEQ ID NO: 1960)<br>(SEQ ID NO: 3069) |
| βc-3620 Target: | 5'-AGGCAACUGGUAAACUGUCCAAAACAA-3'<br>3'-UCCGUUGACCAUUUGACAGGUUUUGUU-5'<br>5'-AGGCAACTGGTAAACTGTCCAAAACAA-3' | (SEQ ID NO: 7506)<br>(SEQ ID NO: 1961)<br>(SEQ ID NO: 3070) |
| βc-3628 Target: | 5'-GGGAUAAAAGGCAACUGGUAAACUGUC-3'<br>3'-CCCUAUUUUCCGUUGACCAUUUGACAG-5'<br>5'-GGGATAAAAGGCAACTGGTAAACTGTC-3' | (SEQ ID NO: 7507)<br>(SEQ ID NO: 1962)<br>(SEQ ID NO: 3071) |
| βc-3629 Target: | 5'-UGGGAUAAAAGGCAACUGGUAAACUGU-3'<br>3'-ACCCUAUUUUCCGUUGACCAUUUGACA-5'<br>5'-TGGGATAAAAGGCAACTGGTAAACTGT-3' | (SEQ ID NO: 7508)<br>(SEQ ID NO: 1963)<br>(SEQ ID NO: 3072) |
| βc-3636 Target: | 5'-ACAACUUUGGGAUAAAAGGCAACUGGU-3'<br>3'-UGUUGAAACCCUAUUUUCCGUUGACCA-5'<br>5'-ACAACTTTGGGATAAAAGGCAACTGGT-3' | (SEQ ID NO: 7509)<br>(SEQ ID NO: 1964)<br>(SEQ ID NO: 3073) |
| βc-3638 Target: | 5'-CAACAACUUUGGGAUAAAAGGCAACUG-3'<br>3'-GUUGUUGAAACCCUAUUUUCCGUUGAC-5'<br>5'-CAACAACTTTGGGATAAAAGGCAACTG-3' | (SEQ ID NO: 7510)<br>(SEQ ID NO: 1965)<br>(SEQ ID NO: 3074) |
| βc-3643 Target: | 5'-GGUUACAACAACUUUGGGAUAAAAGGC-3'<br>3'-CCAAUGUUGUUGAAACCCUAUUUUCCG-5'<br>5'-GGTTACAACAACTTTGGGATAAAAGGC-3' | (SEQ ID NO: 7511)<br>(SEQ ID NO: 1966)<br>(SEQ ID NO: 3075) |
| βc-3644 Target: | 5'-AGGUUACAACAACUUUGGGAUAAAAGG-3'<br>3'-UCCAAUGUUGUUGAAACCCUAUUUUCC-5'<br>5'-AGGTTACAACAACTTTGGGATAAAAGG-3' | (SEQ ID NO: 7512)<br>(SEQ ID NO: 1967)<br>(SEQ ID NO: 3076) |
| βc-3645 Target: | 5'-CAGGUUACAACAACUUUGGGAUAAAAG-3'<br>3'-GUCCAAUGUUGUUGAAACCCUAUUUUC-5'<br>5'-CAGGTTACAACAACTTTGGGATAAAAG-3' | (SEQ ID NO: 7513)<br>(SEQ ID NO: 1968)<br>(SEQ ID NO: 3077) |
| βc-3653 Target: | 5'-UAUCACAGCAGGUUACAACAACUUUGG-3'<br>3'-AUAGUGUCGUCCAAUGUUGUUGAAACC-5'<br>5'-TATCACAGCAGGTTACAACAACTTTGG-3' | (SEQ ID NO: 7514)<br>(SEQ ID NO: 1969)<br>(SEQ ID NO: 3078) |
| βc-3654 Target: | 5'-GUAUCACAGCAGGUUACAACAACUUUG-3'<br>3'-CAUAGUGUCGUCCAAUGUUGUUGAAAC-5'<br>5'-GTATCACAGCAGGTTACAACAACTTTG-3' | (SEQ ID NO: 7515)<br>(SEQ ID NO: 1970)<br>(SEQ ID NO: 3079) |
| βc-3656 Target: | 5'-UCGUAUCACAGCAGGUUACAACAACUU-3'<br>3'-AGCAUAGUGUCGUCCAAUGUUGUUGAA-5'<br>5'-TCGTATCACAGCAGGTTACAACAACTT-3' | (SEQ ID NO: 7516)<br>(SEQ ID NO: 1971)<br>(SEQ ID NO: 3080) |
| βc-3670 Target: | 5'-UUUCUCUUGAAGCAUCGUAUCACAGCA-3'<br>3'-AAAGAGAACUUCGUAGCAUAGUGUCGU-5'<br>5'-TTTCTCTTGAAGCATCGTATCACAGCA-3' | (SEQ ID NO: 7517)<br>(SEQ ID NO: 1972)<br>(SEQ ID NO: 3081) |
| βc-3671 Target: | 5'-UUUUCUCUUGAAGCAUCGUAUCACAGC-3'<br>3'-AAAAGAGAACUUCGUAGCAUAGUGUCG-5'<br>5'-TTTTCTCTTGAAGCATCGTATCACAGC-3' | (SEQ ID NO: 7518)<br>(SEQ ID NO: 1973)<br>(SEQ ID NO: 3082) |

TABLE 13-continued

Additional Selected Anti-β-catenin DsiRNAs, Blunt, Unfrayed Duplexes

| | | |
|---|---|---|
| | 5'-CAUUUCUCUUGAAGCAUCGUAUCACA-3' | (SEQ ID NO: 7519) |
| | 3'-GUAAAAGAGAACUUCGUAGCAUAGUGU-5' | (SEQ ID NO: 1974) |
| βc-3673 Target: | 5'-CATTTCTCTTGAAGCATCGTATCACA-3' | (SEQ ID NO: 3083) |
| | 5'-UUUUUUAUAACCGCAUUUUCUCUUGAA-3' | (SEQ ID NO: 7520) |
| | 3'-AAAAAAUAUUGGCGUAAAAGAGAACUU-5' | (SEQ ID NO: 1975) |
| βc-3686 Target: | 5'-TTTTTTATAACCGCATTTTCTCTTGAA-3' | (SEQ ID NO: 3084) |
| | 5'-AUUUUUUAUAACCGCAUUUUCUCUUGA-3' | (SEQ ID NO: 7521) |
| | 3'-UAAAAAAUAUUGGCGUAAAAGAGAACU-5' | (SEQ ID NO: 1976) |
| βc-3687 Target: | 5'-ATTTTTTATAACCGCATTTTCTCTTGA-3' | (SEQ ID NO: 3085) |
| | 5'-CAUUUUUUAUAACCGCAUUUUCUCUUG-3' | (SEQ ID NO: 7522) |
| | 3'-GUAAAAAAUAUUGGCGUAAAAGAGAAC-5' | (SEQ ID NO: 1977) |
| βc-3688 Target: | 5'-CATTTTTTATAACCGCATTTTCTCTTG-3' | (SEQ ID NO: 3086) |
| | 5'-CCAUUUUUUAUAACCGCAUUUUCUCUU-3' | (SEQ ID NO: 7523) |
| | 3'-GGUAAAAAAUAUUGGCGUAAAAGAGAA-5' | (SEQ ID NO: 1978) |
| βc-3689 Target: | 5'-CCATTTTTTATAACCGCATTTTCTCTT-3' | (SEQ ID NO: 3087) |
| | 5'-CUGAACCAUUUUUUAUAACCGCAUUUU-3' | (SEQ ID NO: 7524) |
| | 3'-GACUUGGUAAAAAAUAUUGGCGUAAAA-5' | (SEQ ID NO: 1979) |
| βc-3694 Target: | 5'-CTGAACCATTTTTTATAACCGCATTTT-3' | (SEQ ID NO: 3088) |
| | 5'-UAAUUCUGAACCAUUUUUUAUAACCGC-3' | (SEQ ID NO: 7525) |
| | 3'-AUUAAGACUUGGUAAAAAAUAUUGGCG-5' | (SEQ ID NO: 1980) |
| βc-3699 Target: | 5'-TAATTCTGAACCATTTTTTATAACCGC-3' | (SEQ ID NO: 3089) |
| | 5'-UUAAUUCUGAACCAUUUUUUAUAACCG-3' | (SEQ ID NO: 7526) |
| | 3'-AAUUAAGACUUGGUAAAAAAUAUUGGC-5' | (SEQ ID NO: 1981) |
| βc-3700 Target: | 5'-TTAATTCTGAACCATTTTTTATAACCG-3' | (SEQ ID NO: 3090) |
| | 5'-UUUAAUUCUGAACCAUUUUUUAUAACC-3' | (SEQ ID NO: 7527) |
| | 3'-AAAUUAAGACUUGGUAAAAAAUAUUGG-5' | (SEQ ID NO: 1982) |
| βc-3701 Target: | 5'-TTTAATTCTGAACCATTTTTTATAACC-3' | (SEQ ID NO: 3091) |
| | 5'-GUUUAAUUCUGAACCAUUUUUUAUAAC-3' | (SEQ ID NO: 7528) |
| | 3'-CAAAUUAAGACUUGGUAAAAAAUAUUG-5' | (SEQ ID NO: 1983) |
| βc-3702 Target: | 5'-GTTTAATTCTGAACCATTTTTTATAAC-3' | (SEQ ID NO: 3092) |
| | 5'-AGUUUAAUUCUGAACCAUUUUUUAUAA-3' | (SEQ ID NO: 7529) |
| | 3'-UCAAAUUAAGACUUGGUAAAAAAUAUU-5' | (SEQ ID NO: 1984) |
| βc-3703 Target: | 5'-AGTTTAATTCTGAACCATTTTTTATAA-3' | (SEQ ID NO: 3093) |
| | 5'-AAGUUUAAUUCUGAACCAUUUUUUAUA-3' | (SEQ ID NO: 7530) |
| | 3'-UUCAAAUUAAGACUUGGUAAAAAAUAU-5' | (SEQ ID NO: 1985) |
| βc-3704 Target: | 5'-AAGTTTAATTCTGAACCATTTTTTATA-3' | (SEQ ID NO: 3094) |
| | 5'-AUUAAAAGUUUAAUUCUGAACCAUUUU-3' | (SEQ ID NO: 7531) |
| | 3'-UAAUUUUCAAAUUAAGACUUGGUAAAA-5' | (SEQ ID NO: 1986) |
| βc-3709 Target: | 5'-ATTAAAAGTTTAATTCTGAACCATTTT-3' | (SEQ ID NO: 3095) |
| | 5'-AAUUAAAAGUUUAAUUCUGAACCAUUU-3' | (SEQ ID NO: 7532) |
| | 3'-UUAAUUUUCAAAUUAAGACUUGGUAAA-5' | (SEQ ID NO: 1987) |
| βc-3710 Target: | 5'-AATTAAAAGTTTAATTCTGAACCATTT-3' | (SEQ ID NO: 3096) |
| | 5'-UGAAUUAAAAGUUUAAUUCUGAACCAU-3' | (SEQ ID NO: 7533) |
| | 3'-ACUUAAUUUUCAAAUUAAGACUUGGUA-5' | (SEQ ID NO: 1988) |
| βc-3712 Target: | 5'-TGAATTAAAAGTTTAATTCTGAACC-3' | (SEQ ID NO: 3097) |
| | 5'-CAAUACAGCUAAAGGAUGAUUUACAGG-3' | (SEQ ID NO: 7534) |
| | 3'-GUUAUGUCGAUUUCCUACUAAAUGUCC-5' | (SEQ ID NO: 1989) |
| βc-2634t2 Target: | 5'-CAATACAGCTAAAGGATGATTTACAGG-3' | (SEQ ID NO: 3098) |
| | 5'-ACAAUACAGCUAAAGGAUGAUUUACAG-3' | (SEQ ID NO: 7535) |
| | 3'-UGUUAUGUCGAUUUCCUACUAAAUGUC-5' | (SEQ ID NO: 1990) |
| βc-2635t2 Target: | 5'-ACAATACAGCTAAAGGATGATTTACAG-3' | (SEQ ID NO: 3099) |
| | 5'-AGACAAUACAGCUAAAGGAUGAUUUAC-3' | (SEQ ID NO: 7536) |
| | 3'-UCUGUUAUGUCGAUUUCCUACUAAAUG-5' | (SEQ ID NO: 1991) |
| βc-2637t2 Target: | 5'-AGACAATACAGCTAAAGGATGATTTAC-3' | (SEQ ID NO: 3100) |
| | 5'-GUUACUCCUAAAGGAUGAUUUACAGGU-3' | (SEQ ID NO: 7537) |
| | 3'-CAAUGAGGAUUUCCUACUAAAUGUCCA-5' | (SEQ ID NO: 1992) |
| βc-2633t3 Target: | 5'-GTTACTCCTAAAGGATGATTTACAGGT-3' | (SEQ ID NO: 3101) |

TABLE 13-continued

Additional Selected Anti-β-catenin DsiRNAs, Blunt, Unfrayed Duplexes

|  |  |  |
|---|---|---|
| βc-2634t3 Target: | 5'-UGUUACUCCUAAAGGAUGAUUUACAGG-3'<br>3'-ACAAUGAGGAUUUCCUACUAAAUGUCC-5'<br>5'-TGTTACTCCTAAAGGATGATTTACAGG-3' | (SEQ ID NO: 7538)<br>(SEQ ID NO: 1993)<br>(SEQ ID NO: 3102) |
| βc-2635t3 Target: | 5'-UUGUUACUCCUAAAGGAUGAUUUACAG-3'<br>3'-AACAAUGAGGAUUUCCUACUAAAUGUC-5'<br>5'-TTGTTACTCCTAAAGGATGATTTACAG-3' | (SEQ ID NO: 7539)<br>(SEQ ID NO: 1994)<br>(SEQ ID NO: 3103) |
| βc-2636t3 Target: | 5'-AUUGUUACUCCUAAAGGAUGAUUUACA-3'<br>3'-UAACAAUGAGGAUUUCCUACUAAAUGU-5'<br>5'-ATTGTTACTCCTAAAGGATGATTTACA-3' | (SEQ ID NO: 7540)<br>(SEQ ID NO: 1995)<br>(SEQ ID NO: 3104) |
| βc-m318 Target: | 5'-GGAUUCCAGAAUCCAAGUAAGACUGCU-3'<br>3'-CCUAAGGUCUUAGGUUCAUUCUGACGA-5'<br>5'-GGATTCCAGAATCCAAGTAAGACTGCT-3' | (SEQ ID NO: 7541)<br>(SEQ ID NO: 1996)<br>(SEQ ID NO: 3105) |
| βc-m417 Target: | 5'-CUUGCUCCCAUUCAUAAAGGACUUGGG-3'<br>3'-GAACGAGGGUAAGUAUUUCCUGAACCC-5'<br>5'-CTTGCTCCCATTCATAAAGGACTTGGG-3' | (SEQ ID NO: 7542)<br>(SEQ ID NO: 1997)<br>(SEQ ID NO: 3106) |
| βc-m462 Target: | 5'-CGUCAAUAUCAGCUACUUGCUCUUGCG-3'<br>3'-GCAGUUAUAGUCGAUGAACGAGAACGC-5'<br>5'-CGTCAATATCAGCTACTTGCTCTTGCG-3' | (SEQ ID NO: 7543)<br>(SEQ ID NO: 1998)<br>(SEQ ID NO: 3107) |
| βc-m463 Target: | 5'-CCGUCAAUAUCAGCUACUUGCUCUUGC-3'<br>3'-GGCAGUUAUAGUCGAUGAACGAGAACG-5'<br>5'-CCGTCAATATCAGCTACTTGCTCTTGC-3' | (SEQ ID NO: 7544)<br>(SEQ ID NO: 1999)<br>(SEQ ID NO: 3108) |
| βc-m468 Target: | 5'-ACUGCCCGUCAAUAUCAGCUACUUGCU-3'<br>3'-UGACGGGCAGUUAUAGUCGAUGAACGA-5'<br>5'-ACTGCCCGTCAATATCAGCTACTTGCT-3' | (SEQ ID NO: 7545)<br>(SEQ ID NO: 2000)<br>(SEQ ID NO: 3109) |
| βc-m613 Target: | 5'-UGUUUCAACAUCUGUGAUGGUUCAGCC-3'<br>3'-ACAAAGUUGUAGACACUACCAAGUCGG-5'<br>5'-TGTTTCAACATCTGTGATGGTTCAGCC-3' | (SEQ ID NO: 7546)<br>(SEQ ID NO: 2001)<br>(SEQ ID NO: 3110) |
| βc-m614 Target: | 5'-AUGUUUCAACAUCUGUGAUGGUUCAGC-3'<br>3'-UACAAAGUUGUAGACACUACCAAGUCG-5'<br>5'-ATGTTTCAACATCTGTGATGGTTCAGC-3' | (SEQ ID NO: 7547)<br>(SEQ ID NO: 2002)<br>(SEQ ID NO: 3111) |
| βc-m624 Target: | 5'-UGACAACUGCAUGUUUCAACAUCUGUG-3'<br>3'-ACUGUUGACGUACAAAGUUGUAGACAC-5'<br>5'-TGACAACTGCATGTTTCAACATCTGTG-3' | (SEQ ID NO: 7548)<br>(SEQ ID NO: 2003)<br>(SEQ ID NO: 3112) |
| βc-m626 Target: | 5'-AUUGACAACUGCAUGUUUCAACAUCUG-3'<br>3'-UAACUGUUGACGUACAAAGUUGUAGAC-5'<br>5'-ATTGACAACTGCATGTTTCAACATCTG-3' | (SEQ ID NO: 7549)<br>(SEQ ID NO: 2004)<br>(SEQ ID NO: 3113) |
| βc-m630 Target: | 5'-UCAAAUUGACAACUGCAUGUUUCAACA-3'<br>3'-AGUUUAACUGUUGACGUACAAAGUUGU-5'<br>5'-TCAAATTGACAACTGCATGTTTCAACA-3' | (SEQ ID NO: 7550)<br>(SEQ ID NO: 2005)<br>(SEQ ID NO: 3114) |
| βc-m636 Target: | 5'-AGUUAAUCAAAUUGACAACUGCAUGUU-3'<br>3'-UCAAUUAGUUUAACUGUUGACGUACAA-5'<br>5'-AGTTAATCAAATTGACAACTGCATGTT-3' | (SEQ ID NO: 7551)<br>(SEQ ID NO: 2006)<br>(SEQ ID NO: 3115) |
| βc-m642 Target: | 5'-CCUGAUAGUUAAUCAAAUUGACAACUG-3'<br>3'-GGACUAUCAAUUAGUUUAACUGUUGAC-5'<br>5'-CCTGATAGTTAATCAAATTGACAACTG-3' | (SEQ ID NO: 7552)<br>(SEQ ID NO: 2007)<br>(SEQ ID NO: 3116) |
| βc-m648 Target: | 5'-CGUCAUCCUGAUAGUUAAUCAAAUUGA-3'<br>3'-GCAGUAGGACUAUCAAUUAGUUUAACU-5'<br>5'-CGTCATCCTGATAGTTAATCAAATTGA-3' | (SEQ ID NO: 7553)<br>(SEQ ID NO: 2008)<br>(SEQ ID NO: 3117) |
| βc-m649 Target: | 5'-GCGUCAUCCUGAUAGUUAAUCAAAUUG-3'<br>3'-CGCAGUAGGACUAUCAAUUAGUUUAAC-5'<br>5'-GCGTCATCCTGATAGTTAATCAAATTG-3' | (SEQ ID NO: 7554)<br>(SEQ ID NO: 2009)<br>(SEQ ID NO: 3118) |
| βc-m702 Target: | 5'-CCUCAUCGUUUAGCAGUUUUGUCAGCU-3'<br>3'-GGAGUAGCAAAUCGUCAAAACAGUCGA-5'<br>5'-CCTCATCGTTTAGCAGTTTTGTCAGCT-3' | (SEQ ID NO: 7555)<br>(SEQ ID NO: 2010)<br>(SEQ ID NO: 3119) |
| βc-m707 Target: | 5'-CUGGUCCUCAUCGUUUAGCAGUUUUGU-3'<br>3'-GACCAGGAGUAGCAAAUCGUCAAAACA-5'<br>5'-CTGGTCCTCATCGTTTAGCAGTTTTGT-3' | (SEQ ID NO: 7556)<br>(SEQ ID NO: 2011)<br>(SEQ ID NO: 3120) |

TABLE 13-continued

Additional Selected Anti-β-catenin DsiRNAs, Blunt, Unfrayed Duplexes

| | | |
|---|---|---|
| βc-m734 Target: | 5'-CAUAACAGCAGCUUUAUUAACUACCAC-3'<br>3'-GUAUUGUCGUCGAAAUAAUUGAUGGUG-5'<br>5'-CATAACAGCAGCTTTATTAACTACCAC-3' | (SEQ ID NO: 7557)<br>(SEQ ID NO: 2012)<br>(SEQ ID NO: 3121) |
| βc-m735 Target: | 5'-CCAUAACAGCAGCUUUAUUAACUACCA-3'<br>3'-GGUAUUGUCGUCGAAAUAAUUGAUGGU-5'<br>5'-CCATAACAGCAGCTTTATTAACTACCA-3' | (SEQ ID NO: 7558)<br>(SEQ ID NO: 2013)<br>(SEQ ID NO: 3122) |
| βc-m738 Target: | 5'-GGACCAUAACAGCAGCUUUAUUAACUA-3'<br>3'-CCUGGUAUUGUCGUCGAAAUAAUUGAU-5'<br>5'-GGACCATAACAGCAGCTTTATTAACTA-3' | (SEQ ID NO: 7559)<br>(SEQ ID NO: 2014)<br>(SEQ ID NO: 3123) |
| βc-m739 Target: | 5'-UGGACCAUAACAGCAGCUUUAUUAACU-3'<br>3'-ACCUGGUAUUGUCGUCGAAAUAAUUGA-5'<br>5'-TGGACCATAACAGCAGCTTTATTAACT-3' | (SEQ ID NO: 7560)<br>(SEQ ID NO: 2015)<br>(SEQ ID NO: 3124) |
| βc-m843 Target: | 5'-CUGUCUCUACAUCAUUUGUAUUCUGCA-3'<br>3'-GACAGAGAUGUAGUAAACAUAAGACGU-5'<br>5'-CTGTCTCTACATCATTTGTATTCTGCA-3' | (SEQ ID NO: 7561)<br>(SEQ ID NO: 2016)<br>(SEQ ID NO: 3125) |
| βc-m844 Target: | 5'-GCUGUCUCUACAUCAUUUGUAUUCUGC-3'<br>3'-CGACAGAGAUGUAGUAAACAUAAGACG-5'<br>5'-GCTGTCTCTACATCATTTGTATTCTGC-3' | (SEQ ID NO: 7562)<br>(SEQ ID NO: 2017)<br>(SEQ ID NO: 3126) |
| βc-m1063 Target: | 5'-GCAACCAUUUUCUGCAGUCCACCAGCU-3'<br>3'-CGUUGGUAAAAGACGUCAGGUGGUCGA-5'<br>5'-GCAACCATTTTCTGCAGTCCACCAGCT-3' | (SEQ ID NO: 7563)<br>(SEQ ID NO: 2018)<br>(SEQ ID NO: 3127) |
| βc-m1065 Target: | 5'-AAGCAACCAUUUUCUGCAGUCCACCAG-3'<br>3'-UUCGUUGGUAAAAGACGUCAGGUGGUC-5'<br>5'-AAGCAACCATTTTCTGCAGTCCACCAG-3' | (SEQ ID NO: 7564)<br>(SEQ ID NO: 2019)<br>(SEQ ID NO: 3128) |
| βc-m1080 Target: | 5'-UUGUUUUGUUGAGCAAAGCAACCAUUU-3'<br>3'-AACAAAACAACUCGUUUCGUUGGUAAA-5'<br>5'-TTGTTTTGTTGAGCAAAGCAACCATTT-3' | (SEQ ID NO: 7565)<br>(SEQ ID NO: 2020)<br>(SEQ ID NO: 3129) |
| βc-m1081 Target: | 5'-UUUGUUUUGUUGAGCAAAGCAACCAUU-3'<br>3'-AAACAAAACAACUCGUUUCGUUGGUAA-5'<br>5'-TTTGTTTTGTTGAGCAAAGCAACCATT-3' | (SEQ ID NO: 7566)<br>(SEQ ID NO: 2021)<br>(SEQ ID NO: 3130) |
| βc-m1098 Target: | 5'-UAGCCAAGAAUUUCACGUUUGUUUUGU-3'<br>3'-AUCGGUUCUUAAAGUGCAAACAAAACA-5'<br>5'-TAGCCAAGAATTTCACGTTTGTTTTGT-3' | (SEQ ID NO: 7567)<br>(SEQ ID NO: 2022)<br>(SEQ ID NO: 3131) |
| βc-m1140 Target: | 5'-CUUGAUUGCCAUAAGCUAAGAUCUGAA-3'<br>3'-GAACUAACGGUAUUCGAUUCUAGACUU-5'<br>5'-CTTGATTGCCATAAGCTAAGATCTGAA-3' | (SEQ ID NO: 7568)<br>(SEQ ID NO: 2023)<br>(SEQ ID NO: 3132) |
| βc-m1145 Target: | 5'-GCUCUCUUGAUUGCCAUAAGCUAAGAU-3'<br>3'-CGAGAGAACUAACGGUAUUCGAUUCUA-5'<br>5'-GCTCTCTTGATTGCCATAAGCTAAGAT-3' | (SEQ ID NO: 7569)<br>(SEQ ID NO: 2024)<br>(SEQ ID NO: 3133) |
| βc-m1217 Target: | 5'-CUUCUCAUAAGUGUAGGUCCUCAUUAU-3'<br>3'-GAAGAGUAUUCACAUCCAGGAGUAAUA-5'<br>5'-CTTCTCATAAGTGTAGGTCCTCATTAT-3' | (SEQ ID NO: 7570)<br>(SEQ ID NO: 2025)<br>(SEQ ID NO: 3134) |
| βc-m1218 Target: | 5'-GCUUCUCAUAAGUGUAGGUCCUCAUUA-3'<br>3'-CGAAGAGUAUUCACAUCCAGGAGUAAU-5'<br>5'-GCTTCTCATAAGTGTAGGTCCTCATTA-3' | (SEQ ID NO: 7571)<br>(SEQ ID NO: 2026)<br>(SEQ ID NO: 3135) |
| βc-m1220 Target: | 5'-AAGCUUCUCAUAAGUGUAGGUCCUCAU-3'<br>3'-UUCGAAGAGUAUUCACAUCCAGGAGUA-5'<br>5'-AAGCTTCTCATAAGTGTAGGTCCTC-3' | (SEQ ID NO: 7572)<br>(SEQ ID NO: 2027)<br>(SEQ ID NO: 3136) |
| βc-m1221 Target: | 5'-GAAGCUUCUCAUAAGUGUAGGUCCUCA-3'<br>3'-CUUCGAAGAGUAUUCACAUCCAGGAGU-5'<br>5'-GAAGCTTCTCATAAGTGTAGGTCCTCA-3' | (SEQ ID NO: 7573)<br>(SEQ ID NO: 2028)<br>(SEQ ID NO: 3137) |
| βc-m1365 Target: | 5'-GAGUCCAAAGACAGUUUUGAACAAGUC-3'<br>3'-CUCAGGUUUCUGUCAAAACUUGUUCAG-5'<br>5'-GAGTCCAAAGACAGTTTTGAACAAGTC-3' | (SEQ ID NO: 7574)<br>(SEQ ID NO: 2029)<br>(SEQ ID NO: 3138) |
| βc-m1366 Target: | 5'-AGAGUCCAAAGACAGUUUUGAACAAGU-3'<br>3'-UCUCAGGUUUCUGUCAAAACUUGUUCA-5'<br>5'-AGAGTCCAAAGACAGTTTTGAACAAGT-3' | (SEQ ID NO: 7575)<br>(SEQ ID NO: 2030)<br>(SEQ ID NO: 3139) |

TABLE 13-continued

Additional Selected Anti-β-catenin DsiRNAs, Blunt, Unfrayed Duplexes

| | | |
|---|---|---|
| βc-m1461 Target: | 5'-CCACAUUUAUAUCAUCGGAACCCAGAA-3'<br>3'-GGUGUAAAUAUAGUAGCCUUGGGUCUU-5'<br>5'-CCACATTTATATCATCGGAACCCAGAA-3' | (SEQ ID NO: 7576)<br>(SEQ ID NO: 2031)<br>(SEQ ID NO: 3140) |
| βc-m1464 Target: | 5'-UGACCACAUUUAUAUCAUCGGAACCCA-3'<br>3'-ACUGGUGUAAAUAUAGUAGCCUUGGGU-5'<br>5'-TGACCACATTTATATCATCGGAACCCA-3' | (SEQ ID NO: 7577)<br>(SEQ ID NO: 2032)<br>(SEQ ID NO: 3141) |
| βc-m1473 Target: | 5'-CUGCACAGGUGACCACAUUUAUAUCAU-3'<br>3'-GACGUGUCCACUGGUGUAAAUAUAGUA-5'<br>5'-CTGCACAGGTGACCACATTTATATC-3' | (SEQ ID NO: 7578)<br>(SEQ ID NO: 2033)<br>(SEQ ID NO: 3142) |
| βc-m1474 Target: | 5'-GCUGCACAGGUGACCACAUUUAUAUCA-3'<br>3'-CGACGUGUCCACUGGUGUAAAUAUAGU-5'<br>5'-GCTGCACAGGTGACCACATTTATATCA-3' | (SEQ ID NO: 7579)<br>(SEQ ID NO: 2034)<br>(SEQ ID NO: 3143) |
| βc-m1510 Target: | 5'-UUGUAAUUAUUGCAAGUGAGGUUAGAG-3'<br>3'-AACAUUAAUAACGUUCACUCCAAUCUC-5'<br>5'-TTGTAATTATTGCAAGTGAGGTTAGAG-3' | (SEQ ID NO: 7580)<br>(SEQ ID NO: 2035)<br>(SEQ ID NO: 3144) |
| βc-m1523 Target: | 5'-CAUCAUCUUGUUUUUGUAAUUAUUGCA-3'<br>3'-GUAGUAGAACAAAAACAUUAAUAACGU-5'<br>5'-CATCATCTTGTTTTTGTAATTATTGCA-3' | (SEQ ID NO: 7581)<br>(SEQ ID NO: 2036)<br>(SEQ ID NO: 3145) |
| βc-m1524 Target: | 5'-CCAUCAUCUUGUUUUUGUAAUUAUUGC-3'<br>3'-GGUAGUAGAACAAAAACAUUAAUAACG-5'<br>5'-CCATCATCTTGTTTTTGTAATTATTGC-3' | (SEQ ID NO: 7582)<br>(SEQ ID NO: 2037)<br>(SEQ ID NO: 3146) |
| βc-m1527 Target: | 5'-ACACCAUCAUCUUGUUUUUGUAAUUAU-3'<br>3'-UGUGGUAGUAGAACAAAAACAUUAAUA-5'<br>5'-ACACCATCATCTTGTTTTTGTAATTAT-3' | (SEQ ID NO: 7583)<br>(SEQ ID NO: 2038)<br>(SEQ ID NO: 3147) |
| βc-m1532 Target: | 5'-UUGGCACACCAUCAUCUUGUUUUUGUA-3'<br>3'-AACCGUGUGGUAGUAGAACAAAAACAU-5'<br>5'-TTGGCACACCATCATCTTGTTTTTGTA-3' | (SEQ ID NO: 7584)<br>(SEQ ID NO: 2039)<br>(SEQ ID NO: 3148) |
| βc-m1752 Target: | 5'-UCAAUCCAACAGUUGCCUUUAUCAGAG-3'<br>3'-AGUUAGGUUGUCAACGGAAAUAGUCUC-5'<br>5'-TCAATCCAACAGTTGCCTTTATCAGAG-3' | (SEQ ID NO: 7585)<br>(SEQ ID NO: 2040)<br>(SEQ ID NO: 3149) |
| βc-m1757 Target: | 5'-UCGAAUCAAUCCAACAGUUGCCUUUAU-3'<br>3'-AGCUUAGUUAGGUUGUCAACGGAAAUA-5'<br>5'-TCGAATCAATCCAACAGTTGCCTTTAT-3' | (SEQ ID NO: 7586)<br>(SEQ ID NO: 2041)<br>(SEQ ID NO: 3150) |
| βc-m1827 Target: | 5'-GCUGAACUAGUCGUGGAAUAGCACCCU-3'<br>3'-CGACUUGAUCAGCACCUUAUCGUGGGA-5'<br>5'-GCTGAACTAGTCGTGGAATAGCACCCT-3' | (SEQ ID NO: 7587)<br>(SEQ ID NO: 2042)<br>(SEQ ID NO: 3151) |
| βc-m1934 Target: | 5'-AGUACACCCUUCUACUAUCUCCUCCAU-3'<br>3'-UCAUGUGGGAAGAUGAUAGAGGAGGUA-5'<br>5'-AGTACACCCTTCTACTATCTCCTCC-3' | (SEQ ID NO: 7588)<br>(SEQ ID NO: 2043)<br>(SEQ ID NO: 3152) |
| βc-m1935 Target: | 5'-CAGUACACCCUUCUACUAUCUCCUCCA-3'<br>3'-GUCAUGUGGGAAGAUGAUAGAGGAGGU-5'<br>5'-CAGTACACCCTTCTACTATCTCCTCCA-3' | (SEQ ID NO: 7589)<br>(SEQ ID NO: 2044)<br>(SEQ ID NO: 3153) |
| βc-m1936 Target: | 5'-CCAGUACACCCUUCUACUAUCUCCUCC-3'<br>3'-GGUCAUGUGGGAAGAUGAUAGAGGAGG-5'<br>5'-CCAGTACACCCTTCTACTATCTCCTCC-3' | (SEQ ID NO: 7590)<br>(SEQ ID NO: 2045)<br>(SEQ ID NO: 3154) |
| βc-m1941 Target: | 5'-GAGCUCCAGUACACCCUUCUACUAUCU-3'<br>3'-CUCGAGGUCAUGUGGGAAGAUGAUAGA-5'<br>5'-GAGCTCCAGTACACCCTTCTACTATCT-3' | (SEQ ID NO: 7591)<br>(SEQ ID NO: 2046)<br>(SEQ ID NO: 3155) |
| βc-m2009 Target: | 5'-AAACAAUGGAAUGGUAUUGAGUCCUCG-3'<br>3'-UUUGUUACCUUACCAUAACUCAGGAGC-5'<br>5'-AAACAATGGAATGGTATTGAGTCCTCG-3' | (SEQ ID NO: 7592)<br>(SEQ ID NO: 2047)<br>(SEQ ID NO: 3156) |
| βc-m2015 Target: | 5'-CUGCACAAACAAUGGAAUGGUAUUGAG-3'<br>3'-GACGUGUUUGUUACCUUACCAUAACUC-5'<br>5'-CTGCACAAACAATGGAATGGTATTGAG-3' | (SEQ ID NO: 7593)<br>(SEQ ID NO: 2048)<br>(SEQ ID NO: 3157) |
| βc-m2016 Target: | 5'-ACUGCACAAACAAUGGAAUGGUAUUGA-3'<br>3'-UGACGUGUUUGUUACCUUACCAUAACU-5'<br>5'-ACTGCACAAACAATGGAATGGTATTGA-3' | (SEQ ID NO: 7594)<br>(SEQ ID NO: 2049)<br>(SEQ ID NO: 3158) |

TABLE 13-continued

Additional Selected Anti-β-catenin DsiRNAs, Blunt, Unfrayed Duplexes

| | | |
|---|---|---|
| βc-m2021 Target: | 5'-AAGCAACUGCACAAACAAUGGAAUGGU-3'<br>3'-UUCGUUGACGUGUUUGUUACCUUACCA-5'<br>5'-AAGCAACTGCACAAACAATGGAATGGT-3' | (SEQ ID NO: 7595)<br>(SEQ ID NO: 2050)<br>(SEQ ID NO: 3159) |
| βc-m2028 Target: | 5'-GAGAAUAAAGCAACUGCACAAACAAUG-3'<br>3'-CUCUUAUUUCGUUGACGUGUUUGUUAC-5'<br>5'-GAGAATAAAGCAACTGCACAAACAATG-3' | (SEQ ID NO: 7596)<br>(SEQ ID NO: 2051)<br>(SEQ ID NO: 3160) |
| βc-m2037 Target: | 5'-UUUCAAUGGGAGAAUAAAGCAACUGCA-3'<br>3'-AAAGUUACCCUCUUAUUUCGUUGACGU-5'<br>5'-TTTCAATGGGAGAATAAAGCAACTGCA-3' | (SEQ ID NO: 7597)<br>(SEQ ID NO: 2052)<br>(SEQ ID NO: 3161) |
| βc-m2038 Target: | 5'-UUUUCAAUGGGAGAAUAAAGCAACUGC-3'<br>3'-AAAAGUUACCCUCUUAUUUCGUUGACG-5'<br>5'-TTTTCAATGGGAGAATAAAGCAACTGC-3' | (SEQ ID NO: 7598)<br>(SEQ ID NO: 2053)<br>(SEQ ID NO: 3162) |
| βc-m2039 Target: | 5'-AUUUUCAAUGGGAGAAUAAAGCAACUG-3'<br>3'-UAAAAGUUACCCUCUUAUUUCGUUGAC-5'<br>5'-ATTTTCAATGGGAGAATAAAGCAACTG-3' | (SEQ ID NO: 7599)<br>(SEQ ID NO: 2054)<br>(SEQ ID NO: 3163) |
| βc-m2043 Target: | 5'-GGAUAUUUUCAAUGGGAGAAUAAAGCA-3'<br>3'-CCUAUAAAAGUUACCCUCUUAUUUCGU-5'<br>5'-GGATATTTTCAATGGGAGAATAAAGCA-3' | (SEQ ID NO: 7600)<br>(SEQ ID NO: 2055)<br>(SEQ ID NO: 3164) |
| βc-m2044 Target: | 5'-UGGAUAUUUUCAAUGGGAGAAUAAAGC-3'<br>3'-ACCUAUAAAAGUUACCCUCUUAUUUCG-5'<br>5'-TGGATATTTTCAATGGGAGAATAAAGC-3' | (SEQ ID NO: 7601)<br>(SEQ ID NO: 2056)<br>(SEQ ID NO: 3165) |
| βc-m2045 Target: | 5'-UUGGAUAUUUUCAAUGGGAGAAUAAAG-3'<br>3'-AACCUAUAAAAGUUACCCUCUUAUUUC-5'<br>5'-TTGGATATTTTCAATGGGAGAATAAAG-3' | (SEQ ID NO: 7602)<br>(SEQ ID NO: 2057)<br>(SEQ ID NO: 3166) |
| βc-m2055 Target: | 5'-CAGCUACUCUUUGGAUAUUUUCAAUGG-3'<br>3'-GUCGAUGAGAAACCUAUAAAAGUUACC-5'<br>5'-CAGCTACTCTTTGGATATTTTCAATGG-3' | (SEQ ID NO: 7603)<br>(SEQ ID NO: 2058)<br>(SEQ ID NO: 3167) |
| βc-m2056 Target: | 5'-GCAGCUACUCUUUGGAUAUUUUCAAUG-3'<br>3'-CGUCGAUGAGAAACCUAUAAAAGUUAC-5'<br>5'-GCAGCTACTCTTTGGATATTTTCAATG-3' | (SEQ ID NO: 7604)<br>(SEQ ID NO: 2059)<br>(SEQ ID NO: 3168) |
| βc-m2231 Target: | 5'-CCGCUUCUUGUAAUCCUGUGGCUUGUC-3'<br>3'-GGCGAAGAACAUUAGGACACCGAACAG-5'<br>5'-CCGCTTCTTGTAATCCTGTGGCTTGTC-3' | (SEQ ID NO: 7605)<br>(SEQ ID NO: 2060)<br>(SEQ ID NO: 3169) |
| βc-m2307 Target: | 5'-CCAGUCCAAGAUCUGCAGUCUCAUUCC-3'<br>3'-GGUCAGGUUCUAGACGUCAGAGUAAGG-5'<br>5'-CCAGTCCAAGATCTGCAGTCTCATTCC-3' | (SEQ ID NO: 7606)<br>(SEQ ID NO: 2061)<br>(SEQ ID NO: 3170) |
| βc-m2385 Target: | 5'-CGUAUCCACCAGAGUGAAAAGAACGGU-3'<br>3'-GCAUAGGUGGUCUCACUUUUCUUGCCA-5'<br>5'-CGTATCCACCAGAGTGAAAAGAACGGT-3' | (SEQ ID NO: 7607)<br>(SEQ ID NO: 2062)<br>(SEQ ID NO: 3171) |
| βc-m2539 Target: | 5'-CAGGCCAGCUGAUUGCUAUCACCUGGG-3'<br>3'-GUCCGGUCGACUAACGAUAGUGGACCC-5'<br>5'-CAGGCCAGCTGATTGCTATCACCTGGG-3' | (SEQ ID NO: 7608)<br>(SEQ ID NO: 2063)<br>(SEQ ID NO: 3172) |
| βc-m2562 Target: | 5'-CGAUUUACAGGUCAGUAUCAAACCAGG-3'<br>3'-GCUAAAUGUCCAGUCAUAGUUUGGUCC-5'<br>5'-CGATTTACAGGTCAGTATCAAACCAGG-3' | (SEQ ID NO: 7609)<br>(SEQ ID NO: 2064)<br>(SEQ ID NO: 3173) |
| βc-m2563 Target: | 5'-ACGAUUUACAGGUCAGUAUCAAACCAG-3'<br>3'-UGCUAAAUGUCCAGUCAUAGUUUGGUC-5'<br>5'-ACGATTTACAGGTCAGTATCAAACCAG-3' | (SEQ ID NO: 7610)<br>(SEQ ID NO: 2065)<br>(SEQ ID NO: 3174) |
| βc-m2578 Target: | 5'-UUUCUUACCUAAAGGACGAUUUACAGG-3'<br>3'-AAAGAAUGGAUUUCCUGCUAAAUGUCC-5'<br>5'-TTTCTTACCTAAAGGACGATTTACAGG-3' | (SEQ ID NO: 7611)<br>(SEQ ID NO: 2066)<br>(SEQ ID NO: 3175) |
| βc-m2580 Target: | 5'-GCUUUCUUACCUAAAGGACGAUUUACA-3'<br>3'-CGAAAGAAUGGAUUUCCUGCUAAAUGU-5'<br>5'-GCTTTCTTACCTAAAGGACGATTTACA-3' | (SEQ ID NO: 7612)<br>(SEQ ID NO: 2067)<br>(SEQ ID NO: 3176) |
| βc-m2589 Target: | 5'-CUUUUAUAAGCUUUCUUACCUAAAGGA-3'<br>3'-GAAAAUAUUCGAAAGAAUGGAUUUCCU-5'<br>5'-CTTTTATAAGCTTTCTTACCTAAAGGA-3' | (SEQ ID NO: 7613)<br>(SEQ ID NO: 2068)<br>(SEQ ID NO: 3177) |

TABLE 13-continued

Additional Selected Anti-β-catenin DsiRNAs, Blunt, Unfrayed Duplexes

| | | |
|---|---|---|
| βc-m2590 Target: | 5'-GCUUUUAUAAGCUUUCUUACCUAAAGG-3'<br>3'-CGAAAAUAUUCGAAAGAAUGGAUUUCC-5'<br>5'-GCTTTTATAAGCTTTCTTACCTAAAGG-3' | (SEQ ID NO: 7614)<br>(SEQ ID NO: 2069)<br>(SEQ ID NO: 3178) |
| βc-m2593 Target: | 5'-CUGGCUUUUAUAAGCUUUCUUACCUAA-3'<br>3'-GACCGAAAAUAUUCGAAAGAAUGGAUU-5'<br>5'-CTGGCTTTTATAAGCTTTCTTACCTAA-3' | (SEQ ID NO: 7615)<br>(SEQ ID NO: 2070)<br>(SEQ ID NO: 3179) |
| βc-m2598 Target: | 5'-CCACACUGGCUUUUAUAAGCUUUCUUA-3'<br>3'-GGUGUGACCGAAAAUAUUCGAAAGAAU-5'<br>5'-CCACACTGGCTTTTATAAGCTTTCTTA-3' | (SEQ ID NO: 7616)<br>(SEQ ID NO: 2071)<br>(SEQ ID NO: 3180) |
| βc-m2604 Target: | 5'-AUUCACCCACACUGGCUUUUAUAAGCU-3'<br>3'-UAAGUGGGUGUGACCGAAAAUAUUCGA-5'<br>5'-ATTCACCCACACTGGCTTTTATAAGCT-3' | (SEQ ID NO: 7617)<br>(SEQ ID NO: 2072)<br>(SEQ ID NO: 3181) |
| βc-m2644 Target: | 5'-CCUACCAAGUCUUUCUGGAGUUCUGCA-3'<br>3'-GGAUGGUUCAGAAAGACCUCAAGACGU-5'<br>5'-CCTACCAAGTCTTTCTGGAGTTCTGCA-3' | (SEQ ID NO: 7618)<br>(SEQ ID NO: 2073)<br>(SEQ ID NO: 3182) |
| βc-m2674 Target: | 5'-AUUUACAAACAGGCCUAAAACCAUUCC-3'<br>3'-UAAAUGUUUGUCCGGAUUUUGGUAAGG-5'<br>5'-ATTTACAAACAGGCCTAAAACCATTCC-3' | (SEQ ID NO: 7619)<br>(SEQ ID NO: 2074)<br>(SEQ ID NO: 3183) |
| βc-m2675 Target: | 5'-GAUUUACAAACAGGCCUAAAACCAUUC-3'<br>3'-CUAAAUGUUUGUCCGGAUUUUGGUAAG-5'<br>5'-GATTTACAAACAGGCCTAAAACCATTC-3' | (SEQ ID NO: 7620)<br>(SEQ ID NO: 2075)<br>(SEQ ID NO: 3184) |
| βc-m2676 Target: | 5'-AGAUUUACAAACAGGCCUAAAACCAUU-3'<br>3'-UCUAAAUGUUUGUCCGGAUUUUGGUAA-5'<br>5'-AGATTTACAAACAGGCCTAAAACCATT-3' | (SEQ ID NO: 7621)<br>(SEQ ID NO: 2076)<br>(SEQ ID NO: 3185) |
| βc-m2710 Target: | 5'-CAUCUCCUUCCAAGGUAUGUAUCUGUU-3'<br>3'-GUAGAGGAAGGUUCCAUACAUAGACAA-5'<br>5'-CATCTCCTTCCAAGGTATGTATCTGTT-3' | (SEQ ID NO: 7622)<br>(SEQ ID NO: 2077)<br>(SEQ ID NO: 3186) |
| βc-m2711 Target: | 5'-ACAUCUCCUUCCAAGGUAUGUAUCUGU-3'<br>3'-UGUAGAGGAAGGUUCCAUACAUAGACA-5'<br>5'-ACATCTCCTTCCAAGGTATGTATCTGT-3' | (SEQ ID NO: 7623)<br>(SEQ ID NO: 2078)<br>(SEQ ID NO: 3187) |
| βc-m2725 Target: | 5'-ACUUCCACACAUGAACAUCUCCUUCCA-3'<br>3'-UGAAGGUGUGUACUUGUAGAGGAAGGU-5'<br>5'-ACTTCCACACATGAACATCTCCTTCCA-3' | (SEQ ID NO: 7624)<br>(SEQ ID NO: 2079)<br>(SEQ ID NO: 3188) |
| βc-m2728 Target: | 5'-GAAACUUCCACACAUGAACAUCUCCUU-3'<br>3'-CUUUGAAGGUGUGUACUUGUAGAGGAA-5'<br>5'-GAAACTTCCACACATGAACATCTCCTT-3' | (SEQ ID NO: 7625)<br>(SEQ ID NO: 2080)<br>(SEQ ID NO: 3189) |
| βc-m2729 Target: | 5'-AGAAACUUCCACACAUGAACAUCUCCU-3'<br>3'-UCUUUGAAGGUGUGUACUUGUAGAGGA-5'<br>5'-AGAAACTTCCACACATGAACATCTCCT-3' | (SEQ ID NO: 7626)<br>(SEQ ID NO: 2081)<br>(SEQ ID NO: 3190) |
| βc-m2730 Target: | 5'-GAGAAACUUCCACACAUGAACAUCUCC-3'<br>3'-CUCUUUGAAGGUGUGUACUUGUAGAGG-5'<br>5'-GAGAAACTTCCACACATGAACATCTCC-3' | (SEQ ID NO: 7627)<br>(SEQ ID NO: 2082)<br>(SEQ ID NO: 3191) |
| βc-m2731 Target: | 5'-UGAGAAACUUCCACACAUGAACAUCUC-3'<br>3'-ACUCUUUGAAGGUGUGUACUUGUAGAG-5'<br>5'-TGAGAAACTTCCACACATGAACATCTC-3' | (SEQ ID NO: 7628)<br>(SEQ ID NO: 2083)<br>(SEQ ID NO: 3192) |
| βc-m2739 Target: | 5'-CAUCAACGUGAGAAACUUCCACACAUG-3'<br>3'-GUAGUUGCACUCUUUGAAGGUGUGUAC-5'<br>5'-CATCAACGTGAGAAACTTCCACACATG-3' | (SEQ ID NO: 7629)<br>(SEQ ID NO: 2084)<br>(SEQ ID NO: 3193) |
| βc-m2742 Target: | 5'-AAACAUCAACGUGAGAAACUUCCACAC-3'<br>3'-UUUGUAGUUGCACUCUUUGAAGGUGUG-5'<br>5'-AAACATCAACGTGAGAAACTTCCACAC-3' | (SEQ ID NO: 7630)<br>(SEQ ID NO: 2085)<br>(SEQ ID NO: 3194) |
| βc-m2743 Target: | 5'-AAAACAUCAACGUGAGAAACUUCCACA-3'<br>3'-UUUUGUAGUUGCACUCUUUGAAGGUGU-5'<br>5'-AAAACATCAACGTGAGAAACTTCCACA-3' | (SEQ ID NO: 7631)<br>(SEQ ID NO: 2086)<br>(SEQ ID NO: 3195) |
| βc-m2744 Target: | 5'-AAAAACAUCAACGUGAGAAACUUCCAC-3'<br>3'-UUUUUGUAGUUGCACUCUUUGAAGGUG-5'<br>5'-AAAAACATCAACGTGAGAAACTTCCAC-3' | (SEQ ID NO: 7632)<br>(SEQ ID NO: 2087)<br>(SEQ ID NO: 3196) |

TABLE 13-continued

Additional Selected Anti-β-catenin DsiRNAs, Blunt, Unfrayed Duplexes

| | | | |
|---|---|---|---|
| βc-m2745 | Target: | 5'-CAAAAACAUCAACGUGAGAAACUUCCA-3'<br>3'-GUUUUUGUAGUUGCACUCUUUGAAGGU-5'<br>5'-CAAAAACATCAACGTGAGAAACTTCCA-3' | (SEQ ID NO: 7633)<br>(SEQ ID NO: 2088)<br>(SEQ ID NO: 3197) |
| βc-m2746 | Target: | 5'-GCAAAAACAUCAACGUGAGAAACUUCC-3'<br>3'-CGUUUUUGUAGUUGCACUCUUUGAAGG-5'<br>5'-GCAAAAACATCAACGTGAGAAACTTCC-3' | (SEQ ID NO: 7634)<br>(SEQ ID NO: 2089)<br>(SEQ ID NO: 3198) |
| βc-m2748 | Target: | 5'-UGGCAAAAACAUCAACGUGAGAAACUU-3'<br>3'-ACCGUUUUUGUAGUUGCACUCUUUGAA-5'<br>5'-TGGCAAAAACATCAACGTGAGAAACTT-3' | (SEQ ID NO: 7635)<br>(SEQ ID NO: 2090)<br>(SEQ ID NO: 3199) |
| βc-m2760 | Target: | 5'-CUGCAAAAGCUGUGGCAAAAACAUCAA-3'<br>3'-GACGUUUUCGACACCGUUUUUGUAGUU-5'<br>5'-CTGCAAAAGCTGTGGCAAAAACATCAA-3' | (SEQ ID NO: 7636)<br>(SEQ ID NO: 2091)<br>(SEQ ID NO: 3200) |
| βc-m2761 | Target: | 5'-GCUGCAAAAGCUGUGGCAAAAACAUCA-3'<br>3'-CGACGUUUUCGACACCGUUUUUGUAGU-5'<br>5'-GCTGCAAAAGCTGTGGCAAAAACATCA-3' | (SEQ ID NO: 7637)<br>(SEQ ID NO: 2092)<br>(SEQ ID NO: 3201) |
| βc-m2778 | Target: | 5'-ACUCAUCUGAGUAUAACGCUGCAAAAG-3'<br>3'-UGAGUAGACUCAUAUUGCGACGUUUUC-5'<br>5'-ACTCATCTGAGTATAACGCTGCAAAAG-3' | (SEQ ID NO: 7638)<br>(SEQ ID NO: 2093)<br>(SEQ ID NO: 3202) |
| βc-m2795 | Target: | 5'-UGAAAACAGCAAAUGUUACUCAUCUGA-3'<br>3'-ACUUUUGUCGUUUACAAUGAGUAGACU-5'<br>5'-TGAAAACAGCAAATGTTACTCATCTGA-3' | (SEQ ID NO: 7639)<br>(SEQ ID NO: 2094)<br>(SEQ ID NO: 3203) |
| βc-m2796 | Target: | 5'-UUGAAAACAGCAAAUGUUACUCAUCUG-3'<br>3'-AACUUUUGUCGUUUACAAUGAGUAGAC-5'<br>5'-TTGAAAACAGCAAATGTTACTCATCTG-3' | (SEQ ID NO: 7640)<br>(SEQ ID NO: 2095)<br>(SEQ ID NO: 3204) |
| βc-m2797 | Target: | 5'-GUUGAAAACAGCAAAUGUUACUCAUCU-3'<br>3'-CAACUUUUGUCGUUUACAAUGAGUAGA-5'<br>5'-GTTGAAAACAGCAAATGTTACTCATCT-3' | (SEQ ID NO: 7641)<br>(SEQ ID NO: 2096)<br>(SEQ ID NO: 3205) |
| βc-m2805 | Target: | 5'-CUAUUAAUGUUGAAAACAGCAAAUGUU-3'<br>3'-GAUAAUUACAACUUUUGUCGUUUACAA-5'<br>5'-CTATTAATGTTGAAAACAGCAAATGTT-3' | (SEQ ID NO: 7642)<br>(SEQ ID NO: 2097)<br>(SEQ ID NO: 3206) |
| βc-m2834 | Target: | 5'-ACACUACAGCUGUAUAGAGAGAAAGGC-3'<br>3'-UGUGAUGUCGACAUAUCUCUCUUUCCG-5'<br>5'-ACACTACAGCTGTATAGAGAGAAAGGC-3' | (SEQ ID NO: 7643)<br>(SEQ ID NO: 2098)<br>(SEQ ID NO: 3207) |
| βc-m2859 | Target: | 5'-CAGGCCAAUCACAAUGCACGUUCAGAC-3'<br>3'-GUCCGGUUAGUGUUACGUGCAAGUCUG-5'<br>5'-CAGGCCAATCACAATGCACGTTCAGAC-3' | (SEQ ID NO: 7644)<br>(SEQ ID NO: 2099)<br>(SEQ ID NO: 3208) |
| βc-m2946 | Target: | 5'-CUGUUCCCAUAGGAAACUCAGCUUGGU-3'<br>3'-GACAAGGGUAUCCUUUGAGUCGAACCA-5'<br>5'-CTGTTCCCATAGGAAACTCAGCTTGGT-3' | (SEQ ID NO: 7645)<br>(SEQ ID NO: 2100)<br>(SEQ ID NO: 3209) |
| βc-m2968 | Target: | 5'-CAGAACAAAAAGCGUACUUCGACUGUU-3'<br>3'-GUCUUGUUUUUCGCAUGAAGCUGACAA-5'<br>5'-CAGAACAAAAAGCGTACTTCGACTGTT-3' | (SEQ ID NO: 7646)<br>(SEQ ID NO: 2101)<br>(SEQ ID NO: 3210) |
| βc-m2974 | Target: | 5'-AAGGACCAGAACAAAAAGCGUACUUCG-3'<br>3'-UUCCUGGUCUUGUUUUUCGCAUGAAGC-5'<br>5'-AAGGACCAGAACAAAAAGCGTACTTCG-3' | (SEQ ID NO: 7647)<br>(SEQ ID NO: 2102)<br>(SEQ ID NO: 3211) |
| βc-m2982 | Target: | 5'-CGACCAAAAAGGACCAGAACAAAAAGC-3'<br>3'-GCUGGUUUUUCCUGGUCUUGUUUUUCG-5'<br>5'-CGACCAAAAAGGACCAGAACAAAAAGC-3' | (SEQ ID NO: 7648)<br>(SEQ ID NO: 2103)<br>(SEQ ID NO: 3212) |
| βc-m2983 | Target: | 5'-UCGACCAAAAAGGACCAGAACAAAAAG-3'<br>3'-AGCUGGUUUUUCCUGGUCUUGUUUUUC-5'<br>5'-TCGACCAAAAAGGACCAGAACAAAAAG-3' | (SEQ ID NO: 7649)<br>(SEQ ID NO: 2104)<br>(SEQ ID NO: 3213) |
| βc-m2990 | Target: | 5'-UUACUCCUCGACCAAAAAGGACCAGAA-3'<br>3'-AAUGAGGAGCUGGUUUUUCCUGGUCUU-5'<br>5'-TTACTCCTCGACCAAAAAGGACCAGAA-3' | (SEQ ID NO: 7650)<br>(SEQ ID NO: 2105)<br>(SEQ ID NO: 3214) |
| βc-m3005 | Target: | 5'-AAUCCAUUUGUAUUGUUACUCCUCGAC-3'<br>3'-UUAGGUAAACAUAACAAUGAGGAGCUG-5'<br>5'-AATCCATTTGTATTGTTACTCCTCGAC-3' | (SEQ ID NO: 7651)<br>(SEQ ID NO: 2106)<br>(SEQ ID NO: 3215) |

TABLE 13-continued

Additional Selected Anti-β-catenin DsiRNAs, Blunt, Unfrayed Duplexes

| | | |
|---|---|---|
| βc-m3006 Target: | 5'-AAAUCCAUUUGUAUUGUUACUCCUCGA-3'<br>3'-UUUAGGUAAACAUAACAAUGAGGAGCU-5'<br>5'-AAATCCATTTGTATTGTTACTCCTCGA-3' | (SEQ ID NO: 7652)<br>(SEQ ID NO: 2107)<br>(SEQ ID NO: 3216) |
| βc-m3007 Target: | 5'-CAAAUCCAUUUGUAUUGUUACUCCUCG-3'<br>3'-GUUUAGGUAAACAUAACAAUGAGGAGC-5'<br>5'-CAAATCCATTTGTATTGTTACTCCTCG-3' | (SEQ ID NO: 7653)<br>(SEQ ID NO: 2108)<br>(SEQ ID NO: 3217) |
| βc-m3008 Target: | 5'-CCAAAUCCAUUUGUAUUGUUACUCCUC-3'<br>3'-GGUUUAGGUAAACAUAACAAUGAGGAG-5'<br>5'-CCAAATCCATTTGTATTGTTACTCCTC-3' | (SEQ ID NO: 7654)<br>(SEQ ID NO: 2109)<br>(SEQ ID NO: 3218) |
| βc-m3015 Target: | 5'-UCACUCCCCAAAUCCAUUUGUAUUGUU-3'<br>3'-AGUGAGGGGUUUAGGUAAACAUAACAA-5'<br>5'-TCACTCCCCAAATCCATTTGTATTGTT-3' | (SEQ ID NO: 7655)<br>(SEQ ID NO: 2110)<br>(SEQ ID NO: 3219) |
| βc-m3047 Target: | 5'-GAUCCAUUCGUGUGCAUUCUUCACUGC-3'<br>3'-CUAGGUAAGCACACGUAAGAAGUGACG-5'<br>5'-GATCCATTCGTGTGCATTCTTCACTGC-3' | (SEQ ID NO: 7656)<br>(SEQ ID NO: 2111)<br>(SEQ ID NO: 3220) |
| βc-m3048 Target: | 5'-UGAUCCAUUCGUGUGCAUUCUUCACUG-3'<br>3'-ACUAGGUAAGCACACGUAAGAAGUGAC-5'<br>5'-TGATCCATTCGTGTGCATTCTTCACTG-3' | (SEQ ID NO: 7657)<br>(SEQ ID NO: 2112)<br>(SEQ ID NO: 3221) |
| βc-m3049 Target: | 5'-GUGAUCCAUUCGUGUGCAUUCUUCACU-3'<br>3'-CACUAGGUAAGCACACGUAAGAAGUGA-5'<br>5'-GTGATCCATTCGTGTGCATTCTTCACT-3' | (SEQ ID NO: 7658)<br>(SEQ ID NO: 2113)<br>(SEQ ID NO: 3222) |
| βc-m3093 Target: | 5'-UAAAACAAAGAACAAGCAAGGCUAGGG-3'<br>3'-AUUUUGUUUCUUGUUCGUUCCGAUCCC-5'<br>5'-TAAAACAAAGAACAAGCAAGGCTAGGG-3' | (SEQ ID NO: 7659)<br>(SEQ ID NO: 2114)<br>(SEQ ID NO: 3223) |
| βc-m3109 Target: | 5'-GCACCACUACAGAUAUUAAAACAAAGA-3'<br>3'-CGUGGUGAUGUCUAUAAUUUUGUUUCU-5'<br>5'-GCACCACTACAGATATTAAAACAAAGA-3' | (SEQ ID NO: 7660)<br>(SEQ ID NO: 2115)<br>(SEQ ID NO: 3224) |
| βc-m3111 Target: | 5'-CAGCACCACUACAGAUAUUAAAACAAA-3'<br>3'-GUCGUGGUGAUGUCUAUAAUUUUGUUU-5'<br>5'-CAGCACCACTACAGATATTAAAACAAA-3' | (SEQ ID NO: 7661)<br>(SEQ ID NO: 2116)<br>(SEQ ID NO: 3225) |
| βc-m3112 Target: | 5'-UCAGCACCACUACAGAUAUUAAAACAA-3'<br>3'-AGUCGUGGUGAUGUCUAUAAUUUUGUU-5'<br>5'-TCAGCACCACTACAGATATTAAAACAA-3' | (SEQ ID NO: 7662)<br>(SEQ ID NO: 2117)<br>(SEQ ID NO: 3226) |
| βc-m3133 Target: | 5'-AAAAAAUAAAAGCAAGCAAAGUCAGCA-3'<br>3'-UUUUUUAUUUUCGUUCGUUUCAGUCGU-5'<br>5'-AAAAAATAAAAGCAAGCAAAGTCAGCA-3' | (SEQ ID NO: 7663)<br>(SEQ ID NO: 2118)<br>(SEQ ID NO: 3227) |
| βc-m3137 Target: | 5'-CUGCAAAAAAUAAAAGCAAGCAAAGUC-3'<br>3'-GACGUUUUUUAUUUUCGUUCGUUUCAG-5'<br>5'-CTGCAAAAAATAAAAGCAAGCAAAGTC-3' | (SEQ ID NO: 7664)<br>(SEQ ID NO: 2119)<br>(SEQ ID NO: 3228) |
| βc-m3142 Target: | 5'-AGUUACUGCAAAAAAUAAAAGCAAGCA-3'<br>3'-UCAAUGACGUUUUUUAUUUUCGUUCGU-5'<br>5'-AGTTACTGCAAAAAATAAAAGCAAGCA-3' | (SEQ ID NO: 7665)<br>(SEQ ID NO: 2120)<br>(SEQ ID NO: 3229) |
| βc-m3148 Target: | 5'-ACUAACAGUUACUGCAAAAAAUAAAAG-3'<br>3'-UGAUUGUCAAUGACGUUUUUUAUUUUC-5'<br>5'-ACTAACAGTTACTGCAAAAAATAAAAG-3' | (SEQ ID NO: 7666)<br>(SEQ ID NO: 2121)<br>(SEQ ID NO: 3230) |
| βc-m3150 Target: | 5'-AAACUAACAGUUACUGCAAAAAAUAAA-3'<br>3'-UUUGAUUGUCAAUGACGUUUUUUAUUU-5'<br>5'-AAACTAACAGTTACTGCAAAAAATAAA-3' | (SEQ ID NO: 7667)<br>(SEQ ID NO: 2122)<br>(SEQ ID NO: 3231) |
| βc-m3152 Target: | 5'-AAAAACUAACAGUUACUGCAAAAAAUA-3'<br>3'-UUUUUGAUUGUCAAUGACGUUUUUUAU-5'<br>5'-AAAAACTAACAGTTACTGCAAAAAATA-3' | (SEQ ID NO: 7668)<br>(SEQ ID NO: 2123)<br>(SEQ ID NO: 3232) |
| βc-m3153 Target: | 5'-UAAAAACUAACAGUUACUGCAAAAAAU-3'<br>3'-AUUUUUGAUUGUCAAUGACGUUUUUUA-5'<br>5'-TAAAAACTAACAGTTACTGCAAAAAAT-3' | (SEQ ID NO: 7669)<br>(SEQ ID NO: 2124)<br>(SEQ ID NO: 3233) |
| βc-m3155 Target: | 5'-CUUAAAAACUAACAGUUACUGCAAAAA-3'<br>3'-GAAUUUUUGAUUGUCAAUGACGUUUUU-5'<br>5'-CTTAAAAACTAACAGTTACTGCAAAAA-3' | (SEQ ID NO: 7670)<br>(SEQ ID NO: 2125)<br>(SEQ ID NO: 3234) |

TABLE 13-continued

Additional Selected Anti-β-catenin DsiRNAs, Blunt, Unfrayed Duplexes

| | | |
|---|---|---|
| βc-m3159 Target: | 5'-ACUACUUAAAAACUAACAGUUACUGCA-3'<br>3'-UGAUGAAUUUUUGAUUGUCAAUGACGU-5'<br>5'-ACTACTTAAAAACTAACAGTTACTGCA-3' | (SEQ ID NO: 7671)<br>(SEQ ID NO: 2126)<br>(SEQ ID NO: 3235) |
| βc-m3161 Target: | 5'-ACACUACUUAAAAACUAACAGUUACUG-3'<br>3'-UGUGAUGAAUUUUUGAUUGUCAAUGAC-5'<br>5'-ACACTACTTAAAAACTAACAGTTACTG-3' | (SEQ ID NO: 7672)<br>(SEQ ID NO: 2127)<br>(SEQ ID NO: 3236) |
| βc-m3165 Target: | 5'-CAUAACACUACUUAAAAACUAACAGUU-3'<br>3'-GUAUUGUGAUGAAUUUUUGAUUGUCAA-5'<br>5'-CATAACACTACTTAAAAACTAACAGTT-3' | (SEQ ID NO: 7673)<br>(SEQ ID NO: 2128)<br>(SEQ ID NO: 3237) |
| βc-m3166 Target: | 5'-ACAUAACACUACUUAAAAACUAACAGU-3'<br>3'-UGUAUUGUGAUGAAUUUUUGAUUGUCA-5'<br>5'-ACATAACACTACTTAAAAACTAACAGT-3' | (SEQ ID NO: 7674)<br>(SEQ ID NO: 2129)<br>(SEQ ID NO: 3238) |
| βc-m3168 Target: | 5'-GAACAUAACACUACUUAAAAACUAACA-3'<br>3'-CUUGUAUUGUGAUGAAUUUUUGAUUGU-5'<br>5'-GAACATAACACTACTTAAAAACTAACA-3' | (SEQ ID NO: 7675)<br>(SEQ ID NO: 2130)<br>(SEQ ID NO: 3239) |
| βc-m3169 Target: | 5'-AGAACAUAACACUACUUAAAAACUAAC-3'<br>3'-UCUUGUAUUGUGAUGAAUUUUUGAUUG-5'<br>5'-AGAACATAACACTACTTAAAAACTAAC-3' | (SEQ ID NO: 7676)<br>(SEQ ID NO: 2131)<br>(SEQ ID NO: 3240) |
| βc-m3170 Target: | 5'-UAGAACAUAACACUACUUAAAAACUAA-3'<br>3'-AUCUUGUAUUGUGAUGAAUUUUUGAUU-5'<br>5'-TAGAACATAACACTACTTAAAAACTAA-3' | (SEQ ID NO: 7677)<br>(SEQ ID NO: 2132)<br>(SEQ ID NO: 3241) |
| βc-m3171 Target: | 5'-CUAGAACAUAACACUACUUAAAAACUA-3'<br>3'-GAUCUUGUAUUGUGAUGAAUUUUUGAU-5'<br>5'-CTAGAACATAACACTACTTAAAAACTA-3' | (SEQ ID NO: 7678)<br>(SEQ ID NO: 2133)<br>(SEQ ID NO: 3242) |
| βc-m3176 Target: | 5'-GUUCACUAGAACAUAACACUACUUAAA-3'<br>3'-CAAGUGAUCUUGUAUUGUGAUGAAUUU-5'<br>5'-GTTCACTAGAACATAACACTACTTAAA-3' | (SEQ ID NO: 7679)<br>(SEQ ID NO: 2134)<br>(SEQ ID NO: 3243) |
| βc-m3178 Target: | 5'-AGGUUCACUAGAACAUAACACUACUUA-3'<br>3'-UCCAAGUGAUCUUGUAUUGUGAUGAAU-5'<br>5'-AGGTTCACTAGAACATAACACTACTTA-3' | (SEQ ID NO: 7680)<br>(SEQ ID NO: 2135)<br>(SEQ ID NO: 3244) |
| βc-m3179 Target: | 5'-CAGGUUCACUAGAACAUAACACUACUU-3'<br>3'-GUCCAAGUGAUCUUGUAUUGUGAUGAA-5'<br>5'-CAGGTTCACTAGAACATAACACTACTT-3' | (SEQ ID NO: 7681)<br>(SEQ ID NO: 2136)<br>(SEQ ID NO: 3245) |
| βc-m3216 Target: | 5'-CCAUUACUCGGUUCUUAGAAAUCAGAA-3'<br>3'-GGUAAUGAGCCAAGAAUCUUUAGUCUU-5'<br>5'-CCATTACTCGGTTCTTAGAAATCAGAA-3' | (SEQ ID NO: 7682)<br>(SEQ ID NO: 2137)<br>(SEQ ID NO: 3246) |
| βc-m3219 Target: | 5'-ACACCAUUACUCGGUUCUUAGAAAUCA-3'<br>3'-UGUGGUAAUGAGCCAAGAAUCUUUAGU-5'<br>5'-ACACCATTACTCGGTTCTTAGAAATCA-3' | (SEQ ID NO: 7683)<br>(SEQ ID NO: 2138)<br>(SEQ ID NO: 3247) |
| βc-m3224 Target: | 5'-GUUCUACACCAUUACUCGGUUCUUAGA-3'<br>3'-CAAGAUGUGGUAAUGAGCCAAGAAUCU-5'<br>5'-GTTCTACACCATTACTCGGTTCTTAGA-3' | (SEQ ID NO: 7684)<br>(SEQ ID NO: 2139)<br>(SEQ ID NO: 3248) |
| βc-m3234 Target: | 5'-AUGAAUUAGUGUUCUACACCAUUACUC-3'<br>3'-UACUUAAUCACAAGAUGUGGUAAUGAG-5'<br>5'-ATGAATTAGTGTTCTACACCATTACTC-3' | (SEQ ID NO: 7685)<br>(SEQ ID NO: 2140)<br>(SEQ ID NO: 3249) |
| βc-m3239 Target: | 5'-UGAUUAUGAAUUAGUGUUCUACACCAU-3'<br>3'-ACUAAUACUUAAUCACAAGAUGUGGUA-5'<br>5'-TGATTATGAATTAGTGTTCTACACC-3' | (SEQ ID NO: 7686)<br>(SEQ ID NO: 2141)<br>(SEQ ID NO: 3250) |
| βc-m3240 Target: | 5'-GUGAUUAUGAAUUAGUGUUCUACACCA-3'<br>3'-CACUAAUACUUAAUCACAAGAUGUGGU-5'<br>5'-GTGATTATGAATTAGTGTTCTACACCA-3' | (SEQ ID NO: 7687)<br>(SEQ ID NO: 2142)<br>(SEQ ID NO: 3251) |
| βc-m3241 Target: | 5'-CGUGAUUAUGAAUUAGUGUUCUACACC-3'<br>3'-GCACUAAUACUUAAUCACAAGAUGUGG-5'<br>5'-CGTGATTATGAATTAGTGTTCTACACC-3' | (SEQ ID NO: 7688)<br>(SEQ ID NO: 2143)<br>(SEQ ID NO: 3252) |
| βc-m3251 Target: | 5'-UUACAAUUAGCGUGAUUAUGAAUUAGU-3'<br>3'-AAUGUUAAUCGCACUAAUACUUAAUCA-5'<br>5'-TTACAATTAGCGTGATTATGAATTAGT-3' | (SEQ ID NO: 7689)<br>(SEQ ID NO: 2144)<br>(SEQ ID NO: 3253) |

TABLE 13-continued

Additional Selected Anti-β-catenin DsiRNAs, Blunt, Unfrayed Duplexes

| | | | |
|---|---|---|---|
| βc-m3252 | Target: | 5'-AUUACAAUUAGCGUGAUUAUGAAUUAG-3'<br>3'-UAAUGUUAAUCGCACUAAUACUUAAUC-5'<br>5'-ATTACAATTAGCGTGATTATGAATTAG-3' | (SEQ ID NO: 7690)<br>(SEQ ID NO: 2145)<br>(SEQ ID NO: 3254) |
| βc-m3256 | Target: | 5'-CCAGAUUACAAUUAGCGUGAUUAUGAA-3'<br>3'-GGUCUAAUGUUAAUCGCACUAAUACUU-5'<br>5'-CCAGATTACAATTAGCGTGATTATGAA-3' | (SEQ ID NO: 7691)<br>(SEQ ID NO: 2146)<br>(SEQ ID NO: 3255) |
| βc-m3267 | Target: | 5'-GUUACACGUCUCCAGAUUACAAUUAGC-3'<br>3'-CAAUGUGCAGAGGUCUAAUGUUAAUCG-5'<br>5'-GTTACACGTCTCCAGATTACAATTAGC-3' | (SEQ ID NO: 7692)<br>(SEQ ID NO: 2147)<br>(SEQ ID NO: 3256) |
| βc-m3269 | Target: | 5'-AUGUUACACGUCUCCAGAUUACAAUUA-3'<br>3'-UACAAUGUGCAGAGGUCUAAUGUUAAU-5'<br>5'-ATGTTACACGTCTCCAGATTACAATTA-3' | (SEQ ID NO: 7693)<br>(SEQ ID NO: 2148)<br>(SEQ ID NO: 3257) |
| βc-m3277 | Target: | 5'-GCUACACAAUGUUACACGUCUCCAGAU-3'<br>3'-CGAUGUGUUACAAUGUGCAGAGGUCUA-5'<br>5'-GCTACACAATGTTACACGTCTCCAGAT-3' | (SEQ ID NO: 7694)<br>(SEQ ID NO: 2149)<br>(SEQ ID NO: 3258) |
| βc-m3279 | Target: | 5'-AGGCUACACAAUGUUACACGUCUCCAG-3'<br>3'-UCCGAUGUGUUACAAUGUGCAGAGGUC-5'<br>5'-AGGCTACACAATGTTACACGTCTCCAG-3' | (SEQ ID NO: 7695)<br>(SEQ ID NO: 2150)<br>(SEQ ID NO: 3259) |
| βc-m3286 | Target: | 5'-AUACAAAAGGCUACACAAUGUUACACG-3'<br>3'-UAUGUUUUCCGAUGUGUUACAAUGUGC-5'<br>5'-ATACAAAAGGCTACACAATGTTACACG-3' | (SEQ ID NO: 7696)<br>(SEQ ID NO: 2151)<br>(SEQ ID NO: 3260) |
| βc-m3287 | Target: | 5'-UAUACAAAAGGCUACACAAUGUUACAC-3'<br>3'-AUAUGUUUUCCGAUGUGUUACAAUGUG-5'<br>5'-TATACAAAAGGCTACACAATGTTACAC-3' | (SEQ ID NO: 7697)<br>(SEQ ID NO: 2152)<br>(SEQ ID NO: 3261) |
| βc-m3291 | Target: | 5'-UAUUUAUACAAAAGGCUACACAAUGUU-3'<br>3'-AUAAAUAUGUUUUCCGAUGUGUUACAA-5'<br>5'-TATTTATACAAAAGGCTACACAATGTT-3' | (SEQ ID NO: 7698)<br>(SEQ ID NO: 2153)<br>(SEQ ID NO: 3262) |
| βc-m3292 | Target: | 5'-CUAUUUAUACAAAAGGCUACACAAUGU-3'<br>3'-GAUAAAUAUGUUUUCCGAUGUGUUACA-5'<br>5'-CTATTTATACAAAAGGCTACACAATGT-3' | (SEQ ID NO: 7699)<br>(SEQ ID NO: 2154)<br>(SEQ ID NO: 3263) |
| βc-m3295 | Target: | 5'-UGUCUAUUUAUACAAAAGGCUACACAA-3'<br>3'-ACAGAUAAAUAUGUUUUCCGAUGUGUU-5'<br>5'-TGTCTATTTATACAAAAGGCTACACAA-3' | (SEQ ID NO: 7700)<br>(SEQ ID NO: 2155)<br>(SEQ ID NO: 3264) |
| βc-m3296 | Target: | 5'-CUGUCUAUUUAUACAAAAGGCUACACA-3'<br>3'-GACAGAUAAAUAUGUUUUCCGAUGUGU-5'<br>5'-CTGTCTATTTATACAAAAGGCTACACA-3' | (SEQ ID NO: 7701)<br>(SEQ ID NO: 2156)<br>(SEQ ID NO: 3265) |
| βc-m3297 | Target: | 5'-UCUGUCUAUUUAUACAAAAGGCUACAC-3'<br>3'-AGACAGAUAAAUAUGUUUUCCGAUGUG-5'<br>5'-TCTGTCTATTTATACAAAAGGCTACAC-3' | (SEQ ID NO: 7702)<br>(SEQ ID NO: 2157)<br>(SEQ ID NO: 3266) |
| βc-m3303 | Target: | 5'-UUUCUAUCUGUCUAUUUAUACAAAAGG-3'<br>3'-AAAGAUAGACAGAUAAAUAUGUUUUCC-5'<br>5'-TTTCTATCTGTCTATTTATACAAAAGG-3' | (SEQ ID NO: 7703)<br>(SEQ ID NO: 2158)<br>(SEQ ID NO: 3267) |
| βc-m3304 | Target: | 5'-AUUUCUAUCUGUCUAUUUAUACAAAAG-3'<br>3'-UAAAGAUAGACAGAUAAAUAUGUUUUC-5'<br>5'-ATTTCTATCTGTCTATTTATACAAAAG-3' | (SEQ ID NO: 7704)<br>(SEQ ID NO: 2159)<br>(SEQ ID NO: 3268) |
| βc-m3305 | Target: | 5'-CAUUUCUAUCUGUCUAUUUAUACAAAA-3'<br>3'-GUAAAGAUAGACAGAUAAAUAUGUUUU-5'<br>5'-CATTTCTATCTGTCTATTTATACAAAA-3' | (SEQ ID NO: 7705)<br>(SEQ ID NO: 2160)<br>(SEQ ID NO: 3269) |
| βc-m3306 | Target: | 5'-CCAUUUCUAUCUGUCUAUUUAUACAAA-3'<br>3'-GGUAAAGAUAGACAGAUAAAUAUGUUU-5'<br>5'-CCATTTCTATCTGTCTATTTATACAAA-3' | (SEQ ID NO: 7706)<br>(SEQ ID NO: 2161)<br>(SEQ ID NO: 3270) |
| βc-m3310 | Target: | 5'-CGGACCAUUUCUAUCUGUCUAUUUAUA-3'<br>3'-GCCUGGUAAAGAUAGACAGAUAAAUAU-5'<br>5'-CGGACCATTTCTATCTGTCTATTTATA-3' | (SEQ ID NO: 7707)<br>(SEQ ID NO: 2162)<br>(SEQ ID NO: 3271) |
| βc-m3311 | Target: | 5'-UCGGACCAUUUCUAUCUGUCUAUUUAU-3'<br>3'-AGCCUGGUAAAGAUAGACAGAUAAAUA-5'<br>5'-TCGGACCATTTCTATCTGTCTATTTAT-3' | (SEQ ID NO: 7708)<br>(SEQ ID NO: 2163)<br>(SEQ ID NO: 3272) |

TABLE 13-continued

Additional Selected Anti-β-catenin DsiRNAs, Blunt, Unfrayed Duplexes

| | | | |
|---|---|---|---|
| βc-m3318 | Target: | 5'-AAACUAAUCGGACCAUUUCUAUCUGUC-3'<br>3'-UUUGAUUAGCCUGGUAAAGAUAGACAG-5'<br>5'-AAACTAATCGGACCATTTCTATCTGTC-3' | (SEQ ID NO: 7709)<br>(SEQ ID NO: 2164)<br>(SEQ ID NO: 3273) |
| βc-m3319 | Target: | 5'-GAAACUAAUCGGACCAUUUCUAUCUGU-3'<br>3'-CUUUGAUUAGCCUGGUAAAGAUAGACA-5'<br>5'-GAAACTAATCGGACCATTTCTATCTGT-3' | (SEQ ID NO: 7710)<br>(SEQ ID NO: 2165)<br>(SEQ ID NO: 3274) |
| βc-m3320 | Target: | 5'-GGAAACUAAUCGGACCAUUUCUAUCUG-3'<br>3'-CCUUUGAUUAGCCUGGUAAAGAUAGAC-5'<br>5'-GGAAACTAATCGGACCATTTCTATCTG-3' | (SEQ ID NO: 7711)<br>(SEQ ID NO: 2166)<br>(SEQ ID NO: 3275) |
| βc-m3321 | Target: | 5'-AGGAAACUAAUCGGACCAUUUCUAUCU-3'<br>3'-UCCUUUGAUUAGCCUGGUAAAGAUAGA-5'<br>5'-AGGAAACTAATCGGACCATTTCTATCT-3' | (SEQ ID NO: 7712)<br>(SEQ ID NO: 2167)<br>(SEQ ID NO: 3276) |
| βc-m3328 | Target: | 5'-AUUAAAAAGGAAACUAAUCGGACCAUU-3'<br>3'-UAAUUUUUCCUUUGAUUAGCCUGGUAA-5'<br>5'-ATTAAAAAGGAAACTAATCGGACCATT-3' | (SEQ ID NO: 7713)<br>(SEQ ID NO: 2168)<br>(SEQ ID NO: 3277) |
| βc-m3334 | Target: | 5'-AAGCAUAUUAAAAAGGAAACUAAUCGG-3'<br>3'-UUCGUAUAAUUUUUCCUUUGAUUAGCC-5'<br>5'-AAGCATATTAAAAAGGAAACTAATCGG-3' | (SEQ ID NO: 7714)<br>(SEQ ID NO: 2169)<br>(SEQ ID NO: 3278) |
| βc-m3335 | Target: | 5'-UAAGCAUAUUAAAAAGGAAACUAAUCG-3'<br>3'-AUUCGUAUAAUUUUUCCUUUGAUUAGC-5'<br>5'-TAAGCATATTAAAAAGGAAACTAATCG-3' | (SEQ ID NO: 7715)<br>(SEQ ID NO: 2170)<br>(SEQ ID NO: 3279) |
| βc-m3339 | Target: | 5'-AUUUUAAGCAUAUUAAAAAGGAAACUA-3'<br>3'-UAAAAUUCGUAUAAUUUUUCCUUUGAU-5'<br>5'-ATTTTAAGCATATTAAAAAGGAAACTA-3' | (SEQ ID NO: 7716)<br>(SEQ ID NO: 2171)<br>(SEQ ID NO: 3280) |
| βc-m3345 | Target: | 5'-CUGCUUAUUUUAAGCAUAUUAAAAAGG-3'<br>3'-GACGAAUAAAAUUCGUAUAAUUUUUCC-5'<br>5'-CTGCTTATTTTAAGCATATTAAAAAGG-3' | (SEQ ID NO: 7717)<br>(SEQ ID NO: 2172)<br>(SEQ ID NO: 3281) |
| βc-m3346 | Target: | 5'-CCUGCUUAUUUUAAGCAUAUUAAAAAG-3'<br>3'-GGACGAAUAAAAUUCGUAUAAUUUUUC-5'<br>5'-CCTGCTTATTTTAAGCATATTAAAAAG-3' | (SEQ ID NO: 7718)<br>(SEQ ID NO: 2173)<br>(SEQ ID NO: 3282) |
| βc-m3352 | Target: | 5'-GAUCCACCUGCUUAUUUUAAGCAUAUU-3'<br>3'-CUAGGUGGACGAAUAAAAUUCGUAUAA-5'<br>5'-GATCCACCTGCTTATTTTAAGCATATT-3' | (SEQ ID NO: 7719)<br>(SEQ ID NO: 2174)<br>(SEQ ID NO: 3283) |
| βc-m3367 | Target: | 5'-CAAAAACAUGAAAUAGAUCCACCUGCU-3'<br>3'-GUUUUUGUACUUUAUCUAGGUGGACGA-5'<br>5'-CAAAAACATGAAATAGATCCACCTGCT-3' | (SEQ ID NO: 7720)<br>(SEQ ID NO: 2175)<br>(SEQ ID NO: 3284) |
| βc-m3368 | Target: | 5'-UCAAAAACAUGAAAUAGAUCCACCUGC-3'<br>3'-AGUUUUUGUACUUUAUCUAGGUGGACG-5'<br>5'-TCAAAAACATGAAATAGATCCACCTGC-3' | (SEQ ID NO: 7721)<br>(SEQ ID NO: 2176)<br>(SEQ ID NO: 3285) |
| βc-m3370 | Target: | 5'-GUUCAAAAACAUGAAAUAGAUCCACCU-3'<br>3'-CAAGUUUUUGUACUUUAUCUAGGUGGA-5'<br>5'-GTTCAAAAACATGAAATAGATCCACCT-3' | (SEQ ID NO: 7722)<br>(SEQ ID NO: 2177)<br>(SEQ ID NO: 3286) |
| βc-m3371 | Target: | 5'-UGUUCAAAAACAUGAAAUAGAUCCACC-3'<br>3'-ACAAGUUUUUGUACUUUAUCUAGGUGG-5'<br>5'-TGTTCAAAAACATGAAATAGATCCACC-3' | (SEQ ID NO: 7723)<br>(SEQ ID NO: 2178)<br>(SEQ ID NO: 3287) |
| βc-m3372 | Target: | 5'-UUGUUCAAAAACAUGAAAUAGAUCCAC-3'<br>3'-AACAAGUUUUUGUACUUUAUCUAGGUG-5'<br>5'-TTGTTCAAAAACATGAAATAGATCCAC-3' | (SEQ ID NO: 7724)<br>(SEQ ID NO: 2179)<br>(SEQ ID NO: 3288) |
| βc-m3377 | Target: | 5'-AGUUUUGUUCAAAAACAUGAAAUAGA-3'<br>3'-UCAAAAACAAGUUUUUGUACUUUAUCU-5'<br>5'-AGTTTTTGTTCAAAAACATGAAATAGA-3' | (SEQ ID NO: 7725)<br>(SEQ ID NO: 2180)<br>(SEQ ID NO: 3289) |
| βc-m3383 | Target: | 5'-CGAUAAAGUUUUGUUCAAAAACAUGA-3'<br>3'-GCUAUUUCAAAAACAAGUUUUUGUACU-5'<br>5'-CGATAAAGTTTTGTTCAAAAACATGA-3' | (SEQ ID NO: 7726)<br>(SEQ ID NO: 2181)<br>(SEQ ID NO: 3290) |
| βc-m3389 | Target: | 5'-UAUCCCCGAUAAAGUUUUGUUCAAAA-3'<br>3'-AUAGGGGCUAUUUCAAAAACAAGUUUU-5'<br>5'-TATCCCCGATAAAGTTTTGTTCAAAA-3' | (SEQ ID NO: 7727)<br>(SEQ ID NO: 2182)<br>(SEQ ID NO: 3291) |

TABLE 13-continued

Additional Selected Anti-β-catenin DsiRNAs, Blunt, Unfrayed Duplexes

| | | |
|---|---|---|
| βc-m3390 Target: | 5'-GUAUCCCCGAUAAAGUUUUUGUUCAAA-3'<br>3'-CAUAGGGGCUAUUUCAAAAACAAGUUU-5'<br>5'-GTATCCCCGATAAAGTTTTTGTTCAAA-3' | (SEQ ID NO: 7728)<br>(SEQ ID NO: 2183)<br>(SEQ ID NO: 3292) |
| βc-m3419 Target: | 5'-ACACCUCUUACUGAUUUACCCUACCGC-3'<br>3'-UGUGGAGAAUGACUAAAUGGGAUGGCG-5'<br>5'-ACACCTCTTACTGATTTACCCTACCGC-3' | (SEQ ID NO: 7729)<br>(SEQ ID NO: 2184)<br>(SEQ ID NO: 3293) |
| βc-m3421 Target: | 5'-UAACACCUCUUACUGAUUUACCCUACC-3'<br>3'-AUUGUGGAGAAUGACUAAAUGGGAUGG-5'<br>5'-TAACACCTCTTACTGATTTACCCTACC-3' | (SEQ ID NO: 7730)<br>(SEQ ID NO: 2185)<br>(SEQ ID NO: 3294) |
| βc-m3422 Target: | 5'-AUAACACCUCUUACUGAUUUACCCUAC-3'<br>3'-UAUUGUGGAGAAUGACUAAAUGGGAUG-5'<br>5'-ATAACACCTCTTACTGATTTACCCTAC-3' | (SEQ ID NO: 7731)<br>(SEQ ID NO: 2186)<br>(SEQ ID NO: 3295) |
| βc-m3423 Target: | 5'-AAUAACACCUCUUACUGAUUUACCCUA-3'<br>3'-UUAUUGUGGAGAAUGACUAAAUGGGAU-5'<br>5'-AATAACACCTCTTACTGATTTACCCTA-3' | (SEQ ID NO: 7732)<br>(SEQ ID NO: 2187)<br>(SEQ ID NO: 3296) |
| βc-m3424 Target: | 5'-AAAUAACACCUCUUACUGAUUUACCCU-3'<br>3'-UUUAUUGUGGAGAAUGACUAAAUGGGA-5'<br>5'-AAATAACACCTCTTACTGATTTACCCT-3' | (SEQ ID NO: 7733)<br>(SEQ ID NO: 2188)<br>(SEQ ID NO: 3297) |
| βc-m3425 Target: | 5'-CAAAUAACACCUCUUACUGAUUUACCC-3'<br>3'-GUUUAUUGUGGAGAAUGACUAAAUGGG-5'<br>5'-CAAATAACACCTCTTACTGATTTACCC-3' | (SEQ ID NO: 7734)<br>(SEQ ID NO: 2189)<br>(SEQ ID NO: 3298) |
| βc-m3431 Target: | 5'-AAGGCUCAAAUAACACCUCUUACUGAU-3'<br>3'-UUCCGAGUUUAUUGUGGAGAAUGACUA-5'<br>5'-AAGGCTCAAATAACACCTCTTACTGAT-3' | (SEQ ID NO: 7735)<br>(SEQ ID NO: 2190)<br>(SEQ ID NO: 3299) |
| βc-m3436 Target: | 5'-AAAACAAGGCUCAAAUAACACCUCUUA-3'<br>3'-UUUUGUUCCGAGUUUAUUGUGGAGAAU-5'<br>5'-AAAACAAGGCTCAAATAACACCTCTTA-3' | (SEQ ID NO: 7736)<br>(SEQ ID NO: 2191)<br>(SEQ ID NO: 3300) |
| βc-m3437 Target: | 5'-CAAAACAAGGCUCAAAUAACACCUCUU-3'<br>3'-GUUUUGUUCCGAGUUUAUUGUGGAGAA-5'<br>5'-CAAAACAAGGCTCAAATAACACCTCTT-3' | (SEQ ID NO: 7737)<br>(SEQ ID NO: 2192)<br>(SEQ ID NO: 3301) |
| βc-m3438 Target: | 5'-CCAAAACAAGGCUCAAAUAACACCUCU-3'<br>3'-GGUUUUGUUCCGAGUUUAUUGUGGAGA-5'<br>5'-CCAAAACAAGGCTCAAATAACACCTCT-3' | (SEQ ID NO: 7738)<br>(SEQ ID NO: 2193)<br>(SEQ ID NO: 3302) |
| βc-m3441 Target: | 5'-UGUCCAAAACAAGGCUCAAAUAACACC-3'<br>3'-ACAGGUUUUGUUCCGAGUUUAUUGUGG-5'<br>5'-TGTCCAAAACAAGGCTCAAATAACACC-3' | (SEQ ID NO: 7739)<br>(SEQ ID NO: 2194)<br>(SEQ ID NO: 3303) |
| βc-m3443 Target: | 5'-ACUGUCCAAAACAAGGCUCAAAUAACA-3'<br>3'-UGACAGGUUUUGUUCCGAGUUUAUUGU-5'<br>5'-ACTGTCCAAAACAAGGCTCAAATAACA-3' | (SEQ ID NO: 7740)<br>(SEQ ID NO: 2195)<br>(SEQ ID NO: 3304) |
| βc-m3448 Target: | 5'-GGUAUACUGUCCAAAACAAGGCUCAAA-3'<br>3'-CCAUAUGACAGGUUUUGUUCCGAGUUU-5'<br>5'-GGTATACTGTCCAAAACAAGGCTCAAA-3' | (SEQ ID NO: 7741)<br>(SEQ ID NO: 2196)<br>(SEQ ID NO: 3305) |
| βc-m3456 Target: | 5'-AGGCAACUGGUAUACUGUCCAAAACAA-3'<br>3'-UCCGUUGACCAUAUGACAGGUUUUGUU-5'<br>5'-AGGCAACTGGTATACTGTCCAAAACAA-3' | (SEQ ID NO: 7742)<br>(SEQ ID NO: 2197)<br>(SEQ ID NO: 3306) |
| βc-m3464 Target: | 5'-GGGAUAAAAGGCAACUGGUAUACUGUC-3'<br>3'-CCCUAUUUUCCGUUGACCAUAUGACAG-5'<br>5'-GGGATAAAAGGCAACTGGTATACTGTC-3' | (SEQ ID NO: 7743)<br>(SEQ ID NO: 2198)<br>(SEQ ID NO: 3307) |
| βc-m3465 Target: | 5'-UGGGAUAAAAGGCAACUGGUAUACUGU-3'<br>3'-ACCCUAUUUUCCGUUGACCAUAUGACA-5'<br>5'-TGGGATAAAAGGCAACTGGTATACTGT-3' | (SEQ ID NO: 7744)<br>(SEQ ID NO: 2199)<br>(SEQ ID NO: 3308) |
| βc-m3472 Target: | 5'-ACAACUUUGGGAUAAAAGGCAACUGGU-3'<br>3'-UGUUGAAACCCUAUUUUCCGUUGACCA-5'<br>5'-ACAACTTTGGGATAAAAGGCAACTGGT-3' | (SEQ ID NO: 7745)<br>(SEQ ID NO: 2200)<br>(SEQ ID NO: 3309) |
| βc-m3474 Target: | 5'-CAACAACUUUGGGAUAAAAGGCAACUG-3'<br>3'-GUUGUUGAAACCCUAUUUUCCGUUGAC-5'<br>5'-CAACAACTTTGGGATAAAAGGCAACTG-3' | (SEQ ID NO: 7746)<br>(SEQ ID NO: 2201)<br>(SEQ ID NO: 3310) |

TABLE 13-continued

Additional Selected Anti-β-catenin DsiRNAs, Blunt, Unfrayed Duplexes

| | | |
|---|---|---|
| βc-m3479 Target: | 5'-GGUUACAACAACUUUGGGAUAAAAGGC-3'<br>3'-CCAAUGUUGUUGAAACCCUAUUUUCCG-5'<br>5'-GGTTACAACAACTTTGGGATAAAAGGC-3' | (SEQ ID NO: 7747)<br>(SEQ ID NO: 2202)<br>(SEQ ID NO: 3311) |
| βc-m3480 Target: | 5'-AGGUUACAACAACUUUGGGAUAAAAGG-3'<br>3'-UCCAAUGUUGUUGAAACCCUAUUUUCC-5'<br>5'-AGGTTACAACAACTTTGGGATAAAAGG-3' | (SEQ ID NO: 7748)<br>(SEQ ID NO: 2203)<br>(SEQ ID NO: 3312) |
| βc-m3481 Target: | 5'-CAGGUUACAACAACUUUGGGAUAAAAG-3'<br>3'-GUCCAAUGUUGUUGAAACCCUAUUUUC-5'<br>5'-CAGGTTACAACAACTTTGGGATAAAAG-3' | (SEQ ID NO: 7749)<br>(SEQ ID NO: 2204)<br>(SEQ ID NO: 3313) |
| βc-m3489 Target: | 5'-UAUCACAGCAGGUUACAACAACUUUGG-3'<br>3'-AUAGUGUCGUCCAAUGUUGUUGAAACC-5'<br>5'-TATCACAGCAGGTTACAACAACTTTGG-3' | (SEQ ID NO: 7750)<br>(SEQ ID NO: 2205)<br>(SEQ ID NO: 3314) |
| βc-m3490 Target: | 5'-GUAUCACAGCAGGUUACAACAACUUUG-3'<br>3'-CAUAGUGUCGUCCAAUGUUGUUGAAAC-5'<br>5'-GTATCACAGCAGGTTACAACAACTTTG-3' | (SEQ ID NO: 7751)<br>(SEQ ID NO: 2206)<br>(SEQ ID NO: 3315) |
| βc-m3492 Target: | 5'-UUGUAUCACAGCAGGUUACAACAACUU-3'<br>3'-AACAUAGUGUCGUCCAAUGUUGUUGAA-5'<br>5'-TTGTATCACAGCAGGTTACAACAACTT-3' | (SEQ ID NO: 7752)<br>(SEQ ID NO: 2207)<br>(SEQ ID NO: 3316) |
| βc-m3509 Target: | 5'-CCGCAUCUGUUGAAGCAUUGUAUCACA-3'<br>3'-GGCGUAGACAACUUCGUAACAUAGUGU-5'<br>5'-CCGCATCTGTTGAAGCATTGTATCACA-3' | (SEQ ID NO: 7753)<br>(SEQ ID NO: 2208)<br>(SEQ ID NO: 3317) |
| βc-m3527 Target: | 5'-UCUGAACCAUUUCUAUAACCGCAUCUG-3'<br>3'-AGACUUGGUAAAGAUAUUGGCGUAGAC-5'<br>5'-TCTGAACCATTTCTATAACCGCATCTG-3' | (SEQ ID NO: 7754)<br>(SEQ ID NO: 2209)<br>(SEQ ID NO: 3318) |
| βc-m3531 Target: | 5'-UAAUUCUGAACCAUUUCUAUAACCGCA-3'<br>3'-AUUAAGACUUGGUAAAGAUAUUGGCGU-5'<br>5'-TAATTCTGAACCATTTCTATAACCGCA-3' | (SEQ ID NO: 7755)<br>(SEQ ID NO: 2210)<br>(SEQ ID NO: 3319) |
| βc-m3533 Target: | 5'-UUUAAUUCUGAACCAUUUCUAUAACCG-3'<br>3'-AAAUUAAGACUUGGUAAAGAUAUUGGC-5'<br>5'-TTTAATTCTGAACCATTTCTATAACCG-3' | (SEQ ID NO: 7756)<br>(SEQ ID NO: 2211)<br>(SEQ ID NO: 3320) |
| βc-m3534 Target: | 5'-GUUUAAUUCUGAACCAUUUCUAUAACC-3'<br>3'-CAAAUUAAGACUUGGUAAAGAUAUUGG-5'<br>5'-GTTTAATTCTGAACCATTTCTATAACC-3' | (SEQ ID NO: 7757)<br>(SEQ ID NO: 2212)<br>(SEQ ID NO: 3321) |
| βc-m3535 Target: | 5'-AGUUUAAUUCUGAACCAUUUCUAUAAC-3'<br>3'-UCAAAUUAAGACUUGGUAAAGAUAUUG-5'<br>5'-AGTTTAATTCTGAACCATTTCTATAAC-3' | (SEQ ID NO: 7758)<br>(SEQ ID NO: 2213)<br>(SEQ ID NO: 3322) |
| βc-m3536 Target: | 5'-AAGUUUAAUUCUGAACCAUUUCUAUAA-3'<br>3'-UUCAAAUUAAGACUUGGUAAAGAUAUU-5'<br>5'-AAGTTTAATTCTGAACCATTTCTATAA-3' | (SEQ ID NO: 7759)<br>(SEQ ID NO: 2214)<br>(SEQ ID NO: 3323) |
| βc-m3541 Target: | 5'-AUUAAAAGUUUAAUUCUGAACCAUUUC-3'<br>3'-UAAUUUUCAAAUUAAGACUUGGUAAAG-5'<br>5'-ATTAAAAGTTTAATTCTGAACCATTTC-3' | (SEQ ID NO: 7760)<br>(SEQ ID NO: 2215)<br>(SEQ ID NO: 3324) |
| βc-m3542 Target: | 5'-AAUUAAAAGUUUAAUUCUGAACCAUUU-3'<br>3'-UUAAUUUUCAAAUUAAGACUUGGUAAA-5'<br>5'-AATTAAAAGTTTAATTCTGAACCATTT-3' | (SEQ ID NO: 7761)<br>(SEQ ID NO: 2216)<br>(SEQ ID NO: 3325) |
| βc-m3544 Target: | 5'-UGAAUUAAAAGUUUAAUUCUGAACCAU-3'<br>3'-ACUUAAUUUUCAAAUUAAGACUUGGUA-5'<br>5'-TGAATTAAAAGTTTAATTCTGAACC-3' | (SEQ ID NO: 7762)<br>(SEQ ID NO: 2217)<br>(SEQ ID NO: 3326) |
| βc-m3550 Target: | 5'-UUUGAAUGAAUUAAAAGUUUAAUUCUG-3'<br>3'-AAACUUACUUAAUUUUCAAAUUAAGAC-5'<br>5'-TTTGAATGAATTAAAAGTTTAATTCTG-3' | (SEQ ID NO: 7763)<br>(SEQ ID NO: 2218)<br>(SEQ ID NO: 3327) |
| βc-m3554 Target: | 5'-UUUUUUUGAAUGAAUUAAAAGUUUAAU-3'<br>3'-AAAAAAACUUACUUAAUUUUCAAAUUA-5'<br>5'-TTTTTTTGAATGAATTAAAAGTTTAAT-3' | (SEQ ID NO: 7764)<br>(SEQ ID NO: 2219)<br>(SEQ ID NO: 3328) |
| βc-m3558 Target: | 5'-UUUUUUUUUUGAAUGAAUUAAAAGUU-3'<br>3'-AAAAAAAAAAACUUACUUAAUUUUCAA-5'<br>5'-TTTTTTTTTTGAATGAATTAAAAGTT-3' | (SEQ ID NO: 7765)<br>(SEQ ID NO: 2220)<br>(SEQ ID NO: 3329) |

TABLE 13-continued

Additional Selected Anti-β-catenin DsiRNAs, Blunt, Unfrayed Duplexes

| | | |
|---|---|---|
| βc-m3559 Target: | 5'-UUUUUUUUUUUUGAAUGAAUUAAAAGU-3'<br>3'-AAAAAAAAAAAACUUACUUAAUUUUCA-5'<br>5'-TTTTTTTTTTTTGAATGAATTAAAAGT-3' | (SEQ ID NO: 7766)<br>(SEQ ID NO: 2221)<br>(SEQ ID NO: 3330) |
| βc-m3560 Target: | 5'-UUUUUUUUUUUUGAAUGAAUUAAAAG-3'<br>3'-AAAAAAAAAAAACUUACUUAAUUUUC-5'<br>5'-TTTTTTTTTTTTGAATGAATTAAAAG-3' | (SEQ ID NO: 7767)<br>(SEQ ID NO: 2222)<br>(SEQ ID NO: 3331) |
| βc-m3561 Target: | 5'-UUUUUUUUUUUUUGAAUGAAUUAAAA-3'<br>3'-AAAAAAAAAAAAACUUACUUAAUUUU-5'<br>5'-TTTTTTTTTTTTTGAATGAATTAAAA-3' | (SEQ ID NO: 7768)<br>(SEQ ID NO: 2223)<br>(SEQ ID NO: 3332) |
| βc-m3562 Target: | 5'-UUUUUUUUUUUUUUGAAUGAAUUAAA-3'<br>3'-AAAAAAAAAAAAAACUUACUUAAUUU-5'<br>5'-TTTTTTTTTTTTTTGAATGAATTAAA-3' | (SEQ ID NO: 7769)<br>(SEQ ID NO: 2224)<br>(SEQ ID NO: 3333) |
| βc-m3563 Target: | 5'-UUUUUUUUUUUUUUUGAAUGAAUUAA-3'<br>3'-AAAAAAAAAAAAAAACUUACUUAAUU-5'<br>5'-TTTTTTTTTTTTTTTGAATGAATTAA-3' | (SEQ ID NO: 7770)<br>(SEQ ID NO: 2225)<br>(SEQ ID NO: 3334) |

Within Tables 2-4 and 9 above, underlined residues indicate 2'-O-methyl residues. In Tables 2-4, 6-9 and 11-13 above, UPPER CASE indicates ribonucleotides, and lower case denotes deoxyribonucleotides. The DsiRNA agents of Tables 2-4 and 9 above are 25/27mer agents possessing a blunt end. The structures and/or modification patterning of the agents of Tables 2-4, 6, 9 and 11 above can be readily adapted to the above generic sequence structures, e.g., the 3' overhang of the second strand can be extended or contracted, 2'-O-methylation of the second strand can be expanded towards the 5' end of the second strand, optionally at alternating sites, etc. Such further modifications are optional, as 25/27mer DsiRNAs with such modifications can also be readily designed from the above DsiRNA agents and are also expected to be functional inhibitors of β-catenin expression. Similarly, the 27mer "blunt/fray" and "blunt/blunt" DsiRNA structures and/or modification patterns of the agents of of Tables 7-8 and 12-13 above can also be readily adapted to the above generic sequence structures, e.g., for application of modification patterning of the antisense strand to such structures and/or adaptation of such sequences to the above generic structures.

In certain embodiments, 27mer DsiRNAs possessing independent strand lengths each of 27 nucleotides are designed and synthesized for targeting of the same sites within the β-catenin transcript as the asymmetric "25/27" structures shown in Tables 2-4, 6, 9 and 11 herein. Exemplary "27/27" DsiRNAs are optionally designed with a "blunt/fray" structure as shown for the DsiRNAs of Tables 7 and 12 above, or with a "blunt/blunt" structure as shown for the DsiRNAs of Tables 8 and 13 above.

In certain embodiments, the DsiRNA agents of the invention require, e.g., at least 19, at least 20, at least 21, at least 22, at least 23, at least 24, at least 25 or at least 26 residues of the first strand to be complementary to corresponding residues of the second strand. In certain related embodiments, these first strand residues complementary to corresponding residues of the second strand are optionally consecutive residues.

As used herein "DsiRNAmm" refers to a DsiRNA having a "mismatch tolerant region" containing one, two, three or four mismatched base pairs of the duplex formed by the sense and antisense strands of the DsiRNA, where such mismatches are positioned within the DsiRNA at a location(s) lying between (and thus not including) the two terminal base pairs of either end of the DsiRNA. The mismatched base pairs are located within a "mismatch-tolerant region" which is defined herein with respect to the location of the projected Ago2 cut site of the corresponding target nucleic acid. The mismatch tolerant region is located "upstream of" the projected Ago2 cut site of the target strand. "Upstream" in this context will be understood as the 5'-most portion of the DsiRNAmm duplex, where 5' refers to the orientation of the sense strand of the DsiRNA duplex. Therefore, the mismatch tolerant region is upstream of the base on the sense (passenger) strand that corresponds to the projected Ago2 cut site of the target nucleic acid (see FIG. 1); alternatively, when referring to the antisense (guide) strand of the DsiRNAmm, the mismatch tolerant region can also be described as positioned downstream of the base that is complementary to the projected Ago2 cut site of the target nucleic acid, that is, the 3'-most portion of the antisense strand of the DsiRNAmm (where position 1 of the antisense strand is the 5' terminal nucleotide of the antisense strand, see FIG. 1).

In one embodiment, for example with numbering as depicted in FIG. 1, the mismatch tolerant region is positioned between and including base pairs 3-9 when numbered from the nucleotide starting at the 5' end of the sense strand of the duplex. Therefore, a DsiRNAmm of the invention possesses a single mismatched base pair at any one of positions 3, 4, 5, 6, 7, 8 or 9 of the sense strand of a right-hand extended DsiRNA (where position 1 is the 5' terminal nucleotide of the sense strand and position 9 is the nucleotide residue of the sense strand that is immediately 5' of the projected Ago2 cut site of the target β-catenin RNA sequence corresponding to the sense strand sequence). In certain embodiments, for a DsiRNAmm that possesses a mismatched base pair nucleotide at any of positions 3, 4, 5, 6, 7, 8 or 9 of the sense strand, the corresponding mismatched base pair nucleotide of the antisense strand not only forms a mismatched base pair with the DsiRNAmm sense strand sequence, but also forms a mismatched base pair with a DsiRNAmm target β-catenin RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target β-catenin RNA sequence). In alternative embodiments, the mismatch base pair nucleotide of the antisense strand of a DsiRNAmm only form a mismatched base pair with a corresponding nucleotide of the sense strand sequence of the DsiRNAmm, yet base pairs with its corresponding target β-catenin RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target β-catenin RNA sequence).

A DsiRNAmm of the invention that possesses a single mismatched base pair within the mismatch-tolerant region (mismatch region) as described above (e.g., a DsiRNAmm harboring a mismatched nucleotide residue at any one of positions 3, 4, 5, 6, 7, 8 or 9 of the sense strand) can further include one, two or even three additional mismatched base pairs. In preferred embodiments, these one, two or three additional mismatched base pairs of the DsiRNAmm occur at position(s) 3, 4, 5, 6, 7, 8 and/or 9 of the sense strand (and at corresponding residues of the antisense strand). In one embodiment where one additional mismatched base pair is present within a DsiRNAmm, the two mismatched base pairs of the sense strand can occur, e.g., at nucleotides of both position 4 and position 6 of the sense strand (with mismatch also occurring at corresponding nucleotide residues of the antisense strand).

In DsiRNAmm agents possessing two mismatched base pairs, mismatches can occur consecutively (e.g., at consecutive positions along the sense strand nucleotide sequence). Alternatively, nucleotides of the sense strand that form mismatched base pairs with the antisense strand sequence can be interspersed by nucleotides that base pair with the antisense strand sequence (e.g., for a DsiRNAmm possessing mismatched nucleotides at positions 3 and 6, but not at positions 4 and 5, the mismatched residues of sense strand positions 3 and 6 are interspersed by two nucleotides that form matched base pairs with corresponding residues of the antisense strand). For example, two residues of the sense strand (located within the mismatch-tolerant region of the sense strand) that form mismatched base pairs with the corresponding antisense strand sequence can occur with zero, one, two, three, four or five matched base pairs located between these mismatched base pairs.

For certain DsiRNAmm agents possessing three mismatched base pairs, mismatches can occur consecutively (e.g., in a triplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiRNAmm possessing mismatched nucleotides at positions 3, 4 and 8, but not at positions 5, 6 and 7, the mismatched residues of sense strand positions 3 and 4 are adjacent to one another, while the mismatched residues of sense strand positions 4 and 8 are interspersed by three nucleotides that form matched base pairs with corresponding residues of the antisense strand). For example, three residues of the sense strand (located within the mismatch-tolerant region of the sense strand) that form mismatched base pairs with the corresponding antisense strand sequence can occur with zero, one, two, three or four matched base pairs located between any two of these mismatched base pairs.

For certain DsiRNAmm agents possessing four mismatched base pairs, mismatches can occur consecutively (e.g., in a quadruplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiRNAmm possessing mismatched nucleotides at positions 3, 5, 7 and 8, but not at positions 4 and 6, the mismatched residues of sense strand positions 7 and 8 are adjacent to one another, while the mismatched residues of sense strand positions 3 and 5 are interspersed by one nucleotide that forms a matched base pair with the corresponding residue of the antisense strand—similarly, the the mismatched residues of sense strand positions 5 and 7 are also interspersed by one nucleotide that forms a matched base pair with the corresponding residue of the antisense strand). For example, four residues of the sense strand (located within the mismatch-tolerant region of the sense strand) that form mismatched base pairs with the corresponding antisense strand sequence can occur with zero, one, two or three matched base pairs located between any two of these mismatched base pairs.

In another embodiment, for example with numbering also as depicted in FIG. 1, a DsiRNAmm of the invention comprises a mismatch tolerant region which possesses a single mismatched base pair nucleotide at any one of positions 17, 18, 19, 20, 21, 22 or 23 of the antisense strand of the DsiRNA (where position 1 is the 5' terminal nucleotide of the antisense strand and position 17 is the nucleotide residue of the antisense strand that is immediately 3' (downstream) in the antisense strand of the projected Ago2 cut site of the target β-catenin RNA sequence sufficiently complementary to the antisense strand sequence). In certain embodiments, for a DsiRNAmm that possesses a mismatched base pair nucleotide at any of positions 17, 18, 19, 20, 21, 22 or 23 of the antisense strand with respect to the sense strand of the DsiRNAmm, the mismatched base pair nucleotide of the antisense strand not only forms a mismatched base pair with the DsiRNAmm sense strand sequence, but also forms a mismatched base pair with a DsiRNAmm target β-catenin RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target β-catenin RNA sequence). In alternative embodiments, the mismatch base pair nucleotide of the antisense strand of a DsiRNAmm only forms a mismatched base pair with a corresponding nucleotide of the sense strand sequence of the DsiRNAmm, yet base pairs with its corresponding target β-catenin RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target β-catenin RNA sequence).

A DsiRNAmm of the invention that possesses a single mismatched base pair within the mismatch-tolerant region as described above (e.g., a DsiRNAmm harboring a mismatched nucleotide residue at positions 17, 18, 19, 20, 21, 22 or 23 of the antisense strand) can further include one, two or even three additional mismatched base pairs. In preferred embodiments, these one, two or three additional mismatched base pairs of the DsiRNAmm occur at position(s) 17, 18, 19, 20, 21, 22 and/or 23 of the antisense strand (and at corresponding residues of the sense strand). In one embodiment where one additional mismatched base pair is present within a DsiRNAmm, the two mismatched base pairs of the antisense strand can occur, e.g., at nucleotides of both position 18 and position 20 of the antisense strand (with mismatch also occurring at corresponding nucleotide residues of the sense strand).

In DsiRNAmm agents possessing two mismatched base pairs, mismatches can occur consecutively (e.g., at consecutive positions along the antisense strand nucleotide sequence). Alternatively, nucleotides of the antisense strand that form mismatched base pairs with the sense strand sequence can be interspersed by nucleotides that base pair with the sense strand sequence (e.g., for a DsiRNAmm possessing mismatched nucleotides at positions 17 and 20, but not at positions 18 and 19, the mismatched residues of antisense strand positions 17 and 20 are interspersed by two nucleotides that form matched base pairs with corresponding residues of the sense strand). For example, two residues of the antisense strand (located within the mismatch-tolerant region of the sense strand) that form mismatched base pairs with the corresponding sense strand sequence can occur with zero, one, two, three, four, five, six or seven matched base pairs located between these mismatched base pairs.

For certain DsiRNAmm agents possessing three mismatched base pairs, mismatches can occur consecutively (e.g., in a triplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 17, 18 and 22, but not at positions 19, 20 and 21, the mismatched residues of antisense strand positions 17 and 18 are adjacent to one another, while the mismatched residues of antisense strand positions 18 and 122 are interspersed by three nucleotides that form matched base pairs with corresponding residues of the sense strand). For example, three residues of the antisense strand (located within the mismatch-tolerant region of the antisense strand) that form mismatched base pairs with the corresponding sense strand sequence can occur with zero, one, two, three, four, five or six matched base pairs located between any two of these mismatched base pairs.

For certain DsiRNAmm agents possessing four mismatched base pairs, mismatches can occur consecutively (e.g., in a quadruplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 18, 20, 22 and 23, but not at positions 19 and 21, the mismatched residues of antisense strand positions 22 and 23 are adjacent to one another, while the mismatched residues of antisense strand positions 18 and 20 are interspersed by one nucleotide that forms a matched base pair with the corresponding residue of the sense strand—similarly, the the mismatched residues of antisense strand positions 20 and 22 are also interspersed by one nucleotide that forms a matched base pair with the corresponding residue of the sense strand). For example, four residues of the antisense strand (located within the mismatch-tolerant region of the antisense strand) that form mismatched base pairs with the corresponding sense strand sequence can occur with zero, one, two, three, four or five matched base pairs located between any two of these mismatched base pairs.

For reasons of clarity, the location(s) of mismatched nucleotide residues within the above DsiRNAmm agents are numbered in reference to the 5' terminal residue of either sense or antisense strands of the DsiRNAmm. The numbering of positions located within the mismatch-tolerant region (mismatch region) of the antisense strand can shift with variations in the proximity of the 5' terminus of the sense or antisense strand to the projected Ago2 cleavage site. Thus, the location(s) of preferred mismatch sites within either antisense strand or sense strand can also be identified as the permissible proximity of such mismatches to the projected Ago2 cut site. Accordingly, in one preferred embodiment, the position of a mismatch nucleotide of the sense strand of a DsiRNAmm is the nucleotide residue of the sense strand that is located immediately 5' (upstream) of the projected Ago2 cleavage site of the corresponding target β-catenin RNA sequence. In other preferred embodiments, a mismatch nucleotide of the sense strand of a DsiRNAmm is positioned at the nucleotide residue of the sense strand that is located two nucleotides 5' (upstream) of the projected Ago2 cleavage site, three nucleotides 5' (upstream) of the projected Ago2 cleavage site, four nucleotides 5' (upstream) of the projected Ago2 cleavage site, five nucleotides 5' (upstream) of the projected Ago2 cleavage site, six nucleotides 5' (upstream) of the projected Ago2 cleavage site, seven nucleotides 5' (upstream) of the projected Ago2 cleavage site, eight nucleotides 5' (upstream) of the projected Ago2 cleavage site, or nine nucleotides 5' (upstream) of the projected Ago2 cleavage site.

Exemplary single mismatch-containing 25/27mer DsiRNAs (DsiRNAmm) include the following structures (such mismatch-containing structures may also be incorporated into other exemplary DsiRNA structures shown herein).

```
5'-XX^MXXXXXXXXXXXXXXXXXXXXDD-3'
3'-XXXX_MXXXXXXXXXXXXXXXXXXXXX-5'
5'-XXX^MXXXXXXXXXXXXXXXXXXXXDD-3'
3'-XXXXX_MXXXXXXXXXXXXXXXXXXXX-5'
5'-XXXX^MXXXXXXXXXXXXXXXXXXXDD-3'
3'-XXXXXX_MXXXXXXXXXXXXXXXXXXX-5'
5'-XXXXX^MXXXXXXXXXXXXXXXXXXDD-3'
3'-XXXXXXX_MXXXXXXXXXXXXXXXXXX-5'
5'-XXXXXX^MXXXXXXXXXXXXXXXXXDD-3'
3'-XXXXXXXX_MXXXXXXXXXXXXXXXXX-5'
5'-XXXXXXX^MXXXXXXXXXXXXXXXXDD-3'
3'-XXXXXXXXX_MXXXXXXXXXXXXXXXX-5'
5'-XXXXXXXX^MXXXXXXXXXXXXXXXDD-3'
3'-XXXXXXCXXX_MXXXXXXXXXXXXXXX-5'
``` wherein "X"=RNA, "D"=DNA and "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown above, can also be used in the above DsiRNAmm agents. For the above mismatch structures, the top strand is the sense strand, and the bottom strand is the antisense strand.

In certain embodiments, a DsiRNA of the invention can contain mismatches that exist in reference to the target β-catenin RNA sequence yet do not necessarily exist as mismatched base pairs within the two strands of the DsiRNA—thus, a DsiRNA can possess perfect complementarity between first and second strands of a DsiRNA, yet still possess mismatched residues in reference to a target β-catenin RNA (which, in certain embodiments, may be advantageous in promoting efficacy and/or potency and/or duration of effect). In certain embodiments, where mismatches occur between antisense strand and target β-catenin RNA sequence, the position of a mismatch is located within the antisense strand at a position(s) that corresponds to a sequence of the sense strand located 5' of the projected Ago2 cut site of the target region— e.g., antisense strand residue(s) positioned within the antisense strand to the 3' of the antisense residue which is complementary to the projected Ago2 cut site of the target sequence.

Exemplary 25/27mer DsiRNAs that harbor a single mismatched residue in reference to target sequences include the following structures.

```
Target RNA Sequence:      5'-...AXXXXXXXXXXXXXXXXXXXX...-3'
DsiRNAmm Sense Strand:    5'-XXXXXXXXXXXXXXXXXXXXXXXDD-3'
DsiRNAmm Antisense Strand: 3'-EXXXXXXXXXXXXXXXXXXXXXXXXX-5'

Target RNA Sequence:      5'-...XAXXXXXXXXXXXXXXXXXXX...-3'
DsiRNAmm Sense Strand:    5'-XXXXXXXXXXXXXXXXXXXXXXXDD-3'
DsiRNAmm Antisense Strand: 3'-XEXXXXXXXXXXXXXXXXXXXXXXXX-5'

Target RNA Sequence:      5'-...AXXXXXXXXXXXXXXXXXX...-3'
DsiRNAmm Sense Strand:    5'-BXXXXXXXXXXXXXXXXXXXXXXXDD-3'
DsiRNAmm Antisense Strand: 3'-XXEXXXXXXXXXXXXXXXXXXXXXXXX-5'

Target RNA Sequence:      5'-...XAXXXXXXXXXXXXXXXXXX...-3'
DsiRNAmm Sense Strand:    5'-XBXXXXXXXXXXXXXXXXXXXXXXDD-3'
DsiRNAmm Antisense Strand: 3'-XXXEXXXXXXXXXXXXXXXXXXXXXXX-5'

Target RNA Sequence:      5'-...XXAXXXXXXXXXXXXXXXXX...-3'
DsiRNAmm Sense Strand:    5'-XXBXXXXXXXXXXXXXXXXXXXXXDD-3'
DsiRNAmm Antisense Strand: 3'-XXXXEXXXXXXXXXXXXXXXXXXXXXX-5'

Target RNA Sequence:      5'-...XXXAXXXXXXXXXXXXXXXX...-3'
DsiRNAmm Sense Strand:    5'-XXXBXXXXXXXXXXXXXXXXXXXXDD-3'
DsiRNAmm Antisense Strand: 3'-XXXXXEXXXXXXXXXXXXXXXXXXXXX-5'

Target RNA Sequence:      5'-...XXXXAXXXXXXXXXXXXXXX...-3'
DsiRNAmm Sense Strand:    5'-XXXXBXXXXXXXXXXXXXXXXXXXDD-3'
DsiRNAmm Antisense Strand: 3'-XXXXXXEXXXXXXXXXXXXXXXXXXXX-5'

Target RNA Sequence:      5'-...XXXXXAXXXXXXXXXXXXXX...-3'
DsiRNAmm Sense Strand:    5'-XXXXXBXXXXXXXXXXXXXXXXXXDD-3'
DsiRNAmm Antisense Strand: 3'-XXXXXXXEXXXXXXXXXXXXXXXXXXX-5'

Target RNA Sequence:      5'-...XXXXXXAXXXXXXXXXXXXX...-3'
DsiRNAmm Sense Strand:    5'-XXXXXXBXXXXXXXXXXXXXXXXXDD-3'
DsiRNAmm Antisense Strand: 3'-XXXXXXXXEXXXXXXXXXXXXXXXXXX-5'

Target RNA Sequence:      5'-...XXXXXXXAXXXXXXXXXXXX...-3'
DsiRNAmm Sense Strand:    5'-XXXXXXXBXXXXXXXXXXXXXXXXDD-3'
DsiRNAmm Antisense Strand: 3'-XXXXXXXXXEXXXXXXXXXXXXXXXXX-5'

Target RNA Sequence:      5'-...XXXXXXXXAXXXXXXXXXXX...-3'
DsiRNAmm Sense Strand:    5'-XXXXXXXXBXXXXXXXXXXXXXXXDD-3'
DsiRNAmm Antisense Strand: 3'-XXXXXXXXXXEXXXXXXXXXXXXXXXX-5'
``` wherein "X"=RNA, "D"=DNA and "E"=Nucleic acid residues (RNA, DNA or non-natural or modified nucleic acids) that do not base pair (hydrogen bond) with corresponding "A" RNA residues of otherwise complementary (target) strand when strands are annealed, yet optionally do base pair with corresponding "B" residues ("B" residues are also RNA, DNA or non-natural or modified nucleic acids). Any of the residues of such agents can optionally be 2'-O-methyl RNA monomers—alternating positioning of 2'-O-methyl RNA monomers that commences from the 3'-terminal residue of the bottom (second) strand, as shown above, can also be used in the above DsiRNA agents.

In addition to the above-exemplified structures, DsiRNAs of the invention can also possess one, two or three additional residues that form further mismatches with the target β-catenin RNA sequence. Such mismatches can be consecutive, or can be interspersed by nucleotides that form matched base pairs with the target β-catenin RNA sequence. Where interspersed by nucleotides that form matched base pairs, mismatched residues can be spaced apart from each other within a single strand at an interval of one, two, three, four, five, six, seven or even eight base paired nucleotides between such mismatch-forming residues.

As for the above-described DsiRNAmm agents, a preferred location within DsiRNAs for antisense strand nucleotides that form mismatched base pairs with target β-catenin RNA sequence (yet may or may not form mismatches with corresponding sense strand nucleotides) is within the antisense strand region that is located 3' (downstream) of the antisense strand sequence which is complementary to the projected Ago2 cut site of the DsiRNA (e.g., in FIG. 1, the region of the antisense strand which is 3' of the projected Ago2 cut site is preferred for mismatch-forming residues and happens to be located at positions 17-23 of the antisense strand for the 25/27mer agent shown in FIG. 1). Thus, in one embodiment, the position of a mismatch nucleotide (in relation to the target β-catenin RNA sequence) of the antisense strand of a DsiRNAmm is the nucleotide residue of the antisense strand that is located immediately 3' (downstream) within the antisense strand sequence of the projected Ago2 cleavage site of the corresponding target β-catenin RNA sequence. In other preferred embodiments, a mismatch nucleotide of the antisense strand of a DsiRNAmm (in relation to the target β-catenin RNA sequence) is positioned at the nucleotide residue of the antisense strand that is located two nucleotides 3' (downstream) of the corresponding projected Ago2 cleavage site, three nucleotides 3' (downstream) of the corresponding projected Ago2 cleavage site, four nucleotides 3' (downstream) of the corresponding projected Ago2 cleavage site, five nucleotides 3' (downstream) of the corresponding projected Ago2 cleavage site, six nucleotides 3' (downstream) of the projected Ago2 cleavage site, seven nucleotides 3' (downstream) of the projected Ago2 cleavage site, eight nucleotides 3' (downstream) of the projected Ago2 cleavage site, or nine nucleotides 3' (downstream) of the projected Ago2 cleavage site.

In DsiRNA agents possessing two mismatch-forming nucleotides of the antisense strand (where mismatch-forming nucleotides are mismatch forming in relation to target β-catenin RNA sequence), mismatches can occur consecutively (e.g., at consecutive positions along the antisense strand nucleotide sequence). Alternatively, nucleotides of the antisense strand that form mismatched base pairs with the target β-catenin RNA sequence can be interspersed by nucleotides that base pair with the target β-catenin RNA sequence (e.g., for a DsiRNA possessing mismatch-forming nucleotides at positions 17 and 20 (starting from the 5' terminus (position 1) of the antisense strand of the 25/27mer agent shown in FIG. 1), but not at positions 18 and 19, the mismatched residues of sense strand positions 17 and 20 are interspersed by two nucleotides that form matched base pairs with corresponding residues of the target β-catenin RNA sequence). For example, two residues of the antisense strand (located within the mismatch-tolerant region of the antisense strand) that form mismatched base pairs with the corresponding target β-catenin RNA sequence can occur with zero, one, two, three, four or five matched base pairs (with respect to target β-catenin RNA sequence) located between these mismatch-forming base pairs.

For certain DsiRNAs possessing three mismatch-forming base pairs (mismatch-forming with respect to target β-catenin RNA sequence), mismatch-forming nucleotides can occur consecutively (e.g., in a triplet along the antisense strand nucleotide sequence). Alternatively, nucleotides of the antisense strand that form mismatched base pairs with the target β-catenin RNA sequence can be interspersed by nucleotides that form matched base pairs with the target β-catenin RNA sequence (e.g., for a DsiRNA possessing mismatched nucleotides at positions 17, 18 and 22, but not at positions 19, 20 and 21, the mismatch-forming residues of antisense strand positions 17 and 18 are adjacent to one another, while the mismatch-forming residues of antisense strand positions 18 and 22 are interspersed by three nucleotides that form matched base pairs with corresponding residues of the target β-catenin RNA). For example, three residues of the antisense strand (located within the mismatch-tolerant region of the antisense strand) that form mismatched base pairs with the corresponding target β-catenin RNA sequence can occur with zero, one, two, three or four matched base pairs located between any two of these mismatch-forming base pairs.

For certain DsiRNAs possessing four mismatch-forming base pairs (mismatch-forming with respect to target β-catenin RNA sequence), mismatch-forming nucleotides can occur consecutively (e.g., in a quadruplet along the sense strand nucleotide sequence). Alternatively, nucleotides of the antisense strand that form mismatched base pairs with the target β-catenin RNA sequence can be interspersed by nucleotides that form matched base pairs with the target β-catenin RNA sequence (e.g., for a DsiRNA possessing mismatch-forming nucleotides at positions 17, 19, 21 and 22, but not at positions 18 and 20, the mismatch-forming residues of antisense strand positions 21 and 22 are adjacent to one another, while the mismatch-forming residues of antisense strand positions 17 and 19 are interspersed by one nucleotide that forms a matched base pair with the corresponding residue of the target β-catenin RNA sequence—similarly, the mismatch-forming residues of antisense strand positions 19 and 21 are also interspersed by one nucleotide that forms a matched base pair with the corresponding residue of the target β-catenin RNA sequence). For example, four residues of the antisense strand (located within the mismatch-tolerant region of the antisense strand) that form mismatched base pairs with the corresponding target β-catenin RNA sequence can occur with zero, one, two or three matched base pairs located between any two of these mismatch-forming base pairs.

The above DsiRNAmm and other DsiRNA structures are described in order to exemplify certain structures of DsiRNAmm and DsiRNA agents. Design of the above DsiRNAmm and DsiRNA structures can be adapted to generate, e.g., DsiRNAmm forms of other DsiRNA structures shown infra. As exemplified above, DsiRNAs can also be designed that possess single mismatches (or two, three or four mismatches) between the antisense strand of the DsiRNA and a target sequence, yet optionally can retain perfect complementarity between sense and antisense strand sequences of a DsiRNA.

It is further noted that the DsiRNA agents exemplified infra can also possess insertion/deletion (in/del) structures within their double-stranded and/or target β-catenin RNA-aligned structures. Accordingly, the DsiRNAs of the invention can be designed to possess in/del variations in, e.g., antisense strand sequence as compared to target β-catenin RNA sequence and/or antisense strand sequence as compared to sense strand sequence, with preferred location(s) for placement of such in/del nucleotides corresponding to those locations described above for positioning of mismatched and/or mismatch-forming base pairs.

It is also noted that the DsiRNAs of the instant invention can tolerate mismatches within the 3'-terminal region of the sense strand/5'-terminal region of the antisense strand, as this region is modeled to be processed by Dicer and liberated from the guide strand sequence that loads into RISC. Exemplary DsiRNA structures of the invention that harbor such mismatches include the following:

```
Target RNA Sequence:      5'-...XXXXXXXXXXXXXXXXXXXXXHXXX...-3'
DsiRNA Sense Strand:      5'-XXXXXXXXXXXXXXXXXXXXXIXDD-3'
DsiRNA Antisense Strand:  3'-XXXXXXXXXXXXXXXXXXXXXXJXXX-5'

Target RNA Sequence:      5'-...XXXXXXXXXXXXXXXXXXXXXHXX...-3'
DsiRNA Sense Strand:      5'-XXXXXXXXXXXXXXXXXXXXXIDD-3'
DsiRNA Antisense Strand:  3'-XXXXXXXXXXXXXXXXXXXXXXJXX-5'

Target RNA Sequence:      5'-...XXXXXXXXXXXXXXXXXXXXXHX...-3'
DsiRNA Sense Strand:      5'-XXXXXXXXXXXXXXXXXXXXXID-3'
DsiRNA Antisense Strand:  3'-XXXXXXXXXXXXXXXXXXXXXXJX-5'

Target RNA Sequence:      5'-...XXXXXXXXXXXXXXXXXXXXXH...-3'
DsiRNA Sense Strand:      5'-XXXXXXXXXXXXXXXXXXXXXDI-3'
DsiRNA Antisense Strand:  3'-XXXXXXXXXXXXXXXXXXXXXXJ-5'
``` wherein "X"=RNA, "D"=DNA and "I" and "J"=Nucleic acid residues (RNA, DNA or non-natural or modified nucleic acids) that do not base pair (hydrogen bond) with one another, yet optionally "J" is complementary to target RNA sequence nucleotide "H". Any of the residues of such agents can optionally be 2'-O-methyl RNA monomers—alternating positioning of 2'-O-methyl RNA monomers that commences from the 3'-terminal residue of the bottom (second) strand, as shown above—or any of the above-described methylation patterns—can also be used in the above DsiRNA agents. The above mismatches can also be combined within the DsiRNAs of the instant invention.

In the below structures, such mismatches are introduced within the asymmetric βc-1569 DsiRNA (newly-introduced mismatch residues are italicized): βc-1569 25/27mer DsiRNA, mismatch position=22 of sense strand (from 5'-terminus)

5'-ACCUCACUUGCAAUAAUUAUA$^C$Gaa-3' (SEQ ID NO: 7775)
3'-AUUGGAGUGAACGUUAUUAAUAU$_U$CUU-5' (SEQ ID NO: 1287)

Optionally, the mismatched "C" residue of position 22 of the sense strand is alternatively "U" or "G".
βc-1569 25/27mer DsiRNA, mismatch position=23 of sense strand 5'-ACCUCACUUGCAAUAAUUAUAC$^U$aa-3' (SEQ ID NO: 7776)
3'-AUUGGAGUGAACGUUAUUAAUAUU$_C$UU-5' (SEQ ID NO: 1287)

Optionally, the mismatched "U" residue of position 23 of the sense strand is alternatively "A" or "C".
βc-1569 25/27mer DsiRNA, mismatch position=24 of sense strand 5'-ACCUCACUUGCAAUAAUUAUAAG$^C$a-3' (SEQ ID NO: 7777)
3'-AUUGGAGUGAACGUUAUUAAUAUUC$_U$U-5' (SEQ ID NO: 1287)

Optionally, the mismatched "c" residue of position 24 of the sense strand is alternatively "t" or "g".
βc-1569 25/27mer DsiRNA, mismatch position=25 of sense strand 5'-ACCUCACUUGCAAUAAUUAUAAGa$^C$-3' (SEQ ID NO: 7778)
3'-AUUGGAGUGAACGUUAUUAAUAUUCU$_U$-5' (SEQ ID NO: 1287)

Optionally, the mismatched "c" residue of position 25 of the sense strand is alternatively "t" or "g".
βc-1569 25/27mer DsiRNA, mismatch position=1 of antisense strand 5'-ACCUCACUUGCAAUAAUUAUAAGa$^a$-3' (SEQ ID NO: 178)
3'-AUUGGAGUGAACGUUAUUAAUAUUCU$_G$-5' (SEQ ID NO: 7779)

Optionally, the mismatched "G" residue of position 1 of the antisense strand is alternatively "A" or "C".
βc-1569 25/27mer DsiRNA, mismatch position=2 of antisense strand 5'-ACCUCACUUGCAAUAAUUAUAAG$^a$a-3' (SEQ ID NO: 178)
3'-AUUGGAGUGAACGUUAUUAAUAUUC$_G$U-5' (SEQ ID NO: 7780)

Optionally, the mismatched "G" residue of position 2 of the antisense strand is alternatively "A" or "C".
βc-1569 25/27mer DsiRNA, mismatch position=3 of antisense strand 5'-ACCUCACUUGCAAUAAUUAUAA$^G$aa-3' (SEQ ID NO: 178)
3'-AUUGGAGUGAACGUUAUUAAUAUU$_A$UU-5' (SEQ ID NO: 7781)

Optionally, the mismatched "A" residue of position 3 of the antisense strand is alternatively "U" or "G".
βc-1569 25/27mer DsiRNA, mismatch position=4 of antisense strand 5'-ACCUCACUUGCAAUAAUUAUA$^A$Gaa-3' (SEQ ID NO: 178)
3'-AUUGGAGUGAACGUUAUUAAUAU$_G$CUU-5' (SEQ ID NO: 7782)

Optionally, the mismatched "G" residue of position 4 of the antisense strand is alternatively "A" or "C".

As an additional example, such mismatches are introduced within the asymmetric βc-3393 DsiRNA (newly-introduced mismatch residues are italicized): βc-3393 25/27mer DsiRNA, mismatch position=22 of sense strand (from 5'-terminus)

5'-UGGUGUAGAACACUAAUUCAU$^C$Atc-3' (SEQ ID NO: 7787)
3'-UUACCACAUCUUGUGAUUAAGUA$_U$UAG-5' (SEQ ID NO: 1506)

Optionally, the mismatched "C" residue of position 22 of the sense strand is alternatively "U" or "G".
βc-3393 25/27mer DsiRNA, mismatch position=23 of sense strand 5'-UGGUGUAGAACACUAAUUCAUA$^C$tc-3' (SEQ ID NO: 7788)
3'-UUACCACAUCUUGUGAUUAAGUAU$_U$AG-5' (SEQ ID NO: 1506)

Optionally, the mismatched "C" residue of position 23 of the sense strand is alternatively "G" or "U".
βc-3393 25/27mer DsiRNA, mismatch position=24 of sense strand 5'-UGGUGUAGAACACUAAUUCAUAA$^C$c-3'  (SEQ ID NO: 7789)
3'-UUACCACAUCUUGUGAUUAAGUAUU$_A$G-5' (SEQ ID NO: 1506)

Optionally, the mismatched "c" residue of position 24 of the sense strand is alternatively "a" or "g".
βc-3393 25/27mer DsiRNA, mismatch position=25 of sense strand

```
5'-UGGUGUAGAACACUAAUUCAUAAtᵃ-3'  (SEQ ID NO: 7790)
3'-UUACCACAUCUUGUGAUUAAGUAUUAG-5' (SEQ ID NO: 1506)
```

Optionally, the mismatched "a" residue of position 25 of the sense strand is alternatively "t" or "g".
βc-3393 25/27mer DsiRNA, mismatch position=1 of antisense strand

```
5'-UGGUGUAGAACACUAAUUCAUAAtᶜ-3' (SEQ ID NO: 397)
3'-UUACCACAUCUUGUGAUUAAGUAUUAₐ-5' (SEQ ID NO: 7791)
```

Optionally, the mismatched "A" residue of position 1 of the antisense strand is alternatively "U" or "C".
βc-3393 25/27mer DsiRNA, mismatch position=2 of antisense strand

```
5'-UGGUGUAGAACACUAAUUCAUAAtc-3' (SEQ ID NO: 397)
3'-UUACCACAUCUUGUGAUUAAGUAUUcG-5' (SEQ ID NO: 7792)
```

Optionally, the mismatched "C" residue of position 2 of the antisense strand is alternatively "G" or "U".
βc-3393 25/27mer DsiRNA, mismatch position=3 of antisense strand

```
5'-UGGUGUAGAACACUAAUUCAUAᴬtc-3' (SEQ ID NO: 397)
3'-UUACCACAUCUUGUGAUUAAGUAUcAG-5' (SEQ ID NO: 7793)
```

Optionally, the mismatched "C" residue of position 3 of the antisense strand is alternatively "U" or "A".
βc-3393 25/27mer DsiRNA, mismatch position=4 of antisense strand

```
5'-UGGUGUAGAACACUAAUUCAUᴬAtc-3' (SEQ ID NO: 397)
3'-UUACCACAUCUUGUGAUUAAGUAcUAG-5' (SEQ ID NO: 7794)
```

Optionally, the mismatched "C" residue of position 4 of the antisense strand is alternatively "U" or "A".

As noted above, introduction of such mismatches can be performed upon any of the DsiRNAs described herein.

The mismatches of such DsiRNA structures can be combined to produce a DsiRNA possessing, e.g., two, three or even four mismatches within the 3'-terminal four nucleotides of the sense strand/5'-terminal four nucleotides of the antisense strand.

Indeed, in view of the flexibility of sequences which can be incorporated into DsiRNAs at the 3'-terminal residues of the sense strand/5'-terminal residues of the antisense strand, in certain embodiments, the sequence requirements of an asymmetric DsiRNA of the instant invention can be represented as the following (minimalist) structure (shown for an exemplary βc-1569 DsiRNA sequence):

```
                                   (SEQ ID NO: 7783)
    5'-ACCUCACUUGCAAUAAUUAUAXXX[X]ₙ-3'

(SEQ ID NO: 7784)
    3'-AUUGGAGUGAACGUUAUUAAUXXXXX[X]ₙ-5'
``` where n=1 to 5, 1 to 10, 1 to 20, 1 to 30, 1 to 50, or 1 to 80 or more.

```
    βc-1569 Target:
                                   (SEQ ID NO: 7785)
    5'-TAACCTCACTTGCAATAATTAXXXXXX-3'
```

The β-catenin target site may also be a site which is targeted by one or more of several oligonucleotides whose complementary target sites overlap with a stated target site. For example, for an exemplary βc-288 DsiRNA, it is noted that certain DsiRNAs targeting overlapping and only slightly offset β-catenin sequences can exhibit activity levels similar to that of βc-288 (specifically, see βc-284, βc-285, βc-286, βc-287, βc-289, βc-290 and βc-291 DsiRNAs of Table 14 below). Thus, in certain embodiments, a designated target sequence region can be effectively targeted by a series of DsiRNAs possessing largely overlapping sequences. (E.g., if considering DsiRNAs surrounding the βc-288 site, a more encompassing β-catenin target sequence might be recited as, e.g., 5'-CAGCGTGGACAATGGCTACTCAAGCTGATTTGAT-3' (SEQ ID NO: 7786), wherein any given DsiRNA (e.g., a DsiRNA selected from βc-284, βc-285, βc-286, βc-287, βc-288, βc-289, βc-290 and βc-291) only targets a sub-sequence within such a sequence region, yet the entire sequence can be considered a viable target for such a series of DsiRNAs).

Additionally and/or alternatively, mismatches within the 3'-terminal four nucleotides of the sense strand/5'-terminal four nucleotides of the antisense strand can be combined with mismatches positioned at other mismatch-tolerant positions, as described above.

In view of the present identification of the above-described Dicer substrate agents (DsiRNAs) as inhibitors of β-catenin levels via targeting of specific β-catenin sequences, it is also recognized that DsiRNAs having structures similar to those described herein can also be synthesized which target other sequences within the β-catenin sequence of SEQ ID NOs: 1-3 or SEQ ID NOs: 5-6, or within variants thereof (e.g., target sequences possessing 80% identity, 90% identity, 95% identity, 96% identity, 97% identity, 98% identity, 99% or more identity to a sequence of SEQ ID NOs: 1-3 or SEQ ID NOs: 5-6).

Anti-β-Catenin DsiRNA Design/Synthesis

It has been found empirically that longer dsRNA species of from 25 to 35 nucleotides (DsiRNAs) and especially from 25 to 30 nucleotides give unexpectedly effective results in terms of potency and duration of action, as compared to 19-23mer siRNA agents. Without wishing to be bound by the underlying theory of the dsRNA processing mechanism, it is thought that the longer dsRNA species serve as a substrate for the Dicer enzyme in the cytoplasm of a cell. In addition to cleaving the dsRNA of the invention into shorter segments, Dicer is thought to facilitate the incorporation of a single-stranded cleavage product derived from the cleaved dsRNA into the RISC complex that is responsible for the destruction of the cytoplasmic RNA (e.g., β-catenin RNA) of or derived from the target gene, β-catenin (or other gene associated with a β-catenin-associated disease or disorder). Prior studies (Rossi et al., U.S. Patent Application No. 2007/0265220) have shown that the cleavability of a dsRNA species (specifically, a DsiRNA agent) by Dicer corresponds with increased potency and duration of action of the dsRNA species.

Certain preferred anti-β-catenin DsiRNA agents were selected from a pre-screened population. Design of DsiRNAs can optionally involve use of predictive scoring algorithms that perform in silico assessments of the projected activity/efficacy of a number of possible DsiRNA agents spanning a region of sequence. Information regarding the design of such scoring algorithms can be found, e.g., in Gong et al. (*BMC Bioinformatics* 2006, 7:516), though a more recent "v3" algorithm represents a theoretically improved algorithm relative to siRNA scoring algorithms previously available in the art. (E.g., the "v3" and "v4" scoring algorithms are machine learning algorithms that are not reliant upon any biases in human sequence. In addition, the "v3" and "v4" algorithms derive from data sets that are many-fold larger than that from which an older "v2" algorithm such as that described in Gong et al. derives.)

The first and second oligonucleotides of the DsiRNA agents of the instant invention are not required to be completely complementary. In fact, in one embodiment, the 3'-terminus of the sense strand contains one or more mismatches. In one aspect, two mismatches are incorporated at the 3' terminus of the sense strand. In another embodiment, the DsiRNA of the invention is a double stranded RNA molecule containing two RNA oligonucleotides each of which is 27 nucleotides in length and, when annealed to each other, have blunt ends and a two nucleotide mismatch on the 3'-terminus of the sense strand (the 5'-terminus of the antisense strand). The use of mismatches or decreased thermodynamic stability (specifically at the 3'-sense/5'-antisense position) has been proposed to facilitate or favor entry of the antisense strand into RISC (Schwarz et al., 2003, *Cell* 115: 199-208; Khvorova et al., 2003, Cell 115: 209-216), presumably by affecting some rate-limiting unwinding steps that occur with entry of the siRNA into RISC. Thus, terminal base composition has been included in design algorithms for selecting active 21mer siRNA duplexes (Ui-Tei et al., 2004, *Nucleic Acids Res* 32: 936-948; Reynolds et al., 2004, *Nat Biotechnol* 22: 326-330). With Dicer cleavage of the dsRNA of this embodiment, the small end-terminal sequence which contains the mismatches will either be left unpaired with the antisense strand (become part of a 3'-overhang) or be cleaved entirely off the final 21-mer siRNA. These "mismatches", therefore, do not persist as mismatches in the final RNA component of RISC. The finding that base mismatches or destabilization of segments at the 3'-end of the sense strand of Dicer substrate improved the potency of synthetic duplexes in RNAi, presumably by facilitating processing by Dicer, was a surprising finding of past works describing the design and use of 25-30mer dsRNAs (also termed "DsiRNAs" herein; Rossi et al., U.S. Patent Application Nos. 2005/0277610, 2005/0244858 and 2007/0265220).

Modification of Anti-β-Catenin DsiRNAs

One major factor that inhibits the effect of double stranded RNAs ("dsRNAs") is the degradation of dsRNAs (e.g., siRNAs and DsiRNAs) by nucleases. A 3'-exonuclease is the primary nuclease activity present in serum and modification of the 3'-ends of antisense DNA oligonucleotides is crucial to prevent degradation (Eder et al., 1991, *Antisense Res Dev,* 1: 141-151). An RNase-T family nuclease has been identified called ERI-1 which has 3' to 5' exonuclease activity that is involved in regulation and degradation of siRNAs (Kennedy et al., 2004, *Nature* 427: 645-649; Hong et al., 2005, *Biochem J,* 390: 675-679). This gene is also known as Thex1 (NM_02067) in mice or THEX1 (NM_153332) in humans and is involved in degradation of histone mRNA; it also mediates degradation of 3'-overhangs in siRNAs, but does not degrade duplex RNA (Yang et al., 2006, *J Biol Chem,* 281: 30447-30454). It is therefore reasonable to expect that 3'-end-stabilization of dsRNAs, including the DsiRNAs of the instant invention, will improve stability.

XRN1 (NM_019001) is a 5' to 3' exonuclease that resides in P-bodies and has been implicated in degradation of mRNA targeted by miRNA (Rehwinkel et al., 2005, RNA 11: 1640-1647) and may also be responsible for completing degradation initiated by internal cleavage as directed by a siRNA. XRN2 (NM_012255) is a distinct 5' to 3' exonuclease that is involved in nuclear RNA processing.

RNase A is a major endonuclease activity in mammals that degrades RNAs. It is specific for ssRNA and cleaves at the 3'-end of pyrimidine bases. SiRNA degradation products consistent with RNase A cleavage can be detected by mass spectrometry after incubation in serum (Turner et al., 2007, *Mol Biosyst* 3: 43-50). The 3'-overhangs enhance the susceptibility of siRNAs to RNase degradation. Depletion of RNase A from serum reduces degradation of siRNAs; this degradation does show some sequence preference and is worse for sequences having poly A/U sequence on the ends (Haupenthal et al., 2006 *Biochem Pharmacol* 71: 702-710). This suggests the possibility that lower stability regions of the duplex may "breathe" and offer transient single-stranded species available for degradation by RNase A. RNase A inhibitors can be added to serum and improve siRNA longevity and potency (Haupenthal et al., 2007, *Int J. Cancer* 121: 206-210).

In 21mers, phosphorothioate or boranophosphate modifications directly stabilize the internucleoside phosphate linkage. Boranophosphate modified RNAs are highly nuclease resistant, potent as silencing agents, and are relatively non-toxic. Boranophosphate modified RNAs cannot be manufactured using standard chemical synthesis methods and instead are made by in vitro transcription (IVT) (Hall et al., 2004, *Nucleic Acids Res* 32: 5991-6000; Hall et al., 2006, *Nucleic Acids Res* 34: 2773-2781). Phosphorothioate (PS) modifications can be easily placed in the RNA duplex at any desired position and can be made using standard chemical synthesis methods. The PS modification shows dose-dependent toxicity, so most investigators have recommended limited incorporation in siRNAs, favoring the 3'-ends where protection from nucleases is most important (Harborth et al., 2003, *Antisense Nucleic Acid Drug Dev* 13: 83-105; Chiu and Rana, 2003, *Mol Cell* 10: 549-561; Braasch et al., 2003, *Biochemistry* 42: 7967-7975; Amarzguioui et al., 2003, *Nucleic Acids Research* 31: 589-595). More extensive PS modification can be compatible with potent RNAi activity; however, use of sugar modifications (such as 2'-O-methyl RNA) may be superior (Choung et al., 2006, *Biochem Biophys Res Commun* 342: 919-927).

A variety of substitutions can be placed at the 2'-position of the ribose which generally increases duplex stability ($T_m$) and can greatly improve nuclease resistance. 2'-O-methyl RNA is a naturally occurring modification found in mammalian ribosomal RNAs and transfer RNAs. 2'-O-methyl modification in siRNAs is known, but the precise position of modified bases within the duplex is important to retain potency and complete substitution of 2'-O-methyl RNA for RNA will inactivate the siRNA. For example, a pattern that employs alternating 2'-O-methyl bases can have potency equivalent to unmodified RNA and is quite stable in serum (Choung et al., 2006, *Biochem Biophys Res Commun* 342: 919-927; Czauderna et al., 2003, *Nucleic Acids Research* 31: 2705-2716).

The 2'-fluoro (2'-F) modification is also compatible with dsRNA (e.g., siRNA and DsiRNA) function; it is most commonly placed at pyrimidine sites (due to reagent cost and availability) and can be combined with 2'-O-methyl modification at purine positions; 2'-F purines are available and can also be used. Heavily modified duplexes of this kind can be potent triggers of RNAi in vitro (Allerson et al., 2005, *J Med Chem* 48: 901-904; Prakash et al., 2005, *J Med Chem* 48: 4247-4253; Kraynack and Baker, 2006, *RNA* 12: 163-176) and can improve performance and extend duration of action when used in vivo (Morrissey et al., 2005, *Hepatology* 41: 1349-1356; Morrissey et al., 2005, *Nat Biotechnol* 23: 1002-1007). A highly potent, nuclease stable, blunt 19mer duplex containing alternative 2'-F and 2'-O-Me bases is taught by Allerson. In this design, alternating 2'-O-Me residues are positioned in an identical pattern to that employed by Czauderna, however the remaining RNA residues are converted to 2'-F modified bases. A highly potent, nuclease resistant siRNA employed by Morrissey employed a highly potent, nuclease resistant siRNA in vivo. In addition to 2'-O-Me RNA and 2'-F RNA, this duplex includes DNA, RNA, inverted abasic residues, and a 3'-terminal PS internucleoside linkage. While extensive modification has certain benefits, more limited modification of the duplex can also improve in vivo performance and is both simpler and less costly to manufacture. Soutschek et al. (2004, *Nature* 432: 173-178) employed a duplex in vivo and was mostly RNA with two 2'-O-Me RNA bases and limited 3'-terminal PS internucleoside linkages.

Locked nucleic acids (LNAs) are a different class of 2'-modification that can be used to stabilize dsRNA (e.g., siRNA and DsiRNA). Patterns of LNA incorporation that retain potency are more restricted than 2'-O-methyl or 2'-F bases, so limited modification is preferred (Braasch et al., 2003, *Biochemistry* 42: 7967-7975; Grunweller et al., 2003, *Nucleic Acids Res* 31: 3185-3193; Elmen et al., 2005, *Nucleic Acids Res* 33: 439-447). Even with limited incorporation, the use of LNA modifications can improve dsRNA performance in vivo and may also alter or improve off target effect profiles (Mook et al., 2007, *Mol Cancer Ther* 6: 833-843).

Synthetic nucleic acids introduced into cells or live animals can be recognized as "foreign" and trigger an immune response Immune stimulation constitutes a major class of off-target effects which can dramatically change experimental results and even lead to cell death. The innate immune system includes a collection of receptor molecules that specifically interact with DNA and RNA that mediate these responses, some of which are located in the cytoplasm and some of which reside in endosomes (Marques and Williams, 2005, *Nat Biotechnol* 23: 1399-1405; Schlee et al., 2006, *Mol Ther* 14: 463-470). Delivery of siRNAs by cationic lipids or liposomes exposes the siRNA to both cytoplasmic and endosomal compartments, maximizing the risk for triggering a type 1 interferon (IFN) response both in vitro and in vivo (Morrissey et al., 2005, *Nat Biotechnol* 23: 1002-1007; Sioud and Sorensen, 2003, *Biochem Biophys Res Commun* 312: 1220-1225; Sioud, 2005, *J Mol Biol* 348: 1079-1090; Ma et al., 2005, *Biochem Biophys Res Commun* 330: 755-759). RNAs transcribed within the cell are less immunogenic (Robbins et al., 2006, *Nat Biotechnol* 24: 566-571) and synthetic RNAs that are immunogenic when delivered using lipid-based methods can evade immune stimulation when introduced unto cells by mechanical means, even in vivo (Heidel et al., 2004, *Nat Biotechnol* 22: 1579-1582). However, lipid based delivery methods are convenient, effective, and widely used. Some general strategy to prevent immune responses is needed, especially for in vivo application where all cell types are present and the risk of generating an immune response is highest. Use of chemically modified RNAs may solve most or even all of these problems.

In certain embodiments, modifications can be included in the anti-β-catenin DsiRNA agents of the present invention so long as the modification does not prevent the DsiRNA agent from possessing β-catenin inhibitory activity. In one embodiment, one or more modifications are made that enhance Dicer processing of the DsiRNA agent (an assay for determining Dicer processing of a DsiRNA is described supra). In a second embodiment, one or more modifications are made that result in more effective β-catenin inhibition (as described herein, β-catenin inhibition/β-catenin inhibitory activity of a DsiRNA can be assayed via art-recognized methods for determining RNA levels, or for determining β-catenin polypeptide levels, should such levels be assessed in lieu of or in addition to assessment of, e.g., (β-catenin mRNA levels). In a third embodiment, one or more modifications are made that support greater β-catenin inhibitory activity (means of determining (β-catenin inhibitory activity are described supra). In a fourth embodiment, one or more modifications are made that result in greater potency of β-catenin inhibitory activity per each DsiRNA agent molecule to be delivered to the cell (potency of (β-catenin inhibitory activity is described supra). Modifications can be incorporated in the 3'-terminal region, the 5'-terminal region, in both the 3'-terminal and 5'-terminal region or in some instances in various positions within the sequence. With the restrictions noted above in mind, numbers and combinations of modifications can be incorporated into the DsiRNA agent. Where multiple modifications are present, they may be the same or different. Modifications to bases, sugar moieties, the phosphate backbone, and their combinations are contemplated. Either 5'-terminus can be phosphorylated.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003, *Nucleic Acids Research* 31: 589-595). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858, 988 and 6,291,438 and in U.S. published patent application No. 2004/0203145 A1. Other modifications are disclosed in Herdewijn (2000, *Antisense Nucleic Acid Drug Dev* 10: 297-310), Eckstein (2000, *Antisense Nucleic Acid Drug Dev* 10: 117-21), Rusckowski et al. (2000, *Antisense Nucleic Acid Drug Dev* 10: 333-345), Stein et al. (2001, *Antisense Nucleic Acid Drug Dev* 11: 317-25); Vorobjev et al. (2001, *Antisense Nucleic Acid Drug Dev* 11: 77-85).

One or more modifications contemplated can be incorporated into either strand. The placement of the modifications in the DsiRNA agent can greatly affect the characteristics of the DsiRNA agent, including conferring greater potency and stability, reducing toxicity, enhance Dicer processing, and minimizing an immune response. In one embodiment, the antisense strand or the sense strand or both strands have one or more 2'-O-methyl modified nucleotides. In another embodiment, the antisense strand contains 2'-O-methyl modified nucleotides. In another embodiment, the antisense stand contains a 3' overhang that is comprised of 2'-O-methyl modified nucleotides. The antisense strand could also include additional 2'-O-methyl modified nucleotides.

In certain embodiments of the present invention, the anti-β-catenin DsiRNA agent has one or more of the following properties: (i) the DsiRNA agent is asymmetric, e.g., has a 3' overhang on the antisense strand and (ii) the DsiRNA agent has a modified 3' end on the sense strand to direct orientation of Dicer binding and processing of the dsRNA to an active siRNA. According to this embodiment, the longest strand in the dsRNA comprises 25-35 nucleotides (e.g., 25, 26, 27, 28, 29, 30, 31, 32, 33, 34 or 35 nucleotides). In certain such embodiments, the DsiRNA agent is asymmetric such that the sense strand comprises 25-34 nucleotides and the 3' end of the sense strand forms a blunt end with the 5' end of the antisense strand while the antisense strand comprises 26-35 nucleotides and forms an overhang on the 3' end of the antisense strand. In one embodiment, the DsiRNA agent is asymmetric such that the sense strand comprises 25-28 nucleotides and the antisense strand comprises 25-30 nucleotides. Thus, the resulting dsRNA has an overhang on the 3' end of the antisense strand. The overhang is 1-4 nucleotides, for example 2 nucleotides. The sense strand may also have a 5' phosphate.

In other embodiments, the sense strand of the DsiRNA agent is modified for Dicer processing by suitable modifiers located at the 3' end of the sense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotides modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the DsiRNA agent to direct the orientation of Dicer processing of the antisense strand. In a further embodiment of the present invention, two terminal DNA bases are substituted for two ribonucleotides on the 3'-end of the sense strand forming a blunt end of the duplex on the 3' end of the sense strand and the 5' end of the antisense strand, and a two-nucleotide RNA overhang is located on the 3'-end of the antisense strand. This is an asymmetric composition with DNA on the blunt end and RNA bases on the overhanging end.

The sense and antisense strands of a DsiRNA agent of the instant invention anneal under biological conditions, such as the conditions found in the cytoplasm of a cell. In addition, a region of one of the sequences, particularly of the antisense strand, of the DsiRNA agent has a sequence length of at least 15 (in certain embodiments, 19) nucleotides, wherein these nucleotides are adjacent to the 3' end of antisense strand (e.g., in the 21-nucleotide region adjacent to the 3' end of the antisense strand) and are sufficiently complementary to a nucleotide sequence of the target β-catenin RNA.

Additionally, the DsiRNA agent structure can be optimized to ensure that the oligonucleotide segment generated from Dicer's cleavage will be the portion of the oligonucleotide that is most effective in inhibiting gene expression. For example, in one embodiment of the invention, a 27-bp oligonucleotide of the DsiRNA agent structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

The DsiRNA agent can also have one or more of the following additional properties: (a) the antisense strand has a right shift from the typical 21mer (e.g., the DsiRNA comprises a length of antisense strand nucleotides that extends to the 5' of a projected Dicer cleavage site within the DsiRNA, with such antisense strand nucleotides base paired with corresponding nucleotides of the sense strand extending 3' of a projected Dicer cleavage site in the sense strand), (b) the strands may not be completely complementary, i.e., the strands may contain simple mismatched base pairs (in certain embodiments, the DsiRNAs of the invention possess 1, 2, 3, 4 or even 5 or more mismatched base pairs, provided that β-catenin inhibitory activity of the DsiRNA possessing mismatched base pairs is retained at sufficient levels (e.g., retains at least 50% β-catenin inhibitory activity or more, at least 60% β-catenin inhibitory activity or more, at least 70% β-catenin inhibitory activity or more, at least 80% β-catenin inhibitory activity or more, at least 90% β-catenin inhibitory activity or more or at least 95% β-catenin inhibitory activity or more as compared to a corresponding DsiRNA not possessing mismatched base pairs. In certain embodiments, mismatched base pairs exist between the antisense and sense strands of a DsiRNA. In some embodiments, mismatched base pairs exist (or are predicted to exist) between the antisense strand and the target RNA. In certain embodiments, the presence of a mismatched base pair(s) between an antisense strand residue and a corresponding residue within the target RNA that is located 3' in the target RNA sequence of a projected Ago2 cleavage site retains and may even enhance (β-catenin inhibitory activity of a DsiRNA of the invention) and (c) base modifications such as locked nucleic acid(s) may be included in the 5' end of the sense strand. A "typical" 21mer siRNA is designed using conventional techniques. In one technique, a variety of sites are commonly tested in parallel or pools containing several distinct siRNA duplexes specific to the same target with the hope that one of the reagents will be effective (Ji et al., 2003, *FEBS Lett* 552: 247-252). Other techniques use design rules and algorithms to increase the likelihood of obtaining active RNAi effector molecules (Schwarz et al., 2003, *Cell* 115: 199-208; Khvorova et al., 2003, *Cell* 115: 209-216; Ui-Tei et al., 2004, *Nucleic Acids Res* 32: 936-948; Reynolds et al., 2004, *Nat Biotechnol* 22: 326-330; Krol et al., 2004, *J Biol Chem* 279: 42230-42239; Yuan et al., 2004, *Nucl Acids Res* 32(Webserver issue):W130-134; Boese et al., 2005, *Methods Enzymol* 392: 73-96). High throughput selection of siRNA has also been developed (U.S. published patent application No. 2005/0042641 A1). Potential target sites can also be analyzed by secondary structure predictions (Heale et al., 2005, *Nucleic Acids Res* 33(3): e30). This 21mer is then used to design a right shift to include 3-9 additional nucleotides on the 5' end of the 21mer. The sequence of these additional nucleotides is not restricted. In one embodiment, the added ribonucleotides are based on the sequence of the target gene. Even in this embodiment, full complementarity between the target sequence and the antisense siRNA is not required.

The first and second oligonucleotides of a DsiRNA agent of the instant invention are not required to be completely complementary. They only need to be sufficiently complementary to anneal under biological conditions and to provide a substrate for Dicer that produces a siRNA sufficiently complementary to the target sequence. Locked nucleic acids, or LNA's, are well known to a skilled artisan (Elmen et al., 2005, *Nucleic Acids Res* 33: 439-447; Kurreck et al., 2002, *Nucleic Acids Res* 30: 1911-1918; Crinelli et al., 2002, *Nucleic Acids Res* 30: 2435-2443; Braasch and Corey, 2001, *Chem Biol* 8: 1-7; Bondensgaard et al., 2000, *Chemistry* 6: 2687-2695; Wahlestedt et al., 2000, *Proc Natl Acad Sci USA* 97: 5633-5638). In one embodiment, an LNA is incorporated at the 5' terminus of the sense strand. In another embodiment, an LNA is incorporated at the 5' terminus of the sense strand in duplexes designed to include a 3' overhang on the antisense strand.

In certain embodiments, the DsiRNA agent of the instant invention has an asymmetric structure, with the sense strand having a 25-base pair length, and the antisense strand having a 27-base pair length with a 2 base 3'-overhang. In other embodiments, this DsiRNA agent having an asymmetric structure further contains 2 deoxynucleotides at the 3' end of the sense strand in place of two of the ribonucleotides.

Certain DsiRNA agent compositions containing two separate oligonucleotides can be linked by a third structure. The third structure will not block Dicer activity on the DsiRNA agent and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the DsiRNA agent in a manner such that a hairpin structure is produced upon annealing of the two oligonucleotides making up the dsRNA composition. The hairpin structure will not block Dicer activity on the DsiRNA agent and will not interfere with the directed destruction of the β-catenin RNA.

In certain embodiments, the anti-β-catenin DsiRNA agent of the invention has several properties which enhance its processing by Dicer. According to such embodiments, the DsiRNA agent has a length sufficient such that it is processed by Dicer to produce an siRNA and at least one of the following properties: (i) the DsiRNA agent is asymmetric, e.g., has a 3' overhang on the sense strand and (ii) the DsiRNA agent has a modified 3' end on the antisense strand to direct orientation of Dicer binding and processing of the dsRNA to an active siRNA. According to these embodiments, the longest strand in the DsiRNA agent comprises 25-30 nucleotides. In one embodiment, the sense strand comprises 25-30 nucleotides and the antisense strand comprises 25-28 nucleotides. Thus, the resulting dsRNA has an overhang on the 3' end of the sense strand. The overhang is 1-4 nucleotides, such as 2 nucleotides. The antisense strand may also have a 5' phosphate.

In certain embodiments, the sense strand of a DsiRNA agent is modified for Dicer processing by suitable modifiers located at the 3' end of the sense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thia-cytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the sense strand in place of two ribonucleotides forming a blunt end of the duplex on the 5' end of the antisense strand and the 3' end of the sense strand, and a two-nucleotide RNA overhang is located on the 3'-end of the antisense strand. This is an asymmetric composition with DNA on the blunt end and RNA bases on the overhanging end.

In certain other embodiments, the antisense strand of a DsiRNA agent is modified for Dicer processing by suitable modifiers located at the 3' end of the antisense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is also an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the target β-catenin RNA.

Additionally, the DsiRNA agent structure contains two portions based on Dicer cleavage, a first portion which survives the Dicer-cleavage process and proceeds to actively engage the target RNA as part of the RISC complex and a second portion which is not active in RISC. The first portion will contain the sequence known to be most effective at RNA interference at the target RNA/RISC level, whereas the second portion may or may not be complementary to the target sequence. For example, in one embodiment of the invention, a 27-bp oligonucleotide of the DsiRNA agent structure is synthesized wherein the anticipated 21 to 22-bp segment that forms a hybrid with the target nucleic acid and thereby inhibits gene expression is located on the 3'-end of the antisense strand. The remaining bases located on the 5'-end of the antisense strand will be cleaved by Dicer and thus will not be a contiguous part of the Dicer-cleaved RNAi molecule. This second portion can be homologous (i.e., based on the sequence of the target sequence) or non-homologous and added to extend the nucleic acid strand.

US 2007/0265220 discloses that 27mer DsiRNAs show improved stability in serum over comparable 21mer siRNA compositions, even absent chemical modification. Modifications of DsiRNA agents, such as inclusion of 2'-O-methyl RNA in the antisense strand, in patterns such as detailed above, when coupled with addition of a 5' Phosphate, can improve stability of DsiRNA agents. Addition of 5'-phosphate to all strands in synthetic RNA duplexes may be an inexpensive and physiological method to confer some limited degree of nuclease stability.

The chemical modification patterns of the dsRNA agents of the instant invention are designed to enhance the efficacy of such agents. Accordingly, such modifications are designed to avoid reducing potency of dsRNA agents; to avoid interfering with Dicer processing of DsiRNA agents; to improve stability in biological fluids (reduce nuclease sensitivity) of dsRNA agents; or to block or evade detection by the innate immune system. Such modifications are also designed to avoid being toxic and to avoid increasing the cost or impact the ease of manufacturing the instant dsRNA agents of the invention.

β-Catenin Biology and Biochemistry

Known human and mouse β-catenin cDNA and polypeptide sequences include the following:

Human Wild-Type β-Catenin (Cadherin-Associated Protein) Sequence, Transcript Variant 1 (SEQ ID NO: 1; *Homo sapiens* CTNNB1, Transcript Variant 1; GenBank Accession No. NM_001904.3):

AGGATACAGCGGCTTCTGCGCGACTTATAAGAGCTCCTTGTGCGGCGCCA

TTTTAAGCCTCTCGGTCTGTGGCAGCAGCGTTGGCCCGGCCCCGGGAGCG

GAGAGCGAGGGGAGGCGGAGACGGAGGAAGGTCTGAGGAGCAGCTTCAGT

CCCCGCCGAGCCGCCACCGCAGGTCGAGGACGGTCGGACTCCCGCGGCGG

GAGGAGCCTGTTCCCCTGAGGGTATTTGAAGTATACCATACAACTGTTTT

GAAAATCCAGCGTGGACAATGGCTACTCAAGCTGATTTGATGGAGTTGGA

CATGGCCATGGAACCAGACAGAAAAGCGGCTGTTAGTCACTGGCAGCAAC

AGTCTTACCTGGACTCTGGAATCCATTCTGGTGCCACTACCACAGCTCCT

TCTCTGAGTGGTAAAGGCAATCCTGAGGAAGAGGATGTGGATACCTCCCA

AGTCCTGTATGAGTGGGAACAGGGATTTTCTCAGTCCTTCACTCAAGAAC

AAGTAGCTGATATTGATGGACAGTATGCAATGACTCGAGCTCAGAGGGTA

CGAGCTGCTATGTTCCCTGAGACATTAGATGAGGGCATGCAGATCCCATC

TACACAGTTTGATGCTGCTCATCCCACTAATGTCCAGCGTTTGGCTGAAC

CATCACAGATGCTGAAACATGCAGTTGTAAACTTGATTAACTATCAAGAT

GATGCAGAACTTGCCACACGTGCAATCCCTGAACTGACAAAACTGCTAAA

TGACGAGGACCAGGTGGTGGTTAATAAGGCTGCAGTTATGGTCCATCAGC

TTTCTAAAAAGGAAGCTTCCAGACACGCTATCATGCGTTCTCCTCAGATG

GTGTCTGCTATTGTACGTACCATGCAGAATACAAATGATGTAGAAACAGC

TCGTTGTACCGCTGGGACCTTGCATAACCTTTCCCATCATCGTGAGGGCT

TACTGGCCATCTTTAAGTCTGGAGGCATTCCTGCCCTGGTGAAAATGCTT

GGTTCACCAGTGGATTCTGTGTTGTTTTATGCCATTACAACTCTCCACAA

CCTTTTATTACATCAAGAAGGAGCTAAAATGGCAGTGCGTTTAGCTGGTG

GGCTGCAGAAAATGGTTGCCTTGCTCAACAAAACAAATGTTAAATTCTTG

GCTATTACGACAGACTGCCTTCAAATTTTAGCTTATGGCAACCAAGAAAG

CAAGCTCATCATACTGGCTAGTGGTGGACCCCAAGCTTTAGTAAATATAA

TGAGGACCTATACTTACGAAAAACTACTGTGGACCACAAGCAGAGTGCTG

AAGGTGCTATCTGTCTGCTCTAGTAATAAGCCGGCTATTGTAGAAGCTGG

TGGAATGCAAGCTTTAGGACTTCACCTGACAGATCCAAGTCAACGTCTTG

TTCAGAACTGTCTTTGGACTCTCAGGAATCTTTCAGATGCTGCAACTAAA

CAGGAAGGGATGGAAGGTCTCCTTGGGACTCTTGTTCAGCTTCTGGGTTC

AGATGATATAAATGTGGTCACCTGTGCAGCTGGAATTCTTTCTAACCTCA

CTTGCAATAATTATAAGAACAAGATGATGGTCTGCCAAGTGGGTGGTATA

GAGGCTCTTGTGCGTACTGTCCTTCGGGCTGGTGACAGGGAAGACATCAC

TGAGCCTGCCATCTGTGCTCTTCGTCATCTGACCAGCCGACACCAAGAAG

CAGAGATGGCCCAGAATGCAGTTCGCCTTCACTATGGACTACCAGTTGTG

GTTAAGCTCTTACACCCACCATCCCACTGGCCTCTGATAAAGGCTACTGT

TGGATTGATTCGAAATCTTGCCCTTTGTCCCGCAAATCATGCACCTTTGC

GTGAGCAGGGTGCCATTCCACGACTAGTTCAGTTGCTTGTTCGTGCACAT

CAGGATACCCAGCGCCGTACGTCCATGGGTGGGACACAGCAGCAATTTGT

GGAGGGGGTCCGCATGGAAGAAATAGTTGAAGGTTGTACCGGAGCCCTTC

ACATCCTAGCTCGGGATGTTCACAACCGAATTGTTATCAGAGGACTAAAT

ACCATTCCATTGTTTGTGCAGCTGCTTTATTCTCCCATTGAAAACATCCA

AAGAGTAGCTGCAGGGGTCCTCTGTGAACTTGCTCAGGACAAGGAAGCTG

CAGAAGCTATTGAAGCTGAGGGAGCCACAGCTCCTCTGACAGAGTTACTT

CACTCTAGGAATGAAGGTGTGGCGACATATGCAGCTGCTGTTTTGTTCCG

AATGTCTGAGGACAAGCCACAAGATTACAAGAAACGGCTTTCAGTTGAGC

TGACCAGCTCTCTCTTCAGAACAGAGCCAATGGCTTGGAATGAGACTGCT

GATCTTGGACTTGATATTGGTGCCCAGGGAGAACCCCTTGGATATCGCCA

GGATGATCCTAGCTATCGTTCTTTTCACTCTGGTGGATATGGCCAGGATG

CCTTGGGTATGGACCCCATGATGGAACATGAGATGGGTGGCCACCACCCT

GGTGCTGACTATCCAGTTGATGGGCTGCCAGATCTGGGGCATGCCCAGGA

CCTCATGGATGGGCTGCCTCCAGGTGACAGCAATCAGCTGGCCTGGTTTG

ATACTGACCTGTAAATCATCCTTTAGGTAAGAAGTTTTAAAAAGCCAGTT

TGGGTAAAATACTTTTACTCTGCCTACAGAACTTCAGAAAGACTTGGTTG

GTAGGGTGGGAGTGGTTTAGGCTATTTGTAAATCTGCCACAAAAACAGGT

ATATACTTTGAAAGGAGATGTCTTGGAACATTGGAATGTTCTCAGATTTC

```
TGGTTGTTATGTGATCATGTGTGGAAGTTATTAACTTTAATGTTTTTTGC
CACAGCTTTTGCAACTTAATACTCAAATGAGTAACATTTGCTGTTTTAAA
CATTAATAGCAGCCTTTCTCTCTTTATACAGCTGTATTGTCTGAACTTGC
ATTGTGATTGGCCTGTAGAGTTGCTGAGAGGGCTCGAGGGGTGGGCTGGT
ATCTCAGAAAGTGCCTGACACACTAACCAAGCTGAGTTTCCTATGGGAAC
AATTGAAGTAAACTTTTTGTTCTGGTCCTTTTTGGTCGAGGAGTAACAAT
ACAAATGGATTTTGGGAGTGACTCAAGAAGTGAAGAATGCACAAGAATGG
ATCACAAGATGGAATTTATCAAACCCTAGCCTTGCTTGTTAAATTTTTTT
TTTTTTTTTTTAAGAATATCTGTAATGGTACTGACTTTGCTTGCTTTGA
AGTAGCTCTTTTTTTTTTTTTTTTTTTTTGCAGTAACTGTTTTTTA
AGTCTCTCGTAGTGTTAAGTTATAGTGAATACTGCTACAGCAATTTCTAA
TTTTTAAGAATTGAGTAATGGTGTAGAACACTAATTCATAATCACTCTAA
TTAATTGTAATCTGAATAAAGTGTAACAATTGTGTAGCCTTTTTGTATAA
AATAGACAAATAGAAAATGGTCCAATTAGTTTCCTTTTTAATATGCTTAA
AATAAGCAGGTGGATCTATTTCATGTTTTTGATCAAAAACTATTTGGGAT
ATGTATGGGTAGGGTAAATCAGTAAGAGGTGTTATTTGGAACCTTGTTTT
GGACAGTTTACCAGTTGCCTTTTATCCCAAAGTTGTTGTAACCTGCTGTG
ATACGATGCTTCAAGAGAAAATGCGGTTATAAAAAATGGTTCAGAATTAA
ACTTTTAATTCATTCGATTG
```

Human Wild-Type β-Catenin (Cadherin-Associated Protein) Sequence, Transcript Variant 2 (SEQ ID NO: 2; *Homo sapiens* CTNNB1, Transcript Variant 2; GenBank Accession No. NM_001098209.1):

```
AGGATACAGCGGCTTCTGCGCGACTTATAAGAGCTCCTTGTGCGGCGCCA
TTTTAAGCCTCTCGGTCTGTGGCAGCAGCGTTGGCCCGGCCCCGGGAGCG
GAGAGCGAGGGGAGGCGGAGACGGAGGAAGGTCTGAGGAGCAGCTTCAGT
CCCCGCCGAGCCGCCACCGCAGGTCGAGGACGGTCGGACTCCCGCGGCGG
GAGGAGCCTGTTCCCCTGAGGGTATTTGAAGTATACCATACAACTGTTTT
GAAAATCCAGCGTGGACAATGGCTACTCAAGCTGATTTGATGGAGTTGGA
CATGGCCATGGAACCAGACAGAAAAGCGGCTGTTAGTCACTGGCAGCAAC
AGTCTTACCTGGACTCTGGAATCCATTCTGGTGCCACTACCACAGCTCCT
TCTCTGAGTGGTAAAGGCAATCCTGAGGAAGAGGATGTGGATACCTCCCA
AGTCCTGTATGAGTGGGAACAGGGATTTTCTCAGTCCTTCACTCAAGAAC
AAGTAGCTGATATTGATGGACAGTATGCAATGACTCGAGCTCAGAGGGTA
CGAGCTGCTATGTTCCCTGAGACATTAGATGAGGGCATGCAGATCCCATC
TACACAGTTTGATGCTGCTCATCCCACTAATGTCCAGCGTTTGGCTGAAC
CATCACAGATGCTGAAACATGCAGTTGTAAACTTGATTAACTATCAAGAT
GATGCAGAACTTGCCACACGTGCAATCCCTGAACTGACAAAACTGCTAAA
TGACGAGGACCAGGTGGTGGTTAATAAGGCTGCAGTTATGGTCCATCAGC
TTTCTAAAAAGGAAGCTTCCAGACACGCTATCATGCGTTCTCCTCAGATG
GTGTCTGCTATTGTACGTACCATGCAGAATACAAATGATGTAGAAACAGC
```

```
TCGTTGTACCGCTGGGACCTTGCATAACCTTTCCCATCATCGTGAGGGCT
TACTGGCCATCTTTAAGTCTGGAGGCATTCCTGCCCTGGTGAAAATGCTT
GGTTCACCAGTGGATTCTGTGTTGTTTTATGCCATTACAACTCTCCACAA
CCTTTTATTACATCAAGAAGGAGCTAAAATGGCAGTGCGTTTAGCTGGTG
GGCTGCAGAAAATGGTTGCCTTGCTCAACAAAACAAATGTTAAATTCTTG
GCTATTACGACAGACTGCCTTCAAATTTTAGCTTATGGCAACCAAGAAAG
CAAGCTCATCATACTGGCTAGTGGTGGACCCCAAGCTTTAGTAAATATAA
TGAGGACCTATACTTACGAAAAACTACTGTGGACCACAAGCAGAGTGCTG
AAGGTGCTATCTGTCTGCTCTAGTAATAAGCCGGCTATTGTAGAAGCTGG
TGGAATGCAAGCTTTAGGACTTCACCTGACAGATCCAAGTCAACGTCTTG
TTCAGAACTGTCTTTGGACTCTCAGGAATCTTTCAGATGCTGCAACTAAA
CAGGAAGGGATGGAAGGTCTCCTTGGGACTCTTGTTCAGCTTCTGGGTTC
AGATGATATAAATGTGGTCACCTGTGCAGCTGGAATTCTTTCTAACCTCA
CTTGCAATAATTATAAGAACAAGATGATGGTCTGCCAAGTGGGTGGTATA
GAGGCTCTTGTGCGTACTGTCCTTCGGGCTGGTGACAGGGAAGACATCAC
TGAGCCTGCCATCTGTGCTCTTCGTCATCTGACCAGCCGACACCAAGAAG
CAGAGATGGCCCAGAATGCAGTTCGCCTTCACTATGGACTACCAGTTGTG
GTTAAGCTCTTACACCCACCATCCCACTGGCCTCTGATAAAGGCTACTGT
TGGATTGATTCGAAATCTTGCCCTTTGTCCCGCAAATCATGCACCTTTGC
GTGAGCAGGGTGCCATTCCACGACTAGTTCAGTTGCTTGTTCGTGCACAT
CAGGATACCCAGCGCCGTACGTCCATGGGTGGGACACAGCAGCAATTTGT
GGAGGGGGTCCGCATGGAAGAAATAGTTGAAGGTTGTACCGGAGCCCTTC
ACATCCTAGCTCGGGATGTTCACAACCGAATTGTTATCAGAGGACTAAAT
ACCATTCCATTGTTTGTGCAGCTGCTTTATTCTCCCATTGAAAACATCCA
AAGAGTAGCTGCAGGGGTCCTCTGTGAACTTGCTCAGGACAAGGAAGCTG
CAGAAGCTATTGAAGCTGAGGGAGCCACAGCTCCTCTGACAGAGTTACTT
CACTCTAGGAATGAAGGTGTGGCGACATATGCAGCTGCTGTTTTGTTCCG
AATGTCTGAGGACAAGCCACAAGATTACAAGAAACGGCTTTCAGTTGAGC
TGACCAGCTCTCTCTTCAGAACAGAGCCAATGGCTTGGAATGAGACTGCT
GATCTTGGACTTGATATTGGTGCCCAGGGAGAACCCCTTGGATATCGCCA
GGATGATCCTAGCTATCGTTCTTTTCACTCTGGTGGATATGGCCAGGATG
CCTTGGGTATGGACCCCATGATGGAACATGAGATGGGTGGCCACCACCCT
GGTGCTGACTATCCAGTTGATGGGCTGCCAGATCGGGGCATGCCCAGGA
CCTCATGGATGGGCTGCCTCCAGGTGACAGCAATCAGCTGGCCTGGTTTG
ATACTGACCTGTAAATCATCCTTTAGCTGTATTGTCTGAACTTGCATTGT
GATTGGCCTGTAGAGTTGCTGAGAGGGCTCGAGGGGTGGGCTGGTATCTC
AGAAAGTGCCTGACACACTAACCAAGCTGAGTTTCCTATGGGAACAATTG
AAGTAAACTTTTTGTTCTGGTCCTTTTTGGTCGAGGAGTAACAATACAAA
TGGATTTTGGGAGTGACTCAAGAAGTGAAGAATGCACAAGAATGGATCAC
AAGATGGAATTTATCAAACCCTAGCCTTGCTTGTTAAATTTTTTTTTTTT
```

TTTTTTTAAGAATATCTGTAATGGTACTGACTTTGCTTGCTTTGAAGTAG
CTCTTTTTTTTTTTTTTTTTTTTTTGCAGTAACTGTTTTTTAAGTCT
CTCGTAGTGTTAAGTTATAGTGAATACTGCTACAGCAATTTCTAATTTTT
AAGAATTGAGTAATGGTGTAGAACACTAATTCATAATCACTCTAATTAAT
TGTAATCTGAATAAAGTGTAACAATTGTGTAGCCTTTTTGTATAAAATAG
ACAAATAGAAAATGGTCCAATTAGTTTCCTTTTTAATATGCTTAAAATAA
GCAGGTGGATCTATTTCATGTTTTTGATCAAAAACTATTTGGGATATGTA
TGGGTAGGGTAAATCAGTAAGAGGTGTTATTTGGAACCTTGTTTTGGACA
GTTTACCAGTTGCCTTTTATCCCAAAGTTGTTGTAACCTGCTGTGATACG
ATGCTTCAAGAGAAAATGCGGTTATAAAAAATGGTTCAGAATTAAACTTT
TAATTCATTCGATTG

Human Wild-Type β-Catenin (Cadherin-Associated Protein) Sequence, Transcript Variant 3 (SEQ ID NO: 3; *Homo sapiens* CTNNB1, Transcript Variant 3; GenBank Accession No. NM_001098210.1):

AGGATACAGCGGCTTCTGCGCGACTTATAAGAGCTCCTTGTGCGGCGCCA
TTTTAAGCCTCTCGGTCTGTGGCAGCAGCGTTGGCCCGGCCCCGGGAGCG
GAGAGCGAGGGGAGGCGGAGACGGAGGAAGGTCTGAGGAGCAGCTTCAGT
CCCCGCCGAGCCGCCACCGCAGGTCGAGGACGGTCGGACTCCCGCGGCGG
GAGGAGCCTGTTCCCCTGAGGGTATTTGAAGTATACCATACAACTGTTTT
GAAAATCCAGCGTGGACAATGGCTACTCAAGCTGATTTGATGGAGTTGGA
CATGGCCATGGAACCAGACAGAAAAGCGGCTGTTAGTCACTGGCAGCAAC
AGTCTTACCTGGACTCTGGAATCCATTCTGGTGCCACTACCACAGCTCCT
TCTCTGAGTGGTAAAGGCAATCCTGAGGAAGAGGATGTGGATACCTCCCA
AGTCCTGTATGAGTGGGAACAGGGATTTTCTCAGTCCTTCACTCAAGAAC
AAGTAGCTGATATTGATGGACAGTATGCAATGACTCGAGCTCAGAGGGTA
CGAGCTGCTATGTTCCCTGAGACATTAGATGAGGGCATGCAGATCCCATC
TACACAGTTTGATGCTGCTCATCCCACTAATGTCCAGCGTTTGGCTGAAC
CATCACAGATGCTGAAACATGCAGTTGTAAACTTGATTAACTATCAAGAT
GATGCAGAACTTGCCACACGTGCAATCCCTGAACTGACAAAACTGCTAAA
TGACGAGGACCAGGTGGTGGTTAATAAGGCTGCAGTTATGGTCCATCAGC
TTTCTAAAAGGAAGCTTCCAGACACGCTATCATGCGTTCTCCTCAGATG
GTGTCTGCTATTGTACGTACCATGCAGAATACAAATGATGTAGAAACAGC
TCGTTGTACCGCTGGGACCTTGCATAACCTTTCCCATCATCGTGAGGGCT
TACTGGCCATCTTTAAGTCTGGAGGCATTCCTGCCCTGGTGAAAATGCTT
GGTTCACCAGTGGATTCTGTGTTGTTTTATGCCATTACAACTCTCCACAA
CCTTTTATTACATCAAGAAGGAGCTAAAATGGCAGTGCGTTTAGCTGGTG
GGCTGCAGAAAATGGTTGCCTTGCTCAACAAAACAAATGTTAAATTCTTG
GCTATTACGACAGACTGCCTTCAAATTTTAGCTTATGGCAACCAAGAAAG
CAAGCTCATCATACTGGCTAGTGGTGGACCCCAAGCTTTAGTAAATAAA
TGAGGACCTATACTTACGAAAAACTACTGTGGACCACAAGCAGAGTGCTG

AAGGTGCTATCTGTCTGCTCTAGTAATAAGCCGGCTATTGTAGAAGCTGG
TGGAATGCAAGCTTTAGGACTTCACCTGACAGATCCAAGTCAACGTCTTG
TTCAGAACTGTCTTTGGACTCTCAGGAATCTTTCAGATGCTGCAACTAAA
CAGGAAGGGATGGAAGGTCTCCTTGGGACTCTTGTTCAGCTTCTGGGTTC
AGATGATATAAATGTGGTCACCTGTGCAGCTGGAATTCTTTCTAACCTCA
CTTGCAATAATTATAAGAACAAGATGATGGTCTGCCAAGTGGGTGGTATA
GAGGCTCTTGTGCGTACTGTCCTTCGGGCTGGTGACAGGGAAGACATCAC
TGAGCCTGCCATCTGTGCTCTTCGTCATCTGACCAGCCGACACCAAGAAG
CAGAGATGGCCCAGAATGCAGTTCGCCTTCACTATGGACTACCAGTTGTG
GTTAAGCTCTTACACCCACCATCCCACTGGCCTCTGATAAAGGCTACTGT
TGGATTGATTCGAAATCTTGCCCTTTGTCCCGCAAATCATGCACCTTTGC
GTGAGCAGGGTGCCATTCCACGACTAGTTCAGTTGCTTGTTCGTGCACAT
CAGGATACCCAGCGCCGTACGTCCATGGGTGGGACACAGCAGCAATTTGT
GGAGGGGGTCCGCATGGAAGAAATAGTTGAAGGTTGTACCGGAGCCCTTC
ACATCCTAGCTCGGGATGTTCACAACCGAATTGTTATCAGAGGACTAAAT
ACCATTCCATTGTTTGTGCAGCTGCTTTATTCTCCCATTGAAAACATCCA
AAGAGTAGCTGCAGGGGTCCTCTGTGAACTTGCTCAGGACAAGGAAGCTG
CAGAAGCTATTGAAGCTGAGGGAGCCACAGCTCCTCTGACAGAGTTACTT
CACTCTAGGAATGAAGGTGTGGCGACATATGCAGCTGCTGTTTTGTTCCG
AATGTCTGAGGACAAGCCACAAGATTACAAGAAACGGCTTTCAGTTGAGC
TGACCAGCTCTCTCTTCAGAACAGAGCCAATGGCTTGGAATGAGACTGCT
GATCTTGGACTTGATATTGGTGCCCAGGGAGAACCCCTTGGATATCGCCA
GGATGATCCTAGCTATCGTTCTTTTCACTCTGGTGGATATGGCCAGGATG
CCTTGGGTATGGACCCCATGATGGAACATGAGATGGGTGGCCACCACCCT
GGTGCTGACTATCCAGTTGATGGGCTGCCAGATCTGGGGCATGCCCAGGA
CCTCATGGATGGGCTGCCTCCAGGTGACAGCAATCAGCTGGCCTGGTTTG
ATACTGACCTGTAAATCATCCTTTAGGAGTAACAATACAAATGGATTTTG
GGAGTGACTCAAGAAGTGAAGAATGCACAAGAATGGATCACAAGATGGAA
TTTATCAAACCCTAGCCTTGCTTGTTAAATTTTTTTTTTTTTTTTTAA
GAATATCTGTAATGGTACTGACTTTGCTTGCTTTGAAGTAGCTCTTTTTT
TTTTTTTTTTTTTTTTTGCAGTAACTGTTTTTAAGTCTCTCGTAGTG
TTAAGTTATAGTGAATACTGCTACAGCAATTTCTAATTTTTAAGAATTGA
GTAATGGTGTAGAACACTAATTCATAATCACTCTAATTAATTGTAATCTG
AATAAAGTGTAACAATTGTGTAGCCTTTTGTATAAAATAGACAAATAGA
AAATGGTCCAATTAGTTTCCTTTTTAATATGCTTAAAATAAGCAGGTGGA
TCTATTTCATGTTTTTGATCAAAAACTATTTGGGATATGTATGGGTAGGG
TAAATCAGTAAGAGGTGTTATTTGGAACCTTGTTTTGGACAGTTTACCAG
TTGCCTTTTATCCCAAAGTTGTTGTAACCTGCTGTGATACGATGCTTCAA
GAGAAAATGCGGTTATAAAAAATGGTTCAGAATTAAACTTTTAATTCATT
CGATTG

Human Wild-Type β-Catenin Sequence, Amino Acid Sequence NP_001895.1 (SEQ ID NO: 4; Translation of NM_001904.3, NM_001098209.1 or NM_001098210.1):

MATQADLMELDMAMEPDRKAAVSHWQQQSYLDSGIHSGATTTAPSLSGKG
NPEEEDVDTSQVLYEWEQGFSQSFTQEQVADIDGQYAMTRAQRVRAAMFP
ETLDEGMQIPSTQFDAAHPTNVQRLAEPSQMLKHAVVNLINYQDDAELAT
RAIPELTKLLNDEDQVVVNKAAVMVHQLSKKEASRHAIMRSPQMVSAIVR
TMQNTNDVETARCTAGTLHNLSHHREGLLAIFKSGGIPALVKMLGSPVDS
VLFYAITTLHNLLLHQEGAKMAVRLAGGLQKMVALLNKTNVKFLAITTDC
LQILAYGNQESKLIILASGGPQALVNIMRTYTYEKLLWTTSRVLKVLSVC
SSNKPAIVEAGGMQALGLHLTDPSQRLVQNCLWTLRNLSDAATKQEGMEG
LLGTLVQLLGSDDINVVTCAAGILSNLTCNNYKNKMMVCQVGGIEALVRT
VLRAGDREDITEPAICALRHLTSRHQEAEMAQNAVRLHYGLPVVVKLLHP
PSHWPLIKATVGLIRNLALCPANHAPLREQGAIPRLVQLLVRAHQDTQRR
TSMGGTQQQFVEGVRMEEIVEGCTGALHILARDVHNRIVIRGLNTIPLFV
QLLYSPIENIQRVAAGVLCELAQDKEAAEAIEAEGATAPLTELLHSRNEG
VATYAAAVLFRMSEDKPQDYKKRLSVELTSSLFRTEPMAWNETADLGLDI
GAQGEPLGYRQDDPSYRSFHSGGYGQDALGMDPMMEHEMGGHHPGADYPV
DGLPDLGHAQDLMDGLPPGDSNQLAWFDTDL

Mouse Wild-Type β-Catenin Sequence (SEQ ID NO: 5; *Mus musculus* Catenin (Cadherin Associated Protein), Beta 1 (Ctnnb1), Transcript Variant 1 in C57BL/6;
GenBank Accession No. NM_007614.3; Note: Mouse DsiRNA Target Sequence Positions Correspond to NM_007614.2 Below):

GCGCGGCGGAACGCTCCGCGCGGAGCGGCAGCGGCAGGATACACGGTGCC
GCGCCGCTTATAAATCGCTCCTTGTGCGGCGCCATCTTAAGCCCTCGCTC
GGTGGCGGCCGCGTCAGCTCGTGTCCTGTGAAGCCCGCGGCCCGGGGAGG
CGGAGACGGAGCACGGTGGGCGCCGAGCCGTCAGTGCAGGAGGCCGAGGC
CGAGCGGGCGGCCGCGAGTGAGCAGCGCGCGGGCCTGAGGGTACCTGAAG
CTCAGCGCACAGCTGCTGTGACACCGCTGCGTGGACAATGGCTACTCAAG
CTGACCTGATGGAGTTGGACATGGCCATGGAGCCGGACAGAAAAGCTGCT
GTCAGCCACTGGCAGCAGCAGTCTTACTTGGATTCTGGAATCCATTCTGG
TGCCACCACCACAGCTCCTTCCCTGAGTGGCAAGGGCAACCCTGAGGAAG
AAGATGTTGACACCTCCCAAGTCCTTTATGAATGGGAGCAAGGCTTTTCC
CAGTCCTTCACGCAAGAGCAAGTAGCTGATATTGACGGGCAGTATGCAAT
GACTAGGGCTCAGAGGGTCCGAGCTGCCATGTTCCCTGAGACGCTAGATG
AGGGCATGCAGATCCCATCCACGCAGTTTGACGCTGCTCATCCCACTAAT
GTCCAGCGCTTGGCTGAACCATCACAGATGTTGAAACATGCAGTTGTCAA
TTTGATTAACTATCAGGATGACGCGGAACTTGCCACACGTGCAATTCCTG
AGCTGACAAAACTGCTAAACGATGAGGACCAGGTGGTAGTTAATAAAGCT
GCTGTTATGGTCCATCAGCTTTCCAAAAAGGAAGCTTCCAGACATGCCAT

CATGCGCTCCCCTCAGATGGTGTCTGCCATTGTACGCACCATGCAGAATA
CAAATGATGTAGAGACAGCTCGTTGTACTGCTGGGACTCTGCACAACCTT
TCTCACCACCGCGAGGGCTTGCTGGCCATCTTTAAGTCTGGTGGCATCCC
AGCGCTGGTGAAAATGCTTGGGTCACCAGTGGATTCTGTACTGTTCTACG
CCATCACGACACTGCATAATCTCCTGCTCCATCAGGAAGGAGCTAAAATG
GCAGTGCGCCTAGCTGGTGGACTGCAGAAAATGGTTGCTTTGCTCAACAA
AACAAACGTGAAATTCTTGGCTATTACAACAGACTGCCTTCAGATCTTAG
CTTATGGCAATCAAGAGAGCAAGCTCATCATTCTGGCCAGTGGTGGACCC
CAAGCCTTAGTAAACATAATGAGGACCTACACTTATGAGAAGCTTCTGTG
GACCACAAGCAGAGTGCTGAAGGTGCTGTCTGTCTGCTCTAGCAACAAGC
CGGCCATTGTAGAAGCTGGTGGGATGCAGGCACTGGGGCTTCATCTGACA
GACCCAAGTCAGCGACTTGTTCAAAACTGTCTTTGGACTCTCAGAAACCT
TTCAGATGCAGCGACTAAGCAGGAAGGGATGGAAGGCCTCCTTGGGACTC
TAGTGCAGCTTCTGGGTTCCGATGATATAAATGTGGTCACCTGTGCAGCT
GGAATTCTCTCTAACCTCACTTGCAATAATTACAAAAACAAGATGATGGT
GTGCCAAGTGGGTGGCATAGAGGCTCTTGTACGCACCGTCCTTCGTGCTG
GTGACAGGGAAGACATCACTGAGCCTGCCATCTGTGCTCTTCGTCATCTG
ACCAGCCGGCATCAGGAAGCCGAGATGGCCCAGAATGCCGTTCGCCTTCA
TTATGGACTGCCTGTTGTGGTTAAACTCCTGCACCCACCATCCCACTGGC
CTCTGATAAAGGCAACTGTTGGATTGATTCGAAACCTTGCCCTTTGCCCA
GCAAATCATGCGCCTTTGCGGGAACAGGGTGCTATTCCACGACTAGTTCA
GCTGCTTGTACGAGCACATCAGGACACCCAACGGCGCACCTCCATGGGTG
GAACGCAGCAGCAGTTTGTGGAGGGCGTGCGCATGGAGGAGATAGTAGAA
GGGTGTACTGGAGCTCTCCACATCCTTGCTCGGGACGTTCACAACCGGAT
TGTAATCCGAGGACTCAATACCATTCCATTGTTTGTGCAGTTGCTTTATT
CTCCCATTGAAAATATCCAAAGAGTAGCTGCAGGGGTCCTCTGTGAACTT
GCTCAGGACAAGGAGGCTGCAGAGGCCATTGAAGCTGAGGGAGCCACAGC
TCCCCTGACAGAGTTACTCCACTCCAGGAATGAAGGCGTGGCAACATACG
CAGCTGCTGTCCTATTCCGAATGTCTGAGGACAAGCCACAGGATTACAAG
AAGCGGCTTTCAGTCGAGCTGACCAGTTCCCTCTTCAGGACAGAGCCAAT
GGCTTGGAATGAGACTGCAGATCTTGGACTGGACATTGGTGCCCAGGGAG
AAGCCCTTGGATATCGCCAGGATGATCCCAGCTACCGTTCTTTTCACTCT
GGTGGATACGGCCAGGATGCCTTGGGGATGGACCCTATGATGGAGCATGA
GATGGGTGGCCACCACCCTGGTGCTGACTATCCAGTTGATGGGCTGCCTG
ATCTGGGACACGCCCAGGACCTCATGGATGGGCTGCCCCAGGTGATAGC
AATCAGCTGGCCTGGTTTGATACTGACCTGTAAATCGTCCTTTAGGTAAG
AAAGCTTATAAAAGCCAGTGTGGGTGAATACTTTACTCTGCCTGCAGAAC
TCCAGAAAGACTTGGTAGGGTGGGAATGGTTTTAGGCCTGTTTGTAAATC
TGCCACCAAACAGATACATACCTTGGAAGGAGATGTTCATGTGTGGAAGT
TTCTCACGTTGATGTTTTGCCACAGCTTTTGCAGCGTTATACTCAGATG
AGTAACATTTGCTGTTTTCAACATTAATAGCAGCCTTTCTCTCTATACAG

CTGTAGTGTCTGAACGTGCATTGTGATTGGCCTGTAGAGTTGCTGAGAGG

GCTCGAGGGGTGGGCTGGTATCTCAGAAAGTGCCTGACACACTAACCAAG

CTGAGTTTCCTATGGGAACAGTCGAAGTACGCTTTTTGTTCTGGTCCTTT

TTGGTCGAGGAGTAACAATACAAATGGATTTGGGGAGTGACTCACGCAGT

GAAGAATGCACACGAATGGATCACAAGATGGCGTTATCAAACCCTAGCCT

TGCTTGTTCTTTGTTTTAATATCTGTAGTGGTGCTGACTTTGCTTGCTTT

TATTTTTTGCAGTAACTGTTAGTTTTTAAGTAGTGTTATGTTCTAGTGAA

CCTGCTACAGCAATTTCTGATTTCTAAGAACCGAGTAATGGTGTAGAACA

CTAATTCATAATCACGCTAATTGTAATCTGGAGACGTGTAACATTGTGTA

GCCTTTTGTATAAATAGACAGATAGAAATGGTCCGATTAGTTTCCTTTTT

AATATGCTTAAAATAAGCAGGTGGATCTATTTCATGTTTTTGAACAAAAA

CTTTATCGGGGATACGTGCGGTAGGGTAAATCAGTAAGAGGTGTTATTTG

AGCCTTGTTTTGGACAGTATACCAGTTGCCTTTTATCCCAAAGTTGTTGT

AACCTGCTGTGATACAATGCTTCAACAGATGCGGTTATAGAAATGGTTCA

GAATTAAACTTTTAATTCATTCAAAAAAAAAAAAAAAAA

Mouse Wild-Type β-Catenin Sequence (SEQ ID NO: 6; *Mus musculus* Catenin (Cadherin Associated Protein), Beta 1 (Ctnnb1) in C57BL/6; GenBank Accession No. NM_007614.2; Mouse DsiRNA Target Sequence Positions Correspond to NM_007614.2):

GCGGCGCCATCTTAAGCCCTCGCTCGGTGGCGGCCGCGTCAGCTCGTGTC

CTGTGAAGCCCGCGGCCCGGGGAGGCGGAGACGGAGCACGGTGGGCGCCG

AGCCGTCAGTGCAGGAGGCCGAGGCCGAGCGGGCGGCCGCGAGTGAGCAG

CGCGCGGGCCTGAGGGTACCTGAAGCTCAGCGCACAGCTGCTGTGACACC

GCTGCGTGGACAATGGCTACTCAAGCTGACCTGATGGAGTTGGACATGGC

CATGGAGCCGGACAGAAAAGCTGCTGTCAGCCACTGGCAGCAGCAGTCTT

ACTTGGATTCTGGAATCCATTCTGGTGCCACCACCACAGCTCCTTCCCTG

AGTGGCAAGGGCAACCCTGAGGAAGAAGATGTTGACACCTCCCAAGTCCT

TTATGAATGGGAGCAAGGCTTTTCCCAGTCCTTCACGCAAGAGCAAGTAG

CTGATATTGACGGGCAGTATGCAATGACTAGGGCTCAGAGGGTCCGAGCT

GCCATGTTCCCTGAGACGCTAGATGAGGGCATGCAGATCCCATCCACGCA

GTTTGACGCTGCTCATCCCACTAATGTCCAGCGCTTGGCTGAACCATCAC

AGATGTTGAAACATGCAGTTGTCAATTTGATTAACTATCAGGATGACGCG

GAACTTGCCACACGTGCAATTCCTGAGCTGACAAAACTGCTAAACGATGA

GGACCAGGTGGTAGTTAATAAAGCTGCTGTTATGGTCCATCAGCTTTCCA

AAAAGGAAGCTTCCAGACATGCCATCATGCGCTCCCCTCAGATGGTGTCT

GCCATTGTACGCACCATGCAGAATACAAATGATGTAGAGACAGCTCGTTG

TACTGCTGGGACTCTGCACAACCTTTCTCACCACCGCGAGGGCTTGCTGG

CCATCTTTAAGTCTGGTGGCATCCCAGCGCTGGTGAAAATGCTTGGGTCA

CCAGTGGATTCTGTACTGTTCTACGCCATCACGACACTGCATAATCTCCT

GCTCCATCAGGAAGGAGCTAAAATGGCAGTGCGCCTAGCTGGTGGACTGC

AGAAAATGGTTGCTTTGCTCAACAAAACAAACGTGAAATTCTTGGCTATT

ACAACAGACTGCCTTCAGATCTTAGCTTATGGCAATCAAGAGAGCAAGCT

CATCATTCTGGCCAGTGGTGGACCCCAAGCCTTAGTAAACATAATGAGGA

CCTACACTTATGAGAAGCTTCTGTGGACCACAAGCAGAGTGCTGAAGGTG

CTGTCTGTCTGCTCTAGCAACAAGCCGGCCATTGTAGAAGCTGGTGGGAT

GCAGGCACTGGGGCTTCATCTGACAGACCCAAGTCAGCGACTTGTTCAAA

ACTGTCTTTGGACTCTCAGAAACCTTTCAGATGCAGCGACTAAGCAGGAA

GGGATGGAAGGCCTCCTTGGGACTCTAGTGCAGCTTCTGGGTTCCGATGA

TATAAATGTGGTCACCTGTGCAGCTGGAATTCTCTCTAACCTCACTTGCA

ATAATTACAAAAACAAGATGATGGTGTGCCAAGTGGGTGGCATAGAGGCT

CTTGTACGCACCGTCCTTCGTGCTGGTGACAGGGAAGACATCACTGAGCC

TGCCATCTGTGCTCTTCGTCATCTGACCAGCCGGCATCAGGAAGCCGAGA

TGGCCCAGAATGCCGTTCGCCTTCATTATGGACTGCCTGTTGTGGTTAAA

CTCCTGCACCCACCATCCCACTGGCCTCTGATAAAGGCAACTGTTGGATT

GATTCGAAACCTTGCCCTTTGCCCAGCAAATCATGCGCCTTTGCGGGAAC

AGGGTGCTATTCCACGACTAGTTCAGCTGCTTGTACGAGCACATCAGGAC

ACCCAACGGCGCACCTCCATGGGTGGAACGCAGCAGCAGTTTGTGGAGGG

CGTGCGCATGGAGGAGATAGTAGAAGGGTGTACTGGAGCTCTCCACATCC

TTGCTCGGGACGTTCACAACCGGATTGTAATCCGAGGACTCAATACCATT

CCATTGTTTGTGCAGTTGCTTTATTCTCCCATTGAAAATATCCAAAGAGT

AGCTGCAGGGGTCCTCTGTGAACTTGCTCAGGACAAGGAGGCTGCAGAGG

CCATTGAAGCTGAGGGAGCCACAGCTCCCCTGACAGAGTTACTCCACTCC

AGGAATGAAGGCGTGGCAACATACGCAGCTGCTGTCCTATTCCGAATGTC

TGAGGACAAGCCACAGGATTACAAGAAGCGGCTTTCAGTCGAGCTGACCA

GTTCCCTCTTCAGGACAGAGCCAATGGCTTGGAATGAGACTGCAGATCTT

GGACTGGACATTGGTGCCCAGGGAGAAGCCCTTGGATATCGCCAGGATGA

TCCCAGCTACCGTTCTTTTCACTCTGGTGGATACGCCAGGATGCCTTGG

GGATGGACCCTATGATGGAGCATGAGATGGGTGGCCACCACCCTGGTGCT

GACTATCCAGTTGATGGGCTGCCTGATCTGGGACACGCCCAGGACCTCAT

GGATGGGCTGCCCCAGGTGATAGCAATCAGCTGGCCTGGTTTGATACTG

ACCTGTAAATCGTCCTTTAGGTAAGAAAGCTTATAAAAGCCAGTGTGGGT

GAATACTTTACTCTGCCTGCAGAACTCCAGAAAGACTTGGTAGGGTGGGA

ATGGTTTTAGGCCTGTTTGTAAATCTGCCACCAAACAGATACATACCTTG

GAAGGAGATGTTCATGTGTGGAAGTTTCTCACGTTGATGTTTTTGCCACA

GCTTTTGCAGCGTTATACTCAGATGAGTAACATTTGCTGTTTTCAACATT

AATAGCAGCCTTTCTCTCTATACAGCTGTAGTGTCTGAACGTGCATTGTG

ATTGGCCTGTAGAGTTGCTGAGAGGGCTCGAGGGGTGGGCTGGTATCTCA

GAAAGTGCCTGACACACTAACCAAGCTGAGTTTCCTATGGGAACAGTCGA

AGTACGCTTTTGTTCTGGTCCTTTTGGTCGAGGAGTAACAATACAAAT

GGATTTGGGGAGTGACTCACGCAGTGAAGAATGCACACGAATGGATCACA

-continued

```
AGATGGCGTTATCAAACCCTAGCCTTGCTTGTTCTTTGTTTTAATATCTG

TAGTGGTGCTGACTTTGCTTGCTTTTATTTTTTGCAGTAACTGTTAGTTT

TTAAGTAGTGTTATGTTCTAGTGAACCTGCTACAGCAATTTCTGATTTCT

AAGAACCGAGTAATGGTGTAGAACACTAATTCATAATCACGCTAATTGTA

ATCTGGAGACGTGTAACATTGTGTAGCCTTTTGTATAAATAGACAGATAG

AAATGGTCCGATTAGTTTCCTTTTTAATATGCTTAAAATAAGCAGGTGGA

TCTATTTCATGTTTTTGAACAAAAACTTTATCGGGGATACGTGCGGTAGG

GTAAATCAGTAAGAGGTGTTATTTGAGCCTTGTTTTGGACAGTATACCAG

TTGCCTTTTATCCCAAAGTTGTTGTAACCTGCTGTGATACAATGCTTCAA

CAGATGCGGTTATAGAAATGGTTCAGAATTAAACTTTTAATTCATTCAAA

AAAAAAAAAAAAAAA
```

Mouse Wild-Type β-Catenin Amino Acid Sequence NP_031640.1 (SEQ ID NO: 7; Translation of NM_007614.2 or NM_007614.3):

```
MATQADLMELDMAMEPDRKAAVSHWQQQSYLDSGIHSGATTTAPSLSGKG

NPEEEDVDTSQVLYEWEQGFSQSFTQEQVADIDGQYAMTRAQRVRAAMFP

ETLDEGMQIPSTQFDAAHPTNVQRLAEPSQMLKHAVVNLINYQDDAELAT

RAIPELTKLLNDEDQVVVNKAAVMVHQLSKKEASRHAIMRSPQMVSAIVR

TMQNTNDVETARCTAGTLHNLSHHREGLLAIFKSGGIPALVKMLGSPVDS

VLFYAITTLHNLLLHQEGAKMAVRLAGGLQKMVALLNKTNVKFLAITTDC

LQILAYGNQESKLIILASGGPQALVNIMRTYTYEKLLWTTSRVLKVLSVC

SSNKPAIVEAGGMQALGLHLTDPSQRLVQNCLWTLRNLSDAATKQEGMEG

LLGTLVQLLGSDDINVVTCAAGILSNLTCNNYKNKMMVCQVGGIEALVRT

VLRAGDREDITEPAICALRHLTSRHQEAEMAQNAVRLHYGLPVVVKLLHP

PSHWPLIKATVGLIRNLALCPANHAPLREQGAIPRLVQLLVRAHQDTQRR

TSMGGTQQQFVEGVRMEEIVEGCTGALHILARDVHNRIVIRGLNTIPLFV

QLLYSPIENIQRVAAGVLCELAQDKEAAEAIEAEGATAPLTELLHSRNEG

VATYAAAVLFRMSEDKPQDYKKRLSVELTSSLFRTEPMAWNETADLGLDI

GAQGEALGYRQDDPSYRSFHSGGYGQDALGMDPMMEHEMGGHHPGADYPV

DGLPDLGHAQDLMDGLPPGDSNQLAWFDTDL
```

β-catenin is a protein that in humans is encoded by the CTNNB1 gene (Kraus et al. Genomics 23: 272-4)—accordingly, reference herein to the human "β-catenin gene" specifically refers to the CTNNB1 gene. β-catenin is a subunit of the cadherin protein complex and has been demonstrated to be an integral component in the Wnt signaling pathway. Drosophila armadillo is a β-catenin homolog, rendering β-catenin a member of the armadillo family.

As a member of the armadillo family, the β-catenin protein contains multiple copies of the so-called armadillo repeat domain, which is a domain specialized for protein-protein binding. When β-catenin is not associated with cadherins and alpha-catenin, it can interact with other proteins such as ICAT and APC.

Functionally, cadherin complexes constitute adherens junctions (Ajs), which are required for creation and maintenance of epithelial cell layers via regulation of cell growth and adhesion between neighboring cells. β-catenin also anchors the actin cytoskeleton and is modeled to be responsible for transmitting contact inhibition signals that cause cells to stop dividing once an epithelial sheet is complete (EntrezGene: catenin). β-catenin has been shown to play a significant role in liver biology, e.g., liver development (both embryonic and postnatal), liver regeneration following partial hepatectomy, HGF-induced hepatomegaly, liver zonation, and pathogenesis of liver cancer (Thompson and Monga. Hepatology 45: 1298-1305).

Without being bound by theory, β-catenin is modeled to function in the Wnt signaling pathway in the following manner. When Wnt is not present, GSK-3 (a kinase) constitutively phosphorylates the β-catenin protein. β-catenin is associated with axin (scaffolding protein) complexed with GSK3 and APC (adenomatosis polyposis coli). The creation of this complex acts to substantially increase the phosphorylation of β-catenin by facilitating the action of GSK3. When β-catenin is phosphorylated, it is degraded and, thus, β-catenin does not build up in the cell to a significant level. When Wnt binds to frizzled (Fz), its receptor, disheveled (Dsh), is recruited to the membrane. GSK3 is inhibited by the activation of Dsh by Fz. Because of this, β-catenin is permitted to build up in the cytosol and can be subsequently translocated into the nucleus, where it performs a variety of functions. β-catenin can act in conjunction with TCF and LEF to activate specific target genes involved in different processes.

β-catenin is an oncogene. An increase in β-catenin production has been noted in subjects with basal cell carcinoma, and such increase leads to the increase in proliferation of related tumors (Saldanha et al. Br. J Dermatol. 151: 157-64). Mutations in β-catenin are a cause of colorectal cancer (CRC), pilomatrixoma (PTR), medulloblastoma (MDB), and ovarian cancer. β-catenin also binds to the product of the APC gene, which is mutated in adenomatous polyposis of the colon.

The ability of β-catenin to bind to other proteins is regulated by tyrosine kinases (Lilien and Balsamo Curr. Opin. Cell Biol. 17: 459-65) and serine kinases such as GSK-3 (Castellone et al. Science 310: 1504-10). When β-catenin is not assembled in complexes with cadherins, it can form a complex with axin. While bound to axin, β-catenin can be phosphorylated by GSK-3, which creates a signal for the rapid ubiquitin-dependent degradation of β-catenin by proteosomes. Various signals such as the Wnt signalling pathway can inhibit GSK-3-mediated phosphorylation of β-catenin (Liu et al. Curr. Biol. 15: 1989-97), allowing β-catenin to go to the cell nucleus, interact with transcription factors, and regulate gene transcription.

β-catenin can be phosphorylated by other kinases such as protein kinase A (PKA). Phosphorylation of β-catenin by PKA has been associated with reduced degradation of β-catenin, increased levels of β-catenin in the nucleus and interaction of β-catenin with TCF family transcription factors to regulate gene expression (Hino et al. Mol. Cell. Biol. 25: 9063-72).

β-catenin has also been shown to interact with the following proteins: Androgen receptor, APC, AXIN1, CBY1, CDH1, CDH2, CDH3, CDK5R1, CHUK, CTNNA1, CTNND1, EGFR, FHL2, GSK3B, HER2/neu, HNF4A, IKK2, LEF1, MAGI1, MUC1, NR5A1, PCAF, PHF17, Plakoglobin, PTPN14, PTPRF, PRPRK, PSEN1, RuvB-like 1, SMAD7, SLC9A3R1, SMARCA4, USP9X and VE-cadherin (http://en.wikipedia.org/wiki/Beta-catenin).

In Vitro Assay to Assess DsiRNA β-Catenin Inhibitory Activity

An in vitro assay that recapitulates RNAi in a cell-free system can be used to evaluate DsiRNA constructs targeting β-catenin RNA sequence(s), and thus to assess β-cateninspecific gene inhibitory activity (also referred to herein as (β-catenin inhibitory activity) of a DsiRNA. The assay comprises the system described by Tuschl et al., 1999, Genes and Development, 13, 3191-3197 and Zamore et al., 2000, Cell, 101, 25-33 adapted for use with DsiRNA agents directed against β-catenin RNA. A *Drosophila* extract derived from syncytial blastoderm is used to reconstitute RNAi activity in vitro. Target RNA is generated via in vitro transcription from a selected β-catenin expressing plasmid using T7 RNA polymerase or via chemical synthesis. Sense and antisense DsiRNA strands (for example 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol] lysis buffer containing DsiRNA (10 nM final concentration). The reaction mixture also contains 10 mM creatine phosphate, 10 ug/ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and preincubated at 25° C. for 10 minutes before adding RNA, then incubated at 25° C. for an additional 60 minutes. Reactions are quenched with 4 volumes of 1.25× Passive Lysis Buffer (Promega). Target RNA cleavage is assayed by RT-PCR analysis or other methods known in the art and are compared to control reactions in which DsiRNA is omitted from the reaction.

Alternately, internally-labeled target RNA for the assay is prepared by in vitro transcription in the presence of [alpha-$^{32}$P] CTP, passed over a G50 Sephadex column by spin chromatography and used as target RNA without further purification. Optionally, target RNA is 5'-$^{32}$P-end labeled using T4 polynucleotide kinase enzyme. Assays are performed as described above and target RNA and the specific RNA cleavage products generated by RNAi are visualized on an autoradiograph of a gel. The percentage of cleavage is determined by PHOSPHOR IMAGER® (autoradiography) quantitation of bands representing intact control RNA or RNA from control reactions without DsiRNA and the cleavage products generated by the assay.

In one embodiment, this assay is used to determine target sites in the β-catenin RNA target for DsiRNA mediated RNAi cleavage, wherein a plurality of DsiRNA constructs are screened for RNAi mediated cleavage of the β-catenin RNA target, for example, by analyzing the assay reaction by electrophoresis of labeled target RNA, or by northern blotting, as well as by other methodology well known in the art.

In certain embodiments, a DsiRNA of the invention is deemed to possess β-catenin inhibitory activity if, e.g., a 50% reduction in β-catenin RNA levels is observed in a system, cell, tissue or organism, relative to a suitable control. Additional metes and bounds for determination of β-catenin inhibitory activity of a DsiRNA of the invention are described supra.

Conjugation and Delivery of Anti-β-Catenin DsiRNA Agents

In certain embodiments the present invention relates to a method for treating a subject having a β-catenin-associated disease or disorder, or at risk of developing a β-catenin-associated disease or disorder. In such embodiments, the DsiRNA can act as novel therapeutic agents for controlling the β-catenin-associated disease or disorder. The method comprises administering a pharmaceutical composition of the invention to the patient (e.g., human), such that the expression, level and/or activity of a β-catenin RNA is reduced. The expression, level and/or activity of a polypeptide encoded by a β-catenin RNA might also be reduced by a DsiRNA of the instant invention, even where said DsiRNA is directed against a non-coding region of the β-catenin transcript (e.g., a targeted 5' UTR or 3' UTR sequence). Because of their high specificity, the DsiRNAs of the present invention can specifically target β-catenin sequences of cells and tissues, optionally in an allele-specific manner where polymorphic alleles exist within an individual and/or population.

In the treatment of a β-catenin-associated disease or disorder, the DsiRNA can be brought into contact with the cells or tissue of a subject, e.g., the cells or tissue of a subject exhibiting disregulation of β-catenin and/or otherwise targeted for reduction of β-catenin levels. For example, DsiRNA substantially identical to all or part of a β-catenin RNA sequence, may be brought into contact with or introduced into such a cell, either in vivo or in vitro. Similarly, DsiRNA substantially identical to all or part of a β-catenin RNA sequence may administered directly to a subject having or at risk of developing a β-catenin-associated disease or disorder.

Therapeutic use of the DsiRNA agents of the instant invention can involve use of formulations of DsiRNA agents comprising multiple different DsiRNA agent sequences. For example, two or more, three or more, four or more, five or more, etc. of the presently described agents can be combined to produce a formulation that, e.g., targets multiple different regions of the β-catenin RNA, or that not only target β-catenin RNA but also target, e.g., cellular target genes associated with a β-catenin-associated disease or disorder. A DsiRNA agent of the instant invention may also be constructed such that either strand of the DsiRNA agent independently targets two or more regions of β-catenin RNA, or such that one of the strands of the DsiRNA agent targets a cellular target gene of β-catenin known in the art.

Use of multifunctional DsiRNA molecules that target more then one region of a target nucleic acid molecule can also provide potent inhibition of β-catenin RNA levels and expression. For example, a single multifunctional DsiRNA construct of the invention can target both the βc-1569 and βc-1683 sites simultaneously; additionally and/or alternatively, single or multifunctional agents of the invention can be designed to selectively target one splice variant of β-catenin over another.

Thus, the DsiRNA agents of the instant invention, individually, or in combination or in conjunction with other drugs, can be used to treat, inhibit, reduce, or prevent a β-catenin-associated disease or disorder. For example, the DsiRNA molecules can be administered to a subject or can be administered to other appropriate cells evident to those skilled in the art, individually or in combination with one or more drugs under conditions suitable for the treatment.

The DsiRNA molecules also can be used in combination with other known treatments to treat, inhibit, reduce, or prevent a β-catenin-associated disease or disorder in a subject or organism. For example, the described molecules could be used in combination with one or more known compounds, treatments, or procedures to treat, inhibit, reduce, or prevent a β-catenin-associated disease or disorder in a subject or organism as are known in the art.

A DsiRNA agent of the invention can be conjugated (e.g., at its 5' or 3' terminus of its sense or antisense strand) or unconjugated to another moiety (e.g. a non-nucleic acid moiety such as a peptide), an organic compound (e.g., a dye, cholesterol, or the like). Modifying DsiRNA agents in this way may improve cellular uptake or enhance cellular targeting activities of the resulting DsiRNA agent derivative as compared to the corresponding unconjugated DsiRNA agent, are useful for tracing the DsiRNA agent derivative in the cell, or improve the stability of the DsiRNA agent derivative compared to the corresponding unconjugated DsiRNA agent.

Methods of Introducing Nucleic Acids, Vectors, and Host Cells

DsiRNA agents of the invention may be directly introduced into a cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The DsiRNA agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities enhance nucleic acid uptake by the cell or other-wise increase inhibition of the target β-catenin RNA.

A cell having a target β-catenin RNA may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target β-catenin RNA sequence and the dose of DsiRNA agent material delivered, this process may provide partial or complete loss of function for the β-catenin RNA. A reduction or loss of RNA levels or expression (either β-catenin RNA expression or encoded polypeptide expression) in at least 50%, 60%, 70%, 80%, 90%, 95% or 99% or more of targeted cells is exemplary Inhibition of β-catenin RNA levels or expression refers to the absence (or observable decrease) in the level of β-catenin RNA or β-catenin RNA-encoded protein. Specificity refers to the ability to inhibit the β-catenin RNA without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). Inhibition of target β-catenin RNA sequence(s) by the DsiRNA agents of the invention also can be measured based upon the effect of administration of such DsiRNA agents upon development/progression of a β-catenin-associated disease or disorder, e.g., tumor formation, growth, metastasis, etc., either in vivo or in vitro. Treatment and/or reductions in tumor or cancer cell levels can include halting or reduction of growth of tumor or cancer cell levels or reductions of, e.g., 10%, 20%, 30%, 40%, 50%, 60%, 70%, 80%, 90%, 95% or 99% or more, and can also be measured in logarithmic terms, e.g., 10-fold, 100-fold, 1000-fold, $10^5$-fold, $10^6$-fold, $10^7$-fold reduction in cancer cell levels could be achieved via administration of the DsiRNA agents of the invention to cells, a tissue, or a subject.

For RNA-mediated inhibition in a cell line or whole organism, expression a reporter or drug resistance gene whose protein product is easily assayed can be measured. Such reporter genes include acetohydroxyacid synthase (AHAS), alkaline phosphatase (AP), β galactosidase (LacZ), β glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention.

Lower doses of injected material and longer times after administration of RNA silencing agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target β-catenin RNA or translation of target protein. As an example, the efficiency of inhibition may be determined by assessing the amount of gene product in the cell; RNA may be detected with a hybridization probe having a nucleotide sequence outside the region used for the inhibitory DsiRNA, or translated polypeptide may be detected with an antibody raised against the polypeptide sequence of that region.

The DsiRNA agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

Pharmaceutical Compositions

In certain embodiments, the present invention provides for a pharmaceutical composition comprising the DsiRNA agent of the present invention. The DsiRNA agent sample can be suitably formulated and introduced into the environment of the cell by any means that allows for a sufficient portion of the sample to enter the cell to induce gene silencing, if it is to occur. Many formulations for dsRNA are known in the art and can be used so long as the dsRNA gains entry to the target cells so that it can act. See, e.g., U.S. published patent application Nos. 2004/0203145 A1 and 2005/0054598 A1. For example, the DsiRNA agent of the instant invention can be formulated in buffer solutions such as phosphate buffered saline solutions, liposomes, micellar structures, and capsids. Formulations of DsiRNA agent with cationic lipids can be used to facilitate transfection of the DsiRNA agent into cells. For example, cationic lipids, such as lipofectin (U.S. Pat. No. 5,705,188), cationic glycerol derivatives, and polycationic molecules, such as polylysine (published PCT International Application WO 97/30731), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; cHeLating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The compounds can also be administered by a method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a nucleic acid molecule (i.e., an effective dosage) depends on the nucleic acid selected. For instance, if a plasmid encoding a DsiRNA agent is selected, single dose amounts in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The expression constructs may be constructs suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, e.g., Tuschl (2002, *Nature Biotechnol* 20: 500-505).

It can be appreciated that the method of introducing DsiRNA agents into the environment of the cell will depend on the type of cell and the make up of its environment. For example, when the cells are found within a liquid, one preferable formulation is with a lipid formulation such as in lipofectamine and the DsiRNA agents can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate DsiRNA agents in a buffer or saline solution and directly inject the formulated DsiRNA agents into cells, as in studies with oocytes. The direct injection of DsiRNA agents duplexes may also be done. For suitable methods of introducing dsRNA (e.g., DsiRNA agents), see U.S. published patent application No. 2004/0203145 A1.

Suitable amounts of a DsiRNA agent must be introduced and these amounts can be empirically determined using standard methods. Typically, effective concentrations of individual DsiRNA agent species in the environment of a cell will be 50 nanomolar or less, 10 nanomolar or less, or compositions in which concentrations of 1 nanomolar or less can be used. In another embodiment, methods utilizing a concentration of 200 picomolar or less, 100 picomolar or less, 50 picomolar or less, 20 picomolar or less, and even a concentration of 10 picomolar or less, 5 picomolar or less, 2 picomolar or less or 1 picomolar or less can be used in many circumstances.

The method can be carried out by addition of the DsiRNA agent compositions to an extracellular matrix in which cells can live provided that the DsiRNA agent composition is formulated so that a sufficient amount of the DsiRNA agent can enter the cell to exert its effect. For example, the method is amenable for use with cells present in a liquid such as a liquid culture or cell growth media, in tissue explants, or in whole organisms, including animals, such as mammals and especially humans.

The level or activity of a β-catenin RNA can be determined by a suitable method now known in the art or that is later developed. It can be appreciated that the method used to measure a target RNA and/or the "expression" of a target gene can depend upon the nature of the target gene and its encoded RNA. For example, where the target β-catenin RNA sequence encodes a protein, the term "expression" can refer to a protein or the β-catenin RNA/transcript derived from the β-catenin gene (either genomic or of exogenous origin). In such instances the expression of the target β-catenin RNA can be determined by measuring the amount of β-catenin RNA/transcript directly or by measuring the amount of β-catenin protein. Protein can be measured in protein assays such as by staining or immunoblotting or, if the protein catalyzes a reaction that can be measured, by measuring reaction rates. All such methods are known in the art and can be used. Where target β-catenin RNA levels are to be measured, art-recognized methods for detecting RNA levels can be used (e.g., RT-PCR, Northern Blotting, etc.). In targeting β-catenin RNAs with the DsiRNA agents of the instant invention, it is also anticipated that measurement of the efficacy of a DsiRNA agent in reducing levels of β-catenin RNA or protein in a subject, tissue, in cells, either in vitro or in vivo, or in cell extracts can also be used to determine the extent of reduction of β-catenin-associated phenotypes (e.g., disease or disorders, e.g., cancer or tumor formation, growth, metastasis, spread, etc.). The above measurements can be made on cells, cell extracts, tissues, tissue extracts or other suitable source material.

The determination of whether the expression of a β-catenin RNA has been "reduced" can be by a suitable method that can reliably detect changes in RNA levels. Typically, the determination is made by introducing into the environment of a cell undigested DsiRNA such that at least a portion of that DsiRNA agent enters the cytoplasm, and then measuring the level of the target RNA. The same measurement is made on identical untreated cells and the results obtained from each measurement are compared.

The DsiRNA agent can be formulated as a pharmaceutical composition which comprises a pharmacologically effective amount of a DsiRNA agent and pharmaceutically acceptable carrier. A pharmacologically or therapeutically effective amount refers to that amount of a DsiRNA agent effective to produce the intended pharmacological, therapeutic or preventive result. The phrases "pharmacologically effective amount" and "therapeutically effective amount" or simply "effective amount" refer to that amount of an RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

Suitably formulated pharmaceutical compositions of this invention can be administered by means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general, a suitable dosage unit of dsRNA will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the dsRNA can be administered once daily. However, the therapeutic agent may also be dosed in dosage units containing two, three, four, five, six or more sub-doses administered at appropriate intervals throughout the day. In that case, the dsRNA contained in each sub-dose must be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. In this embodiment, the dosage unit contains a corresponding multiple of the daily dose. Regardless of the formulation, the pharmaceutical composition must contain dsRNA in a quantity sufficient to inhibit expression of the target gene in the animal or human being treated. The composition can be compounded in such a way that the sum of the multiple units of dsRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

The pharmaceutical compositions can be included in a kit, container, pack, or dispenser together with instructions for administration.

Methods of Treatment

The present invention provides for both prophylactic and therapeutic methods of treating a subject at risk of (or susceptible to) a disease or disorder caused, in whole or in part, by β-catenin (e.g., misregulation and/or elevation of β-catenin transcript and/or (β-catenin protein levels), or treatable via selective targeting of β-catenin.

"Treatment", or "treating" as used herein, is defined as the application or administration of a therapeutic agent (e.g., a DsiRNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above (including, e.g., prevention of the commencement of transforming events within a subject via inhibition of (β-catenin expression), by administering to the subject a therapeutic agent (e.g., a DsiRNA agent or vector or transgene encoding same). Subjects at risk for the disease can be identified by, for example, one or a combination of diagnostic or prognostic assays as described herein. Administration of a prophylactic agent can occur prior to the detection of, e.g., cancer in a subject, or the manifestation of symptoms characteristic of the disease or disorder, such that the disease or disorder is prevented or, alternatively, delayed in its progression.

Another aspect of the invention pertains to methods of treating subjects therapeutically, i.e., altering the onset of symptoms of the disease or disorder. These methods can be performed in vitro (e.g., by culturing the cell with the DsiRNA agent) or, alternatively, in vivo (e.g., by administering the DsiRNA agent to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target β-catenin RNA molecules of the present invention or target β-catenin RNA modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in a selected animal model. For example, a DsiRNA agent (or expression vector or transgene encoding same) as described herein can be used in an animal model to determine the efficacy, toxicity, or side effects of treatment with said agent. Alternatively, an agent (e.g., a therapeutic agent) can be used in an animal model to determine the mechanism of action of such an agent.

Models Useful to Evaluate the Down-Regulation of β-Catenin mRNA Levels and Expression Cell Culture The DsiRNA agents of the invention can be tested for cleavage activity in vivo, for example, using the following procedure. The nucleotide sequences within the β-catenin cDNA targeted by the DsiRNA agents of the invention are shown in the above β-catenin sequences.

The DsiRNA reagents of the invention can be tested in cell culture using HeLa or other mammalian cells to determine the extent of β-catenin RNA and β-catenin protein inhibition. DsiRNA reagents (e.g., see FIG. 1, and above-recited structures) are selected against the β-catenin target as described herein. β-catenin RNA inhibition is measured after delivery of these reagents by a suitable transfection agent to, for example, cultured HeLa cells or other transformed or non-transformed mammalian cells in culture. Relative amounts of target β-catenin RNA are measured versus actin or other appropriate control using real-time PCR monitoring of amplification (e.g., ABI 7700 TAQMAN®). A comparison is made to a mixture of oligonucleotide sequences made to unrelated targets or to a randomized DsiRNA control with the same overall length and chemistry, but randomly substituted at each position, or simply to appropriate vehicle-treated or untreated controls. Primary and secondary lead reagents are chosen for the target and optimization performed. After an optimal transfection agent concentration is chosen, a RNA time-course of inhibition is performed with the lead DsiRNA molecule.

TAQMAN® (Real-Time PCR Monitoring of Amplification) and Lightcycler Quantification of mRNA Total RNA is prepared from cells following DsiRNA delivery, for example, using Ambion Rnaqueous 4-PCR purification kit for large scale extractions, or Promega SV96 for 96-well assays. For Taqman analysis, dual-labeled probes are synthesized with, for example, the reporter dyes FAM or VIC covalently linked at the 5'-end and the quencher dye TAMARA conjugated to the 3'-end. PCR amplifications are performed on, for example, an ABI PRISM 7700 Sequence detector using 50 uL reactions consisting of 10 uL total RNA, 100 nM forward primer, 100 mM reverse primer, 100 nM probe, 1× TaqMan PCR reaction buffer (PE-Applied Biosystems), 5.5 mM MgCl2, 100 uM each dATP, dCTP, dGTP and dTTP, 0.2U RNase Inhibitor (Promega), 0.025U AmpliTaq Gold (PE-Applied Biosystems) and 0.2U M-MLV Reverse Transcriptase (Promega). The thermal cycling conditions can consist of 30 minutes at 48° C., 10 minutes at 95° C., followed by 40 cycles of 15 seconds at 95° C. and 1 minute at 60° C. Quantitation of target β-catenin mRNA level is determined relative to standards generated from serially diluted total cellular RNA (300, 100, 30, 10 ng/rxn) and normalizing to, for example, 36B4 mRNA in either parallel or same tube TaqMan reactions.

Western Blotting

Cellular protein extracts can be prepared using a standard micro preparation technique (for example using RIPA buffer). Cellular protein extracts are run on 4-12% Tris-Glycine polyacrylamide gel and transferred onto membranes. Non-specific binding can be blocked by incubation, for example, with 5% non-fat milk for 1 hour followed by primary antibody for 16 hours at 4° C. Following washes, the secondary antibody is applied, for example (1:10,000 dilution) for 1 hour at room temperature and the signal detected on a VersaDoc imaging system In several cell culture systems, cationic lipids have been shown to enhance the bioavailability of oligonucleotides to cells in culture (Bennet, et al., 1992, Mol. Pharmacology, 41, 1023-1033). In one embodiment, DsiRNA molecules of the invention are complexed with cationic lipids for cell culture experiments. DsiRNA and cationic lipid mixtures are prepared in serum-free OptimMEM (InVitrogen) immediately prior to addition to the cells. OptiMEM is warmed to room temperature (about 20-25° C.) and cationic lipid is added to the final desired concentration. DsiRNA molecules are added to OptiMEM to the desired concentration and the solution is added to the diluted DsiRNA and incubated for 15 minutes at room temperature. In dose response experiments, the RNA complex is serially diluted into OptiMEM prior to addition of the cationic lipid.

Animal Models

Evaluating the efficacy of anti-β-catenin DsiRNA agents in animal models is performed as follows. Animal models of cancer and/or proliferative diseases, conditions, or disorders as are known in the art can be used for evaluation of the efficacy, potency, toxicity, etc. of anti-β-catenin DsiRNAs. Suitable animal models of proliferative disease include, e.g., transgenic rodents (e.g., mice, rats) bearing gain of function proto-oncogenes (e.g., Myc, Src) and/or loss of function of tumour suppressor proteins (e.g., p53, Rb) or rodents that have been exposed to radiation or chemical mutagens that induce DNA changes that facilitate neoplastic transformation. Many such animal models are commercially available, for example, from The Jackson Laboratory, Bar Harbor, Me., USA. These animal models may be used as a source cells or tissue for assays of the compositions of the invention. Such models can also be used or adapted for use for pre-clinical evaluation of the efficacy of DsiRNA compositions of the invention in modulating β-catenin gene expression toward therapeutic use.

As in cell culture models, the most β-catenin relevant mouse tumor xenografts are those derived from cancer cells that express β-catenin proteins, such as SW480 or HCT116 colon cancer cells. Xenograft models of colon cancer relevant to study of the anti-tumor effect of modulating β-catenin have been described by various groups. A xenograft animal model useful according to the invention is described in Verma et al. 2003, *Clinical Cancer Research* 9: 1291-1300. Use of these models has demonstrated that inhibition of β-catenin expression by anti-β-catenin agents causes inhibition of tumor growth in animals.

Such models can be used in evaluating the efficacy of DsiRNA molecules of the invention to inhibit β-catenin levels, expression, tumor/cancer formation, growth, spread, development of other β-catenin-associated phenotypes, diseases or disorders, etc. These models and others can similarly be used to evaluate the safety/toxicity and efficacy of DsiRNA molecules of the invention in a pre-clinical setting.

Examples of animal model systems useful for evaluation of the β-catenin-targeting DsiRNAs of the invention include wild-type mice, and orthotopic or subcutaneous SW480 or HCT116 xenograft tumor model mice. In an exemplary in vivo experiment, DsiRNAs of the invention are tail vein injected into such mouse models at doses ranging from 1 to 10 mg/kg or, alternatively, repeated doses are administered at single-dose $IC_{50}$ levels, and organs (e.g., prostate, liver, kidney, lung, pancreas, colon, skin, spleen, bone marrow, lymph nodes, mammary fat pad, etc.) are harvested 24 hours after administration of the final dose. Such organs are then evaluated for mouse and/or human β-catenin levels, depending upon the model used. Duration of action can also be examined at, e.g., 1, 4, 7, 14, 21 or more days after final DsiRNA administration.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N. Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The present invention is described by reference to the following Examples, which are offered by way of illustration and are not intended to limit the invention in any manner. Standard techniques well known in the art or the techniques specifically described below were utilized.

Anti-β-Catenin DsiRNAs

Anti-β-catenin DsiRNA agents were provided as follows.

Example 1

Preparation and Assessment of Double-Stranded RNA Oligonucleotides

Oligonucleotide Synthesis and Purification

DsiRNA molecules according to the invention target sites on human β-catenin sequences or mouse β-catenin sequences (such DsiRNAs are termed "common" DsiRNAs). The sequence of one strand of each DsiRNA molecule was complementary to the target β-catenin site sequences described above. The DsiRNA molecules were chemically synthesized using methods described herein. Generally, DsiRNA constructs were synthesized using solid phase oligonucleotide synthesis methods as described for 19-23mer siRNAs (see for example Usman et al., U.S. Pat. Nos. 5,804, 683; 5,831,071; 5,998,203; 6,117,657; 6,353,098; 6,362,323; 6,437,117; 6,469,158; Scaringe et al., U.S. Pat. Nos. 6,111, 086; 6,008,400; 6,111,086).

Individual RNA strands were synthesized and HPLC purified according to standard methods (Integrated DNA Technologies, Coralville, Iowa). For example, RNA oligonucleotides were synthesized using solid phase phosphoramidite chemistry, deprotected and desalted on NAP-5 columns (Amersham Pharmacia Biotech, Piscataway, N.J.) using standard techniques (Damha and Olgivie, 1993, *Methods Mol Biol* 20: 81-114; Wincott et al., 1995, *Nucleic Acids Res* 23: 2677-84). The oligomers were purified using ion-exchange high performance liquid chromatography (IE-HPLC) on an Amersham Source 15Q column (1.0 cm×25 cm; Amersham Pharmacia Biotech, Piscataway, N.J.) using a 15 min step-linear gradient. The gradient varies from 90:10 Buffers A:B to 52:48 Buffers A:B, where Buffer A is 100 mM Tris pH 8.5 and Buffer B is 100 mM Tris pH 8.5, 1 M NaCl. Samples were monitored at 260 nm and peaks corresponding to the full-length oligonucleotide species are collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 µm inner diameter and contains ssDNA 100R Gel (Beckman-Coulter). Typically, about 0.6 nmole of oligonucleotide was injected into a capillary, run in an electric field of 444 V/cm and detected by UV absorbance at 260 nm Denaturing Tris-Borate-7 M-urea running buffer was purchased from Beckman-Coulter. Oligoribonucleotides were obtained that are at least 90% pure as assessed by CE for use in experiments described below. Compound identity was verified by matrix-assisted laser desorption ionization time-of-flight (MALDI-TOF) mass spectroscopy on a Voyager DE™ Biospectometry Work Station (Applied Biosystems, Foster City, Calif.) following the manufacturer's recommended protocol. Relative molecular masses of all oligomers were obtained, often within 0.2% of expected molecular mass.

Preparation of Duplexes

Single-stranded RNA (ssRNA) oligomers were resuspended, e.g., at 100 µM concentration in duplex buffer consisting of 100 mM potassium acetate, 30 mM HEPES, pH 7.5. Complementary sense and antisense strands were mixed in equal molar amounts to yield a final solution of, e.g., 50 µM duplex. Samples were heated to 100° C. for 5' in RNA buffer (IDT) and allowed to cool to room temperature before use. Double-stranded RNA (dsRNA) oligomers were stored at −20° C. Single-stranded RNA oligomers were stored lyophilized or in nuclease-free water at −80° C.

Nomenclature

For consistency, the following nomenclature has been employed in the instant specification. Names given to duplexes indicate the length of the oligomers and the presence or absence of overhangs. A "25/27" is an asymmetric duplex having a 25 base sense strand and a 27 base antisense strand with a 2-base 3'-overhang. A "27/25" is an asymmetric duplex having a 27 base sense strand and a 25 base antisense strand.

Cell Culture and RNA Transfection

HeLa cells were obtained from ATCC and maintained in DMEM (HyClone) supplemented with 10% fetal bovine serum (HyClone) at 37° C. under 5% $CO_2$. Hepa 1-6 cells were obtained from ATCC and maintained in DMEM (HyClone) supplemented with 10% fetal bovine serum (HyClone) at 37° C. under 5% $CO_2$. For RNA transfections, cells were transfected with DsiRNAs as indicated at a final concentration of 1 nM or 0.1 nM using Lipofectamine™ RNAiMAX (Invitrogen) and following manufacturer's instructions. Briefly, an aliquot of stock solution of each DsiRNA was mixed with Opti-MEM I (Invitrogen) to reach a volume of 87.5 uL; Lipofectamine™ RNAiMAX was diluted in OptiMEM to 87.5 uL. The resulting 1504, mix was added at 50 uL per well into triplicate individual wells of 96 well plates and incubated for 20 min at RT to allow DsiRNA:Lipofectamine™ RNAiMAX complexes to form. Meanwhile, HeLa cells were trypsinized and resuspended in medium. Finally, 100 uL of the cell suspension were added to each well (final volume 150 uL) and plates were placed into the incubator for 24 hours.

Assessment of β-Catenin Inhibition

β-catenin target gene knockdown was determined by qRT-PCR, with values normalized to HPRT and SFRS9 housekeeping genes, and to transfections with control DsiRNAs.

RNA Isolation and Analysis

Media was aspirated, and total RNA was extracted using the SV96 kit (Promega). Approximately 100 ng of total RNA was reverse-transcribed using SuperscriptII, Oligo dT, and random hexamers following manufacturer's instructions. Typically, one-sixth of the resulting cDNA was analyzed by qPCR using primers and probes specific for both the β-catenin gene and for the human genes HPRT-1 and SFRS9. An ABI 7700 was used for the amplification reactions. Each sample was tested in triplicate. Relative β-catenin RNA levels were normalized to HPRT1 and SFRS9 RNA levels and compared with RNA levels obtained in control samples treated with the control DsiRNAs.

Example 2

DsiRNA Inhibition of β-Catenin—Primary Screen

DsiRNA molecules targeting β-catenin were designed and synthesized as described above and tested in HeLa cells for inhibition. For transfection, annealed DsiRNAs were mixed with the transfection reagent (Lipofectamine™ RNAiMAX, Invitrogen) in a volume of 50 µl/well and incubated for 20 minutes at room temperature. The HeLa (human) or Hepa 1-6 (mouse) cells were trypsinized, resuspended in media, and added to wells (100 uL per well) to give a final DsiRNA concentration of 1 nM in a volume of 150 µl. Each DsiRNA transfection mixture was added to 3 wells for triplicate DsiRNA treatments. Cells were incubated at 37° C. for 24 hours in the continued presence of the DsiRNA transfection mixture. At 24 hours, RNA was prepared from each well of treated cells. The supernatants with the transfection mixtures were first removed and discarded, then the cells were lysed and RNA prepared from each well. Target β-catenin RNA levels following treatment were evaluated by qRT-PCR for the β-catenin target gene, with values normalized to those obtained for controls. Triplicate data was averaged and the % error determined for each treatment. Normalized data were graphed and the reduction of target mRNA by active DsiRNAs in comparison to controls was determined β-catenin targeting DsiRNAs of Tables 2-4 above were examined for β-catenin inhibitory efficacy.

488 asymmetric DsiRNAs (tested DsiRNAs possessed a 25/27mer structure) were prepared and tested for β-catenin inhibitory efficacy in human HeLa and mouse Hepa 1-6 cells incubated in the presence of such DsiRNAs at a concentration of 1 nM. Sequences and structures of all 488 tested asymmetric DsiRNAs are shown above in Tables 2-4, with underlined nucleotide residues indicating 2'-O-methyl modified residues; ribonucleotide residues are shown as UPPER CASE, while deoxyribonucleotide residues are shown as lower case.

Assay of these 488 β-catenin targeting DsiRNAs in human HeLa and mouse Hepa 1-6 cells at 1 nM revealed the following β-catenin inhibitory efficacies, presented in Tables 14-17. β-catenin levels were determined using qPCR assays positioned at locations within the β-catenin transcript (for human HeLa cell experiments, paired qPCR assays were performed for the human β-catenin 1297-1397 amplicon (Yakima Yellow) and the human β-catenin 3506-3659 amplicon (FAM); for mouse Hepa 1-6 cell experiments, paired qPCR assays were performed for the mouse β-catenin 1232-1394 amplicon (FAM) and mouse β-catenin 2848-2930 amplicon (MAX); values presented in Tables 14-17 below are averaged values of these paired qPCR assays).

TABLE 14

β-Catenin Inhibitory Efficacy of DsiRNAs Assayed at 1 nM in Human HeLa Cells

| Tested DsiRNA (Target Location in human β-catenin transcript variant 1) | Mouse β-catenin Target Location (in NM_007614.2) | % Remaining β-catenin mRNA ± % Error |
|---|---|---|
| βc-240 | | 5 ± 21.1 |
| βc-244 | | 3.8 ± 2.8 |

TABLE 14-continued

β-Catenin Inhibitory Efficacy of DsiRNAs Assayed at 1 nM in Human HeLa Cells

| Tested DsiRNA (Target Location in human β-catenin transcript variant 1) | Mouse β-catenin Target Location (in NM_007614.2) | % Remaining β-catenin mRNA ± % Error |
|---|---|---|
| βc-253 | | 5.5 ± 1.7 |
| βc-259 | | 3.6 ± 11.3 |
| βc-264 | | 4.1 ± 9.5 |
| βc-496 | | 3.9 ± 5.3 |
| βc-516 | | 4.4 ± 6.5 |
| βc-522 | | 8.6 ± 11.7 |
| βc-524 | | 6.7 ± 10.9 |
| βc-540 | | 5.3 ± 4.7 |
| βc-582 | | 3.8 ± 6.8 |
| βc-686 | | 2.1 ± 2.8 |
| βc-692 | | 2.2 ± 4.9 |
| βc-697 | | 3.9 ± 4.4 |
| βc-707 | | 4.3 ± 6.9 |
| βc-753 | | 5.2 ± 6.1 |
| βc-870 | | 3 ± 7.7 |
| βc-889 | | 2.9 ± 4.9 |
| βc-1060 | | 4 ± 3.6 |
| βc-1065 | | 7.7 ± 4.6 |
| βc-1070 | | 4.6 ± 2.1 |
| βc-1076 | | 7.1 ± 5.1 |
| βc-1154 | | 3.2 ± 10.7 |
| βc-1180 | | 4.8 ± 4 |
| βc-1185 | | 7.6 ± 9 |
| βc-1260 | | 8.7 ± 5.5 |
| βc-1294 | | 16.7 ± 6.2 |
| βc-1412 | | 6.4 ± 12.1 |
| βc-1418 | | 6.1 ± 10.4 |
| βc-1423 | | 153.2 ± 5.2 |
| βc-1520 | | 8.5 ± 10.4 |
| βc-1561 | | 7.5 ± 5.8 |
| βc-1571 | | 5 ± 3.4 |
| βc-1579 | | 5.9 ± 4.4 |
| βc-1620 | | 3.7 ± 4.1 |
| βc-1816 | | 4.9 ± 3.4 |
| βc-1987 | | 8.2 ± 3.1 |
| βc-1989 | | 10.6 ± 4.9 |
| βc-2111 | | 12.1 ± 2.2 |
| βc-2282 | | 6.2 ± 5.6 |
| βc-2624 | | 12 ± 46.4 |
| βc-2647 | | 103.1 ± 4.4 |
| βc-2770 | | 121.5 ± 5.1 |
| βc-2848 | | 107.6 ± 4.3 |
| βc-2874 | | 44.2 ± 3.3 |
| βc-2909 | | 100.8 ± 4.9 |
| βc-3074 | | 81.1 ± 5.5 |
| βc-3197 | | 8.4 ± 11.8 |
| βc-3203 | | 5.1 ± 8.3 |
| βc-3273 | | 67.6 ± 5.1 |
| βc-3333 | | 5.5 ± 8.4 |
| βc-3349 | | 6.5 ± 4 |
| βc-3354 | | 5.6 ± 11.1 |
| βc-3371 | | 15.5 ± 16.8 |
| βc-3376 | | 21.5 ± 9.1 |
| βc-3411 | | 8.7 ± 7.5 |
| βc-3426 | | 5.9 ± N/A |
| βc-3431 | | 3.4 ± 7 |
| βc-3437 | | 6.5 ± 5 |
| βc-3458 | | 9.2 ± 2.3 |
| βc-3468 | | 7.1 ± 4.5 |
| βc-3488 | | 7.5 ± 4.3 |
| βc-3496 | | 9.2 ± 5.1 |
| βc-3552 | | 25.9 ± 4 |
| βc-3600 | | 8.2 ± 7.4 |
| βc-3605 | | 6.2 ± 5.8 |
| βc-3615 | | 5.4 ± 3.9 |
| βc-3674 | | 5.8 ± 4.1 |
| βc-3686 | | 6.4 ± 4 |
| βc-3691 | | 4.6 ± 3 |
| βc-3700 | | 8.7 ± 4 |
| βc-3707 | | 7.2 ± 4.6 |
| βc-284 | 228 | 4.9 ± 14.1 |
| βc-285 | 229 | 6.7 ± 3.2 |
| βc-286 | 230 | 6.7 ± 6.3 |
| βc-287 | 231 | 7.8 ± 7.4 |
| βc-288 | 232 | 5.3 ± 4 |
| βc-289 | 233 | 5.9 ± 13.9 |
| βc-290 | 234 | 6.7 ± 3.2 |
| βc-291 | 235 | 6.1 ± 6.2 |
| βc-312 | 256 | 13.1 ± 3.1 |
| βc-313 | 257 | 14 ± 5.3 |
| βc-314 | 258 | 17.7 ± 8.9 |
| βc-315 | 259 | 40.2 ± 5 |
| βc-316 | 260 | 23.2 ± 3.6 |
| βc-317 | 261 | 12.4 ± 2.7 |
| βc-318 | 262 | 18 ± 4.7 |
| βc-389 | 333 | 51.5 ± 3.8 |
| βc-390 | 334 | 10.9 ± 4.8 |
| βc-391 | 335 | 7.6 ± 9.4 |
| βc-392 | 336 | 15.7 ± 3.9 |
| βc-393 | 337 | 7.8 ± 2.5 |
| βc-600 | 544 | 63.1 ± 4.6 |
| βc-601 | 545 | 59.2 ± 3.7 |
| βc-602 | 546 | 31.8 ± 2.5 |
| βc-603 | 547 | 14.9 ± 9 |
| βc-604 | 548 | 21.9 ± 4 |
| βc-605 | 549 | 10.1 ± 1.4 |
| βc-638 | 582 | 9.9 ± 2.7 |
| βc-639 | 583 | 4.6 ± 7.8 |
| βc-640 | 584 | 100.3 ± 11.7 |
| βc-641 | 585 | 10.4 ± 2.3 |
| βc-642 | 586 | 13.5 ± 4.2 |
| βc-643 | 587 | 41.8 ± 5.2 |
| βc-644 | 588 | 32.5 ± N/A |
| βc-645 | 589 | 10.5 ± 2.5 |
| βc-665 | 609 | 8.8 ± 5.6 |
| βc-666 | 610 | 6.7 ± 2 |
| βc-667 | 611 | 8.9 ± 3.2 |
| βc-731 | 675 | 7.3 ± 6.9 |
| βc-732 | 676 | 53.9 ± 6.1 |
| βc-809 | 753 | 8.6 ± 1.7 |
| βc-810 | 754 | 12.2 ± 8.3 |
| βc-830 | 774 | 5.8 ± 3 |
| βc-831 | 775 | 10.5 ± 2.6 |
| βc-893 | 837 | 3.6 ± 6.2 |
| βc-894 | 838 | 3.5 ± 2 |
| βc-895 | 839 | 3.6 ± 2.1 |
| βc-896 | 840 | 4.3 ± 10.3 |
| βc-897 | 841 | 4.9 ± 8.8 |
| βc-898 | 842 | 7.9 ± 9.3 |
| βc-899 | 843 | 6.8 ± 6.3 |
| βc-900 | 844 | 3.9 ± 2.8 |
| βc-977 | 921 | 10.4 ± 5 |
| βc-978 | 922 | 28.1 ± 2.4 |
| βc-1091 | 1035 | 8.8 ± 7.7 |
| βc-1092 | 1036 | 25.4 ± 3.2 |
| βc-1093 | 1037 | 11.9 ± 1.6 |
| βc-1094 | 1038 | 10.1 ± 3.4 |
| βc-1095 | 1039 | 7.9 ± 4.5 |
| βc-1301 | 1245 | 12.4 ± 5.2 |
| βc-1302 | 1246 | 14.2 ± 5.8 |
| βc-1303 | 1247 | 10 ± 4.8 |
| βc-1304 | 1248 | 8.4 ± 3.8 |
| βc-1305 | 1249 | 6.8 ± 8 |
| βc-1306 | 1250 | 6.1 ± 9.5 |
| βc-1307 | 1251 | 5.7 ± 3.6 |
| βc-1308 | 1252 | 5.7 ± 5.1 |
| βc-1309 | 1253 | 6.9 ± 3.7 |
| βc-1310 | 1254 | 4.5 ± 3.2 |
| βc-1311 | 1255 | 5.3 ± 4.5 |
| βc-1312 | 1256 | 9.8 ± 1.2 |
| βc-1313 | 1257 | 5.7 ± 6.3 |
| βc-1314 | 1258 | 5.2 ± 5.9 |
| βc-1430 | 1374 | 20.6 ± 7.8 |
| βc-1431 | 1375 | 17.5 ± 4 |

TABLE 14-continued

β-Catenin Inhibitory Efficacy of DsiRNAs Assayed at 1 nM in Human HeLa Cells

| Tested DsiRNA (Target Location in human β-catenin transcript variant 1) | Mouse β-catenin Target Location (in NM_007614.2) | % Remaining β-catenin mRNA ± % Error |
|---|---|---|
| βc-1526 | 1470 | 35.8 ± 4.5 |
| βc-1527 | 1471 | 40.7 ± 10.2 |
| βc-1528 | 1472 | 22.8 ± 4.2 |
| βc-1529 | 1473 | 21.8 ± 7.6 |
| βc-1530 | 1474 | 17.3 ± 11.4 |
| βc-1531 | 1475 | 62.1 ± 8.3 |
| βc-1532 | 1476 | 37.8 ± 19.1 |
| βc-1533 | 1477 | 16.3 ± 6.2 |
| βc-1534 | 1478 | 80.7 ± 17 |
| βc-1535 | 1479 | 27.1 ± 6.7 |
| βc-1536 | 1480 | 13.3 ± 4.3 |
| βc-1537 | 1481 | 12.9 ± 4.1 |
| βc-1538 | 1482 | 11.9 ± 3 |
| βc-1539 | 1483 | 10.9 ± 8.9 |
| βc-1540 | 1484 | 5 ± 6.1 |
| βc-1541 | 1485 | 4.2 ± 9.8 |
| βc-1542 | 1486 | 9.8 ± 2.1 |
| βc-1543 | 1487 | 5.7 ± 6.4 |
| βc-1544 | 1488 | 4.8 ± 5.8 |
| βc-1545 | 1489 | 4 ± 5.5 |
| βc-1565 | 1509 | 6.5 ± 8.5 |
| βc-1566 | 1510 | 3.6 ± 6.6 |
| βc-1567 | 1511 | 3.5 ± 17.3 |
| βc-1568 | 1512 | 3.2 ± 8.4 |
| βc-1569 | 1513 | 2.7 ± 13 |
| βc-1652 | 1596 | 5.1 ± 14.3 |
| βc-1653 | 1597 | 5.8 ± 13.2 |
| βc-1654 | 1598 | 26.4 ± 2.6 |
| βc-1655 | 1599 | 17.8 ± 3.9 |
| βc-1656 | 1600 | 18.7 ± 7.4 |
| βc-1657 | 1601 | 35.4 ± 7.7 |
| βc-1658 | 1602 | 10 ± 4.4 |
| βc-1659 | 1603 | 10.2 ± 10.5 |
| βc-1660 | 1604 | 31.5 ± 2.4 |
| βc-1661 | 1605 | 14.3 ± 5 |
| βc-1662 | 1606 | 5 ± 4.4 |
| βc-1663 | 1607 | 21.7 ± 4.7 |
| βc-1664 | 1608 | 67 ± 8.6 |
| βc-1665 | 1609 | 16.6 ± 14.3 |
| βc-1666 | 1610 | 11.3 ± 6.3 |
| βc-1667 | 1611 | 6.2 ± 19.5 |
| βc-1668 | 1612 | 33.5 ± 6.3 |
| βc-1669 | 1613 | 26.1 ± 3 |
| βc-1670 | 1614 | 27.7 ± 3.8 |
| βc-1671 | 1615 | 9.3 ± 2.2 |
| βc-1672 | 1616 | 23.4 ± 5.4 |
| βc-1673 | 1617 | 21.7 ± 9.1 |
| βc-1674 | 1618 | 15.1 ± 4 |
| βc-1675 | 1619 | 31 ± 5.9 |
| βc-1676 | 1620 | 12.1 ± 10.6 |
| βc-1677 | 1621 | 23.2 ± 15.4 |
| βc-1678 | 1622 | 6.9 ± 10.8 |
| βc-1679 | 1623 | 13 ± 9.6 |
| βc-1680 | 1624 | 5 ± 10.6 |
| βc-1681 | 1625 | 4 ± 6.5 |
| βc-1682 | 1626 | 2.8 ± 6.2 |
| βc-1683 | 1627 | 2.8 ± 5.7 |
| βc-1684 | 1628 | 7.4 ± 2.7 |
| βc-1685 | 1629 | 11.3 ± 6.3 |
| βc-1686 | 1630 | 15.6 ± 4.3 |
| βc-1687 | 1631 | 7.6 ± 4.4 |
| βc-1688 | 1632 | 17.8 ± 5 |
| βc-1689 | 1633 | 23.7 ± 7.5 |
| βc-1690 | 1634 | 8.1 ± 3 |
| βc-1691 | 1635 | 8.5 ± 4.6 |
| βc-1692 | 1636 | 33.9 ± 28.1 |
| βc-1693 | 1637 | 45.6 ± 4.8 |
| βc-1694 | 1638 | 12.7 ± 3.4 |
| βc-1695 | 1639 | 9.4 ± 5.6 |
| βc-1787 | 1731 | 46.4 ± 6.2 |
| βc-1788 | 1732 | 28 ± 3.8 |
| βc-1789 | 1733 | 28.6 ± 6.5 |
| βc-1790 | 1734 | 65.2 ± 5.1 |
| βc-1791 | 1735 | 13.6 ± 4 |
| βc-1792 | 1736 | 10.2 ± 16.3 |
| βc-1793 | 1737 | 18.7 ± 7.7 |
| βc-1794 | 1738 | 36.7 ± 5 |
| βc-1795 | 1739 | 31.2 ± 9.1 |
| βc-1796 | 1740 | 8.5 ± 5 |
| βc-1797 | 1741 | 23.8 ± 4.1 |
| βc-1798 | 1742 | 49.2 ± 3.1 |
| βc-1799 | 1743 | 58 ± 3 |
| βc-1800 | 1744 | 26.3 ± 5.7 |
| βc-1820 | 1764 | 3.8 ± 7.8 |
| βc-1821 | 1765 | 4.8 ± 13.4 |
| βc-2072 | 2016 | 7.6 ± 14 |
| βc-2073 | 2017 | 12.4 ± 8.5 |
| βc-2074 | 2018 | 10.8 ± 6.2 |
| βc-2075 | 2019 | 7.6 ± 1.9 |
| βc-2076 | 2020 | 13.5 ± 6.5 |
| βc-2077 | 2021 | 12.1 ± 7 |
| βc-2097 | 2041 | 3.9 ± 2.7 |
| βc-2098 | 2042 | 6.2 ± 3.6 |
| βc-2099 | 2043 | 6 ± 3.8 |
| βc-2100 | 2044 | 11.4 ± 8.6 |
| βc-2141 | 2085 | 8.3 ± 8.7 |
| βc-2142 | 2086 | 17.9 ± 2.4 |
| βc-2143 | 2087 | 6.2 ± 11.2 |
| βc-2144 | 2088 | 4.4 ± 16.1 |
| βc-2145 | 2089 | 8.8 ± 12.2 |
| βc-2146 | 2090 | 9.4 ± 9.6 |
| βc-2147 | 2091 | 10.5 ± 12.2 |
| βc-2148 | 2092 | 6.5 ± 2.7 |
| βc-2149 | 2093 | 16.3 ± 5.8 |
| βc-2150 | 2094 | 10.7 ± 5.2 |
| βc-2151 | 2095 | 5.7 ± 3.2 |
| βc-2183 | 2127 | 38.1 ± 2.9 |
| βc-2184 | 2128 | 41.5 ± 4.3 |
| βc-2185 | 2129 | 83.7 ± 2.3 |
| βc-2270 | 2214 | 23.8 ± 12.6 |
| βc-2271 | 2215 | 18.8 ± 9.6 |
| βc-2272 | 2216 | 6.7 ± 3.5 |
| βc-2273 | 2217 | 8.4 ± 5.5 |
| βc-2274 | 2218 | 6.2 ± 4.4 |
| βc-2275 | 2219 | 7.2 ± 5.8 |
| βc-2276 | 2220 | 7.1 ± 2.4 |
| βc-2277 | 2221 | 4.8 ± 2.8 |
| βc-2345 | 2289 | 8.5 ± 2.5 |
| βc-2346 | 2290 | 7 ± 4.5 |
| βc-2347 | 2291 | 6.8 ± 5.9 |
| βc-2348 | 2292 | 12.3 ± 14.8 |
| βc-2349 | 2293 | 6.2 ± 12.8 |
| βc-2350 | 2294 | 4.1 ± 11.7 |
| βc-2351 | 2295 | 6.9 ± 9.1 |
| βc-2352 | 2296 | 11.5 ± 13 |
| βc-2353 | 2297 | 19.1 ± 4.7 |
| βc-2354 | 2298 | 17.1 ± 3.6 |
| βc-2355 | 2299 | 8.1 ± 6.5 |
| βc-2411 | 2355 | 6.6 ± 2.1 |
| βc-2412 | 2356 | 8.1 ± 3.9 |
| βc-2413 | 2357 | 10.1 ± 3.5 |
| βc-2414 | 2358 | 9.8 ± 1 |
| βc-2415 | 2359 | 10.9 ± 4.3 |
| βc-2441 | 2385 | 9.5 ± 3 |
| βc-2442 | 2386 | 5.2 ± 5 |
| βc-2443 | 2387 | 8.8 ± 11.9 |
| βc-2444 | 2388 | 10.2 ± 4 |
| βc-2445 | 2389 | 5.3 ± 6.4 |
| βc-2501 | 2445 | 74.5 ± 3.1 |
| βc-2502 | 2446 | 95.4 ± 4.2 |
| βc-2503 | 2447 | 116.5 ± 5 |
| βc-2504 | 2448 | 108.9 ± 5.3 |
| βc-2505 | 2449 | 98.7 ± 5 |
| βc-2506 | 2450 | 43.5 ± 2.7 |

TABLE 14-continued

β-Catenin Inhibitory Efficacy of DsiRNAs Assayed at 1 nM in Human HeLa Cells

| Tested DsiRNA (Target Location in human β-catenin transcript variant 1) | Mouse β-catenin Target Location (in NM_007614.2) | % Remaining β-catenin mRNA ± % Error |
|---|---|---|
| βc-2507 | 2451 | 89.5 ± 1.9 |
| βc-2508 | 2452 | 54.6 ± 7 |
| βc-2509 | 2453 | 19.4 ± 10.5 |
| βc-2510 | 2454 | 47.1 ± 3.5 |
| βc-2511 | 2455 | 60.7 ± 4.9 |
| βc-2512 | 2456 | 53.7 ± 9.7 |
| βc-2513 | 2457 | 18 ± N/A |
| βc-2514 | 2458 | 6.5 ± 4.9 |
| βc-2515 | 2459 | 13.5 ± 3.7 |
| βc-2516 | 2460 | 11.3 ± 3 |
| βc-2517 | 2461 | 6.2 ± 3.5 |
| βc-2518 | 2462 | 6.9 ± 4.8 |
| βc-2519 | 2463 | 9.1 ± 2.8 |
| βc-2520 | 2464 | 6.6 ± 4 |
| βc-2521 | 2465 | 6.4 ± 3.9 |
| βc-2522 | 2466 | 7.6 ± 5.6 |
| βc-2523 | 2467 | 6.1 ± 7.6 |
| βc-2524 | 2468 | 5.5 ± 3 |
| βc-2525 | 2469 | 3.6 ± 1.3 |
| βc-2526 | 2470 | 4.9 ± 2.8 |
| βc-2527 | 2471 | 58 ± 9.2 |
| βc-2528 | 2472 | 22.5 ± 5.3 |
| βc-2529 | 2473 | 24.5 ± 9.5 |
| βc-2530 | 2474 | 53.5 ± 1.3 |
| βc-2531 | 2475 | 19.3 ± 9.1 |
| βc-2532 | 2476 | 17.2 ± 11.5 |
| βc-2533 | 2477 | 21.5 ± 9.8 |
| βc-2534 | 2478 | 77.4 ± 2.4 |
| βc-2535 | 2479 | 55.4 ± 4.3 |
| βc-2567 | 2511 | 77.9 ± 4.1 |
| βc-2568 | 2512 | 51.2 ± 9.2 |
| βc-2569 | 2513 | 38.2 ± 2.8 |
| βc-2603 | 2547 | 11 ± 7.7 |
| βc-2604 | 2548 | 9.7 ± 5.6 |
| βc-2605 | 2549 | 29.1 ± 4.2 |
| βc-2606 | 2550 | 23.4 ± 4.4 |
| βc-2607 | 2551 | 10.6 ± 2.6 |
| βc-2608 | 2552 | 16 ± 6.4 |
| βc-2609 | 2553 | 23.3 ± 15.2 |
| βc-2610 | 2554 | 16.2 ± 5.1 |
| βc-2611 | 2555 | 3.8 ± 1.4 |
| βc-2612 | 2556 | 2.2 ± 4.6 |
| βc-2613 | 2557 | 8.4 ± 2.3 |
| βc-2614 | 2558 | 4.9 ± 3.4 |
| βc-2615 | 2559 | 6.7 ± 6.4 |
| βc-2616 | 2560 | 8.4 ± 7.7 |
| βc-2617 | 2561 | 6.2 ± 6.3 |
| βc-2618 | 2562 | 6.6 ± 6.2 |
| βc-2619 | 2563 | 6 ± 4.1 |
| βc-2620 | 2564 | 5.9 ± 11.4 |
| βc-2621 | 2565 | 9.5 ± 13.2 |
| βc-2622 | 2566 | 7.3 ± 10 |
| βc-2623 | 2567 | 7.2 ± 9.8 |
| βc-2869 | 2765 | 86.5 ± 9.1 |
| βc-2902 | 2798 | 67.7 ± 3.1 |
| βc-2923 | 2819 | 76.5 ± 3.1 |
| βc-2925 | 2821 | 88.6 ± 5.6 |
| βc-2927 | 2823 | 79.9 ± 6.5 |
| βc-2929 | 2825 | 71.1 ± 1.2 |
| βc-2973 | 2867 | 49.8 ± 6.9 |
| βc-2975 | 2869 | 46.3 ± 5.6 |
| βc-2977 | 2871 | 43.2 ± 1.4 |
| βc-2979 | 2873 | 59.3 ± 4.3 |
| βc-2981 | 2875 | 47 ± 5.2 |
| βc-2983 | 2877 | 59.8 ± 1.9 |
| βc-2985 | 2879 | 50.9 ± 3.1 |
| βc-2987 | 2881 | 54.5 ± 2.8 |
| βc-2989 | 2883 | 50.7 ± 2.4 |
| βc-3015 | 2909 | 72.2 ± 2.5 |
| βc-3017 | 2911 | 56.9 ± 3.9 |
| βc-3019 | 2913 | 62.5 ± 4.1 |
| βc-3021 | 2915 | 59.5 ± 3.2 |
| βc-3046 | 2940 | 77.4 ± 19.4 |
| βc-3048 | 2942 | 45.3 ± 15.3 |
| βc-3050 | 2944 | 60.2 ± 10.5 |
| βc-3052 | 2946 | 58.5 ± 5.3 |
| βc-3054 | 2948 | 84.7 ± 5.1 |
| βc-3056 | 2950 | 64.8 ± 7.4 |
| βc-3087 | 2981 | 58.7 ± 6.6 |
| βc-3089 | 2983 | 47.4 ± 6 |
| βc-3091 | 2985 | 52.6 ± 6 |
| βc-3093 | 2987 | 45.7 ± 14.5 |
| βc-3095 | 2989 | 49.7 ± 3.8 |
| βc-3097 | 2991 | 72.3 ± 13.4 |
| βc-3099 | 2993 | 39.7 ± 3.4 |
| βc-3101 | 2995 | 31.4 ± 13.3 |
| βc-3103 | 2997 | 35.6 ± 9 |
| βc-3105 | 2999 | 16 ± 7.7 |
| βc-3107 | 3001 | 41.3 ± 33.6 |
| βc-3109 | 3003 | 5.3 ± 35.8 |
| βc-3111 | 3005 | 4.5 ± 7.6 |
| βc-3113 | 3007 | 7.5 ± 9.8 |
| βc-3115 | 3009 | 5.1 ± 15.4 |
| βc-3191 | 3084 | 10.2 ± 9.9 |
| βc-3193 | 3086 | 9.3 ± 5.5 |
| βc-3195 | 3088 | 4.4 ± 3.1 |
| βc-3387 | 3232 | 4.8 ± 7.8 |
| βc-3389 | 3234 | 3.6 ± 6 |
| βc-3391 | 3236 | 4.7 ± 7.2 |
| βc-3393 | 3238 | 2.7 ± 7.1 |
| βc-3395 | 3240 | 4.9 ± 3.7 |
| βc-3397 | 3242 | 4.8 ± 3.1 |
| βc-3399 | 3244 | 3.9 ± 9.3 |
| βc-3401 | 3246 | 4.8 ± 9.8 |
| βc-3500 | 3336 | 5.7 ± 3.4 |
| βc-3502 | 3338 | 8.3 ± 3.9 |
| βc-3504 | 3340 | 7 ± 6.2 |
| βc-3506 | 3342 | 9.7 ± 2.3 |
| βc-3508 | 3344 | 9.2 ± 2.9 |
| βc-3509 | 3345 | 13.8 ± 4.2 |
| βc-3510 | 3346 | 56.3 ± 5 |
| βc-3512 | 3348 | 20.8 ± 4.6 |
| βc-3514 | 3350 | 9.7 ± 3.3 |
| βc-3516 | 3352 | 12.7 ± 7.4 |
| βc-3518 | 3354 | 7.5 ± 5.7 |
| βc-3520 | 3356 | 6.6 ± 2.6 |
| βc-3522 | 3358 | 7.5 ± 7.1 |
| βc-3524 | 3360 | 10.5 ± 4.4 |
| βc-3526 | 3362 | 9.4 ± N/A |
| βc-3528 | 3364 | 8.2 ± 8.9 |
| βc-3530 | 3366 | 8.2 ± 9 |
| βc-3532 | 3368 | 7.5 ± 5.4 |
| βc-3534 | 3370 | 5.6 ± 11.9 |
| βc-3536 | 3372 | 5.7 ± 2.8 |
| βc-3538 | 3374 | 7.5 ± 2.8 |
| βc-3583 | 3420 | 10 ± 5.2 |
| βc-3585 | 3422 | 9.4 ± 7.8 |
| βc-3587 | 3424 | 7 ± 5 |
| βc-3589 | 3426 | 6.5 ± 5.6 |
| βc-3591 | 3428 | 5.4 ± 6.6 |
| βc-3593 | 3430 | 11.5 ± 5.7 |
| βc-3633 | 3469 | 14.6 ± 3.9 |
| βc-3635 | 3471 | 9.5 ± 3.6 |
| βc-3637 | 3473 | 11.6 ± 5 |
| βc-3639 | 3475 | 18.9 ± 10.1 |
| βc-3641 | 3477 | 8.4 ± 5.4 |
| βc-3643 | 3479 | 10.8 ± 5.6 |
| βc-3645 | 3481 | 12.6 ± 3.2 |
| βc-3647 | 3483 | 15.1 ± 2.7 |
| βc-3649 | 3485 | 14.4 ± 3.1 |
| βc-3651 | 3487 | 7.2 ± 11.1 |
| βc-3653 | 3489 | 6.3 ± 5.7 |
| βc-3655 | 3491 | 10.9 ± 7.7 |
| βc-3657 | 3493 | 7 ± 3.5 |

TABLE 14-continued

β-Catenin Inhibitory Efficacy of DsiRNAs Assayed at 1 nM in Human HeLa Cells

| Tested DsiRNA (Target Location in human β-catenin transcript variant 1) | Mouse β-catenin Target Location (in NM_007614.2) | % Remaining β-catenin mRNA ± % Error |
|---|---|---|
| βc-3659 | 3495 | 5.4 ± 8.4 |
| βc-3708 | 3540 | 6.3 ± 11.3 |
| βc-3710 | 3542 | 5.5 ± 11.8 |
| βc-3712 | 3544 | 4.8 ± 8.1 |
| βc-3714 | 3546 | 7.4 ± 3.6 |
| βc-3716 | 3548 | 20.2 ± 11.6 |

Figure 2:
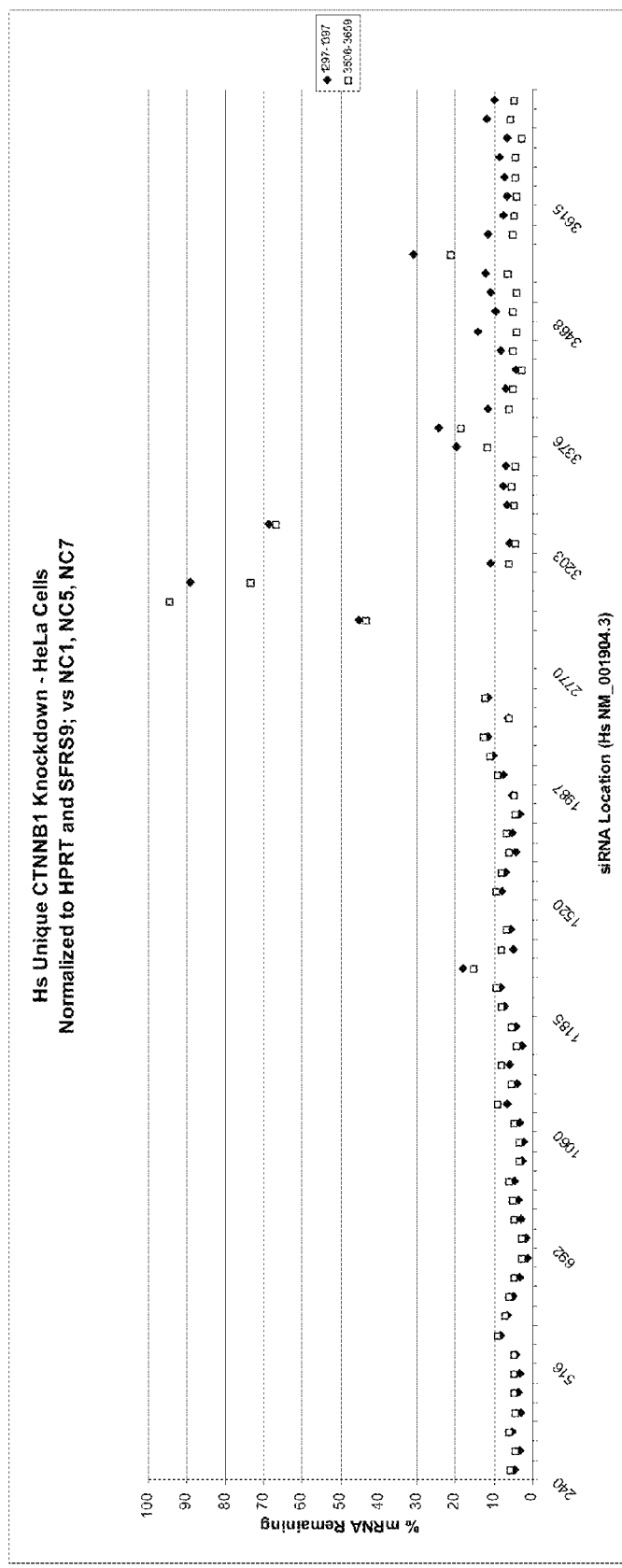
FIGS. 2 and 3 show plots of human β-catenin inhibitory efficacies observed at 1 nM in the environment of HeLa cells for DsiRNAs targeting sites progressing from 5' to 3' across the human β-catenin transcript. Human β-catenin levels were normalized to HPRT and SFRS9 levels.
Figure 3:
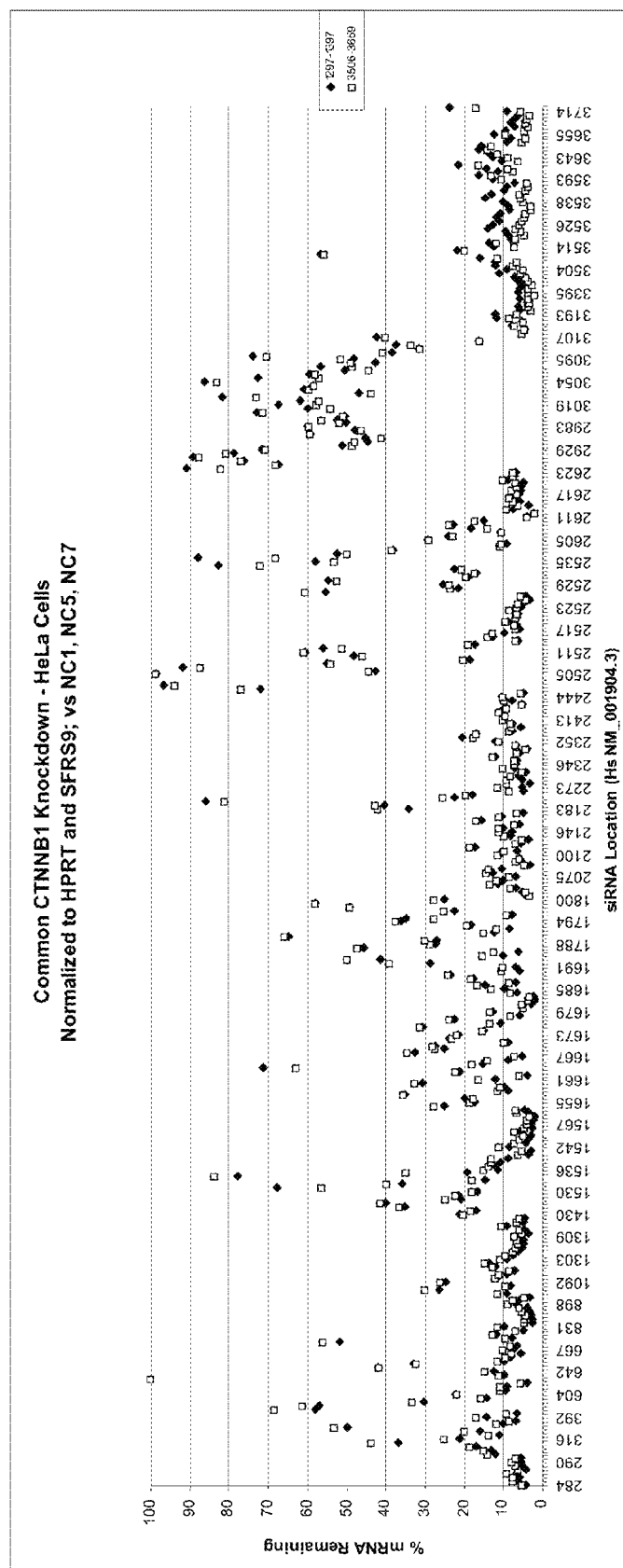

The data shown in above Table 14 were also plotted graphically (see FIGS. 2 and 3).

TABLE 15

100 Human β-Catenin-Targeting DsiRNAs (Rank Ordered by Inhibition)

| Tested DsiRNA (Target Location in human β-catenin transcript variant 1) | Mouse β-catenin Target Location (in NM_007614.2) | % Remaining β-catenin mRNA ± % Error |
|---|---|---|
| βc-686 |  | 2.1 ± 2.8 |
| βc-692 |  | 2.2 ± 4.9 |
| βc-2612 | 2556 | 2.2 ± 4.6 |
| βc-1569 | 1513 | 2.7 ± 13 |
| βc-3393 | 3238 | 2.7 ± 7.1 |
| βc-1682 | 1626 | 2.8 ± 6.2 |
| βc-1683 | 1627 | 2.8 ± 5.7 |
| βc-889 |  | 2.9 ± 4.9 |
| βc-870 |  | 3 ± 7.7 |
| βc-1154 |  | 3.2 ± 10.7 |
| βc-1568 | 1512 | 3.2 ± 8.4 |
| βc-3431 |  | 3.4 ± 7 |
| βc-894 | 838 | 3.5 ± 2 |
| βc-1567 | 1511 | 3.5 ± 17.3 |
| βc-259 |  | 3.6 ± 11.3 |
| βc-893 | 837 | 3.6 ± 6.2 |
| βc-895 | 839 | 3.6 ± 2.1 |
| βc-1566 | 1510 | 3.6 ± 6.6 |
| βc-2525 | 2469 | 3.6 ± 1.3 |
| βc-3389 | 3234 | 3.6 ± 6 |
| βc-1620 |  | 3.7 ± 4.1 |
| βc-244 |  | 3.8 ± 2.8 |
| βc-582 |  | 3.8 ± 6.8 |
| βc-1820 | 1764 | 3.8 ± 7.8 |
| βc-2611 | 2555 | 3.8 ± 1.4 |
| βc-496 |  | 3.9 ± 5.3 |
| βc-697 |  | 3.9 ± 4.4 |
| βc-900 | 844 | 3.9 ± 2.8 |
| βc-2097 | 2041 | 3.9 ± 2.7 |
| βc-3399 | 3244 | 3.9 ± 9.3 |
| βc-1060 |  | 4 ± 3.6 |
| βc-1545 | 1489 | 4 ± 5.5 |
| βc-1681 | 1625 | 4 ± 6.5 |
| βc-264 |  | 4.1 ± 9.5 |
| βc-2350 | 2294 | 4.1 ± 11.7 |
| βc-1541 | 1485 | 4.2 ± 9.8 |
| βc-707 |  | 4.3 ± 6.9 |
| βc-896 | 840 | 4.3 ± 10.3 |
| βc-516 |  | 4.4 ± 6.5 |
| βc-2144 | 2088 | 4.4 ± 16.1 |
| βc-3195 | 3088 | 4.4 ± 3.1 |
| βc-1310 | 1254 | 4.5 ± 3.2 |
| βc-3111 | 3005 | 4.5 ± 7.6 |
| βc-1070 |  | 4.6 ± 2.1 |
| βc-3691 |  | 4.6 ± 3 |
| βc-639 | 583 | 4.6 ± 7.8 |
| βc-3391 | 3236 | 4.7 ± 7.2 |
| βc-1180 |  | 4.8 ± 4 |
| βc-1544 | 1488 | 4.8 ± 5.8 |
| βc-1821 | 1765 | 4.8 ± 13.4 |

TABLE 15-continued

100 Human β-Catenin-Targeting DsiRNAs (Rank Ordered by Inhibition)

| Tested DsiRNA (Target Location in human β-catenin transcript variant 1) | Mouse β-catenin Target Location (in NM_007614.2) | % Remaining β-catenin mRNA ± % Error |
|---|---|---|
| βc-2277 | 2221 | 4.8 ± 2.8 |
| βc-3387 | 3232 | 4.8 ± 7.8 |
| βc-3397 | 3242 | 4.8 ± 3.1 |
| βc-3401 | 3246 | 4.8 ± 9.8 |
| βc-3712 | 3544 | 4.8 ± 8.1 |
| βc-1816 |  | 4.9 ± 3.4 |
| βc-284 | 228 | 4.9 ± 14.1 |
| βc-897 | 841 | 4.9 ± 8.8 |
| βc-2526 | 2470 | 4.9 ± 2.8 |
| βc-2614 | 2558 | 4.9 ± 3.4 |
| βc-3395 | 3240 | 4.9 ± 3.7 |
| βc-240 |  | 5 ± 21.1 |
| βc-1571 |  | 5 ± 3.4 |
| βc-1540 | 1484 | 5 ± 6.1 |
| βc-1662 | 1606 | 5 ± 4.4 |
| βc-1680 | 1624 | 5 ± 10.6 |
| βc-3203 |  | 5.1 ± 8.3 |
| βc-1652 | 1596 | 5.1 ± 14.3 |
| βc-3115 | 3009 | 5.1 ± 15.4 |
| βc-753 |  | 5.2 ± 6.1 |
| βc-1314 | 1258 | 5.2 ± 5.9 |
| βc-2442 | 2386 | 5.2 ± 5 |
| βc-540 |  | 5.3 ± 4.7 |
| βc-288 | 232 | 5.3 ± 4 |
| βc-1311 | 1255 | 5.3 ± 4.5 |
| βc-2445 | 2389 | 5.3 ± 6.4 |
| βc-3109 | 3003 | 5.3 ± 35.8 |
| βc-3615 |  | 5.4 ± 3.9 |
| βc-3591 | 3428 | 5.4 ± 6.6 |
| βc-3659 | 3495 | 5.4 ± 8.4 |
| βc-253 |  | 5.5 ± 1.7 |
| βc-3333 |  | 5.5 ± 8.4 |
| βc-2524 | 2468 | 5.5 ± 3 |
| βc-3710 | 3542 | 5.5 ± 11.8 |
| βc-3354 |  | 5.6 ± 11.1 |
| βc-3534 | 3370 | 5.6 ± 11.9 |
| βc-1307 | 1251 | 5.7 ± 3.6 |
| βc-1308 | 1252 | 5.7 ± 5.1 |
| βc-1313 | 1257 | 5.7 ± 6.3 |
| βc-1543 | 1487 | 5.7 ± 6.4 |
| βc-2151 | 2095 | 5.7 ± 3.2 |
| βc-3500 | 3336 | 5.7 ± 3.4 |
| βc-3536 | 3372 | 5.7 ± 2.8 |
| βc-3674 |  | 5.8 ± 4.1 |
| βc-830 | 774 | 5.8 ± 3 |
| βc-1653 | 1597 | 5.8 ± 13.2 |
| βc-1579 |  | 5.9 ± 4.4 |
| βc-3426 |  | 5.9 ± N/A |
| βc-289 | 233 | 5.9 ± 13.9 |
| βc-2620 | 2564 | 5.9 ± 11.4 |

TABLE 16

β-Catenin Inhibitory Efficacy of DsiRNAs at 1 nM in Mouse Hepa 1-6 Cells

| Tested DsiRNA/ Mouse β-catenin Target Location (in NM_007614.2) | Tested DsiRNA/ Human β-catenin transcript variant 1 Target Location | % Remaining β-catenin mRNA ± % Error |
|---|---|---|
| 228 | βc-284 | 32 ± 23 |
| 229 | βc-285 | 27.2 ± 10.7 |
| 230 | βc-286 | 24.5 ± 14.5 |
| 231 | βc-287 | 35.9 ± 19.7 |
| 232 | βc-288 | 43.1 ± 12 |
| 233 | βc-289 | 34.8 ± 7 |
| 234 | βc-290 | 41.6 ± 15.9 |
| 235 | βc-291 | 48.4 ± 25.1 |

TABLE 16-continued

β-Catenin Inhibitory Efficacy of DsiRNAs at 1 nM in Mouse Hepa 1-6 Cells

| Tested DsiRNA/ Mouse β-catenin Target Location (in NM_007614.2) | Tested DsiRNA/ Human β-catenin transcript variant 1 Target Location | % Remaining β-catenin mRNA ± % Error |
|---|---|---|
| 256 | βc-312 | 109.7 ± N/A |
| 257 | βc-313 | 68.5 ± 6.7 |
| 258 | βc-314 | 93.4 ± 8.6 |
| 259 | βc-315 | 69.4 ± 3.4 |
| 260 | βc-316 | 101 ± 3.4 |
| 261 | βc-317 | 67.6 ± 10.5 |
| 262 | βc-318 | 88 ± 11 |
| 333 | βc-389 | 107.4 ± 6.7 |
| 334 | βc-390 | 99.2 ± 14.4 |
| 335 | βc-391 | 68.5 ± 7.4 |
| 336 | βc-392 | 77.4 ± 5.5 |
| 337 | βc-393 | 53.8 ± 6.8 |
| 544 | βc-600 | 65.9 ± 7.7 |
| 545 | βc-601 | 54.1 ± 6.3 |
| 546 | βc-602 | 44.1 ± 12.9 |
| 547 | βc-603 | 37.3 ± 7.3 |
| 548 | βc-604 | 83 ± 14.5 |
| 549 | βc-605 | 44.6 ± 9.2 |
| 582 | βc-638 | 22.6 ± 5.9 |
| 583 | βc-639 | 12.2 ± 15.4 |
| 584 | βc-640 | 102.1 ± 8.4 |
| 585 | βc-641 | 24.4 ± 9 |
| 586 | βc-642 | 32.3 ± 29.7 |
| 587 | βc-643 | 62.1 ± 10.6 |
| 588 | βc-644 | 56.1 ± 6.8 |
| 589 | βc-645 | 18.4 ± 6.2 |
| 609 | βc-665 | 23.7 ± 7 |
| 610 | βc-666 | 23.3 ± 7.2 |
| 611 | βc-667 | 18.5 ± 6.1 |
| 675 | βc-731 | 34.4 ± 13.7 |
| 676 | βc-732 | 127.2 ± 3.4 |
| 753 | βc-809 | 56 ± 7.6 |
| 754 | βc-810 | 82.4 ± 5.4 |
| 774 | βc-830 | 26.5 ± 6.2 |
| 775 | βc-831 | 16.1 ± 7.3 |
| 837 | βc-893 | 9.2 ± 9.5 |
| 838 | βc-894 | 10.5 ± 9.4 |
| 839 | βc-895 | 12.5 ± 16.7 |
| 840 | βc-896 | 14.1 ± 19.2 |
| 841 | βc-897 | 25.7 ± 10 |
| 842 | βc-898 | 20.1 ± 19.7 |
| 843 | βc-899 | 21.5 ± 13.6 |
| 844 | βc-900 | 13.8 ± 9.7 |
| 921 | βc-977 | 44.1 ± 12 |
| 922 | βc-978 | 58.4 ± 43 |
| 1035 | βc-1091 | 97.2 ± 10.9 |
| 1036 | βc-1092 | 111.4 ± 10.5 |
| 1037 | βc-1093 | 122 ± 13.4 |
| 1038 | βc-1094 | 54.1 ± 3.6 |
| 1039 | βc-1095 | 53.2 ± 6.9 |
| 1245 | βc-1301 | 25.5 ± 3.9 |
| 1246 | βc-1302 | 28.7 ± 5.2 |
| 1247 | βc-1303 | 33.5 ± 3.2 |
| 1248 | βc-1304 | 31.2 ± 11.2 |
| 1249 | βc-1305 | 22.1 ± 17.3 |
| 1250 | βc-1306 | 23.5 ± 15.8 |
| 1251 | βc-1307 | 15.7 ± 13.3 |
| 1252 | βc-1308 | 16.4 ± 13.6 |
| 1253 | βc-1309 | 13.5 ± 4.8 |
| 1254 | βc-1310 | 14.9 ± 8.1 |
| 1255 | βc-1311 | 17.6 ± 12.9 |
| 1256 | βc-1312 | 33.4 ± 6.4 |
| 1257 | βc-1313 | 16.8 ± 11.1 |
| 1258 | βc-1314 | 18.4 ± 4.8 |
| 1374 | βc-1430 | 57.1 ± 4.4 |
| 1375 | βc-1431 | 42.3 ± 7.5 |
| 1470 | βc-1526 | 64.7 ± 8.8 |
| 1471 | βc-1527 | 36.8 ± 12.4 |
| 1472 | βc-1528 | 31.6 ± 18.8 |
| 1473 | βc-1529 | 25.7 ± 13.3 |
| 1474 | βc-1530 | 30.3 ± 13.7 |
| 1475 | βc-1531 | 56.3 ± 2.2 |
| 1476 | βc-1532 | 31.5 ± 5 |
| 1477 | βc-1533 | 21.2 ± 2.6 |
| 1478 | βc-1534 | 77.6 ± 5.7 |
| 1479 | βc-1535 | 34.3 ± 8.3 |
| 1480 | βc-1536 | 14.7 ± 3.6 |
| 1481 | βc-1537 | 14.1 ± 9 |
| 1482 | βc-1538 | 21.1 ± 4 |
| 1483 | βc-1539 | 19.5 ± 8.4 |
| 1484 | βc-1540 | 11.7 ± N/A |
| 1485 | βc-1541 | 7.3 ± 7.1 |
| 1486 | βc-1542 | 14.7 ± 7.8 |
| 1487 | βc-1543 | 11.7 ± 5.9 |
| 1488 | βc-1544 | 8.2 ± 8.2 |
| 1489 | βc-1545 | 7.4 ± 10.1 |
| 1509 | βc-1565 | 21.2 ± 9.1 |
| 1510 | βc-1566 | 9 ± 18.1 |
| 1511 | βc-1567 | 10.7 ± 16.4 |
| 1512 | βc-1568 | 8.3 ± 14.9 |
| 1513 | βc-1569 | 7 ± 12.8 |
| 1596 | βc-1652 | 10.1 ± 13.9 |
| 1597 | βc-1653 | 23.4 ± 32.9 |
| 1598 | βc-1654 | 67.3 ± 27.6 |
| 1599 | βc-1655 | 38.5 ± 12.3 |
| 1600 | βc-1656 | 26.3 ± 14.2 |
| 1601 | βc-1657 | 38 ± 8.9 |
| 1602 | βc-1658 | 12.7 ± 6.8 |
| 1603 | βc-1659 | 25.9 ± 7.6 |
| 1604 | βc-1660 | 56.5 ± 12.8 |
| 1605 | βc-1661 | 27.3 ± 13.4 |
| 1606 | βc-1662 | 12.3 ± 18.1 |
| 1607 | βc-1663 | 46.1 ± 27.2 |
| 1608 | βc-1664 | 71.2 ± 17.1 |
| 1609 | βc-1665 | 25.8 ± 11.4 |
| 1610 | βc-1666 | 15.7 ± 4.7 |
| 1611 | βc-1667 | 20.8 ± 4 |
| 1612 | βc-1668 | 61 ± 29.3 |
| 1613 | βc-1669 | 46.7 ± 11.4 |
| 1614 | βc-1670 | 44.9 ± 1.6 |
| 1615 | βc-1671 | 30.7 ± 20.8 |
| 1616 | βc-1672 | 52.8 ± 12.9 |
| 1617 | βc-1673 | 56.7 ± 11.2 |
| 1618 | βc-1674 | 28 ± 7 |
| 1619 | βc-1675 | 37.5 ± 11.1 |
| 1620 | βc-1676 | 16 ± 7.2 |
| 1621 | βc-1677 | 40.8 ± 3.1 |
| 1622 | βc-1678 | 14.1 ± 10.8 |
| 1623 | βc-1679 | 26.7 ± 14.4 |
| 1624 | βc-1680 | 14.8 ± 7.4 |
| 1625 | βc-1681 | 10.7 ± 5 |
| 1626 | βc-1682 | 10.9 ± 21.3 |
| 1627 | βc-1683 | 7.3 ± 11 |
| 1628 | βc-1684 | 11.1 ± 3.3 |
| 1629 | βc-1685 | 21.5 ± 18 |
| 1630 | βc-1686 | 23.4 ± 4.7 |
| 1631 | βc-1687 | 15.2 ± 16.6 |
| 1632 | βc-1688 | 21.6 ± 4.9 |
| 1633 | βc-1689 | 33.6 ± 34.5 |
| 1634 | βc-1690 | 24.1 ± 10.9 |
| 1635 | βc-1691 | 33.7 ± 10.9 |
| 1636 | βc-1692 | 42.5 ± 3.9 |
| 1637 | βc-1693 | 83.4 ± 14 |
| 1638 | βc-1694 | 19.8 ± 2.6 |
| 1639 | βc-1695 | 15.9 ± 10.9 |
| 1731 | βc-1787 | 65.2 ± 8.7 |
| 1732 | βc-1788 | 33.4 ± 25.5 |
| 1733 | βc-1789 | 35.4 ± 16.3 |
| 1734 | βc-1790 | 46.6 ± 16.4 |
| 1735 | βc-1791 | 15 ± 9.5 |
| 1736 | βc-1792 | 12.8 ± 4.4 |
| 1737 | βc-1793 | 15.8 ± 8.3 |
| 1738 | βc-1794 | 28.4 ± 7.1 |
| 1739 | βc-1795 | 23.5 ± 17.2 |

TABLE 16-continued

β-Catenin Inhibitory Efficacy of DsiRNAs at 1 nM in Mouse Hepa 1-6 Cells

| Tested DsiRNA/ Mouse β-catenin Target Location (in NM_007614.2) | Tested DsiRNA/ Human β-catenin transcript variant 1 Target Location | % Remaining β-catenin mRNA ± % Error |
|---|---|---|
| 1740 | βc-1796 | 9 ± 14.1 |
| 1741 | βc-1797 | 26.1 ± 6.6 |
| 1742 | βc-1798 | 50.2 ± 10.2 |
| 1743 | βc-1799 | 55.9 ± 2.7 |
| 1744 | βc-1800 | 36.3 ± 6.5 |
| 1764 | βc-1820 | 7.3 ± 37.9 |
| 1765 | βc-1821 | 5.6 ± 13.9 |
| 2016 | βc-2072 | 12.3 ± 15 |
| 2017 | βc-2073 | 12.4 ± 10.3 |
| 2018 | βc-2074 | 16.3 ± 14.8 |
| 2019 | βc-2075 | 8.2 ± 15.3 |
| 2020 | βc-2076 | 9.8 ± 7.1 |
| 2021 | βc-2077 | 16.9 ± 42 |
| 2041 | βc-2097 | 5.6 ± 10.2 |
| 2042 | βc-2098 | 7.4 ± 6 |
| 2043 | βc-2099 | 12.6 ± 21.8 |
| 2044 | βc-2100 | 28.7 ± 7.6 |
| 2085 | βc-2141 | 29.7 ± 14.1 |
| 2086 | βc-2142 | 46.2 ± 4.4 |
| 2087 | βc-2143 | 16 ± 10.8 |
| 2088 | βc-2144 | 13.8 ± 18.6 |
| 2089 | βc-2145 | 29.6 ± 10.3 |
| 2090 | βc-2146 | 40.5 ± 5.3 |
| 2091 | βc-2147 | 27.9 ± 11.4 |
| 2092 | βc-2148 | 21.8 ± 2.2 |
| 2093 | βc-2149 | 60.3 ± 4.4 |
| 2094 | βc-2150 | 42.8 ± 3.9 |
| 2095 | βc-2151 | 29 ± 2.4 |
| 2127 | βc-2183 | 75 ± 4.7 |
| 2128 | βc-2184 | 76.5 ± 4.7 |
| 2129 | βc-2185 | 129.6 ± 16.4 |
| 2214 | βc-2270 | 65.8 ± 4.7 |
| 2215 | βc-2271 | 40.8 ± N/A |
| 2216 | βc-2272 | 13.5 ± 8.5 |
| 2217 | βc-2273 | 21.5 ± 3 |
| 2218 | βc-2274 | 17.6 ± 6.2 |
| 2219 | βc-2275 | 28.9 ± 6.2 |
| 2220 | βc-2276 | 21.2 ± 5.4 |
| 2221 | βc-2277 | 26.9 ± 2.8 |
| 2289 | βc-2345 | 20.8 ± 8.7 |
| 2290 | βc-2346 | 13.6 ± 7.2 |
| 2291 | βc-2347 | 17 ± 12.8 |
| 2292 | βc-2348 | 19.2 ± 3.3 |
| 2293 | βc-2349 | 9.6 ± 6.4 |
| 2294 | βc-2350 | 10.4 ± 12.8 |
| 2295 | βc-2351 | 17 ± 8.9 |
| 2296 | βc-2352 | 31.2 ± 13.1 |
| 2297 | βc-2353 | 37.1 ± N/A |
| 2298 | βc-2354 | 32.4 ± 6 |
| 2299 | βc-2355 | 21.5 ± 5.3 |
| 2355 | βc-2411 | 16.6 ± 6.3 |
| 2356 | βc-2412 | 12.8 ± 8 |
| 2357 | βc-2413 | 18.6 ± 5.8 |
| 2358 | βc-2414 | 16.3 ± 12.4 |
| 2359 | βc-2415 | 27.2 ± 11.4 |
| 2385 | βc-2441 | 20.1 ± 18.9 |
| 2386 | βc-2442 | 9.2 ± 4 |
| 2387 | βc-2443 | 14.4 ± 8.1 |
| 2388 | βc-2444 | 14.2 ± 3.4 |
| 2389 | βc-2445 | 9.8 ± 7.6 |
| 2445 | βc-2501 | 67.3 ± 5.1 |
| 2446 | βc-2502 | 72.4 ± 6.2 |
| 2447 | βc-2503 | 96.8 ± 6.3 |
| 2448 | βc-2504 | 112.6 ± 7.5 |
| 2449 | βc-2505 | 68.5 ± 9.4 |
| 2450 | βc-2506 | 128.8 ± 10.4 |
| 2451 | βc-2507 | 144.3 ± 12.9 |
| 2452 | βc-2508 | 99.5 ± 8.8 |
| 2453 | βc-2509 | 80.5 ± 8.4 |
| 2454 | βc-2510 | 88.6 ± 10.6 |
| 2455 | βc-2511 | 105.9 ± 8.8 |
| 2456 | βc-2512 | 126.3 ± 18.2 |
| 2457 | βc-2513 | 30.4 ± 13.7 |
| 2458 | βc-2514 | 22.6 ± 2.4 |
| 2459 | βc-2515 | 45.2 ± 30.1 |
| 2460 | βc-2516 | 27.6 ± 7.2 |
| 2461 | βc-2517 | 19.7 ± N/A |
| 2462 | βc-2518 | 21.9 ± 10.5 |
| 2463 | βc-2519 | 29.9 ± 14.6 |
| 2464 | βc-2520 | 27.2 ± 6.1 |
| 2465 | βc-2521 | 11.5 ± N/A |
| 2466 | βc-2522 | 17.9 ± 8.4 |
| 2467 | βc-2523 | 18.5 ± 4.5 |
| 2468 | βc-2524 | 16.8 ± 6.6 |
| 2469 | βc-2525 | 19.4 ± 14.4 |
| 2470 | βc-2526 | 10.7 ± 6.8 |
| 2471 | βc-2527 | 62.5 ± 8.1 |
| 2472 | βc-2528 | 64.5 ± 14.2 |
| 2473 | βc-2529 | 41.4 ± 12.6 |
| 2474 | βc-2530 | 73.5 ± 7.1 |
| 2475 | βc-2531 | 32.2 ± 10.4 |
| 2476 | βc-2532 | 23.9 ± 18.7 |
| 2477 | βc-2533 | 40 ± 10 |
| 2478 | βc-2534 | 60.4 ± N/A |
| 2479 | βc-2535 | 81.3 ± 4.9 |
| 2511 | βc-2567 | 104.5 ± 12.9 |
| 2512 | βc-2568 | 53 ± 9 |
| 2513 | βc-2569 | 67.1 ± 3.6 |
| 2547 | βc-2603 | 18.1 ± 7.9 |
| 2548 | βc-2604 | 14.2 ± 2.5 |
| 2549 | βc-2605 | 28.9 ± 5.9 |
| 2550 | βc-2606 | 23.7 ± 6.8 |
| 2551 | βc-2607 | 17.1 ± 16.7 |
| 2552 | βc-2608 | 18.1 ± 3.6 |
| 2553 | βc-2609 | 23.8 ± N/A |
| 2554 | βc-2610 | 22.6 ± 21.5 |
| 2555 | βc-2611 | 9.4 ± 7.6 |
| 2556 | βc-2612 | 5.1 ± 4.1 |
| 2557 | βc-2613 | 16.3 ± 7.8 |
| 2558 | βc-2614 | 11 ± 8.5 |
| 2559 | βc-2615 | 11.6 ± 4 |
| 2560 | βc-2616 | 14.8 ± 4.1 |
| 2561 | βc-2617 | 9.8 ± 8.1 |
| 2562 | βc-2618 | 12 ± 8.8 |
| 2563 | βc-2619 | 10.7 ± 13.7 |
| 2564 | βc-2620 | 9.2 ± 18.9 |
| 2565 | βc-2621 | 16.9 ± 9.6 |
| 2566 | βc-2622 | 15.5 ± 7.2 |
| 2567 | βc-2623 | 15 ± 6.1 |
| 2765 | βc-2869 | 24.5 ± 26.4 |
| 2798 | βc-2902 | 10.1 ± 9.5 |
| 2819 | βc-2923 | 16.9 ± 2 |
| 2821 | βc-2925 | 11.2 ± 6.3 |
| 2823 | βc-2927 | 15.4 ± 9.6 |
| 2825 | βc-2929 | 9.8 ± 10 |
| 2867 | βc-2973 | 16.6 ± 5.2 |
| 2869 | βc-2975 | 28.7 ± 12.7 |
| 2871 | βc-2977 | 17 ± 9.7 |
| 2873 | βc-2979 | 20 ± 13 |
| 2875 | βc-2981 | 20 ± 17.9 |
| 2877 | βc-2983 | 29 ± 5.7 |
| 2879 | βc-2985 | 12.1 ± 13 |
| 2881 | βc-2987 | 18.3 ± 7.6 |
| 2883 | βc-2989 | 12.4 ± 6.9 |
| 2909 | βc-3015 | 12 ± 9.6 |
| 2911 | βc-3017 | 18.6 ± 21.3 |
| 2913 | βc-3019 | 15.8 ± 16.6 |
| 2915 | βc-3021 | 24 ± 5.9 |
| 2940 | βc-3046 | 24.3 ± 5.1 |
| 2942 | βc-3048 | 10.8 ± 18.4 |
| 2944 | βc-3050 | 15.9 ± 7.1 |
| 2946 | βc-3052 | 16 ± 15.8 |
| 2948 | βc-3054 | 13.4 ± 8.2 |
| 2950 | βc-3056 | 35.2 ± 11.8 |

TABLE 16-continued

β-Catenin Inhibitory Efficacy of DsiRNAs at 1 nM in Mouse Hepa 1-6 Cells

| Tested DsiRNA/ Mouse β-catenin Target Location (in NM_007614.2) | Tested DsiRNA/ Human β-catenin transcript variant 1 Target Location | % Remaining β-catenin mRNA ± % Error |
|---|---|---|
| 2981 | βc-3087 | 8.9 ± 27.7 |
| 2983 | βc-3089 | 11.3 ± 3.5 |
| 2985 | βc-3091 | 26.6 ± 4.1 |
| 2987 | βc-3093 | 7.3 ± 6.4 |
| 2989 | βc-3095 | 16.1 ± 7 |
| 2991 | βc-3097 | 6.7 ± 4.3 |
| 2993 | βc-3099 | 12.5 ± 5.7 |
| 2995 | βc-3101 | 11.4 ± 3.3 |
| 2997 | βc-3103 | 7.4 ± 9.7 |
| 2999 | βc-3105 | 7.4 ± 3 |
| 3001 | βc-3107 | 8.6 ± 5.1 |
| 3003 | βc-3109 | 6.3 ± 9.2 |
| 3005 | βc-3111 | 5.8 ± 6.9 |
| 3007 | βc-3113 | 8 ± 3.6 |
| 3009 | βc-3115 | 7.9 ± 8.8 |
| 3084 | βc-3191 | 15.9 ± 4.2 |
| 3086 | βc-3193 | 22.1 ± 8.4 |
| 3088 | βc-3195 | 11.1 ± 14.2 |
| 3232 | βc-3387 | 8.3 ± 12.4 |
| 3234 | βc-3389 | 6.1 ± 16.4 |
| 3236 | βc-3391 | 7.5 ± 12.1 |
| 3238 | βc-3393 | 5.9 ± 14.7 |
| 3240 | βc-3395 | 9.6 ± 8.1 |
| 3242 | βc-3397 | 12.7 ± 2.5 |
| 3244 | βc-3399 | 5.4 ± 9.6 |
| 3246 | βc-3401 | 9.4 ± 10.7 |
| 3336 | βc-3500 | 10.2 ± 1.6 |
| 3338 | βc-3502 | 8 ± 6.6 |
| 3340 | βc-3504 | 9 ± 3 |
| 3342 | βc-3506 | 17.7 ± 3.3 |
| 3344 | βc-3508 | 23.8 ± 4 |
| 3345 | βc-3509 | 25.3 ± 3.6 |
| 3346 | βc-3510 | 63.9 ± 10.6 |
| 3348 | βc-3512 | 25.2 ± 6.4 |
| 3350 | βc-3514 | 10.1 ± 2 |
| 3352 | βc-3516 | 17.9 ± 1.9 |
| 3354 | βc-3518 | 11.1 ± 5.4 |
| 3356 | βc-3520 | 8.5 ± 2.6 |
| 3358 | βc-3522 | 12.5 ± 8.6 |
| 3360 | βc-3524 | 15.4 ± 7.4 |
| 3362 | βc-3526 | 7 ± 7.7 |
| 3364 | βc-3528 | 10.5 ± 10.7 |
| 3366 | βc-3530 | 12.9 ± 11.6 |
| 3368 | βc-3532 | 7.2 ± 15.4 |
| 3370 | βc-3534 | 7.7 ± 13.4 |
| 3372 | βc-3536 | 9.7 ± 15.8 |
| 3374 | βc-3538 | 12.6 ± 8.8 |
| 3420 | βc-3583 | 19.8 ± 4 |
| 3422 | βc-3585 | 10.6 ± 2.4 |
| 3424 | βc-3587 | 8.7 ± 2.9 |
| 3426 | βc-3589 | 9.7 ± 1.7 |
| 3428 | βc-3591 | 7.5 ± 4.2 |
| 3430 | βc-3593 | 22 ± 1.7 |
| 3469 | βc-3633 | 14.2 ± 5.1 |
| 3471 | βc-3635 | 12.1 ± 7.6 |
| 3473 | βc-3637 | 17.3 ± 5.6 |
| 3475 | βc-3639 | 9.8 ± 5.4 |
| 3477 | βc-3641 | 9.7 ± 6.5 |
| 3479 | βc-3643 | 11 ± 5.2 |
| 3481 | βc-3645 | 6.9 ± 8.9 |
| 3483 | βc-3647 | 17.5 ± 5 |
| 3485 | βc-3649 | 16.7 ± 1.8 |
| 3487 | βc-3651 | 12.2 ± 4.3 |
| 3489 | βc-3653 | 16.5 ± 3.3 |
| 3491 | βc-3655 | 11.4 ± 14.1 |
| 3493 | βc-3657 | 10 ± 10.2 |
| 3495 | βc-3659 | 8.7 ± 5 |
| 3540 | βc-3708 | 7.4 ± 7 |
| 3542 | βc-3710 | 8.7 ± 3.2 |
| 3544 | βc-3712 | 6 ± 9.4 |
| 3546 | βc-3714 | 11.9 ± 2.9 |
| 3548 | βc-3716 | 27 ± 7.1 |
| | βc-m314 | 77.1 ± 15.6 |
| | βc-m325 | 99.1 ± 19.3 |
| | βc-m408 | 50.4 ± 23.7 |
| | βc-m460 | 58.7 ± 16.5 |
| | βc-m526 | 12.9 ± 4.5 |
| | βc-m631 | 13.7 ± 11.2 |
| | βc-m636 | 16.5 ± 19.9 |
| | βc-m642 | 10.8 ± 8.5 |
| | βc-m723 | 13.7 ± 12.1 |
| | βc-m970 | 12.3 ± 10.9 |
| | βc-m976 | 12 ± 9.5 |
| | βc-m981 | 15.3 ± 4.1 |
| | βc-m1066 | 11.3 ± 8.6 |
| | βc-m1106 | 10.6 ± 7.8 |
| | βc-m1354 | 9.7 ± 6.1 |
| | βc-m1363 | 11.1 ± 3.3 |
| | βc-m1373 | 11.8 ± N/A |
| | βc-m1508 | 11.5 ± 7.1 |
| | βc-m1515 | 9.4 ± 6.9 |
| | βc-m1682 | 11.8 ± 11.4 |
| | βc-m1693 | 16 ± 14 |
| | βc-m1698 | 13.5 ± 6 |
| | βc-m1705 | 10.7 ± 5.3 |
| | βc-m1763 | 7.7 ± 14.2 |
| | βc-m2008 | 18.3 ± 3.5 |
| | βc-m2226 | 11.7 ± 10 |
| | βc-m2427 | 30.8 ± 2.4 |
| | βc-m2568 | 9.7 ± 3.9 |
| | βc-m2614 | 13.3 ± 4.1 |
| | βc-m2770 | 17.5 ± 4.9 |
| | βc-m2777 | 29.8 ± 17.2 |
| | βc-m2784 | 16 ± 15.1 |
| | βc-m2806 | 8.6 ± 8 |
| | βc-m2850 | 13.4 ± 3.1 |
| | βc-m2965 | 12.5 ± 10.3 |
| | βc-m2970 | 11.6 ± 7.6 |
| | βc-m2976 | 12.8 ± 4.3 |
| | βc-m3092 | 7.5 ± 29.8 |
| | βc-m3097 | 11.6 ± 2.7 |
| | βc-m3198 | 14.7 ± 9.3 |
| | βc-m3207 | 7.9 ± N/A |
| | βc-m3433 | 15.4 ± 6.4 |
| | βc-m3439 | 14.3 ± 4.4 |
| | βc-m3444 | 9.7 ± 8.4 |
| | βc-m3449 | 9.9 ± 15.8 |
| | βc-m3522 | 10.3 ± 5.5 |
| | βc-m3533 | 10 ± 5.2 |
| | βc-m3538 | 10.1 ± 4.5 |

Figure 4:
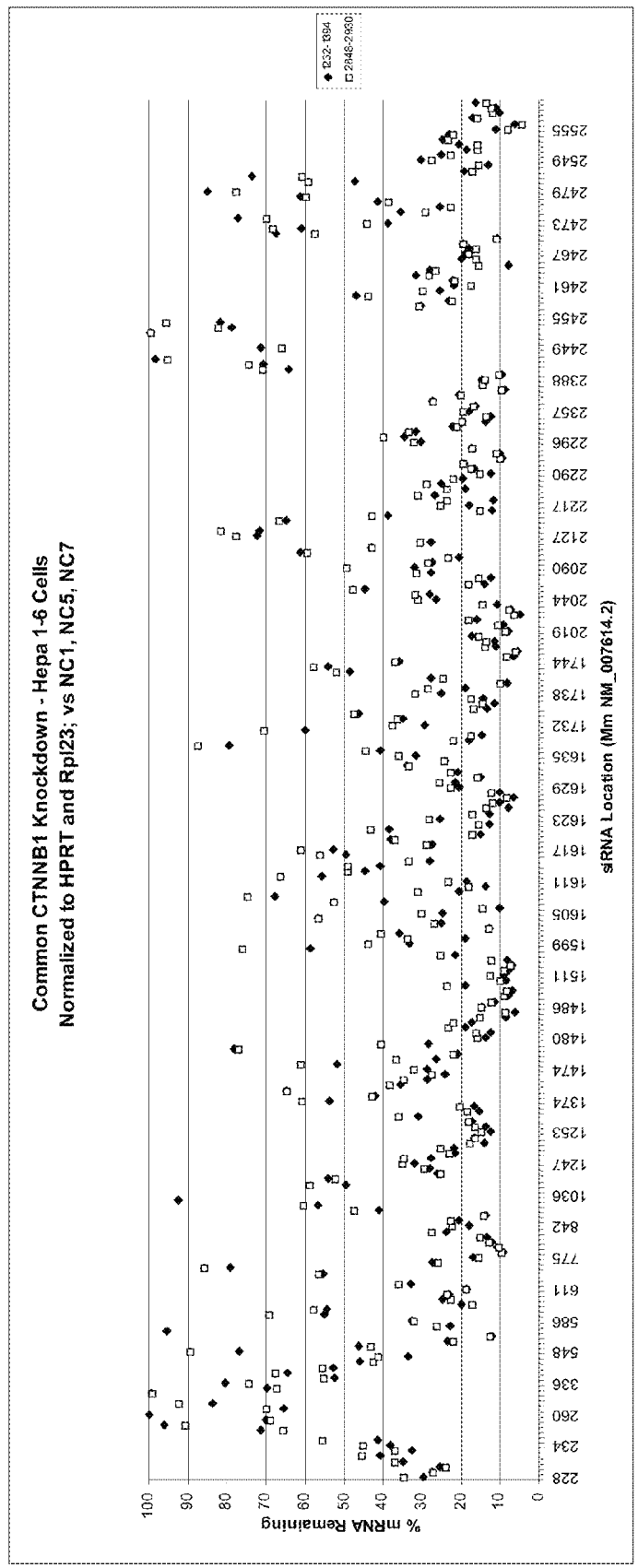
FIGS. 4 and 5 show plots of mouse β-catenin inhibitory efficacies observed at 1 nM in the environment of Hepa 1-6 cells for DsiRNAs targeting sites progressing from 5' to 3' across the mouse β-catenin transcript. Mouse β-catenin levels were normalized to HPRT and Rpl23 levels.
Figure 5:
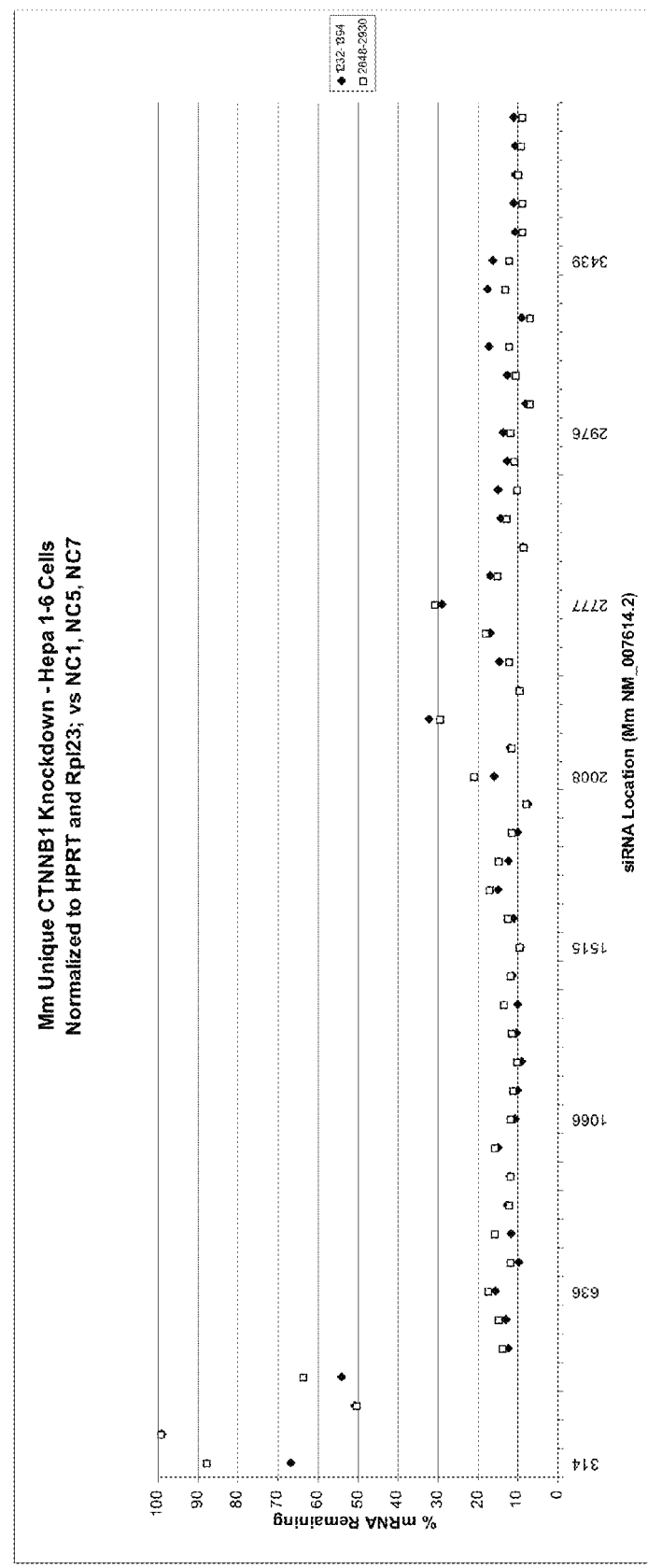

The data shown in above Table 16 were also plotted graphically (see FIGS. 4 and 5).

TABLE 17

100 Mouse β-Catenin-Targeting DsiRNAs (Rank Ordered by Inhibition)

| Tested DsiRNA/ Mouse β-catenin Target Location (in NM_007614.2) | Tested DsiRNA/ Human β-catenin transcript variant 1 Target Location | % Remaining β-catenin mRNA ± % Error |
|---|---|---|
| 2556 | βc-2612 | 5.1 ± 4.1 |
| 3244 | βc-3399 | 5.4 ± 9.6 |
| 1765 | βc-1821 | 5.6 ± 13.9 |
| 2041 | βc-2097 | 5.6 ± 10.2 |
| 3005 | βc-3111 | 5.8 ± 6.9 |
| 3238 | βc-3393 | 5.9 ± 14.7 |
| 3544 | βc-3712 | 6 ± 9.4 |
| 3234 | βc-3389 | 6.1 ± 16.4 |
| 3003 | βc-3109 | 6.3 ± 9.2 |

TABLE 17-continued

100 Mouse β-Catenin-Targeting DsiRNAs (Rank Ordered by Inhibition)

| Tested DsiRNA/ Mouse β-catenin Target Location (in NM_007614.2) | Tested DsiRNA/ Human β-catenin transcript variant 1 Target Location | % Remaining β-catenin mRNA ± % Error |
|---|---|---|
| 2991 | βc-3097 | 6.7 ± 4.3 |
| 3481 | βc-3645 | 6.9 ± 8.9 |
| 1513 | βc-1569 | 7 ± 12.8 |
| 3362 | βc-3526 | 7 ± 7.7 |
| 3368 | βc-3532 | 7.2 ± 15.4 |
| 1485 | βc-1541 | 7.3 ± 7.1 |
| 1627 | βc-1683 | 7.3 ± 11 |
| 1764 | βc-1820 | 7.3 ± 37.9 |
| 2987 | βc-3093 | 7.3 ± 6.4 |
| 1489 | βc-1545 | 7.4 ± 10.1 |
| 2042 | βc-2098 | 7.4 ± 6 |
| 2997 | βc-3103 | 7.4 ± 9.7 |
| 2999 | βc-3105 | 7.4 ± 3 |
| 3540 | βc-3708 | 7.4 ± 7 |
| 3236 | βc-3391 | 7.5 ± 12.1 |
| 3428 | βc-3591 | 7.5 ± 4.2 |
| βc-m3092 | | 7.5 ± 29.8 |
| 3370 | βc-3534 | 7.7 ± 13.4 |
| βc-m1763 | | 7.7 ± 14.2 |
| 3009 | βc-3115 | 7.9 ± 8.8 |
| βc-m3207 | | 7.9 ± N/A |
| 3007 | βc-3113 | 8 ± 3.6 |
| 3338 | βc-3502 | 8 ± 6.6 |
| 1488 | βc-1544 | 8.2 ± 8.2 |
| 2019 | βc-2075 | 8.2 ± 15.3 |
| 1512 | βc-1568 | 8.3 ± 14.9 |
| 3232 | βc-3387 | 8.3 ± 12.4 |
| 3356 | βc-3520 | 8.5 ± 2.6 |
| 3001 | βc-3107 | 8.6 ± 5.1 |
| βc-m2806 | | 8.6 ± 8 |
| 3424 | βc-3587 | 8.7 ± 2.9 |
| 3495 | βc-3659 | 8.7 ± 5 |
| 3542 | βc-3710 | 8.7 ± 3.2 |
| 2981 | βc-3087 | 8.9 ± 27.7 |
| 1510 | βc-1566 | 9 ± 18.1 |
| 1740 | βc-1796 | 9 ± 14.1 |
| 3340 | βc-3504 | 9 ± 3 |
| 837 | βc-893 | 9.2 ± 9.5 |
| 2386 | βc-2442 | 9.2 ± 4 |
| 2564 | βc-2620 | 9.2 ± 18.9 |
| 2555 | βc-2611 | 9.4 ± 7.6 |
| 3246 | βc-3401 | 9.4 ± 10.7 |
| βc-m1515 | | 9.4 ± 6.9 |
| 2293 | βc-2349 | 9.6 ± 6.4 |
| 3240 | βc-3395 | 9.6 ± 8.1 |
| 3372 | βc-3536 | 9.7 ± 15.8 |
| 3426 | βc-3589 | 9.7 ± 1.7 |
| 3477 | βc-3641 | 9.7 ± 6.5 |
| βc-m1354 | | 9.7 ± 6.1 |
| βc-m2568 | | 9.7 ± 3.9 |
| βc-m3444 | | 9.7 ± 8.4 |
| 2020 | βc-2076 | 9.8 ± 7.1 |
| 2389 | βc-2445 | 9.8 ± 7.6 |
| 2561 | βc-2617 | 9.8 ± 8.1 |
| 2825 | βc-2929 | 9.8 ± 10 |
| 3475 | βc-3639 | 9.8 ± 5.4 |
| βc-m3449 | | 9.9 ± 15.8 |
| 3493 | βc-3657 | 10 ± 10.2 |
| βc-m3533 | | 10 ± 5.2 |
| 1596 | βc-1652 | 10.1 ± 13.9 |
| 2798 | βc-2902 | 10.1 ± 9.5 |
| 3350 | βc-3514 | 10.1 ± 2 |
| βc-m3538 | | 10.1 ± 4.5 |
| 3336 | βc-3500 | 10.2 ± 1.6 |
| βc-m3522 | | 10.3 ± 5.5 |
| 2294 | βc-2350 | 10.4 ± 12.8 |
| 838 | βc-894 | 10.5 ± 9.4 |
| 3364 | βc-3528 | 10.5 ± 10.7 |
| 3422 | βc-3585 | 10.6 ± 2.4 |
| βc-m1106 | | 10.6 ± 7.8 |
| 1511 | βc-1567 | 10.7 ± 16.4 |
| 1625 | βc-1681 | 10.7 ± 5 |
| 2470 | βc-2526 | 10.7 ± 6.8 |
| 2563 | βc-2619 | 10.7 ± 13.7 |
| βc-m1705 | | 10.7 ± 5.3 |
| 2942 | βc-3048 | 10.8 ± 18.4 |
| βc-m642 | | 10.8 ± 8.5 |
| 1626 | βc-1682 | 10.9 ± 21.3 |
| 2558 | βc-2614 | 11 ± 8.5 |
| 3479 | βc-3643 | 11 ± 5.2 |
| 1628 | βc-1684 | 11.1 ± 3.3 |
| 3088 | βc-3195 | 11.1 ± 14.2 |
| 3354 | βc-3518 | 11.1 ± 5.4 |
| βc-m1363 | | 11.1 ± 3.3 |
| 2821 | βc-2925 | 11.2 ± 6.3 |
| 2983 | βc-3089 | 11.3 ± 3.5 |
| βc-m1066 | | 11.3 ± 8.6 |
| 2995 | βc-3101 | 11.4 ± 3.3 |
| 3491 | βc-3655 | 11.4 ± 14.1 |
| 2465 | βc-2521 | 11.5 ± N/A |
| βc-m1508 | | 11.5 ± 7.1 |

As shown in above Table 14, 348 of 440 asymmetric DsiRNAs examined in human HeLa cells showed greater than 70% reduction of human β-catenin levels in HeLa cells at 1 nM. Of these 348 DsiRNAs, 317 exhibited 80% or greater reduction of human β-catenin levels in HeLa cells at 1 nM, and 229 exhibited 90% or greater reduction of human β-catenin levels in HeLa cells cells at 1 nM. A number of these DsiRNAs uniquely targeted human β-catenin.

As shown in above Table 16, 295 of 416 asymmetric DsiRNAs examined in in mouse Hepa 1-6 cells showed greater than 70% reduction of mouse β-catenin levels in Hepa 1-6 cells at 1 nM. Of these 295 DsiRNAs, 225 exhibited 80% or greater reduction of mouse β-catenin levels in Hepa 1-6 cells at 1 nM, and 68 exhibited 90% or greater reduction of mouse β-catenin levels in Hepa 1-6 cells at 1 nM. A number of these DsiRNAs uniquely targeted mouse β-catenin.

Example 3

β-Catenin Targeting DsiRNAs Effectively Reduced β-Catenin RNA Levels in Tumor Cells and Inhibited Tumor Cell Growth Cell Culture, RNA Transfection and Analysis HCT116 cells were maintained in McCoy's 5a Medium with 10% Fetal Bovine Serum (FBS); HepG2 cells were maintained in MEM with 10% FBS (both media contained penicillin and streptomycin). For transfection, cells were seeded into 24-well plates at 40,000 cells per well the day before transfection, in antibiotic-free medium. To transfect, DsiRNAs were complexed with the lipid transfection reagent RNAiMAX, in OptiMem medium and then added to the cells in medium to yield the indicated final DsiRNA concentrations. Controls included Untransfected cells, Mock cells treated with RNAiMAX without DsiRNA, and Control DsiRNA #114 (with non-specific sequence). After six hours of exposure, the cell culture medium was removed, cells were washed, and fresh medium was added.

For RNA expression analysis, RNA was isolated one day after transfection, using the Promega SV96 RNA isolation kit. RNA was reverse-transcribed, and then Taqman quantitative PCR was performed on a BioRad CFX96, in multiplex using primer and probe sets specific for CTNNB1/B-catenin and the housekeeping gene HPRT1 for normalization.

Cell growth was assayed three days after transfection, using the Promega Cell Titer Blue (CTB) reagent. Briefly, culture medium was replaced with fresh medium containing CTB reagent; after one hour, fluorescence at the appropriate wavelength was measured one a plate reader. Cell number values were graphed relative to Mock treatments.

Figure 6:
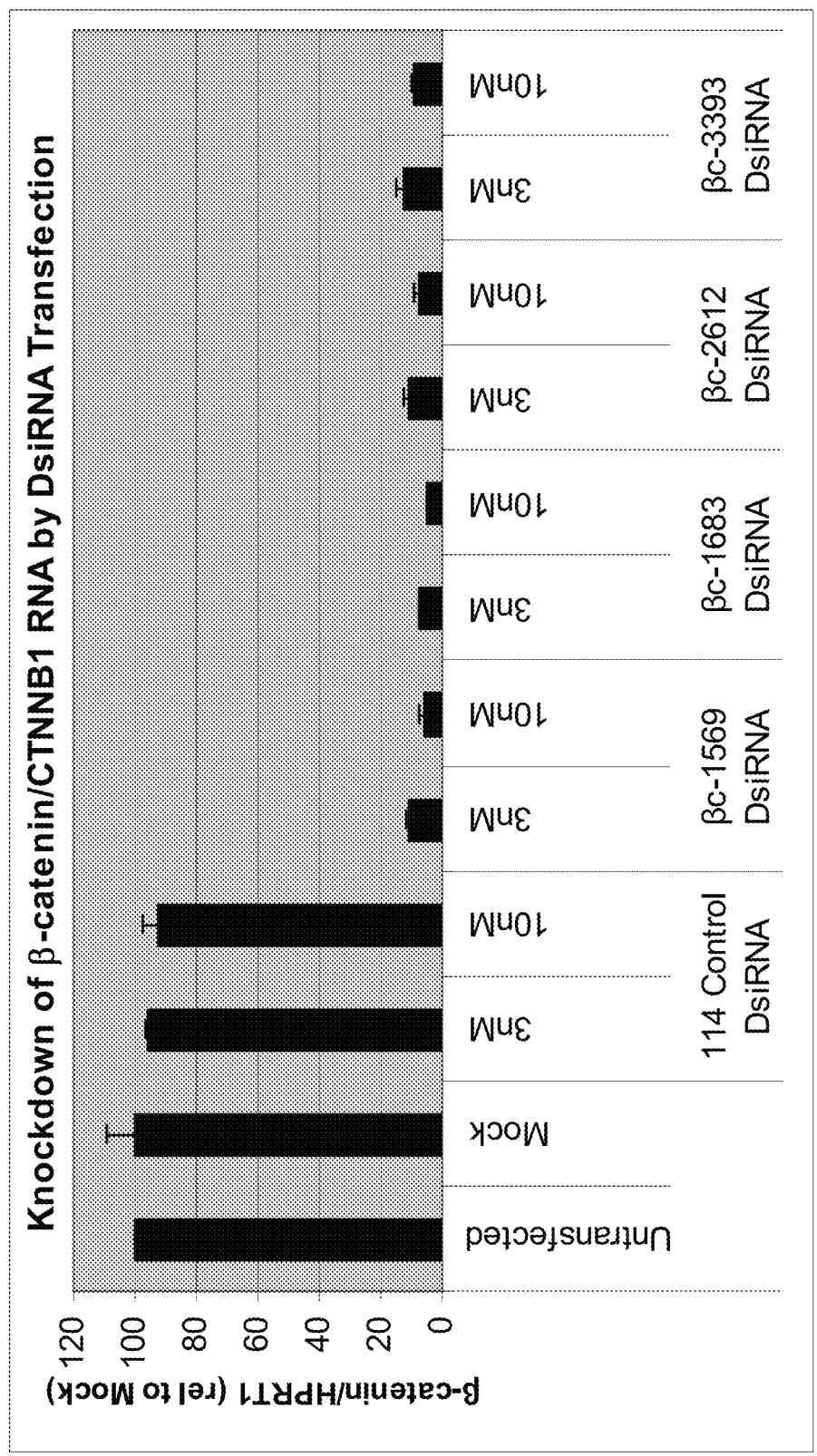
FIG. 6 shows that human β-catenin targeting DsiRNAs effectively reduced β-catenin RNA levels by 90% or more in human HCT116 colon carcinoma cells. HCT116 cells were transfected in vitro with indicated DsiRNAs at 3 nM or 10 nM, and cells were assayed for β-catenin RNA levels at a 24 hour timepoint.

To examine whether human β-catenin targeting DsiRNAs identified as effective at reducing β-catenin transcript levels in HeLa cells were also effective inhibitors of β-catenin in colon cancer cells, four DsiRNAs (βc-1569, βc-1683, βc-2612 and (βc-3393) were transfected into colon carcinoma cell line HCT116. As shown in FIG. 6, βc-1569, βc-1683, βc-2612 and βc-3393 DsiRNAs dramatically (>80%) reduced human β-catenin transcript levels in colon carcinoma cell line HCT116 cells at both 3 nM and 10 nM concentrations in the environment of these cells.

Figure 7:
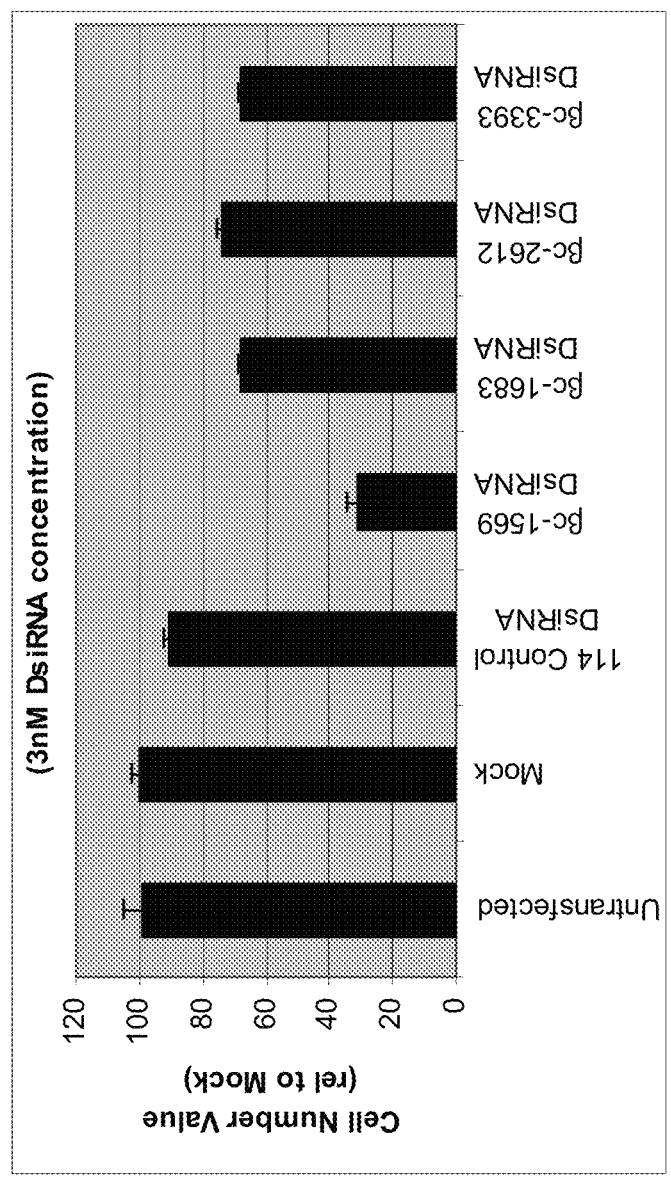
FIG. 7 shows that human β-catenin targeting DsiRNAs significantly inhibited growth of human HepG2 hepatocarcinoma cells. HepG2 cells were transfected in vitro with indicated DsiRNAs at 3 nM, and HepG2 cell lines were assayed for growth at a three day timepoint.
Figure 8:
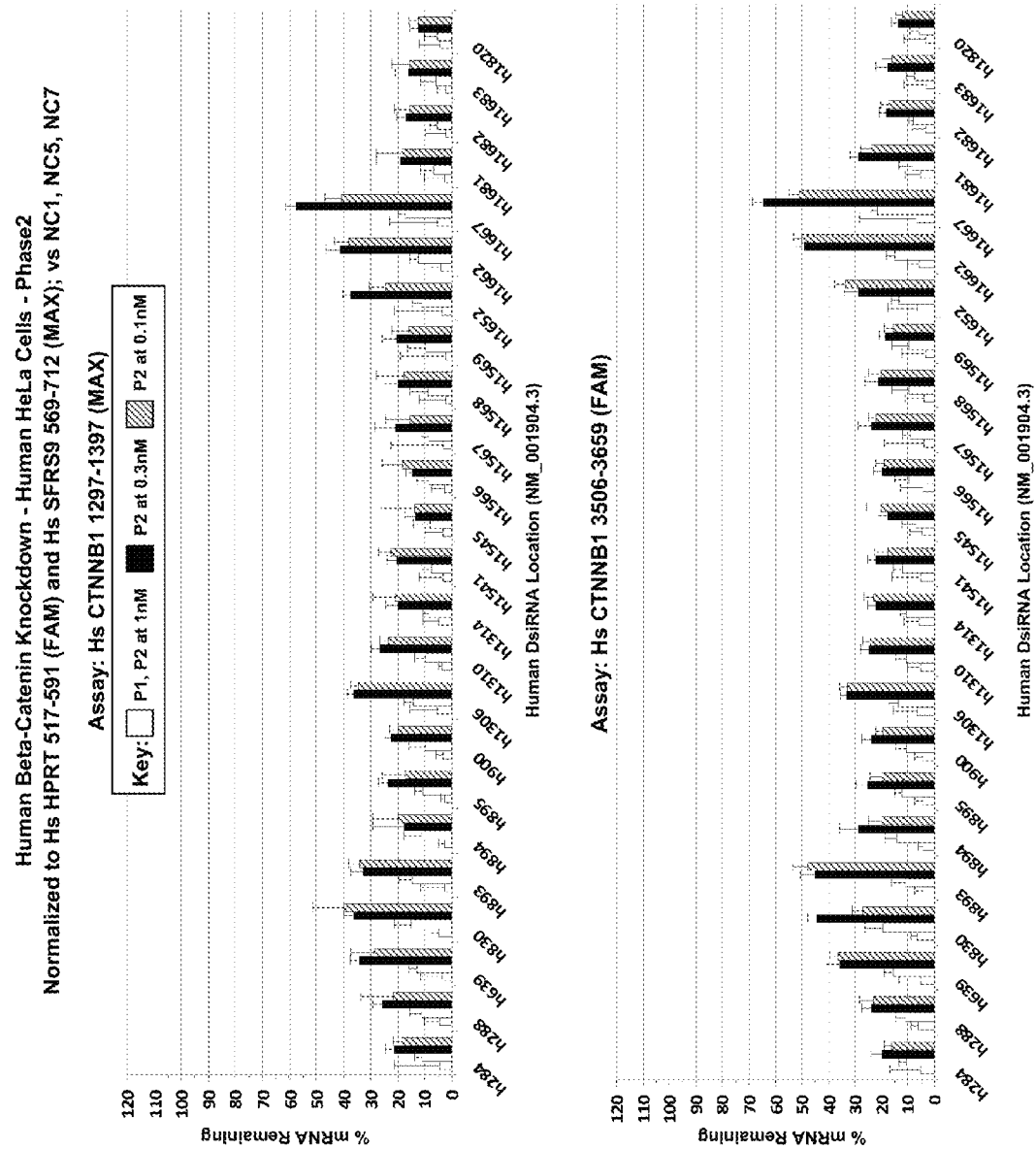
Figure 9:
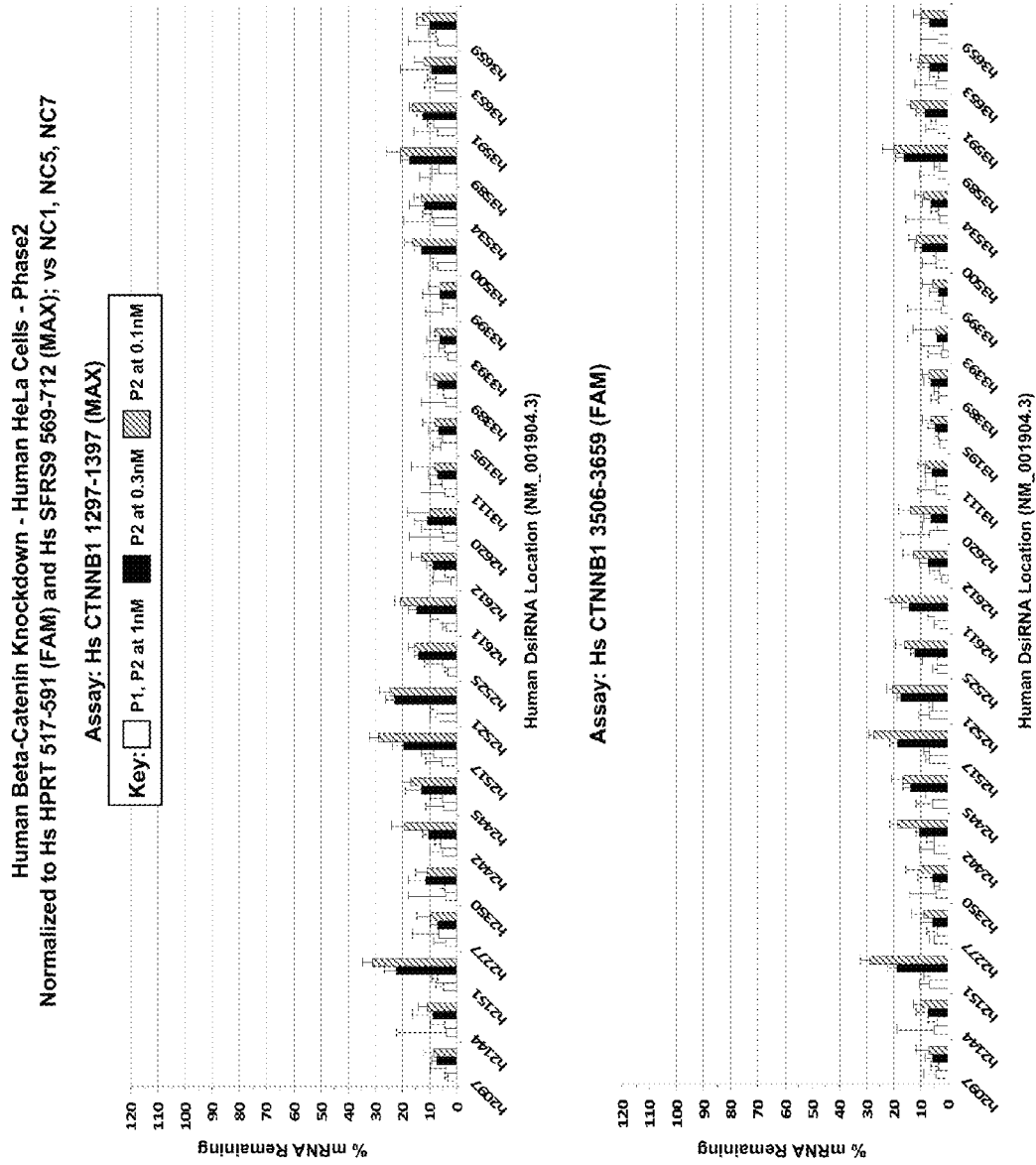
Figure 10:
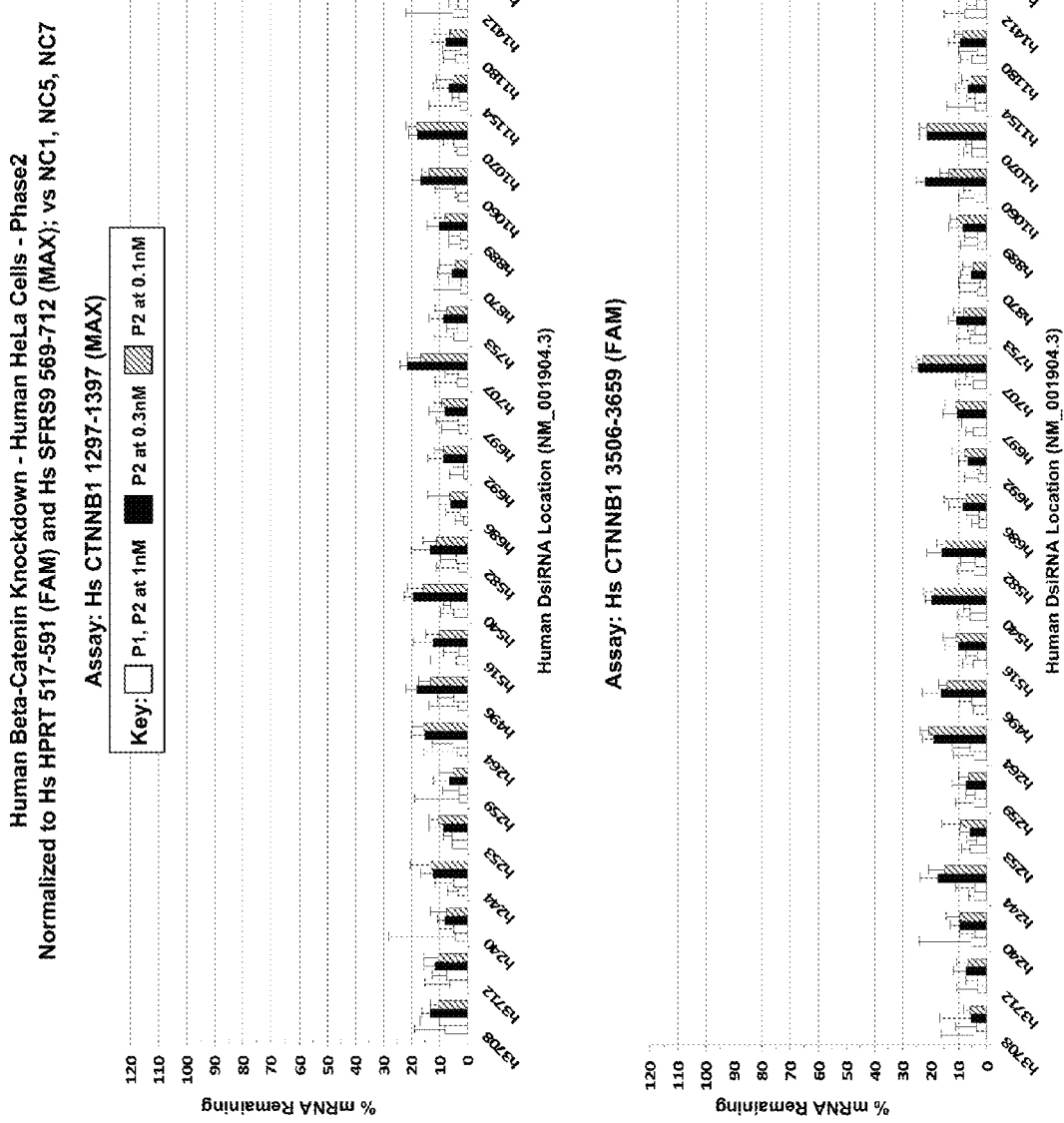
Figure 12:
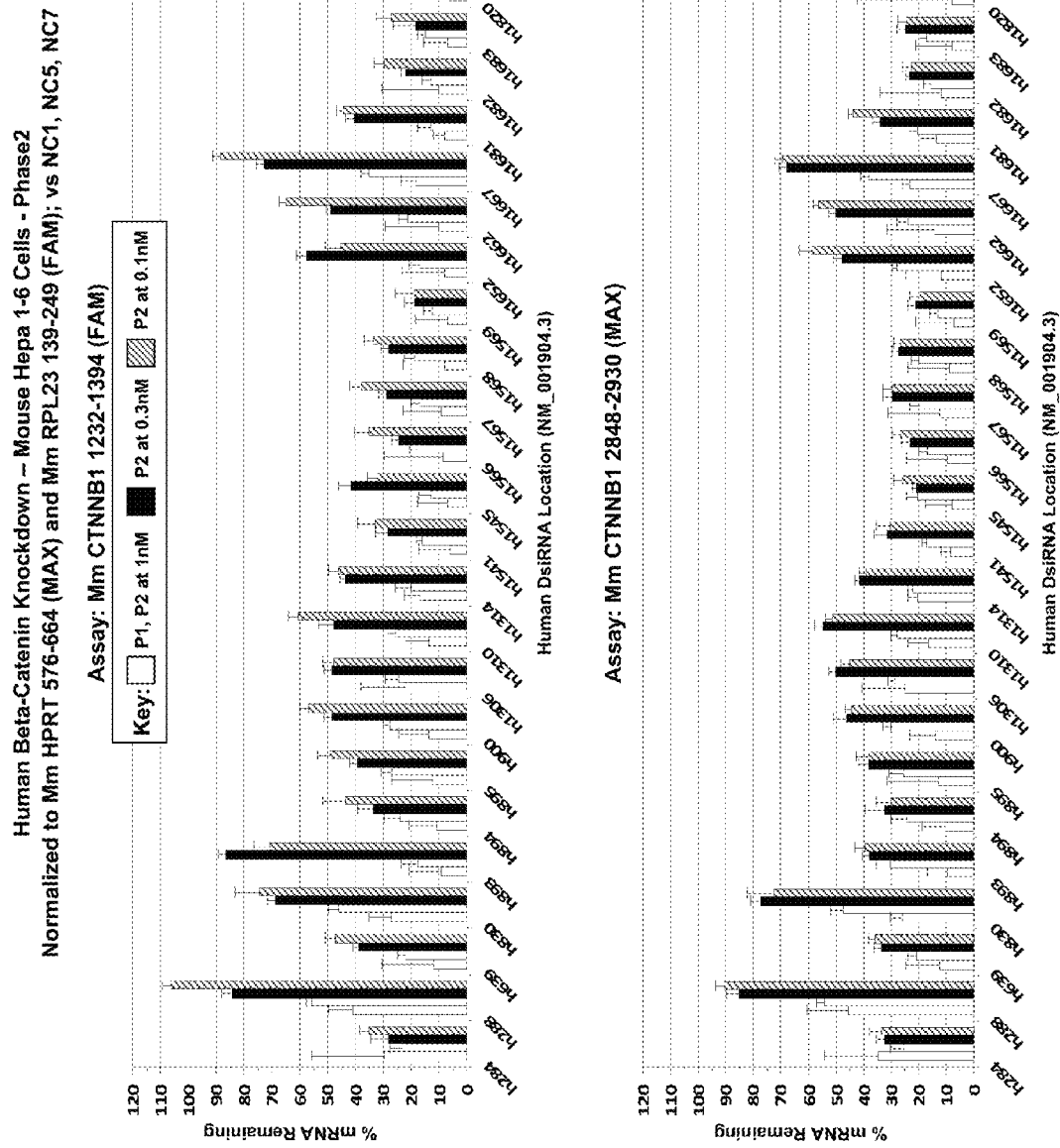
FIGS. 12-15 show histograms of mouse β-catenin inhibitory efficacies observed for indicated DsiRNAs. "P1" indicates phase 1, while "P2" indicates phase 2. In phase 1, DsiRNAs were tested at 1 nM in the environment of mouse Hepa 1-6 cells. In phase 2, DsiRNAs were tested at 1 nM, at 0.3 nM and at 0.1 nM in the environment of mouse Hepa 1-6 cells. Individual bars represent average human β-catenin levels observed in triplicate, with standard errors shown. Human β-catenin levels were normalized to HPRT and RPL23 levels. Expression levels were assayed with probe amplicons positioned at both positions 1232-1394 and 2848-2930 in Mm CTNNB1. (It is noted that the histograms of FIG. 13 reflect phase 2 values obtained for a subpar transfection.)
Figure 13:
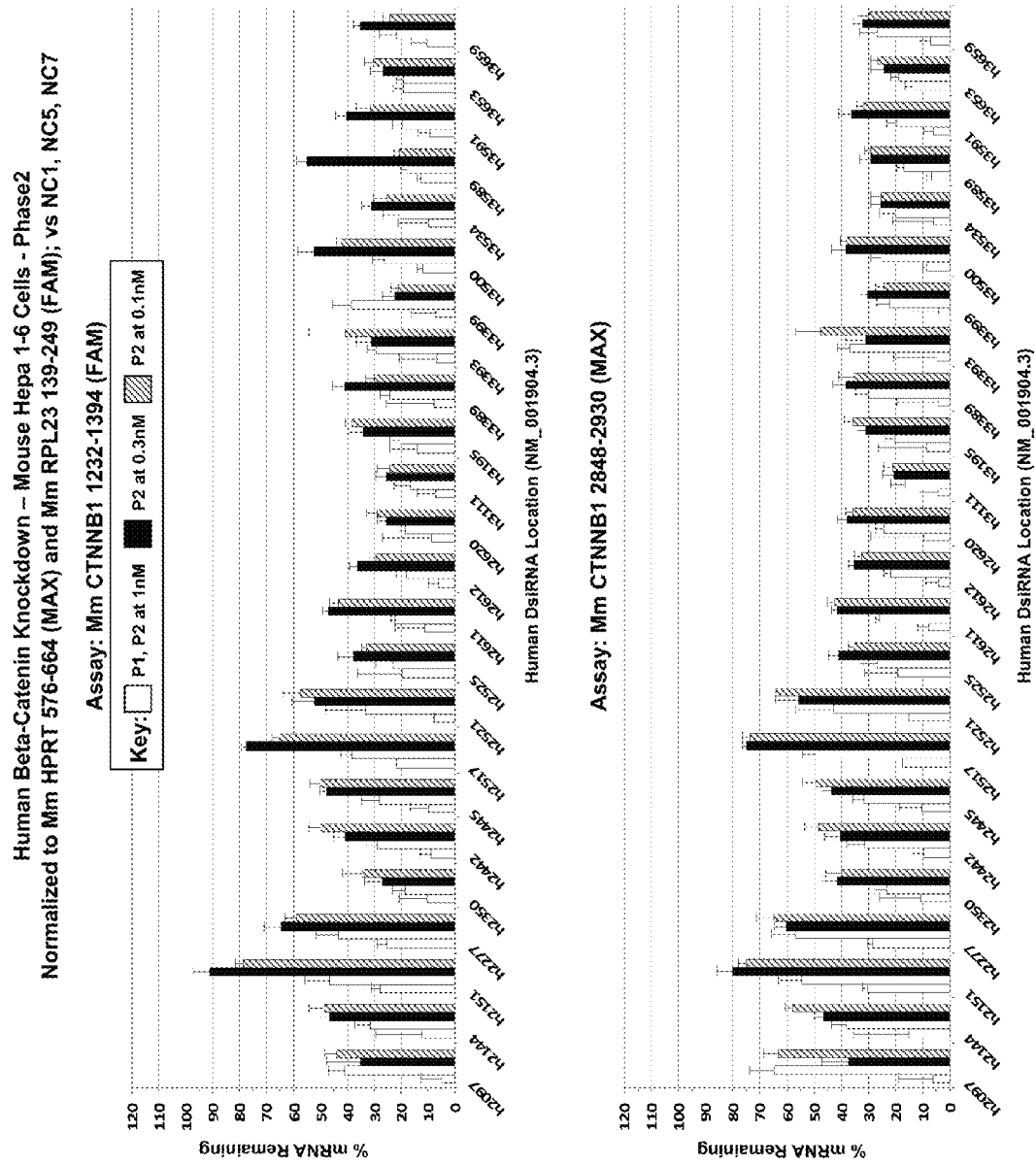
Figure 14:
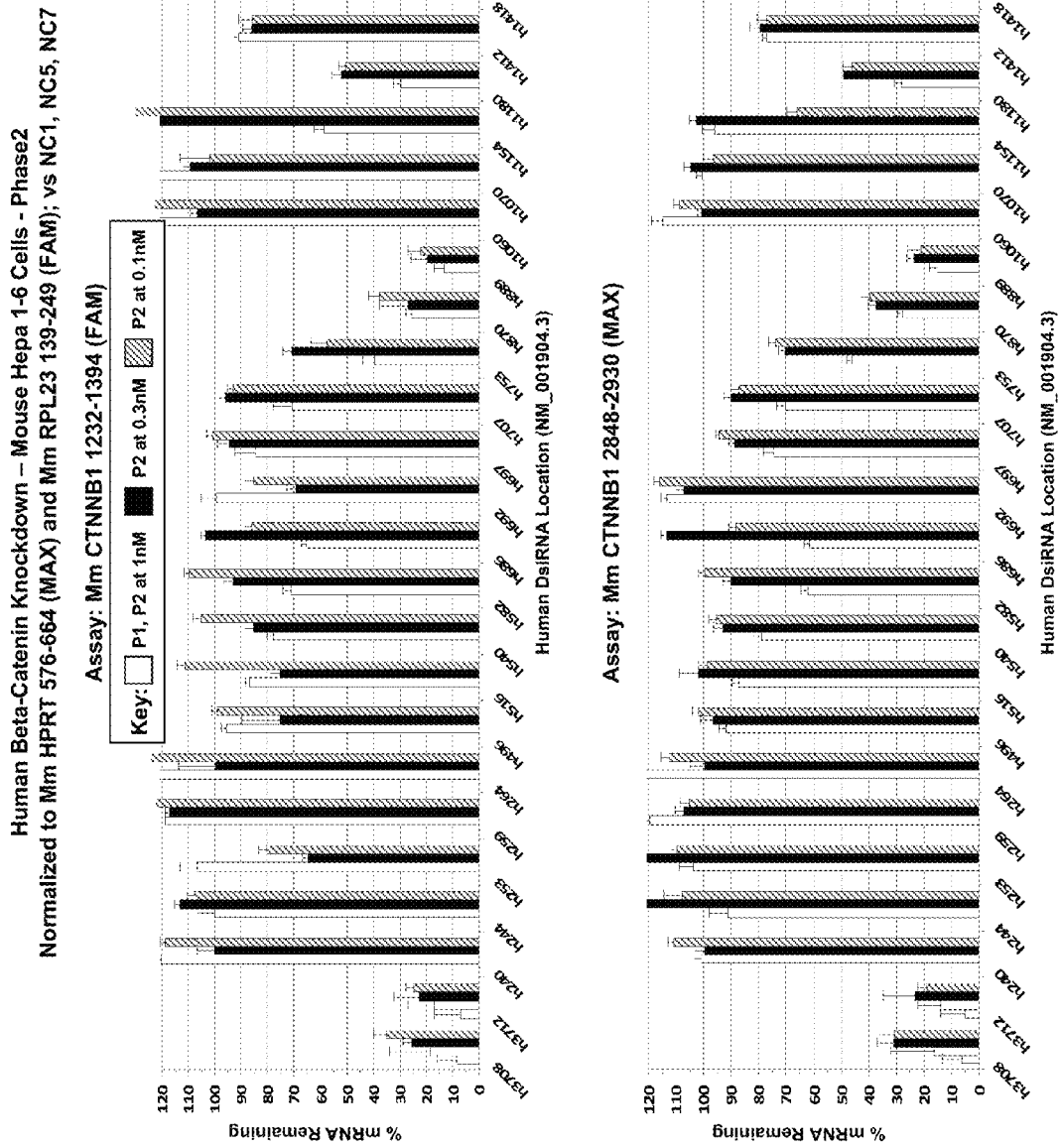
Figure 15:
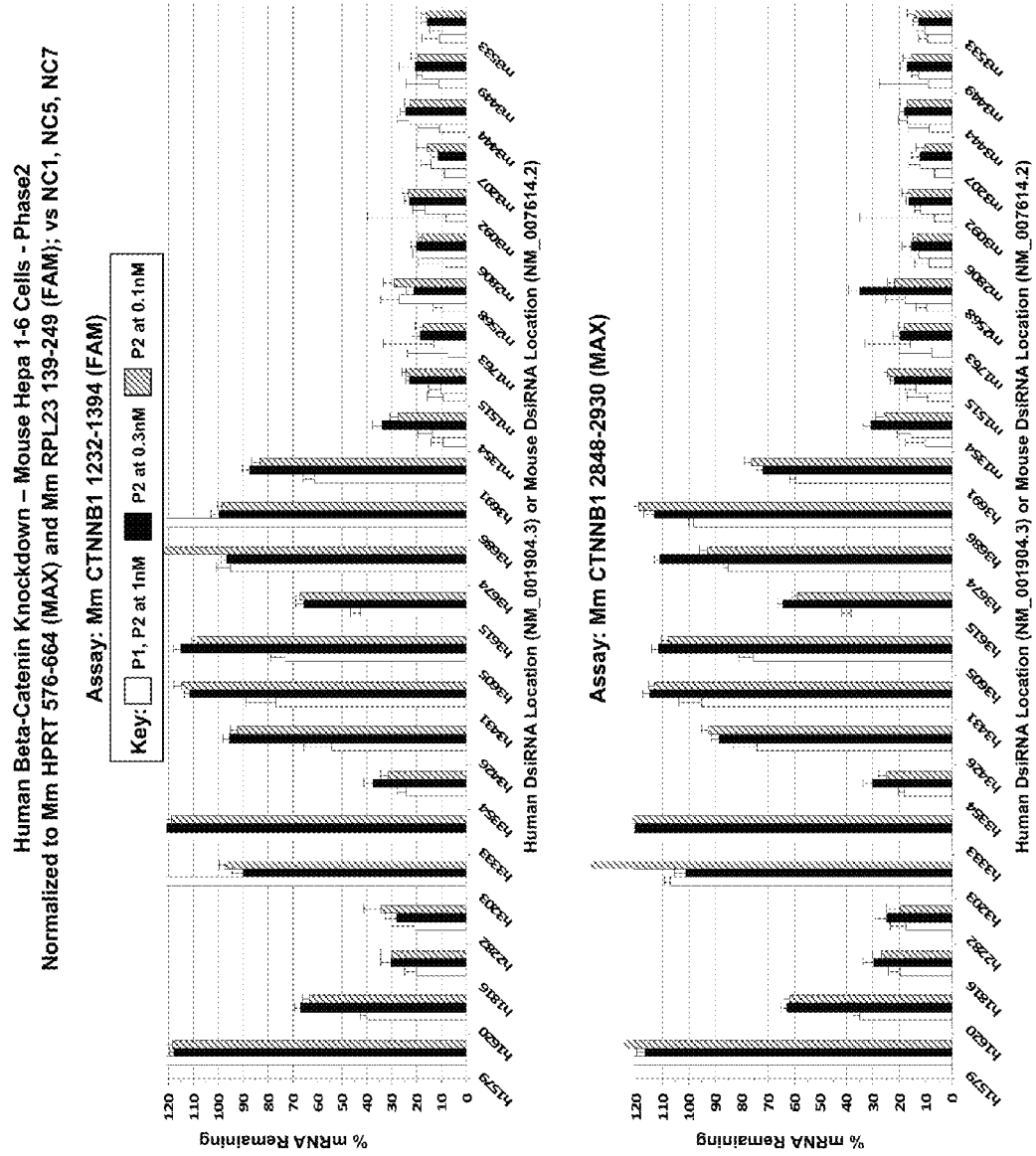

The effects of β-catenin targeting DsiRNAs βc-1569, βc-1683, βc-2612 and βc-3393 were also examined in hepatocarcinoma cell line HepG2, with the effect of DsiRNA treatment upon growth of the hepatocarcinoma cell line assessed. As shown in FIG. 7, following three days of incubation at 3 nM concentration in the environment of HepG2 cells, all four assayed β-catenin targeting DsiRNAs showed significant reduction in tumor cell number (relative to mock-treated and control DsiRNA-treated cells, approximately 30% to 60% or greater cell growth inhibition was observed at day 3 post-transfection). Notably, the β-catenin targeting βc-1569 DsiRNA exhibited approximately 70% reduction in tumor cell numbers, demonstrating the remarkable efficacy of this β-catenin targeting DsiRNA upon a phenotype of therapeutic significance.

Example 4

DsiRNA Inhibition of β-Catenin—Secondary Screen 96 asymmetric DsiRNAs of the above experiment are examined in a secondary assay ("Phase 2"). Specifically, 96 asymmetric DsiRNAs (e.g., βc-284, βc-288, βc-639, βc-830, βc-893, βc-894, βc-895, βc-900, βc-1306, βc-1310, βc-1314, βc-1541, βc-1545, βc-1566, βc-1567, βc-1568, βc-1569, βc-1652, βc-1662, βc-1667, βc-1681, βc-1682, βc-1683, βc-1820, βc-2097, βc-2144, βc-2151, βc-2277, βc-2350, βc-2442, βc-2445, βc-2517, βc-2521, βc-2525, βc-2611, βc-2612, βc-2620, βc-3111, βc-3195, βc-3389, βc-3393, βc-3399, βc-3500, βc-3534, βc-3589, βc-3591, βc-3653, βc-3659, βc-3708, βc-3712, βc-240, βc-244, βc-253, βc-259, βc-264, βc-496, βc-516, βc-540, βc-582, βc-686, βc-692, βc-697, βc-707, βc-753, βc-870, βc-889, βc-1060, βc-1070, βc-1154, βc-1180, βc-1412, βc-1418, βc-1579, βc-1620, βc-1816, βc-2282, βc-3203, βc-3333, βc-3354, βc-3426, βc-3431, βc-3605, βc-3615, βc-3674, βc-3686, βc-3691, βc-m1354, βc-m1515, βc-m1763, βc-m2568, βc-m2806, βc-m3092, βc-m3207, βc-m3444, βc-m3449 and βc-m3533) were assessed for inhibition of human β-catenin at 1 nM, 0.3 nM and 0.1 nM in the environment of human HeLa cells. These 96 asymmetric DsiRNAs are also assessed for inhibition of mouse β-catenin at 1 nM, 0.3 nM and 0.1 nM in the environment of mouse Hepa 1-6 cells. As shown in FIGS. 8-11, a remarkable number of asymmetric DsiRNAs reproducibly exhibited robust human β-catenin inhibitory efficacies at sub-nanomolar concentrations when assayed in the environment of HeLa cells. In addition, as shown in FIGS. 12-15, a number of these asymmetric DsiRNAs also showed robust mouse HIF-1α inhibitory efficacies at 1 nM, 300 pM and 100 pM when assayed in the environment of mouse Hepa 1-6 cells. (Meanwhile, both human β-catenin-specific and mouse β-catenin-specific inhibitory asymmetric DsiRNAs were also identified.)

While $IC_{50}$ values were not formally calculated during secondary screening, it is clear from FIGS. 8-11 that sub-nanomolar (and, indeed, sub-100 pM) $IC_{50}$ values were observed for the vast majority of DsiRNAs. Thus, β-catenin-targeting DsiRNAs were demonstrated to be remarkably potent and effective inhibitors of β-catenin expression.

Example 5

Figure 16:
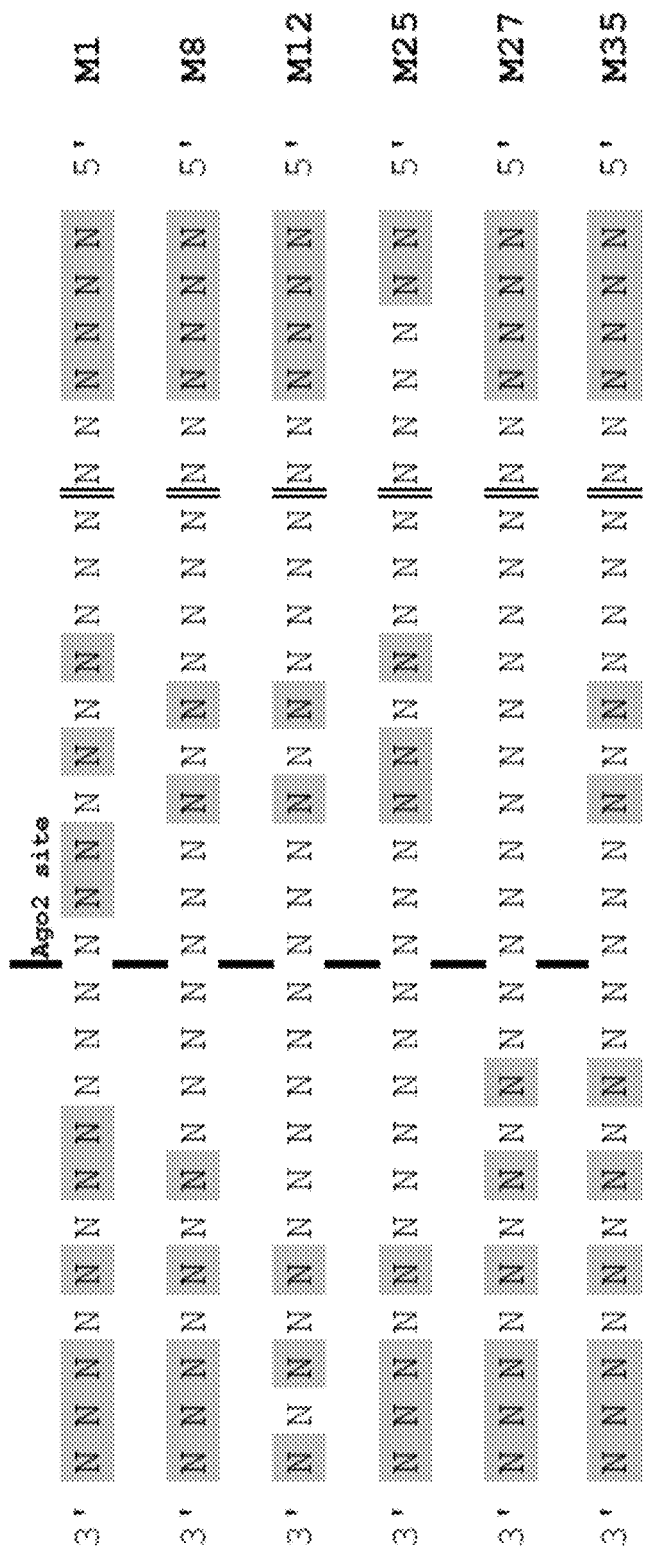
FIG. 16 shows antisense (guide) strand 2'-O-methyl modification patterns employed in phase 3 assays.
Figure 17:
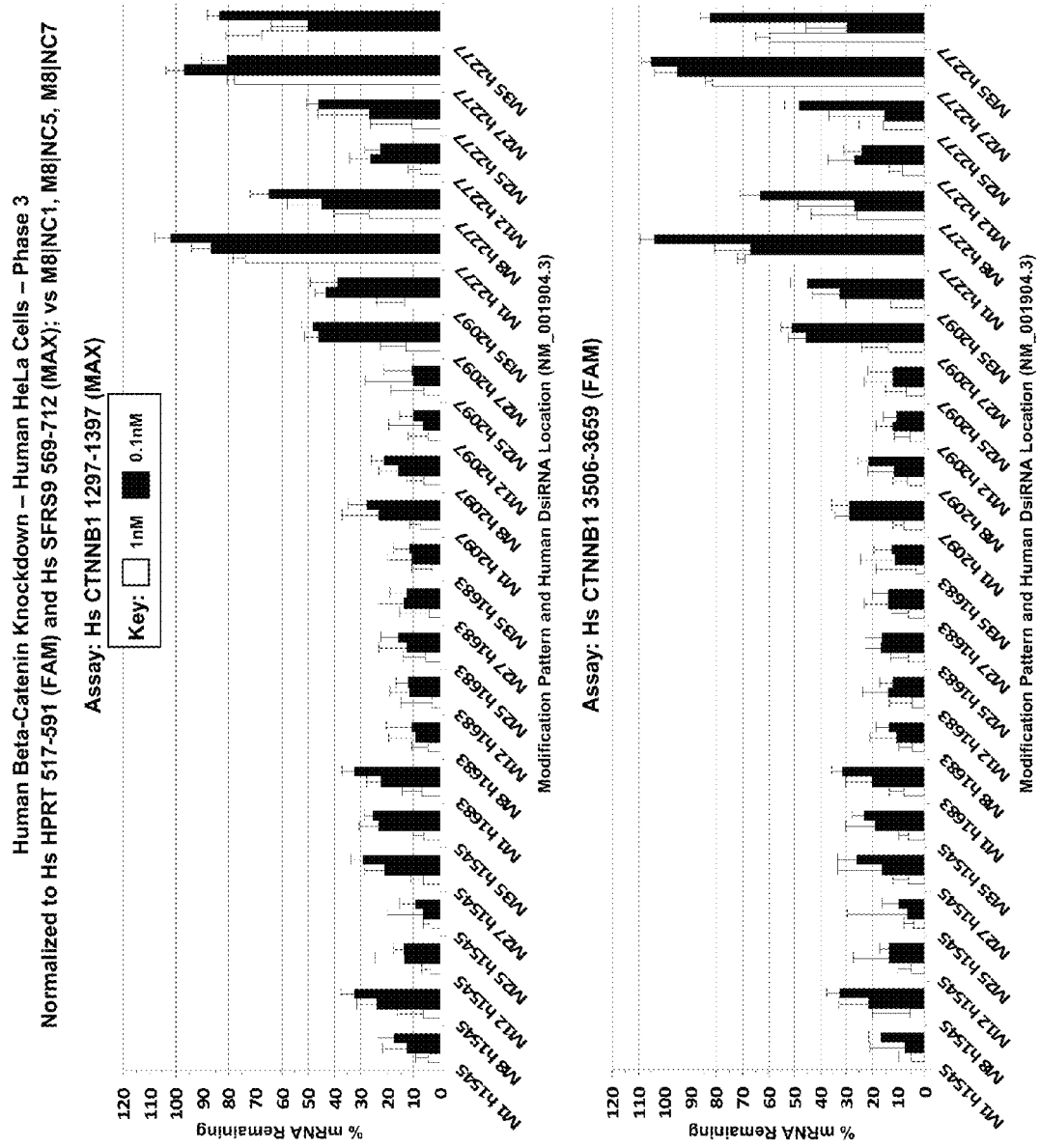
FIGS. 17-24 present histograms showing phase 3 efficacy data for six different guide strand modification patterns each across 32 β-catenin-targeting DsiRNAs in human HeLa cells at 0.1 nM (parallel assays) and 1 nM. Expression levels were assayed with probe amplicons positioned at both positions 1297-1397 and 3506-3659 in Hs CTNNB1, with human β-catenin levels normalized to HPRT and SFRS9 levels.
Figure 18:
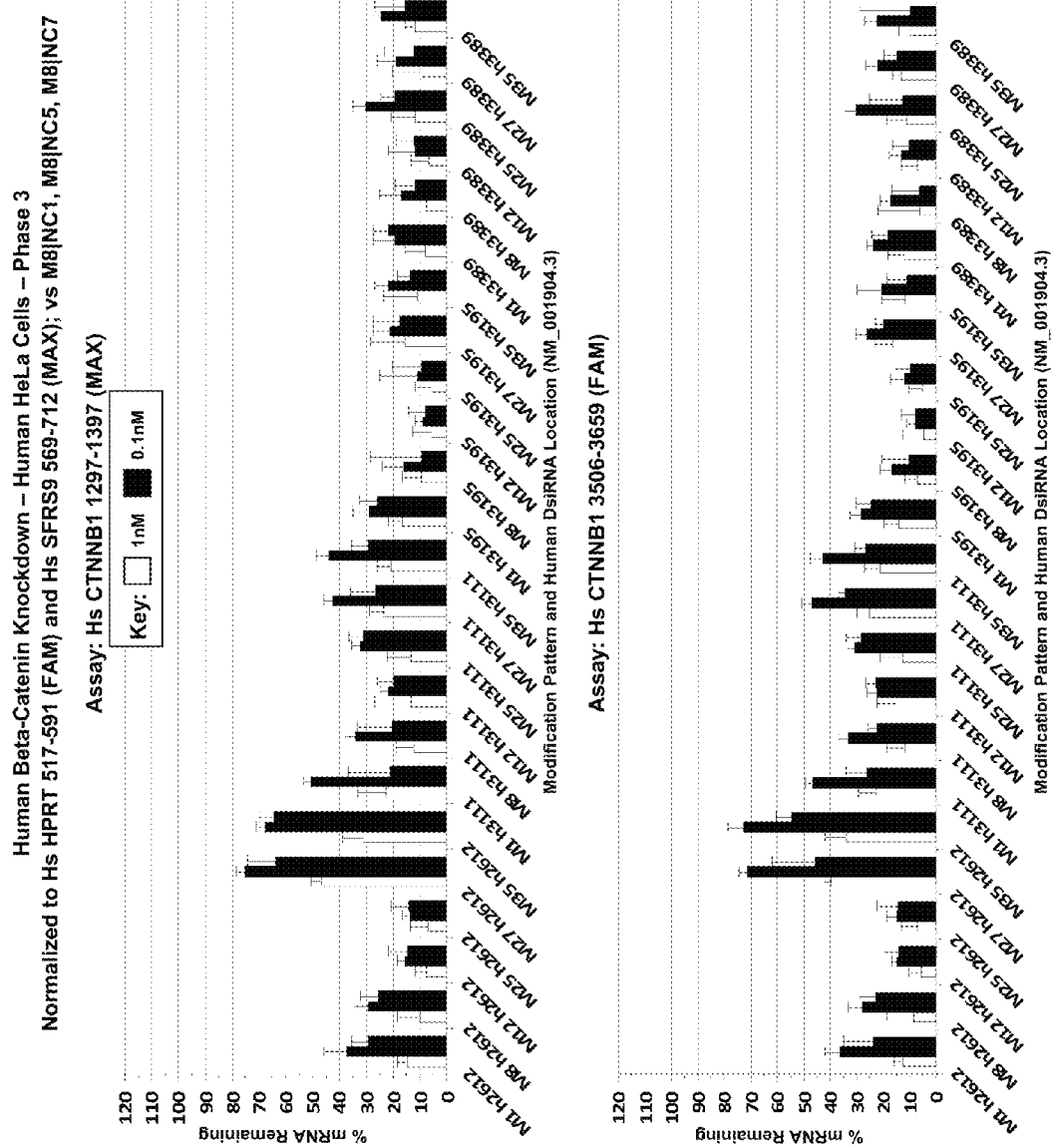
Figure 19:
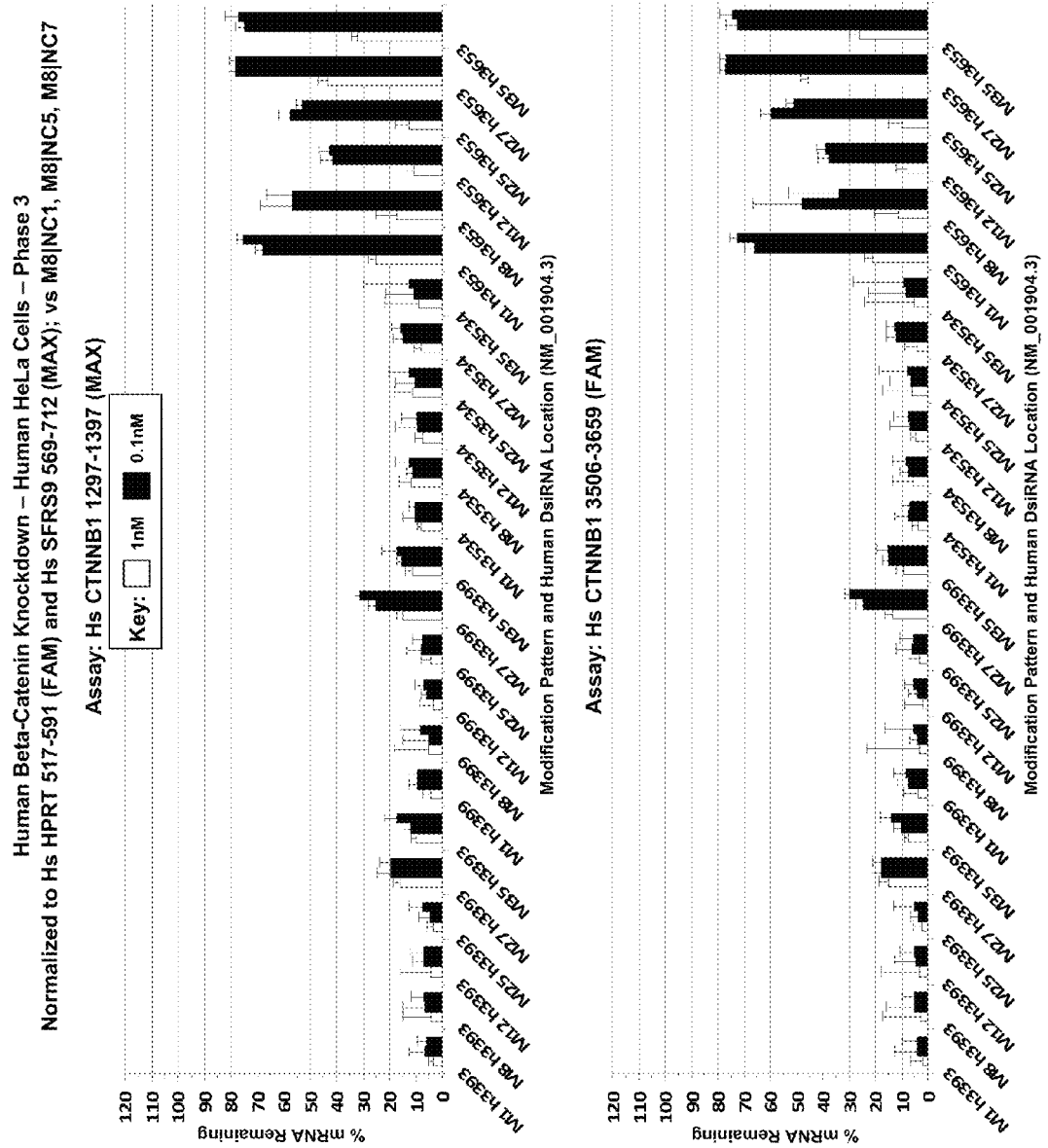
Figure 20:
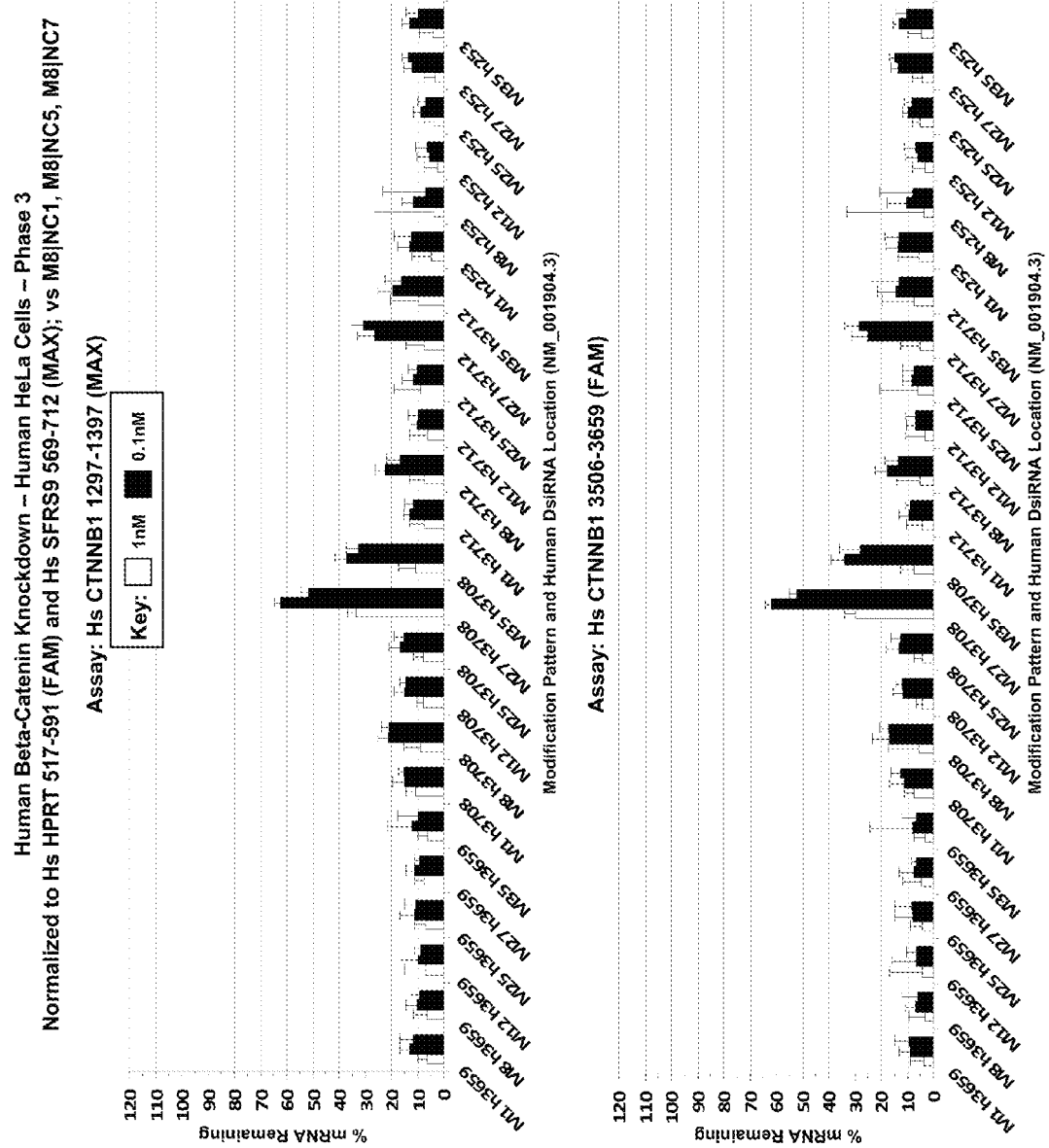
Figure 21:
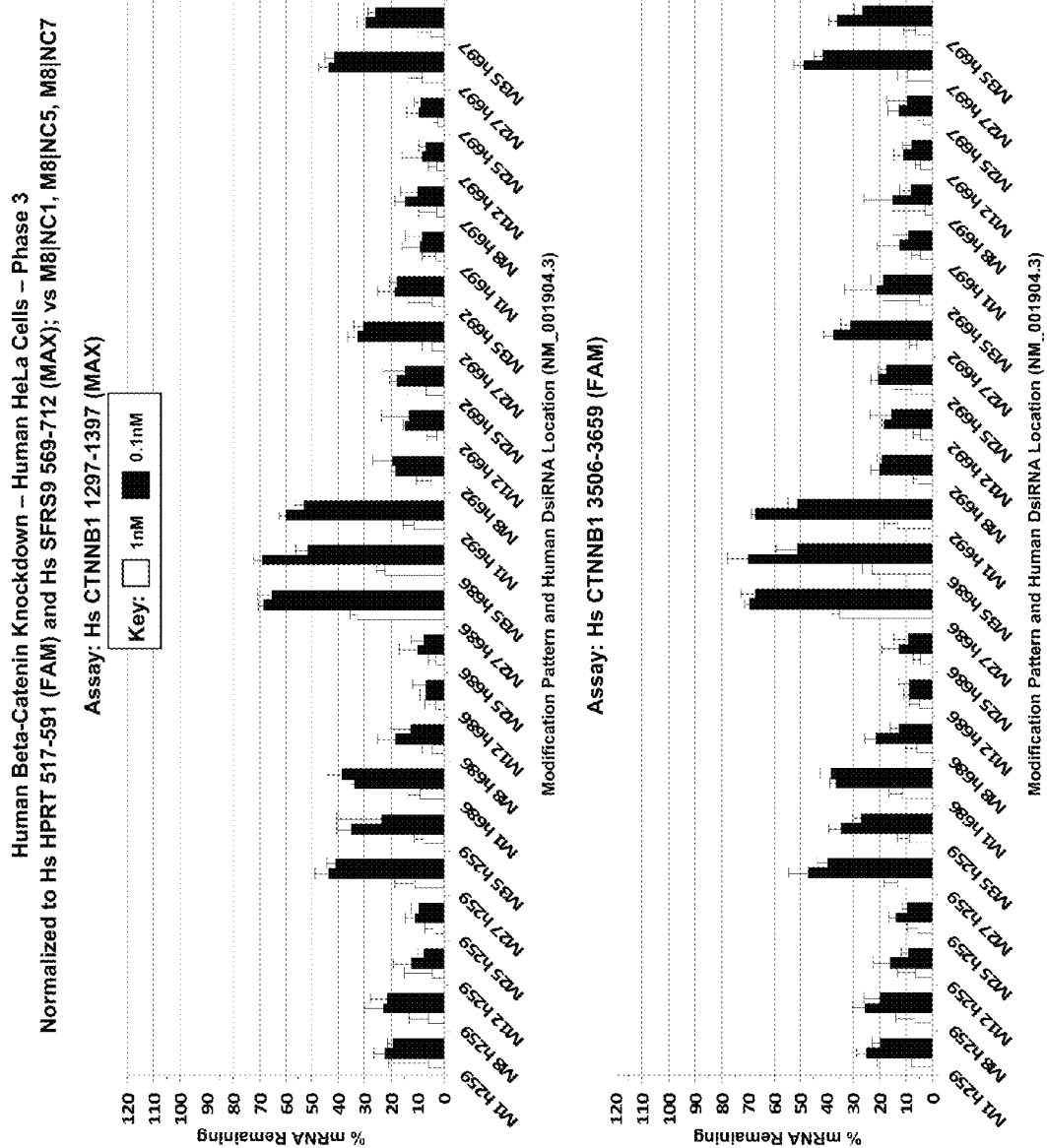
Figure 22:
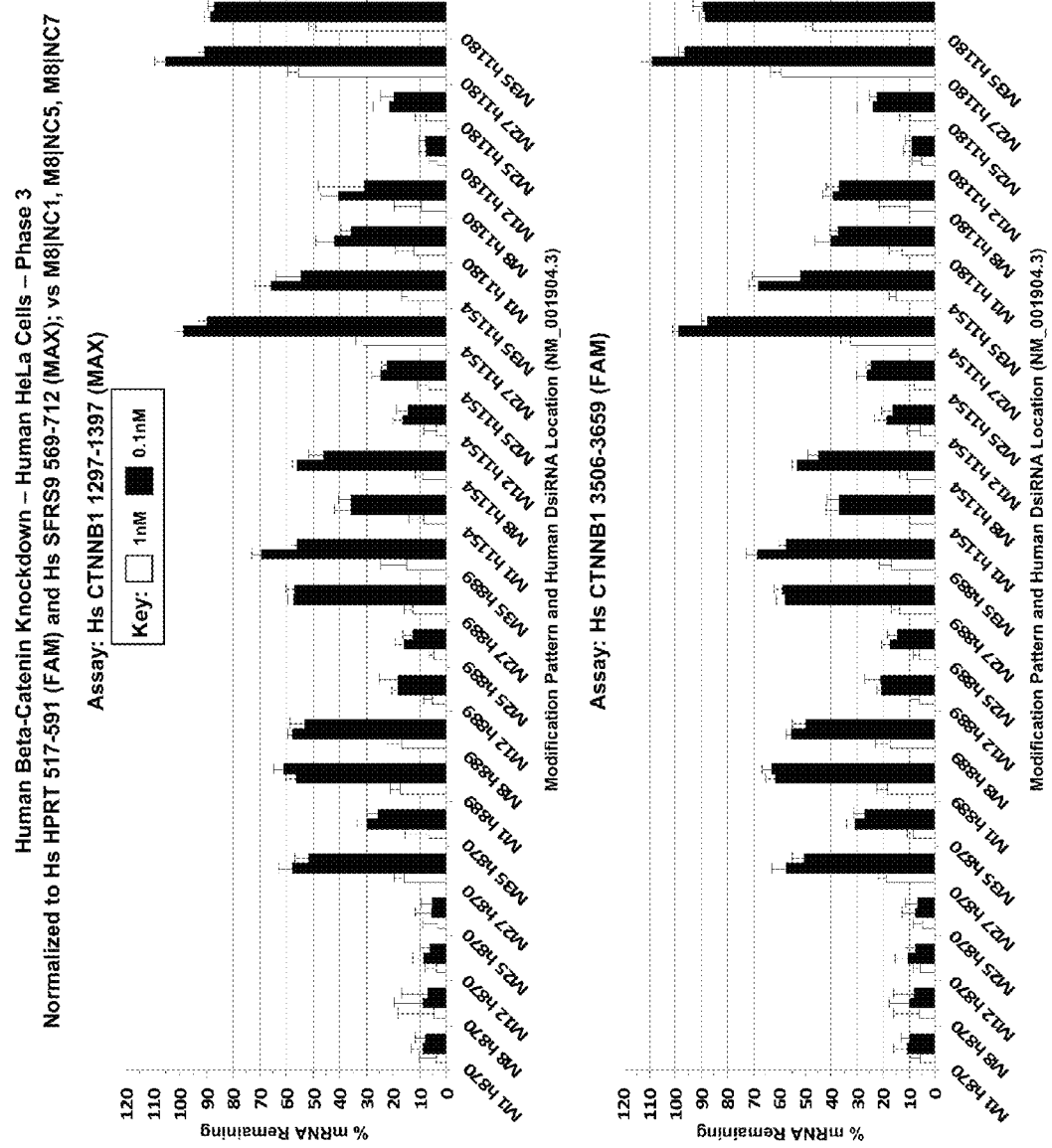
Figure 23:
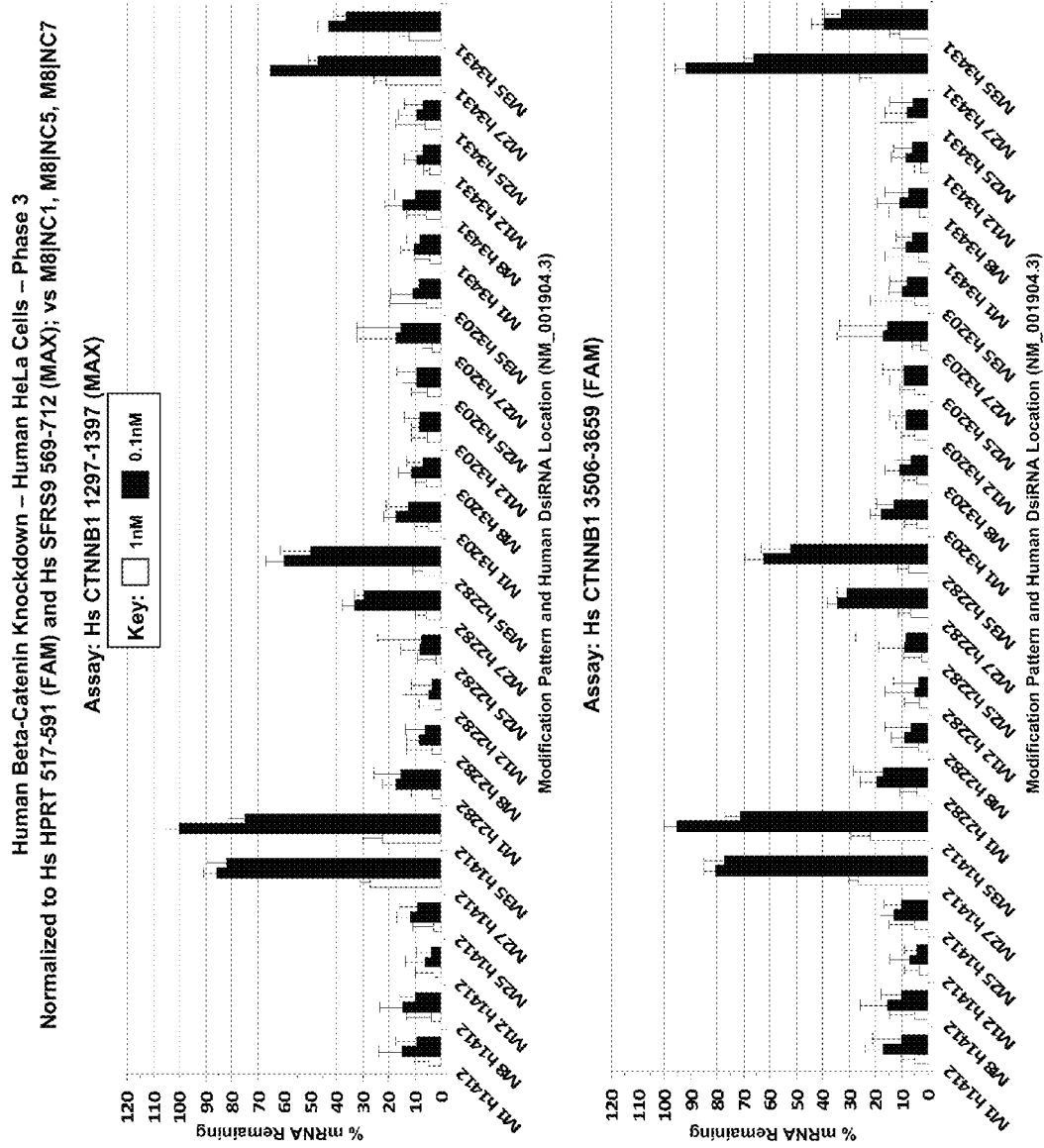
Figure 24:
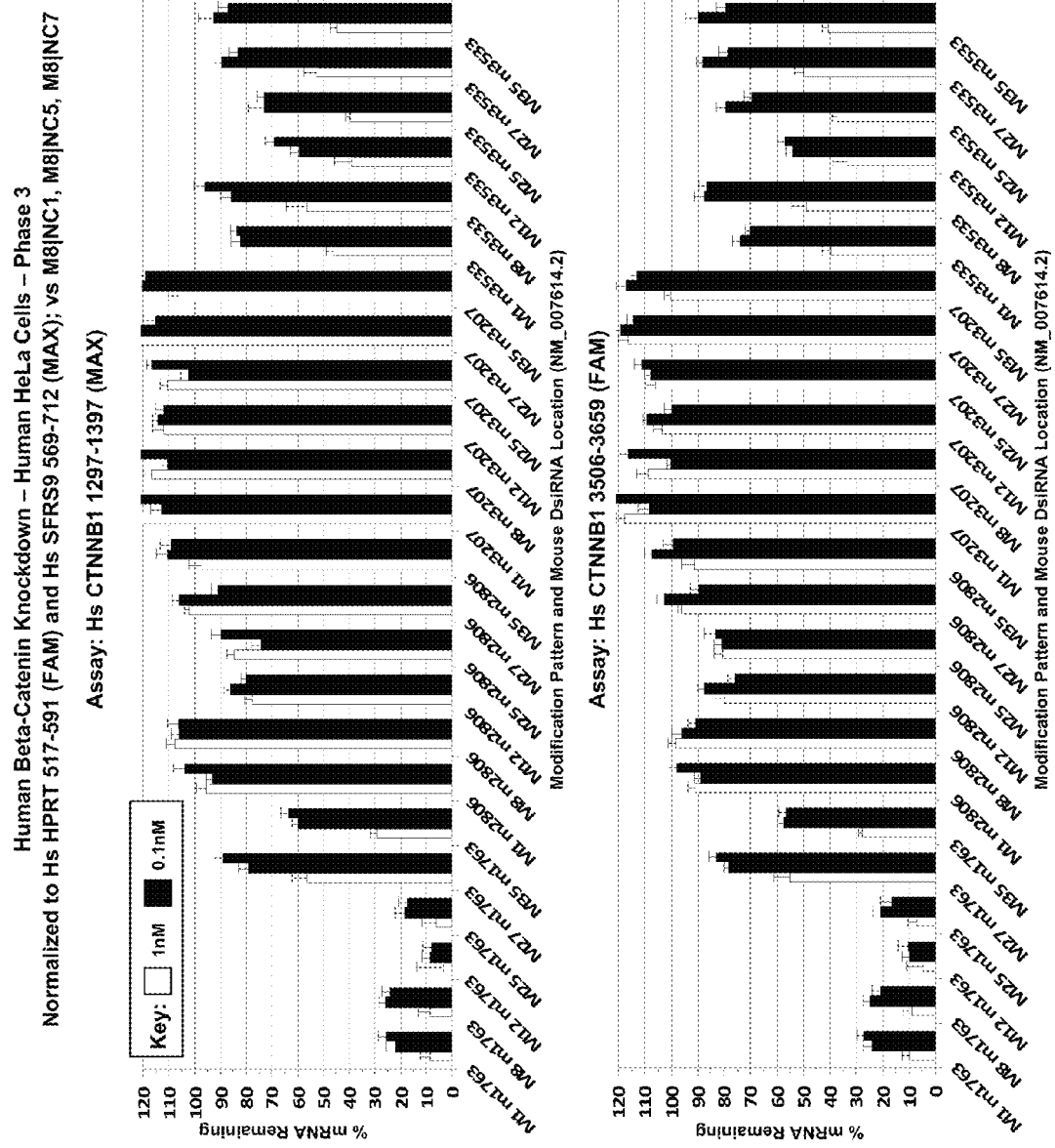

Modified Forms of β-Catenin-Targeting DsiRNAs Reduce 13-Catenin Levels In Vitro 32 β-catenin-targeting DsiRNAs (βc-1545, βc-1683, βc-2097, βc-2277, βc-2612, βc-3111, βc-3195, βc-3389, βc-3393, βc-3399, βc-3534, βc-3653, βc-3659, βc-3708, βc-3712, βc-253, βc-259, βc-686, βc-692, βc-697, βc-870, βc-889, βc-1154, βc-1180, βc-1412, βc-2282, βc-3203, βc-3431, βc-m1763, βc-m2806, βc-m3207 and βc-m3533) were prepared with 2'-O-methyl modification patterns as shown in schematic of FIG. 16. For each of the 32 DsiRNA sequences, DsiRNAs possessing each of the six antisense (guide) strand modification patterns were assayed for β-catenin inhibition in human HeLa cells at 0.1 nM (in parallel assays) and 1.0 nM concentrations in the environment of the HeLa cells. Results of these experiments are presented as histograms in FIGS. 17 to 24. In general, the 32 DsiRNA sequences exhibited a trend towards somewhat reduced efficacy of β-catenin inhibition as the extent of 2'-O-methyl modification of the guide strand increased. However, for almost all DsiRNA sequences examined, a modification pattern could be identified that allowed the DsiRNA to retain significant β-catenin inhibitory efficacy in vitro. It was also notable that many DsiRNAs (e.g., βc-1545, βc-1683, βc-3195, βc-3389, βc-3393, βc-3399, βc-3534, βc-3659, βc-3712, βc-253 and βc-3203) exhibited robust β-catenin inhibitory efficacy in even the most highly modified states examined. These data confirm that it is possible to identify highly effective β-catenin inhibitory DsiRNAs that are robustly tolerant to modification, such that levels of modification sufficient to stabilize such DsiRNAs and/or reduce immunogenicity of such DsiRNAs when therapeutically administered to a subject in vivo can be applied to these DsiRNAs.

In certain embodiments, the invention provides a DsiRNA selected from among one or more of the following:

TABLE 18

Select β-Catenin-Targeting DsiRNAs

| DsiRNA Name | 27 nt Target Sequence | 21 nt Target Sequence |
|---|---|---|
| βc-496 | SEQ ID NO: 2231 | SEQ ID NO: 4449 |
| βc-540 | SEQ ID NO: 2235 | SEQ ID NO: 4453 |
| βc-639 | SEQ ID NO: 2325 | SEQ ID NO: 4543 |
| βc-900 | SEQ ID NO: 2348 | SEQ ID NO: 4566 |
| βc-1545 | SEQ ID NO: 2391 | SEQ ID NO: 4609 |
| βc-2151 | SEQ ID NO: 2477 | SEQ ID NO: 4695 |
| βc-3203 | SEQ ID NO: 2274 | SEQ ID NO: 4492 |
| βc-3399 | SEQ ID NO: 2618 | SEQ ID NO: 4836 |
| βc-3591 | SEQ ID NO: 2645 | SEQ ID NO: 4863 |
| βc-3708 | SEQ ID NO: 2661 | SEQ ID NO: 4879 |

Among the DsiRNAs of Table 18 that were tested in the above-described modified DsiRNA assays, βc-1545, βc-3203 and βc-3399 were shown to be robustly effective DsiRNA sequences even when modified (and βc-1545 and βc-3399 were observed to be highly effective inhibitors of β-catenin under all modification conditions examined).

Example 6

β-Catenin-Targeting DsiRNAs Reduced Axin-2 Levels In Vitro

Figure 26:
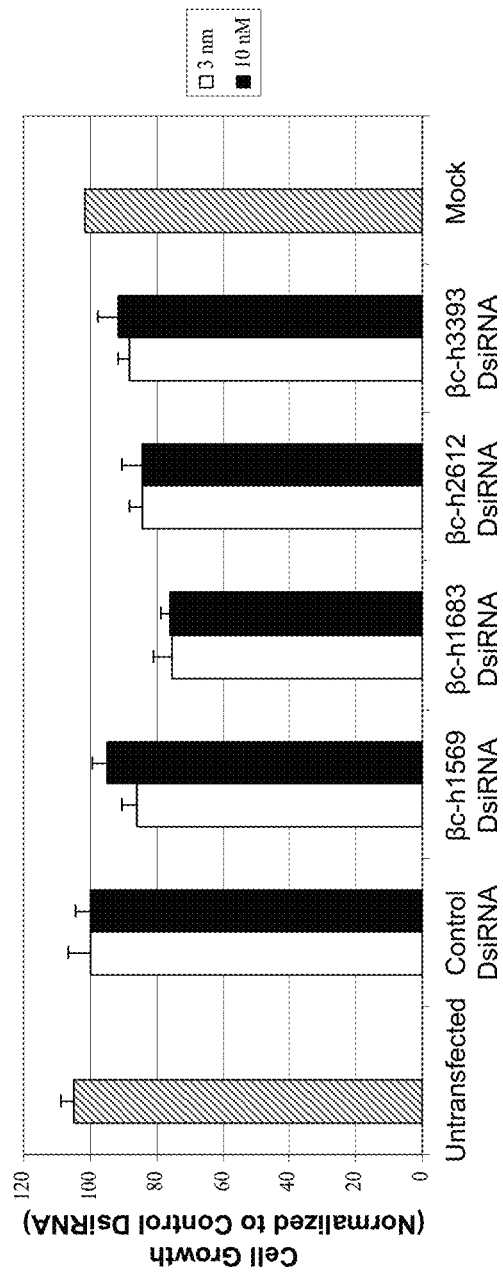
FIG. 26 shows that transfection of human colorectal cancer cell line HCT116 cells with certain DsiRNAs targeting human β-catenin (βc-h1683, βc-h2612 and βc-h3393) inhibited the growth of such cells at five days post-transfection, as compared to cells administered a control DsiRNA. Cell growth inhibition was assayed using a CellTiter-Blue® Cell Viability Assay (Promega) at five days post-transfection.

The impact of β-catenin-targeting DsiRNAs upon Axin-2, a known downstream target of β-catenin was examined in both HCT116 (colon carcinoma) and HepG2 (hepatocellular carcinoma) cell lines. As shown in FIG. 26, βcat-h1569, βcat-h1683, βcat-h2612 and βcat-h3393 were all robust inhibitors of Axin-2, with approximately 80%-90% knockdown observed for each of these DsiRNAs in both cell lines. Cells were assayed at two days post-transfection at indicated concentrations (3 nM and 10 nM) with designated DsiRNAs. Thus, the effect of β-catenin knockdown was also observed in the mRNA levels of the downstream target of β-catenin, Axin-2.

Example 7

β-Catenin Targeting DsiRNAs Inhibited Tumor Cell Growth in Colorectal and Hepatocellular Carcinoma Cell Lines As described above, FIG. 7 shows the growth inhibitory impact of β-catenin-targeting DsiRNAs upon HepG2 hepatocellular carcinoma cells. To identify whether such cell growth inhibitory effects could also be observed in other cancer cell lines, the impact of β-catenin-targeting DsiRNAs upon growth of both HCT116 (colorectal carcinoma) and HuH7 (hepatocellular carcinoma) cell lines was also examined. As shown in FIG. 26, transfection of human colorectal cancer cell line HCT116 cells with certain DsiRNAs targeting human β-catenin (βc-1683, βc-2612 and βc-3393) inhibited the growth of such cells at five days post-transfection, as compared to cells administered a control DsiRNA. Cell growth inhibition was assayed using a CellTiter-Blue® Cell Viability Assay (Promega) at five days post-transfection.

Figure 27:
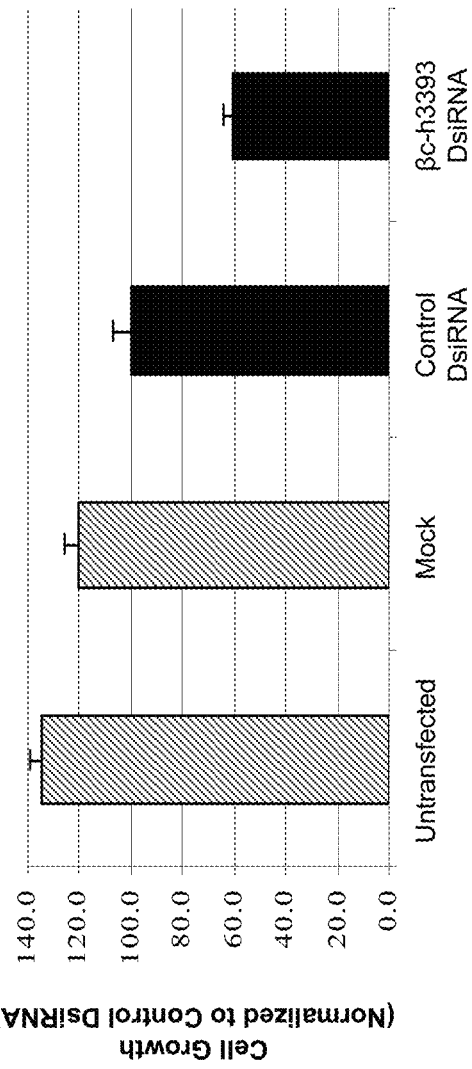
FIG. 27 shows that transfection of human hepatocellular carcinoma cell line HuH7 cells with a DsiRNA targeting human β-catenin inhibited the growth of such cells at five days post-transfection, as compared to cells administered a control DsiRNA. Cell growth inhibition was assayed using a CellTiter-Blue® Cell Viability Assay (Promega) at five days post-transfection.

More robust inhibition of cancer cell line growth was observed following administration of βc-3393 DsiRNA to human hepatocellular carcinoma cell line HuH7 cells (FIG. 27). At five days post-transfection, approximately 40% inhibition of HuH7 cell growth was observed, as compared to cells administered a control DsiRNA. Cell growth inhibition was assayed using a CellTiter-Blue® Cell Viability Assay (Promega) at five days post-transfection. Thus, the cancer cell line growth inhibitory effect of β-catenin-targeting DsiRNAs was observed to be generalizable across at least three distinct cell lines (and was surprisingly robust in the two distinct hepatocellular carcinoma cell lines examined, HepG2 and HuH7).

Figure 28:
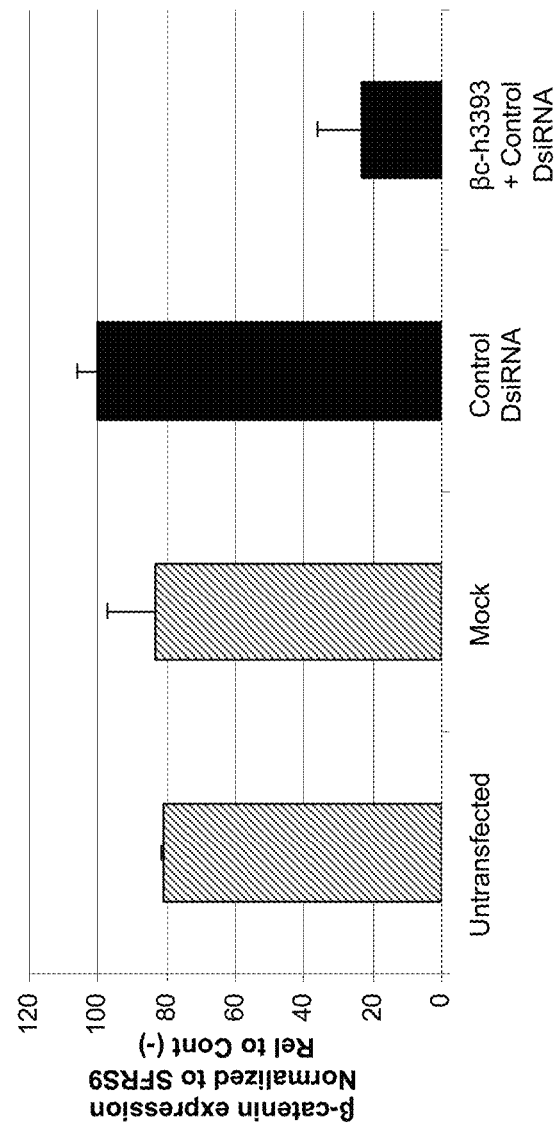
FIG. 28 shows that transfection of human hepatocellular carcinoma cell line HuH7 cells with a DsiRNA targeting human β-catenin (specifically, a βc-h3393 25/27mer possessing an "M11" modified antisense (guide) strand consisting of 2'-O-methyl modifications at the following positions starting from the 5'-terminus (position 1) of the antisense strand: 1, 2, 3, 4, 11, 13, 25 and 27) produced knockdown of β-catenin levels of approximately 80% at two days post-transfection, when administered with a control DsiRNA, as compared to cells administered only the control DsiRNA.

As shown in FIG. 28, transfection of human hepatocellular carcinoma cell line HuH7 cells with a DsiRNA targeting human β-catenin (specifically, a βc-3393 25/27mer possessing an "M11" modified antisense (guide) strand consisting of 2'-O-methyl modifications at the following positions starting from the 5'-terminus (position 1) of the antisense strand: 1, 2, 3, 4, 11, 13, 25 and 27) produced knockdown of 3-catenin mRNA levels of approximately 80% at two days post-transfection, when administered with a control DsiRNA, as compared to cells administered only the control DsiRNA. Thus, β-catenin-targeting DsiRNAs were potent inhibitors of both β-catenin expression levels and of cell growth in hepatocellular carcinoma cell lines HepG2 and HuH7.

Figure 29:
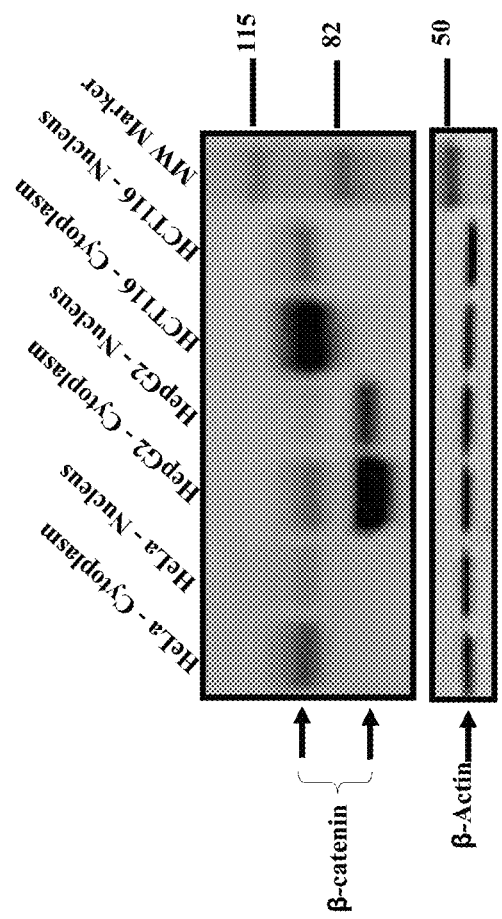
FIG. 29 shows fractionated human β-catenin protein levels found in HeLa (cervical cancer), HepG2 (hepatocellular liver carcinoma) and HCT116 (colorectal carcinoma) cell lines. Nuclear and cytoplasmic levels of β-catenin were identified for each cell line via Western blot, with β-actin levels assayed as an internal control. Cell extracts were obtained from confluent six well pates, using a NE-PER Nuclear and Cytoplasmic Extraction Reagents Kit (Thermo Fisher Scientific Inc). 75 ug of protein was loaded from each cell line. A known truncation mutant form of β-catenin protein was observed in HepG2 cells.

The expression of β-Catenin in human HeLa, HepG2 and HCT116 carcinoma cell lines was confirmed in vitro, with subcellular distribution of expressed β-Catenin protein also examined. Nuclear and cytoplasmic levels of β-catenin were identified for each cell line via Western blot (FIG. 29), with 3-actin levels assayed as an internal control. Cell extracts were obtained from confluent six well pates, using a NE-PER Nuclear and Cytoplasmic Extraction Reagents Kit (Thermo Fisher Scientific Inc). 75 ug of protein was loaded from each cell line. HeLa (cervical cancer), HepG2 (hepatocellular liver carcinoma) and HCT116 (colorectal carcinoma) cell lines each expressed β-Catenin protein at robust levels, with β-Catenin protein primarily found in the cytoplasm of each cell type (though significant nuclear fractions were also observed for each cell type). Notably, a known truncation mutant form of β-catenin protein was observed in HepG2 cells.

Example 8

β-Catenin-Targeting DsiRNAs Reduced 13-Catenin mRNA and Protein Levels In Vivo

Figure 30:
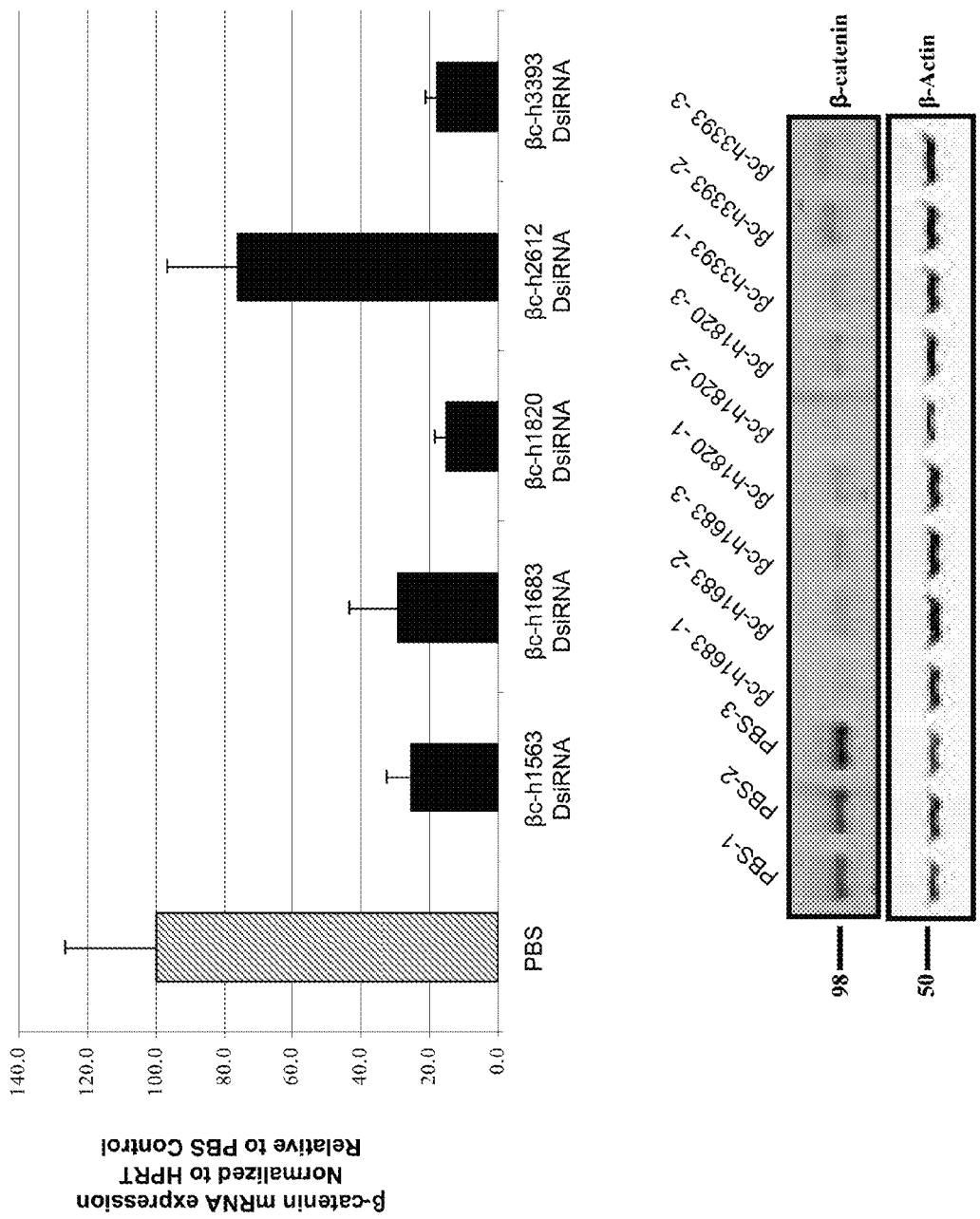
FIG. 30 demonstrates that DsiRNAs targeting human β-catenin were active in vivo in normal mouse liver, inhibiting both β-catenin mRNA (top panel) and protein (bottom panel) levels significantly (e.g., in many instances, approximately 70-90% knockdown was observed) when administered as a single dose intravenously to normal mice (n=5 mice per group) at 10 mg/kg and formulated in Invivofectamine® 2.0 (Invitrogen™, Carlsbad, Calif.). Liver tissue was harvested at 72 hours post-administration. All DsiRNAs targeting human β-catenin possessed "M11" modified antisense (guide) strands.

The impact of β-Catenin-targeting DsiRNAs upon β-Catenin expression levels was examined in vivo. Specifically, human β-catenin-targeting DsiRNAs βc-1683, βc-1820 and βc-3393 (previously noted as also being active inhibitors of mouse β-Catenin) were demonstrated to be remarkably effective inhibitors of mouse β-catenin expression in vivo in normal mouse liver, inhibiting both β-catenin mRNA (FIG. 30, top panel) and protein (FIG. 30, bottom panel) levels significantly (e.g., for these DsiRNAs, approximately 70-90% knockdown was observed) when administered as a single dose intravenously to normal mice (n=5 mice per group) at 10 mg/kg and formulated in Invivofectamine® 2.0 (Invitrogen™, Carlsbad, Calif.). In such experiments, liver tissue was harvested at 72 hours post-administration. All DsiRNAs targeting β-catenin possessed "M11" modified antisense (guide) strands. Notably, βc-1563 also exhibited robust inhibition of β-catenin mRNA levels in vivo; however, corresponding β-catenin protein levels were not assessed for this DsiRNA. Meanwhile, βc-2612 was also observed to inhibit β-catenin mRNA levels, even if not to the extent observed for βc-1563, βc-1683, βc-1820 and βc-3393, or to the extent observed for certain modified forms of βc-2612 in additional experiments described below.

Figure 31:
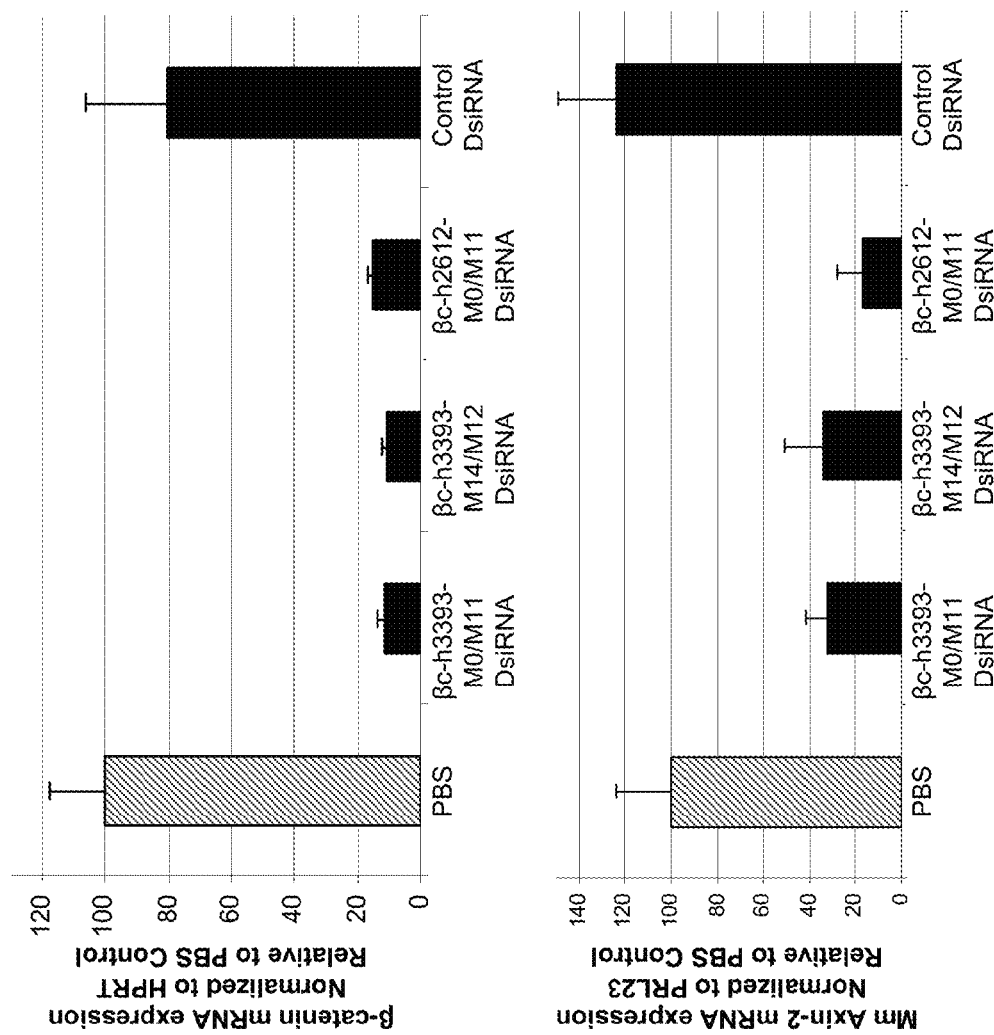
FIG. 31 shows that DsiRNAs targeting human β-catenin were active in vivo in normal mouse liver, inhibiting both β-catenin mRNA (top panel) and Axin-2 mRNA (bottom panel) levels significantly (e.g., in many instances, approximately 70-90% knockdown was observed) when administered as a single dose intravenously to normal mice (n=5 mice per group) at 10 mg/kg and formulated in Invivofectamine® 2.0 (Invitrogen™, Carlsbad, Calif.). Liver tissue was harvested at 72 hours post-administration. DsiRNAs targeting human β-catenin possessed varying modification patterns as indicated, with, e.g., an "M0/M11" pattern corresponding to a 25/27mer DsiRNA possessing an unmodified sense (passenger) strand and a modified antisense (guide) strand having the "M11" pattern of 2'-O-methylation. It is noted that the "M14" modification pattern of the sense strand corresponds to modification of the sense strand at the following positions, starting from the 5'-terminus (position 1) of the sense strand: 2, 4, 6, 8, 12, 14, 16 and 18.

The above in vivo results were confirmed and expanded upon under differing conditions in subsequent experiments that also employed modified forms of certain DsiRNAs. As shown in FIG. 31, DsiRNAs targeting β-catenin were shown to be active in vivo inhibitors of both β-catenin and Axin-2 in normal mouse liver, inhibiting both β-catenin mRNA (top panel) and Axin-2 mRNA (bottom panel) levels significantly (e.g., in many instances, approximately 70-90% knockdown was observed) when administered as a single dose intravenously to normal mice (n=5 mice per group) at 10 mg/kg and formulated in Invivofectamine® 2.0 (Invitrogen™, Carlsbad, Calif.). For such experiments, liver tissue was harvested at 72 hours post-administration. In these experiments, βc-3393 and βc-2612 DsiRNAs possessed varying modification patterns as indicated in FIG. 31, with, e.g., an "M0/M11" pattern corresponding to a 25/27mer DsiRNA possessing an unmodified sense (passenger) strand and a modified antisense (guide) strand having the "M11" pattern of 2'-O-methlyation. (Meanwhile, the "M14" modification pattern of the sense strand employed for βc-3393-M14/M12 corresponds to modification of the sense strand at the following positions, starting from the 5'-terminus (position 1) of the sense strand: 2, 4, 6, 8, 12, 14, 16 and 18. All three assayed DsiRNAs (βc-2612-M0/M11 and parallel differentially modified forms of βc-3393) showed greater than 80% inhibition of β-catenin levels in vivo in normal mouse liver, and at least 60% knockdown of Axin-2.

Figure 32:
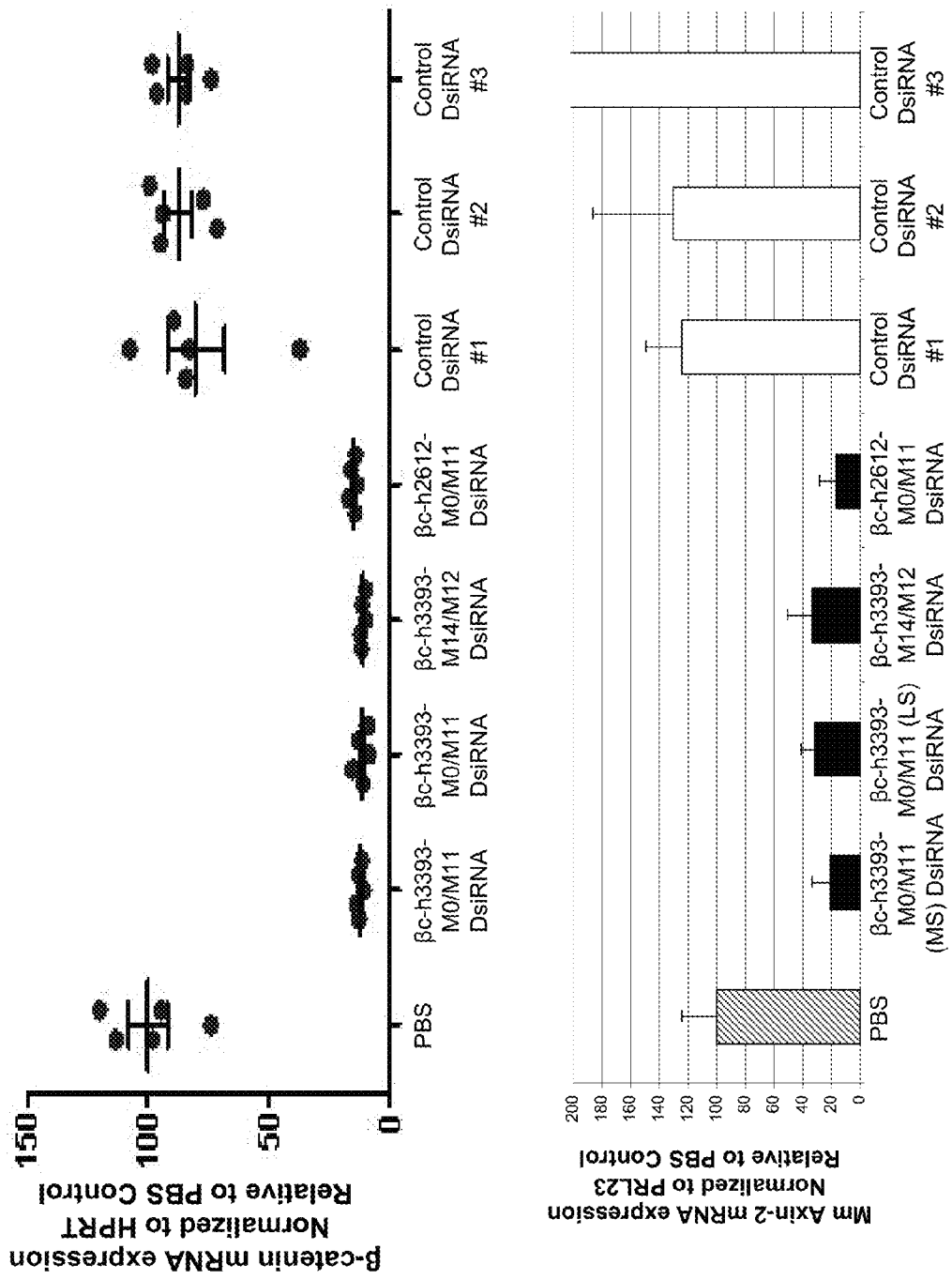
FIG. 32 demonstrates that DsiRNAs targeting human β-catenin were also active at a 48 hour timepoint in vivo in normal mouse liver, inhibiting both β-catenin mRNA (top panel) and Axin-2 mRNA (bottom panel) levels significantly (e.g., in many instances, approximately 70-90% knockdown was observed) when administered as a single dose intravenously to normal mice (n=5 mice per group) at 10 mg/kg and formulated in Invivofectamine® 2.0 (Invitrogen™, Carlsbad, Calif.). Liver tissue was harvested at 48 hours post-administration. DsiRNAs targeting human β-catenin possessed varying modification patterns as indicated and as described above. Control DsiRNAs possessed similar patterns of modification of sense and antisense strands.

Modified forms of βc-3393 and βc-2612 DsiRNAs were also observed to be active inhibitors of β-catenin and Axin-2 expression at a 48 hour timepoint in vivo in normal mouse liver. Specifically, as shown in FIG. 32, βc-3393-M0/M11 (MS), βc-3393-M0/M11 (LS), βc-3393-M14/M12 and βc-2612-M0/M11 DsiRNAs all robustly inhibited both β-catenin mRNA (top panel) and Axin-2 mRNA (bottom panel) levels significantly (e.g., in all instances, approximately 70-90% knockdown was observed) when administered as a single dose intravenously to normal mice (n=5 mice per group) at 10 mg/kg and formulated in Invivofectamine® 2.0 (Invitrogen™, Carlsbad, Calif.). In these experiments, liver tissue was harvested at 48 hours post-administration. DsiRNAs targeting β-catenin possessed varying modification patterns as indicated in FIG. 32 and as described above. Control DsiRNAs possessed similar patterns of modification of sense and antisense strands.

Thus, β-catenin DsiRNAs were observed to be surprisingly potent and effective inhibitors of β-catenin expression in vivo.

Example 9

Inhibition of β-Catenin by Additional Preferred DsiRNAs

The remaining DsiRNA molecules shown in Table 9, possessing sense and antisense strand sequences as shown and targeting β-catenin wild-type sequences (and variant sequences where applicable) are designed and synthesized as described above and tested in HeLa cells (and, optionally, in mouse Hepa 1-6 cells) for inhibitory efficacy as described in Examples 3 and 4 above. The ability of these DsiRNA agents to inhibit β-catenin expression is optionally assessed in comparison to corresponding β-catenin target sequence-directed 21mer siRNAs (21 nucleotide target sequences of β-catenin dsRNA agents described herein are presented in Tables 5 and 10 above). These additional DsiRNAs and the DsiRNAs tested herein are also examined for the ability to outperform cognate siRNAs, as determined via measurement of efficacy in decreasing levels of β-catenin target relative to a cognate 21mer siRNA agent. The duration of such inhibitory effects is also examined at both 24 hours and 48 hours post-administration, with concentrations of 0.1 nM, 0.3 nM, 1 nM and 5 nM tested. DsiRNAs of the instant invention are examined for the ability to outperform their cognate 21mer siRNA, as determined via measurement of potency and/or duration of effect.

Optionally, the DsiRNA molecules shown in Tables 6-8 and 11-13 above are also similarly synthesized and tested.

Example 10

Indications

As described herein, the nucleic acid molecules of the present invention are used in assays to diagnose disease state related to β-catenin levels. In addition, the nucleic acid molecules can be used to treat disease state related to β-catenin misregulation, levels, etc.

Particular disorders and disease states that can be associated with β-catenin expression modulation include, but are not limited to cancer and/or proliferative diseases, conditions, or disorders and other diseases, conditions or disorders that are related to or will respond to the levels of β-catenin in a cell or tissue, alone or in combination with other therapies. Particular degenerative and disease states that are associated with β-catenin expression modulation include but are not limited to, for example prostate cancer, lung cancer, colorectal cancer, bladder cancer, pancreatic cancer, and breast cancer.

In certain therapeutic embodiments, the disease or disorder to be treated is selected from the group consisting of a hyperproliferative disorder, such as cancer, such as a cancer selected from the group consisting of colorectal cancer, hepatocellular cancer, endometrial cancer, malignant melanoma, ovarian cancer, pancreatic cancer, pituitary cancer, oesophageal cancer, lung cancer, breast cancer, kidney cancer, haematopoetic system cancer, cervical cancer, CNS cancer, bone cancer, biliary tract cancer and adrenal gland cancer. Optionally, the disease or disorder is a cancer selected from the group consisting of colorectal cancer, hepatocellular cancer, endometrial cancer, and malignant melanoma. In certain embodiments, the disorder is a cancer selected from the group consisting of liver cancer and kidney cancer. In certain embodiments, the disease or disorder is associated with a mutation in the β-catenin gene or a gene whose protein product is associated with or interacts with β-catenin, such as the APC gene. Therefore, in various embodiments, the target mRNA is a mutated form of the β-catenin sequence, for example it may comprise one or more single point mutations, such as SNPs associated with cancer.

Examples of such diseases where mutations in the β-catenin or APC gene lead to abnormal levels of β-catenin activity are: (1) Colorectal cancer, APC and β-catenin are mutually mutated in more than 70% of all cases (Powell et al., Nature, 1992; Morin et al., Science, 1997; Sparks et al., Cancer Res, 1998); (2) Hepatocellular cancer, β-catenin are mutated in more than 25% of cases (de La Coste A, PNAS, 1998); (3) Endometrial cancer, β-catenin are mutated >10%; and (4) Malignant melanoma, β-catenin are mutated >10% (Rubinfeld et al., Science, 1997).

Further examples of such diseases are cancer of the ovary, pancreas, pituitary, oesophagus, lung, breast, kidney, haematopoetic system, cervix, CNS, bone, biliary tract and adrenal gland. It has been shown that mutations in the β-catenin or APC gene are associated with these diseases (Catalogue of Somatic Mutations in Cancer available from the Sanger Institute (United Kingdom) homepage http://www.sanger.ac.uk/).

In certain embodiments, the disease or disorder is associated with abnormal levels of a mutated form of β-catenin. In certain embodiments, the disease or disorder is associated with abnormal levels of a wild-type form of β-catenin. One aspect of the invention is directed to a method of treating a mammal suffering from or susceptible to conditions associated with abnormal levels of β-catenin, comprising administering to the mammal a therapeutically effective amount of a DsiRNA of the invention targeted to β-catenin or various compositions or conjugates thereof.

Gemcytabine and cyclophosphamide are non-limiting examples of chemotherapeutic agents that can be combined with or used in conjunction with the nucleic acid molecules (e.g. DsiRNA molecules) of the instant invention. Those skilled in the art will recognize that other drugs such as anti-cancer compounds and therapies can be similarly be readily combined with the nucleic acid molecules of the instant invention (e.g. DsiRNA molecules) and are hence within the scope of the instant invention. Such compounds and therapies are well known in the art (see for example Cancer: Principles and Practice of Oncology, Volumes 1 and 2, eds Devita, V. T., Hellman, S., and Rosenberg, S. A., J.B. Lippincott Company, Philadelphia, USA) and include, without limitations, antifolates; fluoropyrimidines; cytarabine; purine analogs; adenosine analogs; amsacrine; topoisomerase I inhibitors; anthrapyrazoles; retinoids; antibiotics such as bleomycin, anthacyclins, mitomycin C, dactinomycin, and mithramycin; hexamethylmelamine; dacarbazine; 1-asperginase; platinum analogs; alkylating agents such as nitrogen mustard, melphalan, chlorambucil, busulfan, ifosfamide, 4-hydroperoxycyclophosphamide, nitrosoureas, thiotepa; plant derived compounds such as vinca alkaloids, epipodophylotoxins, taxol; Tamoxifen; radiation therapy; surgery; nutritional supplements; gene therapy; radiotherapy such as 3D-CRT; immunotoxin therapy such as ricin, monoclonal antibodies Herceptin; and the like. For combination therapy, the nucleic acids of the invention are prepared in one of two ways. First, the agents are physically combined in a preparation of nucleic acid and chemotherapeutic agent, such as a mixture of a nucleic acid of the invention encapsulated in liposomes and ifosfamide in a solution for intravenous administration, wherein both agents are present in a therapeutically effective concentration (e.g., ifosfamide in solution to deliver 1000-1250 mg/m2/day and liposome-associated nucleic acid of the invention in the same solution to deliver 0.1-100 mg/kg/day). Alternatively, the agents are administered separately but simultaneously in their respective effective doses (e.g., 1000-1250 mg/m2/d ifosfamide and 0.1 to 100 mg/kg/day nucleic acid of the invention).

Those skilled in the art will recognize that other compounds and therapies used to treat the diseases and conditions described herein can similarly be combined with the nucleic acid molecules of the instant invention (e.g. siNA molecules) and are hence within the scope of the instant invention.

Example 11

Serum Stability of DsiRNAs

Serum stability of DsiRNA agents is assessed via incubation of DsiRNA agents in 50% fetal bovine serum for various periods of time (up to 24 h) at 37° C. Serum is extracted and the nucleic acids are separated on a 20% non-denaturing PAGE and can be visualized with Gelstar stain. Relative levels of protection from nuclease degradation are assessed for DsiRNAs (with and without modifications).

Example 12

Use of Additional Cell Culture Models to Evaluate the Down-Regulation of β-Catenin Gene Expression A variety of endpoints have been used in cell culture models to look at β-catenin-mediated effects after treatment with anti-β-catenin agents. Phenotypic endpoints include inhibition of cell proliferation, RNA expression, and reduction of β-catenin protein expression. Because β-catenin mutations are directly associated with increased proliferation of certain tumor cells, a proliferation endpoint for cell culture assays can be used as a screen, e.g., as documented in the above examples. There are several methods by which this endpoint can be measured. Following treatment of cells with DsiRNA, cells are allowed to grow (typically 5 days), after which the cell viability, the incorporation of bromodeoxyuridine (BrdU) into cellular DNA and/or the cell density are measured. The assay of cell density can be done in a 96-well format, e.g. by using commercially available fluorescent nucleic acid stains (such as Syto® 13 or CyQuant®). As a secondary, confirmatory endpoint, a DsiRNA-mediated decrease in the level of β-catenin protein expression can be evaluated using a β-catenin-specific ELISA.

Example 13

Evaluation of Anti-β-Catenin DsiRNA Efficacy in a Mouse Model of β-Catenin Misregulation Anti-β-catenin DsiRNA chosen from in vitro assays can be further tested in mouse models, including, e.g., xenograft and other animal models as recited above. In one example, mice possessing misregulated (e.g., elevated) β-catenin levels are administered a DsiRNA agent of the present invention via hydrodynamic tail vein injection. 3-4 mice per group (divided based upon specific DsiRNA agent tested) are injected with 50 μg or 200 μg of DsiRNA. Levels of β-catenin RNA are evaluated using RT-qPCR. Additionally or alternatively, levels of β-catenin (e.g., (β-catenin protein levels and/or cancer cell/tumor formation, growth or spread) can be evaluated using an art-recognized method, or phenotypes associated with misregulation of β-catenin (e.g., tumor formation, growth, metastasis, etc.) are monitored (optionally as a proxy for measurement of β-catenin transcript or (β-catenin protein levels). Active DsiRNA in such animal models can also be subsequently tested in combination with standard chemotherapies.

Example 14

Diagnostic Uses

The DsiRNA molecules of the invention can be used in a variety of diagnostic applications, such as in the identification of molecular targets (e.g., RNA) in a variety of applications, for example, in clinical, industrial, environmental, agricultural and/or research settings. Such diagnostic use of DsiRNA molecules involves utilizing reconstituted RNAi systems, for example, using cellular lysates or partially purified cellular lysates. DsiRNA molecules of this invention can be used as diagnostic tools to examine genetic drift and mutations within diseased cells. The close relationship between DsiRNA activity and the structure of the target β-catenin RNA allows the detection of mutations in a region of the β-catenin molecule, which alters the base-pairing and three-dimensional structure of the target β-catenin RNA. By using multiple DsiRNA molecules described in this invention, one can map nucleotide changes, which are important to RNA structure and function in vitro, as well as in cells and tissues. Cleavage of target β-catenin RNAs with DsiRNA molecules can be used to inhibit gene expression and define the role of specified gene products in the progression of a β-catenin-associated disease or disorder. In this manner, other genetic targets can be defined as important mediators of the disease. These experiments will lead to better treatment of the disease progression by affording the possibility of combination therapies (e.g., multiple DsiRNA molecules targeted to different genes, DsiRNA molecules coupled with known small molecule inhibitors, or intermittent treatment with combinations of DsiRNA molecules and/or other chemical or biological molecules). Other in vitro uses of DsiRNA molecules of this invention are well known in the art, and include detection of the presence of RNAs associated with a disease or related condition. Such RNA is detected by determining the presence of a cleavage product after treatment with a DsiRNA using standard methodologies, for example, fluorescence resonance emission transfer (FRET).

In a specific example, DsiRNA molecules that cleave only wild-type or mutant or polymorphic forms of the target β-catenin RNA are used for the assay. The first DsiRNA molecules (i.e., those that cleave only wild-type forms of target β-catenin RNA) are used to identify wild-type β-catenin RNA present in the sample and the second DsiRNA molecules (i.e., those that cleave only mutant or polymorphic forms of target RNA) are used to identify mutant or polymorphic β-catenin RNA in the sample. As reaction controls, synthetic substrates of both wild-type and mutant or polymorphic β-catenin RNA are cleaved by both DsiRNA molecules to demonstrate the relative DsiRNA efficiencies in the reactions and the absence of cleavage of the "non-targeted" β-catenin RNA species. The cleavage products from the synthetic substrates also serve to generate size markers for the analysis of wild-type and mutant β-catenin RNAs in the sample population. Thus, each analysis requires two DsiRNA molecules, two substrates and one unknown sample, which is combined into six reactions. The presence of cleavage products is determined using an RNase protection assay so that full-length and cleavage fragments of each β-catenin RNA can be analyzed in one lane of a polyacrylamide gel. It is not absolutely required to quantify the results to gain insight into the expression of mutant or polymorphic β-catenin RNAs and putative risk of β-catenin-associated phenotypic changes in target cells. The expression of β-catenin mRNA whose protein product is implicated in the development of the phenotype (i.e., disease related/associated) is adequate to establish risk. If probes of comparable specific activity are used for both transcripts, then a qualitative comparison of β-catenin RNA levels is adequate and decreases the cost of the initial diagnosis. Higher mutant or polymorphic form to wild-type ratios are correlated with higher risk whether β-catenin RNA levels are compared qualitatively or quantitatively.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying DsiRNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09428752B2). An electronic copy of the "Sequence Listing" will also be available from the USPTO upon request and payment of the fee set forth in 37 CFR 1.19(b)(3).

We claim:

1. A double-stranded RNA (dsRNA) comprising first and second nucleic acid strands and a duplex region of at least 25 base pairs, wherein said first strand is 25-35 nucleotides in length and said second strand of said dsRNA comprises 5'-GCUGUUUCUACAUCAUUUGUAUUCUGC-3' (SEQ ID NO: 1239), wherein said dsRNA reduces β-catenin target gene expression when said double stranded nucleic acid is introduced into a mammalian cell.

2. The dsRNA of claim 1, wherein said dsRNA possesses a modified nucleotide or backbone modification.

3. The dsRNA of claim 2, wherein the dsRNA possesses one or more modifications selected from the group consisting of a 2'-O-methyl nucleotide, a 2'-methoxyethoxy nucleotide, a 2'-fluoro nucleotide, a 2'-allyl nucleotide, a 2'-O-[2-(methylamino)-2-oxoethyl] nucleotide, a 4'-thio nucleotide, a 4'-CH2-O-2'-bridge, a 4'-(CH2)2-O-2'-bridge, a locked nucleic acid (LNA), a 2'-amino, a 2'-O—(N-methlycarbamate), a 2'-O-alkyl ribonucleotide, a deoxyribonucleotide, a dideoxyribonucleotide, an acyclonucleotide, a 3'-deoxyadenosine (cordycepin), a 3'-azido-3'-deoxythymidine (AZT), a 2',3'-dideoxyinosine (ddI), a 2',3'-dideoxy-3'-thiacytidine (3TC), a 2',3'-didehydro-2',3'-dideoxythymidine (d4T), a monophosphate nucleotide of 3'-azido-3'-deoxythymidine (AZT), a 2',3'-dideoxy-3'-thiacytidine (3TC) and a monophosphate nucleotide of 2',3'-didehydro-2',3'-dideoxythymidine (d4T), a 4-thiouracil, a 5-bromouracil, a 5-iodouracil, a 5-(3-aminoallyl)-uracil, a phosphonate backbone modification, a phosphorothioate backbone modification and a phosphotriesterphosphate backbone modification.

4. The dsRNA of claim 1, wherein starting from the first nucleotide (position 1) at the 3' terminus of the first strand, position 1, 2 and/or 3 is substituted with one or more modified nucleotides.

5. The dsRNA of claim 4, wherein said modified nucleotide is a deoxyribonucleotide.

6. The dsRNA of claim 2, wherein starting from the first nucleotide (position 1) at the 3' terminus of the first strand, positions 1 and 2 are substituted with a deoxyribonucleotide.

7. The dsRNA of claim 2, wherein starting from the first nucleotide (position 1) at the 3' terminus of the second strand, positions 1, 2 and 3 are substituted with a 2'-O-methyl ribonucleotide.

8. The dsRNA of claim 1, wherein said first strand comprises 5'-AGAAUACAAAUGAUGUAGAAACAGC-3' (SEQ ID NO: 130).

9. The dsRNA of claim 1, wherein said first strand consists of 5'-AGAAUACAAAUGAUGUAGAAACAGC-3' (SEQ ID NO: 130).

10. The dsRNA of claim 1, wherein the first and second strands are joined by a chemical linker.

11. The dsRNA of claim 1, wherein said second strand comprises 1-5 single-stranded nucleotides at its 3' terminus.

12. The dsRNA of claim 1, wherein said first strand is 25 nucleotides in length.

13. The dsRNA of claim 1, wherein said first strand is 26 nucleotides in length.

14. The dsRNA of claim 1, wherein said second strand is up to 50 nucleotides in length.

* * * * *